(12) United States Patent
Axten et al.

(10) Patent No.: US 11,773,078 B2
(45) Date of Patent: Oct. 3, 2023

(54) FURIN INHIBITORS

(71) Applicant: Glaxosmithkline Intellectual Property Development Limited, Brentford (GB)

(72) Inventors: Jeffrey Michael Axten, King of Prussia, PA (US); Mui Cheung, King of Prussia, PA (US); Michael P. Demartino, Collegeville, PA (US); Huiping Amy Guan, Acton, MA (US); Yan Hu, Shanghai (CN); Aaron Bayne Miller, Research Triangle Park, NC (US); Donghui Qin, Malvern, PA (US); Chengde Wu, Shanghai (CN); Zhiliu Zhang, Shanghai (CN); Xiaojuan Lin, Shanghai (CN)

(73) Assignee: Glaxosmithkline Intellectual Property Development Limited, Brentford (GB)

( * ) Notice: Subject to any disclaimer, the term of this patent is extended or adjusted under 35 U.S.C. 154(b) by 254 days.

(21) Appl. No.: 17/054,491

(22) PCT Filed: May 10, 2019

(86) PCT No.: PCT/EP2019/062098
§ 371 (c)(1),
(2) Date: Nov. 10, 2020

(87) PCT Pub. No.: WO2019/215341
PCT Pub. Date: Nov. 14, 2019

(65) Prior Publication Data
US 2022/0315556 A1 Oct. 6, 2022

Related U.S. Application Data

(60) Provisional application No. 62/670,050, filed on May 11, 2018.

(51) Int. Cl.
*C07D 401/12* (2006.01)
*C07D 401/14* (2006.01)
*A61P 11/00* (2006.01)
*C07D 211/26* (2006.01)
*C07D 487/08* (2006.01)

(52) U.S. Cl.
CPC ............ *C07D 401/14* (2013.01); *A61P 11/00* (2018.01); *C07D 211/26* (2013.01); *C07D 401/12* (2013.01); *C07D 487/08* (2013.01)

(58) Field of Classification Search
CPC ............................ C07D 401/12; C07D 401/14
See application file for complete search history.

(56) References Cited

U.S. PATENT DOCUMENTS

| | | |
|---|---|---|
| 2006/0058308 A1 | 3/2006 | Norman et al. |
| 2009/0131328 A1 | 5/2009 | Smith et al. |
| 2015/0051138 A1 | 2/2015 | Strongin et al. |
| 2015/0073054 A1 | 3/2015 | Strongin et al. |
| 2015/0232428 A1 | 8/2015 | Haidle et al. |
| 2023/0011571 A1 | 1/2023 | Wilcoxen et al. |

FOREIGN PATENT DOCUMENTS

| | | |
|---|---|---|
| CN | 101952275 A | 1/2011 |
| CN | 107441094 A | 12/2017 |
| CN | 107624110 A | 1/2018 |
| JP | 2006-514118 A | 4/2006 |
| RU | 2576402 C2 | 3/2016 |
| WO | WO 2005/047268 A1 | 5/2005 |
| WO | WO 2006/031852 A1 | 3/2006 |
| WO | WO 2007/046781 A1 | 4/2007 |
| WO | WO 2009/023306 A2 | 2/2009 |
| WO | WO 2013/138665 A1 | 9/2013 |
| WO | WO 2013/138666 A1 | 9/2013 |
| WO | WO 2014/031438 A2 | 2/2014 |
| WO | WO 2014/152716 A1 | 9/2014 |

(Continued)

OTHER PUBLICATIONS

International Search Report and Written Opinion for PCT/EP2019/062098, dated Jul. 30, 2019.

(Continued)

*Primary Examiner* — Brian E McDowell
(74) *Attorney, Agent, or Firm* — Wolf, Greenfield & Sacks, P.C.

(57) ABSTRACT

This invention relates to novel compounds according to Formula (I) which are inhibitors of furin, to pharmaceutical compositions containing them, to processes for their preparation, and to their use in therapy for the treatment of fibrotic diseases, including pulmonary fibrosis, renal fibrosis, liver fibrosis, skin fibrosis, ocular fibrosis, cardiac fibrosis, and other miscellaneous fibrotic conditions. The disclosed compounds may also be useful for treating other furin-mediated conditions, including but not limited to, hypertension, cancer, infectious diseases, and genetic disorders (e.g., cystic fibrosis (CF)), and neurodegenerative disorders.

(I)

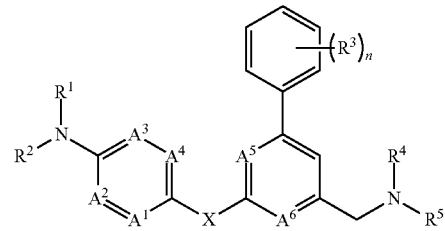

22 Claims, 16 Drawing Sheets
Specification includes a Sequence Listing.

(56) References Cited

FOREIGN PATENT DOCUMENTS

| WO | WO 2016/144702 A1 | 9/2016 |
|---|---|---|
| WO | WO 2019/215341 A1 | 11/2019 |

OTHER PUBLICATIONS

Bennett et al., A furin-like convertase mediates propeptide cleavage of BACE, the Alzheimer's beta-secretase. J Biol Chem. Dec. 1, 2000;275(48):37712-7. doi: 10.1074/jbc.M005339200. Erratum in: J Biol Chem May 4, 2001;276(18):15561. PMID: 10956649.

Biernacka et al., TGF-β signaling in fibrosis. Growth Factors. Oct. 2011;29(5):196-202. doi: 10.3109/08977194.2011.595714. Epub Jul. 11, 2011. PMID: 21740331; PMCID: PMC4408550.

Bonnans et al., Remodelling the extracellular matrix in development and disease. Nat Rev Mol Cell Biol. Dec. 2014;15(12):786-801. doi: 10.1038/nrm3904. PMID: 25415508; PMCID: PMC4316204.

Constam, Regulation of TGFβ and related signals by precursor processing. Semin Cell Dev Biol. Aug. 2014;32:85-97. doi: 10.1016/j.semcdb.2014.01.008. Epub Feb. 5, 2014. PMID: 24508081.

Constam et al., Tissue-specific requirements for the proprotein convertase furin/SPC1 during embryonic turning and heart looping. Development. Jan. 2000;127(2):245-54. PMID: 10603343.

Cousin et al., Soluble form of the (pro)renin receptor generated by intracellular cleavage by furin is secreted in plasma. Hypertension. Jun. 2009;53(6):1077-82. doi: 10.1161/HYPERTENSIONAHA.108.127258. Epub Apr. 20, 2009. PMID: 19380613.

Couture et al., Therapeutic uses of furin and its inhibitors: a patent review. Expert Opin Ther Pat. Apr. 2015;25(4):379-96. doi: 10.1517/13543776.2014.1000303. Epub Jan. 7, 2015. PMID: 25563687.

Crews et al., Molecular mechanisms of neurodegeneration in Alzheimer's disease. Hum Mol Genet. Apr. 15, 2010;19(R1):R12-20. doi: 10.1093/hmg/ddq160. Epub Apr. 22, 2010. PMID: 20413653; PMCID: PMC2875049.

Dai et al., The genes associated with early-onset Alzheimer's disease. Oncotarget. Dec. 15, 2017;9(19):15132-15143. doi: 10.18632/oncotarget.23738. PMID: 29599933; PMCID: PMC5871104.

Dubois et al., Evidence that furin is an authentic transforming growth factor-beta1-converting enzyme. Am J Pathol. Jan. 2001;158(1):305-16. doi: 10.1016/s0002-9440(10)63970-3. PMID: 11141505; PMCID: PMC1850265.

Ehret et al., Genetic variants in novel pathways influence blood pressure and cardiovascular disease risk. Nature. Sep. 11, 2011;478(7367):103-9. doi: 10.1038/nature10405. PMID: 21909115; PMCID: PMC3340926.

Ganesh et al., Loci influencing blood pressure identified using a cardiovascular gene-centric array. Hum Mol Genet. Apr. 15, 2013;22(8):1663-78. doi: 10.1093/hmg/dds555. Epub Jan. 8, 2013. Erratum in: Hum Mol Genet. Aug. 15, 2013;22(16):3394-5. Van Setten, Jessic A [corrected to Van Setten, Jessica]. PMID: 23303523; PMCID: PMC3657476.

Garten et al., Processing of viral glycoproteins by the subtilisin-like endoprotease furin and its inhibition by specific peptidylchloroalkylketones. Biochimie. 1994;76(3-4):217-25. doi: 10.1016/0300-9084(94)90149-x. PMID: 7819326.

Hoffman et al., Cystic fibrosis therapeutics: the road ahead. Chest. Jan. 2013;143(1):207-213. doi: 10.1378/chest.12-1639. PMID: 23276843; PMCID: PMC3610617.

Jaaks et al., The proprotein convertase furin in tumour progression. Int J Cancer. Aug. 15, 2017;141(4):654-663. doi: 10.1002/ijc.30714. Epub May 15, 2017. PMID: 28369813.

Joukov et al., Proteolytic processing regulates receptor specificity and activity of VEGF-C. EMBO J. Jul. 1, 1997;16(13):3898-911. doi: 10.1093/emboj/16.13.3898. PMID: 9233800; PMCID: PMC1170014.

Kang et al., Activation of membrane-type matrix metalloproteinase 3 zymogen by the proprotein convertase furin in the trans-Golgi network. Cancer Res. Feb. 1, 2002;62(3):675-81. PMID: 11830519.

Klein-Szanto et al., Proprotein convertase inhibition: Paralyzing the cell's master switches. Biochem Pharmacol. Sep. 15, 2017;140:8-15. doi: 10.1016/j.bcp.2017.04.027. Epub Apr. 27, 2017. PMID: 28456517; PMCID: PMC5586041.

Loechel et al., Human ADAM 12 (meltrin alpha) is an active metalloprotease. J Biol Chem. Jul. 3, 1998;273(27):16993-7. doi: 10.1074/jbc.273.27.16993. PMID: 9642263.

Maquoi et al., Inhibition of matrix metalloproteinase 2 maturation and HT1080 invasiveness by a synthetic furin inhibitor. FEBS Lett. Mar. 13, 1998;424(3):262-6. doi: 10.1016/s0014-5793(98)00187-2. PMID: 9539163.

McColl et al., Proprotein convertases promote processing of VEGF-D, a critical step for binding the angiogenic receptor VEGFR-2. FASEB J. Apr. 2007;21(4):1088-98. doi: 10.1096/fj.06-7060com. Epub Jan. 22, 2007. PMID: 17242158.

Myerburg et al., Acute regulation of the epithelial sodium channel in airway epithelia by proteases and trafficking. Am J Respir Cell Mol Biol. Dec. 2010;43(6):712-9. doi: 10.1165/rcmb.2009-0348OC. Epub Jan. 22, 2010. PMID: 20097829; PMCID: PMC2993091.

Nakayama, Furin: a mammalian subtilisin/Kex2p-like endoprotease involved in processing of a wide variety of precursor proteins. Biochem J. Nov. 1, 1997;327 ( Pt 3)(Pt 3):625-35. doi: 10.1042/bj3270625. PMID: 9599222; PMCID: PMC1218878.

Nanthakumar et al., Dissecting fibrosis: therapeutic insights from the small-molecule toolbox. Nat Rev Drug Discov. Oct. 2015;14(10):693-720. doi: 10.1038/nrd4592. Epub Sep. 4, 2015. PMID: 26338155.

Pesu et al., T-cell-expressed proprotein convertase furin is essential for maintenance of peripheral immune tolerance. Nature. Sep. 11, 2008;455(7210):246-50. doi: 10.1038/nature07210. PMID: 18701887; PMCID: PMC2758057.

Pohlers et al., TGF-beta and fibrosis in different organs—molecular pathway imprints. Biochim Biophys Acta. Aug. 2009;1792(8):746-56. doi: 10.1016/j.bbadis.2009.06.004. Epub Jun. 17, 2009. PMID: 19539753.

Rangachari et al., Cause and consequence of Aβ—Lipid interactions in Alzheimer disease pathogenesis. Biochim Biophys Act. Sep. 2018. 1860(9):1652-1662.

Reihill et al., Inhibition of Protease-Epithelial Sodium Channel Signaling Improves Mucociliary Function in Cystic Fibrosis Airways. Am J Respir Crit Care Med. Sep. 15, 2016;194(6):701-10. doi: 10.1164/rccm.201511-2216OC. PMID: 27014936.

Robertson et al., Latent TGF-β-binding proteins. Matrix Biol. Sep. 2015;47:44-53. doi: 10.1016/j.matbio.2015.05.005. Epub May 8, 2015. PMID: 25960419; PMCID: PMC4844006.

Roebroek et al., Failure of ventral closure and axial rotation in embryos lacking the proprotein convertase Furin. Development. Dec. 1998;125(24):4863-76. PMID: 9811571.

Roebroek et al., Limited redundancy of the proprotein convertase furin in mouse liver. J Biol Chem. Dec. 17, 2004;279(51):53442-50. doi: 10.1074/jbc.M407152200. Epub Oct. 7, 2004. PMID: 15471862.

Schlöndorff et al., Intracellular maturation and localization of the tumour necrosis factor alpha convertase (TACE). Biochem J. Apr. 1, 2000;347 Pt 1(Pt 1):131-8. PMID: 10727411; PMCID: PMC1220940.

Seidah et al., The biology and therapeutic targeting of the proprotein convertases. Nat Rev Drug Discov. May 2012;11(5):367-83. doi: 10.1038/nrd3699. PMID: 22679642.

Shiryaev et al., High-resolution analysis and functional mapping of cleavage sites and substrate proteins of furin in the human proteome. PLoS One. 2013;8(1):e54290. doi: 10.1371/journal.pone.0054290. Epub Jan. 15, 2013. PMID: 23335997; PMCID: PMC3545927.

Susan-Resiga et al., Furin is the major processing enzyme of the cardiac-specific growth factor bone morphogenetic protein 10. J Biol Chem. Jul. 1, 2011;286(26):22785-94. doi: 10.1074/jbc.M111.233577. Epub May 5, 2011. PMID: 21550985; PMCID: PMC3123046.

Thomas et al., In the Shadow of Fibrosis: Innate Immune Suppression Mediated by Transforming Growth Factor-β. Am J Respir Cell Mol Biol. Dec. 2016;55(6):759-766. doi: 10.1165/rcmb.2016-0248PS. PMID: 27603223.

Thomas, Furin at the cutting edge: from protein traffic to embryogenesis and disease. Nat Rev Mol Cell Biol. Oct. 2002;3(10):753-66. doi: 10.1038/nrm934. PMID: 12360192; PMCID: PMC1964754.

(56) References Cited

OTHER PUBLICATIONS

Turpeinen et al., Genetics of the first seven proprotein convertase enzymes in health and disease. Curr Genomics. Nov. 2013;14(7):453-67. doi: 10.2174/1389202911314050010. PMID: 24396277; PMCID: PMC3867721.

Wang et al., Shedding of membrane type matrix metalloproteinase 5 by a furin-type convertase: a potential mechanism for down-regulation. J. Biol. Chem. Sep. 21, 2001;276(38):35953-60. doi: 10.1074/jbc.M103680200. Epub Jul. 26, 2001. PMID: 11470782.

Yana et al., Regulation of membrane type-1 matrix metalloproteinase activation by proprotein convertases. Mol Biol Cell. Jul. 2000;11(7):2387-401. doi: 10.1091/mbc.11.7.2387. PMID: 10888676; PMCID: PMC14927.

Zhang, Non-Smad pathways in TGF-beta signaling. Cell Res. Jan. 2009;19(1):128-39. doi: 10.1038/cr.2008.328. PMID: 19114990; PMCID: PMC2635127.

International Preliminary Report on Patentability, dated Nov. 26, 2020 for Application No. PCT/EP2019/062098.

International Search Report and Written Opinion, dated Mar. 3, 2021 for Application No. PCT/US2020/060108.

International Preliminary Report on Patentability, dated May 27, 2022 for Application No. PCT/US2020/060108.

International Search Report and Written Opinion, dated Jul. 20, 2021 for Application No. PCT/US2021/025382.

International Preliminary Report on Patentability, dated Oct. 13, 2022 for Application No. PCT/US2021/025382.

International Search Report and Written Opinion, dated Apr. 20, 2022 for Application No. PCT/US2022/015098.

Alexander et al., History of highly pathogenic avian influenza. Rev Sci Tech. Apr. 2009;28(1):19-38. doi: 10.20506/rst.28.1.1856.

Andersen et al., The proximal origin of SARS-CoV-2. Nat Med. Apr. 2020;26(4):450-452. doi: 10.1038/s41591-020-0820-9.

Bagdonaite et al., Global aspects of viral glycosylation. Glycobiology. Jul. 1, 2018;28(7):443-467. doi: 10.1093/glycob/cwy021.

Belouzard et al., Activation of the SARS coronavirus spike protein via sequential proteolytic cleavage at two distinct sites. Proc Natl Acad Sci U S A. Apr. 7, 2009;106(14):5871-6. doi: 10.1073/pnas.0809524106. Epub Mar. 24, 2009.

Bergeron et al., Implication of proprotein convertases in the processing and spread of severe acute respiratory syndrome coronavirus. Biochem Biophys Res Commun. Jan. 21, 2005;326(3):554-63. doi: 10.1016/j.bbrc.2004.11.063.

Braun et al., Furin-mediated protein processing in infectious diseases and cancer. Clin Transl Immunology. Aug. 5, 2019;8(8):e1073. doi: 10.1002/cti2.1073.

Chan et al., Genomic characterization of the 2019 novel human-pathogenic coronavirus isolated from a patient with atypical pneumonia after visiting Wuhan. Emerg Microbes Infect. Jan. 28, 2020;9(1):221-236. doi: 10.1080/22221751.2020.1719902. Erratum in: Emerg Microbes Infect. Dec. 2020;9(1):540.

Cheng et al., The S2 Subunit of QX-type Infectious Bronchitis Coronavirus Spike Protein Is an Essential Determinant of Neurotropism. Viruses. Oct. 22, 2019;11(10):972. doi: 10.3390/v11100972.

Claas et al., Human influenza A H5N1 virus related to a highly pathogenic avian influenza virus. Lancet. Feb. 14, 1998;351(9101):472-7. doi: 10.1016/S0140-6736(97)11212-0. Erratum in: Lancet Apr. 25, 1998;351(9111):1292.

Clark et al., GNF-2 Inhibits Dengue Virus by Targeting Abl Kinases and the Viral E Protein. Cell Chem Biol. Apr. 21, 2016;23(4):443-52. doi: 10.1016/j.chembiol.2016.03.010.

Coutard et al., The spike glycoprotein of the new coronavirus 2019-nCoV contains a furin-like cleavage site absent in CoV of the same clade. Antiviral Res. Apr. 2020;176:104742. doi: 10.1016/j.antiviral.2020.104742. Epub Feb. 10, 2020.

De Wispelaere et al., Inhibition of Flaviviruses by Targeting a Conserved Pocket on the Viral Envelope Protein. Cell Chem Biol. Aug. 16, 2018;25(8):1006-1016.e8. doi: 10.1016/j.chembiol.2018.05.011. Epub Jun. 21, 2018.

Douglas et al., Furin Inhibition as a Mechanism to Reduce Aberrant ENaC-Mediated Sodium Transport and Rehydrate the Airways in Cystic Fibrosis Lung Disease. FASEB J. Apr. 1, 2019;33(S1). 3 pages. Abstract Only. Retrieved from <https://faseb.onlinelibrary.wiley.com/doi/10.1096/fasebj.2019.33. 1_supplement.802.26>.

Essalmani et al., Furin cleaves SARS-CoV-2 spike-glycoprotein at S1/S2 and S2' for viral fusion/entry: indirect role of TMPRSS2. bioRxiv. Dec. 20, 2020. 46 pages, doi: 10.1101/2020.12.18.423106.

Ito et al., Generation of a highly pathogenic avian influenza A virus from an avirulent field isolate by passaging in chickens. J Virol. May 2001;75(9):4439-43. doi: 10.1128/JVI.75.9.4439-4443.2001.

Jaimes et al., Structural modeling of 2019-novel coronavirus (nCoV) spike protein reveals a proteolytically-sensitive activation loop as a distinguishing feature compared to SARS-CoV and related SARS-like coronaviruses. bioRxiv [Preprint]. Feb. 18, 2020. 36 pages, doi: 10.1101/2020.02.10.942185.

Jin et al., Virus strain from a mild COVID-19 patient in Hangzhou represents a new trend in SARS-CoV-2 evolution potentially related to Furin cleavage site. Emerg Microbes Infect. Dec. 2020;9(1):1474-1488. doi: 10.1080/22221751.2020.1781551.

Klimpel et al., Anthrax toxin protective antigen is activated by a cell surface protease with the sequence specificity and catalytic properties of furin. Proc Natl Acad Sci U S A. Nov. 1, 1992;89(21):10277-81. doi: 10.1073/pnas.89.21.10277.

Menachery et al., Trypsin Treatment Unlocks Barrier for Zoonotic Bat Coronavirus Infection. J Virol. Feb. 14, 2020;94(5):e01774-19. doi: 10.1128/JVI.01774-19.

Millet et al., Host cell entry of Middle East respiratory syndrome coronavirus after two-step, furin-mediated activation of the spike protein. Proc Natl Acad Sci U S A. Oct. 21, 2014;111(42):15214-9. doi: 10.1073/pnas.1407087111. Epub Oct. 6, 2014.

Millet et al., Host cell proteases: Critical determinants of coronavirus tropism and pathogenesis. Virus Res. Apr. 16, 2015;202:120-34. doi: 10.1016/j.virusres.2014.11.021. Epub Nov. 22, 2014.

Mukherjee et al., Enhancing dengue virus maturation using a stable furin over-expressing cell line. Virology. Oct. 2016;497:33-40. doi: 10.1016/j.virol.2016.06.022. Epub Jul. 13, 2016.

Neumann et al., Proteolytic processing of the Ebola virus glycoprotein is not critical for Ebola virus replication in nonhuman primates. J Virol. Mar. 2007;81(6):2995-8. doi: 10.1128/JVI.02486-06. Epub Jan. 17, 2007.

Rabaan et al., SARS-CoV-2, SARS-CoV, and MERS-COV: A comparative overview. Infez Med. 2020 Ahead Of Print Jun. 1;28(2):174-184.

Ramos-Molina et al., Identification of potent and compartment-selective small molecule furin inhibitors using cell-based assays. Biochem Pharmacol. Jul. 15, 2015;96(2):107-18. doi: 10.1016/j.bcp.2015.05.008. Epub May 21, 2015.

Steiner et al., Insulin biosynthesis: evidence for a precursor. Science. Aug. 11, 1967;157(3789):697-700. doi: 10.1126/science.157.3789.697.

Steinhauer D.A., Role of hemagglutinin cleavage for the pathogenicity of influenza virus. Virology. May 25, 1999;258(1):1-20. doi: 10.1006/viro.1999.9716.

Tian et al., FurinDB: A database of 20-residue furin cleavage site motifs, substrates and their associated drugs. Int J Mol Sci. Feb. 8, 2011;12(2):1060-5. doi: 10.3390/ijms12021060.

Van De Ven et al., Furin is a subtilisin-like proprotein processing enzyme in higher eukaryotes. Mol Biol Rep. Nov. 1990;14(4):265-75. doi: 10.1007/BF00429896.

Walls et al., Structure, Function, and Antigenicity of the SARS-CoV-2 Spike Glycoprotein. Cell. Apr. 16, 2020;181(2):281-292.e6. doi: 10.1016/j.cell.2020.02.058. Epub Mar. 9, 2020. Erratum in: Cell. Dec. 10, 2020;183(6):1735.

Wilen et al., Strategies in optical resolutions. Tetrahedron. 1977;33:2725-36. doi: 10.1016/0040-4020(77)80264-0.

Yamada et al., Proteolytic activation of the spike protein at a novel RRRR/S motif is implicated in furin-dependent entry, syncytium formation, and infectivity of coronavirus infectious bronchitis virus in cultured cells. J Virol. Sep. 2009;83(17):8744-58. doi: 10.1128/JVI.00613-09. Epub Jun. 24, 2009.

ated to attainment of the page content.

FURIN INHIBITORS

RELATED APPLICATIONS

The present application is a national stage filing under 35 U.S.C. § 371 of International PCT Application, PCT/EP2019/062098, filed May 10, 2019, which claims priority under 35 U.S.C. § 119(e) to U.S. provisional application, U.S. Ser. No. 62/670,050, filed May 11, 2018, the entire contents of each of which is incorporated herein by reference.

FIELD OF THE INVENTION

This invention relates to compounds which inhibit furin and thus are useful for the treatment of diseases mediated by furin, including fibrotic diseases. The disclosed compounds may also be useful for treating other furin-mediated conditions, including but not limited to, hypertension, cancer, infectious diseases, genetic disorders, and neurodegenerative disorders.

BACKGROUND OF THE INVENTION

Inactive precursor proteins of many enzymes, receptors and secreted proteins require processing and maturation to exert their biological functions (Thomas G. *Nat. Rev. Mol. Cell. Biol.* 2002, 3(10), 753-766). The proteolytic cleavage of pro-peptide sequences is dependent on the proprotein convertase (PC) family of calcium-dependent endoproteases. This PC family consists of the following serine proteases: proprotein convertase subtilisin kexin 1 (PCSK1), PCSK2, Furin/PCSK3, PCSK4, PCSK5, PCSK6/paired basic amino acid cleaving enzyme 4 (PACE4), PCSK7, PCSK8/subtilisin kexin isoenzyme 1 (SK-1)/membrane bound transcription factor peptidase site 1 (MBTPS1) and PCSK9 (Thomas G. *Nat. Rev. Mol. Cell. Biol.* 2002, 3(10), 753-766; Nakayama K. *Biochem. J.* 1997, 327(3), 625-635; Klein-Szanto A J, Bassi D E. *Biochem. Pharmacol.* 2017, 140, 8-15; Turpeinen H, Ortutay Z, Pesu M. *Curr. Genomics* 2013, 14(7), 453-467) (https://www.genenames.org). Among these PCSKs, furin (PCSK3) is well characterized and the most widely studied family member with diverse biological functions.

Furin is a 794 amino-acid type 1 transmembrane protein that is ubiquitously expressed in many cell types (Thomas G. *Nat. Rev. Mol. Cell. Biol.* 2002, 3(10), 753-766). It consists of the highly-conserved domain structure commonly found in PCSKs, including an N-terminal signal peptide, an inhibitory prodomain, a catalytic peptidase S8/S53 domain, a P domain, and a cysteine-rich region and a cytoplasmic domain (Thomas G. *Nat. Rev. Mol. Cell. Biol.* 2002, 3(10), 753-766; Turpeinen H, Ortutay Z, Pesu M. *Curr. Genomics* 2013, 14(7), 453-467). The prodomain is essential for the proper folding, activation and transport of furin, whereas the P domain regulates enzyme activity of the catalytic domain by modulating pH/calcium-dependent autoproteolytic cleavage process (Thomas G. *Nat. Rev. Mol. Cell. Biol.* 2002, 3(10), 753-766; Turpeinen H, Ortutay Z, Pesu M. *Curr. Genomics* 2013, 14(7), 453-467). Lastly, the cytoplasmic domain of furin allows for both efficient internalization from the plasma membrane and fast retrieval from the plasma membrane to the trans-Golgi network (TGN) (Thomas G. *Nat. Rev. Mol. Cell. Biol.* 2002, 3(10), 753-766).

Furin is predominantly localized in the trans-Golgi network (TGN) and the endosomal system, where it processes most of its diverse substrates in vivo. Furin's endoprotease activity is unmasked by release of its prodomain fragment, enabling furin to functionally process substrates in trans (Thomas G. *Nat. Rev. Mol. Cell. Biol.* 2002, 3(10), 753-766). Positioned after the carboxy-terminal arginine (Arg) residue, the consensus site that furin cleaves is the sequence -Arg-X-Lys/Arg-Arg←-(Lys is lysine, X is any amino acid and ← identifies the cleavage site). Based on this substrate peptide amino acid motif, furin has >400 predicted target protein substrates, including hormones, growth factors, enzymes, receptors, neuropeptides, and infective agents (Turpeinen H, Ortutay Z, Pesu M. *Curr. Genomics* 2013, 14(7), 453-467; Shiryaev S A, Chernov A V, Golubkov V S, Thomsen E R, Chudin E, Chee M S, et al. *PLoS One* 2013, 8(1), e54290) (https://www.ebi.ac.uk/merops). The importance of the biological role of furin-dependent proteolytic processing can be further exemplified by the phenotypes of various studies with knock-out mice.

Germ-line furin knock-out mice studies demonstrate an important role for furin in embryonic development with embryonic lethality occurring between day 10.5 and 11.5. Failure of ventral closure and axial rotation as well as the absence of chorioallantoic fusion was observed. The impact of furin knock-down in endothelial cells resulted in cardiovascular defects, which included septal and valvular defects that may be attributed to impaired processing of TGF-β (Turpeinen H, Ortutay Z, Pesu M. *Curr. Genomics* 2013, 14(7), 453-467; Roebroek A J, Umans L, Pauli I G, Robertson E J, van Leuven F, Van de Ven W J, et al. *Development* 1998, 125(24), 4863-4876; Seidah N G, Prat A. *Nat. Rev. Drug Discov.* 2012, 11(5), 367-383; Constam D B, Robertson E J. *Development* 2000, 127(2), 245-254; Susan-Resiga D, Essalmani R, Hamelin J, Asselin M C, Benjannet S, Chamberland A, et al. *J. Biol. Chem.* 2011, 286(26), 22785-22794). However, knock-out of Furin in the liver of adult mice (inducible Mx1-Cre transgene) is not lethal and typical substrates of furin were cleaved although less efficiently pointing to possible redundancy among the PCSKs (Klein-Szanto A J, Bassi D E. *Biochem. Pharmacol.* 2017, 140, 8-15; Roebroek A J, Taylor N A, Louagie E, Pauli I, Smeijers L, Snellinx A, et al. *J. Biol. Chem.* 2004, 279(51), 53442-53450). In addition, targeted deletion of furin in T cells caused functional impairment of regulatory and effector T cells as a result of defective TGFβ1 signaling (Pesu M, Watford W T, Wei L, Xu L, Fuss I, Strober W, et al. *Nature* 2008, 455(7210), 246-250). These observations implicate the role of furin in TGFβ biology and the potential therapeutic use of furin inhibitors for TGFβ-dependent diseases.

Organ fibrosis is the result of aberrant wound healing response, resulting in excessive collagen deposition. Connective tissue scarring leads to progressive loss of tissue function and eventual organ failure (Nanthakumar C B, Hatley R J, Lemma S, Gauldie J, Marshall R P, Macdonald S J. *Nat. Rev. Drug Discov.* 2015, 14(10), 693-720). TGFβ family members play a key role in fibrosis (Dubois C M, Blanchette F, Laprise M H, Leduc R, Grondin F, Seidah N G. *Am. J. Pathol.* 2001, 158(1), 305-316), and TGFβ1 is elevated in fibrotic organs such as heart, lung, and kidney (Pohlers D, Brenmoehl J, Löffler I, Müller CK, Leipner C, Schultze-Mosgau S, et al. *Biochimica et Biophysica Acta (BBA) —Molecular Basis of Disease* 2009, 1792(8), 746-756; Thomas B J, Kan O K, Loveland K L, Elias J A, Bardin P G. *Am. J. Respir. Cell. Mol. Biol.* 2016, 55(6), 759-766). Pre-pro-TGFβ1 is synthesized by most cells as a single 390 amino acid peptide. The furin-dependent processing event is predicted to occur following an Arg-His-Arg-Arg sequence immediately preceding the $NH_2$-terminal Ala 279 residue of the growth factor (Constam D B. *Seminars in Cell &*

Developmental Biology 2014, 32, 85-97). Mature TGFβ forms a 25 KDa dimer, which is complexed with specific binding proteins such as the TGFβ latency-associated peptide (LAP) (NH$_2$-terminal part of the precursor sequence) and the large latent binding protein (LTBP) before secretion into the extracellular matrix (Constam D B. Seminars in Cell & Developmental Biology 2014, 32, 85-97; Robertson I B, Horiguchi M, Zilberberg L, Dabovic B, Hadjiolova K, Rifkin D B. Matrix biology, Journal of the International Society for Matrix Biology 2015, 47, 44-53). Active mature TGFβ1 must be liberated from the latent complex before it can exert its biological effects. The biological effects of TGFβ are mediated through the canonical SMAD-dependent signaling and the noncanonical pathways involving PI3K/ATK, Erk, and p38 upon receptor activation (Zhang Y E. Cell Research 2009, 19(1), 128-139). TGF01 drives the profibrotic responses by promoting the transformation of normal epithelial cell to active fibroblasts and the subsequent synthesis and deposition of collagen (Biernacka A, Dobaczewski M, Frangogiannis N G. Growth Factors (Chur, Switzerland) 2011, 29(5), 196-202). Thus, therapeutic intervention using a furin inhibitor would prevent the proper processing of Pre-pro-TGFβ1, and therefore provide benefit by depleting the bioactive TGFβ in fibrotic disease.

Given the diversity in its substrates, therapeutic intervention of furin could also be beneficial for diseases such as hypertension, cancer, infectious, respiratory and neurondegeneration diseases (Thomas G. Nat. Rev. Mol. Cell. Biol. 2002, 3(10), 753-766; Nakayama K. Biochem. J. 1997, 327(3), 625-635; Shiryaev S A, Chernov A V, Golubkov V S, Thomsen E R, Chudin E, Chee M S, et al. PLoS One 2013, 8(1), e54290; Bennett B D, Denis P, Haniu M, Teplow D B, Kahn S, Louis J C, et al. J. Biol. Chem. 2000, 275(48), 37712-37717; Takahashi R H, Nagao T, Gouras G K. Pathology International 2017, 67(4), 185-193). Hypertension is a condition in which blood exerts increased force against the walls of the arteries. The renin-angiotensin system and molecules that regulate sodium-electrolyte balance can impact blood pressure and are associated with Furin activity (Turpeinen H, Ortutay Z, Pesu M. Curr. Genomics 2013, 14(7), 453-467; Cousin C, Bracquart D, Contrepas A, Corvol P, Muller L, Nguyen G. Hypertension 2009, 53(6), 1077-1082). Two recent large-scale genetic association studies (GWAS) demonstrated a role for Furin genetics as a risk factor for hypertension. One study utilized a GWAS approach to study over 200,000 subjects of European descent, thereby identifying a single nucleotide polymorphism (SNP; rs2521501) in the Furin-FES loci associated with elevations in systolic and diastolic blood pressure (Ehret G B, Munroe P B, Rice K M, Bochud M, Johnson A D, et al. Nature 2011, 478(7367), 103-109). Two additional Furin polymorphisms, rs2071410 and rs6227, which are associated with systolic and diastolic blood pressure respectively were identified in a second multi-center study that genotyped 50,000 SNPs amongst 2100 candidate genes (Turpeinen H, Ortutay Z, Pesu M. Curr. Genomics 2013, 14(7), 453-467; Ganesh S K, Tragante V, Guo W, Guo Y, Lanktree M B, Smith E N, et al. Hum. Mol. Genet. 2013, 22(8), 1663-1678). Given such strong human genetic evidence, modulation of furin activity could be a therapeutic approach for hypertension.

Cancer is a set of diseases involving abnormal, uncontrolled growth of cells which may spread to other parts of the body (metastasis). There are furin substrates associated with various processes involved in cancer progression, such as proliferation, anti-apoptosis, migration/invasion, metastasis, and angiogenesis. The substrates that furin targets in these processes are growth factors and their receptors, matrix metalloproteases, cell adhesion molecules and angiogenic/ lymphangiogenic factors (Shiryaev S A, Chernov A V, Golubkov V S, Thomsen E R, Chudin E, Chee M S, et al. PLoS One 2013, 8(1), e54290; Jaaks P, Bernasconi M. Int. J. Cancer 2017, 141(4), 654-663; Bassi D E, Mahloogi H, Al-Saleem L, Lopez De Cicco R, Ridge J A, Klein-Szanto A J. Mol. Carcinog. 2001, 31(4), 224-232). Many growth factors and their receptors are important for the balance between apoptotic and prosurvival mechanisms. Therefore, dysregulation of growth factors plays a role in the development of cancer. In addition to uncontrolled growth, extracellular matrix (ECM) degradation is necessary for cancer cells to escape the primary site. Similarly, ECM remodeling is required for the development of the metastatic niche that enables disseminated cancer cells to survive, colonize, and proliferate at the metastatic site (Bonnans C, Chou J, Werb Z. Nat. Rev. Mol. Cell. Biol. 2014, 15(12), 786-801). Many of such enzymes like MMPs and ADAM proteases that mediate ECM degradation require proteolytic activation by furin (Maquoi E, Noel A, Frankenne F, Angliker H, Murphy G, Foidart J M. FEBS Lett. 1998, 424(3), 262-266; Yana I, Weiss S J. Mol. Biol. Cell 2000, 11(7), 2387-2401; Kang T, Nagase H, Pei D. Cancer Res. 2002, 62(3), 675-681; Wang X, Pei D. J. Biol. Chem. 2001, 276(38), 35953-35960; Loechel F, Gilpin B J, Engvall E, Albrechtsen R, Wewer U M. J. Biol. Chem. 1998, 273(27), 16993-16997; Schlondorff J, Becherer J D, Blobel C P. Biochem. J. 2000, 347(1), 131-138). Finally, angiogenesis, a process of blood vessels formation supports the growth of tumors. Vascular endothelial growth factors VEGF-C and VEGF-D are processed by furin, rendering them capable of promoting VEGF signaling, thereby stimulating angiogenesis and lymphangiogenesis (Joukov V, Sorsa T, Kumar V, Jeltsch M, Claesson-Welsh L, Cao Y, et al. EMBO J. 1997, 16(13), 3898-3911; McColl B K, Paavonen K, Karnezis T, Harris N C, Davydova N, Rothacker J, et al. FASEB J. 2007, 21(4), 1088-1098). Therefore, therapeutic intervention of furin activities would limit the growth of cancer cells by blocking multiple key biological processes that promote the growth and spread of cancer cells.

Infectious diseases may be spread from one person to another and are caused by pathogenic microorganisms such as bacteria, viruses, parasites or fungi. Pathogenicity is the ability of a microbial agent to cause disease and virulence is the degree to which an organism is pathogenic. In order for viruses to enter host cells and replicate, the envelope glycoproteins must be proteolytically activated (Nakayama K. Biochem. J. 1997, 327(3), 625-635). The processing of envelope glycoproteins may in some cases impact viral pathogenicity (Nakayama K. Biochem. J. 1997, 327(3), 625-635). The glycoprotein precursors of many virulent viruses, such as human immunodeficiency virus (HIV), avian influenza virus, measles virus, respiratory syncytial virus (RSV), Ebola virus, anthrax, and Zika virus (ZIKV) are cleaved at a site marked by a consensus sequence consistent with furin recognition (Thomas G. Nat. Rev. Mol. Cell. Biol. 2002, 3(10), 753-766; 2, 36-38). The cleavage of HIV glycoprotein160 and infectious virus production are blocked when the furin inhibitor α1-PDX is expressed in cells (Nakayama K. Biochem. J. 1997, 327(3), 625-635). It is thus conceivable for the therapeutic use of furin inhibitor in a pandemic situation or biological warfare.

Cystic fibrosis (CF) is a common life-limiting autosomal-recessive genetic disease in Europe and North America (Hoffman L R, Ramsey B W. CHEST 2013, 143(1), 207-213). A thin film of fluid lines the conducting airways of the lung facilitating mucociliary clearance, which contributes to innate immune defense by removing inhaled pathogens. The volume of this fluid is regulated by chloride and sodium transport across the airway epithelium. This regulation is lost in cystic fibrosis due to the absence of the cystic fibrosis transmembrane conduction regulator (CFTR), which mediates chloride secretion and subsequent sodium reabsorption & fluid balance across the epithelium. Epithelial sodium channel (ENaC) hyperabsorption is a contributing factor in the depletion of the fluid layer beginning the CF pathophysiology. Channel activating proteases (CAPs) such as furin catalyze endoproteolysis of ENaC, and increase sodium channel conductance which would otherwise remain low (Reihill J A, Walker B, Hamilton R A, Ferguson T E, Elborn J S, Stutts M J, et al. *Am. J. Respir. Crit. Care Med.* 2016, 194(6), 701-710; Myerburg M M, Harvey P R, Heidrich E M, Pilewski J M, Butterworth M B. *Am. J. Respir. Cell. Mol. Biol.* 2010, 43(6), 712-719). A furin inhibitor is effective in blocking sodium reabsorption (Reihill J A, Walker B, Hamilton R A, Ferguson T E, Elborn J S, Stutts M J, et al. *Am. J. Respir. Crit. Care Med.* 2016, 194(6), 701-710) and thus providing proof of concept evidence for the potential use of a furin inhibitor for the treatment CF.

Alzheimer's disease (AD) is a progressive, multifactorial, and heterogeneous neurodegenerative disease leading to progressive cognitive decline. Amyloid-β (Aβ)-containing plaques and neurofibrillary tangles composed of hyperphosphorylated tau in the brain are the neuropathological hallmarks of AD (Takahashi R H, Nagao T, Gouras G K. *Pathology International* 2017, 67(4), 185-193; Rangachari V, Dean D N, Rana P, Vaidya A, Ghosh P. *Biochimica et Biophysica Acta (BBA) —Biomembranes* 2018, https://doi.org/10.1016/j.bbamem.2018.03.004; Crews L, Masliah E. *Human Molecular Genetics* 2010, 19(R1), R12-R20). The amyloid precursor protein (APP) is an integral membrane protein containing a single transmembrane domain (Takahashi R H, Nagao T, Gouras G K. *Pathology International* 2017, 67(4), 185-193; Rangachari V, Dean D N, Rana P, Vaidya A, Ghosh P. *Biochimica et Biophysica Acta (BBA) —Biomembranes* 2018, https://doi.org/10.1016/j.bbamem.2018.03.004). Amyloid peptides can form by sequential cleavage of APP by the aspartyl proteases, β-(BACE) and γ-secretases (Takahashi R H, Nagao T, Gouras G K. *Pathology International* 2017, 67(4), 185-193; Rangachari V, Dean D N, Rana P, Vaidya A, Ghosh P. *Biochimica et Biophysica Acta (BBA) —Biomembranes* 2018, https://doi.org/10.1016/j.bbamem.2018.03.004; Fiala J C. *Acta Neuropathologica* 2007, 114(6), 551-571). Proteolytic cleavage of APP results in the generation of the Aβ1-42 monomer, which under pathological conditions can assemble into potentially toxic oligomers and form of plaques (Takahashi R H, Nagao T, Gouras G K. *Pathology International* 2017, 67(4), 185-193; Rangachari V, Dean D N, Rana P, Vaidya A, Ghosh P. *Biochimica et Biophysica Acta (BBA) —Biomembranes* 2018, https://doi.org/10.1016/j.bbamem.2018.03.004; Fiala J C. *Acta Neuropathologica* 2007, 114(6), 551-571). It is suggested that amyloid deposition is initiated by glia that secrete Aβ. The protein spontaneously aggregates into amyloid filaments that activate microglia. Activated microglia then secrete oxidative species and inflammatory cytokines that cause axonal dystrophy and cell death (Rangachari V, Dean D N, Rana P, Vaidya A, Ghosh P. *Biochimica et Biophysica Acta (BBA) —Biomembranes* 2018, https://doi.org/10.1016/j.bbamem.2018.03.004; Crews L, Masliah E. *Human Molecular Genetics* 2010, 19(R1), R12-R20; Fiala J C. *Acta Neuropathologica* 2007, 114(6), 551-571). Mutations of APP and presenilins, components of the γ-secretases complex, lead to alteration of the APP processing by secretases and increase in production of pro-plaque forming Aβ peptides (Dai M H, Zheng H, Zeng L D, Zhang Y. *Oncotarget* 2018, 9(19), 15132-15143), suggesting the importance of secretases in disease progression. Therefore, pharmacological modulation of APP processing has been a prominent strategy for the treatment of AD, with both BACE and γ-secretases inhibitors being evaluated in recent clinical trials (Panza F, Seripa D, Solfrizzi V, Imbimbo B P, Lozupone M, Leo A, et al. *Expert Opinion* on Emerging Drugs 2016, 21(4), 377-391). BACE pro-peptide shares a consensus sequence for furin, and processing of BACE pro-peptide is shown to be dependent on active furin (Bennett B D, Denis P, Haniu M, Teplow D B, Kahn S, Louis J C, et al. *J. Biol. Chem.* 2000, 275(48), 37712-37717). Thus, selective furin inhibitor can potentially be used for the treatment of AD and neurodegenerative diseases associated with dysregulated furin processing.

Known furin inhibitors are peptidic in nature and derived from the natural substrate motif sequence, or are designed peptidomimetic compounds with lysine and arginine side-chains to enable high affinity binding to furin. A potent peptidic furin inhibitor was identified by incorporating a reactive chloromethyl ketone (CMK) moiety (WO 2009/023306 A2; Garten W, Hallenberger S, Ortmann D, Schafer W, Vey M, Angliker H, et al. *Biochimie* 1994, 76(3-4), 217-225). This non-selective CMK peptide (Decanoyl-Arg-Val-Lys-Arg-CMK) engages the active site of furin at the catalytic Ser368 residue to give a tetrahedral hemiketal that irreversibly alkylates the His194 residue. This well-known irreversible protease inhibition mechanism of a halomethylketone provides very high and durable potency, however also can account for non-selective protease inhibition, particularly against other PCSK family members. Furin inhibitors have been found to protect macrophages from processing of anthrax (WO 2013/138666 A1) and to restore fluid balance in CF cells (Reihill J A, Walker B, Hamilton R A, Ferguson T E, Elborn J S, Stutts M J, et al. *Am. J. Respir. Crit. Care Med.* 2016, 194(6), 701-710). Another strategy for pharmacological furin inhibition is the use of an engineered variant of naturally occurring α-1-antitrypsin serum protease inhibitor α1-PDX. α1-PDX is a serpin superfamily wide protease inhibitor with high specificity for furin and PCSK 5/6 with $K_i$ values as low as 600 pM (Couture F, Kwiatkowska A, Dory Y L, Day R. *Expert Opinion on Therapeutic Patents* 2015, 25(4), 379-396). α1-PDX forms an SDS-resistant complex with furin through the formation of a tetrahedral adduct with the catalytic serine. Cancer cells expressing either α1-PDX or the prosegment of furin (as a proprotein inhibitor) were injected into immunocompromised mice leading to a decrease in the number of a variety of tumors and metastases.

Thus far, potent inhibitors of furin reported are peptide derivatives or peptidomimetics containing polybasic residues in order to achieve high inhibitory potency. As a consequence of the highly basic nature of the inhibitors, reactivity, and peptide structure, their chemical and pharmacokinetics properties limit use as clinical therapeutic agents. Furin plays a diverse biological role in health and diseases with high unmet medical need. Therefore, potent and selective small molecule furin inhibitors with drug-like properties are desirable as an attractive approach to provide therapeutic benefit in many diseases such as organ fibrosis, hypertension, cancer, infectious disease, neurodegenerative disease, and CF. The present invention describes the structure and biological properties of novel furin inhibitors.

SUMMARY OF THE INVENTION

The present invention relates to compounds according to Formula (I) or pharmaceutically acceptable salts thereof:

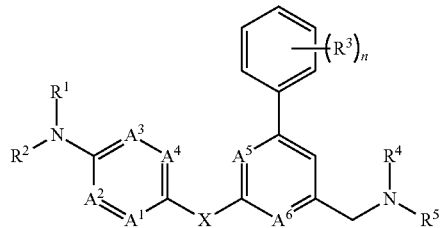

wherein:
$A^1, A^2, A^3, A^4, A^5$, and $A^6$ are each independently N, CH, or $CR^6$;
X is O or $NR^8$;
$R^1$ and $R^2$ are each independently hydrogen, $(C_1-C_4)$alkyl, or $H_2N(C_1-C_4)$alkyl-;
or $R^1$ and $R^2$ taken together with the nitrogen atom to which they are attached represent a 4-11 membered monocyclic or fused, bridged, or spiro bicyclic saturated ring, optionally containing one or two additional heteroatoms independently selected from oxygen, nitrogen, and sulfur, wherein said ring is optionally substituted by one, two, or three substituents independently selected from halogen, hydroxyl, oxo, —OCONR$^8$R$^9$, —CO$_2$R$^8$, —C(O)CO$_2$R$^8$, R$^7$, —OR$^7$, —NHR$^8$, —NR$^7$R$^8$, —C(O)R$^7$, —CONHR$^8$, —CONR$^7$R$^8$, and —SO$_2$R$^7$;
each $R^3$ is independently selected from the group consisting of halogen, methyl, fluoromethyl, difluoromethyl, and trifluoromethyl;
$R^4$ and $R^5$ are each independently hydrogen, $(C_1-C_4)$alkyl, or $(C_1-C_4)$alkoxy$(C_2-C_4)$alkyl-;
or $R^4$ and $R^5$ taken together with the nitrogen atom to which they are attached represent a 4-11 membered monocyclic or fused, bridged, or spiro bicyclic saturated ring, optionally containing one or two additional heteroatoms independently selected from oxygen, nitrogen, and sulfur, wherein said ring is optionally substituted by one, two, or three substituents independently selected from halogen, hydroxyl, oxo, —OCONR$^8$R$^9$, —CO$_2$R$^8$, —C(O)CO$_2$R$^8$, —SO$_2$(C$_1$-C$_4$)alkyl, R$^7$, —OR$^7$, —NHR$^8$, —NR$^7$R$^8$, —N(R$^8$)C(O)R$^9$, —N(R$^8$)SO$_2$R$^9$, —N(R$^8$)CONR$^8$R$^9$, —N(R$^8$)CON(R$^8$)SO$_2$R$^9$, —C(O)R$^7$, —CONHR$^8$, —CONR$^7$R$^8$, and —P(O)R$^8$R$^9$;
each $R^6$ is independently selected from the group consisting of halogen, $(C_1-C_4)$alkyl, halo$(C_1-C_4)$alkyl, hydroxyl, and $(C_1-C_4)$alkoxy;
each $R^7$ is independently selected from the group consisting of $(C_1-C_6)$alkyl, $(C_2-C_6)$alkenyl, halo$(C_1-C_6)$alkyl, $(C_3-C_6)$cycloalkyl, and $(C_3-C_6)$cycloalkyl$(C_1-C_4)$alkyl-, each of which is optionally substituted by one or two substituents independently selected from triazolyl, tetrazolyl, —CO$_2$R$^8$, —CONR$^8$R$^9$, —CON(R$^8$)CO$_2$(C$_1$-C$_4$)alkyl, hydroxyl, oxo, $(C_1-C_4)$alkoxy, —OCONR$^8$R$^9$, —OCON(R$^8$)C(O)R$^9$, $(C_1-C_4)$alkyl, HO(C$_1$-C$_4$)alkyl-, —NR$^8$R$^9$, —N(O)R$^8$R$^9$, —N(R$^8$)C(O)R$^9$, —N(R$^8$)CO$_2$(C$_1$-C$_4$)alkyl, —N(R$^8$)CH$_2$CO$_2$R$^9$, —N(R$^8$)CONR$^8$R$^9$, —N(R$^8$)CON(R$^8$)C(O)R$^9$, —N(R$^8$)CON(R$^8$)CO$_2$(C$_1$-C$_4$)alkyl, —N(R$^8$)SO$_2$R$^9$, —N(R$^8$)CON(R$^8$)SO$_2$R$^9$, —SO(C$_1$-C$_4$)alkyl, —SO$_2$(C$_1$-C$_4$)alkyl, —SO$_3$R$^8$, —SO$_2$NR$^8$R$^9$, —B(OH)$_2$, —P(O)R$^8$R$^9$, and —P(O)(OR$^8$)(OR$^9$);
each $R^8$ and $R^9$ is independently hydrogen, $(C_1-C_4)$alkyl, or $(C_3-C_6)$cycloalkyl; and
n is 1, 2, 3, or 4;
or a pharmaceutically acceptable salt thereof.

Another aspect of the invention relates to pharmaceutical compositions comprising compounds of Formula (I) and pharmaceutically acceptable excipients.

In another aspect, there is provided the use of a compound of Formula (I) or a pharmaceutically acceptable salt or solvate thereof, in the manufacture of a medicament for use in the treatment of a disorder mediated by furin, such as fibrotic diseases.

In another aspect, this invention provides a compound of Formula (I) or a pharmaceutically acceptable salt thereof for use in the treatment of diseases mediated by furin. The invention further provides a compound of Formula (I) or a pharmaceutically acceptable salt thereof as an active therapeutic substance for use in the treatment of a disease mediated by furin.

In another aspect, the invention provides a compound of Formula (I) or a pharmaceutically acceptable salt thereof for use in therapy.

In another aspect, the invention provides a compound of Formula (I) or a pharmaceutically acceptable salt thereof for use in the treatment of fibrotic diseases.

In another aspect, the invention provides methods of co-administering the presently invented compounds of Formula (I) with other active ingredients.

Another aspect of the invention relates to pharmaceutical compositions comprising compounds of Formula (I-a) and pharmaceutically acceptable excipients.

In another aspect, there is provided the use of a compound of Formula (I-a) or a pharmaceutically acceptable salt or solvate thereof, in the manufacture of a medicament for use in the treatment of a disorder mediated by furin, such as fibrotic diseases.

In another aspect, this invention provides a compound of Formula (I-a) or a pharmaceutically acceptable salt thereof for use in the treatment of diseases mediated by furin. The invention further provides a compound of Formula (I-a) or a pharmaceutically acceptable salt thereof as an active therapeutic substance for use in the treatment of a disease mediated by furin.

In another aspect, the invention provides a compound of Formula (I-a) or a pharmaceutically acceptable salt thereof for use in therapy.

In another aspect, the invention provides a compound of Formula (I-a) or a pharmaceutically acceptable salt thereof for use in the treatment of fibrotic diseases.

In another aspect, the invention provides methods of co-administering the presently invented compounds of Formula (I-a) with other active ingredients.

DETAILED DESCRIPTION OF THE INVENTION

Figure 1:
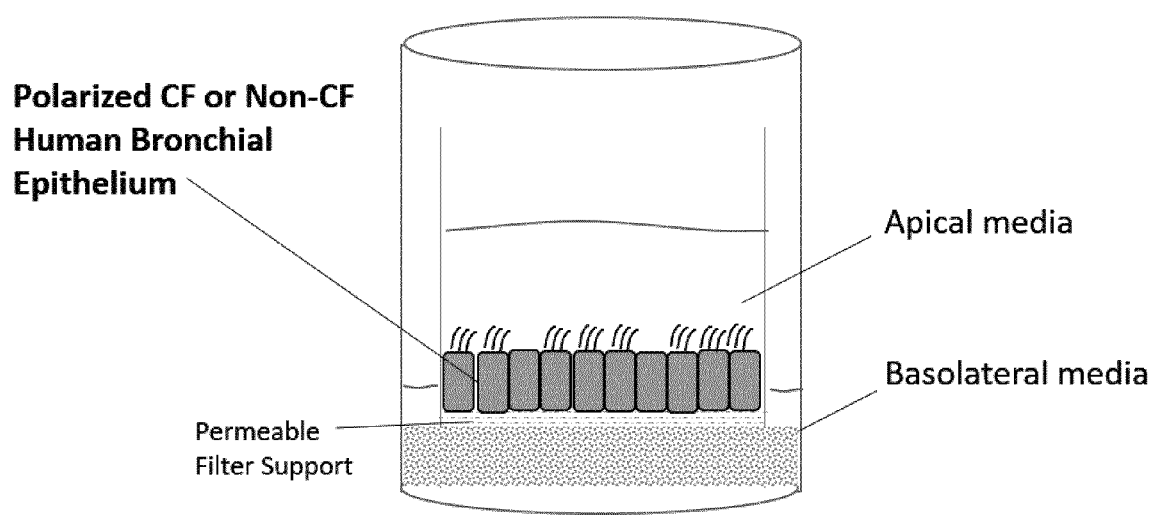
FIG. 1 depicts transepithelial electrical resistance (TEER) assays with polarized CF or non-CF human bronchial epithelium.
Figure 2:
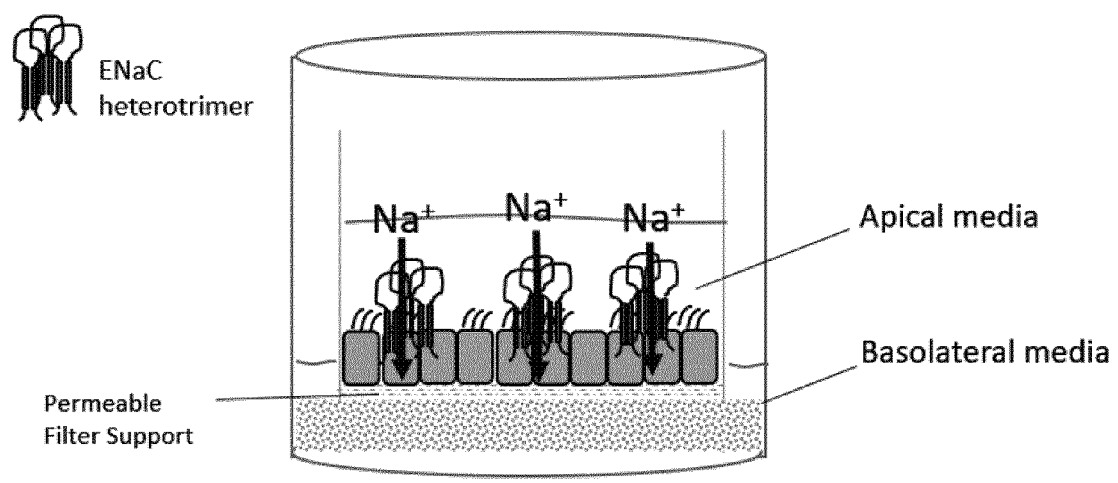
FIG. 2 depicts TEER assays when the epithelial sodium channel is active.
Figure 3:
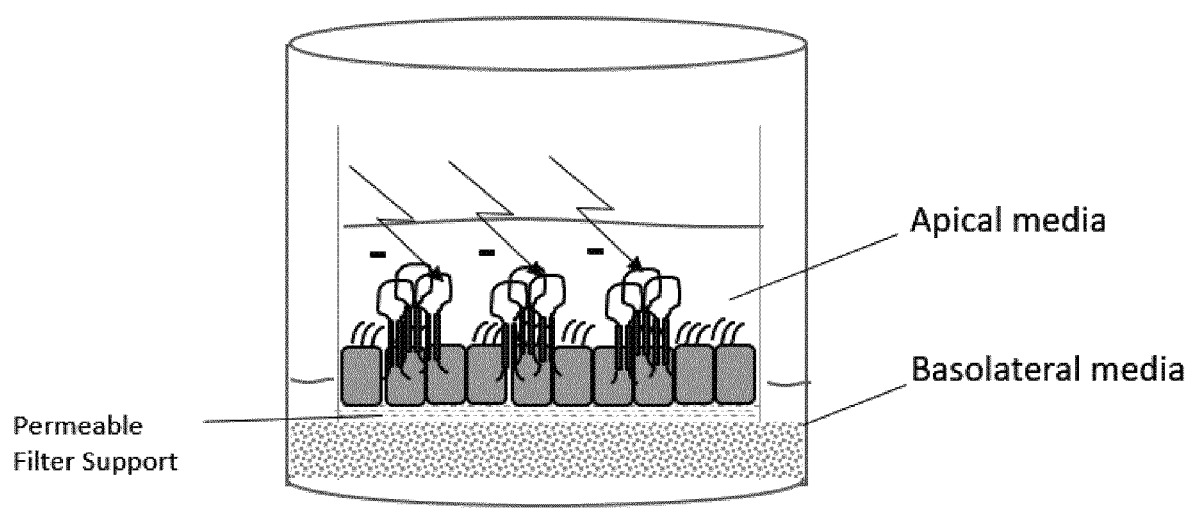
FIG. 3 depicts TEER assays when the epithelial sodium channel is closed (inhibited).
Figure 4:
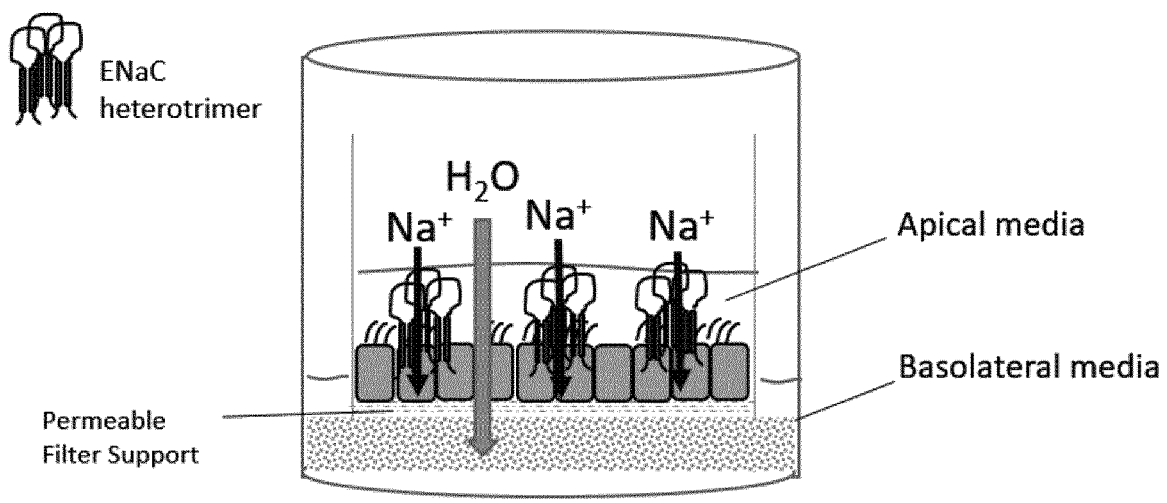
FIG. 4 depicts an osmotic driving force for fluid absorption in the TEER assays when the epithelial sodium channel is active.
Figure 5:
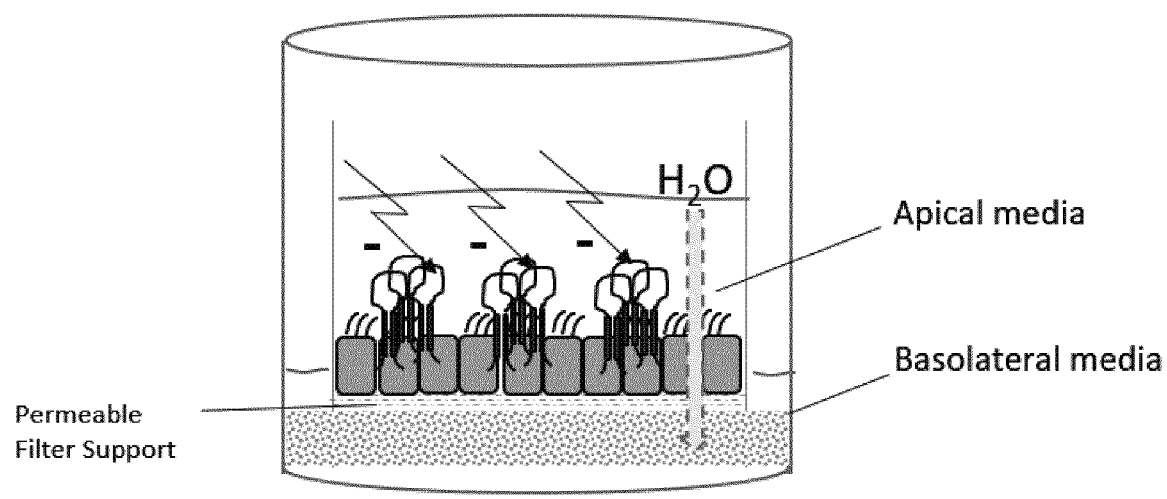
FIG. 5 depicts no osmotic driving force for fluid absorption in the TEER assays when the epithelial sodium channel is closed.

This invention relates to compounds of the Formula (I) as defined above or pharmaceutically acceptable salts thereof.

This invention also relates to compounds of the Formula (I-a):

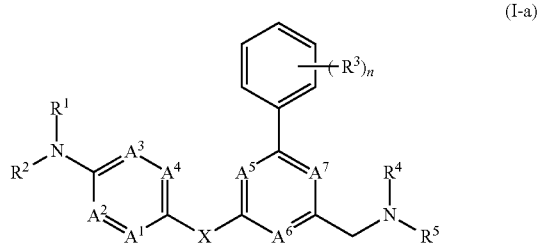

(I-a)

wherein:
$A^1, A^2, A^3, A^4, A^5, A^6$, and $A^7$ are each independently N, CH, or $CR^6$;

X is O or $NR^8$;

$R^1$ and $R^2$ are each independently hydrogen, $(C_1-C_4)$alkyl, or $H_2N(C_1-C_4)$alkyl-;

or $R^1$ and $R^2$ taken together with the nitrogen atom to which they are attached represent a 4-11 membered monocyclic or fused, bridged, or spiro bicyclic saturated ring, optionally containing one or two additional heteroatoms independently selected from oxygen, nitrogen, and sulfur, wherein said ring is optionally substituted by one, two, or three substituents independently selected from halogen, hydroxyl, oxo, —OCONR$^8$R$^9$, —CO$_2$R$^8$, —C(O)CO$_2$R$^8$, R$^7$, —OR$^7$, —NHR$^8$, —NR$^7$R$^8$, —C(O)R$^7$, —CONHR$^8$, —CONR$^7$R$^8$, and —SO$_2$R$^7$;

each $R^3$ is independently selected from the group consisting of halogen, methyl, fluoromethyl, difluoromethyl, and trifluoromethyl;

$R^4$ and $R^5$ are each independently hydrogen, $(C_1-C_4)$alkyl, or $(C_1-C_4)$alkoxy$(C_2-C_4)$alkyl-;

or $R^4$ and $R^5$ taken together with the nitrogen atom to which they are attached represent a 4-11 membered monocyclic or fused, bridged, or spiro bicyclic saturated ring, optionally containing one or two additional heteroatoms independently selected from oxygen, nitrogen, and sulfur, wherein said ring is optionally substituted by one, two, or three substituents independently selected from halogen, hydroxyl, oxo, —OCONR$^8$R$^9$, —CO$_2$R$^8$, —C(O)CO$_2$R$^8$, —SO$_2$(C$_1$-C$_4$)alkyl, R$^7$, —OR$^7$, —NHR$^8$, —NR$^7$R$^8$, —N(R$^8$)C(O)R$^9$, —N(R$^8$)SO$_2$R$^9$, —N(R$^8$)CONR$^8$R$^9$, —N(R$^8$)CON(R$^8$)SO$_2$R$^9$, —C(O)R$^7$, —CONHR$^8$, —CONR$^7$R$^8$, and —P(O)R$^8$R$^9$;

each $R^6$ is independently selected from the group consisting of halogen, $(C_1-C_4)$alkyl, halo$(C_1-C_4)$alkyl, hydroxyl, and $(C_1-C_4)$alkoxy;

each $R^7$ is independently selected from the group consisting of $(C_1-C_6)$alkyl, $(C_2-C_6)$alkenyl, halo$(C_1-C_6)$alkyl, $(C_3-C_6)$cycloalkyl, and $(C_3-C_6)$cycloalkyl$(C_1-C_4)$alkyl-, each of which is optionally substituted by one or two substituents independently selected from triazolyl, tetrazolyl, —CO$_2$R$^8$, —CONR$^8$R$^9$, —CON(R$^8$)CO$_2$(C$_1$-C$_4$)alkyl, hydroxyl, oxo, (C$_1$-C$_4$)alkoxy, —OCONR$^8$R$^9$, —OCON(R$^8$)C(O)R$^9$, (C$_1$-C$_4$)alkyl, HO(C$_1$-C$_4$)alkyl-, —NR$^8$R$^9$, —N(O)R$^8$R$^9$, —N(R$^8$)C(O)R$^9$, —N(R$^8$)CO$_2$(C$_1$-C$_4$)alkyl, —N(R$^8$)CH$_2$CO$_2$R$^9$, —N(R$^8$)CONR$^8$R$^9$, —N(R$^8$)CON(R$^8$)C(O)R$^9$, —N(R$^8$)CON(R$^8$)CO$_2$(C$_1$-C$_4$)alkyl, —N(R$^8$)SO$_2$R$^9$, —N(R$^8$)CON(R$^8$)SO$_2$R$^9$, —SO(C$_1$-C$_4$)alkyl, —SO$_2$(C$_1$-C$_4$)alkyl, —SO$_3$R$^8$, —SO$_2$NR$^8$R$^9$, —B(OH)$_2$, —P(O)R$^8$R$^9$, and —P(O)(OR$^8$)(OR$^9$);

each $R^8$ and $R^9$ is independently hydrogen, $(C_1-C_4)$alkyl, or $(C_3-C_6)$cycloalkyl; and n is 1, 2, 3, or 4;

or a pharmaceutically acceptable salt thereof.

This invention also relates to compounds of the Formula (II):

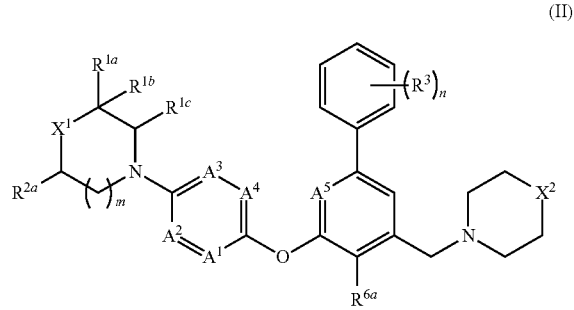

(II)

wherein:
- $A^1$, $A^2$, $A^3$, $A^4$, and $A^5$ are each independently N or CH, wherein one, two, or three of $A^1$, $A^2$, $A^3$, $A^4$, and $A^5$ are N;
- $X^1$ and $X^2$ are each independently $NR^{10}$ or $C(R^{11})R^{12}$;
- $R^{1a}$, $R^{1b}$, $R^{1c}$, and $R^{2a}$ are each independently hydrogen, fluoro, $(C_1\text{-}C_4)$alkyl, $HO(C_1\text{-}C_4)$alkyl-, hydroxyl, or —$CONR^8R^9$, wherein at least two of $R^{1a}$, $R^{1b}$, $R^{1c}$, and $R^{2a}$ are hydrogen;
- or $X^1$ is $NR^{10}$, $R^{1a}$ and $R^{2a}$ taken together represent —$CH_2$— or —$(CH_2)_2$—, and $R^{1b}$ and $R^{1c}$ are each hydrogen;
- or $X^1$ is $NR^{10}$, $R^1$ and $R^{2a}$ taken together represent —$CH_2$— or —$(CH_2)_2$—, and $R^{1a}$ and $R^{1b}$ are each hydrogen;
- or $X^1$ is $NR^{10}$, $R^1$ and $R^{10}$ taken together represent —$CH_2$— or —$(CH_2)_2$—, and $R^{1a}R^{1b}$, and $R^{2a}$ are each hydrogen;
- or $X^1$ is $NR^{10}$, $R^{1a}$ and $R^{1b}$ taken together with the carbon atom to which they are attached represent $(C_3\text{-}C_6)$cycloalkyl, and $R^1$ and $R^{2a}$ are each hydrogen;
- each $R^3$ is independently selected from the group consisting of fluoro, chloro, methyl, fluoromethyl, difluoromethyl, and trifluoromethyl;
- $R^{6a}$ is hydrogen, fluoro, chloro, or methyl;
- each $R^7$ is independently selected from the group consisting of $(C_1\text{-}C_4)$alkyl, $(C_2\text{-}C_4)$alkenyl, halo$(C_1\text{-}C_4)$alkyl, $(C_3\text{-}C_6)$cycloalkyl, and $(C_3\text{-}C_6)$cycloalkyl$(C_1\text{-}C_2)$alkyl-, each of which is optionally substituted by one or two substituents independently selected from —$CO_2R^8$, —$CONR^8R^9$, hydroxyl, oxo, $(C_1\text{-}C_4)$alkoxy, —$OCONR^8R^9$, $HO(C_1\text{-}C_4)$alkyl-, —$NR^8R^9$, —$N(R^8)C(O)R^9$, —$N(R^8)CO_2(C_1\text{-}C_4)$alkyl, —$N(R^8)CH_2CO_2R^9$, —$N(R^8)CONR^8R^9$, —$N(R^8)SO_2R^9$, —$SO(C_1\text{-}C_4)$alkyl, —$SO_2(C_1\text{-}C_4)$alkyl, —$SO_3R^8$, —$SO_2NR^8R^9$, and —$P(O)(OR^8)(OR^9)$;
- each $R^8$ and $R^9$ is independently hydrogen or $(C_1\text{-}C_4)$alkyl;
- each $R^{10}$ is independently selected from the group consisting of hydrogen, $R^7$, —$C(O)R^7$, —$CONHR^8$, —$CONR^7R^8$, —$C(O)CO_2R^8$, and —$SO_2R^7$;
- each $R^{11}$ is independently selected from the group consisting of hydrogen, —$OR^7$, —$NHR^8$, —$NR^7R^8$, and $R^7$;
- each $R^{12}$ is independently selected from the group consisting of hydrogen, halogen, hydroxyl, —$CO_2R^8$, —$CONHR^8$, and —$CONR^8R^9$, wherein when $R^{12}$ is hydroxyl, $R^{11}$ is hydrogen or $R^7$;
- m is 1 or 2; and
- n is 1, 2, or 3;

or a pharmaceutically acceptable salt thereof.

This invention further relates to compounds of the Formula (III):

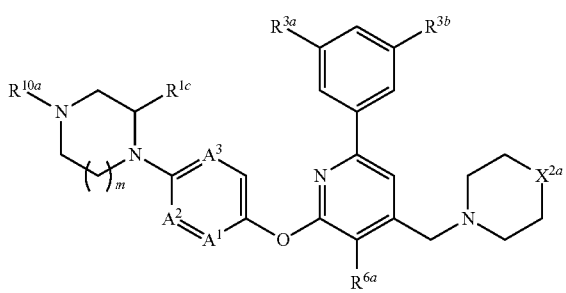

(III)

wherein:
- $A^1$, $A^2$, and $A^3$ are each independently N or CH, wherein one or two of $A^1$, $A^2$, and $A^3$ are N;
- $X^2a$ is $NR^{10b}$ or $C(R^{11a})R^{12a}$;
- $R^{1c}$ is hydrogen;
- $R^{3a}$ and $R^{3b}$ are each independently fluoro or chloro;
- $R^{6a}$ is hydrogen, fluoro, chloro, or methyl;
- $R^{10a}$ is hydrogen, $(C_1\text{-}C_4)$alkyl, or $(C_3\text{-}C_6)$cycloalkyl, wherein said $(C_1\text{-}C_4)$alkyl or $(C_3\text{-}C_6)$cycloalkyl is optionally substituted by —$CO_2H$, —$CONH_2$, —$CONH(C_1\text{-}C_4)$alkyl, —$CON((C_1\text{-}C_4)$alkyl$)((C_1\text{-}C_4)$alkyl), hydroxyl, $(C_1\text{-}C_4)$alkoxy, —$SO_2(C_1\text{-}C_4)$alkyl, or —$SO_2NH_2$;
- or $R^{1c}$ and $R^{10a}$ taken together represent —$CH_2$— or —$(CH_2)_2$—;
- $R^{10b}$ is $(C_1\text{-}C_4)$alkyl which is optionally substituted by —$CONH_2$, —$CONH(C_1\text{-}C_4)$alkyl, or —$CON((C_1\text{-}C_4)$alkyl$)((C_1\text{-}C_4)$alkyl);
- $R^{11a}$ is $(C_1\text{-}C_4)$alkyl or $(C_1\text{-}C_4)$alkoxy, each of which is optionally substituted by one or two substituents independently selected from —$CO_2H$, —$CONH_2$, —$CONH(C_1\text{-}C_4)$alkyl, —$CON((C_1\text{-}C_4)$alkyl$)((C_1\text{-}C_4)$alkyl), hydroxyl, —$OCONH(C_1\text{-}C_4)$alkyl, —$NHCO(C_1\text{-}C_4)$alkyl, —$NHCO_2(C_1\text{-}C_4)$alkyl, and —$NHCONH(C_1\text{-}C_4)$alkyl;
- $R^{12a}$ is hydrogen, hydroxyl, or fluoro, wherein when $R^{12a}$ is hydroxyl, $R^{11a}$ is $(C_1\text{-}C_4)$alkyl which is optionally substituted by one or two substituents independently selected from —$CO_2H$, —$CONH_2$, —$CONH(C_1\text{-}C_4)$alkyl, —$CON((C_1\text{-}C_4)$alkyl$)((C_1\text{-}C_4)$alkyl), hydroxyl, —$OCONH(C_1\text{-}C_4)$alkyl, —$NHCO(C_1\text{-}C_4)$alkyl, —$NHCO_2(C_1\text{-}C_4)$alkyl, and —$NHCONH(C_1\text{-}C_4)$alkyl; and
- m is 1 or 2;

or a pharmaceutically acceptable salt thereof.

This invention further relates to compounds of the Formula (IV):

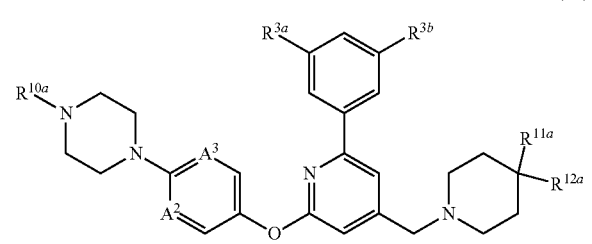

(IV)

wherein:
- $A^2$, and $A^3$ are each independently N or CH, wherein at least one of $A^2$ or $A^3$ are N;
- $R^{3a}$ and $R^{3b}$ are each independently fluoro or chloro;
- $R^{10a}$ is hydrogen, $(C_1\text{-}C_4)$alkyl, or $(C_3\text{-}C_6)$cycloalkyl, wherein said $(C_1\text{-}C_4)$alkyl or $(C_3\text{-}C_6)$cycloalkyl is optionally substituted by —$CO_2H$, —$CONH_2$, —$CONH(C_1\text{-}C_4)$alkyl, —$CON((C_1\text{-}C_4)$alkyl$)((C_1\text{-}C_4)$alkyl), hydroxyl, $(C_1\text{-}C_4)$alkoxy, —$SO_2(C_1\text{-}C_4)$alkyl, or —$SO_2NH_2$;
- $R^{11a}$ is $(C_1\text{-}C_4)$alkyl or $(C_1\text{-}C_4)$alkoxy, each of which is optionally substituted by one or two substituents independently selected from —$CO_2H$, —$CONH_2$, —$CONH(C_1\text{-}C_4)$alkyl, —$CON((C_1\text{-}C_4)$alkyl$)((C_1\text{-}C_4)$alkyl), hydroxyl, —$OCONH(C_1\text{-}C_4)$alkyl, —$NHCO$ ($C_1$-$C_4$)alkyl, —NHCO$_2$($C_1$-$C_4$)alkyl, and —NHCONH($C_1$-$C_4$)alkyl; and $R^{12a}$ is hydrogen, hydroxyl, or fluoro, wherein when $R^{12a}$ is hydroxyl, $R^{11a}$ is ($C_1$-$C_4$)alkyl which is optionally substituted by one or two substituents independently selected from —CO$_2$H, —CONH$_2$, —CONH($C_1$-$C_4$)alkyl, —CON(($C_1$-$C_4$)alkyl)(($C_1$-$C_4$)alkyl), hydroxyl, —OCONH($C_1$-$C_4$)alkyl, —NHCO($C_1$-$C_4$)alkyl, —NHCO$_2$($C_1$-$C_4$)alkyl, and —NHCONH($C_1$-$C_4$)alkyl;

or a pharmaceutically acceptable salt thereof.

In one embodiment, $A^1$, $A^2$, $A^3$, $A^4$, $A^5$, $A^6$, and $A^7$ are each independently N, CH, or CR$^6$, wherein zero, one, two, or three of $A^1$, $A^2$, $A^3$, $A^4$, $A^5$, $A^6$, and $A^7$ are N. In another embodiment, $A^1$, $A^2$, $A^3$, $A^4$, $A^5$, $A^6$, and $A^7$ are each independently N, CH, or CR$^6$, wherein two or three of $A^1$, $A^2$, $A^3$, $A^4$, $A^5$, $A^6$, and $A^7$ are N. In one embodiment, $A^1$, $A^2$, $A^3$, $A^4$, $A^5$, and $A^6$ are each independently N, CH, or CR$^6$, wherein zero, one, two, or three of $A^1$, $A^2$, $A^3$, $A^4$, $A^5$, and $A^6$ are N. In another embodiment, $A^1$, $A^2$, $A^3$, $A^4$, $A^5$, and $A^6$ are each independently N, CH, or CR$^6$, wherein two or three of $A^1$, $A^2$, $A^3$, $A^4$, $A^5$, and $A^6$ are N. In another embodiment, $A^1$, $A^2$, $A^3$, $A^4$, and $A^5$ are each independently N or CH, wherein two or three of $A^1$, $A^2$, $A^3$, $A^4$, and $A^5$ are N. In another embodiment, $A^1$, $A^2$, $A^3$, $A^4$, and $A^5$ are each independently N or CH, wherein three of $A^1$, $A^2$, $A^3$, $A^4$, and $A^5$ are N. In another embodiment, $A^1$, $A^2$, $A^3$, $A^4$, and $A^5$ are each independently N or CH, wherein two of $A^1$, $A^2$, $A^3$, $A^4$, and $A^5$ are N. In another embodiment, $A^1$, $A^2$, and $A^3$ are each independently N or CH, wherein two of $A^1$, $A^2$, and $A^3$ are N. In another embodiment, A, $A^2$, and $A^3$ are each independently N or CH, wherein one of $A^1$, $A^2$, and $A^3$ is N. In another embodiment, one of A and $A^2$ is N and the other is CH. In another embodiment, $A^1$ and $A^2$ are each CH. In another embodiment, $A^1$ is N or CH. In another embodiment, $A^2$ is N or CH. In another embodiment, $A^3$ is N or CH. In another embodiment, $A^4$ is N or CH. In another embodiment, $A^5$ is N or CH. In another embodiment, $A^6$ is N or CH. In another embodiment, $A^6$ is CH or CR$^6$. In a specific embodiment, $A^1$ is N. In another specific embodiment, $A^1$ is CH. In another specific embodiment, $A^2$ is N. In another specific embodiment, $A^2$ is CH. In another specific embodiment, $A^3$ is N. In another specific embodiment, $A^3$ is CH. In another specific embodiment, $A^4$ is N. In another specific embodiment, $A^4$ is CH. In another specific embodiment, $A^5$ is N. In another specific embodiment, $A^5$ is CH. In another specific embodiment, $A^6$ is N. In another specific embodiment, $A^6$ is CH. In another specific embodiment, $A^7$ is N. In another specific embodiment, $A^7$ is CH. In another specific embodiment, $A^1$ and $A^2$ are each N. In another specific embodiment, $A^1$ and $A^3$ are each N. In another specific embodiment, $A^2$ and $A^3$ are each N. In another specific embodiment, $A^1$ and $A^4$ are each N. In another specific embodiment, $A^3$ and $A^5$ are each N. In another specific embodiment, $A^4$ and $A^6$ are each CH. In another specific embodiment, $A^5$ and $A^7$ are each N.

In one embodiment, X is O or NR, wherein R is ($C_1$-$C_4$)alkyl. In another embodiment, X is NR, wherein R is ($C_1$-$C_4$)alkyl. In a specific embodiment, X is O.

In one embodiment, $R^1$ and $R^2$ are each independently hydrogen, ($C_1$-$C_4$)alkyl, or H$_2$N($C_1$-$C_4$)alkyl-. In another embodiment, $R^1$ and $R^2$ are each independently hydrogen or H$_2$N($C_1$-$C_4$)alkyl-. In another embodiment, $R^1$ and $R^2$ taken together with the nitrogen atom to which they are attached represent a 4-11 membered monocyclic or fused, bridged, or spiro bicyclic saturated ring, optionally containing one or two additional heteroatoms independently selected from oxygen, nitrogen, and sulfur, wherein said ring is optionally substituted by one, two, or three substituents independently selected from halogen, hydroxyl, oxo, —OCONR$^8$R$^9$, —CO$_2$R$^8$, —C(O)CO$_2$R, R$^7$, —OR$^7$, —NHR, —NR$^7$R$^8$, —C(O)R$^7$, —CONHR$^8$, —CONR$^7$R$^8$, and —SO$_2$R$^7$. In another embodiment, $R^1$ and $R^2$ taken together with the nitrogen atom to which they are attached represent a 4-11 membered monocyclic or fused, bridged, or spiro bicyclic saturated ring, optionally containing one or two additional nitrogen heteroatoms, wherein said ring is optionally substituted by one, two, or three substituents independently selected from halogen, hydroxyl, oxo, R$^7$, —OR$^7$, —NHR$^8$, —NR$^7$R$^8$, and —C(O)R$^7$. In another embodiment, $R^1$ and $R^2$ taken together with the nitrogen atom to which they are attached represent a 4-11 membered monocyclic or fused, bridged, or spiro bicyclic saturated ring, optionally containing one additional nitrogen heteroatom, wherein said ring is optionally substituted by one substituent which is R$^7$. In another embodiment, $R^1$ and $R^2$ taken together with the nitrogen atom to which they are attached represent a 6- or 7-membered monocyclic ring, optionally containing one or two additional heteroatoms independently selected from oxygen, nitrogen, and sulfur, wherein said ring is optionally substituted by one, two, or three substituents independently selected from halogen, hydroxyl, oxo, —OCONR$^8$R$^9$, —CO$_2$R$^8$, —C(O)CO$_2$R$^8$, R$^7$, —OR$^7$, —NHR$^8$, —NR$^7$R$^8$, —C(O)R$^7$, —CONHR$^8$, —CONR$^7$R$^8$, and —SO$_2$R$^7$. In another embodiment, $R^1$ and $R^2$ taken together with the nitrogen atom to which they are attached represent a 6- or 7-membered monocyclic ring, optionally containing one or two additional nitrogen heteroatoms, wherein said ring is optionally substituted by one, two, or three substituents independently selected from halogen, hydroxyl, oxo, R$^7$, —OR$^7$, —NHR$^8$, —NR$^7$R$^8$, and —C(O)R$^7$. In another embodiment, $R^1$ and $R^2$ taken together with the nitrogen atom to which they are attached represent a 6- or 7-membered monocyclic ring, optionally containing one additional nitrogen heteroatom, wherein said ring is optionally substituted by one substituent which is R$^7$.

In one embodiment, each $R^3$ is independently selected from the group consisting of halogen, methyl, and difluoromethyl. In another embodiment, each $R^3$ is independently selected from the group consisting of fluoro, chloro, bromo, methyl, and difluoromethyl. In one embodiment, each $R^3$ is independently halogen. In another embodiment, each $R^3$ is independently selected from the group consisting of fluoro, chloro, and bromo. In another embodiment, each $R^3$ is independently fluoro or chloro. In a specific embodiment, each $R^3$ is chloro.

In one embodiment, $R^4$ and $R^5$ are each independently hydrogen, ($C_1$-$C_4$)alkyl, or ($C_1$-$C_4$)alkoxy($C_2$-$C_4$)alkyl-. In another embodiment, $R^4$ and $R^5$ taken together with the nitrogen atom to which they are attached represent a 4-11 membered monocyclic or fused, bridged, or spiro bicyclic saturated ring, optionally containing one or two additional heteroatoms independently selected from oxygen, nitrogen, and sulfur, wherein said ring is optionally substituted by one, two, or three substituents independently selected from halogen, hydroxyl, oxo, —OCONR$^8$R$^9$, —CO$_2$R$^8$, —C(O)CO$_2$R$^8$, —SO$_2$($C_1$-$C_4$)alkyl, R$^7$, —OR$^7$, —NHR$^8$, —NR$^7$R$^8$, —N(R$^8$)C(O)R$^9$, —N(R$^8$)SO$_2$R$^9$, —N(R$^8$)CONR$^8$R$^9$, —N(R$^8$)CON(R$^8$)SO$_2$R$^9$, —C(O)R$^7$, —CONHR$^8$, —CONR$^7$R$^8$, and —P(O)R$^8$R$^9$. In another embodiment, $R^4$ and $R^5$ taken together with the nitrogen atom to which they are attached represent a 4-11 membered monocyclic or fused, bridged, or spiro bicyclic saturated ring, optionally containing one or two additional heteroatoms independently selected from oxygen and nitrogen, wherein said ring is optionally substituted by one or two substituents independently selected from halogen, hydroxyl, oxo, —$CO_2R^8$, $R^7$, —$OR^7$, —$NHR^8$, —$N(R^8)C(O)R^9$, —$N(R^8)SO_2R^9$, —$N(R^8)CONR^8R^9$, —$N(R^8)CON(R^8)SO_2R^9$, —$C(O)R^7$, and —$P(O)R^8R^9$. In another embodiment, $R^4$ and $R^5$ taken together with the nitrogen atom to which they are attached represent a 4-11 membered monocyclic or fused, bridged, or spiro bicyclic saturated ring, optionally containing one or two additional heteroatoms independently selected from oxygen and nitrogen, wherein said ring is optionally substituted by one substituent which is $R^7$. In another embodiment, $R^4$ and $R^5$ taken together with the nitrogen atom to which they are attached represent a 6- or 7-membered monocyclic ring, optionally containing one or two additional heteroatoms independently selected from oxygen and nitrogen, wherein said ring is optionally substituted by one, two, or three substituents independently selected from halogen, hydroxyl, oxo, —$OCONR^8R^9$, —$CO_2R^8$, —$C(O)CO_2R^8$, —$SO_2(C_1-C_4)$alkyl, $R^7$, —$OR^7$, —$NHR^8$, —$NR^7R^8$, —$N(R^8)C(O)R^9$, —$N(R^8)SO_2R^9$, —$N(R^8)CONR^8R^9$, —$N(R^8)CON(R^8)SO_2R^9$, —$C(O)R^7$, —$CONHR^8$, —$CONR^7R^8$, and —$P(O)R^8R^9$. In another embodiment, $R^4$ and $R^5$ taken together with the nitrogen atom to which they are attached represent a 6- or 7-membered monocyclic ring, optionally containing one or two additional heteroatoms independently selected from oxygen and nitrogen, wherein said ring is optionally substituted by one or two substituents independently selected from halogen, hydroxyl, oxo, —$CO_2R^8$, $R^7$, —$OR^7$, —$NHR^8$, —$N(R^8)C(O)R^9$, —$N(R^8)SO_2R^9$, —$N(R^8)CONR^8R^9$, —$N(R^8)CON(R^8)SO_2R^9$, —$C(O)R^7$, and —$P(O)R^8R^9$. In another embodiment, $R^4$ and $R^5$ taken together with the nitrogen atom to which they are attached represent a 6- or 7-membered monocyclic ring, optionally containing one or two additional heteroatoms independently selected from oxygen and nitrogen, wherein said ring is optionally substituted by one substituent which is $R^7$. In another embodiment, $R^4$ and $R^5$ taken together with the nitrogen atom to which they are attached represent a 6-membered monocyclic ring, wherein said ring is optionally substituted by one, two, or three substituents independently selected from halogen, hydroxyl, oxo, —$OCONR^8R^9$, —$CO_2R^8$, —$C(O)CO_2R^8$, —$SO_2(C_1-C_4)$alkyl, $R^7$, —$OR^7$, —$NHR^8$, —$NR^7R^8$, —$N(R^8)C(O)R^9$, —$N(R^8)SO_2R^9$, —$N(R^8)CONR^8R^9$, —$N(R^8)CON(R^8)SO_2R^9$, —$C(O)R^7$, —$CONHR^8$, —$CONR^7R^8$, and —$P(O)R^8R^9$. In another embodiment, $R^4$ and $R^5$ taken together with the nitrogen atom to which they are attached represent a 6-membered monocyclic ring, wherein said ring is optionally substituted by one or two substituents independently selected from halogen, hydroxyl, oxo, —$CO_2R^8$, $R^7$, —$OR^7$, —$NHR^8$, —$N(R^8)C(O)R^9$, —$N(R^8)SO_2R^9$, —$N(R^8)CONR^8R^9$, —$N(R^8)CON(R^8)SO_2R^9$, —$C(O)R^7$, and —$P(O)R^8R^9$. In another embodiment, $R^4$ and $R^5$ taken together with the nitrogen atom to which they are attached represent a 6-membered monocyclic ring, wherein said ring is optionally substituted by one substituent which is $R^7$.

In one embodiment, each $R^6$ is independently selected from the group consisting of halogen and $(C_1-C_4)$alkyl. In another embodiment, each $R^6$ is independently halogen. In another embodiment, each $R^6$ is independently selected from the group consisting of fluoro, chloro, bromo, and methyl. In another embodiment, each $R^6$ is independently selected from the group consisting of fluoro, chloro, and bromo. In another embodiment, each $R^6$ is independently fluoro or chloro. In a specific embodiment, each $R^6$ is fluoro. In another specific embodiment, each $R^6$ is chloro. In another embodiment, each $R^6$ is independently $(C_1-C_4)$alkyl. In another specific embodiment, each $R^6$ is methyl. In one embodiment, each $R^7$ is independently selected from the group consisting of $(C_1-C_6)$alkyl, halo$(C_1-C_6)$alkyl, $(C_3-C_6)$cycloalkyl, and $(C_3-C_6)$cycloalkyl$(C_1-C_4)$alkyl-, each of which is optionally substituted by one or two substituents independently selected from triazolyl, tetrazolyl, —$CO_2R^8$, —$CONR^8R^9$, —$CON(R^8)CO_2(C_1-C_4)$alkyl, hydroxyl, $(C_1-C_4)$alkoxy, —$OCONR^8R^9$, —$OCON(R^8)C(O)R^9$, $(C_1-C_4)$alkyl, $HO(C_1-C_4)$alkyl-, —$NR^8R^9$, —$N(O)R^8R^9$, —$N(R^8)C(O)R^9$, —$N(R^8)CO_2(C_1-C_4)$alkyl, —$N(R^8)CONR^8R^9$, —$N(R^8)CON(R^8)C(O)R^9$, —$N(R^8)CON(R^8)CO_2(C_1-C_4)$alkyl, —$N(R^8)SO_2R^9$, —$N(R^8)CON(R^8)SO_2R^9$, —$SO(C_1-C_4)$alkyl, —$SO_2(C_1-C_4)$alkyl, —$SO_3R^8$, —$SO_2NR^8R^9$, —$B(OH)_2$, —$P(O)R^8R^9$, and —$P(O)(OR^8)(OR^9)$. In another embodiment, each $R^7$ is independently selected from the group consisting of $(C_1-C_4)$alkyl, $(C_2-C_4)$alkenyl, halo$(C_1-C_4)$alkyl, $(C_3-C_6)$cycloalkyl, and $(C_3-C_6)$cycloalkyl$(C_1-C_2)$alkyl-, each of which is optionally substituted by one or two substituents independently selected from —$CO_2R^8$, —$CONR^8R^9$, hydroxyl, oxo, $(C_1-C_4)$alkoxy, —$OCONR^8R^9$, $HO(C_1-C_4)$alkyl-, —$NR^8R^9$, —$N(R^8)C(O)R^9$, —$N(R^8)CO_2(C_1-C_4)$alkyl, —$N(R^8)CH_2CO_2R^9$, —$N(R^8)CONR^8R^9$, —$N(R^8)SO_2R^9$, —$SO(C_1-C_4)$alkyl, —$SO_2(C_1-C_4)$alkyl, —$SO_3R^8$, —$SO_2NR^8R^9$, and —$P(O)(OR^8)(OR^9)$. In another embodiment, each $R^7$ is independently selected from the group consisting of $(C_1-C_4)$alkyl, $(C_2-C_4)$alkenyl, halo$(C_1-C_4)$alkyl, $(C_3-C_6)$cycloalkyl, and $(C_3-C_6)$cycloalkyl$(C_1-C_2)$alkyl-, each of which is optionally substituted by one or two substituents independently selected from —$CO_2R^8$, —$CONR^8R^9$, hydroxyl, $(C_1-C_4)$alkoxy, —$OCONR^8R^9$, $HO(C_1-C_4)$alkyl-, —$NR^8R^9$, —$N(R^8)C(O)R^9$, —$N(R^8)CO_2(C_1-C_4)$alkyl, —$N(R^8)CONR^8R^9$, —$N(R^8)SO_2R^9$, —$SO(C_1-C_4)$alkyl, —$SO_2(C_1-C_4)$alkyl, —$SO_3R^8$, —$SO_2NR^8R^9$, and —$P(O)(OR^8)(OR^9)$. In another embodiment, each $R^7$ is $(C_1-C_6)$alkyl which is optionally substituted by one substituent which is —$CO_2H$, hydroxyl, —$N(R^8)C(O)R^9$, or —$SO(C_1-C_4)$alkyl. In another embodiment, each $R^7$ is $(C_1-C_4)$alkyl which is optionally substituted by one substituent which is —$CO_2H$, hydroxyl, —$N(R^8)C(O)R^9$, or —$SO(C_1-C_4)$alkyl.

In one embodiment, each $R^8$ and $R^9$ is independently hydrogen or $(C_1-C_4)$alkyl. In another embodiment, each $R^8$ and $R^9$ is independently $(C_1-C_4)$alkyl. In another embodiment, $R^8$ and $R^9$ are each methyl. In another embodiment, each $R^8$ and $R^9$ is hydrogen. In another embodiment, $R^8$ is hydrogen and $R^9$ is $(C_1-C_4)$alkyl. In another embodiment, $R^8$ is hydrogen and $R^9$ is methyl. In another embodiment, $R^8$ is $(C_1-C_4)$alkyl. In another embodiment, $R^8$ is methyl. In another embodiment, $R^8$ is hydrogen. In another embodiment, $R^9$ is $(C_1-C_4)$alkyl. In another embodiment, $R^9$ is methyl. In another embodiment, $R^9$ is hydrogen.

In one embodiment, n is 1, 2, or 3. In another embodiment, n is 2 or 3. In another embodiment, n is 2.

In one embodiment, $X^1$ and $X^2$ are each independently $NR^{10}$. In another embodiment, $X^1$ and $X^2$ are each independently $C(R^{11})R^{12}$. In another embodiment, $X^1$ is $NR^{10}$. In another embodiment, $X^1$ is $C(R^{11})R^{12}$. In another embodiment, $X^2$ is $NR^{10}$. In another embodiment, $X^2$ is $C(R^{11})R^{12}$. In another embodiment, $X^1$ is $NR^{10}$ and $X^2$ is $C(R^{11})R^{12}$. In another embodiment, $X^1$ is $C(R^{11})R^{12}$ and $X^2$ is $NR^{10}$.

In one embodiment, $X^{2a}$ is $NR^{10b}$. In another embodiment, $X^{2a}$ is $C(R^{11a})R^{12a}$. In one embodiment, $R^{1a}$, $R^{1b}$, $R^{1c}$, and $R^{2a}$ are each independently hydrogen, fluoro, $(C_1-C_4)$alkyl, $HO(C_1-C_4)$alkyl-, hydroxyl, or —$CONR^8R^9$, wherein at least two of $R^{1a}$, $R^{1b}$, $R^{1c}$, and $R^{2a}$ are hydrogen. In another embodiment, $R^{1a}$, $R^{1b}$, $R^{1c}$, and $R^{2a}$ are each hydrogen. In a specific embodiment, $R^{1c}$ is hydrogen.

In one embodiment, $X^1$ is $NR^{10}$, $R^{1a}$ and $R^{2a}$ taken together represent —$CH_2$— or —$(CH_2)_2$—, and $R^{1b}$ and $R^{1c}$ are each hydrogen. In another embodiment, $X^1$ is $NR^{10}$, $R^{1c}$ and $R^{2a}$ taken together represent —$CH_2$— or —$(CH_2)_2$—, and $R^{1a}$ and $R^{1b}$ are each hydrogen. In another embodiment, $X^1$ is $NR^{10}$, $R^{1c}$ and $R^{10}$ taken together represent —$CH_2$— or —$(CH_2)_2$—, and $R^{1a}$, $R^{1b}$, and $R^{2a}$ are each hydrogen. In another embodiment, $X^1$ is $NR^{10}$, $R^{1a}$ and $R^{1b}$ taken together with the carbon atom to which they are attached represent $(C_3$-$C_6)$cycloalkyl, and $R^{1c}$ and $R^{2a}$ are each hydrogen.

In one embodiment, $R^{3a}$ and $R^{3b}$ are each fluoro. In another embodiment, $R^{3a}$ and $R^{3b}$ are each chloro. In another embodiment, $R^{3a}$ is fluoro and $R^{3b}$ is chloro.

In one embodiment, $R^{6a}$ is hydrogen or methyl.

In one embodiment, each $R^{10}$ is independently selected from the group consisting of hydrogen, $R^7$, —$C(O)R^7$, —$CONHR^8$, —$CONR^7R^8$, —$C(O)CO_2R^8$, and —$SO_2R^7$. In another embodiment, each $R^{10}$ is independently selected from the group consisting of hydrogen and $R^7$. In another embodiment, each $R^{10}$ is $R^7$.

In one embodiment, $R^{10a}$ is hydrogen, $(C_1$-$C_4)$alkyl, or $(C_3$-$C_6)$cycloalkyl, wherein said $(C_1$-$C_4)$alkyl or $(C_3$-$C_6)$cycloalkyl is optionally substituted by —$CO_2H$, —$CONH_2$, —$CONH(C_1$-$C_4)$alkyl, —$CON((C_1$-$C_4)$alkyl)($(C_1$-$C_4)$alkyl), hydroxyl, $(C_1$-$C_4)$alkoxy, —$SO_2(C_1$-$C_4)$alkyl, or —$SO_2NH_2$. In another embodiment, $R^{10a}$ is $(C_1$-$C_4)$alkyl which is optionally substituted by —$CO_2H$, —$CONH_2$, —$CONH(C_1$-$C_4)$alkyl, —$CON((C_1$-$C_4)$alkyl)($(C_1$-$C_4)$alkyl), hydroxyl, $(C_1$-$C_4)$alkoxy, —$SO_2(C_1$-$C_4)$alkyl, or —$SO_2NH_2$. In another embodiment, $R^{10a}$ is $(C_1$-$C_4)$alkyl which is optionally substituted by —$CO_2H$, hydroxyl, or —$SO_2(C_1$-$C_4)$alkyl.

In one embodiment, $R^{1c}$ and $R^{10a}$ taken together represent —$CH_2$— or —$(CH_2)_2$—.

In one embodiment, each $R^{11}$ is $R^7$. In another embodiment, $R^{10}$ and $R^{11}$ are each independently $R^7$.

In one embodiment, $R^{11a}$ is $(C_1$-$C_4)$alkyl which is optionally substituted by one or two substituents independently selected from —$CO_2H$, —$CONH_2$, —$CONH(C_1$-$C_4)$alkyl, —$CON((C_1$-$C_4)$alkyl)($(C_1$-$C_4)$alkyl), hydroxyl, —$OCONH(C_1$-$C_4)$alkyl, —$NHCO(C_1$-$C_4)$alkyl, —$NHCO_2(C_1$-$C_4)$alkyl, and —$NHCONH(C_1$-$C_4)$alkyl. In another embodiment, $R^{11a}$ is $(C_1$-$C_4)$alkyl which is optionally substituted by one substituent which is —$CO_2H$ or —$NHCO(C_1$-$C_4)$alkyl.

In one embodiment, each $R^{12}$ is independently selected from the group consisting of hydrogen, halogen, and hydroxyl. In another embodiment, each $R^{12}$ is hydrogen.

In one embodiment, $R^{12a}$ is hydrogen.

In one embodiment, m is 1. In another embodiment, m is 2.

In one embodiment, this invention relates to compounds of Formula (I) wherein:
  $A^1$, $A^2$, $A^3$, $A^4$, $A^5$, and $A^6$ are each independently N, CH, or $CR^6$, wherein zero, one, two, or three of $A^1$, $A^2$, $A^3$, $A^4$, $A^5$, and $A^6$ are N;
  X is O or $NR^8$;
  $R^1$ and $R^2$ are each independently hydrogen or $H_2N(C_1$-$C_4)$alkyl-;
  or $R^1$ and $R^2$ taken together with the nitrogen atom to which they are attached represent a 4-11 membered monocyclic or fused, bridged, or spiro bicyclic saturated ring, optionally containing one or two additional nitrogen heteroatoms, wherein said ring is optionally substituted by one, two, or three substituents independently selected from halogen, hydroxyl, oxo, $R^7$, —$OR^7$, —$NHR^8$, —$NR^7R^8$, and —$C(O)R^7$;
  each $R^3$ is independently selected from the group consisting of halogen, methyl, and difluoromethyl;
  $R^4$ and $R^5$ are each independently hydrogen, $(C_1$-$C_4)$alkyl, or $(C_1$-$C_4)$alkoxy$(C_2$-$C_4)$alkyl-;
  or $R^4$ and $R^5$ taken together with the nitrogen atom to which they are attached represent a 4-11 membered monocyclic or fused, bridged, or spiro bicyclic saturated ring, optionally containing one or two additional heteroatoms independently selected from oxygen and nitrogen, wherein said ring is optionally substituted by one or two substituents independently selected from halogen, hydroxyl, oxo, —$CO_2R^8$, $R^7$, —$OR^7$, —$NHR^8$, —$N(R^8)C(O)R^9$, —$N(R^8)SO_2R^9$, —$N(R^8)CONR^8R^9$, —$N(R^8)CON(R^8)SO_2R^9$, —$C(O)R^7$, and —$P(O)R^8R^9$;
  each $R^6$ is independently selected from the group consisting of halogen and $(C_1$-$C_4)$alkyl;
  each $R^7$ is independently selected from the group consisting of $(C_1$-$C_6)$alkyl, halo$(C_1$-$C_6)$alkyl, $(C_3$-$C_6)$cycloalkyl, and $(C_3$-$C_6)$cycloalkyl$(C_1$-$C_4)$alkyl-, each of which is optionally substituted by one or two substituents independently selected from triazolyl, tetrazolyl, —$CO_2R^8$, —$CONR^8R^9$, —$CON(R^8)CO_2(C_1$-$C_4)$alkyl, hydroxyl, $(C_1$-$C_4)$alkoxy, —$OCONR^8R^9$, —$OCON(R^8)C(O)R^9$, $(C_1$-$C_4)$alkyl, $HO(C_1$-$C_4)$alkyl-, —$NR^8R^9$, —$N(O)R^8R^9$, —$N(R^8)C(O)R^9$, —$N(R^8)CO_2(C_1$-$C_4)$alkyl, —$N(R^8)CONR^8R^9$, —$N(R^8)CON(R^8)C(O)R^9$, —$N(R^8)CON(R^8)CO_2(C_1$-$C_4)$alkyl, —$N(R^8)SO_2R^9$, —$N(R^8)CON(R^8)SO_2R^9$, —$SO(C_1$-$C_4)$alkyl, —$SO_2(C_1$-$C_4)$alkyl, —$SO_3R^8$, —$SO_2NR^8R^9$, —$B(OH)_2$, —$P(O)R^8R^9$, and —$P(O)(OR^8)(OR^9)$;
  each $R^8$ and $R^9$ is independently hydrogen, $(C_1$-$C_4)$alkyl, or $(C_3$-$C_6)$cycloalkyl; and
  n is 2 or 3;
  or a pharmaceutically acceptable salt thereof.

In another embodiment, this invention relates to compounds of Formula (I) wherein:
  $A^1$ and $A^2$ are each CH;
  or one of $A^1$ and $A^2$ is N and the other is CH;
  $A^3$ and $A^5$ are each N;
  $A^4$ is CH;
  $A^6$ is CH or $CR^6$;
  X is O;
  $R^1$ and $R^2$ taken together with the nitrogen atom to which they are attached represent a 6- or 7-membered monocyclic ring, optionally containing one additional nitrogen heteroatom, wherein said ring is optionally substituted by one substituent which is $R^7$;
  each $R^3$ is independently selected from the group consisting of fluoro, chloro, and bromo;
  $R^4$ and $R^5$ taken together with the nitrogen atom to which they are attached represent a 6-membered monocyclic ring, wherein said ring is optionally substituted by one substituent which is $R^7$;
  $R^6$ is methyl;
  each $R^7$ is $(C_1$-$C_6)$alkyl which is optionally substituted by one substituent which is —$CO_2H$, hydroxyl, —$N(R^8)C(O)R^9$, or —$SO(C_1$-$C_4)$alkyl;
  each $R^8$ and $R^9$ is independently hydrogen or $(C_1$-$C_4)$alkyl; and
  n is 2;
  or a pharmaceutically acceptable salt thereof.

In one embodiment, this invention relates to compounds of Formula (II) wherein:
$A^1$, $A^2$, $A^3$, $A^4$, and $A^5$ are each independently N or CH, wherein two or three of $A^1$, $A^2$, $A^3$, $A^4$, and $A^5$ are N;
$X^1$ and $X^2$ are each independently $NR^{10}$ or $C(R^{11})R^{12}$;
$R^{1a}$, $R^{1b}$, $R^{1c}$, and $R^{2a}$ are each hydrogen;
or $X^1$ is $NR^{10}$, $R^{1a}$ and $R^{2a}$ taken together represent —CH$_2$— or —(CH$_2$)$_2$—, and $R^{1b}$ and $R^{1c}$ are each hydrogen;
or $X^1$ is $NR^{10}$, $R^{1c}$ and $R^{2a}$ taken together represent —CH$_2$— or —(CH$_2$)$_2$—, and $R^{1a}$ and $R^{1b}$ are each hydrogen;
or $X^1$ is $NR^{10}$, $R^{1c}$ and $R^{10}$ taken together represent —CH$_2$— or —(CH$_2$)$_2$—, and $R^{1a}$, $R^{1b}$, and $R^{2a}$ are each hydrogen;
each $R^3$ is independently selected from the group consisting of halogen, methyl, and difluoromethyl;
$R^{6a}$ is hydrogen, fluoro, chloro, or methyl;
each $R^7$ is independently selected from the group consisting of (C$_1$-C$_4$)alkyl, (C$_2$-C$_4$)alkenyl, halo(C$_1$-C$_4$)alkyl, (C$_3$-C$_6$)cycloalkyl, and (C$_3$-C$_6$)cycloalkyl(C$_1$-C$_2$)alkyl-, each of which is optionally substituted by one or two substituents independently selected from —CO$_2$R$^8$, —CONR$^8$R$^9$, hydroxyl, (C$_1$-C$_4$)alkoxy, —OCONR$^8$R$^9$, HO(C$_1$-C$_4$)alkyl-, —NR$^8$R$^9$, —N(R$^8$)C(O)R$^9$, —N(R$^8$)CO$_2$(C$_1$-C$_4$)alkyl, —N(R$^8$)CONR$^8$R$^9$, —N(R$^8$)SO$_2$R$^9$, —SO(C$_1$-C$_4$)alkyl, —SO$_2$(C$_1$-C$_4$)alkyl, —SO$_3$R$^8$, —SO$_2$NR$^8$R$^9$, and —P(O)(OR$^8$)(OR$^9$);
each $R^8$ and $R^9$ is independently hydrogen or (C$_1$-C$_4$) alkyl;
each $R^{10}$ is independently selected from the group consisting of hydrogen and $R^7$;
each $R^{11}$ is $R^7$;
each $R^{12}$ is independently selected from the group consisting of hydrogen, halogen, and hydroxyl;
m is 1 or 2; and
n is 2 or 3;
or a pharmaceutically acceptable salt thereof.

In another embodiment, this invention relates to compounds of Formula (II) wherein:
$A^1$ and $A^2$ are each CH;
or one of $A^1$ and $A^2$ is N and the other is CH;
$A^3$ and $A^5$ are each N;
$A^4$ is CH;
$X^1$ is $NR^{10}$ and $X^2$ is $C(R^{11})R^{12}$;
$R^{1a}$, $R^{1b}$, $R^{1c}$, and $R^{2a}$ are each hydrogen;
or $X^1$ is $NR^{10}$, $R^{1c}$ and $R^{10}$ taken together represent —CH$_2$— or —(CH$_2$)$_2$—, and $R^{1a}$, $R^{1b}$, and $R^{2a}$ are each hydrogen;
each $R^3$ is independently fluoro or chloro;
$R^{6a}$ is hydrogen or methyl;
each $R^7$ is (C$_1$-C$_4$)alkyl which is optionally substituted by one substituent which is —CO$_2$H, hydroxyl, —N(R$^8$)C(O)R$^9$, or —SO(C$_1$-C$_4$)alkyl;
each $R^8$ and $R^9$ is independently hydrogen or (C$_1$-C$_4$) alkyl;
$R^{10}$ and $R^{11}$ are each independently $R^7$;
$R^{12}$ is hydrogen;
m is 1 or 2; and
n is 2 or 3;
or a pharmaceutically acceptable salt thereof.

In one embodiment, this invention relates to compounds of Formula (III) wherein:
$A^1$ and $A^2$ are each CH;
or one of $A^1$ and $A^2$ is N and the other is CH;
$A^3$ is N;
$X^{2a}$ is $C(R^{11a})R^{12a}$;

$R^{1c}$ is hydrogen;
$R^{3a}$ and $R^{3b}$ are each chloro;
$R^{6a}$ is hydrogen or methyl;
$R^{10a}$ is (C$_1$-C$_4$)alkyl which is optionally substituted by —CO$_2$H, hydroxyl, or —SO$_2$(C$_1$-C$_4$)alkyl;
or $R^{1c}$ and $R^{10a}$ taken together represent —CH$_2$— or —(CH$_2$)$_2$—;
$R^{11a}$ is (C$_1$-C$_4$)alkyl which is optionally substituted by one substituent which is —CO$_2$H or —NHCO(C$_1$-C$_4$) alkyl;
$R^{12a}$ is hydrogen; and
m is 1 or 2;
or a pharmaceutically acceptable salt thereof.

Specific compounds of this invention include:
2-(4-((2-(3,5-dichlorophenyl)-6-((6-(piperazin-1-yl)pyridin-3-yl)oxy)pyridin-4-yl)methyl)piperazin-1-yl)-N-methylacetamide;
N-((1-((2-(3,5-dichlorophenyl)-6-((6-(piperazin-1-yl)pyridin-3-yl)oxy)pyridin-4-yl)methyl)-4-hydroxypiperidin-4-yl)methyl)acetamide;
3-(1-((2-(3,5-dichlorophenyl)-6-((6-(piperazin-1-yl)pyridin-3-yl)oxy)pyridin-4-yl)methyl)piperidin-4-yl)propanoic acid;
2-(1-((2-(3,5-dichlorophenyl)-6-((6-(piperazin-1-yl)pyridin-3-yl)oxy)pyridin-4-yl)methyl)piperidin-4-yl)acetic acid;
1-((1-((2-(3,5-dichlorophenyl)-6-((6-(piperazin-1-yl)pyridin-3-yl)oxy)pyridin-4-yl)methyl)-4-hydroxypiperidin-4-yl)methyl)-3-methylurea;
methyl ((1-((2-(3,5-dichlorophenyl)-6-((6-(piperazin-1-yl)pyridin-3-yl)oxy)pyridin-4-yl)methyl)-4-hydroxypiperidin-4-yl)methyl)carbamate;
2-(1-((2-(3,5-dichlorophenyl)-6-((6-(piperazin-1-yl)pyridin-3-yl)oxy)pyridin-4-yl)methyl)piperidin-4-yl)ethanesulfonic acid;
(1-((2-(3,5-dichlorophenyl)-6-((6-(piperazin-1-yl)pyridin-3-yl)oxy)pyridin-4-yl)methyl)piperidin-4-yl)methanesulfonic acid;
N-((1-((2-(3,5-dichlorophenyl)-6-((6-(piperazin-1-yl)pyridin-3-yl)oxy)pyridin-4-yl)methyl)piperidin-4-yl)methyl)acetamide;
2-(4-(5-((4-((4-(acetamidomethyl)piperidin-1-yl)methyl)-6-(3,5-dichlorophenyl)pyridin-2-yl)oxy)pyridin-2-yl)piperazin-1-yl)acetic acid;
3-(4-(5-((4-((4-(acetamidomethyl)piperidin-1-yl)methyl)-6-(3,5-dichlorophenyl)pyridin-2-yl)oxy)pyridin-2-yl)piperazin-1-yl)propanoic acid;
N-((1-((2-(3,5-dichlorophenyl)-6-((6-(4-(2-(methylsulfonyl)ethyl)piperazin-1-yl)pyridin-3-yl)oxy)pyridin-4-yl)methyl)piperidin-4-yl)methyl)acetamide;
3-(4-(5-((4-((4-(acetamidomethyl)piperidin-1-yl)methyl)-6-(3,5-dichlorophenyl)pyridin-2-yl)oxy)pyridin-2-yl)piperazin-1-yl)propanamide;
N-((1-((2-((6-(4-(2-(1H-tetrazol-5-yl)ethyl)piperazin-1-yl)pyridin-3-yl)oxy)-6-(3,5-dichlorophenyl)pyridin-4-yl)methyl)piperidin-4-yl)methyl)acetamide;
N-((1-((2-(3,5-dichlorophenyl)-6-((6-(4-(2-(methylsulfinyl)ethyl)piperazin-1-yl)pyridin-3-yl)oxy)pyridin-4-yl)methyl)piperidin-4-yl)methyl)acetamide;
N-((1-((2-(3,5-dichlorophenyl)-6-((6-(4-(4-(methylsulfonyl)butan-2-yl)piperazin-1-yl)pyridin-3-yl)oxy)pyridin-4-yl)methyl)piperidin-4-yl)methyl)acetamide;
1-((1-((2-(3,5-dichlorophenyl)-6-((2-(4-(3-(methyl sulfinyl)butyl)piperazin-1-yl)pyrimidin-5-yl)oxy)pyridin-4-yl)methyl)piperidin-4-yl)methyl)-3-methylurea;
1-((1-((2-(3,5-dichlorophenyl)-6-((2-(4-(4-(methylsulfonyl)butan-2-yl)piperazin-1-yl)pyrimidin-5-yl)oxy)pyridin-4-yl)methyl)piperidin-4-yl)methyl)-3-methylurea;

N-((1-((2-(3,5-dichlorophenyl)-6-((2-(4-(4-(methylsulfonyl)butan-2-yl)piperazin-1-yl)pyrimidin-5-yl)oxy)pyridin-4-yl)methyl)piperidin-4-yl)methyl)acetamide;

1-((1-((2-(3,5-dichlorophenyl)-6-((2-(4-(4-hydroxybutan-2-yl)piperazin-1-yl)pyrimidin-5-yl)oxy)pyridin-4-yl)methyl)piperidin-4-yl)methyl)-3-methylurea;

2-(1-((2-(3,5-dichlorophenyl)-6-((2-(4-(1-hydroxypropan-2-yl)piperazin-1-yl)pyrimidin-5-yl)oxy)pyridin-4-yl)methyl)piperidin-4-yl)acetic acid;

2-(1-((2-(3,5-dichlorophenyl)-6-((2-(4-(3-hydroxycyclobutyl)piperazin-1-yl)pyrimidin-5-yl)oxy)pyridin-4-yl)methyl)piperidin-4-yl)acetic acid;

2-(1-((2-(3,5-dichlorophenyl)-6-((2-(4-(1,3-dihydroxypropan-2-yl)piperazin-1-yl)pyrimidin-5-yl)oxy)pyridin-4-yl)methyl)piperidin-4-yl)acetic acid;

2-(1-((2-(3,5-dichlorophenyl)-6-((2-(4-((1s,3s)-3-hydroxy-3-methylcyclobutyl)piperazin-1-yl)pyrimidin-5-yl)oxy)pyridin-4-yl)methyl)piperidin-4-yl)acetic acid;

2-(1-((2-(3,5-dichlorophenyl)-6-((2-(4-((1r,3r)-3-hydroxy-3-methylcyclobutyl)piperazin-1-yl)pyrimidin-5-yl)oxy)pyridin-4-yl)methyl)piperidin-4-yl)acetic acid;

N-((1-((2-(3,5-dichlorophenyl)-6-((6-(4-((trans)-3-(methylsulfonamido)cyclobutyl)piperazin-1-yl)pyridin-3-yl)oxy)pyridin-4-yl)methyl)piperidin-4-yl)methyl)acetamide;

N-((1-((2-(3,5-dichlorophenyl)-6-((6-(4-((cis)-3-(methylsulfonamido)cyclobutyl)piperazin-1-yl)pyridin-3-yl)oxy)pyridin-4-yl)methyl)piperidin-4-yl)methyl)acetamide;

N-((1-((2-((6-(4-(2-aminoethyl)piperazin-1-yl)pyridin-3-yl)oxy)-6-(3,5-dichlorophenyl)pyridin-4-yl)methyl)piperidin-4-yl)methyl)acetamide;

N-((1-((2-(3,5-dichlorophenyl)-6-((6-(4-(2,4-dihydroxybutyl)piperazin-1-yl)pyridin-3-yl)oxy)pyridin-4-yl)methyl)piperidin-4-yl)methyl)acetamide;

(2-(4-(5-((4-((4-(acetamidomethyl)piperidin-1-yl)methyl)-6-(3,5-dichlorophenyl)pyridin-2-yl)oxy)pyridin-2-yl)piperazin-1-yl)ethyl)phosphonic acid;

2-(4-(5-((4-((4-(acetamidomethyl)piperidin-1-yl)methyl)-6-(3,5-dichlorophenyl)pyridin-2-yl)oxy)pyridin-2-yl)piperazin-1-yl)ethyl carbamate;

N-((1-((2-(3,5-dichlorophenyl)-6-((6-(4-(2-(N-methylmethylsulfonamido)ethyl)piperazin-1-yl)pyridin-3-yl)oxy)pyridin-4-yl)methyl)piperidin-4-yl)methyl)acetamide;

4-(4-(5-((4-((4-(acetamidomethyl)piperidin-1-yl)methyl)-6-(3,5-dichlorophenyl)pyridin-2-yl)oxy)pyridin-2-yl)piperazin-1-yl)-4-oxobutanoic acid;

N-((1-((2-(3,5-dichlorophenyl)-6-((6-(4-((1-(hydroxymethyl)cyclopropyl)methyl)piperazin-1-yl)pyridin-3-yl)oxy)pyridin-4-yl)methyl)piperidin-4-yl)methyl)acetamide;

N-((1-((2-(3,5-dichlorophenyl)-6-((6-(4-((1-hydroxycyclopropyl)methyl)piperazin-1-yl)pyridin-3-yl)oxy)pyridin-4-yl)methyl)piperidin-4-yl)methyl)acetamide;

2-(1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)-N-ethylacetamide;

1-(2-(3,5-dichlorophenyl)-6-((2-(4-(3-(methylsulfonyl)propyl)piperazin-1-yl)pyrimidin-5-yl)oxy)pyridin-4-yl)-N-methylmethanamine;

3-(4-(5-((6-(3,5-dichlorophenyl)-4-((4-(sulfamoylmethyl)piperidin-1-yl)methyl)pyridin-2-yl)oxy)pyridin-2-yl)piperazin-1-yl)propanoic acid;

3-(4-(5-((6-(3,5-dichlorophenyl)-4-((4-((methylsulfonyl)methyl)piperidin-1-yl)methyl)pyridin-2-yl)oxy)pyridin-2-yl)piperazin-1-yl)propanoic acid;

1-((1-((2-(3,5-dichlorophenyl)-6-((6-(4-(2-hydroxyethyl)piperazin-1-yl)pyridin-3-yl)oxy)pyridin-4-yl)methyl)piperidin-4-yl)methyl)-3-methylurea;

3-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)propanoic acid;

N-((1-((5-(4-aminophenoxy)-3',5'-dichloro-[1,1'-biphenyl]-3-yl)methyl)piperidin-4-yl)methyl) acetamide;

N-((1-((5-((5-aminopyrimidin-2-yl)oxy)-3',5'-dichloro-[1,1'-biphenyl]-3-yl)methyl)piperidin-4-yl)methyl)acetamide;

3-(4-(5-((6-(3,5-dichlorophenyl)-4-((4-(methylsulfonamidoethyl)piperidin-1-yl)methyl)pyridin-2-yl)oxy)pyridin-2-yl)piperazin-1-yl)propanoic acid;

N-((1-((5-((5-aminopyridin-2-yl)oxy)-3',5'-dichloro-[1,1'-biphenyl]-3-yl)methyl)piperidin-4-yl)methyl)acetamide;

N-((1-((5-((6-amino-5-fluoropyridin-3-yl)oxy)-3',5'-dichloro-[1,1'-biphenyl]-3-yl)methyl)piperidin-4-yl)methyl)acetamide;

1-((1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)methyl)-3-methylurea;

3-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)propane-1-sulfonamide;

methyl ((1-((2-(3,5-dichlorophenyl)-6-((2-(piperazin-1-yl)pyrimidin-5-yl)oxy)pyridin-4-yl)methyl)piperidin-4-yl)methyl)carbamate;

3-(4-(5-((6-(3,5-dichlorophenyl)-4-((methylamino)methyl)pyridin-2-yl)oxy)pyridin-2-yl)piperazin-1-yl)propanoic acid;

3-(4-(5-((6-(3,5-dichlorophenyl)-4-((4-fluoro-4-(((methoxycarbonyl)amino)methyl)piperidin-1-yl)methyl)pyridin-2-yl)oxy)pyrimidin-2-yl)piperazin-1-yl)propanoic acid;

2-(1-((2-(3,5-dichlorophenyl)-6-((2-(4-methylpiperazin-1-yl)pyrimidin-5-yl)oxy)pyridin-4-yl)methyl)piperidin-4-yl)ethanol;

2-((1-((2-(3,5-dichlorophenyl)-6-((2-(4-methylpiperazin-1-yl)pyrimidin-5-yl)oxy)pyridin-4-yl)methyl)piperidin-4-yl)oxy)acetic acid;

3-(4-(5-((4-((4-(2-(carbamoyloxy)ethyl)piperazin-1-yl)methyl)-6-(3,5-dichlorophenyl)pyridin-2-yl)oxy)pyrimidin-2-yl)piperazin-1-yl)propanoic acid;

3-(4-(5-((4-((4-(2-(carbamoyloxy)ethyl)piperazin-1-yl)methyl)-6-(3,5-dichlorophenyl)pyridin-2-yl)oxy)pyridin-2-yl)piperazin-1-yl)propanoic acid;

3-(3-(5-((6-(3,5-dichlorophenyl)-4-((4-(((methoxycarbonyl)amino)methyl)piperidin-1-yl)methyl)pyridin-2-yl)oxy)pyrimidin-2-yl)-3,8-diazabicyclo[3.2.1]octan-8-yl)propanoic acid;

4-(4-(5-((6-(3,5-dichlorophenyl)-4-((4-(2-hydroxyethyl)piperidin-1-yl)methyl)pyridin-2-yl)oxy)pyrimidin-2-yl)piperazin-1-yl)-2-methylbutanoic acid;

3-(4-(5-((4-((4-(cyclopropanecarboxamidomethyl)piperidin-1-yl)methyl)-6-(3,5-dichlorophenyl)pyridin-2-yl)oxy)pyridin-2-yl)piperazin-1-yl)propanoic acid;

4-(4-(5-((6-(3,5-dichlorophenyl)-4-((4-(propionamidomethyl)piperidin-1-yl)methyl)pyridin-2-yl)oxy)pyrimidin-2-yl)piperazin-1-yl)-2-methylbutanoic acid;

4-(4-(5-((6-(3,5-dichlorophenyl)-4-((4-fluoropiperidin-1-yl)methyl)pyridin-2-yl)oxy)pyrimidin-2-yl)piperazin-1-yl)butan-2-ol;

3-(4-(5-((4-((4-(acetamidomethyl)piperidin-1-yl)methyl)-6-(3-chloro-5-(difluoromethyl)phenyl)pyridin-2-yl)oxy)pyrimidin-2-yl)piperazin-1-yl)propanoic acid;

3-(4-(5-((6-(3,5-dichlorophenyl)-4-((4-(((methoxycarbonyl)amino)methyl)piperidin-1-yl)methyl)pyridin-2-yl)oxy)pyrimidin-2-yl)piperazin-1-yl)propanoic acid;

methyl ((1-((2-(3,5-dichlorophenyl)-6-((2-(4-methylpiperazin-1-yl)pyrimidin-5-yl)oxy)pyridin-4-yl)methyl)piperidin-4-yl)methyl)carbamate;
N-((1-((2-(3,5-dichlorophenyl)-6-((2-(4-methylpiperazin-1-yl)pyrimidin-5-yl)oxy)pyridin-4-yl)methyl)piperidin-4-yl)methyl)acetamide;
methyl ((1-((2-(3,5-dichlorophenyl)-6-((6-(4-methylpiperazin-1-yl)pyridin-3-yl)oxy)pyridin-4-yl)methyl)piperidin-4-yl)methyl)carbamate;
(1-((2-(3,5-dichlorophenyl)-6-((2-(4-methylpiperazin-1-yl)pyrimidin-5-yl)oxy)pyridin-4-yl)methyl)piperidin-4-yl)methyl methylcarbamate;
(1-((2-(3,5-dichlorophenyl)-6-((6-(4-methylpiperazin-1-yl)pyridin-3-yl)oxy)pyridin-4-yl)methyl)piperidin-4-yl)methyl methylcarbamate;
N-((1-((3',5'-dichloro-5-((2-(4-methylpiperazin-1-yl)pyrimidin-5-yl)oxy)-[1,1'-biphenyl]-3-yl)methyl)piperidin-4-yl)methyl)acetamide;
1-((1-((2-(3,5-dichlorophenyl)-6-((6-(4-methylpiperazin-1-yl)pyridin-3-yl)oxy)pyridin-4-yl)methyl)piperidin-4-yl)methyl)-3-methylurea;
1-((1-((2-(3,5-dichlorophenyl)-6-((2-(4-methylpiperazin-1-yl)pyrimidin-5-yl)oxy)pyridin-4-yl)methyl)piperidin-4-yl)methyl)-3-methylurea;
N-((1-((2-(3,5-dichlorophenyl)-6-((2-(8-methyl-3,8-diazabicyclo[3.2.1]octan-3-yl)pyrimidin-5-yl)oxy)pyridin-4-yl)methyl)piperidin-4-yl)methyl)acetamide;
5-((4-((4-((1H-tetrazol-5-yl)methyl)piperidin-1-yl)methyl)-6-(3,5-dichlorophenyl)pyridin-2-yl)oxy)-2-(4-methylpiperazin-1-yl)pyrimidine;
(1-((2-(3,5-dichlorophenyl)-6-((2-(piperazin-1-yl)pyrimidin-5-yl)oxy)pyridin-4-yl)methyl)piperidin-4-yl)methyl methylcarbamate;
(1-((2-(3,5-dichlorophenyl)-6-((6-(piperazin-1-yl)pyridin-3-yl)oxy)pyridin-4-yl)methyl)piperidin-4-yl)methyl methylcarbamate;
1-((1-((2-(3,5-dichlorophenyl)-6-((2-(piperazin-1-yl)pyrimidin-5-yl)oxy)pyridin-4-yl)methyl)piperidin-4-yl)methyl)-3-methylurea;
methyl ((1-((2-(3,5-dichlorophenyl)-6-((6-(piperazin-1-yl)pyridin-3-yl)oxy)pyridin-4-yl)methyl)piperidin-4-yl)methyl)carbamate;
3-(4-(5-((6-(3,5-dichlorophenyl)-4-((4-(((methylcarbamoyl)oxy)methyl)piperidin-1-yl)methyl)pyridin-2-yl)oxy)pyrimidin-2-yl)piperazin-1-yl)propanoic acid;
3-(4-(5-((4-((4-(3-amino-3-oxopropyl)piperazin-1-yl)methyl)-6-(3,5-dichlorophenyl)pyridin-2-yl)oxy)pyrimidin-2-yl)piperazin-1-yl)propanoic acid;
3-(4-(5-((4-((4-(2-amino-2-oxoethyl)piperazin-1-yl)methyl)-6-(3,5-dichlorophenyl)pyridin-2-yl)oxy)pyrimidin-2-yl)piperazin-1-yl)propanoic acid;
3-(4-(5-((6-(3,5-dichlorophenyl)-4-(((1R,7S,8r)-8-(methylsulfonamido)-4-azabicyclo[5.1.0]octan-4-yl)methyl)pyridin-2-yl)oxy)pyrimidin-2-yl)piperazin-1-yl)propanoic acid;
4-(4-(5-((6-(3,5-dichlorophenyl)-4-(((1R,7S,8r)-8-(methylsulfonamido)-4-azabicyclo[5.1.0]octan-4-yl)methyl)pyridin-2-yl)oxy)pyrimidin-2-yl)piperazin-1-yl)-2-methylbutanoic acid;
4-(4-(5-((4-(((1R,7S,8r)-8-acetamido-4-azabicyclo[5.1.0]octan-4-yl)methyl)-6-(3,5-dichlorophenyl)pyridin-2-yl)oxy)pyrimidin-2-yl)piperazin-1-yl)-2-methylbutanoic acid;
4-(4-(5-((6-(3,5-dichlorophenyl)-4-(pyrrolidin-1-ylmethyl)pyridin-2-yl)oxy)pyrimidin-2-yl)piperazin-1-yl)-2-methylbutanoic acid;
3-(4-(5-((4-((4-(cyclopropanecarboxamidomethyl)piperidin-1-yl)methyl)-6-(3,5-dichlorophenyl)pyridin-2-yl)oxy)pyrimidin-2-yl)piperazin-1-yl)propanoic acid;
3-(4-(5-((6-(3,5-dichlorophenyl)-4-((4-((dimethylphosphoryl)methyl)piperidin-1-yl)methyl)pyridin-2-yl)oxy)pyridin-2-yl)piperazin-1-yl)propanoic acid;
2-(1-((2-(3,5-dichlorophenyl)-6-((2-(piperazin-1-yl)pyrimidin-5-yl)oxy)pyridin-4-yl)methyl)piperidin-4-yl)acetamide;
2-(1-((2-(3,5-dichlorophenyl)-6-((2-(4-methylpiperazin-1-yl)pyrimidin-5-yl)oxy)pyridin-4-yl)methyl)piperidin-4-yl)ethanesulfonamide;
3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanamide;
N-((1-((2-(3,5-dichlorophenyl)-6-((6-(piperazin-1-yl)pyridin-3-yl)oxy)pyridin-4-yl)methyl)piperidin-4-yl)methyl)acetamide;
N-((1-((6-(3,5-dichlorophenyl)-2-((6-(piperazin-1-yl)pyridin-3-yl)oxy)pyridin-4-yl)methyl)piperidin-4-yl)methyl)acetamide;
N-((1-((2-(3,5-dichlorophenyl)-6-((5-fluoro-6-(piperazin-1-yl)pyridin-3-yl)oxy)pyridin-4-yl)methyl)-4-hydroxypiperidin-4-yl)methyl)acetamide;
N-((1-((2-(3,5-dichlorophenyl)-6-((2-(piperazin-1-yl)pyrimidin-5-yl)oxy)pyridin-4-yl)methyl)piperidin-4-yl)methyl)acetamide;
N-((1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)methyl)acetamide;
3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-N-methylpropanamide;
3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)butanamide;
4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)butanamide;
1-(5-((3',5'-dichloro-5-(((2-methoxyethyl)amino)methyl)-[1,1'-biphenyl]-3-yl)oxy)pyridin-2-yl)-N-methylpiperidin-4-amine;
1-(3',5'-dichloro-5-((6-(hexahydropyrrolo[3,4-c]pyrrol-2(1H)-yl)pyridin-3-yl)oxy)-[1,1'-biphenyl]-3-yl)-N-methylmethanamine;
N1-(5-((3',5'-dichloro-5-(morpholinomethyl)-[1,1'-biphenyl]-3-yl)oxy)pyridin-2-yl)ethane-1,2-diamine;
1-(5-((3',5'-dichloro-5-((methylamino)methyl)-[1,1'-biphenyl]-3-yl)oxy)pyridin-2-yl)piperidin-4-amine;
N1-(5-((3',5'-dichloro-5-((methylamino)methyl)-[1,1'-biphenyl]-3-yl)oxy)pyridin-2-yl)propane-1,3-diamine;
1-(3',5'-dichloro-5-((6-(3,3-dimethylpiperazin-1-yl)pyridin-3-yl)oxy)-[1,1'-biphenyl]-3-yl)-N-methylmethanamine;
1-(5-((6-(1,4-diazepan-1-yl)pyridin-3-yl)oxy)-3',5'-dichloro-[1,1'-biphenyl]-3-yl)-N-methylmethanamine;
1-(3',5'-dichloro-5-((6-(4-methylpiperazin-1-yl)pyridin-3-yl)oxy)-[1,1'-biphenyl]-3-yl)-N-methylmethanamine;
N-((1-((5-((6-((2-amino-2-methylpropyl)amino)pyridin-3-yl)oxy)-3',5'-dichloro-[1,1'-biphenyl]-3-yl)methyl)piperidin-4-yl)methyl)acetamide;
N-((1-((5-((6-((3S,4R)-4-amino-3-fluoropiperidin-1-yl)pyridin-3-yl)oxy)-3',5'-dichloro-[1,1'-biphenyl]-3-yl)methyl)piperidin-4-yl)methyl)acetamide;
N-((1-((3',5'-dichloro-5-((6-(3-oxohexahydroimidazo[1,5-a]pyrazin-7(1H)-yl)pyridin-3-yl)oxy)-[1,1'-biphenyl]-3-yl)methyl)piperidin-4-yl)methyl)acetamide;

1-(5-((6-(3-chloro-5-methylphenyl)-4-((methylamino) methyl)pyridin-2-yl)oxy)pyridin-2-yl)piperidin-4-amine;

N-((1-((2-(3,5-dichlorophenyl)-6-((5-(piperazin-1-yl) pyrazin-2-yl)oxy)pyridin-4-yl)methyl)piperidin-4-yl) methyl)acetamide;

N-((1-((2-(3,5-dichlorophenyl)-6-((5-(4-methylpiperazin-1-yl)pyrazin-2-yl)oxy)pyridin-4-yl)methyl)piperidin-4-yl) methyl)acetamide;

3-(4-(5-((4-((4-(acetamidomethyl)piperidin-1-yl)methyl)-6-(3,5-dichlorophenyl)pyridin-2-yl)oxy)pyrazin-2-yl)piperazin-1-yl)propanoic acid;

2-(1-((2-(3,5-dichlorophenyl)-6-((5-(piperazin-1-yl) pyrazin-2-yl)oxy)pyridin-4-yl)methyl)piperidin-4-yl)acetic acid;

N-((1-((3',5'-dichloro-5-((2-(4-(3-hydroxypropyl)piperazin-1-yl)pyrimidin-5-yl)oxy)-[1,1'-biphenyl]-3-yl)methyl)piperidin-4-yl)methyl)acetamide;

3-(1-((3',5'-dichloro-5-((2-(4-(2-hydroxyethyl)piperazin-1-yl)pyrimidin-5-yl)oxy)-[1,1'-biphenyl]-3-yl)methyl)piperidin-4-yl)propanoic acid;

3-(4-(5-((4-((4-(acetamidomethyl)piperidin-1-yl)methyl)-6-(3-chloro-5-fluorophenyl)pyridin-2-yl)oxy)pyridin-2-yl) piperazin-1-yl)propanoic acid;

3-(4-(5-((4-((4-(acetamidomethyl)piperidin-1-yl)methyl)-6-(3-bromo-5-fluorophenyl)pyridin-2-yl)oxy)pyridin-2-yl) piperazin-1-yl)propanoic acid;

2-(1-((3',5'-dichloro-5-((2-(4-methylpiperazin-1-yl)pyrimidin-5-yl)oxy)-[1,1'-biphenyl]-3-yl)methyl)piperidin-4-yl) acetic acid;

N-((1-((2-((2-(1,4-diazepan-1-yl)pyrimidin-5-yl)oxy)-6-(3,5-dichlorophenyl)pyridin-4-yl)methyl)piperidin-4-yl) methyl)acetamide;

N-((1-((2-((2-(4-aminopiperidin-1-yl)pyrimidin-5-yl)oxy)-6-(3,5-dichlorophenyl)pyridin-4-yl)methyl)piperidin-4-yl)methyl)acetamide;

2-(1-((2-(3,5-dichlorophenyl)-6-((6-(piperazin-1-yl)pyridin-3-yl)oxy)pyridin-4-yl)methyl)piperidin-4-yl)-N,N-dimethylethanamine oxide;

N-((1-((2-(3,5-dichlorophenyl)-6-((5-fluoro-6-(piperazin-1-yl)pyridin-3-yl)oxy)pyridin-4-yl)methyl)piperidin-4-yl) methyl)acetamide;

2-((1-((2-(3,5-dichlorophenyl)-6-((2-(piperazin-1-yl)pyrimidin-5-yl)oxy)pyridin-4-yl)methyl)piperidin-4-yl) oxy)acetic acid;

2-(1-((2-(3,5-dichlorophenyl)-6-((2-(6-hydroxy-1,4-diazepan-1-yl)pyrimidin-5-yl)oxy)pyridin-4-yl)methyl)piperidin-4-yl)acetic acid;

2-(1-((2-((2-(4-amino-4-(2-hydroxyethyl)piperidin-1-yl)pyrimidin-5-yl)oxy)-6-(3,5-dichlorophenyl)pyridin-4-yl) methyl)piperidin-4-yl)acetic acid;

((1-((2-(3,5-dichlorophenyl)-6-((2-(piperazin-1-yl)pyrimidin-5-yl)oxy)pyridin-4-yl)methyl)piperidin-4-yl)methyl) dimethylphosphine oxide;

2-(1-((2-(3,5-dichlorophenyl)-6-((2-(4-methyl-1,4-diazepan-1-yl)pyrimidin-5-yl)oxy)pyridin-4-yl)methyl)piperidin-4-yl)acetic acid;

3-(1-((2-(3,5-dichlorophenyl)-6-((2-(4-methylpiperazin-1-yl)pyrimidin-5-yl)oxy)pyridin-4-yl)methyl)azetidin-3-yl) butanoic acid;

2-((1-((2-(3,5-dichlorophenyl)-6-((2-(4-methylpiperazin-1-yl)pyrimidin-5-yl)oxy)pyridin-4-yl)methyl)pyrrolidin-3-yl)oxy)acetic acid;

2-(2-((2-(3,5-dichlorophenyl)-6-((2-(4-methylpiperazin-1-yl)pyrimidin-5-yl)oxy)pyridin-4-yl)methyl)octahydrocyclopenta[c]pyrrol-5-yl)acetic acid;

3-(1-((2-(3,5-dichlorophenyl)-6-((2-(4-methylpiperazin-1-yl)pyrimidin-5-yl)oxy)pyridin-4-yl)methyl)piperidin-4-yl)propanoic acid;

3-(1-((2-(3,5-dichlorophenyl)-6-((2-(4-methylpiperazin-1-yl)pyrimidin-5-yl)oxy)pyridin-4-yl)methyl)piperidin-4-yl)-2-methylpropanoic acid;

2-(1-((2-((2-(1,4-diazepan-1-yl)pyrimidin-5-yl)oxy)-6-(3,5-dichlorophenyl)pyridin-4-yl)methyl)piperidin-4-yl)acetic acid;

2-(1-((2-(3,5-dichlorophenyl)-6-((2-(5-methylhexahydropyrrolo[3,4-c]pyrrol-2(1H)-yl)pyrimidin-5-yl)oxy)pyridin-4-yl)methyl)piperidin-4-yl)acetic acid;

(S)-3-(1-((2-(3,5-dichlorophenyl)-6-((2-(4-methylpiperazin-1-yl)pyrimidin-5-yl)oxy)pyridin-4-yl)methyl)piperidin-4-yl)-2-methylpropanoic acid;

1-(7-((2-(3,5-dichlorophenyl)-6-((2-(4-methylpiperazin-1-yl)pyrimidin-5-yl)oxy)pyridin-4-yl)methyl)-2,7-diazaspiro[3.5]nonan-2-yl)-2-hydroxyethanone;

(1R,7S,8r)-4-((2-(3,5-dichlorophenyl)-6-((6-(4-methylpiperazin-1-yl)pyridin-3-yl)oxy)pyridin-4-yl)methyl)-4-azabicyclo[5.1.0]octane-8-carboxylic acid;

(R)-3-(1-((2-(3,5-dichlorophenyl)-6-((2-(4-methylpiperazin-1-yl)pyrimidin-5-yl)oxy)pyridin-4-yl)methyl)piperidin-4-yl)-2-methylpropanoic acid;

1-(1-((2-(3,5-dichlorophenyl)-6-((2-(4-methylpiperazin-1-yl)pyrimidin-5-yl)oxy)pyridin-4-yl)methyl)piperidin-4-yl)propan-2-ol;

3-(1-((2-(3,5-dichlorophenyl)-6-((2-(4-methylpiperazin-1-yl)pyrimidin-5-yl)oxy)pyridin-4-yl)methyl)piperidin-4-yl)-2-hydroxypropanoic acid;

2-((1-((2-(3,5-dichlorophenyl)-6-((2-(4-methyl-1,4-diazepan-1-yl)pyrimidin-5-yl)oxy)pyridin-4-yl)methyl)piperidin-4-yl)oxy)acetic acid;

9-((2-(3,5-dichlorophenyl)-6-((6-(4-methylpiperazin-1-yl) pyridin-3-yl)oxy)pyridin-4-yl)methyl)-2-oxa-4,9-diazaspiro[5.5]undecan-3-one;

2-(1-((2-(3,5-dichlorophenyl)-6-((2-(4-methylpiperazin-1-yl)pyrimidin-5-yl)oxy)pyridin-4-yl)methyl)piperidin-4-yl)acetamide;

1-((1-((2-(3,5-dichlorophenyl)-6-((2-(4-methylpiperazin-1-yl)pyrimidin-5-yl)oxy)pyridin-4-yl)methyl)piperidin-4-yl)oxy)cyclopropanecarboxylic acid;

2-(1-((2-(3,5-dichlorophenyl)-6-((2-(6-methoxy-4-methyl-1,4-diazepan-1-yl)pyrimidin-5-yl)oxy)pyridin-4-yl) methyl)piperidin-4-yl)acetic acid;

N-((1-((2-(3,5-dichlorophenyl)-6-((6-(6-fluoro-4-methyl-1,4-diazepan-1-yl)pyridin-3-yl)oxy)pyridin-4-yl)methyl) piperidin-4-yl)methyl)acetamide;

2-(1-((2-(3,5-dichlorophenyl)-6-((2-(6-hydroxy-4,6-dimethyl-1,4-diazepan-1-yl)pyrimidin-5-yl)oxy)pyridin-4-yl) methyl)piperidin-4-yl)acetic acid;

2-(1-((2-(3,5-dichlorophenyl)-6-((2-(6-fluoro-4-methyl-1,4-diazepan-1-yl)pyrimidin-5-yl)oxy)pyridin-4-yl)methyl) piperidin-4-yl)acetic acid;

2-(1-((2-(3,5-dichlorophenyl)-6-((4-methyl-2-(4-methylpiperazin-1-yl)pyrimidin-5-yl)oxy)pyridin-4-yl)methyl)piperidin-4-yl)acetic acid;

2-(1-((2-(3,5-dichlorophenyl)-6-((2-methyl-6-(4-methylpiperazin-1-yl)pyridin-3-yl)oxy)pyridin-4-yl)methyl)piperidin-4-yl)acetic acid;

2-(1-((2-(3,5-dichlorophenyl)-6-(4-(4-methylpiperazin-1-yl)phenoxy)pyridin-4-yl)methyl)piperidin-4-yl)acetic acid;

2-(1-((2-(3,5-dichlorophenyl)-6-((5-fluoro-6-(4-methylpiperazin-1-yl)pyridin-3-yl)oxy)pyridin-4-yl)methyl)piperidin-4-yl)acetic acid;

2-(1-((2-(3,5-dichlorophenyl)-6-((2-(3-(methylamino)pyrrolidin-1-yl)pyrimidin-5-yl)oxy)pyridin-4-yl)methyl)piperidin-4-yl)acetic acid;

(S)-2-(4-((2-(3,5-dichlorophenyl)-6-((2-(4-methylpiperazin-1-yl)pyrimidin-5-yl)oxy)pyridin-4-yl)methyl)-1,4-oxazepan-7-yl)ethanol;

N-((1R,5S,6r)-3-((2-(3,5-dichlorophenyl)-6-((2-(4-methyl-1,4-diazepan-1-yl)pyrimidin-5-yl)oxy)pyridin-4-yl)methyl)-3-azabicyclo[3.1.0]hexan-6-yl)acetamide;

1-(1-((2-(3,5-dichlorophenyl)-6-((2-(4-methylpiperazin-1-yl)pyrimidin-5-yl)oxy)pyridin-4-yl)methyl)piperidin-4-yl)propan-2-one;

2-(1-((2-(3,5-dichlorophenyl)-6-((6-(4-methyl-1,4-diazepan-1-yl)pyridin-3-yl)oxy)pyridin-4-yl)methyl)piperidin-4-yl)acetic acid;

N-((1-((2-(3,5-dichlorophenyl)-6-((6-(4-methylpiperazin-1-yl)pyridazin-3-yl)oxy)pyridin-4-yl)methyl)piperidin-4-yl)methyl)acetamide;

2-(1-((2-((2-(4-aminopiperidin-1-yl)pyrimidin-5-yl)oxy)-6-(3,5-dichlorophenyl)pyridin-4-yl)methyl)piperidin-4-yl)acetic acid;

(S)-2-(1-((2-(3,5-dichlorophenyl)-6-((2-(3-methylpiperazin-1-yl)pyrimidin-5-yl)oxy)pyridin-4-yl)methyl)piperidin-4-yl)acetic acid;

2-(1-((2-(3,5-dichlorophenyl)-6-((2-(3,3-dimethylpiperazin-1-yl)pyrimidin-5-yl)oxy)pyridin-4-yl)methyl)piperidin-4-yl)acetic acid;

2-(1-((2-(3,5-dichlorophenyl)-6-((2-(hexahydropyrrolo[3,4-c]pyrrol-2(1H)-yl)pyrimidin-5-yl)oxy)pyridin-4-yl)methyl)piperidin-4-yl)acetic acid;

2-(1-((2-((2-(3,6-diazabicyclo[3.1.1]heptan-3-yl)pyrimidin-5-yl)oxy)-6-(3,5-dichlorophenyl)pyridin-4-yl)methyl)piperidin-4-yl)acetic acid;

2-(1-((2-((2-(3,8-diazabicyclo[3.2.1]octan-3-yl)pyrimidin-5-yl)oxy)-6-(3,5-dichlorophenyl)pyridin-4-yl)methyl)piperidin-4-yl)acetic acid;

2-(1-((2-((2-(4,7-diazaspiro[2.5]octan-7-yl)pyrimidin-5-yl)oxy)-6-(3,5-dichlorophenyl)pyridin-4-yl)methyl)piperidin-4-yl)acetic acid;

2-(1-((2-((2-(4-amino-4-(hydroxymethyl)piperidin-1-yl)pyrimidin-5-yl)oxy)-6-(3,5-dichlorophenyl)pyridin-4-yl)methyl)piperidin-4-yl)acetic acid;

2-(1-((2-((6-(1,4-diazepan-1-yl)pyridin-3-yl)oxy)-6-(3,5-dichlorophenyl)pyridin-4-yl)methyl)piperidin-4-yl)acetic acid;

N-((1-((3',5'-dichloro-5-((2-(4-(2-(methylsulfonyl)ethyl)piperazin-1-yl)pyrimidin-5-yl)oxy)-[1,1'-biphenyl]-3-yl)methyl)piperidin-4-yl)methyl) acetamide;

3-(4-(5-((5-((4-(acetamidomethyl)piperidin-1-yl)methyl)-3',5'-dichloro-[1,1'-biphenyl]-3-yl)oxy)pyrimidin-2-yl)piperazin-1-yl)propanoic acid;

3-(4-(6-((4-((4-(acetamidomethyl)piperidin-1-yl)methyl)-6-(3,5-dichlorophenyl)pyridin-2-yl)oxy)pyridazin-3-yl)piperazin-1-yl)propanoic acid;

3-(4-(5-((5-((4-(acetamidomethyl)piperidin-1-yl)methyl)-3',5'-dichloro-[1,1'-biphenyl]-3-yl)oxy)pyrimidin-2-yl)piperazin-1-yl)propanamide;

1-((1-((2-(3,5-dichlorophenyl)-6-((2-(4-(3-hydroxypropyl)piperazin-1-yl)pyrimidin-5-yl)oxy)pyridin-4-yl)methyl)piperidin-4-yl)methyl)-3-methylurea;

methyl (3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoyl)carbamate;

1-(2-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)ethyl)cyclopropanecarboxylic acid;

4-(4-(5-((4-((4-(acetamidomethyl)piperidin-1-yl)methyl)-6-(3,5-dichlorophenyl)pyridin-2-yl)oxy)pyridin-2-yl)piperazin-1-yl)-2-methylbutanoic acid;

methyl (3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoyl)carbamate;

methyl (3-(4-(5-((4-((4-(acetamidomethyl)piperidin-1-yl)methyl)-6-(3,5-dichlorophenyl)pyridin-2-yl)oxy)pyridin-2-yl)piperazin-1-yl)propanoyl)carbamate;

2-(1-((2-(3,5-dichlorophenyl)-6-((2-(4-(2,3-dihydroxypropyl)piperazin-1-yl)pyrimidin-5-yl)oxy)pyridin-4-yl)methyl)piperidin-4-yl)acetic acid;

4-(5-((4-((4-(acetamidomethyl)piperidin-1-yl)methyl)-6-(3,5-dichlorophenyl)pyridin-2-yl)oxy)pyridin-2-yl)-1-methylpiperazine 1-oxide;

4-(5-((4-((4-(acetamidomethyl)piperidin-1-yl)methyl)-6-(3,5-dichlorophenyl)pyridin-2-yl)oxy)pyridin-2-yl)-1,1-bis(2-hydroxyethyl)piperazin-1-ium;

N-((1-((2-(3,5-dichlorophenyl)-6-((6-(4-(2-hydroxyethyl)piperazin-1-yl)pyridin-3-yl)oxy)pyridin-4-yl)methyl)piperidin-4-yl)methyl)acetamide;

4-(5-((4-((4-(acetamidomethyl)piperidin-1-yl)methyl)-6-(3,5-dichlorophenyl)pyridin-2-yl)oxy)pyridin-2-yl)-1,1-dimethylpiperazin-1-ium;

N-((1-((2-(((6-(4-amino-3-fluoropiperidin-1-yl)pyridin-3-yl)oxy)-6-(3,5-dichlorophenyl)pyridin-4-yl)methyl)piperidin-4-yl)methyl)acetamide;

N-((1-((2-(3,5-dichlorophenyl)-6-((6-((1S,4S)-5-(2-(methylsulfonyl)ethyl)-2,5-diazabicyclo[2.2.1]heptan-2-yl)pyridin-3-yl)oxy)pyridin-4-yl)methyl)piperidin-4-yl)methyl) acetamide;

N-((1-((2-((6-((3S,4R)-3-(aminomethyl)-4-hydroxypyrrolidin-1-yl)pyridin-3-yl)oxy)-6-(3,5-dichlorophenyl)pyridin-4-yl)methyl)piperidin-4-yl)methyl) acetamide;

3-((1R,5S)-3-(5-((4-((4-(acetamidomethyl)piperidin-1-yl)methyl)-6-(3,5-dichlorophenyl)pyridin-2-yl)oxy)pyridin-2-yl)-3,8-diazabicyclo[3.2.1]octan-8-yl)propanoic acid;

(S)-3-(4-(5-((4-((4-(acetamidomethyl)piperidin-1-yl)methyl)-6-(3,5-dichlorophenyl)pyridin-2-yl)oxy)pyridin-2-yl)-2-methylpiperazin-1-yl)propanoic acid;

2-(1-((2-((6-((1S,4S)-2,5-diazabicyclo[2.2.1]heptan-2-yl)pyridin-3-yl)oxy)-6-(3,5-dichlorophenyl)pyridin-4-yl)methyl)piperidin-4-yl)acetic acid;

4-(4-(5-((4-((4-(acetamidomethyl)piperidin-1-yl)methyl)-6-(3,5-dichlorophenyl)pyridin-2-yl)oxy)pyridin-2-yl)piperazin-1-yl)-2-ethylbutanoic acid;

3-(4-(5-((4-((4-(acetamidomethyl)piperidin-1-yl)methyl)-6-(3,5-dichlorophenyl)pyridin-2-yl)oxy)pyridin-2-yl)piperazin-1-yl)-2,2-dimethylpropanoic acid;

3-(4-(5-((4-((4-(acetamidomethyl)piperidin-1-yl)methyl)-6-(3,5-dichlorophenyl)pyridin-2-yl)oxy)pyridin-2-yl)-1,4-diazepan-1-yl)propanoic acid;

3-(4-(5-((4-((4-(acetamidomethyl)piperidin-1-yl)methyl)-6-(3,5-dichlorophenyl)pyridin-2-yl)oxy)pyridin-2-yl)-2,2-dimethylpiperazin-1-yl)propanoic acid;

N-((1-((2-((6-(1,4-diazepan-1-yl)pyridin-3-yl)oxy)-6-(3,5-dichlorophenyl)pyridin-4-yl)methyl)piperidin-4-yl)methyl)acetamide;

N-((1-((2-(3,5-dichlorophenyl)-6-((6-(4-(methylamino)piperidin-1-yl)pyridin-3-yl)oxy)pyridin-4-yl)methyl)piperidin-4-yl)methyl)acetamide;

N-((1-((2-(3,5-dichlorophenyl)-6-((6-(hexahydropyrrolo[3,4-c]pyrrol-2(1H)-yl)pyridin-3-yl)oxy)pyridin-4-yl)methyl)piperidin-4-yl)methyl)acetamide;

N-((1-((2-(3,5-dichlorophenyl)-6-((6-(3-(hydroxymethyl)piperazin-1-yl)pyridin-3-yl)oxy)pyridin-4-yl)methyl)piperidin-4-yl)methyl)acetamide;

N-((1-((2-((6-(4-aminopiperidin-1-yl)pyridin-3-yl)oxy)-6-(3,5-dichlorophenyl)pyridin-4-yl)methyl)piperidin-4-yl)methyl)acetamide;

N-((1-((2-(3,5-dichlorophenyl)-6-((6-(3,3-dimethylpiperazin-1-yl)pyridin-3-yl)oxy)pyridin-4-yl)methyl)piperidin-4-yl)methyl)acetamide;

N-((1-((2-((6-(4-amino-3,3-dimethylpiperidin-1-yl)pyridin-3-yl)oxy)-6-(3,5-dichlorophenyl)pyridin-4-yl)methyl)piperidin-4-yl)methyl)acetamide;

N-((1-((2-((6-(2,7-diazaspiro[4.4]nonan-2-yl)pyridin-3-yl)oxy)-6-(3,5-dichlorophenyl)pyridin-4-yl)methyl)piperidin-4-yl)methyl)acetamide;

N-((1-((2-(3,5-dichlorophenyl)-6-((6-(4-methylpiperazin-1-yl)pyridin-3-yl)oxy)pyridin-4-yl)methyl)piperidin-4-yl)methyl)acetamide;

1-(3',5'-dichloro-5-((6-(hexahydropyrrolo[3,4-c]pyrrol-2(1H)-yl)pyridin-3-yl)oxy)-[1,1'-biphenyl]-3-yl)-N-methylmethanamine;

1-(5-((6-((1S,4S)-2,5-diazabicyclo[2.2.1]heptan-2-yl)pyridin-3-yl)oxy)-3',5'-dichloro-[1,1'-biphenyl]-3-yl)-N-methylmethanamine;

2-(1-((2-(3,5-dichlorophenyl)-6-((6-((1S,4S)-5-methyl-2,5-diazabicyclo[2.2.1]heptan-2-yl)pyridin-3-yl)oxy)pyridin-4-yl)methyl)piperidin-4-yl)acetic acid;

2-(1-((2-(3,5-dichlorophenyl)-6-((2-(4-(3-(methylsulfinyl)butyl)piperazin-1-yl)pyrimidin-5-yl)oxy)pyridin-4-yl)methyl)piperidin-4-yl)acetic acid;

2-(1-((2-(3,5-dichlorophenyl)-6-((2-(4-(3-(methylsulfonyl)butyl)piperazin-1-yl)pyrimidin-5-yl)oxy)pyridin-4-yl)methyl)piperidin-4-yl)acetic acid;

2-(1-((2-(3,5-dichlorophenyl)-6-((2-(piperazin-1-yl)pyrimidin-5-yl)oxy)pyridin-4-yl)methyl)piperidin-4-yl)acetic acid;

2-(1-((2-(3,5-dichlorophenyl)-6-((2-(4-methylpiperazin-1-yl)pyrimidin-5-yl)oxy)pyridin-4-yl)methyl)piperidin-4-yl)acetic acid;

4-(4-(5-((6-(3,5-dichlorophenyl)-4-((4-(((methylcarbamoyl)oxy)methyl)piperidin-1-yl)methyl)pyridin-2-yl)oxy)pyrimidin-2-yl)piperazin-1-yl)pentanoic acid;

(1-((2-(3,5-dichlorophenyl)-6-((2-(4-(4-hydroxybutan-2-yl)piperazin-1-yl)pyrimidin-5-yl)oxy)pyridin-4-yl)methyl)piperidin-4-yl)methyl methylcarbamate;

(1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)methyl methylcarbamate;

3-(4-(5-((6-(3,5-dichlorophenyl)-4-((4-(((methylcarbamoyl)oxy)methyl)piperidin-1-yl)methyl)pyridin-2-yl)oxy)pyrimidin-2-yl)piperazin-1-yl)cyclobutanecarboxylic acid;

2-(1-((2-(3,5-dichlorophenyl)-6-((6-(4-methylpiperazin-1-yl)pyridin-3-yl)oxy)pyridin-4-yl)methyl)piperidin-4-yl)acetic acid;

3-(1-((2-(3,5-dichlorophenyl)-6-((6-(4-methylpiperazin-1-yl)pyridin-3-yl)oxy)pyridin-4-yl)methyl)piperidin-4-yl)-2-methylpropanoic acid;

N-((1-((2-(3,5-dichlorophenyl)-6-((2-(4-(3-(methylsulfonyl)butyl)piperazin-1-yl)pyrimidin-5-yl)oxy)pyridin-4-yl)methyl)piperidin-4-yl)methyl)acetamide;

4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)pentanoic acid;

3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)cyclobutanecarboxylic acid;

methyl ((1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)methyl)carbamate;

N-((1-((2-(3,5-dichlorophenyl)-6-((6-(4-(3-(methylsulfonyl)butyl)piperazin-1-yl)pyridin-3-yl)oxy)pyridin-4-yl)methyl)piperidin-4-yl)methyl)acetamide;

1-((1-((2-(3,5-dichlorophenyl)-6-((6-(4-(3-(methylsulfonyl)butyl)piperazin-1-yl)pyridin-3-yl)oxy)pyridin-4-yl)methyl)piperidin-4-yl)methyl)-3-methylurea;

1-((1-((2-(3,5-dichlorophenyl)-6-((2-(4-(3-(methyl sulfonyl)butyl)piperazin-1-yl)pyrimidin-5-yl)oxy)pyridin-4-yl)methyl)piperidin-4-yl)methyl)-3-methylurea;

3-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)cyclobutanecarboxylic acid;

4-(4-(5-((6-(3,5-dichlorophenyl)-4-((4-(((methoxycarbonyl)amino)methyl)piperidin-1-yl)methyl)pyridin-2-yl)oxy)pyrimidin-2-yl)piperazin-1-yl)pentanoic acid;

methyl ((1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)methyl)carbamate;

2-((1R,7S,8r)-4-((2-(3,5-dichlorophenyl)-6-((2-(4-methylpiperazin-1-yl)pyrimidin-5-yl)oxy)pyridin-4-yl)methyl)-4-azabicyclo[5.1.0]octan-8-yl)acetic acid;

2-((1-((2-(3,5-dichlorophenyl)-6-((2-(4-methylpiperazin-1-yl)pyrimidin-5-yl)oxy)pyridin-4-yl)methyl)piperidin-4-yl)oxy)-2-methylpropanoic acid;

2-(1-((2-(3,5-dichlorophenyl)-6-((2-(6-hydroxy-4-methyl-1,4-diazepan-1-yl)pyrimidin-5-yl)oxy)pyridin-4-yl)methyl)piperidin-4-yl)acetic acid;

2-(1-((2-(3,5-dichlorophenyl)-6-((2-(4-(dimethylamino)piperidin-1-yl)pyrimidin-5-yl)oxy)pyridin-4-yl)methyl)piperidin-4-yl)acetic acid;

2-(1-((2-(3,5-dichlorophenyl)-6-((2-(6-methyl-3,6-diazabicyclo[3.1.1]heptan-3-yl)pyrimidin-5-yl)oxy)pyridin-4-yl)methyl)piperidin-4-yl)acetic acid;

2-(1-((2-(3,5-dichlorophenyl)-6-((2-(4-((1-hydroxycyclopropyl)methyl)piperazin-1-yl)pyrimidin-5-yl)oxy)pyridin-4-yl)methyl)piperidin-4-yl)acetic acid;

2-(1-((2-(3,5-dichlorophenyl)-6-((2-(4-ethyl-1,4-diazepan-1-yl)pyrimidin-5-yl)oxy)pyridin-4-yl)methyl)piperidin-4-yl)acetic acid;

2-(1-((2-(3,5-dichlorophenyl)-6-((2-((1S,4S)-5-methyl-2,5-diazabicyclo[2.2.1]heptan-2-yl)pyrimidin-5-yl)oxy)pyridin-4-yl)methyl)piperidin-4-yl)acetic acid;

2-(1-((2-(3,5-dichlorophenyl)-6-((2-((1S,4S)-5-ethyl-2,5-diazabicyclo[2.2.1]heptan-2-yl)pyrimidin-5-yl)oxy)pyridin-4-yl)methyl)piperidin-4-yl)acetic acid;

2-(1-((2-((2-(4-cyclopropylpiperazin-1-yl)pyrimidin-5-yl)oxy)-6-(3,5-dichlorophenyl)pyridin-4-yl)methyl)piperidin-4-yl)acetic acid;

2-(1-((2-(3,5-dichlorophenyl)-6-((2-(4-ethylpiperazin-1-yl)pyrimidin-5-yl)oxy)pyridin-4-yl)methyl)piperidin-4-yl)acetic acid;

2-(1-((2-(3,5-dichlorophenyl)-6-((2-(4-isopropylpiperazin-1-yl)pyrimidin-5-yl)oxy)pyridin-4-yl)methyl)piperidin-4-yl)acetic acid;

2-(1-((2-(3,5-dichlorophenyl)-6-((2-(4-(2-fluoroethyl)piperazin-1-yl)pyrimidin-5-yl)oxy)pyridin-4-yl)methyl)piperidin-4-yl)acetic acid;

2-(1-((2-(3,5-dichlorophenyl)-6-((2-(4-(3-hydroxybutyl)piperazin-1-yl)pyrimidin-5-yl)oxy)pyridin-4-yl)methyl)piperidin-4-yl)acetic acid;

2-(1-((2-(3,5-dichlorophenyl)-6-((2-(4-(4-hydroxybutan-2-yl)piperazin-1-yl)pyrimidin-5-yl)oxy)pyridin-4-yl)methyl)piperidin-4-yl)acetic acid;

2-(1-((2-(3,5-dichlorophenyl)-6-((2-(4-(4-(methylamino)butan-2-yl)piperazin-1-yl)pyrimidin-5-yl)oxy)pyridin-4-yl)methyl)piperidin-4-yl)acetic acid;

2-(1-((2-(3,5-dichlorophenyl)-6-((2-(4-(4-(dimethylamino)butan-2-yl)piperazin-1-yl)pyrimidin-5-yl)oxy)pyridin-4-yl)methyl)piperidin-4-yl)acetic acid;
2-(1-((2-(3,5-dichlorophenyl)-6-((2-(4-(2-((methylcarbamoyl)oxy)ethyl)piperazin-1-yl)pyrimidin-5-yl)oxy)pyridin-4-yl)methyl)piperidin-4-yl)acetic acid;
2-(1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)acetic acid;
2-(1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)acetic acid;
2-(1-((2-(3,5-dichlorophenyl)-6-((6-(4-(2-methoxyethyl)piperazin-1-yl)pyridin-3-yl)oxy)pyridin-4-yl)methyl)piperidin-4-yl)acetic acid;
N-((1-((2-(3,5-dichlorophenyl)-6-((2-(4-(2-methoxyethyl)piperazin-1-yl)pyrimidin-5-yl)oxy)pyridin-4-yl)methyl)piperidin-4-yl)methyl)acetamide;
2-(1-((2-(3,5-dichlorophenyl)-6-((2-(4-(3-sulfamoylpropyl)piperazin-1-yl)pyrimidin-5-yl)oxy)pyridin-4-yl)methyl)piperidin-4-yl)acetic acid;
2-(1-((2-(3,5-dichlorophenyl)-6-((2-(4-(2-methoxyethyl)piperazin-1-yl)pyrimidin-5-yl)oxy)pyridin-4-yl)methyl)piperidin-4-yl)acetic acid;
3-(4-(5-((6-(3,5-dichlorophenyl)-4-((4-(((methylcarbamoyl)oxy)methyl)piperidin-1-yl)methyl)pyridin-2-yl)oxy)pyrimidin-2-yl)piperazin-1-yl)propanoic acid;
4-(4-(5-((4-((4-(acetamidomethyl)piperidin-1-yl)methyl)-6-(3,5-dichlorophenyl)pyridin-2-yl)oxy)pyridin-2-yl)piperazin-1-yl)butanoic acid;
N-((1-((2-(3,5-dichlorophenyl)-6-((6-(4-(2-methoxyethyl)piperazin-1-yl)pyridin-3-yl)oxy)pyridin-4-yl)methyl)piperidin-4-yl)methyl)acetamide;
N-((1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)methyl)acetamide;
2-(1-((2-(3,5-dichlorophenyl)-6-((6-(4-(3-sulfamoylpropyl)piperazin-1-yl)pyridin-3-yl)oxy)pyridin-4-yl)methyl)piperidin-4-yl)acetic acid;
N-((1-((2-(3,5-dichlorophenyl)-6-((2-(4-(3-sulfamoylpropyl)piperazin-1-yl)pyrimidin-5-yl)oxy)pyridin-4-yl)methyl)piperidin-4-yl)methyl)acetamide;
1-((1-((2-(3,5-dichlorophenyl)-6-((6-(4-(2-methoxyethyl)piperazin-1-yl)pyridin-3-yl)oxy)pyridin-4-yl)methyl)piperidin-4-yl)methyl)-3-methylurea;
1-((1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)methyl)-3-methylurea;
3-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)propanoic acid;
1-((1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)methyl)-3-methylurea;
3-(4-(5-((5-((4-(acetamidomethyl)piperidin-1-yl)methyl)-3',5'-dichloro-[1,1'-biphenyl]-3-yl)oxy)pyridin-2-yl)piperazin-1-yl)propanoic acid;
N-((1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)methyl)acetamide;
3-(4-(5-((6-(3,5-dichlorophenyl)-4-((4-((3-methylureido)methyl)piperidin-1-yl)methyl)pyridin-2-yl)oxy)pyridin-2-yl)piperazin-1-yl)propane-1-sulfonamide;
3-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)propanamide;
1-((1-((2-(3,5-dichlorophenyl)-6-((2-(4-(2-methoxyethyl)piperazin-1-yl)pyrimidin-5-yl)oxy)pyridin-4-yl)methyl)piperidin-4-yl)methyl)-3-methylurea;
3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoic acid;
2-(1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)acetamide;
3-(4-(5-((6-(3,5-dichlorophenyl)-4-((4-hydroxy-4-((3-methylureido)methyl)piperidin-1-yl)methyl)pyridin-2-yl)oxy)pyrimidin-2-yl)piperazin-1-yl)propanamide;
3-(4-(5-((4-((4-(acetamidomethyl)piperidin-1-yl)methyl)-6-(3,5-dichlorophenyl)pyridin-2-yl)oxy)-3-fluoropyridin-2-yl)piperazin-1-yl)propanoic acid;
3-(4-(5-((6-(3,5-dichlorophenyl)-4-((4-(((ethoxycarbonyl)amino)methyl)piperidin-1-yl)methyl)pyridin-2-yl)oxy)pyrimidin-2-yl)piperazin-1-yl)propanoic acid;
3-(4-(5-((6-(3,5-dichlorophenyl)-4-((4-(2-(ethylamino)-2-oxoethyl)piperidin-1-yl)methyl)pyridin-2-yl)oxy)pyrimidin-2-yl)piperazin-1-yl)propanoic acid;
3-(1-((2-(3,5-dichlorophenyl)-6-((2-(piperazin-1-yl)pyrimidin-5-yl)oxy)pyridin-4-yl)methyl)piperidin-4-yl)-2-methylpropanoic acid;
3-(4-(5-((6-(3,5-dichlorophenyl)-4-((4-((3-methylureido)methyl)piperidin-1-yl)methyl)pyridin-2-yl)oxy)-3-fluoropyridin-2-yl)piperazin-1-yl)propanoic acid;
3-(1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)propanoic acid;
3-(1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)propanoic acid;
3-(4-(5-((4-((4-(acetamidomethyl)piperidin-1-yl)methyl)-6-(3-chloro-4,5-difluorophenyl)pyridin-2-yl)oxy)pyrimidin-2-yl)piperazin-1-yl)propanamide;
1-((1-((2-(3-chloro-5-fluorophenyl)-6-((2-(4-(3-(methylsulfonyl)propyl)piperazin-1-yl)pyrimidin-5-yl)oxy)pyridin-4-yl)methyl)piperidin-4-yl)methyl)-3-methylurea;
methyl ((1-((2-(3-chloro-5-fluorophenyl)-6-((2-(piperazin-1-yl)pyrimidin-5-yl)oxy)pyridin-4-yl)methyl)piperidin-4-yl)methyl)carbamate;
3-(4-(5-((6-(3,5-dichlorophenyl)-4-((4-(2-(methylsulfonyl)ethyl)piperidin-1-yl)methyl)pyridin-2-yl)oxy)pyridin-2-yl)piperazin-1-yl)propanoic acid;
3-(4-(5-((6-(3,5-dichlorophenyl)-4-((4-(2-sulfamoylethyl)piperidin-1-yl)methyl)pyridin-2-yl)oxy)pyridin-2-yl)piperazin-1-yl)propanoic acid;
2-(1-((2-(3,5-dichlorophenyl)-6-((2-(4-(2-(1-hydroxycyclopropyl)ethyl)piperazin-1-yl)pyrimidin-5-yl)oxy)pyridin-4-yl)methyl)piperidin-4-yl)acetic acid;
2-(1-((2-(3,5-dichlorophenyl)-6-((2-(4-(3-hydroxy-3-methylbutyl)piperazin-1-yl)pyrimidin-5-yl)oxy)pyridin-4-yl)methyl)piperidin-4-yl)acetic acid;
2-(1-((2-(3,5-dichlorophenyl)-6-((2-(4-(3-hydroxy-2,2-dimethylpropyl)piperazin-1-yl)pyrimidin-5-yl)oxy)pyridin-4-yl)methyl)piperidin-4-yl)acetic acid;
3-(4-(5-((4-((4-(acetamidomethyl)piperidin-1-yl)methyl)-6-(3,5-dichlorophenyl)pyridin-2-yl)oxy)pyridin-2-yl)piperazin-1-yl)butanoic acid;
3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)butanoic acid;
3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-methylpropanoic acid;

3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-methylpropanamide;

N-((1-((2-(3,5-dichlorophenyl)-6-((2-(4-(2-(methylsulfonyl)ethyl)piperazin-1-yl)pyrimidin-5-yl)oxy)pyridin-4-yl)methyl)piperidin-4-yl)methyl)acetamide;

N-((1-((2-(3,5-dichlorophenyl)-6-((2-(4-(2-sulfamoylethyl)piperazin-1-yl)pyrimidin-5-yl)oxy)pyridin-4-yl)methyl)piperidin-4-yl)methyl)acetamide;

2-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)ethanesulfonic acid;

2-((4-(5-((4-((4-(acetamidomethyl)piperidin-1-yl)methyl)-6-(3,5-dichlorophenyl)pyridin-2-yl)oxy)pyrimidin-2-yl)piperazin-1-yl)methyl)butanoic acid;

N-((1-((2-(3,5-dichlorophenyl)-6-((6-(4-(2-sulfamoylethyl)piperazin-1-yl)pyridin-3-yl)oxy)pyridin-4-yl)methyl)piperidin-4-yl)methyl)acetamide;

1-((1-((2-(3,5-dichlorophenyl)-6-((6-(4-(2-(methylsulfonyl)ethyl)piperazin-1-yl)pyridin-3-yl)oxy)pyridin-4-yl)methyl)piperidin-4-yl)methyl)-3-methylurea;

3-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)-2-methylpropanamide;

3-(4-(5-((3',5'-dichloro-5-((4-((3-methylureido)methyl)piperidin-1-yl)methyl)-[1,1'-biphenyl]-3-yl)oxy)pyrimidin-2-yl)piperazin-1-yl)-2-methylpropanoic acid;

N-((1-((3',5'-dichloro-5-((6-(4-(2-(methylsulfonyl)ethyl)piperazin-1-yl)pyridin-3-yl)oxy)-[1,1'-biphenyl]-3-yl)methyl)piperidin-4-yl)methyl) acetamide;

(S)-3-(4-(5-((6-(3,5-dichlorophenyl)-4-((4-(((methoxycarbonyl)amino)methyl)piperidin-1-yl)methyl)pyridin-2-yl)oxy)pyrimidin-2-yl)-2-methylpiperazin-1-yl)propanoic acid;

1-((1-((2-(3,5-dichlorophenyl)-6-((2-(4-(3-hydroxybutyl)piperazin-1-yl)pyrimidin-5-yl)oxy)pyridin-4-yl)methyl)piperidin-4-yl)methyl)-3-methylurea;

3-(3-(5-((4-((4-(acetamidomethyl)piperidin-1-yl)methyl)-6-(3,5-dichlorophenyl)pyridin-2-yl)oxy)pyrimidin-2-yl)-3,8-diazabicyclo[3.2.1]octan-8-yl)propanoic acid;

methyl 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoate;

(R)-2-(1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)acetic acid;

(R)-2-(1-((2-(3,5-dichlorophenyl)-6-((6-(4-(2-hydroxypropyl)piperazin-1-yl)pyridin-3-yl)oxy)pyridin-4-yl)methyl)piperidin-4-yl)acetic acid;

2-(1-((2-(3,5-dichlorophenyl)-6-((6-(4-(2-hydroxyethyl)piperazin-1-yl)pyridin-3-yl)oxy)pyridin-4-yl)methyl)piperidin-4-yl)acetic acid;

3-(1-((2-(3,5-dichlorophenyl)-6-((2-(4-((R)-2-hydroxypropyl)piperazin-1-yl)pyrimidin-5-yl)oxy)pyridin-4-yl)methyl)piperidin-4-yl)-2-methylpropanoic acid;

(R)—N-((1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)methyl)acetamide;

N-((1-((2-(3,5-dichlorophenyl)-6-((2-(4-(2-hydroxy-2-methylpropyl)piperazin-1-yl)pyrimidin-5-yl)oxy)pyridin-4-yl)methyl)piperidin-4-yl)methyl)acetamide;

N-((1-((2-(3,5-dichlorophenyl)-6-((2-(4-(3-fluoro-2-hydroxypropyl)piperazin-1-yl)pyrimidin-5-yl)oxy)pyridin-4-yl)methyl)piperidin-4-yl)methyl)acetamide;

(R)-1-((2-(3,5-dichlorophenyl)-6-((6-(4-(2-hydroxypropyl)piperazin-1-yl)pyridin-3-yl)oxy)pyridin-4-yl)methyl)piperidin-4-yl)methyl methylcarbamate;

2-(1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)acetic acid;

(1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)methyl methylcarbamate;

(R)-(1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)methyl methylcarbamate;

(R)-1-((1-((2-(3,5-dichlorophenyl)-6-((6-(4-(2-hydroxypropyl)piperazin-1-yl)pyridin-3-yl)oxy)pyridin-4-yl)methyl)piperidin-4-yl)methyl)-3-methylurea;

(R)-1-((1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)methyl)-3-methylurea;

methyl ((1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)methyl)carbamate;

(R)-methyl ((1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)methyl)carbamate;

1-((1-((3',5'-dichloro-5-((2-(4-(2-hydroxyethyl)piperazin-1-yl)pyrimidin-5-yl)oxy)-[1,1'-biphenyl]-3-yl)methyl)piperidin-4-yl)methyl)-3-methylurea;

3-(1-((2-(3,5-dichlorophenyl)-6-((6-(4-(2-hydroxyethyl)piperazin-1-yl)pyridin-3-yl)oxy)pyridin-4-yl)methyl)piperidin-4-yl)propanoic acid;

N-((1-((2-(3-chloro-5-fluorophenyl)-6-((2-(4-(2-hydroxyethyl)piperazin-1-yl)pyrimidin-5-yl)oxy)pyridin-4-yl)methyl)piperidin-4-yl)methyl)acetamide;

3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-hydroxypropanoic acid;

(R)-2-((1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)oxy)acetic acid;

((1-((2-(3,5-dichlorophenyl)-6-((2-(4-methylpiperazin-1-yl)pyrimidin-5-yl)oxy)pyridin-4-yl)methyl)piperidin-4-yl)methyl)boronic acid;

(2-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)ethyl)boronic acid;

((1-((2-(3,5-dichlorophenyl)-6-((2-(4-methylpiperazin-1-yl)pyrimidin-5-yl)oxy)pyridin-4-yl)methyl)piperidin-4-yl)methyl)dimethylphosphine oxide;

(1R,7S,8r)-4-((2-(3,5-dichlorophenyl)-6-((2-(4-methylpiperazin-1-yl)pyrimidin-5-yl)oxy)pyridin-4-yl)methyl)-4-azabicyclo[5.1.0]octane-8-carboxylic acid;

((1-((2-(3,5-dichlorophenyl)-6-((2-(4-methyl-1,4-diazepan-1-yl)pyrimidin-5-yl)oxy)pyridin-4-yl)methyl)piperidin-4-yl)methyl)boronic acid;

(2-(1-((2-(3,5-dichlorophenyl)-6-((2-(4-methylpiperazin-1-yl)pyrimidin-5-yl)oxy)pyridin-4-yl)methyl)piperidin-4-yl)ethyl)boronic acid;

(1-((2-(3,5-dichlorophenyl)-6-((6-(4-methylpiperazin-1-yl)pyridin-3-yl)oxy)pyridin-4-yl)methyl)piperidin-4-yl)methyl acetylcarbamate;

N-1-((1-((2-(3,5-dichlorophenyl)-6-((2-(4-methylpiperazin-1-yl)pyrimidin-5-yl)oxy)pyridin-4-yl)methyl)piperidin-4-yl)methyl)-N'-methoxylcarbonylurea;

N-(((1-((2-(3,5-dichlorophenyl)-6-((2-(4-methylpiperazin-1-yl)pyrimidin-5-yl)oxy)pyridin-4-yl)methyl)piperidin-4-yl)methyl)carbamoyl)methanesulfonamide;

N-(((1-((2-(3,5-dichlorophenyl)-6-((2-(4-methylpiperazin-1-yl)pyrimidin-5-yl)oxy)pyridin-4-yl)methyl)piperidin-4-yl)methyl)carbamoyl)acetamide;

N-((1-((2-(3,5-dichlorophenyl)-6-((2-(4-methylpiperazin-1-yl)pyrimidin-5-yl)oxy)pyridin-4-yl)methyl)piperidin-4-yl)carbamoyl)methanesulfonamide;
1-(1-((2-(3,5-dichlorophenyl)-6-((2-(4-methylpiperazin-1-yl)pyrimidin-5-yl)oxy)pyridin-4-yl)methyl)piperidin-4-yl)urea;
(S)-(4-((2-(3,5-dichlorophenyl)-6-((2-(4-methylpiperazin-1-yl)pyrimidin-5-yl)oxy)pyridin-4-yl)methyl)-1,4-oxazepan-7-yl)methanol;
(1-((2-(3,5-dichlorophenyl)-6-((2-(4-methylpiperazin-1-yl)pyrimidin-5-yl)oxy)pyridin-4-yl)methyl)piperidin-4-yl)dimethylphosphine oxide;
2-(1-((2-(3,5-dichlorophenyl)-6-((2-(4-methylpiperazin-1-yl)pyrimidin-5-yl)amino)pyridin-4-yl)methyl)piperidin-4-yl)acetic acid;
2-(1-((6-(3,5-dichlorophenyl)-3-methyl-2-((5-(4-methylpiperazin-1-yl)pyrazin-2-yl)oxy)pyridin-4-yl)methyl)piperidin-4-yl)acetic acid;
2-(1-((2-((2-(1,4-diazabicyclo[3.2.1]octan-4-yl)pyrimidin-5-yl)oxy)-6-(3,5-dichlorophenyl)pyridin-4-yl)methyl)piperidin-4-yl)acetic acid;
N-((1-((2-((2-(3,8-diazabicyclo[3.2.1]octan-3-yl)pyrimidin-5-yl)oxy)-6-(3,5-dichlorophenyl)pyridin-4-yl)methyl)piperidin-4-yl)methyl)acetamide;
methyl ((1-((2-((2-(1,4-diazabicyclo[3.2.1]octan-4-yl)pyrimidin-5-yl)oxy)-6-(3,5-dichlorophenyl)pyridin-4-yl)methyl)piperidin-4-yl)methyl)carbamate;
(1R,7S,8r)-4-((2-((2-(1,4-diazabicyclo[3.2.1]octan-4-yl)pyrimidin-5-yl)oxy)-6-(3,5-dichlorophenyl)pyridin-4-yl)methyl)-4-azabicyclo[5.1.0]octane-8-carboxylic acid;
4-(5-((6-(3,5-dichlorophenyl)-4-((4-fluoropiperidin-1-yl)methyl)pyridin-2-yl)oxy)pyrimidin-2-yl)-1,4-diazabicyclo[3.2.1]octane;
2-(1-((2-(3,5-dichlorophenyl)-6-((5-(4-methylpiperazin-1-yl)pyrazin-2-yl)oxy)pyridin-4-yl)methyl)piperidin-4-yl)acetic acid;
2-(1-((2-(3,5-dichlorophenyl)-6-((5-(4-methyl-1,4-diazepan-1-yl)pyrazin-2-yl)oxy)pyridin-4-yl)methyl)piperidin-4-yl)acetic acid;
4-(4-(5-((6-(3,5-dichlorophenyl)-4-((4-(2-hydroxyethyl)piperidin-1-yl)methyl)pyridin-2-yl)oxy)pyrazin-2-yl)piperazin-1-yl)-2-methylbutanoic acid;
2-(1-((2-(3,5-dichlorophenyl)-6-((5-(piperazin-1-yl)pyrazin-2-yl)oxy)pyridin-4-yl)methyl)piperidin-4-yl)ethanol;
2-(1-((2-(3,5-dichlorophenyl)-6-((5-(4-(2-hydroxy-2-methylpropyl)piperazin-1-yl)pyrazin-2-yl)oxy)pyridin-4-yl)methyl)piperidin-4-yl)acetic acid;
2-(1-((2-((6-(1,4-diazabicyclo[3.2.1]octan-4-yl)pyridazin-3-yl)oxy)-6-(3,5-dichlorophenyl)pyridin-4-yl)methyl)piperidin-4-yl)acetic acid;
2-(1-((2-(3,5-dichlorophenyl)-6-((5-(4-ethyl-1,4-diazepan-1-yl)pyrazin-2-yl)oxy)pyridin-4-yl)methyl)piperidin-4-yl)acetic acid;
2-(1-((2-(3,5-dichlorophenyl)-6-((5-((1S,4S)-5-methyl-2,5-diazabicyclo[2.2.1]heptan-2-yl)pyrazin-2-yl)oxy)pyridin-4-yl)methyl)piperidin-4-yl)acetic acid;
2-(1-((2-(3,5-dichlorophenyl)-6-((5-(4-isopropylpiperazin-1-yl)pyrazin-2-yl)oxy)pyridin-4-yl)methyl)piperidin-4-yl)acetic acid;
2-(1-((2-((5-(1,4-diazabicyclo[3.2.1]octan-4-yl)pyrazin-2-yl)oxy)-6-(3,5-dichlorophenyl)pyridin-4-yl)methyl)piperidin-4-yl)acetic acid;
2-(1-((2-(3,5-dichlorophenyl)-6-((5-(4-(3-hydroxybutyl)piperazin-1-yl)pyrazin-2-yl)oxy)pyridin-4-yl)methyl)piperidin-4-yl)acetic acid;
2-(1-((2-(3,5-dichlorophenyl)-6-((5-(4-methylpiperazin-1-yl)pyrazin-2-yl)oxy)pyridin-4-yl)methyl)piperidin-4-yl)ethanol;
3-(1-((2-(3,5-dichlorophenyl)-6-((5-(4-methyl-1,4-diazepan-1-yl)pyrazin-2-yl)oxy)pyridin-4-yl)methyl)piperidin-4-yl)-2-methylpropanoic acid;
2-(1-((2-(3,5-dichlorophenyl)-6-((5-(6-methyl-3,6-diazabicyclo[3.1.1]heptan-3-yl)pyrazin-2-yl)oxy)pyridin-4-yl)methyl)piperidin-4-yl)acetic acid;
1-((1-((2-(3,5-dichlorophenyl)-6-((5-(4-methylpiperazin-1-yl)pyrazin-2-yl)oxy)pyridin-4-yl)methyl)piperidin-4-yl)oxy)cyclopropanecarboxylic acid;
2-(1-((2-(3,5-dichlorophenyl)-6-((5-(4-(3-(methylsulfonyl)propyl)piperazin-1-yl)pyrazin-2-yl)oxy)pyridin-4-yl)methyl)piperidin-4-yl)acetic acid;
2-(1-((2-(3,5-dichlorophenyl)-6-((6-(4-ethyl-1,4-diazepan-1-yl)pyridazin-3-yl)oxy)pyridin-4-yl)methyl)piperidin-4-yl)acetic acid;
2-(1-((2-(3,5-dichlorophenyl)-6-((6-(4-methyl-1,4-diazepan-1-yl)pyridazin-3-yl)oxy)pyridin-4-yl)methyl)piperidin-4-yl)acetic acid;
2-(1-((2-(3,5-dichlorophenyl)-6-((6-((1S,4S)-5-methyl-2,5-diazabicyclo[2.2.1]heptan-2-yl)pyridazin-3-yl)oxy)pyridin-4-yl)methyl)piperidin-4-yl)acetic acid;
2-(1-((2-(3,5-dichlorophenyl)-6-((6-(4-ethylpiperazin-1-yl)pyridazin-3-yl)oxy)pyridin-4-yl)methyl)piperidin-4-yl)acetic acid;
2-(1-((2-(3,5-dichlorophenyl)-6-((6-(4-methylpiperazin-1-yl)pyridazin-3-yl)oxy)pyridin-4-yl)methyl)piperidin-4-yl)acetic acid;
2-(1-((2-(3,5-dichlorophenyl)-6-((6-(4-methylpiperazin-1-yl)pyridazin-3-yl)oxy)pyridin-4-yl)methyl)piperidin-4-yl)ethanol;
(1R,7S,8r)-4-((2-(3,5-dichlorophenyl)-6-((6-(4-methylpiperazin-1-yl)pyridazin-3-yl)oxy)pyridin-4-yl)methyl)-4-azabicyclo[5.1.0]octane-8-carboxylic acid;
(1R,7S,8r)-4-((2-(3,5-dichlorophenyl)-6-((6-(4-methyl-1,4-diazepan-1-yl)pyridazin-3-yl)oxy)pyridin-4-yl)methyl)-4-azabicyclo[5.1.0]octane-8-carboxylic acid;
3-(4-(6-((4-((4-(acetamidomethyl)piperidin-1-yl)methyl)-6-(3,5-dichlorophenyl)pyridin-2-yl)oxy)pyridazin-3-yl)piperazin-1-yl)-2-methylpropanoic acid;
(R)-3-(1-((2-(3,5-dichlorophenyl)-6-((6-(4-methylpiperazin-1-yl)pyridazin-3-yl)oxy)pyridin-4-yl)methyl)piperidin-4-yl)-2-methylpropanoic acid;
(S)-3-(1-((2-(3,5-dichlorophenyl)-6-((6-(4-methylpiperazin-1-yl)pyridazin-3-yl)oxy)pyridin-4-yl)methyl)piperidin-4-yl)-2-methylpropanoic acid;
2-(1-((2-(3,5-dichlorophenyl)-6-((6-((1S,4S)-5-ethyl-2,5-diazabicyclo[2.2.1]heptan-2-yl)pyridazin-3-yl)oxy)pyridin-4-yl)methyl)piperidin-4-yl)acetic acid;
3-(4-(5-((4-(((1R,7S,8r)-8-acetamido-4-azabicyclo[5.1.0]octan-4-yl)methyl)-6-(3,5-dichlorophenyl)pyridin-2-yl)oxy)pyrimidin-2-yl)piperazin-1-yl)propanoic acid;
methyl 4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-methylbutanoate;
4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-methylbutanoic acid;
4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2,2-dimethylbutanoic acid;
2-(1-((6-(3,5-dichlorophenyl)-3-methyl-2-((6-(4-methylpiperazin-1-yl)pyridazin-3-yl)oxy)pyridin-4-yl)methyl)piperidin-4-yl)acetic acid;

N-((1-((2-(3-chloro-5-fluorophenyl)-6-((2-(4-(4-(methylsulfonyl)butan-2-yl)piperazin-1-yl)pyrimidin-5-yl)oxy)pyridin-4-yl)methyl)piperidin-4-yl)methyl) acetamide;

1-((1-((2-(3-chloro-5-fluorophenyl)-6-((2-(4-(4-(methylsulfonyl)butan-2-yl)piperazin-1-yl)pyrimidin-5-yl)oxy)pyridin-4-yl)methyl)piperidin-4-yl)methyl)-3-methylurea;

2-(1-((2-(3-chloro-5-fluorophenyl)-6-((2-(4-methyl-1,4-diazepan-1-yl)pyrimidin-5-yl)oxy)pyridin-4-yl)methyl)piperidin-4-yl)acetic acid;

2-(1-((2-(3,5-dichlorophenyl)-6-(isopropyl(2-(4-methylpiperazin-1-yl)pyrimidin-5-yl)amino)pyridin-4-yl)methyl)piperidin-4-yl)acetic acid;

2-(1-((3',5'-dichloro-4-fluoro-5-((2-(4-methylpiperazin-1-yl)pyrimidin-5-yl)oxy)-[1,1'-biphenyl]-3-yl)methyl)piperidin-4-yl)acetic acid;

2-(1-((6-(3,5-dichlorophenyl)-3-fluoro-2-((6-(4-methylpiperazin-1-yl)pyridin-3-yl)oxy)pyridin-4-yl)methyl)piperidin-4-yl)acetic acid;

2-(1-((6-(3,5-dichlorophenyl)-3-fluoro-2-((2-(8-methyl-3,8-diazabicyclo[3.2.1]octan-3-yl)pyrimidin-5-yl)oxy)pyridin-4-yl)methyl)piperidin-4-yl)acetic acid;

2-(1-((6-(3,5-dichlorophenyl)-3-fluoro-2-((2-(4-methylpiperazin-1-yl)pyrimidin-5-yl)oxy)pyridin-4-yl)methyl)piperidin-4-yl)acetic acid;

2-(1-((6-(3,5-dichlorophenyl)-3-fluoro-2-((4-methyl-2-(4-methylpiperazin-1-yl)pyrimidin-5-yl)oxy)pyridin-4-yl)methyl)piperidin-4-yl)acetic acid;

4-(4-(5-((4-((4-(acetamidomethyl)piperidin-1-yl)methyl)-6-(3,5-dichlorophenyl)-3-fluoropyridin-2-yl)oxy)pyrimidin-2-yl)piperazin-1-yl)-2-methylbutanoic acid;

2-(1-((2-((2-(3,8-diazabicyclo[3.2.1]octan-3-yl)pyrimidin-5-yl)oxy)-6-(3,5-dichlorophenyl)-3-fluoropyridin-4-yl)methyl)piperidin-4-yl)acetic acid;

2-(1-((6-(3,5-dichlorophenyl)-3-fluoro-2-((2-methyl-6-(4-methylpiperazin-1-yl)pyridin-3-yl)oxy)pyridin-4-yl)methyl)piperidin-4-yl)acetic acid;

2-(1-((6-(3,5-dichlorophenyl)-3-fluoro-2-((6-(4-methylpiperazin-1-yl)pyridazin-3-yl)oxy)pyridin-4-yl)methyl)piperidin-4-yl)acetic acid;

methyl 3-(4-(5-((4-((4-(acetamidomethyl)piperidin-1-yl)methyl)-6-(3,5-dichlorophenyl)pyridin-2-yl)oxy)pyridin-2-yl)piperazin-1-yl)propanoate;

2-(1-((6-(3,5-dichlorophenyl)-3-methyl-2-((6-(4-methylpiperazin-1-yl)pyridin-3-yl)oxy)pyridin-4-yl)methyl)piperidin-4-yl)acetic acid;

2-(1-((2-((2-(4-((1H-1,2,3-triazol-5-yl)methyl)piperazin-1-yl)pyrimidin-5-yl)oxy)-6-(3,5-dichlorophenyl)pyridin-4-yl)methyl)piperidin-4-yl)acetic acid;

2-(1-((2-(3,5-dichlorophenyl)-6-(methyl(2-(4-methylpiperazin-1-yl)pyrimidin-5-yl)amino)pyridin-4-yl)methyl)piperidin-4-yl)acetic acid;

2-(1-((2-(3,5-dichlorophenyl)-6-(ethyl(2-(4-methylpiperazin-1-yl)pyrimidin-5-yl)amino)pyridin-4-yl)methyl)piperidin-4-yl)acetic acid;

2-(1-((6-(3,5-dichlorophenyl)-3-fluoro-2-((5-(4-methylpiperazin-1-yl)pyrazin-2-yl)oxy)pyridin-4-yl)methyl)piperidin-4-yl)acetic acid;

3-(4-(5-((4-((4-(acetamidomethyl)piperidin-1-yl)methyl)-6-(3,5-dichlorophenyl)pyridin-2-yl)oxy)pyrazin-2-yl)piperazin-1-yl)propanamide;

4-(4-(5-((6-(3,5-dichlorophenyl)-4-((4-(propionamidomethyl)piperidin-1-yl)methyl)pyridin-2-yl)oxy)pyrazin-2-yl)piperazin-1-yl)-2-methylbutanoic acid;

N-((1-((2-(3,5-dichlorophenyl)-6-((5-(4-(1-hydroxypropan-2-yl)piperazin-1-yl)pyrazin-2-yl)oxy)pyridin-4-yl)methyl)piperidin-4-yl)methyl)acetamide;

1-((1-((2-(3,5-dichlorophenyl)-6-((5-(4-methylpiperazin-1-yl)pyrazin-2-yl)oxy)pyridin-4-yl)methyl)piperidin-4-yl)methyl)-3-methylurea;

methyl ((1-((2-(3,5-dichlorophenyl)-6-((5-(4-methylpiperazin-1-yl)pyrazin-2-yl)oxy)pyridin-4-yl)methyl)piperidin-4-yl)methyl)carbamate;

4-(4-(5-((4-((4-(acetamidomethyl)piperidin-1-yl)methyl)-6-(3,5-dichlorophenyl)pyridin-2-yl)oxy)pyrazin-2-yl)piperazin-1-yl)-2-methylbutanoic acid;

(1R,7S,8r)-4-((2-(3,5-dichlorophenyl)-6-((2-(4-methyl-1,4-diazepan-1-yl)pyrimidin-5-yl)oxy)pyridin-4-yl)methyl)-4-azabicyclo[5.1.0]octane-8-carboxylic acid;

2-(1-((2-(3,5-dichlorophenyl)-6-((2-(8-methyl-3,8-diazabicyclo[3.2.1]octan-3-yl)pyrimidin-5-yl)oxy)pyridin-4-yl)methyl)piperidin-4-yl)acetic acid; and 2-(1-((2-(3,5-dichlorophenyl)-6-((2-(6-fluoro-1,4-diazepan-1-yl)pyrimidin-5-yl)oxy)pyridin-4-yl)methyl)piperidin-4-yl)acetic acid;

or pharmaceutically acceptable salts thereof.

Specific compounds of this invention which are of particular interest include:

3-(4-(5-((4-((4-(acetamidomethyl)piperidin-1-yl)methyl)-6-(3,5-dichlorophenyl)pyridin-2-yl)oxy)pyridin-2-yl)piperazin-1-yl)propanoic acid;

N-((1-((2-(3,5-dichlorophenyl)-6-((6-(4-(2-(methylsulfonyl)ethyl)piperazin-1-yl)pyridin-3-yl)oxy)pyridin-4-yl)methyl)piperidin-4-yl)methyl)acetamide;

2-(1-((2-(3,5-dichlorophenyl)-6-((2-(4-methyl-1,4-diazepan-1-yl)pyrimidin-5-yl)oxy)pyridin-4-yl)methyl)piperidin-4-yl)acetic acid;

N-((1-((2-(3,5-dichlorophenyl)-6-((6-(4-(2-hydroxyethyl)piperazin-1-yl)pyridin-3-yl)oxy)pyridin-4-yl)methyl)piperidin-4-yl)methyl)acetamide;

2-(1-((2-(3,5-dichlorophenyl)-6-((2-(4-methylpiperazin-1-yl)pyrimidin-5-yl)oxy)pyridin-4-yl)methyl)piperidin-4-yl)acetic acid;

3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoic acid;

2-(1-((6-(3,5-dichlorophenyl)-3-methyl-2-((5-(4-methylpiperazin-1-yl)pyrazin-2-yl)oxy)pyridin-4-yl)methyl)piperidin-4-yl)acetic acid;

2-(1-((2-((2-(1,4-diazabicyclo[3.2.1]octan-4-yl)pyrimidin-5-yl)oxy)-6-(3,5-dichlorophenyl)pyridin-4-yl)methyl)piperidin-4-yl)acetic acid;

2-(1-((2-(3,5-dichlorophenyl)-6-((5-(4-methylpiperazin-1-yl)pyrazin-2-yl)oxy)pyridin-4-yl)methyl)piperidin-4-yl)acetic acid; and 4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-methylbutanoic acid;

or pharmaceutically acceptable salts thereof.

Specific compounds of this invention which are of highest interest include:

3-(4-(5-((4-((4-(acetamidomethyl)piperidin-1-yl)methyl)-6-(3,5-dichlorophenyl)pyridin-2-yl)oxy)pyridin-2-yl)piperazin-1-yl)propanoic acid;

2-(1-((2-(3,5-dichlorophenyl)-6-((2-(4-methyl-1,4-diazepan-1-yl)pyrimidin-5-yl)oxy)pyridin-4-yl)methyl)piperidin-4-yl)acetic acid;

2-(1-((2-(3,5-dichlorophenyl)-6-((2-(4-methylpiperazin-1-yl)pyrimidin-5-yl)oxy)pyridin-4-yl)methyl)piperidin-4-yl)acetic acid;

2-(1-((2-((2-(1,4-diazabicyclo[3.2.1]octan-4-yl)pyrimidin-5-yl)oxy)-6-(3,5-dichlorophenyl)pyridin-4-yl)methyl)piperidin-4-yl)acetic acid; and 4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-methylbutanoic acid;

or pharmaceutically acceptable salts thereof.

Typically, but not absolutely, the salts of the present invention are pharmaceutically acceptable salts. Salts of the disclosed compounds containing a basic amine or other basic functional group may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N-bisdehydroabietylamine, glucamine, N-methylglucamine, collidine, quinine, quinoline, and basic amino acid such as lysine and arginine.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

The compound of Formula (I) may exist in a crystalline or noncrystalline form, or as a mixture thereof. The compound of Formula (I-a) may also exist in a crystalline or noncrystalline form, or as a mixture thereof. The skilled artisan will appreciate that pharmaceutically acceptable solvates may be formed for crystalline or non-crystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that the compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The compound of Formula (I) or a salt thereof may exist in stereoisomeric forms (e.g., it contains one or more asymmetric carbon atoms). The compound of Formula (I-a) or a salt thereof may also exist in stereoisomeric forms. The individual stereoisomers (enantiomers and diastereomers) and mixtures of these are included within the scope of the present invention. Likewise, it is understood that a compound or salt of Formula (I) or Formula (I-a) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. It is to be understood that the present invention includes all combinations and subsets of the particular groups defined hereinabove.

The subject invention also includes isotopically-labeled compounds, which are identical to those recited in Formula (I) and following, but for the fact that one or more atoms are replaced by an atom having an atomic mass or mass number different from the atomic mass or mass number usually found in nature. The subject invention also includes isotopically-labeled compounds of Formula (I-a). Examples of isotopes that can be incorporated into compounds of the invention and pharmaceutically acceptable salts thereof include isotopes of hydrogen, carbon, nitrogen, oxygen, phosphorous, sulfur, fluorine, chlorine, and iodine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$, and $^{125}I$.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of Formula (I) and following of this invention can generally be prepared by carrying out the procedures disclosed in the Schemes and/or in the Examples below, by substituting a readily available isotopically labeled reagent for a non-isotopically labeled reagent. Isotopically labeled compounds of Formula (I-a) can also generally be prepared by carrying out the procedures disclosed in the Schemes and/or in the Examples below, by substituting a readily available isotopically labeled reagent for a non-isotopically labeled reagent.

The invention further provides a pharmaceutical composition (also referred to as pharmaceutical formulation) comprising a compound of Formula (I) or pharmaceutically acceptable salt thereof and one or more excipients (also referred to as carriers and/or diluents in the pharmaceutical arts). The disclosure also provides a pharmaceutical composition comprising a compound of Formula (I-a) or pharmaceutically acceptable salt thereof and one or more excipients. The excipients are acceptable in the sense of being compatible with the other ingredients of the formulation and not deleterious to the recipient thereof (i.e., the patient).

In certain embodiments, the compounds described herein are provided in an effective amount in the pharmaceutical composition. In certain embodiments, the effective amount is a therapeutically effective amount. In certain embodiments, the effective amount is a prophylactically effective amount. In certain embodiments, a therapeutically effective amount is an amount effective for inhibiting the aberrant activity of furin. In certain embodiments, a therapeutically effective amount is an amount effective for treating a disease (e.g., a disease associated with aberrant activity of furin (e.g., fibrotic diseases including pulmonary fibrosis (e.g., idiopathic pulmonary fibrosis, non-specific interstitial pneumonia (NSIP), usual interstitial pneumonia (UIP), Hermansky-Pudlak syndrome, progressive massive fibrosis (a complication of coal workers' pneumoconiosis), connective tissue disease-related pulmonary fibrosis, airway fibrosis in asthma and COPD, acute respiratory distress syndrome (ARDS) associated fibrosis, acute lung injury; radiation-induced fibrosis; familial pulmonary fibrosis; pulmonary hypertension), renal fibrosis (e.g., diabetic nephropathy, IgA nephropathy, lupus nephritis; focal segmental glomerulosclerosis (FSGS), transplant nephropathy, autoimmune nephropathy, drug-induced nephropathy, hypertension-related nephropathy, nephrogenic systemic fibrosis), liver fibrosis (e.g., viral-induced fibrosis (e.g. hepatitis C or B), autoimmune hepatitis, primary biliary cirrhosis, alcoholic liver disease, non-alcoholic fatty liver disease including non-alcoholic steatohepatitis (NASH), congenital hepatic fibrosis, primary sclerosing cholangitis, drug-induced hepatitis, hepatic cirrhosis), skin fibrosis (e.g., hypertrophic scars, scleroderma, keloids, dermatomyositis, eosinophilic fasciitis, Dupytrens contracture, Ehlers-Danlos syndrome, Peyronie's disease epidermolysis bullosa dystrophica, oral submucous fibrosis), ocular fibrosis (e.g., AMD, diabetic macular oedema, dry eye, glaucoma), cardiac fibrosis (e.g., congestive heart failure, endomyocardial fibrosis, hypertrophic cardiomyopathy (HCM), dilated cardiomyopathy (DCM), arrhythmogenic right ventricular cardiomyopathy (ARVC), hypertensive heart disease, cardiac sarcoidosis and other forms of heart failure) and other miscellaneous fibrotic conditions (e.g., mediastinal fibrosis, myelofibrosis, retroperitoneal fibrosis, Crohn's disease, neurofibromatosis, uterine leiomyomas (fibroids), chronic organ transplant rejection)).

In certain embodiments, the effective amount is an amount effective for inhibiting the activity of a furin by at least 10%, at least 20%, at least 30%, at least 40%, at least 50%, at least 60%, at least 70%, at least 80%, at least 90%, at least 95%, or at least 98%. In certain embodiments, the effective amount is an amount effective for inhibiting the activity of a furin by not more than 10%, not more than 20%, not more than 30%, not more than 40%, not more than 50%, not more than 60%, not more than 70%, not more than 80%, not more than 90%, not more than 95%, or not more than 98%.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Pharmaceutical compositions may be in unit dose form containing a predetermined amount of active ingredient per unit dose. Such a unit may contain a therapeutically effective dose of the compound of Formula (I) or salt thereof or a fraction of a therapeutically effective dose such that multiple unit dosage forms might be administered at a given time to achieve the desired therapeutically effective dose. Such a unit may contain a therapeutically effective dose of the compound of Formula (I-a) or salt thereof or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules; powders or granules; solutions or suspensions in aqueous or non-aqueous liquids; edible foams or whips; oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a suitable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In the present invention, tablets and capsules are preferred oral forms of delivery of the pharmaceutical composition.

In another aspect, the invention is directed to a dosage form adapted for administration to a patient by inhalation. Inhalation refers to administration into the patient's lungs whether inhaled through the mouth or through the nasal passages. For example, the compound of the invention may be inhaled into the lungs as a dry powder, an aerosol, a suspension, or a solution.

Dry powder compositions for delivery to the lung by inhalation typically comprise a compound of the invention as a finely divided powder together with one or more pharmaceutically acceptable excipients as finely divided powders. Pharmaceutically acceptable excipients particularly suited for use in dry powders are known to those skilled in the art and include lactose, starch, mannitol, and mono-, di-, and polysaccharides.

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 μg-10 mg of the compound of the invention.

Aerosols may be formed by suspending or dissolving a compound of the invention in a liquefied propellant. Suitable propellants include halocarbons, hydrocarbons, and other liquefied gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of the invention will typically be administered to a patient via a metered dose inhaler (MDI). Such devices are known to those skilled in the art.

The aerosol may contain additional pharmaceutically acceptable excipients typically used with multiple dose inhalers such as surfactants, lubricants, cosolvents and other excipients to improve the physical stability of the formulation, to improve valve performance, to improve solubility, or to improve taste.

Suspensions and solutions comprising a compound of the invention may also be administered to a patient via a nebulizer. The solvent or suspension agent utilized for nebulization may be any pharmaceutically acceptable liquid such as water, aqueous saline, alcohols or glycols, e.g. ethanol, isopropyl alcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g. sodium chloride, potassium chloride or organic salts, such as potassium, sodium and ammonium salts or organic acids, e.g. ascorbic acid, citric acid, acetic acid, tartaric acid, etc. may be used for this purpose.

Other pharmaceutically acceptable excipients may be added to the suspension or solution. The compound of the invention may be stabilized by the addition of an inorganic acid, e.g. hydrochloric acid, nitric acid, sulfuric acid and/or phosphoric acid; an organic acid, e.g. ascorbic acid, citric acid, acetic acid, and tartaric acid, etc., a complexing agent such as EDTA or citric acid and salts thereof; or an antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

Pharmaceutical compositions adapted for rectal administration may be presented as suppositories or as enemas.

Pharmaceutical compositions adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the pharmaceutical compositions may include other agents conventional in the art having regard to the type of formulation in question, for example those suitable for oral administration may include flavoring agents.

Pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the Formula (I), depending on the condition being treated, the route of administration and the age, weight and condition of the patient, or pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the Formula (I-a), or pharmaceutical compositions may be presented in unit dose forms containing a predetermined amount of active ingredient per unit dose. Preferred unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of Formula (I) for the treatment of pulmonary fibrosis will generally be in the range of 0.001 to 100 mg/kg body weight of recipient per day, suitably in the range of 0.01 to 10 mg/kg body weight per day. However, an effective amount of a compound of Formula (I-a) for the treatment of pulmonary fibrosis will generally be in the range of 0.001 to 100 mg/kg body weight of recipient per day, suitably in the range of 0.01 to 10 mg/kg body weight per day. For a 70 kg adult mammal, the actual amount per day would suitably be from 7 to 700 mg and this amount may be given in a single dose per day or in a number (such as two, three, four, five or six) of sub-doses per day such that the total daily dose is the same. Inhaled daily dosages range from 10 µg-10 mg/day, with preferred 10 µg-2 mg/day, and more preferred 50 µg-500 µg/day. An effective amount of a salt or solvate, etc., may be determined as a proportion of the effective amount of the compound of Formula (I) or Formula (I-a) per se. It is envisaged that similar dosages would be appropriate for treatment of the other conditions referred to above.

In accordance with another aspect of the invention there is provided a process for the preparation of a pharmaceutical composition comprising mixing (or admixing) a compound of Formula (I) or salt thereof with at least one excipient. In accordance with another aspect of the invention there is provided a process for the preparation of a pharmaceutical composition comprising mixing (or admixing) a compound of Formula (I-a) or salt thereof with at least one excipient.

The present invention also provides a method of treatment in a mammal, especially a human. Disease states which can be treated by the methods and compositions provided herein include, but are not limited to, fibrotic diseases. Fibrotic diseases involve the formation of excess fibrous connective tissue in an organ or tissue in a reparative or reactive process. Diseases may include but are not limited to pulmonary fibrosis, e.g. idiopathic pulmonary fibrosis, non-specific interstitial pneumonia (NSIP), usual interstitial pneumonia (UIP), Hermansky-Pudlak syndrome, progressive massive fibrosis (a complication of coal workers' pneumoconiosis), connective tissue disease-related pulmonary fibrosis, airway fibrosis in asthma and COPD, acute respiratory distress syndrome (ARDS) associated fibrosis, acute lung injury; radiation-induced fibrosis; familial pulmonary fibrosis; pulmonary hypertension); renal fibrosis (diabetic nephropathy, IgA nephropathy, lupus nephritis; focal segmental glomerulosclerosis (FSGS), transplant nephropathy, autoimmune nephropathy, drug-induced nephropathy, hypertension-related nephropathy, nephrogenic systemic fibrosis); liver fibrosis (viral-induced fibrosis (e.g. hepatitis C or B), autoimmune hepatitis, primary biliary cirrhosis, alcoholic liver disease, non-alcoholic fatty liver disease including non-alcoholic steatohepatitis (NASH), congenital hepatic fibrosis, primary sclerosing cholangitis, drug-induced hepatitis, hepatic cirrhosis); skin fibrosis (hypertrophic scars, scleroderma, keloids, dermatomyositis, eosinophilic fasciitis, Dupytrens contracture, Ehlers-Danlos syndrome, Peyronie's disease epidermolysis bullosa dystrophica, oral submucous fibrosis); ocular fibrosis (AMD, diabetic macular oedema, dry eye, glaucoma); cardiac fibrosis (congestive heart failure, endomyocardial fibrosis, hypertrophic cardiomyopathy (HCM), dilated cardiomyopathy (DCM), arrhythmogenic right ventricular cardiomyopathy (ARVC), hypertensive heart disease, cardiac sarcoidosis and other forms of heart failure) and other miscellaneous fibrotic conditions (mediastinal fibrosis, myelofibrosis, retroperitoneal fibrosis, Crohn's disease, neurofibromatosis, uterine leiomyomas (fibroids), chronic organ transplant rejection).

Additional disease states which can be treated by the methods and compositions provided herein include, but are not limited to, hypertension, cancer, infectious (such as human immunodeficiency virus (HIV), avian influenza virus, measles virus, respiratory syncytial virus (RSV), Ebola virus, anthrax, and Zika virus (ZIKV)), respiratory (such as cystic fibrosis (CF)) and neurondegeneration (such as Alzheimer's disease (AD)) diseases.

The instant compounds can be combined with or co-administered with other therapeutic agents, particularly agents that may enhance the activity or time of disposition of the compounds. Combination therapies according to the invention comprise the administration of at least one compound of the invention and the use of at least one other treatment method, including administration of one or more other therapeutic agents. Other therapeutic agents which may be used in combination with a compound of the invention include, but are not limited to, antigen immunotherapy, anti-histamines, corticosteroids (e.g., fluticasone propionate, fluticasone furoate, beclomethasone dipropionate, budesonide, ciclesonide, mometasone furoate, triamcinolone, fhmisolide), NSAIDs, leukotriene modulators (e.g. montelukast, zafirlukast, pranlukast) iNOS inhibitors, tryptase inhibitors, IKK2 inhibitors, p38 inhibitors, Syk inhibitors, elastase inhibitors, beta-2 integrin antagonists, adenosine a2a agonists, chemokine antagonists such as CCR3 antagonists or CCR4 antagonists, mediator release inhibitors such as sodium chromoglycate, 5-lipoxygenase inhibitors (zyflo), DPI antagonists, DP2 antagonists, pI3K delta inhibitors, ITK inhibitors, LP (lysophosphatidic) inhibitors or FLAP (5-lipoxygenase activating protein) inhibitors (e.g. sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate), methotrexate, and similar agents; monoclonal antibody therapy such as anti-IgE, anti-TNF, anti-IL-5, anti-IL-6, anti-IL-12, anti-IL-1 and similar agents; receptor therapies e.g. etanercept and similar agents; antigen non-specific immunotherapies (e.g. interferon or other cytokines/chemokines, cytokine/chemokine receptor modulators, cytokine agonists or antagonists, TLR agonists and similar agents)), inhibitors of TGFβ synthesis, for example pirfenidone, tyrosine kinase inhibitors targeting the vascular endothelial growth factor (VEGF), platelet-derived growth factor (PDGF) and fibroblast growth factor (FGF) receptor kinases, for example intedanib (BIBF-1120) and imatinib mesylate (Gleevec), endothelin receptor antagonists, for example ambrisentan or macitentan, anti-oxidants, such as N-acetylcysteine (NAC or fluimucil), broad-spectrum antibiotics, such as tetracyclines, for example minocycline hydrochloride, phosphodiesterase 5 (PDE5) inhibitors for example sildenafil, or $\alpha_v\beta_6$ integrin antagonists, e.g. monoclonal antibodies such as those described in WO 2003/100033 A2.

By the term "co-administration" and derivatives thereof as used herein refers to either simultaneous administration or any manner of separate sequential administration of a furin inhibiting compound, as described herein, and a further active ingredient or ingredients. The term further active ingredient or ingredients, as used herein, includes any compound or therapeutic agent known to or that demonstrates advantageous properties when administered to a patient in need of treatment. Preferably, if the administration is not simultaneous, the compounds are administered in a close time proximity to each other. Furthermore, it does not matter if the compounds are administered in the same dosage form, e.g. one compound may be administered orally and another compound may be administered intravenously.

Another aspect of the present disclosure relates to kits comprising a container with a compound, or pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition. A kit described herein may also include information (e.g., prescribing information) as required by a regulatory agency, such as the U.S. Food and Drug Administration (FDA).

The details of one or more embodiments of the invention are set forth herein. Other features, objects, and advantages of the invention will be apparent from the Detailed Description, Examples, Figures, and Claims.

Definitions

Terms are used within their accepted meanings. The following definitions are meant to clarify, but not limit, the terms defined.

As used herein, the term "alkyl" represents a saturated, straight or branched hydrocarbon moiety having the specified number of carbon atoms. The term "$(C_1-C_6)$alkyl" refers to an alkyl moiety containing from 1 to 6 carbon atoms. Exemplary alkyls include, but are not limited to, methyl, ethyl, n-propyl, isopropyl, n-butyl, isobutyl, s-butyl, t-butyl, pentyl, and hexyl.

"Alkoxy" refers to a group containing an alkyl radical, defined hereinabove, attached through an oxygen linking atom. The term "$(C_1-C_4)$alkoxy" refers to a straight- or branched-chain hydrocarbon radical having at least 1 and up to 4 carbon atoms attached through an oxygen linking atom. Exemplary "$(C_1-C_4)$alkoxy" groups useful in the present invention include methoxy, ethoxy, n-propoxy, isopropoxy, n-butoxy, s-butoxy, isobutoxy, and t-butoxy.

When the term "alkyl" is used in combination with other substituent groups, such as "halo$(C_1-C_6)$alkyl", "$(C_3-C_6)$cycloalkyl$(C_1-C_4)$alkyl-", or "$(C_1-C_4)$alkoxy$(C_2-C_4)$alkyl-", the term "alkyl" is intended to encompass a divalent straight or branched-chain hydrocarbon radical, wherein the point of attachment is through the alkyl moiety. The term "halo$(C_1-C_6)$alkyl" is intended to mean a radical having one or more halogen atoms, which may be the same or different, at one or more carbon atoms of an alkyl moiety containing from 1 to 6 carbon atoms, which is a straight or branched-chain carbon radical. Examples of "halo$(C_1-C_6)$alkyl" groups useful in the present invention include, but are not limited to, —CH$_2$F (fluoromethyl), —CHF$_2$ (difluoromethyl), —CF$_3$ (trifluoromethyl), —CCl$_3$ (trichloromethyl), 1,1-difluoroethyl, 2-fluoro-2-methylpropyl, 2,2-difluoropropyl, 2,2,2-trifluoroethyl, and hexafluoroisopropyl. Examples of "$(C_3-C_6)$cycloalkyl$(C_1-C_4)$alkyl-" groups useful in the present invention include, but are not limited to, cyclobutylmethyl, cyclopentylmethyl, cyclohexylmethyl, cyclobutylethyl, cyclopentylethyl, and cyclohexylethyl. Examples of "$(C_1-C_4)$alkoxy$(C_2-C_4)$alkyl-" groups useful in the present invention include, but are not limited to, methoxyethyl, methoxyisopropyl, ethoxyethyl, ethoxyisopropyl, isopropoxyethyl, isopropoxyisopropyl, t-butoxyethyl, and t-butoxyisopropyl.

When the term "alkenyl" (or "alkenylene") is used it refers to straight or branched hydrocarbon chains containing the specified number of carbon atoms and at least 1 and up to 3 carbon-carbon double bonds. Examples include ethenyl (or ethenylene) and propenyl (or propenylene).

As used herein, the term "cycloalkyl" refers to a non-aromatic, saturated, cyclic hydrocarbon ring containing the specified number of carbon atoms. The term "$(C_3-C_6)$cycloalkyl" refers to a non aromatic cyclic hydrocarbon ring having from three to six ring carbon atoms. Exemplary "$(C_3-C_6)$cycloalkyl" groups useful in the present invention include cyclopropyl, cyclobutyl, cyclopentyl, and cyclohexyl.

The terms "halogen" and "halo" represent fluoro, chloro, bromo, or iodo substituents.

"Oxo" represents a double-bonded oxygen moiety; for example, if attached directly to a carbon atom forms a carbonyl moiety (C=O).

"Hydroxy" or "hydroxyl" is intended to mean the radical —OH.

As used herein, the term "optionally" means that the subsequently described event(s) may or may not occur, and includes both event(s) that occur and event(s) that do not occur.

As used herein, the term "treatment" refers to alleviating the specified condition, eliminating or reducing one or more symptoms of the condition, slowing or eliminating the progression of the condition, and delaying the reoccurrence of the condition in a previously afflicted or diagnosed patient or subject.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula (I), as well as salts thereof, may be administered as the raw chemical. For use in therapy, therapeutically effective amounts of a compound of Formula (I-a), as well as salts thereof, may be administered as the raw chemical. Additionally, the active ingredient may be presented as a pharmaceutical composition.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, respiratory disease (e.g., cystic fibrosis), neurodegenerative disorders (e.g., Alzheimer's disease), and coronary artery disease.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease.

The term "inhibition," "inhibiting," "inhibit," or "inhibitor" refer to the ability of a compound to reduce, slow, halt, or prevent activity of a particular biological process (e.g., Furin activity) in a cell relative to vehicle.

In certain embodiments, a kit described herein includes a first container comprising a compound or pharmaceutical composition described herein. In certain embodiments, a kit described herein is useful in treating and/or preventing diseases, such as fibrotic diseases including pulmonary fibrosis, other miscellaneous fibrotic conditions, hypertension, cancer, infectious diseases, genetic disorders, or neurodegenerative disorders.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating fibrotic disease, other miscellaneous fibrotic conditions, hypertension, cancer, infectious diseases, genetic disorders, or neurodegenerative disorders. A kit described herein may include one or more additional pharmaceutical agents described herein as a separate composition.

Compound Preparation

Abbreviations $Ac_2O$ acetic anhydride
AcOH acetic acid
AIBN azobisisobutyronitrile
aq. aqueous
$BBr_3$ boron tribromide
$BF_3 \cdot OEt_2$ boron trifluoride diethyl etherate
$BH_3 \cdot DMS$ borane dimethyl sulfide complex
(±)-BINAP racemic 2,2'-bis(diphenylphosphino)-1,1'-binaphthalene
Bn benzyl
BnOH benzyl alcohol
$Boc_2O$ di-tert-butyl decarbonate
BPin 4,4,5,5-tetramethyl-1,3,2-dioxaborolane
$Br_2$ bromine
$CaCl_2$ calcium chloride
$CBr_4$ carbon tetrabromide
CbzCl benzyl chloroformate
$CCl_4$ carbon tetrachloride
CDI 1,1'-carbonyldiimidazole
$Cl_2$ chlorine gas
$Cs_2CO_3$ cesium carbonate
CuI copper(I) iodide
$CuSO_4$ copper(II) sulfate
DAST diethylaminosulfur trifluoride
DCE dichloroethane
DCM or $CH_2Cl_2$ dichloromethane
DEAD diethyl azodicarboxylate
Dess-Martin 1,1,1-tris(acetyloxy)-1,1-dihydro-1,2-benziodoxol-3-(1H)-one
DIAD diisopropyl azodicarboxylate
DIEA diisopropylethylamine
DMF N,N-dimethylformamide
DMSO dimethylsulfoxide
DPPA diphenylphosphoryl azide
EA or EtOAc ethyl acetate
EDC 1-ethyl-3-(3-dimethylaminopropyl)carbodiimide
ES-LCMS electrospray liquid chromatography-mass spectrometry
EtI ethyl iodide
EtMgBr ethylmagnesium bromide
$Et_3N$ triethylamine
EtOH ethanol
g gram(s)
Grubbs I benzylidene-bis(tricyclohexylphosphine)dichlororuthenium
h hour(s)
$H_2$ hydrogen gas
HATU O-(7-azabenzotriazol-1-yl)-N,N,N',N''-tetramethyluronium hexafluorophosphate
HCl hydrochloric acid
$H_2O$ water
HOBt hydroxybenzotriazole
HPLC high performance liquid chromatography
in vacuo under vacuum
i-PrOH isopropyl alcohol
$[Ir(COD)OMe]_2$ di-μ-methoxobis(1,5-cyclooctadiene)diiridium(I)
KCN potassium cyanide
$K_2CO_3$ potassium carbonate
KI potassium iodide
KOAc potassium acetate
$K_3PO_4$ potassium phosphate tribasic
L liter(s)
LAH or $LiAlH_4$ lithium aluminium hydride
LCMS liquid chromatography-mass spectrometry
LiHMDS lithium bis(trimethylsilyl)amide
LiOH lithium hydroxide
$LiOH \cdot H_2O$ lithium hydroxide monohydrate
M molar
m-CPBA meta-chloroperoxybenzoic acid
MeCN acetonitrile
MeI methyl iodide
MeMgBr methylmagnesium bromide
$MeNH_2$ methylamine
MeOH methanol
$MgSO_4$ magnesium sulfate
min minute(s)
mL milliliter(s)
mmol millimole(s)
mol mole(s)
MsCl methanesulfonyl chloride
MTBE methyl tert-butyl ether
N normal
$N_2$ nitrogen gas
$NaBH_4$ sodium borohydride
$NaBH_3CN$ sodium cyanoborohydride
$NaBH(OAc)_3$ sodium triacetoxyborohydride
NaCN sodium cyanide
NaH sodium hydride
$NaHCO_3$ sodium bicarbonate
NaOH sodium hydroxide
$Na_2SO_4$ sodium sulfate
NBS N-bromosuccinimide
n-BuLi n-butyllithium
n-BuMgCl n-butylmagnesium chloride
$NH_3$ ammonia
$NH_4Cl$ ammonium chloride
$NH_4OAC$ ammonium acetate
$NH_4OH$ ammonium hydroxide
NMP A-methyl-2-pyrrolidone
NMR nuclear magnetic resonance
OTf trifluoromethanesulfonate
Oxone® potassium peroxymonosulfate
$Pd(OAc)_2$ palladium(II) acetate
Pd/C palladium on carbon
$PdCl_2(dppf)$ [1,1'-bis(diphenylphosphino)ferrocene]dichloropalladium(II)
$Pd_2(dba)_3$ tris(dibenzylideneacetone)dipalladium(0)
$Pd(OH)_2$ palladium(II) hydroxide
$Pd(PPh_3)_2Cl_2$ bis(triphenylphosphine)palladium(II) dichloride
PE petroleum ether
$POCl_3$ phosphoryl chloride
$PPh_3$ triphenylphosphine
p-TsCl para-toluenesulfonyl chloride
p-TSOH para-toluenesulfonic acid
SFC supercritical fluid chromatography
$SOCl_2$ thionyl chloride
TBAF tetra-n-butylammonium fluoride
TBS tert-butyldimethylsilyl TBSCl tert-butyldimethylsilyl chloride
t-BuOH tert-butyl alcohol
t-BuOK potassium tert-butoxide
t-BuONa sodium tert-butoxide
TFA trifluoroacetic acid
Tf$_2$O trifluoromethanesulfonic anhydride
THF tetrahydrofuran
TFC thin layer chromotography
TMS-N$_3$ trimethylsilyl azide
TosMIC para-toluenesulfonylmethyl isocyanide
Xantphos 4,5-bis(diphenylphosphino)-9,9-dimethylxanthene
Zn zinc metal Generic Synthesis Schemes The compounds of this invention may be made by a variety of methods, including well-known standard synthetic methods. Illustrative general synthetic methods are set out below and then specific compounds of the invention are prepared in the working examples. The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts, (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention. Starting materials are commercially available or are made from commercially available starting materials using methods known to those skilled in the art.

Certain compounds of Formula (I) can be prepared according to Schemes 1, 2, or 3 or analogous methods.

Scheme 1

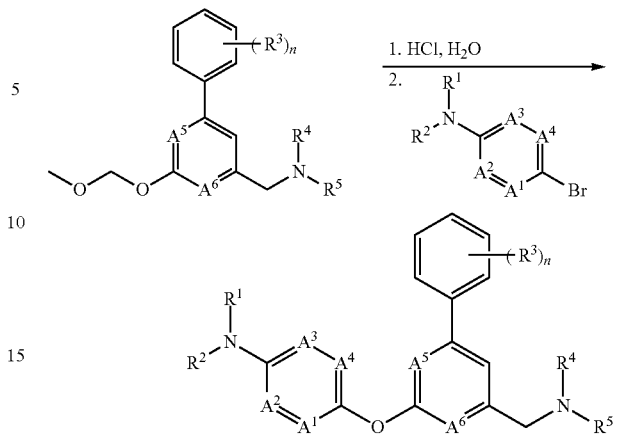

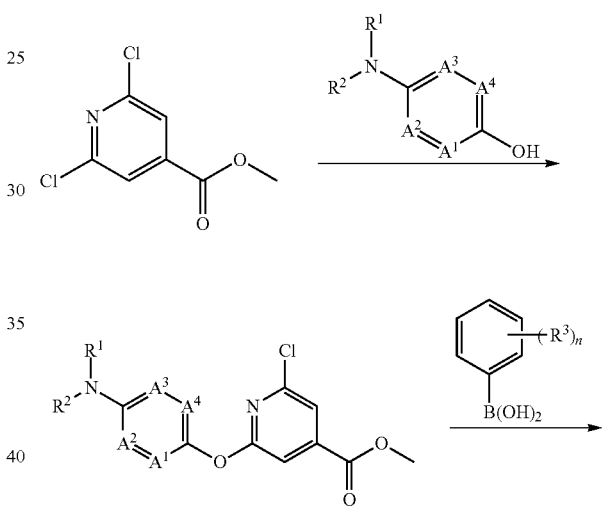

Scheme 2

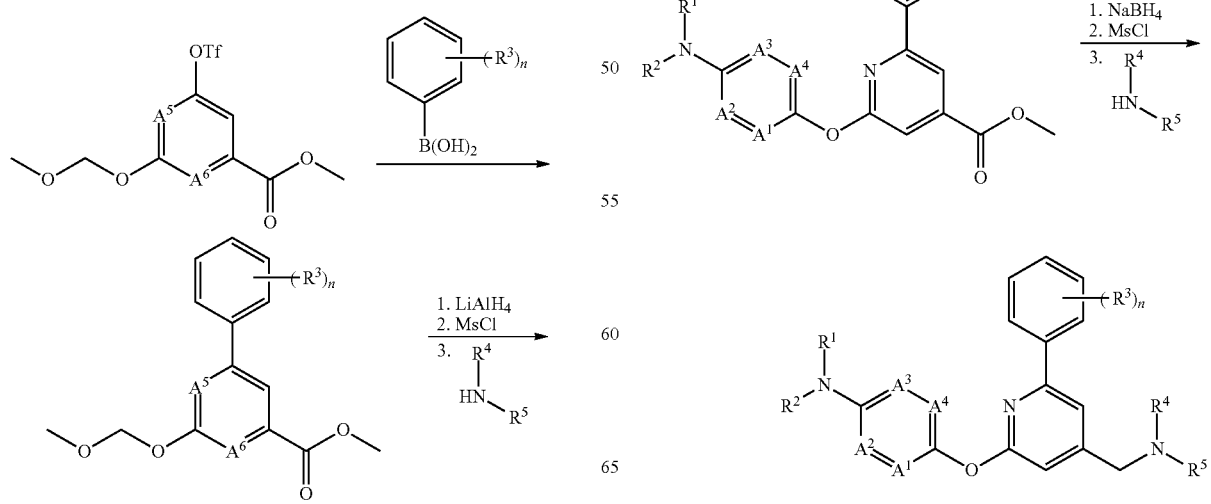

Scheme 3

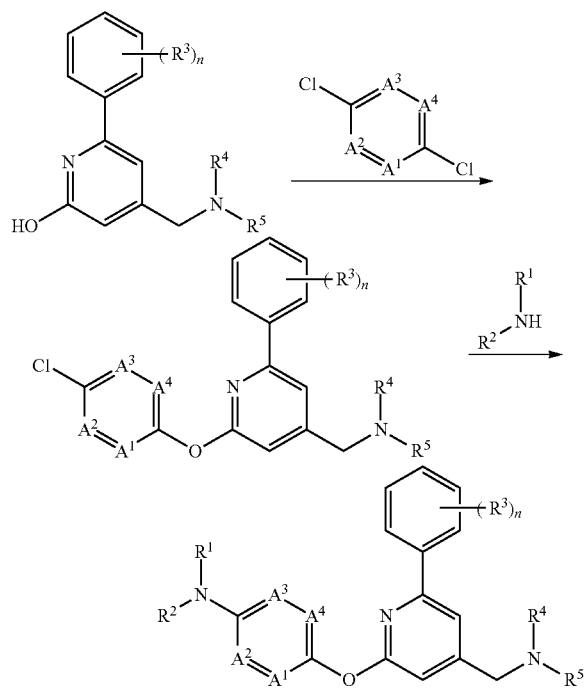

EXPERIMENTALS

The following examples illustrate in the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention. Unless otherwise noted, reagents are commercially available or are prepared according to procedures in the literature. The symbols and conventions used in the descriptions of processes, schemes, and examples are consistent with those used in the contemporary scientific literature, for example, the Journal of the American Chemical Society or the Journal of Biological Chemistry.

In the Examples:

Preparative HPLC was performed on a Gilson UV/VIS-156 with UV detection at 220/254 nm Gilson 281 automatic collection. HPLC column commonly used ASB-C18 21.2× 150 mm or Phenomenex 21.2×150 mm. HPLC Gradient (acidic condition, 0.01% HCl or 0.1% formic acid) used 0-100% acetonitrile with water and corresponding acid, the gradient shape was optimized for individual separations. Unless specially mentioned, compounds are isolated in HCl system and thus obtained as HCl salts. However, the compounds can also be isolated and used as the free base. HPLC Gradient (basic condition, 0.05% $NH_3H_2O$ or neutral condition, 0.01% $NH_4HCO_3$) was optimized for individual separation.

Chemical shifts are expressed in parts per million (ppm) units. Coupling constants (J) are in units of hertz (Hz). Splitting patterns describe apparent multiplicities and are designated as s (single), d (double), t (triplet), dd (double doublet), dt (double triplet), dq (double quartet), m (multiplet), br (broad).

Flash column chromatography was performed on silica gel.

The naming programs used are ACDLABs 11.0 Namebatch, ACD IUPAC, or ChemDraw.

Intermediates

Intermediate 1: Methyl 2,6-dichloroisonicotinate, hydrochloride

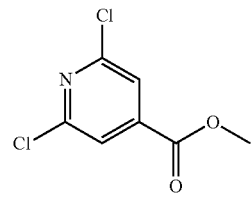

To a solution of 2,6-dichloroisonicotinic acid (300 g, 1563 mmol) in MeOH (2 L) was added $SOCl_2$ (0.228 L, 3125 mmol) in portion at 0° C. The mixture was stirred at 70° C. for 14 h. The reaction mixture was concentrated and saturated aqueous $NaHCO_3$ solution (500 mL) was added. The mixture was extracted with DCM (500 mL×3). The combined organic layers were washed with brine (200 mL), dried over $Na_2SO_4$, filtered and concentrated to yield methyl 2,6-dichloroisonicotinate (300 g, 1311 mmol, 84.0% yield) as an off white solid: $^1H$ NMR (400 MHz, $CD_3OD$) δ ppm 7.87 (s, 2H), 3.96 (s, 3H); ES-LCMS m/z 206.1, 208.1 $[M+H]^+$.

Intermediate 2: N-(Piperidin-4-ylmethyl)acetamide, hydrochloride

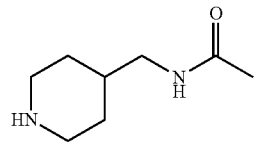

Step 1: tert-Butyl 4-(acetamidomethyl)piperidine-1-carboxylate

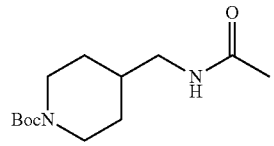

To a mixture of tert-butyl 4-(aminomethyl)piperidine-1-carboxylate (150 g, 700 mmol) in DCM (1.2 L) was added $Ac_2O$ (93 g, 910 mmol) dropwise. The mixture was stirred at 15° C. for 2 h. The solution was concentrated to yield a pale yellow oil of tert-butyl 4-(acetamidomethyl)piperidine-1-carboxylate (180 g, 697 mmol, 100.0% yield): $^1H$ NMR (400 MHz, $CDCl_3$) δ ppm 5.67 (br. s, 1H), 4.09 (br. s, 2H), 3.18-2.99 (m, 2H), 2.66 (t, J=11.7 Hz, 2H), 1.98 (s, 3H), 1.71-1.55 (m, 3H), 1.43 (s, 9H), 1.10 (m, 2H); ES-LCMS m/z 157.1 [M−t−Bu+H]⁺.

Step 2: N-(Piperidin-4-ylmethyl)acetamide, hydrochloride

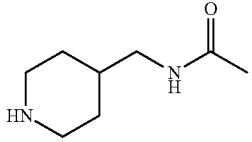

tert-Butyl 4-(acetamidomethyl)piperidine-1-carboxylate (360 g, 1404 mmol) was dissolved in HCl solution (4 M in EtOAc, 1 L, 4 mol). Then the reaction mixture was stirred at 15° C. for 0.5 h. A large amount of solid formed and the reaction was completed. The product N-(piperidin-4-ylmethyl)acetamide, hydrochloride was obtained by filtration as a white solid (265 g, 1307 mmol, 93.0% yield): $^1$H NMR (400 MHz, CD$_3$OD) δ ppm 3.41 (d, J=12.1 Hz, 2H), 3.22 (d, J=6.4 Hz, 2H), 2.99 (t, J=12.3 Hz, 2H), 2.13 (s, 3H), 1.99-1.85 (m, 3H), 1.52-1.39 (m, 2H).

Intermediate 3: Methyl 2-(piperidin-4-yl)acetate, hydrochloride

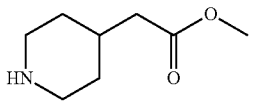

To a solution of 2-(1-(tert-butoxycarbonyl)piperidin-4-yl)acetic acid (62 g, 255 mmol) in MeOH (300 mL) was added sulfurous dichloride (40 mL, 353 mmol). The mixture was stirred at 50° C. for 10 h then concentrated to yield a white solid of methyl 2-(piperidin-4-yl)acetate, hydrochloride (50 g, 245 mmol, 96.0% yield): $^1$H NMR (400 MHz, CD$_3$OD) δ ppm 3.68 (s, 3H), 3.43-3.33 (m, 2H), 3.01 (t, J=12.8 Hz, 2H), 2.40-2.29 (m, 2H), 2.09 (m, 1H), 1.97 (d, J=14.1 Hz, 2H), 1.57-1.41 (m, 2H); ES-LCMS m/z 158.2 [M+H]⁺.

Intermediate 4: tert-Butyl 4-(5-((6-(3,5-dichlorophenyl)-4-(((methylsulfonyl)oxy)methyl)pyridin-2-yl)oxy)pyrimidin-2-yl)piperazine-1-carboxylate

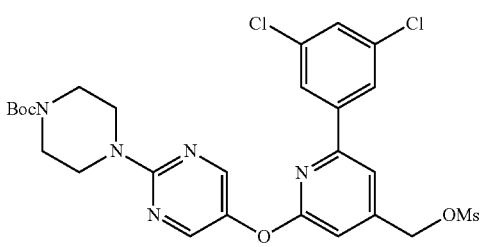

Step 1: 5-(Benzyloxy)-2-chloropyrimidine

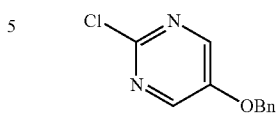

To a mixture of 2-chloropyrimidin-5-ol (45 g, 345 mmol) in DMF (1 L) was added Cs$_2$CO$_3$ (337 g, 1034 mmol) and (bromomethyl)benzene (49.1 mL, 414 mmol). The mixture was stirred at 15° C. for 8 h under N$_2$ atmosphere. Then the mixture was concentrated and saturated aqueous NaHCO$_3$ solution (150 mL) was added. The aqueous layer was extracted with EtOAc (500 mL×2), and the combined extracts were washed with brine (150 mL×2), dried over Na$_2$SO$_4$, filtered and concentrated to yield a yellow oil of 5-(benzyloxy)-2-chloropyrimidine (78 g, 318 mmol, 92.0% yield): $^1$H NMR (400 MHz, CD$_3$OD) δ ppm 8.45 (s, 2H), 7.52-7.29 (m, 5H), 5.23 (s, 2H); ES-LCMS m/z 221.2, 223.1 [M+H]⁺.

Step 2: tert-Butyl 4-(5-(benzyloxy)pyrimidin-2-yl)piperazine-1-carboxylate

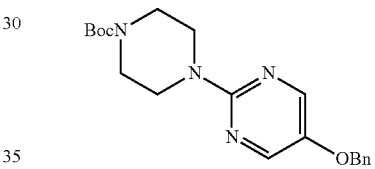

To a mixture of 5-(benzyloxy)-2-chloropyrimidine (15 g, 61.2 mmol) and tert-butyl piperazine-1-carboxylate (17.09 g, 92 mmol) in DMF (200 mL) was added Cs$_2$CO$_3$ (59.8 g, 184 mmol). The mixture was stirred at 120° C. for 10 h. The reaction mixture was concentrated and purified by silica gel column chromatography (PE/EtOAc=5/1). All fractions found to contain product by TLC (PE/EA=3/1, R$_f$=0.6) were combined and concentrated to yield a white solid of tert-butyl 4-(5-(benzyloxy)pyrimidin-2-yl)piperazine-1-carboxylate (10 g, 25.6 mmol, 41.9% yield): $^1$H NMR (400 MHz, CDCl$_3$) δ ppm 8.13 (s, 2H), 7.43-7.31 (m, 5H), 5.03 (s, 2H), 3.75-3.65 (m, 4H), 3.56-3.43 (m, 4H), 1.49 (s, 9H); ES-LCMS m/z 371.3 [M+H]⁺.

Step 3: tert-Butyl 4-(5-hydroxypyrimidin-2-yl)piperazine-1-carboxylate

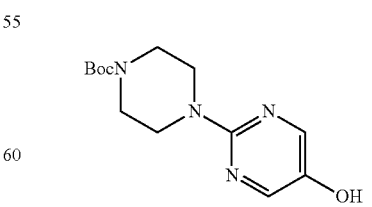

To a solution of tert-butyl 4-(5-(benzyloxy)pyrimidin-2-yl)piperazine-1-carboxylate (10 g, 25.6 mmol) in MeOH (30 mL) was added Pd/C (10 wt %, 2.73 g, 2.56 mmol). The mixture was stirred under 1 atm H$_2$ atmosphere at 15° C. for 0.5 h. The mixture was filtered and concentrated to yield a light yellow solid of tert-butyl 4-(5-hydroxypyrimidin-2-yl)piperazine-1-carboxylate (7.5 g, 22.74 mmol, 89.0% yield): ¹H NMR (400 MHz, CD₃OD)<5 ppm 8.03 (s, 2H), 3.70-3.59 (m, 4H), 3.50 (d, J=4.5 Hz, 4H), 1.50 (s, 9H); ES-LCMS m/z 225.2 [M–t–Bu+H]⁺.

Step 4: tert-Butyl 4-(5-((6-chloro-4-(methoxycarbonyl)pyridin-2-yl)oxy)pyrimidin-2-yl)piperazine-1-carboxylate

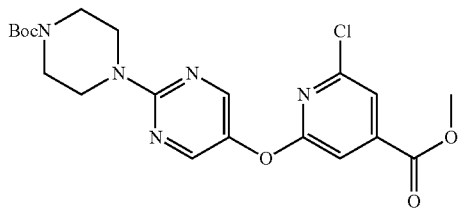 [SMILES: COC(=O)c1cc(Cl)nc(Oc2cnc(N3CCN(C(=O)OC(C)(C)C)CC3)nc2)c1]

To a mixture of methyl 2,6-dichloroisonicotinate, hydrochloride (6.7 g, 27.4 mmol) and tert-butyl 4-(5-hydroxypyrimidin-2-yl)piperazine-1-carboxylate (7.4 g, 22.44 mmol) in DMF (80 mL) was added K₂CO₃ (9.30 g, 67.3 mmol). The mixture was stirred at 50° C. for 10 h. Then the solution was concentrated and saturated aqueous NaHCO₃ solution (150 mL) was added. The aqueous layer was extracted with DCM (500 mL×2), and the combined extracts were washed with brine (150 mL×2), dried over Na₂SO₄, filtered and concentrated. The crude material was purified by silica gel column chromatography (PE/EtOAc=5/1). All fractions found to contain product by TLC (PE/EA=3/1, R_f=0.5) were combined and concentrated to yield a yellow oil of tert-butyl 4-(5-((6-chloro-4-(methoxycarbonyl)pyridin-2-yl)oxy)pyrimidin-2-yl)piperazine-1-carboxylate (8.4 g, 16.80 mmol, 74.9% yield): ¹H NMR (400 MHz, CD₃OD) δ ppm 8.31 (s, 2H), 7.62 (s, 1H), 7.51 (s, 1H), 3.99 (s, 3H), 3.90-3.80 (m, 4H), 3.55 (m, 4H), 1.51 (s, 9H); ES-LCMS m/z 394.2, 396.1 [M–t–Bu+H]⁺.

Step 5: tert-Butyl 4-(5-((6-(3,5-dichlorophenyl)-4-(methoxycarbonyl)pyridin-2-yl)oxy)pyrimidin-2-yl)piperazine-1-carboxylate

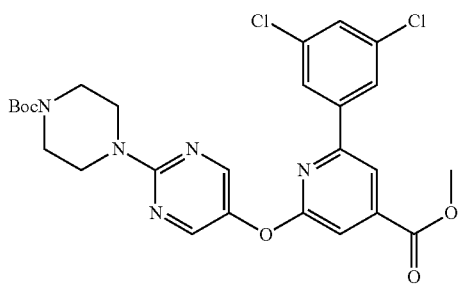 [SMILES: COC(=O)c1cc(Oc2cnc(N3CCN(C(=O)OC(C)(C)C)CC3)nc2)nc(-c2cc(Cl)cc(Cl)c2)c1]

To a mixture of tert-butyl 4-(5-((6-chloro-4-(methoxycarbonyl)pyridin-2-yl)oxy)pyrimidin-2-yl)piperazine-1-carboxylate (8 g, 16.00 mmol) and (3,5-dichlorophenyl)boronic acid (7.63 g, 40.0 mmol) in DMF (100 mL) was added K₂CO₃ (6.64 g, 48.0 mmol) and PdCl₂(dppf) (0.586 g, 0.800 mmol). The mixture was stirred at 80° C. for 2 h under N₂ atmosphere. The mixture was concentrated and purified by silica gel column chromatography (PE/EtOAc=5/1). All fractions found to contain product by TLC (PE/EA=3/1, R_f=0.4) were combined and concentrated to yield a colorless oil of tert-butyl 4-(5-((6-(3,5-dichlorophenyl)-4-(methoxycarbonyl)pyridine-2-yl)oxy)pyrimidin-2-yl)piperazine-1-carboxylate (7.4 g, 11.22 mmol, 70.1% yield): ¹H NMR (400 MHz, CDCl₃) δ ppm 8.30 (s, 2H), 7.95 (s, 1H), 7.75 (d, J=1.3 Hz, 2H), 7.48 (s, 1H), 7.37 (s, 1H), 4.00 (s, 3H), 3.89-3.75 (m, 4H), 3.60-3.45 (m, 4H), 1.49 (s, 9H); ES-LCMS m/z 504.1, 506.1 [M–t–Bu+H]⁺.

Step 6: tert-Butyl 4-(5-((6-(3,5-dichlorophenyl)-4-(hydroxymethyl)pyridin-2-yl)oxy)pyrimidin-2-yl)piperazine-1-carboxylate

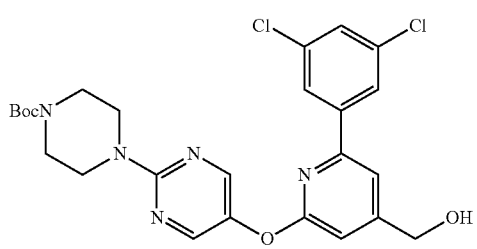

To a mixture of tert-butyl 4-(5-((6-(3,5-dichlorophenyl)-4-(methoxycarbonyl)pyridin-2-yl)oxy)pyrimidin-2-yl)piperazine-1-carboxylate (7.4 g, 11.22 mmol) in MeOH (150 mL) was added NaBH₄ (2.123 g, 56.1 mmol). The mixture was stirred at 15° C. for 10 min under N₂ atmosphere then concentrated and saturated aqueous NaHCO₃ solution (150 mL) was added. The aqueous layer was extracted with DCM (500 mL×2) and the combined extracts were washed with brine (150 mL×2), dried over Na₂SO₄, filtered and concentrated to yield a yellow oil of tert-butyl 4-(5-((6-(3,5-dichlorophenyl)-4-(hydroxymethyl)pyridine-2-yl)oxy)pyrimidin-2-yl)piperazine-1-carboxylate (7.2 g, 10.82 mmol, 96.0% yield): ¹H NMR (400 MHz, CD₃OD) δ ppm 8.35 (s, 2H), 7.81 (s, 2H), 7.60 (s, 1H), 7.44 (s, 1H), 7.06 (s, 1H), 4.75 (s, 2H), 3.89-3.82 (m, 4H), 3.54 (m, 4H), 1.51 (s, 9H); ES-LCMS m/z 532.2, 534.2 [M+H]⁺.

Step 7: tert-Butyl 4-(5-((6-(3,5-dichlorophenyl)-4-(((methylsulfonyl)oxy)methyl)pyridin-2-yl)oxy)pyrimidin-2-yl)piperazine-1-carboxylate

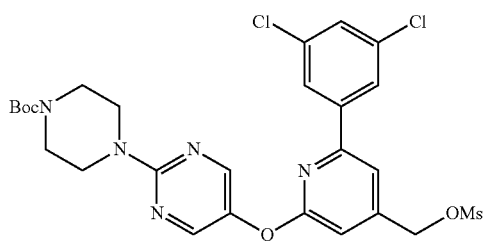

To a mixture of tert-butyl 4-(5-((6-(3,5-dichlorophenyl)-4-(hydroxymethyl)pyridin-2-yl)oxy)pyrimidin-2-yl)piperazine-1-carboxylate (4.5 g, 6.76 mmol) in DCM (150 mL) was added MsCl (0.79 mL, 10.14 mmol) and DIEA (3.54 mL, 20.28 mmol). The mixture was stirred at 15° C. for 10 min under N₂ atmosphere. Then the solution was concentrated and saturated aqueous NaHCO$_3$ solution (150 mL) was added. The aqueous layer was extracted with DCM (500 mL×2), and the combined extracts were washed with brine (150 mL×2), dried over Na$_2$SO$_4$, filtered and concentrated to yield a yellow oil of tert-butyl 4-(5-((6-(3,5-dichlorophenyl)-4-(((methylsulfonyl)oxy)methyl)pyridin-2-yl)oxy)pyrimidin-2-yl)piperazine-1-carboxylate (5 g, 6.55 mmol, 97.0% yield): $^1$H NMR (400 MHz, CD$_3$OD) δ ppm 8.37 (s, 2H), 7.85 (s, 2H), 7.48 (s, 1H), 7.41 (s, 1H), 7.16 (s, 1H), 3.86 (d, J=5.5 Hz, 6H), 3.55 (s, 4H), 3.25-3.23 (m, 3H), 1.51 (s, 9H); ES-LCMS m/z 554.2, 556.2 [M−t−Bu+H]$^+$.

Intermediate 5: tert-Butyl 4-(5-((6-(3,5-dichlorophenyl)-4-(((methylsulfonyl)oxy)methyl)pyridin-2-yl)oxy)pyrimidin-2-yl)-1,4-diazepane-1-carboxylate

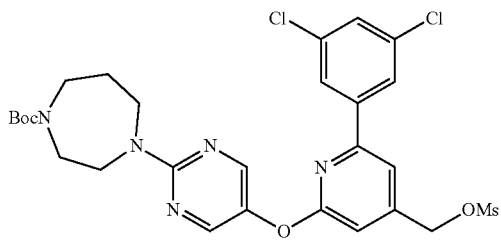 [SMILES: CC(C)(C)OC(=O)N1CCCN(c2ncc(Oc3cc(COS(C)(=O)=O)cc(-c4cc(Cl)cc(Cl)c4)n3)cn2)CC1]

Step 1: 1-(5-(Benzyloxy)pyrimidin-2-yl)-1,4-diazepane

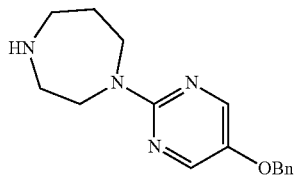 [SMILES: c1ccc(COc2cnc(N3CCCNCC3)nc2)cc1]

To a solution of 5-(benzyloxy)-2-chloropyrimidine (4 g, 17.22 mmol) and Cs$_2$CO$_3$ (11.22 g, 34.4 mmol) in DMF (50 mL) was added 1,4-diazepane (3.45 g, 34.4 mmol). Then the reaction mixture was stirred at 130° C. for 12 h. The solid was filtered off and the solution was concentrated to yield the crude product which was purified by silica gel chromatography (PE/EtOAc=1/0 to 1/2). All fractions found to contain product by TLC (PE/EtOAc=2/1, R$_f$=0.15) were combined and concentrated to yield a pale yellow solid of 1-(5-(benzyloxy)pyrimidin-2-yl)-1,4-diazepane (4.0 g, 12.97 mmol, 75.0% yield): $^1$H NMR (400 MHz, CDCl$_3$) δ ppm 8.17-7.97 (m, 2H), 7.45-7.25 (m, 5H), 5.00 (s, 2H), 3.92-3.65 (m, 4H), 3.12-2.96 (m, 2H), 2.90-2.71 (m, 2H), 1.95-1.82 (m, 2H); ES-LCMS m/z 285.2 [M+H]$^+$.

Step 2: tert-Butyl 4-(5-(benzyloxy)pyrimidin-2-yl)-1,4-diazepane-1-carboxylate

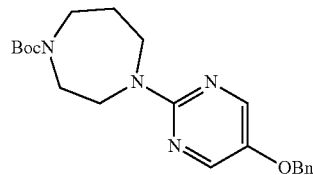 [SMILES: CC(C)(C)OC(=O)N1CCCN(c2ncc(OCc3ccccc3)cn2)CC1]

To a solution of 1-(5-(benzyloxy)pyrimidin-2-yl)-1,4-diazepane (4 g, 12.97 mmol) and DIEA (5.03 g, 38.9 mmol) in DCM (50 mL) was added Boc$_2$O (3.61 mL, 15.57 mmol). Then the reaction mixture was stirred at 20° C. for 12 h. DCM (50 mL) was added and washed with aqueous citric acid (50 mL×3). The organic layers was dried over Na$_2$SO$_4$ and concentrated to yield a pale yellow solid of tert-butyl 4-(5-(benzyloxy)pyrimidin-2-yl)-1,4-diazepane-1-carboxylate (3.9 g, 9.13 mmol, 70.4% yield): $^1$H NMR (400 MHz, CDCl$_3$) δ ppm 8.11 (d, J=2.6 Hz, 2H), 7.44-7.28 (m, 5H), 5.05 (d, J=3.1 Hz, 2H), 3.82 (t, J=5.1 Hz, 2H), 3.72 (q, J=5.6 Hz, 2H), 3.55 (td, J=5.7, 19.4 Hz, 2H), 3.39-3.31 (m, 2H), 1.92-1.81 (m, 2H), 1.32 (s, 9H); ES-LCMS m/z 385.2 [M+H]$^+$.

Step 3: tert-Butyl 4-(5-hydroxypyrimidin-2-yl)-1,4-diazepane-1-carboxylate

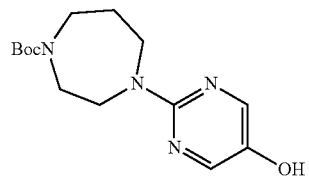 [SMILES: CC(C)(C)OC(=O)N1CCCN(c2ncc(O)cn2)CC1]

To a solution of tert-butyl 4-(5-(benzyloxy)pyrimidin-2-yl)-1,4-diazepane-1-carboxylate (3.9 g, 9.13 mmol) in MeOH (50 mL) was added Pd/C (10 wt %, 0.972 g, 0.913 mmol). Then the reaction mixture was stirred at 20° C. for 1 h under H$_2$ atmosphere (15 psi). The solid was filtered off and the solution was concentrated to yield a yellow oil of tert-butyl 4-(5-hydroxypyrimidin-2-yl)-1,4-diazepane-1-carboxylate (2.9 g, 8.87 mmol, 97.0% yield): $^1$H NMR (400 MHz, CDCl$_3$) δ ppm 7.97 (d, J=2.2 Hz, 2H), 3.80 (t, J=5.7 Hz, 2H), 3.70 (q, J=5.6 Hz, 2H), 3.61-3.52 (m, 2H), 3.36 (s, 2H), 1.91-1.79 (m, 2H), 1.36 (d, J=15.9 Hz, 9H); ES-LCMS m/z 295.2 [M+H]$^+$.

Step 4: tert-Butyl 4-(5-((6-chloro-4-(methoxycarbonyl)pyridin-2-yl)oxy)pyrimidin-2-yl)-1,4-diazepane-1-carboxylate

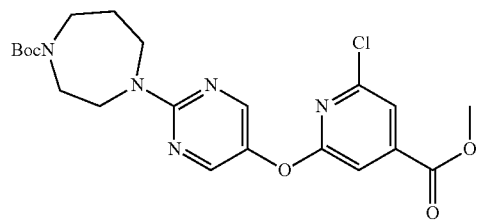 [SMILES: COC(=O)c1cc(Cl)nc(Oc2cnc(N3CCCN(C(=O)OC(C)(C)C)CC3)nc2)c1]

To a solution of tert-butyl 4-(5-hydroxypyrimidin-2-yl)-1,4-diazepane-1-carboxylate (2.9 g, 8.87 mmol) and methyl 2,6-dichloroisonicotinate (3.08 g, 13.30 mmol) in DMF (50 mL) was added K$_2$CO$_3$ (2.451 g, 17.73 mmol). Then the reaction mixture was stirred at 80° C. for 2 h. The solid was filtered off and the solution was concentrated to yield the crude product which was purified by column chromatography (PE/EtOAc=1/0 to 1/1). All fractions found to contain product by TLC (PE/EtOAc=5/1, R$_f$=0.45) were combined and concentrated to yield a pale yellow solid of tert-butyl 4-(5-((6-chloro-4-(methoxycarbonyl)pyridin-2-yl)oxy)pyrimidin-2-yl)-1,4-diazepane-1-carboxylate (3.2 g, 6.78 mmol, 76.0% yield): $^1$H NMR (400 MHz, CDCl$_3$) δ ppm 8.22 (s, 2H), 7.56 (s, 1H), 7.39 (s, 1H), 3.96 (s, 3H), 3.92-3.85 (m, 2H), 3.80-3.74 (m, 2H), 3.57 (s, 2H), 3.42-3.29 (m, 2H), 1.97 (q, J=6.1 Hz, 2H), 1.43 (d, J=7.9 Hz, 9H); ES-LCMS m/z 464.2, 466.2 [M+H]$^+$.

Step 5: tert-Butyl 4-(5-((6-(3,5-dichlorophenyl)-4-(methoxycarbonyl)pyridin-2-yl)oxy)pyrimidin-2-yl)-1,4-diazepane-1-carboxylate

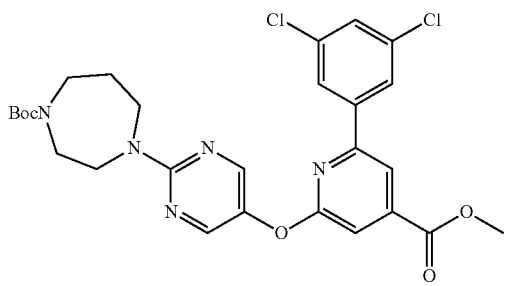 [SMILES: COC(=O)c1cc(Oc2cnc(N3CCCN(C(=O)OC(C)(C)C)CC3)nc2)nc(-c2cc(Cl)cc(Cl)c2)c1]

To a solution of tert-butyl 4-(5-((6-chloro-4-(methoxycarbonyl)pyridin-2-yl)oxy)pyrimidin-2-yl)-1,4-diazepane-1-carboxylate (3.2 g, 6.78 mmol) and (3,5-dichlorophenyl)boronic acid (1.940 g, 10.17 mmol) in DMF (50 mL) was added K$_2$CO$_3$ (1.873 g, 13.55 mmol) and PdCl$_2$(dppf) (0.248 g, 0.339 mmol) under N$_2$ atmosphere. Then the reaction mixture was stirred at 80° C. for 2 h. The solution was concentrated to yield the crude product which was purified by column chromatography (PE/EtOAc=1/0 to 1/1). All fractions found to contain product by TLC (PE/EtOAc=3/1, R$_f$=0.55) were combined and concentrated to yield a pale yellow solid of tert-butyl 4-(5-((6-(3,5-dichlorophenyl)-4-(methoxycarbonyl)pyridin-2-yl)oxy)pyrimidin-2-yl)-1,4-diazepane-1-carboxylate (3.1 g, 4.88 mmol, 72.0% yield): $^1$H NMR (400 MHz, CDCl$_3$) δ ppm 8.29 (s, 2H), 7.96 (s, 1H), 7.77 (d, J=0.9 Hz, 2H), 7.49 (s, 1H), 7.37 (s, 1H), 4.00 (s, 3H), 3.94-3.86 (m, 2H), 3.79 (d, J=5.3 Hz, 2H), 3.58 (d, J=4.4 Hz, 2H), 3.40-3.27 (m, 2H), 2.04-1.97 (m, 2H), 1.45 (d, J=6.2 Hz, 9H); ES-LCMS m/z 574.2, 576.2 [M+H]$^+$.

Step 6: tert-Butyl 4-(5-((6-(3,5-dichlorophenyl)-4-(hydroxymethyl)pyridin-2-yl)oxy)pyrimidin-2-yl)-1,4-diazepane-1-carboxylate

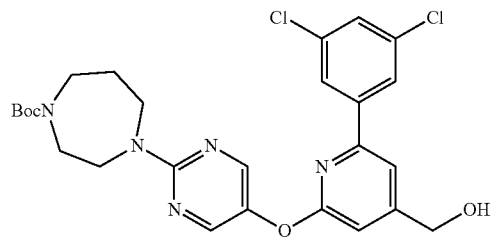 [SMILES: CC(C)(C)OC(=O)N1CCCN(c2ncc(Oc3cc(CO)cc(-c4cc(Cl)cc(Cl)c4)n3)cn2)CC1]

To a solution of tert-butyl 4-(5-((6-(3,5-dichlorophenyl)-4-(methoxycarbonyl)pyridin-2-yl)oxy)pyrimidin-2-yl)-1,4-diazepane-1-carboxylate (1.2 g, 1.889 mmol) in MeOH (50 mL) was added NaBH$_4$ (0.429 g, 11.33 mmol) in portions at 20° C. Then the reaction mixture was stirred at 20° C. for 1 h. TLC (PE/EtOAc=3/1, R$_f$=0.55) showed the reaction was completed. The solution was concentrated and DCM (50 mL) was added. The organic layer was washed with water (50 mL) and brine (50 mL). The combined organic layers dried over Na$_2$SO$_4$ and concentrated to yield a pale yellow solid of tert-butyl 4-(5-((6-(3,5-dichlorophenyl)-4-(hydroxymethyl)pyridin-2-yl)oxy)pyrimidin-2-yl)-1,4-diazepane-1-carboxylate (1.1 g, 1.707 mmol, 90.0% yield): $^1$H NMR (400 MHz, CDCl$_3$) δ ppm 8.15-8.00 (m, 2H), 7.56 (s, 2H), 7.30-7.22 (m, 1H), 7.17 (s, 1H), 6.78 (s, 1H), 4.65 (s, 2H), 3.74 (s, 2H), 3.63 (d, J=4.9 Hz, 2H), 3.42 (s, 2H), 3.24-3.09 (m, 2H), 1.86 (s, 2H), 1.29 (d, J=4.4 Hz, 9H); ES-LCMS m/z 546.2, 548.2 [M+H]$^+$.

Step 7: tert-Butyl 4-(5-((6-(3,5-dichlorophenyl)-4-(((methylsulfonyl)oxy)methyl)pyridin-2-yl)oxy)pyrimidin-2-yl)-1,4-diazepane-1-carboxylate

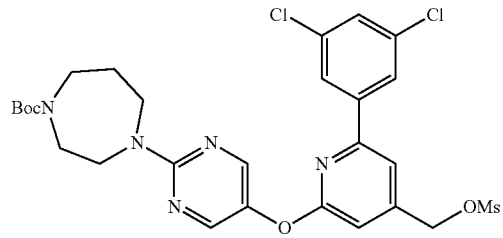 [SMILES: CC(C)(C)OC(=O)N1CCCN(c2ncc(Oc3cc(COS(C)(=O)=O)cc(-c4cc(Cl)cc(Cl)c4)n3)cn2)CC1]

To a solution of tert-butyl 4-(5-((6-(3,5-dichlorophenyl)-4-(hydroxymethyl)pyridin-2-yl)oxy)pyrimidin-2-yl)-1,4-diazepane-1-carboxylate (1.1 g, 1.707 mmol) and DIEA (0.662 g, 5.12 mmol) in DCM (20 mL) was added MsCl (0.2 mL, 2.56 mmol). Then the reaction mixture was stirred at 0° C. for 10 mins. Water (50 mL) was added and extracted with DCM (25 mL×3). The combined organic layers were dried over Na$_2$SO$_4$ and concentrated to yield a yellow solid of tert-butyl 4-(5-((6-(3,5-dichlorophenyl)-4-(((methylsulfonyl)oxy)methyl)pyridin-2-yl)oxy)pyrimidin-2-yl)-1,4-diazepane-1-carboxylate (1.25 g, 1.629 mmol, 95.0% yield): $^1$H NMR (400 MHz, CDCl$_3$) δ ppm 8.28 (s, 2H), 7.72 (s, 2H), 7.42 (s, 1H), 7.37 (s, 1H), 6.96 (s, 1H), 5.29 (s, 2H), 3.96-3.88 (m, 2H), 3.79 (d, J=5.0 Hz, 2H), 3.58 (d, J=4.0 Hz, 2H), 3.39-3.28 (m, 2H), 3.13 (s, 3H), 2.02 (m, 2H), 1.45 (d, J=5.5 Hz, 9H); ES-LCMS m/z 624.2, 626.2 [M+H]⁺.

Intermediate 6: tert-Butyl 4-(5-((6-(3,5-dichlorophenyl)-4-(((methylsulfonyl)oxy)methyl)pyridin-2-yl)oxy)pyridin-2-yl)piperazine-1-carboxylate

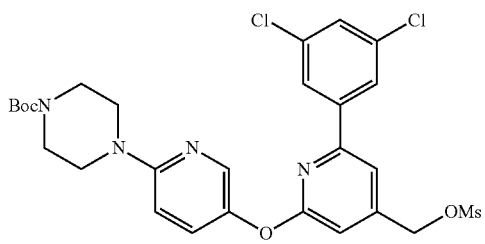

Step 1: 5-(Benzyloxy)-2-bromopyridine

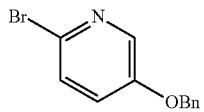 [SMILES: Brc1ccc(OCc2ccccc2)cn1]

To a solution of 6-bromopyridin-3-ol (30 g, 172 mmol) and (bromomethyl)benzene (35.4 g, 207 mmol) in DMF (300 mL) was added K₂CO₃ (35.7 g, 259 mmol). The mixture was stirred at 20° C. for 2 h. Then the mixture was filtered and the filtration was concentrated and separated between DCM (500 mL) and saturated aqueous NaHCO₃ (300 mL) solution. The combined organic extract was washed with brine (200 mL), dried over Na₂SO₄, filtered and concentrated. The crude material was purified by silica gel column chromatography (PE/EtOAc=5/1). All fractions found to contain product by TLC (PE/EtOAc=5/1, R$_f$=0.6) were combined and concentrated to yield a brown solid of 5-(benzyloxy)-2-bromopyridine (40 g, 148 mmol, 86.0% yield): ¹H NMR (400 MHz, CDCl₃) δ ppm 8.13 (d, J=2.9 Hz, 1H), 7.49-7.29 (m, 6H), 7.21-7.09 (m, 1H), 5.08 (s, 2H); ES-LCMS m/z 264.0, 266.0 [M+H]⁺.

Step 2: tert-Butyl 4-(5-(benzyloxy)pyridin-2-yl)piperazine-1-carboxylate

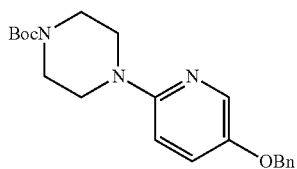 [SMILES: CC(C)(C)OC(=O)N1CCN(c2ccc(OCc3ccccc3)cn2)CC1]

To a mixture of tert-butyl piperazine-1-carboxylate (30.5 g, 164 mmol) and Cs₂CO₃ (89 g, 273 mmol) in THF (500 mL) was added Pd₂(dba)₃ (12.48 g, 13.63 mmol), 5-(benzyloxy)-2-bromopyridine (36 g, 136 mmol) and (±)-BINAP (8.49 g, 13.63 mmol) under N₂ atmosphere. The mixture was stirred at 70° C. for 12 h then concentrated, separated between DCM (500 mL) and saturated aqueous NaHCO₃ (200 mL) solution. The combined organic extract was washed with brine (200 mL), dried over Na₂SO₄, filtered and concentrated. The crude material was purified by silica gel column chromatography (PE/EtOAc=4/1). All fractions found to contain product by TLC (PE/EtOAc=4/1, R$_f$=0.6) were combined and concentrated to yield a light yellow solid of tert-butyl 4-(5-(benzyloxy)pyridin-2-yl)piperazine-1-carboxylate (50 g, 122 mmol, 89.0% yield): ¹H NMR (400 MHz, CDCl₃) δ ppm 8.39 (d, J=2.6 Hz, 1H), 8.23 (d, J=8.8 Hz, 1H), 7.99 (d, J=3.1 Hz, 1H), 7.40-7.36 (m, 5H), 5.03 (s, 2H), 3.53 (d, J=5.3 Hz, 4H), 3.39 (d, J=5.3 Hz, 4H), 1.48 (s, 9H); ES-LCMS m/z 370.3 [M+H]⁺.

Step 3: tert-Butyl 4-(5-hydroxypyridin-2-yl)piperazine-1-carboxylate

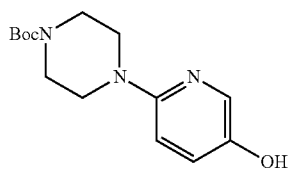

To a solution of tert-butyl 4-(5-(benzyloxy)pyridin-2-yl)piperazine-1-carboxylate (45 g, 122 mmol) in MeOH (500 mL) was added Pd/C (10 wt %, 12.96 g, 12.18 mmol). The mixture was stirred at 20° C. under H₂ atmosphere at 50 psi for 10 h. The solution was filtered and concentrated to yield light yellow oil of tert-butyl 4-(5-hydroxypyridin-2-yl)piperazine-1-carboxylate (26 g, 88 mmol, 72.6% yield): ¹H NMR (400 MHz, CDCl₃) δ ppm 7.86 (br. s, 1H), 7.18-7.04 (m, 1H), 6.61 (d, J=8.8 Hz, 1H), 3.62-3.47 (m, 4H), 3.33 (d, J=4.0 Hz, 4H), 1.47 (s, 9H); ES-LCMS m/z 280.2 [M+H]⁺.

Step 4: tert-Butyl 4-(5-((6-chloro-4-(methoxycarbonyl)pyridin-2-yl)oxy)pyridin-2-yl)piperazine-1-carboxylate

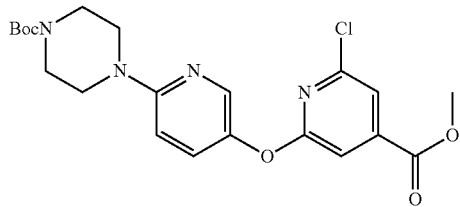

To a mixture of methyl 2,6-dichloroisonicotinate (8 g, 38.8 mmol) and K₂CO₃ (10.73 g, 78 mmol) in DMF (200 mL) was added tert-butyl 4-(5-hydroxypyridin-2-yl)piperazine-1-carboxylate (14.10 g, 50.5 mmol). The mixture was stirred at 80° C. for 2 h. Then the solution was concentrated, separated between DCM (600 mL) and saturated NaHCO₃ solution (300 mL). The combined organic extract was washed with brine (200 mL), dried over Na₂SO₄, filtered and concentrated. The crude material was purified by silica gel column chromatography (PE/EtOAc=1/1). All fractions found to contain product by TLC (PE/EtOAc=1/1, R$_f$=0.3) were combined and concentrated to yield a light yellow solid of tert-butyl 4-(5-((6-chloro-4-(methoxycarbonyl)pyridin-2-yl)oxy)pyridin-2-yl)piperazine-1-carboxylate (15 g, 30.1 mmol, 77.0% yield): ¹H NMR (400 MHz, CDCl₃) δ ppm 8.07 (d, J=2.6 Hz, 1H), 7.54 (s, 1H), 7.37-7.27 (m, 2H), 6.68

(d, J=8.8 Hz, 1H), 3.95-3.91 (m, 3H), 3.56-3.54 (m, 8H), 1.48 (s, 9H); ES-LCMS m/z 449.1, 451.1 [M+H]⁺.

Step 5: tert-Butyl 4-(5-((6-(3,5-dichlorophenyl)-4-(methoxycarbonyl)pyridin-2-yl)oxy)pyridin-2-yl)piperazine-1-carboxylate

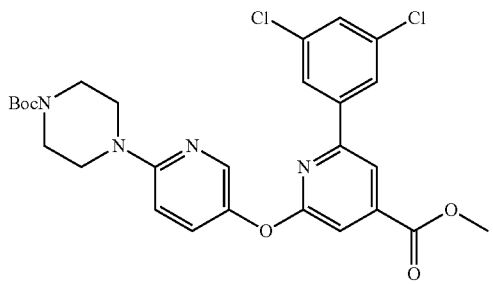 [SMILES: COC(=O)c1cc(Oc2ccc(N3CCN(C(=O)OC(C)(C)C)CC3)nc2)nc(-c2cc(Cl)cc(Cl)c2)c1]

To a solution of tert-butyl 4-(5-((6-chloro-4-(methoxycarbonyl)pyridin-2-yl)oxy)pyridin-2-yl)piperazine-1-carboxylate (15 g, 33.4 mmol) and (3,5-dichlorophenyl)boronic acid (8.93 g, 46.8 mmol) in 1,4-dioxane (200 mL) was added PdCl₂(dppf) (2.445 g, 3.34 mmol) and K₂CO₃ (13.85 g, 100 mmol) under N₂ atmosphere. The mixture was stirred at 90° C. for 4 h. Water (200 mL) was added then extracted with DCM (200 mL×3). The organic layers were combined, dried over Na₂SO₄, filtered and concentrated. The crude material was purified by column chromatography (PE/EtOAc=1/1) to yield a brown solid of tert-butyl 4-(5-((6-(3,5-dichlorophenyl)-4-(methoxycarbonyl)pyridin-2-yl)oxy)pyridin-2-yl)piperazine-1-carboxylate (10 g, 16.27 mmol, 48.7% yield): ¹H NMR (400 MHz, CDCl₃) δ ppm 8.13 (d, J=2.6 Hz, 1H), 7.93 (s, 1H), 7.78 (d, J=1.3 Hz, 2H), 7.54-7.38 (m, 2H), 7.38-7.33 (m, 1H), 6.73 (d, J=9.3 Hz, 1H), 3.98 (s, 3H), 3.56-3.54 (m, 8H), 1.49 (s, 9H); ES-LCMS m/z 559.1, 561.1 [M+H]⁺.

Step 6: tert-Butyl 4-(5-((6-(3,5-dichlorophenyl)-4-(hydroxymethyl)pyridin-2-yl)oxy)pyridin-2-yl)piperazine-1-carboxylate

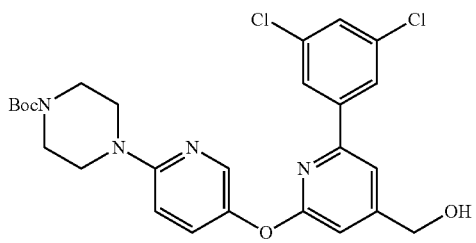 [SMILES: CC(C)(C)OC(=O)N1CCN(c2ccc(Oc3cc(CO)cc(-c4cc(Cl)cc(Cl)c4)n3)cn2)CC1]

To a solution of tert-butyl 4-(5-((6-(3,5-dichlorophenyl)-4-(methoxycarbonyl)pyridin-2-yl)oxy)pyridin-2-yl)piperazine-1-carboxylate (9.9 g, 17.70 mmol) in MeOH (300 mL) was added NaBH₄ (2.008 g, 53.1 mmol). The solution was stirred at 20° C. for 0.5 h. Saturated aqueous NH₄Cl solution (10 mL) was added and the solution was concentrated, separated between DCM (300 mL) and saturated NaHCO₃ solution (100 mL). The combined organic extract was washed with brine, dried over Na₂SO₄, filtered and concentrated. The crude material was purified by silica gel column chromatography (PE/EtOAc=1/1). All fractions found to contain product by TLC (PE/EtOAc=1/1, R_f=0.6) were combined and concentrated to yield light yellow oil of tert-butyl 4-(5-((6-(3,5-dichlorophenyl)-4-(hydroxymethyl)pyridin-2-yl)oxy)pyridin-2-yl)piperazine-1-carboxylate (8 g, 13.55 mmol, 77.0% yield): ¹H NMR (400 MHz, CDCl₃) δ ppm 8.10 (d, J=2.6 Hz, 1H), 7.75 (d, J=1.8 Hz, 2H), 7.44-7.38 (m, 2H), 7.33 (s, 1H), 6.84 (s, 1H), 6.72 (d, J=8.8 Hz, 1H), 4.78 (d, J=3.5 Hz, 2H), 3.56-3.54 (m, 8H), 1.49 (s, 9H); ES-LCMS m/z 531.1, 533.1 [M+H]⁺.

Step 7: tert-Butyl 4-(5-((6-(3,5-dichlorophenyl)-4-(((methylsulfonyl)oxy)methyl)pyridin-2-yl)oxy)pyridin-2-yl)piperazine-1-carboxylate

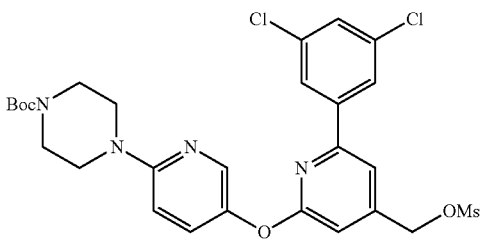 [SMILES: CC(C)(C)OC(=O)N1CCN(c2ccc(Oc3cc(COS(C)(=O)=O)cc(-c4cc(Cl)cc(Cl)c4)n3)cn2)CC1]

To a solution of tert-butyl 4-(5-((6-(3,5-dichlorophenyl)-4-(hydroxymethyl)pyridin-2-yl)oxy)pyridin-2-yl)piperazine-1-carboxylate (6 g, 11.29 mmol) and DIEA (2.92 g, 22.58 mmol) in DCM (200 mL) was added MsCl (1.552 g, 13.55 mmol). The solution was stirred at 20° C. for 0.5 h. Then the solution was washed with water (100 mL×3). The organic layer was dried over Na₂SO₄, filtered and concentrated to yield brown oil of tert-butyl 4-(5-((6-(3,5-dichlorophenyl)-4-(((methylsulfonyl)oxy)methyl)pyridin-2-yl)oxy)pyridin-2-yl)piperazine-1-carboxylate (6 g, 8.86 mmol, 78.0% yield): ¹H NMR (400 MHz, CDCl₃) δ ppm 8.12 (d, J=2.6 Hz, 1H), 7.73 (d, J=1.8 Hz, 2H), 7.46-7.32 (m, 3H), 6.88 (s, 1H), 6.73 (d, J=9.3 Hz, 1H), 5.26 (s, 2H), 3.58-3.55 (m, 8H), 3.10 (s, 3H), 1.49 (s, 9H); ES-LCMS m/z 609.1, 611.1 [M+H]⁺.

Intermediate 7: (2-(3,5-Dichlorophenyl)-6-((6-(piperazin-1-yl)pyridin-3-yl)oxy)pyridine-4-yl)methanol, 3 hydrochloride

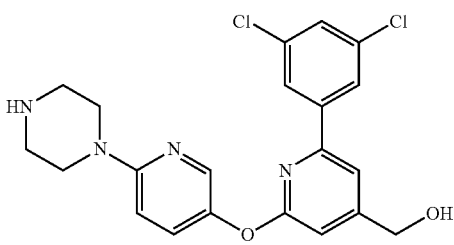 [SMILES: OCc1cc(Oc2ccc(N3CCNCC3)nc2)nc(-c2cc(Cl)cc(Cl)c2)c1]

To a solution of tert-butyl 4-(5-((6-(3,5-dichlorophenyl)-4-(hydroxymethyl)pyridin-2-yl)oxy)pyridin-2-yl)piperazine-1-carboxylate (2.5 g, 3.39 mmol) in MeOH (20 mL) was added HCl solution (4 M in MeOH, 20 mL, 80 mmol). The mixture was stirred at 20° C. for 0.5 h. The mixture was concentrated to yield a brown solid of (2-(3,5-dichlorophenyl)-6-((6-(piperazin-1-yl)pyridin-3-yl)oxy)pyridin-4-yl)methanol, 3 hydrochloride (1.8 g, 2.483 mmol, 73.3% yield): ¹H NMR (400 MHz, CD₃OD) δ ppm 8.29-8.19 (m, 2H), 7.83 (d, J=1.5 Hz, 2H), 7.70 (s, 1H), 7.66-7.61 (m, 1H), 7.49 (s, 1H), 7.19 (s, 1H), 4.79 (s, 2H), 4.11-4.06 (m, 4H), 3.56-3.51 (m, 4H); ES-LCMS m/z 431.1, 433.1 [M+H]⁺.

Intermediate 8: Ethyl 3-((4-(5-((6-(3,5-dichlorophenyl)-4-(((methylsulfonyl)oxy)methyl)pyridin-2-yl)oxy)pyridin-2-yl)piperazin-1-yl)propanoate

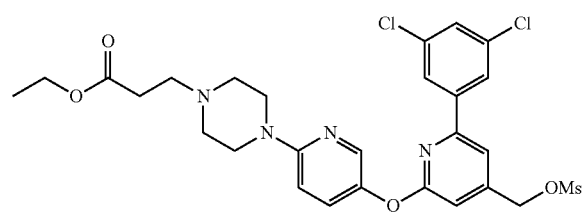 [SMILES: CCOC(=O)CCN1CCN(c2ccc(Oc3cc(COS(C)(=O)=O)cc(-c4cc(Cl)cc(Cl)c4)n3)cn2)CC1]

Step 1: Ethyl 3-(4-(5-((6-(3,5-dichlorophenyl)-4-(hydroxymethyl)pyridin-2-yl)oxy)pyridin-2-yl)piperazin-1-yl)propanoate

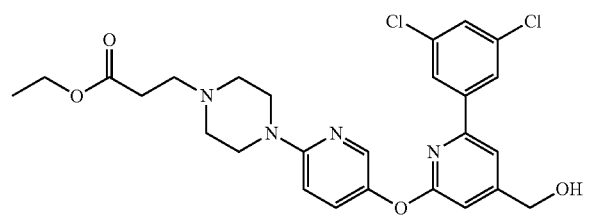 [SMILES: CCOC(=O)CCN1CCN(c2ccc(Oc3cc(CO)cc(-c4cc(Cl)cc(Cl)c4)n3)cn2)CC1]

To a mixture of (2-(3,5-dichlorophenyl)-6-((6-(piperazin-1-yl)pyridin-3-yl)oxy)pyridin-4-yl)methanol, 3 hydrochloride (1.8 g, 2.483 mmol), K₂CO₃ (1.030 g, 7.45 mmol) in DMF (5 mL) was added ethyl 3-bromopropanoate (1.349 g, 7.45 mmol). The mixture was stirred at 80° C. for 3 h then concentrated and the residue was diluted with DCM (100 mL) and water (100 mL). The aqueous phase was extracted with DCM (100 mL×2). The combined organic layers were dried over Na₂SO₄, filtered and concentrated to yield crude product which was purified by silica gel column chromatography on silica gel (DCM/MeOH=1/0 to 10/1). All fractions found to contain product by TLC (DCM/MeOH=10/1, R$_f$=0.5) were combined and concentrated to yield a brown solid of ethyl 3-(4-(5-((6-(3,5-dichlorophenyl)-4-(hydroxymethyl)pyridin-2-yl)oxy)pyridin-2-yl)piperazin-1-yl)propanoate (1.2 g, 2.073 mmol, 83.0% yield): ¹H NMR (400 MHz, CDCl₃) δ ppm 8.08 (d, J=2.6 Hz, 1H), 7.78-7.73 (m, 2H), 7.39 (td, J=5.8, 3.0 Hz, 2H), 7.32 (s, 1H), 6.81 (s, 1H), 6.70 (d, J=9.3 Hz, 1H), 4.79-4.72 (m, 2H), 4.14 (q, J=7.1 Hz, 2H), 3.52 (d, J=5.3 Hz, 4H), 2.77-2.72 (m, 2H), 2.63-2.54 (m, 6H), 1.25 (t, J=7.1 Hz, 3H); ES-LCMS m/z 531.1, 533.1 [M+H]⁺.

Step 2: Ethyl 3-(4-(5-((6-(3,5-dichlorophenyl)-4-(((methylsulfonyl)oxy)methyl)pyridin-2-yl)oxy)pyridin-2-yl)piperazin-1-yl)propanoate

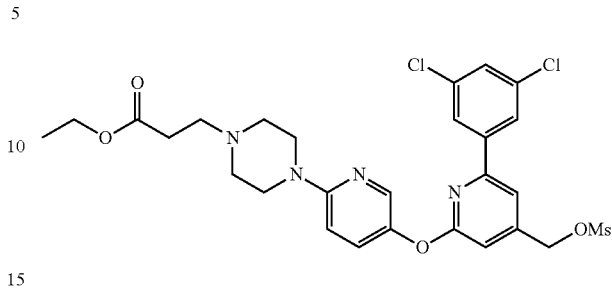

To a mixture of ethyl 3-(4-(5-((6-(3,5-dichlorophenyl)-4-(hydroxymethyl)pyridin-2-yl)oxy)pyridin-2-yl)piperazin-1-yl)propanoate (0.15 g, 0.259 mmol), DIEA (0.136 mL, 0.777 mmol) in DCM (50 mL) was added MsCl (0.040 mL, 0.518 mmol). The mixture was stirred at 20° C. for 0.5 h followed by addition of water (50 mL) and extraction with DCM (50 mL×2). The combined organic layers were dried over Na₂SO₄, filtered and concentrated to yield a brown solid of ethyl 3-(4-(5-((6-(3,5-dichlorophenyl)-4-(((methylsulfonyl)oxy)methyl)pyridin-2-yl)oxy)pyridin-2-yl)piperazin-1-yl)propanoate (160 mg, 0.191 mmol, 73.5% yield): ¹H NMR (400 MHz, CDCl₃) δ ppm 8.07 (br. s, 1H), 7.71 (br. s, 2H), 7.40-7.33 (m, 2H), 7.20 (br. s, 1H), 6.82 (d, J=11.5 Hz, 1H), 6.69 (d, J=8.8 Hz, 1H), 5.28-5.18 (m, 2H), 4.15-4.07 (m, 2H), 3.51 (br. s, 4H), 3.13-3.03 (m, 3H), 2.76-2.66 (m, 2H), 2.60-2.49 (m, 6H), 1.27-1.20 (m, 3H); ES-LCMS m/z 609.2, 611.2 [M+H]⁺.

Intermediate 9: tert-Butyl 4-(5-bromopyrimidin-2-yl)piperazine-1-carboxylate

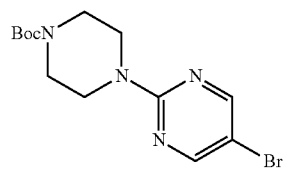 [SMILES: CC(C)(C)OC(=O)N1CCN(c2ncc(Br)cn2)CC1]

To a solution of tert-butyl piperazine-1-carboxylate (28.9 g, 155 mmol) in DML (200 mL) was added 5-bromo-2-chloropyrimidine (20 g, 103 mmol) and Cs₂CO₃ (101 g, 310 mmol). The mixture was stirred at 80° C. for 10 h. Then crude product was separated between DCM (500 mL) and saturated NaHCO₃ solution (300 mL). The combined organic extract was washed with brine (200 mL), dried over Na₂SO₄, filtered and concentrated. The crude material was purified by silica gel column chromatography (PE/EtOAc=3/1). All fractions found to contain product by TLC (PE/EtOAc=3/1, R$_f$=0.6) were combined and concentrated to yield a white solid of tert-butyl 4-(5-bromopyrimidin-2-yl)piperazine-1-carboxylate (38 g, 100 mmol, 96.0% yield): ¹H NMR (400 MHz, CD₃OD) δ ppm 8.39 (s, 2H), 3.87-3.74 (m, 4H), 3.50 (s, 4H), 1.57-1.45 (m, 9H); ES-LCMS m/z 287.1, 289.1 [M−t−Bu+H]⁺.

Intermediate 10: tert-Butyl 4-(5-((3',5'-dichloro-5-(hydroxymethyl)-[1,1'-biphenyl]-3-yl)oxy)pyrimidin-2-yl)piperazine-1-carboxylate

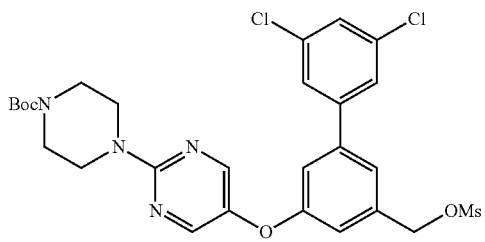 [SMILES: CC(C)(C)OC(=O)N1CCN(c2ncc(Oc3cc(COS(C)(=O)=O)cc(-c4cc(Cl)cc(Cl)c4)c3)cn2)CC1]

Step 1: 3-Bromo-5-hydroxybenzaldehyde

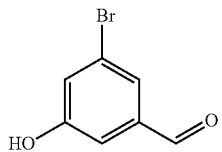

To a mixture of toluene (200 mL) and n-BuLi (3.0 M in THF, 167 mL, 417 mmol) was added n-BuMgCl (2.0 M in THF, 59.5 mL, 119 mmol) at −10° C. The reaction mixture was stirred at −10° C. for 0.5 h then a solution of 3,5-dibromophenol (50 g, 198 mmol) in toluene (200 mL) was added dropwise over a period of 0.5 h. After stirring at −10° C. for another 0.5 h, the reaction mixture was cooled to −40° C. and DMF (309 mL, 3.97 mol) was added dropwise over 0.4 h. The reaction mixture was then slowly warmed to 20° C. and stirred for 10.5 h. The reaction was carefully quenched at 0° C. with aq. HCl (10%) and extracted with EtOAc (500 mL×3). The combined organic extracts were washed with water (500 mL×2) and brine (500 mL×3), dried over Na$_2$SO$_4$ and filtered. The crude material was purified by silica gel column chromatography (PE/EtOAc=7/1 to 4/1). All fractions found to contain product by TLC (PE/EA=3/1, R$_f$=0.4) were combined and concentrated to yield a light yellow solid of 3-bromo-5-hydroxybenzaldehyde (15 g, 52.2 mmol, 26.3% yield): $^1$H NMR (400 MHz, CD$_3$OD) δ ppm 9.82 (s, 1H), 7.47 (s, 1H), 7.22 (d, J=2.0 Hz, 2H); ES-LCMS m/z 201.2 [M+H]$^+$.

Step 2: 3',5'-Dichloro-5-hydroxy-[1,1'-biphenyl]-3-carbaldehyde

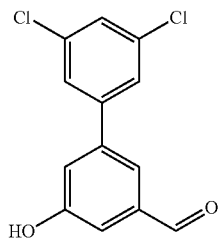

To a solution of (3,5-dichlorophenyl)boronic acid (84 g, 438 mmol) and 3-bromo-5-hydroxybenzaldehyde (80 g, 398 mmol) in 1,4-dioxane (2 L) was added Cs$_2$CO$_3$ (389 g, 1194 mmol) and PdCl$_2$(dppf) (1.456 g, 1.990 mmol). Then the mixture was stirred at 80° C. for 8 h under N$_2$ atmosphere. The mixture was adjusted to pH=6 with diluted HCl (aq., 1.0 M) and concentrated to yield a brown solid, which was further diluted with H$_2$O (2 L), filtered to yield a white solid of 3',5'-dichloro-5-hydroxy-[1,1'-biphenyl]-3-carbaldehyde (110 g, 268 mmol, 67.3% yield): $^1$H NMR (400 MHz, CD$_3$OD) δ ppm 9.96 (s, 1H), 7.62 (d, J=1.5 Hz, 3H), 7.52 (d, J=2.0 Hz, 1H), 7.31 (d, J=4.4 Hz, 2H); ES-LCMS m/z 267.1 [M+H]$^+$.

Step 3: 3',5'-Dichloro-5-(hydroxymethyl)-[1,1'-biphenyl]-3-ol

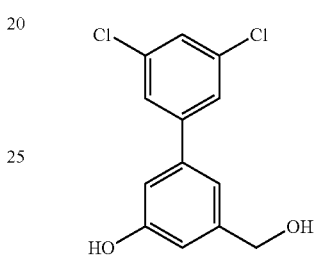

To a solution of 3',5'-dichloro-5-hydroxy-[1,1'-biphenyl]-3-carbaldehyde (3 g, 8.99 mmol) in MeOH (50 mL) was added NaBH$_4$ (2 g, 52.9 mmol). Then, the mixture was stirred at 20° C. for 1 h. Saturated aqueous NH$_4$Cl (40 mL) solution was added and the solution was concentrated then separated between DCM (50 mL) and saturated NaHCO$_3$ (30 mL) solution. The combined organic layers were dried over Na$_2$SO$_4$, filtered and concentrated to yield crude product which was purified by silica gel column chromatography (PE/EtOAc=3/1). All fractions found to contain product by TLC (PE/EtOAc=3/1, R$_f$=0.2) were combined and concentrated to yield a white solid of 3',5'-dichloro-5-(hydroxymethyl)-[1,1'-biphenyl]-3-ol (2.5 g, 8.52 mmol, 95.0% yield): $^1$H NMR (400 MHz, CD$_3$OD) δ ppm 7.55 (d, J=2.0 Hz, 2H), 7.41 (t, J=1.8 Hz, 1H), 7.07 (s, 1H), 6.90 (d, J=16.1 Hz, 2H), 4.62 (s, 2H).

Step 4: tert-Butyl 4-(5-((3',5'-dichloro-5-(hydroxymethyl)-[1,1'-biphenyl]-3-yl)oxy)pyrimidin-2-yl)piperazine-1-carboxylate

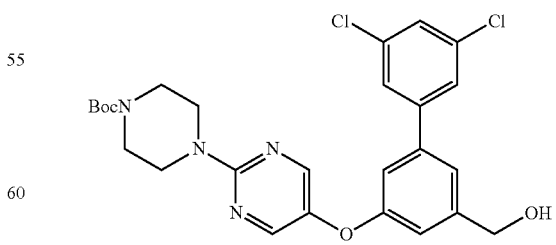

To a mixture of tert-butyl 4-(5-bromopyrimidin-2-yl)piperazine-1-carboxylate (2.89 g, 7.58 mmol) and 3',5'-dichloro-5-(hydroxymethyl)-[1,1'-biphenyl]-3-ol (2 g, 6.32 mmol) in DMSO (10 mL) was added CuI (0.060 g, 0.316 mmol), picolinic acid (0.039 g, 0.316 mmol) and K₃PO₄ (4.02 g, 18.95 mmol). The solution was stirred at 130° C. for 10 h under N₂ atmosphere. Saturated aqueous NH₄Cl (40 mL) was added and the solution was concentrated followed by separation between DCM (50 mL) and saturated NaHCO₃ (50 mL) solution. The combined organic extract was washed with brine (50 mL), dried over Na₂SO₄, filtered and concentrated. The crude material was purified by silica gel column chromatography (PE/EtOAc=1/0 to 1/1). All fractions found to contain product by TLC (PE/EtOAc=3/1, R_f=0.45) were combined and concentrated to yield a brown solid of tert-butyl 4-(5-((3',5'-dichloro-5-(hydroxymethyl)-[1,1'-biphenyl]-3-yl)oxy)pyrimidin-2-yl)piperazine-1-carboxylate (850 mg, 1.441 mmol, 22.8% yield): ¹H NMR (400 MHz, CDCl₃) δ ppm 8.19 (s, 2H), 7.39 (s, 2H), 7.33 (t, J=1.9 Hz, 1H), 7.21 (s, 1H), 7.00 (s, 1H), 6.94 (s, 1H), 4.71 (s, 2H), 3.78 (d, J=5.3 Hz, 4H), 3.50 (d, J=4.9 Hz, 4H), 1.48 (s, 9H); ES-LCMS m/z 475.2, 477.2 [M−t−Bu+H]⁺.

Step 5: tert-Butyl 4-(5-((3',5'-dichloro-5-(hydroxymethyl)-[1,1'-biphenyl]-3-yl)oxy)pyrimidin-2-yl)piperazine-1-carboxylate

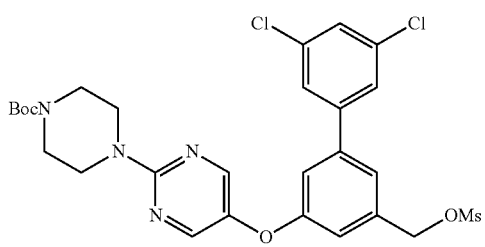 [SMILES: CC(C)(C)OC(=O)N1CCN(c2ncc(Oc3cc(COS(C)(=O)=O)cc(-c4cc(Cl)cc(Cl)c4)c3)cn2)CC1]

To a solution of tert-butyl 4-(5-((3',5'-dichloro-5-(hydroxymethyl)-[1,1'-biphenyl]-3-yl)oxy)pyrimidin-2-yl)piperazine-1-carboxylate (850 mg, 1.441 mmol) and DIEA (559 mg, 4.32 mmol) in DCM (10 mL) was added MsCl (0.168 mL, 2.162 mmol) at 0° C. Then the reaction mixture was stirred at 0° C. for 10 min. Water (50 mL) was added and the aqueous phase was extracted with DCM (25 mL×3). The combined organic layers were dried over Na₂SO₄, filtered and concentrated to yield a yellow oil of tert-butyl 4-(5-((3',5'-dichloro-5-(((methylsulfonyl)oxy)methyl)-[1,1'-biphenyl]-3-yl)oxy)pyrimidin-2-yl)piperazine-1-carboxylate (950 mg, 1.403 mmol, 97.0% yield): ¹H NMR (400 MHz, CD₃OD) δ ppm 8.30-8.26 (m, 2H), 7.73 (d, J=3.1 Hz, 1H), 7.61-7.57 (m, 2H), 7.28-7.23 (m, 1H), 7.07 (s, 1H), 6.77 (d, J=9.0 Hz, 1H), 5.28 (s, 2H), 3.80 (d, J=5.1 Hz, 4H), 3.56-3.52 (m, 4H), 3.10 (s, 3H), 1.48 (s, 9H); ES-LCMS m/z 553.1, 555.1 [M−t−Bu+H]⁺.

Intermediate 11: tert-Butyl 4-((5-((6-((3-chloro-5-fluorophenyl)-4-(((methylsulfonyl)oxy)methyl)pyridin-2-yl)oxy)pyrimidin-2-yl)piperazine-1-carboxylate

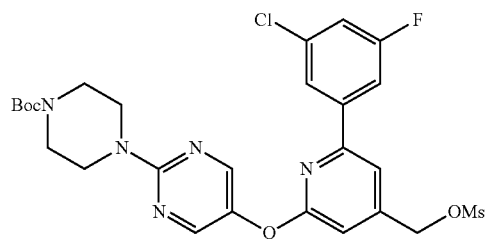 [SMILES: CC(C)(C)OC(=O)N1CCN(c2ncc(Oc3cc(COS(C)(=O)=O)cc(-c4cc(F)cc(Cl)c4)n3)cn2)CC1]

Step 1: tert-Butyl 4-(5-((6-(3-chloro-5-fluorophenyl)-4-(methoxycarbonyl)pyridin-2-yl)oxy)pyrimidin-2-yl)piperazine-1-carboxylate To a solution of tert-butyl 4-(5-((6-chloro-4-(methoxycarbonyl)pyridin-2-yl)oxy)pyrimidin-2-yl)piperazine-1-carboxylate (750 mg, 1.167 mmol) in DMF (5 mL) was added (3-chloro-5-fluorophenyl)boronic acid (305 mg, 1.750 mmol), PdCl₂(dppf) (85 mg, 0.117 mmol) and K₂CO₃ (484 mg, 3.50 mmol). The mixture was stirred at 80° C. for 1 h under N₂ atmosphere. The mixture was concentrated and purified by silica gel column chromatography (PE/EtOAc=3/1). All fractions found to contain product by TLC (PE/EA=3/1, R_f=0.5) were combined and concentrated to yield a yellow solid of tert-butyl 4-(5-((6-(3-chloro-5-fluorophenyl)-4-(methoxycarbonyl)pyridin-2-yl)oxy)pyrimidin-2-yl)piperazine-1-carboxylate (500 mg, 0.643 mmol, 55.1% yield): ¹H NMR (400 MHz, CD₃OD) δ ppm 8.38 (s, 1H), 7.45-7.35 (3H), 7.16-7.15 (m, 1H), 6.61-6.60 (m, 1H), 6.51-6.40 (m, 1H), 3.75 (s, 3H), 3.50-3.40 (m, 8H), 1.45 (s, 9H); ES-LCMS m/z 488.2 [M−t−Bu+H]⁺.

Step 2: tert-Butyl 4-(5-((6-(3-chloro-5-fluorophenyl)-4-(hydroxymethyl)pyridin-2-yl)oxy)pyrimidin-2-yl)piperazine-1-carboxylate

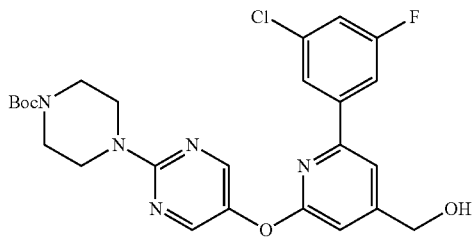 [SMILES: CC(C)(C)OC(=O)N1CCN(c2ncc(Oc3cc(CO)cc(-c4cc(F)cc(Cl)c4)n3)cn2)CC1]

To a mixture of tert-butyl 4-(5-((6-(3-chloro-5-fluorophenyl)-4-(methoxycarbonyl)pyridin-2-yl)oxy)pyrimidin-2-yl)piperazine-1-carboxylate (500 mg, 0.643 mmol) in MeOH (20 mL) was added NaBH$_4$ (48.7 mg, 1.287 mmol). The mixture was stirred at 15° C. for 20 min then concentrated. Water (50 mL) was added and the mixture was extracted with DCM (50 mL×2). The combine organic layers were dried over Na$_2$SO$_4$, filtered and concentrated to yield a white solid of tert-butyl 4-(5-((6-(3-chloro-5-fluorophenyl)-4-(hydroxymethyl)pyridin-2-yl)oxy)pyrimidin-2-yl)piperazine-1-carboxylate (400 mg, 0.543 mmol, 84.0% yield): $^1$H NMR (400 MHz, CD$_3$OD) δ ppm 8.32 (s, 1H), 7.71 (s, 1H), 7.59-7.53 (m, 2H), 7.33-7.30 (m, 1H), 7.22-7.18 (m, 1H), 7.04 (s, 1H), 4.73 (s, 2H), 3.84-3.80 (m, 4H), 3.52 (s, 4H), 1.49 (s, 9H); ES-LCMS m/z 516.2, 518.2 [M+H]$^+$.

Step 3: tert-Butyl 4-(5-((6-(3-chloro-5-fluorophenyl)-4-(((methylsulfonyl)oxy)methyl)pyridin-2-yl)oxy)pyrimidin-2-yl)piperazine-1-carboxylate

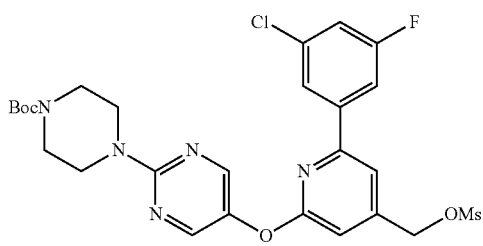 [SMILES: CC(C)(C)OC(=O)N1CCN(c2ncc(Oc3cc(COS(C)(=O)=O)cc(-c4cc(F)cc(Cl)c4)n3)cn2)CC1]

To a mixture of tert-butyl 4-(5-((6-(3-chloro-5-fluorophenyl)-4-(hydroxymethyl)pyridin-2-yl)oxy)pyrimidin-2-yl)piperazine-1-carboxylate (1 g, 1.357 mmol) in DCM (20 mL) was added MsCl (0.159 mL, 2.035 mmol) and DIEA (0.711 mL, 4.07 mmol). The mixture was stirred at 25° C. for 20 min before H$_2$O (100 mL) was added. The mixture was extracted with DCM (100 mL×2) and the combine organic layers were dried over Na$_2$SO$_4$, filtered and concentrated to yield a yellow oil of tert-butyl 4-(5-((6-(3-chloro-5-fluorophenyl)-4-(((methylsulfonyl)oxy)methyl)pyridin-2-yl)oxy)pyrimidin-2-yl)piperazine-1-carboxylate (800 mg, 0.902 mmol, 66.5% yield): $^1$H NMR (400 MHz, CD$_3$OD) δ ppm 8.80 (s, 1H), 7.77 (s, 1H), 7.73-7.70 (m, 2H), 7.60-7.57 (m, 1H), 7.29-7.19 (m, 2H), 5.45 (s, 2H), 3.97-3.89 (m, 4H), 3.73-3.59 (m, 4H), 3.21 (s, 3H), 1.49 (s, 9H); ES-LCMS m/z 538.2, 540.2 [M+H]$^+$.

Intermediate 12: tert-Butyl 4-(5-((6-(3-chloro-4,5-difluorophenyl)-4-(((methylsulfonyl)oxy)methyl)pyridin-2-yl)oxy)pyrimidin-2-yl)piperazine-1-carboxylate

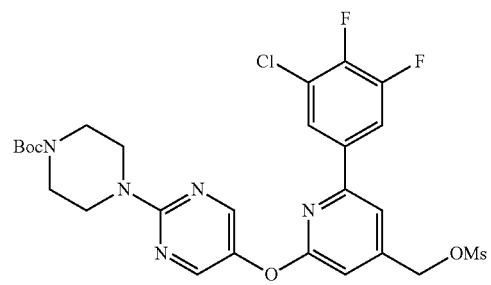 [SMILES: CC(C)(C)OC(=O)N1CCN(c2ncc(Oc3cc(COS(C)(=O)=O)cc(-c4cc(F)c(F)c(Cl)c4)n3)cn2)CC1]

Step 1: (E)-2,6-Diisopropyl-N-(pyridin-2-ylmethylene)aniline

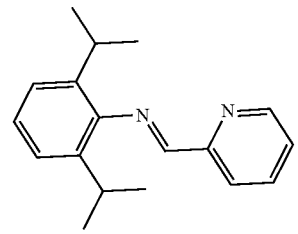 [SMILES: CC(C)c1cccc(C(C)C)c1/N=C/c1ccccn1]

2,6-Diisopropylaniline (2.70 mL, 11.28 mmol) was added to a solution of picolinaldehyde (0.822 mL, 11.28 mmol) in toluene (100 mL) in a round bottom flask equipped with a Dean-Stark trap, followed by the addition of a catalytic amount of p-TsOH (0.1 g). The reaction mixture was refluxed at 140° C. for 24 h to remove water. The reaction mixture was cooled to 25° C. and then washed once with water (100 mL), and the solution was concentrated. The resulting residue was purified by silica gel column chromatography (PE/EtOAc=4/1). All fractions found to contain product by TLC (DCM/MeOH=30/1, R$_f$=0.7) were combined and concentrated to yield brown oil of (E)-2,6-diisopropyl-N-(pyridin-2-ylmethylene)aniline (450 mg, 1.351 mmol, 12.0% yield): $^1$H NMR (400 MHz, CDCl$_3$) δ ppm 8.73 (d, J=4.9 Hz, 1H), 8.31 (s, 1H), 8.27 (d, J=7.9 Hz, 1H), 7.85 (t, J=7.3 Hz, 1H), 7.41 (dd, J=5.3, 6.6 Hz, 1H), 7.20-7.11 (m, 3H), 2.97 (d, J=6.7, 13.9 Hz, 2H), 1.18 (d, J=6.6 Hz, 12H).

Step 2: 2-(3-Chloro-4,5-difluorophenyl)-4,4,5,5-tetramethyl-1,3,2-dioxaborolane

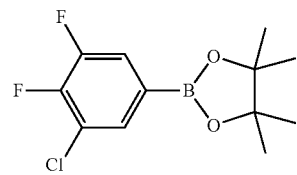 [SMILES: CC1(C)OB(c2cc(F)c(F)c(Cl)c2)OC1(C)C]

To a solution of 1-chloro-2,3-difluorobenzene (3 g, 20.20 mmol) and 4,4,4',4',5,5,5',5'-octamethyl-2,2'-bi(1,3,2-dioxaborolane) (6.15 g, 24.24 mmol) in n-heptane (30 mL) was added (E)-2,6-diisopropyl-N-(pyridin-2-ylmethylene)aniline (0.336 g, 1.010 mmol) and chloro(1,5-cyclooctadiene)iridium(I)dimer (0.678 g, 1.010 mmol). The reaction mixture was stirred at 110° C. for 12 h under $N_2$ atmosphere. Then DCM was added (50 mL) and the mixture was washed with aqueous $NaHCO_3$ (20 mL). The aqueous phase was extracted with DCM (50 mL×2) and combined organic layers were washed with brine (20 mL), dried over $Na_2SO_4$, filtered, concentrated, followed by purification with silica gel column chromatography (PE/EA=1/0). All fractions found to contain product by TLC (PE/EA=2/1, $R_f$=0.3) were combined and concentrated to yield a colorless oil of 2-(3-chloro-4,5-difluorophenyl)-4,4,5,5-tetramethyl-1,3,2-dioxaborolane (800 mg, 2.62 mmol, 12.9% yield): $^1$H NMR (400 MHz, $CDCl_3$) δ ppm 7.60 (d, J=6.6 Hz, 1H), 7.48 (t, J=8.2 Hz, 1H), 1.33 (s, 12H); ES-LCMS m/z 275.1 $[M+H]^+$.

Step 3: tert-Butyl 4-(5-((6-(3-chloro-4,5-difluorophenyl)-4-(methoxycarbonyl)pyridin-2-yl)oxy)pyrimidin-2-yl)piperazine-1-carboxylate

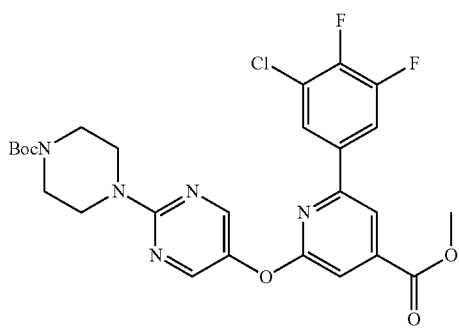 [SMILES: COC(=O)c1cc(Oc2cnc(N3CCN(C(=O)OC(C)(C)C)CC3)nc2)nc(-c2cc(F)c(F)c(Cl)c2)c1]

To a mixture of tert-butyl 4-(5-((6-chloro-4-(methoxycarbonyl)pyridin-2-yl)oxy)pyrimidin-2-yl)piperazine-1-carboxylate (700 mg, 1.400 mmol) and 2-(3-chloro-4,5-difluorophenyl)-4,4,5,5-tetramethyl-1,3,2-dioxaborolane (700 mg, 2.295 mmol) in 1,4-dioxane (20 mL) was added $K_2CO_3$ (581 mg, 4.20 mmol) and $PdCl_2$(dppf) (51.2 mg, 0.070 mmol). The mixture was stirred at 80° C. under $N_2$ atmosphere for 6 h. The mixture was concentrated and purified by silica gel column chromatography (PE/EtOAc=5/1). All fractions found to contain product by TLC (PE/EA=3/1, $R_f$=0.4) were combined and concentrated to yield a colorless oil of tert-butyl 4-(5-((6-(3-chloro-4,5-difluorophenyl)-4-(methoxycarbonyl)pyridin-2-yl)oxy)pyrimidin-2-yl)piperazine-1-carboxylate (800 mg, 1.025 mmol, 73.2% yield): $^1$H NMR (400 MHz, $CDCl_3$) δ ppm 8.30 (s, 1H), 8.25 (s, 1H), 7.93 (s, 1H), 7.73 (d, J=5.7 Hz, 1H), 7.68-7.60 (m, 1H), 7.48 (s, 1H), 4.01 (s, 3H), 3.83 (d, J=5.3 Hz, 4H), 3.53 (d, J=3.5 Hz, 4H), 1.50 (s, 9H); ES-LCMS m/z 506.1 $[M-t-Bu+H]^+$.

Step 4: tert-Butyl 4-(5-((6-(3-chloro-4,5-difluorophenyl)-4-(hydroxymethyl)pyridin-2-yl)oxy)pyrimidin-2-yl)piperazine-1-carboxylate

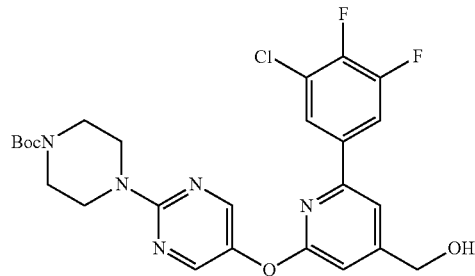 [SMILES: CC(C)(C)OC(=O)N1CCN(c2ncc(Oc3cc(CO)cc(-c4cc(F)c(F)c(Cl)c4)n3)cn2)CC1]

To a mixture of tert-butyl 4-(5-((6-(3-chloro-4,5-difluorophenyl)-4-(methoxycarbonyl)pyridin-2-yl)oxy)pyrimidin-2-yl)piperazine-1-carboxylate (750 mg, 0.961 mmol) in MeOH (15 mL) was added $NaBH_4$ (327 mg, 8.65 mmol). The mixture was stirred at 15° C. for 20 min. Then the solution was concentrated and saturated $NaHCO_3$ solution (150 mL) was added. The aqueous layer was extracted with DCM (500 mL×3), and the combined extracts were washed with brine (150 mL×2), dried over $Na_2SO_4$, filtered and concentrated to yield a yellow oil of tert-butyl 4-(5-((6-(3-chloro-4,5-difluorophenyl)-4-(hydroxymethyl)pyridin-2-yl)oxy)pyrimidin-2-yl)piperazine-1-carboxylate (750 mg, 0.843 mmol, 88.0% yield): $^1$H NMR (400 MHz, $CDCl_3$) δ ppm 8.29 (s, 2H), 7.69 (d, J=5.5 Hz, 1H), 7.65-7.55 (m, 1H), 7.40 (s, 1H), 6.92 (s, 1H), 4.81 (s, 2H), 3.81 (d, J=5.0 Hz, 4H), 3.52 (d, J=3.5 Hz, 4H), 1.50 (s, 9H); ES-LCMS m/z 478.2 $[M-t-Bu+H]^+$.

Step 5: tert-Butyl 4-(5-((6-(3-chloro-4,5-difluorophenyl)-4-(((methylsulfonyl)oxy)methyl)pyridin-2-yl)oxy)pyrimidin-2-yl)piperazine-1-carboxylate

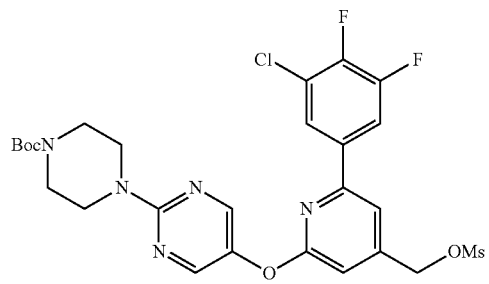 [SMILES: CC(C)(C)OC(=O)N1CCN(c2ncc(Oc3cc(COS(C)(=O)=O)cc(-c4cc(F)c(F)c(Cl)c4)n3)cn2)CC1]

To a mixture of tert-butyl 4-(5-((6-(3-chloro-4,5-difluorophenyl)-4-(hydroxymethyl)pyridin-2-yl)oxy)pyrimidin-2-yl)piperazine-1-carboxylate (750 mg, 0.843 mmol) in DCM (15 mL) was added DIEA (0.442 mL, 2.53 mmol). MsCl (0.079 mL, 1.011 mmol) was added at 15° C. then the mixture was stirred for 15 min under $N_2$ atmosphere. The mixture was concentrated and saturated $NaHCO_3$ solution (150 mL) was added. The aqueous layer was extracted with DCM (150 mL×2), and the combined extracts were washed with brine (150 mL×2), dried over $Na_2SO_4$, filtered and concentrated to yield a yellow oil of tert-butyl 4-(5-((6-(3-chloro-4,5-difluorophenyl)-4-(((methylsulfonyl)oxy)methyl)pyridin-2-yl)oxy)pyrimidin-2-yl)piperazine-1-carboxylate (880 mg, 0.820 mmol, 97.0% yield): $^1$H NMR (400 MHz, CDCl$_3$) δ ppm 8.30 (s, 2H), 7.68 (d, J=5.0 Hz, 1H), 7.64-7.55 (m, 1H), 7.41-7.37 (m, 1H), 6.96 (s, 1H), 5.32-5.28 (m, 2H), 3.83 (d, J=4.5 Hz, 4H), 3.54 (s, 4H), 3.13 (d, J=7.0 Hz, 3H), 1.50 (s, 9H); ES-LCMS m/z 556.1[M−t−Bu+H]$^+$.

Intermediate 13: tert-Butyl ((5-((6-bromopyridin-3-yl)oxy)-3',5'-dichloro-[1,1'-biphenyl]-3-yl)methyl)(methyl)carbamate

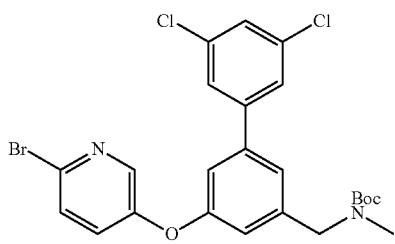 [SMILES: CN(Cc1cc(Oc2ccc(Br)nc2)cc(-c2cc(Cl)cc(Cl)c2)c1)C(=O)OC(C)(C)C]

Step 1: 3',5'-Dichloro-5-((methylamino)methyl)-[1,1'-biphenyl]-3-ol

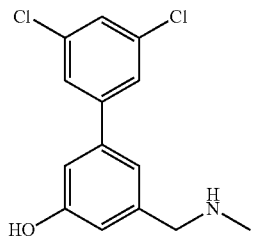 [SMILES: CNCc1cc(O)cc(-c2cc(Cl)cc(Cl)c2)c1]

To a solution of 3',5'-dichloro-5-hydroxy-[1,1'-biphenyl]-3-carbaldehyde (90 g, 337 mmol) in DCM (2 L) was added MeNH$_2$ in EtOH (192 g, 674 mmol). Then the mixture was stirred at 20° C. for 8 h under N$_2$ atmosphere. AcOH was added to adjust pH to 6, and NaBH(OAc)$_3$ (143 g, 674 mmol) was added to the mixture at 0° C. The mixture was stirred at 20° C. for 4 h then the solution was filtered and concentrated. The crude material was purified by silica gel column chromatography (DCM/MeOH=10/1). All fractions found to contain product by TLC (DCM/MeOH=10/1, R$_f$=0.5) were combined and concentrated to yield a light yellow solid of 3',5'-dichloro-5-((methylamino)methyl)-[1,1'-biphenyl]-3-ol (85 g, 271 mmol, 80.0% yield): $^1$H NMR (400 MHz, CD$_3$OD) δ ppm 7.55 (d, J=2.0 Hz, 2H), 7.41 (t, J=1.7 Hz, 1H), 7.19 (s, 1H), 7.05 (s, 1H), 6.94 (s, 1H), 4.11 (s, 2H), 2.67 (s, 3H); ES-LCMS m/z 282.0, 284.0 [M+H]$^+$.

Step 2: tert-Butyl ((3',5'-dichloro-5-hydroxy-[1,1'-biphenyl]-3-yl)methyl)(methyl)carbamate

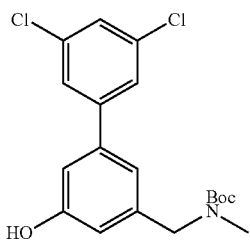 [SMILES: CN(Cc1cc(O)cc(-c2cc(Cl)cc(Cl)c2)c1)C(=O)OC(C)(C)C]

To a suspension of 3',5'-dichloro-5-((methylamino)methyl)-[1,1'-biphenyl]-3-ol (85 g, 301 mmol) and DIEA (58.4 g, 452 mmol) in DCM (2 L) was added (Boc)$_2$O (64.4 g, 295 mmol) at 0° C., and the reaction mixture was stirred for 12 h under N$_2$ atmosphere at 20° C. The reaction mixture was diluted with DCM (1 L) and washed with saturated NaHCO$_3$ solution (2 L×2). The organic phase was dried over Na$_2$SO$_4$ and filtered. The crude material was purified by silica gel column chromatography (PE/EtOAc=10/1 to 5/1). All fractions found to contain product by TLC (PE/EA=5/1, R$_f$=0.5) were combined and concentrated to yield a light yellow solid of tert-butyl ((3',5'-dichloro-5-hydroxy-[1,1'-biphenyl]-3-yl)methyl)(methyl)carbamate (50 g, 105 mmol, 34.7% yield): $^1$H NMR (400 MHz, CD$_3$OD) δ ppm 7.49 (d, J=2.0 Hz, 2H), 7.39 (s, 1H), 6.90 (d, J=7.1 Hz, 2H), 6.71 (s, 1H), 4.41 (s, 2H), 2.84 (s, 3H), 1.47 (s, 9H); ES-LCMS m/z 325.9, 327.9 [M−t−Bu+H]$^+$.

Step 3: tert-Butyl ((5-((6-bromopyridin-3-yl)oxy)-3',5'-dichloro-[1,1'-biphenyl]-3-yl)methyl)(methyl)carbamate

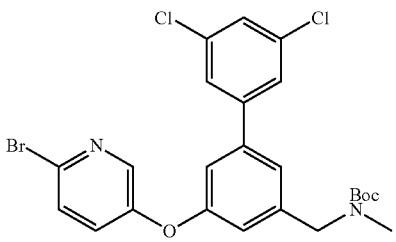 [SMILES: CN(Cc1cc(Oc2ccc(Br)nc2)cc(-c2cc(Cl)cc(Cl)c2)c1)C(=O)OC(C)(C)C]

To a solution of tert-butyl ((3',5'-dichloro-5-hydroxy-[1,1'-biphenyl]-3-yl)methyl)(methyl)carbamate (1 g, 2.62 mmol) and 2-bromo-5-fluoropyridine (1.381 g, 7.85 mmol) in DMF (30 mL) was added Cs$_2$CO$_3$ (4.26 g, 13.08 mmol). The mixture was stirred at 80° C. for 8 h. The mixture was filtered, concentrated and purified by silica gel (PE/EtOAc=4/1) to yield tert-butyl ((5-((6-bromopyridin-3-yl)oxy)-3',5'-dichloro-[1,1'-biphenyl]-3-yl)methyl)(methyl)carbamate (1.3 g, 2.294 mmol, 88.0% yield): $^1$H NMR (400 MHz, CDCl$_3$) δ ppm 8.22-8.14 (m, 1H), 7.53-7.42 (m, 1H), 7.42-7.32 (m, 3H), 7.22-7.17 (m, 2H), 7.07 (br. s, 1H), 6.89 (br. s, 1H), 4.45 (br. s, 2H), 2.84 (s, 3H), 1.46 (br. s, 9H); ES-LCMS m/z 480.9, 482.9, 484.9 [M−t−Bu+H]$^+$.

Intermediate 14: N-((1-((3',5'-Dichloro-5-hydroxy-[1,1'-biphenyl]-3-yl)methyl)piperidin-4-yl)methyl)acetamide

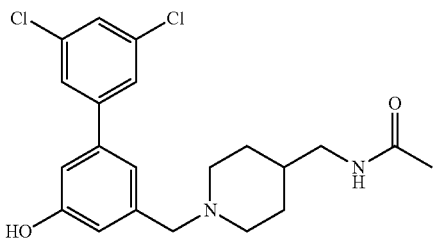 [SMILES: CC(=O)NCC1CCN(Cc2cc(O)cc(-c3cc(Cl)cc(Cl)c3)c2)CC1]

Step 1: Methyl 3-hydroxy-5-(methoxymethoxy)benzoate

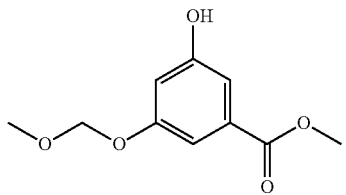

To a mixture of methyl 3,5-dihydroxybenzoate (200 g, 1189 mmol) in acetone (1 L) was added dropwise chloro(methoxy)methane (105 g, 1308 mmol), K$_2$CO$_3$ (493 g, 3568 mmol) at 0° C. The mixture was stirred at 0° C. for 20 h then concentrated. The residue was dissolved in DCM (1 L) and the solution was washed with water (1 L×3). The organic phase was dried over Na$_2$SO$_4$, filtered, concentrated and purified by silica gel (EtOAc/PE, 0-50%). The fractions (EtOAc/PE=5/1, R$_f$=0.4) were combined and was concentrated to yield a white solid of methyl 3-hydroxy-5-(methoxymethoxy)benzoate (60 g, 226 mmol, 19.0% yield): $^1$H NMR (400 MHz, CD$_3$OD) δ ppm 7.28-7.25 (m, 1H), 7.18 (d, J=1.10 Hz, 1H), 6.75 (t, J=2.32 Hz, 1H), 5.18-5.16 (m, 2H), 3.89 (s, 3H), 3.47 (s, 3H); ES-LCMS m/z 213.1 [M+H]$^+$.

Step 2: Methyl 3-hydroxy-5-(((trifluoromethyl)sulfonyl)oxy)benzoate

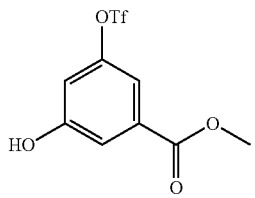 [SMILES: COC(=O)c1cc(O)cc(OS(=O)(=O)C(F)(F)F)c1]

To a mixture of methyl 3-hydroxy-5-(methoxymethoxy)benzoate (200 g, 943 mmol) in DCM (1 L) was added Tf$_2$O (175 mL, 1037 mmol), DIEA (247 mL, 1414 mmol) at 20° C. The mixture was stirred at 20° C. for 2 h then washed with water (1 L×3). The organic phase was dried over Na$_2$SO$_4$ and filtered. The filtrate was concentrated to yield a brown solid of methyl 3-hydroxy-5-(((trifluoromethyl)sulfonyl)oxy)benzoate (220 g, 586 mmol, 62.2% yield): $^1$H NMR (400 MHz, CDCl$_3$) δ ppm 7.71 (s, 1H), 7.46 (s, 1H), 7.29 (s, 1H), 3.90 (s, 3H); ES-LCMS m/z 301.0 [M+H]$^+$.

Step 3: Methyl 3',5'-dichloro-5-hydroxy-[1,1'-biphenyl]-3-carboxylate

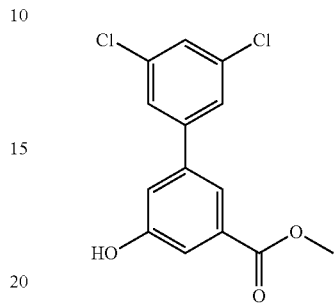

To a mixture of methyl 3-hydroxy-5-(((trifluoromethyl)sulfonyl)oxy)benzoate (100 g, 333 mmol) in 1,4-dioxane (1.5 L) and water (500 mL) was added (3,5-dichlorophenyl)boronic acid (63.6 g, 333 mmol), K$_2$CO$_3$ (138 g, 999 mmol), PdCl$_2$(dppf)-CH$_2$Cl$_2$ adduct (27.2 g, 33.3 mmol) at 80° C. under N$_2$ atmosphere. The mixture was stirred at 80° C. for 4 h under N$_2$ atmosphere. Then the reaction mixture was concentrated and the residue was dissolved in DCM (1 L), washed with water (1 L×3). The organic phase was dried over Na$_2$SO$_4$, filtered, concentrated and purified by silica gel (EtOAc/PE=3/1, R$_f$=0.4) to a white solid yield methyl 3',5'-dichloro-5-hydroxy-[1,1'-biphenyl]-3-carboxylate (80 g, 215 mmol, 64.7% yield): $^1$H NMR (400 MHz, CDCl$_3$) δ ppm 7.72 (s, 1H), 7.46 (s, 1H), 7.43-7.37 (m, 2H), 7.33-7.28 (m, 1H), 7.15 (s, 1H), 3.88 (s, 3H); ES-LCMS m/z 297.1 [M+H]$^+$.

Step 4: Methyl 3',5'-dichloro-5-(methoxymethoxy)-[1,1'-biphenyl]-3-carboxylate

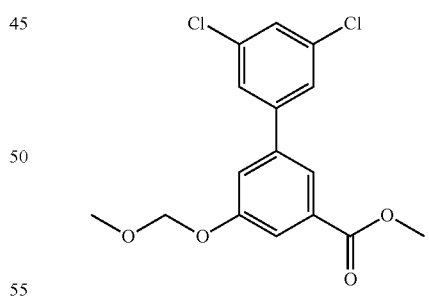

To a mixture of methyl 3',5'-dichloro-5-hydroxy-[1,1'-biphenyl]-3-carboxylate (80 g, 269 mmol) in DCM (1 L) was added chloro(methoxy)methane (26.0 mL, 538 mmol), DIEA (188 mL, 1077 mmol) at 20° C. The mixture was stirred at 20° C. for 2 h then concentrated, and the resulting crude was dissolved in DCM (1 L). The mixture was washed with water (1 L×3) and the organic phase was dried over Na$_2$SO$_4$, filtered, and concentrated. The crude was purified by silica column chromatography on silica gel (EtOAc/PE=5/1, R$_f$=0.4) yield a brown solid of methyl 3',5'-dichloro-5-(methoxymethoxy)-[1,1'-biphenyl]-3-carboxylate (60 g, 141 mmol, 52.3% yield): $^1$H NMR (400 MHz, CDCl$_3$) δ ppm 7.88-7.81 (m, 1H), 7.75-7.69 (m, 1H), 7.46 (d, J=1.71 Hz, 2H), 7.40-7.32 (m, 2H), 5.25 (s, 2H), 3.96-3.91 (m, 3H), 3.52-3.48 (m, 3H); ES-LCMS m/z 341.1 [M+H]$^+$.

Step 5: (3',5'-Dichloro-5-(methoxymethoxy)-[1,1'-biphenyl]-3-yl)methanol

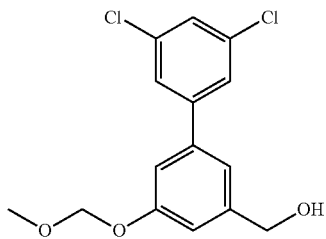 [SMILES: COCOc1cc(CO)cc(-c2cc(Cl)cc(Cl)c2)c1]

To a solution of methyl 3',5'-dichloro-5-(methoxymethoxy)-[1,1'-biphenyl]-3-carboxylate (8.3 g, 19.46 mmol) in THF (80 mL) was added LiAlH$_4$ (0.886 g, 23.35 mmol) at −10° C. The mixture was stirred at −10° C. for 20 min then was quenched by addition of water (1 mL) and NaOH (aq., 10%, 1 mL). The mixture was filtered and concentrated to yield a yellow oil of (3',5'-dichloro-5-(methoxymethoxy)-[1,1'-biphenyl]-3-yl)methanol (8 g, 19.16 mmol, 98.0% yield): $^1$H NMR (400 MHz, CD$_3$OD) δ ppm 7.54 (d, J=1.5 Hz, 2H), 7.40 (s, 1H), 7.21 (s, 1H), 7.12 (d, J=9.5 Hz, 2H), 5.26 (s, 2H), 4.65 (s, 2H), 3.49 (s, 3H); ES-LCMS m/z 335.1, 337.1 [M+Na]$^+$.

Step 6: (3',5'-Dichloro-5-(methoxymethoxy)-[1,1'-biphenyl]-3-yl)methyl methanesulfonate

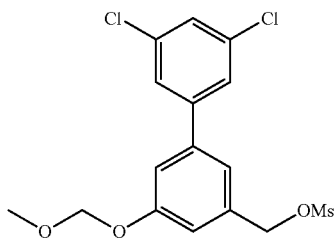 [SMILES: COCOc1cc(COS(C)(=O)=O)cc(-c2cc(Cl)cc(Cl)c2)c1]

To a solution of (3',5'-dichloro-5-(methoxymethoxy)-[1,1'-biphenyl]-3-yl)methanol (8 g, 19.16 mmol) in DCM (80 mL) was added MsCl (1.792 mL, 22.99 mmol) and DIEA (10.23 mL, 57.5 mmol). The mixture was stirred at 10° C. for 0.5 h then concentrated and distributed between DCM (300 mL) and saturated NaHCO$_3$ (300 mL) solution. The combined organic extract was washed with brine (200 mL), dried over Na$_2$SO$_4$, filtered and concentrated to yield a yellow oil of (3',5'-dichloro-5-(methoxymethoxy)-[1,1'-biphenyl]-3-yl)methyl methanesulfonate (8 g, 15.33 mmol, 80.0% yield): $^1$H NMR (400 MHz, CD$_3$OD) δ ppm 7.54 (s, 2H), 7.42 (s, 1H), 7.29 (s, 1H), 7.25 (s, 1H), 7.17 (s, 1H), 5.27 (s, 2H), 4.88 (s, 2H), 3.50 (s, 3H), 3.12 (s, 3H); ES-LCMS m/z 413.1, 415.1 [M+Na]$^+$.

Step 7: N-((1-((3',5'-Dichloro-5-(methoxymethoxy)-[1,1'-biphenyl]-3-yl)methyl)piperidin-4-yl)methyl) acetamide

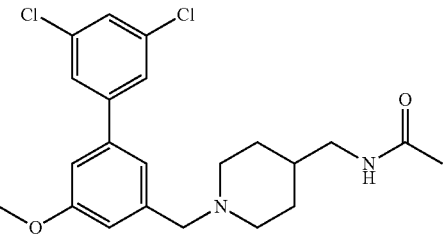

To a mixture of (3',5'-dichloro-5-(methoxymethoxy)-[1,1'-biphenyl]-3-yl)methyl methanesulfonate (8 g, 15.33 mmol) in DML (50 mL) was added K$_2$CO$_3$ (8.48 g, 61.3 mmol) and N-(piperidin-4-ylmethyl)acetamide, hydrochloride (6.22 g, 30.7 mmol). The mixture was stirred at 15° C. for 10 h under N$_2$ atmosphere then concentrated and saturated NaHCO$_3$ solution (150 mL) was added. The aqueous layer was extracted with DCM (300 mL×2) and the combined extracts were washed with brine (150 mL×2), dried over Na$_2$SO$_4$, filtered and concentrated. The crude material was purified by silica gel column chromatography (DCM/MeOH=5/1). All fractions found to contain product by TLC (DCM/MeOH=10/1, R$_f$=0.5) were combined and concentrated to yield a yellow oil of N-((1-((3',5'-dichloro-5-(methoxymethoxy)-[1,1'-biphenyl]-3-yl)methyl)piperidin-4-yl)methyl)acetamide (7 g, 12.41 mmol, 81.0% yield): $^1$H NMR (400 MHz, CD$_3$OD) δ ppm 7.58 (d, J=1.5 Hz, 2H), 7.44 (d, J=1.5 Hz, 1H), 7.25 (s, 1H), 7.19 (s, 1H), 7.09 (s, 1H), 5.31-5.22 (m, 2H), 3.58-3.54 (m, 2H), 3.52-3.48 (m, 3H), 3.08 (d, J=6.5 Hz, 2H), 2.96 (d, J=11.3 Hz, 2H), 2.06 (t, J=10.9 Hz, 2H), 1.95 (s, 3H), 1.73 (d, J=12.5 Hz, 2H), 1.61-1.45 (m, 1H), 1.39-1.23 (m, 2H); ES-LCMS m/z 451.3, 453.3 [M+H]$^+$.

Step 8: N-((1-((3',5'-Dichloro-5-hydroxy-[1,1'-biphenyl]-3-yl)methyl)piperidin-4-yl)methyl)acetamide

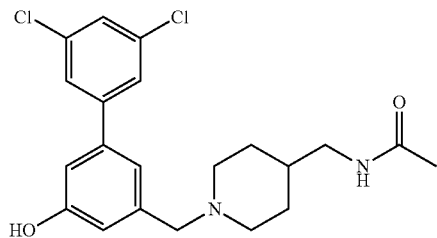 [SMILES: CC(=O)NCC1CCN(Cc2cc(O)cc(-c3cc(Cl)cc(Cl)c3)c2)CC1]

To a mixture of N-((1-((3',5'-dichloro-5-(methoxymethoxy)-[1,1'-biphenyl]-3-yl)methyl)piperidin-4-yl)methyl)acetamide (7 g, 12.41 mmol) in water (30 mL) was added concentrated HCl (30 mL, 238 mmol). The mixture was stirred at 15° C. for 10 h under N$_2$ atmosphere then was concentrated to yield a yellow solid of N-((1-((3', 5'-dichloro-5-hydroxy-[1,1'-biphenyl]-3-yl)methyl)piperidin-4-yl)methyl)acetamide (6.2 g, 12.18 mmol, 98.0% yield): $^1$H NMR (400 MHz, CD$_3$OD) δ ppm 7.63 (d, J=1.5 Hz, 2H), 7.46 (s, 1H), 7.32 (s, 1H), 7.14 (s, 1H), 7.05 (s, 1H), 4.36-4.27 (m, 2H), 3.56 (d, J=12.0 Hz, 2H), 3.20 (d, J=6.0 Hz, 2H), 3.10 (br. s, 2H), 2.09 (br. s, 3H), 1.99 (d, J=14.1 Hz, 2H), 1.90-1.87 (m, 1H), 1.68-1.50 (m, 2H); ES-LCMS m/z 407.2, 409.2 [M+H]+.

Intermediate 15: N-((1-((2-((6-Bromopyridin-3-yl)oxy)-6-(3,5-dichlorophenyl)pyridin-4-yl)methyl)piperidin-4-yl)methyl)acetamide

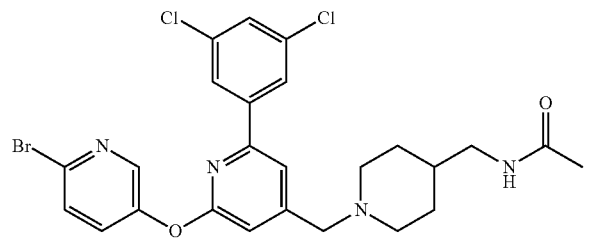 [SMILES: CC(=O)NCC1CCN(Cc2cc(Oc3ccc(Br)nc3)nc(-c3cc(Cl)cc(Cl)c3)c2)CC1]

Step 1: Methyl 2-(benzyloxy)-6-chloroisonicotinate

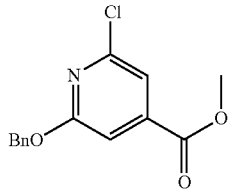 [SMILES: COC(=O)c1cc(Cl)nc(OCc2ccccc2)c1]

To a solution of phenylmethanol (15.75 g, 146 mmol) in DMF (500 mL) was added NaH (7.57 g, 189 mmol) at 25° C. After the mixture was stirred at 25° C. for 0.5 h, methyl 2,6-dichloroisonicotinate (30 g, 146 mmol) in DMF (100 mL) was added and the mixture was stirred at 25° C. for 12 h. The mixture was filtered and the filtrate was concentrated to yield a residue which was purified by column chromatography to yield a colorless oil of methyl 2-(benzyloxy)-6-chloroisonicotinate (16 g, 57.6 mmol, 39.6% yield): 1H NMR (400 MHz, CDCl3) d ppm 7.43-7.36 (m, 3H), 7.36-7.26 (m, 4H), 5.32 (s, 2H), 3.87 (s, 3H); ES-LCMS m/z 278.1 [M+H]+.

Step 2: Methyl 2-(benzyloxy)-6-(3,5-dichlorophenyl)isonicotinate

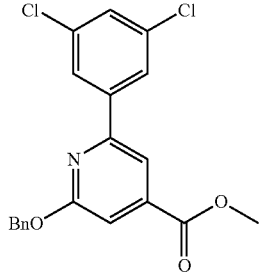

A mixture of methyl 2-(benzyloxy)-6-chloroisonicotinate (12 g, 43.2 mmol), (3,5-dichlorophenyl)boronic acid (12.37 g, 64.8 mmol), PdCl2(dppf) (6.32 g, 8.64 mmol) and K2CO3 (11.94 g, 86 mmol) in 1,4-dioxane (200 mL) was stirred at 80° C. for 12 h under N2 atmosphere. The mixture was filtered and the filtrate was concentrated. The residue was purified by column chromatography to yield a colorless oil of methyl 2-(benzyloxy)-6-(3,5-dichlorophenyl)isonicotinate (13 g, 33.5 mmol, 77.0% yield): 1H NMR (400 MHz, CDCl3) δ ppm 7.96-7.92 (m, 1H), 7.91-7.87 (m, 2H), 7.85-7.80 (m, 2H), 7.42-7.38 (m, 5H), 5.50 (s, 2H), 3.92 (d, J=2.0 Hz, 3H); ES-LCMS m/z 388.0, 389.9 [M+H]+.

Step 3: (2-(Benzyloxy)-6-(3,5-dichlorophenyl)pyridin-4-yl)methanol

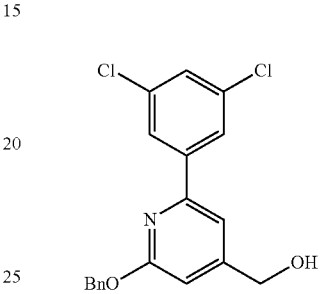

To a solution of methyl 2-(benzyloxy)-6-(3,5-dichlorophenyl)isonicotinate (12 g, 30.9 mmol) in THF (300 mL) was added LiAlH4 (2.35 g, 61.8 mmol) at −78° C. The mixture was allowed to warm up to 25° C. for 12 h. The reaction was quenched by addition of aqueous NaOH (20%, 10 mL) at 0° C. then was filtered and concentrated. The residue was purified by column chromatography to yield a yellow oil of (2-(benzyloxy)-6-(3,5-dichlorophenyl)pyridin-4-yl)methanol (10.7 g, 29.7 mmol, 96.0% yield): 1H NMR (400 MHz, CDCl3) δ ppm 7.83-7.78 (m, 1H), 7.46-7.41 (m, 1H), 7.40-7.36 (m, 1H), 7.30 (d, J=4.0 Hz, 4H), 7.23 (s, 3H), 5.29 (s, 2H), 4.68 (d, J=4.9 Hz, 2H); ES-LCMS m/z 359.9, 362.0 [M+H]+.

Step 4: (2-(Benzyloxy)-6-(3,5-dichlorophenyl)pyridin-4-yl)methyl methanesulfonate

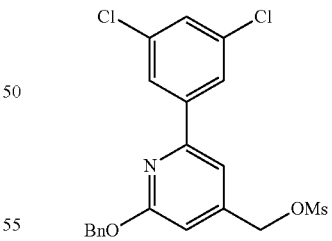

To a solution of (2-(benzyloxy)-6-(3,5-dichlorophenyl)pyridin-4-yl)methanol (3.0 g, 8.33 mmol) and DIEA (2.91 mL, 16.66 mmol) in DCM (40 mL) was added MsCl (0.779 mL, 9.99 mmol) at 0° C. The mixture was stirred at 25° C. for 3 h. DCM (100 mL) was added, washed with water (30 mL×3) and dried over Na2SO4. The organic phase was concentrated to yield a yellow oil of (2-(benzyloxy)-6-(3,5-dichlorophenyl)pyridin-4-yl)methyl methanesulfonate (3.0 g, 6.84 mmol, 82.0% yield): 1H NMR (400 MHz, CDCl3) δ ppm 7.80-7.78 (m, 2H), 7.43-7.41 (m, 2H), 7.40-7.36 (m, 1H), 7.36-7.31 (m, 5H), 5.42 (s, 2H), 5.16 (s, 2H), 3.01 (s, 3H); ES-LCMS m/z 437.9, 439.9 [M+H]⁺.

Step 5: N-((1-((2-(benzyloxy)-6-(3,5-dichlorophenyl)pyridin-4-yl)methyl)piperidin-4-yl)methyl)acetamide

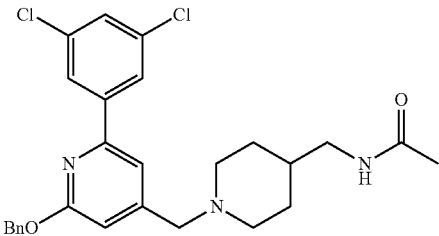 [SMILES: CC(=O)NCC1CCN(Cc2cc(OCc3ccccc3)nc(-c3cc(Cl)cc(Cl)c3)c2)CC1]

To a solution of (2-(benzyloxy)-6-(3,5-dichlorophenyl)pyridin-4-yl)methyl methanesulfonate (3.0 g, 6.84 mmol) and K₂CO₃ (1.892 g, 13.69 mmol) in DMF (30 mL) was added N-(piperidin-4-ylmethyl/acetamide (1.069 g, 6.84 mmol). The mixture was stirred at 80° C. for 12 h. After cooling to room temperature, the mixture was filtered and the filtrate was concentrated. The residue was purified by column chromatography to yield a yellow oil of N-((1-((2-(benzyloxy)-6-(3,5-dichlorophenyl)pyridin-4-yl)methyl)piperidin-4-yl)methyl)acetamide (3.0 g, 6.02 mmol, 88.0% yield): $^1$H NMR (400 MHz, CDCl₃) δ ppm 7.93-7.84 (m, 2H), 7.53-7.47 (m, 2H), 7.46-7.42 (m, 1H), 7.41-7.34 (m, 4H), 7.34-7.30 (m, 1H), 5.47-5.44 (m, 2H), 3.54-3.50 (m, 2H), 3.18-3.11 (m, 2H), 2.91-2.77 (m, 4H), 2.11-2.07 (m, 3H), 1.71-1.67 (m, 2H), 1.55-1.49 (m, 1H), 1.32-1.23 (m, 2H); ES-LCMS m/z 498.1, 500.1 [M+H]⁺.

Step 6: N-((1-((2-(3,5-dichlorophenyl)-6-hydroxypyridin-4-yl)methyl)piperidin-4-yl)methyl)acetamide

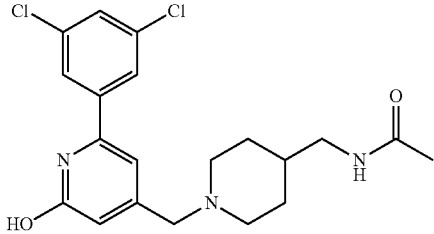 [SMILES: CC(=O)NCC1CCN(Cc2cc(O)nc(-c3cc(Cl)cc(Cl)c3)c2)CC1]

To a solution of N-((1-((2-(benzyloxy)-6-(3,5-dichlorophenyl)pyridin-4-yl)methyl)piperidin-4-yl)methyl)acetamide (2.0 g, 4.01 mmol) in THF (20 mL) was added concentrated HCl (15 mL, 180 mmol). The mixture was stirred at 80° C. for 4 h then concentrated. The residue was purified by column chromatography to yield a brown solid of N-((1-((2-(3,5-dichlorophenyl)-6-hydroxypyridin-4-yl/methyl)piperidin-4-yl)methyl)acetamide (1.0 g, 2.449 mmol, 61.0% yield): $^1$H NMR (400 MHz, CD₃OD) δ ppm 7.74-7.66 (m, 2H), 7.61-7.54 (m, 1H), 6.81-6.72 (m, 1H), 6.57-6.48 (m, 1H), 3.44 (s, 2H), 3.09-3.02 (m, 2H), 2.95-2.86 (m, 2H), 2.12-2.00 (m, 2H), 1.92 (s, 3H), 1.76-1.65 (m, 2H), 1.60-1.45 (m, 1H), 1.38-1.21 (m, 2H); ES-LCMS m/z 408.2, 410.1 [M+H]⁺.

Step 7: N-((1-((2-((6-Bromopyridin-3-yl)oxy)-6-(3,5-dichlorophenyl)pyridin-4-yl)methyl)piperidin-4-yl)methyl)acetamide

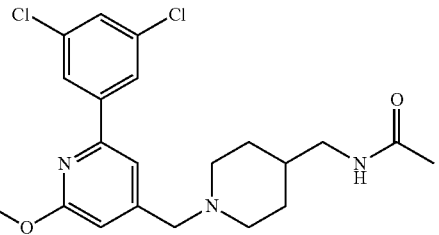

A mixture of N-((1-((2-(3,5-dichlorophenyl)-6-hydroxypyridin-4-yl)methyl)piperidin-4-yl)methyl)acetamide (1 g, 2.449 mmol), 2-bromo-5-fluoropyridine (0.646 g, 3.67 mmol) and Cs₂CO₃ (3.99 g, 12.25 mmol) in NMP (15 mL) was stirred at 130° C. for 16 h. The mixture was cooled to room temperature and filtered. The filtrate was concentrated and the residue was purified twice by silica gel column chromatography (MeOH/DCM=1/10). All fractions found to contain product by TLC (MeOH/DCM=1/10) were combined and concentrated to yield a brown solid of N-((1-((2-((6-bromopyridin-3-yl)oxy)-6-(3,5-dichlorophenyl)pyridin-4-yl)methyl)piperidin-4yl)methyl)acetamide (580 mg, 0.504 mmol, 20.6% yield): $^1$H NMR (400 MHz, CDCl₃) δ ppm 8.36-8.30 (m, 1H), 7.73 (d, J=1.7 Hz, 1H), 7.68 (d, J=1.7 Hz, 1H), 7.54-7.51 (m, 1H), 7.50-7.47 (m, 1H), 7.45 (s, 1H), 7.35-7.31 (m, 1H), 7.01-6.93 (m, 1H), 3.53 (s, 2H), 3.18-3.14 (m, 2H), 2.88 (d, J=10.8 Hz, 2H), 2.00-1.96 (m, 5H), 1.73-1.60 (m, 2H), 1.53 (d, J=4.2 Hz, 1H), 1.32 (d, J=7.6 Hz, 2H); ES-LCMS m/z 563.0, 564.9 [M+H]⁺.

Intermediate 16: Methyl 2-(1-((2-((6-bromopyridin-3-yl)oxy)-6-(3,5-dichlorophenyl)pyridin-4-yl)methyl)piperidin-4-yl)acetate

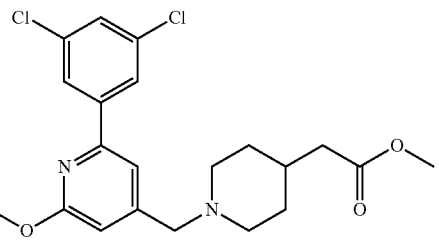

Step 1: Methyl 2-(1-((2-(benzyloxy)-6-(3,5-dichlorophenyl)pyridin-4-yl)methyl)piperidin-4-yl)acetate

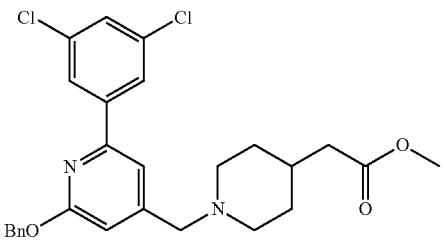 [SMILES: COC(=O)CC1CCN(Cc2cc(OCc3ccccc3)nc(-c3cc(Cl)cc(Cl)c3)c2)CC1]

To a mixture of (2-(benzyloxy)-6-(3,5-dichlorophenyl) pyridin-4-yl)methyl methanesulfonate (27 g, 52.7 mmol) and methyl 2-(piperidin-4-yl)acetate, hydrochloride (12.90 g, 63.3 mmol) in DMF (400 mL) was added K$_2$CO$_3$ (21.86 g, 158 mmol). The mixture was stirred at 70° C. for 10 h before being concentrated. The residue was mixed with DCM (300 mL) and filtered. The filtrate was concentrated to yield a yellow oil of methyl 2-(1-((2-(benzyloxy)-6-(3,5-dichlorophenyl)pyridin-4-yl)methyl)piperidin-4-yl)acetate (25 g, 46.3 mmol, 88.0% yield): $^1$H NMR (400 MHz, CD$_3$OD) δ ppm 7.97 (s, 2H), 7.50-7.45 (m, 4H), 7.39-7.35 (m, 2H), 7.28-7.26 (m, 1H), 6.83 (s, 1H), 5.47 (s, 2H), 3.65 (s, 3H), 3.55 (s, 2H), 2.91-2.89 (m, 2H), 2.28-2.27 (m, 2H), 2.08-2.06 (m, 2H), 1.78-1.71 (m, 3H), 1.36-1.32 (m, 2H); ES-LCMS m/z 499.3, 501.3 [M+H]$^+$.

Step 2: Methyl 2-(1-((2-(3,5-dichlorophenyl)-6-hydroxypyridin-4-yl)methyl)piperidin-4-yl)acetate

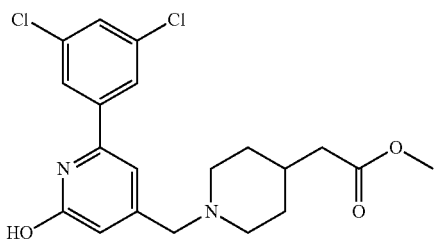 [SMILES: COC(=O)CC1CCN(Cc2cc(O)nc(-c3cc(Cl)cc(Cl)c3)c2)CC1]

A mixture of methyl 2-(1-((2-(benzyloxy)-6-(3,5-dichlorophenyl)pyridin-4-yl)methyl)piperidin-4-yl)acetate (25 g, 46.3 mmol) and TFA (300 mL, 3894 mmol) was stirred at 50° C. for 1 h. The mixture was concentrated. The residue was poured into ice water (200 mL), neutralized with saturated Na$_2$CO$_3$ solution to pH to 8 then extracted with DCM/MeOH (10/1, 100 mL×3). The combined organic layers were concentrated and the residue was purified on silica gel column chromatography (DCM/MeOH=1/0 to 10/1). All fractions found to contain product by TLC (DCM/MeOH=10/1, R$_f$=0.6) were combined and concentrated to yield a yellow oil. The yellow oil was triturated in PE/EtOAc (5/1, 100 mL) then filtered. The filter cake was washed with PE/EtOAc (5/1, 10 mL) and dried to yield a yellow solid of methyl 2-(1-((2-(3,5-dichlorophenyl)-6-hydroxypyridin-4-yl)methyl)piperidin-4-yl)acetate (17 g, 34.7 mmol, 74.9% yield): $^1$H NMR (400 MHz, CD$_3$OD) δ ppm 7.80 (s, 2H), 7.64 (s, 1H), 6.92 (s, 1H), 6.70 (s, 1H), 4.16 (s, 2H), 3.69 (s, 3H), 3.50-3.48 (m, 2H), 3.01-2.98 (m, 2H), 2.39-2.37 (m, 2H), 2.03-2.00 (m, 3H), 1.56-1.54 (m, 2H); ES-LCMS m/z 409.2, 411.2 [M+H]$^+$.

Step 3: Methyl 2-(1-((2-((6-bromopyridin-3-yl)oxy)-6-(3,5-dichlorophenyl)pyridin-4-yl)methyl)piperidin-4-yl)acetate

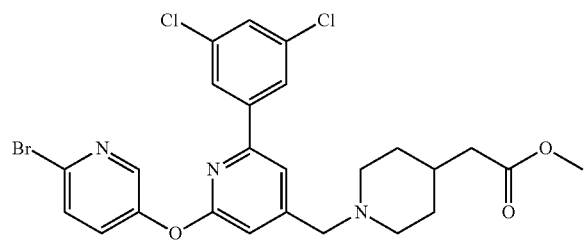 [SMILES: COC(=O)CC1CCN(Cc2cc(Oc3ccc(Br)nc3)nc(-c3cc(Cl)cc(Cl)c3)c2)CC1]

To a mixture of methyl 2-(1-((2-(3,5-dichlorophenyl)-6-hydroxypyridin-4-yl)methyl)piperidin-4-yl)acetate (14.5 g, 29.6 mmol) and 2-bromo-5-fluoropyridine (17.59 mL, 148 mmol) in NMP (300 mL) was added K$_2$CO$_3$ (12.26 g, 89 mmol). The mixture was stirred at 150° C. for 30 h then filtered and the filtrate was concentrated. The residue was purified on silica gel column chromatography (PE/EtOAc=5/1 to 1/1 to DCM/MeOH 15=10/1). All fractions found to contain product by TLC (PE/EtOAc=1/1, R$_f$=0.4) were combined and concentrated to yield a crude product, which was further purified by preparative HPLC (MeCN/H$_2$O as eluents, acidic condition). The desired fraction was combined and concentrated to about 100 mL, followed by being basified with saturated Na$_2$CO$_3$ solution to pH=8 and extracted with DCM/MeOH (10/1, 100 mL×3). The combined organic layers were dried over Na$_2$SO$_4$, filtered and concentrated to yield a white solid of methyl 2-(1-((2-((6-bromopyridin-3-yl)oxy)-6-(3,5-dichlorophenyl)pyridin-4-yl)methyl)piperidin-4-yl)acetate (6.15 g, 10.87 mmol, 36.8% yield): $^1$H NMR (400 MHz, CD$_3$OD) δ ppm 8.34 (s, 1H), 7.82 (s, 2H), 7.77 (s, 1H), 7.75-7.66 (m, 2H), 7.47 (s, 1H), 7.18 (s, 1H), 4.01 (s, 2H), 3.66 (s, 3H), 3.24-3.22 (m, 2H), 2.62-2.60 (m, 2H), 2.34-2.32 (m, 2H), 1.91-1.87 (m, 3H), 1.51-1.43 (m, 2H); ES-LCMS m/z 564.2, 566.1 [M+H]$^+$.

Intermediate 17: tert-Butyl 4-(5-((6-(3,5-dichlorophenyl)-4-(hydroxymethyl)pyridin-2-yl)oxy)-3-fluoropyridin-2-yl)piperazine-1-carboxylate

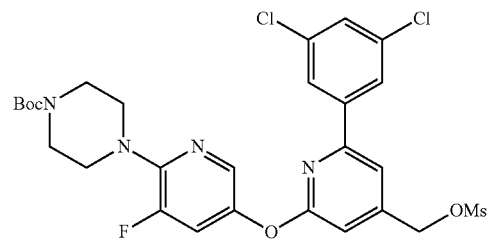 [SMILES: CC(C)(C)OC(=O)N1CCN(c2ncc(Oc3cc(COS(C)(=O)=O)cc(-c4cc(Cl)cc(Cl)c4)n3)cc2F)CC1]

Step 1: 5-(Benzyloxy)-2-chloro-3-fluoropyridine

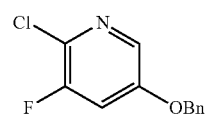 [SMILES: Fc1cc(OCc2ccccc2)cnc1Cl]

To a mixture of 6-chloro-5-fluoropyridin-3-ol (1 g, 6.78 mmol), K$_2$CO$_3$ (2.81 g, 20.33 mmol) in DMF (15 mL) was added (bromomethyl)benzene (2.319 g, 13.56 mmol). The reaction mixture was stirred at 20° C. for 2 h then was filtered and concentrated. The residue was separated between DCM (50 mL) and H$_2$O (20 mL). The aqueous phase was extracted with DCM (50 mL×2). The organic phases were combined and washed with brine (30 mL), dried over Na$_2$SO$_4$, filtered and concentrated to yield a yellow solid of 5-(benzyloxy)-2-chloro-3-fluoropyridine (1.3 g, 4.38 mmol, 64.6% yield): $^1$H NMR (400 MHz, CDCl$_3$) δ ppm 8.04-7.95 (m, 1H), 7.40-7.35 (m, 5H), 7.10 (dd, J=2.6, 9.4 Hz, 1H), 5.09 (s, 2H); ES-LCMS m/z 238.0, 240.0 [M+H]$^+$.

Step 2: tert-Butyl 4-(5-(benzyloxy)-3-fluoropyridin-2-yl)piperazine-1-carboxylate

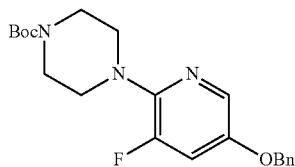 [SMILES: CC(C)(C)OC(=O)N1CCN(c2ncc(OCc3ccccc3)cc2F)CC1]

A mixture of tert-butyl piperazine-1-carboxylate (2.038 g, 10.94 mmol), (±)-BINAP (0.681 g, 1.094 mmol), 5-(benzyloxy)-2-chloro-3-fluoropyridine (1.3 g, 5.47 mmol), $Pd_2(dba)_3$ (0.501 g, 0.547 mmol) and sodium tert-butoxide (1.577 g, 16.41 mmol) in THF (20 mL) was heated to 65° C. for 12 h under $N_2$ atmosphere. The mixture was concentrated to yield the crude product which was purified by silica gel column chromatography (PE/EtOAc=2/1). All fractions found to contain product by TLC (EtOAc/PE=1/3, $R_f$=0.5) were combined and concentrated to yield a yellow solid of tert-butyl 4-(5-(benzyloxy)-3-fluoropyridin-2-yl)piperazine-1-carboxylate (1 g, 2.323 mmol, 42.5% yield): $^1$H NMR (400 MHz, $CDCl_3$) δ ppm 7.82 (d, J=2.5 Hz, 1H), 7.43-7.39 (m, 4H), 7.37-7.33 (m, 1H), 7.02 (dd, J=2.0, 13.1 Hz, 1H), 5.05 (s, 2H), 3.61-3.51 (m, 4H), 3.35-3.22 (m, 4H), 1.48 (s, 9H); ES-LCMS m/z 388.2 $[M+H]^+$.

Step 3: tert-Butyl 4-(3-fluoro-5-hydroxypyridin-2-yl)piperazine-1-carboxylate

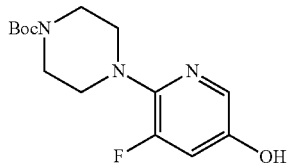 [SMILES: CC(C)(C)OC(=O)N1CCN(c2ncc(O)cc2F)CC1]

A mixture of tert-butyl 4-(5-(benzyloxy)-3-fluoropyridin-2-yl)piperazine-1-carboxylate (1 g, 2.58 mmol), Pd/C (0.275 g, 0.258 mmol) in MeOH (20 mL) was heated to 50° C. for 10 h under $H_2$ atmosphere at 50 psi. The mixture was filtered and concentrated to yield the crude product as a yellow solid of tert-butyl 4-(3-fluoro-5-hydroxypyridin-2-yl)piperazine-1-carboxylate (800 mg, 2.153 mmol, 83.0% yield): $^1$H NMR (400 MHz, $CD_3OD$) δ ppm 7.62 (d, J=2.2 Hz, 1H), 7.05-6.91 (m, 1H), 3.61-3.48 (m, 4H), 3.20-3.12 (m, 4H), 1.49-1.45 (m, 9H); ES-LCMS m/z 298.1 $[M+H]^+$.

Step 4: 2-((6-(4-(tert-Butoxycarbonyl)piperazin-1-yl)-5-fluoropyridin-3-yl)oxy)-6-chloroisonicotinic

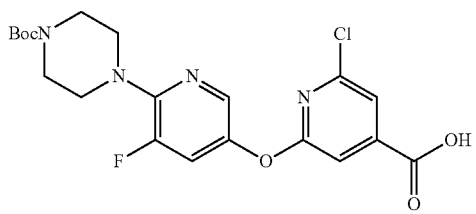 [SMILES: CC(C)(C)OC(=O)N1CCN(c2ncc(Oc3cc(C(=O)O)cc(Cl)n3)cc2F)CC1]

A mixture of tert-butyl 4-(3-fluoro-5-hydroxypyridin-2-yl)piperazine-1-carboxylate (1.3 g, 4.37 mmol), methyl 2,6-dichloroisonicotinate (1.802 g, 8.74 mmol) and $K_2CO_3$ (1.813 g, 13.12 mmol) in THF (10 mL) was heated to 65° C. for 3 h under $N_2$ atmosphere. Volatiles were concentrated to yield the crude product which was purified by silica gel column chromatography (DCM/MeOH=10/1). All fractions found to contain product by TLC (DCM/MeOH=10/1, $R_f$=0.5) were combined and concentrated to yield a yellow solid of 2-((6-(4-(tert-butoxycarbonyl)piperazin-1-yl)-5-fluoropyridin-3-yl)oxy)-6-chloroisonicotinic acid (800 mg, 1.237 mmol, 28.3% yield): $^1$H NMR (400 MHz, $CDCl_3$) δ ppm 7.21-7.09 (m, 1H), 6.60 (br. s, 2H), 6.53-6.47 (m, 1H), 2.78 (br. s, 4H), 2.59 (s, 4H), 0.69 (br. s, 9H); ES-LCMS m/z 397.1, 399.1 $[M-t-Bu+H]^+$.

Step 5: Methyl 2-chloro-6-((5-fluoro-6-(piperazin-1-yl)pyridin-3-yl)oxy)isonicotinate

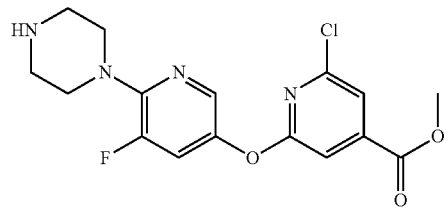 [SMILES: COC(=O)c1cc(Cl)nc(Oc2cnc(N3CCNCC3)c(F)c2)c1]

To a mixture of 2-((6-(4-(tert-butoxycarbonyl)piperazin-1-yl)-5-fluoropyridin-3-yl)oxy)-6-chloroisonicotinic acid (800 mg, 1.767 mmol) in MeOH (10 mL) was added $SOCl_2$ (1.289 mL, 17.67 mmol). The mixture was stirred at 60° C. for 5 h then was cooled and concentrated to yield brown oil of methyl 2-chloro-6-((5-fluoro-6-(piperazin-1-yl)pyridin-3-yl)oxy)isonicotinate (600 mg, 1.472 mmol, 83.0% yield): $^1$H NMR (400 MHz, $CDCl_3$) δ ppm 7.96 (d, J=2.2 Hz, 1H), 7.63-7.57 (m, 1H), 7.41 (s, 1H), 7.28 (d, J=2.2 Hz, 1H), 3.97 (s, 3H), 3.84 (br. s, 4H), 3.37 (d, J=4.4 Hz, 4H); ES-LCMS m/z 367.1, 369.0 $[M+H]^+$.

Step 6: tert-Butyl 4-(5-((6-chloro-4-(methoxycarbonyl)pyridin-2-yl)oxy)-3-fluoropyridin-2-yl)piperazine-1-carboxylate

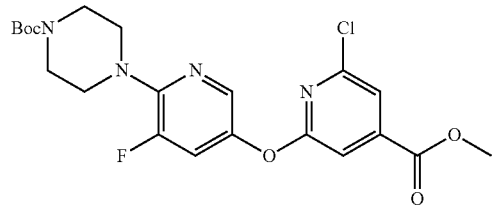 [SMILES: COC(=O)c1cc(Cl)nc(Oc2cnc(N3CCN(C(=O)OC(C)(C)C)CC3)c(F)c2)c1]

A mixture of methyl 2-chloro-6-((5-fluoro-6-(piperazin-1-yl)pyridin-3-yl)oxy)isonicotinate (600 mg, 1.636 mmol), $Boc_2O$ (0.570 mL, 2.454 mmol) and DIEA (0.857 mL, 4.91 mmol) in DCM (10 mL) was stirred at 15° C. for 6 h. The mixture was diluted with water (30 mL) then extracted with DCM (50 mL×3). The organic layers was washed with brine, dried over $Na_2SO_4$, filtered and concentrated. The crude product was purified by silica gel column chromatography (PE/EtOAc=4/1). All fractions found to contain product by TLC (EtOAc/PE=1/1, $R_f$=0.5) were combined and concentrated to yield a yellow oil of tert-butyl 4-(5-((6-chloro-4-(methoxycarbonyl)pyridin-2-yl)oxy)-3-fluoropyridin-2-yl)piperazine-1-carboxylate (800 mg, 1.456 mmol, 89.0% yield): $^1$H NMR (400 MHz, CDCl$_3$) δ ppm 7.95 (d, J=2.2 Hz, 1H), 7.59 (s, 1H), 7.39 (s, 1H), 7.20 (d, J=2.2 Hz, 1H), 3.96 (s, 3H), 3.57 (d, J=4.9 Hz, 4H), 3.42 (br. s, 4H), 1.48 (s, 9H); ES-LCMS m/z 411.0, 413.0 [M−t−Bu+H]$^+$.

Step 7: tert-Butyl 4-(5-((6-(3,5-dichlorophenyl)-4-(methoxycarbonyl)pyridin-2-yl)oxy)-3-fluoropyridin-2-yl)piperazine-1-carboxylate

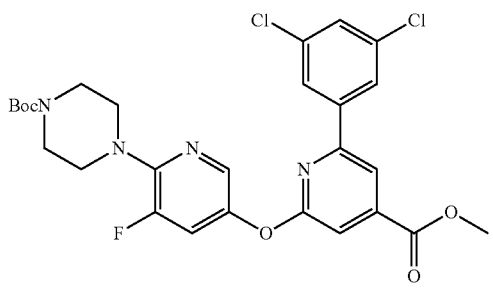 [SMILES: COC(=O)c1cc(Oc2cnc(N3CCN(C(=O)OC(C)(C)C)CC3)c(F)c2)nc(-c2cc(Cl)cc(Cl)c2)c1]

A mixture of tert-butyl 4-(5-((6-chloro-4-(methoxycarbonyl)pyridin-2-yl)oxy)-3-fluoropyridin-2-yl)piperazine-1-carboxylate (0.8 g, 1.713 mmol), PdCl$_2$(dppf) (0.125 g, 0.171 mmol), K$_2$CO$_3$ (0.474 g, 3.43 mmol), (3,5-dichlorophenyl)boronic acid (0.49 g, 2.57 mmol) in 1,4-dioxane (10 mL) and water (1 mL) was heated at 65° C. for 8 h under N$_2$ atmosphere. Volatiles were concentrated to yield the crude product which was distributed between DCM (30 mL) and H$_2$O (20 mL), extracted with DCM (50 mL×2). The combined organic layer was washed with brine (20 mL), dried over Na$_2$SO$_4$, filtered and concentrated. The crude product was purified by silica gel column chromatography (PE/EtOAc=4/1). All fractions found to contain product by TLC (EtOAc/PE=1/3, $R_f$=0.6) were combined and concentrated to yield a light yellow solid of tert-butyl 4-(5-((6-(3,5-dichlorophenyl)-4-(methoxycarbonyl)pyridin-2-yl)oxy)-3-fluoropyridin-2yl)piperazine-1-carboxylate (800 mg, 1.178 mmol, 68.7% yield): $^1$H NMR (400 MHz, CD$_3$OD) (δ ppm 8.11 (s, 1H), 8.02 (d, J=1.8 Hz, 1H), 7.85 (d, J=1.3 Hz, 2H), 7.57-7.52 (m, 2H), 7.48 (s, 1H), 4.02-3.96 (m, 3H), 3.59 (br. s, 4H), 3.44 (d, J=5.3 Hz, 4H), 1.49 (s, 9H); ES-LCMS m/z 577.1, 579.1 [M+H]$^+$.

Step 8: tert-Butyl 4-(5-((6-(3,5-dichlorophenyl)-4-(hydroxymethyl)pyridin-2-yl)oxy)-3-fluoropyridin-2-yl)piperazine-1-carboxylate

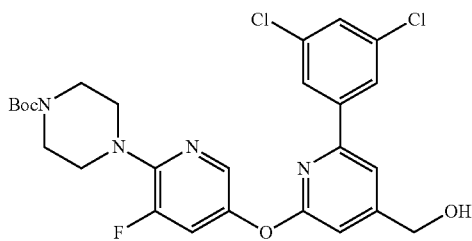 [SMILES: CC(C)(C)OC(=O)N1CCN(c2ncc(Oc3cc(CO)cc(-c4cc(Cl)cc(Cl)c4)n3)cc2F)CC1]

A mixture of tert-butyl 4-(5-((6-(3,5-dichlorophenyl)-4-(methoxycarbonyl)pyridin-2-yl)oxy)-3-fluoropyridin-2-yl)piperazine-1-carboxylate (800 mg, 1.385 mmol), NaBH$_4$ (524 mg, 13.85 mmol) in MeOH (10 mL) was stirred at 25° C. for 2 h. Volatiles were concentrated to yield the crude product which was separated between DCM (50 mL) and H$_2$O (20 mL). The aqueous phase was extracted with DCM (50 mL×2) and the combined organic layer was washed with brine (20 mL), dried over Na$_2$SO$_4$, filtered and concentrated. The crude product was purified by silica gel column chromatography (DCM/MeOH=4/1). All fractions found to contain product by TLC (DCM/MeOH=1/1, $R_f$=0.4) were combined and concentrated to yield a light yellow solid of tert-butyl 4-(5-((6-(3,5-dichlorophenyl)-4-(hydroxymethyl)pyridin-2-yl)oxy)-3-fluoropyridin-2-yl)piperazine-1-carboxylate (500 mg, 0.819 mmol, 59.1% yield): $^1$H NMR (400 MHz, CDCl$_3$) δ ppm 8.04-7.98 (m, 1H), 7.75 (d, J=1.5 Hz, 2H), 7.45 (s, 1H), 7.36 (s, 1H), 7.30 (dd, J=2.0, 12.5 Hz, 1H), 6.92 (s, 1H), 4.87-4.76 (m, 2H), 3.63-3.54 (m, 4H), 3.44 (d, J=5.0 Hz, 4H), 1.50 (s, 9H); ES-LCMS m/z 549.1, 551.1 [M+H]$^+$.

Step 9: tert-Butyl 4-(5-((6-(3,5-dichlorophenyl)-4-(hydroxymethyl)pyridin-2-yl)oxy)-3-fluoropyridin-2-yl)piperazine-1-carboxylate

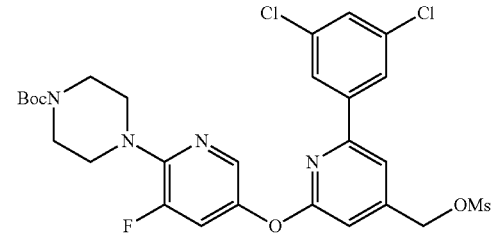 [SMILES: CC(C)(C)OC(=O)N1CCN(c2ncc(Oc3cc(COS(C)(=O)=O)cc(-c4cc(Cl)cc(Cl)c4)n3)cc2F)CC1]

To a mixture of tert-butyl 4-(5-((6-(3,5-dichlorophenyl)-4-(hydroxymethyl)pyridin-2-yl)oxy)-3-fluoropyridin-2-yl)piperazine-1-carboxylate (500 mg, 0.910 mmol), DIEA (0.477 mL, 2.73 mmol) in DCM (10 mL) was added MsCl (0.106 mL, 1.365 mmol) at 25° C. The mixture was stirred for 20 min before NaHCO$_3$ solution (aq., 5 wt %, 10 mL) was added. The mixture was extracted with DCM (50 mL×2) and the combined organic layer was washed with brine (20 mL), dried over Na$_2$SO$_4$, filtered and concentrated to yield a yellow oil of tert-butyl 4-(5-((6-(3,5-dichlorophenyl)-4-(((methylsulfonyl)oxy)methyl)pyridin-2-yl)oxy)-3-fluoropyridin-2-yl)piperazine-1-carboxylate (500 mg, 0.637 mmol, 70.0% yield): $^1$H NMR (400 MHz, CDCl$_3$) δ ppm 8.04-7.99 (m, 1H), 7.73 (d, J=1.5 Hz, 2H), 7.47-7.43 (m, 1H), 7.39-7.36 (m, 1H), 7.31 (dd, J=2.0, 12.5 Hz, 1H), 6.95 (s, 1H), 4.63-4.57 (m, 2H), 3.62-3.56 (m, 4H), 3.45 (d, J=5.5 Hz, 4H), 2.79 (s, 3H), 1.43 (s, 9H); ES-LCMS m/z 627.1, 629.1 [M+H]$^+$.

Intermediate 18: tert-Butyl 4-(5-((3',5'-dichloro-5-(((methylsulfonyl)oxy)methyl)-[1,1'-biphenyl]-3-yl)oxy)pyridin-2-yl)piperazine-1-carboxylate

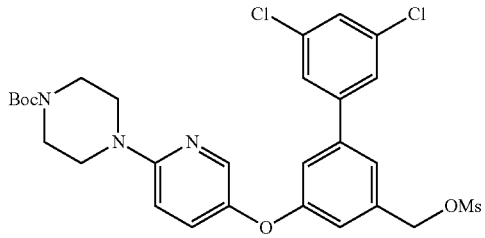 [SMILES: CC(C)(C)OC(=O)N1CCN(c2ccc(Oc3cc(COS(C)(=O)=O)cc(-c4cc(Cl)cc(Cl)c4)c3)cn2)CC1]

Step 1: Methyl 5-((6-bromopyridin-3-yl)oxy)-3',5'-dichloro-[1,1'-biphenyl]-3-carboxylate

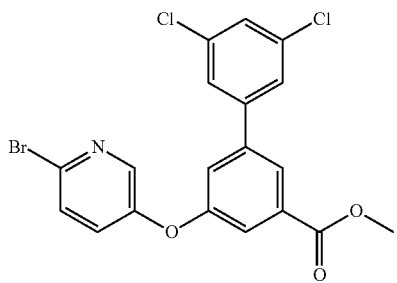 [SMILES: COC(=O)c1cc(Oc2ccc(Br)nc2)cc(-c2cc(Cl)cc(Cl)c2)c1]

To a mixture of 2-bromo-5-fluoropyridine (1.895 g, 10.77 mmol) in DMF (50 mL) was added methyl 3',5'-dichloro-5-hydroxy-[1,1'-biphenyl]-3-carboxylate (2 g, 5.38 mmol), K₂CO₃ (2.233 g, 16.15 mmol). The mixture was stirred at 120° C. for 5 h then was concentrated and partitioned between DCM (100 mL) and H₂O (100 mL). The aqueous phase was extracted with DCM (100 mL×2) and the combined organic layers were dried over Na₂SO₄, filtered and concentrated to yield crude product. The crude material was purified by silica gel column chromatography (PE/EtOAc=20/1 to 5/1). All fractions found to contain product by TLC (PE/EtOAc=3/1, R$_f$=0.6) were combined and concentrated to yield a brown solid of methyl 5-((6-bromopyridin-3-yl)oxy)-3',5'-dichloro-[1,1'-biphenyl]-3-carboxylate (1500 mg, 2.65 mmol, 49.2% yield): ¹H NMR (400 MHz, CDCl₃) δ ppm 8.21 (d, J=3.0 Hz, 1H), 8.02 (s, 1H), 7.65 (s, 1H), 7.46 (d, J=1.5 Hz, 3H), 7.41-7.37 (m, 2H), 7.28-7.24 (m, 1H), 3.95-3.91 (m, 3H); ES-LCMS m/z 452.0, 454.0 [M+H]⁺.

Step 2: tert-Butyl 4-(5-((3',5'-dichloro-5-(methoxycarbonyl)-[1,1'-biphenyl]-3-yl)oxy)pyridin-2-yl)piperazine-1-carboxylate

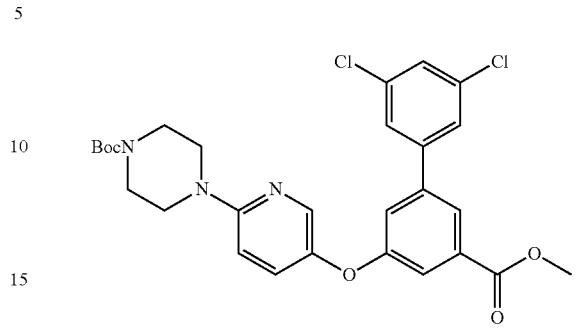

To a mixture of methyl 5-((6-bromopyridin-3-yl)oxy)-3',5'-dichloro-[1,1'-biphenyl]-3-carboxylate (1.5 g, 2.65 mmol) in THF (20 mL) was added tert-butyl piperazine-1-carboxylate (0.740 g, 3.97 mmol), Pd₂(dba)₃ (0.073 g, 0.079 mmol), Cs₂CO₃ (2.59 g, 7.95 mmol) and Xantphos (0.766 g, 1.324 mmol). The mixture was stirred at 70° C. for 4 h under N₂ atmosphere then was concentrated and partitioned between DCM (100 mL) and H₂O (100 mL). The aqueous phase was extracted with DCM (100 mL×2) and the combined organic layers were dried over Na₂SO₄, filtered and concentrated to yield crude product. The crude product was purified by silica gel column chromatography (DCM/MeOH=20/1 to 5/1). All fractions found to contain product by TLC (DCM/MeOH=30/1, R$_f$=0.5) were combined and concentrated to yield a green solid of tert-butyl 4-(5-((3',5'-dichloro-5-(methoxycarbonyl)-[1,1'-biphenyl]-3-yl)oxy)pyridin-2-yl)piperazine-1-carboxylate (1.6 g, 2.292 mmol, 87.0% yield): ¹H NMR (400 MHz, CDCl₃) δ ppm 8.09-8.04 (m, 1H), 7.88 (s, 1H), 7.57-7.53 (m, 1H), 7.43 (d, J=1.8 Hz, 1H), 7.40-7.37 (m, 1H), 7.31-7.28 (m, 1H), 6.93 (t, J=7.7 Hz, 1H), 6.69 (d, J=9.3 Hz, 1H), 6.52 (dd, J=1.5, 7.3 Hz, 1H), 3.95-3.89 (m, 3H), 3.56 (d, J=5.3 Hz, 4H), 3.53-3.49 (m, 4H), 1.48 (s, 9H); ES-LCMS m/z 558.2, 560.2 [M+H]⁺.

Step 3: tert-Butyl 4-(5-((3',5'-dichloro-5-(hydroxymethyl)-[1,1'-biphenyl]-3-yl)oxy)pyridin-2-yl)piperazine-1-carboxylate

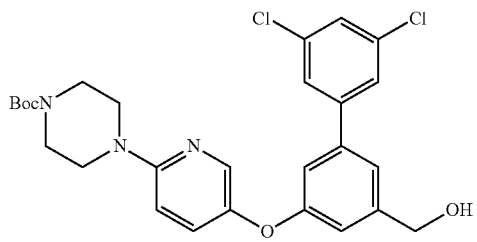

To a mixture of tert-butyl 4-(5-((3',5'-dichloro-5-(methoxycarbonyl)-[1,1'-biphenyl]-3-yl)oxy)pyridin-2-yl)piperazine-1-carboxylate (1.6 g, 2.292 mmol) in THF (20 mL) was added LiAlH₄ (0.096 g, 2.52 mmol) at −20° C. The mixture was stirred at −20° C. for 4 h. The mixture was quenched by H₂O (0.1 mL), followed by 10% NaOH solution H₂O (0.1 mL), then filtered and the filtrate was concentrated to yield a green solid of crude product tert-butyl 4-(5-((3',5'-dichloro-5-(hydroxymethyl)-[1,1'-biphenyl]-3-yl)oxy)pyridin-2-yl)piperazine-1-carboxylate (1.4 g, 2.111 mmol, 92.0% yield): $^1$H NMR (400 MHz, CDCl$_3$) δ ppm 8.03-7.96 (m, 1H), 7.34 (d, J=1.8 Hz, 1H), 7.27 (t, J=1.8 Hz, 1H), 7.19 (s, 1H), 6.95 (s, 1H), 6.91-6.83 (m, 2H), 6.67-6.58 (m, 1H), 6.49-6.43 (m, 1H), 4.74-4.58 (m, 2H), 3.50 (d, J=5.7 Hz, 4H), 3.46-3.41 (m, 4H), 1.42 (s, 9H); ES-LCMS m/z 530.1, 532.1 [M+H]$^+$.

Step 4: tert-Butyl 4-(5-((3',5'-dichloro-5-(((methylsulfonyl)oxy)methyl)-[1,1'-biphenyl]-3-yl)oxy)pyridin-2-yl)piperazine-1-carboxylate

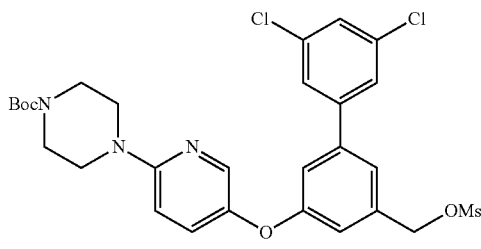 [SMILES: CC(C)(C)OC(=O)N1CCN(c2ccc(Oc3cc(COS(C)(=O)=O)cc(-c4cc(Cl)cc(Cl)c4)c3)cn2)CC1]

To a mixture of tert-butyl 4-(5-((3',5'-dichloro-5-(hydroxymethyl)-[1,1'-biphenyl]-3-yl)oxy)pyridin-2-yl)piperazine-1-carboxylate (600 mg, 0.905 mmol), DIEA (0.5 mL, 2.86 mmol) in DCM (50 mL) was added MsCl (0.106 mL, 1.357 mmol) at 30° C. The mixture was stirred at 30° C. for 0.5 h then was washed with water (50 mL×3). The organic phase was dried over Na$_2$SO$_4$ and filtered. The filtrate was concentrated to yield a brown solid of tert-butyl 4-(5-((3',5'-dichloro-5-(((methylsulfonyl)oxy)methyl)-[1,1'-biphenyl]-3-yl)oxy)pyridin-2-yl)piperazine-1-carboxylate (700 mg, 0.663 mmol, 73.2% yield): $^1$H NMR (400 MHz, CDCl$_3$) δ ppm 7.32 (br. s, 1H), 7.28 (d, J=2.2 Hz, 2H), 7.26-7.20 (m, 2H), 7.15 (br. s, 1H), 7.03 (br. s, 1H), 6.92-6.89 (m, 1H), 6.64 (d, J=9.3 Hz, 1H), 5.26 (s, 2H), 3.50-3.48 (m, 8H), 2.94 (s, 3H), 1.47 (s, 9H); ES-LCMS m/z 608.1, 610.1 [M+H]$^+$.

Intermediate 19: (2-((2-(4-((tert-Butoxycarbonyl)amino)piperidin-1-yl)pyrimidin-5-yl)oxy)-6-(3,5-dichlorophenyl)pyridin-4-yl)methyl methanesulfonate

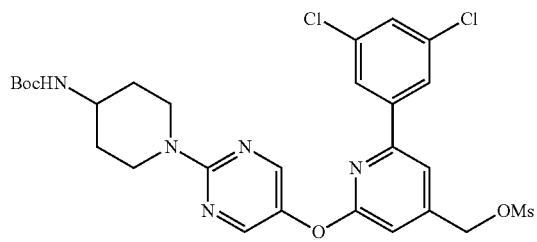 [SMILES: CC(C)(C)OC(=O)NC1CCN(c2ncc(Oc3cc(COS(C)(=O)=O)cc(-c4cc(Cl)cc(Cl)c4)n3)cn2)CC1]

Step 1: tert-Butyl (1-(5-(benzyloxy)pyrimidin-2-yl)piperidin-4-yl)carbamate

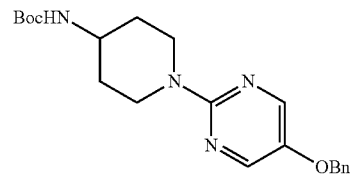 [SMILES: CC(C)(C)OC(=O)NC1CCN(c2ncc(OCc3ccccc3)cn2)CC1]

To a mixture of 5-(benzyloxy)-2-chloropyrimidine (4 g, 16.32 mmol) and tert-butyl piperidin-4-ylcarbamate (6.54 g, 32.6 mmol) in DML (100 mL) was added Cs$_2$CO$_3$ (15.95 g, 48.9 mmol). The reaction mixture was stirred at 80° C. for 10 h then filtered, concentrated and the residue was purified by silica gel column chromatography (PE/EtOAc=5/1). All fractions found to contain product by TLC (PE/EA=3/1, R$_f$=0.6) were combined and concentrated to yield a white solid of tert-butyl (1-(5-(benzyloxy)pyrimidin-2-yl)piperidin-4-yl)carbamate (3.5 g, 8.65 mmol, 53.0% yield): $^1$H NMR (400 MHz, CDCl$_3$) δ ppm 8.09 (s, 2H), 7.37-7.32 (m, 5H), 4.99 (s, 2H), 4.49-4.46 (m, 3H), 3.02-2.96 (m, 2H), 2.02-1.97 (m, 2H), 1.43 (s, 9H), 1.35-1.33 (m, 2H); ES-LCMS m/z 385.2 [M+H]$^+$.

Step 2: tert-Butyl (1-(5-hydroxypyrimidin-2-yl)piperidin-4-yl)carbamate

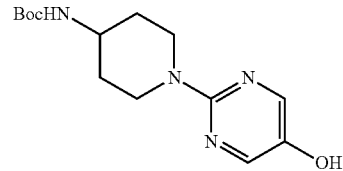 [SMILES: CC(C)(C)OC(=O)NC1CCN(c2ncc(O)cn2)CC1]

A mixture of tert-butyl (1-(5-(benzyloxy)pyrimidin-2-yl)piperidin-4-yl)carbamate (3.5 g, 8.65 mmol), Pd/C (0.920 g, 0.865 mmol) in MeOH (50 mL) was stirred at 25° C. for 0.5 h under H$_2$ atmosphere at 15 psi. The mixture was filtered and concentrated to yield a yellow solid of tert-butyl (1-(5-hydroxypyrimidin-2-yl)piperidin-4-yl)carbamate (1.5 g, 4.08 mmol, 47.1% yield): $^1$H NMR (400 MHz, CD$_3$OD) δ ppm 7.95 (s, 2H), 4.38 (d, J=13.2 Hz, 2H), 3.74 (m, 1H), 3.16-3.05 (m, 2H), 2.00-1.80 (m, 2H), 1.43 (s, 9H), 1.38-1.36 (m, 2H); ES-LCMS m/z 295.2 [M+H]$^+$.

Step 3: Methyl 2-((2-(4-((tert-butoxycarbonyl)amino)piperidin-1-yl)pyrimidin-5-yl)oxy)-6-chloroisonicotinate

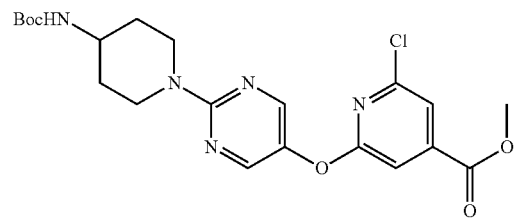 [SMILES: COC(=O)c1cc(Cl)nc(Oc2cnc(N3CCC(NC(=O)OC(C)(C)C)CC3)nc2)c1]

To a mixture of methyl 2,6-dichloroisonicotinate (0.923 g, 4.08 mmol) and tert-butyl (1-(5-hydroxypyrimidin-2-yl)piperidin-4-yl)carbamate (1.5 g, 4.08 mmol) in DMF (30 mL) was added K$_2$CO$_3$ (1.690 g, 12.23 mmol). The mixture was stirred at 50° C. for 10 h followed by concentration and addition of saturated NaHCO$_3$ solution (150 mL). The aqueous layer was extracted with DCM (150 mL×2) and the combined extracts were washed with brine (150 mL×2), dried over Na$_2$SO$_4$, filtered and concentrated. The crude material was purified by silica gel column chromatography (PE/EtOAc=5/1). All fractions found to contain product by TLC (PE/EA=3/1, R$_f$=0.6) were combined and concentrated to yield a yellow oil of methyl 2-((2-(4-((tert-butoxycarbonyl)amino)piperidin-1-yl)pyrimidin-5-yl)oxy)-6-chloroisonicotinate (600 mg, 1.203 mmol, 29.5% yield): $^1$H NMR (400 MHz, CDCl$_3$) δ ppm 8.21 (s, 2H), 7.55 (s, 1H), 7.38-7.36 (m, 1H), 4.66-4.60 (m, 2H), 4.46 (br. s, 1H), 3.95 (s, 3H), 3.71-3.67 (m, 1H), 3.11-2.07 (m, 2H), 2.02-1.99 (m, 2H), 1.44 (s, 9H), 1.40-1.38 (m, 2H); ES-LCMS m/z 464.1, 466.1 [M+H]$^+$.

Step 4: Methyl 2-((2-(4-((tert-butoxycarbonyl)amino)piperidin-1-yl)pyrimidin-5-yl)oxy)-6-(3,5-dichlorophenyl)isonicotinate

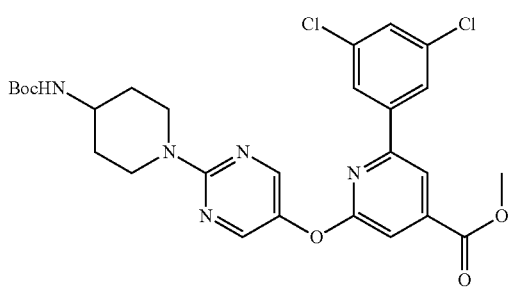 [SMILES: COC(=O)c1cc(Oc2cnc(N3CCC(NC(=O)OC(C)(C)C)CC3)nc2)nc(-c2cc(Cl)cc(Cl)c2)c1]

To a mixture of methyl 2-((2-(4-((tert-butoxycarbonyl)amino)piperidin-1-yl)pyrimidin-5-yl)oxy)-6-chloroisonicotinate (0.6 g, 1.203 mmol) and (3,5-dichlorophenyl)boronic acid (0.574 g, 3.01 mmol) in DMF (10 mL) was added K$_2$CO$_3$ (0.499 g, 3.61 mmol) and PdCl$_2$(dppf) (0.044 g, 0.060 mmol). The mixture was stirred at 80° C. under N$_2$ atmosphere for 0.5 h. The mixture was concentrated and purified by silica gel column chromatography (PE/EtOAc=5/1). All fractions found to contain product by TLC (PE/EA=3/1, R$_f$=0.4) were combined and concentrated to yield a yellow solid of methyl 2-((2-(4-((tert-butoxycarbonyl)amino)piperidin-1-yl)pyrimidin-5-yl)oxy)-6-(3,5-dichlorophenyl)isonicotinate (700 mg, 1.097 mmol, 91.0% yield): $^1$H NMR (400 MHz, CDCl$_3$) δ ppm 8.27 (s, 2H), 7.95 (s, 1H), 7.78-7.70 (m, 2H), 7.50-7.43 (m, 1H), 7.38-7.26 (m, 1H), 4.74-4.59 (m, 2H), 4.46 (br. s, 1H), 4.01-3.93 (m, 3H), 3.83-3.66 (m, 1H), 3.10 (t, J=11.2 Hz, 2H), 2.03 (t, J=5.1 Hz, 2H), 1.45 (s, 9H), 1.40-1.38 (m, 2H); ES-LCMS m/z 574.2, 576.2 [M+H]$^+$.

Step 5: tert-Butyl (1-(5-((6-(3,5-dichlorophenyl)-4-(hydroxymethyl)pyridin-2-yl)oxy)pyrimidin-2-yl)piperidin-4-yl)carbamate

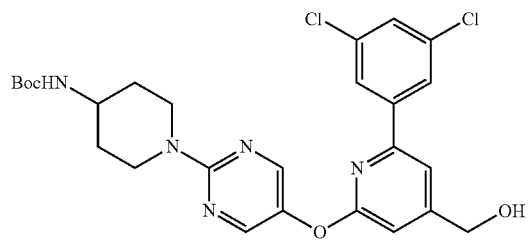 [SMILES: CC(C)(C)OC(=O)NC1CCN(c2ncc(Oc3cc(CO)cc(-c4cc(Cl)cc(Cl)c4)n3)cn2)CC1]

A mixture of methyl 2-((2-(4-((tert-butoxycarbonyl)amino)piperidin-1-yl)pyrimidin-5-yl)oxy)-6-(3,5-dichlorophenyl)isonicotinate (0.7 g, 1.097 mmol), NaBH$_4$ (0.415 g, 10.97 mmol) in MeOH (20 mL) was stirred at 25° C. for 5 h. Volatiles were concentrated to and the residue was partitioned between DCM (50 mL) and H$_2$O (20 mL). The aqueous phase was extracted with DCM (50 mL×2) and the combined organic layer was washed with brine (20 mL), dried over Na$_2$SO$_4$, filtered and concentrated to yield a yellow solid of tert-butyl (1-(5-((6-(3,5-dichlorophenyl)-4-(hydroxymethyl)pyridin-2-yl)oxy)pyrimidin-2-yl)piperidin-4-yl)carbamate (500 mg, 0.668 mmol, 60.9% yield): $^1$H NMR (400 MHz, CD$_3$OD) δ ppm 8.28 (s, 2H), 7.80 (d, J=1.8 Hz, 2H), 7.57 (s, 1H), 7.41 (t, J=1.8 Hz, 1H), 7.02 (s, 1H), 4.75-4.71 (m, 2H), 4.64-4.60 (m, 2H), 3.70-3.57 (m, 1H), 3.18-3.04 (m, 2H), 1.93 (d, J=10.1 Hz, 2H), 1.44 (s, 9H), 1.40-1.38 (m, 2H); ES-LCMS m/z 546.1, 548.1 [M+H]$^+$.

Step 6: (2-((2-(4-((tert-Butoxycarbonyl)amino)piperidin-1-yl)pyrimidin-5-yl)oxy)-6-(3,5-dichlorophenyl)pyridin-4-yl)methyl methanesulfonate

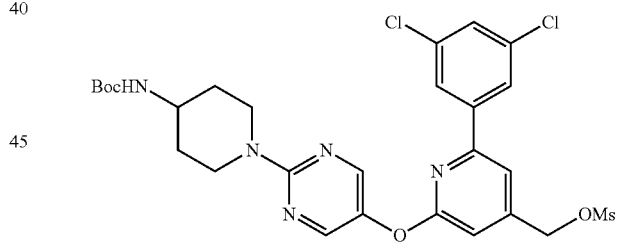

To a mixture of tert-butyl (1-(5-((6-(3,5-dichlorophenyl)-4-(hydroxymethyl)pyridin-2-yl)oxy)pyrimidin-2-yl)piperidin-4-yl)carbamate (500 mg, 0.668 mmol), DIEA (0.350 mL, 2.004 mmol) and MsCl (0.078 mL, 1.002 mmol) in DCM (10 mL) was stirred at 25° C. for 20 min. The reaction was added 5% NaHCO$_3$ (10 mL) and extracted with DCM (50 mL×2). The organic extract was washed with brine (20 mL), dried over Na$_2$SO$_4$, filtered and concentrated to yield a yellow oil of (2-((2-(4-((tert-butoxycarbonyl)amino)piperidin-1-yl)pyrimidin-5-yl)oxy)-6-(3,5-dichlorophenyl)pyridin-4-yl)methyl methanesulfonate (580 mg, 0.650 mmol, 97.0% yield): $^1$H NMR (400 MHz, CDCl$_3$) δ ppm 8.20 (s, 2H), 7.68-7.65 (m, 2H), 7.39-7.28 (m, 2H), 6.88 (s, 1H), 5.21 (s, 2H), 4.57 (d, J=13.7 Hz, 2H), 4.41 (br. s, 1H), 3.09-3.06 (m, 2H), 3.04 (s, 3H), 1.98-1.96 (m, 2H), 1.39 (s, 9H), 1.38-1.36 (m, 2H); ES-LCMS m/z 624.1, 626.1 [M+H]$^+$.

Intermediate 20: (A)-tert-Butyl 4-(5-((6-(3,5-dichlorophenyl)-4-(((methylsulfonyl)oxy)methyl)pyridin-2-yl)oxy)pyrimidin-2-yl)-2-methylpiperazine-1-carboxylate

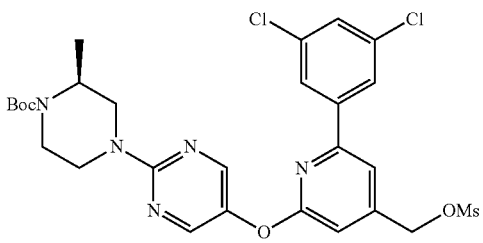 [SMILES: C[C@H]1CN(c2ncc(Oc3cc(COS(C)(=O)=O)cc(-c4cc(Cl)cc(Cl)c4)n3)cn2)CCN1C(=O)OC(C)(C)C]

Step 1: (S)-tert-Butyl 4-(5-(benzyloxy)pyrimidin-2-yl)-2-methylpiperazine-1-carboxylate

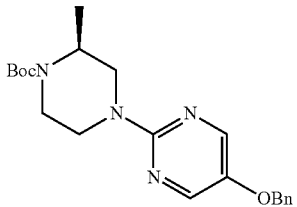 [SMILES: C[C@H]1CN(c2ncc(OCc3ccccc3)cn2)CCN1C(=O)OC(C)(C)C]

To a mixture of 5-(benzyloxy)-2-chloropyrimidine (3 g, 12.92 mmol) in DMF (100 mL) was added (S)-tert-butyl 2-methylpiperazine-1-carboxylate (5 g, 24.97 mmol) and Cs$_2$CO$_3$ (8.42 g, 25.8 mmol). The mixture was stirred at 130° C. for 12 h. The mixture was concentrated and purified by silica gel column chromatography (PE/EtOAc=3/1). All fractions found to contain product by TLC (PE/EA=3/1, R$_f$=0.6) were combined and concentrated to yield a light yellow solid of (S)-tert-butyl 4-(5-(benzyloxy)pyrimidin-2-yl)-2-methylpiperazine-1-carboxylate (3 g, 5.61 mmol, 43.4% yield): $^1$H NMR (400 MHz, CD$_3$OD) δ ppm 8.13 (s, 2H), 7.43-7.32 (m, 5H), 5.06 (s, 2H), 4.36 (d, J=13.2 Hz, 3H), 3.84 (br. s, 1H), 3.15-3.05 (m, 2H), 2.91 (d, J=4.0 Hz, 1H), 1.47 (s, 9H), 1.12 (d, J=6.6 Hz, 3H); ES-LCMS m/z 385.2 [M+H]$^+$.

Step 2: (S)-tert-Butyl 4-(5-hydroxypyrimidin-2-yl)-2-methylpiperazine-1-carboxylate

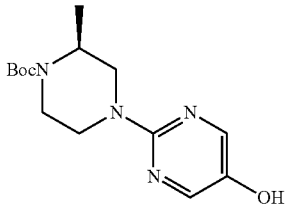 [SMILES: C[C@H]1CN(c2ncc(O)cn2)CCN1C(=O)OC(C)(C)C]

To a solution of (S)-tert-butyl 4-(5-(benzyloxy)pyrimidin-2-yl)-2-methylpiperazine-1-carboxylate (2.5 g, 4.68 mmol) in EtOAc (50 mL) was added Pd/C (10 wt %, 0.8 g, 0.752 mmol). The mixture was stirred at 25° C. for 0.5 h under H$_2$ (15 psi). The mixture was filtered and concentrated to yield a yellow solid of (S)-tert-butyl 4-(5-hydroxypyrimidin-2-yl)-2-methylpiperazine-1-carboxylate (1.8 g, 4.53 mmol, 97.0% yield): $^1$H NMR (400 MHz, CD$_3$OD) δ ppm 7.99 (s, 2H), 4.42-4.27 (m, 3H), 3.85 (br. s, 1H), 3.16-3.06 (m, 2H), 2.89 (d, J=3.5 Hz, 1H), 1.47 (s, 9H), 1.14 (d, J=6.6 Hz, 3H); ES-LCMS m/z 239.2 [M−t−Bu+H]$^+$.

Step 3: (S)-tert-Butyl 4-(5-((6-chloro-4-(methoxycarbonyl)pyridin-2-yl)oxy)pyrimidin-2-yl)-2-methylpiperazine-1-carboxylat

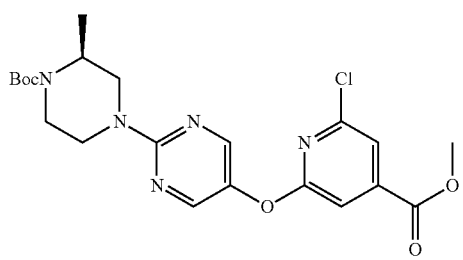 [SMILES: COC(=O)c1cc(Cl)nc(Oc2cnc(N3CCN(C(=O)OC(C)(C)C)[C@@H](C)C3)nc2)c1]

To a solution of (S)-tert-butyl 4-(5-hydroxypyrimidin-2-yl)-2-methylpiperazine-1-carboxylate (1.8 g, 4.53 mmol) in DMF (50 mL) was added K$_2$CO$_3$ (1.876 g, 13.58 mmol) and methyl 2,6-dichloroisonicotinate (1.571 g, 6.79 mmol). The mixture was stirred at 80° C. for 2 h. The mixture was filtered and concentrated to yield a light yellow solid of (S)-tert-butyl 4-(5-((6-chloro-4-(methoxycarbonyl)pyridin-2-yl)oxy)pyrimidin-2-yl)-2-methylpiperazine-1-carboxylate (3 g, 4.20 mmol, 93.0% yield): $^1$H NMR (400 MHz, CD$_3$OD) δ ppm 8.30-8.19 (m, 2H), 7.58 (s, 1H), 7.49-7.42 (m, 1H), 4.61-4.47 (m, 2H), 4.37-4.29 (m, 1H), 3.92 (s, 3H), 3.85 (br. s, 1H), 3.24 (dd, J=3.7, 13.0 Hz, 2H), 3.04 (d, J=3.1 Hz, 1H), 1.48 (s, 9H), 1.17 (d, J=6.6 Hz, 3H); ES-LCMS m/z 408.1, 410.1 [M−t−Bu+H]$^+$.

Step 4: (S)-tert-Butyl 4-(5-((6-(3,5-dichlorophenyl)-4-(methoxycarbonyl)pyridin-2-yl)oxy)pyrimidin-2-yl)-2-methylpiperazine-1-carboxylate

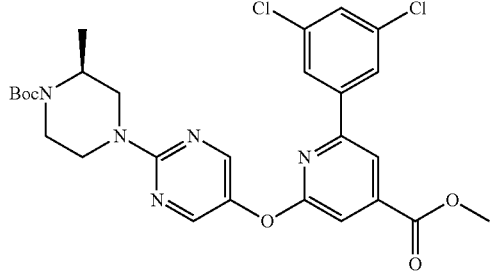 [SMILES: COC(=O)c1cc(Oc2cnc(N3CCN(C(=O)OC(C)(C)C)[C@@H](C)C3)nc2)nc(-c2cc(Cl)cc(Cl)c2)c1]

To a solution of (S)-tert-butyl 4-(5-((6-chloro-4-(methoxycarbonyl)pyridin-2-yl)oxy)pyrimidin-2-yl)-2-methylpiperazine-1-carboxylate (2.9 g, 4.06 mmol) in DMF (60 mL) was added (3,5-dichlorophenyl)boronic acid (1.163 g, 6.09 mmol), K$_2$CO$_3$ (1.685 g, 12.19 mmol) and PdCl$_2$(dppf) (0.297 g, 0.406 mmol). The mixture was stirred at 80° C. for 2 h under N$_2$ atmosphere. The mixture was concentrated and purified by silica gel column chromatography (PE/EtOAc=5/1). All fractions found to contain product by TLC (PE/EtOAc=5/1, R$_f$=0.5) were combined and concentrated to yield a yellow solid of (S)-tert-butyl 4-(5-((6-(3,5-dichlorophenyl)-4-(methoxycarbonyl)pyridin-2-yl)oxy)pyrimidin-2-yl)-2-methylpiperazine-1-carboxylate (2.3 g, 3.56 mmol, 88.0% yield): $^1$H NMR (400 MHz, CD$_3$OD) δ ppm 8.30 (s, 2H), 7.98 (s, 1H), 7.74 (d, J=1.8 Hz, 2H), 7.49-7.36 (m, 2H), 4.62-4.51 (m, 2H), 4.38-4.29 (m, 1H), 3.99 (s, 3H), 3.90 (d, J=13.2 Hz, 1H), 3.28-3.19 (m, 2H), 3.05 (br. s, 1H), 1.49 (s, 9H), 1.16 (d, J=6.6 Hz, 3H); ES-LCMS m/z 518.1, 520.1 [M−t−Bu+H]$^+$.

Step 5: (S)-tert-Butyl 4-(5-((6-(3,5-dichlorophenyl)-4-(hydroxymethyl)pyridin-2-yl)oxy)pyrimidin-2-yl)-2-methylpiperazine-1-carboxylate

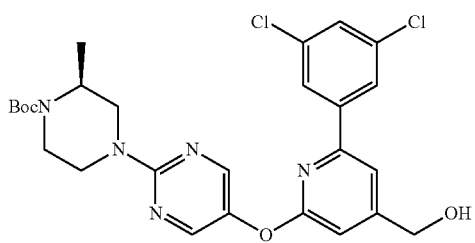 [SMILES: C[C@H]1CN(c2ncc(Oc3cc(CO)cc(-c4cc(Cl)cc(Cl)c4)n3)cn2)CCN1C(=O)OC(C)(C)C]

To a solution of (S)-tert-butyl 4-(5-((6-(3,5-dichlorophenyl)-4-(methoxycarbonyl)pyridin-2-yl)oxy)pyrimidin-2-yl)-2-methylpiperazine-1-carboxylate (2.2 g, 3.41 mmol) in MeOH (50 mL) was added NaBH$_4$ (0.645 g, 17.04 mmol). The mixture was stirred at 20° C. for 0.5 h then concentrated. Water (200 mL) was added and the mixture was extracted with DCM (200 mL×2), the combine organic layers was dried over Na$_2$SO$_4$, filtered and concentrated to yield a yellow solid of (S)-tert-butyl 4-(5-((6-(3,5-dichlorophenyl)-4-(hydroxymethyl)pyridin-2-yl)oxy)pyrimidin-2-yl)-2-methyl piperazine-1-carboxylate (2.2 g, 3.08 mmol, 90.0% yield): $^1$H NMR (400 MHz, CD$_3$OD) δ ppm 8.32 (s, 2H), 7.82 (s, 2H), 7.61 (s, 1H), 7.44 (s, 1H), 7.07 (s, 1H), 4.75 (s, 2H), 4.65-4.58 (m, 2H), 4.34 (br. s, 1H), 3.93 (d, J=13.1 Hz, 1H), 3.25 (d, J=11.0 Hz, 2H), 3.08 (br. s, 1H), 1.51 (s, 9H), 1.19 (d, J=6.5 Hz, 3H); ES-LCMS m/z 490.1, 492.1 [M−t−Bu+H]$^+$.

Step 6: (S)-tert-Butyl 4-(5-((6-(3,5-dichlorophenyl)-4-(((methylsulfonyl)oxy)methyl)pyridin-2-yl)oxy)pyrimidin-2-yl)-2-methylpiperazine-1-carboxylate

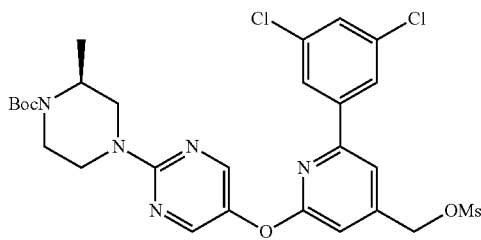 [SMILES: C[C@H]1CN(c2ncc(Oc3cc(COS(C)(=O)=O)cc(-c4cc(Cl)cc(Cl)c4)n3)cn2)CCN1C(=O)OC(C)(C)C]

To a solution of (S)-tert-butyl 4-(5-((6-(3,5-dichlorophenyl)-4-(hydroxymethyl)pyridin-2-yl)oxy)pyrimidin-2-yl)-2-methylpiperazine-1-carboxylate (1 g, 1.400 mmol) in DCM (30 mL) was added DIEA (0.734 mL, 4.20 mmol) and MsCl (0.164 mL, 2.100 mmol). The mixture was stirred at 20° C. for 20 min. Water (50 mL) was added and the mixture was extracted with DCM (100 mL×2), the combine organic layers were dried over Na$_2$SO$_4$, filtered and concentrated to yield a yellow oil of (S)-tert-butyl 4-(5-((6-(3,5-dichlorophenyl)-4-(((methylsulfonyl)oxy)methyl)pyridin-2-yl)oxy)pyrimidin-2-yl)-2-methylpiperazine-1-carboxylate (1 g, 1.078 mmol, 77.0% yield): $^1$H NMR (400 MHz, CD$_3$OD) δ ppm 8.31 (s, 2H), 7.78 (s, 2H), 7.65 (d, J=12.5 Hz, 1H), 7.44-7.39 (m, 1H), 7.11 (d, J=5.5 Hz, 1H), 5.29 (s, 2H), 4.57 (d, J=14.6 Hz, 2H), 4.33 (br. s, 1H), 3.91 (d, J=13.6 Hz, 1H), 3.29-3.20 (m, 3H), 2.87 (m, 3H), 1.50 (s, 9H), 1.17 (br. s, 3H); ES-LCMS m/z 568.1, 570.1 [M−t−Bu+H]$^+$.

Intermediate 21: Ethyl 3-(4-(5-((6-(3,5-dichlorophenyl)-4-(((methylsulfonyl)oxy)methyl)pyridin-2-yl)oxy)pyrimidin-2-yl)piperazin-1-yl)propanoate

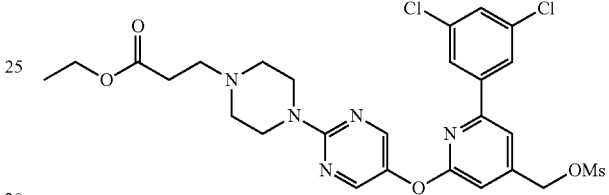

Step 1: (2-(3,5-Dichlorophenyl)-6-((2-(piperazin-1-yl)pyrimidin-5-yl)oxy)pyridin-4-yl)methanol

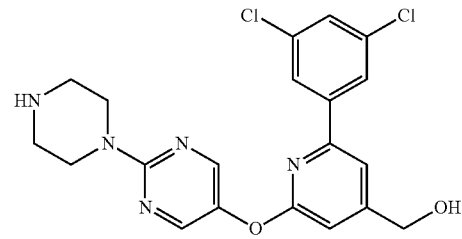 [SMILES: OCc1cc(Oc2cnc(N3CCNCC3)nc2)nc(-c2cc(Cl)cc(Cl)c2)c1]

To a solution of tert-butyl 4-(5-((6-(3,5-dichlorophenyl)-4-(hydroxymethyl)pyridin-2-yl)oxy)pyrimidin-2-yl)piperazine-1-carboxylate (1 g, 1.690 mmol) in MeOH (10 mL) was added HCl solution (4 M in MeOH, 2 mL, 8.00 mmol). The mixture was stirred at 20° C. for 0.2 h then concentrated. The residue was partitioned between DCM (30 mL) and saturated NaHCO$_3$ (20 mL) solution. The aqueous phase was extracted with DCM (10 mL 10×2). The combined organic extracts were washed with brine (20 mL), dried over Na$_2$SO$_4$, filtered and concentrated to yield a yellow solid of (2-(3,5-dichlorophenyl)-6-((2-(piperazin-1-yl) pyrimidin-5-yl)oxy)pyridin-4-yl)methanol (0.7 g, 1.376 mmol, 81.0% yield): $^1$H NMR (400 MHz, CD$_3$OD) δ ppm 8.54 (s, 2H), 7.80 (d, J=1.8 Hz, 2H), 7.62 (s, 1H), 7.45 (t, J=1.8 Hz, 1H), 7.10 (s, 1H), 4.74 (s, 2H), 4.19-4.11 (m, 4H), 3.38-3.33 (m, 4H); ES-LCMS m/z 432.1, 434.0 [M+H]$^+$.

Step 2: Ethyl 3-(4-(5-((6-(3,5-dichlorophenyl)-4-(hydroxymethyl)pyridin-2-yl)oxy)pyrimidin-2-yl)piperazin-1-yl)propanoate

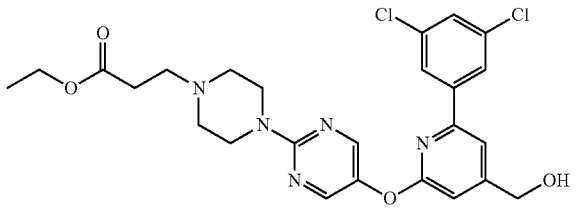 [SMILES: CCOC(=O)CCN1CCN(c2ncc(Oc3cc(CO)cc(-c4cc(Cl)cc(Cl)c4)n3)cn2)CC1]

To a solution of (2-(3,5-dichlorophenyl)-6-((2-(piperazin-1-yl)pyrimidin-5-yl)oxy)pyridin-4-yl)methanol (0.5 g, 0.983 mmol) in DMF (5.00 mL) was added ethyl 3-bromopropanoate (0.214 g, 1.180 mmol) and K$_2$CO$_3$ (0.272 g, 1.966 mmol). The mixture was stirred at 80° C. for 2 h. Then the solution was filtered and concentrated. The crude product was partitioned between DCM (30 mL) and saturated NaHCO$_3$ (20 mL) solution. The aqueous phase was extracted with DCM (10 mL×2). The combined organic extracts were washed with brine (20 mL), dried over Na$_2$SO$_4$, filtered and concentrated to yield a yellow solid of ethyl 3-(4-(5-((6-(3,5-dichlorophenyl)-4-(hydroxymethyl)pyridin-2-yl)oxy)pyrimidin-2-yl)piperazin-1-yl)propanoate (0.5 g, 0.808 mmol, 82.0% yield): $^1$H NMR (400 MHz, CD$_3$OD) δ ppm 8.31 (s, 2H), 7.81 (d, J=1.8 Hz, 2H), 7.59 (s, 1H), 7.42 (s, 1H), 7.04 (s, 1H), 4.72 (s, 2H), 4.15 (q, J=7.1 Hz, 2H), 3.90-3.78 (m, 4H), 2.79-2.70 (m, 2H), 2.63-2.52 (m, 6H), 1.31-1.23 (m, 3H); ES-LCMS m/z 532.1, 534.1 [M+H]$^+$.

Step 3: Ethyl 3-(4-(5-((6-(3,5-dichlorophenyl)-4-(((methylsulfonyl)oxy)methyl)pyridin-2-yl)oxy)pyrimidin-2-yl)piperazin-1-yl)propanoate

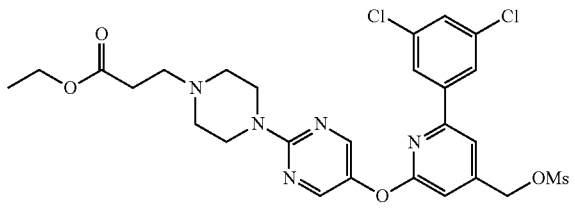 [SMILES: CCOC(=O)CCN1CCN(c2ncc(Oc3cc(COS(C)(=O)=O)cc(-c4cc(Cl)cc(Cl)c4)n3)cn2)CC1]

To a solution of ethyl 3-(4-(5-((6-(3,5-dichlorophenyl)-4-(hydroxymethyl)pyridin-2-yl)oxy)pyrimidin-2-yl)piperazin-1-yl)propanoate (0.5 g, 0.808 mmol) in DCM (10 mL) was added DIEA (0.209 g, 1.615 mmol) and MsCl (0.370 g, 3.23 mmol). The mixture was stirred at 30° C. for 0.5 h then concentrated. The crude product was purified by silica gel column chromatography (DCM/MeOH=10/1 to 5/1). All fractions found to contain product by TLC (PE/EtOAc=5/1, R$_f$=0.4) were combined and concentrated to yield a light yellow solid of ethyl 3-(4-(5-((6-(3,5-dichlorophenyl)-4-(((methylsulfonyl)oxy)methyl)pyridin-2-yl)oxy)pyrimidin-2-yl)piperazin-1-yl)propanoate (0.5 g, 0.704 mmol, 87.0% yield): $^1$H NMR (400 MHz, CD$_3$OD) δ ppm 8.37-8.29 (m, 2H), 7.86-7.79 (m, 2H), 7.70-7.66 (m, 1H), 7.49-7.43 (m, 1H), 7.12 (s, 1H), 5.29 (s, 2H), 4.18 (q, J=7.1 Hz, 2H), 3.89-3.83 (m, 4H), 3 3.05 (s, 3H), 2.81-2.70 (m, 2H), 2.57 (t, J=5.1 Hz, 6H), 1.23-1.19 (m, 3H); ES-LCMS m/z 610.0, 612.1 [M+H]$^+$.

Intermediate 22: 3-Chloropropane-1-sulfonamide

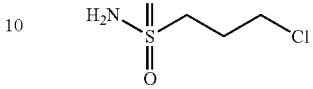

Gaseous ammonia was bubbled to a cold (−78° C.) solution of 3-chloropropane-1-sulfonyl chloride (5 g, 28.2 mmol) in THF (40 mL). The solution was stirred at −78° C. for 0.5 h then concentrated and partitioned between DCM (50 mL) and saturated NaHCO$_3$ (30 mL) solution. The combined organic extract was washed with brine (20 mL), dried over Na$_2$SO$_4$, filtered and concentrated to yield a brown solid of 3-chloropropane-1-sulfonamide (3 g, 18.08 mmol, 64.0% yield): $^1$H NMR (400 MHz, CD$_3$OD) δ ppm 3.72 (t, J=6.4 Hz, 2H), 3.27-3.19 (m, 2H), 2.32-2.21 (m, 2H).

Intermediate 23: Ethenesulfonamide

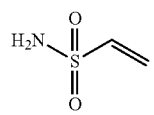

Step 1: 2-Bromoethanesulfonate

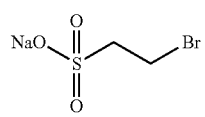

A mixture of 1,2-dibromoethane (100 g, 532 mmol) and sodium sulfite (22.14 g, 176 mmol) in EtOH (250 mL) and H$_2$O (250 mL) was stirred at 100° C. for 10 h then the reaction mixture was concentrated. EtOH (500 mL) was added and filtered. The filtrate was concentrated to yield a white solid of sodium 2-bromoethanesulfonate (15 g, 56.9 mmol, 10.7% yield): $^1$H NMR (400 MHz, D$_2$O) δ ppm 3.62 (t, J=7.5 Hz, 2H), 3.46-3.34 (m, 2H).

Step 2: 2-Bromoethanesulfonyl chloride

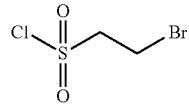

A mixture of pentachlorophosphorane (2.5 g, 12.01 mmol) and sodium 2-bromoethanesulfonate (4 g, 15.17 mmol) was stirred at 110° C. for 2 h. The reaction mixture was cooled and then poured into ice. The mixture was extracted with DCM (150 mL×2) and the organic layer was washed successively with water (150 mL×2), NaHCO₃ solution (150 mL×2) and water (150 mL×2). The organic solution was dried over MgSO₄ and concentrated to yield brown oil of 2-bromoethanesulfonyl chloride (1.5 g, 5.78 mmol, 38.1% yield): ¹H NMR (400 MHz, CD₃OD) δ ppm 4.54-4.46 (m, 2H), 3.91-3.83 (m, 2H).

Step 3: Ethenesulfonamide

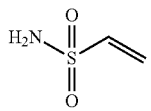

A solution of 2-bromoethanesulfonyl chloride (1.5 g, 5.78 mmol) in THF (35 mL) was cooled to −40° C. then ammonia gas was slowly bubbled to the mixture for 1 h. The reaction was filtered and concentrated to yield a brown solid of ethenesulfonamide (500 mg, 3.27 mmol, 56.5% yield): ¹H NMR (400 MHz, CD₃OD) δ ppm 6.80 (dd, J=9.9, 16.5 Hz, 1H), 6.15 (d, J=16.3 Hz, 1H), 5.88 (d, J=10.1 Hz, 1H); ES-LCMS m/z 130.2 [M+Na]⁺.

Intermediate 24: 3-(Methylsulfonyl)butanal

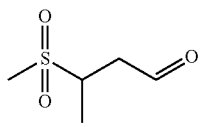

Step 1: 3-(Methylthio(butan-1-ol

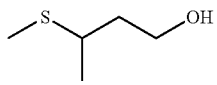

To a solution of 3-(methylthio)butanal (2.5 g, 21.15 mmol) in MeOH (10 mL) was added NaBH₄ (1.600 g, 42.3 mmol). The mixture was stirred at 25° C. for 0.5 h. The reaction was monitored by TLC (PE/EA=1/1, R_f=0.6). The mixture was filtered and concentrated to yield a yellow oil of 3-(methylthio)butan-1-ol (2 g, 13.31 mmol, 62.9% yield): ¹H NMR (400 MHz, CD₃OD) δ ppm 3.76-3.50 (m, 2H), 2.96-2.69 (m, 1H), 2.05 (s, 3H), 1.84-1.58 (m, 2H), 1.28 (d, J=6.6 Hz, 3H)

Step 2: 3-(Methylsulfonyl)butan-1-ol

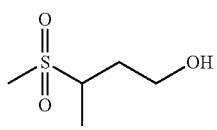

To a solution of 3-(methylthio)butan-1-ol (2 g, 13.31 mmol) in DCM (150 mL) was added m-CPBA (3.28 g, 13.31 mmol). The mixture was stirred at 25° C. for 10 h. Water (50 mL) was added and the mixture was extracted with DCM (50 mL×2). The combine organic layers were dried over Na₂SO₄, filtered, concentrated and purified by silica gel column chromatography (DCM/MeOH=10/1). All fractions found to contain product by TLC (DCM/MeOH=10/1, R_f=0.4) were combined and concentrated to yield a yellow oil of 3-(methylsulfonyl)butan-1-ol (500 mg, 2.63 mmol, 19.7% yield): ¹H NMR (400 MHz, CD₃OD) δ ppm 3.82-3.71 (m, 1H), 3.65 (ddd, J=5.3, 8.8, 11.0 Hz, 1H), 3.28-3.16 (m, 1H), 2.91 (s, 3H), 2.30-2.15 (m, 1H), 1.71-1.55 (m, 1H), 1.39 (d, J=7.1 Hz, 3H)

Step 3: 3-(Methylsulfonyl)butanal

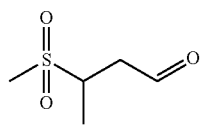

To a solution of oxalyl dichloride (400 mg, 3.15 mmol) in DCM (5 mL) was added DMSO (0.448 mL, 6.31 mmol, dissolved in 5.0 mL of DCM) at −78° C. over 5 min. Then a solution of 3-(methylsulfonyl)butan-1-ol (400 mg, 2.102 mmol) in DCM (5 mL) was added drop-wise over 10 min followed by addition of a solution of DIEA (2.203 mL, 12.61 mmol) in 5 mL of DCM. The mixture was allowed to stir at −78° C. for 10 min then warm to room temperature. Ice-cold hydrochloric acid solution (1.0 M, 30 mL) was added to quench the reaction. The two phases were separated and the aqueous phase was extracted with DCM (50 mL×3). The combined organic phases were combined, dried with anhydrous Na₂SO₄ and concentrated to yield a yellow oil of 3-(methylsulfonyl)butanal (500 mg, 1.997 mmol, 95.0% yield): ¹H NMR (400 MHz, CDCCl₃) δ ppm 9.78 (s, 1H), 3.32-3.19 (m, 2H), 3.14-3.01 (m, 1H), 2.87 (s, 3H), 1.50 (d, J=6.6 Hz, 3H)

Intermediate 25:
2-(Piperidin-4-yl)ethanesulfonamide

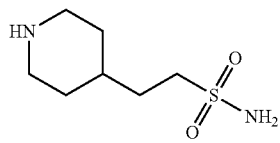 [SMILES: NS(=O)(=O)CCC1CCNCC1]

Step 1: 2-(Piperidin-4-yl)ethanol, hydrochloride

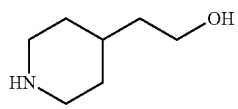

To a solution of tert-butyl 4-(2-hydroxyethyl)piperidine-1-carboxylate (8 g, 33.1 mmol) in MeOH (50 mL) was added HCl solution (4 M in MeOH, 10 mL, 40.0 mmol). The mixture was stirred at 30° C. for 0.5 h then concentrated to yield a brown solid of 2-(piperidin-4-yl)ethanol, hydrochloride (5.5 g, 28.2 mmol, 85.0% yield): $^1$H NMR (400 MHz, CD$_3$OD) δ ppm 3.61 (t, J=6.4 Hz, 2H), 3.36 (d, J=12.8 Hz, 2H), 2.95 (t, J=12.8 Hz, 2H), 1.94 (d, J=14.1 Hz, 2H), 1.77 (m, 1H), 1.51 (q, J=6.6 Hz, 2H), 1.46-1.32 (m, 2H).

Step 2: Benzyl 4-(2-hydroxyethyl)piperidine-1-carboxylate

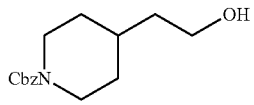

To a mixture of 2-(piperidin-4-yl)ethanol, hydrochloride (5.5 g, 28.2 mmol), Na$_2$CO$_3$ (11.85 g, 141 mmol) in 1,4-dioxane (100 mL) and water (100 mL) was added the dropwise CbzCl (5.78 g, 33.9 mmol). Then the mixture was stirred at 30° C. for 10 h. The mixture was concentrated, and the residue was diluted with water (200 mL), extracted with EtOAc (100 mL×2). The combined organic phase was washed with water (200 mL×2), dried over Na$_2$SO$_4$, filtered, and concentrated. The crude was purified by silica column chromatography on silica gel (DCM/MeOH=20/1, R$_f$=0.6) to yield brown oil of benzyl 4-(2-hydroxyethyl)piperidine-1-carboxylate (7 g, 25.9 mmol, 92.0% yield): $^1$H NMR (400 MHz, CDCl$_3$) δ ppm 7.43-7.30 (m, 5H), 5.14 (s, 2H), 4.25-4.10 (m, 2H), 3.72 (t, J=6.65 Hz, 2H), 2.80 (br. s, 2H), 1.80-1.57 (m, 5H), 1.24-1.09 (m, 2H); ES-LCMS m/z 264.2 [M+H]$^+$.

Step 3: Benzyl 4-(2-((methylsulfonyl)oxy)ethyl)piperidine-1-carboxylate

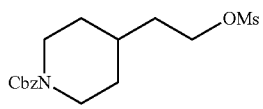 [SMILES: CS(=O)(=O)OCCC1CCN(C(=O)OCc2ccccc2)CC1]

To a mixture of benzyl 4-(2-hydroxyethyl)piperidine-1-carboxylate (5.5 g, 20.33 mmol), DIEA (7.10 mL, 40.7 mmol) in DCM (20 mL) was added MsCl (1.901 mL, 24.40 mmol). The mixture was stirred at 30° C. for 0.5 h then concentrated. The residue was partitioned between DCM (200 mL) and water (200 mL), extracted with DCM (200 mL×2). The combined organic layers were dried over Na$_2$SO$_4$, filtered and concentrated to yield a yellow solid of benzyl 4-(2-((methylsulfonyl)oxy)ethyl)piperidine-1-carboxylate (6 g, 14.06 mmol, 69.2% yield): $^1$H NMR (400 MHz, CDCl$_3$) δ ppm 7.31 (d, J=15.4 Hz, 5H), 5.08 (d, J=15.4 Hz, 2H), 4.34-4.03 (m, 4H), 3.08 (s, 3H), 2.74-2.72 (m, 2H), 1.66-1.50 (m, 5H), 1.14-1.09 (m, 2H); ES-LCMS m/z 342.2 [M+H]$^+$.

Step 4: Benzyl 4-(2-(acetylthio)ethyl)piperidine-1-carboxylate

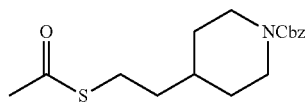 [SMILES: CC(=O)SCCC1CCN(C(=O)OCc2ccccc2)CC1]

To a mixture of benzyl 4-(2-((methylsulfonyl)oxy)ethyl) piperidine-1-carboxylate (6 g, 14.06 mmol), K$_2$CO$_3$ (5.83 g, 42.2 mmol) in DMF (50 mL) was added ethanethioic S-acid (2.140 g, 28.1 mmol). The mixture was stirred at 25° C. for 3 h until LCMS showed the reaction was completed. The mixture was filtered and the filtrate was concentrated, diluted with DCM (100 mL) and water (100 mL), extracted with DCM (100 mL×2). The combined organic layers were dried over Na$_2$SO$_4$, filtered and concentrated to yield crude product, which was purified by column chromatography on silica gel (PE/EtOAc=5/1, R$_f$ 10=0.3) to yield a brown solid of benzyl 4-(2-(acetylthio)ethyl)piperidine-1-carboxylate (5 g, 12.44 mmol, 89.0% yield): $^1$H NMR (400 MHz, CDCl$_3$) δ ppm 7.51-7.16 (m, 5H), 5.21-5.00 (m, 2H), 4.14 (br. s, 2H), 2.90-2.67 (m, 4H), 2.39-2.20 (m, 3H), 1.68-1.60 (d, J=10.1 Hz, 5H), 1.10 (br. s, 2H); ES-LCMS m/z 322.1 [M+H]$^+$.

Step 5: Dibenzyl 4,4'-(disulfanediylbis(ethane-2,1-diyl))bis(piperidine-1-carboxylate)

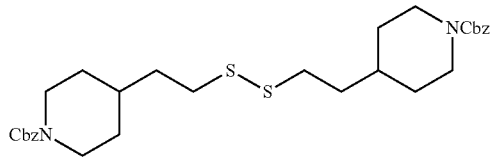 [SMILES: O=C(OCc1ccccc1)N1CCC(CCSSCCC2CCN(C(=O)OCc3ccccc3)CC2)CC1]

To a solution of benzyl 4-(2-(acetylthio)ethyl)piperidine-1-carboxylate (5 g, 12.44 mmol) in MeOH (50 mL) and water (100 mL) was added K$_2$CO$_3$ (8.60 g, 62.2 mmol). The mixture was stirred at 30° C. for 2 h then concentrated. The residue was diluted with water (100 mL), extracted with DCM (100 mL×2). The combined organic layers were dried over Na$_2$SO$_4$, filtered and concentrated to yield a brown solid dibenzyl 4,4'-(disulfanediylbis(ethane-2,1-diyl))bis(piperidine-1-carboxylate) (3.6 g, 5.56 mmol, 89.4% yield): $^1$H NMR (400 MHz, CDCl$_3$) δ ppm 7.36-7.12 (m, 10H), 5.05 (s, 4H), 4.10 (br. s, 4H), 2.81-2.56 (m, 8H), 1.59 (d, J=13.7 Hz, 10H), 1.07 (d, J=8.8 Hz, 4H); ES-LCMS m/z 557.3 [M+H]$^+$.

Step 6: Benzyl 4-(2-mercaptoethyl)piperidine-1-carboxylate

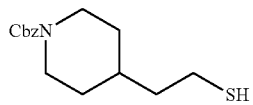

To a mixture of dibenzyl 4,4'-(disulfanediylbis(ethane-2,1-diyl))bis(piperidine-1-carboxylate) (1 g, 1.545 mmol) in AcOH (10 mL, 175 mmol) was added Zn powder (0.505 g, 7.72 mmol). The mixture was stirred at 30° C. for 5 h then filtered. The filtrate was concentrated to yield a brown solid benzyl 4-(2-mercaptoethyl)piperidine-1-carboxylate (0.90 g, 3.332 mmol, 75.0% yield): ¹H NMR (400 MHz, CDCl₃) δ ppm 7.50-7.17 (m, 5H), 5.11 (br. s, 2H), 4.17 (br. s, 2H), 2.76 (br. s, 2H), 2.64-2.46 (m, 2H), 1.65 (d, J=11.5 Hz, 4H), 1.39-1.28 (m, 1H), 1.12-1.10 (m, 2H); ES-LCMS m/z 280.2 [M+H]⁺.

Step 7: Benzyl 4-(2-(chlorosulfonyl)ethyl)piperidine-1-carboxylate

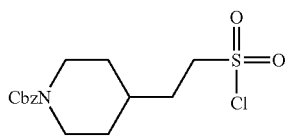

A stirred suspension of benzyl 4-(2-mercaptoethyl)piperidine-1-carboxylate (900 mg, 2.332 mmol) in water (10 mL) and THF (10 mL) was cooled to −10° C., then Cl₂ gas was bubbled through the reaction mixture for 10 min at −10° C. to 0° C. The mixture was flushed under N₂ to remove excess chlorine before concentration. The residue was diluted with DCM (50 mL) and water (50 mL), extracted with DCM (50 mL×2). The combined organic layers were dried over Na₂SO₄, filtered and concentrated to yield brown oil of benzyl 4-(2-(chlorosulfonyl)ethyl)piperidine-1-carboxylate (1 g, 1.521 mmol, 65.2% yield): ¹H NMR (400 MHz, CDCl₃) δ ppm 7.35-7.23 (m, 5H), 5.06 (s, 2H), 4.15 (d, J=11.9 Hz, 2H), 2.71-2.69 (m, 2H), 2.60-2.50 (m, 2H), 1.97-1.91 (m, 4H), 1.64 (d, J=13.7 Hz, 1H). 1.22-1.16 (m, 2H); ES-LCMS m/z 346.2 [M+H]⁺.

Step 8: Benzyl 4-(2-sulfamoylethyl)piperidine-1-carboxylate

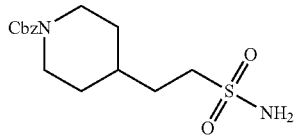 [SMILES: NS(=O)(=O)CCC1CCN(C(=O)OCc2ccccc2)CC1]

To a solution of benzyl 4-(2-(chlorosulfonyl)ethyl)piperidine-1-carboxylate (1 g, 1.521 mmol) in THF (10 mL) was bubbled ammonia gas at −40° C. for 20 min. The mixture was concentrated to yield the crude product which was purified by preparative HPLC (MeCN/H₂O as eluents, acidic condition) and dried by lyophilization to yield a white solid of benzyl 4-(2-sulfamoylethyl)piperidine-1-carboxylate (200 mg, 0.613 mmol, 40.3% yield): ¹H NMR (400 MHz, CD₃OD) δ ppm 7.42-7.28 (m, 5H), 5.12 (s, 2H), 4.16 (d, J=13.1 Hz, 2H), 3.17-3.09 (m, 2H), 2.85 (br s, 2H), 1.82-1.71 (m, 4H), 1.66 (t, J=7.3 Hz, 1H), 1.19-1.08 (m, 2H); ES-LCMS m/z 327.2 [M+H]⁺.

Step 9: 2-(Piperidin-4-yl)ethanesulfonamide

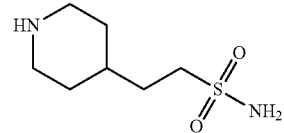

To a solution of benzyl 4-(2-sulfamoylethyl)piperidine-1-carboxylate (200 mg, 0.613 mmol) in MeOH (15 mL) was added Pd/C (10 wt %, 65.2 mg, 0.061 mmol). The mixture was stirred at 20° C. for 0.5 h under H₂ atmosphere (15 psi). The mixture was filtered and the filtrate was concentrated to yield a brown solid of 2-(piperidin-4-yl)ethanesulfonamide (130 mg, 0.541 mmol, 88.0% yield): ¹H NMR (400 MHz, CD₃OD) δ ppm 3.24-3.16 (m, 1H), 3.14-3.06 (m, 2H), 2.93-2.86 (m, 2H), 2.77 (dt, J=2.8, 12.7 Hz, 1H), 1.80-1.71 (m, 4H), 1.48-1.39 (m, 1H), 1.31-1.22 (m, 2H); ES-LCMS m/z 193.5 [M+H]⁺.

Intermediate 26: Ethyl 3-(piperidin-4-yl)propanoate

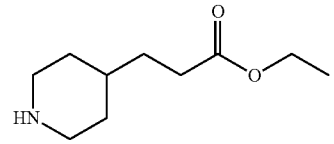

Step 1: (E)-tert-Butyl 4-(3-ethoxy-3-oxoprop-1-en-1-yl)piperidine-1-carboxylate

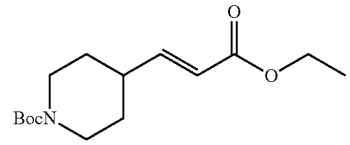 [SMILES: CCOC(=O)/C=C/C1CCN(C(=O)OC(C)(C)C)CC1]

To a solution of ethyl 2-(diethoxyphosphoryl)acetate (32.0 mL, 211 mmol) in THF (300 mL) was added t-BuOK (23.68 g, 211 mmol). After stirring at 25° C. for 0.5 h, tert-butyl 4-formylpiperidine-1-carboxylate (30 g, 141 mmol) was added. The mixture was stirred at the same temperature for 1.5 h. TLC (PE/EtOAc=3/1, R_f=0.61) showed the reaction was completed. The mixture was concentrated and water (500 mL) was added. The mixture was extracted with DCM (200 mL×3) and the combined organic layers were dried over Na₂SO₄, concentrated to yield the crude product which was purified by flash chromatography on 120 g silica gel (PE/EtOAc=1/0 to 2/1). All fractions found to contain product by TLC (PE/EtOAc=3/1, R_f=0.61) were combined and concentrated to yield a pale yellow oil of (E)-tert-butyl 4-(3-ethoxy-3-oxoprop-1-en-1-yl)piperidine-1-carboxylate (32 g, 102 mmol, 72.3% yield): ¹H NMR (400 MHz, CDCl₃) δ ppm 6.88 (dd, J=6.4, 15.7 Hz, 1H), 5.81-5.74 (m, 1H), 4.21-4.15 (m, 2H), 4.14-4.03 (m, 2H), 2.74 (t, J=11.9 Hz, 2H), 2.27 (dd, J=3.7, 7.3 Hz, 1H), 1.71 (d, J=12.8 Hz, 2H), 1.44 (s, 9H), 1.33-1.23 (m, 5H); ES-LCMS m/z 184.2 [M−Boc+H]⁺.

Step 2: tert-Butyl 4-(3-ethoxy-3-oxopropyl)piperidine-1-carboxylate

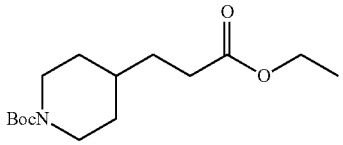 [SMILES: CCOC(=O)CCC1CCN(C(=O)OC(C)(C)C)CC1]

To a solution of (E)-tert-butyl 4-(3-ethoxy-3-oxoprop-1-en-1-yl)piperidine-1-carboxylate (32 g, 102 mmol) in MeOH (300 mL) was added Pd/C (10 wt %, 5 g, 4.70 mmol). The mixture was stirred at 25° C. for 12 h at 50 psi under $H_2$ atmosphere. The mixture was filtered and the filtrate was concentrated to yield a pale yellow oil of tert-butyl 4-(3-ethoxy-3-oxopropyl)piperidine-1-carboxylate (27 g, 85 mmol, 84.0% yield): $^1$H NMR (400 MHz, CDCl$_3$) δ ppm 4.11 (q, J=7.4 Hz, 4H), 2.64 (t, J=11.9 Hz, 2H), 2.30 (t, J=7.7 Hz, 2H), 1.63 (d, J=13.7 Hz, 2H), 1.59-1.53 (m, 2H), 1.43 (s, 9H), 1.37 (td, J=3.7, 7.5 Hz, 1H), 1.24 (t, J=7.1 Hz, 3H), 1.12-1.00 (m, 2H); ES-LCMS m/z 186.2 [M−Boc+H]$^+$.

Step 3: Ethyl 3-(piperidin-4-yl)propanoate

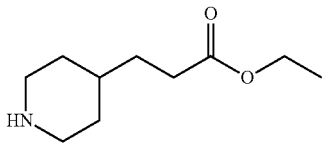

tert-Butyl 4-(3-ethoxy-3-oxopropyl)piperidine-1-carboxylate (13 g, 41.0 mmol) was dissolved in HCl solution (4.0 M in MeOH, 60 mL, 240 mmol). The reaction mixture was stirred at 15° C. for 10 min then concentrated. Aqueous NaHCO$_3$ was added and extracted with DCM (50 mL×5). The combined organic layers were dried over Na$_2$SO$_4$ and concentrated to yield a pale yellow oil of ethyl 3-(piperidin-4-yl)propanoate (8 g, 38.9 mmol, 95.0% yield): $^1$H NMR (400 MHz, CDCl$_3$) δ ppm 4.11 (q, J=7.1 Hz, 2H), 3.10 (d, J=12.3 Hz, 2H), 2.56 (s, 2H), 2.30 (t, J=7.7 Hz, 2H), 1.68 (d, J=12.8 Hz, 2H), 1.60-1.52 (m, 2H), 1.43-1.34 (m, 1H), 1.28-1.08 (m, 5H); ES-LCMS m/z 186.2 [M+H]$^+$.

Intermediate 27: Ethyl 2-methyl-3-(piperidin-4-yl)propanoate, hydrochloride

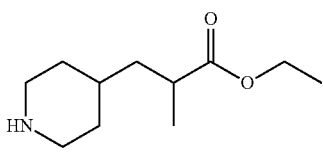

Step 1: tert-Butyl 4-(3-ethoxy-2-methyl-3-oxopropyl)piperidine-1-carboxylate

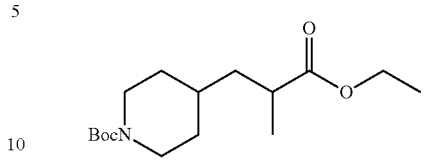

To a solution of tert-butyl 4-(3-ethoxy-3-oxopropyl)piperidine-1-carboxylate (3 g, 9.46 mmol) in THF (40 mL) was added LiHMDS (3.17 g, 18.92 mmol) at 0° C. The mixture was stirred at 0° C. for 0.5 h. Then MeI (1.611 g, 11.35 mmol) was added and the mixture was stirred at 25° C. for 7.5 h. The mixture was quenched with 5 mL of saturated aqueous NH$_4$Cl solution. The organic phase was separate, concentrated and purified by silica gel column chromatography (PE/EtOAc=0-100/30). All fractions found to contain product by TLC (PE/EtOAc=3/1, R$_f$=0.5) were combined and concentrated to yield a colorless oil tert-butyl 4-(3-ethoxy-2-methyl-3-oxopropyl)piperidine-1-carboxylate (2 g, 6.01 mmol, 63.5% yield): $^1$H NMR (400 MHz, CDCl$_3$) δ ppm 4.16-3.92 (m, 4H), 2.63 (t, J=11.2 Hz, 2H), 2.55-2.44 (m, 1H), 1.72-1.52 (m, 4H), 1.43 (s, 10H), 1.23 (t, J=7.1 Hz, 3H), 1.16-0.99 (m, 5H); ES-LCMS m/z 200.2 [M−Boc+H]$^+$.

Step 2: Ethyl 2-methyl-3-(piperidin-4-yl)propanoate, hydrochloride

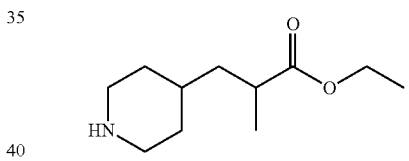

tert-Butyl 4-(3-ethoxy-2-methyl-3-oxopropyl)piperidine-1-carboxylate (2 g, 6.01 mmol) was dissolved HCl solution (4.0 M in EtOAc, 24 mL, 96 mmol). The mixture was stirred at 20° C. for 0.5 h then concentrated to yield a brown solid of ethyl 2-methyl-3-(piperidin-4-yl)propanoate, hydrochloride (1.5 g, 5.09 mmol, 85.0% yield): $^1$H NMR (400 MHz, CDCl$_3$) δ ppm 4.17-4.09 (m, 4H), 4.46-3.50 (m, 2H), 2.86-2.70 (m, 2H), 2.53-2.40 (m, 1H), 2.10-2.01 (m, 4H), 1.82-1.56 (m, 4H), 1.41-1.29 (m, 3H); ES-LCMS m/z 200.3 [M+H]$^+$.

Intermediate 28: tert-Butyl 4-(aminomethyl)-4-((tert-butyldimethylsilyl)oxy)piperidine-1-carboxylate

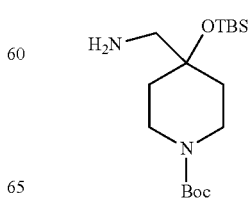

Step 1: tert-Butyl 1-oxa-6-azaspiro[2.5]octane-6-carboxylate

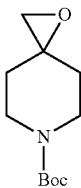

To a solution of trimethylsulfoxonium iodide (26.5 g, 120 mmol) in DMSO (100 mL) was added NaH (4.82 g, 120 mmol) at 0° C. After the mixture was stirred at 0° C. for 0.5 h, tert-butyl 4-oxopiperidine-1-carboxylate (20 g, 100 mmol) was added and the solution was stirred at 25° C. for 12 h. The solution was poured into ice water (500 mL), extracted with EtOAc (200 mL×3). The combined organic phases were dried over Na$_2$SO$_4$, concentrated. The residue was purified by a column chromatography eluted with PE/EtOAc=3/1 to yield a colorless oil of tert-butyl 1-oxa-6-azaspiro[2.5]octane-6-carboxylate (13 g, 54.9 mmol, 54.7% yield): $^1$H NMR (400 MHz, CDCl$_3$) δ ppm 3.77-3.62 (m, 2H), 3.48-3.35 (m, 2H), 2.67 (s, 2H), 1.86-1.73 (m, 2H), 1.54-1.37 (m, 11H); ES-LCMS m/z 158.1 [M−t−Bu+H]$^+$.

Step 2: tert-Butyl 4-(aminomethyl)-4-hydroxypiperidine-1-carboxylate

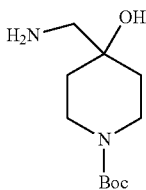

A solution of tert-butyl 1-oxa-6-azaspiro[2.5]octane-6-carboxylate (26 g, 122 mmol) in aqueous ammonia (200 mL, 3484 mmol) was stirred at 50° C. for 12 h. The mixture was concentrated to yield a colorless oil of tert-butyl 4-(aminomethyl)-4-hydroxypiperidine-1-carboxylate (27 g, 94 mmol, 77.0% yield): $^1$H NMR (400 MHz, CDCl$_3$) δ ppm 3.90-3.75 (m, 2H), 3.60-3.49 (m, 1H), 3.43-3.32 (m, 1H), 3.23-3.07 (m, 2H), 2.70 (s, 2H), 1.55 (br. s, 2H), 1.43 (s, 9H); ES-LCMS m/z 175.0 [M−t−Bu+H]$^+$.

Step 3: tert-Butyl 4-(aminomethyl)-4-((tert-butyldimethylsilyl)oxy)piperidine-1-carboxylate

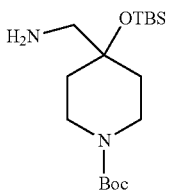

To a solution of tert-butyl 4-(aminomethyl)-4-hydroxypiperidine-1-carboxylate (25 g, 109 mmol) and imidazole (11.08 g, 163 mmol) in DCM (200 mL) was added TBSCl (19.63 g, 130 mmol) in DCM (100 mL) at 0° C. Then, the mixture was stirred at 25° C. for 12 h. The solution was dissolved in DCM (300 mL) and washed with water (100 mL×3). The organic phase was dried over Na$_2$SO$_4$ and concentrated to yield brown oil of tert-butyl 4-(aminomethyl)-4-((tert-butyldimethylsilyl)oxy)piperidine-1-carboxylate (36 g, 84 mmol, 77.0% yield): $^1$H NMR (400 MHz, CDCl$_3$) δ ppm 3.71-3.60 (m, 2H), 3.48-3.38 (m, 1H), 3.31-3.21 (m, 2H), 3.19-3.09 (m, 1H), 2.68 (s, 2H), 1.55-1.52 (m, 2H), 1.44 (s, 9H), 0.85 (s, 9H), 0.03-0.02 (m, 6H); ES-LCMS m/z 289.2 [M+H]$^+$.

Intermediate 29: Ethyl (piperidin-4-ylmethyl)carbamate, hydrochloride

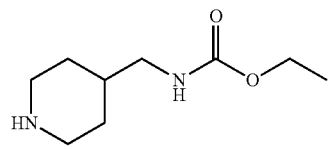

Step 1: tert-Butyl 4-(((ethoxycarbonyl)amino)methyl)piperidine-1-carboxylate

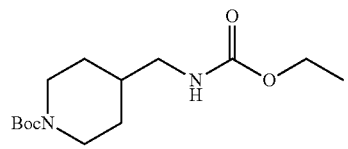 [SMILES: CCOC(=O)NCC1CCN(C(=O)OC(C)(C)C)CC1]

To a solution of tert-butyl 4-(aminomethyl)piperidine-1-carboxylate (10 g, 46.7 mmol) and DIEA (12.06 g, 93 mmol) in DCM (100 mL) was added ethyl carbonochloridate (5.57 g, 51.3 mmol) dropwise. The mixture was stirred at 0° C. for 0.5 h. DCM (500 mL) was added and the mixture was washed successively with 1 N HCl (100 mL), aq. NaHCO$_3$ (300 mL) solution and water (300 mL×2). The organic layer was dried over Na$_2$SO$_4$, filtered and concentrated to yield light yellow oil of tert-butyl 4-(((ethoxycarbonyl)amino)methyl)piperidine-1-carboxylate (9 g, 28.3 mmol, 60.6% yield): $^1$H NMR (400 MHz, CDCl$_3$) δ ppm 4.80 (br. s, 1H), 4.23-3.93 (m, 4H), 3.03 (br. s, 2H), 2.64 (t, J=11.7 Hz, 2H), 1.68-1.56 (m, 3H), 1.42 (s, 9H), 1.20 (t, J=6.8 Hz, 3H), 1.13-1.03 (m, 2H); ES-LCMS m/z 231.2. [M−t−Bu+H]$^+$.

Step 2: Ethyl (piperidin-4-ylmethyl)carbamate, hydrochloride

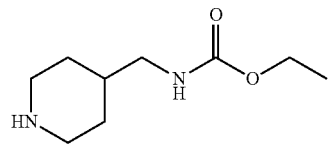

To a solution of tert-butyl 4-(((ethoxycarbonyl)amino)methyl)piperidine-1-carboxylate (9 g, 28.3 mmol) in EtOAc (50 mL) was added HCl solution (4.0 M in EtOAc, 30 mL, 120 mmol) dropwise. The mixture was stirred at 25° C. for 0.5 h then concentrated to yield a pink solid ethyl (piperidin-4-ylmethyl)carbamate, hydrochloride (7.5 g, 26.9 mmol, 95.0% yield): $^1$H NMR (400 MHz, CD$_3$OD) δ ppm 4.11-4.01 (m, 2H), 3.40 (d, J=12.8 Hz, 2H), 3.04 (d, J=6.6 Hz, 2H), 2.97 (t, J=12.3 Hz, 2H), 1.92 (d, J=13.7 Hz, 2H), 1.49-1.35 (m, 3H), 1.25-1.18 (m, 3H); ES-LCMS m/z 187.2 [M+H]$^+$.

Intermediate 30:
N-Ethyl-2-(piperidin-4-yl)acetamide, hydrochloride

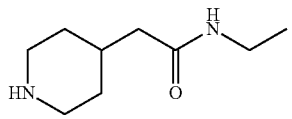

Step 1: tert-Butyl 4-(2-(ethylamino)-2-oxoethyl)piperidine-1-carboxylate

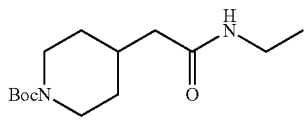 [SMILES: CCNC(=O)CC1CCN(C(=O)OC(C)(C)C)CC1]

To a solution of 2-(1-(tert-butoxycarbonyl)piperidin-4-yl)acetic acid (10 g, 32.9 mmol) and ethanamine, hydrochloride (5.36 g, 65.8 mmol) in DCM (100 mL) was added DIEA (34.5 mL, 197 mmol) and HATU (25.00 g, 65.8 mmol). The reaction mixture was stirred at 30° C. for 8 h until TLC (PE/EtOAc=3/1) showed the reaction was completed. The mixture was concentrated and the residue was purified by flash chromatography (PE/EtOAc=10/1 to 1/1). All fractions found to contain product by TLC (PE/EtOAc=3/1, R$_f$=0.25) were combined and concentrated to yield a colorless oil tert-butyl 4-(2-(ethylamino)-2-oxoethyl)piperidine-1-carboxylate (5 g, 14.79 mmol, 45.0% yield): $^1$H NMR (400 MHz, CDCl$_3$) δ ppm 3.33-3.21 (m, 2H), 2.77-2.56 (m, 4H), 2.11-1.98 (m, 2H), 1.95-1.93 (m, 1H), 1.64 (d, J=13.2 Hz, 2H), 1.41 (s, 9H), 1.40-1.38 (m, 2H), 1.10 (t, J=7.3 Hz, 3H); ES-LCMS m/z 215.0 [M−t−Bu+H]$^+$.

Step 2: N-Ethyl-2-(piperidin-4-yl)acetamide, hydrochloride

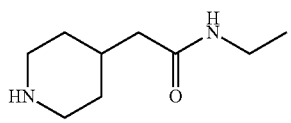

tert-Butyl 4-(2-(ethylamino)-2-oxoethyl)piperidine-1-carboxylate (5 g, 14.79 mmol) was dissolved in HCl solution (4.0 M in MeOH, 24 mL, 96 mmol). The mixture was stirred at 20° C. for 0.5 h then concentrated to yield a brown solid N-ethyl-2-(piperidin-4-yl)acetamide, hydrochloride (3 g, 10.16 mmol, 68.7% yield): $^1$H NMR (400 MHz, CDCl$_3$) δ ppm 3.77-3.55 (m, 2H), 3.19-2.87 (m, 4H), 2.86 (m, 2H), 1.97-1.78 (m, 1H), 1.51 (br. s, 4H), 1.42 (d, J=4.4 Hz, 3H).

Intermediate 31: Ethyl 3-(azetidin-3-yl)butanoate, TFA salt

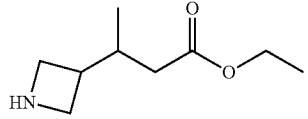

Step 1: tert-Butyl 3-(methoxy(methyl)carbamoyl)azetidine-1-carboxylate

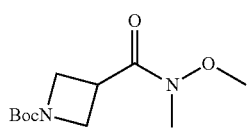 [SMILES: CON(C)C(=O)C1CN(C(=O)OC(C)(C)C)C1]

CDI (6.04 g, 37.3 mmol) was added in portions to a solution of 1-(tert-butoxycarbonyl)azetidine-3-carboxylic acid (5 g, 24.85 mmol) in THF (50 mL). The mixture was stirred at 15° C. for 2 h. A suspension of N,O-dimethylhydroxylamine, hydrochloride (3.64 g, 37.3 mmol) and DIEA (13.02 mL, 74.5 mmol) in MeCN (50 mL) was added. The resulting mixture was stirred at 15° C. for 8 h. Volatiles were concentrated then water (100 mL) and EtOAc (100 mL) were added. The organic layer was separated, washed successively with 5% aqueous citric acid (100 mL), water (100 mL) and brine (100 mL) then dried over anhydrous MgSO$_4$ and concentrated to yield a pale yellow oil of tert-butyl 3-(methoxy(methyl)carbamoyl)azetidine-1-carboxylate (5 g, 17.40 mmol, 70.0% yield): $^1$H NMR (400 MHz, CD$_3$OD) δ ppm 4.11-3.97 (m, 4H), 3.85-3.74 (m, 1H), 3.69 (s, 3H), 3.20 (s, 3H), 1.43 (s, 9H); ES-LCMS m/z 189.1[M−t−Bu+H]$^+$.

Step 2: tert-Butyl 3-acetylazetidine-1-carboxylate

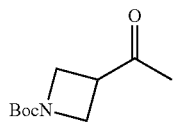

A solution of tert-butyl 3-(methoxy(methyl)carbamoyl)azetidine-1-carboxylate (4 g, 13.92 mmol) in THF (70 mL) was added drop wise to a solution of MeMgBr (13.92 mL, 41.8 mmol) in THF (30 mL) over 0.5 h. The reaction temperature was kept at 0° C. After the addition, the mixture was stirred at 15° C. for 2.5 h. The mixture was cooled to 0° C. and 10% aqueous citric acid (50 mL) was added. The organic layer was separated and the aqueous layer was extracted with EtOAc (200 mL). The combined organic layers were dried over Na$_2$SO$_4$, filtered and concentrated to yield a yellow oil of tert-butyl 3-acetylazetidine-1-carboxylate (3 g, 12.05 mmol, 87.0% yield): $^1$H NMR (400 MHz, CD$_3$OD) δ ppm 4.10-3.97 (m, 4H), 3.59 (s, 1H), 2.18 (s, 3H), 1.45 (s, 9H); ES-LCMS m/z 144.1 [M−t−Bu+H]$^+$.

Step 3: (E)-tert-Butyl 3-(4-ethoxy-4-oxobut-2-en-2-yl)azetidine-1-carboxylate

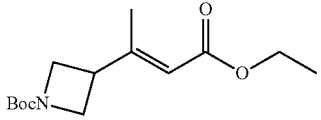 [SMILES: CCOC(=O)/C=C(\C)C1CN(C(=O)OC(C)(C)C)C1]

To a solution of ethyl 2-(diethoxyphosphoryl)acetate (2.70 g, 12.05 mmol) in THF (30 mL) was added t-BuOK (1.352 g, 12.05 mmol). The mixture was stirred at 15° C. for 2 h followed by addition of a solution of tert-butyl 3-acetylazetidine-1-carboxylate (2 g, 8.03 mmol) in THF (20 mL). The mixture was stirred at 15° C. for 6 h before quenched with H$_2$O (50 mL). The mixture was extracted with DCM (200 mL×2), the combine organic layers were dried over Na$_2$SO$_4$, filtered and concentrated to yield crude product which was purified by silica gel column chromatography (PE/EtOAc=2/1). All fractions found to contain product by TLC (PE/EtOAc=2/1, R$_f$=0.5) were combined and concentrated to yield a colorless oil of (E)-tert-butyl 3-(4-ethoxy-4-oxobut-2-en-2-yl)azetidine-1-carboxylate (2.5 g, 7.43 mmol, 92.0% yield): $^1$H NMR (400 MHz, CD$_3$OD) δ ppm 5.77 (s, 1H), 4.20-4.10 (m, 4H), 3.87 (t, J=7.0 Hz, 2H), 3.49-3.37 (m, 1H), 2.23-2.04 (m, 3H), 1.47-1.45 (m, 9H), 1.31-1.26 (m, 3H); ES-LCMS m/z 270.2 [M+H]$^+$

Step 4: tert-Butyl 3-(4-ethoxy-4-oxobutan-2-yl)azetidine-1-carboxylate

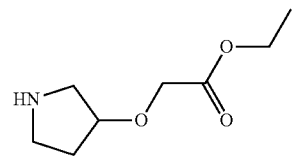

To a solution of (E)-tert-butyl 3-(4-ethoxy-4-oxobut-2-en-2-yl)azetidine-1-carboxylate (2 g, 5.94 mmol) in MeOH (50 mL) was added Pd/C (10 wt %, 1.897 g, 1.782 mmol). The mixture was stirred at 15° C. for 0.5 h under H$_2$ atmosphere (15 psi) then filtered and concentrated to yield a colorless oil of tert-butyl 3-(4-ethoxy-4-oxobutan-2-yl)azetidine-1-carboxylate (2 g, 5.53 mmol, 93.0% yield): $^1$H NMR (400 MHz, CD$_3$OD) δ ppm 4.15 (q, J=7.4 Hz, 2H), 3.96 (d, J=8.0 Hz, 2H), 3.64 (br. s, 2H), 2.32 (d, J=10.0 Hz, 2H), 2.17-2.01 (m, 2H), 1.45 (s, 9H), 1.27 (t, J=7.3 Hz, 3H), 0.94 (d, J=6.0 Hz, 3H); ES-LCMS m/z 216.2 [M−t−Bu+H]$^+$.

Step 5: Ethyl 3-(azetidin-3-yl)butanoate, TFA salt

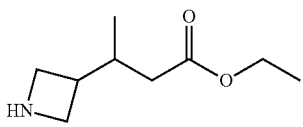

To a solution of tert-butyl 3-(4-ethoxy-4-oxobutan-2-yl)azetidine-1-carboxylate (1 g, 2.76 mmol) in DCM (10 mL) was added TFA (2 mL, 26.0 mmol). The mixture was stirred at 15° C. for 0.5 h then concentrated to yield a colorless oil of ethyl 3-(azetidin-3-yl)butanoate, TFA salt (1 g, 2.454 mmol, 89.0% yield): $^1$H NMR (400 MHz, CD$_3$OD) δ ppm 4.23-3.79 (m, 6H), 2.82-2.71 (m, 1H), 2.45-2.39 (m, 3H) 1.23-1.19 (m, 3H), 0.89 (d, J=5.3 Hz, 3H); ES-LCMS m/z 172.2[M+H]$^+$.

Intermediate 32: Ethyl 2-(pyrrolidin-3-yloxy)acetate, hydrochloride

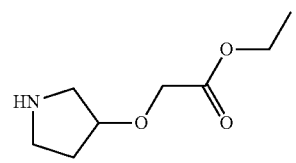

Step 1: tert-Butyl 3-(2-ethoxy-2-oxoethoxy)pyrrolidine-1-carboxylate

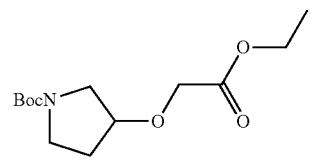 [SMILES: CCOC(=O)COC1CCN(C(=O)OC(C)(C)C)C1]

To a suspension of tert-butyl 3-hydroxypyrrolidine-1-carboxylate (3 g, 16.02 mmol) in THF (50 mL) was added NaH (0.961 g, 24.03 mmol) under N$_2$ atmosphere at 0° C. The reaction mixture was stirred at 0° C. for 0.5 h then ethyl 2-bromoacetate (5.35 g, 32.0 mmol) was added. The reaction mixture was stirred at 20° C. for 9.5 h under N$_2$ atmosphere. The mixture was quenched with saturated aqueous NH$_4$Cl solution (30 mL), extracted with EtOAc (30 mL×3). The combined organic layers were dried over Na$_2$SO$_4$, filtered and concentrated to yield crude. The crude was purified by flash chromatography (PE/EtOAc=3/1, R$_f$=0.5) and the desired fraction was concentrated to yield a colorless oil tert-butyl 3-(2-ethoxy-2-oxoethoxy)pyrrolidine-1-carboxylate (3 g, 8.78 mmol, 54.8% yield): $^1$H NMR (400 MHz, CDCl$_3$) δ ppm 4.22 (q, J=7.1 Hz, 2H), 4.15 (br. s, 1H), 4.11-4.02 (m, 2H), 3.57-3.34 (m, 4H), 2.11-1.88 (m, 2H), 1.45 (s, 9H), 1.31-1.25 (m, 3H); ES-LCMS m/z 218.2 [M−t−Bu+H]$^+$.

Step 2: Ethyl 2-(pyrrolidin-3-yloxy)acetate, hydrochloride

To a suspension of tert-butyl 3-(2-ethoxy-2-oxoethoxy) pyrrolidine-1-carboxylate (3 g, 8.78 mmol) in DCM (30 mL) was added HCl solution (4.0 M in EtOAc, 20 mL, 80 mmol). The reaction mixture was stirred at 15° C. for 0.5 h then concentrated to yield a colorless gum crude of ethyl 2-(pyrrolidin-3-yloxy)acetate, hydrochloride (1.5 g, 5.72 mmol, 65.2% yield): $^1$H NMR (400 MHz, CDCl$_3$) δ ppm 4.37 (br. s, 1H), 4.21 (q, J=7.3 Hz, 2H), 4.13-4.07 (m, 2H), 3.92 (br. s, 1H), 3.62-3.38 (m, 4H), 2.25 (dd, J=5.6, 13.9 Hz, 1H), 2.15-2.05 (m, 1H), 1.31-1.25 (m, 3H).

Intermediate 33: Ethyl 2-(octahydrocyclopenta[c]pyrrol-5-yl)acetate, hydrochloride

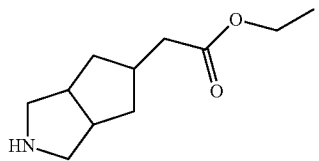

Step 1: tert-Butyl 5-(2-ethoxy-2-oxoethylidene)hexahydrocyclopenta[c]pyrrole-2(1H)-carboxylate

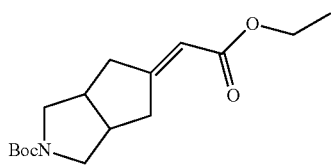 [SMILES: CCOC(=O)C=C1CC2CN(C(=O)OC(C)(C)C)CC2C1]

To a solution of ethyl 2-(diethoxyphosphoryl)acetate (1.493 g, 6.66 mmol) in THF (10 mL) was added t-BuOK (0.747 g, 6.66 mmol). After stirring at 15° C. for 0.5 h, tert-butyl 5-oxohexahydrocyclopenta[c]pyrrole-2(1H)-carboxylate (1 g, 4.44 mmol) was added. The mixture was stirred at the same temperature for 11.5 h until TLC (PE/EtOAc=3/1, R$_f$=0.58) showed the reaction was completed. Volatiles were concentrated and water (50 mL) was added. The mixture was extracted with DCM (20 mL×3) and the combined organic layers were dried over Na$_2$SO$_4$ and concentrated to yield the crude product which was purified by flash chromatography (PE/EtOAc=1/0 to 2/1, PE/EtOAc=3/1, R$_f$=0.58) to yield a pale yellow oil tert-butyl 5-(2-ethoxy-2-oxoethylidene)hexahydrocyclopenta[c]pyrrole-2(1H)-carboxylate (600 mg, 1.844 mmol, 41.5% yield): $^1$H NMR (400 MHz, CDCl$_3$) δ ppm 5.76 (s, 1H), 4.06 (q, J=7.1 Hz, 2H), 3.46 (d, J=7.1 Hz, 2H), 3.07 (dd, J=4.2, 10.8 Hz, 1H), 3.02-2.90 (m, 2H), 2.76-2.55 (m, 4H), 2.36 (d, J=14.1 Hz, 1H), 1.38 (s, 9H), 1.23-1.12 (m, 3H); ES-LCMS m/z 240.2 [M−t−Bu+H]$^+$.

Step 2: tert-Butyl 5-(2-ethoxy-2-oxoethyl)hexahydrocyclopenta[c]pyrrole-2(1H)-carboxylate

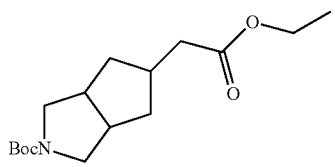 [SMILES: CCOC(=O)CC1CC2CN(C(=O)OC(C)(C)C)CC2C1]

To a solution of tert-butyl 5-(2-ethoxy-2-oxoethylidene)hexahydrocyclopenta[c]pyrrole-2(1H)-carboxylate (600 mg, 1.844 mmol) in MeOH (20 mL) was added Pd/C (10 wt %, 200 mg, 0.188 mmol) under H$_2$ atmosphere (15 psi). The mixture was stirred at 15° C. for 8 h then filtered. The filtrate was concentrated to yield a colorless oil tert-butyl 5-(2-ethoxy-2-oxoethyl)hexahydrocyclopenta[c]pyrrole-2(1H)-carboxylate (500 mg, 1.429 mmol, 77.0% yield): $^1$H NMR (400 MHz, CDCl$_3$) δ ppm 4.11 (q, J=7.1 Hz, 2H), 3.41 (s, 2H), 3.21 (s, 2H), 2.59 (s, 2H), 2.38-2.21 (m, 3H), 2.18-2.05 (m, 2H), 1.44 (s, 9H), 1.24 (t, J=7.1 Hz, 3H), 1.07 (s, 2H). ES-LCMS m/z 242.2 [M−t−Bu+H]$^+$.

Step 3: Ethyl 2-(octahydrocyclopenta[c]pyrrol-5-yl)acetate, hydrochloride

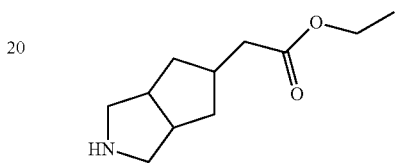

tert-Butyl 5-(2-ethoxy-2-oxoethyl)hexahydrocyclopenta[c]pyrrole-2(1H)-carboxylate (500 mg, 1.429 mmol) was dissolved in HCl solution (4.0 M in EtOAc, 6 mL, 24.00 mmol). The reaction mixture was stirred at 15° C. for 0.5 h. The solution was concentrated to yield a pale yellow oil of ethyl 2-(octahydrocyclopenta[c]pyrrol-5-yl)acetate, hydrochloride (380 mg, 1.382 mmol, 97.0% yield): $^1$H NMR (400 MHz, CDCl$_3$) δ ppm 4.13-4.05 (m, 2H), 3.21 (s, 4H), 2.91-2.81 (m, 2H), 2.42 (d, J=6.2 Hz, 2H), 2.27-2.12 (m, 3H), 1.39-1.28 (m, 2H), 1.26-1.18 (m, 3H); ES-LCMS m/z 198.3 [M+H]$^+$.

Intermediate 34: Benzyl (3,3-dimethylpiperidin-4-yl)carbamate

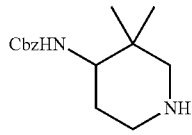 [SMILES: CC1(C)CNCCC1NC(=O)OCc1ccccc1]

Step 1: tert-Butyl 4-amino-3,3-dimethylpiperidine-1-carboxylate

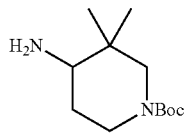

To a solution of tert-butyl 3,3-dimethyl-4-oxopiperidine-1-carboxylate (1.2 g, 5.28 mmol) in MeOH (10 mL) was added NH$_4$OAc (4.07 g, 52.8 mmol). The mixture was stirred at 15° C. for 10 h under N$_2$ atmosphere then NaBH$_3$CN (0.995 g, 15.84 mmol) was added and stirred for another 2 h. The mixture was filtered and concentrated to yield a colorless oil of tert-butyl 4-amino-3,3-dimethylpiperidine-1-carboxylate (600 mg, 2.102 mmol, 39.8% yield): $^1$H NMR (400 MHz, CD$_3$OD) δ ppm 4.00 (d, J=13.2 Hz, 2H), 3.64 (d, J=13.2 Hz, 2H), 2.49 (dd, J=4.2, 11.0 Hz, 1H), 1.67-1.52 (m, 2H), 1.43 (s, 9H), 0.93 (s, 3H), 0.81 (s, 3H); ES-LCMS m/z 173.1 [M+H]$^+$.

Step 2: tert-Butyl 4-(((benzyloxy)carbonyl)amino)-3,3-dimethylpiperidine-1-carboxylate

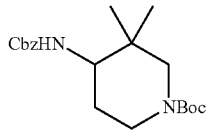

To a mixture of tert-butyl 4-amino-3,3-dimethylpiperidine-1-carboxylate (400 mg, 1.752 mmol) and DIEA (679 mg, 5.26 mmol) in DCM (8 mL) was added CbzCl (448 mg, 2.63 mmol). The mixture was stirred at 15° C. for 1 h then concentrated. The residue was purified by preparative TLC (PE/EtOAc=10/3, R$_f$=0.6) to yield a yellow oil of tert-butyl 4-(((benzyloxy)carbonyl)amino)-3,3-dimethylpiperidine-1-carboxylate (500 mg, 1.104 mmol, 63.0% yield): $^1$H NMR (400 MHz, CDCl$_3$) δ ppm 7.40-7.29 (m, 5H), 5.15-5.05 (m, 2H), 4.60 (d, J=9.5 Hz, 1H), 3.83-3.60 (m, 1H), 3.57-3.45 (m, 1H), 2.80 (br. s, 1H), 2.62 (br. s, 1H), 1.77-1.67 (m, 1H), 1.55-1.47 (m, 1H), 1.45 (s, 9H), 0.94 (s, 3H), 0.82 (s, 3H); ES-LCMS m/z 263.2 [M−Boc+H]$^+$.

Step 3: Benzyl (3,3-dimethylpiperidin-4-yl)carbamate

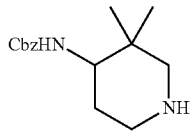

To a solution of tert-butyl 4-(((benzyloxy)carbonyl)amino)-3,3-dimethylpiperidine-1-carboxylate (300 mg, 0.828 mmol) in DCM (10 mL) was added TFA (1887 mg, 16.55 mmol). The mixture was stirred at 15° C. for 0.5 h then water (50 mL) was added. The aqueous phase was adjusted to pH=9 with solid Na$_2$CO$_3$ then extracted with DCM (15 mL×2). The combined extracts were washed with brine (15 mL×2), dried over Na$_2$SO$_4$, filtered and concentrated to yield a yellow oil of benzyl (3,3-dimethylpiperidin-4-yl)carbamate (200 mg, 0.686 mmol, 83.0% yield): $^1$H NMR (400 MHz, CDCl$_3$) δ ppm 7.40-7.29 (m, 5H), 5.14-5.04 (m, 2H), 4.61 (d, J=9.5 Hz, 1H), 3.55-3.46 (m, 1H), 3.04 (d, J=12.6 Hz, 1H), 2.72-2.59 (m, 2H), 2.48 (d, J=12.6 Hz, 1H), 1.72-1.67 (m, 1H), 1.42-1.40 (m, 1H), 0.90 (d, J=3.7 Hz, 6H); ES-LCMS m/z 263.2 [M+H]$^+$.

Intermediate 35: 2-(Piperidin-4-yl)acetamide

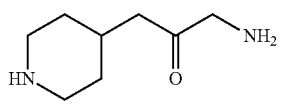 [SMILES: NCC(=O)CC1CCNCC1]

Step 1: tert-Butyl 4-(2-amino-2-oxoethyl)piperidine-1-carboxylate

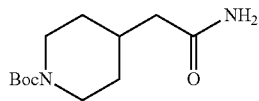 [SMILES: CC(C)(C)OC(=O)N1CCC(CC(N)=O)CC1]

To a solution of 2-(1-(tert-butoxycarbonyl)piperidin-4-yl) acetic acid (5 g, 20.55 mmol) and DIEA (14.36 mL, 82 mmol) in DCM (100 mL) was added NH$_4$Cl (10.99 g, 206 mmol) and HATU (15.63 g, 41.1 mmol). The reaction mixture was stirred at 30° C. for 8 h then concentrated and purified by flash chromatography (DCM/MeOH=100/1 to 10/1). All fractions found to contain product by TLC (DCM/MeOH=10/1), R$_f$=0.6) were combined and concentrated to yield a white solid of tert-butyl 4-(2-amino-2-oxoethyl) piperidine-1-carboxylate (3 g, 9.90 mmol, 48.2% yield): $^1$H NMR (400 MHz, CDCl$_3$) δ ppm 5.82-5.52 (m, 2H), 4.12-3.95 (m, 2H), 2.77-2.61 (m, 2H), 2.06-1.88 (m, 2H), 1.72 (d, J=12.8 Hz, 2H), 1.54-1.40 (m, 9H), 1.13 (dq, J=4.0, 12.3 Hz, 2H); ES-LCMS m/z 187.2 [M−t−Bu+H]$^+$.

Step 2: 2-(Piperidin-4-yl)acetamide, hydrochloride

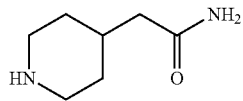

tert-Butyl 4-(2-amino-2-oxoethyl)piperidine-1-carboxylate (0.8 g, 2.64 mmol) was dissolved in HCl solution (4.0 M in EtOAc, 10 mL, 40 mmol). The mixture was stirred at 20° C. for 0.5 h. The mixture concentrated to yield a white solid of 2-(piperidin-4-yl)acetamide, hydrochloride (0.5 g, 2.239 mmol, 85.0% yield): $^1$H NMR (400 MHz, CDCl$_3$) δ ppm 3.16-3.10 (m, 4H), 2.12-2.02 (m, 2H), 1.43-1.40 (m, 5H).

Intermediate 36: 4-(2-(Methylsulfonyl)ethyl)piperidine, hydrochloride

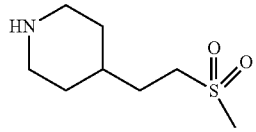

Step 1: tert-Butyl 4-(2-(methylthio)ethyl)piperidine-1-carboxylate

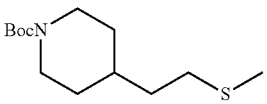

To a solution of tert-butyl 4-(2-((methylsulfonyl)oxy)ethyl)piperidine-1-carboxylate (3.75 g, 9.76 mmol) and sodium methanethiolate (2.74 g, 39.0 mmol) in DMF (50 mL) was added $K_2CO_3$ (2.70 g, 19.52 mmol) at 25° C. The reaction mixture was stirred at 25° C. for 12 h then filtered. The filtrate was concentrated to yield the crude product which was purified by flash chromatography on silica gel column chromatography (PE/EtOAc=1/0 to 1/1, PE/EtOAc=3/1, $R_f$=0.45) to yield a yellow oil of tert-butyl 4-(2-(methylthio)ethyl)piperidine-1-carboxylate (1.5 g, 5.20 mmol, 53.3% yield): $^1$H NMR (400 MHz, $CDCl_3$) δ ppm 4.06 (s, 2H), 2.67 (t, J=11.9 Hz, 2H), 2.54-2.46 (m, 2H), 2.11-2.02 (m, 3H), 1.65 (d, J=12.8 Hz, 2H), 1.55-1.48 (m, 3H), 1.44 (s, 9H), 1.13-1.03 (m, 2H); ES-LCMS m/z 160.2 [M−Boc+H]$^+$.

Step 2: tert-Butyl 4-(2-(methylsulfonyl)ethyl)piperidine-1-carboxylate

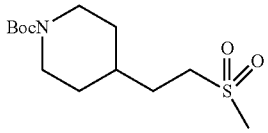

To a solution of tert-butyl 4-(2-(methylthio)ethyl)piperidine-1-carboxylate (500 mg, 1.735 mmol) in DCM (10 mL) was added m-CPBA (704 mg, 3.47 mmol) at 25° C. The reaction mixture was stirred at 25° C. for 12 h. The solid was filtered off and the mixture was concentrated to yield the crude product which was purified by silica gel column chromatography (PE/EtOAc=1/0 to 1/3, PE/EtOAc=1/1, $R_f$=0.25) to yield a pale yellow solid of tert-butyl 4-(2-(methylsulfonyl)ethyl)piperidine-1-carboxylate (350 mg, 0.961 mmol, 55.4% yield): $^1$H NMR (400 MHz, $CDCl_3$) δ ppm 4.15-4.07 (m, 2H), 2.78-2.65 (m, 4H), 2.58 (s, 3H), 1.84-1.77 (m, 1H), 1.69-1.64 (m, 2H), 1.63-1.48 (m, 2H), 1.56 (s, 9H), 1.17-1.09 (m, 2H); ES-LCMS m/z 236.1 [M−t−Bu+H]$^+$.

Step 3: 4-(2-(Methylsulfonyl)ethyl)piperidine, hydrochloride

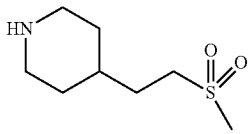

tert-Butyl 4-(2-(methylsulfonyl)ethyl)piperidine-1-carboxylate (350 mg, 0.961 mmol) was dissolved in HCl solution (4.0 M in EtOAc, 8 mL, 32.0 mmol). The reaction mixture was stirred at 15° C. for 10 min. Then the mixture was concentrated to yield a white solid of 4-(2-(methylsulfonyl)ethyl)piperidine, hydrochloride (235 mg, 0.929 mmol, 97.0% yield): $^1$H NMR (400 MHz, $CD_3OD$) δ ppm 3.40 (d, J=12.8 Hz, 2H), 3.24-3.14 (m, 2H), 3.04-2.90 (m, 5H), 1.99 (d, J=12.8 Hz, 2H), 1.83-1.72 (m, 3H), 1.48-1.36 (m, 2H).

Intermediate 37: (1S,4S)-tert-Butyl 2,5-diazabicyclo[2.2.1]heptane-2-carboxylate

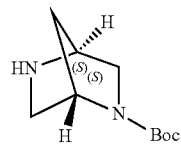

Step 1: (2S,4R)-Methyl 4-hydroxypyrrolidine-2-carboxylate, hydrochloride

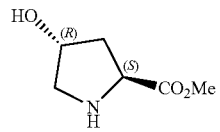

To a suspension of (2S,4R)-4-hydroxypyrrolidine-2-carboxylic acid (90 g, 686 mmol) in MeOH (1 L) was added $SOCl_2$ (100 mL, 1373 mmol) dropwise under −15° C. The mixture was stirred at 20° C. for 20 h then concentrated to yield a white solid of (2S,4R)-methyl 4-hydroxypyrrolidine-2-carboxylate, hydrochloride (100 g, 523 mmol, 76.0% yield): $^1$H NMR (400 MHz, DMSO-$d_6$) δ ppm 9.89 (br. s, 1H), 5.64 (br. s, 1H), 4.53-4.35 (m, 2H), 3.74 (s, 3H), 3.36 (dd, J=4.4, 11.9 Hz, 1H), 3.06 (d, J=12.0 Hz, 1H), 2.23-2.15 (m, 1H), 2.13-2.03 (m, 1H); ES-LCMS m/z 146.2 [M+H]$^+$.

Step 2: (2S,4R)-Methyl 4-hydroxy-1-tosylpyrrolidine-2-carboxylate

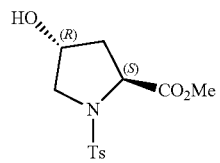

To a suspension of (2S,4R)-methyl 4-hydroxypyrrolidine-2-carboxylate, hydrochloride (100 g, 523 mmol) and $Et_3N$ (219 mL, 1569 mmol) in DCM (1500 mL) was added p-TsCl (120 g, 628 mmol) in portions at 0° C. The mixture was stirred at 20° C. for 18 h then water (500 mL) was added. The organic extract was washed with saturated $NaHCO_3$ solution (500 mL×2), brine (500 mL), dried over $Na_2SO_4$, filtered and concentrated to yield a pale yellow solid of (2S,4R)-methyl 4-hydroxy-1-tosylpyrrolidine-2-carboxylate (105 g, 228 mmol, 43.5% yield): $^1$H NMR (400 MHz, $CDCl_3$) δ ppm 7.78 (d, J=8.0 Hz, 2H), 7.33 (d, J=8.0 Hz, 2H), 4.51-4.36 (m, 2H), 3.78-3.71 (m, 3H), 3.62 (dd, J=11.6, 4.0 Hz, 1H), 3.39 (d, J=11.6 Hz, 1H), 2.43 (s, 3H), 2.26-2.18 (m, 1H), 2.16-2.05 (m, 1H); ES-LCMS m/z 300.1 [M+H]$^+$.

Step 3: (3S,5S)-5-(Hydroxymethyl)-1-tosylpyrrolidin-3-ol

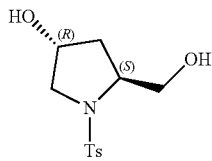

LiAlH$_4$ (12.34 g, 325 mmol) was suspended in 800 mL of anhydrous THF under N$_2$ atmosphere and cooled to 0° C. with vigorous stirring. A solution of (2S,4R)-methyl 4-hydroxy-1-tosylpyrrolidine-2-carboxylate (100 g, 217 mmol) in 400 mL of dry THF was added dropwise below 5° C. The reaction was allowed to warm to 20° C. and stirred for 18 h. Then the reaction mixture was cooled to 0° C. and water (13 mL) was added, followed by addition of 15% NaOH (13 mL) and water (39 mL). The suspension was stirred for 20 min and diluted with EtOAc (200 mL), treated with 80 g of MgSO$_4$, then stirred for additional 20 min. The solid was filtered off and the filtrate was concentrated to yield a pale yellow solid of (3S,5S)-5-(hydroxymethyl)-1-tosylpyrrolidin-3-ol (74.29 g, 210 mmol, 97.0% yield): $^1$H NMR (400 MHz, DMSO-$d_6$) δ ppm 7.72-7.64 (m, 2H), 7.45-7.36 (m, 2H), 4.85-4.69 (m, 2H), 4.26-4.16 (m, 1H), 3.63-3.52 (m, 2H), 3.42-3.39 (m, 2H), 2.91 (dd, J=10.0, 4.8 Hz, 1H), 2.42-2.36 (m, 3H), 1.92 (d, J=12.4, 5.2 Hz, 1H), 1.52-1.43 (m, 1H); ES-LCMS m/z 272.2 [M+H]$^+$.

Step 4: ((2S,4R)-4-((Methylsulfonyl)oxy)-1-tosylpyrrolidin-2-yl)methyl methanesulfonate

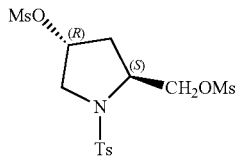

To a solution of (3S,5S)-5-(hydroxymethyl)-1-tosylpyrrolidin-3-ol (78 g, 221 mmol) and Et$_3$N (139 mL, 994 mmol) in DCM (1.3 L) was added dropwise MsCl (157 mL, 2010 mmol) at 0° C. The mixture was allowed to warm to 20° C. and stirred at 20° C. for 20 h. The reaction was quenched with water (500 mL). The aqueous phase was extracted with DCM (600 mL×2). The organic phases were combined and washed with saturated NaHCO$_3$ solution (500 mL×2), dried with Na$_2$SO$_4$, filtered and concentrated to yield a yellow oil of ((2S,4R)-4-((methyl sulfonyl)oxy)-1-tosylpyrrolidin-2-yl)methyl methanesulfonate (100 g, 161 mmol, 73.0% yield): $^1$H NMR (400 MHz, CDCl$_3$) δ ppm 7.81-7.74 (m, 2H), 7.38 (d, J=8.0 Hz, 2H), 5.10 (br. s, 1H), 4.62-4.54 (m, 1H), 4.47 (dd, J=10.8, 2.4 Hz, 1H), 4.05-3.96 (m, 1H), 3.75-3.68 (m, 2H), 3.14-3.09 (m, 3H), 2.73-2.65 (m, 3H), 2.45 (s, 3H), 2.36-2.24 (m, 2H); ES-LCMS m/z 428.1 [M+H]$^+$.

Step 5: (1S,4S)-2-Benzyl-5-tosyl-2,5-diazabicyclo[2.2.1]heptane

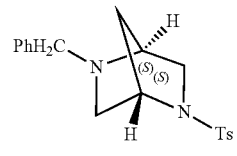

To a suspension of ((2S,4R)-4-((methyl sulfonyl)oxy)-1-tosyl pyrrolidin-2-yl)methyl methanesulfonate (100 g, 161 mmol) in toluene (1 L) was added phenylmethanamine (60.5 g, 564 mmol). The mixture was stirred at 100° C. for 18 h. The mixture was cooled to room temperature and filtered. The filtrate was concentrated and the residue was washed with PE, filtered and dried to yield a pale yellow solid of (1S,4S)-2-benzyl-5-tosyl-2,5-diazabicyclo[2.2.1]heptane (60 g, 154 mmol, 96.0% yield): $^1$H NMR (400 MHz, CDCl$_3$) δ ppm 7.74 (d, J=8.0 Hz, 2H), 7.36-7.23 (m, 7H), 4.28 (br. s, 1H), 3.72-3.59 (m, 3H), 3.46-3.38 (m, 1H), 3.03 (dd, J=9.6, 2.0 Hz, 1H), 2.83 (dd, J=10.0, 2.4 Hz, 1H), 2.71-2.62 (m, 1H), 2.48-2.41 (m, 3H), 1.71 (d, J=9.6 Hz, 1H), 1.11 (d, J=9.6 Hz, 1H); ES-LCMS m/z 343.2 [M+H]$^+$.

Step 6: (1S,4S)-2-Benzyl-2,5-diazabicyclo[2.2.1]heptanes, 2 hydrobromide

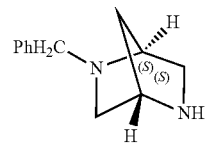

To a suspension of (1S,4S)-2-benzyl-5-tosyl-2,5-diazabicyclo[2.2.1]heptane (60 g, 154 mmol) in acetic acid (600 mL) was added hydrogen bromide in acetic acid (120 mL, 419 mmol). The mixture was stirred at 70° C. for 20 h. The resulting suspension was cooled and the precipitate was filtered, washed with PE and dried to yield a yellow solid of (1S,4S)-2-benzyl-2,5-diazabicyclo[2.2.1]heptane, 2 hydrobromide (60 g, 146 mmol, 95.0% yield): $^1$H NMR (400 MHz, DMSO-$d_6$) δ ppm 9.54-9.18 (m, 2H), 7.66 (d, J=3.6 Hz, 2H), 7.56-7.37 (m, 3H), 4.67-4.31 (m, 4H), 3.74-3.61 (m, 1H), 3.47 (br. s, 3H), 2.07 (d, J=11.6 Hz, 2H).

Step 7: (1S,4S)-tert-Butyl 5-benzyl-2,5-diazabicyclo[2.2.1]heptane-2-carboxylate

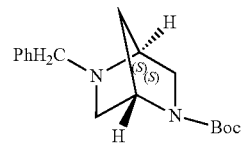

(1S4S)-2-Benzyl-2,5-diazabicyclo[2.2.1]heptane, 2 hydrobromide (60 g, 146 mmol) and Et$_3$N (60.9 mL, 437 mmol) was dissolved in DCM (600 mL). The reaction mixture was cooled to 0° C. Boc$_2$O (35.5 mL, 153 mmol) was added to the above solution at 0° C. The mixture was stirred at 20° C.

for 18 h then quenched with water (300 mL). The organic phase was washed with saturated aqueous NaHCO₃ (aq., 300 mL×2), dried with Na₂SO₄, filtered and concentrated to yield the crude product which was purified by silica gel column chromatography (PE/EtOAc=20/1 to 5/1). All fractions found to contain product by TLC (PE/EtOAc=3/1, $R_f$=0.4) were combined and concentrated to yield a pale yellow solid of (1S,4S)-tert-butyl 5-benzyl-2,5-diazabicyclo[2.2.1]heptane-2-carboxylate (45 g, 140 mmol, 96.0% yield): ¹H NMR (400 MHz, CDCl₃) δ ppm 7.48-7.18 (m, 5H), 4.44-4.24 (m, 1H), 3.77 (d, J=8.0 Hz, 2H), 3.69-3.45 (m, 2H), 3.26-3.14 (m, 1H), 3.01-2.86 (m, 1H), 2.80-2.55 (m, 1H), 1.93-1.84 (m, 1H), 1.77-1.65 (m, 1H), 1.50 (br. s, 9H); ES-LCMS m/z 289.3 [M+H]⁺.

Step 8: (1S,4S) tert-Butyl 2,5-diazabicyclo[2.2.1]heptane-2-carboxylate

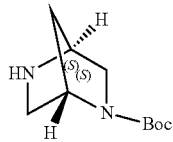

To a suspension of (1S,4S)-tert-butyl 5-benzyl-2,5-diazabicyclo[2.2.1]heptane-2-carboxylate (15 g, 46.8 mmol) in MeOH (150 mL) was added Pd/C (10 wt %, 4.98 g, 4.68 mmol). The mixture was stirred at 50° C. for 18 h under H₂ atmosphere (50 psi). The solution was filtered and concentrated to yield the residue, which was dissolved in DCM (120 mL), dried with Na₂SO₄, filtered and concentrated to yield an off white solid of (1S,4S)-tert-butyl 2,5-diazabicyclo[2.2.1]heptane-2-carboxylate (8 g, 39.9 mmol, 85.0% yield): ¹H NMR (400 MHz, CDCl₃) δ ppm 4.49-4.25 (m, 1H), 3.69 (br. s, 1H), 3.44-3.29 (m, 1H), 3.16 (dd, J=17.2, 10.4 Hz, 1H), 3.09-2.93 (m, 2H), 1.79-1.63 (m, 2H), 1.58 (br. s, 1H), 1.45 (d, J=4.8 Hz, 9H); ES-LCMS m/z 199.2 [M+H]⁺.

Intermediate 38: Ethyl 2-methylenebutanoate

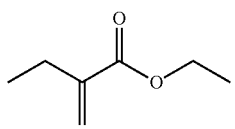

Step 1: Ethyl 2-(diethoxyphosphoryl)butanoate

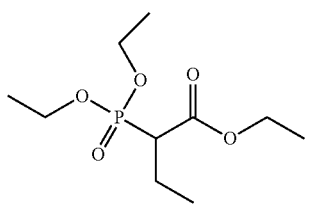

To a solution of ethyl 2-(diethoxyphosphoryl)acetate (15 g, 66.9 mmol) in DMSO (50 mL) was added t-BuOK (9.01 g, 80 mmol) and EtI (12.52 g, 80 mmol). The mixture was stirred at 50° C. for 1 h. The mixture was dissolved in EtOAc (200 mL) and washed with saturated NH₄Cl solution (100 mL×2). The organic phase was concentrated to yield a yellow oil of ethyl 2-(diethoxyphosphoryl)butanoate (16 g, 57.1 mmol, 85.0% yield): ¹H NMR (400 MHz, CDCl₃) δ ppm 4.25-3.98 (m, 6H), 2.86-2.71 (m, 1H), 1.95-1.80 (m, 2H), 1.30-1.15 (m, 9H), 0.91 (t, J=7.3 Hz, 3H); ES-LCMS m/z 253.1 [M+H]⁺.

Step 2: Ethyl 2-methylenebutanoate

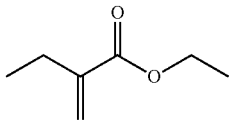

To a solution of ethyl 2-(diethoxyphosphoryl)butanoate (16 g, 57.1 mmol) and paraformaldehyde (5.14 g, 171 mmol) in THF (10 mL) and water (80 mL) was added K₂CO₃ (15.78 g, 114 mmol). The mixture was stirred at 80° C. for 3 h. TLC (PE/EtOAc=10/1, $R_f$=0.5) showed the reaction was completed. The mixture was extracted with DCM (200 mL×2) and the combined organic layers were dried over Na₂SO₄, concentrated to yield a colorless oil of ethyl 2-methylenebutanoate (10 g, 54.6 mmol, 96.0% yield): ¹H NMR (400 MHz, CDCl₃) δ ppm 6.12 (s, 1H), 5.50 (s, 1H), 4.20 (q, J=1.4 Hz, 2H), 2.48-2.13 (m, 2H), 1.28 (d, J=7.1 Hz, 3H), 1.07 (t, 7=7.5 Hz, 3H).

Intermediate 39: 3-(Methylsulfonyl)propyl methanesulfonate

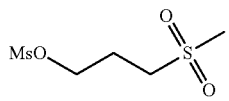

Step 1: 3-(Methylsulfonyl)propan-1-ol

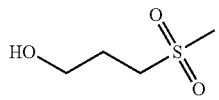

To a solution of 3-(methylthio)propan-1-ol (20 g, 188 mmol) in DCM (200 mL) was added m-CPBA (98 g, 565 mmol) at 15° C. Then the reaction mixture was stirred at 15° C. for 12 h until TLC showed the reaction was completed. The solid was filtered off. H₂O (200 mL) was added to the filtrate and extracted with DCM (250 mL×2), the combined organic layers were washed with aqueous NaHSO₃ (200 mL) and brine (200 mL), dried over Na₂SO₄ and concentrated to yield the crude product. The crude product was purified by silica gel column chromatography (MeOH/DCM=5/95). All fractions found to contain product by TLC (DCM/MeOH=10/1, $R_f$=0.5) were combined and concentrated to yield a yellow oil of 3-(methylsulfonyl)propan-1-ol (2.5 g, 16.28 mmol, 8.6% yield): ¹H NMR (400 MHz, CDCl₃) δ ppm 3.78 (t, J=6.0 Hz, 2H), 3.21-3.10 (m, 2H), 2.92 (s, 3H), 2.18 (br. s, 1H), 2.13-1.99 (m, 2H).

Step 2: 3-(Methylsulfonyl)propyl methanesulfonate

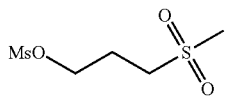

To a solution of 3-(methylsulfonyl)propan-1-ol (0.5 g, 3.26 mmol) in DCM (10 mL) was added MsCl (0.381 mL, 4.88 mmol), DIEA (1.706 mL, 9.77 mmol) at 15° C. The reaction mixture was stirred at 15° C. for 20 min then DCM (50 mL) was added. The mixture was washed with saturated aqueous NaHCO₃ (20 mL) solution. The organic layer was washed with brine, dried over Na₂SO₄ and concentrated to yield a brown solid of 3-(methylsulfonyl)propyl methanesulfonate (0.4 g, 1.480 mmol, 45.4% yield): ¹H NMR (400 MHz, CDCl₃) δ ppm 4.39 (t, J=6.0 Hz, 2H), 3.18 (t, J=7.5 Hz, 2H), 3.04 (s, 3H), 2.95 (s, 3H), 2.38-2.28 (m, 2H)

Intermediate 40: 3-(Methylsulfonyl)propanal

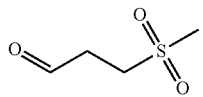

To a solution of oxalyl dichloride (8.38 mL, 98 mmol) in DCM (120 mL) was added DMSO (15.27 g, 195 mmol) dropwise at −78° C. under N₂ atmosphere. After the mixture was stirred for 1 h, 3-(methylsulfonyl)propan-1-ol (10 g, 65.1 mmol) was added to the mixture during 0.5 h at −78° C. under N₂ atmosphere. The mixture was stirred for 1 h and DIEA (68.3 mL, 391 mmol) was added to the reaction at −78° C. under N₂ atmosphere. Then the mixture was allowed to warm to 0° C. over 0.5 h and stirred at 0° C. for another 1 h. The reaction solution was extracted with DCM (250 mL×3), and the combined organic phases were dried with anhydrous Na₂SO₄ and concentrated under reduced pressure. The crude product was purified by silica gel column chromatography (DCM/MeOH=10/1). All fractions found to contain product by TLC (DCM/MeOH=10/1, R$_f$=0.6) were combined and concentrated to yield a light yellow oil of 3-(methylsulfonyl)propanal (2.5 g, 14.69 mmol, 22.6% yield): ¹H NMR (400 MHz, CDCl₃) δ ppm 9.82 (s, 1H), 3.37-3.33 (m, 2H), 3.09 (t, J=7.1 Hz, 2H), 2.95 (s, 3H).

Intermediate 41: 1-Methyl-3-(piperidin-4-ylmethyl)urea, hydrochloride

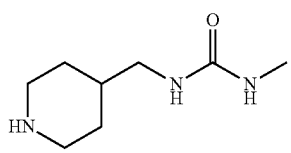

Step 1: tert-Butyl 4-((3-methylureido)methyl)piperidine-1-carboxylate

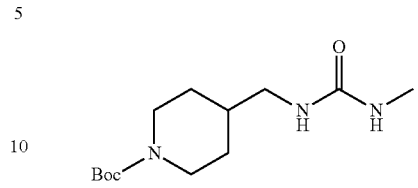

To a mixture of tert-butyl 4-(aminomethyl)piperidine-1-carboxylate (70 g, 327 mmol) and Et₃N (45.5 mL, 327 mmol) in DCM (1 L) was added methylcarbamic chloride (24.77 mL, 392 mmol) dropwise at 0° C. The mixture was stirred at 25° C. for 12 h then DCM (500 mL) and water (800 mL) was added. The aqueous layer was extracted with DCM (500 mL×2). The combined organic layers were washed with 5% HCl solution (500 mL), 10% NaHCO₃ solution (500 mL) and water (500 mL). The organic phase was dried over Na₂SO₄, filtered, and concentrated to yield a white solid of tert-butyl 4-((3-methylureido)methyl)piperidine-1-carboxylate (88 g, 292 mmol, 89.0% yield): ¹H NMR (400 MHz, CDCl₃) δ ppm 4.55 (br. s, 1H), 4.40 (br. s, 1H), 4.03 (m, 2H), 3.12-2.92 (m, 2H), 2.70 (s, 3H), 2.60 (m, 2H), 1.72-1.58 (m, 4H), 1.38 (s, 9H), 1.03 (dd, J=3.79, 12.10 Hz, 1H); ES-LCMS m/z 216.0 [M−t−Bu+H]⁺.

Step 2: 1-Methyl-3-(piperidin-4-ylmethyl)urea, hydrochloride

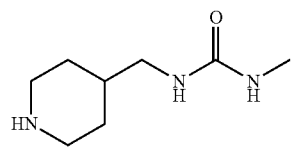

A solution of tert-butyl 4-((3-methylureido)methyl)piperidine-1-carboxylate (85 g, 313 mmol) in MeOH (600 mL) with HCl solution (4.0 M in MeOH, 250 mL, 1.0 mol) at 30° C. was stirred for 2 h. The mixture was concentrated to yield a yellow solid of 1-methyl-3-(piperidin-4-ylmethyl)urea, hydrochloride (70 g, 303 mmol, 97.0% yield): ¹H NMR (400 MHz, CD₃OD) δ ppm 3.42 (d, J=13.05 Hz, 2H), 3.18-3.09 (m, 2H), 3.05-2.93 (m, 2H), 2.76 (s, 3H), 1.96 (d, J=13.55 Hz, 2H), 1.89-1.78 (m, 1H), 1.52-1.34 (m, 2H).

Intermediate 42: Methyl (piperidin-4-ylmethyl)carbamate, hydrochloride

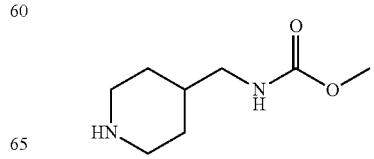

Step 1: tert-Butyl 4-(((methoxycarbonyl)amino) methyl)piperidine-1-carboxylate

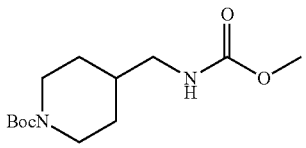 [SMILES: COC(=O)NCC1CCN(C(=O)OC(C)(C)C)CC1]

To a solution of tert-butyl 4-(aminomethyl)piperidine-1-carboxylate (70 g, 327 mmol) and DIEA (211 g, 1633 mmol) in DCM (1 L) was added methyl carbonochloridate (37 g, 392 mmol) in dropwise. The mixture was stirred at 0° C. for 0.5 h then DCM (500 mL) was added. The mixture was washed with 1 N HCl (300 mL), saturated NaHCO$_3$ solution (300 mL) and water (300 mL×2). The organic layer was dried over Na$_2$SO$_4$, filtered and concentrated to yield light yellow oil of tert-butyl 4-(((methoxycarbonyl)amino) methyl)piperidine-1-carboxylate (85 g, 297 mmol, 91.0% yield): $^1$H NMR (400 MHz, CDCl$_3$) δ ppm 4.08 (br. s, 2H), 3.71-3.60 (m, 3H), 3.04 (br. s, 2H), 2.64 (br. s, 2H), 1.69-1.54 (m, 3H), 1.42 (s, 9H), 1.16-1.01 (m, 2H); ES-LCMS m/z 295.0 [M+Na]$^+$.

Step 2: Methyl (piperidin-4-ylmethyl)carbamate, hydrochloride

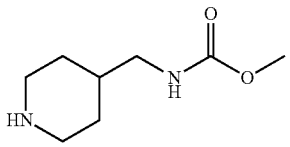

To a solution of tert-butyl 4-(((methoxycarbonyl)amino) methyl)piperidine-1-carboxylate (86 g, 316 mmol) in MeOH (500 mL) was added HCl solution (4.0 M in MeOH, 400 mL, 1.6 mol). The solution was stirred at 20° C. for 0.5 h then concentrated to yield a white solid of methyl (piperidin-4-ylmethyl)carbamate, hydrochloride (65 g, 296 mmol, 94.0% yield): $^1$H NMR (400 MHz, CD$_3$OD) δ ppm 3.69-3.58 (m, 3H), 3.44-3.35 (m, 2H), 3.04 (d, J=6.8 Hz, 2H), 2.95 (t, J=12.5 Hz, 2H), 1.97-1.87 (m, 2H), 1.85-1.72 (m, 1H), 1.47-1.31 (m, 2H).

Intermediate 43: N-((4-((tert-butyldimethylsilyl) oxy)piperidin-4-yl)methyl) acetamide

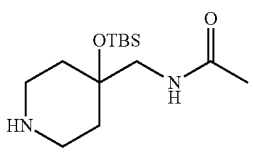

Step 1: tert-Butyl 1-oxa-6-azaspiro[2.5]octane-6-carboxylate

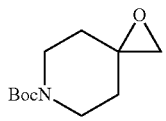 [SMILES: CC(C)(C)OC(=O)N1CCC2(CC1)CO2]

To a solution of trimethylsulfonium iodide (23.19 g, 105 mmol) in DMSO (350 mL) at room temperature was added NaH (4.22 g, 105 mmol) in portions. After stirring at the same temperature for 2 h, tert-butyl 4-oxopiperidine-1-carboxylate (20 g, 100 mmol) was added. Then the reaction mixture was stirred at 20° C. for 12 h. The solvent was removed in vacuo and water (500 mL) was added, then extracted with MTBE (200 mL×3). The organic layer was removed in vacuo to give the crude product which was purified by flash chromatography on 120 g silica gel (from PE/EA=10/1 to PE/EA=8/1) to provide tert-butyl 1-oxa-6-azaspiro[2.5]octane-6-carboxylate (13 g, 54.9 mmol, 54.7% yield) as an off-white solid: $^1$H NMR (400 MHz, CDCl$_3$) δ ppm 3.70 (d, J=12.8 Hz, 2H), 3.41 (ddd, J=3.6, 9.6, 13.2 Hz, 2H), 2.72-2.63 (m, 2H), 1.80-1.75 (m, 2H), 1.50-1.35 (m, 11H); ES-LCMS m/z 157.9 [M−t−Bu+H]$^+$.

Step 2: tert-Butyl 4-(aminomethyl)-4-hydroxypiperidine-1-carboxylate

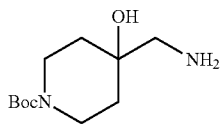 [SMILES: CC(C)(C)OC(=O)N1CCC(O)(CN)CC1]

tert-Butyl 1-oxa-6-azaspiro[2.5]octane-6-carboxylate (11 g, 51.6 mmol) was dissolved in NH$_3$/H$_2$O (120 mL) at room temperature. Then the reaction mixture was stirred at 50° C. for 12 h. Solvent was removed in vacuo to give tert-butyl 4-(aminomethyl)-4-hydroxypiperidine-1-carboxylate (11.5 g, 44.9 mmol, 87.0% yield): $^1$H NMR (400 MHz, CDCl$_3$) δ ppm 3.85-3.73 (m, 2H), 3.18 (br s, 2H), 2.60-2.48 (m, 2H), 1.58-1.43 (m, 13H); ES-LCMS m/z 175.1 [M−t−Bu+H]$^+$.

Step 3: tert-Butyl 4-(aminomethyl)-4-((tert-butyldimethylsilyl)oxy)piperidine-1-carboxylate

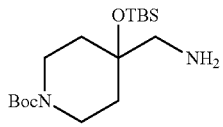 [SMILES: CC(C)(C)OC(=O)N1CCC(CN)(O[Si](C)(C)C(C)(C)C)CC1]

To a solution of tert-butyl 4-(aminomethyl)-4-hydroxypiperidine-1-carboxylate (9 g, 39.1 mmol) and 4H-imidazole (3.99 g, 58.6 mmol) in DCM (200 mL) at room temperature was added TBSCl (7.07 g, 46.9 mmol). Then the reaction mixture was stirred at 15° C. for 12 h. The solvent was removed in vacuo to give the crude product which was purified by flash chromatography on 80 g silica gel (from PE:EA=1:1 to PE:EA=0:1 for 50 minutes) to provide tert-butyl 4-(aminomethyl)-4-((tert-butyldimethylsilyl)oxy)piperidine-1-carboxylate (6 g, 15.67 mmol, 40.1% yield) as an off-white solid: $^1$H NMR (400 MHz, CDCl$_3$) δ ppm 3.59 (brs, 2H), 3.31 (ddd, J=3.4, 9.6, 13.1 Hz, 2H), 2.58 (s, 2H), 1.74-1.62 (m, 2H), 1.42 (dd, J=3.8, 9.2 Hz, 2H), 1.36 (s, 9H), 0.78 (s, 3H), 0.00 (s, 2H); ES-LCMS m/z 289.1 [M−t−Bu+H]$^+$.

Step 4: tert-Butyl 4-(acetamidomethyl)-4-((tert-butyldimethylsilyl)oxy)piperidine-1-carboxylate

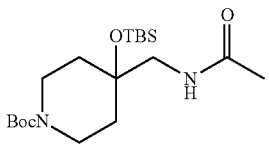

To a solution of tert-butyl 4-(aminomethyl)-4-((tert-butyldimethylsilyl)oxy)piperidine-1-carboxylate (3.1 g, 9.00 mmol) and A-ethyl-A-isopropylpropan-2-amine (3.49 g, 27.0 mmol) in DCM (60 mL) at room temperature was added acetyl chloride (0.902 mL, 10.80 mmol). Then the reaction mixture was stirred at 15° C. for 1 h. Water (60 mL) was added and extracted with DCM (30 mL×2). The combined organic layer was dried over Na$_2$SO$_4$ and concentrated in vacuo to give tert-butyl 4-(acetamidomethyl)-4-((tert-butyldimethylsilyl)oxy)piperidine-1-carboxylate (3.5 g, 8.15 mmol, 91.0% yield) as off-white oil: $^1$H NMR (400 MHz, CDCl$_3$) δ ppm 5.50 (s, 1H), 3.38-3.20 (m, 6H), 1.87 (s, 3H), 1.35-1.31 (m, 9H), 1.10 (d, J=6.1 Hz, 4H), 0.78 (s, 9H), 0.00 (s, 6H); ES-LCMS m/z 287.1 [M−Boc+H]$^+$.

Step 5: N-((4-((tert-Butyldimethylsilyl)oxy)piperidin-4-yl)methyl)acetamide

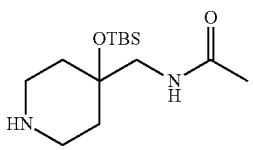 [SMILES: CC(=O)NCC1(O[Si](C)(C)C(C)(C)C)CCNCC1]

To a solution of tert-butyl 4-(acetamidomethyl)-4-((tert-butyldimethylsilyl)oxy)piperidine-1-carboxylate (3.5 g, 9.05 mmol) in DCM (50 mL) at room temperature was added 2,2,2-trifluoroacetic acid (12 mL, 9.05 mmol). Then the reaction mixture was stirred at 15° C. for 2 h. Solvent was removed in vacuo and saturated aqueous NaHCO$_3$ (60 mL) solution was added, extracted with DCM (50 mL×2). The combined organic layers were dried over Na$_2$SO$_4$, filtered and concentrated to give N-((4-(((tert-butyldimethylsilyl)oxy)piperidin-4-yl)methyl)acetamide (2.6 g, 8.17 mmol, 90.0% yield) as an off-white solid: $^1$H NMR (400 MHz, CDCl$_3$) δ ppm 3.54 (qd, J=6.6, 10.5 Hz, 1H), 3.28 (d, J=6.1 Hz, 2H), 3.14 (s, 2H), 3.01-2.92 (m, 1H), 1.92 (s, 3H), 1.89-1.81 (m, 2H), 1.59 (d, J=14.2 Hz, 2H), 0.74 (s, 9H), 0.06 (s, 6H); ES-LCMS m/z 287.1 [M+H]$^+$.

Intermediate 44:
N,N-Dimethyl-2-(piperidin-4-yl)ethanamine oxide, hydrochloride

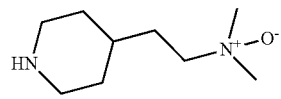

Step 1: tert-Butyl 4-(2-(1,3-dioxoisoindolin-2-yl)ethyl)piperidine-1-carboxylate

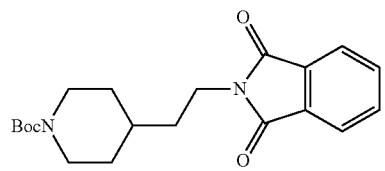 [SMILES: CC(C)(C)OC(=O)N1CCC(CCN2C(=O)c3ccccc3C2=O)CC1]

To a mixture of tert-butyl 4-(2-hydroxyethyl)piperidine-1-carboxylate (2.7 g, 11.77 mmol) and isoindoline-1,3-dione (1.906 g, 12.95 mmol) in THF (30 mL) was added PPh$_3$ (4.01 g, 15.31 mmol) and DIAD (3.43 mL, 17.66 mmol). The mixture was stirred at 15° C. under N$_2$ atmosphere for 10 h then concentrated. The residue was purified by silica gel column chromatography (PE/EtOAc=5/1). All fractions found to contain product by TLC (PE/EtOAc=3/1, R$_f$=0.5) were combined and concentrated to yield a light yellow solid of tert-butyl 4-(2-(1,3-dioxoisoindolin-2-yl)ethyl)piperidine-1-carboxylate (3 g, 7.11 mmol, 60.4% yield): $^1$H NMR (400 MHz, CD$_3$OD) δ ppm 7.91-7.76 (m, 4H), 4.07 (d, J=13.1 Hz, 2H), 3.74 (t, J=7.3 Hz, 2H), 2.74 (br. s, 2H), 1.82 (d, J=12.5 Hz, 2H), 1.63 (q, J=7.0 Hz, 2H), 1.47 (m, 9H), 1.31 (t, J=6.0 Hz, 1H), 1.12 (dq, J=4.0, 12.4 Hz, 2H); ES-LCMS m/z 259.2 [M−Boc+H]$^+$.

Step 2: tert-Butyl 4-(2-aminoethyl)piperidine-1-carboxylate

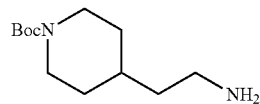

To a solution of tert-butyl 4-(2-(1,3-dioxoisoindolin-2-yl)ethyl)piperidine-1-carboxylate (2 g, 5.58 mmol) in DCM (10 mL) was added hydrazine hydrate (85%, 1.972 g, 33.5 mmol). The mixture was stirred at 15° C. for 1 h then filtrated. The filtrate was concentrated to yield a yellow oil of tert-butyl 4-(2-aminoethyl)piperidine-1-carboxylate (1.4 g, 5.21 mmol, 93.0% yield): $^1$H NMR (400 MHz, CD$_3$OD) δ ppm 4.04 (d, J=12.8 Hz, 2H), 2.83-2.60 (m, 4H), 1.68 (d, J=12.3 Hz, 2H), 1.58-1.51 (m, 1H), 1.49-1.37 (m, 10H), 1.31-1.21 (m, 1H), 1.15-0.99 (m, 2H); ES-LCMS m/z 173.2 [M−t−Bu+H]$^+$.

Step 3: tert-Butyl 4-(2-(dimethylamino)ethyl)piperidine-1-carboxylate

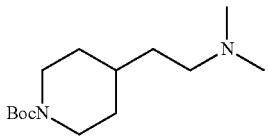

To a solution of tert-butyl 4-(2-aminoethyl)piperidine-1-carboxylate (1.4 g, 6.13 mmol) in MeOH (15 mL) was added formaldehyde (aq., 30%, 5.40 mL, 36.8 mmol) and formic acid (0.235 mL, 6.13 mmol). The mixture was stirred at 15° C. for 11 h under $N_2$ atmosphere then $NaBH_3CN$ (3.08 g, 49.1 mmol) was added and stirred for another 1 h. The solution was concentrated and saturated $NaHCO_3$ solution (15 mL) was added. The aqueous layer was extracted with DCM (150 mL×2) and the combined extracts were washed with brine (15 mL×2), dried over $Na_2SO_4$, filtered and concentrated. The crude material was purified by silica gel column chromatography (DCM/MeOH=5/1). All fractions found to contain product by TLC (DCM/MeOH=10/1, $R_f$=0.4) were combined and concentrated to yield light yellow oil of tert-butyl 4-(2-(dimethylamino)ethyl)piperidine-1-carboxylate (1.3 g, 4.06 mmol, 66.2% yield): $^1H$ NMR (400 MHz, $CD_3OD$) δ ppm 4.08 (d, J=13.6 Hz, 2H), 3.06-2.96 (m, 2H), 2.86-2.69 (m, 8H), 1.73 (d, J=12.5 Hz, 2H), 1.67-1.55 (m, 3H), 1.47 (s, 9H), 1.22-1.06 (m, 2H); ES-LCMS m/z 257.3 $[M+H]^+$.

Step 4: 2-(1-(tert-Butoxycarbonyl)piperidin-4-yl)-N,N-dimethylethanamine oxide

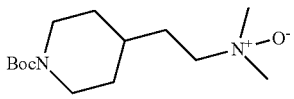

To a mixture of tert-butyl 4-(2-(dimethylamino)ethyl) piperidine-1-carboxylate (1 g, 3.90 mmol) in DCM (15 mL) was added m-CPBA (1.010 g, 5.85 mmol). The mixture was stirred at 15° C. for 1 h. The mixture was concentrated and purified by silica gel column chromatography (DCM/MeOH=5/1). All fractions found to contain product by TLC (DCM/MeOH=10/1, $R_f$=0.3) were combined and concentrated to yield a yellow oil of 2-(1-(tert-butoxycarbonyl) piperidin-4-yl)-N,N-dimethylethanamine oxide (950 mg, 2.96 mmol, 76.0% yield): $^1H$ NMR (400 MHz, $CD_3OD$) δ ppm 4.08 (d, J=13.1 Hz, 2H), 3.40 (dd, J=4.3, 7.8 Hz, 2H), 3.21 (s, 6H), 2.78 (br. s, 2H), 1.88-1.78 (m, 2H), 1.73 (d, J=12.0 Hz, 2H), 1.58-1.46 (m, 10H), 1.18 (dq, J=4.0, 12.2 Hz, 2H); ES-LCMS m/z 273.3 $[M+H]^+$.

Step 5: N,N-dimethyl-2-(piperidin-4-yl)ethanamine oxide, hydrochloride

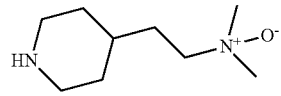

A mixture of 2-(1-(tert-butoxycarbonyl)piperidin-4-yl)-N,N-dimethylethanamine oxide (950 mg, 3.49 mmol) in HCl (4.0 M in isopropylether, 3 mL, 12 mmol) was stirred at 15° C. for 0.5 h. The reaction mixture was concentrated to yield a yellow solid of N,N-dimethyl-2-(piperidin-4-yl) ethanamine oxide, hydrochloride (950 mg, 3.41 mmol, 98.0% yield): $^1H$ NMR (400 MHz, $CD_3OD$) δ ppm 3.80-3.76 (m, 2H), 3.54 (br. s, 6H), 3.44-3.41 (m, 2H), 3.06-3.03 (m, 2H), 2.02-2.00 (m, 2H), 1.94-1.91 (m, 2H), 1.81-1.78 (m, 1H), 1.56-1.53 (m, 2H); ES-LCMS m/z 173.4 $[M+H]^+$.

Intermediate 45: 4-(((tert-Butyldimethylsilyl)oxy)methyl)-6-(3,5-dichlorophenyl)-3-methylpyridin-2-ol

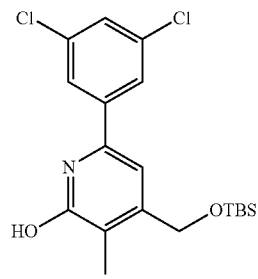

Step 1: 6-(3,5-Dichlorophenyl)-4-(hydroxymethyl)pyridin-2-ol

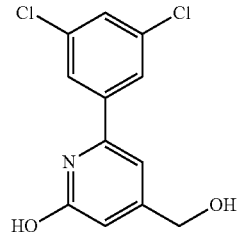 [SMILES: OCc1cc(O)nc(-c2cc(Cl)cc(Cl)c2)c1]

(2-(Benzyloxy)-6-(3,5-dichlorophenyl)pyridin-4-yl) methanol (20 g, 55.5 mmol) was dissolved in TFA (90 mL, 1168 mmol). The mixture was stirred at 50° C. for 4 h. The residue was added MeOH (200 mL) and DIEA (20 mL) and stirred at 25° C. for 2 h. The mixture was concentrated to yield 6-(3,5-dichlorophenyl)-4-(hydroxymethyl)pyridin-2-ol (15 g, 52.8 mmol, 95.0% yield) as a yellow solid: $^1H$ NMR (400 MHz, $CDCl_3$) δ ppm 7.40-7.35 (m, 3H), 7.29-7.28 (m, 1H), 7.19-7.08 (m, 1H), 4.69 (s, 2H); ES-LCMS m/z 270.0, 272.0 $[M+H]^+$.

Step 2: 4-(((tert-Butyldimethylsilyl)oxy)methyl)-6-(3,5-dichlorophenyl)pyridin-2-ol

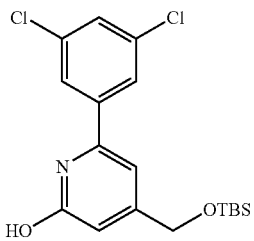 [SMILES: CC(C)(C)[Si](C)(C)OCc1cc(O)nc(-c2cc(Cl)cc(Cl)c2)c1]

A mixture of TBSCl (26.5 g, 176 mmol), 6-(3,5-dichlorophenyl)-4-(hydroxymethyl)pyridin-2-ol (10 g, 35.2 mmol) and imidazole (23.94 g, 352 mmol) in CHCl₃ (150 mL) was stirred at 80° C. for 10 h. The mixture was added H₂O (150 mL). Then the mixture was extracted with DCM (100 mL×3). The combined organic layer was washed with brine (150 mL), dried over Na₂SO₄, filtered and concentrated. The crude material was purified by flash chromatography (PE/EtOAc=10/1 to 2/1, TLC: PE/EtOAc=3/1, $R_f$=0.6) to yield 4-(((tert-butyldimethylsilyl)oxy)methyl)-6-(3,5-dichlorophenyl)pyridin-2-ol (15 g, 32.8 mmol, 93.0% yield): ¹H NMR (400 MHz, CDCl₃) δ ppm 7.62 (d, J=2.0 Hz, 2H), 7.43 (t, J=1.9 Hz, 1H), 6.63 (q, 7=1.1 Hz, 1H), 6.44 (d, J=1.3 Hz, 1H), 4.64 (d, J=1.1 Hz, 2H), 0.99-0.94 (m, 9H), 0.16-0.10 (m, 6H); ES-LCMS m/z 384.1, 386.1 [M+H]⁺.

Step 3: 3-Bromo-4-(((tert-butyldimethylsilyl)oxy)methyl)-6-(3,5-dichlorophenyl)pyridin-2-ol

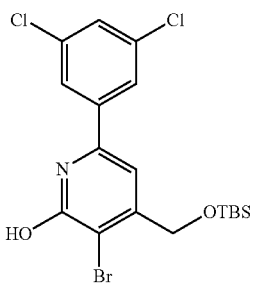 [SMILES: CC(C)(C)[Si](C)(C)OCc1cc(-c2cc(Cl)cc(Cl)c2)nc(O)c1Br]

To a mixture of 4-(((tert-butyldimethylsilyl)oxy)methyl)-6-(3,5-dichlorophenyl)pyridin-2-(2.5 g, 5.46 mmol) and NH₄OAc (0.421 g, 5.46 mmol) in AcOH (50 mL) was added a solution of Br₂ (0.225 mL, 4.37 mmol) in AcOH (20 mL) dropwise. The mixture was stirred at 20° C. for 5 min. To the mixture was added H₂O (200 mL), and a white precipitate formed. After filtration, the filter cake was washed with water (50 mL×3). The filter cake was dried in vacuo to yield 3-bromo-4-(((tert-butyldimethylsilyl)oxy)methyl)-6-(3,5-dichlorophenyl)pyridin-2-ol (2.5 g, 4.50 mmol, 82.0% yield) as a white solid: ¹H NMR (400 MHz, CDCl₃) δ ppm 7.74 (d, J=1.8 Hz, 2H), 7.47 (t, J=1.8 Hz, 1H), 6.91 (s, 1H), 4.69 (s, 2H), 1.01-0.98 (m, 9H), 0.18-0.16 (m, 6H); ES-LCMS m/z 462.0, 464.0, 466.0 [M+H]⁺.

Step 4: 4-(((tert-Butyldimethylsilyl)oxy)methyl)-6-(3,5-dichlorophenyl)-3-methylpyridin-2-ol

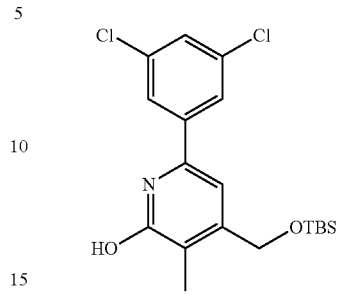

To a mixture of 3-bromo-4-(((tert-butyldimethylsilyl)oxy)methyl)-6-(3,5-dichlorophenyl)pyridin-2-ol (1.7 g, 3.06 mmol), 2,4,6-trimethyl-1,3,5,2,4,6-trioxatriborinane (15.37 g, 122 mmol) and K₂CO₃ (1.269 g, 9.18 mmol) in 1,4-dioxane (45 mL) and water (4.5 mL) was added PdCl₂(dppf)-CH₂Cl₂ adduct (0.750 g, 0.918 mmol) under N₂ atmosphere. Then the reaction mixture was stirred at 110° C. for 2 h under N₂ atmosphere. The mixture was filtered and the filtrate was concentrated. The residue was purified by flash chromatography (from PE/EtOAc=5/1 to 2/1, TLC: PE/EtOAc=3/1, $R_f$=0.6) to yield 4-(((tert-butyldimethylsilyl)oxy)methyl)-6-(3,5-dichlorophenyl)-3-methylpyridin-2-ol (540 mg, 1.220 mmol, 39.9% yield) as an off white solid: ¹H NMR (400 MHz, CDCl₃) δ ppm 7.64 (d, J=1.5 Hz, 2H), 7.27-7.21 (m, 1H), 6.72 (s, 1H), 4.51 (s, 2H), 1.98 (s, 3H), 0.83 (s, 9H), 0.00 (s, 6H); ES-LCMS m/z 398.1, 400.1 [M+H]⁺.

Intermediate 46: Methyl 2-(1-((2-(3,5-dichlorophenyl)-6-((2-)methylsulfinyl)pyrimidin-5-yl)oxy)pyridin-4-yl)methyl)piperidin-4-yl)acetate

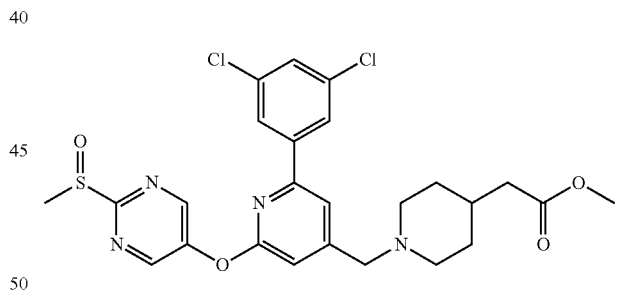

Step 1: 2-(Methylthio)-5-(4,4,5,5-tetramethyl-1,3,2-dioxaborolan-2-yl)pyrimidine

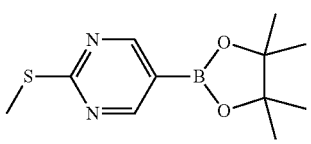

To a solution of 5-bromo-2-(methylthio)pyrimidine (3 g, 14.63 mmol) and 4,4,4',4',5,5,5',5'-octamethyl-2,2'-bi(1,3,2-dioxaborolane) (4.46 g, 17.55 mmol) in 1,4-dioxane (200 mL) was added potassium acetate (2.154 g, 21.94 mmol) and PdCl₂(dppf) (0.535 g, 0.731 mmol). Then the reaction mixture was stirred at 80° C. for 12 h under N₂ atmosphere. The solvent was concentrated to give the crude product which was purified on g silica gel (from pure PE to PE/EtOAc=3/1, R_f=0.40 (PE/EtOAc=3/1)) to yield a pale yellow solid of 2-(methylthio)-5-(4,4,5,5-tetramethyl-1,3,2-dioxaborolan-2-yl)pyrimidine (2.1 g, 7.50 mmol, 51.2% yield): ¹H NMR (400 MHz, CDCl₃) δ ppm 8.75 (s, 2H), 2.56 (s, 3H), 1.31 (s, 12H); ES-LCMS m/z 171.2 [M−pin+H]⁺.

Step 2: 2-(Methylthio)pyrimidin-5-ol

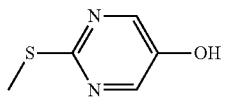

To a solution of 2-(methylthio)-5-(4,4,5,5-tetramethyl-1,3,2-dioxaborolan-2-yl)pyrimidine (2.05 g, 7.32 mmol) in THF (20 mL) and water (20.00 mL) was added sodium perborate tetrahydrate (3.38 g, 21.95 mmol) at 10° C. Then the mixture was stirred for 12 h. Saturated NH₄Cl (50 mL) solution was added to quench the reaction and extracted with DCM (30 mL×10). The combined organic layers were dried over Na₂SO₄ and concentrated to yield a pale yellow solid of 2-(methylthio)pyrimidin-5-ol (1.1 g, 6.96 mmol, 95.0% yield): ¹H NMR (400 MHz, CDCl₃) δ ppm 8.16-8.12 (m, 2H), 2.49 (s, 3H); ES-LCMS m/z 143.2 [M+H]⁺.

Step 3: Methyl 2-chloro-6-((2-(methylthio)pyrimidin-5-yl)oxy)isonicotinate

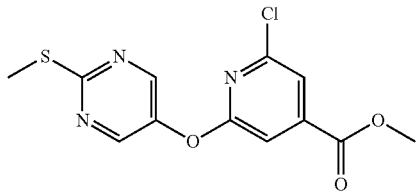

To a solution of 2-(methylthio)pyrimidin-5-ol (1.1 g, 6.96 mmol) and methyl 2,6-dichloroisonicotinate (2.295 g, 11.14 mmol) in DMF (20 mL) was added K₂CO₃ (2.89 g, 20.89 mmol). Then the reaction mixture was heated to 80° C. for 2 h. The solid was filtered off and solvent was concentrated to give the crude product which was purified by flash chromatography (from pure PE to PE/EtOAc=3/1, TLC: R_f=0.50) to yield a pale yellow solid of methyl 2-chloro-6-((2-(methylthio)pyrimidin-5-yl)oxy)isonicotinate (1.2 g, 3.46 mmol, 49.8% yield): ¹H NMR (400 MHz, CDCl₃) δ ppm 8.46 (s, 2H), 7.60 (s, 1H), 7.45 (s, 1H), 3.95 (s, 3H), 2.57 (s, 3H); ES-LCMS m/z 312.1, 314.2 [M+H]⁺. Step 4: Methyl 2-(3,5-dichlorophenyl)-6-((2-(methylthio)pyrimidin-5-yl)oxy)isonicotinate

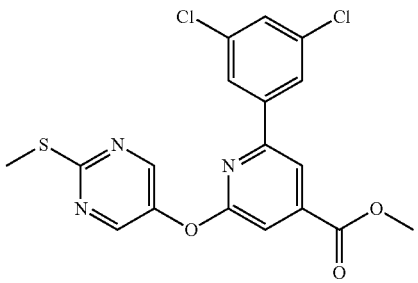

To a solution of methyl 2-chloro-6-((2-(methylthio)pyrimidin-5-yl)oxy)isonicotinate (1.2 g, 3.46 mmol) and (3,5-dichlorophenyl)boronic acid (1.058 g, 5.54 mmol) in DMF (12 mL) was added K₂CO₃ (0.958 g, 6.93 mmol) and PdCl₂(dppf) (0.127 g, 0.173 mmol) under N₂ atmosphere. Then the reaction mixture was stirred at 80° C. for 2 h. After filtration, the filtrate was concentrated to give the crude product which was purified by flash chromatography on 40 g silica gel (from pure PE to PE/EtOAc=3/1, R_f=0.55 (PE/EtOAc=3/1)) to yield a pale yellow solid of methyl 2-(3,5-dichlorophenyl)-6-((2-(methylthio)pyrimidin-5-yl)oxy)isonicotinate (1.2 g, 2.56 mmol, 73.8% yield): ¹H NMR (400 MHz, CDCl₃) δ ppm 8.59-8.49 (m, 2H), 8.00 (d, J=1.1 Hz, 1H), 7.71 (d, J=2.0 Hz, 2H), 7.54 (d, J=0.9 Hz, 1H), 7.39-7.34 (m, 1H), 4.01 (s, 3H), 2.63-2.59 (m, 3H); ES-LCMS m/z 422.1, 424.1 [M+H]⁺.

Step 5: (2-(3,5-Dichlorophenyl)-6-((2-(methylthio)pyrimidin-5-yl)oxy)pyridin-4-yl)methanol

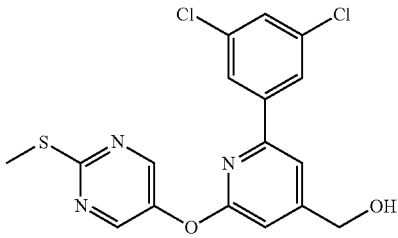 [SMILES: CSc1ncc(Oc2cc(CO)cc(-c3cc(Cl)cc(Cl)c3)n2)cn1]

To a solution of methyl 2-(3,5-dichlorophenyl)-6-((2-(methylthio)pyrimidin-5-yl)oxy)isonicotinate (6 g, 12.79 mmol) in THF (100 mL) was added LAH (0.388 g, 10.23 mmol) in portions at −40° C. Then the reaction mixture was stirred at −40° C. for 30 min. Aqueous NaOH solution (1 mL, 10%) and H₂O (1 mL) was added to quench the reaction. The solid was filtered off and solvent was removed. The crude residue was added petroleum ether (500 mL) and EtOAc (100 mL), the mixture was stirred at 40° C. for 1 h. The mixture was filtered, the filter cake was washed with petroleum ether (100 mL×2) to give (2-(3,5-dichlorophenyl)-6-((2-(methylthio)pyrimidin-5-yl)oxy)pyridin-4-yl)methanol (4.5 g, 8.27 mmol, 64.7% yield) as a brown solid: ¹H NMR (400 MHz, CDCl₃) δ ppm 8.49-8.46 (m, 2H), 7.63 (s, 2H), 7.40 (s, 1H), 7.19 (s, 1H), 6.94 (s, 1H), 4.78 (d, J=5.3 Hz, 2H), 2.55 (s, 3H); ES-LCMS m/z 394.0, 396.1 [M+H]⁺.

Step 6: (2-(3,5-Dichlorophenyl)-6-((2-(methylthio)pyrimidin-5-yl)oxy)pyridin-4-yl)methyl methanesulfonate

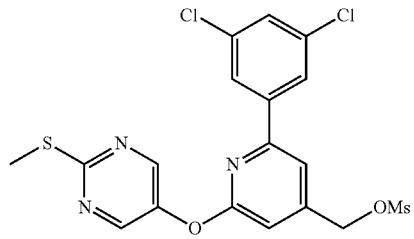 [SMILES: CSc1ncc(Oc2cc(COS(C)(=O)=O)cc(-c3cc(Cl)cc(Cl)c3)n2)cn1]

To a solution of (2-(3,5-dichlorophenyl)-6-((2-(methylthio)pyrimidin-5-yl)oxy)pyridin-4-yl)methanol (7 g, 12.87 mmol) and DIEA (4.05 mL, 23.21 mmol) in DCM (150 mL) was added MsCl (1.304 mL, 16.73 mmol) at 0° C. Then the reaction mixture was stirred at 0° C. for 0.5 h. Water (100 mL) was added and extracted with DCM (200 mL×2). The combined organic layers were dried over Na$_2$SO$_4$ and concentrated to yield a yellow solid of (2-(3,5-dichlorophenyl)-6-((2-(methylthio)pyrimidin-5-yl)oxy)pyridin-4-yl)methyl methanesulfonate (7.5 g, 11.11 mmol, 86.0% yield): $^1$H NMR (400 MHz, CDCl$_3$) δ ppm 8.55-8.51 (m, 2H), 7.66 (d, J=1.8 Hz, 2H), 7.44 (s, 1H), 7.37 (d, J=2.0 Hz, 1H), 7.02 (s, 1H), 5.31-5.27 (m, 2H), 3.13 (s, 3H), 2.61 (s, 3H); ES-LCMS m/z 472.0, 474.0 [M+H]$^+$.

Step 7: Methyl 2-(1-((2-(3,5-dichlorophenyl)-6-((2-(methylthio)pyrimidin-5-yl)oxy)pyridin-4-yl)methyl)piperidin-4-yl)acetate

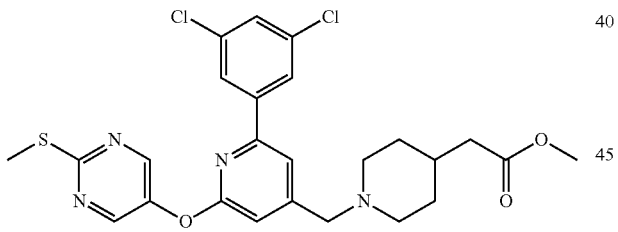

To a mixture of (2-(3,5-dichlorophenyl)-6-((2-(methylthio)pyrimidin-5-yl)oxy)pyridin-4-yl)methylmethanesulfonate (7.5 g, 11 mmol) and DIEA (9.71 mL, 55.6 mmol) in DMF (150 mL) was added methyl 2-(piperidin-4-yl)acetate, hydrochloride (5.4 g, 25.09 mmol). The reaction mixture was stirred at 30° C. for 12 h. The mixture was concentrated to yield the crude product. The crude material was purified by flash chromatography (from pure DCM to DCM/MeOH=10/1, TLC: DCM/MeOH=10/1, R$_f$=0.6) to yield methyl 2-(1-((2-(3,5-dichlorophenyl)-6-((2-(methylthio)pyrimidin-5-yl)oxy)pyridin-4-yl)methyl)piperidin-4-yl)acetate (7.2 g, 9.45 mmol, 85.0% yield) as a yellow solid: $^1$H NMR (400 MHz, CDCl$_3$) δ ppm 8.55 (s, 2H), 7.74 (s, 2H), 7.35 (s, 1H), 7.27 (s, 1H), 7.22 (s, 1H), 3.99 (s, 2H), 3.67 (s, 3H), 3.29 (s, 2H), 3.14-3.05 (m, 2H), 2.62 (s, 3H), 2.33 (d, J=6.2 Hz, 2H), 2.05-1.95 (m, 2H), 1.87 (s, 3H); ES-LCMS m/z 533.2, 535.2 [M+H]$^+$.

Step 8: Methyl 2-(1-((2-(3,5-dichlorophenyl)-6-((2-(methylsulfinyl)pyrimidin-5-yl)oxy)pyridin-4-yl)methyl)piperidin-4-yl)acetate

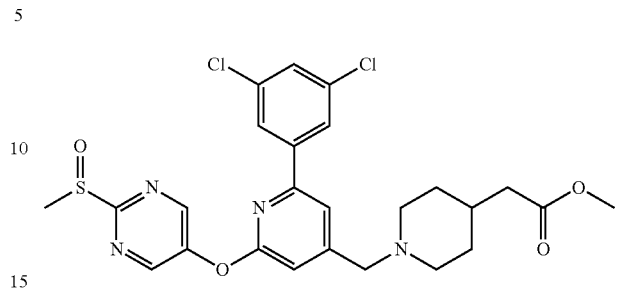

To a solution of methyl 2-(1-((2-(3,5-dichlorophenyl)-6-((2-(methylthio)pyrimidin-5-yl)oxy)pyridin-4-yl)methyl)piperidin-4-yl)acetate (7.2 g, 9.45 mmol) in MeOH (100 mL) was added Oxone (4.65 g, 7.56 mmol). Then the reaction mixture was stirred at 20° C. for 12 h. The solid was filtered off and aqueous Na$_2$SO$_3$ (80 mL) was added and extracted with DCM (200 mL×2). The combined organic layers were dried over Na$_2$SO$_4$ and concentrated to give the residue. The crude material was purified by flash chromatography (from pure DCM to DCM/MeOH=10/1, TLC: DCM/MeOH=10/1, R$_f$=0.3) to yield methyl 2-(1-((2-(3,5-dichlorophenyl)-6-((2-(methylsulfinyl)pyrimidin-5-yl)oxy)pyridin-4-yl)methyl)piperidin-4-yl)acetate (4.5 g, 6.55 mmol, 69.3% yield) as a brown solid: $^1$H NMR (400 MHz, CDCl$_3$) δ ppm 8.88 (s, 2H), 7.65 (d, J=1.8 Hz, 2H), 7.51 (s, 1H), 7.35 (t, J=1.9 Hz, 1H), 7.07 (s, 1H), 3.67 (s, 3H), 3.57 (s, 2H), 2.99 (s, 3H), 2.89-2.85 (m, 2H), 2.27 (d, J=1.1 Hz, 2H), 2.14-2.08 (m, 2H), 1.84 (dt, J=3.7, 7.5 Hz, 1H), 1.74 (d, J=12.1 Hz, 2H), 1.42-1.35 (m, 2H); ES-LCMS m/z 549.2, 551.2 [M+H]$^+$.

Intermediate 47: 14-Diazabicyclo[3.2.1]octane

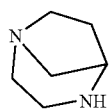

Step 1: Ethyl 2-(3-oxopiperazin-2-yl)acetate

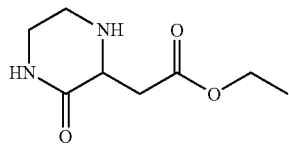

A mixture of ethane-1,2-diamine (30 g, 499 mmol) and diethyl maleate (86 g, 499 mmol) in i-PrOH (1200 mL) was stirred at 60° C. for 16 h. This mixture was concentrated to yield ethyl 2-(3-oxopiperazin-2-yl)acetate (100 g, 483 mmol, 97.0% yield) as a white solid: $^1$H NMR (400 MHz, CD$_3$OD) δ ppm 4.22-4.08 (m, 2H), 3.74-3.57 (m, 1H), 3.44-3.21 (m, 2H), 3.12-2.79 (m, 2H), 2.78-2.55 (m, 2H), 1.25 (tt, J=4.3, 7.2 Hz, 3H).

Step 2: Ethyl 2-(1-benzyl-3-oxopiperazin-2-yl)acetate

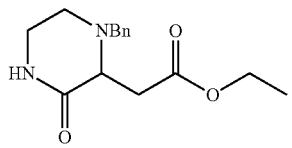 [SMILES: CCOC(=O)CC1C(=O)NCCN1Cc1ccccc1]

To a suspension of ethyl 2-(3-oxopiperazin-2-yl)acetate (84 g, 406 mmol) in EtOH (500 mL) was added (bromomethyl)benzene (76 g, 447 mmol). The reaction mixture was stirred at 60° C. for 12 h. This reaction mixture was concentrated to yield the residue which was dissolved in a mixture of water (200 mL) and EtOAc (200 mL), adjusted with 2 M HCl to pH=1. The mixture was extracted with EtOAc (200 mL×2), the aqueous layer was adjusted to pH=11 with 2 N NaOH solution, extracted with EtOAc (200 mL×2), dried over Na$_2$SO$_4$, concentrated to yield the residue. To the residue was added PE (200 mL). After filtration, the filter cake was collected to yield ethyl 2-(1-benzyl-3-oxopiperazin-2-yl)acetate (65 g, 115 mmol, 28.4% yield) as a white solid: $^1$H NMR (400 MHz, DMSO) δ ppm 7.85 (s, 1H), 7.33-7.16 (m, 5H), 4.10-3.94 (m, 2H), 3.85 (d, J=13.5 Hz, 1H), 3.36 (s, 1H), 3.23 (t, J=5.3 Hz, 1H), 3.15-2.98 (m, 2H), 2.93-2.84 (m, 1H), 2.80-2.69 (m, 2H), 2.32 (ddd, J=4.0, 8.4, 12.3 Hz, 1H), 1.13 (t, J=7.2 Hz, 3H); ES-LCMS m/z 277.3 [M+H]$^+$.

Step 3: 2-(1-Benzylpiperazin-2-yl)ethanol

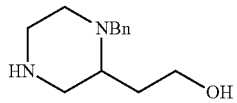

To a suspension of ethyl 2-(1-benzyl-3-oxopiperazin-2-yl)acetate (20 g, 35.5 mmol) in THF (400 mL) at 0° C. was added LAH (8.08 g, 213 mmol) portion wise. The reaction mixture was stirred at 20° C. for 16 h under N$_2$ atmosphere. This reaction mixture was quenched with H$_2$O (8.08 mL), followed by 10% NaOH solution (8.08 mL) at 0° C. Then the mixture was filtered and the filtrate was concentrated to yield 2-(1-benzylpiperazin-2-yl)ethanol (10 g, 34.0 mmol, 96.0% yield) as light yellow oil: $^1$H NMR (400 MHz, CD$_3$OD) δ ppm 7.48-7.12 (m, 5H), 4.07 (d, J=13.2 Hz, 1H), 3.73-3.57 (m, 2H), 3.22 (d, J=13.2 Hz, 1H), 3.01-2.92 (m, 1H), 2.82-2.73 (m, 1H), 2.72-2.59 (m, 3H), 2.49-2.41 (m, 1H), 2.16-2.08 (m, 1H), 2.01 (dtd, J=3.2, 7.2, 14.3 Hz, 1H), 1.72 (qd, J=7.1, 13.8 Hz, 1H).

Step 4: 4-Benzyl-1,4-diazabicyclo[3.2.1]octane

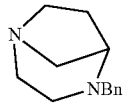

To a suspension of PPh$_3$ (17.86 g, 68.1 mmol) in THF (600 mL) at 0° C. was added DEAD (10.78 mL, 68.1 mmol). The reaction mixture was stirred at 20° C. for 0.5 h under N$_2$ atmosphere. The solution of 2-(1-benzylpiperazin-2-yl)ethanol (10 g, 34.0 mmol) in THF (200 mL) was added to the reaction mixture and the mixture was stirred at 20° C. for 11.5 h. This reaction mixture was concentrated. The residue was dissolved in EtOAc (100 mL) and water (100 mL), adjusted to pH=1 with 2 N HCl solution. The aqueous layer was separated, washed with EtOAc (100 mL×2), and then adjusted to pH=11 with 2 N NaOH solution. The mixture was extracted with EtOAc (100 mL×2). The combined organic layers were washed with brine (100 mL), dried over Na$_2$SO$_4$, filtered and concentrated. The crude material was purified by flash chromatography (from DCM/MeOH=100/1 to 10/1, TLC: DCM/MeOH=10/1, R$_f$=0.3) to yield 4-benzyl-1,4-diazabicyclo[3.2.1]octane (6 g, 26.7 mmol, 78.0% yield) as a yellow solid: $^1$H NMR (400 MHz, CD$_3$OD) δ ppm 7.60-7.02 (m, 5H), 3.49-3.39 (m, 2H), 3.25-3.19 (m, 1H), 3.01-2.80 (m, 4H), 2.63 (dd, J=4.4, 13.5 Hz, 1H), 2.52 (dd, J=4.5, 12.2 Hz, 2H), 2.45-2.35 (m, 1H), 2.14 (dddd, J=2.3, 5.6, 8.2, 13.7 Hz, 1H), 1.56 (tdd, J=5.3, 10.7, 13.6 Hz, 1H); ES-LCMS m/z 203.2 [M+H]$^+$.

Step 5: 1,4-Diazabicyclo[3.2.1]octane

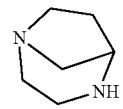

To a solution of 4-benzyl-1,4-diazabicyclo[3.2.1]octane (12 g, 53.4 mmol) in MeOH (150 mL) was added Pd/C (10 wt %, 11.36 g, 10.68 mmol) under N$_2$ atmosphere. The mixture was stirred under H$_2$ atmosphere (50 psi) at 50° C. for 36 h. Then the mixture was filtered and the filtrate was concentrated to yield 1,4-diazabicyclo[3.2.1]octane (4.7 g, 35.6 mmol, 66.7% yield) as light yellow oil: $^1$H NMR (400 MHz, CD$_3$OD) δ ppm 3.60 (d, J=2.9 Hz, 1H), 3.19-3.02 (m, 5H), 2.79 (dt, J=4.3, 12.1 Hz, 2H), 2.69 (d, J=11.5 Hz, 1H), 2.12-2.02 (m, 2H).

Intermediate 48: Methyl 2-(3,5-dichlorophenyl)-6-((2-(methyl thio)pyrimidin-5-yl)amino)isonicotinate

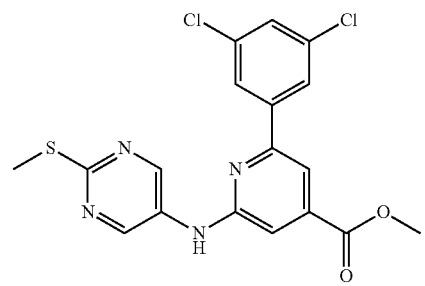

Step 1: Methyl 2-((tert-butoxycarbonyl)amino)-6-chloroisonicotinate

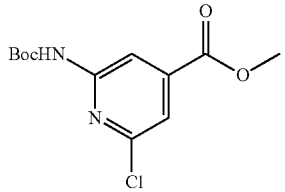 [SMILES: COC(=O)c1cc(Cl)nc(NC(=O)OC(C)(C)C)c1]

To a mixture of methyl 2,6-dichloroisonicotinate (1000 mg, 4.85 mmol), tert-butyl carbamate (910 mg, 7.77 mmol), Xantphos (281 mg, 0.485 mmol), $K_3PO_4$ (3085 mg, 14.56 mmol) in THF (40 mL) was added $Pd_2(dba)_3$ (444 mg, 0.485 mmol). The reaction mixture was stirred at 80° C. for 12 h under $N_2$ atmosphere. The mixture was filtered and concentrated. The crude material was purified by flash chromatography (from pure PE to PE/EtOAc=3/1, TLC: PE/EtOAc=3/1, $R_f$=0.7) to yield methyl 2-((tert-butoxycarbonyl)amino)-6-chloroisonicotinate (1.1 g, 3.45 mmol, 71.1% yield) as a pale yellow solid: $^1$H NMR (400 MHz, $CD_3OD$) δ ppm 8.37 (d, J=1.1 Hz, 1H), 7.46 (d, J=1.1 Hz, 1H), 3.93 (s, 3H), 1.52 (s, 9H); ES-LCMS m/z 231.1, 233.1 [M−t−Bu+H]$^+$.

Step 2: Methyl 2-((tert-butoxycarbonyl)amino)-6-(3,5-dichlorophenyl)isonicotinate

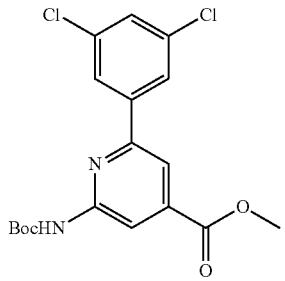 [SMILES: COC(=O)c1cc(NC(=O)OC(C)(C)C)nc(-c2cc(Cl)cc(Cl)c2)c1]

To a solution of methyl 2-((tert-butoxycarbonyl)amino)-6-chloroisonicotinate (1100 mg, 3.45 mmol) and (3,5-dichlorophenyl)boronic acid (1977 mg, 10.36 mmol) in DMF (30 mL) was added $K_2CO_3$ (1432 mg, 10.36 mmol) and $PdCl_2(dppf)$ (253 mg, 0.345 mmol) under $N_2$ atmosphere. Then the reaction mixture was stirred at 85° C. for 3 h. The mixture was filtered and concentrated. The crude material was purified by flash chromatography (from pure PE to PE/EtOAc=5/1, TLC: PE/EtOAc=5/1, $R_f$=0.6) to yield methyl 2-((tert-butoxycarbonyl)amino)-6-(3,5-dichlorophenyl)isonicotinate (1.1 g, 2.215 mmol, 64.2% yield) as a pale yellow solid: $^1$H NMR (400 MHz, $CDCl_3$) δ ppm 8.47 (d, J=0.9 Hz, 1H), 7.93 (d, J=1.1 Hz, 1H), 7.90 (d, J=2.0 Hz, 2H), 7.40 (t, J=1.9 Hz, 1H), 3.98 (s, 3H), 0.00 (s, 9H); ES-LCMS m/z 341.0, 343.0 [M−t−Bu+H]$^+$.

Step 3: Methyl 2-amino-6-(3,5-dichlorophenyl)isonicotinate

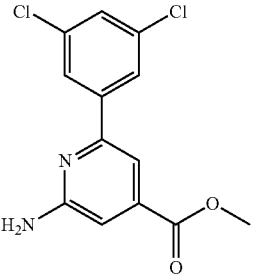 [SMILES: COC(=O)c1cc(N)nc(-c2cc(Cl)cc(Cl)c2)c1]

Methyl 2-((tert-butoxycarbonyl)amino)-6-(3,5-dichlorophenyl)isonicotinate (1.0800 g, 2.175 mmol) was dissolved in TFA (5 mL, 64.9 mmol) and DCM (15 mL). The mixture was stirred at 20° C. for 0.5 h. The reaction mixture was concentrated. The residue was partitioned between DCM (100 mL) and saturated aqueous $Na_2CO_3$ solution (80 mL). The mixture was extracted with DCM (50 mL×3). The organic layer was washed with brine (80 mL), dried over $Na_2SO_4$, filtered and concentrated. The crude material was purified by flash chromatography (PE/EtOAc=5/1 to 2/1, TLC: PE/EtOAc=5/1, $R_f$=0.5) to yield methyl 2-amino-6-(3,5-dichlorophenyl)isonicotinate (750 mg, 2.019 mmol, 93.0% yield) as a pale yellow solid: $^1$H NMR (400 MHz, $CD_3OD$) δ ppm 7.91 (d, J=1.8 Hz, 2H), 7.47 (d, J=1.1 Hz, 1H), 7.44 (t, J=1.9 Hz, 1H), 7.08 (d, J=1.1 Hz, 1H), 3.92 (s, 3H); ES-LCMS m/z 297.0, 299.0 [M+H]$^+$.

Step 4: Methyl 2-(3,5-dichlorophenyl)-6-((2-(methylthio)pyrimidin-5-yl)amino)isonicotinate

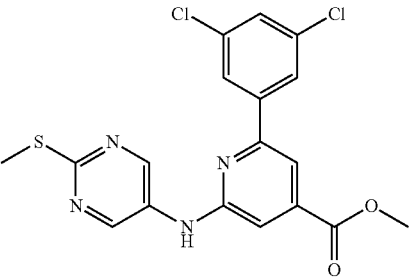

To a mixture of methyl 2-amino-6-(3,5-dichlorophenyl)isonicotinate (650 mg, 1.750 mmol), 5-bromo-2-(methylthio)pyrimidine (538 mg, 2.63 mmol), Xantphos (101 mg, 0.175 mmol), $K_3PO_4$ (1112 mg, 5.25 mmol) in THF (30 mL) was added $Pd_2(dba)_3$ (160 mg, 0.175 mmol). The reaction mixture was stirred at 80° C. for 12 h under $N_2$ atmosphere. The mixture was filtered and concentrated. The crude material was purified by flash chromatography (from pure DCM to DCM/MeOH=20/1, TLC: DCM/MeOH=20/1, $R_f$=0.65) to yield methyl 2-(3,5-dichlorophenyl)-6-((2-(methylthio)pyrimidin-5-yl)amino)isonicotinate (750 mg, 1.424 mmol, 81.0% yield) as a pale yellow solid: $^1$H NMR (400 MHz, $CD_3OD$) δ ppm 7.95 (d, J=1.8 Hz, 2H), 7.75 (s, 1H), 7.52-7.50 (m, 1H), 7.38 (br s, 1H), 7.37-7.35 (m, 1H), 7.32-7.30 (m, 1H), 3.97 (s, 3H), 2.66-2.53 (m, 3H); ES-LCMS m/z 421.0, 423.0 [M+H]$^+$.

Intermediate 49: Ethyl 2-(1-((2-(3,5-dichlorophenyl)-6-hydroxypyridin-4-yl)methyl)piperidin-4-yl)acetate

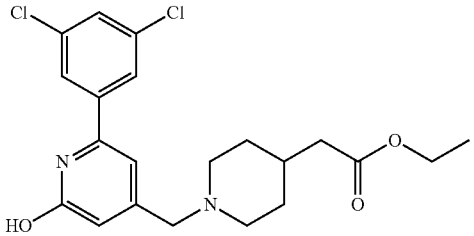 [SMILES: CCOC(=O)CC1CCN(Cc2cc(O)nc(-c3cc(Cl)cc(Cl)c3)c2)CC1]

Step 1: Ethyl 2-(1-((2-(benzyloxy)-6-(3,5-dichlorophenyl)pyridin-4-yl)methyl)piperidin-4-yl)acetate

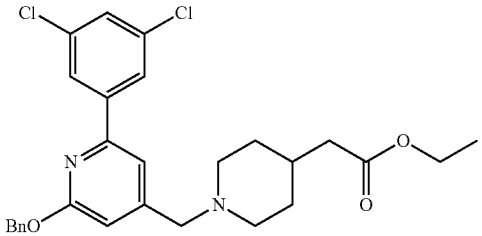 [SMILES: CCOC(=O)CC1CCN(Cc2cc(OCc3ccccc3)nc(-c3cc(Cl)cc(Cl)c3)c2)CC1]

To a solution of (2-(benzyloxy)-6-(3,5-dichlorophenyl)pyridin-4-yl)methyl methanesulfonate (39.6 g, 81 mmol) and ethyl 2-(piperidin-4-yl)acetate, hydrochloride (28.1 g, 122 mmol) in DMF (450 mL) was added K$_2$CO$_3$ (33.7 g, 244 mmol). The mixture was stirred at 60° C. for 12 h. The solid was filtered off and solvent was removed in vacuo to give the crude product which was purified by flash chromatography (from pure DCM to DCM/MeOH=10/1, TLC: DCM/MeOH=10/1, R$_f$=0.65) to afford ethyl 2-(1-((2-(benzyloxy)-6-(3,5-dichlorophenyl)pyridin-4-yl)methyl)piperidin-4-yl)acetate (42 g, 77 mmol, 95.0% yield) as a pale yellow solid: $^1$H NMR (400 MHz, CDCl$_3$) δ ppm 7.96 (s, 3H), 7.48 (br d, J=7.5 Hz, 2H), 7.43-7.28 (m, 4H), 6.92 (br s, 1H), 5.46 (s, 2H), 4.17-4.10 (m, 2H), 3.65 (s, 1H), 3.51-3.24 (m, 2H), 3.09-3.05 (m, 1H), 2.62 (br s, 2H), 2.30 (br s, 2H), 1.97-1.72 (m, 5H), 1.24 (d, J=7.9 Hz, 3H); ES-LCMS m/z 513.2, 515.2 [M+H]$^+$.

Step 2: Ethyl 2-(1-((2-(3,5-dichlorophenyl)-6-hydroxypyridin-4-yl)methyl)piperidin-4-yl)acetate

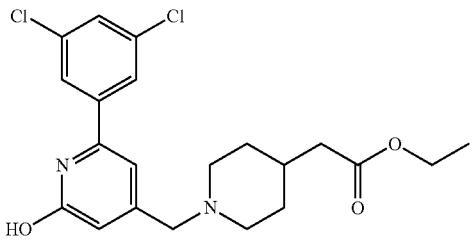 [SMILES: CCOC(=O)CC1CCN(Cc2cc(O)nc(-c3cc(Cl)cc(Cl)c3)c2)CC1]

To a solution of ethyl 2-(1-((2-(benzyloxy)-6-(3,5-dichlorophenyl)pyridin-4-yl)methyl)piperidin-4-yl)acetate (42 g, 77 mmol) in DCM (150 mL) was added TFA (150 mL, 1947 mmol). Then the reaction mixture was stirred at 25° C. for 12 h. The solvent was removed in vacuo and saturated aqueous NaHCO$_3$ solution (500 mL) was added. The mixture was extracted with DCM (200 mL×3). The combined organic layers were dried over Na$_2$SO$_4$, filtered and concentrated in vacuo to yield ethyl 2-(1-((2-(3,5-dichlorophenyl)-6-hydroxypyridin-4-yl)methyl)piperidin-4-yl)acetate (34 g, 68.3 mmol, 88.0% yield) as a pale yellow solid: $^1$H NMR (400 MHz, CDCl$_3$) δ ppm 7.61 (s, 2H), 7.42 (s, 1H), 6.90 (s, 1H), 6.54 (s, 1H), 4.14-4.08 (m, 2H), 4.02 (s, 2H), 3.68-3.55 (m, 2H), 2.69 (s, 2H), 2.30 (d, J=6.6 Hz, 2H), 1.95 (d, J=14.1 Hz, 3H), 1.80-1.69 (m, 2H), 1.25-1.19 (m, 3H); ES-LCMS m/z 423.2, 425.1 [M+H]$^+$.

Intermediate 50: (1R,7S,8r)-Benzyl 8-amino-4-azabicyclo[5.1.0]octane-4-carboxylate, hydrochloride

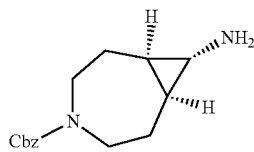 [SMILES: N[C@@H]1[C@H]2CCN(C(=O)OCc3ccccc3)CC[C@@H]12]

Step 1: N-Benzyl-N-(but-3-en-1-yl)but-3-en-1-amine

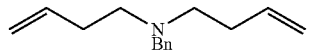 [SMILES: C=CCCN(CCC=C)Cc1ccccc1]

To a solution of 4-bromobut-1-ene (151 g, 1120 mmol) and phenylmethanamine (60 g, 560 mmol) in DMF (500 mL) was added K$_2$CO$_3$ (232 g, 1680 mmol). The mixture was stirred at 80° C. for 12 h. After filtration, the filtrate was concentrated. The crude residue was purified by flash chromatography (from pure PE to PE/EtOAc=100/1 to 10/1, TLC: PE/EtOAc=10/1, R$_f$=0.65) to yield N-benzyl-N-(but-3-en-1-yl)but-3-en-1-amine (75 g, 327 mmol, 58.5% yield) as light yellow oil: $^1$H NMR (400 MHz, CDCl$_3$) δ ppm 7.29-7.13 (m, 5H), 5.71 (tdd, J=6.7, 10.3, 17.1 Hz, 2H), 5.08-4.80 (m, 4H), 3.53 (s, 2H), 2.50-2.43 (m, 4H), 2.21-2.12 (m, 4H); ES-LCMS m/z 216.2 [M+H]$^+$.

Step 2: Benzyl di(but-3-en-1-yl)carbamate

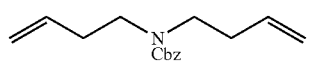 [SMILES: C=CCCN(CCC=C)C(=O)OCc1ccccc1]

To a solution of N-benzyl-N-(but-3-en-1-yl)but-3-en-1-amine (75 g, 327 mmol) in toluene (500 mL) was added CbzCl (56.1 mL, 393 mmol). The mixture was stirred at 110° C. for 12 h. The mixture was concentrated. The crude residue was purified by flash chromatography (from pure PE to PE/EtOAc=10/1, TLC: PE/EtOAc=10/1, R$_f$=0.5) to yield benzyl di(but-3-en-1-yl)carbamate (73 g, 197 mmol, 60.2% yield) as light yellow oil: ¹H NMR (400 MHz, CDCl₃) δ ppm 7.39-7.30 (m, 5H), 5.87-5.57 (m, 2H), 5.13 (s, 2H), 5.12-4.92 (m, 4H), 3.31 (s, 4H), 2.39-2.21 (m, 4H); ES-LCMS m/z 260.2 [M+H]⁺.

Step 3: Benzyl 2,3,6,7-tetrahydro-1H-azepine-1-carboxylate

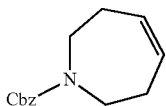

To a suspension of benzyl di(but-3-en-1-yl)carbamate (36 g, 97 mmol) in DCM (3600 mL) was added Grubbs I (4.07 g, 4.86 mmol). The reaction mixture was stirred at 40° C. for 12 h under N₂ atmosphere. The reaction mixture was concentrated to afford the crude. The crude material was purified by flash chromatography (from pure PE to PE/EtOAc=10/1, TLC: PE/EtOAc=10/1, R_f=0.6) to yield benzyl 2,3,6,7-tetrahydro-1H-azepine-1-carboxylate (22.2 g, 87 mmol, 90.0% yield) as a yellow oil: ¹H NMR (400 MHz, CD₃OD) δ ppm 7.38-7.24 (m, 5H), 5.77-5.67 (m, 2H), 5.12 (s, 2H), 3.55-3.45 (m, 4H), 2.28 (d, J=4.2 Hz, 4H); ES-LCMS m/z 232.2 [M+H]⁺.

Step 4: (1R,7S,8r)-4-Benzyl 8-ethyl 4-azabicyclo[5.1.0]octane-4,8-dicarboxylate

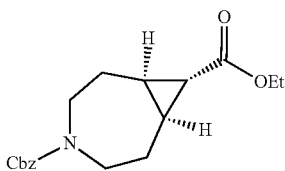 [SMILES: CCOC(=O)[C@H]1[C@@H]2CCN(C(=O)OCc3ccccc3)CC[C@@H]21]

To a suspension of benzyl 2,3,6,7-tetrahydro-1H-azepine-1-carboxylate (23 g, 90 mmol) and CuSO₄ (1.444 g, 9.05 mmol) stirred under N₂ atmosphere at 110° C. was added ethyl diazoacetate (94 mL, 905 mmol) during 2 h. The reaction mixture was stirred at 110° C. for h. The reaction mixture concentrated to afford the crude. This reaction mixture was concentrated to afford crude. The crude material was purified by flash chromatography (from pure PE to PE/EtOAc=90/5, TLC: PE/EtOAc=10/1, R_f=0.6) were combined and concentrated to yield light yellow oil which was purified by preparative HPLC (MeCN/H₂O as eluents, acid condition) and lyophilized to afford (1R,7S,8r)-4-benzyl 8-ethyl 4-azabicyclo[5.1.0]octane-4,8-dicarboxylate (8.9 g, 26.6 mmol, 29.4% yield) as a yellow oil: ¹H NMR (400 MHz, CD₃OD) δ ppm 7.38-7.27 (m, 5H), 5.09 (d, J=1.5 Hz, 2H), 4.11-4.06 (m, 2H), 3.52-3.37 (m, 4H), 2.24 (d, J=9.5 Hz, 2H), 1.70-1.59 (m, 5H), 1.25-1.21 (m, 3H); ES-LCMS m/z 318.2 [M+H]⁺.

Step 5: (1R,7S',8r)-4-((Benzyloxy)carbonyl)-4-azabicyclo[5.1.0]octane-8-carboxylic acid

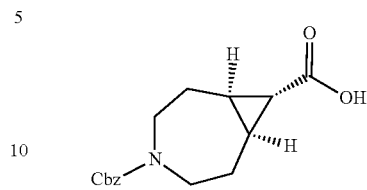

To a solution of (1R,7S,8r)-4-benzyl 8-ethyl 4-azabicyclo[5.1.0]octane-4,8-dicarboxylate (8 g, 23.95 mmol) in MeOH (100 mL) and H₂O (20 mL) was added LiOH·H₂O (5.02 g, 120 mmol). The mixture was stirred at 50° C. for 2 h. The mixture was concentrated. The residue was added H₂O (50 mL), acidified with 1 N HCl to pH=6.5-7. The precipitate was filtered and dried in vacuo to yield (1R,7S,8r)-4-((benzyloxy)carbonyl)-4-azabicyclo[5.1.0]octane-8-carboxylic acid (5.6 g, 18.58 mmol, 78.0% yield) as a white solid: ¹H NMR (400 MHz, CDCl₃) δ ppm 7.43-7.27 (m, 5H), 5.11 (s, 2H), 3.42 (br s, 4H), 2.29 (br s, 2H), 1.75 (br s, 2H), 1.71-1.58 (m, 3H); ES-LCMS m/z: 290.1 [M+H]⁺.

Step 6: (1R,7S,8r)-Benzyl 8-(azidocarbonyl)-4-azabicyclo[5.1.0]octane-4-carboxylate

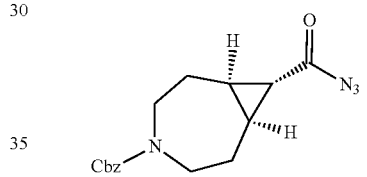

To a solution of (1R,7S,8r)-4-((benzyloxy)carbonyl)-4-azabicyclo[5.1.0]octane-8-carboxylic acid (1.5 g, 4.98 mmol) in DCM (20 mL) and DMF (0.2 mL) was added oxalyl dichloride (0.509 mL, 5.97 mmol) at 0° C. After stirring at the same temperature for 1 h, the reaction mixture was concentrated and dissolved in acetone (20 mL). Sodium azide (0.971 g, 14.93 mmol) in water (2 mL) was added. Then the reaction was stirred at 25° C. for another 2.5 h. Saturated aqueous NaHCO₃ (50 mL) solution was added and extracted with DCM (30 mL×2). The combined organic layers were dried over Na₂SO₄, filtered and concentrated to give (1R,7S,8r-benzyl 8-(azidocarbonyl)-4-azabicyclo[5.1.0]octane-4-carboxylate (1.55 g, 4.44 mmol, 89.0% yield) as pale yellow oil: ¹H NMR (400 MHz, CDCl₃) δ ppm 7.43-7.24 (m, 5H), 5.11 (d, J=1.98 Hz, 2H), 3.65-3.38 (m, 4H), 2.49-2.08 (m, 3H), 1.81-1.43 (m, 4H); ES-LCMS m/z: 315.2 [M+H]⁺.

Step 7: (1R,7S,8r)-Benzyl 8-((tert-butoxycarbonyl)amino)-4-azabicyclo[5.1.0]octane-4-carboxylate

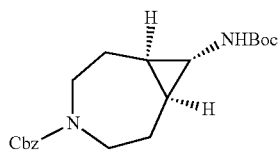 [SMILES: CC(C)(C)OC(=O)N[C@H]1[C@@H]2CCN(C(=O)OCc3ccccc3)CC[C@@H]21]

To a solution of (1R,7S,8r)-benzyl 8-(azidocarbonyl)-4-azabicyclo[5.1.0]octane-4-carboxylate (1.55 g, 4.44 mmol) in t-BuOH (15 mL) was stirred at 100° C. for 2 h. Saturated aqueous NaHCO₃ (60 mL) solution was added and extracted with DCM (50 mL×2). The combined organic layers were dried over Na₂SO₄, filtered and concentrated to give (1R,7S,8r)-benzyl 8-((tert-butoxycarbonyl)amino)-4-azabicyclo[5.1.0]octane-4-carboxylate (1.75 g, 3.88 mmol, 88.0% yield) as pale yellow oil: ¹H NMR (400 MHz, CDCl₃) δ ppm 7.32-7.20 (m, 5H), 5.03 (s, 2H), 4.65 (br s, 1H), 3.71-3.42 (m, 2H), 3.24-3.08 (m, 2H), 2.38-2.14 (m, 3H), 1.57 (br s, 2H), 1.37 (s, 9H), 1.07 (br s, 2H); ES-LCMS m/z 305.2 [M−t−Bu+H]⁺.

Step 8: (1R,7S,8r)-Benzyl 8-amino-4-azabicyclo[5.1.0]octane-4-carboxylate, hydrochloride

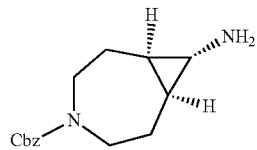 [SMILES: N[C@@H]1[C@H]2CCN(C(=O)OCc3ccccc3)CC[C@@H]12]

(1R,7S,8r)-Benzyl 8-((tert-butoxycarbonyl)amino)-4-azabicyclo[5.1.0]octane-4-carboxylate (1.75 g, 3.88 mmol) was dissolved in HCl solution (4 M in MeOH, 20 mL, 80 mmol). Then the reaction mixture was stirred at 20° C. for 0.5 h. The reaction mixture was concentrated to give (1R,1S,8r)-benzyl 8-amino-4-azabicyclo[5.1.0]octane-4-carboxylate, hydrochloride (1.35 g, 3.64 mmol, 94.0% yield) as a pale yellow solid: ¹H NMR (400 MHz, CD₃OD) δ ppm 7.47-7.12 (m, 5H), 5.07 (brs, 2H), 3.64-3.41 (m, 3H), 2.65-2.14 (m, 4H), 1.67-1.35 (m, 4H); ES-LCMS m/z 261.0 [M+H]⁺.

Intermediate 51: Methyl 4-bromo-2-methylbutanoate

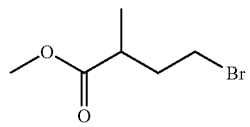

To a solution of 3-methyldihydrofuran-2(3H)-one (30 g, 300 mmol) in DCM (500 mL) was added BBr₃ (34.0 mL, 360 mmol) in portions at 0° C. The reaction mixture was stirred at 30° C. for 8 h. MeOH (100 mL) was added to the mixture and stirred for 8 h. The mixture was added to DCM (500 mL) and saturated aqueous NaHCO₃ (600 mL) solution. The mixture was extracted with DCM (150 mL×2). The organic layer was washed brine (200 mL), dried over Na₂SO₄, filtered and concentrated to give the crude product as a yellow oil of methyl 4-bromo-2-methylbutanoate (50 g, 244 mmol, 81.0% yield): ¹H NMR (400 MHz, CDCl₃) δ ppm 3.70 (s, 3H), 3.50-3.36 (m, 2H), 2.72 (t, J=7.03 Hz, 1H), 2.35-2.17 (m, 1H), 2.00-1.85 (m, 1H), 1.20 (d, J=7.28 Hz, 3H); ES-LCMS m/z 195.0, 197.0 [M+H]⁺.

Intermediate 52: Dimethyl(piperidin-4-yl methyl)phosphine oxide

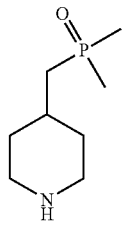

Step 1: Benzyl 4-((dimethylphosphoryl)(hydroxy)methyl)piperidine-1-carboxylate

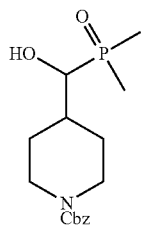

To a solution of benzyl 4-formylpiperidine-1-carboxylate (2 g, 8.09 mmol) and dimethylphosphine oxide (0.757 g, 9.71 mmol) in i-PrOH (20 mL) was added Et₃N (2.455 g, 24.26 mmol). Then the reaction mixture was stirred at 90° C. for 10 h. Water (30 mL) was added and extracted with DCM (50 mL×2). The combined organic layers were dried over Na₂SO₄ and concentrated to yield the crude product. The crude material was purified by flash chromatography (from pure DCM to DCM/MeOH=10/1, TLC: DCM/MeOH=10/1, R_f=0.4) to yield benzyl 4-((dimethylphosphoryl)(hydroxy)methyl)piperidine-1-carboxylate (1.5 g, 3.69 mmol, 45.6% yield) as a yellow solid: ¹H NMR (400 MHz, CDCl₃) δ ppm 7.33-7.16 (m, 5H), 5.04 (br s, 2H), 4.37 (br s, 1H), 4.15 (br s, 2H), 3.49 (br s, 1H), 2.72 (br s, 2H), 2.11-1.73 (m, 4H), 1.44 (dd, J=4.5, 12.7 Hz, 6H); ES-LCMS m/z 326.2 [M+H]⁺.

Step 2: Benzyl 4-((dimethylphosphoryl)methylene)piperidine-1-carboxylate

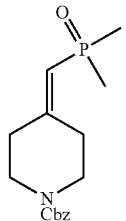 [SMILES: CP(C)(=O)C=C1CCN(C(=O)OCc2ccccc2)CC1]

To a solution of benzyl 4-((dimethylphosphoryl)(hydroxy)methyl)piperidine-1-carboxylate (1200 mg, 2.95 mmol) in DCM (30 mL) was added DAST (1.170 mL, 8.85 mmol) at 20° C. Then, the mixture was stirred at 20° C. for 3 h under N₂ atmosphere. The reaction mixture was quenched by the addition of saturated aqueous NaHCO₃ solution (50 mL) at 0° C. The mixture was extracted with DCM (100 mL×3). The combined organic layers were washed with brine (50 mL), dried over Na₂SO₄, filtered and concentrated. The crude product was purified by preparative HPLC (MeCN/H₂O as eluents, acidic condition) and dried by lyophilization to yield benzyl 4-((dimethylphosphoryl)methylene)piperidine-1-carboxylate (210 mg, 0.608 mmol, 20.6% yield) as colorless oil: ¹H NMR (400 MHz, CD₃OD) δ ppm 7.29 (d, J=2.2 Hz, 5H), 5.46-5.27 (m, 1H), 5.07 (d, J=8.6 Hz, 2H), 3.57-3.46 (m, 4H), 2.81 (br s, 2H), 2.22 (br s, 2H), 1.53-1.49 (m, 6H); ES-LCMS m/z 308.2 [M+H]⁺.

Step 3: Dimethyl(piperidin-4-ylmethyl)phosphine oxide

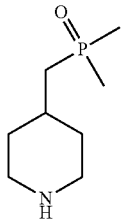

A mixture of benzyl 4-((dimethylphosphoryl)methylene)piperidine-1-carboxylate (200 mg, 0.579 mmol) and Pd/C (10 wt %, 339 mg, 0.319 mmol) in MeOH (20 mL) was stirred at 20° C. for 1 h under H₂ (15 psi). The mixture was filtered and the filtrate was concentrated to yield dimethyl (piperidin-4-ylmethyl)phosphine oxide (140 mg, 0.479 mmol, 83.0% yield) as a brown solid: ¹H NMR (400 MHz, CD₃OD) δ ppm 3.03 (s, 2H), 2.30 (s, 2H), 2.08-1.99 (m, 4H), 1.75 (d, J=11.5 Hz, 3H), 1.50-1.48 (m, 6H).

Intermediate 53: 1-(2-Bromoethyl)cyclopropanol

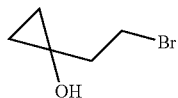

To a solution of ethyl 3-bromopropanoate (500 mg, 2.76 mmol) in THF (30 mL) cooled to 0° C. was added tetraisopropoxytitanium (79 mg, 0.276 mmol), followed by EtMgBr (1 M in THF, 8.29 mL, 8.29 mmol). The mixture was stirred at 0° C. for 2 h. The mixture was quenched with saturated aqueous NH₄Cl solution (2 mL) at 0° C. The mixture was partitioned between EtOAc (15 mL) and water (15 mL). The combined organic layer was dried over Na₂SO₄, filtered and concentrated to give a crude product which was purified by flash chromatography (PE/EtOAc=5/1) to give 1-(2-bromoethyl)cyclopropanol (400 mg, 2.181 mmol, 79.0% yield) as a yellow oil: ¹H NMR (400 MHz, CDCl₃) δ ppm 3.66-3.55 (m, 2H), 2.14-2.10 (m, 2H), 0.85-0.78 (m, 2H), 0.59-0.52 (m, 2H).

Intermediate 54: Methyl 1-(2-bromoethyl)cyclopropanecarboxylate

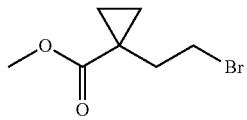

Step 1: 5-Oxaspiro[2.4]heptan-4-one

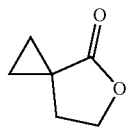

To a solution of 3-methylenedihydrofuran-2(3/7)-one (5 g, 51.0 mmol), BF₃·OEt₂ (0.646 mL, 5.10 mmol) and Pd(OAc)₂ (0.080 g, 0.357 mmol) in ether (50 mL) was added trimethylsilyldiazomethane (15.72 g, 138 mmol) dropwise at 0° C. under N₂ atmosphere. Then the mixture was stirred at 26° C. for 5 h under N₂ atmosphere. The mixture was filtered and concentrated. The crude material was purified by flash chromatography (from PE/EtOAc=50/1 to 4/1, TLC: PE/EtOAc=5/1, R_f=0.7) to yield 5-oxaspiro[2.4]heptan-4-one (150 mg, 1.204 mmol, 2.4% yield) as a yellow oil: ¹H NMR (400 MHz, CDCl₃) δ ppm 4.35 (t, J=7.5 Hz, 2H), 2.24 (t, J=7.5 Hz, 2H), 1.22-1.15 (m, 2H), 0.93-0.85 (m, 2H); ES-LCMS m/z 113.1 [M+H]⁺.

Step 2: Methyl 1-(2-bromoethyl)cyclopropanecarboxylate

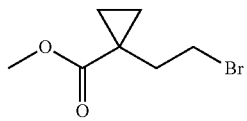

A mixture of 5-oxaspiro[2.4]heptan-4-one (150 mg, 1.204 mmol) in DCM (10 mL) was added BBr₃ (0.171 mL, 1.806 mmol) at 0° C. under N₂ atmosphere. Then the mixture was stirred at 25° C. for 8 h under N₂ atmosphere. MeOH (10.0 mL) was added to the mixture and stirred at 25° C. for 8 h. The reaction mixture was quenched by the addition of saturated aqueous NaHCO₃ solution (30 mL) at 0° C. The mixture was extracted with EtOAc (50 mL×3). The combined organic layers were washed with brine (30 mL), dried over Na₂SO₄, filtered and concentrated to yield methyl 1-(2-bromoethyl)cyclopropanecarboxylate (200 mg, 0.676 mmol, 56.2% yield) as brown oil: ¹H NMR (400 MHz, CDCl₃) δ ppm 3.69-3.65 (m, 3H), 3.60-3.58 (m, 2H), 2.41-2.38 (m, 2H), 1.95 (d, J=2.4 Hz, 2H), 1.81 (t, J=2.1 Hz, 2H).

Intermediate 55: Methyl 2-hydroxy-3-(piperidin-4-yl)propanoate, hydrochloride

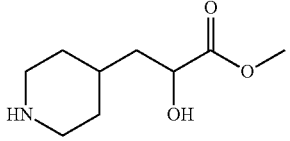

Step 1: tert-Butyl 4-(2-Methoxy-2-oxoethyl)piperidine-1-carboxylate

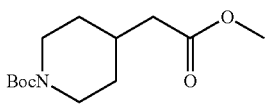 [SMILES: COC(=O)CC1CCN(C(=O)OC(C)(C)C)CC1]

To a solution of methyl 2-(piperidin-4-yl)acetate, hydrochloride (15 g, 69.7 mmol) and DIEA (27.0 g, 209 mmol) in DCM (300 mL) was added Boc$_2$O (19.42 mL, 84 mmol). Then the reaction mixture was stirred at 20° C. for 12 h. The mixture was washed with aqueous acetic acid (200 mL×2) and saturated aqueous NaHCO$_3$ (200 mL) solution, dried over Na$_2$SO$_4$ and concentrated in vacuo to give tert-butyl 4-(2-methoxy-2-oxoethyl)piperidine-1-carboxylate (17 g, 59.5 mmol, 85.0% yield) as pale yellow oil: $^1$H NMR (400 MHz, CDCl$_3$) δ 4.07 (s, 2H), 3.70 (t, J=5.5 Hz, 2H), 2.69 (t, J=11.5 Hz, 2H), 1.75-1.60 (m, 3H), 1.55-1.49 (m, 2H), 1.48-1.30 (m, 9H), 1.18-1.03 (m, 2H); ES-LCMS m/z 202.2 [M−t−Bu+H]$^+$.

Step 2: tert-Butyl 4-(2-hydroxyethyl)piperidine-1-carboxylate

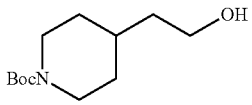

To a solution of tert-butyl 4-(2-methoxy-2-oxoethyl)piperidine-1-carboxylate (17 g, 59.5 mmol) in THF (300 mL) was added LAH (2.482 g, 65.4 mmol) in portions. Then the reaction mixture was stirred at 0° C. for 30 min. Water (2.5 mL) and aqueous NaOH (2.5 mL, 10%) was added to quench the reaction. The solid was filtered off and solvent was removed in vacuo to give tert-butyl 4-(2-hydroxyethyl)piperidine-1-carboxylate (12 g, 49.7 mmol, 84.0% yield) as pale yellow oil: $^1$H NMR (400 MHz, CDCl$_3$) δ ppm 4.07 (s, 2H), 3.70 (t, J=5.5 Hz, 2H), 2.69 (t, J=11.5 Hz, 2H), 1.75-1.60 (m, 3H), 1.55-1.49 (m, 2H), 1.48-1.30 (m, 9H), 1.18-1.03 (m, 2H); ES-LCMS m/z: 174.2 [M−t−Bu+H]$^+$.

Step 3: tert-Butyl 4-(2-oxoethyl)piperidine-1-carboxylate

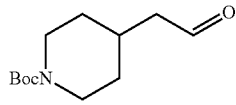

A solution of oxalyl dichloride (2.65 mL, 31.1 mmol) in 40 mL of DCM was cooled to −78° C. A solution of DMSO (4.41 mL, 62.1 mmol) in DCM (30 mL) was added dropwise over 30 minutes. At the end of the addition the reaction solution was warmed to −70° C. over a period of 20 min, then a solution of tert-butyl 4-(2-hydroxyethyl)piperidine-1-carboxylate (5 g, 20.71 mmol) in DCM (30 mL) was added dropwise over 30 min. The dropping funnel was washed with 5-mL portions of methylene chloride, then charged with a solution of DIEA (21.71 mL, 124 mmol) in 20 mL of DCM was added over 20 min, then the reaction flask was removed from the bath and allowed to warm to 0° C. over 60 min. The mixture was monitored by TLC (PE:EtOAc=2:1, R$_f$=0.55). The reaction solution was transferred to a 250 mL separatory funnel charged with 30 mL of ice-cold 1 M HCl solution. The two phases were separated, the aqueous phase was extracted with methylene chloride (50 mL×3), and the combined organic phases are washed with pH=7 aqueous phosphate buffer (100 mL×4), then dried with anhydrous sodium sulfate and concentrated under reduced pressure to give pale yellow oil of tert-butyl 4-(2-oxoethyl) piperidine-1-carboxylate (4.8 g, 19.01 mmol, 92.0% yield): $^1$H NMR (400 MHz, CDCl$_3$) δ ppm 9.78 (d, J=1.3 Hz, 1H), 4.08 (s, 2H), 2.73 (t, J=11.7 Hz, 2H), 2.38 (d, J=7.1 Hz, 2H), 2.11-1.96 (m, 1H), 1.68 (d, J 2.8 Hz, 2H), 1.61-134 (m, 9H), 1.30-1.08 (m, 2H); ES-LCMS m/z: 172.2 [M−t−Bu+H]$^+$.

Step 4: tert-Butyl 4-(2-cyano-2-hydroxyethyl)piperidine-1-carboxylate

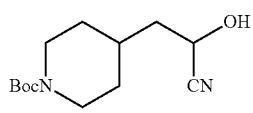

To a solution of tert-butyl 4-(2-oxoethyl)piperidine-1-carboxylate (2 g, 7.92 mmol) in water (20 mL) was added sodium metabisulfite (1.505 g, 7.92 mmol). After stirring at 15° C. for 2 h, NaCN (0.776 g, 15.84 mmol) was added. Then the mixture was stirred at 15° C. for 10 h. Water (50 mL) was added and extracted with DCM (50 mL×2), and the combined organic phases were washed with saturated aqueous NaHCO$_3$ (50 mL) solution and brine (50 mL), then dried with anhydrous sodium sulfate and concentrated to give pale yellow oil of tert-butyl 4-(2-cyano-2-hydroxyethyl)piperidine-1-carboxylate (2 g, 7.08 mmol, 89.0% yield): $^1$H NMR (400 MHz, CDCl$_3$) δ 4.63-4.52 (m, 1H), 4.09 (s, 2H), 3.81-3.66 (m, 2H), 2.71 (s, 2H), 1.76-1.63 (m, 3H), 1.55-1.35 (m, 9H), 1.25-1.06 (m, 2H); ES-LCMS m/z: 199.2 [M−t−Bu+H]$^+$.

Step 5: Methyl 2-hydroxy-3-(piperidin-4-yl)propanoate, hydrochloride

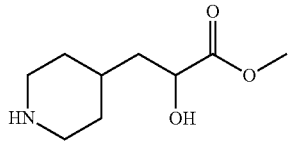

tert-Butyl 4-(2-cyano-2-hydroxyethyl)piperidine-1-carboxylate (1.9 g, 6.72 mmol) was dissolved in HCl solution (4 M in MeOH, 30 mL, 120 mmol). Then the mixture was stirred at 15° C. for 12 h. The solvent was removed in vacuo to give methyl 2-hydroxy-3-(piperidin-4-yl)propanoate, hydrochloride (1.5 g, 5.70 mmol, 85.0% yield) as a pale yellow solid: $^1$H NMR (400 MHz, CDCl$_3$) δ ppm 4.58 (dd, J=3.5, 9.7 Hz, 1H), 4.31-4.04 (m, 3H), 3.43-3.36 (m, 2H), 3.05-2.97 (m, 2H), 2.07 (d, J=14.1 Hz, 1H), 1.94 (d, J=11.9 Hz, 2H), 1.77-1.66 (m, 2H), 1.54-1.42 (m, 2H).

Intermediate 56: N-((1R,7S,8r)-4-azabicyclo[5.1.0]octan-8-yl) acetamide, trifluoroacetic acid salt

Step 1: (1R,7S,8r)-Benzyl 8-acetamido-4-azabicyclo[5.1.0]octane-4-carboxylate

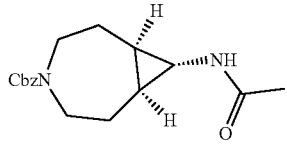 [SMILES: CC(=O)N[C@H]1[C@@H]2CCN(C(=O)OCc3ccccc3)CC[C@@H]21]

To a solution of (1R,7S,8r)-benzyl 8-amino-4-azabicyclo[5.1.0]octane-4-carboxylate, hydrochloride (500 mg, 1.348 mmol) in DCM (10 mL) was added DIEA (209 mg, 1.617 mmol) and Ac$_2$O (165 mg, 1.617 mmol) at 25° C. Then the mixture was stirred at 25° C. for 12 h. The solvent was concentrated to give the crude product which was purified by flash chromatography (from pure DCM to DCM/MeOH=10/1, R$_f$=0.50 (DCM/MeOH=10/1)) to yield a pale yellow oil of (1R,7S,8r)-benzyl 8-acetamido-4-azabicyclo[5.1.0]octane-4-carboxylate (415 mg, 1.167 mmol, 87.0% yield): $^1$H NMR (400 MHz, CDCl$_3$) δ ppm 7.40-7.28 (m, 5H), 5.55 (brs, 1H), 5.10 (s, 2H), 3.77-3.47 (m, 2H), 3.34-3.15 (m, 2H), 2.63-2.21 (m, 3H), 1.64 (s, 3H), 1.62-1.44 (m, 2H), 1.26-1.10 (m, 2H); ES-LCMS m/z 303.0 [M+H]$^+$.

Step 2: N-((1R,7S,8r)-4-azabicyclo[5.1.0]octan-8-yl)acetamide, trifluoroacetic acid salt

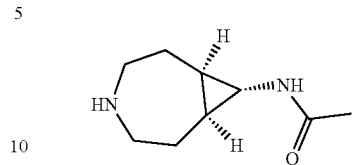

(1R,7S,8r)-Benzyl 8-(methylsulfonamido)-4-azabicyclo[5.1.0]octane-4-carboxylate (360 mg, 1.064 mmol) in TFA (5 mL, 64.9 mmol) was stirred at 50° C. for 1.5 h. The mixture was concentrated to give N-((1R,7S,8r)-4-azabicyclo[5.1.0]octan-8-yl)acetamide, trifluoroacetic acid (400 mg, 1.134 mmol, 97.0% yield) as a yellow oil: $^1$H NMR (400 MHz, CD$_3$OD) δ ppm 3.39-3.34 (m, 2H), 3.12-3.02 (m, 2H), 2.52-2.42 (m, 3H), 1.87 (s, 3H), 1.49 (dd, J=9.26, 17.20 Hz, 2H), 1.25 (s, 2H); ES-LCMS m/z 169.2 [M+H]$^+$.

Intermediate 57: N-(Piperidin-4-ylmethyl)cyclopropanecarboxamide, trifluoroacetic acid salt

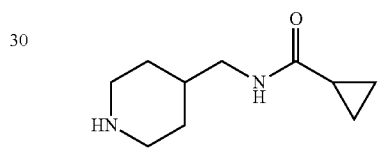

Step 1: tert-Butyl 4-(cyclopropanecarboxamidomethyl)piperidine-1-carboxylate

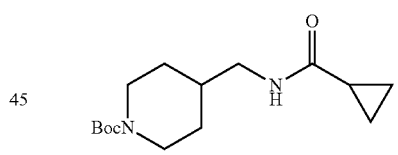

To a solution of cyclopropanecarboxylic acid (1 g, 11.62 mmol), DIEA (6.09 mL, 34.8 mmol) and EDC (4.45 g, 23.23 mmol) in DMF (30 mL) was added tert-butyl 4-(aminomethyl)piperidine-1-carboxylate (2.74 g, 12.78 mmol) and HOBt (3.56 g, 23.23 mmol). Then the mixture was stirred at 26° C. for 12 h. The mixture was concentrated and then 10% citric acid (40 mL) was added. The mixture was extracted with DCM (100 mL×3). The combined organic layers were washed with brine (40 mL), dried over Na$_2$SO$_4$, filtered and concentrated. The crude material was purified by flash chromatography (from PE/EtOAc=20/1 to 1/1, TLC: PE/EtOAc=1/1, R$_f$=0.5) to yield tert-butyl 4-(cyclopropanecarboxamidomethyl)piperidine-1-carboxylate (1.4 g, 4.46 mmol, 38.4% yield) as colorless oil: $^1$H NMR (400 MHz, CDCl$_3$) δ ppm 5.88 (s, 1H), 4.15-4.06 (m, 2H), 3.15 (s, 2H), 2.66 (s, 2H), 1.71-1.59 (m, 3H), 1.43 (s, 9H), 1.36-1.29 (m, 1H), 1.17-1.05 (m, 2H), 1.00-0.90 (m, 2H), 0.77-0.66 (m, 2H); ES-LCMS m/z 227.2 [M+H-t-Bu]$^+$.

Step 2: N-(Piperidin-4-yl methyl)cyclopropanecarboxamide, trifluoroacetic acid salt

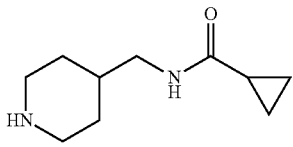 [SMILES: O=C(NCC1CCNCC1)C1CC1]

To a solution of tert-butyl 4-(cyclopropanecarboxamidomethyl)piperidine-1-carboxylate (700 mg, 2.231 mmol) in DCM (5 mL) was added TFA (1 mL, 12.98 mmol). The mixture was stirred at 25° C. for 0.5 h. The mixture was concentrated to yield N-(piperidin-4-ylmethyl)cyclopropanecarboxamide, trifluoroacetic acid (0.7 g, 2.126 mmol, 95.0% yield) as colorless oil: $^1$H NMR (400 MHz, CD$_3$OD) δ ppm 3.39 (d, J=12.5 Hz, 2H), 3.14 (d, J=6.5 Hz, 2H), 2.96 (dt, J=2.5, 12.8 Hz, 2H), 1.93 (d, J=14.1 Hz, 2H), 1.87-1.74 (m, 1H), 1.59-1.54 (m, 1H), 1.46-1.34 (m, 2H), 0.86-0.79 (m, 2H), 0.78-0.71 (m, 2H); ES-LCMS m/z 183.2 [M+H]$^+$.

Intermediate 58: ten-Butyl 6-fluoro-4-(5-hydroxypyrimidin-2-yl)-1,4-diazepane-1-carboxylate

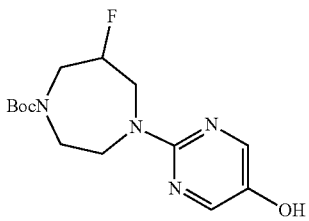 [SMILES: CC(C)(C)OC(=O)N1CCN(c2ncc(O)cn2)CC(F)C1]

Step 1: tert-Butyl 4-(5-(benzyloxy)pyrimidin-2-yl)-6-fluoro-1,4-diazepane-1-carboxylate

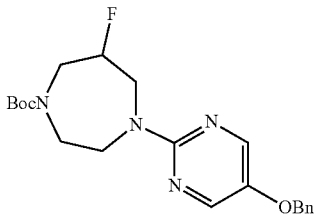 [SMILES: CC(C)(C)OC(=O)N1CCN(c2ncc(OCc3ccccc3)cn2)CC(F)C1]

To a solution of tert-butyl 4-(5-(benzyloxy)pyrimidin-2-yl)-6-hydroxy-1,4-diazepane-1-carboxylate (760 mg, 1.708 mmol) in DCM (20 mL) was added DAST (0.237 mL, 1.793 mmol). The mixture was stirred at 20° C. for 15 min. Then the mixture was concentrated to give the residue which was distributed between DCM (30 mL) and H$_2$O (20 mL), extracted with DCM (30 mL×2). The combined organic layers were washed with brine (20 mL), dried over Na$_2$SO$_4$, filtered and concentrated. The crude product was purified by flash chromatography (20% EtOAc: 80% Petroleum ether, TLC: PE/EtOAc=5/1) to yield a light yellow solid of tert-butyl 4-(5-(benzyloxy)pyrimidin-2-yl)-6-fluoro-1,4-diazepane-1-carboxylate (700 mg, 1.652 mmol, 97.0% yield): $^1$H NMR (400 MHz, CD$_3$OD) δ ppm 8.15 (d, J=13.9 Hz, 2H), 7.43-7.28 (m, 5H), 5.10-5.05 (m, 2H), 4.42-4.24 (m, 1H), 4.24-4.16 (m, 2H), 3.76-3.41 (m, 6H), 1.48-1.29 (m, 9H); ES-LCMS m/z 403.3 [M+H]$^+$.

Step 2: tert-Butyl 6-fluoro-4-(5-hydroxypyrimidin-2-yl)-1,4-diazepane-1-carboxylate

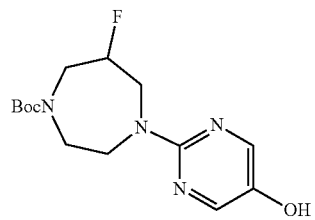 [SMILES: CC(C)(C)OC(=O)N1CCN(c2ncc(O)cn2)CC(F)C1]

To a solution of tert-butyl 4-(5-(benzyloxy)pyrimidin-2-yl)-6-fluoro-1,4-diazepane-1-carboxylate (650 mg, 1.534 mmol) in MeOH (50 mL) was added Pd/C (10 wt %, 163 mg, 0.153 mmol). Then the reaction mixture was stirred at 20° C. for 1 h under H$_2$ atmosphere (16 psi). The solid was filtered off and solvent was removed in vacuo to give tert-butyl 6-fluoro-4-(5-hydroxypyrimidin-2-yl)-1,4-diazepane-1-carboxylate (500 mg, 1.281 mmol, 83.0% yield) as a yellow oil: $^1$H NMR (400 MHz, CD$_3$OD) § 7.98 (s, 2H), 4.35-4.31 (m, 1H), 4.35-4.28 (m, 1H), 4.25-4.12 (m, 2H), 3.78-3.60 (m, 2H), 3.53-3.44 (m, 4H), 1.38 (d, J=19.0 Hz, 9H); ES-LCMS m/z 313.3 [M+H]$^+$.

Intermediate 59: 2-(3-Chloro-5-(difluoromethyl)phenyl)-4,4,5,5-tetramethyl-1,3,2-dioxaborolane

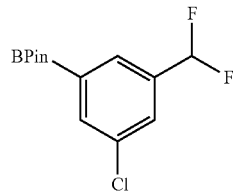

Step 1: 3-Chloro-5-(difluoromethyl)phenol

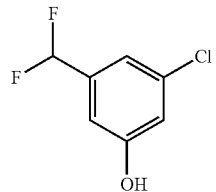 [SMILES: Oc1cc(Cl)cc(C(F)F)c1]

To a solution of 3-chloro-5-hydroxybenzaldehyde (2 g, 12.77 mmol) in DCM (20 mL) was added DAST (3.38 mL, 25.5 mmol) dropwise. The mixture was stirred at 10° C. for 2 h. Water (50 mL) was added and the mixture was extracted with DCM (2×50 mL), the combine organic layers were dried over Na$_2$SO$_4$, filtered and concentrated to give yellow oil of 3-chloro-5-(difluoromethyl)phenol (1.5 g, 6.72 mmol, 52.6% yield): $^1$H NMR (400 MHz, CD$_3$OD) δ ppm 6.97 (s, 1H), 6.90 (s, 1H), 6.85 (s, 1H), 6.80-6.50 (m, 1H)

Step 2: 3-Chloro-5-(difluoromethyl)phenyl trifluoromethanesulfonate

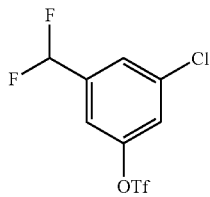

To a solution of 3-chloro-5-(difluoromethyl)phenol (700 mg, 3.14 mmol) in DCM (20 mL) was added DIEA (1.643 mL, 9.41 mmol) and Tf$_2$O (1.060 mL, 6.27 mmol). The mixture was stirred at 10° C. for 3 h. Water (50 mL) was added and the mixture was extracted with DCM (2×50 mL), the combine organic layers were dried over Na$_2$SO$_4$, filtered and concentrated to give yellow oil of 3-chloro-5-(difluoromethyl)phenyl trifluoromethanesulfonate (1 g, 1.610 mmol, 51.3% yield): $^1$H NMR (400 MHz, CD$_3$OD) δ ppm 7.72 (s, 1H), 7.67 (s, 1H), 7.55 (s, 1H), 7.04-6.69 (m, 1H)

Step 3: 2-(3-Chloro-5-(difluoromethyl)phenyl)-4,4,5,5-tetramethyl-1,3,2-dioxaborolane

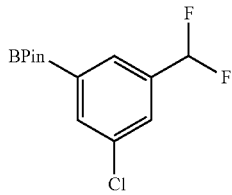

To a suspension of 3-chloro-5-(difluoromethyl)phenyl trifluoromethanesulfonate (1 g, 1.610 mmol), 4,4,4',4',5,5,5',5'-octamethyl-2,2'-bi(1,3,2-dioxaborolane) (0.613 g, 2.414 mmol) and KOAc (0.474 g, 4.83 mmol) in 1,4-dioxane (10 mL) stirred under N$_2$ atmosphere was added PdCl$_2$(dppf) (0.118 g, 0.161 mmol). The reaction mixture was stirred at 80° C. for 5 h under N$_2$ atmosphere. After filtration, the filtrate was concentrated. The residue was added DCM (30 mL) and water (30 mL), extracted with DCM (30 mL×3). The combined organic layers were dried over Na$_2$SO$_4$, filtered and evaporated to afford crude 2-(3-chloro-5-(difluoromethyl)phenyl)-4,4,5,5-tetramethyl-1,3,2-dioxaborolane (0.8 g, 1.386 mmol, 86.0% yield) as dark oil, which was used for the next step directly: $^1$H NMR (400 MHz, CD$_3$OD) δ ppm 7.86-7.68 (m, 1H), 7.65-7.49 (m, 2H), 7.08-6.62 (m, 1H), 1.24-1.21 (m, 12H)

Intermediate 60: Ethyl 2-(piperidin-4-yloxy)acetate, hydrochloride

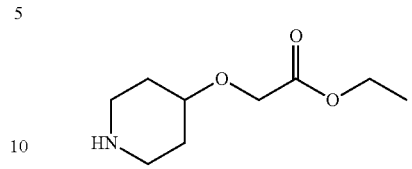

Step 1: tert-Butyl 4-(2-ethoxy-2-oxoethoxy)piperidine-1-carboxylate

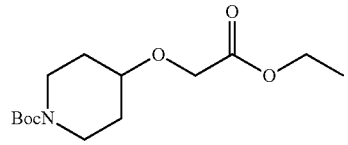

To a solution of tert-butyl 4-hydroxypiperidine-1-carboxylate (10 g, 49.7 mmol) in THF (200 mL) was added 60% NaH (3.97 g, 99 mmol) at 15° C. under N$_2$ atmosphere. The mixture was stirred at 15° C. for 1 h. Then, ethyl 2-bromoacetate (16.60 g, 99 mmol) was added and the mixture was stirred at 50° C. for 9 h. Water (2 mL) was added and the mixture was concentrated to give the residue which was distributed between DCM (150 mL) and saturated aqueous NaHCO$_3$ solution (150 mL), extracted with DCM (150 mL×2). The combined organic layers were dried over Na$_2$SO$_4$, filtered and evaporated to give tert-butyl 4-(2-ethoxy-2-oxoethoxy)piperidine-1-carboxylate (3 g, 7.31 mmol, 14.7% yield) as colorless oil: $^1$H NMR (400 MHz, CD$_3$OD) δ ppm 4.23-4.09 (m, 4H), 3.76-3.58 (m, 3H), 3.14 (t, J=10.4 Hz, 2H), 1.89-1.81 (m, 2H), 1.57-1.48 (m, 2H), 1.45 (s, 9H), 1.27 (t, J=7.2 Hz, 3H); ES-LCMS m/z 232.1 [M−t−Bu+H]$^+$.

Step 2: Ethyl 2-(piperidin-4-yloxy)acetate, hydrochloride

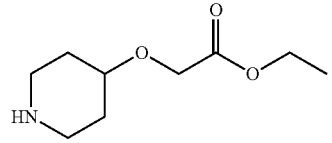

To a solution of tert-butyl 4-(2-ethoxy-2-oxoethoxy)piperidine-1-carboxylate (3 g, 7.31 mmol) in DCM (10 mL) was added HCl solution (4 M in EtOAc, 10 mL, 40.0 mmol). The mixture was stirred at 10° C. for 20 min. The mixture was concentrated to give a yellow solid of ethyl 2-(piperidin-4-yloxy)acetate, hydrochloride (2 g, 7.15 mmol, 98.0% yield): $^1$H NMR (400 MHz, CD$_3$OD) δ ppm 4.21-4.12 (m, 4H), 3.90-3.72 (m, 1H), 3.37-3.31 (m, 2H), 3.18-3.03 (m, 2H), 2.08-1.94 (m, 4H), 1.31-1.25 (m, 3H); ES-LCMS m/z 188.1 [M+H]$^+$.

Intermediate 61: (S)-Methyl 2-(1,4-oxazepan-7-yl)acetate

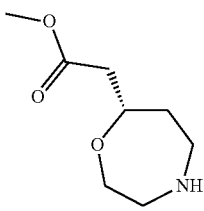

Step 1: (S)-4-(Benzylamino)-2-hydroxybutanoic acid

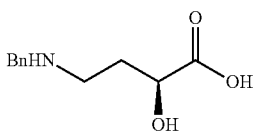

To a solution of (S)-4-amino-2-hydroxybutanoic acid (13.5 g, 113 mmol), NaOH (4.85 g, 121 mmol) in water (120 mL) was added benzaldehyde (12.26 mL, 121 mmol) at 25° C. Then the mixture was stirred at 25° C. for 30 min. The mixture was cooled to 0° C. and NaBH$_4$ (2.92 g, 77 mmol) was added during 30 min. The mixture was stirred for 11 h at 25° C. The mixture was washed with EtOAc (100 mL). The aqueous phase was acidified to pH=6 with 12 N HCl solution and the solid was collected and dried to yield 0S')-4-(benzylamino)-2-hydroxybutanoic acid (23 g, 33.0 mmol, 29.1% yield) as a white solid: $^1$H NMR (400 MHz, CD$_3$OD) δ ppm 7.40-7.20 (m, 5H), 4.01-3.91 (m, 1H), 3.82-3.72 (m, 2H), 2.90-2.71 (m, 2H), 2.08-1.94 (m, 1H), 1.89-1.75 (m, 1H); ES-LCMS m/z 210.2 [M+H]$^+$.

Step 2: (S)-4-Benzyl-3-oxo-1,4-oxazepane-7-carboxylic acid

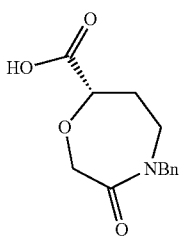 [SMILES: O=C(O)[C@@H]1CCN(Cc2ccccc2)C(=O)CO1]

To a solution of (S)-4-(benzylamino)-2-hydroxybutanoic acid (23 g, 33.0 mmol), NaOH (14 g, 350 mmol) in water (150 mL) was added 2-chloroacetyl chloride (11.2 mL, 141 mmol) dropwise at 0° C. Then the mixture was stirred at 25° C. for 12 h. The reaction mixture was extracted with DCM (15 mL×2), the aqueous phase was acidified to pH=3 with 12 M HCl solution. The solid was filtered and dried to yield light oil, which was purified by preparative HPLC (MeCN/H$_2$O as eluents, acidic condition), followed by lyophilization to yield (N)-4-benzyl-3-oxo-1,4-oxazepane-7-carboxylic acid (7 g, 27.1 mmol, 82.0% yield) as colorless oil: $^1$H NMR (400 MHz, CD$_3$OD) δ ppm 7.40-7.21 (m, 5H), 4.61 (d, J=2.4 Hz, 2H), 4.52-4.36 (m, 2H), 4.29 (dd, J=4.6, 9.5 Hz, 1H), 3.64-3.44 (m, 2H), 2.32-2.18 (m, 1H), 2.05-1.92 (m, 1H); ES-LCMS m/z 250.3 [M+H]$^+$.

Step 3: (S)-(4-Benzyl-1,4-oxazepan-7-yl)methanol

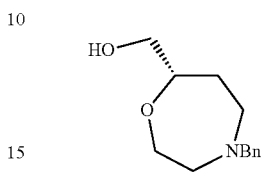

To a solution of (S)-4-benzyl-3-oxo-1,4-oxazepane-7-carboxylic acid (5 g, 19.35 mmol) in THF (80 mL) was added LAH (2.204 g, 58.1 mmol) portion wise at 0° C. Then the mixture was stirred at 25° C. for 12 h. The mixture was quenched by H$_2$O (2.2 mL), followed by 10% NaOH solution (2.2 mL). Then the mixture was filtered and the filtrate was concentrated to yield (S)-(4-benzyl-1,4-oxazepan-7-yl)methanol (3.8 g, 14.60 mmol, 75.0% yield) as light yellow oil: $^1$H NMR (400 MHz, CD$_3$OD) δ ppm 7.39-7.19 (m, 5H), 3.93-3.84 (m, 1H), 3.83-3.75 (m, 1H), 3.71-3.58 (m, 3H), 3.51-3.37 (m, 2H), 2.79-2.71 (m, 1H), 2.68-2.60 (m, 2H), 1.96-1.85 (m, 1H), 1.79-1.66 (m, 1H); ES-LCMS m/z 222.2 [M+H]$^+$.

Step 4: (S)-(1,4-Oxazepan-7-yl)methanol

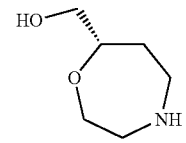

To a solution of (S)-(4-benzyl-1,4-oxazepan-7-yl)methanol (3.8 g, 14.60 mmol) in MeOH (50 mL) was added Pd/C (10 wt %, 1.553 g, 1.460 mmol) under N$_2$ atmosphere. Then the mixture was stirred at 25° C. under H$_2$ atmosphere (50 psi) for 12 h. Then the mixture was filtered and the filtrate was concentrated to yield (S)-(1,4-oxazepan-7-yl)methanol (1.9 g, 12.31 mmol, 84.0% yield) as light yellow oil: $^1$H NMR (400 MHz, CD$_3$OD) δ ppm 4.18-4.02 (m, 1H), 3.88-3.66 (m, 2H), 3.59-3.34 (m, 2H), 2.89-2.66 (m, 4H), 2.04 (m, 1H), 1.94-1.90 (m, 1H).

Step 5: (S)-Benzyl 7-(hydroxymethyl)-1,4-oxazepane-4-carboxylate

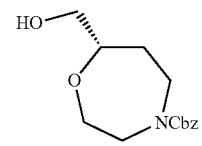

To a solution of (S)-(1,4-oxazepan-7-yl)methanol (1.9 g, 12.31 mmol) and DIEA (4.30 mL, 24.62 mmol) in DCM (80 mL) was added CbzCl (1.933 mL, 13.54 mmol) dropwise.

Then the mixture was stirred at 25° C. for 2 h. The mixture was concentrated and then water (30 mL) was added. The mixture was extracted with DCM (50 mL×2). The combined organic layers were washed with brine (50 mL), dried over Na$_2$SO$_4$, filtered and concentrated. The crude material was purified by flash chromatography (PE/EtOAc=5/1 to 1/1, TLC: PE/EtOAc=1/1, R$_f$=0.2) to yield (S)-benzyl 7-(hydroxymethyl)-1,4-oxazepane-4-carboxylate (1.7 g, 5.84 mmol, 47.5% yield) as a yellow oil: $^1$H NMR (400 MHz, CD$_3$OD) δ ppm 7.40-7.25 (m, 5H), 5.20-5.08 (m, 2H), 4.00 (m, 1H), 3.80-3.33 (m, 8H), 1.98-1.83 (m, 1H), 1.65-1.50 (m, 1H); ES-LCMS m/z 288.2 [M+Na]$^+$.

Step 6: (S)-Benzyl 7-(((methylsulfonyl)oxy)methyl)-1,4-oxazepane-4-carboxylate

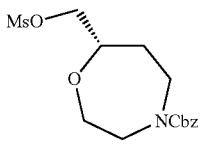 [SMILES: CS(=O)(=O)OC[C@@H]1CCN(C(=O)OCc2ccccc2)CCO1]

To a solution of (S)-benzyl 7-(hydroxymethyl)-1,4-oxazepane-4-carboxylate (850 mg, 2.92 mmol), Et$_3$N (0.865 mL, 4.38 mmol) in DCM (30 mL) was added MsCl (0.250 mL, 3.21 mmol) at 0° C. Then the mixture was stirred for 10 min. To the mixture was added water (20 mL). The mixture was extracted with DCM (30 mL×2). The combined organic layers were washed with brine (20 mL), dried over Na$_2$SO$_4$, filtered and concentrated to yield (S)-benzyl 7-(((methylsulfonyl)oxy)methyl)-1,4-oxazepane-4-carboxylate (1.1 g, 2.81 mmol, 96.0% yield) as light yellow oil: $^1$H NMR (400 MHz, CD$_3$OD) δ ppm 7.40-7.27 (m, 5H), 5.19-5.11 (m, 2H), 4.21-4.11 (m, 2H), 4.07-3.97 (m, 1H), 3.75 (d, J=13.2 Hz, 2H), 3.66-3.43 (m, 4H), 3.06 (s, 3H), 2.02-1.90 (m, 1H), 1.75-1.58 (m, 1H); ES-LCMS m/z 344.2 [M+H]$^+$.

Step 7: (S)-Benzyl 7-(cyanomethyl)-1,4-oxazepane-4-carboxylate

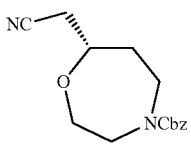 [SMILES: N#CC[C@@H]1CCN(C(=O)OCc2ccccc2)CCO1]

To a solution of (S)-benzyl 7-(((methylsulfonyl)oxy)methyl)-1,4-oxazepane-4-carboxylate (1.1 g, 2.81 mmol) in DMSO (20 mL) was added KCN (0.549 g, 8.44 mmol). Then the mixture was stirred for 10 h at 80° C. To the mixture was added saturated aqueous NaHCO$_3$ solution (30 mL). The mixture was extracted with DCM (50 mL×2). The combined organic layers were washed with brine (50 mL), dried over Na$_2$SO$_4$, filtered and concentrated. The crude material was purified by flash chromatography (PE/EtOAc=5/1 to 1/1, TLC: PE/EtOAc=1/1, R$_f$=0.45) to yield (S)-benzyl 7-(cyanomethyl)-1,4-oxazepane-4-carboxylate (700 mg, 2.493 mmol, 89.0% yield) as light yellow oil: $^1$H NMR (400 MHz, CD$_3$OD) δ ppm 7.46-7.16 (m, 5H), 5.18-5.10 (m, 2H), 4.07-3.96 (m, 1H), 3.82-3.42 (m, 6H), 2.73-2.53 (m, 2H), 2.06-1.92 (m, 1H), 1.80-1.65 (m, 1H); ES-LCMS m/z 275.2 [M+H]$^+$.

Step 8: (S)-Benzyl 7-(2-methoxy-2-oxoethyl)-1,4-oxazepane-4-carboxylate

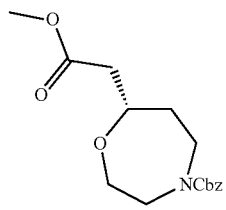 [SMILES: COC(=O)C[C@@H]1CCN(C(=O)OCc2ccccc2)CCO1]

A solution of (S)-benzyl 7-(cyanomethyl)-1,4-oxazepane-4-carboxylate (700 mg, 2.493 mmol) in HCl solution (4 M in MeOH, 15 mL, 60.0 mmol) was stirred for 72 h at 20° C. The mixture was concentrated to yield (S)-benzyl 7-(2-methoxy-2-oxoethyl)-1,4-oxazepane-4-carboxylate (580 mg, 1.887 mmol, 76.0% yield) as a light yellow solid: $^1$H NMR (400 MHz, CD$_3$OD) δ ppm 7.38-7.23 (m, 5H), 5.16-5.07 (m, 2H), 4.05-3.79 (m, 3H), 3.66-3.63 (m, 3H), 3.61-3.41 (m, 4H), 2.56-2.40 (m, 2H), 1.99-1.89 (m, 1H), 1.69-1.56 (m, 1H); ES-LCMS m/z 330.1 [M+Na]$^+$ Step 9: (S)-Methyl 2-(1,4-oxazepan-7-yl)acetate, trifluoroacetic acid salt

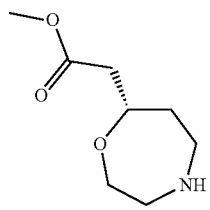

A solution of (S)-benzyl 7-(2-methoxy-2-oxoethyl)-1,4-oxazepane-4-carboxylate (350 mg, 0.994 mmol) in TFA (10 mL, 130 mmol) was stirred at 50° C. for 2 h. Then the mixture was concentrated to yield (S)-methyl 2-(1,4-oxazepan-7-yl)acetate, trifluoroacetic acid (300 mg, 0.909 mmol, 91.0% yield) as light yellow oil: $^1$H NMR (400 MHz, CD$_3$OD) δ ppm 4.18-4.08 (m, 1H), 4.00 (d, J=4.8, 13.8 Hz, 1H), 3.79 (ddd, J=3.9, 7.9, 14.1 Hz, 1H), 3.66 (s, 3H), 3.46-3.31 (m, 4H), 2.59-2.49 (m, 2H), 2.20-2.13 (m, 1H), 1.98-1.86 (m, 1H).

Intermediate 62: Benzyl (1R,5S,6r)-3-azabicyclo[3.1.0]hexan-6-ylcarbamate

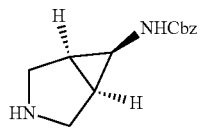 [SMILES: O=C(N[C@@H]1[C@@H]2CNC[C@@H]21)OCc1ccccc1]

Step 1: (1R,5S,6s)-3-tert-Butyl 6-ethyl 3-azabicyclo[3.1.0]hexane-3,6-dicarboxylate

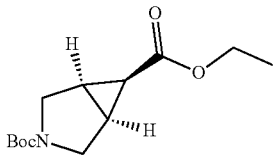 [SMILES: CCOC(=O)[C@@H]1[C@@H]2CN(C(=O)OC(C)(C)C)C[C@@H]21]

To a mixture of tert-butyl 2,5-dihydro-1H-pyrrole-1-carboxylate (10 g, 59.1 mmol) and Rhodium(II) acetate dimer (1.828 g, 4.14 mmol) in DCM (120 mL) was added ethyl diazoacetate (7.36 mL, 70.9 mmol) drop wise at 25° C. The reaction mixture was stirred at 25° C. for 12 h. The mixture was filtered and the filtrate was concentrated. The crude material was purified by flash chromatography (from pure PE to PE/EtOAc=3/1, TLC: PE/EtOAc=3/1, $R_f$=0.7) to yield (1S,5S,6s)-3-tert-butyl 6-ethyl 3-azabicyclo[3.1.0]hexane-3,6-dicarboxylate (1.3 g, 4.58 mmol, 7.8% yield) as colorless liquid: $^1$H NMR (400 MHz, CDCl$_3$) δ ppm 4.10 (q, J=6.9 Hz, 2H), 3.80-3.70 (m, 2H), 3.43 (t, J=9.9 Hz, 2H), 1.90-1.84 (m, 2H), 1.79-1.75 (m, 1H), 1.43 (s, 9H), 1.25 (t, J=7.2 Hz, 3H); ES-LCMS m/z: 200.1 [M+H-t-Bu]$^+$.

Step 2: (1R,5S,6s)-3-(tert-Butoxycarbonyl)-3-azabicyclo[3.1.0]hexane-6-carboxylic acid

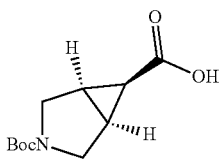

To a solution of (1R,5S,6S)-3-tert-butyl 6-ethyl 3-azabicyclo[3.1.0]hexane-3,6-dicarboxylate (500.00 mg, 1.763 mmol) in THF (6.00 mL) and H$_2$O (6.00 mL) was added LiOH·H$_2$O (740 mg, 17.63 mmol). The reaction mixture was stirred at 25° C. for 12 h. The reaction mixture was concentrated and dissolved by H$_2$O (30 mL). The mixture was adjusted pH to 4 with 1 N HCl. The mixture was extracted with DCM (100 mL×2). The combined organic layers were washed with brine (30 mL), dried over Na$_2$SO$_4$, filtered and concentrated to yield (1R,5S,6s)-3-(tert-butoxycarbonyl)-3-azabicyclo[3.1.0]hexane-6-carboxylic acid (350 mg, 1.386 mmol, 79.0% yield) as a pale yellow solid: $^1$H NMR (400 MHz, CDCl$_3$) δ ppm 3.75 (d, J=11.5 Hz, 2H), 3.50 (d, J=11.0 Hz, 2H), 2.00-1.95 (m, 2H), 1.81-1.75 (m, 1H), 1.43 (s, 9H); ES-LCMS m/z: 172.1 [M+H-t-Bu]$^+$.

Step 3: (1R,5S,6r)-tert-Butyl 6-(((benzyloxy)carbonyl)amino)-3-azabicyclo[3.1.0]hexane-3-carboxylate

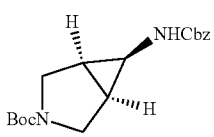 [SMILES: CC(C)(C)OC(=O)N1C[C@@H]2[C@H](C1)[C@@H]2NC(=O)OCc1ccccc1]

To a mixture of (1R,5S,6s)-3-(tert-butoxycarbonyl)-3-azabicyclo[3.1.0]hexane-6-carboxylic acid (350 mg, 1.386 mmol), DPPA (0.329 mL, 1.525 mmol) and Et$_3$N (0.386 mL, 2.77 mmol) in toluene (10 mL) was added BnOH (300 mg, 2.77 mmol). The mixture was stirred at 115° C. for 12 h under N$_2$ atmosphere. Then the mixture was concentrated to yield the crude material. The crude material was purified by flash chromatography (from pure PE to PE/EtOAc=1/1, TLC: PE/EtOAc=1/1, $R_f$=0.5) to yield (1R,5S,6r)-tert-butyl 6-(((benzyloxy)carbonyl)amino)-3-azabicyclo[3.1.0]hexane-3-carboxylate (380 mg, 1.029 mmol, 74.2% yield) as a brown solid: $^1$H NMR (400 MHz, CDCl$_3$) δ ppm 7.38-7.32 (m, 5H), 5.12 (s, 2H), 3.62-3.48 (m, 3H), 3.39 (d, J=10.6 Hz, 1H), 2.90 (s, 1H), 1.80 (s, 2H), 1.40 (s, 9H); ES-LCMS m/z: 277.1 [M+H-t-Bu]$^+$.

Step 4: Benzyl (1S,5S,6r)-3-azabicyclo[3.1.0]hexan-6-ylcarbamate, hydrochloride

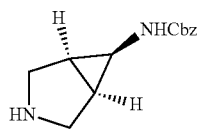 [SMILES: O=C(N[C@@H]1[C@@H]2CNC[C@@H]21)OCc1ccccc1]

A mixture of (1R,5S,6r)-tert-butyl 6-(((benzyloxy)carbonyl)amino)-3-azabicyclo[3.1.0]hexane-3-carboxylate (380 mg, 1.029 mmol) in HCl solution (4 M in EtOAc) (10 mL, 40.0 mmol) was stirred at 25° C. for 0.5 h. The mixture was concentrated to yield benzyl (1R,5S,6r)-3-azabicyclo[3.1.0]hexan-6-ylcarbamate, hydrochloride (300 mg, 1.005 mmol, 98.0% yield) as a brown solid: $^1$H NMR (400 MHz, CD$_3$OD) δ ppm 7.43-7.28 (m, 5H), 5.13 (s, 2H), 3.65-3.56 (m, 2H), 3.33 (s, 1H), 3.30 (s, 1H), 2.78 (t, J=6.8 Hz, 1H), 2.17-2.12 (m, 2H); ES-LCMS m/z: 233.2 [M+H]$^+$.

Intermediate 63: 4-(((tert-Butyldimethylsilyl)oxy)methyl)-2-chloro-6-(3,5-dichlorophenyl)-3-fluoropyridine

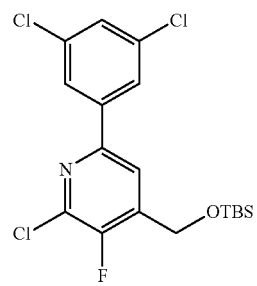 [SMILES: CC(C)(C)[Si](C)(C)OCc1cc(-c2cc(Cl)cc(Cl)c2)nc(Cl)c1F]

Step 1: Methyl 2-bromo-5-fluoroisonicotinate

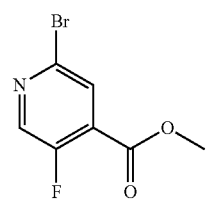

To a solution of 2-bromo-5-fluoroisonicotinic acid (25 g, 114 mmol) in MeOH (150 mL) was added SOCl$_2$ (25 mL, 343 mmol) and the mixture was stirred at 25° C. for 18 h. The reaction mixture was concentrated and DCM (40 mL) was added. The mixture was neutralized with 4 N NaOH to pH=7-8. The mixture was extracted with DCM (50 mL×3). The combined organic layers were washed with brine (50 mL), dried over Na$_2$SO$_4$, filtered and concentrated. The crude material was purified by flash chromatography (from PE/EtOAc=10/1 to 8/1, TLC: PE/EtOAc=2/1, $R_f$=0.7) to yield methyl 2-bromo-5-fluoroisonicotinate (25 g, 89 mmol, 78.0% yield) as a colorless solid: $^1$H NMR (400 MHz, CDCl$_3$) δ ppm 8.34 (d, J=1.5 Hz, 1H), 7.88 (d, J=4.9 Hz, 1H), 3.94-3.93 (m, 3H); ES-LCMS m/z 233.9, 235.9 [M+H]$^+$.

Step 2: Methyl 2-(3,5-dichlorophenyl)-5-fluoroisonicotinate

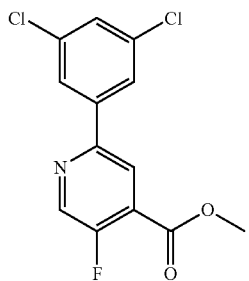 [SMILES: COC(=O)c1cc(-c2cc(Cl)cc(Cl)c2)ncc1F]

A solution of methyl 2-bromo-5-fluoroisonicotinate (7 g, 24.86 mmol), (3,5-dichlorophenyl)boronic acid (7.11 g, 37.3 mmol), K$_2$CO$_3$ (7.56 g, 54.7 mmol) and PdCl$_2$(dppf) (1.5 g, 2.050 mmol) in 1,4-dioxane (6 mL) was stirred at 80° C. for 4 h under N$_2$ atmosphere. The crude material was purified by flash chromatography (from PE/EtOAc=5/1 to 2/1, TLC: PE/EtOAc=3/1, $R_f$=0.6) to yield methyl 2-(3,5-dichlorophenyl)-5-fluoroisonicotinate (8 g, 21.33 mmol, 86.0% yield) as a white solid: $^1$H NMR (400 MHz, CDCl$_3$) δ ppm 9.27-9.17 (m, 1H), 8.77-8.67 (m, 1H), 8.47-8.37 (m, 2H), 8.02-7.90 (m, 1H), 4.60-4.56 (m, 3H); ES-LCMS m/z 300.0, 302.0 [M+H]$^+$.

Step 3: 2-(3,5-Dichlorophenyl)-5-fluoro-4-(methoxycarbonyl)pyridine 1-oxide

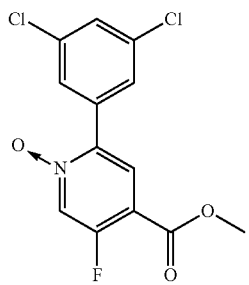

To a solution of methyl 2-(3,5-dichlorophenyl)-5-fluoroisonicotinate (9 g, 23.99 mmol) in MeOH (30.0 mL) and DCM (90 mL) was added m-CPBA (14.79 g, 60.0 mmol) and the mixture was stirred at 25° C. for 66 h. The mixture was neutralized with 2 N NaOH to pH=8. The mixture was extracted with DCM (70 mL×3). The combined organic layers were washed with brine (50 mL), dried over Na$_2$SO$_4$, filtered and concentrated. The crude material was purified by flash chromatography (from PE/EtOAc=20/1 to 15/1, TLC: PE/EtOAc=5/1, $R_f$=0.5) to yield 2-(3,5-dichlorophenyl)-5-fluoro-4-(methoxycarbonyl)pyridine 1-oxide (5 g, 13.35 mmol, 55.6% yield) as a white solid: $^1$H NMR (400 MHz, CDCl$_3$) δ ppm 8.26 (t, J=5.6 Hz, 1H), 7.96 (m, J=5.8, 8.5 Hz, 1H), 7.62 (m, J=1.9, 5.8 Hz, 2H), 7.45 (m, J=1.9, 3.9 Hz, 1H), 3.97 (d, J=6.0 Hz, 3H); ES-LCMS m/z 316.1, 318.0 [M+H]$^+$.

Step 4: Methyl 2-chloro-6-(3,5-dichlorophenyl)-3-fluoroisonicotinate

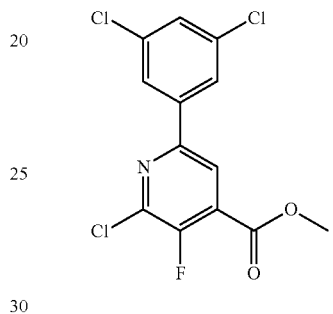

A solution of 2-(3,5-dichlorophenyl)-5-fluoro-4-(methoxycarbonyl)pyridine 1-oxide (3 g, 8.01 mmol) in POCl$_3$ (31.4 mL, 337 mmol) was stirred at 80° C. for 16 h. The reaction mixture was concentrated to yield the residue. DCM (10 mL) was added and the mixture was added into 10% NaOH (50 mL) slowly. The mixture was extracted with DCM (20 mL×3). The combined organic layers were washed with brine (30 mL), dried over Na$_2$SO$_4$, filtered and concentrated. The crude material was purified by flash chromatography (from PE/EtOAc=19/1 to 16/1, TLC: PE/EtOAc=3/1, $R_f$=0.7) to yield methyl 2-chloro-6-(3,5-dichlorophenyl)-3-fluoroisonicotinate (1.5 g, 3.59 mmol, 67.2% yield) as a white solid: $^1$H NMR (400 MHz, CDCl$_3$) δ ppm 8.01 (d, J=4.0 Hz, 1H), 7.82-7.78 (m, 2H), 7.38-7.34 (m, 1H), 3.96 (s, 3H); ES-LCMS m/z 334.0, 336.0 [M+H]$^+$.

Step 5: (2-Chloro-6-(3,5-dichlorophenyl)-3-fluoropyridin-4-yl)methanol

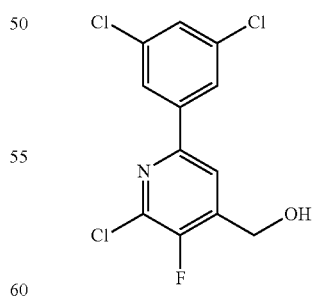

To a solution of methyl 2-chloro-6-(3,5-dichlorophenyl)-3-fluoroisonicotinate (3 g, 7.62 mmol) in MeOH (40 mL) was added NaBH$_4$ (0.577 g, 15.24 mmol) and the mixture was stirred at 25° C. for 40 min. The reaction mixture was quenched by the addition of saturated aqueous NH$_4$Cl solution (50 mL). The mixture was extracted with DCM (50 mL×3). The combined organic layers were washed with brine (50 mL), dried over $Na_2SO_4$, filtered and concentrated. The crude material was purified by flash chromatography (from PE/EtOAc=20/1 to 10/1, TLC: PE/EtOAc=5/1, $R_f$=0.6) to yield (2-chloro-6-(3,5-dichlorophenyl)-3-fluoropyridin-4-yl)methanol (3 g, 7.19 mmol, 94.0% yield) as a white solid: $^1$H NMR (400 MHz, $CDCl_3$) δ ppm 8.36 (d, J=3.5 Hz, 1H), 8.35-8.28 (m, 2H), 7.86 (d, J=1.8 Hz, 1H), 5.26 (s, 2H); ES-LCMS m/z 306.0, 308.0 $[M+H]^+$ Step 6: 4-(((tert-Butyldimethylsilyl)oxy)methyl)-2-chloro-6-(3,5-dichlorophenyl)-3-fluoropyridine

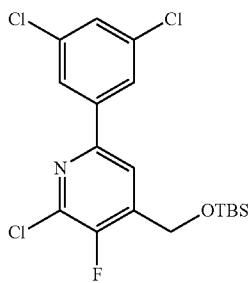 [SMILES: CC(C)(C)[Si](C)(C)OCc1cc(-c2cc(Cl)cc(Cl)c2)nc(Cl)c1F]

To a solution of (2-chloro-6-(3,5-dichlorophenyl)-3-fluoropyridin-4-yl)methanol (3.3 g, 7.91 mmol) in DCM (60 mL) was added 1H-imidazole (2.155 g, 31.6 mmol) and TBSCl (4.77 g, 31.6 mmol) and the mixture was stirred at 40° C. for 1 h. $H_2O$ (60 mL) was added. The mixture was extracted with DCM (50 mL×3). The combined organic layers were washed with brine (50 mL), dried over $Na_2SO_4$, filtered and concentrated. The crude material was purified by flash chromatography (from PE/EtOAc=10/1 to 5/1, TLC: PE/EtOAc=5/1, $R_f$=0.6) to yield 4-(((tert-butyldimethylsilyl)oxy)methyl)-2-chloro-6-(3,5-dichlorophenyl)-3-fluoropyridine (3.5 g, 7.07 mmol, 89.0% yield) as a white solid: $^1$H NMR (400 MHz, $CDCl_3$) δ ppm 7.86-7.84 (m, 2H), 7.83 (d, J=4.4 Hz, 1H), 7.45-7.38 (m, 1H), 4.87 (s, 2H), 1.00 (s, 9H), 0.18 (s, 6H); ES-LCMS m/z 419.8, 421.8 $[M+H]^+$.

Intermediate 64: 4-(2-(4,4,5,5-tetramethyl-1,3,2-dioxaborolan-2-yl)ethyl)piperidine

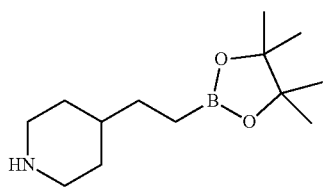 [SMILES: CC1(C)OB(CCC2CCNCC2)OC1(C)C]

Step 1: tert-Butyl 4-(2,2-dibromovinyl)piperidine-1-carboxylate

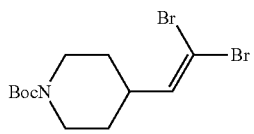

To a mixture of tert-butyl 4-formylpiperidine-1-carboxylate (9 g, 42.2 mmol) and $PPh_3$ (22.14 g, 84 mmol) in DCM (100 mL) was added $CBr_4$ (28.0 g, 84 mmol) in portions at 0° C. The reaction mixture was stirred at 0° C. for 3 h under $N_2$ atmosphere. Then the reaction mixture was stirred at 20° C. for 12 h under $N_2$ atmosphere. The reaction mixture was filtered and the filtrate was concentrated. The crude material was purified by flash chromatography (from pure PE to PE/EtOAc=5/1, $R_f$=0.7 (PE/EtOAc=5/1)) to yield tert-butyl 4-(2,2-dibromovinyl)piperidine-1-carboxylate (6.91 g, 16.82 mmol, 39.9% yield) as a white solid: $^1$H NMR (400 MHz, $CDCl_3$) δ ppm 6.16 (d, J=8.8 Hz, 1H), 4.00 (s, 2H), 2.70 (t, J=12.0 Hz, 2H), 2.43-2.31 (m, 1H), 1.64 (d, J=10.8 Hz, 2H), 1.39 (s, 9H), 1.31-1.21 (m, 2H); ES-LCMS m/z 312.0, 314.0, 316.0 $[M-t-Bu+H]^+$.

Step 2: (E)-tert-butyl 4-(2-bromovinyl)piperidine-1-carboxylate

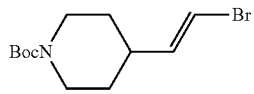

To a mixture of tert-butyl 4-(2,2-dibromovinyl)piperidine-1-carboxylate (5.91 g, 14.39 mmol) in MeOH (40 mL) and THF (20.00 mL) was added $NH_4Cl$ (6.16 g, 115 mmol) at 0° C., the reaction mixture was stirred at 0° C. for 30 min under $N_2$ atmosphere. Then zinc (3.76 g, 57.6 mmol) was added and the whole reaction mixture was stirred at 20° C. for 12 h under $N_2$ atmosphere. After filtration, the filtrate was concentrated to yield (E)-tert-butyl 4-(2-bromovinyl)piperidine-1-carboxylate (4.3 g, 14.08 mmol, 98.0% yield) as a white solid: $^1$H NMR (400 MHz, $CDCl_3$) δ ppm 6.21-5.85 (m, 2H), 4.06 (s, 2H), 2.82-2.64 (m, 2H), 2.21-2.05 (m, 1H), 1.66 (d, J=13.0 Hz, 2H), 1.44-1.42 (m, 9H), 1.35-1.21 (m, 2H); ES-LCMS m/z 234.0, 236.0 $[M-t-Bu+H]^+$.

Step 3: (E)-tert-Butyl 4-(2-(4,4,5,5-tetramethyl-1,3,2-dioxaborolan-2-yl)vinyl)piperidine-1-carboxylate

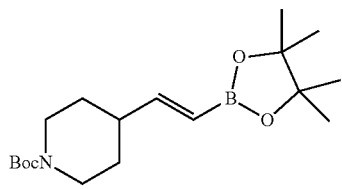 [SMILES: CC(C)(C)OC(=O)N1CCC(/C=C/B2OC(C)(C)C(C)(C)O2)CC1]

A mixture of (E)-tert-butyl 4-(2-bromovinyl)piperidine-1-carboxylate (2.3 g, 7.53 mmol), 4,4,4',4',5,5,5',5'-octamethyl-2,2'-bi(1,3,2-dioxaborolane) (2.87 g, 11.29 mmol), $PPh_3$ (0.197 g, 0.753 mmol), KOAc (1.478 g, 15.06 mmol) and $Pd_2(dba)_3$ (0.345 g, 0.376 mmol) in 1,4-dioxane (30 mL) was stirred at 110° C. for 12 h. The reaction mixture was filtered and the filtrate was concentrated. The crude material was purified by flash chromatography (from pure PE to PE/EtOAc=5/1, $R_f$=0.7 (PE/EtOAc=5/1)) to yield (E)-tert-butyl 4-(2-(4,4,5,5-tetramethyl-1,3,2-dioxaborolan-2-yl)vinyl)piperidine-1-carboxylate (2 g, 2.97 mmol, 39.4% yield) as a white solid: $^1$H NMR (400 MHz, $CDCl_3$) δ ppm 5.43 (dd, J=1.5, 18.1 Hz, 1H), 5.03-4.96 (m, 1H), 2.78-2.70 (m, 4H), 2.22-2.15 (m, 1H), 1.69 (d, J=16.3 Hz, 4H), 1.45 (s, 9H), 1.27 (s, 12H); ES-LCMS m/z 238.2 [M−Boc+H]+.

Step 4: tert-Butyl 4-(2-(4,4,5,5-tetramethyl-1,3,2-dioxaborolan-2-yl)ethyl)piperidine-1-carboxylate

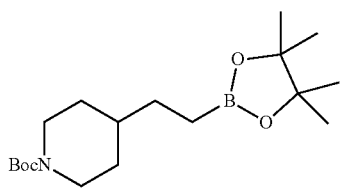 [SMILES: CC(C)(C)OC(=O)N1CCC(CCB2OC(C)(C)C(C)(C)O2)CC1]

A mixture of (E)-tert-butyl 4-(2-(4,4,5,5-tetramethyl-1,3,2-dioxaborolan-2-yl)vinyl)piperidine-1-carboxylate (2 g, 2.97 mmol) in MeOH (30 mL) was added Pd/C (10 wt %, 3.16 g, 2.97 mmol). The mixture was stirred at 20° C. for 10 min under H₂ atmosphere (15 psi). The reaction mixture was filtered and the filtrate was concentrated to yield tert-butyl 4-(2-(4,4,5,5-tetramethyl-1,3,2-dioxaborolan-2-yl)ethyl)piperidine-1-carboxylate (1.6 g, 2.358 mmol, 80.0% yield) as a yellow oil: ¹H NMR (400 MHz, CDCl₃) δ ppm 2.70-2.57 (m, 4H), 1.62 (d, J=12.3 Hz, 2H), 1.42 (d, J=2.0 Hz, 9H), 1.21 (s, 12H), 1.09-0.93 (m, 4H), 0.88-0.84 (m, 1H), 0.78-0.70 (m, 2H); ES-LCMS m/z 240.2 [M+H]+. Step 5: 4-(2-(4,4,5,5-Tetramethyl-1,3,2-dioxaborolan-2-yl)ethyl)piperidine, trifluoroacetic acid salt

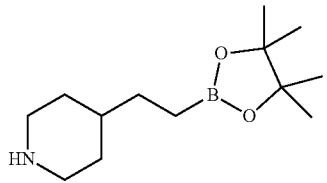 [SMILES: CC1(C)OB(CCC2CCNCC2)OC1(C)C]

To a solution of tert-butyl 4-(2-(4,4,5,5-tetramethyl-1,3,2-dioxaborolan-2-yl)ethyl)piperidine-1-carboxylate (600 mg, 0.884 mmol) in DCM (16 mL) was added TFA (4 mL, 51.9 mmol). The mixture was stirred at 30° C. for 0.5 h. The mixture was concentrated to yield 4-(2-(4,4,5,5-tetramethyl-1,3,2-dioxaborolan-2-yl)ethyl)piperidine, trifluoroacetic acid salt (420 mg, 0.595 mmol, 67.2% yield) as brown oil: ¹H NMR (400 MHz, CDCl₃) δ ppm 3.47 (d, J=11.0 Hz, 2H), 2.93 (d, J=11.0 Hz, 2H), 1.93 (d, J=12.3 Hz, 2H), 1.47-1.38 (m, 4H), 1.36-1.34 (m, 1H), 1.28-1.25 (m, 12H), 0.91-0.75 (m, 2H); ES-LCMS m/z 240.1 [M+H]+.

Intermediate 65: Methyl 2,2-dimethyl-3-(piperazin-1-yl)propanoate

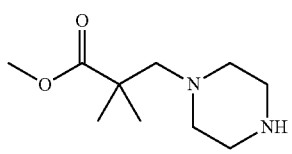

Step 1: tert-Butyl 4-(3-hydroxy-2,2-dimethylpropanoyl)piperazine-1-carboxylate

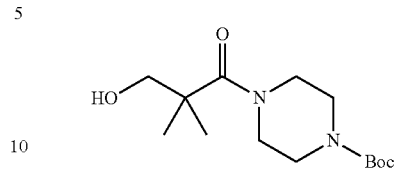

To a solution of 3-hydroxy-2,2-dimethylpropanoic acid (3 g, 25.4 mmol), DIEA (13.31 mL, 76 mmol) and tert-butyl piperazine-1-carboxylate (5.68 g, 30.5 mmol) in DCM (100 mL) was added EDC (9.74 g, 50.8 mmol) and HOBt (7.78 g, 50.8 mmol). Then the mixture was stirred at 26° C. for 8 h. The mixture was added water (80 mL). The mixture was extracted with EtOAc (100 mL×3). The combined organic layers were washed with brine (60 mL), dried over Na₂SO₄, filtered and concentrated. The crude material was purified by flash chromatography (from PE/EtOAc=20/1 to 2/1, TLC: PE/EtOAc=3/1, R_f=0.4) to yield tert-butyl 4-(3-hydroxy-2,2-dimethylpropanoyl)piperazine-1-carboxylate (6 g, 18.86 mmol, 74.3% yield) as a white solid: ¹H NMR (400 MHz, CDCl₃) δ ppm 3.63-3.58 (m, 4H), 3.52-3.48 (m, 2H), 3.45-3.38 (m, 4H), 1.49-1.47 (m, 9H), 1.30-1.25 (m, 6H); ES-LCMS m/z 287.1 [M+H]+.

Step 2: tert-Butyl 4-(3-hydroxy-2,2-dimethylpropyl)piperazine-1-carboxylate

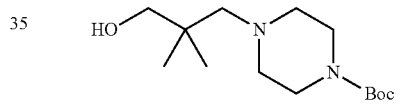

To a solution of tert-butyl 4-(3-hydroxy-2,2-dimethylpropanoyl)piperazine-1-carboxylate (5 g, 15.71 mmol) in THF (70 mL) was added BH₃·DMS (3.14 mL, 31.4 mmol) in portions at 26° C. Then the mixture was stirred at 80° C. for 3 h. The mixture was quenched with MeOH (10 mL) and concentrated. The crude material was purified by flash chromatography (from PE/EtOAc=5/1 to 1/1, TLC: PE/EtOAc=3/1, R_f=0.3) to yield tert-butyl 4-(3-hydroxy-2,2-dimethylpropyl)piperazine-1-carboxylate (3 g, 9.91 mmol, 63.1% yield) as colorless oil: ¹H NMR (400 MHz, CDCl₃) δ ppm 3.50 (s, 2H), 3.42 (brs, 4H), 2.54 (brs, 4H), 2.39 (s, 2H), 1.47-1.43 (m, 9H), 0.93 (s, 6H); ES-LCMS m/z 273.2 [M+H]+.

Step 3: 2,2-Dimethyl-3-(piperazin-1-yl)propan-1-ol, 2 hydrochloride

To a solution of tert-butyl 4-(3-hydroxy-2,2-dimethylpropyl)piperazine-1-carboxylate (2 g, 6.61 mmol) in EtOAc (10 mL) was added HCl solution (4 M in EtOAc, 5 mL, 20.00 mmol). The mixture was stirred at 26° C. for 0.5 h. The mixture was concentrated to give a white solid of 2,2-dimethyl-3-(piperazin-1-yl)propan-1-ol, 2 hydrochloride (1.6 g, 5.55 mmol, 84.0% yield): $^1$H NMR (400 MHz, CD$_3$OD) δ ppm 3.90 (br s, 1H), 3.77-3.59 (m, 6H), 3.58-3.51 (m, 3H), 3.34 (s, 2H), 1.12 (s, 6H); ES-LCMS m/z 173.2 [M+H]$^+$.

Step 4: Benzyl 4-(3-hydroxy-2,2-dimethylpropyl)piperazine-1-carboxylate

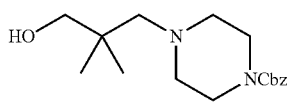 [SMILES: CC(C)(CO)CN1CCN(C(=O)OCc2ccccc2)CC1]

To a solution of 2,2-dimethyl-3-(piperazin-1-yl)propan-1-ol, 2 hydrochloride (1.6 g, 5.55 mmol) and DIEA (2.91 mL, 16.64 mmol) in DCM (50 mL) was added CbzCl (1.188 mL, 8.32 mmol) dropwise at 0° C. Then the mixture was stirred at 26° C. for 8 h. The mixture was quenched with water (20 mL). The mixture was extracted with DCM (100 mL×3). The combined organic layers were washed with brine (50 mL), dried over Na$_2$SO$_4$, filtered and concentrated. The crude material was purified by flash chromatography (from PE/EtOAc=5/1 to 1/1, TLC: PE/EtOAc=3/1, R$_f$=0.5) to yield benzyl 4-(3-hydroxy-2,2-dimethylpropyl)piperazine-1-carboxylate (1.8 g, 5.29 mmol, 95.0% yield) as pale yellow oil: $^1$H NMR (400 MHz, CDCl$_3$) δ ppm 7.37-7.27 (m, 5H), 5.10 (s, 2H), 3.57-3.44 (m, 6H), 2.54 (br s, 4H), 2.38 (s, 2H), 0.91 (s, 6H); ES-LCMS m/z 307.3 [M+H]$^+$.

Step 5: 3-(4-((Benzyloxy)carbonyl)piperazin-1-yl)-2,2-dimethylpropanoic acid

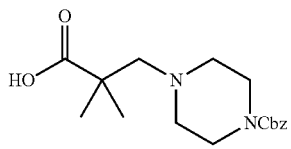 [SMILES: CC(C)(CN1CCN(C(=O)OCc2ccccc2)CC1)C(=O)O]

To a solution of benzyl 4-(3-hydroxy-2,2-dimethylpropyl)piperazine-1-carboxylate (1.3 g, 3.82 mmol) in acetone (5 mL) was added Jones' reagent (5 mL) (Jones' reagent: chromium(VI) oxide (1 g, 10.00 mmol) in H$_2$SO$_4$ (1 mL, 18.76 mmol) was diluted with water to 5 mL) at 0° C. The mixture was stirred at 26° C. for 4 h. The reaction mixture was quenched by i-PrOH (10 mL) at 0° C. The mixture was stirred at 0° C. for 10 min. Ammonium hydroxide (10 mL) was added to the mixture. Then the mixture was filtered and concentrated to give 3-(4-((benzyloxy)carbonyl)piperazin-1-yl)-2,2-dimethylpropanoic acid (300 mg, 0.655 mmol, 44.6% yield) as brown oil. $^1$H NMR (400 MHz, CDCl$_3$) δ ppm 7.28 (br s, 5H), 5.11 (br s, 2H), 3.64-3.41 (m, 6H), 2.79-2.50 (m, 4H), 1.47-0.66 (m, 6H); ES-LCMS m/z 321.2 [M+H]$^+$.

Step 6: Benzyl 4-(3-methoxy-2,2-dimethyl-3-oxopropyl)piperazine-1-carboxylate

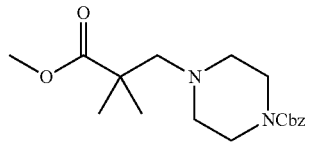 [SMILES: COC(=O)C(C)(C)CN1CCN(C(=O)OCc2ccccc2)CC1]

To a solution of 3-(4-((benzyloxy)carbonyl)piperazin-1-yl)-2,2-dimethylpropanoic acid (1500 mg, 3.28 mmol) in MeOH (10.0 mL) and DCM (10.0 mL) was added (diazomethyl)trimethylsilane (2 M in hexane) (3.28 mL, 6.55 mmol) at 0° C. The reaction mixture was stirred at 0° C. for 1 h. Then the mixture was concentrated to give the residue. The crude material was purified by flash chromatography (from PE/EtOAc=20/1 to 2/1, TLC: PE/EtOAc=3/1, R$_f$=0.6) to yield benzyl 4-(3-methoxy-2,2-dimethyl-3-oxopropyl)piperazine-1-carboxylate (600 mg, 1.669 mmol, 50.9% yield) as pale yellow oil: $^1$H NMR (400 MHz, CDCl$_3$) δ ppm 7.40-7.24 (m, 5H), 5.09 (d, J=4.0 Hz, 2H), 3.63 (d, J=4.2 Hz, 3H), 3.41 (d, J=4.9 Hz, 4H), 2.51-2.31 (m, 6H), 1.14 (d, J=4.2 Hz, 6H); ES-LCMS m/z 335.2 [M+H]$^+$.

Step 7: Methyl 2,2-dimethyl-3-(piperazin-1-yl)propanoate

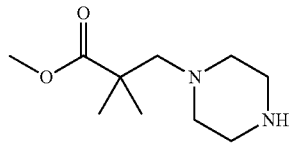

To a solution of benzyl 4-(3-methoxy-2,2-dimethyl-3-oxopropyl)piperazine-1-carboxylate (600 mg, 1.669 mmol) in MeOH (10.0 mL) was added Pd/C (10 wt %, 1776 mg, 1.669 mmol) at 26° C. The reaction mixture was stirred at 26° C. for 2 h under H$_2$ atmosphere at 15 psi. Then the mixture was filtered and concentrated to give yellow oil of methyl 2,2-dimethyl-3-(piperazin-1-yl)propanoate (250 mg, 0.999 mmol, 59.8% yield): $^1$H NMR (400 MHz, CD$_3$OD) δ ppm 3.67-3.60 (m, 3H), 2.85-2.76 (m, 3H), 2.57-2.34 (m, 7H), 1.16-1.11 (m, 6H); ES-LCMS m/z 201.2 [M+H]$^+$.

Intermediate 66: 1-((1-(((tert-butyldimethylsilyl)oxy)cyclopropyl)methyl)piperazine

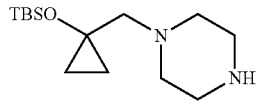

Step 1: Benzyl 4-(1-hydroxycyclopropanecarbonyl) piperazine-1-carboxylate

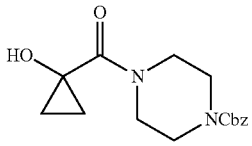 [SMILES: O=C(OCc1ccccc1)N1CCN(C(=O)C2(O)CC2)CC1]

To a mixture of benzyl piperazine-1-carboxylate (5 g, 22.70 mmol), 1-hydroxycyclopropanecarboxylic acid (2.78 g, 27.2 mmol), DIEA (39.6 mL, 227 mmol) in DCM (150 mL) was added EDC (6.53 g, 34.0 mmol) and HOBt (5.21 g, 34.0 mmol). Then, the mixture was stirred at 20° C. for 10 h. The mixture was concentrated and the residue was diluted with DCM (100 mL) and water (100 mL), extracted with DCM (200 mL×2). The combined organic layers were dried over Na$_2$SO$_4$, filtered and evaporated to afford crude product. The crude product was purified by flash chromatography (DCM/MeOH=20:1, R$_f$=0.5) to give benzyl 4-(1-hydroxycyclopropanecarbonyl)piperazine-1-carboxylate (6 g, 18.89 mmol, 83.0% yield) as a white solid: $^1$H NMR (400 MHz, CDCl$_3$) δ ppm 7.40-7.29 (m, 5H), 5.15 (s, 2H), 3.71 (br. s., 4H), 3.57-3.50 (m, 4H), 1.09-1.04 (m, 2H), 0.95-0.91 (m, 2H); ES-LCMS m/z 305.2 [M+H]$^+$.

Step 2: Benzyl 4-((1-hydroxycyclopropyl)methyl) piperazine-1-carboxylate

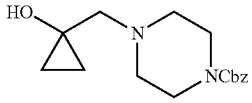 [SMILES: O=C(OCc1ccccc1)N1CCN(CC2(O)CC2)CC1]

To a solution of benzyl 4-(1-hydroxycyclopropanecarbonyl)piperazine-1-carboxylate (5.5 g, 17.62 mmol) in THF (100 mL) was added BH$_3$·DMS (4 mL, 40.0 mmol). Then, the mixture was stirred at 50° C. for 4 h. The reaction solution was quenched by MeOH (20 mL). The mixture was concentrated to afford crude product. The crude product was purified by flash chromatography (DCM/MeOH=20:1, R$_f$=0.5) to give benzyl 4-((1-hydroxycyclopropyl)methyl) piperazine-1-carboxylate (3 g, 8.27 mmol, 46.9% yield) as colorless oil: $^1$H NMR (400 MHz, CDCl$_3$) δ ppm 7.04-6.88 (m, 5H), 4.76 (s, 2H), 3.23-3.10 (m, 4H), 2.20 (br. s., 4H), 2.12 (s, 2H), 0.45 (t, J=5.7 Hz, 2H), 0.06-0.03 (m, 2H); ES-LCMS m/z 291.2 [M+H]$^+$.

Step 3: Benzyl 4-((1-((tert-butyldimethylsilyl)oxy) cyclopropyl)methyl)piperazine-1-carboxylate

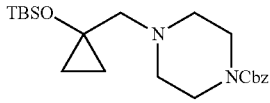 [SMILES: CC(C)(C)[Si](C)(C)OC1(CN2CCN(C(=O)OCc3ccccc3)CC2)CC1]

To a solution of benzyl 4-((1-hydroxycyclopropyl) methyl)piperazine-1-carboxylate (3 g, 8.27 mmol), 1H-imidazole (1.688 g, 24.80 mmol) in DCM (100 mL) was added TBSCl (2.492 g, 16.53 mmol). Then, the mixture was stirred at 40° C. for 16 h. The reaction mixture was diluted with DCM (50 mL) and water (100 mL), extracted with DCM (100 mL×2). The combined organic layers were dried over Na$_2$SO$_4$, filtered and evaporated to afford crude product. The crude product was purified by flash chromatography (PE/EtOAc=5:1, R$_f$=0.5) to give benzyl 4-((1-((tert-butyldimethylsilyl)oxy)cyclopropyl)methyl)piperazine-1-carboxylate (3 g, 7.31 mmol, 88.0% yield) as colorless oil: $^1$H NMR (400 MHz, CDCl$_3$) δ ppm 7.31-7.19 (m, 5H), 5.03 (s, 2H), 3.44-3.37 (m, 4H), 2.40 (br. s., 4H), 2.34 (s, 2H), 0.74 (s, 9H), 0.64-0.59 (m, 2H), 0.41-0.36 (m, 2H), 0.00 (s, 6H); ES-LCMS m/z 405.3 [M+H]$^+$.

Step 4: 1-((1-(((tert-Butyldimethylsilyl)oxy)cyclopropyl)methyl)piperazine

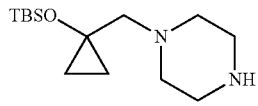 [SMILES: CC(C)(C)[Si](C)(C)OC1(CN2CCNCC2)CC1]

To a mixture of benzyl 4-((1-((tert-butyldimethylsilyl) oxy)cyclopropyl)methyl)piperazine-1-carboxylate (3 g, 7.31 mmol) in MeOH (40 mL) was added Pd/C (10 wt %, 0.778 g, 0.731 mmol). The mixture was stirred at 20° C. for 10 h under H$_2$ atmosphere (40 psi). Then the solution was filtered and concentrated to yield 1-((1-((tert-butyldimethylsilyl) oxy)cyclopropyl)methyl)piperazine (2 g, 6.28 mmol, 86.0% yield) as colorless oil: $^1$H NMR (400 MHz, CDCl$_3$) δ ppm 2.90 (t, J=4.5 Hz, 4H), 2.54 (br. s., 4H), 2.36 (s, 2H), 0.75 (s, 9H), 0.64-0.58 (m, 2H), 0.40-0.37 (m, 2H), 0.00 (s, 6H); ES-LCMS m/z 271.2 [M+H]$^+$.

Intermediate 67: 2-Oxa-4,9-diazaspiro[5.5]undecan-3-one

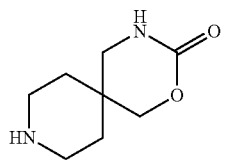 [SMILES: O=C1NCC2(CCNCC2)CO1]

Step 1: tert-Butyl 4-cyanopiperidine-1-carboxylate

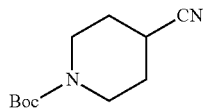 [SMILES: CC(C)(C)OC(=O)N1CCC(C#N)CC1]

To a solution of tert-butyl 4-oxopiperidine-1-carboxylate (5 g, 25.09 mmol), TosMIC (7.35 g, 37.6 mmol) and EtOH (2.93 mL, 50.2 mmol) in DME (150 mL) was added t-BuOK (8.45 g, 75 mmol) at −10° C. The reaction mixture was stirred at −10° C. for 2 h. Then the reaction mixture was warmed to 25° C. and stirred for 12 h. Then the mixture was filtered and concentrated. The crude material was purified by flash chromatography (from pure PE to PE/EtOAc=3/1, TLC: PE/EtOAc=5/1, R$_f$=0.4) to yield tert-butyl 4-cyanopiperidine-1-carboxylate (3.5 g, 14.15 mmol, 56.4% yield) as brown oil: $^1$H NMR (400 MHz, CDCl$_3$) δ ppm 3.64 (ddd, J=3.7, 7.1, 13.6 Hz, 2H), 3.32 (ddd, J=3.6, 7.8, 13.9 Hz, 2H), 2.79 (tt, J=4.1, 7.8 Hz, 1H), 1.91-1.74 (m, 4H), 1.44 (s, 9H); ES-LCMS m/z 155.1 [M−t−Bu+H]$^+$.

Step 2: 1-tert-Butyl 4-ethyl 4-cyanopiperidine-1,4-dicarboxylate

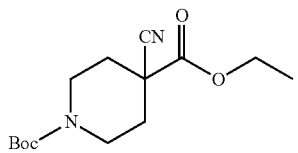 [SMILES: CCOC(=O)C1(C#N)CCN(C(=O)OC(C)(C)C)CC1]

To a solution of tert-butyl 4-cyanopiperidine-1-carboxylate (3.50 g, 14.15 mmol) in THF (50 mL) was added LiHMDS (1 M in THF, 28.3 mL, 28.3 mmol) at −78° C. under N$_2$ atmosphere. The reaction mixture was stirred for 1 h. Then ethyl chloroformate (3 mL, 31.2 mmol) was added. The reaction mixture was stirred for 1 h. Then the mixture was stirred at 25° C. for 12 h. The mixture was quenched by saturated aqueous NH$_4$Cl solution. Then the mixture was distributed between DCM (100 mL) and H$_2$O (100 mL), extracted with DCM (150 mL×3). The combined organic layers were washed with brine (100 mL), dried over Na$_2$SO$_4$, filtered and concentrated. The crude material was purified by flash chromatography (from pure PE to PE/EtOAc=5/1, TLC: PE/EtOAc=5/1, R$_f$=0.6) to yield 1-tert-butyl 4-ethyl 4-cyanopiperidine-1,4-dicarboxylate (3.9 g, 11.64 mmol, 82.0% yield) as colorless oil: $^1$H NMR (400 MHz, CDCl$_3$) δ ppm 4.30-4.20 (m, 2H), 4.08 (s, 2H), 3.08 (s, 2H), 2.07-1.89 (m, 4H), 1.45-1.40 (m, 9H), 1.34-1.26 (m, 3H); ES-LCMS m/z 183.1 [M−Boc+H]$^+$.

Step 3: tert-Butyl 4-cyano-4-(hydroxymethyl)piperidine-1-carboxylate

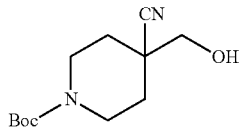 [SMILES: CC(C)(C)OC(=O)N1CCC(C#N)(CO)CC1]

To a solution of 1-tert-butyl 4-ethyl 4-cyanopiperidine-1,4-dicarboxylate (3.8 g, 11.35 mmol) in MeOH (30 mL) was added NaBH$_4$ (1.288 g, 34.0 mmol). The reaction mixture was stirred at 25° C. for 0.5 h. The mixture was quenched by saturated aqueous NH$_4$Cl solution (20 mL) and extracted with DCM (100 mL×3). The combined organic layers were washed with brine (50 mL), dried over Na$_2$SO$_4$, filtered and concentrated. The crude material was purified by flash chromatography (from PE/EtOAc=10/1 to 3/1, TLC: PE/EtOAc=3/1, R$_f$=0.3) to yield tert-butyl 4-cyano-4-(hydroxymethyl)piperidine-1-carboxylate (2.6 g, 9.74 mmol, 86.0% yield) as an off white solid: $^1$H NMR (400 MHz, CDCl$_3$) δ ppm 4.16 (s, 2H), 3.66 (d, J=6.2 Hz, 2H), 3.02 (s, 2H), 2.37 (t, J=6.4 Hz, 1H), 1.95 (d, J=13.2 Hz, 2H), 1.45 (s, 11H); ES-LCMS m/z 141.2 [M+H−Boc]$^+$.

Step 4: tert-Butyl 4-(aminomethyl)-4-(hydroxymethyl)piperidine-1-carboxylate

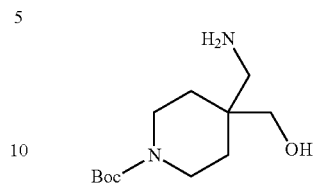

To a solution of tert-butyl 4-cyano-4-(hydroxymethyl)piperidine-1-carboxylate (1.5 g, 5.62 mmol) in THF (15 mL) was added LiAlH$_4$ (0.640 g, 16.85 mmol) at 0° C. under N$_2$ atmosphere. The reaction mixture was stirred at 0° C. for 1 h. The mixture was quenched by H$_2$O (1.5 mL), followed by 10% NaOH solution (1.5 mL). The mixture was filtered and the filtrate was concentrated to yield tert-butyl 4-(aminomethyl)-4-(hydroxymethyl)piperidine-1-carboxylate (1.2 g, 2.95 mmol, 52.5% yield) as colorless oil: $^1$H NMR (400 MHz, CDCl$_3$) δ ppm 4.34 (s, 2H), 3.73-3.66 (m, 4H), 2.83-2.80 (m, 4H), 2.27 (s, 2H), 1.44 (s, 9H); ES-LCMS m/z 189.2 [M−t−Bu+H]$^+$.

Step 5: tert-Butyl 3-oxo-2-oxa-4,9-diazaspiro[5.5]undecane-9-carboxylate

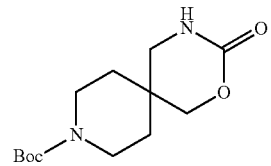 [SMILES: CC(C)(C)OC(=O)N1CCC2(CC1)CNC(=O)OC2]

To a mixture of tert-butyl 4-(aminomethyl)-4-(hydroxymethyl)piperidine-1-carboxylate (1.2 g, 2.95 mmol) and DIEA (1.029 mL, 5.89 mmol) in DCM (10 mL) was added di(1H-imidazol-1-yl)methanone (0.573 g, 3.54 mmol). Then the mixture was stirred at 25° C. for 3 h. The combined reaction mixture was concentrated to give crude material. The crude material was purified by preparative HPLC (MeCN/H$_2$O as eluents, acidic condition) followed by lyophilization to yield tert-butyl 3-oxo-2-oxa-4,9-diazaspiro[5.5]undecane-9-carboxylate (50 mg, 0.175 mmol, 5.9% yield) as a white solid: $^1$H NMR (400 MHz, CD$_3$OD) δ ppm 4.11 (s, 2H), 3.54 (d, J=13.2 Hz, 2H), 3.40-3.35 (m, 2H), 3.18 (s, 2H), 1.53 (t, J=5.8 Hz, 4H), 1.45 (s, 9H). ES-LCMS m/z 215.1 [M−t−Bu+H]$^+$.

Step 6: 2-Oxa-4,9-diazaspiro[5.5]undecan-3-one, hydrochloride

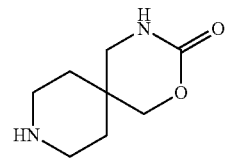 [SMILES: O=C1NCC2(CCNCC2)CO1]

A mixture of tert-butyl 3-oxo-2-oxa-4,9-diazaspiro[5.5]undecane-9-carboxylate (50 mg, 0.175 mmol) and HCl solution (4 M in EtOAc, 3 mL, 12.00 mmol) was stirred at 20° C. for 0.5 h. Then the mixture was concentrated to yield 2-oxa-4,9-diazaspiro[5.5]undecan-3-one, hydrochloride (35 mg, 0.152 mmol, 87.0% yield) as an off white solid: $^1$H NMR (400 MHz, CD$_3$OD) δ ppm 4.18 (s, 2H), 3.27-3.23 (m, 4H), 1.81 (t, J=5.7 Hz, 4H), 1.38 (d, J=6.0 Hz, 2H).

Intermediate 68: 1-(Piperidin-4-yl)propan-2-ol, trifluoroacetic acid salt

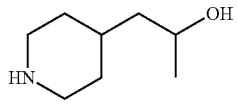

Step 1: tert-Butyl 4-(2-oxoethyl)piperidine-1-carboxylate

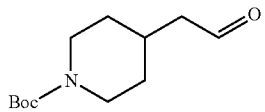

To a solution of oxalyl dichloride (13.39 mL, 157 mmol) in DCM (160 mL) cooled to −78° C. was added a solution of DMSO (16.71 mL, 235 mmol) in DCM (120 mL) dropwise over 30 minutes. After the addition completed, the mixture was warmed to −70° C. over a period of 20 min. Then to the mixture was added a solution of tert-butyl 4-(2-hydroxyethyl)piperidine-1-carboxylate (20 g, 78 mmol) in DCM (120 mL) dropwise over 30 min. Subsequently, a solution of DIEA (82 mL, 471 mmol) in DCM (80 mL) was added over 20 min, then the reaction flask was removed from the bath and allowed to warm to 0° C. over 60 min. The reaction solution was transferred to a 1000 mL separatory funnel charged with ice-cold 0.5 N HCl solution (240 mL). The two phases were separated, the aqueous phase was extracted with DCM (200 mL×3). The combined organic phases were dried over Na$_2$SO$_4$, filtered and concentrated to give pale yellow oil of tert-butyl 4-(2-oxoethyl)piperidine-1-carboxylate (16.5 g, 65.3 mmol, 83.0% yield): $^1$H NMR (400 MHz, CDCl$_3$) δ ppm 9.77 (s, 1H), 4.07 (s, 2H), 2.73 (bt, J=12.5 Hz, 2H), 2.37 (dd, J=1.7, 6.7 Hz, 2H), 2.11-1.93 (m, 1H), 1.68 (d, J=13.2 Hz, 2H), 1.48-1.38 (m, 9H), 1.26-1.03 (m, 2H)

Step 2: tert-Butyl 4-(2-hydroxypropyl)piperidine-1-carboxylate

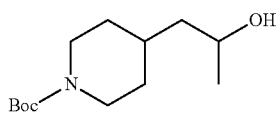

To a solution of tert-butyl 4-(2-oxoethyl)piperidine-1-carboxylate (1 g, 3.96 mmol) in THF (20 mL) cooled to 0° C. was added MeMgBr (3 M in THF, 1.980 mL, 5.94 mmol) dropwise under N$_2$ atmosphere. The mixture was stirred at 0° C. for 2 h. The mixture was quenched with saturated aqueous NH$_4$Cl solution (20 mL), extracted with EtOAc (30 mL×2). The organic layers were dried over Na$_2$SO$_4$, filtered and concentrated. The residue was purified by flash chromatography (from pure PE to PE/EtOAc=5/1, TLC: PE/EtOAc=3:1, R$_f$=0.3) to yield a colorless oil of tert-butyl 4-(2-hydroxypropyl)piperidine-1-carboxylate (700 mg, 2.59 mmol, 65.4% yield): $^1$H NMR (400 MHz, CDCl$_3$) δ ppm 4.08-4.01 (m, 2H), 3.86 (s, 1H), 2.66-2.63 (m, 2H), 1.67-1.65 (m, 1H), 1.57-1.54 (m, 2H), 1.38 (s, 9H), 1.24-1.19 (m, 6H), 1.14-1.13 (m, 2H); ES-LCMS m/z: 188.1 [M−t−Bu+H]$^+$.

Step 3: 1-(Piperidin-4-yl)propan-2-ol, trifluoroacetic acid salt

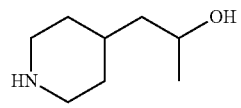

To a solution of tert-butyl 4-(2-hydroxypropyl)piperidine-1-carboxylate (700 mg, 2.59 mmol) in DCM (20 mL) was added TFA (5 mL, 64.9 mmol). The mixture was stirred at 20° C. for 2 h. The mixture was concentrated to give brown oil of 1-(piperidin-4-yl)propan-2-ol, trifluoro acetic acid (700 mg, 2.313 mmol, 89.0% yield): $^1$H NMR (400 MHz, CD$_3$OD) δ ppm 5.28-5.20 (m, 1H), 3.38-3.34 (m, 2H), 2.98-2.95 (m, 2H), 2.00-1.98 (m, 2H), 1.79-1.77 (m, 2H), 1.64-1.55 (m, 1H), 1.49-1.40 (m, 2H), 1.38-1.37 (m, 3H); ES-LCMS m/z: 144.1 [M+H]$^+$.

Intermediate 69: Ethyl 2-(4-aminopiperidin-4-yl)acetate, 2 hydrochloride

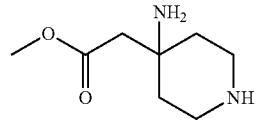

Step 1: tert-Butyl 4-amino-4-(2-ethoxy-2-oxoethyl)piperidine-1-carboxylate

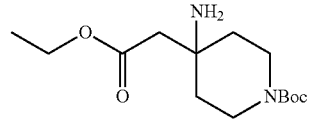 [SMILES: CCOC(=O)CC1(N)CCN(C(=O)OC(C)(C)C)CC1]

To a mixture of 3-ethoxy-3-oxopropanoic acid (13.26 g, 100 mmol) and NH$_4$OAc (10.83 g, 141 mmol) in EtOH (200 mL) was added tert-butyl 4-oxopiperidine-1-carboxylate (20 g, 100 mmol) in batches at 85° C. under N$_2$ atmosphere. Then the reaction mixture was stirred at 85° C. for 3 h. The mixture was concentrated and then saturated aqueous NaHCO$_3$ (100 mL) solution was added. The mixture was extracted with DCM (100 mL×3). The combined organic layers were washed with brine (50 mL), dried over Na$_2$SO$_4$, filtered and concentrated. The crude product was purified by flash chromatography (from pure DCM to DCM/MeOH=10/

1; TLC: DCM/MeOH=8/1, $R_f$=0.5) to yield tert-butyl 4-amino-4-(2-ethoxy-2-oxoethyl)piperidine-1-carboxylate (12 g, 33.5 mmol, 33.4% yield) as brown oil: $^1$H NMR (400 MHz, CDCl$_3$) δ ppm 4.23-4.13 (m, 2H), 3.73-3.59 (m, 2H), 3.42 (d, J=13.5 Hz, 2H), 2.77 (s, 2H), 2.02-1.87 (m, 2H), 1.79 (s, 2H), 1.43 (s, 9H), 1.31-1.20 (m, 3H); ES-LCMS m/z 287.4 [M+H]$^+$.

Step 2: Ethyl 2-(4-aminopiperidin-4-yl)acetate, 2 hydrochloride

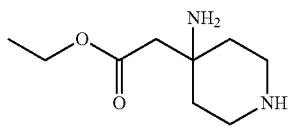

To a mixture of tert-butyl 4-amino-4-(2-ethoxy-2-oxo-ethyl)piperidine-1-carboxylate (15 g, 41.9 mmol) was added HCl solution (4 M in EtOAc, 100 mL) in batches at 25° C. Then the reaction mixture was stirred at 25° C. for 0.5 h. The mixture was concentrated to yield ethyl 2-(4-aminopiperidin-4-yl)acetate, 2 hydrochloride (12 g, 37.0 mmol, 88.0% yield) as a white solid: $^1$H NMR (400 MHz, CDCl$_3$) δ ppm 4.27-4.15 (m, 2H), 3.47-3.34 (m, 2H), 3.29-3.25 (m, 2H), 2.99 (s, 2H), 2.27-2.12 (m, 4H), 1.31-1.23 (m, 3H).

Intermediate 70: tert-Butyl 6-((tert-butyldimethylsilyl)oxy)-4-(5-hydroxypyrimidin-2-yl)-1,4-diazepane-1-carboxylate

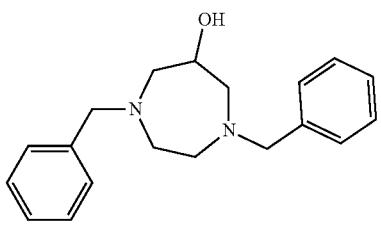

Step 1: N$^1$,N$^2$-Dibenzylethane-1,2-diamine

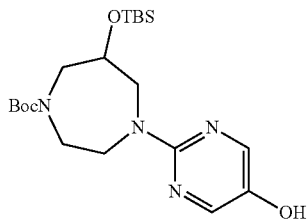 [SMILES: CC(C)(C)OC(=O)N1CCN(c2ncc(O)cn2)CC(O[Si](C)(C)C(C)(C)C)C1]

To a mixture of ethane-1,2-diamine (22.27 mL, 333 mmol) and 4 Å molecular sieves (8 g, 333 mmol) in MeOH (400 mL) was added benzaldehyde (67.3 mL, 666 mmol). Then, the mixture was stirred at 80° C. for 4 h under N$_2$ atmosphere and then cooled via an ice bath. Then NaBH$_4$ (54.1 g, 1431 mmol) was added slowly and the mixture was stirred at 0° C. for 4 h. Saturated aqueous NH$_4$Cl solution (800 mL) was added to the mixture slowly. The mixture was filtered and concentrated to give the residue which was distributed between DCM (500 mL) and saturated aqueous NaHCO$_3$ solution (500 mL), extracted with DCM (500 mL×2). The combined organic layers were dried over Na$_2$SO$_4$, filtered and concentrated. The crude product was purified by flash chromatography (DCM/MeOH=20:1 to 10/1, TLC: DCM/MeOH=10:1, $R_f$=0.5) to yield N$^1$,N$^2$-dibenzylethane-1,2-diamine (42 g, 140 mmol, 42.0% yield) as a pale yellow solid: $^1$H NMR (400 MHz, CD$_3$OD) δ ppm 7.31 (d, J=4.4 Hz, 10H), 3.71 (s, 4H), 2.71 (s, 4H); ES-LCMS m/z 241.3 [M+H]$^+$.

Step 2: 1,4-Dibenzyl-1,4-diazepan-6-ol

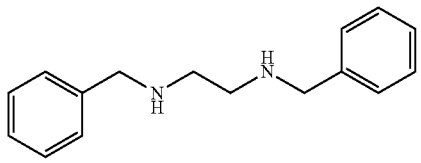 [SMILES: c1ccc(CNCCNCc2ccccc2)cc1]

To a solution of N$^1$,N$^2$-dibenzylethane-1,2-diamine (5 g, 16.64 mmol) in toluene (100 mL) was added 1,3-dibromopropan-2-ol (3.81 g, 17.47 mmol) and Et$_3$N (4.64 mL, 33.3 mmol). The mixture was stirred at 125° C. for 7 h. The mixture was concentrated to give the residue which was distributed between DCM (30 mL) and H$_2$O (20 mL), extracted with DCM (30 mL×2). The combined organic layers were washed with brine (20 mL), dried over Na$_2$SO$_4$, filtered and concentrated. The crude product was purified by flash chromatography (DCM/MeOH=20/1 to 10/1, TLC: PE/EtOAc=1:1 $R_f$=0.5) to yield a pale yellow oil of 1,4-dibenzyl-1,4-diazepan-6-ol (3.8 g, 10.26 mmol, 61.6% yield): $^1$H NMR (400 MHz, CD$_3$OD) δ ppm 7.40-7.17 (m, 10H), 3.85-3.78 (m, 1H), 3.71-3.61 (m, 4H), 2.89 (dd, J=4.4, 12.8 Hz, 2H), 2.73-2.59 (m, 6H); ES-LCMS m/z 297.1 [M+H]$^+$.

Step 3: 1,4-Diazepan-6-ol

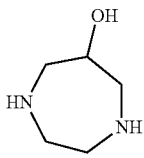

To a solution of 1,4-dibenzyl-1,4-diazepan-6-ol (3.8 g, 10.26 mmol) in MeOH (10 mL) was added Pd/C (10 wt %, 800 mg, 0.752 mmol). The mixture was stirred at 25° C. for 8 h under H$_2$ atmosphere (50 psi). The mixture was filtered and concentrated to yield a yellow oil of 1,4-diazepan-6-ol (1.2 g, 8.26 mmol, 81.0% yield): $^1$H NMR (400 MHz, CDCl$_3$) δ ppm 3.80-3.73 (m, 1H), 3.05-2.94 (m, 4H), 2.90-2.77 (m, 4H), 2.30 (br.s, 2H).

Step 4: 1-(5-(Benzyloxy)pyrimidin-2-yl)-1,4-diazepan-6-ol

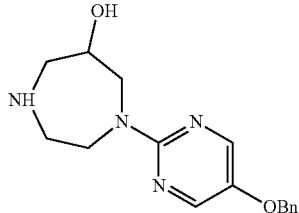 [SMILES: OC1CNCCN(c2ncc(OCc3ccccc3)cn2)C1]

To a mixture of 5-(benzyloxy)-2-chloropyrimidine (850 mg, 3.66 mmol) and 1,4-diazepan-6-ol (1063 mg, 7.32 mmol) in DMSO (100 mL) was added DIEA (0.639 mL, 3.66 mmol). The mixture was stirred at 130° C. for 8 h. The mixture was concentrated to give the crude product which was purified by flash chromatography (from pure DCM to DCM/MeOH=10/1, TLC: DCM/MeOH=10/1, $R_f$=0.12) to afford 1-(5-(benzyloxy)pyrimidin-2-yl)-1,4-diazepan-6-ol (1 g, 3.06 mmol, 84.0% yield) as a pale yellow solid: $^1$H NMR (400 MHz, CDCl$_3$) δ 8.01 (s, 2H), 7.35-7.20 (m, 5H), 4.94 (s, 2H), 4.13 (td, J=4.2, 8.7 Hz, 1H), 4.03-3.76 (m, 4H), 3.16-3.07 (m, 1H), 3.01-2.86 (m, 3H); ES-LCMS m/z 301.1 [M+H]$^+$.

Step 5: tert-Butyl 4-(5-(benzyloxy)pyrimidin-2-yl)-6-hydroxy-1,4-diazepane-1-carboxylate

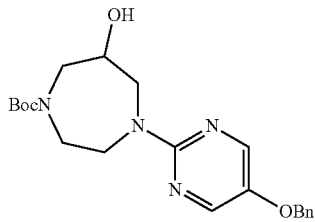 [SMILES: CC(C)(C)OC(=O)N1CCN(c2ncc(OCc3ccccc3)cn2)CC(O)C1]

To a solution of 1-(5-(benzyloxy)pyrimidin-2-yl)-1,4-diazepan-6-ol (1 g, 3.06 mmol) and DIEA (1.188 g, 9.19 mmol) in DCM (50 mL) was added Boc$_2$O (0.711 mL, 3.06 mmol). Then the reaction mixture was stirred at 20° C. for 12 h. DCM (50 mL) was added and washed with aqueous citric acid (10%, 50 mL×3). The organic layers was dried over Na$_2$SO$_4$ and concentrated in vacuo to give tert-butyl 4-(5-(benzyloxy)pyrimidin-2-yl)-6-hydroxy-1,4-diazepane-1-carboxylate (1 g, 2.460 mmol, 80.0% yield) as a pale yellow solid: $^1$H NMR (400 MHz, CDCl$_3$) δ ppm 8.02 (s, 2H), 7.35-7.27 (m, 5H), 4.95 (s, 2H), 4.01 (d, J=13.7 Hz, 1H), 3.90 (dd, J=6.0, 14.3 Hz, 1H), 3.78-3.66 (m, 1H), 3.64-3.45 (m, 2H), 3.38 (dd, J=4.9, 15.4 Hz, 1H), 3.11-3.01 (m, 1H), 2.94-2.83 (m, 1H), 2.51 (dd, J=9.0, 14.3 Hz, 1H), 1.40 (s, 9H); ES-LCMS m/z 401.2 [M+H]$^+$.

Step 6: tert-Butyl 4-(5-(benzyloxy)pyrimidin-2-yl)-6-((tert-butyldimethylsilyl)oxy)-1,4-diazepane-1-carboxylate

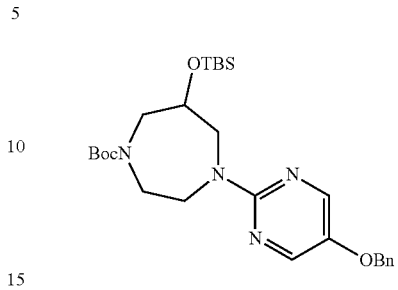

To a solution of tert-butyl 4-(5-(benzyloxy)pyrimidin-2-yl)-6-hydroxy-1,4-diazepane-1-carboxylate (1 g, 2.460 mmol), 1H-imidazole (0.502 g, 7.38 mmol) in DCM (100 mL) was added TBSCl (0.741 g, 4.92 mmol). Then, the mixture was stirred at 40° C. for 20 h. The mixture was concentrated and this reaction mixture was diluted with DCM (100 mL) and water (100 mL), extracted with DCM (100 mL×2). The combined organic layers were dried over Na$_2$SO$_4$, filtered and concentrated. The crude residue was purified by flash chromatography (from PE/EtOAc=8/1 to 5/1, TLC: PE/EtOAc=5:1, $R_f$=0.5) to give tert-butyl 4-(5-(benzyloxy)pyrimidin-2-yl)-6-((tert-butyldimethylsilyl)oxy)-1,4-diazepane-1-carboxylate (1.3 g, 2.432 mmol, 99.0% yield) as a pale yellow solid: $^1$H NMR (400 MHz, CDCl$_3$) δ ppm 7.96 (s, 2H), 7.32-7.19 (m, 5H), 4.87 (d, J=3.5 Hz, 2H), 4.30-4.11 (m, 2H), 3.86-3.75 (m, 1H), 3.65 (dd, J=3.5, 14.1 Hz, 1H), 3.24-3.11 (m, 1H), 3.07-2.95 (m, 2H), 2.80 (dd, J=9.0, 13.9 Hz, 1H), 2.66 (dd, J=9.5, 13.5 Hz, 1H), 1.25-1.15 (m, 9H), 0.84-0.73 (m, 9H), 0.08-0.02 (m, 6H); ES-LCMS m/z 515.3 [M+H]$^+$.

Step 7: tert-Butyl 6-((tert-butyldimethylsilyl)oxy)-4-(5-hydroxypyrimidin-2-yl)-1,4-diazepane-1-carboxylate

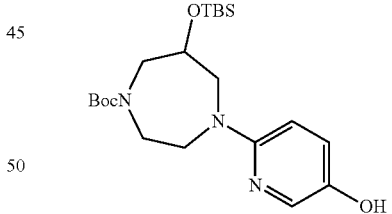

To a solution of tert-butyl 4-(5-(benzyloxy)pyrimidin-2-yl)-6-((tert-butyldimethylsilyl)oxy)-1,4-diazepane-1-carboxylate (1.3 g, 2.432 mmol) in MeOH (50 mL) was added Pd/C (10 wt %, 0.259 g, 0.243 mmol). Then the reaction mixture was stirred at 20° C. for 1 h under H$_2$ atmosphere (16 psi). After filtration, the filtrate was concentrated to yield tert-butyl 6-((tert-butyldimethylsilyl)oxy)-4-(5-hydroxypyrimidin-2-yl)-1,4-diazepane-1-carboxylate (1 g, 2.256 mmol, 93.0% yield) as a yellow oil: $^1$H NMR (400 MHz, CD$_3$OD) δ ppm 7.99-7.92 (m, 2H), 4.44-4.33 (m, 2H), 4.14-3.91 (m, 3H), 3.88-3.76 (m, 1H), 3.15-3.03 (m, 2H), 2.90 (dt, J=4.2, 13.6 Hz, 1H), 1.30 (d, J=9.3 Hz, 9H), 0.96-0.90 (m, 9H), 0.21-0.13 (m, 6H); ES-LCMS m/z 425.3 [M+H]$^+$.

Intermediate 71: 6-Fluoro-1,4-diazepane

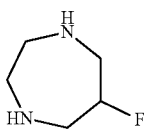

Step 1: 1,4-Dibenzyl-6-fluoro-1,4-diazepane

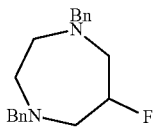

To a mixture of 1,4-dibenzyl-1,4-diazepan-6-ol (3 g, 8.10 mmol) in DCM (50 mL) was added DAST (1.605 mL, 12.15 mmol) at 0° C. The mixture was stirred at 20° C. for 0.5 h. The reaction mixture was quenched by the addition of saturated aqueous NaHCO$_3$ solution (50 mL) at 0° C. The mixture was extracted with DCM (50 mL×3). The combined organic layers were washed with brine (50 mL), dried over Na$_2$SO$_4$, filtered and concentrated. The crude product was purified by flash chromatography (from EtOAc/PE=0/1 to 1/2, TLC: EtOAc/PE=1/3, R$_f$=0.5) to afford 1,4-dibenzyl-6-fluoro-1,4-diazepane (900 mg, 2.56 mmol, 31.7% yield) as a pale yellow solid: $^1$H NMR (400 MHz, CD$_3$OD) δ ppm 7.31-7.18 (m, 10H), 4.59 (dd, J=4.4, 9.9 Hz, 1H), 4.10-3.96 (m, 2H), 3.54-3.47 (m, 2H), 2.80-2.64 (m, 4H), 2.37-2.13 (m, 4H); ES-LCMS m/z 298.8 [M+H]$^+$.

Step 2: 6-Fluoro-1,4-diazepane

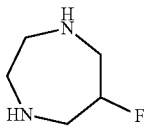

A mixture of 1,4-dibenzyl-6-fluoro-1,4-diazepane (300 mg, 0.855 mmol) in MeOH (10 mL) was added Pd/C (10 wt %, 455 mg, 0.427 mmol). The mixture was stirred at 50° C. for 12 h under H$_2$ (50 psi). The mixture was filtered, washed with MeOH (20 mL×2). The filtrate was concentrated to yield 6-fluoro-1,4-diazepane (110 mg, 0.745 mmol, 87.0% yield) as a pale yellow solid: $^1$H NMR (400 MHz, CD$_3$OD) δ ppm 4.44-4.36 (m, 1H), 2.99-2.91 (m, 4H), 2.83-2.34 (m, 4H).

Intermediate 72: Methyl 2-ethyl-4-(piperazin-1-yl)butanoate, 2 hydrochloride

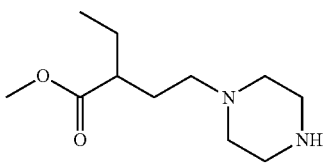

Step 1: tert-Butyl 4-(4-methoxy-4-oxobutyl)piperazine-1-carboxylate

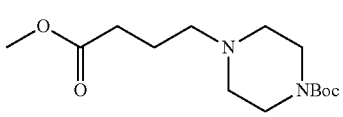 [SMILES: COC(=O)CCCN1CCN(C(=O)OC(C)(C)C)CC1]

A mixture of tert-butyl piperazine-1-carboxylate (3 g, 16.11 mmol), methyl 4-bromobutanoate (4.37 g, 24.16 mmol) and K$_2$CO$_3$ (6.68 g, 48.3 mmol) in MeCN (60 mL) was stirred at 80° C. for 6 h. The mixture was filtered and concentrated. The crude material was purified by flash chromatography (from PE/EtOAc=10/1 to 2/1, TLC: PE/EtOAc=3/1, R$_f$=0.4) to yield tert-butyl 4-(4-methoxy-4-oxobutyl)piperazine-1-carboxylate (4.5 g, 14.14 mmol, 88.0% yield) as a yellow oil: $^1$H NMR (400 MHz, CDCl$_3$) δ ppm 3.67 (s, 3H), 3.45-3.35 (m, 4H), 2.36 (dt, J=1.4, 7.2 Hz, 8H), 1.81 (q, J=7.2 Hz, 2H), 1.46 (s, 9H); ES-LCMS m/z 287.2 [M+H]$^+$.

Step 2: tert-Butyl 4-(3-(methoxycarbonyl)pentyl)piperazine-1-carboxylate

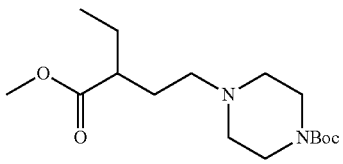 [SMILES: CCC(CCN1CCN(C(=O)OC(C)(C)C)CC1)C(=O)OC]

A mixture of diisopropylamine (1.792 mL, 12.57 mmol) in THF (50 mL) was added dropwise n-BuLi (2.5 M in hexane, 5.03 mL, 12.57 mmol) at −78° C. Then the mixture was stirred at −78° C. for 0.5 h. tert-Butyl 4-(4-methoxy-4-oxobutyl)piperazine-1-carboxylate (2 g, 6.29 mmol) was added dropwise to the mixture at −78° C. under N$_2$ atmosphere. Then the mixture was stirred at 0° C. for 0.5 h under N$_2$ atmosphere. Iodoethane (1.524 mL, 18.86 mmol) was added to the mixture at −78° C. Then the mixture was stirred at 26° C. for 7 h under N$_2$ atmosphere. The mixture was quenched by the addition of saturated aqueous NH$_4$Cl solution (20 mL) at 0° C. The mixture was extracted with EtOAc (100 mL×3). The combined organic layers were washed with brine (50 mL), dried over Na$_2$SO$_4$, filtered and concentrated. The crude material was purified by flash chromatography (from PE/EtOAc=5/1 to 2/1, TLC: PE/EtOAc=5/1, R$_f$=0.6) to yield tert-butyl 4-(3-(methoxycarbonyl)pentyl)piperazine-1-carboxylate (1.5 g, 4.29 mmol, 68.3% yield) as pale yellow oil. NMR (400 MHz, CDCl$_3$) δ ppm 3.65 (s, 3H), 3.37 (d, J=4.0 Hz, 4H), 2.37-2.20 (m, 7H), 1.68-1.49 (m, 4H), 1.43 (s, 9H), 0.87 (t, J=7.4 Hz, 3H); ES-LCMS m/z 315.3 [M+H]$^+$.

Step 3: Methyl 2-ethyl-4-(piperazin-1-yl)butanoate, 2 hydrochloride

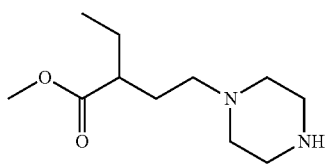

To a solution of tert-butyl 4-(3-(methoxycarbonyl)pentyl)piperazine-1-carboxylate (500 mg, 1.431 mmol) in EtOAc (10 mL) was added HCl solution (4 M in EtOAc) (5 mL, 20.00 mmol) at 26° C. Then the mixture was stirred at 26° C. for 0.5 h. The mixture was concentrated to give methyl 2-ethyl-4-(piperazin-1-yl)butanoate, 2 hydrochloride (450 mg, 1.332 mmol, 93.0% yield) as a pale solid: $^1$H NMR (400 MHz, CD$_3$OD) δ ppm 4.17-3.39 (m, 11H), 3.28-3.18 (m, 2H), 2.53-2.41 (m, 1H), 2.16-1.90 (m, 2H), 1.77-1.57 (m, 2H), 0.92 (t, J=7.4 Hz, 3H); ES-LCMS m/z 215.1 [M+H]$^+$.

Intermediate 73: tert-Butyl 4,7-diazaspiro[2.5]octane-4-carboxylate

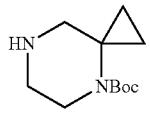

Step 1: 1-((tert-Butoxycarbonyl)amino)cyclopropanecarboxylic acid

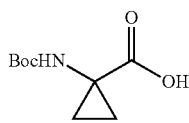

To a solution of 1-aminocyclopropanecarboxylic acid (30 g, 297 mmol) and tetramethylammonium hydroxide (27.0 g, 297 mmol) in MeCN (400 mL) was added Boc$_2$O (130 g, 593 mmol). Then the reaction mixture was stirred at 15° C. for 24 h. The mixture was concentrated and dissolved with EtOAc (500 mL). The mixture was washed with saturated citric acid solution (200 mL×2). The organic phase was dried over Na$_2$SO$_4$, concentrated to give 1-((tert-butoxycarbonyl)amino)cyclopropanecarboxylic acid (30 g, 142 mmol, 47.7% yield) as a white solid: $^1$H NMR (400 MHz, DMSO-d$_6$) δ ppm 12.26 (br. s., 1H), 7.40 (s, 1H), 1.37 (s, 9H), 1.29-1.22 (m, 2H), 1.02-0.89 (m, 2H); ES-LCMS m/z 146.1 [M−t−Bu+H]$^+$.

Step 2: Ethyl 2-(N-benzyl-1-((ten-butoxycarbonyl)amino)cyclopropanecarboxamido)acetate

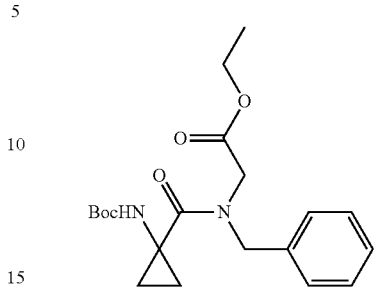

To a solution of ethyl 2-(benzylamino)acetate (27.4 g, 142 mmol), EDC (32.6 g, 170 mmol), HOBt (26.0 g, 170 mmol) and 1-((tert-butoxycarbonyl)amino)cyclopropanecarboxylic acid (30 g, 142 mmol) in DMF (500 mL) was added DIEA (124 mL, 708 mmol). Then the reaction mixture was stirred at 15° C. for 12 h. The mixture was concentrated and dissolved with DCM (1 L). The mixture was washed with saturated citric acid solution (500 mL×2) and 10% aqueous NaOH solution (500 mL). The organic phase was dried over Na$_2$SO$_4$, concentrated to give ethyl 2-(N-benzyl-1-((tert-butoxycarbonyl)amino)cyclopropanecarboxamido)acetate (40 g, 94 mmol, 66.7% yield) as a white solid: $^1$H NMR (400 MHz, CDCl$_3$) δ ppm 7.38-7.27 (m, 3H), 7.21 (d, J=7.0 Hz, 2H), 5.30-4.49 (m, 4H), 4.19-4.14 (m, 2H), 1.35 (s, 9H), 1.27-1.23 (m, 3H), 1.23-0.76 (m, 4H); ES-LCMS m/z 321.1 [M−t−Bu+H]$^+$.

Step 3: tert-Butyl (1-((benzyl(2-hydroxyethyl)amino)methyl)cyclopropyl)carbamate

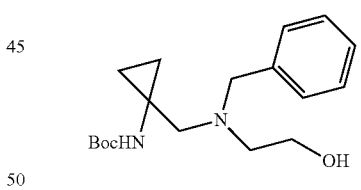

Ethyl 2-(N-benzyl-1-((tert-butoxycarbonyl)amino)cyclopropanecarboxamido)acetate (15 g, 35.4 mmol) in THF (100 mL) was added to the mixture of LiAlH$_4$ (13.45 g, 354 mmol) in THF (400 mL) dropwise. Then the reaction mixture was stirred at 0° C. for 1 h. To the solution was added H$_2$O (13.5 mL), 10% aqueous NaOH solution (13.5 mL) and H$_2$O (40.5 mL). Then the mixture was filtered and concentrated to give the crude product which was purified by flash chromatography (from pure DCM to DCM/MeOH=10/1, TLC: DCM/MeOH=10/1, R$_f$=0.53) to yield tert-butyl (1-((benzyl(2-hydroxyethyl)amino)methyl)cyclopropyl)carbamate (3.75 g, 11.7 mmol, 22.5% yield) as brown oil: $^1$H NMR (400 MHz, CDCl$_3$) δ ppm 7.37-7.22 (m, 5H), 3.75-3.64 (m, 2H), 3.59 (t, J=5.1 Hz, 2H), 2.80-2.68 (m, 2H), 2.61 (s, 2H), 1.44 (s, 9H), 0.84-0.74 (m, 2H), 0.65-0.52 (m, 2H); ES-LCMS m/z 321.3 [M+H]$^+$.

Step 4: 2-(((1-Aminocyclopropyl)methyl)(benzyl)amino)ethanol

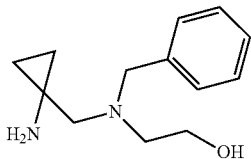 [SMILES: NC1(CN(CCO)Cc2ccccc2)CC1]

tert-Butyl (1-((benzyl(2-hydroxyethyl)amino)methyl)cyclopropyl)carbamate (10 g, 28.1 mmol) was dissolved in HCl solution (4 M in EtOAc, 50 mL, 200 mmol). The mixture was stirred at 20° C. for 0.5 h. The mixture concentrated and dissolved with DCM (100 mL). The mixture was washed with saturated aqueous NaHCO$_3$ solution (50 mL) and dried over Na$_2$SO$_4$, concentrated to give 2-(((1-aminocyclopropyl)methyl)(benzyl)amino)ethanol (6 g, 24.51 mmol, 87.0% yield) as brown oil: $^1$H NMR (400 MHz, CDCl$_3$) δ ppm 6.98-6.86 (m, 5H), 3.37-3.30 (m, 2H), 3.25 (t, J=5.1 Hz, 2H), 2.35 (t, J=4.9 Hz, 2H), 2.10 (s, 2H), 0.32-0.14 (m, 2H), 0.06-0.07 (m, 2H); ES-LCMS m/z 221.1 [M+H]$^+$.

Step 5: 7-Benzyl-4,7-diazaspiro[2.5]octane

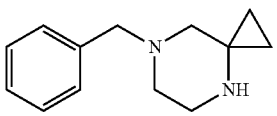 [SMILES: c1ccc(CN2CCNC3(CC3)C2)cc1]

To a solution of 2-(((1-aminocyclopropyl)methyl)(benzyl)amino)ethanol (6 g, 24.51 mmol) and PPh$_3$ (9.64 g, 36.8 mmol) in THF (50 mL) was added DIAD (7.15 mL, 36.8 mmol). Then the reaction mixture was stirred at 15° C. for 8 h under N$_2$ atmosphere. The mixture was diluted with EtOAc (100 mL), and washed with saturated aqueous NaHCO$_3$ solution (50 mL). Then the organic phase was distributed between EtOAc (150 mL) and 1 N HCl solution (50 mL). The aqueous phase was adjusted to pH=9 with NaOH solid and extracted with EtOAc (200 mL×2). The combined organic phase was dried over Na$_2$SO$_4$, concentrated to give 7-benzyl-4,7-diazaspiro[2.5]octane (7 g, 20.76 mmol, 85.0% yield) as brown oil: $^1$H NMR (400 MHz, CDCl$_3$) δ ppm 7.38-7.25 (m, 5H), 3.49 (s, 2H), 2.97 (t, J=4.9 Hz, 2H), 2.55-2.37 (m, 2H), 2.22 (s, 2H), 0.65-0.54 (m, 2H), 0.48-0.36 (m, 2H).

Step 6: tert-Butyl 7-benzyl-4,7-diazaspiro[2.5]octane-4-carboxylate

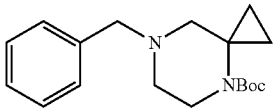 [SMILES: CC(C)(C)OC(=O)N1CCN(Cc2ccccc2)CC12CC2]

To a solution of 7-benzyl-4,7-diazaspiro[2.5]octane (7 g, 20.76 mmol) and DIEA (14.50 mL, 83 mmol) in DCM (200 mL) was added Boc$_2$O (9.64 mL, 41.5 mmol). Then the reaction mixture was stirred at 15° C. for 8 h. The mixture was concentrated and purified by flash chromatography (from pure DCM to DCM/MeOH=10/1, TLC: DCM/MeOH=10/1, R$_f$=0.7) to yield tert-butyl 7-benzyl-4,7-diazaspiro[2.5]octane-4-carboxylate (6 g, 17.86 mmol, 86.0% yield) as a brown solid: $^1$H NMR (400 MHz, CDCl$_3$) δ ppm 7.37-7.24 (m, 5H), 3.64-3.52 (m, 2H), 3.47 (s, 2H), 2.47 (s, 2H), 2.20 (s, 2H), 1.52-1.43 (m, 9H), 0.95 (s, 2H), 0.67 (s, 2H); ES-LCMS m/z 303.3 [M+H]$^+$.

Step 7: tert-Butyl 4,7-diazaspiro[2.5]octane-4-carboxylate

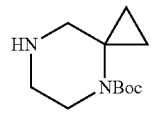

To a solution of tert-butyl 7-benzyl-4,7-diazaspiro[2.5]octane-4-carboxylate (6 g, 17.86 mmol) in MeOH (50 mL) was added Pd/C (10 wt %, 1.900 g, 1.786 mmol) under N$_2$ atmosphere. Then the reaction mixture was stirred at 15° C. for 8 h under H$_2$ atmosphere (15 psi). The mixture was filtered and concentrated to give tert-butyl 4,7-diazaspiro[2.5]octane-4-carboxylate (3.9 g, 16.53 mmol, 93.0% yield) as a white solid: NMR (400 MHz, CDCl$_3$) δ ppm 3.60-3.37 (m, 2H), 2.83 (d, J=4.4 Hz, 2H), 2.64 (s, 2H), 1.51-1.38 (m, 9H), 1.05-0.85 (m, 2H), 0.70 (s, 2H); ES-LCMS m/z 303.3 [M+H]$^+$.

Intermediate 74: 2,2,3,3,9,9,10,10-Octamethyl-4,8-dioxa-3,9-disilaundecan-6-one

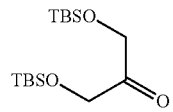

To a solution of 1,3-dihydroxypropan-2-one (5 g, 55.5 mmol) and 1H-imidazole (11.34 g, 167 mmol) in DCM (80 mL) was added TBSCl (16.73 g, 111 mmol). Then, the mixture was stirred at 40° C. for 16 h. To the mixture was added saturated aqueous NH$_4$Cl solution (30 mL), extracted with DCM (80 mL×2). The combined organic layers were washed with brine (30 mL) and dried over Na$_2$SO$_4$, filtered and concentrated. The crude material was purified by flash chromatography (from pure PE to PE/EtOAc=10:1, TLC PE/EtOAc=10:1, R$_f$=0.7) to yield a colorless oil of 2,2,3,3,9,9,10,10-octamethyl-4,8-dioxa-3,9-disilaundecan-6-one (7.277 g, 18.27 mmol, 32.9% yield): $^1$H NMR (400 MHz, CDCl$_3$) δ ppm 4.40 (s, 4H), 0.91 (s, 18H), 0.08 (s, 12H).

Intermediate 75: tert-Butyl (1-(5-(benzyloxy)pyrimidin-2-yl)-4-(hydroxymethyl)piperidin-4-yl) carbamate

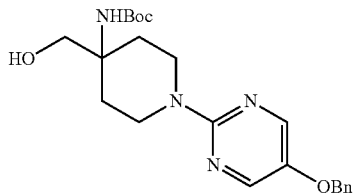 [SMILES: CC(C)(C)OC(=O)NC1(CO)CCN(c2ncc(OCc3ccccc3)cn2)CC1]

Step 1: Methyl 4-aminopiperidine-4-carboxylate, 2 hydrochloride

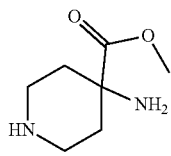

A mixture of 4-amino-1-(tert-butoxycarbonyl)piperidine-4-carboxylic acid (3 g, 12.28 mmol) in HCl solution (4 M in MeOH) (50 mL, 200 mmol) was stirred at 80° C. for 1 h. Then the mixture was concentrated to yield methyl 4-aminopiperidine-4-carboxylate, 2 hydrochloride (2.8 g, 11.51 mmol, 94.0% yield) as an off white solid: $^1$H NMR (400 MHz, CD$_3$OD) δ ppm 3.91 (s, 3H), 3.53-3.46 (m, 2H), 3.44-3.35 (m, 2H), 2.47 (d, J=14.8 Hz, 2H), 2.23 (ddd, J=4.6, 10.9, 14.9 Hz, 2H); ES-LCMS m/z 159.2 [M+H]$^+$.

Step 2: Methyl 4-amino-1-(5-(benzyloxy)pyrimidin-2-yl)piperidine-4-carboxylate

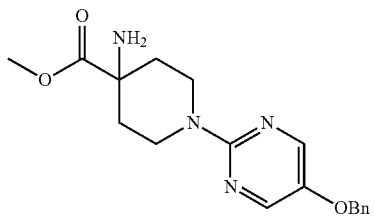 [SMILES: COC(=O)C1(N)CCN(c2ncc(OCc3ccccc3)cn2)CC1]

A mixture of methyl 4-aminopiperidine-4-carboxylate, 2 hydrochloride (2.8 g, 11.51 mmol), 5-(benzyloxy)-2-chloropyrimidine (3.17 g, 13.81 mmol) and DIEA (8.04 mL, 46.0 mmol) in DMSO (30 mL) was stirred at 120° C. for 12 h under N$_2$ atmosphere. Then water (50 mL) was added. The mixture was extracted with DCM (150 mL×3). The combined organic layers were washed with brine (50 mL), dried over Na$_2$SO$_4$, filtered and concentrated to yield the crude material. The crude material was purified by flash chromatography (from pure DCM to DCM/MeOH=10/1, TLC: DCM/MeOH=10/1, R$_f$=0.4) to yield methyl 4-amino-1-(5-(benzyloxy)pyrimidin-2-yl)piperidine-4-carboxylate (1.5 g, 3.94 mmol, 34.3% yield) as brown oil: $^1$H NMR (400 MHz, CDCl$_3$) δ ppm 8.09 (s, 2H), 7.40-7.28 (m, 5H), 4.99 (s, 2H), 3.99 (td, J=4.8, 13.5 Hz, 2H), 3.71 (s, 3H), 3.65 (ddd, J=3.3, 9.8, 13.3 Hz, 2H), 2.05 (ddd, J=4.1, 9.7, 13.6 Hz, 2H), 1.57-1.50 (m, 2H); ES-LCMS m/z 343.4 [M+H]$^+$.

Step 3: (4-Amino-1-(5-(benzyloxy)pyrimidin-2-yl)piperidin-4-yl)methanol

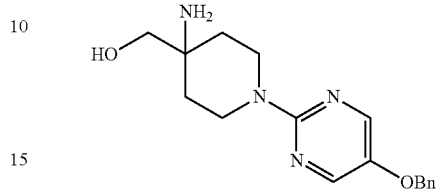

To a solution of methyl 4-amino-1-(5-(benzyloxy)pyrimidin-2-yl)piperidine-4-carboxylate (1.5 g, 3.94 mmol) in THF (20 mL) was added LiAlH$_4$ (0.299 g, 7.89 mmol) at 0° C. Then the mixture was stirred at 0° C. for 1 h under N$_2$ atmosphere. Then the mixture was quenched with 2 M aqueous NaOH solution (3 mL). Then the mixture was filtered and concentrated to yield (4-amino-1-(5-(benzyloxy)pyrimidin-2-yl)piperidin-4-yl)methanol (1.2 g, 3.44 mmol, 87.0% yield) as an off white solid: $^1$H NMR (400 MHz, CDCl$_3$) δ ppm 8.04 (s, 2H), 7.35-7.25 (m, 5H), 4.94 (s, 2H), 4.02-3.94 (m, 2H), 3.44 (ddd, J=3.4, 9.9, 13.6 Hz, 2H), 3.32 (s, 2H), 1.59-1.52 (m, 2H), 1.45-1.38 (m, 2H); ES-LCMS m/z 315.3 [M+H]$^+$.

Step 4: tert-Butyl (1-(5-(benzyloxy)pyrimidin-2-yl)-4-(hydroxymethyl)piperidin-4-yl)carbamate

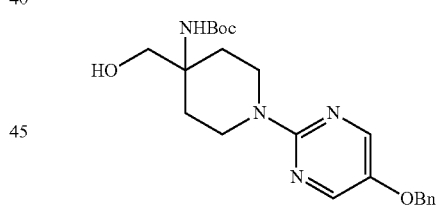

To a solution of (4-amino-1-(5-(benzyloxy)pyrimidin-2-yl)piperidin-4-yl)methanol (550 mg, 1.575 mmol) in DCM (10 mL) was added DIEA (0.550 mL, 3.15 mmol) and Boc$_2$O (0.731 mL, 3.15 mmol) at 20° C. Then the mixture was stirred at 20° C. for 12 h. Then the mixture was concentrated. The crude material was purified by flash chromatography (from pure PE to PE/EtOAc=1/1, TLC: PE/EtOAc=1/1, R$_f$=0.5) to yield tert-butyl (1-(5-(benzyloxy)pyrimidin-2-yl)-4-(hydroxymethyl)piperidin-4-yl)carbamate (500 mg, 1.113 mmol, 70.7% yield) as a white solid: $^1$H NMR (400 MHz, CDCl$_3$) δ ppm 8.10 (s, 2H), 7.40-7.28 (m, 5H), 5.00 (s, 2H), 4.10 (td, J=4.5, 13.8 Hz, 2H), 3.71 (d, J=5.7 Hz, 2H), 3.35 (ddd, J=3.1, 10.4, 13.6 Hz, 2H), 1.93 (d, J=13.9 Hz, 2H), 1.67 (ddd, J=4.2, 10.1, 13.9 Hz, 2H), 1.42 (s, 9H); ES-LCMS m/z: 415.2 [M+H]$^+$.

Intermediate 76: Ethyl 2-methyl-2-(piperidin-4-yloxy)propanoate

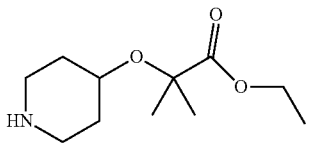

Step 1: Benzyl 4-hydroxypiperidine-1-carboxylate

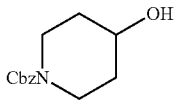

To a mixture of piperidin-4-ol (7 g, 69.2 mmol), NaOH (8.30 g, 208 mmol) in 1,4-dioxane (100 mL) and H$_2$O (100 mL) was added benzyl carbonochloridate (23.61 g, 138 mmol). Then, the mixture was stirred at 20° C. for 16 h. The mixture was diluted with DCM (200 mL) and water (200 mL), extracted with DCM (200 mL×2). The combined organic layers were dried over Na$_2$SO$_4$, filtered and concentrated. The crude product was purified by flash chromatography (from pure PE to PE/EtOAc=1/1, TLC: PE/EtOAc=1/1, R$_f$=0.3) to give benzyl 4-hydroxypiperidine-1-carboxylate (13 g, 49.7 mmol, 71.9% yield) as brown oil: $^1$H NMR (400 MHz, CDCl$_3$) δ ppm 7.40-7.25 (m, 5H), 5.12 (s, 2H), 3.96-3.82 (m, 3H), 3.14 (ddd, J=3.2, 9.8, 13.3 Hz, 2H), 1.85 (br s, 2H), 1.48 (d, J=8.6 Hz, 2H); ES-LCMS m/z 236.2 [M+H]$^+$.

Step 2: Benzyl 4-((1-ethoxy-2-methyl-1-oxopropan-2-yl)oxy)piperidine-1-carboxylate

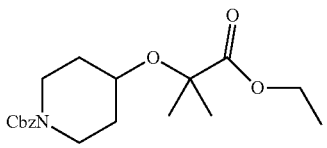 [SMILES: CCOC(=O)C(C)(C)OC1CCN(C(=O)OCc2ccccc2)CC1]

To a mixture of benzyl 4-hydroxypiperidine-1-carboxylate (4 g, 15.30 mmol) in DMF (20 mL) was added 60% NaH (0.918 g, 22.95 mmol) at 0° C. under N$_2$ atmosphere. The solution was stirred at 0° C. for 30 min. Then, ethyl 2-bromo-2-methylpropanoate (4.48 g, 22.95 mmol) was added to the mixture and the mixture was stirred at 100° C. for 11.5 h under N$_2$ atmosphere. The reaction mixture was concentrated and this reaction mixture was diluted with DCM (100 mL) and water (100 mL), extracted with DCM (100 mL×2). The combined organic layers were dried over Na$_2$SO$_4$, filtered and concentrated. The crude product was purified by flash chromatography (from pure PE to PE/EtOAc=3/1, TLC: PE/EtOAc=3/1, R$_f$=0.7) to give benzyl 4-((1-ethoxy-2-methyl-1-oxopropan-2-yl)oxy)piperidine-1-carboxylate (2 g, 1.145 mmol, 7.48% yield) as brown oil: $^1$H NMR (400 MHz, DMSO-d$_6$) δ ppm 7.41-7.38 (m, 5H), 5.10-5.09 (m, 2H), 4.19-3.99 (m, 2H), 3.65-3.61 (m, 3H), 3.42-3.39 (m, 2H), 1.89 (s, 6H), 1.86 (d, J=3.5 Hz, 2H), 1.61-1.58 (m, 2H), 1.25-1.16 (m, 3H); ES-LCMS m/z 350.2 [M+H]$^+$.

Step 3: Ethyl 2-methyl-2-(piperidin-4-yloxy)propanoate

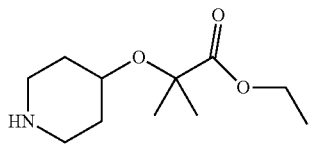

To a mixture of benzyl 4-((1-ethoxy-2-methyl-1-oxopropan-2-yl)oxy)piperidine-1-carboxylate (2000 mg, 1.145 mmol) in EtOH (50 mL) was added Pd/C (10 wt %, 365 mg, 0.343 mmol) under N$_2$ atmosphere. The mixture was stirred at 20° C. for 10 h under H$_2$ atmosphere (40 psi). Then the solution was filtered and concentrated to yield ethyl 2-methyl-2-(piperidin-4-yloxy)propanoate (1 g, 0.929 mmol, 81.0% yield) as colorless oil: $^1$H NMR (400 MHz, CDCl$_3$) δ ppm 4.28-4.07 (m, 2H), 3.09 (br s, 3H), 2.85-2.82 (m, 2H), 1.97-1.94 (m, 2H), 1.68-1.65 (m, 2H), 1.41 (br s, 6H), 1.33-1.27 (m, 3H); ES-LCMS m/z 216.2 [M+H]$^+$.

Intermediate 77: 1-(Piperidin-4-yloxy)cyclopropanecarboxylic acid, trifluoroacetic acid salt

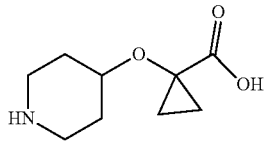 [SMILES: O=C(O)C1(OC2CCNCC2)CC1]

Step 1: tert-Butyl 4-bromopiperidine-1-carboxylate

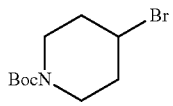

To a mixture of tert-butyl 4-hydroxypiperidine-1-carboxylate (20 g, 99 mmol) and CBr$_4$ (33.0 g, 99 mmol) in DCM (200 mL) was added PPh$_3$ (26.1 g, 99 mmol). The solution was stirred at 20° C. for 5 h. The solution was concentrated and purified by flash chromatography (from PE/EtOAc=50/1 to 3/1, TLC: PE/EtOAc=3/1, R$_f$=0.6) to yield tert-butyl 4-bromopiperidine-1-carboxylate (14 g, 47.7 mmol, 48.0% yield) as colorless oil: $^1$H NMR (400 MHz, CDCl$_3$) δ ppm 4.38-4.24 (m, 1H), 3.75-3.54 (m, 2H), 3.35-3.18 (m, 2H), 2.19-1.97 (m, 2H), 1.97-1.78 (m, 2H), 1.57-1.29 (m, 9H); ES-LCMS m/z 208.1, 210.1 [M−t−Bu+H]$^+$.

Step 2: 1-((1-(tert-Butoxycarbonyl)piperidin-4-yl)oxy)cyclopropanecarboxylic acid

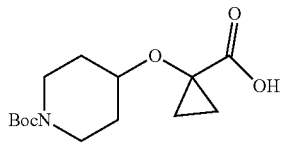

To a mixture of 1-hydroxycyclopropanecarboxylic acid (1.5 g, 14.69 mmol) in DMF (50 mL) was added 60% NaH (1.293 g, 32.3 mmol) at 0° C. under N₂ atmosphere. The solution was stirred at 0° C. for 30 mins. Then, tert-butyl 4-bromopiperidine-1-carboxylate (4.31 g, 14.69 mmol) and KI (7.32 g, 44.1 mmol) was added to the mixture and the mixture was stirred at 30° C. for 11.5 h under N₂ atmosphere. The reaction mixture was concentrated. The mixture was purified by preparative HPLC (MeCN/H₂O as eluents, acidic condition) and lyophilized to yield 1-((1-(tert-butoxycarbonyl)piperidin-4-yl)oxy)cyclopropanecarboxylic acid as a white solid (300 mg, 0.841 mmol, 5.72% yield): $^1$H NMR (400 MHz, CD₃OD) δ ppm 3.63 (d, J=4.9 Hz, 2H), 3.26-3.19 (m, 1H), 2.11 (dd, J=4.9, 14.3 Hz, 1H), 1.97-1.81 (m, 3H), 1.66-1.56 (m, 2H), 1.45 (s, 9H), 1.29-1.25 (m, 2H), 1.08-1.01 (m, 2H); ES-LCMS m/z 308.2 [M+Na]$^+$

Step 3: 1-(Piperidin-4-yloxy)cyclopropanecarboxylic acid, trifluoroacetic acid salt

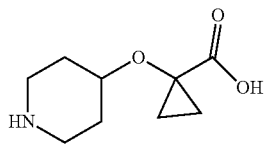

To a mixture of 1-((1-(tert-butoxycarbonyl)piperidin-4-yl)oxy)cyclopropanecarboxylic acid (300 mg, 0.841 mmol) in DCM (10 mL) was added TFA (5 mL, 64.9 mmol). Then the mixture was stirred at 20° C. for 30 min followed by concentration to yield 1-(piperidin-4-yloxy)cyclopropanecarboxylic acid, trifluoroacetic acid (280 mg, 0.655 mmol, 78.0% yield) as a yellow solid: $^1$H NMR (400 MHz, CD₃OD) δ ppm 3.97-3.95 (m, 1H), 3.38 (br s, 2H), 3.12 (br s, 2H), 2.01 (d, J=3.5 Hz, 2H), 1.77 (d, J=3.5 Hz, 2H), 1.25-1.21 (m, 2H), 1.06-1.02 (m, 2H).

Intermediate 78: tert-Butyl 4-(5-hydroxy-4-methylpyrimidin-2-yl)piperazine-1-carboxylate

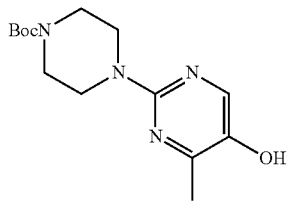 [SMILES: Cc1nc(N2CCN(C(=O)OC(C)(C)C)CC2)ncc1O]

Step 1: 2-Chloro-5-methoxy-4-methylpyrimidine

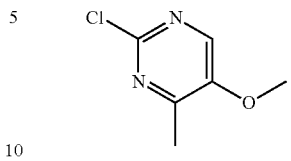

To a solution of 2,4,6-trimethyl-1,3,5,2,4,6-trioxatriborinane (5.26 g, 41.9 mmol) and 2,4-dichloro-5-methoxypyrimidine (5 g, 27.9 mmol) in THF (100 mL) was added K₃PO₄ (11.86 g, 55.9 mmol) and Pd(PPh₃)₂Cl₂ (1.961 g, 2.79 mmol). Then the mixture was stirred at 80° C. for 16 h under N₂ atmosphere. The mixture was concentrated to give the residue. Then the residue was dissolved in water (50 mL). The mixture was extracted with EtOAc (100 mL×3). The combined organic layers were washed with brine (50 mL), dried over Na₂SO₄, filtered and concentrated. The crude material was purified by flash chromatography (from PE/EtOAc=50/1 to 4/1, TLC: PE/EtOAc=5/1, R$_f$=0.7) to yield 2-chloro-5-methoxy-4-methylpyrimidine (2 g, 12.11 mmol, 43.3% yield) as a white solid: $^1$H NMR (400 MHz, CDCl₃) δ ppm 8.05 (s, 1H), 3.92 (s, 3H), 2.53-2.40 (m, 3H); ES-LCMS m/z 159.0, 161.0 [M+H]$^+$.

Step 2: tert-Butyl 4-(5-methoxy-4-methylpyrimidin-2-yl)piperazine-1-carboxylate

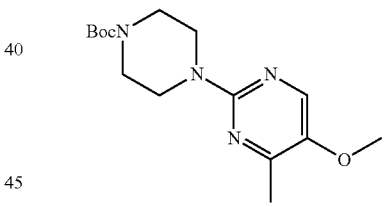

To a solution of tert-butyl piperazine-1-carboxylate (7.89 g, 42.4 mmol) and 2-chloro-5-methoxy-4-methylpyrimidine (2.8 g, 16.95 mmol) in DMSO (50 mL) was added DIEA (8.88 mL, 50.8 mmol). The mixture was stirred at 120° C. for 8 h under N₂ atmosphere. The mixture was added water (80 mL). The mixture was extracted with EtOAc (100 mL×3). The combined organic layers were washed with brine (60 mL), dried over Na₂SO₄, filtered and concentrated. The crude material was purified by flash chromatography (from PE/EtOAc=20/1 to 2/1, TLC: PE/EtOAc=3/1, R$_f$=0.6) to yield tert-butyl 4-(5-methoxy-4-methylpyrimidin-2-yl)piperazine-1-carboxylate (4 g, 11.67 mmol, 68.9% yield) as a yellow solid: $^1$H NMR (400 MHz, CDCl₃) δ ppm 7.89 (s, 1H), 3.78 (s, 3H), 3.72-3.65 (m, 4H), 3.48 (dd, J=4.1, 6.1 Hz, 4H), 2.32 (s, 3H), 1.48 (s, 9H); ES-LCMS m/z 309.2 [M+H]$^+$.

Step 3: 4-Methyl-2-(piperazin-1-yl)pyrimidin-5-ol

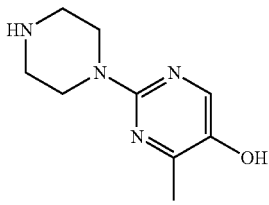

To a solution of tert-butyl 4-(5-methoxy-4-methylpyrimidin-2-yl)piperazine-1-carboxylate (3.5 g, 10.21 mmol) in DCM (100 mL) was dropwise added BBr$_3$ (3.86 mL, 40.9 mmol) at −78° C. under N$_2$ atmosphere. Then the mixture was stirred at 26° C. for 8 h under N$_2$ atmosphere. The mixture quenched with MeOH (20 mL) at −78° C. The mixture was concentrated to give 4-methyl-2-(piperazin-1-yl)pyrimidin-5-ol (4.5 g, 9.27 mmol, 91.0% yield) as a red solid: $^1$H NMR (400 MHz, CD$_3$OD) δ ppm 7.94-7.69 (m, 1H), 4.18-4.10 (m, 4H), 3.50-3.42 (m, 4H), 2.56 (s, 3H); ES-LCMS m/z 195.3 [M+H]$^+$.

Step 4: tert-Butyl 4-(5-((tert-butoxycarbonyl)oxy)-4-methylpyrimidin-2-yl)piperazine-1-carboxylate

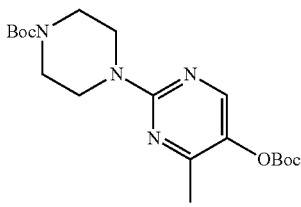

To a solution of 4-methyl-2-(piperazin-1-yl)pyrimidin-5-ol (4.5 g, 9.27 mmol) and DIEA (4.86 mL, 27.8 mmol) in DCM (20 mL) was added Boc$_2$O (3.23 mL, 13.90 mmol) in portions at 26° C. Then the mixture was stirred at 26° C. for 8 h. The mixture was concentrated to give the residue. The crude material was purified by flash chromatography (from PE/EtOAc=10/1 to 3/1, TLC: PE/EtOAc=3/1, R$_f$=0.7) to yield tert-butyl 4-(5-((tert-butoxycarbonyl)oxy)-4-methylpyrimidin-2-yl)piperazine-1-carboxylate (3.8 g, 9.15 mmol, 99.0% yield) as a yellow solid: $^1$H NMR (400 MHz, CDCl$_3$) δ ppm 8.02 (s, 1H), 3.81-3.66 (m, 4H), 3.50-3.38 (m, 4H), 2.26 (s, 3H), 1.53 (s, 9H), 1.47 (s, 9H); ES-LCMS m/z 395.2 [M+H]$^+$.

Step 5: tert-Butyl 4-(5-hydroxy-4-methylpyrimidin-2-yl)piperazine-1-carboxylate

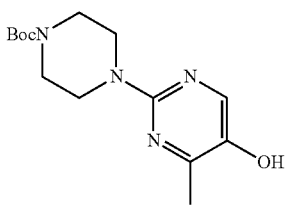 [SMILES: Cc1nc(N2CCN(C(=O)OC(C)(C)C)CC2)ncc1O]

A mixture of tert-butyl 4-(5-((tert-butoxycarbonyl)oxy)-4-methylpyrimidin-2-yl)piperazine-1-carboxylate (3.8 g, 9.15 mmol) and K$_2$CO$_3$ (6.32 g, 45.8 mmol) in MeOH (50 mL) was stirred at 26° C. for 1 h. The mixture was filtered and concentrated to give tert-butyl 4-(5-hydroxy-4-methylpyrimidin-2-yl)piperazine-1-carboxylate (2.7 g, 8.90 mmol, 97.0% yield) as a yellow solid: $^1$H NMR (400 MHz, CD$_3$OD) δ ppm 7.81-7.53 (m, 1H), 3.50-3.39 (m, 8H), 2.29 (s, 3H), 1.46 (s, 9H); ES-LCMS m/z 295.2 [M+H]$^+$.

Intermediate 79: 3-((tert-Butyldimethylsilyl)oxy)-3-methylcyclobutanone

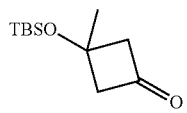

Step 1: 3-(Benzyloxy)-1-methylcyclobutanol

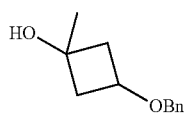

To a solution of 3-(benzyloxy)cyclobutanone (1 g, 5.67 mmol) in toluene (10 mL) and THF (1 mL) was added MeMgBr (3 M in ether, 2.84 mL, 8.51 mmol) at −78° C. under N$_2$ atmosphere. Then the reaction mixture was stirred at −78° C. for 1 h. The mixture was quenched by saturated aqueous NH$_4$Cl solution (50 mL). The mixture was extracted with DCM (150 mL×3). The combined organic layers were washed with brine (50 mL), dried over Na$_2$SO$_4$, filtered and concentrated. The crude material was purified by flash chromatography (from pure PE to PE/EtOAc=1/1, TLC: PE/EtOAc=3/1, R$_f$=0.3) to yield 3-(benzyloxy)-1-methylcyclobutanol (850 mg, 3.98 mmol, 70.1% yield) as colorless liquid: $^1$H NMR (400 MHz, CDCl$_3$) δ ppm 7.36-7.29 (m, 5H), 4.42-4.38 (m, 2H), 3.71 (quin, J=6.8 Hz, 1H), 2.47-2.38 (m, 2H), 2.12-2.04 (m, 2H), 1.29 (s, 3H).

Step 2: (3-(Benzyloxy)-1-methylcyclobutoxy)(tert-butyl)dimethylsilane

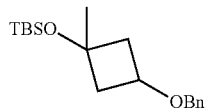

To a solution of 3-(benzyloxy)-1-methylcyclobutanol (0.85 g, 3.98 mmol) in DCM (15 mL) was added imidazole (0.813 g, 11.94 mmol) and TBSCl (1.799 g, 11.94 mmol) at 20° C. Then the mixture was stirred at 20° C. for 12 h. Then water (50 mL) was added. The mixture was extracted with DCM (100 mL×3). The combined organic layers were washed with brine (50 mL), dried over Na$_2$SO$_4$, filtered and concentrated. The crude material was purified by flash chromatography (from pure PE to PE/EtOAc=1/1, TLC:

PE/EtOAc=3/1, $R_f$=0.7) to yield (3-(benzyloxy)-1-methyl-cyclobutoxy)(tert-butyl)dimethylsilane (1 g, 2.94 mmol, 73.8% yield) as colorless oil: $^1$H NMR (400 MHz, CDCl$_3$) δ ppm 7.28-7.20 (m, 5H), 4.35-4.30 (m, 2H), 3.59 (q, J=6.9 Hz, 1H), 2.34-2.26 (m, 2H), 2.11-2.02 (m, 2H), 1.21 (s, 3H), 0.82-0.79 (m, 9H), 0.00 (s, 6H).

Step 3: 3-((tert-Butyldimethylsilyl)oxy)-3-methylcyclobutanol

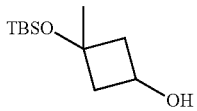

To a solution of (3-(benzyloxy)-1-methylcyclobutoxy)(tert-butyl/dimethyl si lane (1 g, 2.94 mmol) in MeOH (30 mL) was added Pd/C (10 wt %, 0.625 g, 0.587 mmol) under N$_2$ atmosphere. Then the mixture was stirred at 50° C. for 12 h under H$_2$ atmosphere (50 psi). The mixture was filtered and the filtrate was concentrated to yield 3-((tert-butyldimethylsilyl)oxy)-3-methylcyclobutanol (0.7 g, 2.91 mmol, 99.0% yield) as colorless oil: $^1$H NMR (400 MHz, CDCl$_3$) δ ppm 3.91-3.80 (m, 1H), 2.42-2.35 (m, 2H), 2.04-1.94 (m, 2H), 1.22 (s, 3H), 0.83-0.80 (m, 9H), 0.01-0.00 (m, 6H).

Step 4: 3-((tert-Butyldimethylsilyl)oxy)-3-methylcyclobutanone

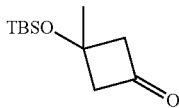

To a solution of 3-((tert-butyldimethylsilyl)oxy)-3-methylcyclobutanol (500 mg, 2.080 mmol) in DCM (10 mL) was added Dess-Martin (1323 mg, 3.12 mmol). Then the mixture was stirred at 20° C. for 12 h under N$_2$ atmosphere. The mixture was quenched by saturated aqueous NaHCO$_3$ solution (50 mL). The mixture was extracted with DCM (100 mL×3). The combined organic layers were washed with brine (30 mL), dried over Na$_2$SO$_4$, filtered and concentrated. The crude material was purified by flash chromatography (from pure PE to PE/EtOAc=1/1, TLC: PE/EtOAc=3/1, $R_f$=0.7) to yield 3-((tert-butyldimethylsilyl)oxy)-3-methylcyclobutanone (400 mg, 1.679 mmol, 81.0% yield) as brown oil: $^1$H NMR (400 MHz, CDCl$_3$) δ ppm 3.12-3.03 (m, 2H), 2.89-2.80 (m, 2H), 1.48 (s, 3H), 0.77 (s, 9H), 0.00 (s, 6H); ES-LCMS m/z: 214.5 [M+H]$^+$.

Intermediate 80: Dimethyl(piperidin-4-yl)phosphine oxide

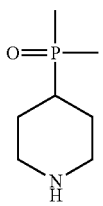

Step 1: Benzyl 4-(dimethylphosphoryl)-4-hydroxypiperidine-1-carboxylate

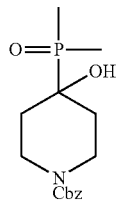 [SMILES: CP(C)(=O)C1(O)CCN(C(=O)OCc2ccccc2)CC1]

To a solution of benzyl 4-oxopiperidine-1-carboxylate (1 g, 4.29 mmol) and dimethylphosphine oxide (0.402 g, 5.14 mmol) in i-PrOH (20 mL) was added Et$_3$N (1.301 g, 12.86 mmol). Then the reaction mixture was stirred at 90° C. for 10 h. H$_2$O (30 mL) was added and extracted with DCM (30 mL×2). The combined organic layers were dried over Na$_2$SO$_4$ and concentrated. The crude material was purified by flash chromatography (from pure DCM to DCM/MeOH=10/1, TLC: DCM/MeOH=10/1, $R_f$=0.3) to yield benzyl 4-(dimethylphosphoryl)-4-hydroxypiperidine-1-carboxylate (600 mg, 1.725 mmol, 40.2% yield) as a yellow solid: $^1$H NMR (400 MHz, CDCl$_3$) δ ppm 7.38-7.27 (m, 5H), 5.12 (s, 2H), 4.11 (d, J=7.1 Hz, 2H), 3.26 (br s, 2H), 1.84-1.75 (m, 2H), 1.66 (br s, 2H), 1.45 (s, 3H), 1.42 (s, 3H); ES-LCMS m/z 312.2 [M+H]$^+$.

Step 2: Benzyl 4-(dimethylphosphoryl)-5,6-dihydropyridine-1 (2/7)-carboxylate

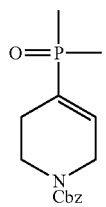 [SMILES: CP(C)(=O)C1=CCN(C(=O)OCc2ccccc2)CC1]

To a mixture of benzyl 4-(dimethylphosphoryl)-4-hydroxypiperidine-1-carboxylate (300 mg, 0.862 mmol) in DCM (5 mL) was added DAST (0.228 mL, 1.725 mmol) at 20° C. Then, the mixture was stirred at 20° C. for 3 h under N$_2$ atmosphere. The reaction mixture was quenched by the addition of saturated aqueous NaHCO$_3$ solution (20 mL) at 0° C. The mixture was extracted with DCM (20 mL×3). The combined organic layers were washed with brine (50 mL), dried over Na$_2$SO$_4$, filtered and concentrated. The crude material was purified by flash chromatography (DCM/MeOH=30/1 to 10/1, TLC: DCM/MeOH=10/1, $R_f$=0.6) to yield benzyl 4-(di methyl phosphoryl)-5,6-dihydropyridine-1 (2H)-carboxylate (120 mg, 0.368 mmol, 42.7% yield) as a yellow oil: $^1$H NMR (400 MHz, CDCl$_3$) δ ppm 7.37-7.29 (m, 5H), 6.60-6.52 (m, 1H), 5.17-5.13 (m, 2H), 4.13 (q, J=3.0 Hz, 2H), 3.63 (t, J=5.4 Hz, 2H), 2.30-2.22 (m, 2H), 1.52 (s, 3H), 1.49 (s, 3H); ES-LCMS m/z 294.2 [M+H]$^+$.

Step 3: Dimethyl(piperidin-4-yl)phosphine oxide

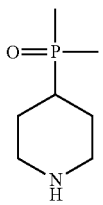

A mixture of benzyl 4-(dimethylphosphoryl)-5,6-dihydropyridine-1 (2/7)-carboxylate (120 mg, 0.368 mmol) and Pd/C (10 wt %, 392 mg, 0.368 mmol) in MeOH (10 mL) was stirred at 20° C. for 1 h under H$_2$ atmosphere (15 psi). The mixture was filtered and the filtrate was concentrated to yield dimethyl(piperidin-4-yl)phosphine oxide (70 mg, 0.304 mmol, 83.0% yield) as brown oil: $^1$H NMR (400 MHz, CD$_3$OD) δ ppm 3.15-3.08 (m, 2H), 3.01-2.96 (m, 2H), 2.64-2.60 (m, 1H), 1.92-1.85 (m, 4H), 1.50 (s, 3H), 1.47 (s, 3H).

Intermediate 81: N-((1R,7S,8r)-4-azabicyclo[5.1.0]octan-8-yl)methanesulfonamide, trifluoroacetic acid salt

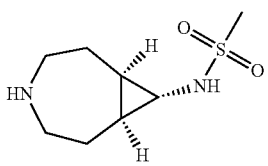

Step 1: (1R,7S,8r)-benzyl 8-(methylsulfonamido)-4-azabicyclo[5.1.0]octane-4-carboxylate

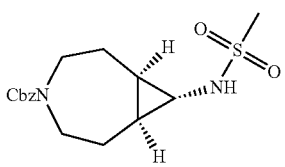

To a solution of (1R,7S,8r)-benzyl 8-amino-4-azabicyclo[5.1.0]octane-4-carboxylate, hydrochloride (750 mg, 2.022 mmol) in DCM (10 mL) was added DIEA (653 mg, 5.05 mmol) and MsCl (278 mg, 2.426 mmol) at 25° C. Then the mixture was stirred at 25° C. for 12 h. The mixture was concentrated to give the which crude product was purified by flash chromatography (from pure DCM to DCM/MeOH=10/1, R$_f$=0.55 (DCM/MeOH=10/1)) to yield a pale yellow oil of (1R,7S,8r)-benzyl 8-(methylsulfonamido)-4-azabicyclo[5.1.0]octane-4-carboxylate (760 mg, 1.797 mmol, 89.0% yield): $^1$H NMR (400 MHz, CDCl$_3$) δ ppm 7.39-7.28 (m, 5H), 5.10 (s, 2H), 3.76-3.57 (m, 2H), 3.29-3.16 (m, 2H), 3.00-2.93 (m, 3H), 2.44-2.24 (m, 3H), 1.52 (s, 2H), 1.41-1.26 (m, 2H); ES-LCMS m/z 338.9 [M+H]$^+$.

Step 2: N-((1R,7S,8r)-4-azabicyclo[5.1.0]octan-8-yl)methanesulfonamide, trifluoroacetic acid salt

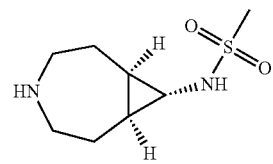

(1R,7S,8r)-benzyl 8-(methylsulfonamido)-4-azabicyclo[5.1.0]octane-4-carboxylate (360 mg, 1.064 mmol) in TFA (5 mL, 64.9 mmol) was stirred at 50° C. for 1.5 h. The mixture was concentrated to give N-((1R,7S,8r)-4-azabicyclo[5.1.0]octan-8-yl)methanesulfonamide, trifluoroacetic acid salt (335 mg, 0.842 mmol, 99.0% yield) as pale yellow oil: $^1$H NMR (400 MHz, CD$_3$OD) δ ppm 3.37 (dd, J=5.84, 13.56 Hz, 2H), 3.10 (t, J=12.02 Hz, 2H), 2.97-2.91 (m, 3H), 2.55-2.42 (m, 3H), 1.53-1.33 (m, 4H).

Intermediate 82: tert-Butyl 2,7-diazaspiro[3.5]nonane-7-carboxylate

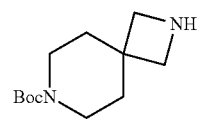

Step 1: 1-tert-butyl 4-ethyl 4-cyanopiperidine-1,4-dicarboxylate

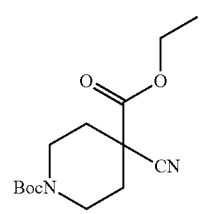 [SMILES: CCOC(=O)C1(C#N)CCN(C(=O)OC(C)(C)C)CC1]

To a solution of tert-butyl 4-cyanopiperidine-1-carboxylate (45 g, 214 mmol) in THF (1 F) cooled to −78° C. was added LiHMDS (1 M in THF, 364 mF, 364 mmol) dropwise under N$_2$ atmosphere. Then the solution was stirred at −78° C. for 0.5 h. Then ethyl carbonochloridate (34.8 g, 321 mmol) was added dropwise. The solution was warmed to 20° C. and stirred for 2 h. The mixture was quenched with addition of saturated aqueous NH$_4$Cl solution (1 L). The mixture was concentrated to remove THF. The residue was extracted with DCM (1 L×2). The combined organic layers were washed with brine (500 mL), dried over Na$_2$SO$_4$, filtered and concentrated to yield 1-tert-butyl 4-ethyl 4-cyanopiperidine-1,4-dicarboxylate (48 g, 119 mmol, 55.6% yield) as brown oil: $^1$H NMR (400 MHz, CDCl$_3$) (δ ppm 4.11 (q, J=7.1 Hz, 2H), 4.00-3.89 (m, 2H), 2.94 (s, 2H), 1.92-1.84 (m, 2H), 1.82-1.74 (m, 2H), 1.28 (s, 9H), 1.16 (t, J=12 Hz, 3H); ES-LCMS m/z 183.2 [M−Boc+H]$^+$.

Step 2: tert-Butyl 4-cyano-4-(hydroxymethyl)piperidine-1-carboxylate

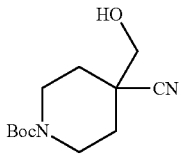 [SMILES: CC(C)(C)OC(=O)N1CCC(C#N)(CO)CC1]

To a solution of 1-tert-butyl 4-ethyl 4-cyanopiperidine-1,4-dicarboxylate (48 g, 119 mmol) in MeOH (1 L) was added NaBH₄ (11.26 g, 298 mmol) in portions. The solution was stirred at 20° C. for 1.5 h. The mixture was quenched with saturated NH₄Cl solution (500 mL) and then concentrated. Then crude product was distributed between DCM (500 mL) and saturated aqueous NaHCO₃ (500 mL) solution. The combined organic extract was washed with brine (200 mL), dried over Na₂SO₄, filtered and concentrated to yield tert-butyl 4-cyano-4-(hydroxymethyl)piperidine-1-carboxylate (40 g, 117 mmol, 98.0% yield) as a brown solid: ¹H NMR (400 MHz, CD₃OD) δ ppm 4.12 (d, J=13.9 Hz, 2H), 3.56 (s, 2H), 3.13-2.88 (m, 2H), 1.89 (d, J=13.5 Hz, 2H), 1.46-1.43 (m, 11H); ES-LCMS m/z 141.2 [M−Boc+H]⁺.

Step 3: tert-Butyl 4-cyano-4-((tosyloxy)methyl)piperidine-1-carboxylate

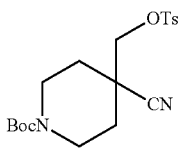

To a solution of tert-butyl 4-cyano-4-(hydroxymethyl)piperidine-1-carboxylate (33 g, 96 mmol) and Et₃N (19.45 g, 192 mmol) in DCM (300 mL) was added DMAP (1.174 g, 9.61 mmol) and 4-methylbenzene-1-sulfonyl chloride (21.99 g, 115 mmol). The mixture was stirred at 20° C. for 10 h. Then the solution was washed with water (500 mL×3). The organic layer was dried over Na₂SO₄, filtered and concentrated. The crude product was purified by flash chromatography (from pure PE to PE/EtOAc=3/1; TLC: PE/EtOAc=3/1, R_f=0.6) to yield tert-butyl 4-cyano-4-((tosyloxy)methyl)piperidine-1-carboxylate (22 g, 50.2 mmol, 52.2% yield) as a yellow solid: ¹H NMR (400 MHz, CDCl₃) δ ppm 7.79 (d, J=8.2 Hz, 2H), 7.36 (d, J=8.4 Hz, 2H), 4.20-4.07 (m, 2H), 3.96 (s, 2H), 2.98 (s, 2H), 2.45 (s, 3H), 1.87 (d, J=13.5 Hz, 2H), 1.49-1.44 (m, 2H), 1.43 (s, 9H); ES-LCMS m/z 295.2 [M−Boc+H]⁺.

Step 4: tert-Butyl 2,7-diazaspiro[3.5]nonane-7-carboxylate

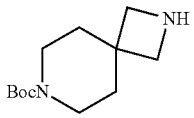

To a suspension of LiAlH₄ (0.173 g, 4.56 mmol) in THF (20 mL) cooled to 0° C. was added tert-butyl 4-cyano-4-((tosyloxy)methyl)piperidine-1-carboxylate (1 g, 2.281 mmol) in portions. The mixture was stirred at 0° C. for 1 h. Water (0.2 mL) and 1 N NaOH (0.2 mL) was added subsequently. After filtration, the filtrate was concentrated to yield tert-butyl 2,7-diazaspiro[3.5]nonane-7-carboxylate (700 mg, 1.547 mmol, 67.8% yield) as a white solid: ¹H NMR (400 MHz, CD₃OD) δ ppm 3.40-3.30 (m, 8H), 1.71-1.67 (m, 4H), 1.42 (s, 9H); ES-LCMS m/z 171.2 [M−t−Bu+H]⁺.

EXAMPLES

Example 1: 2-(4-((2-(3,5-Dichlorophenyl)-6-((6-(piperazin-1-yl)pyridin-3-yl)oxy)pyridin-4-yl)methyl)piperazin-1-yl)-N-methylacetamide, 5 hydrochloride

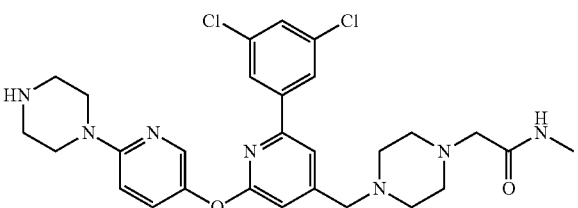

Step 1: tert-Butyl 4-(5-((6-(3,5-dichlorophenyl)-4-((4-(2-(methylamino)-2-oxoethyl)piperazin-1-yl)methyl)pyridin-2-yl)oxy)pyridin-2-yl)piperazine-1-carboxylate

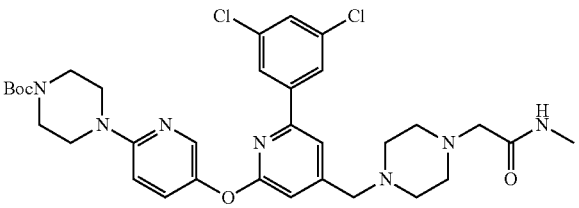 [SMILES: CNC(=O)CN1CCN(Cc2cc(Oc3ccc(N4CCN(C(=O)OC(C)(C)C)CC4)nc3)nc(-c3cc(Cl)cc(Cl)c3)c2)CC1]

To a solution of tert-butyl 4-(5-((6-(3,5-dichlorophenyl)-4-(((methylsulfonyl)oxy)methyl)pyridin-2-yl)oxy)pyridin-2-yl)piperazine-1-carboxylate (600 mg, 0.984 mmol) and K₂CO₃ (272 mg, 1.969 mmol) in DMF (20 mL) was added N-methyl-2-(piperazin-1-yl)acetamide (186 mg, 1.181 mmol). The reaction mixture was stirred at 80° C. for 12 h. The solid was filtered off and the mixture was concentrated to yield the crude product, which was purified by flash chromatography on silica gel (DCM/MeOH=1/0 to 5/1). All fractions found to contain product by TLC (DCM/MeOH=5/1, R_f=0.45) were combined and concentrated to yield a pale yellow solid of tert-butyl 4-(5-((6-(3,5-dichlorophenyl)-4-((4-(2-(methylamino)-2-oxoethyl)piperazin-1-yl)methyl)pyridin-2-yl)oxy)pyridin-2-yl)piperazine-1-carboxylate (500 mg, 0.598 mmol, 60.7% yield): ¹H NMR (400 MHz, CDCl₃) δ ppm 8.12 (d, J=2.9 Hz, 1H), 7.74 (d, J=1.8 Hz, 2H), 7.43 (d, J=6.4 Hz, 1H), 7.39 (s, 1H), 7.33 (t, J=1.8 Hz, 1H), 6.83 (s, 1H), 6.73 (d, J=9.0 Hz, 1H), 3.60-3.50 (m, 12H), 3.03 (s, 2H), 2.84 (d, J=5.1 Hz, 3H), 2.58 (br. s, 6H), 1.49 (s, 9H); ES-LCMS m/z 670.5, 672.0 [M+H]⁺.

Step 2: 2-(4-((2-(3,5-Dichlorophenyl)-6-((6-(piperazin-1-yl)pyridin-3-yl)oxy)pyridin-4-yl)methyl)piperazin-1-yl)-N-methylacetamide, 5 hydrochloride

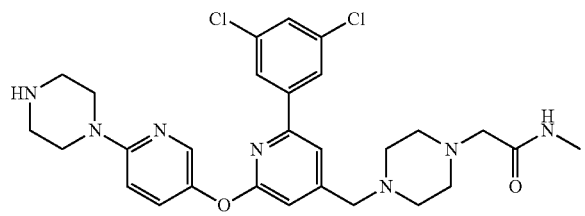 [SMILES: CNC(=O)CN1CCN(Cc2cc(Oc3ccc(N4CCNCC4)nc3)nc(-c3cc(Cl)cc(Cl)c3)c2)CC1]

To a mixture of tert-butyl 4-(5-((6-(3,5-dichlorophenyl)-4-((4-(2-(methylamino)-2-oxoethyl)piperazin-1-yl)methyl)pyridin-2-yl)oxy)pyridin-2-yl)piperazine-1-carboxylate (400 mg, 0.596 mmol) in DCM (10 mL) was added TFA (2 mL, 26 mmol). Then the reaction mixture was stirred at 25° C. for 20 min. The solution was concentrated to yield the crude product which was purified by preparative HPLC (MeCN/H$_2$O as eluents, acidic condition) to yield a yellow solid of 2-(4-((2-(3,5-dichlorophenyl)-6-((6-(piperazin-1-yl)pyridin-3-yl)oxy)pyridin-4-yl)methyl)piperazin-1-yl)-N-methylacetamide, 5 hydrochloride (51.8 mg, 0.068 mmol, 11.4% yield): $^1$H NMR (400 MHz, CD$_3$OD) δ ppm 8.21 (d, J=2.7 Hz, 1H), 8.14 (d, J=7.1 Hz, 1H), 8.00 (s, 1H), 7.89 (d, J=2.0 Hz, 2H), 7.56-7.50 (m, 2H), 7.40 (s, 1H), 4.43 (br. s, 2H), 4.04-3.99 (m, 6H), 3.67 (br. s, 4H), 3.54-3.46 (m, 8H), 2.81 (s, 3H); ES-LCMS m/z 570.3, 572.3 [M+H]$^+$.

Example 2: N-((1-((2-(3,5-Dichlorophenyl)-6-((6-(piperazin-1-yl)pyridine-3-yl)oxy)pyridin-4-yl)methyl)-4-hydroxypiperidin-4-yl)methyl)acetamide

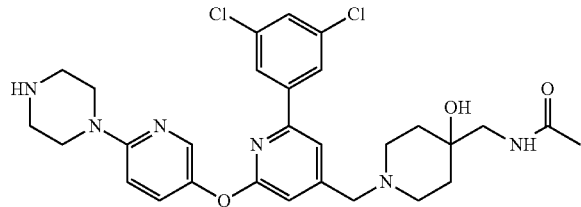 [SMILES: CC(=O)NCC1(O)CCN(Cc2cc(Oc3ccc(N4CCNCC4)nc3)nc(-c3cc(Cl)cc(Cl)c3)c2)CC1]

Step 1: tert-Butyl 4-(5-((4-((4-(acetamidomethyl)-4-hydroxypiperidin-1-yl)methyl)-6-(3,5-dichlorophenyl)pyridin-2-yl)oxy)pyridin-2-yl)piperazine-1-carboxylate

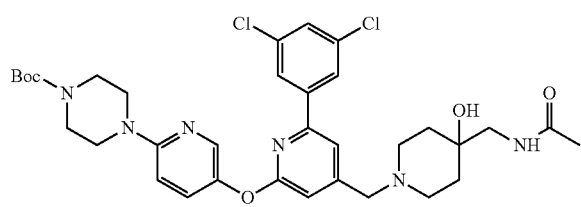 [SMILES: CC(=O)NCC1(O)CCN(Cc2cc(Oc3ccc(N4CCN(C(=O)OC(C)(C)C)CC4)nc3)nc(-c3cc(Cl)cc(Cl)c3)c2)CC1]

To a suspension of tert-butyl 4-(5-((6-(3,5-dichlorophenyl)-4-(((methylsulfonyl)oxy)methyl)pyridin-2-yl)oxy)pyridin-2-yl)piperazine-1-carboxylate (400 mg, 0.656 mmol) and K$_2$CO$_3$ (181 mg, 1.313 mmol) in DMF (15 mL) was added N-((4-hydroxypiperidin-4-yl)methyl) acetamide N-((4-hydroxypiperidin-4-yl)methyl)acetamide (135 mg, 0.787 mmol). Then the reaction mixture was stirred at 80° C. for 12 h. The solid was filtered off and the solution was concentrated to yield the crude product which was purified by flash chromatography column on silica gel (DCM/MeOH=1/0 to 10/1) to yield a pale yellow solid of tert-butyl 4-(5-((4-(4-(acetamidomethyl)-4-hydroxypiperidin-1-yl)methyl)-6-(3,5-dichlorophenyl)pyridin-2-yl)oxy)pyridin-2-yl)piperazine-1-carboxylate (400 mg, 0.475 mmol, 72.4% yield): $^1$H NMR (400 MHz, CDCl$_3$) δ ppm 8.13 (d, J=2.6 Hz, 1H), 7.76 (d, J=1.8 Hz, 2H), 7.46-7.41 (m, 2H), 7.34 (s, 1H), 6.83 (s, 1H), 6.73 (d, J=9.0 Hz, 1H), 3.56 (d, J=8.6 Hz, 12H), 3.31 (d, J=6.0 Hz, 2H), 2.61 (m, 2H), 2.47 (m, 2H), 2.04 (s, 3H), 1.64 (br. s, 4H), 1.49 (s, 9H); ES-LCMS m/z 687.3, 689.0 [M+H]$^+$.

Step 2: N-((1-((2-(3,5-Dichlorophenyl)-6-((6-(piperazin-1-yl)pyridine-3-yl)oxy)pyridin-4-yl)methyl)-4-hydroxypiperidin-4-yl)methyl)acetamide

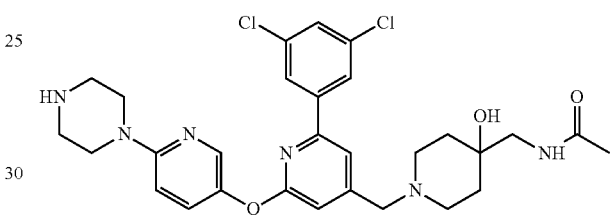

To a mixture of tert-butyl 4-(5-((4-((4-(acetamidomethyl)-4-hydroxypiperidin-1-yl)methyl)-6-(3,5-dichlorophenyl)pyridin-2-yl)oxy)pyridin-2-yl)piperazine-1-carboxylate (400 mg, 0.583 mmol) in DCM (10 mL) was added TFA (2 mL, 26 mmol). Then the reaction mixture was stirred at 25° C. for 16 h. The solution was concentrated to yield the crude product which was purified by preparative HPLC (MeCN/H$_2$O as eluents, acidic condition) to yield a pale yellow solid of N-((1-((2-(3,5-dichlorophenyl)-6-((6-(piperazin-1-yl)pyridin-3-yl)oxy)pyridin-4-yl)methyl)-4-hydroxypiperidin-4-yl)methyl)acetamide, 4 hydrochloride (146.85 mg, 0.201 mmol, 34.4% yield): $^1$H NMR (400 MHz, CD$_3$OD) δ ppm 8.22-8.15 (m, 2H), 8.01 (s, 1H), 7.87 (d, J=1.2 Hz, 2H), 7.56 (d, J=9.0 Hz, 1H), 7.49 (s, 1H), 7.41 (s, 1H), 4.48 (br. s, 2H), 4.03 (br. s, 4H), 3.56-3.29 (m, 8H), 3.26 (s, 2H), 2.06-1.95 (m, 5H), 1.79 (d, J=14.2 Hz, 2H); ES-LCMS m/z 585.3, 587.3 [M+H]$^+$.

Example 3: 3-(1-((2-(3,5-Dichlorophenyl)-6-((6-(piperazin-1-yl)pyridin-3-yl)oxy)pyridin-4-yl)methyl)piperidin-4-yl)propanoic acid, 4 hydrochloride

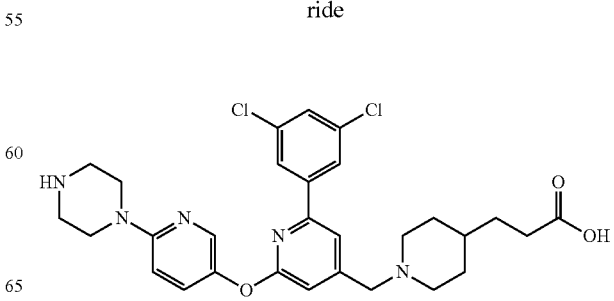

Step 1: tert-Butyl 4-(2-hydroxyethyl)piperidine-1-carboxylate

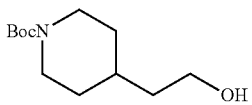

To a solution of 2-(1-(tert-butoxycarbonyl)piperidin-4-yl) acetic acid (30 g, 123 mmol) in THF (200 mL) was added BH$_3$·DMS (61.7 mL, 617 mmol). The mixture was stirred at 20° C. for 2 h. The reaction mixture was quenched with MeOH (100 mL). Then the mixture was concentrated to yield tert-butyl 4-(2-hydroxyethyl)piperidine-1-carboxylate (28 g, 98 mmol, 79.0% yield): $^1$H NMR (400 MHz, CD$_3$OD) δ ppm 4.04 (d, J=13.2 Hz, 2H), 3.70-3.65 (m, 2H), 2.73 (br. s, 2H), 1.82-1.55 (m, 4H), 1.51-1.39 (m, 10H), 1.15-0.99 (m, 2H); ES-LCMS m/z 174.1 [M–t–Bu+H]$^+$.

Step 2: tert-Butyl 4-(2-((methylsulfonyl)oxy)ethyl)piperidine-1-carboxylate

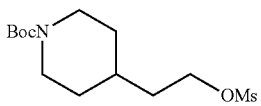

To a solution of tert-butyl 4-(2-hydroxyethyl)piperidine-1-carboxylate (10 g, 43.6 mmol) in DCM (50 mL) was added DIEA (22.85 mL, 131 mmol). MsCl (11.28 mL, 146 mmol) was added and the mixture was stirred at 20° C. for 0.5 h. Then the mixture was concentrated to yield the residue which was partitioned between DCM (300 mL) and H$_2$O (200 mL), extracted with DCM (300 mL×2). The combined organic layers were washed with brine (200 mL), dried over Na$_2$SO$_4$, filtered and concentrated to yield brown oil of tert-butyl 4-(2-((methylsulfonyl)oxy)ethyl)piperidine-1-carboxylate (12 g, 23.42 mmol, 53.7% yield): $^1$H NMR (400 MHz, CD$_3$OD) δ ppm 4.29-4.26 (m, 2H), 4.06 (d, J=2.2 Hz, 2H), 3.04 (s, 3H), 2.74 (br. s, 2H), 1.69 (d, J=5.6 Hz, 4H), 1.43 (s, 10H), 1.12-1.07 (m, 2H); ES-LCMS m/z 252.0 [M–t–Bu+H]$^+$.

Step 3: tert-Butyl 4-(2-cyanoethyl)piperidine-1-carboxylate

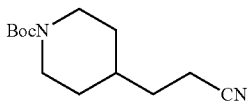

To a solution of tert-butyl 4-(2-((methylsulfonyl)oxy)ethyl)piperidine-1-carboxylate (12 g, 39.0 mmol) in DML (50 mL) was added KCN (7.8 g, 120 mmol). The mixture was stirred at 80° C. for 12 h then concentrated. H$_2$O (200 mL) was added and pH was adjust to 10 followed by extraction with DCM (300 mL×3). The combined organic layers were washed with brine (200 mL), dried over Na$_2$SO$_4$, filtered and concentrated. The crude product was purified by silica gel column chromatography (PE/EtOAc=1/0 to 1/1). All fractions found to contain product by TLC (PE/EtOAc=3/1, R$_f$=0.5) were combined and concentrated to yield brown oil of tert-butyl 4-(2-cyanoethyl)piperidine-1-carboxylate (6.0 g, 20.14 mmol, 51.6% yield): $^1$H NMR (400 MHz, CD$_3$OD) δ ppm 4.11-4.05 (m, 2H), 2.77 (br. s, 2H), 2.48 (m, 2H), 1.74 (d, J=12.3 Hz, 2H), 1.64-1.60 (m, 2H), 1.54-1.31 (m, 10H), 1.16-1.05 (m, 2H); ES-LCMS m/z 183.1 [M–t–Bu+H]$^+$.

Step 4: 3-(1-(tert-Butoxycarbonyl)piperidin-4-yl)propanoic acid

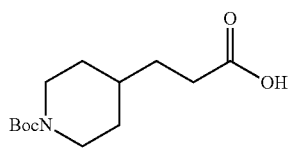 [SMILES: CC(C)(C)OC(=O)N1CCC(CCC(=O)O)CC1]

To a solution of tert-butyl 4-(2-cyanoethyl)piperidine-1-carboxylate (3 g, 12.59 mmol) in MeOH (30 mL) and H$_2$O (30.0 mL) was added NaOH (1.007 g, 25.2 mmol). The mixture was stirred at 20° C. for 12 h then concentrated. The residue was partitioned between DCM (300 mL) and H$_2$O (200 mL). The organic phase was separated and extracted with water (100 mL×2). To the combined aqueous phase was added aqueous HCl solution (1 M, 100 mL) until the pH=6 then extracted with DCM (300 mL×3). The combined organic phase was washed with brine (20 mL), dried over Na$_2$SO$_4$, filtered and concentrated yield yellow solid of 3-(1-(tert-butoxycarbonyl)piperidin-4-yl)propanoic acid (1.3 g, 4.45 mmol, 35.3% yield): $^1$H NMR (400 MHz, CDCl$_3$) δ ppm 4.08 (br. s, 2H), 2.66 (br. s, 2H), 2.38 (t, J=7.6 Hz, 2H), 1.70-1.55 (m, 4H), 1.49-1.37 (m, 10H), 1.09 (dq, J=4.2, 12.2 Hz, 2H); ES-LCMS m/z 202.1 [M–t–Bu+H]$^+$.

Step 5: 3-(Piperidin-4-yl)propanoic acid, trifluoroacetic acid salt

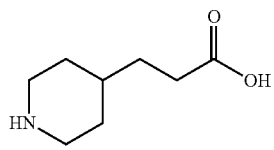

To a mixture of 3-(1-(tert-butoxycarbonyl)piperidin-4-yl)propanoic acid (500 mg, 1.710 mmol) in DCM (10 mL) was added TFA (2 mL, 26.0 mmol). The reaction was stirred at 15° C. for 1 h then concentrated to yield a colorless oil of 3-(piperidin-4-yl)propanoic acid, trifluoroacetic acid salt (300 mg, 0.774 mmol, 45.3% yield): $^1$H NMR (400 MHz, CD$_3$OD) δ ppm 3.39-3.30 (m, 2H), 2.94 (t, J=12.8 Hz, 2H), 2.45-2.26 (m, 2H), 1.94 (d, J=14.1 Hz, 2H), 1.61 (t, J=5.7 Hz, 3H), 1.43-1.32 (m, 2H).

Step 6: 3-(1-((2-((6-(4-(tert-Butoxycarbonyl)piperazin-1-yl)pyridin-3-yl)oxy)-6-(3,5-dichlorophenyl)pyridin-4-yl)methyl)piperidin-4-yl)propanoic acid

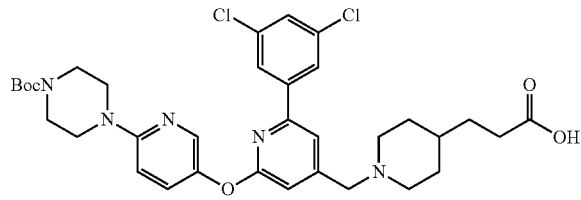 [SMILES: CC(C)(C)OC(=O)N1CCN(c2ccc(Oc3cc(CN4CCC(CCC(=O)O)CC4)cc(-c4cc(Cl)cc(Cl)c4)n3)cn2)CC1]

To a mixture of tert-butyl 4-(5-((6-(3,5-dichlorophenyl)-4-(((methylsulfonyl)oxy)methyl)pyridin-2-yl)oxy)pyridin-2-yl)piperazine-1-carboxylate (500 mg, 0.656 mmol) in DMF (10 mL) was added 3-(piperidin-4-yl)propanoic acid, trifluoroacetic acid salt (305 mg, 0.788 mmol) and K₂CO₃ (272 mg, 1.969 mmol). The reaction was stirred at 60° C. for 5 h. The mixture was filtered and concentrated to yield a yellow oil of 3-(1-((2-((6-(4-(tert-butoxycarbonyl)piperazin-1-yl)pyridin-3-yl)oxy)-6-(3,5-dichlorophenyl)pyridin-4-yl)methyl)piperidin-4-yl)propanoic acid (200 mg, 0.149 mmol, 22.7% yield): $^1$H NMR (400 MHz, CD$_3$OD) δ ppm 8.06-8.02 (m, 1H), 7.81 (d, J=1.8 Hz, 2H), 7.67-7.55 (m, 1H), 7.52-7.47 (m, 1H), 7.43-7.39 (m, 1H), 6.99-6.93 (m, 2H), 4.09 (s, 4H), 3.54 (br. s, 4H), 2.52 (d, J=2.6 Hz, 4H), 2.18 (d, J=7.5 Hz, 4H), 1.71-1.64 (m, 4H), 1.52-1.49 (m, 12H); ES-LCMS m/z 670.3, 672.3 [M+H]$^+$.

Step 7: 3-(1-((2-(3,5-Dichlorophenyl)-6-((6-(piperazin-1-yl)pyridin-3-yl)oxy)pyridine-4-yl)methyl)piperidin-4-yl)propanoic acid, 4 hydrochloride

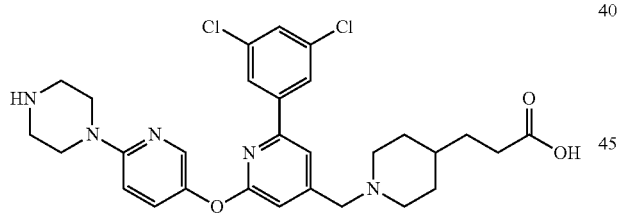

To a solution of 3-(1-((2-((6-(4-(tert-butoxycarbonyl)piperazin-1-yl)pyridin-3-yl)oxy)-6-(3,5-dichlorophenyl)pyridin-4-yl)methyl)piperidin-4-yl)propanoic acid (200 mg, 0.149 mmol) in DCM (20 mL) was added TFA (2 mL, 26.0 mmol). The mixture was stirred at 15° C. for 1 h then concentrated and purified by preparative HPLC (MeCN/H₂O as eluents, acidic condition) and dried by lyophilization to yield a white solid of 3-(1-((2-(3,5-dichlorophenyl)-6-((6-(piperazin-1-yl)pyridin-3-yl)oxy)pyridine-4-yl)methyl)piperidin-4-yl)propanoic acid, 4 hydrochloride (15 mg, 0.021 mmol, 13.9% yield): $^1$H NMR (400 MHz, CD$_3$OD) δ ppm 8.21 (d, J=2.6 Hz, 1H), 8.11 (dd, J=2.2, 9.7 Hz, 1H), 7.97 (s, 1H), 7.88 (d, J=1.8 Hz, 2H), 7.55-7.45 (m, 2H), 7.39 (s, 1H), 4.60-4.39 (m, 2H), 4.10-3.90 (m, 4H), 3.68-3.53 (m, 2H), 3.51-3.42 (m, 4H), 3.11 (t, J=11.7 Hz, 2H), 2.46-2.29 (m, 2H), 2.01 (d, J=13.2 Hz, 2H), 1.73-1.50 (m, 5H); ES-LCMS m/z 570.2, 572.2 [M+H]$^+$.

Example 4: 2-(1-((2-(3,5-Dichlorophenyl)-6-((6-(piperazin-1-yl)pyridin-3-yl)oxy)pyridin-4-yl)methyl)piperidin-4-yl)acetic acid, 4 hydrochloride

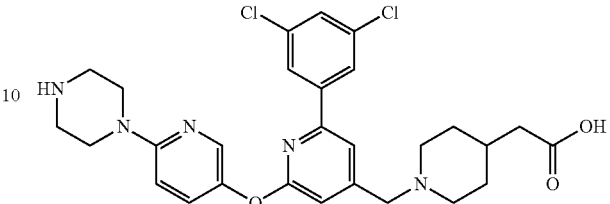

Step 1: Ethyl 2-(piperidin-4-yl)acetate, trifluoroacetic acid salt

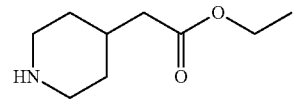

To a mixture of tert-butyl 4-(2-ethoxy-2-oxoethyl)piperidine-1-carboxylate (500 mg, 1.843 mmol) in DCM (10 mL) was added TFA (2 mL, 26.0 mmol). The reaction was stirred at 15° C. for 20 min. The mixture was concentrated to yield a colorless oil of ethyl 2-(piperidin-4-yl)acetate, trifluoroacetic acid salt (750 mg, 1.84 mmol, 100.0% yield): $^1$H NMR (400 MHz, CD$_3$OD) δ ppm 4.14-4.09 (m, 2H), 3.39-3.35 (t, J=12.8 Hz, 2H), 3.05-2.96 (m, 2H), 2.33 (d, J=14.1 Hz, 2H), 1.97-1.93 (d, J=14.1 Hz, 3H), 1.47-1.43 (m, 2H), 1.23-1.21 (t, J=5.7 Hz, 3H); ES-LCMS m/z 172.2 [M+H]$^+$.

Step 2: tert-Butyl 4-(5-((6-(3,5-dichlorophenyl)-4-((4-(2-ethoxy-2-oxoethyl)piperidin-1-yl)methyl)pyridin-2-yl)oxy)pyridin-2-yl)piperazine-1-carboxylate

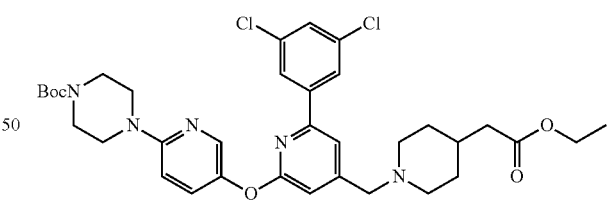

To a mixture of tert-butyl 4-(5-((6-(3,5-dichlorophenyl)-4-(((methylsulfonyl)oxy)methyl)pyridin-2-yl)oxy)pyridin-2-yl)piperazine-1-carboxylate (500 mg, 0.656 mmol) in DMF (20 mL) was added ethyl 2-(piperidin-4-yl)acetate, trifluoroacetic acid salt (401 mg, 0.984 mmol) and K₂CO₃ (272 mg, 1.969 mmol) The reaction was stirred at 60° C. for 5 h. The mixture was filtered and concentrated to yield a yellow solid of tert-butyl 4-(5-((6-(3,5-dichlorophenyl)-4-((4-(2-ethoxy-2-oxoethyl)piperidin-1-yl)methyl)pyridin-2-yl)oxy)pyridin-2-yl)piperazine-1-carboxylate (300 mg, 0.307 mmol, 46.7% yield): $^1$H NMR (400 MHz, CD$_3$OD) δ ppm 8.03 (d, J=2.6 Hz, 1H), 7.80 (d, J=1.8 Hz, 2H), 7.62-7.54 (m, 1H), 7.49-7.44 (m, 1H), 7.40 (t, J=1.8 Hz, 1H), 6.99-6.89 (m, 2H), 4.10-4.08 (m, 2H), 3.58-3.51 (m, 10H), 2.88-2.83 (m, 2H), 2.25 (d, J=6.6 Hz, 2H), 2.09 (m, 2H), 1.79 (m, 1H), 1.72 (d, J=12.8 Hz, 2H), 1.49 (s, 9H), 1.34-1.27 (m, 2H), 1.19 (m, 3H); ES-LCMS m/z 684.3, 686.3 [M+H]+.

Step 3: Methyl 2-(1-((2-(3,5-dichlorophenyl)-6-((6-(piperazin-1-yl)pyridin-3-yl)oxy)pyridin-4-yl)methyl)piperidin-4-yl)acetate, 4 hydrochloride

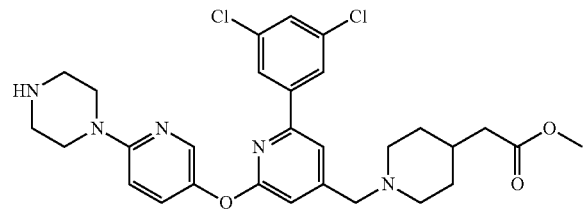 [SMILES: COC(=O)CC1CCN(Cc2cc(Oc3ccc(N4CCNCC4)nc3)nc(-c3cc(Cl)cc(Cl)c3)c2)CC1]

To a solution of tert-butyl 4-(5-((6-(3,5-dichlorophenyl)-4-((4-(2-ethoxy-2-oxoethyl)piperidin-1-yl)methyl)pyridin-2-yl)oxy)pyridin-2-yl)piperazine-1-carboxylate (300 mg, 0.307 mmol) in MeOH (10 mL) was added HCl solution (4.0 M in MeOH, 5 mL, 20.00 mmol). The mixture was stirred at 15° C. for 0.5 h then concentrated to yield a yellow oil of methyl 2-(1-((2-(3,5-dichlorophenyl)-6-((6-(piperazin-1-yl)pyridin-3-yl)oxy)pyridin-4-yl)methyl)piperidin-4-yl)acetate, 4 hydrochloride (200 mg, 0.195 mmol, 63.7% yield): 1H NMR (400 MHz, CD3OD) δ ppm 8.34-8.18 (m, 2H), 8.09-8.05 (m, 2H), 7.90 (d, J=1.8 Hz, 1H), 7.69-7.63 (m, 1H), 7.60-7.35 (m, 2H), 4.47 (s, 2H), 4.13-4.07 (m, 4H), 3.78-3.60 (m, 2H), 3.59-3.43 (m, 6H), 3.18-3.10 (m, 2H), 2.31-2.29 (m, 2H), 2.10-2.07 (m, 1H), 1.71-1.67 (m, 2H), 1.31-1.29 (m, 2H), 1.25 (m, 3H); ES-LCMS m/z 570.3, 572.3 [M+H]+.

Step 4: 2-(1-((2-(3,5-Dichlorophenyl)-6-((6-(piperazin-1-yl)pyridin-3-yl)oxy)pyridin-4-yl)methyl)piperidin-4-yl)acetic acid, 4 hydrochloride

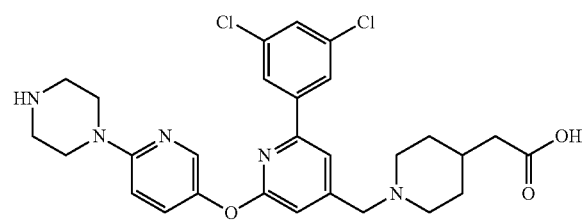

To a mixture of methyl 2-(1-((2-(3,5-dichlorophenyl)-6-((6-(piperazin-1-yl)pyridin-3-yl)oxy)pyridin-4-yl)methyl)piperidin-4-yl)acetate, 4 hydrochloride (200 mg, 0.195 mmol) in MeOH (10 mL) and H2O (2 mL) was added NaOH (46.89 mg, 1.173 mmol). The reaction was stirred at 15° C. for 2 h then concentrated and purified by preparative HPLC (MeCN/H2O as eluents, acidic condition) and dried by lyophilization to yield a white solid of 2-(1-((2-(3,5-dichlorophenyl)-6-((6-(piperazin-1-yl)pyridin-3-yl)oxy)pyridin-4-yl)methyl)piperidin-4-yl)acetic acid, 4 hydrochloride (59.96 mg, 0.084 mmol, 43.1% yield): 1H NMR (400 MHz, CD3OD) δ ppm 8.20 (d, J=2.6 Hz, 1H), 8.03 (dd, J=2.6, 9.3 Hz, 1H), 7.97-7.91 (m, 1H), 7.88 (d, J=1.8 Hz, 2H), 7.51 (t, J=1.8 Hz, 1H), 7.44 (d, J=9.3 Hz, 1H), 7.36 (s, 1H), 4.45 (s, 2H), 3.99-3.95 (m, 4H), 3.59 (d, J=11.9 Hz, 2H), 3.49-3.44 (m, 4H), 3.14 (t, J=11.9 Hz, 2H), 2.37-2.25 (m, 2H), 2.06 (d, J=14.1 Hz, 3H), 1.75-1.58 (m, 2H); ES-LCMS m/z 556.2, 558.2 [M+H]+.

Example 5: 1-((1-((2-(3,5-Dichlorophenyl)-6-((6-(piperazin-1-yl)pyridin-3-yl)oxy)pyridin-4-yl)methyl)-4-hydroxypiperidin-4-yl)methyl)-3-methylurea, 4 hydrochloride

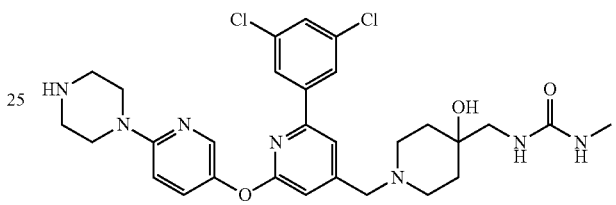

Step 1: tert-Butyl 4-(5-((6-(3,5-dichlorophenyl)-4-((4-hydroxy-4-((3-methylureido)methyl)piperidin-1-yl)methyl)pyridin-2-yl)oxy)pyridin-2-yl)piperazine-1-carboxylate

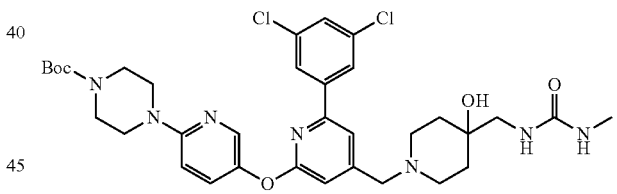

To a solution of tert-butyl 4-(5-((6-(3,5-dichlorophenyl)-4-(((methylsulfonyl)oxy)methyl)pyridin-2-yl)oxy)pyridin-2-yl)piperazine-1-carboxylate (1.1 g, 1.805 mmol) and 1-((4-hydroxypiperidin-4-yl)methyl)-3-methylurea (0.405 g, 2.166 mmol) in DMF (20 mL) was added K2CO3 (0.499 g, 3.61 mmol) at 25° C. The mixture was stirred at 80° C. for 12 h then filtered. The filtrate was concentrated and the residue was dissolved in DCM (100 mL), washed with water (30 mL×3) and dried over Na2SO4. The organic phase was concentrated to yield a yellow solid of tert-butyl 4-(5-((6-(3,5-dichlorophenyl)-4-((4-hydroxy-4-((3-methylureido)methyl)piperidin-1-yl)methyl)pyridin-2-yl)oxy)pyridin-2-yl)piperazine-1-carboxylate (1.2 g, 1.541 mmol, 85.0% yield): 1H NMR (400 MHz, CDCl3) δ ppm 8.08-7.98 (m, 1H), 7.71-7.52 (m, 2H), 7.35-7.22 (m, 2H), 7.19 (s, 1H), 6.73 (s, 1H), 6.63 (d, J=9.2 Hz, 1H), 3.47-3.45 (m, 6H), 3.13 (d, J=6.0 Hz, 2H), 2.97-2.85 (m, 4H), 2.70 (s, 3H), 2.51-2.48 (m, 2H), 2.44-2.40 (m, 2H), 1.70-1.61 (m, 4H), 1.42 (s, 9H); ES-LCMS m/z 700.3, 702.3 [M+H]+.

Step 2: 1-((1-((2-(3,5-Dichlorophenyl)-6-((6-(piperazin-1-yl)pyridin-3-yl)oxy)pyridin-4-yl)methyl)-4-hydroxypiperidin-4-yl)methyl)-3-methylurea, 4 hydrochloride

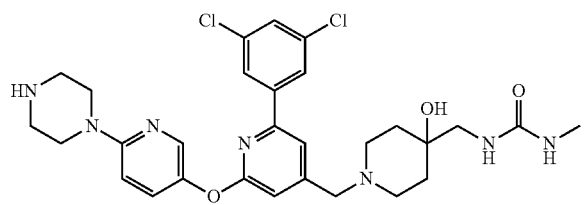 [SMILES: CNC(=O)NCC1(O)CCN(Cc2cc(Oc3ccc(N4CCNCC4)nc3)nc(-c3cc(Cl)cc(Cl)c3)c2)CC1]

To a solution of tert-butyl 4-(5-((6-(3,5-dichlorophenyl)-4-((4-hydroxy-4-((3-methylureido)methyl)piperidin-1-yl)methyl)pyridin-2-yl)oxy)pyridin-2-yl)piperazine-1-carboxylate (1.2 g, 1.713 mmol) in DCM (20 mL) was added TFA (5 mL, 64.9 mmol) at 25° C. The mixture was stirred at 25° C. for 12 h then concentrated. The residue was purified by preparative HPLC (MeCN/H₂O as eluents, acidic condition) and lyophilized to yield a brown solid of 1-((1-((2-(3,5-dichlorophenyl)-6-((6-(piperazin-1-yl)pyridin-3-yl)oxy)pyridin-4-yl)methyl)-4-hydroxypiperidin-4-yl)methyl)-3-methylurea, 4 hydrochloride (182.24 mg, 0.241 mmol, 14.1% yield): $^1$H NMR (400 MHz, CD₃OD) δ ppm 8.23-8.16 (m, 2H), 8.01-7.96 (m, 1H), 7.87 (d, J=1.5 Hz, 2H), 7.61-7.53 (m, 1H), 7.52-7.48 (m, 1H), 7.44-7.38 (m, 1H), 4.47 (s, 2H), 4.07-3.97 (m, 4H), 3.51-3.46 (m, 4H), 3.44-3.35 (m, 4H), 3.26-3.17 (m, 2H), 2.69 (s, 3H), 1.98-1.95 (m, 2H), 1.83-1.74 (m, 2H); ES-LCMS m/z 600.3, 602.2 [M+H]⁺.

Example 6: Methyl ((1-((2-(3,5-dichlorophenyl)-6-((6-(piperazin-1-yl)pyridin-3-yl)oxy)pyridin-4-yl)methyl)-4-hydroxypiperidin-4-yl)methyl)carbamate, 4 hydrochloride

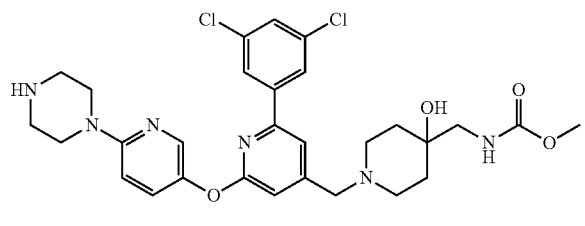

Step 1: tert-Butyl 4-((tert-butyldimethylsilyl)oxy)-4-(((methoxycarbonyl)amino)methyl)piperidine-1-carboxylate

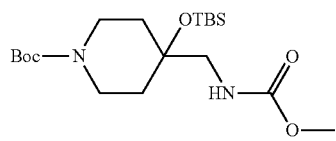 [SMILES: COC(=O)NCC1(O[Si](C)(C)C(C)(C)C)CCN(C(=O)OC(C)(C)C)CC1]

To a solution of tert-butyl 4-(aminomethyl)-4-((tert-butyldimethylsilyl)oxy)piperidine-1-carboxylate (18 g, 52.2 mmol) and DIEA (18.25 mL, 104 mmol) in DCM (200 mL) was added methyl carbonochloridate (7.40 g, 78 mmol) at 0° C. The mixture was stirred at 25° C. for 4 h then was diluted with DCM (250 mL) and washed with water (100 mL×3). The organic phase was dried over Na₂SO₄ and concentrated. The residue was purified by column chromatography eluted with (PE/EA=4/1) to yield a yellow oil of tert-butyl 4-((tert-butyldimethylsilyl)oxy)-4-(((methoxycarbonyl)amino)methyl)piperidine-1-carboxylate (12 g, 20.86 mmol, 39.9% yield): $^1$H NMR (400 MHz, CDCl₃) δ ppm 3.67 (d, J=5.1 Hz, 3H), 3.54-3.45 (m, 2H), 3.43-3.35 (m, 2H), 3.23 (s, 2H), 1.56 (m, 4H), 1.44 (s, 9H), 0.88 (s, 9H), 0.11 (s, 6H); ES-LCMS m/z 303.2 [M−Boc+H]⁺.

Step 2: Methyl ((4-((tert-butyldimethylsilyl)oxy)piperidin-4-yl)methyl/carbamate

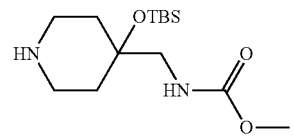

To a solution of tert-butyl 4-((tert-butyldimethylsilyl)oxy)-4-(((methoxycarbonyl)amino)methyl)piperidine-1-carboxylate (2.0 g, 4.97 mmol) in DCM (20 mL) was added TFA (5.0 mL, 64.9 mmol) at 25° C. The mixture was stirred at 25° C. for 1 h then concentrated to yield brown oil of methyl ((4-((ten-butyldimethylsilyl)oxy)piperidin-4-yl)methyl)carbamate (1.4 g, 3.70 mmol, 74.5% yield): $^1$H NMR (400 MHz, CD₃OD) δ ppm 3.45 (s, 3H), 3.09-3.07 (m, 2H), 3.07-2.99 (m, 4H), 1.74-1.67 (m, 2H), 1.56-1.50 (m, 2H), 0.74 (s, 9H), 0.00 (s, 6H); ES-LCMS m/z 303.2 [M+H]⁺.

Step 3: tert-Butyl 4-(5-((4-((4-((tert-butyldimethylsilyl)oxy)-4-(((methoxycarbonyl)amino)methyl)piperidin-1-yl)methyl)-6-(3,5-dichlorophenyl)pyridin-2-yl)oxy)pyridin-2-yl)piperazine-1-carboxylate

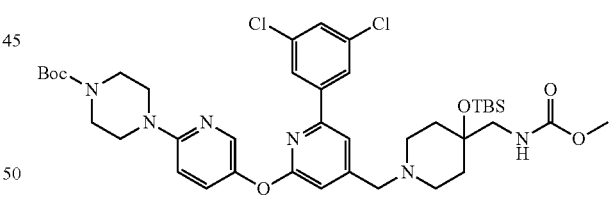

A mixture of tert-butyl 4-(5-((6-(3,5-dichlorophenyl)-4-(((methylsulfonyl)oxy)methyl)pyridin-2-yl)oxy)pyridin-2-yl)piperazine-1-carboxylate (90 mg, 0.148 mmol), methyl ((4-((tert-butyldimethylsilyl)oxy)piperidin-4-yl)methyl)carbamate (53.6 mg, 0.177 mmol) and K₂CO₃ (30.6 mg, 0.221 mmol) in DMF (20 mL) was stirred at 80° C. for 12 h. The mixture was filtered and the filtrate was concentrated to yield brown oil of tert-butyl 4-(5-((4-((4-((tert-butyldimethylsilyl)oxy)-4-(((methoxycarbonyl)amino)methyl)piperidin-1-yl)methyl)-6-(3,5-dichlorophenyl)pyridin-2-yl)oxy)pyridin-2-yl)piperazine-1-carboxylate (110 mg, 0.121 mmol, 82.0% yield): $^1$H NMR (400 MHz, CDCl₃) δ ppm 8.08-8.00 (m, 1H), 7.92-7.88 (m, 1H), 7.69-7.59 (m, 2H), 7.36-7.31 (m, 1H), 7.24-7.21 (m, 1H), 6.73-6.69 (m, 1H), 6.65-6.58 (m, 1H), 3.56 (s, 3H), 3.41 (s, 2H), 3.20-3.15 (m, 4H), 2.90-2.86 (m, 2H), 2.80 (s, 2H), 2.74-2.64 (m, 4H), 2.52-2.41 (m, 2H), 1.60-1.53 (m, 4H), 1.50 (s, 9H), 0.80 (s, 9H), 0.03 (s, 6H); ES-LCMS m/z 815.2, 817.2 [M+H]⁺.

Step 4: Methyl ((4-((tert-butyldimethylsilyl)oxy)-1-((3',5'-dichloro-5-((6-(piperazin-1-yl)pyridin-3-yl)oxy)-[1,1'-biphenyl]-3-yl)methyl)piperidin-4-yl)methyl)carbamate, 4trifluoroacetic acid

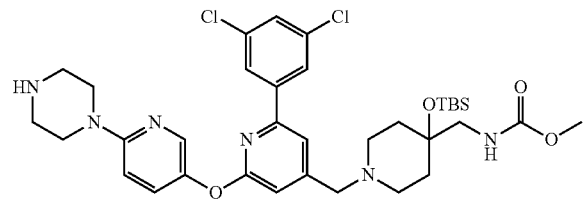 [SMILES: COC(=O)NCC1(O[Si](C)(C)C(C)(C)C)CCN(Cc2cc(Oc3ccc(N4CCNCC4)nc3)nc(-c3cc(Cl)cc(Cl)c3)c2)CC1]

To a solution of tert-butyl 4-(5-((4-((4-((tert-butyldimethylsilyl)oxy)-4-(((methoxycarbonyl)amino)methyl)piperidin-1-yl)methyl)-6-(3,5-dichlorophenyl)pyridin-2-yl)oxy)pyridin-2-yl)piperazine-1-carboxylate (90 mg, 0.110 mmol) in DCM (20 mL) was added TFA (5 mL, 64.9 mmol) at 25° C. The mixture was stirred at 25° C. for 2 h then concentrated to yield brown oil of methyl ((4-((tert-butyldimethylsilyl)oxy)-1-((3',5'-dichloro-5-((6-(piperazin-1-yl)pyridin-3-yl)oxy)-[1,1'-biphenyl]-3-yl)methyl)piperidin-4-yl)methyl)carbamate, 4 trifluoroacetic acid (70 mg, 0.054 mmol, 48.8% yield): ¹H NMR (400 MHz, CD₃OD) δ ppm 7.81-7.76 (m, 1H), 7.65-7.59 (m, 2H), 7.42-7.34 (m, 2H), 7.32-7.28 (m, 1H), 7.09-7.04 (m, 1H), 6.91-6.85 (m, 1H), 3.65 (s, 2H), 3.45 (s, 3H), 3.30-3.15 (m, 6H), 3.08-2.98 (m, 8H), 1.71-1.68 (m, 2H), 1.54-1.50 (m, 2H), 0.74 (s, 9H), 0.00 (s, 6H); ES-LCMS m/z 715.3, 717.4 [M+H]⁺.

Step 5: Methyl ((1-((2-(3,5-dichlorophenyl)-6-((6-(piperazin-1-yl)pyridin-3-yl)oxy)pyridin-4-yl)methyl)-4-hydroxypiperidin-4-yl)methyl)carbamate, 4 hydrochloride

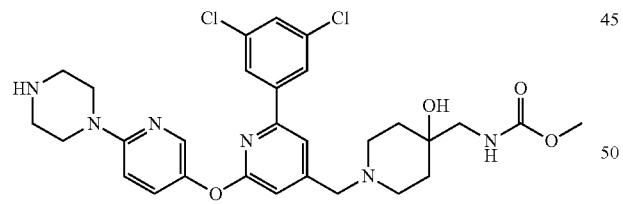

A solution of methyl ((4-((tert-butyldimethylsilyl)oxy)-1-((2-(3,5-dichlorophenyl)-6-((6-(piperazin-1-yl)pyridin-3-yl)oxy)pyridin-4-yl)methyl)piperidin-4-yl)methyl)carbamate, 4 trifluoroacetic acid (70 mg, 0.054 mmol) in 4.0 M HCl in MeOH, (20 mL, 80 mmol) was stirred at 25° C. for 2 h then concentrated. The residue was purified by preparative HPLC (MeCN/H₂O as eluents, acidic condition) and lyophilized to yield a white solid of methyl ((1-((2-(3,5-dichlorophenyl)-6-((6-(piperazin-1-yl)pyridin-3-yl)oxy)pyridin-4-yl)methyl)-4-hydroxypiperidin-4-yl)methyl)carbamate, 4 hydrochloride (31.34 mg, 0.042 mmol, 42.9% yield): ¹H NMR (400 MHz, CD₃OD) δ ppm 8.18-8.13 (m, 1H), 7.91-7.87 (m, 1H), 7.85 (d, J=1.7 Hz, 3H), 7.52-7.48 (m, 1H), 7.32-7.29 (m, 1H), 7.28-7.23 (m, 1H), 4.47-4.42 (m, 2H), 3.93-3.86 (m, 4H), 3.62 (s, 3H), 3.41 (d, J=5.4 Hz, 8H), 3.16 (s, 2H), 1.99-1.85 (m, 2H), 1.82-1.75 (m, 2H); ES-LCMS m/z 601.3, 603.3 [M+H]⁺.

Example 7: 2-(1-((2-(3,5-Dichlorophenyl)-6-((6-(piperazin-1-yl)pyridin-3-yl)oxy)pyridin-4-yl)methyl)piperidin-4-yl)ethanesulfonic acid, 4 hydrochloride

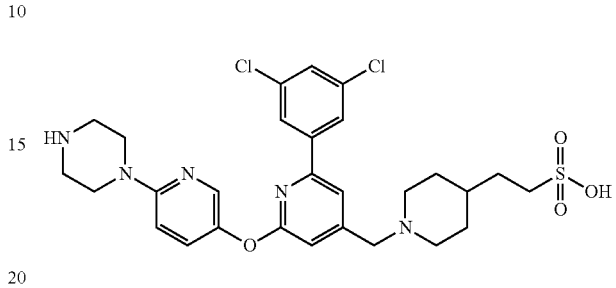

Step 1: 2-(1-(tert-Butoxycarbonyl)piperidin-4-yl)ethanesulfonic acid

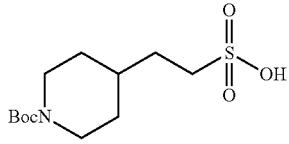 [SMILES: CC(C)(C)OC(=O)N1CCC(CCS(=O)(=O)O)CC1]

To a solution of sodium sulfite (0.861 g, 6.83 mmol) in water (40 mL) was added tert-butyl 4-(2-((methylsulfonyl)oxy)ethyl)piperidine-1-carboxylate (1 g, 2.277 mmol) and EtOH (40.0 mL). The reaction mixture was stirred at 110° C. for 12 h. The mixture was adjusted pH to 6 with 1 N HCl (aq.) then concentrated. To the residue was added MeOH (20 mL), and then the mixture was filtered. The filtrate was evaporated to yield a white solid of 2-(1-(tert-butoxycarbonyl)piperidin-4-yl)ethanesulfonic acid (1 g, 2.045 mmol, 90.0% yield): ¹H NMR (400 MHz, CD₃OD) δ ppm 4.09-4.02 (m, 2H), 3.36 (br. s, 2H), 2.84-2.80 (m, 2H), 1.78-1.68 (m, 5H), 1.44 (s, 9H), 1.38-1.29 (m, 2H); ES-LCMS m/z 238.1 [M−t−Bu+H]⁺.

Step 2: 2-(Piperidin-4-yl)ethanesulfonic acid, hydrochloride

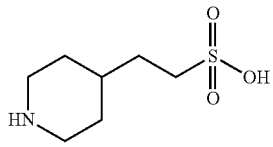 [SMILES: O=S(=O)(O)CCC1CCNCC1]

To a mixture of 2-(1-(tert-butoxycarbonyl)piperidin-4-yl)ethanesulfonic acid (1 g, 2.045 mmol) in EtOAc (5 mL) was added HCl solution (4 M in EtOAc, 5 mL, 20.00 mmol). The reaction was stirred at 25° C. for 0.5 h. The solution was concentrated to yield a yellow solid of 2-(piperidin-4-yl)ethanesulfonic acid, hydrochloride (500 mg, 1.552 mmol, 76.0% yield): ¹H NMR (400 MHz, CD₃OD) δ ppm 3.71-

3.32 (m, 2H), 3.07-2.50 (m, 4H), 2.11-1.66 (m, 3H), 1.62-1.02 (m, 4H); ES-LCMS m/z 194.1 [M+H]⁺.

Step 3: 2-(1-((2-((6-(4-(tert-Butoxycarbonyl)piperazin-1-yl)pyridin-3-yl)oxy)-6-(3,5-dichlorophenyl)pyridin-4-yl)methyl)piperidin-4-yl)ethanesulfonic acid, 3 hydrochloride

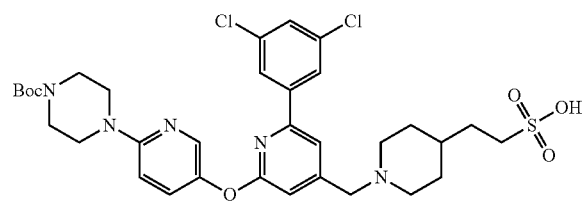 [SMILES: CC(C)(C)OC(=O)N1CCN(c2ccc(Oc3cc(CN4CCC(CCS(=O)(=O)O)CC4)cc(-c4cc(Cl)cc(Cl)c4)n3)cn2)CC1]

To a mixture of tert-butyl 4-(5-((6-(3,5-dichlorophenyl)-4-(((methylsulfonyl)oxy)methyl)pyridin-2-yl)oxy)pyridin-2-yl)piperazine-1-carboxylate (200 mg, 0.246 mmol) in DMF (3 mL) was added 2-(piperidin-4-yl)ethanesulfonic acid (119 mg, 0.369 mmol) and $K_2CO_3$ (102 mg, 0.738 mmol). The reaction was stirred at 60° C. for 5 h. The mixture was filtered, concentrated and purified by preparative HPLC (MeCN/$H_2O$ as eluents, acidic condition) and dried by lyophilization to yield a yellow solid of 2-(1-((2-((6-(4-(tert-butoxycarbonyl)piperazin-1-yl)pyridin-3-yl)oxy)-6-(3,5-dichlorophenyl)pyridin-4-yl)methyl)piperidin-4-yl)ethanesulfonic acid, 3 hydrochloride (80 mg, 0.093 mmol, 37.8% yield): ¹H NMR (400 MHz, $CD_3OD$) δ ppm 8.20 (d, J=2.6 Hz, 1H), 7.87 (d, J=1.8 Hz, 3H), 7.57-7.49 (m, 2H), 7.39-7.32 (m, 2H), 4.45-4.43 (m, 2H), 3.97-3.93 (m, 4H), 3.81-3.78 (m, 2H), 3.70 (br. s, 2H), 3.58 (d, J=11.9 Hz, 2H), 3.10-3.01 (m, 2H), 2.84 (s, 2H), 2.04 (d, J=14.1 Hz, 2H), 1.84-1.67 (m, 5H), 1.56-1.43 (m, 9H); ES-LCMS m/z 706.3, 708.2 [M+H]⁺.

Step 4: 2-(1-((2-(3,5-Dichlorophenyl)-6-((6-(piperazin-1-yl)pyridin-3-yl)oxy)pyridin-4-yl)methyl)piperidin-4-yl)ethanesulfonic acid, 4 hydrochloride

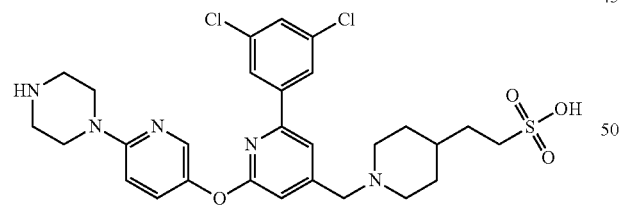

To a mixture of 2-(1-((2-((6-(4-(tert-butoxycarbonyl)piperazin-1-yl)pyridin-3-yl)oxy)-6-(3,5-dichlorophenyl)pyridin-4-yl)methyl)piperidin-4-yl)ethanesulfonic acid, 3 hydrochloride (80 mg, 0.093 mmol) in EtOAc (5 mL) was added HCl solution (4.0 M in EtOAc, 2 mL, 8.00 mmol). The reaction was stirred at 25° C. for 0.5 h then concentrated. Water (20 mL) was added and the mixture was dried by lyophilization to yield a white solid of 2-(1-((2-(3,5-dichlorophenyl)-6-((6-(piperazin-1-yl)pyridin-3-yl)oxy)pyridin-4-yl)methyl)piperidin-4-yl)ethanesulfonic acid, 4 hydrochloride (40.55 mg, 0.054 mmol, 57.9% yield): ¹H NMR (400 MHz, $CD_3OD$) δ ppm 8.20 (d, J=2.5 Hz, 1H), 7.89-7.86 (m, 4H), 7.53 (s, 1H), 7.30 (s, 2H), 4.45 (s, 2H), 3.93 (s, 4H), 3.60 (d, J=11.5 Hz, 2H), 3.44 (d, J=5.0 Hz, 4H), 3.16-3.08 (m, 2H), 2.87 (d, J=7.5 Hz, 2H), 2.07 (d, J=14.6 Hz, 2H), 2.04-1.55 (m, 3H), 1.54-1.44 (m, 2H); ES-LCMS m/z 606.3, 608.3 [M+H]⁺.

Example 8: (1-((2-(3,5-Dichlorophenyl)-6-((6-(piperazin-1-yl)pyridin-3-yl)oxy)pyridin-4-yl)methyl)piperidin-4-yl)methanesulfonic acid, 4 hydrochloride

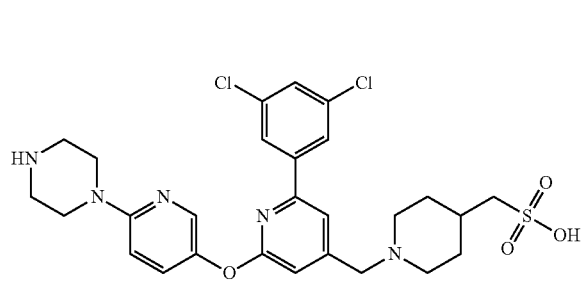 [SMILES: O=S(=O)(O)CC1CCN(Cc2cc(Oc3ccc(N4CCNCC4)nc3)nc(-c3cc(Cl)cc(Cl)c3)c2)CC1]

Step 1: Benzyl 4-(hydroxymethyl)piperidine-1-carboxylate

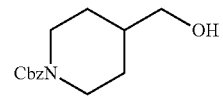

To a mixture of piperidin-4-ylmethanol (8 g, 69.5 mmol), $Na_2CO_3$ (29.2 g, 347 mmol) in 1,4-dioxane (100 mL) and water (100 mL) was added the dropwise CbzCl (14.22 g, 83 mmol). The mixture was stirred at 30° C. for 2 h then concentrated. The resulting crude was partitioned between EtOAc (200 mL) and water (200 mL). The aqueous layer was separated and extracted with EtOAc (100 mL×2), and the organic phase was combined, washed with water (200 mL×2), dried over $Na_2SO_4$, filtered, and concentrated to yield the crude product, which was purified by silica gel column chromatography (PE/EtOAc=20/1 to 10/1 to 5/1, PE/EtOAc=5/1, $R_f$=0.5) to yield brown oil of benzyl 4-(hydroxymethyl)piperidine-1-carboxylate (12 g, 29.1 mmol, 41.9% yield): ¹H NMR (400 MHz, $CDCl_3$) δ ppm 7.39-7.27 (m, 5H), 5.18-5.04 (m, 2H), 4.20 (br. s, 2H), 3.48 (d, J=6.2 Hz, 2H), 2.77 (br. s, 2H), 1.81-1.61 (m, 4H), 1.15 (d, J=10.1 Hz, 1H); ES-LCMS m/z 205.3 [M+H]⁺.

Step 2: Benzyl 4-(((methylsulfonyl)oxy)methyl)piperidine-1-carboxylate

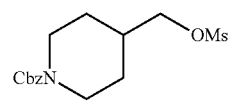

To a solution of benzyl 4-(hydroxymethyl)piperidine-1-carboxylate (5 g, 12.13 mmol) and DIEA (7.84 g, 60.7 mmol) in DCM (120 mL) was added MsCl (4.17 g, 36.4 mmol) at 20° C. The mixture was stirred at 20° C. for 0.5 h then concentrated. The residue was diluted with DCM (100 mL) and water (100 mL), separated and the aqueous phase was extracted with DCM (100 mL×2). The combined organic layers were dried over Na₂SO₄, filtered and concentrated to yield a brown solid of benzyl 4-(((methylsulfonyl)oxy)methyl)piperidine-1-carboxylate (4 g, 9.77 mmol, 81.0% yield): ¹H NMR (400 MHz, CDCl₃) δ ppm 7.38-7.26 (m, 5H), 5.11 (s, 2H), 4.22 (d, J=5.7 Hz, 2H), 4.09 (d, J=5.7 Hz, 2H), 2.99 (s, 3H), 2.84-2.70 (m, 2H), 1.92 (m, 1H), 1.75 (d, J=12.3 Hz, 2H), 1.30-1.14 (m, 2H); ES-LCMS m/z 328.2 [M+H]⁺.

Step 3: (1-((Benzyloxy)carbonyl)piperidin-4-yl)methanesulfonic acid

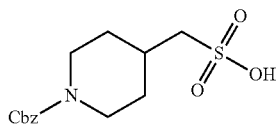 [SMILES: O=C(OCc1ccccc1)N1CCC(CS(=O)(=O)O)CC1]

To a solution of sodium sulfite (0.924 g, 7.33 mmol) in water (40 mL) was added benzyl 4-(((methylsulfonyl)oxy)methyl)piperidine-1-carboxylate (1 g, 2.444 mmol) and EtOH (40.0 mL). The reaction mixture was stirred at 110° C. for 12 h then cooled. The mixture was adjusted pH to 6 with 1 N HCl (aq.) then concentrated. MeOH (20 mL) was added and the mixture was filtered. The filtrate was evaporated to yield a white solid of (1-((benzyloxy)carbonyl)piperidin-4-yl)methanesulfonic acid (1 g, 2.419 mmol, 99.0% yield): ¹H NMR (400 MHz, CD₃OD) δ ppm 7.49-7.14 (m, 5H), 5.10 (br. s, 2H), 4.22-4.00 (m, 2H), 3.01-2.71 (m, 4H), 2.13-1.94 (m, 2H), 1.82-1.57 (m, 1H), 1.32-1.04 (m, 2H); ES-LCMS m/z 314.2 [M+H]⁺.

Step 4: Piperidin-4-ylmethanesulfonic acid, trifluoroacetic acid

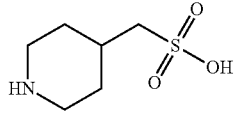

A solution of (1-((benzyloxy)carbonyl)piperidin-4-yl)methanesulfonic acid (900 mg, 2.177 mmol) in TFA (2 mL) was stirred at 60° C. for 12 h. This reaction mixture was concentrated to yield an off white solid of piperidin-4-ylmethanesulfonic acid, trifluoroacetic acid (600 mg, 1.534 mmol, 70.5% yield): ¹H NMR (400 MHz, CD₃OD) δ ppm 3.37 (d, J=13.2 Hz, 2H), 3.09-2.94 (m, 2H), 2.84-2.74 (m, 2H), 2.30-1.89 (m, 3H), 1.63-1.44 (m, 2H).

Step 5: (1-((2-((6-(4-(tert-Butoxycarbonyl)piperazin-1-yl)pyridin-3-yl)oxy)-6-(3,5-dichlorophenyl)pyridin-4-yl)methyl)piperidin-4-yl)methanesulfonic acid, 3 hydrochloride

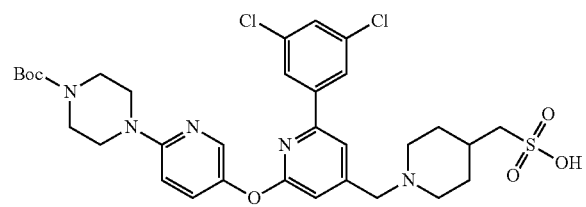 [SMILES: CC(C)(C)OC(=O)N1CCN(c2ccc(Oc3cc(CN4CCC(CS(=O)(=O)O)CC4)cc(-c4cc(Cl)cc(Cl)c4)n3)cn2)CC1]

To a suspension of tert-butyl 4-(5-(((6-(3,5-dichlorophenyl)-4-(((methylsulfonyl)oxy)methyl)pyridin-2-yl)oxy)pyridin-2-yl)piperazine-1-carboxylate (250 mg, 0.308 mmol) and piperidin-4-ylmethanesulfonic acid, trifluoroacetic acid (226 mg, 0.615 mmol) in DMF (10 mF) was added K₂CO₃ (255 mg, 1.846 mmol). The reaction mixture was stirred at 60° C. for 12 h then filtered and concentrated. The residue was purified by preparative HPFC (MeCN/H₂O as eluents, acidic condition) and lyophilized to yield a white solid of (1-((2-((6-(4-(tert-butoxycarbonyl)piperazin-1-yl)pyridin-3-yl)oxy)-6-(3,5-dichlorophenyl)pyridin-4-yl)methyl)piperidin-4-yl)methanesulfonic acid, 3 hydrochloride (150 mg, 0.076 mmol, 24.7% yield): ¹H NMR (400 MHz, CDCl₃) δ ppm 7.91 (br. s, 1H), 7.84 (br. s, 1H), 7.59 (br. s, 2H), 7.20-7.14 (m, 2H), 7.00 (br. s, 1H), 6.88 (d, J=8.8 Hz, 1H), 4.11 (d, J=10.6 Hz, 2H), 3.69 (br. s, 4H), 3.56 (br. s, 2H), 3.48 (br. s, 2H), 3.26 (d, J=12.3 Hz, 2H), 2.84 (br. s, 2H), 2.59 (d, J=5.7 Hz, 2H), 2.04 (d, J=14.6 Hz, 2H), 1.95 (br. s, 1H), 1.51 (br. s, 2H), 1.43-1.23 (m, 9H); ES-LCMS m/z 692.2, 694.2 [M+H]⁺.

Step 6: (1-((2-(3,5-Dichlorophenyl)-6-((6-(piperazin-1-yl)pyridin-3-yl)oxy)pyridin-4-yl)methyl)piperidin-4-yl)methanesulfonic acid, 4 hydrochloride

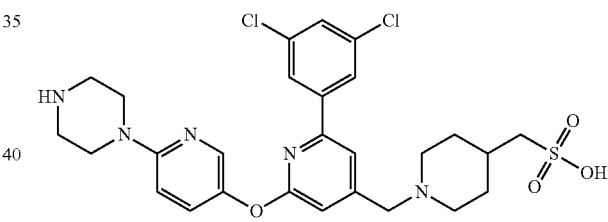

To a suspension of (1-((2-((6-(4-(tert-butoxycarbonyl)piperazin-1-yl)pyridin-3-yl)oxy)-6-(3,5-dichlorophenyl)pyridin-4-yl)methyl)piperidin-4-yl)methanesulfonic acid, 3 hydrochloride (150 mg, 0.076 mmol) in EtOAc (10 mL) was added HCl solution (4.0 M in EtOAc, 5 mL, 20 mmol). The reaction mixture was stirred at 25° C. for 1 h then concentrated. The residue was dissolved in water (10 mL) and lyophilized to yield an off white solid of (1-((2-(3,5-dichlorophenyl)-6-((6-(piperazin-1-yl)pyridin-3-yl)oxy)pyridin-4-yl)methyl)piperidin-4-yl)methanesulfonic acid, 4 hydrochloride (52.92 mg, 0.070 mmol, 92.0% yield): ¹H NMR (400 MHz, CD₃OD) δ ppm 8.16 (d, J=2.6 Hz, 1H), 7.87-7.76 (m, 4H), 7.50 (s, 1H), 7.27-7.20 (m, 2H), 4.41 (s, 2H), 3.92-3.85 (m, 4H), 3.57 (d, J=11.9 Hz, 2H), 3.43-3.37 (m, 4H), 3.16-3.06 (m, 2H), 2.78 (d, J=6.2 Hz, 2H), 2.29 (d, J=14.1 Hz, 2H), 2.17 (br. s, 1H), 1.65-1.52 (m, 2H); ES-LCMS m/z 592.2, 594.2 [M+H]⁺.

Example 9: N-((1-((2-(3,5-Dichlorophenyl)-6-((6-(piperazin-1-yl)pyridin-3-yl)oxy)pyridin-4-yl)methyl)piperidin-4-yl)methyl)acetamide, 4 hydrochloride

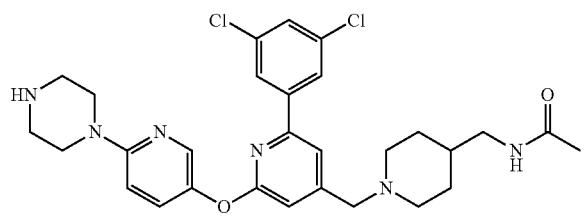

Step 1: tert-Butyl 4-(5-((4-((4-(acetamidomethyl)piperidin-1-yl)methyl)-6-(3,5-dichlorophenyl)pyridin-2-yl)oxy)pyridin-2-yl)piperazine-1-carboxylate

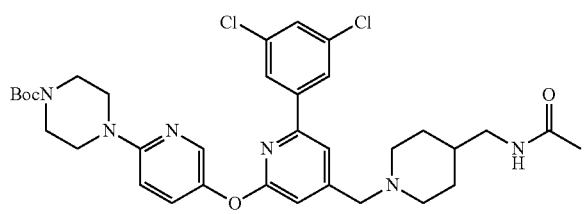 [SMILES: CC(=O)NCC1CCN(Cc2cc(Oc3ccc(N4CCN(C(=O)OC(C)(C)C)CC4)nc3)nc(-c3cc(Cl)cc(Cl)c3)c2)CC1]

A mixture of N-((1-((2-((6-bromopyridin-3-yl)oxy)-6-(3,5-dichlorophenyl)pyridin-4-yl)methyl)piperidin-4-yl)methyl)acetamide (580 mg, 1.028 mmol), tert-butyl piperazine-1-carboxylate (574 mg, 3.08 mmol), (±)-BINAP (12.80 mg, 0.021 mmol), 18-crown-6 (815 mg, 3.08 mmol), Pd$_2$(dba)$_3$ (47.1 mg, 0.051 mmol) and sodium tert-butoxide (296 mg, 3.08 mmol) in THF (15 mL) was stirred at 65° C. under N$_2$ atmosphere for 2 h. The mixture was filtered and the filtrate was concentrated. The residue was dissolved in DCM (50 mL) and washed with brine (50 mL), dried over MgSO$_4$, filtered and concentrated. The crude material was purified by silica gel column chromatography (MeOH/DCM=1/10) then further purified by preparative HPLC (MeCN/H$_2$O as eluents, acidic condition) to yield a pale yellow solid of tert-butyl 4-(5-((4-((4-(acetamidomethyl)piperidin-1-yl)methyl)-6-(3,5-dichlorophenyl)pyridin-2-yl)oxy)pyridin-2-yl)piperazine-1-carboxylate (81 mg, 0.094 mmol, 9.1% yield): $^1$H NMR (400 MHz, CD$_3$OD) δ ppm 8.24-8.17 (m, 1H), 8.00 (d, J=6.8 Hz, 1H), 7.94 (s, 1H), 7.91-7.86 (m, 2H), 7.54 (t, J=1.9 Hz, 1H), 7.44-7.39 (m, 1H), 7.36 (s, 1H), 4.49-4.43 (m, 2H), 4.01-3.94 (m, 4H), 3.62 (d, J=12.3 Hz, 2H), 3.50-3.44 (m, 4H), 3.18-3.07 (m, 4H), 2.06-1.96 (m, 6H), 1.87 (m, 1H), 1.67-1.50 (m, 10H); ES-LCMS m/z 669.3, 671.3 [M+H]$^+$.

Step 2: N-((1-((2-(3,5-Dichlorophenyl)-6-((6-(piperazin-1-yl)pyridin-3-yl)oxy)pyridin-4-yl)methyl)piperidin-4-yl)methyl)acetamide, 4 hydrochloride

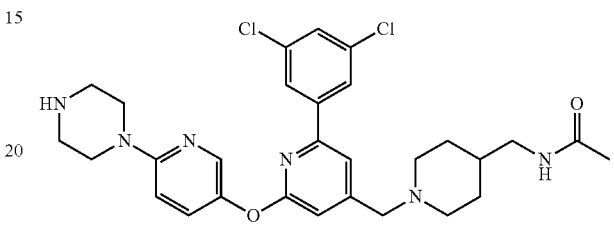

A mixture of tert-butyl 4-(5-((4-((4-(acetamidomethyl)piperidin-1-yl)methyl)-6-(3,5-dichlorophenyl)pyridin-2-yl)oxy)pyridin-2-yl)piperazine-1-carboxylate (81 mg, 0.121 mmol) and TFA (2 mL, 26.0 mmol) in DCM (8 mL) was stirred at 25° C. for 0.5 h. Then the mixture was concentrated and purified by preparative HPLC (MeCN/H$_2$O as eluents, acidic condition) and lyophilized to yield a white solid N-((1-((2-(3,5-dichlorophenyl)-6-((6-(piperazin-1-yl)pyridin-3-yl)oxy)pyridin-4-yl)methyl)piperidin-4-yl)methyl)acetamide, 4 hydrochloride (37.43 mg, 0.052 mmol, 43.1% yield): $^1$H NMR (400 MHz, CD$_3$OD) δ ppm 8.19 (d, J=2.4 Hz, 1H), 8.06 (d, J=9.5 Hz, 1H), 7.92 (s, 1H), 7.86 (d, J=1.7 Hz, 2H), 7.51 (s, 1H), 7.45 (d, J=9.8 Hz, 1H), 7.35 (s, 1H), 4.43 (s, 2H), 4.01-3.93 (m, 4H), 3.59 (d, J=12.7 Hz, 2H), 3.49-3.41 (m, 4H), 3.15-3.03 (m, 4H), 2.03-1.91 (m, 5H), 1.83 (br. s, 1H), 1.63-1.50 (m, 2H); ES-LCMS m/z 569.0, 571.0 [M+H]$^+$.

Example 10: 2-(4-(5-((4-((4-(Acetamidomethyl)piperidin-1-yl)methyl)-6-(3,5-dichlorophenyl)pyridin-2-yl)oxy)pyridin-2-yl)piperazin-1-yl)acetic acid, 4 hydrochloride

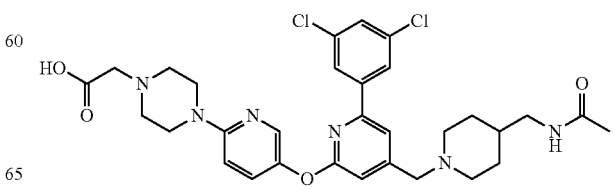

Step 1: Ethyl 2-(4-(5-((4-((4-(acetamidomethyl) piperidin-1-yl)methyl)-6-(3,5-dichlorophenyl)pyridin-2-yl)oxy)pyridin-2-yl)piperazin-1-yl)acetate

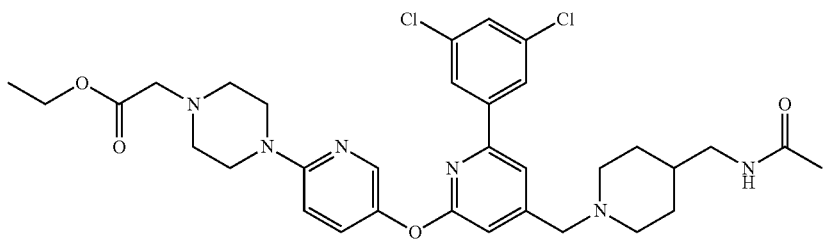 [SMILES: CCOC(=O)CN1CCN(c2ccc(Oc3cc(CN4CCC(CNC(C)=O)CC4)cc(-c4cc(Cl)cc(Cl)c4)n3)cn2)CC1]

To a solution of N-((1-((2-(3,5-dichlorophenyl)-6-((6-(piperazin-1-yl)pyridin-3-yl)oxy)pyridin-4-yl)methyl)piperidin-4-yl)methyl)acetamide (1 g, 1.756 mmol) and ethyl 2-bromoacetate (0.352 g, 2.107 mmol) in DMF (100 mL) was added K$_2$CO$_3$ (0.485 g, 3.51 mmol). The reaction was stirred at 25° C. for 8 h. The mixture was concentrated and purified by silica gel column chromatography. All fractions found to contain product by TLC (MeOH/DCM=1/10, R$_f$=0.4) were combined and concentrated to yield a brown solid of ethyl 2-(4-(5-((4-((4-(acetamidomethyl)piperidin-1-yl)methyl)-6-(3,5-dichlorophenyl)pyridin-2-yl)oxy)pyridin-2-yl)piperazin-1-yl)acetate (0.7 g, 1.07 mmol, 61.3% yield): $^1$H NMR (400 MHz, CDCl$_3$) δ ppm 8.13 (s, 1H), 7.77 (s, 2H), 7.44-7.39 (m, 2H), 7.33 (s, 1H), 6.81 (s, 1H), 6.73 (d, J=9.2 Hz, 1H), 4.23-4.19 (m, 2H), 3.63-3.60 (m, 4H), 3.50 (s, 2H), 3.29 (br. s, 2H), 3.18-3.15 (m, 2H), 2.85-2.79 (m, 2H), 2.75-2.72 (m, 4H), 2.03-2.00 (m, 2H), 1.98 (s, 3H), 1.70-1.45 (m, 3H), 1.32-1.28 (m, 2H), 1.27-1.20 (m, 3H); ES-LCMS m/z 655.3, 657.3 [M+H]$^+$.

Step 2: 2-(4-(5-((4-((4-(Acetamidomethyl)piperidin-1-yl)methyl)-6-(3,5-dichlorophenyl)pyridin-2-yl)oxy)pyridin-2-yl)piperazin-1-yl)acetic acid, 4 hydrochloride

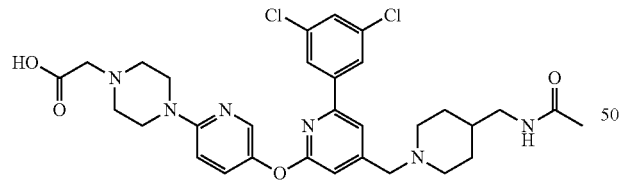

To a solution of ethyl 2-(4-(5-((4-((4-(acetamidomethyl) piperidin-1-yl)methyl)-6-(3,5-dichlorophenyl)pyridin-2-yl) oxy)pyridin-2-yl)piperazin-1-yl)acetate (1.27 g, 1.937 mmol) in MeOH (6 mL) and H$_2$O (1 mL) was added NaOH (0.155 g, 3.87 mmol). The reaction was stirred at 15° C. for 24 h. The mixture was concentrated and purified by preparative HPLC (MeCN/H$_2$O as eluents, acidic condition) to yield a white solid of 2-(4-(5-((4-((4-(acetamidomethyl) piperidin-1-yl)methyl)-6-(3,5-dichlorophenyl)pyridin-2-yl) oxy)pyridin-2-yl)piperazin-1-yl)acetic acid, 4 hydrochloride (716.3 mg, 0.924 mmol, 47.7% yield): $^1$H NMR (400 MHz, CD$_3$OD) δ ppm 8.18 (d, J=2.6 Hz, 1H), 7.90 (br. s, 1H), 7.89-7.73 (m, 3H), 7.51 (t, J=1.8 Hz, 1H), 7.37-7.25 (m, 2H), 4.43 (s, 2H), 4.23 (s, 2H), 4.10-3.90 (br. s, 4H), 3.61-3.58 (m, 6H), 3.12-3.06 (m, 4H), 2.01-1.94 (m, 5H), 1.85-1.76 (m, 1H), 1.60-1.51 (m, 2H); ES-LCMS m/z 627.3, 629.3 [M+H]$^+$.

Example 11: 3-(4-(5-((4-((4-(Acetamidomethyl) piperidin-1-yl)methyl)-6-(3,5-dichlorophenyl)pyridin-2-yl)oxy)pyridin-2-yl)piperazin-1-yl)propanoic acid, 4 hydrochloride

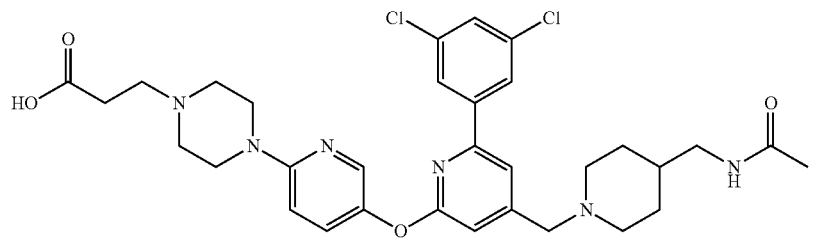 [SMILES: CC(=O)NCC1CCN(Cc2cc(Oc3ccc(N4CCN(CCC(=O)O)CC4)nc3)nc(-c3cc(Cl)cc(Cl)c3)c2)CC1]

Step 1: Ethyl 3-(4-(5-((4-((4-(acetamidomethyl) piperidin-1-yl)methyl)-6-(3,5-dichlorophenyl)pyridin-2-yl)oxy)pyridin-2-yl)piperazin-1-yl)propanoate

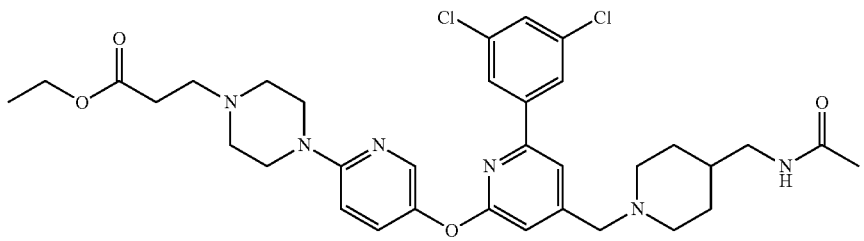 [SMILES: CCOC(=O)CCN1CCN(c2ccc(Oc3cc(CN4CCC(CNC(C)=O)CC4)cc(-c4cc(Cl)cc(Cl)c4)n3)cn2)CC1]

To a solution of N-((1-((2-(3,5-dichlorophenyl)-6-((6-(piperazin-1-yl)pyridin-3-yl)oxy)pyridin-4-yl)methyl)piperidin-4-yl)methyl)acetamide (20 g, 33.4 mmol) and ethyl 3-bromopropanoate (18.12 g, 100 mmol) in DMF (350 mL) was added $K_2CO_3$ (13.83 g, 100 mmol). Then the reaction mixture was stirred at 80° C. for 12 h. The solid was filtered off and solution was concentrated to yield a pale yellow solid of ethyl 3-(4-(5-((4-((4-(acetamidomethyl)piperidin-1-yl)methyl)-6-(3,5-dichlorophenyl)pyridin-2-yl)oxy)pyridin-2-yl)piperazin-1-yl)propanoate (17.6 g, 24.97 mmol, 74.8% yield): $^1$H NMR (400 MHz, $CDCl_3$) δ ppm 8.10 (d, J=3.1 Hz, 1H), 7.74 (d, J=1.8 Hz, 2H), 7.43-7.35 (m, 2H), 7.31 (s, 1H), 6.78 (s, 1H), 6.70 (d, J=9.3 Hz, 1H), 5.55 (br s, 1H), 4.14 (q, J=7.1 Hz, 2H), 3.58-3.50 (m, 4H), 3.47 (s, 2H), 3.14 (t, J=6.4 Hz, 2H), 2.88-2.82 (m, 2H), 2.77-2.70 (m, 2H), 2.64-2.56 (m, 4H), 2.55-2.49 (m, 2H), 2.04-1.94 (m, 5H), 1.66 (d, J=12.8 Hz, 2H), 1.54-1.46 (m, 1H), 1.35-1.21 (m, 5H); ES-LCMS m/z 669.3, 671.3 [M+H]$^+$.

Step 2: 3-(4-(5-((4-((4-(Acetamidomethyl)piperidin-1-yl)methyl)-6-(3,5-dichlorophenyl)pyridin-2-yl) oxy)pyridin-2-yl)piperazin-1-yl)propanoic acid, 4 hydrochloride To a solution of ethyl 3-(4-(5-((4-((4-(acetamidomethyl) piperidin-1-yl)methyl)-6-(3,5-dichlorophenyl)pyridin-2-yl) oxy)pyridin-2-yl)piperazin-1-yl)propanoate (17.6 g, 24.97 mmol) in THF (200 mL) was added $LiOH·H_2O$ (2.096 g, 49.9 mmol) and water (2 mL). Then the reaction mixture was stirred at 25° C. for 12 h. 1N HCl was added to adjust pH to 6 then concentrated to yield the crude product, which was washed with EA/MeOH=10/1 (500 mL) and THF (500 mL). The solid was collected to yield the crude product which was purified by preparative HPLC (MeCN/$H_2O$ as eluents, acidic condition). Concentrated HCl was added to the combined purified fractions to adjust to pH to 2, and lyophilized to yield a pale yellow solid of 3-(4-(5-((4-((4-(acetamidomethyl)piperidin-1-yl)methyl)-6-(3,5-dichlorophenyl)pyridin-2-yl)oxy)pyridine-2-yl)piperazin-1-yl)propanoic acid, 4 hydrochloride (15 g, 23.09 mmol, 92.0% yield): $^1$H NMR (400 MHz, $CD_3OD$) δ ppm 8.23 (s, 1H), 8.20-8.16 (m, 1H), 7.99 (s, 1H), 7.89 (s, 2H), 7.55 (d, J=12 Hz, 1H), 7.51 (s, 1H), 7.40 (s, 1H), 4.46 (s, 2H), 3.80-3.40 (m, 10H), 3.30-3.20 (m, 2H), 3.15-3.07 (m, 4H), 2.96-2.94 (m, 2H), 2.00-1.92 (m, 5H), 1.90-1.79 (m, 1H), 1.62-1.53 (m, 2H); ES-LCMS m/z 641.3, 643.2 [M+H]$^+$.

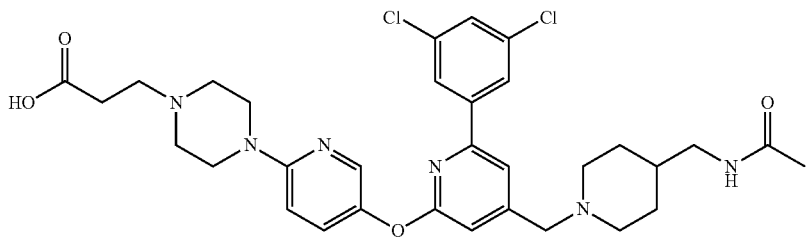 [SMILES: CC(=O)NCC1CCN(Cc2cc(Oc3ccc(N4CCN(CCC(=O)O)CC4)nc3)nc(-c3cc(Cl)cc(Cl)c3)c2)CC1]

Example 12: N-((1-((2-(3,5-Dichlorophenyl)-6-((6-(4-(2-(methylsulfonyl)ethyl)piperazin-1-yl)pyridin-3-yl)oxy)pyridin-4-yl)methyl)piperidin-4-yl)methyl)acetamide, 4 hydrochloride

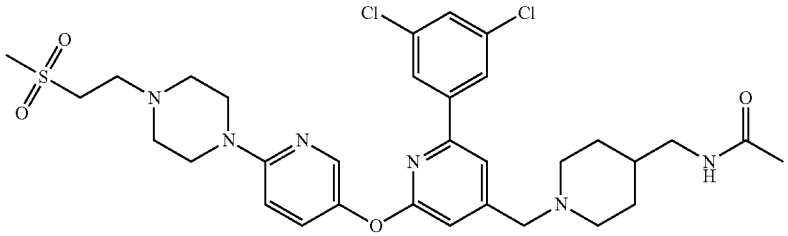 [SMILES: CC(=O)NCC1CCN(Cc2cc(Oc3ccc(N4CCN(CCS(C)(=O)=O)CC4)nc3)nc(-c3cc(Cl)cc(Cl)c3)c2)CC1]

To a solution of N-((1-((2-(3,5-dichlorophenyl)-6-((6-(piperazin-1-yl)pyridin-3-yl)oxy)pyridin-4-yl)methyl)piperidin-4-yl)methyl)acetamide, 4 hydrochloride (1.5 g, 1.887 mmol) and DIEA (1.219 g, 9.44 mmol) in DCM (20 mL) was added (methylsulfonyl)ethene (0.240 g, 2.265 mmol). Then the reaction mixture was stirred at 15° C. for 12 h. The solution was concentrated to yield the crude product which was purified by preparative HPLC (MeCN/H$_2$O as eluents, acidic condition) and lyophilized to yield a white solid of N-((1-((2-(3,5-dichlorophenyl)-6-((6-(4-(2-(methylsulfonyl)ethyl)piperazin-1-yl)pyridine-3-yl)oxy)pyridin-4-yl)methyl)piperidin-4-yl)methyl)acetamide, 4 hydrochloride (672 mg, 0.806 mmol, 42.7% yield): $^1$H NMR (400 MHz, CD$_3$OD) δ ppm 8.26 (d, J=2.5 Hz, 1H), 8.22-8.15 (m, 1H), 8.02 (s, 1H), 7.91 (d, J=1.5 Hz, 2H), 7.59 (d, J=9.5 Hz, 1H), 7.53 (s, 1H), 7.43 (s, 1H), 4.58-4.45 (m, 2H), 4.14 (br. s, 4H), 3.90-3.80 (m, 4H), 3.70 (s, 4H), 3.62 (d, J=12.0 Hz, 2H), 3.23-3.05 (m, 7H), 2.07-1.96 (m, 5H), 1.88 (br. s, 1H), 1.72-1.56 (m, 2H); ES-LCMS m/z 675.2, 677.2 [M+H]$^+$.

Example 13: 3-(4-(5-((4-((4-(Acetamidomethyl)piperidin-1-yl)methyl)-6-(3,5-dichlorophenyl)pyridin-2-yl)oxy)pyrimidin-2-yl)piperazin-1-yl)propanamide, 4 hydrochloride

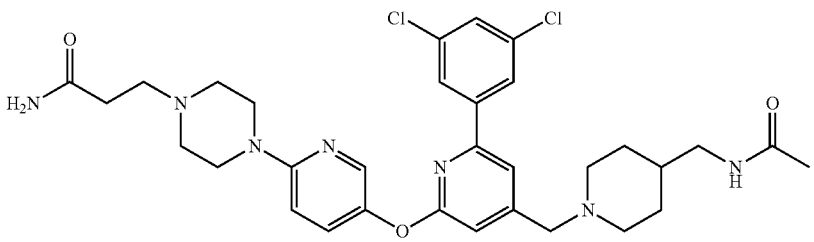 [SMILES: CC(=O)NCC1CCN(Cc2cc(Oc3ccc(N4CCN(CCC(N)=O)CC4)nc3)nc(-c3cc(Cl)cc(Cl)c3)c2)CC1]

To a mixture of N-((1-((2-(3,5-dichlorophenyl)-6-((6-(piperazin-1-yl)pyridin-3-yl)oxy)pyridin-4-yl)methyl)piperidin-4-yl)methyl)acetamide (120 mg, 0.211 mmol) and 3-bromopropanamide (64.0 mg, 0.421 mmol) in DMF (8 mL) was added K$_2$CO$_3$ (58.2 mg, 0.421 mmol). The reaction was stirred at 60° C. for 12 h. The solid was filtered off and solution was concentrated to yield crude product which was purified by preparative HPLC (MeCN/H$_2$O as eluents, acidic condition) to yield a white solid of 3-(4-(5-((4-((4-(acetamidomethyl)piperidin-1-yl)methyl)-6-(3,5-dichlorophenyl)pyridin-2-yl)oxy)pyridin-2-yl)piperazin-1-yl)propanamide, 4 hydrochloride (73.66 mg, 0.093 mmol, 44.2% yield): $^1$H NMR (400 MHz, CD$_3$OD) δ ppm 8.20 (br. s, 1H), 7.94-7.79 (m, 4H), 7.54 (s, 1H), 7.35-7.26 (m, 2H), 4.57 (s, 2H), 3.94 (br. s, 4H), 3.66-3.42 (m, 8H), 3.19-3.05 (m, 4H), 2.85 (t, J=6.5 Hz, 2H), 2.06-1.95 (m, 5H), 1.86 (br. s, 1H), 1.56 (d, J=13.6 Hz, 2H); ES-LCMS m/z 640.3, 642.3 [M+H]$^+$.

Example 14: N-((1-((2-((6-(4-(2-(1H-Tetrazol-5-yl)ethyl)piperazin-1-yl)pyridin-3-yl)oxy)-6-(3,5-dichlorophenyl)pyridin-4-yl)methyl)piperidin-4-yl)methyl)acetamide, 4 hydrochloride

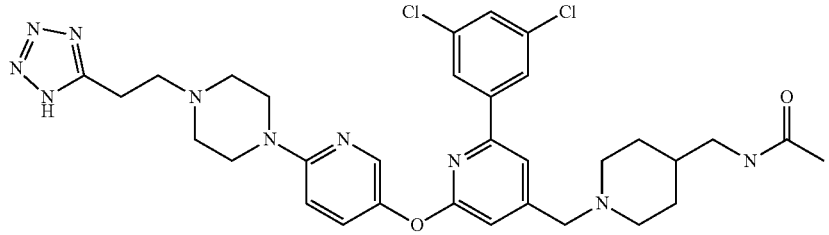 [SMILES: CC(=O)NCC1CCN(Cc2cc(Oc3ccc(N4CCN(CCc5nnn[nH]5)CC4)nc3)nc(-c3cc(Cl)cc(Cl)c3)c2)CC1]

Step 1: N-((1-((2-((6-(4-(2-Cyanoethyl)piperazin-1-yl)pyridin-3-yl)oxy)-6-(3,5-dichlorophenyl)pyridin-4-yl)methyl)piperidin-4-yl)methyl)acetamide

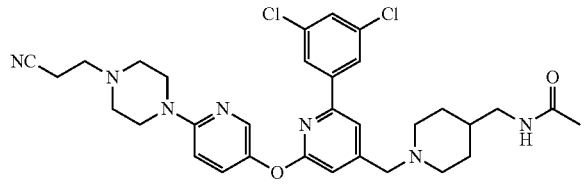

To a mixture of N-((1-((2-(3,5-dichlorophenyl)-6-((6-(piperazin-1-yl)pyridin-3-yl)oxy)pyridin-4-yl)methyl)piperidin-4-yl)methyl)acetamide, 4 hydrochloride (300 mg, 0.377 mmol) in DCM (20 mL) was added acrylonitrile (2.03 g, 38.3 mmol) and DIEA (0.659 mL, 3.77 mmol). The mixture was stirred at 40° C. for 3 h then cooled down and filtered. The filtrate was concentrated and purified by silica gel column chromatography (DCM/MeOH=10/1, $R_f$=0.5) to yield a brown solid of N-((1-((2-((6-(4-(2-cyanoethyl)piperazin-1-yl)pyridin-3-yl)oxy)-6-(3,5-dichlorophenyl)pyridin-4-yl)methyl)piperidin-4-yl)methyl)acetamide (300 mg, 0.270 mmol, 71.5% yield): $^1$H NMR (400 MHz, CDCl$_3$) δ ppm 8.05-8.01 (m, 1H), 7.83 (d, J=1.8 Hz, 2H), 7.68 (s, 1H), 7.49 (dd, J=2.9, 9.0 Hz, 1H), 7.42 (t, J=1.8 Hz, 1H), 7.01 (s, 1H), 6.92 (s, 1H), 3.75-3.68 (m, 4H), 3.57-3.55 (m, 4H), 3.29-3.22 (m, 2H), 3.12-3.01 (m, 4H), 2.75-2.69 (m, 2H), 2.68-2.60 (m, 4H), 1.94 (s, 3H), 1.81-1.68 (m, 3H), 1.64-1.53 (m, 2H); ES-LCMS m/z 622.4, 624.3 [M+H]$^+$.

Step 2: N-((1-((2-((6-(4-(2-(1H-Tetrazol-5-yl)ethyl)piperazin-1-yl)pyridin-3-yl)oxy)-6-(3,5-dichlorophenyl)pyridin-4-yl)methyl)piperidin-4-yl)methyl)acetamide, 4 hydrochloride

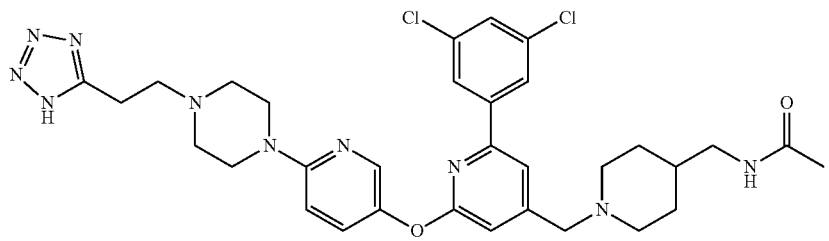 [SMILES: CC(=O)NCC1CCN(Cc2cc(Oc3ccc(N4CCN(CCc5nnn[nH]5)CC4)nc3)nc(-c3cc(Cl)cc(Cl)c3)c2)CC1]

To a mixture of N-((1-((2-((6-(4-(2-cyanoethyl)piperazin-1-yl)pyridin-3-yl)oxy)-6-(3,5-dichlorophenyl)pyridin-4-yl)methyl)piperidin-4-yl)methyl)acetamide (150 mg, 0.135 mmol) in toluene (20 mL) was added azidotributyltin (1 mL, 3.65 mmol). The mixture was stirred at 110° C. for 10 h in autoclave. The reaction mixture was concentrated and purified by preparative HPLC (MeCN/H$_2$O as eluents, acidic condition) and lyophilized to yield a white solid of N-((1-((2-((6-(4-(2-(1H-tetrazol-5-yl)ethyl)piperazin-1-yl)pyridin-3-yl)oxy)-6-(3,5-dichlorophenyl)pyridin-4-yl)methyl)piperidin-4-yl)methyl)acetamide, 4 hydrochloride (28.77 mg, 0.035 mmol, 26.3% yield): $^1$H NMR (400 MHz, CD$_3$OD) δ ppm 8.22 (dd, J=2.5, 10.0 Hz, 1H), 8.17 (d, J=2.5 Hz, 1H), 8.00 (s, 1H), 7.91 (d, J=1.5 Hz, 2H), 7.62 (d, J=9.5 Hz, 1H), 7.55 (s, 1H), 7.43 (s, 1H), 4.48 (s, 2H), 4.12-3.81 (m, 6H), 3.79-3.70 (m, 2H), 3.62-3.60 (m, 2H), 3.45-3.40 (m, 4H), 3.17-3.03 (m, 4H), 2.02-1.95 (m, 5H), 1.88 (br. s, 1H), 1.69-1.54 (m, 2H); ES-LCMS m/z 655.3, 657.3 [M+H]$^+$.

Example 15: N-((1-((2-(3,5-Dichlorophenyl)-6-((6-(4-(2-(methylsulfinyl)ethyl)piperazin-1-yl)pyridin-3-yl)oxy)pyridin-4-yl)methyl)piperidin-4-yl)methyl)acetamide, 4 hydrochloride

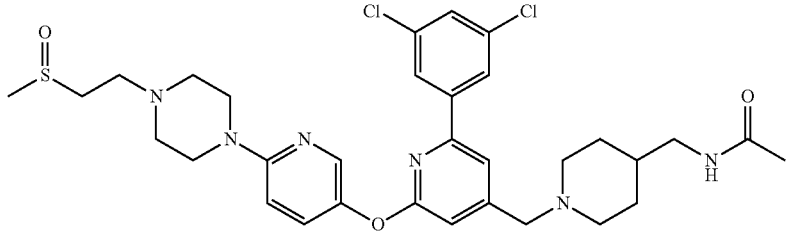 [SMILES: CC(=O)NCC1CCN(Cc2cc(Oc3ccc(N4CCN(CCS(C)=O)CC4)nc3)nc(-c3cc(Cl)cc(Cl)c3)c2)CC1]

Step 1: 2-(Methylthio)acetaldehyde

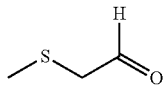

To a solution of oxalyl dichloride (2.78 mL, 32.6 mmol) in DCM (15 mL) was added a solution of DMSO (4.62 mL, 65.1 mmol) in DCM (10 mL) at −78° C. dropwise over 5 minutes. After stirring at the same temperature for 0.5 h, a solution of 2-(methylthio)ethanol (2 g, 21.70 mmol) in DCM (10 mL) was added dropwise over 10 min and stirred for another 0.5 h. Then a solution of DIEA (22.74 mL, 130 mmol) in DCM (10 mL) was added over 5 min. The reaction was allowed to warm to 0° C. over 1.5 h then 30 mL of ice-cold 1 N HCl solution was added. The two phases are separated, the aqueous phase was extracted with DCM (50 mL×3), and the combined organic phases were washed with brine (50 mL), dried with $Na_2SO_4$ and concentrated under reduced pressure to yield a yellow oil of 2-(methylthio)acetaldehyde (800 mg, 7.10 mmol, 32.7% yield): $^1$H NMR (400 MHz, $CDCl_3$) δ ppm 9.39 (t, J=3.5 Hz, 1H), 3.51 (s, 2H), 1.96 (s, 3H).

Step 2: N-((1-((2-(3,5-Dichlorophenyl)-6-((6-(4-(2-(methylthio)ethyl)piperazin-1-yl)pyridin-3-yl)oxy)pyridin-4-yl)methyl)piperidin-4-yl)methyl)acetamide

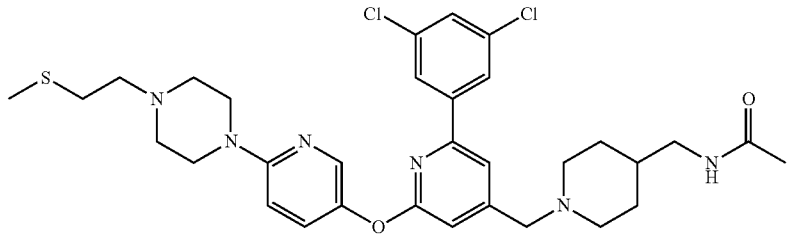 [SMILES: CSCCN1CCN(c2ccc(Oc3cc(CN4CCC(CNC(C)=O)CC4)cc(-c4cc(Cl)cc(Cl)c4)n3)cn2)CC1]

To a solution of 2-(methylthio)acetaldehyde (151 mg, 1.343 mmol), acetic acid (0.05 mL, 0.873 mmol), N-((1-((2-(3,5-dichlorophenyl)-6-((6-(piperazin-1-yl)pyridin-3-yl)oxy)pyridin-4-yl)methyl)piperidin-4-yl)methyl)acetamide (300 mg, 0.448 mmol) in MeOH (10 mL) was added 4 Å molecular sieves (200 mg, 0.448 mmol) and stirred at 50° C. for 70 h. Then, $NaBH_3CN$ (84 mg, 1.343 mmol) was added to the mixture and the mixture was stirred at 25° C. for 2 h. The mixture was filtered and concentrated. The crude product was purified by preparative HPLC (MeCN/$H_2O$ as eluents, acidic condition) and lyophilized to yield a pale yellow solid of N-((1-((2-(3,5-dichlorophenyl)-6-((6-(4-(2-(methylthio)ethyl)piperazin-1-yl)pyridin-3-yl)oxy)pyridin-4-yl)methyl)piperidin-4-yl)methyl)acetamide, 4 hydrochloride (70 mg, 0.079 mmol, 17.7% yield): $^1$H NMR (400 MHz, $CD_3OD$) δ ppm 8.20 (d, J=2.2 Hz, 1H), 8.00 (d, J=7.1 Hz, 1H), 7.94 (s, 1H), 7.88 (d, J=1.8 Hz, 2H), 7.51 (s, 1H), 7.42 (d, J=9.7 Hz, 1H), 7.35 (s, 1H), 4.44 (s, 2H), 3.78 (br. s, 2H), 3.60 (d, J=11.5 Hz, 4H), 3.53-3.39 (m, 4H), 3.27-3.02 (m, 6H), 2.99-2.91 (m, 2H), 2.21 (s, 3H), 2.02-1.93 (m, 5H), 1.85 (s, 1H), 1.63-1.53 (m, 2H); ES-LCMS m/z 643.3, 645.3 [M+H]$^+$.

Step 3: N-((1-((2-(3,5-Dichlorophenyl)-6-((6-(4-(2-(methylsulfinyl)ethyl)piperazin-1-yl)pyridin-3-yl)oxy)pyridin-4-yl)methyl)piperidin-4-yl)methyl)acetamide, 4 hydrochloride

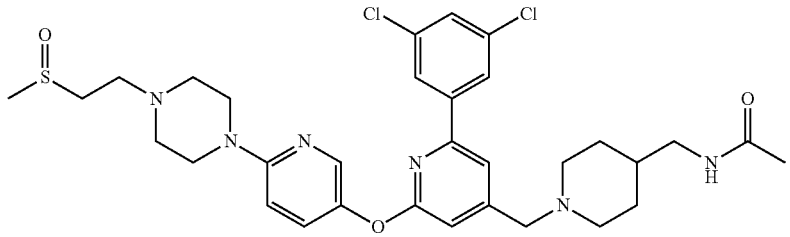 [SMILES: CC(=O)NCC1CCN(Cc2cc(Oc3ccc(N4CCN(CCS(C)=O)CC4)nc3)nc(-c3cc(Cl)cc(Cl)c3)c2)CC1]

To a solution of N-((1-((2-(3,5-dichlorophenyl)-6-((6-(4-(2-(methylthio)ethyl)piperazin-1-yl)pyridin-3-yl)oxy)pyridin-4-yl)methyl)piperidin-4-yl)methyl)acetamide, 4 hydrochloride (60 mg, 0.068 mmol) in MeOH (5 mL) and H$_2$O (1 mL) was added Oxone® (20.90 mg, 0.034 mmol). The mixture was stirred at 25° C. for 2 h then 1 N HCl (aq.) was added to adjust pH to 6-7. The solution was concentrated to yield the crude product which was purified by preparative HPLC (MeCN/H$_2$O as eluents, acidic condition) and lyophilized to yield a pale yellow solid of N-((1-((2-(3,5-dichlorophenyl)-6-((6-(4-(2-(methylsulfinyl)ethyl)piperazin-1-yl)pyridin-3-yl)oxy)pyridin-4-yl)methyl)piperidin-4-yl)methyl)acetamide, 4 hydrochloride (19.81 mg, 0.025 mmol, 36.2% yield): $^1$H NMR (400 MHz, CD$_3$OD) δ ppm 8.23 (d, J=2.2 Hz, 1H), 8.14 (dd, J=2.2, 9.7 Hz, 1H), 7.95 (s, 1H), 7.88 (d, J=1.8 Hz, 2H), 7.58-7.46 (m, 2H), 7.38 (s, 1H), 4.44 (s, 2H), 4.20-4.00 (m, 4H), 3.89-3.54 (m, 8H), 3.53-3.40 (m, 2H), 3.20-3.00 (m, 4H), 2.79 (s, 3H), 2.08-1.89 (m, 5H), 1.85 (s, 1H), 1.67-1.52 (m, 2H); ES-LCMS m/z 659.3, 661.3 [M+H]$^+$.

Examples 16-25 (Table 1) were prepared by procedures analogous to those described for Example 15.

TABLE 1

| Example | Structure/Name | $^1$H NMR | LCMS |
| --- | --- | --- | --- |
| 16 | N-((1-((2-(3,5-dichlorophenyl)-64(6-(4-(4-(methylsulfonyl)butan-2-yl)piperazin-1-yl)pyridin-3-yl)oxy)pyridin-4-yl)methyl)piperidin-4-yl)methyl)acetamide | $^1$H NMR (400 MHz, CD$_3$OD) δ ppm 8.04 (d, J = 2.5 Hz, 1H), 7.84 (d, J = 1.5 Hz, 2H), 7.63 (s, 1H), 7.51 (dd, J = 2.5, 9.0 Hz, 1H), 7.44 (s, 1H), 6.99 (s, 1H), 6.95 (d, J = 9.0 Hz, 1H), 4.62 (s, 2H), 3.61 (m, 2H), 3.60-3.50 (m, 6H), 3.30-3.23 (m, 2H), 3.09 (d, J = 6.4 Hz, 1H), 3.01 (s, 3H), 2.95 (d, J =11.2 Hz, 2H), 2.89-2.74 (m, 3H), 2.66-2.59 (m, 2H), 2.18-2.00 (m, 3H), 1.95 (s, 3H), 1.93-1.83 (m, 1H), 1.74 (d, J = 12.5 Hz, 2H), 1.56 (d, J = 8.5 Hz, 1H), 1.40-1.26 (m, 2H), 1.10 (d, J = 6.5 Hz, 3H) | ES-LCMS m/z 703.2, 705.2 [M + H]$^+$. |
| 17 | 1-((1-((2-(3,5-dichlorophenyl)-6-((2-(4-(3-(methylsulfinyl)butyl)piperazin-1-yl)pyrimidin-5-yl)oxy)pyridin-4-yl)methyl)piperidin-4-yl)methyl)-3-methylurea | $^1$H NMR (400 MHz, CD$_3$OD) δ ppm 8.47 (s, 2H), 7.94 (br, s, 1H), 7.88 (s, 2H), 7.51 (s, 1H), 7.34 (br. s, 1H), 4.60-4.34 (m, 2H), 3.75 (br. s, 2H), 3.60 (br. s, 2H), 3.52-3.34 (m, 6H), 3.30-2.94 (m, 7H), 2.78-2.62 (m, 6H), 2.41-1.95 (m, 4H), 1.83 (br. s, 1H), 1.60 (br. s, 2H), 1.35 (br. s, 3H) | ES-LCMS m/z 703.3, 705.3 [M + H]$^+$. |

TABLE 1-continued

| Example | Structure/Name | ¹H NMR | LCMS |
|---|---|---|---|
| 18 | 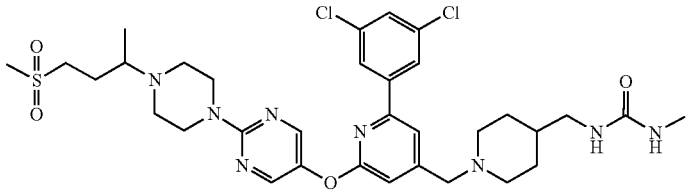<br>1-((1-((2-(3,5-dichlorophenyl)-6-((2-(4-(4-(methylsulfonyl)butan-2-yl)piperazin-1-yl)pyrimidin-5-yl)oxy)pyridin-4-yl)methyl)piperidin-4-yl)methyl)-3-methylurea | ¹H NMR (400 MHz, CD₃OD) δ ppm 8.31 (s, 2H), 7.82 (d, J = 2.2 Hz, 2H), 7.65 (s, 1H), 7.43 (t, J = 1.8 Hz, 1H), 7.04 (s, 1H), 3.84 (d, J = 3.5 Hz, 4H), 3.63 (s, 2H), 3.08 (d, J = 6.6 Hz, 2H), 3.01-2.91 (m, 5H), 2.87-2.79 (m, 2H), 2.75-2.67 (m, 1H), 2.60-2.50 (m, 5H), 2.11 (t, J = 11.9 Hz, 2H), 2.07-1.97 (m, 3H), 1.91-1.80 (m, 1H), 1.73 (d, J = 11.9 Hz, 2H), 1.54 (br.s., 1H), 1.39-1.26 (m, 2H), 1.06 (d, J = 6.6 Hz, 3H) | ES-LCMS m/z 719.3, 721.3 [M + H]⁺. |
| 19 | 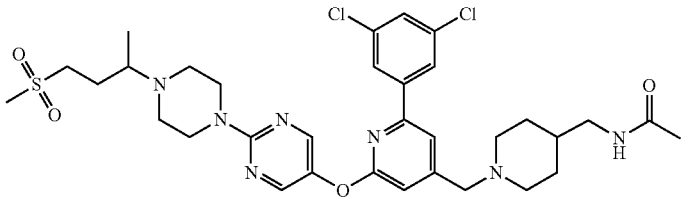 [SMILES: CC(=O)NCC1CCN(Cc2cc(Oc3cnc(N4CCN(C(C)CCS(C)(=O)=O)CC4)nc3)nc(-c3cc(Cl)cc(Cl)c3)c2)CC1]<br>N-((1-((2-(3,5-dichlorophenyl)-6-((2-(4-(4-(methylsulfonyl)butan-2-yl)piperazin-1-yl)pyrimidin-5-yl)oxy)pyridin-4-yl)methyl)piperidin-4-yl)methyl)acetamide | ¹H NMR (400 MHz, CD₃OD) δ ppm 8.31 (s, 2H), 7.82 (d, J = 2.2 Hz, 2H), 7.65 (s, 1H), 7.43 (t, J = 1.8 Hz, 1H), 7.04 (s, 1H), 3.84 (d, J = 3.5 Hz, 4H), 3.63 (s, 2H), 3.34 (br. s, 1H), 3.27-3.18 (m, 1H), 3.08 (d, J = 6.6 Hz, 2H), 3.01-2.91 (m, 5H), 2.87-2.79 (m, 1H), 2.75-2.67 (m, 2H), 2.60-2.50 (m, 2H), 2.11 (t, J = 11.9 Hz, 2H), 2.07-1.97 (m, 1H), 1.93 (s, 3H), 1.91-1.80 (m, 1H), 1.73 (d, J = 11.9 Hz, 2H), 1.54 (br. s, 1H), 1.39-1.26 (m, 2H), 1.06 (d, J = 6.6 Hz, 3H) | ES-LCMS m/z 704.3, 706.3 [M + H]⁺. |
| 20 | 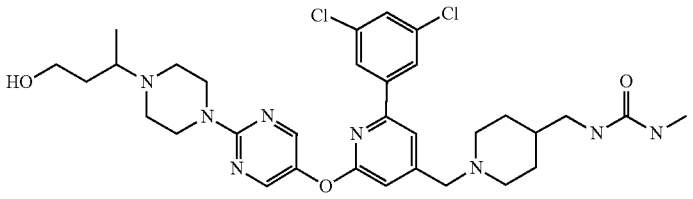 [SMILES: CNC(=O)NCC1CCN(Cc2cc(Oc3cnc(N4CCN(C(C)CCO)CC4)nc3)nc(-c3cc(Cl)cc(Cl)c3)c2)CC1]<br>1-((1-((2-(3,5-dichlorophenyl)-6-((2-(4-(4-hydroxybutan-2-yl)piperazin-1-yl)pyrimidin-5-yl)oxy)pyridin-4-yl)methyl)piperidin-4-yl)methyl)-3-methylurea | ¹H NMR (400 MHz, D₂O) δ ppm 8.39 (s, 2H), 7.60 (d, J = 1.5 Hz, 2H), 7.55 (s, 1H), 7.42 (s, 1H), 7.11 (s, 1H), 4.61 (br.s., 2H), 4.31 (s, 2H), 3.96-3.81 (m, 1H), 3.64 (d, J = 11.0 Hz, 2H), 3.51 (d, J = 11.0 Hz, 2H), 3.40-3.21 (m, 4H), 3.13-3.05 (m, 2H), 3.04-2.92 (m, 4H), 2.57 (s, 3H), 1.97-1.80 (m, 4H), 1.72 (br.s., 1H), 1.46-1.28 (m, 2H), 1.16 (d, J = 6.0 Hz, 3H) | LC-MS m/z 657.3, 659.4 [M + H]⁺. |
| 21 | 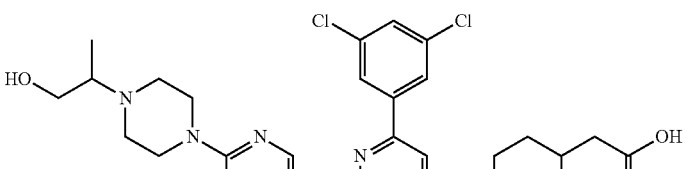<br>2-(1-((2-(3,5-dichlorophenyl)-6-((2-(4-(1-hydroxypropan-2-yl)piperazin-1-yl)pyrimidin-5-yl)oxy)pyridin-4-yl)methyl)piperidin-4-yl)acetic acid | ¹H NMR (400 MHz, CD₃OD) δ ppm 8.37 (s, 2H), 7.84 (d, J = 2.0 Hz, 2H), 7.68 (s, 1H), 7.46 (t, J = 1.8 Hz, 1H), 7.08 (s, 1H), 4.61 (br. s., 2H), 3.97 (br. s., 4H), 3.71 (s, 2H), 3.67 (dd, J = 4.0, 5.5 Hz, 2H), 3.00 (d, J = 6.8 Hz, 4H), 2.91 (br. s., 1H), 2.29-2.23 (m, 2H), 2.20 (d, J = 6.3 Hz, 2H), 1.82 (d, J = 10.0 Hz, 3H), 1.39 (d, J = 10.8 Hz, 2H), 1.17 (s, 3H) | LCMS m/z 615.3, 617.3 [M + H]⁺. |

TABLE 1-continued

| Example | Structure/Name | ¹H NMR | LCMS |
|---|---|---|---|
| 22 | 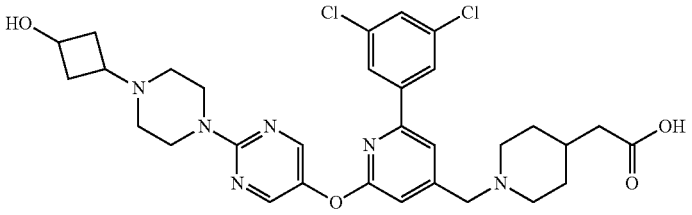 [SMILES: O=C(O)CC1CCN(Cc2cc(Oc3cnc(N4CCN(C5CC(O)C5)CC4)nc3)nc(-c3cc(Cl)cc(Cl)c3)c2)CC1]<br>2-(1-((2-(3,5-dichlorophenyl)-6-((2-(4-(3-hydroxycyclobutyl)piperazin-1-yl)pyrimidin-5-yl)oxy)pyridin-4-yl)methyl)piperidin-4-yl)acetic acid | ¹H NMR (400 MHz, CD₃OD) δ ppm 8.45 (s, 2H), 7.91 (s, 1H), 7.87 (d, J = 1.6 Hz, 2H), 7.50 (s, 1H), 7.31 (s, 1H), 4.95 (d, J = 14.5 Hz, 2H), 4.43 (s, 2H), 4.08 (td, J = 7.3, 14.3 Hz, 1H), 3.58 (d, J = 9.4 Hz, 4H), 3.43-3.32 (m, 3H), 3.14 (t, J = 12.1 Hz, 2H), 3.06-2.93 (m, 2H), 2.84-2.70 (m, 2H), 2.32 (d, J = 6.3 Hz, 2H), 2.25-2.12 (m, 2H), 2.06 (d, J = 13.3 Hz, 3H), 1.70-1.55 (m, 2H) | ES-LCMS m/z 627.3, 629.3 [M + H]⁺. |
| 23 | 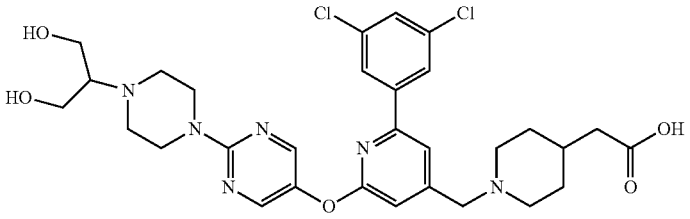 [SMILES: O=C(O)CC1CCN(Cc2cc(Oc3cnc(N4CCN(C(CO)CO)CC4)nc3)nc(-c3cc(Cl)cc(Cl)c3)c2)CC1]<br>2-(1-((2-(3,5-dichlorophenyl)-6-((2-(4-(1,3-dihydroxypropan-2-yl)piperazin-1-yl)pyrimidin-5-yl)oxy)pyridin-4-yl)methyl)piperidin-4-yl)acetic acid | ¹H NMR (400 MHz, CD₃OD) δ ppm 8.49-8.46 (m, 2H), 7.97 (s, 1H), 7.88 (d, J = 2.0 Hz, 2H), 7.48 (t, J = 1.9 Hz, 1H), 7.35 (s, 1H), 4.92 (d, J = 11.5 Hz, 2H), 4.44 (s, 2H), 4.03-3.93 (m, 4H), 3.82-3.74 (m, 2H), 3.60-3.46 (m, 6H), 3.32-3.34 (m, 1H), 3.20-3.10 (m, 2H), 2.38-2.29 (m, 2H), 2.11-1.98 (m, 3H), 1.74-1.61 (m, 2H) | ES-LCMS m/z 631.3, 633.3 [M + H]⁺. |
| 24 | 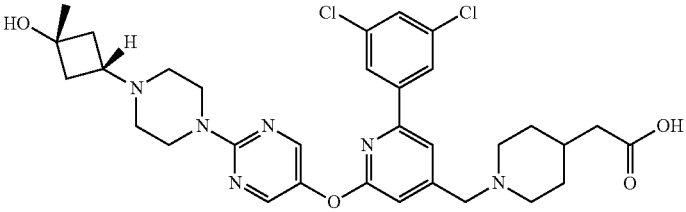 [SMILES: C[C@]1(O)C[C@@H](N2CCN(c3ncc(Oc4cc(CN5CCC(CC(=O)O)CC5)cc(-c5cc(Cl)cc(Cl)c5)n4)cn3)CC2)C1]<br>2-(1-((2-(3,5-dichlorophenyl)-6-((2-(4-((1s,3s)-3-hydroxy-3-methylcyclobutyl)piperazin-1-yl)pyrimidin-5-yl)oxy)pyridin-4-yl)methyl)piperidin-4-yl)acetic acid | ¹H NMR (400 MHz, D₂O) δ ppm 8.25 (s, 2H), 7.43-7.38 (m, 3H), 7.18 (s, 1H), 6.99 (s, 1H), 4.52 (d, J = 14.8 Hz, 2H), 4.21 (s, 2H), 3.52-3.34 (m, 4H), 3.32-3.15 (m, 3H), 2.94 (t, J = 11.8 Hz, 2H), 2.81 (t, J = 11.0 Hz, 2H), 2.46-2.39 (m, 2H), 2.25-2.14 (m, 4H), 1.86 (d, J = 13.5 Hz, 3H), 1.37 (d, J = 13.2 Hz, 2H), 1.22 (s, 3H) | ES-LCMS m/z 641.2, 643.2 [M + H]⁺. |
| 25 | 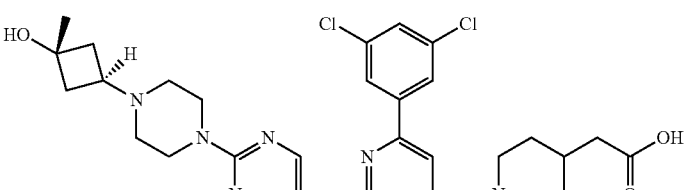<br>2-(1-((2-(3,5-dichlorophenyl)-6-((2-(4-((1r,3r)-3-hydroxy-3-methylcyclobutyl)piperazin-1-yl)pyrimidin-5-yl)oxy)pyridin-4-yl)methyl)piperidin-4-yl)acetic acid | ¹H NMR (400 MHz, D₂O) δ ppm 8.27 (s, 2H), 7.47-7.42 (m, 3H), 7.26 (s, 1H), 7.01 (s, 1H), 4.54 (d, J = 15.0 Hz, 2H), 4.22 (s, 2H), 3.71 (quin, J = 8.2 Hz, 1H), 3.42 (t, J = 13.8 Hz, 4H), 3.22 (t, J = 12.2 Hz, 2H), 2.95 (t, J = 12.0 Hz, 2H), 2.88-2.78 (m, 2H), 2.39-2.31 (m, 2H), 2.26-2.17 (m, 4H), 1.87 (d, J = 13.7 Hz, 3H), 1.38 (d, J = 13.0 Hz, 2H), 1.27 (s, 3H) | ES-LCMS m/z: 641.3, 643.2 [M + H]⁺. |

Example 26: N-((1-((2-(3,5-Dichlorophenyl)-6-((6-(4-((trans)-3-(methylsulfonamido)cyclobutyl)piperazin-1-yl)pyridin-3-yl)oxy)pyridin-4-yl)methyl)piperidin-4-yl)methyl)acetamide

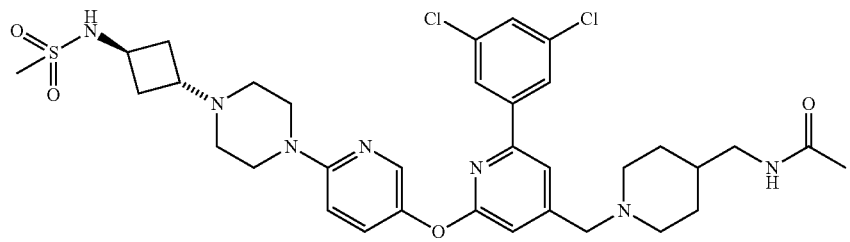 [SMILES: CC(=O)NCC1CCN(Cc2cc(Oc3ccc(N4CCN([C@H]5C[C@H](NS(C)(=O)=O)C5)CC4)nc3)nc(-c3cc(Cl)cc(Cl)c3)c2)CC1]

Example 27: N-((1-((2-(3,5-Dichlorophenyl)-6-((6-(4-((cis)-3-(methylsulfonamido)cyclobutyl)piperazin-1-yl)pyridin-3-yl)oxy)pyridin-4-yl)methyl)piperidin-4-yl)methyl)acetamide

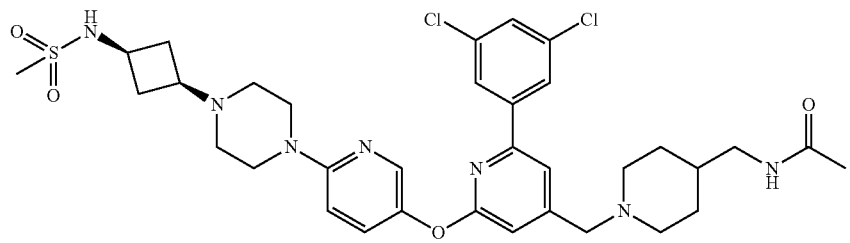 [SMILES: CC(=O)NCC1CCN(Cc2cc(Oc3ccc(N4CCN([C@H]5C[C@@H](NS(C)(=O)=O)C5)CC4)nc3)nc(-c3cc(Cl)cc(Cl)c3)c2)CC1]

Step 1: tert-Butyl (3-(4-(5-((4-((4-(acetamidomethyl)piperidin-1-yl)methyl)-6-(3,5-dichlorophenyl)pyridin-2-yl)oxy)pyridin-2-yl)piperazin-1-yl)cyclobutyl)carbamate

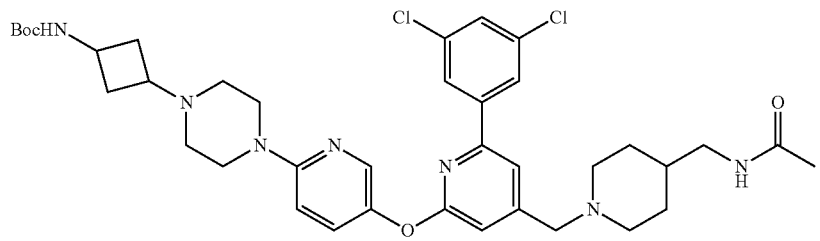 [SMILES: CC(=O)NCC1CCN(Cc2cc(Oc3ccc(N4CCN(C5CC(NC(=O)OC(C)(C)C)C5)CC4)nc3)nc(-c3cc(Cl)cc(Cl)c3)c2)CC1]

A mixture of tert-butyl (3-oxocyclobutyl)carbamate (74.1 mg, 0.400 mmol), acetic acid (2 mg, 0.033 mmol), N-((1-((2-(3,5-dichlorophenyl)-6-((6-(piperazin-1-yl)pyridin-3-yl)oxy)pyridin-4-yl)methyl)piperidin-4-yl)methyl)acetamide (200 mg, 0.334 mmol) and 4 Å molecular sieves (0.2 g) in DCM (8 mL) was stirred at 25° C. for 12 h. Then, NaBH$_3$CN (41.9 mg, 0.667 mmol) was added to the mixture and the mixture was stirred at 25° C. for 2 h. The reaction mixture was concentrated, diluted with additional DCM (50 mL) and washed with saturated NaHCO$_3$ solution (aq., 50 mL×2). The organic phase was dried over Na$_2$SO$_4$, filtered and concentrated to yield a yellow oil of tert-butyl (3-(4-(5-((4-((4-(acetamidomethyl)piperidin-1-yl)methyl)-6-(3,5-dichlorophenyl)pyridin-2-yl)oxy)pyridin-2-yl)piperazin-1-yl)cyclobutyl)carbamate (250 mg, 0.284 mmol, 85.0% yield): $^1$H NMR (400 MHz, CD$_3$OD) δ ppm 8.06 (d, J=3.0 Hz, 1H), 7.85 (d, J=1.5 Hz, 2H), 7.66 (s, 1H), 7.53 (dd, J=2.5, 9.0 Hz, 1H), 7.45 (s, 1H), 7.02 (s, 1H), 6.97 (d, J=9.0 Hz, 1H), 4.20 (t, J=6.0 Hz, 1H), 3.63 (s, 2H), 3.61 (d, J=4.5 Hz, 4H), 3.16-3.03 (m, 6H), 2.62 (m, 4H), 2.39 (m, 1H), 2.16 (m, 4H), 1.96 (s, 3H), 1.77 (d, J=12.0 Hz, 2H), 1.58 (br. s, 1H), 1.45 (br. s, 9H), 1.38 (d, J=15.6 Hz, 2H); ES-LCMS m/z 738.4, 740.3 [M+H]$^+$.

Step 2: N-((1-((2-((6-(4-(3-Aminocyclobutyl)piperazin-1-yl)pyridin-3-yl)oxy)-6-(3,5-dichlorophenyl)pyridin-4-yl)methyl)piperidin-4-yl)methyl)acetamide, 5 trifluoroacetic acid salt

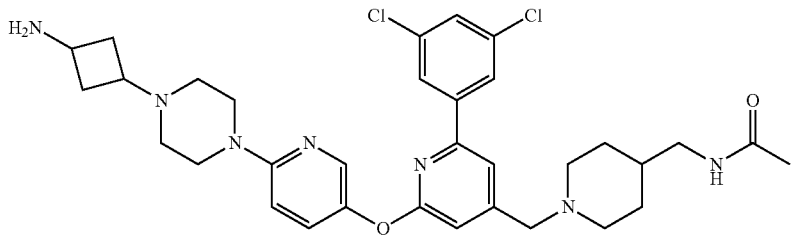 [SMILES: CC(=O)NCC1CCN(Cc2cc(Oc3ccc(N4CCN(C5CC(N)C5)CC4)nc3)nc(-c3cc(Cl)cc(Cl)c3)c2)CC1]

To a solution of tert-butyl (3-(4-(5-((4-((4-(acetamidomethyl)piperidin-1-yl)methyl)-6-(3,5-dichlorophenyl)pyridin-2-yl)oxy)pyridin-2-yl)piperazin-1-yl)cyclobutyl)carbamate (250 mg, 0.284 mmol) in DCM (8 mL) was added TFA (2 mL, 26.0 mmol). The reaction was stirred at 25° C. for 0.5 h then concentrated to yield a yellow oil of N-((1-((2-((6-(4-(3-aminocyclobutyl)piperazin-1-yl)pyridin-3-yl)oxy)-6-(3,5-dichlorophenyl)pyridin-4-yl)methyl)piperidin-4-yl)methyl)acetamide, 5 trifluoroacetic acid salt (300 mg, 0.199 mmol, 69.8% yield): $^1$H NMR (400 MHz, CDCl$_3$) δ ppm 8.11 (br. s, 1H), 7.71-7.59 (m, 4H), 7.35 (s, 1H), 7.01-6.88 (m, 2H), 4.21 (br. s, 2H), 3.98 (m, 1H), 3.51-3.46 (m, 4H), 3.22 (m, 2H), 3.07 (m 2H), 3.00-2.80 (m, 4H), 2.74-2.57 (m, 3H), 1.95 (s, 3H), 1.80-1.75 (m, 4H), 1.62 (m, 3H), 1.29-1.22 (m, 2H); ES-LCMS m/z 638.3, 640.3[M+H]$^+$.

Step 3: N-((1-((2-(3,5-Dichlorophenyl)-6-((6-(4-((trans)-3-(methylsulfonamido)cyclobutyl)piperazin-1-yl)pyridin-3-yl)oxy)pyridin-4-yl)methyl)piperidin-4-yl)methyl)acetamide To a solution of N-((1-((2-((6-(4-(3-aminocyclobutyl)piperazin-1-yl)pyridin-3-yl)oxy)-6-(3,5-dichlorophenyl)pyridin-4-yl)methyl)piperidin-4-yl)methyl)acetamide, 5 trifluoroacetic acid salt (300 mg, 0.199 mmol) in DCM (8 mL) was added DIEA (0.243 mL, 1.390 mmol). MsCl (0.023 mL, 0.298 mmol) was added to the reaction and the reaction was stirred at 25° C. for 0.5 h then concentrated. The residue was purified by preparative HPLC (MeCN/H$_2$O as eluents, basic condition) and lyophilized to yield a white solid of N-((1-((2-(3,5-dichlorophenyl)-6-((6-(4-((trans)-3-(methyl sulfonamido)cyclobutyl)piperazin-1-yl)pyridin-3-yl)oxy)pyridin-4-yl)methyl)piperidin-4-yl)methyl)acetamide (42.14 mg, 0.058 mmol, 29.4% yield) and a white solid of N-((1-((2-(3,5-dichlorophenyl)-6-((6-(4-((cis)-3-(methylsulfonamido)cyclobutyl)piperazin-1-yl)pyridin-3-yl)oxy)pyridin-4-yl)methyl)piperidin-4-yl)methyl)acetamide (18.72 mg, 0.026 mmol, 13.2% yield): (Trans) NMR (400 MHz, CD$_3$OD) δ ppm 8.06 (d, J=2.8 Hz, 1H), 7.84 (d, J=1.8 Hz, 2H), 7.64 (s, 1H), 7.52 (dd, J=2.9, 9.2 Hz, 1H), 7.44 (t, 7=1.8 Hz, 1H), 7.00 (s, 1H), 6.96 (d, J=9.3 Hz, 1H), 4.10-3.97 (m, 1H), 3.63 (s, 2H), 3.62-3.57 (m, 4H), 3.10 (d, J=6.8 Hz, 2H), 2.97 (d, J=11.3 Hz, 3H), 2.93 (s, 3H), 2.57 (t, J=4.6 Hz, 4H), 2.47 (ddd, J=5.4, 8.0, 13.0 Hz, 2H), 2.28-2.17 (m, 2H), 2.12 (t, J=11.0 Hz, 2H), 1.96 (s, 3H), 1.75 (d, J=11.8 Hz, 2H),

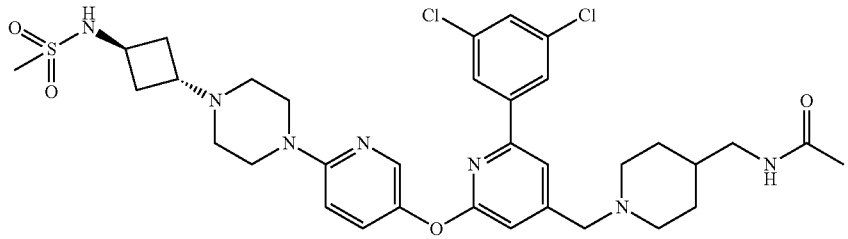 [SMILES: CC(=O)NCC1CCN(Cc2cc(Oc3ccc(N4CCN([C@H]5C[C@H](NS(C)(=O)=O)C5)CC4)nc3)nc(-c3cc(Cl)cc(Cl)c3)c2)CC1]

N-((1-((2-(3,5-Dichlorophenyl)-6-((6-(4-((cis)-3-(methylsulfonamido)cyclobutyl)piperazin-1-yl)pyridin-3-yl)oxy)pyridin-4-yl)methyl)piperidin-4-yl)methyl)acetamide 1.63-1.49 (m, 1H), 1.41-1.27 (m, 2H); ES-LCMS m/z 716.2, 718.2 [M+H]$^+$. (Cis) $^1$H NMR (400 MHz, CD$_3$OD) δ ppm 8.05 (d, J=3.0 Hz, 1H), 7.84 (d, J=1.5 Hz, 2H), 7.64 (s, 1H), 7.52 (dd, J=2.8, 9.3 Hz, 1H), 7.45 (s, 1H), 7.00 (s, 1H), 6.96

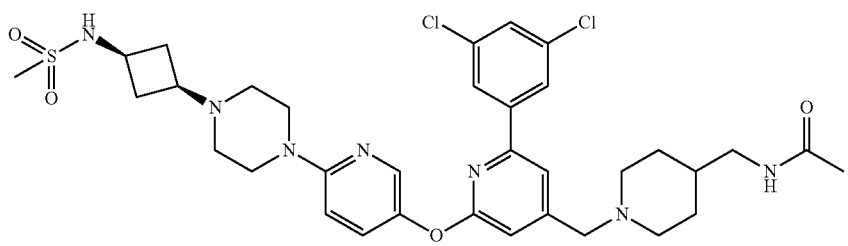 [SMILES: CC(=O)NCC1CCN(Cc2cc(Oc3ccc(N4CCN([C@H]5C[C@@H](NS(C)(=O)=O)C5)CC4)nc3)nc(-c3cc(Cl)cc(Cl)c3)c2)CC1]

(d, J=9.5 Hz, 1H), 3.70-3.55 (m, 7H), 3.10 (d, J=6.5 Hz, 2H), 2.99-2.91 (m, 5H), 2.70-2.49 (m, 7H), 2.10 (t, J=11.0 Hz, 2H), 1.96 (s, 3H), 1.94-1.86 (m, 2H), 1.74 (d, J=12.0 Hz, 2H), 1.55 (br. s, 1H), 1.37-1.30 (m, 2H); ES-LCMS m/z 716.2, 718.2 [M+H]$^+$.

Example 28: N-((1-((2-((6-(4-(2-Aminoethyl)piperazin-1-yl)pyridin-3-yl)oxy)-6-(3,5-dichlorophenyl)pyridin-4-yl)methyl)piperidin-4-yl)methyl)acetamide, 5 hydro chloride

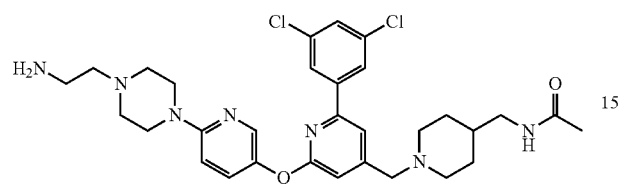

Step 1: tert-Butyl (2-(4-(5-((4-((4-(acetamidomethyl)piperidin-1-yl)methyl)-6-(3,5-dichlorophenyl)pyridin-2-yl)oxy)pyridin-2-yl)piperazin-1-yl)ethyl)carbamate

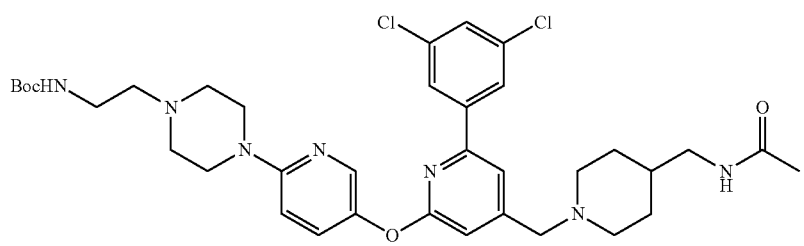 [SMILES: CC(=O)NCC1CCN(Cc2cc(Oc3ccc(N4CCN(CCNC(=O)OC(C)(C)C)CC4)nc3)nc(-c3cc(Cl)cc(Cl)c3)c2)CC1]

To a mixture of N-((1-((2-(3,5-dichlorophenyl)-6-((6-(piperazin-1-yl)pyridin-3-yl)oxy)pyridin-4-yl)methyl)piperidin-4-yl)methyl)acetamide (400 mg, 0.702 mmol) and tert-butyl (2-bromoethyl)carbamate (315 mg, 1.405 mmol) in DMF (20 mL) was added DIEA (0.368 mL, 2.107 mmol). Then the reaction mixture was stirred at 80° C. for 12 h. The solution was concentrated to yield a pale yellow solid of tert-butyl (2-(4-(5-((4-((4-(acetamidomethyl)piperidin-1-yl)methyl)-6-(3,5-dichlorophenyl)pyridin-2-yl)oxy)pyridin-2-yl)piperazin-1-yl)ethyl)carbamate (250 mg, 0.281 mmol, 40.0% yield): $^1$H NMR (400 MHz, CDCl$_3$) δ ppm 8.12 (d, J=9.8 Hz, 1H), 7.85 (d, J=18.8 Hz, 3H), 7.44 (d, J=6.4 Hz, 2H), 7.33 (d, J=5.9 Hz, 1H), 6.77 (dd, J=4.8, 8.9 Hz, 1H), 3.92 (s, 2H), 3.75-3.68 (m, 6H), 3.55-3.48 (m, 4H), 3.32-3.28 (m, 2H), 3.17-3.10 (m, 6H), 1.99 (s, 3H), 1.90-1.75 (m, 5H), 1.45 (s, 9H); ES-LCMS m/z 712.3, 714.3 [M+H]$^+$.

Step 2: N-((1-((2-((6-(4-(2-Aminoethyl)piperazin-1-yl)pyridin-3-yl)oxy)-6-(3,5-dichlorophenyl)pyridin-4-yl)methyl)piperidin-4-yl)methyl)acetamide, 5 hydrochloride

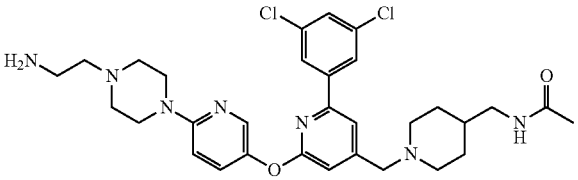 [SMILES: CC(=O)NCC1CCN(Cc2cc(Oc3ccc(N4CCN(CCN)CC4)nc3)nc(-c3cc(Cl)cc(Cl)c3)c2)CC1]

A solution of tert-butyl (2-(4-(5-((4-((4-(acetamidomethyl)piperidin-1-yl)methyl)-6-(3,5-dichlorophenyl)pyridin-2-yl)oxy)pyridin-2-yl)piperazin-1-yl)ethyl)carbamate (250 mg, 0.351 mmol) in 4.0 M in EtOAc (20 mL, 80 mmol) was stirred at 25° C. for 0.5 h. Solution was concentrated and the residue was purified with preparative HPLC (MeCN/H$_2$O as eluents, acidic condition) to yield a pale yellow solid N-((1-((2-((6-(4-(2-aminoethyl)piperazin-1-yl)pyridin-3-yl)oxy)-6-(3,5-dichlorophenyl)pyridin-4-yl)methyl)piperidin-4-yl)methyl)acetamide, 5 hydrochloride (156.68 mg, 0.194 mmol, 55.3% yield): $^1$H NMR (400 MHz, CD$_3$OD) δ ppm 8.28-8.24 (m, 2H), 8.02 (s, 1H), 7.91 (d, J=1.8 Hz, 2H), 7.67-7.63 (m, 1H), 7.56-7.54 (m, 1H), 7.44 (s, 1H), 4.58-4.46 (m, 2H), 4.21 (br. s, 2H), 3.72 (br. s, 2H), 3.60 (dd, J=5.9, 17.4 Hz, 8H), 3.41-3.34 (m, 2H), 3.19-3.11 (m, 4H), 2.03-1.98 (m, 5H), 1.89 (br. s, 1H), 1.71-1.60 (m, 2H); ES-LCMS m/z 612.3, 614.3 [M+H]$^+$.

Example 29: N-((1-((2-(3,5-Dichlorophenyl)-6-((6-(4-(2,4-dihydroxybutyl)piperazin-1-yl)pyridin-3-yl)oxy)pyridin-4-yl)methyl)piperidin-4-yl)methyl)acetamide, 4 hydrochloride

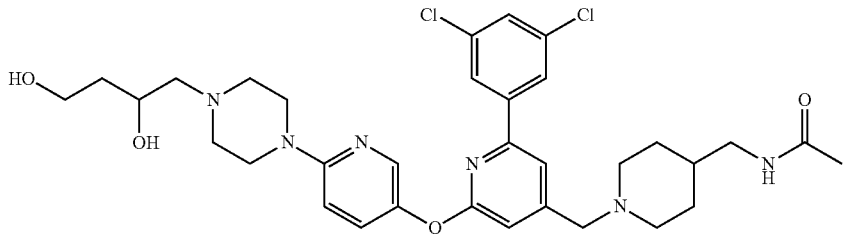 [SMILES: CC(=O)NCC1CCN(Cc2cc(Oc3ccc(N4CCN(CC(O)CCO)CC4)nc3)nc(-c3cc(Cl)cc(Cl)c3)c2)CC1]

Step 1: Ethyl 4-(4-(5-((4-((4-(acetamidomethyl)piperidin-1-yl)methyl)-6-(3,5-dichlorophenyl)pyridin-2-yl)oxy)pyridin-2-yl)piperazin-1-yl)-3-oxobutanoate

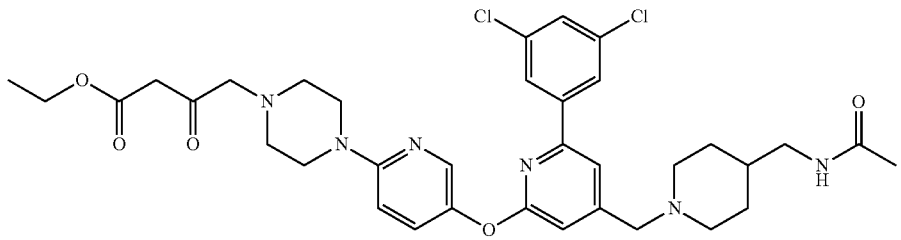 [SMILES: CCOC(=O)CC(=O)CN1CCN(c2ccc(Oc3cc(CN4CCC(CNC(C)=O)CC4)cc(-c4cc(Cl)cc(Cl)c4)n3)cn2)CC1]

To a solution of N-((1-((2-(3,5-dichlorophenyl)-6-((6-(piperazin-1-yl)pyridin-3-yl)oxy)pyridin-4-yl)methyl)piperidin-4-yl)methyl)acetamide (100 mg, 0.176 mmol) and ethyl 4-bromo-3-oxobutanoate (44.0 mg, 0.211 mmol) in DMF (5 mL) was added DIEA (0.031 mL, 0.176 mmol) at 25° C. The mixture was stirred at 25° C. for 12 h. The solution was concentrated. The residue was purified by column chromatography eluted with (PE/DCM=1/1 R$_f$=0.4) to yield brown oil of ethyl 4-(4-(5-((4-((4-(acetamidomethyl)ethyl)piperidin-1-yl)methyl)-6-(3,5-dichlorophenyl)pyridin-2yl)oxy)pyridin-2-yl)piperazin-1-yl)-3-oxobutanoate (100 mg, 0.115 mmol, 65.3% yield): $^1$H NMR (400 MHz, CD$_3$OD) δ ppm 8.23-8.19 (m, 1H), 8.04-7.96 (m, 2H), 7.89 (d, J=1.8 Hz, 2H), 7.55-7.50 (m, 1H), 7.45-7.41 (m, 1H), 7.39-7.36 (m, 1H), 4.61 (s, 2H), 4.46 (s, 2H), 4.14-4.09 (m, 4H), 4.02-3.88 (m, 4H), 3.60 (m, 6H), 3.17-3.04 (m, 4H), 2.04-1.93 (m, 5H), 1.89-1.72 (m, 1H), 1.67-1.51 (m, 2H), 1.31 (t, J=7.1 Hz, 3H); ES-LCMS m/z 697.3, 699.3 [M+H]$^+$.

Step 2: N-((1-((2-(3,5-Dichlorophenyl)-6-((6-(4-(2,4-dihydroxybutyl)piperazin-1-yl)pyridin-3-yl)oxy)pyridin-4-yl)methyl)piperidin-4-yl)methyl)acetamide, 4 hydrochloride

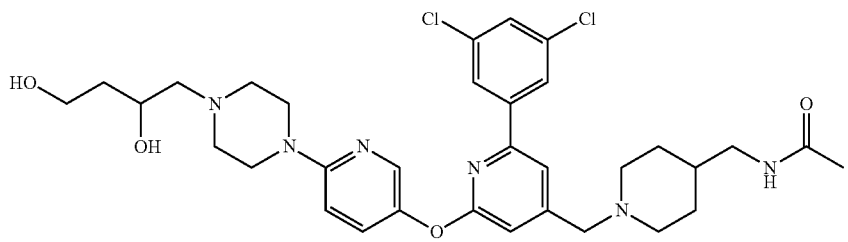 [SMILES: CC(=O)NCC1CCN(Cc2cc(Oc3ccc(N4CCN(CC(O)CCO)CC4)nc3)nc(-c3cc(Cl)cc(Cl)c3)c2)CC1]

To a solution of ethyl 4-(4-(5-((4-((4-(acetamidomethyl)piperidin-1-yl)methyl)-6-(3,5-dichlorophenyl)pyridin-2-yl)oxy)pyridin-2-yl)piperazin-1-yl)-3-oxobutanoate (50 mg, 0.072 mmol) in MeOH (20 mL) was added NaBH$_4$ (10 mg, 0.264 mmol). The mixture was stirred at 25° C. for 1 h. The mixture was concentrated. The residue was purified by preparative HPLC (MeCN/H$_2$O as eluents, acidic condition) to yield a white solid of N-((1-((2-(3,5-dichlorophenyl)-6-((6-(4-(2,4-dihydroxybutyl)piperazin-1-yl)pyridine-3-yl)oxy)pyridin-4-yl)methyl)piperidin-4-yl)methyl)acetamide, 4 hydrochloride (14.88 mg, 0.018 mmol, 25.0% yield): $^1$H NMR (400 MHz, CD$_3$OD) δ ppm 8.19-8.15 (m, 1H), 7.86 (d, J=1.8 Hz, 2H), 7.83-7.76 (m, 2H), 7.55-7.48 (m, 1H), 7.29 (s, 1H), 7.26-7.22 (m, 1H), 4.54-4.35 (m, 5H), 4.25 (br. s, 1H), 3.86-3.69 (m, 4H), 3.60 (d, J=11.9 Hz, 2H), 3.43-3.40 (m, 4H), 3.13 (br. s, 4H), 2.58 (d, J=6.2 Hz, 1H), 2.04-1.92 (m, 5H), 1.83 (br. s, 2H), 1.75-1.71 (m, 1H), 1.53 (d, J=14.1 Hz, 2H); ES-LCMS m/z 657.3, 659.3 [M+H]$^+$.

Example 30: (2-(4-(5-((4-((4-(Acetamidomethyl)piperidin-1-yl)methyl)-6-(3,5-dichlorophenyl)pyridin-2-yl)oxy)pyridin-2-yl)piperazin-1-yl)ethyl)phosphonic acid, 4 hydrochloride

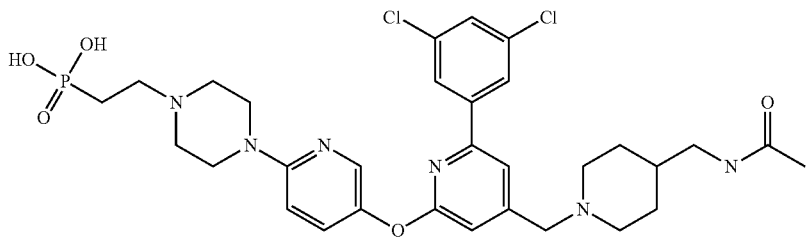 [SMILES: CC(=O)NCC1CCN(Cc2cc(Oc3ccc(N4CCN(CCP(=O)(O)O)CC4)nc3)nc(-c3cc(Cl)cc(Cl)c3)c2)CC1]

Step 1: Diethyl (2-(4-(5-((4-((4-(acetamidomethyl)piperidin-1-yl)methyl)-6-(3,5-dichlorophenyl)pyridin-2-yl)oxy)pyridin-2-yl)piperazin-1-yl)ethyl)phosphonate

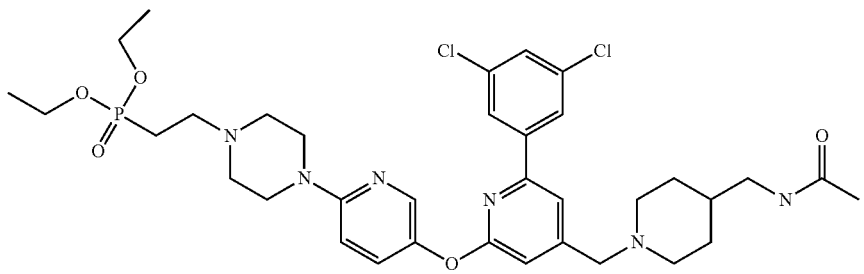 [SMILES: CCOP(=O)(CCN1CCN(c2ccc(Oc3cc(CN4CCC(CNC(C)=O)CC4)cc(-c4cc(Cl)cc(Cl)c4)n3)cn2)CC1)OCC]

A mixture of N-((1-((2-(3,5-dichlorophenyl)-6-((6-(piperazin-1-yl)pyridin-3-yl)oxy)pyridin-4-yl)methyl)piperidin-4-yl)methyl)acetamide, 4 hydrochloride (200 mg, 0.252 mmol), K$_2$CO$_3$ (174 mg, 1.258 mmol) and diethyl vinylphosphonate, (83 mg, 0.503 mmol) (25%) in water (3 mL) and 1,4-dioxane (5 mL) was stirred at 100° C. for 8 h under N$_2$ atmosphere. The reaction mixture was added with water (10 mL) then extracted with DCM (50 mL×3). The organic layer was washed with brine (30 mL), dried over Na$_2$SO$_4$, filtered and concentrated to yield a yellow oil of diethyl (2-(4-(5-((4-((4-(acetamidomethyl)piperidin-1-yl)methyl)-6-(3,5-dichlorophenyl)pyridin-2-yl)oxy)pyridin-2-yl)piperazin-1-yl)ethyl)phosphonate (200 mg, 0.218 mmol, 87.0% yield): $^1$H NMR (400 MHz, CDCl$_3$) δ ppm 8.11 (d, J=2.6 Hz, 1H), 7.75 (d, J=1.8 Hz, 2H), 7.45-7.36 (m, 2H), 7.32 (s, 1H), 6.80 (s, 1H), 6.72 (d, J=8.8 Hz, 1H), 4.10 (m, 4H), 3.54 (d, J=4.9 Hz, 4H), 3.48 (s, 2H), 3.15 (t, J=6.4 Hz, 2H), 2.84 (m, 2H), 2.77-2.66 (m, 2H), 2.63-2.56 (m, 4H), 2.10-1.97 (m, 4H), 1.95 (s, 3H), 1.72-1.60 (m, 5H), 1.31 (m, 6H); ES-LCMS m/z 1332, 735.2 [M+H]$^+$.

Step 2: (2-(4-(5-((4-((4-(Acetamidomethyl)piperidin-1-yl)methyl)-6-(3,5-dichlorophenyl)pyridin-2-yl)oxy)pyridin-2-yl)piperazin-1-yl)ethyl)phosphonic acid, 4 hydrochloride

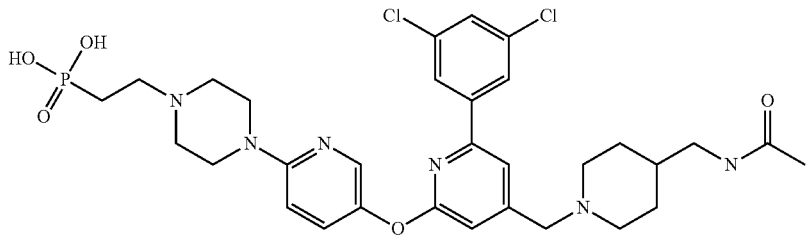 [SMILES: CC(=O)NCC1CCN(Cc2cc(Oc3ccc(N4CCN(CCP(=O)(O)O)CC4)nc3)nc(-c3cc(Cl)cc(Cl)c3)c2)CC1]

To a mixture of diethyl (2-(4-(5-((4-((4-(acetamidomethyl)piperidin-1-yl)methyl)-6-(3,5-dichlorophenyl)pyridin-2-yl)oxy)pyridin-2-yl)piperazin-1-yl)ethyl)phosphonate (150 mg, 0.164 mmol) in concentrated HCl (3 mL) and water (3 mL) was stirred at 100° C. for 3 h. The mixture was concentrated and purified by preparative HPLC (MeCN/H$_2$O as eluents, acidic condition) and dried by lyophilization to yield a white solid of (2-(4-(5-((4-((4-(acetamidomethyl)piperidin-1-yl)methyl)-6-(3,5-dichlorophenyl)pyridin-2-yl)oxy)pyridin-2-yl)piperazin-1-yl)ethyl)phosphonic acid, 4 hydrochloride (70.4 mg, 0.085 mmol, 51.7% yield): $^1$H NMR (400 MHz, CD$_3$OD) δ ppm 8.19 (d, J=2.6 Hz, 1H), 7.91-7.85 (m, 4H), 7.51 (t, J=1.8 Hz, 1H), 7.37-7.29 (m, 2H), 4.80 (s, 2H), 4.57-4.40 (m, 2H), 3.64-3.44 (m, 8H), 3.38-3.33 (m, 2H), 3.18-3.03 (m, 4H), 2.36-2.24 (m, 2H), 2.06-1.91 (m, 6H), 1.64-1.47 (m, 2H); ES-LCMS m/z 6112, 679.1 [M+H]$^+$.

Example 31: 2-(4-(5-((4-((4-(Acetamidomethyl)piperidin-1-yl)methyl)-6-(3,5-dichlorophenyl)pyridin-2-yl)oxy)pyridin-2-yl)piperazin-1-yl)ethyl carbamate, 4 hydrochloride

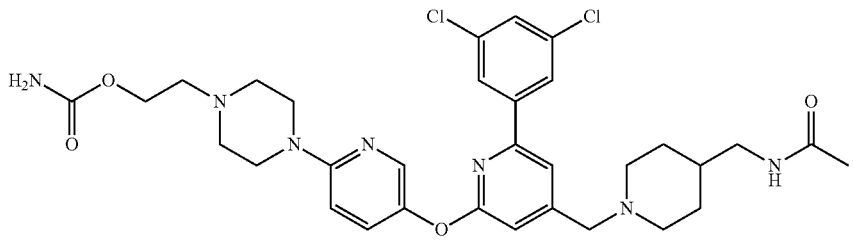 [SMILES: CC(=O)NCC1CCN(Cc2cc(Oc3ccc(N4CCN(CCOC(N)=O)CC4)nc3)nc(-c3cc(Cl)cc(Cl)c3)c2)CC1]

To a solution of N-((1-((2-(3,5-dichlorophenyl)-6-((6-(4-(2-hydroxyethyl)piperazin-1-yl)pyridin-3-yl)oxy)pyridin-4-yl)methyl)piperidin-4-yl)methyl)acetamide (900 mg, 0.587 mmol) in DCM (10 mL) was added CDI (114 mg, 0.704 mmol) and DIEA (0.5 mL, 2.86 mmol). The mixture was stirred at 25° C. for 5 h then ammonium hydroxide (0.2 mL, 5.14 mmol) was added and the mixture was stirred at 25° C. for another 7 h. The reaction mixture was concentrated to yield crude product which was purified by preparative HPLC (MeCN/H$_2$O as eluents, acidic condition) and dried by lyophilization to yield a white solid of 2-(4-(5-((4-((4-(acetamidomethyl)piperidin-1-yl)methyl)-6-(3,5-dichlorophenyl)pyridin-2-yl)oxy)pyridin-2-yl)piperazin-1-yl)ethyl carbamate, 4 hydrochloride (219.42 mg, 0.273 mmol, 46.5% yield): $^1$H NMR (400 MHz, CD$_3$OD) δ ppm 8.22 (br. s, 1H), 7.95 (br. s, 2H), 7.90 (s, 2H), 7.53 (s, 1H), 7.37 (br. s, 2H), 4.52-4.41 (m, 4H), 4.15-4.04 (m, 1H), 3.97 (d, J=5.0 Hz, 1H), 3.84 (br. s, 2H), 3.69-3.50 (m, 6H), 3.42 (br. s, 2H), 3.21-3.05 (m, 4H), 2.07-1.94 (m, 5H), 1.87 (br. s, 1H), 1.68-1.53 (m, 2H); ES-LCMS m/z 656.2, 658.2 [M+H]$^+$.

Example 32: N-((1-((2-(3,5-dichlorophenyl)-6-((6-(4-(2-(N-methylmethylsulfonamido)ethyl)piperazin-1-yl)pyridin-3-yl)oxy)pyridin-4-yl)methyl)piperidin-4-yl)methyl)acetamide, 4 hydrochloride

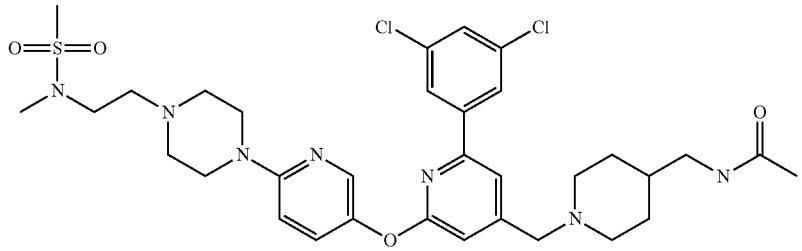 [SMILES: CC(=O)NCC1CCN(Cc2cc(Oc3ccc(N4CCN(CCN(C)S(C)(=O)=O)CC4)nc3)nc(-c3cc(Cl)cc(Cl)c3)c2)CC1]

Step 1: 2-(4-(5-((4-((4-(Acetamidomethyl)piperidin-1-yl)methyl)-6-(3,5-dichlorophenyl)pyridin-2-yl)oxy)pyridin-2-yl)piperazin-1-yl)ethyl methanesulfonate

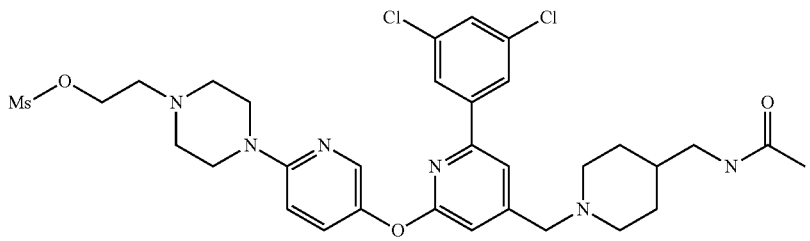 [SMILES: CC(=O)NCC1CCN(Cc2cc(Oc3ccc(N4CCN(CCOS(C)(=O)=O)CC4)nc3)nc(-c3cc(Cl)cc(Cl)c3)c2)CC1]

To a suspension of N-((1-((2-(3,5-dichlorophenyl)-6-((6-(4-(2-hydroxyethyl)piperazin-1-yl)pyridin-3-yl)oxy)pyridin-4-yl)methyl)piperidin-4-yl)methyl)acetamide (200 mg, 0.306 mmol) and DIEA (0.161 mL, 0.919 mmol) in DCM (10 mL) stirred at 0° C. was added MsCl (0.031 mL, 0.398 mmol). The reaction mixture was stirred at 25° C. for 0.5 h. Water (30 mL) was added and extracted with DCM (30 mL×3). The combined organic layers were dried over $Na_2SO_4$, filtered and concentrated to yield a pale yellow gum of 2-(4-(5-((4-((4-(acetamidomethyl)piperidin-1-yl)methyl)-6-(3,5-dichlorophenyl)pyridin-2-yl)oxy)pyridin-2-yl)piperazin-1-yl)ethyl methanesulfonate (260 mg, 0.292 mmol, 95.0% yield): $^1$H NMR (400 MHz, $CDCl_3$) δ ppm 8.08 (d, J=2.6 Hz, 1H), 7.86-7.69 (m, 3H), 7.46 (dd, J=2.6, 9.3 Hz, 1H), 7.33 (s, 1H), 7.06 (br s, 1H), 6.80 (d, J=9.3 Hz, 1H), 4.68 (br s, 1H), 4.20 (br s, 2H), 4.19-3.90 (m, 2H), 3.64-3.61 (m, 2H), 3.57-3.40 (m, 8H), 3.28-3.15 (m, 2H), 3.07 (s, 3H), 2.88-2.73 (m, 4H), 1.92 (s, 3H), 1.82-1.73 (m, 5H); ES-LCMS m/z 691.1, 693.1 $[M+H]^+$.

Step 2: N-((1-((2-(3,5-dichlorophenyl)-6-((6-(4-(2-(methylamino)ethyl)piperazin-1-yl)pyridin-3-yl)oxy)pyridin-4-yl)methyl)piperidin-4-yl)methyl)acetamide

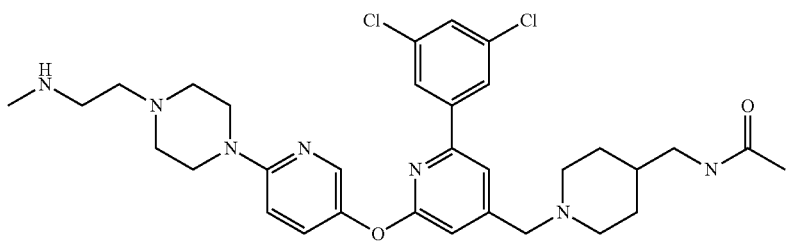 [SMILES: CNCCN1CCN(c2ccc(Oc3cc(CN4CCC(CNC(C)=O)CC4)cc(-c4cc(Cl)cc(Cl)c4)n3)cn2)CC1]

A mixture of 2-(4-(5-((4-((4-(acetamidomethyl)piperidin-1-yl)methyl)-6-(3,5-dichlorophenyl)pyridin-2-yl)oxy)pyridin-2-yl)piperazin-1-yl)ethyl methanesulfonate (260 mg, 0.292 mmol) in methanamine (30% in ethanol, 10 mL, 0.292 mmol) was stirred at 25° C. for 12 h. This reaction mixture was concentrated and the residue was partitioned between DCM (50 mL) and water (30 mL), extracted with DCM (50 mL×2). The combined organic layers were dried over $Na_2SO_4$, filtered and concentrated to yield a pale yellow solid N-((1-((2-(3,5-dichlorophenyl)-6-((6-(4-(2-(methylamino)ethyl)piperazin-1-yl)pyridin-3-yl)oxy)pyridin-4-yl)methyl)piperidin-4-yl)methyl)acetamide (220 mg, 0.278 mmol, 95.0% yield): $^1$H NMR (400 MHz, $CDCl_3$) δ ppm 8.13 (d, J=3.1 Hz, 1H), 7.78 (d, J=1.8 Hz, 2H), 7.46-7.37 (m, 2H), 7.34 (s, 1H), 6.81 (s, 1H), 6.73 (d, J=9.3 Hz, 1H), 5.56 (br. s, 1H), 3.60-3.52 (m, 4H), 3.17 (t, J=6.4 Hz, 2H), 2.88 (d, J=11.5 Hz, 2H), 2.74 (t, J=6.0 Hz, 2H), 2.66-2.53 (m, 8H), 2.48 (s, 3H), 2.08-1.94 (m, 5H), 1.69-1.64 (m, 2H), 1.60-1.53 (m, 1H), 1.36-1.29 (m, 2H); ES-LCMS m/z 626.3, 628.4 $[M+H]^+$.

Step 3: N-((1-((2-(3,5-dichlorophenyl)-6-((6-(4-(2-(N-methylmethylsulfonamido)ethyl)piperazin-1-yl)pyridin-3-yl)oxy)pyridin-4-yl)methyl)piperidin-4-yl)methyl)acetamide, 4 hydrochloride

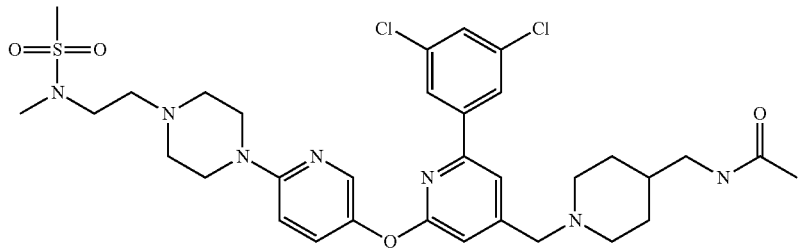 [SMILES: CC(=O)NCC1CCN(Cc2cc(Oc3ccc(N4CCN(CCN(C)S(C)(=O)=O)CC4)nc3)nc(-c3cc(Cl)cc(Cl)c3)c2)CC1]

To a suspension of N-((1-((2-(3,5-dichlorophenyl)-6-((6-(4-(2-(methylamino)ethyl)piperazin-1-yl)pyridin-3-yl)oxy)pyridin-4-yl)methyl)piperidin-4-yl)methyl)acetamide (200 mg, 0.253 mmol) and DIEA (0.133 mL, 0.759 mmol) in DCM (5 mL) was added MsCl (0.030 mL, 0.380 mmol). The reaction mixture was stirred at 25° C. for 1 h. The reaction mixture was concentrated and the residue was purified by preparative HPLC (MeCN/$H_2O$ as eluents, acidic condition) and lyophilized to yield a pale yellow solid N-((1-((2-(3,5-dichlorophenyl)-6-((6-(4-(2-(N-methylmethylsulfonamido)ethyl)piperazin-1-yl)pyridin-3-yl)oxy)pyridin-4-yl)methyl)piperidin-4-yl)methyl)acetamide, 4 hydrochloride (113.21 mg, 0.131 mmol, 51.9% yield): $^1$H NMR (400 MHz, $CD_3OD$) δ ppm 8.22 (d, J=2.6 Hz, 1H), 8.12 (dd, J=2.6, 9.7 Hz, 1H), 7.99 (s, 1H), 7.88 (d, J=1.8 Hz, 2H), 7.56-7.47 (m, 2H), 7.39 (s, 1H), 4.46 (s, 2H), 4.03-3.43 (m, 14H), 3.19-3.05 (m, 4H), 3.03-2.92 (m, 6H), 2.03-1.93 (m, 5H), 1.86 (br. s, 1H), 1.69-1.56 (m, 2H); ES-LCMS m/z 704.2, 706.2 $[M+H]^+$.

Example 33: 4-(4-(5-((4-((4-(Acetamidomethyl)piperidin-1-yl)methyl)-6-(3,5-dichlorophenyl)pyridin-2-yl)oxy)pyridin-2-yl)piperazin-1-yl)-4-oxobutanoic acid, 3 hydrochloride

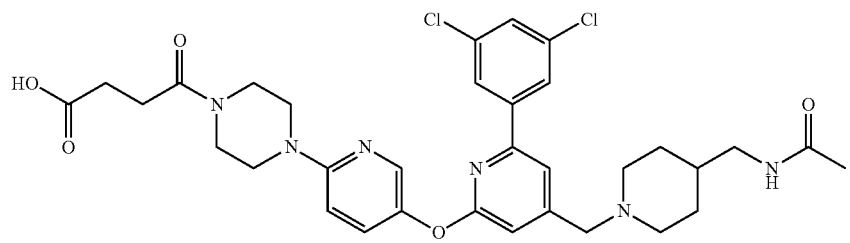 [SMILES: CC(=O)NCC1CCN(Cc2cc(Oc3ccc(N4CCN(C(=O)CCC(=O)O)CC4)nc3)nc(-c3cc(Cl)cc(Cl)c3)c2)CC1]

Step 1: Methyl 4-(4-(5-((4-((4-(acetamidomethyl)piperidin-1-yl)methyl)-6-(3,5-dichlorophenyl)pyridin-2-yl)oxy)pyridin-2-yl)piperazin-1-yl)-4-oxobutanoate

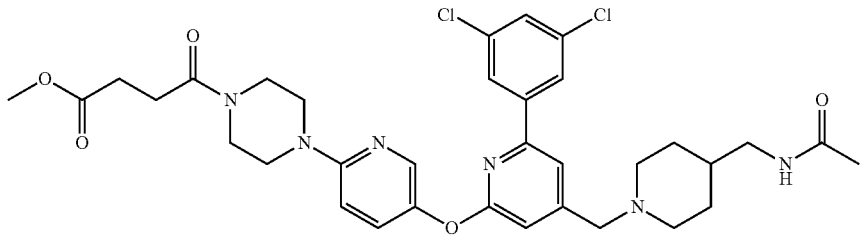 [SMILES: COC(=O)CCC(=O)N1CCN(c2ccc(Oc3cc(CN4CCC(CNC(C)=O)CC4)cc(-c4cc(Cl)cc(Cl)c4)n3)cn2)CC1]

A mixture of N-((1-((2-(3,5-dichlorophenyl)-6-((6-(piperazin-1-yl)pyridin-3-yl)oxy)pyridine-4-yl)methyl)piperidin-4-yl)methyl)acetamide (200 mg, 0.316 mmol), 4-methoxy-4-oxobutanoic acid (50.1 mg, 0.379 mmol), DIEA (0.331 mL, 1.896 mmol) and HATU (180 mg, 0.474 mmol) in DMF (10 mL) was stirred at 20° C. for 10 h. The mixture was concentrated and the residue was partitioned between DCM (30 mL) and H$_2$O (20 mL), extracted with DCM (30 mL×2). The combined organic layers were washed with brine (20 mL), dried over Na$_2$SO$_4$, filtered and concentrated. The crude product was purified by silica gel column chromatography (DCM/MeOH=20/1/10/1). All fractions found to contain product by TLC (DCM/MeOH=10/1, R$_f$=0.5) were combined and concentrated to yield a brown solid of methyl 4-(4-(5-((4-((4-(acetamidomethyl)piperidin-1-yl)methyl)-6-(3,5-dichlorophenyl)pyridin-2-yl)oxy)pyridin-2-yl)piperazin-1-yl)-4-oxobutanoate (200 mg, 0.266 mmol, 84.0% yield): $^1$H NMR (400 MHz, CD$_3$OD) δ ppm 8.58 (d, J=4.0 Hz, 1H), 8.30-8.22 (m, 1H), 8.05 (d, J=2.6 Hz, 1H), 7.80 (d, J=1.8 Hz, 2H), 7.45 (t, J=1.8 Hz, 1H), 7.16 (s, 1H), 6.96 (d, J=9.3 Hz, 1H), 4.31 (s, 2H), 3.76-3.70 (m, 5H), 3.67-3.65 (m, 2H), 3.55-3.45 (m, 4H), 3.26-3.19 (m, 2H), 3.12 (d, J=6.6 Hz, 2H), 3.00-2.97 (m, 2H), 2.79-2.58 (m, 4H), 2.03-1.96 (m, 5H), 1.93-1.81 (m, 1H), 1.64-1.51 (m, 2H); ES-LCMS m/z 683.2, 685.2 [M+H]$^+$.

Step 2: 4-(4-(5-((4-((4-(Acetamidomethyl)piperidin-1-yl)methyl)-6-(3,5-dichlorophenyl)pyridin-2-yl)oxy)pyridin-2-yl)piperazin-1-yl)-4-oxobutanoic acid, 3 hydrochloride

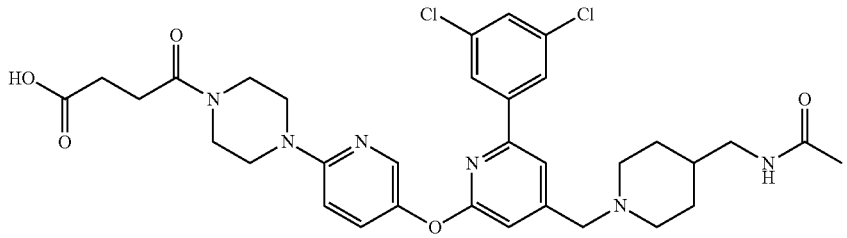 [SMILES: CC(=O)NCC1CCN(Cc2cc(Oc3ccc(N4CCN(C(=O)CCC(=O)O)CC4)nc3)nc(-c3cc(Cl)cc(Cl)c3)c2)CC1]

A mixture of methyl 4-(4-(5-((4-((4-(acetamidomethyl)piperidin-1-yl)methyl)-6-(3,5-dichlorophenyl)pyridin-2-yl)oxy)pyridin-2-yl)piperazin-1-yl)-4-oxobutanoate (200 mg, 0.266 mmol), sodium hydroxide (21.30 mg, 0.532 mmol) in MeOH (5 mL) and water (2 mL) was stirred at 20° C. for 10 h. Then the mixture was concentrated and the residue was purified by preparative HPLC (MeCN/H$_2$O as eluents, acidic condition) and lyophilized to yield a white solid of 4-(4-(5-((4-((4-(acetamidomethyl)piperidin-1-yl)methyl)-6-(3,5-dichlorophenyl)pyridin-2-yl)oxy)pyridin-2-yl)piperazin-1-yl)-4-oxobutanoic acid, 3 hydrochloride (40.34 mg, 0.049 mmol, 18.3% yield): $^1$H NMR (400 MHz, CD$_3$OD) δ ppm 8.21 (d, J=11.5 Hz, 1H), 8.14 (d, J=2.5 Hz, 1H), 7.98 (br. s, 1H), 7.90 (d, J=2.0 Hz, 2H), 7.58 (d, J=10.0 Hz, 1H), 7.55 (s, 1H), 7.42 (s, 1H), 4.48 (s, 2H), 3.95-3.79 (m, 8H), 3.62 (d, J=11.5 Hz, 2H), 3.18-3.07 (m, 4H), 2.76-2.71 (m, 2H), 2.70-2.63 (m, 2H), 2.04-1.97 (m, 5H), 1.88-1.86 (m, 1H), 1.63-1.61 (m, 2H); ES-LCMS m/z 669.2, 671.2 [M+H]$^+$.

Example 34: N-((1-((2-(3,5-Dichlorophenyl)-6-((6-(4-((1-(hydroxymethyl)cyclopropyl)methyl)piperazin-1-yl)pyridin-3-yl)oxy)pyridin-4-yl)methyl)piperidin-4-yl)methyl)acetamide, 4 hydrochloride

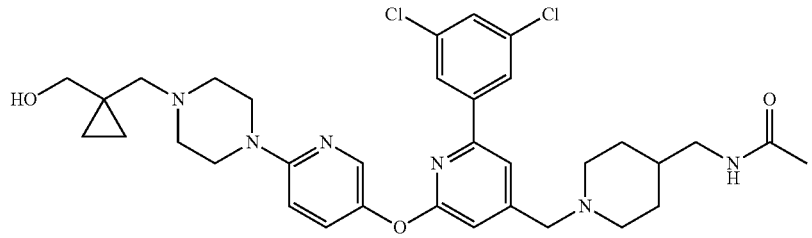 [SMILES: CC(=O)NCC1CCN(Cc2cc(Oc3ccc(N4CCN(CC5(CO)CC5)CC4)nc3)nc(-c3cc(Cl)cc(Cl)c3)c2)CC1]

Step 1: Methyl 1-(4-(5-((6-(3,5-dichlorophenyl)-4-(hydroxymethyl)pyridin-2-yl)oxy)pyridin-2-yl)piperazine-1-carbonyl)cyclopropanecarboxylate

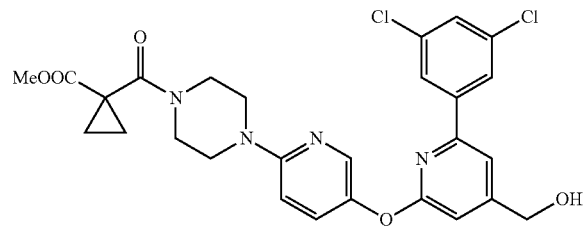 [SMILES: COC(=O)C1(C(=O)N2CCN(c3ccc(Oc4cc(CO)cc(-c5cc(Cl)cc(Cl)c5)n4)cn3)CC2)CC1]

To a mixture of tert-butyl 4-(5-((6-(3,5-dichlorophenyl)-4-(hydroxymethyl)pyridin-2-yl)oxy)pyridin-2-yl)piperazine-1-carboxylate, 3 hydrochloride (2 g, 2.77 mmol), 1-(methoxycarbonyl)cyclopropanecarboxylic acid (0.379 g, 2.63 mmol), DIEA (4.84 mL, 27.7 mmol) in DMF (30 mL) was added HATU (2.105 g, 5.54 mmol). The mixture was stirred at 25° C. for 2 h then concentrated. The residue was diluted with DCM (100 mL) and water (100 mL), extracted with DCM (100 mL×2). The combined organic layers were dried over $Na_2SO_4$, filtered and concentrated to yield crude product which was purified by silica gel column chromatography (DCM/MeOH=10/1, $R_f$=0.6) to yield a yellow solid of methyl 1-(4-(5-((6-(3,5-dichlorophenyl)-4-(hydroxymethyl)pyridin-2-yl)oxy)pyridin-2-yl)piperazine-1-carbonyl)cyclopropanecarboxylate (1.1 g, 1.932 mmol, 69.8% yield): $^1$H NMR (400 MHz, $CD_3OD$) δ ppm 7.98 (d, J=2.8 Hz, 1H), 7.70 (s, 2H), 7.64 (s, 1H), 7.45-7.39 (m, 7H), 6.87-6.81 (m, 2H), 4.63 (s, 2H), 3.71-3.62 (m, 7H), 3.55-3.48 (m, 4H), 1.48-1.43 (m, 2H), 1.30-1.25 (m, 2H); ES-LCMS m/z 557.2, 559.2 [M+H]$^+$.

Step 2: Methyl 1-(4-(5-((6-(3,5-dichlorophenyl)-4-(((methylsulfonyl)oxy)methyl)pyridin-2-yl)oxy)pyridin-2-yl)piperazine-1-carbonyl)cyclopropanecarboxylate

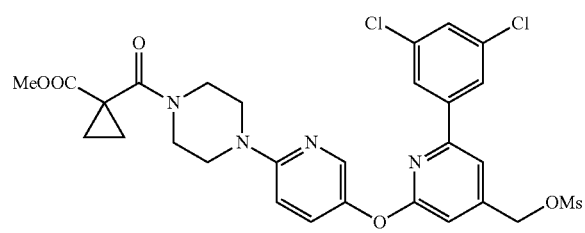 [SMILES: COC(=O)C1(C(=O)N2CCN(c3ccc(Oc4cc(COS(C)(=O)=O)cc(-c5cc(Cl)cc(Cl)c5)n4)cn3)CC2)CC1]

To a solution of methyl 1-(4-(5-((6-(3,5-dichlorophenyl)-4-(hydroxymethyl)pyridin-2-yl)oxy)pyridin-2-yl)piperazine-1-carbonyl)cyclopropanecarboxylate (1.1 g, 1.932 mmol) and DIEA (1.026 mL, 5.79 mmol) in DCM (20 mL) was added MsCl (0.314 mL, 3.86 mmol). The solution was stirred at 20° C. for 0.5 h. Then the solution was washed with water (50 mL×3). The organic layer was dried over $Na_2SO_4$, filtered and concentrated to yield a yellow solid of methyl 1-(4-(5-((6-(3,5-dichlorophenyl)-4-(((methylsulfonyl)oxy)methyl)pyridin-2-yl)oxy)pyridin-2-yl)piperazine-1-carbonyl)cyclopropanecarboxylate (1.2 g, 1.764 mmol, 91.0% yield): $^1$H NMR (400 MHz, $CDCl_3$) δ ppm 8.07 (d, J=2.6 Hz, 1H), 7.66 (d, J=1.8 Hz, 2H), 7.42-7.27 (m, 3H), 6.84 (s, 1H), 6.70 (d, J=8.8 Hz, 1H), 5.20 (s, 2H), 3.77-3.71 (m, 2H), 3.68 (s, 3H), 3.60 (d, J=5.7 Hz, 2H), 3.53 (dd, J=5.3, 15.9 Hz, 4H), 3.05 (s, 3H), 1.50-1.46 (m, 2H), 1.33-1.29 (m, 2H); ES-LCMS m/z 635.1, 637.1[M+H]$^+$.

Step 3: 1-(4-(5-((4-((4-(((tert-Butoxycarbonyl)amino)methyl)piperidin-1-yl)methyl)-6-(3,5-dichlorophenyl)pyridin-2-yl)oxy)pyridin-2-yl)piperazine-1-carbonyl)cyclopropanecarboxylic acid

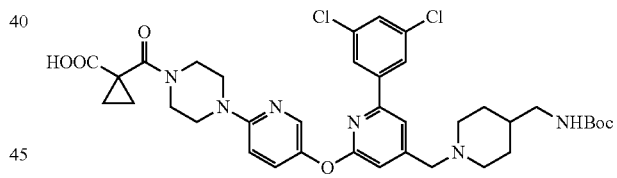

To a mixture of methyl 1-(4-(5-((6-(3,5-dichlorophenyl)-4-(((methylsulfonyl)oxy)methyl)pyridin-2-yl)oxy)pyridin-2-yl)piperazine-1-carbonyl)cyclopropanecarboxylate (1.2 g, 1.764 mmol), $K_2CO_3$ (1.3 g, 9.41 mmol) in DMF (10 mL) was added tert-butyl (piperidin-4-ylmethyl)carbamate (0.567 g, 2.65 mmol). The mixture was stirred at 30° C. for 8 h then cooled down and filtered. The filtrate was concentrated and the residue was purified by silica column chromatography (DCM/MeOH=10/1, $R_f$=0.4) to yield a brown solid of 1-(4-(5-((4-((4-(((tert-butoxycarbonyl)amino)methyl)piperidin-1-yl)methyl)-6-(3,5-dichlorophenyl)pyridin-2-yl)oxy)pyridin-2-yl)piperazine-1-carbonyl)cyclopropanecarboxylic acid (700 mg, 0.757 mmol, 42.9% yield): $^1$H NMR (400 MHz, $CDCl_3$) δ ppm 8.08 (s, 1H), 7.73 (s, 2H), 7.43-7.29 (m, 3H), 7.04 (s, 1H), 6.49 (d, J=7.5 Hz, 1H), 4.80 (s, 2H), 3.82-3.63 (m, 6H), 3.49-3.47 (m, 4H), 3.18-3.16 (m, 2H), 3.04-3.00 (m, 2H), 1.77-1.74 (m, 3H), 1.43 (s, 9H), 1.30-1.26 (m, 4H), 1.24 (s, 2H); ES-LCMS m/z 739.3, 741.3 [M+H]$^+$.

Step 4: tert-Butyl ((1-((2-(3,5-dichlorophenyl)-6-((6-(4-((1-(hydroxymethyl)cyclopropyl)methyl)piperazin-1-yl)pyridin-3-yl)oxy)pyridin-4-yl)methyl)piperidin-4-yl)methyl)carbamate

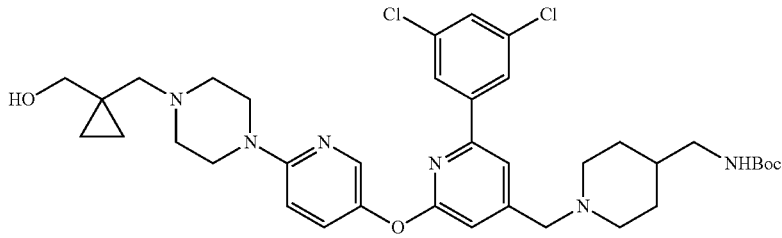 [SMILES: CC(C)(C)OC(=O)NCC1CCN(Cc2cc(Oc3ccc(N4CCN(CC5(CO)CC5)CC4)nc3)nc(-c3cc(Cl)cc(Cl)c3)c2)CC1]

To a mixture of 1-(4-(5-((4-((4-(((tert-butoxycarbonyl)amino)methyl)piperidin-1-yl)methyl)-6-(3,5-dichlorophenyl)pyridin-2-yl)oxy)pyridin-2-yl)piperazine-1-carbonyl)cyclopropanecarboxylic acid (150 mg, 0.162 mmol) in THF (30 mL) was added BH₃·DMS (0.032 mL, 0.324 mmol). The mixture was stirred at 30° C. for 2 h then quenched with MeOH (20 mL). The reaction was concentrated to yield a white solid of tert-butyl ((1-((2-(3,5-dichlorophenyl)-6-((6-(4-((1-(hydroxymethyl)cyclopropyl)methyl)piperazin-1-yl)pyridin-3-yl)oxy)pyridin-4-yl)methyl)piperidin-4-yl)methyl)carbamate (230 mg, 0.090 mmol, 55.8% yield): $^1$H NMR (400 MHz, CDCl₃) δ ppm 8.02 (br. s, 1H), 7.67 (br. s, 2H), 7.38-7.21 (m, 3H), 6.97 (br. s, 1H), 6.45 (br. s, 1H), 4.73 (s, 2H), 3.76-3.56 (m, 5H), 3.42-3.40 (m, 5H), 3.12-3.10 (m, 2H), 2.98-2.97 (m, 2H), 2.52-2.33 (m, 4H), 1.67-1.65 (m, 3H), 1.37 (s, 9H), 1.30-1.18 (m, 6H); ES-LCMS m/z 711.3, 713.3[M+H]⁺.

Step 5: (1-((4-(5-((4-((4-(Aminomethyl)piperidin-1-yl)methyl)-6-(3,5-dichlorophenyl)pyridin-2-yl)oxy)pyridin-2-yl)piperazin-1-yl)methyl)cyclopropyl)methanol, 5 hydrochloride

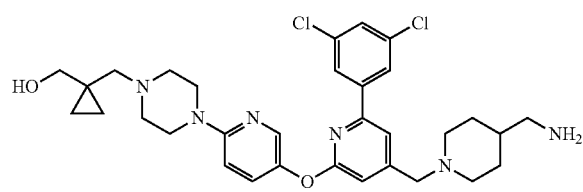 [SMILES: NCC1CCN(Cc2cc(Oc3ccc(N4CCN(CC5(CO)CC5)CC4)nc3)nc(-c3cc(Cl)cc(Cl)c3)c2)CC1]

To a solution of tert-butyl ((1-((2-(3,5-dichlorophenyl)-6-((6-(4-(1-(hydroxymethyl)cyclopropanecarbonyl)piperazin-1-yl)pyridin-3-yl)oxy)pyridin-4-yl)methyl)piperidin-4-yl)methyl)carbamate (230 mg, 0.089 mmol) in MeOH (20 mL) was added HCl solution (4.0 M in MeOH, 10 mL, 40.0 mmol). The mixture was stirred at 30° C. for 0.5 h then concentrated to yield the crude product which was purified by preparative HPLC (MeCN/H₂O as eluents, acidic condition) and dried by lyophilization to yield a brown solid of (1-((4-(5-((4-((4-(aminomethyl)piperidin-1-yl)methyl)-6-(3,5-dichlorophenyl)pyridin-2-yl)oxy)pyridin-2-yl)piperazin-1-yl)methyl)cyclopropyl)methanol, 5 hydrochloride (35 mg, 0.039 mmol, 44.0% yield): $^1$H NMR (400 MHz, CD₃OD) δ ppm 8.17 (d, J=2.6 Hz, 1H), 7.99 (s, 1H), 7.88 (d, J=1.8 Hz, 2H), 7.81 (dd, J=2.6, 9.3 Hz, 1H), 7.49 (s, 1H), 7.34 (s, 1H), 7.25 (d, J=9.3 Hz, 1H), 4.46 (s, 4H), 3.94-3.93 (m, 2H), 3.67-3.58 (m, 4H), 3.51-3.36 (m, 4H), 3.29-3.10 (m, 4H), 2.92 (d, J=6.2 Hz, 2H), 2.11-2.00 (m, 3H), 1.76-1.73 (m, 2H), 0.88-0.75 (m, 4H); ES-LCMS m/z 611.3, 613.3[M+H]⁺.

Step 6: (1-((4-(5-((4-((4-(Acetamidomethyl)piperidin-1-yl)methyl)-6-(3,5-dichlorophenyl)pyridin-2-yl)oxy)pyridin-2-yl)piperazin-1-yl)methyl)cyclopropyl)methyl acetate

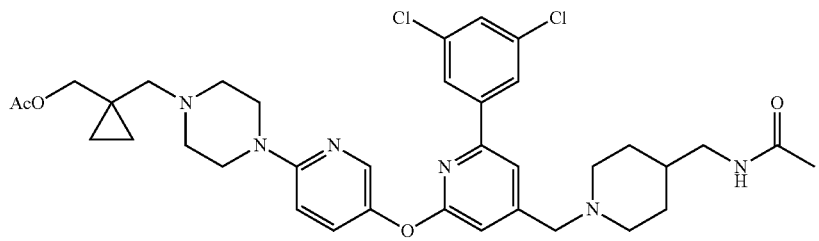 [SMILES: CC(=O)NCC1CCN(Cc2cc(Oc3ccc(N4CCN(CC5(COC(C)=O)CC5)CC4)nc3)nc(-c3cc(Cl)cc(Cl)c3)c2)CC1]

To a solution of (1-((4-(5-((4-((4-(aminomethyl)piperidin-1-yl)methyl)-6-(3,5-dichlorophenyl)pyridin-2-yl)oxy)pyridin-2-yl)piperazin-1-yl)methyl)cyclopropyl)methanol, 5 hydrochloride (30 mg, 0.033 mmol) and DIEA (0.059 mL, 0.335 mmol) in DCM (5 mL) was added Ac₂O (3.79 μL, 0.040 mmol). The solution was stirred at 20° C. for 0.5 h then washed with water (50 mL×3). The organic layer was dried over Na₂SO₄, filtered and concentrated to yield a brown solid of (1-((4-(5-((4-((4-(acetamidomethyl)piperidin-1-yl)methyl)-6-(3,5-dichlorophenyl)pyridin-2-yl)oxy)pyridin-2-yl)piperazin-1-yl)methyl)cyclopropyl)methyl acetate (32 mg, 0.032 mmol, 96.0% yield): $^1$H NMR (400 MHz, CDCl₃) δ ppm 8.05 (s, 1H), 7.70 (d, J=1.8 Hz, 2H), 7.37-7.32 (m, 2H), 7.27 (s, 1H), 6.74 (s, 1H), 6.66 (d, J=9.3 Hz, 1H), 3.61 (d, J=6.6 Hz, 2H), 3.51-3.48 (m, 8H), 3.10 (t, J=6.4 Hz, 2H), 2.82-2.81 (m, 2H), 2.68-2.66 (m, 4H), 2.61-2.49 (m, 2H), 1.94-1.92 (m, 6H), 1.63-1.60 (m, 3H), 1.32-1.15 (m, 2H), 0.52-0.48 (m, 2H), 0.42-0.38 (m, 2H); ES-LCMS m/z 695.3, 697.4 [M+H]⁺.

Step 7: N-((1-((2-(3,5-Dichlorophenyl)-6-((6-(4-((1-(hydroxymethyl)cyclopropyl)methyl)piperazin-1-yl)pyridin-3-yl)oxy)pyridin-4-yl)methyl)piperidin-4-yl)methyl)acetamide, 4 hydrochloride

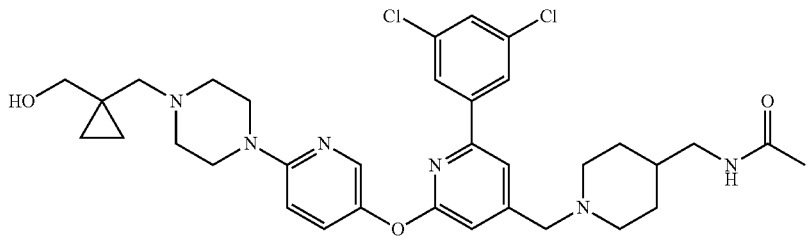 [SMILES: CC(=O)NCC1CCN(Cc2cc(Oc3ccc(N4CCN(CC5(CO)CC5)CC4)nc3)nc(-c3cc(Cl)cc(Cl)c3)c2)CC1]

To a mixture of (1-((4-(5-((4-((4-(acetamidomethyl)piperidin-1-yl)methyl)-6-(3,5-dichlorophenyl)pyridin-2-yl)oxy)pyridin-2-yl)piperazin-1-yl)methyl)cyclopropyl)methyl acetate (32 mg, 0.032 mmol) in THF (5 mL) and water (5 mL) was added LiOH·H₂O (6.76 mg, 0.161 mmol). The mixture was stirred at 30° C. for 20 min then concentrated and purified by preparative HPLC (MeCN/H₂O as eluents, acidic condition) and dried by lyophilization to yield an off white solid of N-((1-((2-(3,5-dichlorophenyl)-6-((6-(4-((1-(hydroxymethyl)cyclopropyl)methyl)piperazin-1-yl)pyridin-3-yl)oxy)pyridin-4-yl)methyl)piperidin-4-yl)methyl)acetamide, 4 hydrochloride (11.13 mg, 0.014 mmol, 43.2% yield): $^1$H NMR (400 MHz, CD₃OD) δ ppm 8.20 (d, J=2.2 Hz, 1H), 8.03 (dd, J=2.4, 9.5 Hz, 1H), 7.93 (s, 1H), 7.87 (d, J=1.3 Hz, 2H), 7.51 (s, 1H), 7.44 (d, J=9.3 Hz, 1H), 7.35 (s, 1H), 4.44 (s, 4H), 3.97-3.95 (m, 2H), 3.64-3.54 (m, 5H), 3.35-3.34 (m, 5H), 3.17-3.02 (m, 4H), 2.06-1.93 (m, 5H), 1.84-1.83 (m, 1H), 1.66-1.53 (m, 2H), 0.81-0.67 (m, 4H); ES-LCMS m/z 653.3, 655.3 [M+H]⁺.

Example 35: N-((1-((2-(3,5-Dichlorophenyl)-6-((6-(4-((1-(hydroxymethyl)cyclopropyl)methyl)piperazin-1-yl)pyridin-3-yl)oxy)pyridin-4-yl)methyl)piperidin-4-yl)methyl) acetamide, 4 hydrochloride Step 1: 1-(4-(5-((6-(3,5-Dichlorophenyl)-4-(hydroxymethyl)pyridin-2-yl)oxy)pyridin-2-yl)piperazin-1-yl)-2,2,2-trifluoroethanone

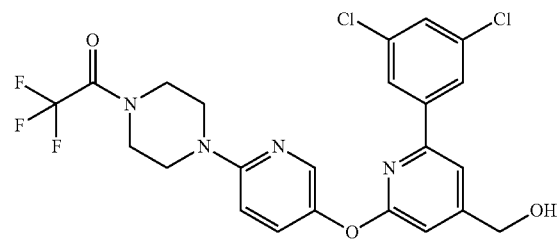 [SMILES: O=C(N1CCN(c2ccc(Oc3cc(CO)cc(-c4cc(Cl)cc(Cl)c4)n3)cn2)CC1)C(F)(F)F]

To a solution of (2-(3,5-dichlorophenyl)-6-((6-(piperazin-1-yl)pyridin-3-yl)oxy)pyridin-4-yl)methanol, 3 hydrochloride (1.9 g, 3.22 mmol) and DIEA (5.69 mL, 32.2 mmol) in DCM (120 mL) was added 2,2,2-trifluoroacetic anhydride (0.749 mL, 3.86 mmol). The solution was stirred at 20° C. for 0.5 h then concentrated, diluted with DCM (100 mL) and water (100 mL) and extracted with DCM (100 mL×2). The combined organic layers were dried over Na₂SO₄, filtered and concentrated to yield a brown solid of 1-(4-(5-((6-(3,5-dichlorophenyl)-4-(hydroxymethyl)pyridin-2-yl)oxy)pyridin-2-yl)piperazin-1-yl)-2,2,2-trifluoroethanone (1.7 g, 2.87 mmol, 89.0% yield): $^1$H NMR (400 MHz, CDCl₃) δ ppm 8.12 (d, J=2.6 Hz, 1H), 7.73 (d, J=1.8 Hz, 2H), 7.47-7.39 (m, 2H), 7.32 (s, 1H), 6.87 (s, 1H), 6.74 (d, J=8.8 Hz, 1H), 4.76 (s, 2H), 3.84-3.81 (m, 2H), 3.75 (d, J=4.9 Hz, 2H), 3.63 (dd, J=5.7, 11.0 Hz, 4H); ES-LCMS m/z 527.1, 529.1[M+H]⁺.

Step 2: (2-(3,5-Dichlorophenyl)-6-((6-(4-(2,2,2-trifluoroacetyl)piperazin-1-yl)pyridin-3-yl)oxy)pyridin-4-yl)methyl methanesulfonate

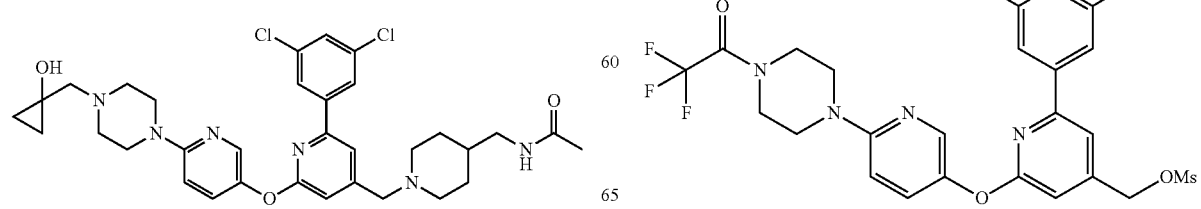

To a mixture of 1-(4-(5-((6-(3,5-dichlorophenyl)-4-(hydroxymethyl)pyridin-2-yl)oxy)pyridin-2-yl)piperazin-1-yl)-2,2,2-trifluoroethanone (1.7 g, 2.87 mmol) and DIEA (2.004 mL, 11.48 mmol) in DCM (50 mL) was added MsCl (0.447 mL, 5.74 mmol). The mixture was stirred at 20° C. for 0.5 h then diluted with DCM (100 mL) and water (100 mL), extracted with DCM (100 mL×2). The combined organic layers were dried over Na₂SO₄, filtered and concentrated to yield a brown solid of (2-(3,5-dichlorophenyl)-6-((6-(4-(2,2,2-trifluoroacetyl)piperazin-1-yl)pyridin-3-yl)oxy)pyridin-4-yl)methyl methanesulfonate (2.2 g, 2.60 mmol, 91.0% yield): $^1$H NMR (400 MHz, CDCl₃) δ ppm 8.08 (d, J=2.2 Hz, 1H), 7.66 (d, J=1.3 Hz, 2H), 7.43-7.27 (m, 3H), 6.85 (s, 1H), 6.70 (d, J=8.8 Hz, 1H), 5.25-5.16 (m, 2H), 3.79 (d, J=4.4 Hz, 2H), 3.72-3.68 (m, 2H), 3.60 (dd, J=5.3, 11.0 Hz, 4H), 3.09-3.02 (m, 3H); ES-LCMS m/z 605.1, 607.1[M+H]⁺.

Step 3: tert-Butyl ((1-((2-(3,5-dichlorophenyl)-6-((6-(4-(2,2,2-trifluoroacetyl)piperazin-1-yl)pyridin-3-yl)oxy)pyridin-4-yl)methyl)piperidin-4-yl)methyl)carbamate

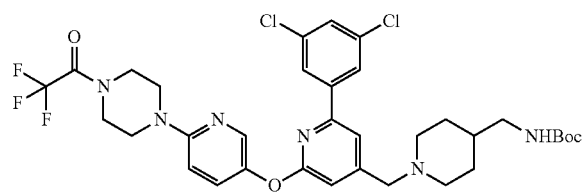 [SMILES: CC(C)(C)OC(=O)NCC1CCN(Cc2cc(Oc3ccc(N4CCN(C(=O)C(F)(F)F)CC4)nc3)nc(-c3cc(Cl)cc(Cl)c3)c2)CC1]

To a mixture of (2-(3,5-dichlorophenyl)-6-((6-(4-(2,2,2-trifluoroacetyl)piperazin-1-yl)pyridin-3-yl)oxy)pyridin-4-yl)methyl methanesulfonate (2.2 g, 2.60 mmol) and K₂CO₃ (1.3 g, 9.41 mmol) in DML (10 mL) was added tert-butyl (piperidin-4-ylmethyl)carbamate (0.836 g, 3.90 mmol). The mixture was stirred at 30° C. for 2 h then cooled down and filtered. The filtrate was concentrated to yield a brown solid of tert-butyl ((1-((2-(3,5-dichlorophenyl)-6-((6-(4-(2,2,2-trifluoroacetyl)piperazin-1-yl)pyridin-3-yl)oxy)pyridin-4-yl)methyl)piperidin-4-yl)methyl)carbamate (2 g, 2.178 mmol, 84.0% yield): $^1$H NMR (400 MHz, CDCl₃) δ ppm 8.11-8.08 (m, 1H), 7.75-7.72 (m, 1H), 7.71-7.68 (m, 1H), 7.47-7.39 (m, 1H), 7.37 (d, J=2.6 Hz, 1H), 7.29 (t, J=1.8 Hz, 1H), 6.84-6.76 (m, 1H), 6.75-6.68 (m, 1H), 3.76-3.69 (m, 4H), 3.65-3.59 (m, 2H), 3.52-3.48 (m, 2H), 3.30 (d, J=12.6 Hz, 2H), 3.02-2.99 (m, 4H), 2.02-1.91 (m, 2H), 1.79 (d, J=12.8 Hz, 2H), 1.65 (d, J=12.6 Hz, 3H), 1.41-1.40 (m, 9H); ES-LCMS m/z 723.3, 725.3 [M+H]⁺.

Step 4: tert-Butyl ((1-((2-(3,5-dichlorophenyl)-6-((6-(4-((1-(hydroxymethyl)cyclopropyl)methyl)piperazin-1-yl)pyridin-3-yl)oxy)pyridin-4-yl)methyl)piperidin-4-yl)methyl)carbamate

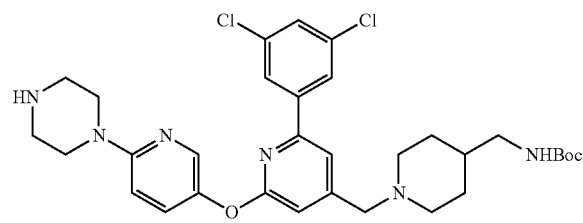 [SMILES: CC(C)(C)OC(=O)NCC1CCN(Cc2cc(Oc3ccc(N4CCNCC4)nc3)nc(-c3cc(Cl)cc(Cl)c3)c2)CC1]

To a mixture of tert-butyl ((1-((2-(3,5-dichlorophenyl)-6-((6-(4-(2,2,2-trifluoroacetyl)piperazin-1-yl)pyridin-3-yl)oxy)pyridin-4-yl)methyl)piperidin-4-yl)methyl)carbamate (1.7 g, 1.851 mmol) in THF (5 mL) and water (5 mL) was added NaOH (0.148 g, 3.70 mmol). The mixture was stirred at 30° C. for 20 min then concentrated, diluted with DCM (100 mL) and water (100 mL), extracted with DCM (100 mL×2). The combined organic layers were dried over Na₂SO₄, filtered and concentrated to yield crude product. The crude product was purified by silica gel column chromatography (DCM/MeOH=20/1, R$_f$=0.5) to yield a brown solid of tert-butyl ((1-((2-(3,5-dichlorophenyl)-6-((6-(piperazin-1-yl)pyridin-3-yl)oxy)pyridin-4-yl)methyl)piperidin-4-yl)methyl)carbamate (1.2 g, 1.663 mmol, 90.0% yield): $^1$H NMR (400 MHz, CDCl₃) δ ppm 8.10 (d, J=2.4 Hz, 1H), 7.77-7.73 (m, 2H), 7.42-7.37 (m, 2H), 7.31 (d, J=1.3 Hz, 1H), 6.79 (s, 1H), 6.75-6.68 (m, 1H), 3.54-3.50 (m, 4H), 3.48 (s, 2H), 3.05-3.00 (m, 6H), 2.85 (d, J=10.8 Hz, 2H), 2.03-1.96 (m, 2H), 1.66 (d, J=12.1 Hz, 3H), 1.41 (s, 9H), 1.33-1.26 (m, 2H); ES-LCMS m/z 627.3, 629.3[M+H]⁺.

Step 5: tert-Butyl ((1-((2-(3,5-dichlorophenyl)-6-((6-(4-(1-hydroxycyclopropanecarbonyl)piperazin-1-yl)pyridin-3-yl)oxy)pyridin-4-yl)methyl)piperidin-4-yl)methyl)carbamate

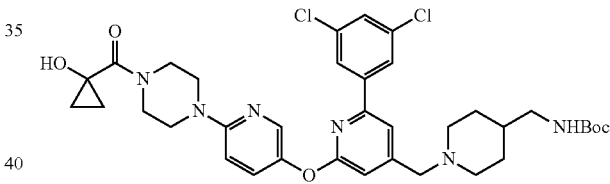

To a mixture of tert-butyl ((1-((2-(3,5-dichlorophenyl)-6-((6-(piperazin-1-yl)pyridin-3-yl)oxy)pyridin-4-yl)methyl)piperidin-4-yl)methyl)carbamate (300 mg, 0.416 mmol), 1-hydroxycyclopropanecarboxylic acid (85 mg, 0.499 mmol), DIEA (0.726 mL, 4.16 mmol) in DMF (5 mL) was added EDC (80 mg, 0.416 mmol) and HOBt (63.7 mg, 0.416 mmol). The mixture was stirred at 25° C. for 10 h then concentrated and diluted with DCM (50 mL) and water (50 mL), extracted with DCM (50 mL×2). The combined organic layers were dried over Na₂SO₄, filtered and concentrated to yield crude product. The crude product was purified by silica gel column chromatography (DCM/MeOH=20/1, R$_f$=0.5) to yield a brown solid tert-butyl ((1-((2-(3,5-dichlorophenyl)-6-((6-(4-(1-hydroxycyclopropanecarbon-yl)piperazin-1-yl)pyridin-3-yl)oxy)pyridin-4-yl)methyl)piperidin-4-yl)methyl)carbamate (240 mg, 0.294 mmol, 70.8% yield): $^1$H NMR (400 MHz, CDCl₃) δ ppm 8.09 (d, J=2.5 Hz, 1H), 7.78 (d, J=8.0 Hz, 1H), 7.68-7.61 (m, 3H), 7.40 (dd, J=2.5, 9.0 Hz, 1H), 6.90 (s, 1H), 6.69-6.60 (m, 1H), 3.88-3.86 (m, 4H), 3.57-3.48 (m, 4H), 3.29 (d, J=11.0 Hz, 2H), 3.02-2.95 (m, 2H), 2.50-2.47 (m, 2H), 1.79-1.76 (m, 2H), 1.70-1.69 (m, 1H), 1.48-1.47 (m, 2H), 1.41 (s, 9H), 1.17-1.07 (m, 2H), 1.04-0.98 (m, 2H), 0.92-0.81 (m, 2H); ES-LCMS m/z 711.4, 713.4 [M+H]⁺.

Step 6: tert-Butyl ((1-((2-(3,5-dichlorophenyl)-6-((6-(4-((1-hydroxycyclopropyl)methyl)piperazin-1-yl)pyridin-3-yl)oxy)pyridin-4-yl)methyl)piperidin-4-yl)methyl)carbamate

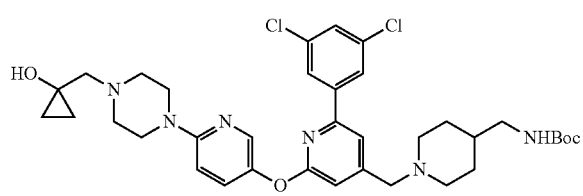 [SMILES: CC(C)(C)OC(=O)NCC1CCN(Cc2cc(Oc3ccc(N4CCN(CC5(O)CC5)CC4)nc3)nc(-c3cc(Cl)cc(Cl)c3)c2)CC1]

To a mixture of tert-butyl ((1-((2-(3,5-dichlorophenyl)-6-((6-(4-(1-hydroxycyclo-propanecarbonyl)piperazin-1-yl)pyridin-3-yl)oxy)pyridin-4-yl)methyl)piperidin-4-yl)methyl)carbamate (230 mg, 0.282 mmol) in THF (5 mL) was added BH₃·DMS (0.085 mL, 0.846 mmol). The mixture was stirred at 30° C. for 2 h. The reaction solution was quenched by MeOH (20 mL). The reaction was concentrated to yield crude product. The crude product was purified by silica gel column chromatography (DCM/MeOH=10/1, $R_f$=0.5) to yield a brown solid of tert-butyl ((1-((2-(3,5-dichlorophenyl)-6-((6-(4-((1-hydroxycyclopropyl)methyl)piperazin-1-yl)pyridin-3-yl)oxy)pyridin-4-yl)methyl)piperidin-4-yl)methyl)carbamate (180 mg, 0.132 mmol, 46.6% yield): ¹H NMR (400 MHz, CDCl₃) δ ppm 8.06 (d, J=2.6 Hz, 1H), 7.68-7.65 (m, 2H), 7.40-7.36 (m, 2H), 7.26 (s, 1H), 6.81 (s, 1H), 6.67 (d, J=9.3 Hz, 1H), 3.73-3.72 (m, 4H), 3.42 (s, 2H), 3.05-3.00 (m, 6H), 2.98-2.96 (m 4H), 2.84 (br. s, 2H), 2.09-2.08 (m, 3H), 1.70-1.65 (m, 2H), 1.39-1.36 (m, 9H), 0.90-0.85 (m, 2H), 0.45-0.40 (m, 2H); ES-LCMS m/z 697.4, 699.4 [M+H]⁺.

Step 7: 1-((4-(5-((4-((4-(Aminomethyl)piperidin-1-yl)methyl)-6-(3,5-dichlorophenyl)pyridin-2-yl)oxy)pyridin-2-yl)piperazin-1-yl)methyl)cyclopropanol, 5 hydrochloride

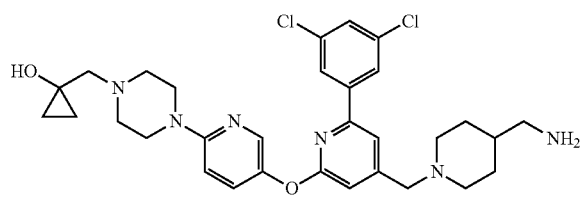 [SMILES: NCC1CCN(Cc2cc(Oc3ccc(N4CCN(CC5(O)CC5)CC4)nc3)nc(-c3cc(Cl)cc(Cl)c3)c2)CC1]

A solution of tert-butyl ((1-((2-(3,5-dichlorophenyl)-6-((6-(4-((1-hydroxycyclopropyl)methyl)piperazin-1-yl)pyridin-3-yl)oxy)pyridin-4-yl)methyl)piperidin-4-yl)methyl)carbamate (180 mg, 0.132 mmol) in HCl solution (4.0 M in EtOAc, 5 mL, 20.00 mmol) was stirred at 20° C. for 1 h. The mixture was concentrated to yield a brown solid of 1-((4-(5-((4-((4-(aminomethyl)piperidin-1-yl)methyl)-6-(3,5-dichlorophenyl)pyridin-2-yl)oxy)pyridin-2-yl)piperazin-1-yl)methyl)cyclopropanol, 5 hydrochloride (110 mg, 0.111 mmol, 85.0% yield): ¹H NMR (400 MHz, CD₃OD) δ ppm 8.20 (br. s, 1H), 8.06-7.94 (m, 2H), 7.92-7.85 (m, 2H), 7.52-7.50 (m, 2H), 7.41-7.36 (m, 1H), 4.51-4.39 (m, 4H), 4.00-3.80 (m, 4H), 3.69-3.55 (m, 4H), 3.50-3.36 (m, 4H), 2.90-2.88 (m, 2H), 2.10-2.00 (m, 3H), 1.80-1.71 (m, 2H), 0.98-0.90 (m, 2H), 0.88-0.77 (m, 2H); ES-LCMS m/z 597.3, 599.3 [M+H]⁺.

Step 8: N-((1-((2-(3,5-Dichlorophenyl)-6-((6-(4-((1-hydroxycyclopropyl)methyl)piperazin-1-yl)pyridin-3-yl)oxy)pyridin-4-yl)methyl)piperidin-4-yl)methyl) acetamide, 4 hydrochloride

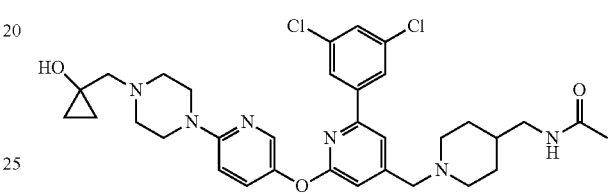

To a solution of 1-((4-(5-((4-((4-(aminomethyl)piperidin-1-yl)methyl)-6-(3,5-dichlorophenyl)pyridin-2-yl)oxy)pyridin-2-yl)piperazin-1-yl)methyl)cyclopropanol, 5 hydrochloride (110 mg, 0.111 mmol) and DIEA (0.197 mL, 1.114 mmol) in DCM (3 mL) was added Ac₂O (0.023 mL, 0.245 mmol). The solution was stirred at 20° C. for 0.5 h then concentrated to yield a brown solid which was dissolved in THF (20 mL) and water (5 mL), then LiOH·H₂O (16.53 mg, 0.394 mmol) was added to the solution. The mixture was stirred at 30° C. for 2 h then concentrated and purified by preparative HPLC (MeCN/H₂O as eluents, acidic condition) and dried by lyophilization to yield a white solid of N-((1-((2-(3,5-dichlorophenyl)-6-((6-(4-((1-hydroxycyclopropyl)methyl)piperazin-1-yl)pyridin-3-yl)oxy)pyridin-4-yl)methyl)piperidin-4-yl)methyl) acetamide, 4 hydrochloride (48.85 mg, 0.062 mmol, 79.0% yield): ¹H NMR (400 MHz, CD₃OD) δ ppm 8.33-8.21 (m, 2H), 8.04 (s, 1H), 7.90 (d, J=1.3 Hz, 2H), 7.67 (d, J=9.7 Hz, 1H), 7.51 (s, 1H), 7.45 (s, 1H), 4.47 (br. s, 4H), 3.96 (d, J=11.5 Hz, 2H), 3.84 (d, J=11.9 Hz, 2H), 3.65-3.49 (m, 4H), 3.44 (s, 2H), 3.22-3.06 (m, 4H), 2.07-1.95 (m, 5H), 1.89 (br. s, 1H), 1.66 (d, J=12.3 Hz, 2H), 1.00-0.93 (m, 2H), 0.87-0.80 (m, 2H); ES-LCMS m/z 639.2, 641.2 [M+H]⁺.

Example 36: 2-(1-((2-(3,5-Dichlorophenyl)-6-((6-(4-(3-(methylsulfonyl)propyl)piperazin-1-yl)pyridin-3-yl)oxy)pyridin-4-yl)methyl)piperidin-4-yl)-N-ethylacetamide

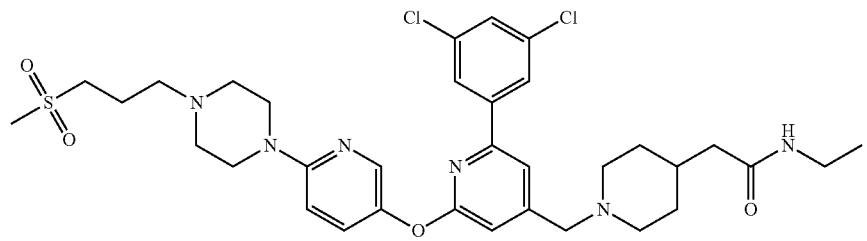 [SMILES: CCNC(=O)CC1CCN(Cc2cc(Oc3ccc(N4CCN(CCCS(C)(=O)=O)CC4)nc3)nc(-c3cc(Cl)cc(Cl)c3)c2)CC1]

Step 1: tert-Butyl 4-(5-((6-(3,5-dichlorophenyl)-4-((4-(2-(ethylamino)-2-oxoethyl)piperidin-1-yl)methyl)pyridin-2-yl)oxy)pyridin-2-yl)piperazine-1-carboxylate

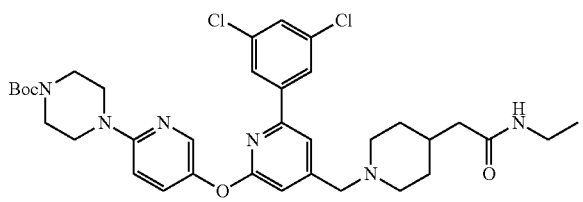 [SMILES: CCNC(=O)CC1CCN(Cc2cc(Oc3ccc(N4CCN(C(=O)OC(C)(C)C)CC4)nc3)nc(-c3cc(Cl)cc(Cl)c3)c2)CC1]

To a mixture of tert-butyl 4-(5-((6-(3,5-dichlorophenyl)-4-(((methylsulfonyl)oxy)methyl)pyridin-2-yl)oxy)pyridin-2-yl)piperazine-1-carboxylate (1.1 g, 1.624 mmol) and $K_2CO_3$ (0.673 g, 4.87 mmol) in DMF (15 mL) was added N-ethyl-2-(piperidin-4-yl)acetamide, hydrochloride (0.576 g, 1.949 mmol). The mixture was stirred at 80° C. for 12 h then filtered and concentrated to yield crude product which was purified by silica gel column chromatography (DCM/MeOH=10/1, $R_f$=0.6) to yield a yellow solid of tert-butyl 4-(5-((6-(3,5-dichlorophenyl)-4-((4-(2-(ethylamino)-2-oxoethyl)piperidin-1-yl)methyl)pyridin-2-yl)oxy)pyridin-2-yl)piperazine-1-carboxylate (800 mg, 0.975 mmol, 60.0% yield): $^1$H NMR (400 MHz, $CDCl_3$) δ ppm 8.29 (s, 2H), 7.99 (s, 1H), 7.70 (d, J=1.3 Hz, 2H), 7.39 (s, 1H), 7.30 (s, 1H), 6.89 (s, 1H), 3.82-3.79 (m, 4H), 3.65-3.64 (m, 4H), 3.53-3.49 (m, 6H), 3.08 (t, J=6.0 Hz, 2H), 2.02-2.00 (m, 2H), 1.84 (br. s, 2H), 1.70-1.68 (m, 3H), 1.48 (s, 9H), 1.29-1.26 (m, 3H); ES-LCMS m/z 683.3, 685.3 [M+H]$^+$.

Step 2: 2-(1-((2-(3,5-Dichlorophenyl)-6-((6-(piperazin-1-yl)pyridin-3-yl)oxy)pyridin-4-yl)methyl)piperidin-4-yl)-N-ethylacetamide, 4 hydrochloride

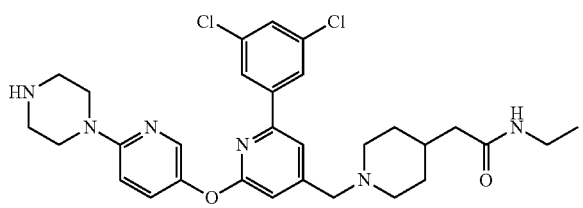 [SMILES: CCNC(=O)CC1CCN(Cc2cc(Oc3ccc(N4CCNCC4)nc3)nc(-c3cc(Cl)cc(Cl)c3)c2)CC1]

A solution of tert-butyl 4-(5-((6-(3,5-dichlorophenyl)-4-((4-(2-(ethylamino)-2-oxoethyl)piperidin-1-yl)methyl)pyridin-2-yl)oxy)pyridin-2-yl)piperazine-1-carboxylate (800 mg, 0.975 mmol) in HCl solution (4.0 M in MeOH, 5 mL, 88 mmol) was stirred at 20° C. for 0.5 h. The reaction was concentrated to yield a brown solid of 2-(1-((2-(3,5-dichlorophenyl)-6-((6-(piperazin-1-yl)pyridin-3-yl)oxy)pyridin-4-yl)methyl)piperidin-4-yl)-Methylacetamide, 4 hydrochloride (800 mg, 0.950 mmol, 97.0% yield): $^1$H NMR (400 MHz, $CD_3OD$) δ ppm 8.28 (dd, J=2.4, 9.9 Hz, 1H), 8.23 (d, J=2.2 Hz, 1H), 8.07 (s, 1H), 7.89 (d, J=1.3 Hz, 2H), 7.66 (d, J=10.1 Hz, 1H), 7.51-7.47 (m, 1H), 7.46-7.42 (m, 1H), 4.47 (s, 2H), 4.11-4.06 (m, 4H), 3.54-3.49 (m, 4H), 3.31-3.29 (m, 2H), 3.24-3.12 (m, 4H), 2.22 (d, J=7.1 Hz, 2H), 2.10 (br. s, 1H), 1.96 (d, J=13.7 Hz, 2H), 1.78-1.68 (m, 2H), 1.12 (t, J=7.3 Hz, 3H); ES-LCMS m/z 583.3, 585.3 [M+H]$^+$.

Step 3: 2-(1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)-N-ethylacetamide

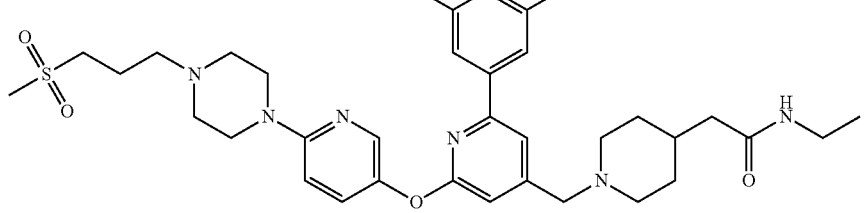

To a mixture of 2-(1-((2-(3,5-dichlorophenyl)-6-((6-(piperazin-1-yl)pyridin-3-yl)oxy)pyridin-4-yl)methyl)piperidin-4-yl)-N-ethylacetamide, 3 hydrochloride (200 mg, 0.250 mmol), AcOH (1.431 µL, 0.025 mmol) and 4 Å molecular sieves (200 mg, 0.250 mmol) in MeOH (10 mL) was added 3-(methylsulfonyl)propanal (170 mg, 1.000 mmol). The mixture was stirred at 20° C. for 10 h under $N_2$ atmosphere then $NaBH_3CN$ (15.71 mg, 0.250 mmol) was added. The mixture was stirred at 20° C. for 0.5 h then filtered and concentrated to yield the residue which was partitioned between DCM (50 mL) and saturated $NaHCO_3$ solution (aq., 50 mL), separated and the aqueous phase was extracted with DCM (50 mL×2). The combined organic layers were dried over $Na_2SO_4$, filtered and concentrated to yield crude product which was purified by preparative HPLC (MeCN/$H_2O$ as eluents, basic condition) and dried by lyophilization to yield a white solid of 2-(1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)-N-ethylacetamide (41.56 mg, 0.059 mmol, 23.6% yield): $^1$H NMR (400 MHz, $CD_3OD$) δ ppm 8.03 (d, J=2.6 Hz, 1H), 7.83 (d, J=1.8 Hz, 2H), 7.63 (s, 1H), 7.50 (dd, J=2.9, 9.0 Hz, 1H), 7.43 (s, 1H), 6.98-6.92 (m, 2H), 4.60 (s, 2H), 3.61-3.54 (m, 6H), 3.22 (d, J=10.1 Hz, 2H), 3.18 (d, J=7.5 Hz, 2H), 2.99 (s, 2H), 2.92 (d, J=11.5 Hz, 2H), 2.65-2.61 (m, 3H), 2.57 (t, J=7.3 Hz, 2H), 2.10 (d, J=6.6 Hz, 2H), 2.07 (d, J=7.5 Hz, 2H), 1.70 (d, J=13.2 Hz, 3H), 1.40-1.28 (m, 4H), 1.10 (t, J=7.3 Hz, 3H); ES-LCMS m/z 703.3, 705.3 [M+H]$^+$.

Example 37: 1-(2-(3,5-Dichlorophenyl)-6-((2-(4-(3-(methylsulfonyl)propyl)piperazin-1-yl)pyrimidin-5-yl)oxy)pyridin-4-yl)-N-methylmethanamine, 4 hydrochloride

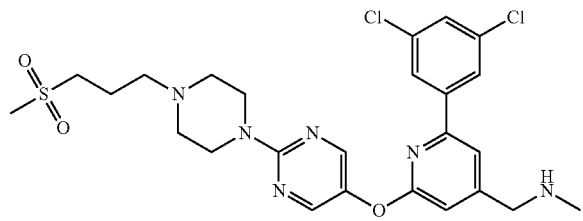

Step 1: tert-Butyl (5-((6-(3,5-dichlorophenyl)-4-((methylamino)methyl)pyridin-2-yl)oxy)pyrimidin-2-yl)piperazine-1-carboxylate

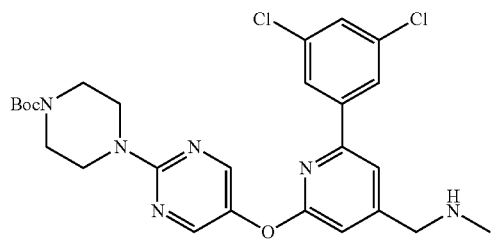 [SMILES: CNCc1cc(Oc2cnc(N3CCN(C(=O)OC(C)(C)C)CC3)nc2)nc(-c2cc(Cl)cc(Cl)c2)c1]

To a solution of tert-butyl 4-(5-((6-(3,5-dichlorophenyl)-4-(((methylsulfonyl)oxy)methyl)pyridin-2-yl)oxy)pyrimidin-2-yl)piperazine-1-carboxylate (1 g, 1.474 mmol) in MeCN (5 mL) was added methanamine (in EtOH, 1.895 g, 7.37 mmol). The mixture was stirred at 20° C. for 10 h then concentrated to yield crude product which was purified by silica gel column chromatography (DCM/MeOH=10/1). All fractions found to contain product by TLC (DCM/MeOH=10/1, R$_f$=0.5) were combined and concentrated to yield a white solid of tert-butyl (5-((6-(3,5-dichlorophenyl)-4-((methylamino)methyl)pyridin-2-yl)oxy)pyrimidin-2-yl)piperazine-1-carboxylate (200 mg, 0.334 mmol, 22.7% yield): $^1$H NMR (400 MHz, CDCl$_3$) δ ppm 8.30 (s, 2H), 7.74 (d, J=1.8 Hz, 2H), 7.43 (s, 1H), 7.34 (d, J=1.8 Hz, 1H), 7.26 (s, 1H), 3.83 (br. s, 6H), 3.53 (d, J=4.4 Hz, 4H), 2.50 (s, 3H), 1.49 (s, 9H); ES-LCMS m/z 545.2, 547.1 [M+H]$^+$.

Step 2: tert-Butyl 4-(5-((4-((((benzyloxy)carbonyl)(methyl)amino)methyl)-6-(3,5-dichlorophenyl)pyridin-2-yl)oxy)pyrimidin-2-yl)piperazine-1-carboxylate

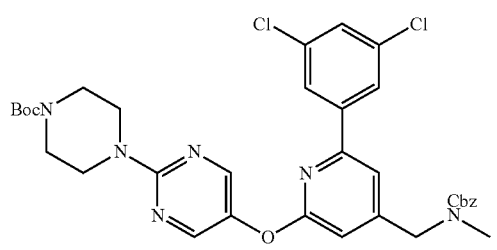 [SMILES: CN(Cc1cc(Oc2cnc(N3CCN(C(=O)OC(C)(C)C)CC3)nc2)nc(-c2cc(Cl)cc(Cl)c2)c1)C(=O)OCc1ccccc1]

To a mixture of tert-butyl 4-(5-((6-(3,5-dichlorophenyl)-4-((methylamino)methyl)pyridin-2-yl)oxy)pyrimidin-2-yl)piperazine-1-carboxylate (200 mg, 0.334 mmol) and DIEA (0.2 mL, 1.145 mmol) in DCM (5 mL) was added CbzCl (0.057 mL, 0.401 mmol). The mixture was stirred at 20° C. for 1 h then concentrated to crude product which was purified by silica gel column chromatography (PE/EtOAc=3/1). All fractions found to contain product by TLC (PE/EtOAc=3/1, R$_f$=0.5) were combined and concentrated to yield a brown solid of tert-butyl 4-(5-((4-((((benzyloxy)carbonyl)(methyl)amino)methyl)-6-(3,5-dichlorophenyl)pyridin-2-yl)oxy)pyrimidin-2-yl)piperazine-1-carboxylate (150 mg, 0.219 mmol, 65.4% yield): $^1$H NMR (400 MHz, CD$_3$OD) δ ppm 8.31 (br. s, 2H), 7.76-7.67 (m, 2H), 7.44-7.33 (m, 4H), 7.25 (br. s, 2H), 6.91-6.78 (m, 2H), 5.21-5.14 (m, 2H), 4.59 (br. s, 2H), 3.84-3.79 (m, 4H), 3.51 (br. s, 4H), 3.02 (br. s, 3H), 1.49 (s, 9H); ES-LCMS m/z 679.2, 681.2 [M+H]$^+$.

Step 3: Benzyl ((2-(3,5-dichlorophenyl)-6-((2-(piperazin-1-yl)pyrimidin-5-yl)oxy)pyridin-4-yl)methyl)(methyl)carbamate, 3 hydrochloride

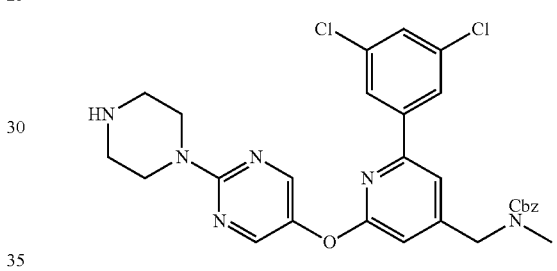

To a solution of tert-butyl 4-(5-((4-((((benzyloxy)carbonyl)(methyl)amino)methyl)-6-(3,5-dichlorophenyl)pyridin-2-yl)oxy)pyrimidin-2-yl)piperazine-1-carboxylate (150 mg, 0.219 mmol) in HCl solution (4 M in EtOAc, 10 mL, 40.0 mmol) was stirred at 20° C. for 0.5 h. The mixture was concentrated to yield a brown solid of benzyl ((2-(3,5-dichlorophenyl)-6-((2-(piperazin-1-yl)pyrimidin-5-yl)oxy)pyridin-4-yl)methyl)(methyl)carbamate, 4 hydrochloride (150 mg, 0.186 mmol, 85.0% yield): $^1$H NMR (400 MHz, CD$_3$OD) δ ppm 8.50-8.46 (m, 2H), 7.77 (br. s, 1H), 7.70 (br. s, 1H), 7.46-7.19 (m, 7H), 6.90-6.85 (m, 1H), 5.22-5.13 (m, 2H), 4.62 (br. s, 2H), 4.14 (t, J=4.9 Hz, 4H), 3.36-3.33 (m, 4H), 3.04 (s, 3H); ES-LCMS m/z 579.1, 581.1 [M+H]$^+$.

Step 4: Benzyl ((2-(3,5-dichlorophenyl)-6-((2-(4-(3-(methylsulfonyl)propyl)piperazin-1-yl)pyrimidin-5-yl)oxy)pyridin-4-yl)methyl)(methyl)carbamate

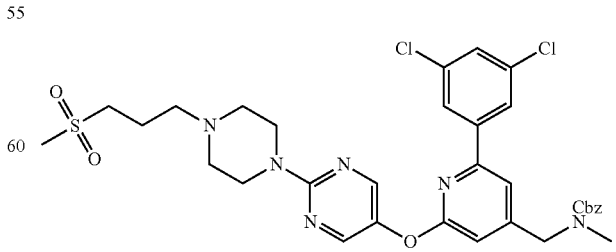

To a mixture of benzyl ((2-(3,5-dichlorophenyl)-6-((2-(piperazin-1-yl)pyrimidin-5-yl)oxy)pyridin-4-yl)methyl)

(methyl)carbamate, 3 hydrochloride (160 mg, 0.188 mmol), AcOH (1.076 µL, 0.019 mmol) and 4 Å molecular sieves (200 mg, 0.188 mmol) in MeOH (10 mL) was added 3-(methylsulfonyl)propanal (128 mg, 0.752 mmol). The mixture was stirred at 20° C. for 4 h under N₂ atmosphere then NaBH₃CN (11.81 mg, 0.188 mmol) was added and the mixture was stirred at 20° C. for another 0.5 h. The reaction was filtered and concentrated to yield the residue which was distributed between DCM (50 mL) and saturated NaHCO₃ aqueous solution (50 mL), separated and extracted with DCM (50 mL×2). The combined organic layers were dried over Na₂SO₄, filtered and concentrated to yield crude product which was purified by preparative TLC and dried by lyophilization to yield a yellow solid of benzyl ((2-(3,5-dichlorophenyl)-6-((2-(4-(3-(methylsulfonyl)propyl)piperazin-1-yl)pyrimidin-5-yl)oxy)pyridin-4-yl)methyl)(methyl) carbamate (120 mg, 0.142 mmol, 76.0% yield): ¹H NMR (400 MHz, CD₃OD) δ ppm 8.32 (br. s, 2H), 7.81-7.69 (m, 2H), 7.48-7.23 (m, 7H), 6.93-6.82 (m, 1H), 5.26-5.12 (m, 2H), 4.62 (s, 2H), 3.89-3.87 (m, 4H), 3.25-3.23 (m, 4H), 3.05 (s, 3H), 2.59-2.57 (m, 4H), 2.17 (s, 3H), 2.11-2.04 (m, 2H); ES-LCMS m/z 699.1, 701.1 [M+H]⁺.

Step 5: 1-(2-(3,5-Dichlorophenyl)-6-((2-(4-(3-(methylsulfonyl)propyl)piperazin-1-yl)pyrimidin-5-yl)oxy)pyridin-4-yl)-N-methylmethanamine, 4 hydrochloride

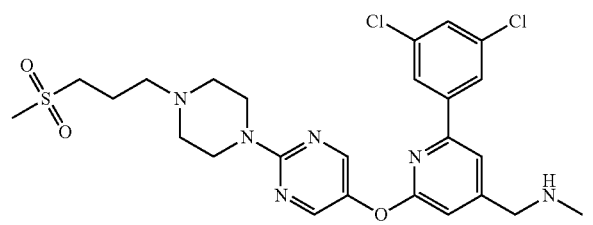

A solution of benzyl ((2-(3,5-dichlorophenyl)-6-((2-(4-(3-(methylsulfonyl)propyl)piperazin-1-yl)pyrimidin-5-yl)oxy)pyridin-4-yl)methyl)(methyl)carbamate (120 mg, 0.142 mmol) in TFA (5 mL, 64.9 mmol) was stirred at 50° C. for 10 h. The reaction was concentrated to yield crude product which was purified by preparative HPLC (MeCN/H₂O as eluents, acidic condition) and dried by lyophilization to yield a white solid of 1-(2-(3,5-dichlorophenyl)-6-((2-(4-(3-(methyl sulfonyl)propyl)piperazin-1-yl)pyrimidin-5-yl)oxy)pyridin-4-yl)-N-methylmethanamine, 4 hydrochloride (43.9 mg, 0.061 mmol, 43.2% yield): ¹H NMR (400 MHz, CD₃OD) δ ppm 8.46 (s, 2H), 7.85 (s, 2H), 7.79 (s, 1H), 7.52 (br. s, 1H), 7.23 (s, 1H), 4.35 (s, 2H), 3.73 (br. s, 2H), 3.50-3.37 (m, 6H), 3.23 (br. s, 4H), 3.06 (s, 3H), 2.83 (s, 3H), 2.40-2.29 (m, 2H); ES-LCMS m/z 565.1, 567.1 [M+H]⁺.

Example 38: 3-((4-(5-((6-(3,5-Dichlorophenyl)-4-((4-(sulfamoylmethyl)piperidin-1-yl)methyl)pyridin-2-yl)oxy)pyridin-2-yl)piperazin-1-yl)propanoic acid, 4 hydrochloride

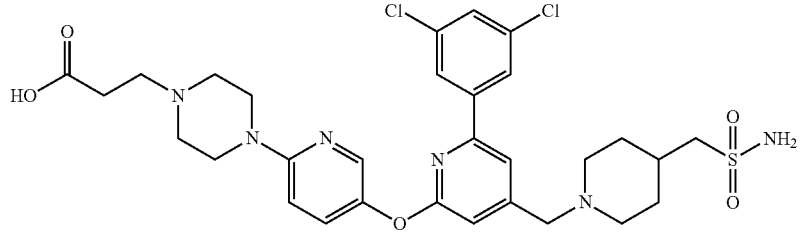 [SMILES: NS(=O)(=O)CC1CCN(Cc2cc(Oc3ccc(N4CCN(CCC(=O)O)CC4)nc3)nc(-c3cc(Cl)cc(Cl)c3)c2)CC1]

Step 1: Benzyl 4-((acetylthio)methyl)piperidine-1-carboxylate

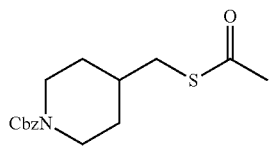 [SMILES: CC(=O)SCC1CCN(C(=O)OCc2ccccc2)CC1]

To a mixture of benzyl 4-(((methylsulfonyl)oxy)methyl)piperidine-1-carboxylate (4 g, 9.77 mmol), K₂CO₃ (4.05 g, 29.3 mmol) in DMF (50 mL) was added ethanethioic S-acid (1.488 g, 19.55 mmol). The mixture was stirred at 25° C. for 3 h then concentrated. The residue was diluted with DCM (100 mL) and water (100 mL), separated and the aqueous phase was extracted with DCM (100 mL×2). The combined organic layers were dried over Na₂SO₄, filtered and concentrated to yield crude product. The crude product was purified by silica gel column chromatography (PE/EtOAc=10/1 to 3/1). All fractions found to contain product by TLC (PE/EtOAc=5/1, R$_f$=0.3) were combined and concentrated to yield a brown solid of benzyl 4-((acetylthio)methyl)piperidine-1-carboxylate (3 g, 7.32 mmol, 74.9% yield): ¹H NMR (400 MHz, CDCl₃) δ ppm 7.47-7.08 (m, 5H), 5.10 (s, 2H), 4.29-4.04 (m, 2H), 2.90-2.59 (m, 4H), 2.32 (s, 3H), 1.81-1.67 (m, 2H), 1.64-1.57 (m, 1H), 1.25-1.06 (m, 2H); ES-LCMS m/z 308.2 [M+H]⁺.

Step 2: Dibenzyl 4,4'-(disulfanediylbis(methylene))bis(piperidine-1-carboxylate)

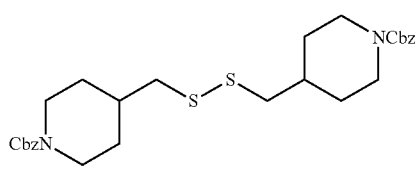 [SMILES: O=C(OCc1ccccc1)N1CCC(CSSCC2CCN(C(=O)OCc3ccccc3)CC2)CC1]

To a solution of benzyl 4-((acetylthio)methyl)piperidine-1-carboxylate (2.4 g, 5.86 mmol) in MeOH (20 mL) and water (10 mL) was added K₂CO₃ (809 mg, 5.86 mmol). The mixture was stirred at 30° C. for 2 h then diluted with water (100 mL), extracted with DCM (100 mL×2). The combined organic layers were dried over Na$_2$SO$_4$, filtered and concentrated to yield a brown solid of dibenzyl 4,4'-(disulfanediylbis(methylene))bis(piperidine-1-carboxylate) (2 g, 2.65 mmol, 90.0% yield): $^1$H NMR (400 MHz, CDCl$_3$) δ ppm 7.40-7.29 (m, 10H), 5.13 (s, 4H), 4.25-4.13 (m, 4H), 2.79 (br. s, 4H), 2.61 (d, J=6.0 Hz, 4H), 1.88-1.78 (m, 6H), 1.17 (d, J=9.5 Hz, 4H); ES-LCMS m/z 529.2 [M+H]$^+$.

Step 3: Benzyl 4-(mercaptomethyl)piperidine-1-carboxylate

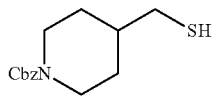

To a mixture of dibenzyl 4,4'-(disulfanediylbis(methylene))bis(piperidine-1-carboxylate) (1900 mg, 2.52 mmol) in acetic acid (10 mL, 175 mmol) was added zinc powder (822 mg, 12.58 mmol). The mixture was stirred at 20° C. for 0.5 h then filtered. The filtrate was concentrated to yield a brown solid of benzyl 4-(mercaptomethyl)piperidine-1-carboxylate (1200 mg, 4.38 mmol, 87.0% yield): $^1$H NMR (400 MHz, CDCl$_3$) δ ppm 7.38-7.24 (m, 5H), 5.11 (s, 2H), 4.19 (br. s, 2H), 2.75 (br. s, 2H), 2.44 (t, J=7.3 Hz, 2H), 1.82 (d, J=12.3 Hz, 2H), 1.59-1.50 (m, 1H), 1.13 (d, J=10.1 Hz, 2H); ES-LCMS m/z 266.2 [M+H]$^+$.

Step 4: Benzyl 4-((chlorosulfonyl)methyl)piperidine-1-carboxylate

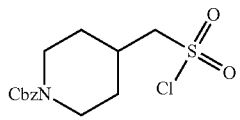

A stirred suspension of benzyl 4-(mercaptomethyl)piperidine-1-carboxylate (600 mg, 2.189 mmol) in water (10 mL) and THF (10 mL) was bubbled at 0-5° C. with chlorine over 20 min. The mixture was flushed under N$_2$ to remove excess chlorine then concentrated. The residue was diluted with DCM (50 mL) and water (50 mL), extracted with DCM (50 mL×2). The combined organic layers were dried over Na$_2$SO$_4$, filtered and concentrated to yield brown oil of benzyl 4-((chlorosulfonyl)methyl)piperidine-1-carboxylate (900 mg, 0.651 mmol, 29.7% yield): $^1$H NMR (400 MHz, CDCl$_3$) δ ppm 7.36-7.23 (m, 5H), 5.08-5.03 (m, 2H), 4.14-4.06 (m, 2H), 2.80-2.77 (m, 2H), 2.56-2.53 (m, 2H), 1.93-1.82 (m, 3H), 1.20-1.15 (m, 2H); ES-LCMS m/z 332.0 [M+H]$^+$.

Step 5: Benzyl 4-(sulfamoylmethyl)piperidine-1-carboxylate

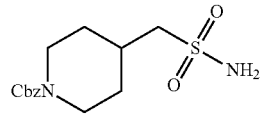 [SMILES: NS(=O)(=O)CC1CCN(C(=O)OCc2ccccc2)CC1]

A solution of benzyl 4-((chlorosulfonyl)methyl)piperidine-1-carboxylate (900 mg, 0.651 mmol) in THF (10 mL) was cooled to −40° C. then ammonia gas was slowly purged at for 20 min. The mixture was concentrated and the residue was taken up with DCM (100 mL) and water (100 mL), extracted with DCM (100 mL×2). The combined organic layers were dried over Na$_2$SO$_4$, filtered and concentrated to yield crude product which was purified by preparative HPLC (MeCN/H$_2$O as eluents, acidic condition) and dried by lyophilization to yield a brown solid of benzyl 4-(sulfamoylmethyl)piperidine-1-carboxylate (110 mg, 0.343 mmol, 52.7% yield): $^1$H NMR (400 MHz, CD$_3$OD) δ ppm 7.40-7.31 (m, 5H), 5.13 (s, 2H), 4.14 (d, J=13.6 Hz, 2H), 3.06 (d, J=6.5 Hz, 2H), 2.92 (br. s, 2H), 2.26-2.17 (m, 1H), 1.98 (d, J=12.5 Hz, 2H), 1.30 (dd, J=3.8, 12.3 Hz, 2H); ES-LCMS m/z 313.1 [M+H]$^+$.

Step 6: Piperidin-4-ylmethanesulfonamide

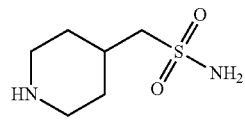

To a solution of benzyl 4-(sulfamoylmethyl)piperidine-1-carboxylate (110 mg, 0.343 mmol) in MeOH (15 mL) was added 10% Pd/C (36.5 mg, 0.034 mmol). The reaction mixture was stirred at 20° C. for 0.5 h under H$_2$ atmosphere (15 psi) then filtered. The filtrate was concentrated to yield a brown solid of piperidin-4-ylmethanesulfonamide (60 mg, 0.303 mmol, 88.0% yield): $^1$H NMR (400 MHz, CD$_3$OD) δ ppm 3.17-2.93 (m, 4H), 2.42-2.13 (m, 3H), 2.11-1.91 (m, 2H), 1.64-1.44 (m, 2H); ES-LCMS m/z 179.1 [M+H]$^+$.

Step 7: Ethyl 3-(4-(5-((6-(3,5-dichlorophenyl)-4-((4-(sulfamoylmethyl)piperidin-1-yl)methyl)pyridin-2-yl)oxy)pyridin-2-yl)piperazin-1-yl)propanoate

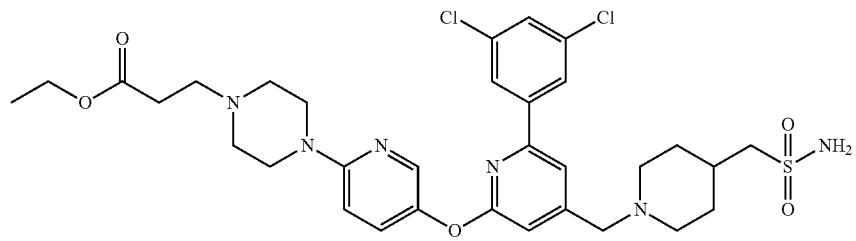 [SMILES: CCOC(=O)CCN1CCN(c2ccc(Oc3cc(CN4CCC(CS(N)(=O)=O)CC4)cc(-c4cc(Cl)cc(Cl)c4)n3)cn2)CC1]

To a mixture of ethyl 3-(4-(5-((6-(3,5-dichlorophenyl)-4-(((methylsulfonyl)oxy)methyl)pyridin-2-yl)oxy)pyridin-2-yl)piperazin-1-yl)propanoate (160 mg, 0.191 mmol) and K$_2$CO$_3$ (132 mg, 0.953 mmol) in DMF (10 mL) was added piperidin-4-ylmethanesulfonamide (60 mg, 0.303 mmol). The mixture was stirred at 20° C. for 0.5 h then concentrated. The residue was taken up with DCM (50 mL) and water (50 mL), extracted with DCM (50 mL×2). The combined organic layers were dried over Na$_2$SO$_4$, filtered and concentrated to yield a brown solid of ethyl 3-(4-(5-((6-(3,5-dichlorophenyl)-4-((4-(sulfamoylmethyl)piperidin-1-yl)methyl)pyridin-2-yl)oxy)pyridin-2-yl)piperazin-1-yl)propanoate (200 mg, 0.085 mmol, 44.6% yield): $^1$H NMR (400 MHz, CDCl$_3$) δ ppm 7.68 (s, 2H), 7.52 (s, 2H), 7.47 (s, 2H), 7.18-7.14 (m, 1H), 7.00 (s, 1H), 4.13 (m, 2H), 3.49-3.45 (m, 12H), 3.17-3.02 (m, 4H), 2.73-2.71 (m, 2H), 2.34-2.31 (m, 2H), 1.98-1.92 (m, 2H), 1.65-1.60 (m, 3H), 1.27-1.21 (m, 3H); ES-LCMS m/z 691.3, 693.2 [M+H]$^+$.

Step 8: 3-(4-(5-((6-(3,5-Dichlorophenyl)-4-((4-(sulfamoylmethyl)piperidin-1-yl)methyl)pyridin-2-yl)oxy)pyridin-2-yl)piperazin-1-yl)propanoic acid, 4 hydrochloride

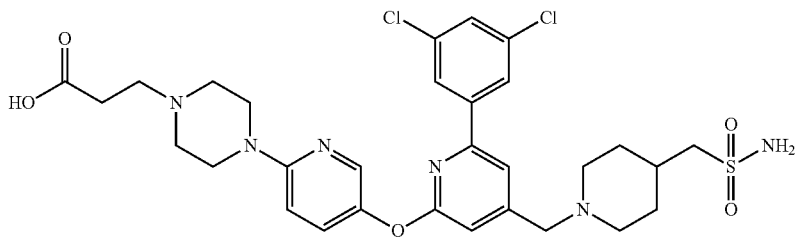 [SMILES: NS(=O)(=O)CC1CCN(Cc2cc(Oc3ccc(N4CCN(CCC(=O)O)CC4)nc3)nc(-c3cc(Cl)cc(Cl)c3)c2)CC1]

To a mixture of ethyl 3-(4-(5-((6-(3,5-dichlorophenyl)-4-((4-(sulfamoylmethyl)piperidin-1-yl)methyl)pyridin-2-yl)oxy)pyridin-2-yl)piperazin-1-yl)propanoate (200 mg, 0.085 mmol) in THF (5 mL) and water (5 mL) was added LiOH·H$_2$O (17.84 mg, 0.425 mmol). The mixture was stirred at 30° C. for 3 h then adjusted pH to 5-7 with HCl solution (aq., 2.0 M). The mixture was concentrated and the residue was purified by preparative HPLC (MeCN/H$_2$O as eluents, acidic condition) and dried by lyophilization to yield a white solid of 3-(4-(5-((6-(3,5-dichlorophenyl)-4-((4-(sulfamoylmethyl)piperidin-1-yl)methyl)pyridin-2-yl)oxy)pyridin-2-yl)piperazin-1-yl)propanoic acid, 4 hydrochloride (10.3 mg, 0.013 mmol, 15.0% yield): $^1$H NMR (400 MHz, CD$_3$OD) δ ppm 8.18 (d, J=2.9 Hz, 1H), 7.90 (s, 1H), 7.87 (d, J=1.8 Hz, 2H), 7.84 (dd, J=2.9, 9.3 Hz, 1H), 7.51 (t, J=1.8 Hz, 1H), 7.31 (s, 1H), 7.27 (d, J=9.5 Hz, 1H), 4.44 (s, 2H), 3.74-3.57 (m, 4H), 3.53 (t, J=6.9 Hz, 4H), 3.34-3.30 (m, 4H), 3.27-3.14 (m, 2H), 3.11 (d, J=6.2 Hz, 2H), 2.93 (t, J=6.9 Hz, 2H), 2.29-2.26 (m, 3H), 1.81-1.66 (m, 2H); ES-LCMS m/z 663.2, 665.2 [M+H]$^+$.

Example 39: 3-(4-(5-((6-(3,5-Dichlorophenyl)-4-((4-((methylsulfonyl)methyl)piperidin-1-yl)methyl)pyridin-2-yl)oxy)pyridin-2-yl)piperazin-1-yl)propanoic acid

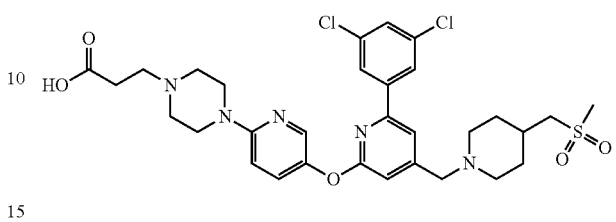

Step 1: tert-Butyl 4-(((methylsulfonyl)oxy)methyl)piperidine-1-carboxylate

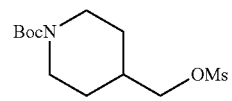

To a solution of tert-butyl 4-(hydroxymethyl)piperidine-1-carboxylate (3 g, 13.93 mmol) and DIEA (5.40 g, 41.8 mmol) in DCM (50 mL) was added MsCl (1.303 mL, 16.72 mmol) at 0° C. The reaction mixture was stirred at 0° C. for 10 min then water (50 mL) was added and extracted with DCM (25 mL×3). The combined organic layers were dried over Na$_2$SO$_4$, filtered and concentrated to yield a yellow oil of tert-butyl 4-(((methylsulfonyl)oxy)methyl)piperidine-1-carboxylate (4 g, 12.95 mmol, 93.0% yield): $^1$H NMR (400 MHz, CDCl$_3$) δ ppm 4.14 (s, 2H), 4.06 (d, J=6.6 Hz, 2H), 3.00 (s, 3H), 2.70 (t, J=12.1 Hz, 2H), 1.95-1.86 (m, 1H), 1.73 (d, J=13.2 Hz, 2H), 1.44 (s, 9H), 1.25-1.18 (m, 2H); ES-LCMS m/z 238.2 [M−t−Bu+H]$^+$.

Step 2: tert-Butyl 4-((methylthio)methyl)piperidine-1-carboxylate

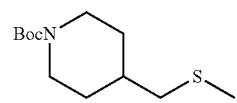

To a solution of tert-butyl 4-(((methylsulfonyl)oxy)methyl)piperidine-1-carboxylate (4 g, 12.95 mmol) and sodium methanethiolate (3.63 g, 51.8 mmol) in DMF (50 mL) was added $K_2CO_3$ (3.58 g, 25.9 mmol) at 25° C. The reaction mixture was stirred at 25° C. for 12 h then filtered and the filtrate was concentrated to yield the crude product which was purified by flash chromatography on silica gel (PE/EtOAc=1/0 to 1/1). All fractions found to contain product by TLC (PE/EtOAc=3/1, $R_f$=0.45) were combined and concentrated to yield a yellow oil of tert-butyl 4-((methylthio)methyl)piperidine-1-carboxylate (1.6 g, 5.87 mmol, 45.3% yield): $^1$H NMR (400 MHz, $CDCl_3$) δ ppm 4.14-4.04 (m, 2H), 2.68 (t, J=12.1 Hz, 2H), 2.41 (d, J=6.6 Hz, 2H), 2.08 (s, 3H), 1.79 (d, J=13.2 Hz, 2H), 1.62-1.60 (m, 1H), 1.44 (s, 9H), 1.17-1.07 (m, 2H); ES-LCMS m/z 190.2 [M−t−Bu+H]$^+$.

Step 3: tert-Butyl 4-((methylsulfonyl)methyl)piperidine-1-carboxylate

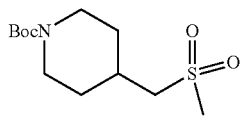

To a solution of tert-butyl 4-((methylthio)methyl)piperidine-1-carboxylate (500 mg, 1.834 mmol) in DCM (10 mL) was added m-CPBA (745 mg, 3.67 mmol) at 25° C. The reaction mixture was stirred at 25° C. for 12 h then filtered. The residue was concentrated to yield the crude product which was purified by flash chromatography on silica gel (PE/EtOAc=1/0 to 1/3). All fractions found to contain product by TLC (PE/EtOAc=1/1, $R_f$=0.25) were combined and concentrated to yield to yield a pale yellow solid of tert-butyl 4-((methylsulfonyl)methyl)piperidine-1-carboxylate (310 mg, 0.894 mmol, 48.8% yield): $^1$H NMR (400 MHz, $CDCl_3$) δ ppm 4.11 (s, 2H), 2.96 (d, J=6.0 Hz, 2H), 2.94 (s, 3H), 2.77 (t, J=11.3 Hz, 2H), 2.28-2.21 (m, 1H), 1.94 (d, J=12.5 Hz, 2H), 1.45 (s, 9H), 1.33-1.29 (m, 2H); ES-LCMS m/z 222.1 [M−t−Bu+H]$^+$.

Step 4: 4-((Methylsulfonyl)methyl)piperidine

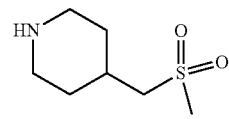

A mixture of tert-butyl 4-((methylsulfonyl)methyl)piperidine-1-carboxylate (200 mg, 0.577 mmol) in 4.0 M HCl in EtOAc, (10 mL, 40.0 mmol) was stirred at 25° C. for 0.5 h. A white precipitate formed. After filtration, the filter cake was dried to yield a white solid of 4-((methylsulfonyl)methyl)piperidine, hydrochloride (130 mg, 0.547 mmol, 95.0% yield): $^1$H NMR (400 MHz, $CD_3OD$) δ ppm 3.39 (d, J=12.8 Hz, 2H), 3.19 (d, J=6.6 Hz, 2H), 3.10-3.03 (m, 2H), 3.01 (s, 3H), 2.42-2.33 (m, 1H), 2.19 (d, J=14.6 Hz, 2H), 1.69-1.57 (m, 2H); ES-LCMS m/z 178.1 [M+H]$^+$.

Step 5: Ethyl 3-(4-(5-((6-(3,5-dichlorophenyl)-4-((4-((methylsulfonyl)methyl)piperidin-1-yl)methyl)pyridin-2-yl)oxy)pyridin-2-yl)piperazin-1-yl)propanoate

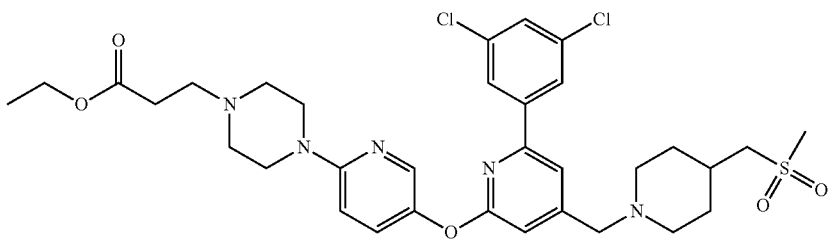 [SMILES: CCOC(=O)CCN1CCN(c2ccc(Oc3cc(CN4CCC(CS(C)(=O)=O)CC4)cc(-c4cc(Cl)cc(Cl)c4)n3)cn2)CC1]

To a solution of ethyl 3-(4-(5-((6-(3,5-dichlorophenyl)-4-(((methylsulfonyl)oxy)methyl)pyridin-2-yl)oxy)pyridin-2-yl)piperazin-1-yl)propanoate (230 mg, 0.287 mmol) and 4-((methylsulfonyl)methyl)piperidine, hydrochloride (130 mg, 0.547 mmol) in DMF (10 mL) was added $K_2CO_3$ (119 mg, 0.862 mmol). The reaction mixture was stirred at 80° C. for 12 h then filtered. The residue was concentrated to yield a yellow solid of ethyl 3-(4-(5-((6-(3,5-dichlorophenyl)-4-((4-((methylsulfonyl)methyl)piperidin-1-yl)methyl)pyridin-2-yl)oxy)pyridin-2-yl)piperazin-1-yl)propanoate (230 mg, 0.200 mmol, 69.6% yield): $^1$H NMR (400 MHz, $CD_3OD$) δ ppm 8.02 (d, J=2.9 Hz, 1H), 7.85-7.76 (m, 2H), 7.61 (s, 1H), 7.50-7.45 (m, 1H), 7.43-7.37 (m, 1H), 6.97 (s, 1H), 6.94-6.89 (m, 1H), 4.15 (q, J=7.1 Hz, 2H), 3.61-3.58 (m, 2H), 3.56-3.51 (m, 4H), 3.11 (d, J=6.4 Hz, 2H), 2.99 (s, 3H), 2.92 (d, J=11.9 Hz, 2H), 2.78-2.74 (m, 2H), 2.65-2.62 (m, 4H), 2.60-2.54 (m, 2H), 2.20-2.11 (m, 2H), 2.08-2.01 (m, 1H), 1.96 (d, J=11.5 Hz, 2H), 1.55-1.43 (m, 2H), 1.26 (t, J=12 Hz, 3H); ES-LCMS m/z 690.3, 692.2 [M+H]$^+$.

Step 6: 3-(4-(5-((6-(3,5-Dichlorophenyl)-4-((4-((methylsulfonyl)methyl)piperidin-1-yl)methyl)pyridin-2-yl)oxy)pyridin-2-yl)piperazin-1-yl)propanoic acid

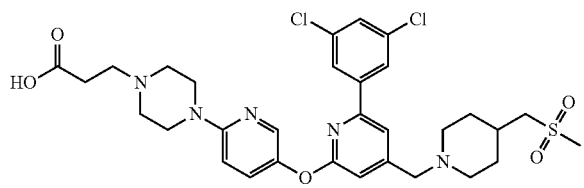 [SMILES: CS(=O)(=O)CC1CCN(Cc2cc(Oc3ccc(N4CCN(CCC(=O)O)CC4)nc3)nc(-c3cc(Cl)cc(Cl)c3)c2)CC1]

To a solution of ethyl 3-(4-(5-((6-(3,5-dichlorophenyl)-4-((4-((methylsulfonyl)methyl)piperidin-1-yl)methyl)pyridin-2-yl)oxy)pyridin-2-yl)piperazin-1-yl)propanoate (230 mg, 0.200 mmol) in MeOH (10 mL) was added NaOH (15.98 mg, 0.400 mmol) in water (1 mL). The reaction mixture was stirred at 25° C. for 12 h. 1N HCl was added to adjust pH to 4-5. The solution was concentrated to yield crude product which was purified by preparative HPLC (MeCN/H₂O as eluents, acidic condition) and lyophilized to yield a white solid of 3-(4-(5-((6-(3,5-dichlorophenyl)-4-((4-((methylsulfonyl)methyl)piperidin-1-yl)methyl)pyridin-2-yl)oxy) pyridin-2-yl)piperazin-1-yl)propanoic acid, 4 hydrochloride (89.96 mg, 0.104 mmol, 52.3% yield): ¹H NMR (400 MHz, CD₃OD) δ ppm 8.23 (d, J=2.5 Hz, 1H), 8.03-7.98 (m, 1H), 7.97 (s, 1H), 7.90 (d, J=1.5 Hz, 2H), 7.54 (s, 1H), 7.42 (d, J=9.5 Hz, 1H), 7.38 (s, 1H), 4.47 (s, 2H), 3.63 (d, J=12.0 Hz, 10H), 3.28-3.11 (m, 6H), 3.03 (s, 3H), 2.97 (t, J=6.8 Hz, 2H), 2.42 (s, 1H), 2.30-2.27 (m, 2H), 1.83 (q, J=2.0 Hz, 2H); ES-LCMS m/z 662.2, 664.2 [M+H]⁺.

Example 40: 1-((1-((2-(3,5-Dichlorophenyl)-6-((6-(4-((2-hydroxyethyl)piperazin-1-yl)pyridin-3-yl)oxy)pyridin-4-yl)methyl)piperidin-4-yl)methyl)-3-methylurea, 4 hydrochloride

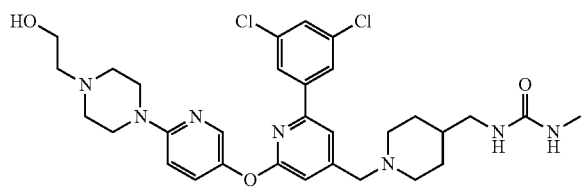 [SMILES: CNC(=O)NCC1CCN(Cc2cc(Oc3ccc(N4CCN(CCO)CC4)nc3)nc(-c3cc(Cl)cc(Cl)c3)c2)CC1]

Step 1: 1-((1-((2-(Benzyloxy)-6-(3,5-dichlorophenyl)pyridin-4-yl)methyl)piperidin-4-yl)methyl)-3-methylurea

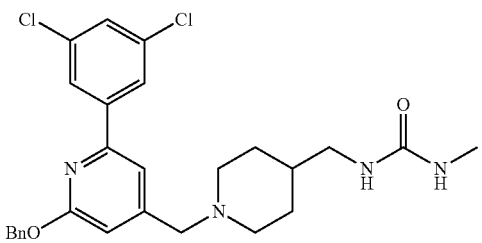 [SMILES: CNC(=O)NCC1CCN(Cc2cc(OCc3ccccc3)nc(-c3cc(Cl)cc(Cl)c3)c2)CC1]

6.3 g of the mixture which contained 2-(benzyloxy)-4-(chloromethyl)-6-(3,5-dichlorophenyl)pyridine (40%) and (2-(benzyloxy)-6-(3,5-dichlorophenyl)pyridin-4-yl)methyl methanesulfonate (60%) was added to a solution of 1-methyl-3-(piperidin-4-ylmethyl)urea hydrochloride (3.46 g, 16.64 mmol) and K₂CO₃ (8.62 mL, 49.9 mmol) in DMF (75 mL). The mixture was stirred at 65° C. for 8 h then cooled down and H₂O (200 mL) was added. A pink precipitate formed. The mixture was filtered and the filter cake was dried to yield a pink solid of 1-((1-((2-(benzyloxy)-6-(3,5-dichlorophenyl)pyridin-4-yl)methyl)piperidin-4-yl)methyl)-3-methylurea (6.7 g, 11.74 mmol, 70.6% yield): ¹H NMR (400 MHz, CDCl₃) δ ppm 7.94-7.81 (m, 2H), 7.50 (d, J=7.3 Hz, 2H), 7.44-7.27 (m, 5H), 6.77 (s, 1H), 5.46 (s, 2H), 4.38 (br. s, 1H), 4.24 (d, J=4.2 Hz, 1H), 3.46 (s, 2H), 3.08 (t, J=6.2 Hz, 2H), 2.86 (d, J=13.5 Hz, 2H), 2.77 (d, J=4.9 Hz, 3H), 2.03-1.92 (m, 2H), 1.50-1.48 (m, 1H), 1.36-1.22 (m, 2H); ES-LCMS m/z 513.2, 515.2 [M+H]⁺.

Step 2: 1-((1-((2-(3,5-Dichlorophenyl)-6-hydroxypyridin-4-yl)methyl)piperidin-4-yl)methyl)-3-methylurea hydrochloride

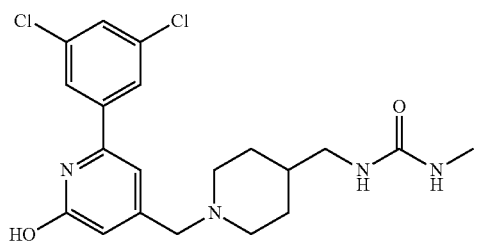 [SMILES: CNC(=O)NCC1CCN(Cc2cc(O)nc(-c3cc(Cl)cc(Cl)c3)c2)CC1]

A mixture of 1-((1-((2-(benzyloxy)-6-(3,5-dichlorophenyl)pyridin-4-yl)methyl)piperidin-4-yl)methyl)-3-methylurea (6.7 g, 12.40 mmol) and concentrated HCl solution (30 mL, 365 mmol) in DCM (30 mL) was stirred at 85° C. for 4 h. The crude material was concentrated to yield a yellow solid of 1-((1-((2-(3,5-dichlorophenyl)-6-hydroxypyridin-4-yl)methyl)piperidin-4-yl)methyl)-3-methylurea hydrochloride (5.3 g, 9.80 mmol, 79.0% yield): ¹H NMR (400 MHz, DMSO-d₆) δ ppm 8.01 (d, J=1.8 Hz, 2H), 7.70 (d, J=1.8 Hz, 2H), 6.78 (s, 1H), 4.27-4.14 (m, 2H), 3.44-3.29 (m, 2H), 3.14-3.10 (m, 2H), 2.90 (s, 3H), 2.72-2.71 (m, 2H), 1.78-1.76 (m, 2H), 1.58-1.55 (m, 3H); ES-LCMS m/z 423.2, 425.2 [M+H]⁺.

Step 3: 1-((1-((2-((6-Bromopyridin-3-yl)oxy)-6-(3,5-dichlorophenyl)pyridin-4-yl)methyl)piperidin-4-yl)methyl)-3-methylurea

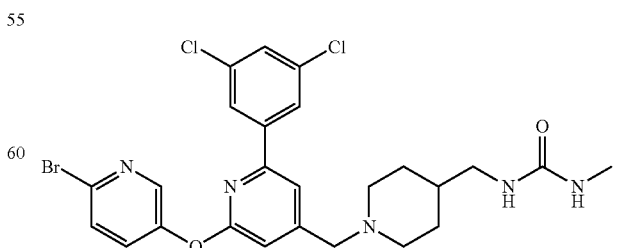

A mixture of 1-((1-((2-(3,5-dichlorophenyl)-6-hydroxypyridin-4-yl)methyl)piperidin-4-yl)methyl)-3-methylurea (2 g, 4.72 mmol), 2-bromo-5-fluoropyridine (4.16 g, 23.62 mmol) and K$_2$CO$_3$ (1.959 g, 14.17 mmol) in DMF (30 mL) was stirred at 140° C. for 8 h. The mixture was concentrated and the residue was partitioned between DCM (100 mL) and H$_2$O (100 mL). The organic layer was separated, dried over Na$_2$SO$_4$, filtered and concentrated. The crude material was purified by silica gel column chromatography (DCM/MeOH=1/0 to 20/1). All fractions found to contain product detected by TLC (DCM/MeOH=20/1, R$_f$=0.25) were combined and concentrated to yield a yellow solid of 1-((1-((2-((6-bromopyridin-3-yl)oxy)-6-(3,5-dichlorophenyl)pyridin-4-yl)methyl)piperidin-4-yl)methyl)-3-methylurea (390 mg, 0.606 mmol, 12.8% yield): $^1$H NMR (400 MHz, CD$_3$OD) δ ppm 8.31 (d, J=2.6 Hz, 1H), 7.83-7.74 (m, 2H), 7.72-7.61 (m, 3H), 7.43 (s, 1H), 7.09 (s, 1H), 3.68-3.58 (m, 2H), 3.07-2.88 (m, 4H), 2.67 (s, 3H), 2.10 (t, J=11.0 Hz, 2H), 1.72 (d, J=11.9 Hz, 2H), 1.50-1.47 (m, 1H), 1.37-1.20 (m, 2H); ES-LCMS m/z 580.1, 582.1 [M+H]$^+$.

Step 4: 1-((1-((2-(3,5-Dichlorophenyl)-6-((6-(4-(2-hydroxyethyl)piperazin-1-yl)pyridin-3-yl)oxy)pyridin-4-yl)methyl)piperidin-4-yl)methyl)-3-methylurea, 4 hydrochloride

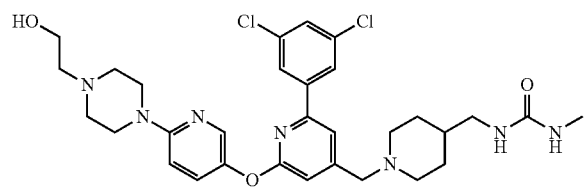 [SMILES: CNC(=O)NCC1CCN(Cc2cc(Oc3ccc(N4CCN(CCO)CC4)nc3)nc(-c3cc(Cl)cc(Cl)c3)c2)CC1]

A mixture of 1-((1-((2-((6-bromopyridin-3-yl)oxy)-6-(3,5-dichlorophenyl)pyridin-4-yl)methyl)piperidin-4-yl)methyl)-3-methylurea (250 mg, 0.432 mmol), 2-(piperazin-1-yl)ethanol (112 mg, 0.863 mmol), Xantphos (24.97 mg, 0.043 mmol), Cs$_2$CO$_3$ (422 mg, 1.295 mmol) and Pd$_2$(dba)$_3$ (19.76 mg, 0.022 mmol) in THF (5 mL) was stirred at 80° C. under N$_2$ atmosphere for 8 h. The mixture was filtered and the filtrate was concentrated. The residue was purified by preparative TLC (DCM/MeOH=9/1, R$_f$=0.15) to yield a yellow solid which was further purified by preparative HPLC (MeCN/H$_2$O as eluents, acidic condition) to yield a white solid of 1-((1-((2-(3,5-dichlorophenyl)-6-((6-(4-(2-hydroxyethyl)piperazin-1-yl)pyridin-3-yl)oxy)pyridin-4-yl)methyl)piperidin-4-yl)methyl)-3-methylurea, 4 hydrochloride (15.26 mg, 0.02 mmol, 4.5% yield): $^1$H NMR (400 MHz, CD$_3$OD) δ ppm 8.06-7.99 (m, 2H), 7.98-7.93 (m, 1H), 7.90 (d, J=1.8 Hz, 2H), 7.52 (s, 1H), 7.37 (s, 1H), 111 (d, J=9.7 Hz, 1H), 4.44 (s, 2H), 4.18 (d, J=14.1 Hz, 2H), 3.94-3.86 (m, 2H), 3.60 (d, J=10.1 Hz, 4H), 3.38-3.33 (m, 2H), 3.24-3.01 (m, 11H), 2.08-1.78 (m, 3H), 1.75-1.54 (m, 2H); ES-LCMS m/z 628.3, 630.3 [M+H]$^+$.

Example 41: 3-(4-(5-((6-(3,5-Dichlorophenyl)-4-((4-((3-methylureido)methyl)piperidin-1-yl)methyl)pyridin-2-yl)oxy)pyridin-2-yl)piperazin-1-yl)propanoic acid, 4 hydrochloride

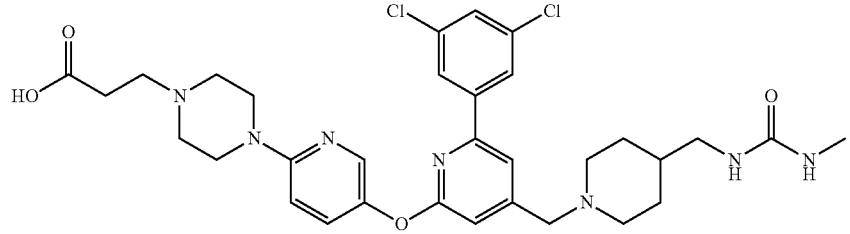 [SMILES: CNC(=O)NCC1CCN(Cc2cc(Oc3ccc(N4CCN(CCC(=O)O)CC4)nc3)nc(-c3cc(Cl)cc(Cl)c3)c2)CC1]

Step 1: tert-Butyl 4-(5-((6-(3,5-dichlorophenyl)-4-((4-((3-methylureido)methyl)piperidin-1-yl)methyl)pyridin-2-yl)oxy)pyridin-2-yl)piperazine-1-carboxylate

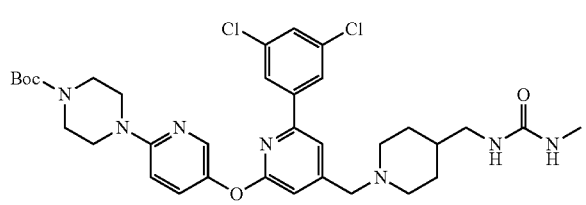 [SMILES: CNC(=O)NCC1CCN(Cc2cc(Oc3ccc(N4CCN(C(=O)OC(C)(C)C)CC4)nc3)nc(-c3cc(Cl)cc(Cl)c3)c2)CC1]

To a mixture of tert-butyl 4-(5-((6-(3,5-dichlorophenyl)-4-(((methylsulfonyl)oxy)methyl)pyridin-2-yl)oxy)pyridin-2-yl)piperazine-1-carboxylate (0.5 g, 0.632 mmol) and 1-methyl-3-(piperidin-4-ylmethyl)urea hydrochloride (0.192 g, 0.758 mmol) in DMF (10 mL) was added K$_2$CO$_3$ (0.262 g, 1.895 mmol). The mixture was stirred at 80° C. for 2 h. Then the solution was filtered and concentrated. The crude product was distributed between DCM (40 mL) and saturated aqueous NaHCO$_3$ (20 mL) solution. The combined organic extract was washed with brine (10 mL), dried over Na$_2$SO$_4$, filtered and concentrated. The crude product was purified by silica gel column chromatography (PE/EtOAc=1/1). All fractions found to contain product by TLC (PE/EtOAc=1/1, R$_f$=0.6) were combined and concentrated to yield a brown solid of tert-butyl 4-(5-((6-(3,5-dichlorophenyl)-4-((4-((3-methylureido)methyl)piperidin-1-yl)methyl)pyridin-2-yl)oxy)pyridin-2-yl)piperazine-1-carboxylate (300 mg, 0.394 mmol, 62.4% yield): $^1$H NMR (400 MHz, CD$_3$OD) δ ppm 8.06-8.01 (m, 1H), 7.81 (d, J=1.8 Hz, 2H), 7.61 (s, 1H), 7.53-7.46 (m, 1H), 7.41 (t, J=1.8 Hz, 1H), 7.00-6.92 (m, 2H), 3.62-3.46 (m, 10H), 3.05-2.98 (m, 2H), 2.93 (d, J=11.5 Hz, 2H), 2.68 (s, 3H), 2.08 (t, J=10.8 Hz, 2H), 1.72 (d, J=11.5 Hz, 2H), 1.49 (s, 10H), 1.35-1.25 (m, 2H); ES-LCMS m/z 684.2, 686.2 [M+H]$^+$.

Step 2: 1-((1-((2-(3,5-Dichlorophenyl)-6-((6-(piperazin-1-yl)pyridin-3-yl)oxy)pyridin-4-yl)methyl)piperidin-4-yl)methyl)-3-methylurea

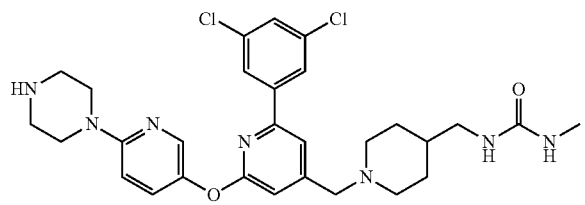

To a solution of tert-butyl 4-(5-((6-(3,5-dichlorophenyl)-4-((4-((3-methylureido)methyl)piperidin-1-yl)methyl)pyridin-2-yl)oxy)pyridin-2-yl)piperazine-1-carboxylate (300 mg, 0.394 mmol) in EtOAc (10 mL) was added HCl solution (4.0 M in EtOAc, 3 mL, 12.00 mmol). The mixture was stirred at 20° C. for 10 min then concentrated and distributed between DCM (50 mL) and saturated aqueous NaHCO₃ (30 mL) solution. The combined organic extract was washed with brine (20 mL), dried over Na₂SO₄, filtered and concentrated to yield a yellow solid of 1-((1-((2-(3,5-dichlorophenyl)-6-((6-(piperazin-1-yl)pyridin-3-yl)oxy)pyridin-4-yl)methyl)piperidin-4-yl)methyl)-3-methylurea (200 mg, 0.294 mmol, 74.6% yield): $^1$H NMR (400 MHz, CD$_3$OD) δ ppm 8.30-8.22 (m, 2H), 8.06 (s, 1H), 7.90 (d, J=1.8 Hz, 2H), 7.65 (d, J=9.7 Hz, 1H), 7.53-7.48 (m, 1H), 7.45 (s, 1H), 4.61-4.45 (m, 2H), 4.13-4.05 (m, 4H), 3.60 (d, J=11.9 Hz, 2H), 3.54-3.49 (m, 4H), 3.16-3.08 (m, 4H), 2.75-2.73 (m, 3H), 1.99 (d, J=13.7 Hz, 2H), 1.87 (br. s, 1H), 1.71-1.58 (m, 2H); ES-LCMS m/z 584.2, 586.2 [M+H]$^+$.

Step 3: Ethyl 3-(4-(5-((6-(3,5-dichlorophenyl)-4-((4-((3-methylureido)methyl)piperidin-1-yl)methyl)pyridin-2-yl)oxy)pyridin-2-yl)piperazin-1-yl)propanoate

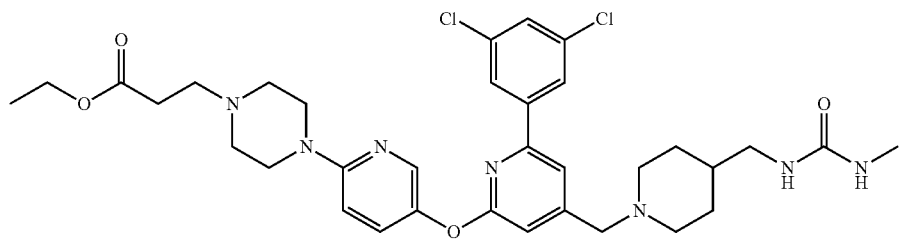 [SMILES: CCOC(=O)CCN1CCN(c2ccc(Oc3cc(CN4CCC(CNC(=O)NC)CC4)cc(-c4cc(Cl)cc(Cl)c4)n3)cn2)CC1]

To a solution of 1-((1-((2-(3,5-dichlorophenyl)-6-((6-(piperazin-1-yl)pyridin-3-yl)oxy)pyridine-4-yl)methyl)piperidin-4-yl)methyl)-3-methylurea (200 mg, 0.342 mmol) in DML (10 mL) was added K₂CO₃ (142 mg, 1.026 mmol) and ethyl 3-bromopropanoate (74.3 mg, 0.411 mmol). The mixture was stirred at 80° C. for 8 h then concentrated. Water (20 mL) was added and the mixture was extracted with DCM (20 mL×2). The combined organic layers were dried over Na₂SO₄, filtered and concentrated to yield a yellow oil of ethyl 3-(4-(5-((6-(3,5-dichlorophenyl)-4-((4-((3-methylureido)methyl)piperidin-1-yl)methyl)pyridin-2-yl)oxy)pyridin-2-yl)piperazin-1-yl)propanoate (150 mg, 0.175 mmol, 51.2% yield): $^1$H NMR (400 MHz, CD$_3$OD) δ ppm 8.01 (d, J=2.6 Hz, 1H), 7.80 (d, J=1.3 Hz, 2H), 7.60 (s, 1H), 7.47 (dd, J=2.6, 9.3 Hz, 1H), 7.40 (s, 1H), 6.96-6.91 (m, 2H), 4.18 (q, J=7.6 Hz, 2H), 3.59-3.58 (m, 2H), 3.33 (s, 3H), 3.03-2.97 (m, 5H), 2.91 (d, J=11.0 Hz, 2H), 2.84 (s, 2H), 2.73-2.68 (m, 4H), 2.66 (s, 3H), 2.06 (t, J=11.0 Hz, 2H), 1.70 (d, J=11.5 Hz, 2H), 1.48-1.42 (m, 2H), 1.28 (br. s, 4H); ES-LCMS m/z 684.2, 686.2 [M+H]$^+$.

Step 4: 3-(4-(5-((6-(3,5-Dichlorophenyl)-4-((4-((3-methylureido)methyl)piperidin-1-yl)methyl)pyridin-2-yl)oxy)pyridin-2-yl)piperazin-1-yl)propanoic acid, 4 hydrochloride

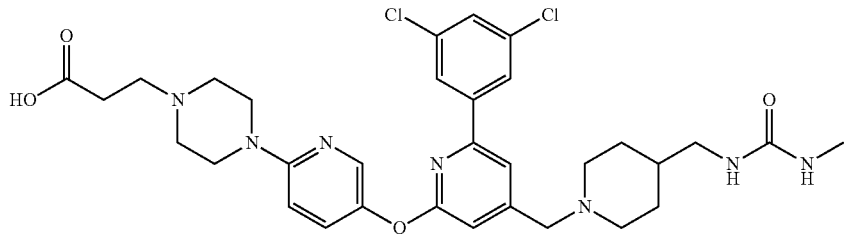 [SMILES: CNC(=O)NCC1CCN(Cc2cc(Oc3ccc(N4CCN(CCC(=O)O)CC4)nc3)nc(-c3cc(Cl)cc(Cl)c3)c2)CC1]

To a solution of ethyl 3-(4-(5-((6-(3,5-dichlorophenyl)-4-((4-((3-methylureido)methyl)piperidin-1-yl)methyl)pyridin-2-yl)oxy)pyridin-2-yl)piperazin-1-yl)propanoate (200 mg, 0.292 mmol) in MeOH (10 mL) and water (2 mL) was added NaOH (23.37 mg, 0.584 mmol). The mixture was stirred at 15° C. for 0.5 h. The mixture was concentrated to yield the crude product which was purified by preparative HPLC (MeCN/H₂O as eluents, acidic condition) and dried by lyophilization to yield a white solid of 3-(4-(5-((6-(3,5-dichlorophenyl)-4-((4-((3-methylureido)methyl)piperidin-1-yl)methyl)pyridin-2-yl)oxy)pyridin-2-yl)piperazin-1-yl)propanoic acid, 4 hydrochloride (38.6 mg, 0.047 mmol, 16.0% yield): $^1$H NMR (400 MHz, CD$_3$OD) δ ppm 8.20 (br. s, 1H), 7.95 (br. s, 1H), 7.86 (br. s, 3H), 7.54-7.29 (m, 3H), 4.55-4.35 (m, 4H), 3.68-3.49 (m, 6H), 3.06 (d, J=5.7 Hz, 5H), 2.95 (br. s, 4H), 2.68 (br. s, 4H), 1.97 (d, J=13.7 Hz, 2H), 1.80 (br. s, 1H), 1.57 (br. s, 2H); ES-LCMS m/z 656.2, 658.2 [M+H]+.

Example 42: N-((1-((5-(4-Aminophenoxy)-3',5'-dichloro-[1,1'-biphenyl]-3-yl)methyl)piperidin-4-yl)methyl)acetamide, 2 hydrochloride

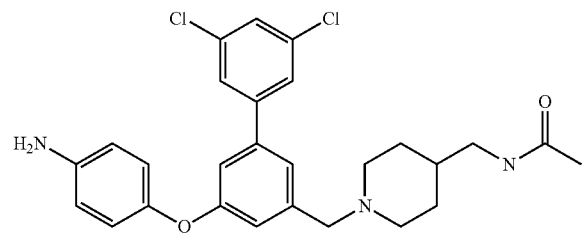 [SMILES: CC(=O)NCC1CCN(Cc2cc(Oc3ccc(N)cc3)cc(-c3cc(Cl)cc(Cl)c3)c2)CC1]

Step 1: N-((1-((3',5'-Dichloro-5-(4-nitrophenoxy)-[1,1'-biphenyl]-3-yl)methyl)piperidin-4-yl)methyl)acetamide

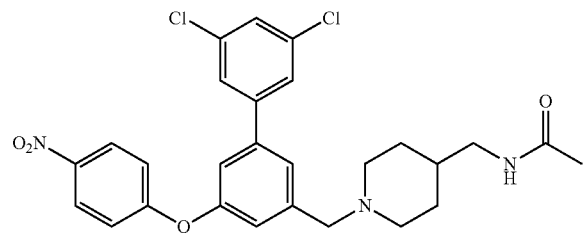

To a solution of N-((1-((3',5'-dichloro-5-hydroxy-[1,1'-biphenyl]-3-yl)methyl)piperidin-4-yl)methyl)acetamide (500 mg, 1.227 mmol) and 1-fluoro-4-nitrobenzene (208 mg, 1.473 mmol) in MeCN (100 mL) was added K₂CO₃ (509 mg, 3.68 mmol). The reaction mixture was stirred at 80° C. for 16 h then filtered. The filtrate was concentrated to yield crude product which was purified by column to yield N-((1-((3',5'-dichloro-5-(4-nitrophenoxy)-[1,1'-biphenyl]-3-yl)methyl)piperidin-4-yl)methyl)acetamide (450 mg, 0.852 mmol, 69.4% yield): $^1$H NMR (400 MHz, CDCl₃) δ ppm 8.22 (d, J=9.2 Hz, 2H), 7.42 (d, J=1.6 Hz, 2H), 7.37-7.35 (m, 2H), 7.12 (d, J=8.8 Hz, 2H), 7.04 (d, J=9.2 Hz, 2H), 5.49 (br. s, 1H), 3.54 (s, 2H), 3.16-3.12 (m, 2H), 2.89-2.87 (m, 2H), 2.01-1.97 (m, 5H), 1.69-1.65 (m, 2H), 1.52-1.51 (m, 1H), 1.32-1.19 (m, 2H); ES-LCMS m/z 528.1, 530.1 [M+H]+.

Step 2: N-((1-((5-(4-Aminophenoxy)-3',5'-dichloro-[1,1'-biphenyl]-3-yl)methyl)piperidin-4-yl)methyl)acetamide, 2 hydrochloride

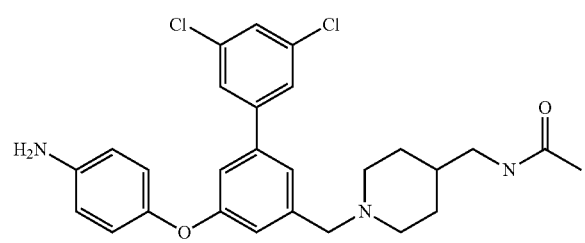

To a solution of N-((1-((3',5'-dichloro-5-(4-nitrophenoxy)-[1,1'-biphenyl]-3-yl)methyl)piperidin-4-yl)methyl)acetamide (350 mg, 0.662 mmol) in AcOH (20 mL) was added Zn powder (433 mg, 6.62 mmol). The reaction mixture was stirred at 80° C. for 16 h then filtered. The filtrate was concentrated and the residue was purified by preparative HPLC (MeCN/H₂O as eluents, acidic condition) to yield N-((1-((5-(4-aminophenoxy)-3',5'-dichloro-[1,1'-biphenyl]-3-yl)methyl)piperidin-4-yl)methyl)acetamide, 2 hydrochloride (157.76 mg, 0.274 mmol, 41.4% yield): $^1$H NMR (400 MHz, CD₃OD) δ ppm 7.69 (s, 1H), 7.64 (m, 2H), 7.48-7.45 (m, 3H), 7.39-7.34 (m, 2H), 7.26-7.24 (m, 2H), 4.37 (s, 2H), 3.55-3.52 (m, 2H), 3.15-3.13 (m, 2H), 3.08-3.02 (m, 2H), 2.00-1.94 (m, 5H), 1.88-1.86 (m, 1H), 1.62-1.53 (m, 2H); ES-LCMS m/z 498.2, 500.2 [M+H]+.

Example 43: N-((1-((5-((5-aminopyrimidin-2-yl)oxy)-3',5'-dichloro-[1,1'-biphenyl]-3-yl)methyl)piperidin-4-yl)methyl)acetamide

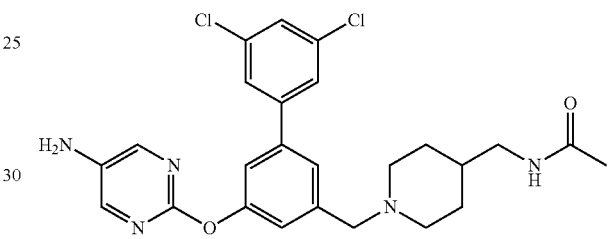

Step 1: N-((1-((3',5'-dichloro-5-((5-nitropyrimidin-2-yl)oxy)-[1,1'-biphenyl]-3-yl)methyl)piperidin-4-yl)methyl)acetamide

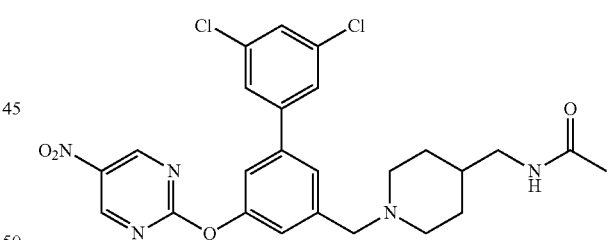

A mixture of N-((1-((3',5'-dichloro-5-hydroxy-[1,1'-biphenyl]-3-yl)methyl)piperidin-4-yl)methyl)acetamide (200 mg, 0.491 mmol), 2-chloro-5-nitropyrimidine (78 mg, 0.491 mmol) and DIEA (0.257 mL, 1.473 mmol) in i-PrOH (2 mL) was stirred at 170° C. for 1 h under microwave. The mixture was concentrated to yield the residue which was purified by preparative TLC (PE/EtOAc=3/1, $R_f$=0.5) to yield N-((1-((3',5'-dichloro-5-((5-nitropyrimidin-2-yl)oxy)-[1,1'-biphenyl]-3-yl)methyl)piperidin-4-yl)methyl)acetamide (40 mg, 0.075 mmol, 15.3% yield): $^1$H NMR (400 MHz, CD₃OD) δ ppm 9.41 (s, 1H), 9.09 (s, 1H), 7.84 (s, 1H), 7.78 (s, 1H), 7.73 (d, J=1.5 Hz, 2H), 7.54 (d, J=1.5 Hz, 2H), 4.45 (s, 2H), 3.62 (d, J=12.5 Hz, 2H), 3.17-3.12 (m, 2H), 3.11-3.02 (m, 2H), 2.01-1.97 (m, 5H), 1.85-1.83 (m, 1H), 1.58-1.46 (m, 2H); ES-LCMS m/z 530.2, 532.2 [M+H]+.

Step 2: N-((1-((5-((5-Aminopyrimidin-2-yl)oxy)-3', 5'-dichloro-[1,1'-biphenyl]-3-yl)methyl)piperidin-4-yl)methyl)acetamide

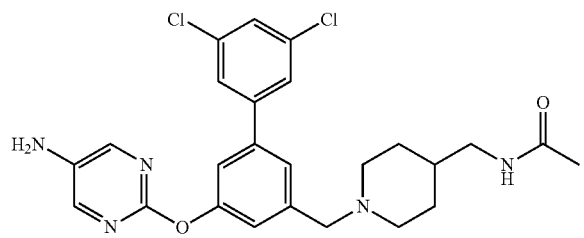 [SMILES: CC(=O)NCC1CCN(Cc2cc(Oc3ncc([N+](=O)[O-])cn3)cc(-c3cc(Cl)cc(Cl)c3)c2)CC1]

A mixture of Pd/C (10 wt %, 4.01 mg, 0.038 mmol), N-((1-(((3',5'-dichloro-5-((5-nitropyrimidin-2-yl)oxy)-[1,1'-biphenyl]-3-yl)methyl)piperidin-4-yl)methyl)acetamide (20 mg, 0.038 mmol) in EtOAc (10 mL) was stirred at 25° C. under H₂ atmosphere (50 psi) for 15 min. The mixture was filtered and the filtrate was concentrated. The residue was purified by preparative HPLC (MeCN/H₂O as eluents, acidic condition) to yield N-((1-((5-((5-aminopyrimidin-2-yl)oxy)-3',5'-dichloro-[1,1'-biphenyl]-3-yl)methyl)piperidin-4-yl)methyl)acetamide, 2 hydrochloride (1.7 mg, 2.94 μmol, 7.8% yield): $^1$H NMR (400 MHz, CD₃OD) δ ppm 8.13 (s, 2H), 7.67-7.62 (m, 3H), 7.55 (br. s, 1H), 7.48 (br. s, 1H), 7.34 (br. s, 1H), 4.36 (s, 2H), 3.56 (d, J=12.3 Hz, 2H), 3.09 (d, J=6.6 Hz, 2H), 3.03 (d, J=12.3 Hz, 2H), 1.99-1.91 (m, 5H), 1.80-1.77 (m, 1H), 1.43 (m, 2H); ES-LCMS m/z 500.1, 502.1 [M+H]$^+$.

Example 44: 3-(4-(5-((6-(3,5-Dichlorophenyl)-4-((4-(methylsulfonamidoethyl)piperidin-1-yl)methyl)pyridin-2-yl)oxy)pyridin-2-yl)piperazin-1-yl)propanoic acid, 4 hydrochloride

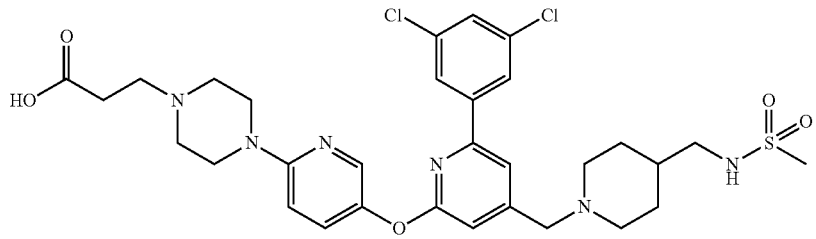 [SMILES: CS(=O)(=O)NCC1CCN(Cc2cc(Oc3ccc(N4CCN(CCC(=O)O)CC4)nc3)nc(-c3cc(Cl)cc(Cl)c3)c2)CC1]

Step 1: Ethyl 3-(4-(5-((4-((4-(((tert-butoxycarbonyl)amino)methyl)piperidin-1-yl)methyl)-6-(3,5-dichlorophenyl)pyridin-2-yl)oxy)pyridin-2-yl)piperazin-1-yl)propanoate

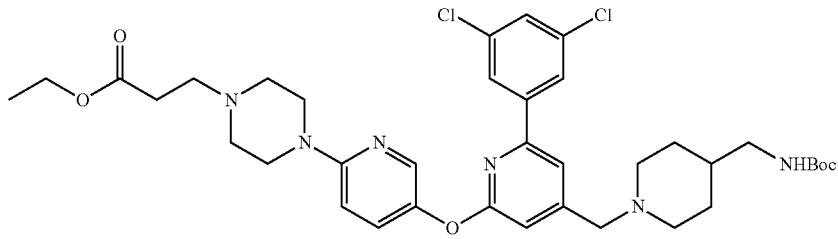 [SMILES: CCOC(=O)CCN1CCN(c2ccc(Oc3cc(CN4CCC(CNC(=O)OC(C)(C)C)CC4)cc(-c4cc(Cl)cc(Cl)c4)n3)cn2)CC1]

To a solution of ethyl 3-(4-(5-((6-(3,5-dichlorophenyl)-4-(((methylsulfonyl)oxy)methyl)pyridin-2-yl)oxy)pyridin-2-yl)piperazin-1-yl)propanoate (830 mg, 1.157 mmol) and tert-butyl (piperidin-4-ylmethyl)carbamate (496 mg, 2.315 mmol) in DMF (10 mL) was added K₂CO₃ (480 mg, 3.47 mmol). The reaction mixture was stirred at 80° C. for 12 h. The solid was filtered off and solution was concentrated to yield the crude product which was purified by flash chromatography column (from pure DCM to DCM/MeOH=10/1, DCM/MeOH=10/1, R$_f$=0.55) to yield a pale yellow solid ethyl 3-(4-(5-((4-((4-(((tert-butoxycarbonyl)amino)methyl)piperidin-1-yl)methyl)-6-(3,5-dichlorophenyl)pyridin-2-yl)oxy)pyridin-2-yl)piperazin-1-yl)propanoate (750 mg, 0.928 mmol, 80.0% yield): $^1$H NMR (400 MHz, CD₃OD) δ ppm 8.05 (s, 1H), 7.84 (s, 2H), 7.65 (s, 1H), 7.51 (d, J=3.2 Hz, 1H), 7.45 (s, 1H), 6.97-6.94 (m, 2H), 4.20-4.16 (m, 2H), 3.58 (s, 2H), 3.57-3.56 (m, 4H), 2.97-2.94 (m, 4H), 2.80-2.75 (m, 2H), 2.67-2.61 (m, 4H), 2.60-2.52 (m, 2H), 2.15-2.08 (m, 2H), 1.76-1.70 (m, 2H), 1.50-1.45 (m, 10H), 1.30-1.27 (m, 5H); ES-LCMS m/z 727.4, 729.4 [M+H]$^+$.

Step 2: Ethyl 3-(4-(5-((4-((4-(aminomethyl)piperidin-1-yl)methyl)-6-(3,5-dichlorophenyl)pyridin-2-yl)oxy)pyridin-2-yl)piperazin-1-yl)propanoate

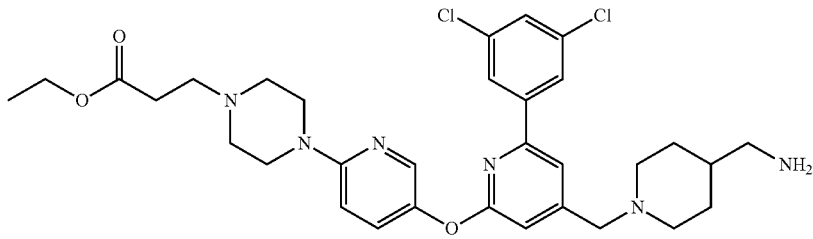 [SMILES: CCOC(=O)CCN1CCN(c2ccc(Oc3cc(CN4CCC(CN)CC4)cc(-c4cc(Cl)cc(Cl)c4)n3)cn2)CC1]

Ethyl 3-(4-(5-((4-((4-(((tert-butoxycarbonyl)amino)methyl)piperidin-1-yl)methyl)-6-(3,5-dichlorophenyl)pyridin-2-yl)oxy)pyridin-2-yl)piperazin-1-yl)propanoate (750 mg, 0.928 mmol) was dissolved in HCl solution (4.0 M in EtOAc, 3 mL, 12.00 mmol). The reaction mixture was stirred at 15° C. for 10 min then concentrated to yield a pale yellow solid of ethyl 3-(4-(5-((4-((4-(aminomethyl)piperidin-1-yl)methyl)-6-(3,5-dichlorophenyl)pyridin-2-yl)oxy)pyridin-2-yl)piperazin-1-yl)propanoate, 5 hydrochloride (850 mg, 0.873 mmol, 94.0% yield): $^1$H NMR (400 MHz, CD$_3$OD) δ ppm 8.29-8.26 (m, 1H), 8.12 (s, 1H), 8.03 (s, 1H), 7.93 (d, J=1.5 Hz, 2H), 7.67 (d, J=9.5 Hz, 1H), 7.57-7.48 (m, 2H), 4.62-4.37 (m, 4H), 4.25 (q, J=7.2 Hz, 2H), 3.93-3.72 (m, 4H), 3.70-3.48 (m, 6H), 3.30-3.19 (m, 2H), 3.05 (s, 2H), 2.95 (d, J=6.0 Hz, 2H), 2.09 (d, J=12.0 Hz, 3H), 1.88-1.75 (m, 2H), 1.37-1.25 (m, 3H); ES-LCMS m/z 627.4, 629.4 [M+H]$^+$.

Step 3: Ethyl 3-(4-(5-((6-(3,5-dichlorophenyl)-4-((4-(methylsulfonamidoethyl)piperidin-1-yl)methyl)pyridin-2-yl)oxy)pyridin-2-yl)piperazin-1-yl)propanoate

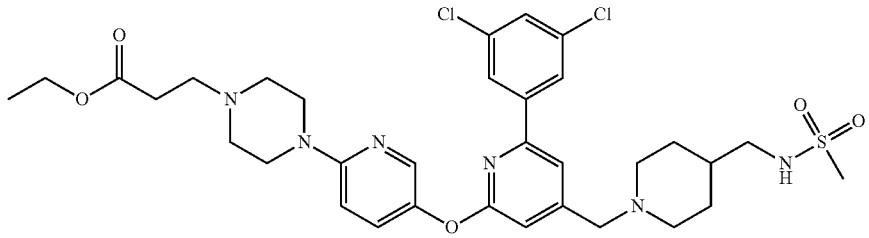 [SMILES: CCOC(=O)CCN1CCN(c2ccc(Oc3cc(CN4CCC(CNS(C)(=O)=O)CC4)cc(-c4cc(Cl)cc(Cl)c4)n3)cn2)CC1]

To a solution of ethyl 3-(4-(5-((4-((4-(aminomethyl)piperidin-1-yl)methyl)-6-(3,5-dichlorophenyl)pyridin-2-yl)oxy)pyridin-2-yl)piperazin-1-yl)propanoate, 5 hydrochloride (150 mg, 0.154 mmol) and DIEA (159 mg, 1.232 mmol) in DCM (5 mL) was added MsCl (21.17 mg, 0.185 mmol). The reaction mixture was stirred at 15° C. for 12 h then concentrated to yield a yellow solid of ethyl 3-(4-(5-((6-(3,5-dichlorophenyl)-4-((4-(methylsulfonamidoethyl)piperidin-1-yl)methyl)pyridin-2-yl)oxy)pyridin-2-yl)piperazin-1-yl)propanoate (180 mg, 0.128 mmol, 83.0% yield): $^1$H NMR (400 MHz, CDCl$_3$) δ ppm 8.05 (d, J=2.9 Hz, 1H), 7.71-7.67 (m, 2H), 7.38-7.32 (m, 2H), 7.28-7.25 (m, 1H), 6.74 (s, 1H), 6.65 (d, J=9.3 Hz, 1H), 4.09 (q, J=7.1 Hz, 2H), 3.51-3.47 (m, 4H), 3.44-3.41 (m, 2H), 2.97 (t, J=6.5 Hz, 2H), 2.89 (s, 3H), 2.83-2.76 (m, 2H), 2.72-2.68 (m, 2H), 2.55 (d, J=4.9 Hz, 4H), 2.49-2.44 (m, 2H), 1.96-1.91 (m, 2H), 1.68 (d, J=11.9 Hz, 2H), 1.50-1.42 (m, 3H), 1.17-1.12 (m, 3H); ES-LCMS m/z 705.3, 707.3 [M+H]$^+$.

Step 4: 3-(4-(5-((6-(3,5-Dichlorophenyl)-4-((4-(methylsulfonamidoethyl)piperidin-1-yl)methyl)pyridin-2-yl)oxy)pyridin-2-yl)piperazin-1-yl)propanoic acid, 4 hydrochloride

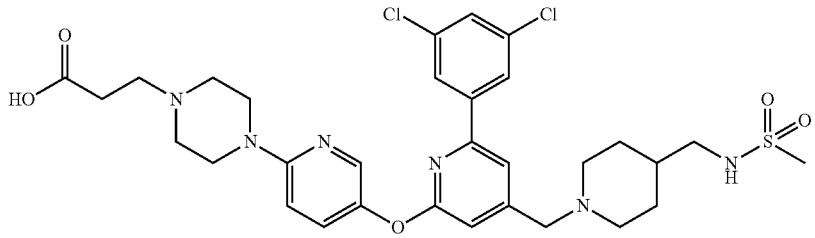 [SMILES: CS(=O)(=O)NCC1CCN(Cc2cc(Oc3ccc(N4CCN(CCC(=O)O)CC4)nc3)nc(-c3cc(Cl)cc(Cl)c3)c2)CC1]

To a solution of ethyl 3-(4-(5-((6-(3,5-dichlorophenyl)-4-((4-(methylsulfonamidoethyl)piperidin-1-yl)methyl)pyridin-2-yl)oxy)pyridin-2-yl)piperazin-1-yl)propanoate (180 mg, 0.128 mmol) in MeOH (10 mL) was added NaOH (10.20 mg, 0.255 mmol) in water (1 mL). The reaction mixture was stirred at 15° C. for 12 h then 1 N HCl was added to adjust pH to 6. The solution was concentrated to yield the crude product which was purified by preparative HPLC (MeCN/H₂O as eluents, acidic condition) and dried by lyophilization to yield a white solid of 3-(4-(5-((6-(3,5-dichlorophenyl)-4-((4-(methylsulfonamidoethyl)piperidin-1-yl)methyl)pyridin-2-yl)oxy)pyridin-2-yl)piperazin-1-yl)propanoic acid, 4 hydrochloride (20.10 mg, 0.024 mmol, 19.1% yield): $^1$H NMR (400 MHz, CD$_3$OD) δ ppm 8.23 (br. s, 1H), 8.16 (s, 1H), 7.98 (s, 1H), 7.89 (s, 2H), 7.55 (s, 1H), 7.51 (s, 1H), 7.41 (s, 1H), 4.46 (s, 4H), 3.96-3.37 (m, 10H), 3.30-3.27 (m, 2H), 3.13-3.10 (m, 2H), 3.01-3.00 (m, 2H), 2.93 (s, 3H), 2.06 (d, J=11.5 Hz, 2H), 1.88-1.86 (m, 1H), 1.66-1.63 (m, 2H); ES-LCMS m/z 6113, 679.3 [M+H]$^+$.

Example 45: N-((1-((5-((5-Aminopyridin-2-yl)oxy)-3',5'-dichloro-[1,1'-biphenyl]-3-yl)methyl)piperidin-4-yl)methyl)acetamide, 3 hydrochloride

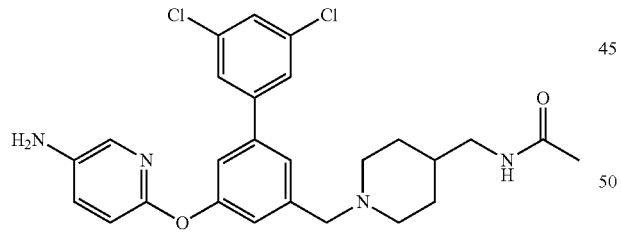

A mixture of N-((1-((3',5'-dichloro-5-hydroxy-[1,1'-biphenyl]-3-yl)methyl)piperidin-4-yl)methyl)acetamide (100 mg, 0.245 mmol) and 2-fluoro-5-nitropyridine (41.9 mg, 0.295 mmol) in DMF (50 mL) was added K$_2$CO$_3$ (67.9 mg, 0.491 mmol). The mixture was stirred at 80° C. under N$_2$ atmosphere for 4 h. The mixture was filtered through a Celite® pad. The filtrate was concentrated and water (30 mL) was added. The aqueous layer was extracted with DCM (30 mL×3) and the organic layer was dried over MgSO$_4$ and concentrated to yield a black solid which was dissolved in EtOAc (50 mL). Then Pd/C (10 wt %, 30 mg) was added under N$_2$ atmosphere and the mixture was stirred under H$_2$ atmosphere (50 psi) at 25° C. for 16 h. After filtration, the filtrate was concentrated and the residue was purified by preparative HPLC (MeCN/H₂O as eluents, acidic condition) to yield brown oil of N-((1-((5-((5-aminopyridin-2-yl)oxy)-3',5'-dichloro-[1,1'-biphenyl]-3-yl)methyl)piperidin-4-yl)methyl)acetamide, 3 hydrochloride (6.53 mg, 10.60 μmol, 5.6% yield): $^1$H NMR (400 MHz, CD$_3$OD) δ ppm 8.17-8.16 (m, 1H), 7.93-7.90 (m, 1H), 7.75 (s, 1H), 7.68-7.67 (m, 2H), 7.59-7.58 (m, 1H), 7.49-7.48 (m, 2H), 7.28-7.26 (m, 1H), 4.39 (s, 2H), 3.58-3.55 (m, 2H), 3.30-3.28 (m, 2H), 3.12-3.01 (m, 2H), 1.98-1.95 (m, 2H), 1.84-1.79 (m, 3H), 1.57-1.54 (m, 1H), 1.51-1.47 (m, 2H); ES-LCMS m/z 499.1, 501.1 [M+H]$^+$.

Example 46: N-((1-((5-((6-Amino-5-fluoropyridin-3-yl)oxy)-3',5'-dichloro-[1,1'-biphenyl]-3-yl)methyl)piperidin-4-yl)methyl)acetamide, 2 hydrochloride

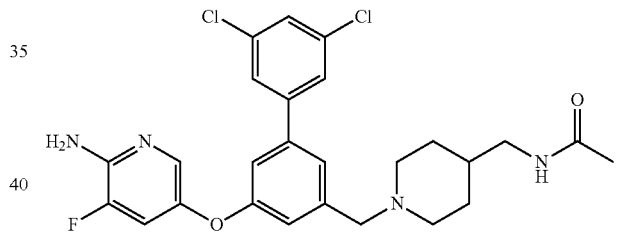

Step 1: 5-Bromo-N-(2,4-dimethoxybenzyl)-3-fluoropyridin-2-amine

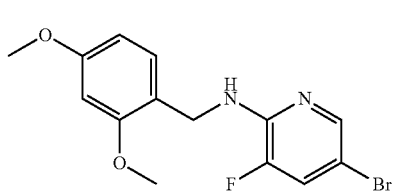 [SMILES: COc1ccc(CNc2ncc(Br)cc2F)c(OC)c1]

A mixture of 5-bromo-2,3-difluoropyridine (71 mg, 0.366 mmol) and (2,4-dimethoxyphenyl)methanamine (1.5 g, 8.78 mmol) was stirred at 100° C. for 16 h. The mixture was purified with silica gel column chromatography (PE/EtOAc=2/1) to yield 5-bromo-N-(2,4-dimethoxybenzyl)-3-fluoropyridin-2-amine (60 mg, 0.158 mmol, 43.2% yield): $^1$H NMR (400 MHz, CDCl$_3$) δ ppm 7.95 (s, 1H), 7.24-7.22 (m, 2H), 6.47 (s, 1H), 6.45-6.41 (m, 1H), 4.55 (s, 2H), 3.83 (s, 3H), 3.77 (s, 3H); ES-LCMS m/z 341.0, 343.0 [M+H]$^+$.

Step 2: N-((1-(((3',5'-Dichloro-5-((6-((2,4-dimethoxybenzyl)amino)-5-fluoropyridin-3-yl)oxy)-[1,1'-biphenyl]-3-yl)methyl)piperidin-4-yl)methyl)acetamide

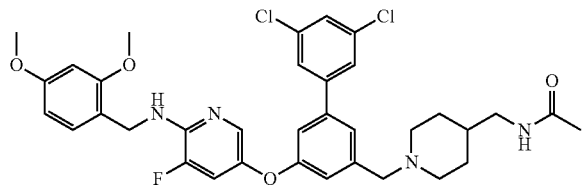 [SMILES: COc1ccc(CNc2ncc(Oc3cc(CN4CCC(CNC(C)=O)CC4)cc(-c4cc(Cl)cc(Cl)c4)c3)cc2F)c(OC)c1]

A mixture of N-((1-((3',5'-dichloro-5-hydroxy-[1,1'-biphenyl]-3-yl)methyl)piperidin-4-yl)methyl)acetamide (84 mg, 0.205 mmol), 5-bromo-N-(2,4-dimethoxybenzyl)-3-fluoropyridin-2-amine (60 mg, 0.176 mmol), picolinic acid (3.79 mg, 0.031 mmol), $K_3PO_4$ (131 mg, 0.616 mmol) and CuI (3.91 mg, 0.021 mmol) in DMSO (15 mL) was stirred at 140° C. for 24 h. The mixture was concentrated and purified with column chromatography (DCM/MeOH=15/1) to yield N-((1-(((3',5'-dichloro-5-((6-((2,4-dimethoxybenzyl)amino)-5-fluoropyridin-3-yl)oxy)-[1,1'-biphenyl]-3-yl)methyl)piperidin-4-yl)methyl)acetamide (30 mg, 0.036 mmol, 17.5% yield): $^1$H NMR (400 MHz, CD$_3$OD) δ ppm 7.70-7.67 (m, 3H), 7.55-7.50 (m, 2H), 7.45-7.42 (m, 2H), 7.31-7.30 (m, 1H), 7.21-7.15 (m, 2H), 6.97 (s, 1H), 3.90-3.85 (m, 5H), 3.82-3.78 (m, 5H), 3.10-3.05 (m, 6H), 1.93 (s, 3H), 1.80-1.75 (m, 2H), 1.27-1.23 (m, 3H); ES-LCMS m/z 667.1, 669.1 [M+H]$^+$.

Step 3: N-((1-(((5-((6-Amino-5-fluoropyridin-3-yl)oxy)-3',5'-dichloro-[1,1'-biphenyl]-3-yl)methyl)piperidin-4-yl)methyl)acetamide, 2 hydrochloride

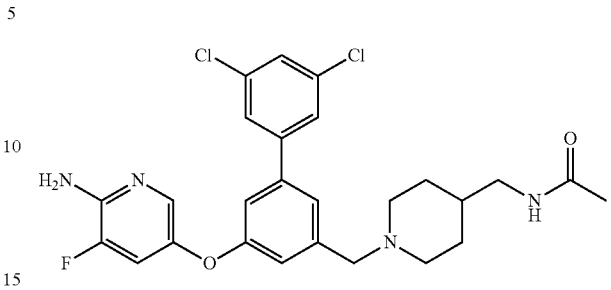

A mixture of N-((1-(((3',5'-dichloro-5-((6-((2,4-dimethoxybenzyl)amino)-5-fluoropyridin-3-yl)oxy)-[1,1'-biphenyl]-3-yl)methyl)piperidin-4-yl)methyl)acetamide (30 mg, 0.045 mmol) in TFA (2 mL) was stirred at 25° C. for 2 h. The mixture was concentrated and purified by preparative HPLC (MeCN/H$_2$O as eluents, acidic condition) to yield of N-((1-(((5-((6-amino-5-fluoropyridin-3-yl)oxy)-3',5'-dichloro-[1,1'-biphenyl]-3-yl)methyl)piperidin-4-yl)methyl)acetamide, 2 hydrochloride (1.41 mg, 2.285 μmol, 5.1% yield): $^1$H NMR (400 MHz, CD$_3$OD) δ ppm 7.92 (d, J=2.4 Hz, 1H), 7.89 (s, 1H), 7.73 (s, 2H), 7.67 (m, 1H), 7.61-7.48 (m, 2H), 7.36 (s, 1H), 4.35 (s, 2H), 3.54-3.51 (m, 2H), 3.11-3.09 (m, 2H), 3.04-2.98 (m, 2H), 2.02-1.93 (m, 7H), 1.55-1.48 (m, 1H); ES-LCMS m/z 517.1, 519.1 [M+H]$^+$.

Example 47: 1-((1-((2-(3,5-Dichlorophenyl)-6-((2-(4-(2-hydroxyethyl)piperazin-1-yl)pyrimidin-5-yl)oxy)pyridin-4-yl)methyl)piperidin-4-yl)methyl)-3-methylurea, 4 hydrochloride

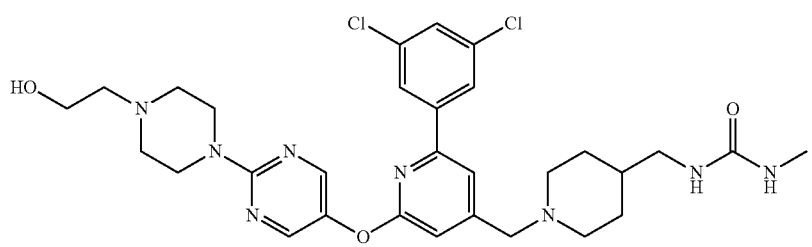 [SMILES: CNC(=O)NCC1CCN(Cc2cc(Oc3cnc(N4CCN(CCO)CC4)nc3)nc(-c3cc(Cl)cc(Cl)c3)c2)CC1]

Step 1: Ethyl 2-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)acetate

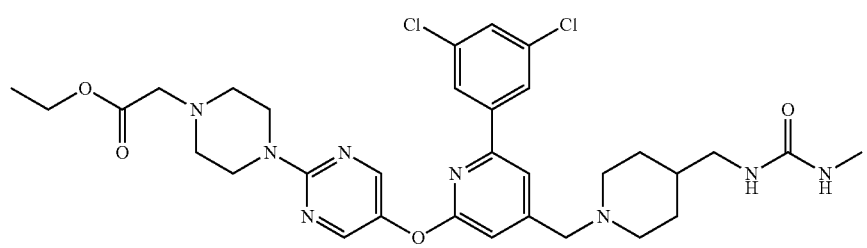 [SMILES: CCOC(=O)CN1CCN(c2ncc(Oc3cc(CN4CCC(CNC(=O)NC)CC4)cc(-c4cc(Cl)cc(Cl)c4)n3)cn2)CC1]

To a mixture of 1-((1-((2-(3,5-dichlorophenyl)-6-((2-(piperazin-1-yl)pyrimidin-5-yl)oxy)pyridin-4-yl)methyl)piperidin-4-yl)methyl)-3-methylurea, 4 hydrochloride (400 mg, 0.438 mmol) in MeCN (5 mL) was added DIEA (0.391 mL, 2.188 mmol) and ethyl 2-bromoacetate (0.053 mL, 0.481 mmol). The reaction was stirred at 15° C. for 10 h under $N_2$ atmosphere then concentrated. Saturated aqueous $NaHCO_3$ solution (15 mL) was added and the aqueous layer was extracted with DCM (150 mL×2). The combined extracts were washed with brine (150 mL×2), dried over $Na_2SO_4$, filtered and concentrated to yield a yellow solid of ethyl 2-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)acetate (300 mg, 0.313 mmol, 71.5% yield): $^1$H NMR (400 MHz, $CD_3OD$) δ ppm 8.34 (s, 2H), 7.84 (d, J=1.5 Hz, 2H), 7.68 (s, 1H), 7.46 (s, 1H), 7.07 (s, 1H), 4.24-4.19 (m, 2H), 3.95-3.84 (m, 4H), 3.66 (s, 2H), 3.28-3.23 (m, 4H), 3.08-3.03 (m, 2H), 2.98 (d, J=11.0 Hz, 2H), 2.72-2.68 (m, 5H), 2.14 (t, J=10.5 Hz, 2H), 1.76 (d, J=11.5 Hz, 2H), 1.53-1.50 (m, 1H), 1.37-1.35 (m, 2H), 1.32-1.29 (m, 3H); ES-LCMS m/z 671.3, 673.3 [M+H]$^+$.

Step 2: 1-((1-((2-(3,5-Dichlorophenyl)-6-((2-(4-(2-hydroxyethyl)piperazin-1-yl)pyrimidin-5-yl)oxy)pyridin-4-yl)methyl)piperidin-4-yl)methyl)-3-methylurea, 4 hydrochloride

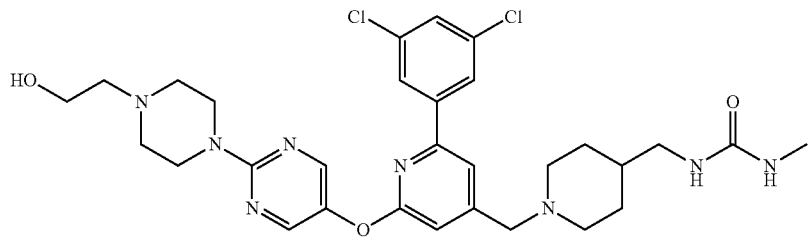 [SMILES: CNC(=O)NCC1CCN(Cc2cc(Oc3cnc(N4CCN(CCO)CC4)nc3)nc(-c3cc(Cl)cc(Cl)c3)c2)CC1]

To a mixture of ethyl 2-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)acetate (300 mg, 0.313 mmol) in THF (10 mL) was added $LiAlH_4$ (17.80 mg, 0.469 mmol). The reaction was stirred at −20° C. for 10 min then quenched with 1 mL of water. The mixture was filtered and concentrated. The mixture was purified by preparative HPLC (MeCN/$H_2O$ as eluents, acidic condition) and dried by lyophilization to yield a white solid of 1-((1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)methyl)-3-methylurea, 4 hydrochloride (37.11 mg, 0.048 mmol, 15.3% yield): $^1$H NMR (400 MHz, $CD_3OD$) δ ppm 8.48 (s, 2H), 7.92-7.85 (m, 3H), 7.54 (s, 1H), 7.33 (s, 1H), 4.93 (br. s, 2H), 4.45 (s, 2H), 4.01-3.92 (m, 2H), 3.75 (d, J=12.0 Hz, 2H), 3.62 (d, J=12.5 Hz, 2H), 3.55-3.43 (m, 2H), 3.38 (d, J=5.5 Hz, 2H), 3.28-3.22 (m, 2H), 3.17-3.04 (m, 4H), 2.73-2.68 (m, 3H), 2.02 (d, J=14.1 Hz, 3H), 1.55 (d, J=14.1 Hz, 2H); ES-LCMS m/z 629.4, 631.4 [M+H]$^+$.

Example 48: 3-((4-(5-((6-(3,5-Dichlorophenyl)-4-((4-((3-methylureido)methyl)piperidin-1-yl)methyl)pyridin-2-yl)oxy)pyrimidin-2-yl)piperazin-1-yl)propane-1-sulfonamide. 4 hydrochloride

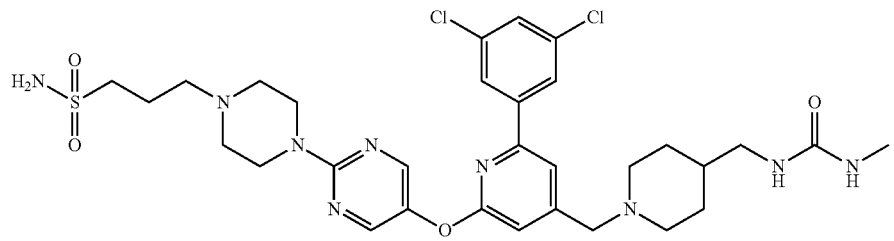 [SMILES: CNC(=O)NCC1CCN(Cc2cc(Oc3cnc(N4CCN(CCCS(N)(=O)=O)CC4)nc3)nc(-c3cc(Cl)cc(Cl)c3)c2)CC1]

To a solution of 1-((1-((2-(3,5-dichlorophenyl)-6-((2-(piperazin-1-yl)pyrimidin-5-yl)oxy)pyridin-4-yl)methyl)piperidin-4-yl)methyl)-3-methylurea (250 mg, 0.367 mmol) in NMP (5 mL) was added 3-chloropropane-1-sulfonamide (152 mg, 0.918 mmol) and DIEA (0.192 mL, 1.102 mmol). The solution was stirred at 120° C. for 3 h under microwave. Then the mixture was concentrated to give the residue which was purified by preparative HPLC (MeCN/H$_2$O as eluents, acidic condition) and lyophilized to yield a white solid 3-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)propane-1-sulfonamide, 4 hydrochloride (21.98 mg, 0.026 mmol, 7.0% yield): $^1$H NMR (400 MHz, CD$_3$OD) δ ppm 8.48-8.44 (m, 2H), 7.91 (s, 1H), 7.87 (d, J=1.3 Hz, 2H), 7.50 (s, 1H), 7.31 (s, 1H), 4.94 (d, J=14.6 Hz, 2H), 4.43 (s, 2H), 3.72 (d, J=12.3 Hz, 2H), 3.59 (d, J=11.9 Hz, 2H), 3.50-3.37 (m, 5H), 3.27-3.15 (m, 5H), 3.12-3.03 (m, 4H), 2.72-2.66 (m, 3H), 2.38-2.29 (m, 2H), 1.98 (d, J=13.7 Hz, 2H), 1.80 (br. s, 1H), 1.61-1.48 (m, 2H); ES-LCMS m/z 706.2, 708.2 [M+H]$^+$.

Example 49: Methyl((1-((2-(3,5-dichlorophenyl)-6-((2-(piperazin-1-yl)pyrimidin-5-yl)oxy)pyridin-4-yl)methyl)piperidin-4-yl)methyl)carbamate, 4 hydrochloride

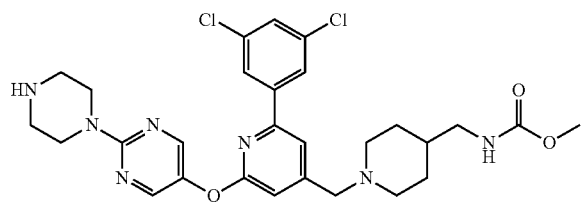 [SMILES: COC(=O)NCC1CCN(Cc2cc(Oc3cnc(N4CCNCC4)nc3)nc(-c3cc(Cl)cc(Cl)c3)c2)CC1]

Step 1: tert-Butyl 4-(5-((6-(3,5-dichlorophenyl)-4-((4-(((methoxycarbonyl)amino)methyl)piperidin-1-yl)methyl)pyridin-2-yl)oxy)pyrimidin-2-yl)piperazine-1-carboxylate

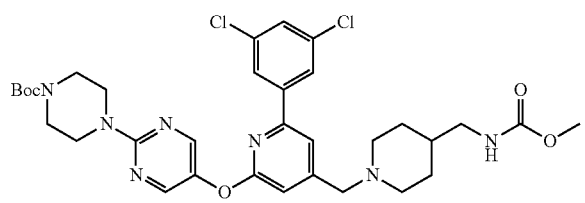 [SMILES: COC(=O)NCC1CCN(Cc2cc(Oc3cnc(N4CCN(C(=O)OC(C)(C)C)CC4)nc3)nc(-c3cc(Cl)cc(Cl)c3)c2)CC1]

To a solution of tert-butyl 4-(5-((6-(3,5-dichlorophenyl)-4-(((methylsulfonyl)oxy)methyl)pyridin-2-yl)oxy)pyrimidin-2-yl)piperazine-1-carboxylate (4 g, 5.44 mmol) and methyl(piperidin-4-ylmethyl)carbamate hydrochloride (1.433 g, 6.53 mmol) in DMF (20 mL) was added K$_2$CO$_3$ (3.69 g, 16.31 mmol). The mixture was stirred at 20° C. for 6 h then filtered and concentrated. The residue was distributed between DCM (30 mL) and saturated NaHCO$_3$ solution (20 mL) and the aqueous phase was extracted with DCM (10 mL×2). The combined organic extracts were washed with brine (20 mL), dried over Na$_2$SO$_4$, filtered and concentrated to yield a yellow solid of tert-butyl 4-(5-((6-(3,5-dichlorophenyl)-4-((4-(((methoxycarbonyl)amino)methyl)piperidin-1-yl)methyl)pyridin-2-yl)oxy)pyrimidin-2-yl)piperazine-1-carboxylate (3.8 g, 5.15 mmol, 95.0% yield): $^1$H NMR (400 MHz, CD$_3$OD) δ ppm 8.32 (s, 2H), 7.81-7.76 (m, 2H), 7.62 (s, 1H), 7.41 (t, J=1.8 Hz, 1H), 7.02 (s, 1H), 3.87-3.78 (m, 4H), 3.69-3.56 (m, 5H), 3.51-3.50 (m, 4H), 3.04-2.95 (m, 2H), 2.92 (d, J=11.0 Hz, 2H), 2.07 (t, J=10.8 Hz, 2H), 1.71 (d, J=11.9 Hz, 2H), 1.50-1.49 (m, 10H), 1.36-1.23 (m, 2H); ES-LCMS m/z 686.2, 688.2 [M+H]$^+$.

Step 2: Methyl((1-((2-(3,5-dichlorophenyl)-6-((2-(piperazin-1-yl)pyrimidin-5-yl)oxy)pyridin-4-yl)methyl)piperidin-4-yl)methyl)carbamate, 4 hydrochloride

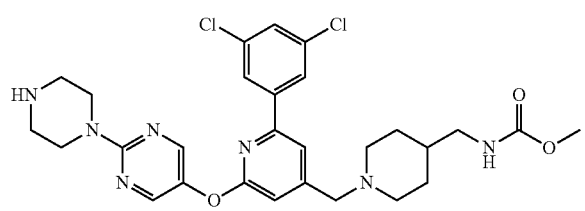 [SMILES: COC(=O)NCC1CCN(Cc2cc(Oc3cnc(N4CCNCC4)nc3)nc(-c3cc(Cl)cc(Cl)c3)c2)CC1]

To a solution of tert-butyl 4-(5-((6-(3,5-dichlorophenyl)-4-((4-(((methoxycarbonyl)amino)methyl)piperidin-1-yl)methyl)pyridin-2-yl)oxy)pyrimidin-2-yl)piperazine-1-carboxylate (3.8 g, 5.15 mmol) in MeOH (30 mL) was added in HCl solution (4.0 M in EtOAc, 10 mL, 40.0 mmol). The mixture was stirred at 20° C. for 0.2 h. Then the solution was concentrated and distributed between DCM (50 mL) and saturated NaHCO$_3$ (30 mL) solution. The aqueous phase was extracted with DCM (30 mL×2). The combined organic extracts were washed with brine (20 mL), dried over Na$_2$SO$_4$, filtered and concentrated to yield a white solid of methyl((1-((2-(3,5-dichlorophenyl)-6-((2-(piperazin-1-yl)pyrimidin-5-yl)oxy)pyridin-4-yl)methyl)piperidin-4-yl)methyl)carbamate (3.4 g, 4.99 mmol, 97% yield). 150 mg of the crude product was dissolved in DMSO (5 mL) was purified by preparative HPLC (MeCN/H$_2$O as eluent, acidic condition) and dried by lyophilization to yield a white solid of methyl((1-((2-(3,5-dichlorophenyl)-6-((2-(piperazin-1-yl)pyrimidin-5-yl)oxy)pyridin-4-yl)methyl)piperidin-4-yl)methyl)carbamate, 4 hydrochloride (63.37 mg, 0.086 mmol, 39.1% yield): $^1$H NMR (400 MHz, CD$_3$OD) δ ppm 8.48 (s, 2H), 7.99 (s, 1H), 7.87 (d, J=1.8 Hz, 2H), 7.47 (t, J=1.8 Hz, 1H), 7.38-7.33 (m, 1H), 4.56-4.55 (m, 2H), 4.21-4.09 (m, 4H), 3.66-3.56 (m, 5H), 3.40-3.34 (m, 4H), 3.12 (t, J=12.1 Hz, 2H), 3.04 (d, J=6.2 Hz, 2H), 1.97 (d, J=13.2 Hz, 2H), 1.83-1.80 (m, 1H), 1.68-1.52 (m, 2H); ES-LCMS m/z 586.3, 588.2 [M+H]$^+$.

Example 50: 3-(4-(5-((6-(3,5-Dichlorophenyl)-4-((methylamino)methyl)pyridin-2-yl)oxy)pyridin-2-yl)piperazin-1-yl)propanoic acid, 4 hydrochloride

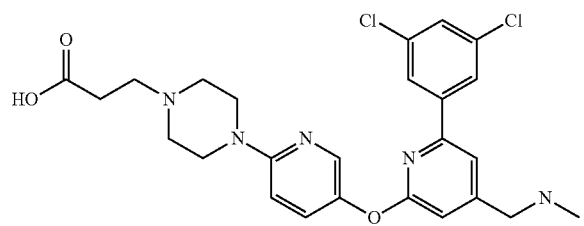 [SMILES: CNCc1cc(Oc2ccc(N3CCN(CCC(=O)O)CC3)nc2)nc(-c2cc(Cl)cc(Cl)c2)c1]

303

Step 1: tert-Butyl 4-(5-((6-(3,5-dichlorophenyl)-4-((methylamino)methyl)pyridin-2-yl)oxy)pyridin-2-yl)piperazine-1-carboxylate

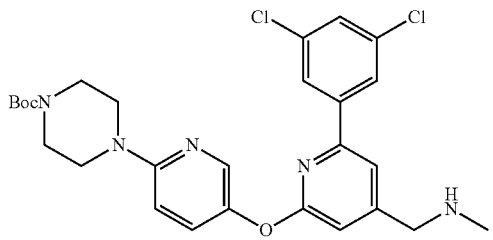 [SMILES: CNCc1cc(Oc2ccc(N3CCN(C(=O)OC(C)(C)C)CC3)nc2)nc(-c2cc(Cl)cc(Cl)c2)c1]

tert-Butyl 4-(5-((6-(3,5-dichlorophenyl)-4-(((methylsulfonyl)oxy)methyl)pyridin-2-yl)oxy)pyridine-2-yl)piperazine-1-carboxylate (0.55 g, 0.902 mmol) was dissolved in methanamine (30% in EtOH, 20 mL, 0.902 mmol). The reaction was stirred at 15° C. for 12 h then concentrated to yield brown oil of tert-butyl 4-(5-((6-(3,5-dichlorophenyl)-4-((methylamino)methyl)pyridin-2-yl)oxy)pyridin-2-yl)piperazine-1-carboxylate (0.6 g, 0.771 mmol, 85.0% yield): $^1$H NMR (400 MHz, CDCl$_3$) δ ppm 8.15-8.05 (m, 1H), 7.81-7.73 (m, 1H), 7.67 (d, J=1.8 Hz, 1H), 7.46-7.26 (m, 3H), 6.81 (d, J=8.4 Hz, 1H), 6.75-6.62 (m, 1H), 3.84 (s, 2H), 3.64-3.16 (m, 8H), 2.49 (s, 3H), 1.47 (s, 9H); ES-LCMS m/z 544.3, 546.3 [M+H]$^+$.

Step 2: tert-Butyl 4-(5-((4-((((benzyloxy)carbonyl)(methyl)amino)methyl)-6-(3,5-dichlorophenyl)pyridin-2-yl)oxy)pyridin-2-yl)piperazine-1-carboxylate

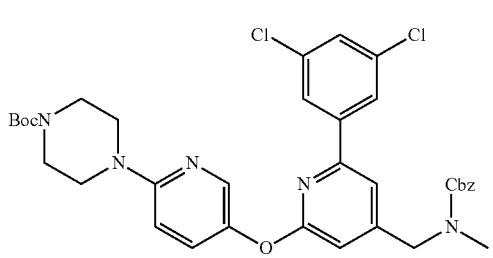 [SMILES: CN(Cc1cc(Oc2ccc(N3CCN(C(=O)OC(C)(C)C)CC3)nc2)nc(-c2cc(Cl)cc(Cl)c2)c1)C(=O)OCc1ccccc1]

To a solution of tert-butyl 4-(5-((6-(3,5-dichlorophenyl)-4-((methylamino)methyl)pyridin-2-yl)oxy)pyridin-2-yl)piperazine-1-carboxylate (0.5 g, 0.918 mmol) and DIEA (0.321 mL, 1.837 mmol) in DCM (40 mL) was added CbzCl (0.262 mL, 1.837 mmol). The mixture was stirred for 1.5 h at 0° C. The organic phase was washed with saturated aqueous NaHCO$_3$ (50 mL×2) and brine (50 mL), dried over Na$_2$SO$_4$, filtered and concentrated to yield brown oil of tert-butyl 4-(5-((4-((((benzyloxy)carbonyl)(methyl)amino)methyl)-6-(3,5-dichlorophenyl)pyridine-2-yl)oxy)pyridin-2-yl)piperazine-1-carboxylate (0.59 g, 0.696 mmol, 76.0% yield): $^1$H NMR (400 MHz, CDCl$_3$) δ ppm 8.21-8.06 (m, 1H), 7.81-7.59 (m, 2H), 7.41-7.30 (m, 8H), 6.82-6.62 (m, 2H), 5.19 (d, J=16.6 Hz, 2H), 4.53 (d, J=12.5 Hz, 2H), 3.57 (br. s, 4H), 3.54 (d, J=5.5 Hz, 3H), 3.05-2.91 (m, 4H), 1.50 (s, 9H); ES-LCMS m/z 678.3, 680.3 [M+H]$^+$.

304

Step 3: Benzyl ((2-(3,5-dichlorophenyl)-6-((6-(piperazin-1-yl)pyridin-3-yl)oxy)pyridine-4-yl)methyl)(methyl)carbamate

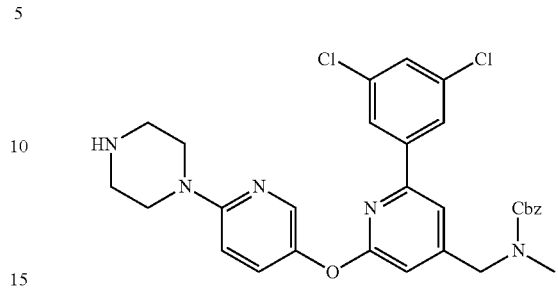

tert-Butyl 4-(5-((4-((((benzyloxy)carbonyl)(methyl)amino)methyl)-6-(3,5-dichlorophenyl)pyridin-2-yl)oxy)pyridin-2-yl)piperazine-1-carboxylate (0.59 g, 0.869 mmol) was dissolved in 4.0 M HCl in EtOAc (30 mL, 120 mmol). The mixture was stirred at 25° C. for 1 h then concentrated. The residue was dissolved in DCM (50 mL), washed with saturated NaHCO$_3$ solution (20 mL). The organic phase was concentrated to yield a brown solid of benzyl((2-(3,5-dichlorophenyl)-6-((6-(piperazin-1-yl)pyridin-3-yl)oxy)pyridin-4-yl)methyl)(methyl)carbamate (0.55 g, 0.761 mmol, 87.0% yield): $^1$H NMR (400 MHz, CDCl$_3$) δ ppm 10.09-9.73 (m, 1H), 8.20-7.92 (m, 1H), 7.52 (d, J=16.8 Hz, 2H), 7.35-7.21 (m, 9H), 6.98-6.64 (m, 1H), 5.16 (d, J=15.0 Hz, 2H), 4.64-4.51 (m, 2H), 4.50-4.11 (m, 4H), 3.98-3.46 (m, 4H), 3.01-2.86 (m, 3H); ES-LCMS m/z 578.3, 580.3 [M+H]$^+$.

Step 4: Ethyl 3-(4-(5-((4-((((benzyloxy)carbonyl)(methyl)amino)methyl)-6-(3,5-dichlorophenyl)pyridin-2-yl)oxy)pyridin-2-yl)piperazin-1-yl)propanoate

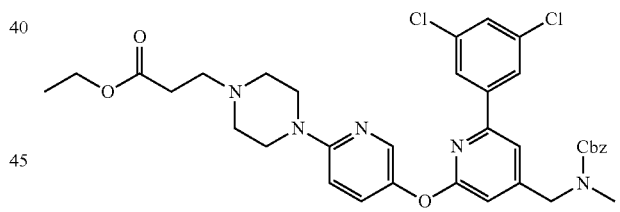

To a solution of benzyl ((2-(3,5-dichlorophenyl)-6-((6-(piperazin-1-yl)pyridin-3-yl)oxy)pyridine-4-yl)methyl)(methyl)carbamate (0.55 g, 0.951 mmol) and ethyl 3-bromopropanoate (0.207 g, 1.141 mmol) in DMF (30 mL) was added K$_2$CO$_3$ (0.263 g, 1.902 mmol). The reaction was stirred at 80° C. for 12 h then concentrated and purified by silica gel chromatography (DCM/MeOH=20/1). All fractions found to contain product by TLC (MeOH/DCM=1/10, R$_f$=0.4) were combined and concentrated to yield a brown solid of ethyl 3-(4-(5-((4-((((benzyloxy)carbonyl)(methyl)amino)methyl)-6-(3,5-dichlorophenyl)pyridin-2-yl)oxy)pyridin-2-yl)piperazin-1-yl)propanoate (0.7 g, 0.825 mmol, 87.0% yield): $^1$H NMR (400 MHz, CDCl$_3$) δ ppm 8.11-8.00 (m, 1H), 7.93 (s, 2H), 7.71-7.57 (m, 2H), 7.35-7.27 (m, 6H), 6.75-6.57 (m, 2H), 5.13 (d, J=17.2 Hz, 2H), 4.65-4.58 (m, 2H), 4.55-4.40 (m, 2H), 4.10 (q, J=7.1 Hz, 2H), 3.53-3.47 (m, 4H), 3.38 (s, 3H), 3.02-2.92 (m, 4H), 2.72 (t, J=7.7 Hz, 2H), 1.22 (t, J=7.1 Hz, 3H); ES-LCMS m/z 678.3, 680.3 [M+H]$^+$.

Step 5: 3-(4-(5-((4-((((Benzyloxy)carbonyl)(methyl) amino)methyl)-6-(3,5-dichlorophenyl)pyridin-2-yl) oxy)pyridin-2-yl)piperazin-1-yl)propanoic acid

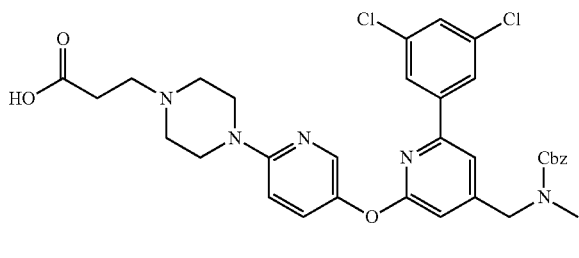

To a solution of ethyl 3-(4-(5-((4-(((((benzyloxy)carbonyl) (methyl)amino)methyl)-6-(3,5-dichlorophenyl)pyridin-2-yl)oxy)pyridin-2-yl)piperazin-1-yl)propanoate (0.70 g, 1.032 mmol) in MeOH (30 mL) and H₂O (1 mL) was added NaOH (0.083 g, 2.063 mmol). The reaction mixture was stirred for 8 h at 25° C., then adjust pH to 7 by 1 N HCl solution. The mixture was concentrated to yield a white solid of 3-(4-(5-((4-((((benzyloxy)carbonyl)(methyl)amino) methyl)-6-(3,5-dichlorophenyl)pyridin-2-yl)oxy)pyridin-2-yl)piperazin-1-yl)propanoic acid (0.8 g, 0.861 mmol, 83.0% yield): $^1$H NMR (400 MHz, CD$_3$OD) δ ppm 8.19 (s, 3H), 7.97 (s, 2H), 7.87 (s, 3H), 7.74 (s, 1H), 7.57-7.50 (m, 4H), 5.10 (d, J=11.2 Hz, 2H), 4.43 (s, 2H), 4.38-4.36 (m, 2H), 3.63-3.50 (m, 4H), 3.32-3.22 (m, 4H), 3.05-3.03 (m, 2H), 2.83 (s, 3H); ES-LCMS m/z 650.3, 652.3 [M+H]$^+$.

Step 6: 3-(4-(5-((6-(3,5-Dichlorophenyl)-4-((methylamino)methyl)pyridin-2-yl)oxy)pyridin-2-yl)piperazin-1-yl)propanoic acid, 4 hydrochloride

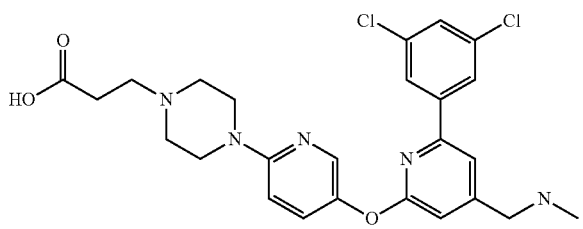

3-(4-(5-((4-((((Benzyloxy)carbonyl)(methyl)amino) methyl)-6-(3,5-dichlorophenyl)pyridin-2-yl)oxy)pyridin-2-yl)piperazin-1-yl)propanoic acid (0.5 g, 0.769 mmol) was dissolved in TFA (30 mL) and stirred at 50° C. for 2 h then concentrated and purified by preparative HPLC (MeCN/H₂O as eluent, acidic condition) to yield a white solid of 3-(4-(5-((6-(3,5-dichlorophenyl)-4-((methylamino)methyl) pyridin-2-yl)oxy)pyridin-2-yl)piperazin-1-yl)propanoic acid, 4 hydrochloride (66.24 mg, 0.096 mmol, 12.5% yield): $^1$H NMR (400 MHz, CD$_3$OD) δ ppm 8.21 (d, J=2.5 Hz, 1H), 7.96 (dd, J=2.5, 9.5 Hz, 1H), 7.91-7.82 (m, 3H), 7.53 (s, 1H), 7.40 (d, J=9.5 Hz, 1H), 7.28 (s, 1H), 4.38 (s, 4H), 3.94-3.38 (m, 8H), 2.97 (t, J=7.0 Hz, 2H), 2.85 (s, 3H); ES-LCMS m/z 516.2, 518.2 [M+H]$^+$.

Example 51: 3-((4-(5-((6-(3,5-Dichlorophenyl)-4-((4-fluoro-4-(((methoxycarbonyl)amino)methyl) piperidin-1-yl)methyl)pyridin-2-yl)oxy)pyrimidin-2-yl)piperazin-1-yl)propanoic acid, 4 hydrochloride

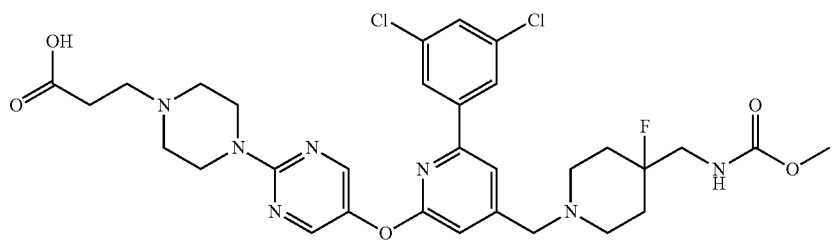 [SMILES: COC(=O)NCC1(F)CCN(Cc2cc(Oc3cnc(N4CCN(CCC(=O)O)CC4)nc3)nc(-c3cc(Cl)cc(Cl)c3)c2)CC1]

Step 1: tert-Butyl 4-((tert-butyldimethylsilyl)oxy)-4-(((methoxycarbonyl)amino)methyl)piperidine-1-carboxylate

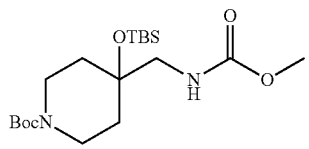 [SMILES: COC(=O)NCC1(O[Si](C)(C)C(C)(C)C)CCN(C(=O)OC(C)(C)C)CC1]

To a solution of tert-butyl 4-(aminomethyl)-4-((tert-butyldimethylsilyl)oxy)piperidine-1-carboxylate (5 g, 11.61 mmol), DIEA (8.11 mL, 46.4 mmol) in DCM (50 mL) was added methyl carbonochloridate (1.371 mL, 17.41 mmol) at 0° C. The reaction mixture was stirred at 0° C. for 0.5 h then filtered, concentrated and purified by flash chromatography (PE/EtOAc=100/0 to 4/1). All fractions found to contain product by TLC (PE/EtOAc=3/1), R$_f$=0.4) were combined and concentrated to yield a white solid tert-butyl 4-((tert-butyldimethylsilyl)oxy)-4-(((methoxycarbonyl)amino) methyl)piperidine-1-carboxylate (3.3 g, 6.56 mmol, 56.5% yield): $^1$H NMR (400 MHz, CDCl$_3$) δ ppm 3.67 (d, J=4.4 Hz, 3H), 3.49 (br. s, 2H), 3.44-3.34 (m, 2H), 3.26 (br. s, 2H), 1.56 (br. s, 4H), 1.45 (d, J=4.9 Hz, 9H), 1.02-0.77 (m, 9H), 0.27-0.03 (m, 6H); ES-LCMS m/z 425.2 [M+Na]$^+$.

Step 2: tert-Butyl 4-hydroxy-4-(((methoxycarbonyl)amino)methyl)piperidine-1-carboxylate

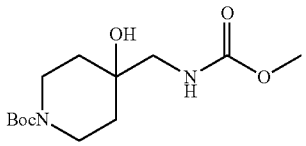 [SMILES: COC(=O)NCC1(O)CCN(C(=O)OC(C)(C)C)CC1]

To a solution of tert-butyl 4-((tert-butyldimethylsilyl)oxy)-4-(((methoxycarbonyl)amino)methyl)piperidine-1-carboxylate (3.3 g, 6.56 mmol) in THF (30 mL) was added TBAF (1 M in THF, 13.11 mL, 13.11 mmol). The reaction mixture was stirred at 25° C. for 6 h. Water (50 mL) was added and extracted with DCM (50 mL×3). The combined organic layers were dried over Na$_2$SO$_4$ and concentrated and purified by flash chromatography (DCM/MeOH=100/0 to 10/1). All fractions found to contain product by TLC (DCM/MeOH=20/1, R$_f$=0.15) were combined and concentrated to yield a colorless oil of tert-butyl 4-hydroxy-4-(((methoxycarbonyl)amino)methyl)piperidine-1-carboxylate (1.9 g, 5.93 mmol, 90.0% yield): $^1$H NMR (400 MHz, CDCl$_3$) δ ppm 3.83-3.64 (m, 2H), 3.59 (s, 3H), 3.10 (br. s, 4H), 1.59-1.39 (m, 4H), 1.39-1.32 (m, 9H)

Step 3: tert-Butyl 4-fluoro-4-(((methoxycarbonyl)amino)methyl)piperidine-1-carboxylate

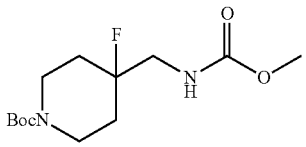 [SMILES: COC(=O)NCC1(F)CCN(C(=O)OC(C)(C)C)CC1]

To a solution of tert-butyl 4-hydroxy-4-(((methoxycarbonyl)amino)methyl)piperidine-1-carboxylate (1.9 g, 5.93 mmol) in DCM (30 mL) was added DAST (1.019 mL, 7.71 mmol) at −78° C. The reaction mixture was stirred at −78° C. for 2 h then concentrated and purified by flash chromatography (PE/EA=100/0 to 4/1). All fractions found to contain product by TLC (PE/EA=3/1, R$_f$=0.3) were combined and concentrated to yield a white solid of tert-butyl 4-fluoro-4-(((methoxycarbonyl)amino)methyl)piperidine-1-carboxylate (0.3 g, 0.827 mmol, 13.9% yield): $^1$H NMR (400 MHz, CDCl$_3$) δ ppm 3.67 (br. s, 3H), 3.49 (d, J=4.9 Hz, 2H), 3.36 (d, J=19.4 Hz, 2H), 3.07 (br. s, 2H), 1.85-1.75 (m, 2H), 1.67-1.51 (m, 2H), 1.50-1.44 (m, 9H).

Step 4: Methyl ((4-fluoropiperidin-4-yl)methyl)carbamate

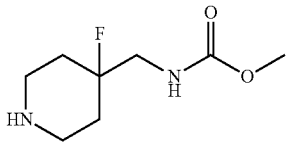

tert-Butyl 4-fluoro-4-(((methoxycarbonyl)amino)methyl)piperidine-1-carboxylate (0.3 g, 0.827 mmol) was dissolved in HCl solution (4.0 M in EtOAc, 10 mL, 40 mmol). The reaction was stirred at 20° C. for 0.5 h then concentrated to yield a brown solid of methyl((4-fluoropiperidin-4-yl)methyl)carbamate, hydrochloride (0.2 g, 0.706 mmol, 85.0% yield): $^1$H NMR (400 MHz, CDCl$_3$) δ ppm 3.80-3.62 (m, 3H), 3.60 (br. s, 2H), 3.48-3.11 (m, 4H), 2.49-1.85 (m, 4H)

Step 5: tert-Butyl 4-(5-((6-(3,5-dichlorophenyl)-4-((4-fluoro-4-(((methoxycarbonyl)amino)methyl)piperidin-1-yl)methyl)pyridin-2-yl)oxy)pyrimidin-2-yl)piperazine-1-carboxylate

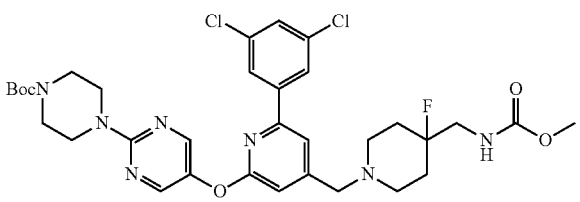 [SMILES: COC(=O)NCC1(F)CCN(Cc2cc(Oc3cnc(N4CCN(C(=O)OC(C)(C)C)CC4)nc3)nc(-c3cc(Cl)cc(Cl)c3)c2)CC1]

To a solution of tert-butyl 4-(5-((6-(3,5-dichlorophenyl)-4-(((methylsulfonyl)oxy)methyl)pyridin-2-yl)oxy)pyrimidin-2-yl)piperazine-1-carboxylate (0.4 g, 0.516 mmol) and methyl((4-fluoropiperidin-4-yl)methyl)carbamate, hydrochloride (0.175 g, 0.619 mmol) in MeCN (15 mL) was added K$_2$CO$_3$ (0.214 g, 1.547 mmol). The reaction mixture was stirred at 80° C. for 6 h then filtered, concentrated and purified by preparative TLC (PE/EtOAc=1/1, R$_f$=0.5) to yield a brown solid of tert-butyl 4-(5-((6-(3,5-dichlorophenyl)-4-((4-fluoro-4-(((methoxycarbonyl)amino)methyl)piperidin-1-yl)methyl)pyridine-2-yl)oxy)pyrimidin-2-yl)piperazine-1-carboxylate (0.2 g, 0.255 mmol, 49.5% yield): $^1$H NMR (400 MHz, CDCl$_3$) δ ppm 8.34 (s, 2H), 8.30 (s, 2H), 7.71 (s, 1H), 7.43 (s, 1H), 7.34 (s, 1H), 6.91 (s, 1H), 3.84-3.81 (m, 4H), 3.68 (s, 3H), 3.57-3.54 (m, 2H), 3.53-3.52 (m, 4H), 3.51-3.37 (m, 2H), 2.70-2.68 (m, 2H), 2.42-2.40 (m, 2H), 1.87-1.84 (m, 2H), 1.62-1.58 (m, 2H), 1.49 (s, 9H); ES-LCMS m/z 704.2, 706.2 [M+H]$^+$.

Step 6: Methyl((1-((2-(3,5-dichlorophenyl)-6-((2-(piperazin-1-yl)pyrimidin-5-yl)oxy)pyridin-4-yl)methyl)-4-fluoropiperidin-4-yl)methyl)carbamate

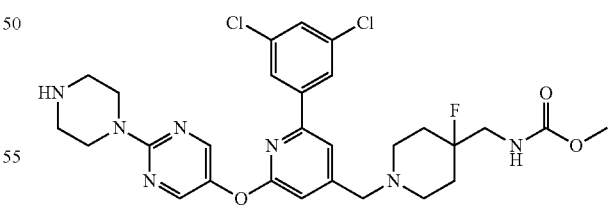

tert-Butyl 4-(5-((6-(3,5-dichlorophenyl)-4-((4-fluoro-4-(((methoxycarbonyl)amino)methyl)piperidin-1-yl)methyl)pyridin-2-yl)oxy)pyrimidin-2-yl)piperazine-1-carboxylate (0.2 g, 0.255 mmol) was dissolved in 4.0 M HCl in EtOAc, (10 mL, 40 mmol). The reaction was stirred at 20° C. for 0.5 h then concentrated and dissolved in DCM (30 mL). The mixture was washed with saturated NaHCO$_3$ solution and dried over Na$_2$SO$_4$, concentrated to yield a brown solid of methyl((1-((2-(3,5-dichlorophenyl)-6-((2-(piperazin-1-yl)

pyrimidin-5-yl)oxy)pyridin-4-yl)methyl)-4-fluoropiperidin-4-yl)methyl)carbamate (0.16 g, 0.245 mmol, 96.0% yield): ¹H NMR (400 MHz, CDCl₃) δ ppm 8.34-8.26 (m, 2H), 7.74 (d, J=1.8 Hz, 2H), 7.47-7.39 (m, 1H), 7.36 (s, 1H), 6.91 (s, 1H), 3.94-3.80 (m, 4H), 3.70 (s, 3H), 3.58 (s, 2H), 3.50-3.32 (m, 2H), 3.08-2.95 (m, 4H), 2.70 (d, J=11.5 Hz, 2H), 2.41 (t, J=10.6 Hz, 2H), 1.99-1.78 (m, 4H); ES-LCMS m/z 604.2, 606.3 [M+H]⁺.

Step 7: 3-(4-(5-((6-(3,5-Dichlorophenyl)-4-((4-fluoro-4-(((methoxycarbonyl)amino)methyl)piperidin-1-yl)methyl)pyridin-2-yl)oxy)pyrimidin-2-yl)piperazin-1-yl)propanoic acid, 4 hydrochloride

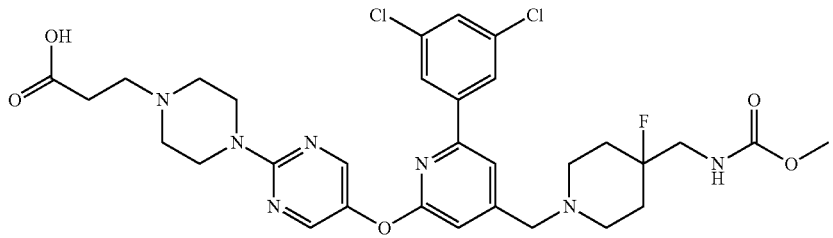 [SMILES: COC(=O)NCC1(F)CCN(Cc2cc(Oc3cnc(N4CCN(CCC(=O)O)CC4)nc3)nc(-c3cc(Cl)cc(Cl)c3)c2)CC1]

To a solution of methyl((1-((2-(3,5-dichlorophenyl)-6-((2-(piperazin-1-yl)pyrimidin-5-yl)oxy)pyridin-4-yl)methyl)-4-fluoropiperidin-4-yl)methyl)carbamate (0.14 g, 0.214 mmol) and 3-bromopropanoic acid (0.983 g, 6.42 mmol) in MeCN (30 mL) was added DIEA (0.935 mL, 5.35 mmol). The reaction mixture was stirred at 80° C. for 5 h then concentrated to yield crude product which was purified by preparative HPLC (MeCN/H₂O as eluents, acidic condition) and lyophilized to yield a white solid of 3-(4-(5-((6-(3,5-dichlorophenyl)-4-((4-fluoro-4-(((methoxycarbonyl)amino)methyl)piperidin-1-yl)methyl)pyridin-2-yl)oxy)pyrimidin-2-yl)piperazin-1-yl)propanoic acid, 4 hydrochloride (76.72 mg, 0.093 mmol, 43.5% yield): ¹H NMR (400 MHz, CD₃OD) δ ppm 8.45 (s, 2H), 8.00-7.94 (m, 1H), 7.87 (d, J=1.8 Hz, 2H), 7.48 (s, 1H), 7.35 (s, 1H), 4.50 (s, 2H), 3.85-3.57 (m, 6H), 3.56-3.47 (m, 4H), 3.47-3.30 (m, 7H), 3.29-3.15 (m, 2H), 2.92 (t, J=7.1 Hz, 2H), 2.25-2.01 (m, 4H); ES-LCMS m/z 676.3, 678.2 [M+H]⁺.

Example 52: 2-(1-((2-(3,5-Dichlorophenyl)-6-((2-(4-methylpiperazin-1-yl)pyrimidin-5-yl)oxy)pyridin-4-yl)methyl)piperidin-4-yl)ethanol

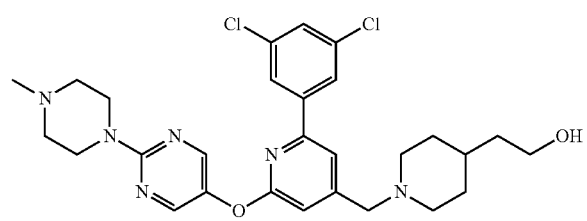 [SMILES: CN1CCN(c2ncc(Oc3cc(CN4CCC(CCO)CC4)cc(-c4cc(Cl)cc(Cl)c4)n3)cn2)CC1]

Step 1: 2-(Piperidin-4-yl)ethanol

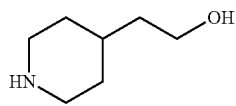

To a mixture of tert-butyl 4-(2-hydroxyethyl)piperidine-1-carboxylate (800 mg, 2.79 mmol) in DCM (20 mL) was added HCl solution (4.0 M in EtOAc, 20 mL, 80 mmol) at 20° C. The mixture was stirred at 20° C. for 0.5 h then concentrated. The residue was partitioned between DCM (250 mL) and saturated aqueous NaHCO₃ (250 mL) solution. Separated and the aqueous phase was extracted with DCM (250 mL×2). The combined organic layers were dried over Na₂SO₄, filtered and concentrated to yield a brown solid of 2-(piperidin-4-yl)ethanol (400 mg, 2.477 mmol, 89.0% yield): ¹H NMR (400 MHz, CD₃OD) δ ppm 3.62 (t, J=6.6 Hz, 2H), 3.37 (d, J=12.8 Hz, 2H), 2.97 (t, J=12.6 Hz, 2H), 1.95 (d, J=14.1 Hz, 2H), 1.78 (m, 1H), 1.53 (q, J=6.6 Hz, 2H), 1.47-1.35 (m, 2H).

Step 2: tert-Butyl 4-(5-((6-(3,5-dichlorophenyl)-4-((4-(2-hydroxyethyl)piperidin-1-yl)methyl)pyridin-2-yl)oxy)pyrimidin-2-yl)piperazine-1-carboxylate

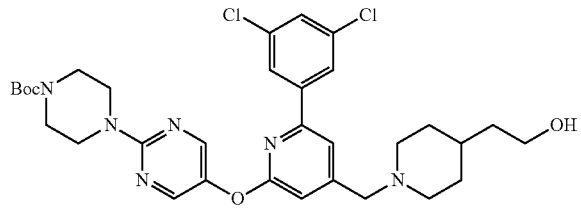 [SMILES: CC(C)(C)OC(=O)N1CCN(c2ncc(Oc3cc(CN4CCC(CCO)CC4)cc(-c4cc(Cl)cc(Cl)c4)n3)cn2)CC1]

To a mixture of tert-butyl 4-(5-((6-(3,5-dichlorophenyl)-4-(((methylsulfonyl)oxy)methyl)pyridin-2-yl)oxy)pyrimidin-2-yl)piperazine-1-carboxylate (600 mg, 0.835 mmol) in DML (50 mL) was added K₂CO₃ (346 mg, 2.506 mmol) and 2-(piperidin-4-yl)ethanol (337 mg, 2.088 mmol). The mixture was stirred at 25° C. for 7 h then filtered, concentrated and purified by silica gel column chromatography (DCM/MeOH=10/1). All fractions found to contain product by TLC analysis (DCM/MeOH=10/1, R_f=0.6) were combined and concentrated to yield a yellow solid of tert-butyl 4-(5-((6-(3,5-dichlorophenyl)-4-((4-(2-hydroxyethyl)piperidin-1-yl)methyl)pyridin-2-yl)oxy)pyrimidin-2-yl)piperazine-1-carboxylate (400 mg, 0.398 mmol, 47.6% yield): ¹H NMR (400 MHz, CDCl₃) δ ppm 8.30 (s, 2H), 7.74-7.67 (m, 2H), 7.41 (s, 1H), 7.33 (br. s, 1H), 6.91-6.87 (m, 1H), 4.06 (br. s, 2H), 3.82 (br. s, 4H), 3.70 (br. s, 4H), 2.74-2.62 (m, 2H), 2.02 (t, J=11.2 Hz, 2H), 1.71-1.60 (m, 5H), 1.44 (s, 9H), 1.35-1.25 (m, 2H), 1.15-1.04 (m, 2H); LC-MS m/z 643.4, 645.4 [M+H]+.

Step 3: 2-(1-((2-(3,5-Dichlorophenyl)-6-((2-(piperazin-1-yl)pyrimidin-5-yl)oxy)pyridine-4-yl)methyl)piperidin-4-yl)ethanol

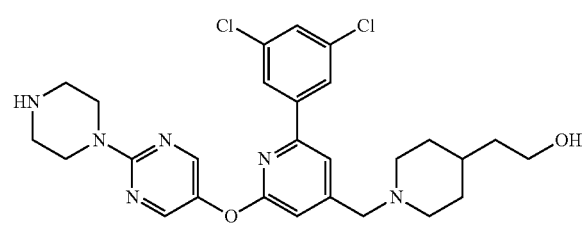 [SMILES: OCCC1CCN(Cc2cc(Oc3cnc(N4CCNCC4)nc3)nc(-c3cc(Cl)cc(Cl)c3)c2)CC1]

To a mixture of tert-butyl 4-(5-((6-(3,5-dichlorophenyl)-4-((4-(2-hydroxyethyl)piperidin-1-yl)methyl)pyridin-2-yl)oxy)pyrimidin-2-yl)piperazine-1-carboxylate (400 mg, 0.398 mmol) in EtOAc (5 mL) was added HCl solution (4.0 M in EtOAc, 5 mL, 20.00 mmol). The reaction was stirred at 25° C. for 20 min then saturated NaHCO₃ solution (10 mL) was added and the mixture was extracted with DCM (20 mL×2). The combined organic layers were dried over Na₂SO₄, filtered and concentrated to yield a yellow solid of 2-(1-((2-(3,5-dichlorophenyl)-6-((2-(piperazin-1-yl)pyrimidin-5-yl)oxy)pyridin-4-yl)methyl)piperidin-4-yl)ethanol (308 mg, 0.385 mmol, 97.0% yield): ¹H NMR (400 MHz, CD₃OD) δ ppm 8.74-8.69 (m, 2H), 8.12-8.08 (m, 2H), 7.91 (d, J=1.8 Hz, 1H), 7.83-7.79 (m, 1H), 7.47-7.44 (m, 1H), 4.48 (s, 2H), 4.26-4.19 (m, 4H), 3.44 (d, J=4.4 Hz, 4H), 3.39 (br. s, 2H), 3.15 (t, J=11.9 Hz, 2H), 3.01-2.96 (m, 2H), 1.95 (d, J=15.4 Hz, 3H), 1.66 (d, J=11.5 Hz, 2H), 1.46-1.40 (m, 2H); LC-MS m/z 543.3, 545.3 [M+H]+.

Step 4: 2-(1-((2-(3,5-Dichlorophenyl)-6-((2-(4-methylpiperazin-1-yl)pyrimidin-5-yl)oxy)pyridin-4-yl)methyl)piperidin-4-yl)ethanol

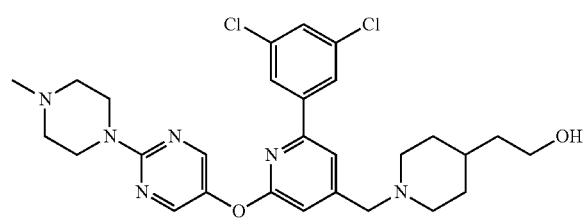 [SMILES: CN1CCN(c2ncc(Oc3cc(CN4CCC(CCO)CC4)cc(-c4cc(Cl)cc(Cl)c4)n3)cn2)CC1]

To a solution of 2-(1-((2-(3,5-dichlorophenyl)-6-((2-(piperazin-1-yl)pyrimidin-5-yl)oxy)pyridine-4-yl)methyl)piperidin-4-yl)ethanol (308 mg, 0.385 mmol) in MeOH (5 mL) and DCM (5 mL) was added paraformaldehyde (34.7 mg, 1.156 mmol), AcOH (4.41 μL, 0.077 mmol) and 4 Å molecular sieves (300 mg, 0.385 mmol). The reaction mixture was stirred at 25° C. for 5 h under N₂ atmosphere then NaBH₃CN (72.7 mg, 1.156 mmol) was added. The reaction was stirred at 25° C. for 2 h then filtered, concentrated to yield the residue which was distributed between DCM (30 mL) and H₂O (20 mL), extracted with DCM (30 mL×2). The combined organic layers were washed with brine (20 mL), dried over Na₂SO₄, filtered and concentrated. The crude product was purified by preparative HPLC (MeCN/H₂O as eluents, basic condition) and lyophilized to yield a white solid of 2-(1-((2-(3,5-dichlorophenyl)-6-((2-(4-methylpiperazin-1-yl)pyrimidin-5-yl)oxy)pyridin-4-yl)methyl)piperidin-4-yl)ethanol (51.2 mg, 0.092 mmol, 23.8% yield): ¹H NMR (400 MHz, CD₃OD) δ ppm 8.31 (s, 2H), 7.81 (s, 2H), 7.64 (s, 1H), 7.42 (br. s, 1H), 7.03 (s, 1H), 3.86 (br. s, 4H), 3.60 (br. s, 4H), 2.92 (d, J=9.7 Hz, 2H), 2.53 (br. s, 4H), 2.34 (s, 3H), 2.09 (t, J=11.5 Hz, 2H), 1.73 (d, J=12.8 Hz, 2H), 1.49 (br. s, 3H), 1.30 (d, J=10.6 Hz, 2H); LC-MS m/z 557.4, 559.3 [M+H]+.

Example 53: 2-((1-((2-(3,5-Dichlorophenyl)-6-((2-(4-methylpiperazin-1-yl)pyrimidin-5-yl)oxy)pyridin-4-yl)methyl)piperidin-4-yl)oxy)acetic acid, 4 hydrochloride

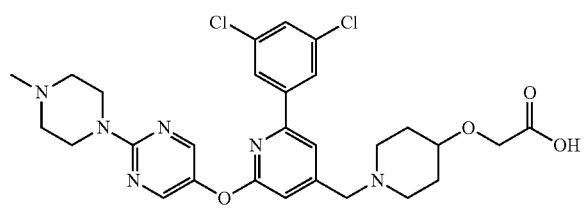 [SMILES: CN1CCN(c2ncc(Oc3cc(CN4CCC(OCC(=O)O)CC4)cc(-c4cc(Cl)cc(Cl)c4)n3)cn2)CC1]

Step 1: tert-Butyl 4-(2-ethoxy-2-oxoethoxy)piperidine-1-carboxylate

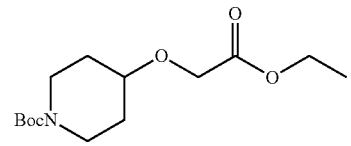 [SMILES: CCOC(=O)COC1CCN(C(=O)OC(C)(C)C)CC1]

To a solution of tert-butyl 4-hydroxypiperidine-1-carboxylate (3 g, 14.91 mmol) in THF (20 mL) was added NaH (0.894 g, 22.36 mmol) at 20° C. under N₂ atmosphere for 1 h. Then, ethyl 2-bromoacetate (7.47 g, 44.7 mmol) was added and the mixture was stirred at 50° C. for 9 h. Water (2 mL) was added and the mixture was concentrated to yield the residue which was partitioned between DCM (50 mL) and saturated aqueous NaHCO₃ solution (50 mL), extracted with DCM (50 mL×2). The combined organic layers were dried over Na₂SO₄, filtered and concentrated to yield crude product. The crude product was purified by silica gel column chromatography (PE/EtOAc=1/2). All fractions found to contain product by TLC (EtOAc=100%, R_f=0.6) were combined and concentrated to yield a colorless oil of tert-butyl 4-(2-ethoxy-2-oxoethoxy)piperidine-1-carboxylate (1.2 g, 3.76 mmol, 25.2% yield): ¹H NMR (400 MHz, CDCl₃) δ ppm 4.26-4.16 (m, 2H), 4.13-4.05 (m, 2H), 3.77 (br. s, 2H), 3.62-3.51 (m, 1H), 3.13-3.00 (m, 2H), 1.84 (br. s, 2H), 1.62-1.53 (m, 2H), 1.45 (s, 9H), 1.31-1.23 (m, 3H); ES-LCMS m/z 232.2 [M−t−Bu+H]+.

Step 2: Methyl 2-(piperidin-4-yloxy)acetate, hydrochloride

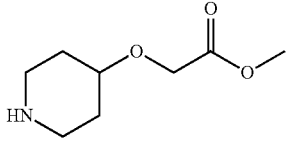

A solution of tert-butyl 4-(2-ethoxy-2-oxoethoxy)piperidin-1-carboxylate (1.2 g, 3.76 mmol) in 4.0 M in MeOH, (10 mL, 40.0 mmol) was stirred at 20° C. for 10 min then concentrated to yield a white solid of methyl 2-(piperidin-4-yloxy)acetate, hydrochloride (0.8 g, 3.62 mmol, 96.0% yield): $^1$H NMR (400 MHz, CD$_3$OD) δ ppm 4.24-4.18 (m, 2H), 3.77-3.72 (m, 3H), 3.38-3.29 (m, 4H), 3.14 (d, J=6.6 Hz, 1H), 2.07-2.00 (m, 2H), 1.97-1.89 (m, 2H); ES-LCMS m/z 174.1 [M+H]$^+$.

Step 3: tert-Butyl 4-(5-((6-(3,5-dichlorophenyl)-4-((4-(2-methoxy-2-oxoethoxy)piperidin-1-yl)methyl)pyridin-2-yl)oxy)pyrimidin-2-yl)piperazine-1-carboxylate

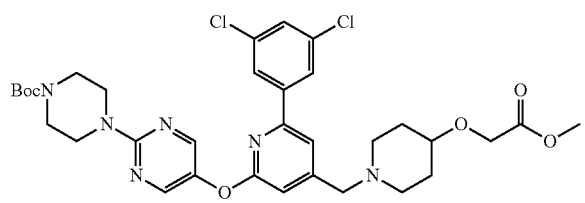 [SMILES: COC(=O)COC1CCN(Cc2cc(Oc3cnc(N4CCN(C(=O)OC(C)(C)C)CC4)nc3)nc(-c3cc(Cl)cc(Cl)c3)c2)CC1]

To a mixture of tert-butyl 4-(5-((6-(3,5-dichlorophenyl)-4-(((methylsulfonyl)oxy)methyl)pyridin-2-yl)oxy)pyrimidin-2-yl)piperazine-1-carboxylate (600 mg, 0.885 mmol) and K$_2$CO$_3$ (367 mg, 2.65 mmol) in DMF (10 mL) was added methyl 2-(piperidin-4-yloxy)acetate, hydrochloride (400 mg, 1.812 mmol). The mixture was stirred at 20° C. for 10 h then filtered and concentrated to yield the crude product, which was purified by silica gel column chromatography (DCM/MeOH=10/1). All fractions found to contain product by TLC (DCM/MeOH=10/1, R$_f$=0.6) were combined and concentrated to yield a white solid of tert-butyl 4-(5-((6-(3,5-dichlorophenyl)-4-((4-(2-methoxy-2-oxoethoxy)piperidin-1-yl)methyl)pyridin-2-yl)oxy)pyrimidin-2-yl)piperazine-1-carboxylate (500 mg, 0.637 mmol, 72.0% yield): $^1$H NMR (400 MHz, CDCl$_3$) δ ppm 8.24 (s, 2H), 7.76-7.67 (m, 3H), 7.26 (s, 2H), 4.07 (s, 2H), 3.77 (m, 4H), 3.69 (s, 3H), 3.62 (s, 2H), 3.47 (m, 4H), 3.13-2.90 (m, 4H), 1.85 (m, 4H), 1.43 (s, 9H); ES-LCMS m/z 687.4, 689.3 [M+H]$^+$.

Step 4: Methyl 2-((1-((2-(3,5-dichlorophenyl)-6-((2-(piperazin-1-yl)pyrimidin-5-yl)oxy)pyridin-4-yl)methyl)piperidin-4-yl)oxy)acetate, 4 hydrochloride

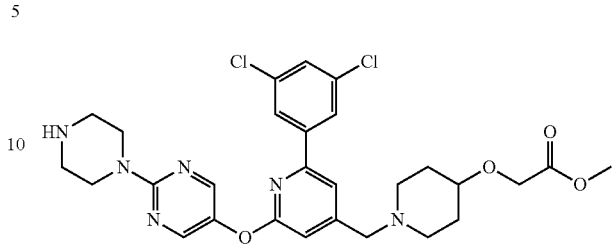

A solution of tert-butyl 4-(5-((6-(3,5-dichlorophenyl)-4-((4-(2-methoxy-2-oxoethoxy)piperidin-1-yl)methyl)pyridin-2-yl)oxy)pyrimidin-2-yl)piperazine-1-carboxylate (500 mg, 0.637 mmol) in HCl solution (4.0 M in MeOH, 5 mL, 20.0 mmol) was stirred at 20° C. for 15 min. The reaction mixture was concentrated to yield a yellow solid of methyl 2-((1-((2-(3,5-dichlorophenyl)-6-((2-(piperazin-1-yl)pyrimidin-5-yl)oxy)pyridin-4-yl)methyl)piperidin-4-yl)oxy)acetate, 4 hydrochloride (420 mg, 0.428 mmol, 67.3% yield): $^1$H NMR (400 MHz, CD$_3$OD) δ ppm 8.60 (s, 2H), 8.04 (br. s, 1H), 7.90 (d, J=1.8 Hz, 2H), 7.49 (s, 1H), 7.40 (s, 1H), 4.51-4.45 (m, 2H), 4.23-4.21 (m, 2H), 4.20-4.16 (m, 4H), 3.77-3.68 (m, 4H), 3.39-3.32 (m, 6H), 3.21-3.11 (m, 2H), 2.15 (m, 3H), 1.91 (m, 1H); ES-LCMS m/z 587.0, 589.0 [M+H]$^+$.

Step 5: Methyl 2-((1-((2-(3,5-dichlorophenyl)-6-((2-(4-methylpiperazin-1-yl)pyrimidin-5-yl)oxy)pyridin-4-yl)methyl)piperidin-4-yl)oxy)acetate

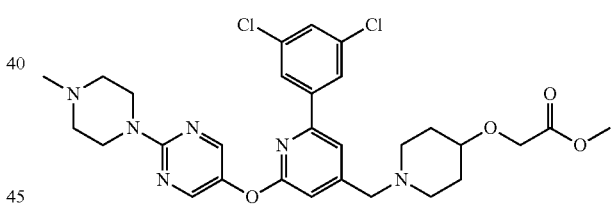

To a mixture of methyl 2-((1-((2-(3,5-dichlorophenyl)-6-((2-(piperazin-1-yl)pyrimidin-5-yl)oxy)pyridin-4-yl)methyl)piperidin-4-yl)oxy)acetate, 4 hydrochloride (400 mg, 0.408 mmol), formic acid (0.036 mL, 0.816 mmol) and 4 Å molecular sieves (600 mg, 0.408 mmol) in MeOH (10 mL) was added paraformaldehyde (61.3 mg, 2.040 mmol). The mixture was stirred at 20° C. for 10 h under N$_2$ atmosphere. Then NaBH$_3$CN (77 mg, 1.224 mmol) was added and the mixture was stirred at 20° C. for 0.5 h. The reaction mixture was filtered and concentrated to yield the residue which was distributed between DCM (20 mL) and saturated aqueous NaHCO$_3$ solution (20 mL), extracted with DCM (20 mL×2). The combined organic layers were dried over Na$_2$SO$_4$, filtered and concentrated to yield a white solid of methyl 2-((1-((2-(3,5-dichlorophenyl)-6-((2-(4-methylpiperazin-1-yl)pyrimidin-5-yl)oxy)pyridine-4-yl)methyl)piperidin-4-yl)oxy)acetate (220 mg, 0.296 mmol, 72.6% yield): $^1$H NMR (400 MHz, CDCl$_3$) δ ppm 8.28-8.19 (m, 2H), 7.66 (s, 2H), 7.35 (s, 1H), 7.27 (br. s, 1H), 6.82 (s, 1H), 4.07 (s, 2H), 3.81 (br. s, 4H), 3.69 (s, 3H), 3.64 (m, 1H), 3.47

(s, 2H), 3.40 (br. s, 1H), 2.71 (m, 2H), 2.46 (m, 4H), 2.30 (s, 3H), 2.18 (m, 2H), 1.86 (m, 2H), 1.66 (m, 2H); ES-LCMS m/z 601.3, 603.3 [M+H]$^+$.

Step 6: 2-((1-((2-(3,5-Dichlorophenyl)-6-((2-(4-methylpiperazin-1-yl)pyrimidin-5-yl)oxy)pyridin-4-yl)methyl)piperidin-4-yl)oxy)acetic acid, 4 hydrochloride

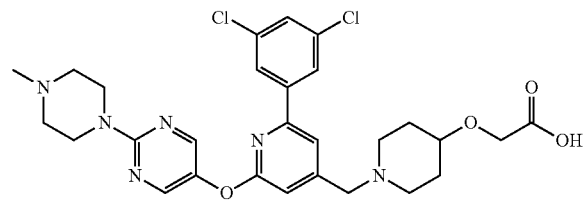 [SMILES: CN1CCN(c2ncc(Oc3cc(CN4CCC(OCC(=O)O)CC4)cc(-c4cc(Cl)cc(Cl)c4)n3)cn2)CC1]

To a solution of methyl 2-((1-((2-(3,5-dichlorophenyl)-6-((2-(4-methylpiperazin-1-yl)pyrimidin-5-yl)oxy)pyridin-4-yl)methyl)piperidin-4-yl)oxy)acetate (220 mg, 0.296 mmol) in THF (5 mL) and water (5.00 mL) was added NaOH (59.2 mg, 1.481 mmol). The mixture was stirred at 50° C. for 10 h then concentrated to yield crude product, which was purified by preparative HPLC (MeCN/H$_2$O as eluents, acidic condition) and dried by lyophilization to yield a white solid of 2-((1-((2-(3,5-dichlorophenyl)-6-((2-(4-methylpiperazin-1-yl)pyrimidin-5-yl)oxy)pyridin-4-yl)methyl)piperidin-4-yl)oxy)acetic acid, 4 hydrochloride (155.57 mg, 0.212 mmol, 71.6% yield): $^1$H NMR (400 MHz, CD$_3$OD) δ ppm 8.46 (s, 2H), 7.95 (br. s, 1H), 7.88 (d, J=1.8 Hz, 2H), 7.50 (s, 1H), 7.33 (br. s, 1H), 4.94 (s, 2H), 4.48-4.42 (m, 2H), 4.18 (s, 2H), 3.86 (br. s, 1H), 3.61 (d, J=12.3 Hz, 2H), 3.49-3.33 (m, 5H), 3.23-3.14 (m, 3H), 2.96 (s, 3H), 2.21-2.13 (m, 2H), 2.07 (d, J=11.9 Hz, 2H); ES-LCMS m/z 587.3, 589.3 [M+H]$^+$.

Example 54: 3-(4-(5-((4-((4-(2-(Carbamoyloxy) ethyl)piperazin-1-yl)methyl)-6-(3,5-dichlorophenyl) pyridin-2-yl)oxy)pyrimidin-2-yl)piperazin-1-yl)propanoic acid, 5 hydrochloride

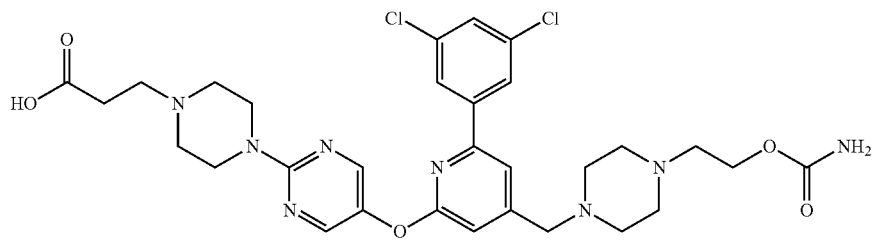 [SMILES: NC(=O)OCCN1CCN(Cc2cc(Oc3cnc(N4CCN(CCC(=O)O)CC4)nc3)nc(-c3cc(Cl)cc(Cl)c3)c2)CC1]

Step 1: tert-Butyl 4-(5-((6-(3,5-dichlorophenyl)-4-((4-(2-hydroxyethyl)piperazin-1-yl)methyl)pyridin-2-yl)oxy)pyrimidin-2-yl)piperazine-1-carboxylate

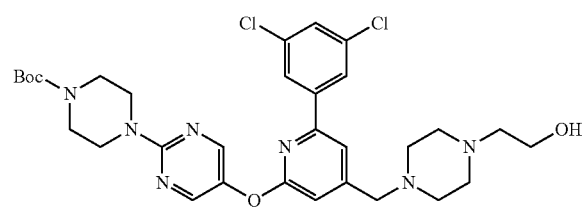 [SMILES: CC(C)(C)OC(=O)N1CCN(c2ncc(Oc3cc(CN4CCN(CCO)CC4)cc(-c4cc(Cl)cc(Cl)c4)n3)cn2)CC1]

To a suspension of tert-butyl 4-(5-((6-(3,5-dichlorophenyl)-4-(((methylsulfonyl)oxy)methyl)pyridin-2-yl)oxy)pyrimidin-2-yl)piperazine-1-carboxylate (500 mg, 0.614 mmol) and 2-(piperazin-1-yl)ethanol (120 mg, 0.921 mmol) in DMF (10 mL) was added Cs$_2$CO$_3$ (600 mg, 1.843 mmol). The reaction mixture was stirred at 30° C. for 12 h then filtered and concentrated to yield crude product, which was purified by silica gel column chromatography (MeOH/DCM=1/9). All fractions found to contain product by TLC (MeOH/DCM=1/10, R$_f$=0.4) were combined and concentrated to yield a light yellow solid of tert-butyl 4-(5-((6-(3,5-dichlorophenyl)-4-((4-(2-hydroxyethyl)piperazin-1-yl)methyl)pyridin-2-yl)oxy)pyrimidin-2-yl)piperazine-1-carboxylate (400 mg, 0.589 mmol, 96.0% yield): $^1$H NMR (400 MHz, CDCl$_3$) δ ppm 8.29-8.27 (m, 2H), 7.73-7.65 (m, 2H), 7.41 (s, 1H), 7.33 (br. s, 1H), 6.90 (s, 1H), 3.81 (m, 4H), 3.62 (t, J=5.1 Hz, 2H), 3.54 (s, 2H), 3.52 (m, 4H), 2.66-2.45 (m, 10H), 1.48 (s, 9H); ES-LCMS m/z 644.2, 646.2 [M+H]$^+$.

Step 2: tert-Butyl 4-(5-((4-((4-(2-(carbamoyloxy) ethyl)piperazin-1-yl)methyl)-6-(3,5-dichlorophenyl) pyridin-2-yl)oxy)pyrimidin-2-yl)piperazine-1-carboxylate

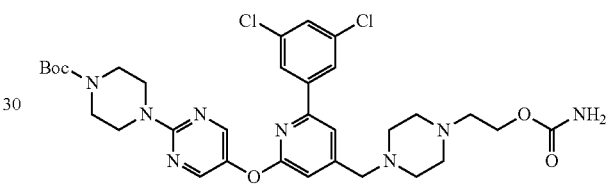

To a suspension of tert-butyl 4-(5-((6-(3,5-dichlorophenyl)-4-((4-(2-hydroxyethyl)piperazin-1-yl)methyl)pyridin-2-yl)oxy)pyrimidin-2-yl)piperazine-1-carboxylate (350 mg, 0.515 mmol), DIEA (0.9 mL, 5.15 mmol) in DCM (5 mL) was added CDI (418 mg, 2.58 mmol). The reaction mixture was stirred at 30° C. for 2 h then NH$_4$OH (5 mL, 0.515 mmol) was added. The mixture was stirred at 30° C. for another 10 h then partitioned between DCM (50 mL) and water (30 mL), extracted with DCM (50 mL×3). The combined organic layers were dried over Na$_2$SO$_4$, filtered and evaporated to yield crude product, which was purified by silica gel column chromatography (MeOH/DCM=1/9). All fractions found to contain product by TLC (MeOH/DCM=1/10, R$_f$=0.45) were combined and concentrated to yield a pale yellow solid of tert-butyl 4-(5-((4-((4-(2-(carbamoyloxy) ethyl)piperazin-1-yl)methyl)-6-(3,5-dichlorophenyl)pyridin-2-yl)oxy)pyrimidin-2-yl)piperazine-1-carboxylate (360 mg, 0.492 mmol, 95.0% yield): $^1$H NMR (400 MHz, CDCl$_3$) δ ppm 8.32 (s, 2H), 7.73 (d, J=1.8 Hz, 2H), 7.42 (s, 1H), 7.35 (s, 1H), 6.93 (s, 1H), 4.65 (br. s, 2H), 4.22 (t, J=5.7 Hz, 2H), 3.91-3.78 (m, 4H), 3.62-3.49 (m, 6H), 3.05 (br. s, 2H), 2.68 (t, J=5.5 Hz, 2H), 2.58-2.46 (m, 6H), 1.50 (s, 9H); ES-LCMS m/z 687.3, 689.3[M+H]+.

Step 3: 2-(4-((2-(3,5-Dichlorophenyl)-6-((2-(piperazin-1-yl)pyrimidin-5-yl)oxy)pyridin-4-yl)methyl) piperazin-1-yl)ethyl carbamate, 5 hydrochloride

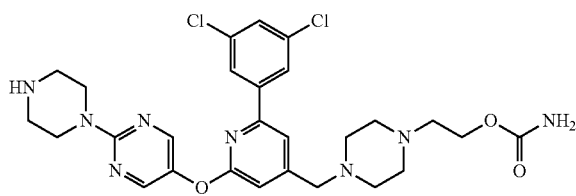 [SMILES: NC(=O)OCCN1CCN(Cc2cc(Oc3cnc(N4CCNCC4)nc3)nc(-c3cc(Cl)cc(Cl)c3)c2)CC1]

To a suspension of tert-butyl 4-(5-((4-((4-(2-(carbamoyloxy)ethyl)piperazin-1-yl)methyl)-6-(3,5-dichlorophenyl)pyridin-2-yl)oxy)pyrimidin-2-yl)piperazine-1-carboxylate (360 mg, 0.492 mmol) in EtOAc (10 mL) was added HCl solution (4.0 M in EtOAc, 10 mL, 96 mmol). The reaction mixture was stirred at 25° C. for 0.5 h then concentrated to yield crude 2-(4-((2-(3,5-dichlorophenyl)-6-((2-(piperazin-1-yl)pyrimidin-5-yl)oxy)pyridin-4-yl)methyl)piperazin-1-yl)ethyl carbamate, 5 hydrochloride (300 mg, 0.238 mmol, 48.5% yield): 1H NMR (400 MHz, CD3OD) δ ppm 8.47 (s, 2H), 8.01 (s, 1H), 7.91 (d, J=1.8 Hz, 2H), 7.51 (t, J=1.9 Hz, 1H), 7.37 (s, 1H), 4.50-4.40 (m, 4H), 4.19-4.14 (m, 4H), 3.80 (d, J=11.5 Hz, 4H), 3.65-3.57 (m, 6H), 3.36 (d, J=5.3 Hz, 4H); ES-LCMS m/z 587.2, 589.3 [M+H]+.

Step 4: Ethyl 3-(4-(5-((4-((4-(2-(carbamoyloxy)ethyl)piperazin-1-yl)methyl)-6-(3,5-dichlorophenyl)pyridin-2-yl)oxy)pyrimidin-2-yl)piperazin-1-yl)propanoate

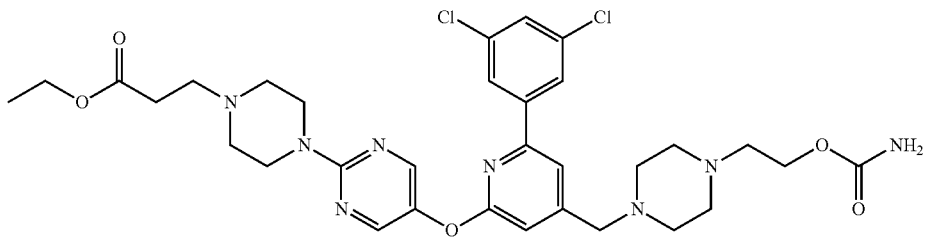 [SMILES: CCOC(=O)CCN1CCN(c2ncc(Oc3cc(CN4CCN(CCOC(N)=O)CC4)cc(-c4cc(Cl)cc(Cl)c4)n3)cn2)CC1]

To a suspension of 2-(4-((2-(3,5-dichlorophenyl)-6-((2-(piperazin-1-yl)pyrimidin-5-yl)oxy)pyridin-4-yl)methyl) piperazin-1-yl)ethyl carbamate, 5 hydrochloride (300 mg, 0.238 mmol) and ethyl 3-bromopropanoate (129 mg, 0.715 mmol) in DMF (10 mL) was added K2CO3 (263 mg, 1.906 mmol). The reaction mixture was stirred at 70° C. for 12 h then filtered and concentrated to yield crude product, which was purified by silica gel column chromatography (MeOH/DCM=1/9). All fractions found to contain product by TLC (DCM:MeOH=10/1, Rf=0.5) were combined and concentrated to yield a light yellow solid of ethyl 3-(4-(5-((4-((4-(2-(carbamoyloxy)ethyl)piperazin-1-yl)methyl)-6-(3,5-dichlorophenyl)pyridin-2-yl)oxy)pyrimidin-2-yl)piperazin-1-yl)propanoate (200 mg, 0.218 mmol, 92.0% yield): 1H NMR (400 MHz, CDCl3) δ ppm 8.30 (s, 2H), 7.74 (s, 2H), 7.42 (s, 1H), 7.35 (s, 1H), 6.91 (s, 1H), 4.70 (br. s, 2H), 4.22 (t, J=5.7 Hz, 2H), 4.18 (m, 2H), 3.86 (m, 6H), 2.78 (t, J=7.3 Hz, 2H), 2.66-2.39 (m, 16H), 1.23 (m, 3H); ES-LCMS m/z 687.2, 689.2 [M+H]+.

Step 5: 3-(4-(5-((4-((4-(2-(Carbamoyloxy)ethyl) piperazin-1-yl)methyl)-6-(3,5-dichlorophenyl)pyridin-2-yl)oxy)pyrimidin-2-yl)piperazin-1-yl)propanoic acid, 5 hydrochloride

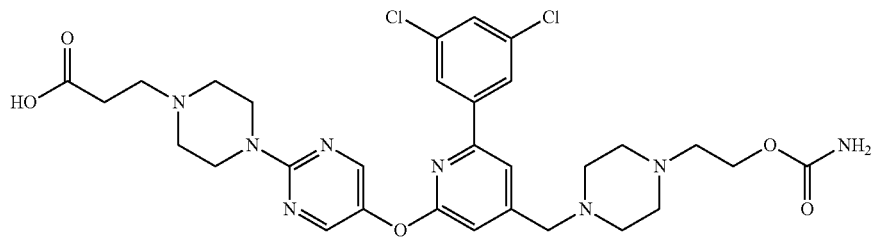 [SMILES: NC(=O)OCCN1CCN(Cc2cc(Oc3cnc(N4CCN(CCC(=O)O)CC4)nc3)nc(-c3cc(Cl)cc(Cl)c3)c2)CC1]

To a suspension of ethyl 3-(4-(5-((4-((4-(2-(carbamoyloxy)ethyl)piperazin-1-yl)methyl)-6-(3,5-dichlorophenyl) pyridin-2-yl)oxy)pyrimidin-2-yl)piperazin-1-yl)propanoate (200 mg, 0.218 mmol) in THF (5 mL) was added LiOH·H2O (45.8 mg, 1.091 mmol) in water (5 mL). The reaction mixture was stirred at 25° C. for 12 h then adjusted pH to 7 with 1 N HCl and this crude was purified by preparative HPLC (MeCN/H2O as eluents, acidic condition) and the desired fraction was lyophilized to yield a white solid of 3-(4-(5-((4-((4-(2-(carbamoyloxy)ethyl)piperazin-1-yl) methyl)-6-(3,5-dichlorophenyl)pyridin-2-yl)oxy)pyrimidin-2-yl)piperazin-1-yl)propanoic acid, 5 hydrochloride (93.71 mg, 0.111 mmol, 51.0% yield): 1H NMR (400 MHz, CD3OD) δ ppm 8.43 (s, 2H), 7.81 (d, J=1.3 Hz, 2H), 7.77-7.72 (m, 1H), 7.50-7.44 (m, 1H), 7.23-7.18 (m, 1H), 4.44-4.35 (m, 2H), 4.04-3.96 (m, 2H), 3.95-3.88 (m, 1H), 3.69 (br. s, 2H), 3.60-3.37 (m, 10H), 3.35 (d, J=4.9 Hz, 1H), 3.25-3.02 (m, 6H), 2.93 (t, J=7.1 Hz, 2H); ES-LCMS m/z 659.2, 661.2 [M+H]+.

Examples 55-61 (Table 2) were prepared by procedures analogous to those described for example 54.

TABLE 2

| Example | Structure/Name | ¹H NMR | LCMS |
|---|---|---|---|
| 55 | 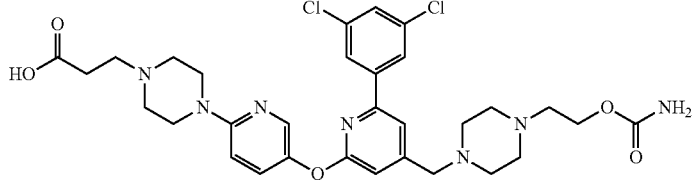 [SMILES: NC(=O)OCCN1CCN(Cc2cc(Oc3ccc(N4CCN(CCC(=O)O)CC4)nc3)nc(-c3cc(Cl)cc(Cl)c3)c2)CC1]<br>3-(4-(5-((4-((4-(2-(carbamoyloxy)ethyl)piperazin-1-yl)methyl)-6-(3,5-dichlorophenyl)pyridin-2-yl)oxy)pyridin-2-yl)piperazin-1-yl)propanoic acid | ¹H NMR (400 MHz, CD$_3$OD) δ ppm 8.22 (d, J = 2.2 Hz, 1H), 8.14 (dd, J = 2.2, 9.7 Hz, 1H), 8.06 (d, J = 5.7 Hz, 1H), 7.89 (s, 2H), 7.54 (d, J = 9.7 Hz, 1H), 7.48 (s, 1H), 7.43 (d, J = 5.3 Hz, 1H), 4.55 (d, J = 14.1 Hz, 2H), 4.48-4.39 (m, 2H), 4.03-3.91 (m, 2H), 3.84 (br. s, 6H), 3.69 (br. s, 6H), 3.62-3.54 (m, 4H), 3.52-3.41 (m, 2H), 2.97 (t, J = 7.1 Hz, 2H) | ES-LCMS m/z 658.2, 660.2 [M + H]⁺. |
| 56 | 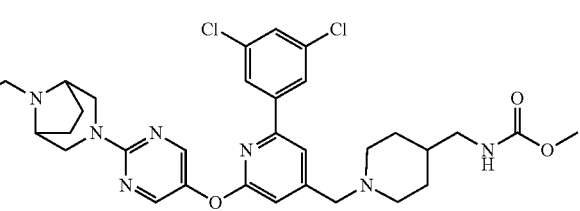<br>3-(3-(5-((6-(3,5-dichlorophenyl)-4-((4-(((methoxycarbonyl)amino)methyl)piperidin-1-yl)methyl)pyridin-2-yl)oxy)pyrimidin-2-yl)-3,8-diazabicyclo[3.2.1]octan-8-yl)propanoic acid | ¹H NMR (400 MHz, CD$_3$OD) δ 8.42 (br. s., 2H), 7.92-7.82 (m, 3H), 7.50 (br. s., 1H), 7.30 (br. s., 1H), 4.76 (d, J = 14.6 Hz, 2H), 4.56-4.38 (m, 3H), 4.25 (br. s., 2H), 3.66-3.55 (m, 4H), 3.47 (d, J = 14.1 Hz, 2H), 3.41 (br. s., 2H), 3.14-3.01 (m, 3H), 2.94 (br. s., 2H), 2.33 (br. s., 2H), 2.08-1.93 (m, 4H), 1.82 (br. s., 2H), 1.61-1.46 (m, 2H) | ES-LCMS m/z 684.3, 686.3 [M + H]⁺. |
| 57 | 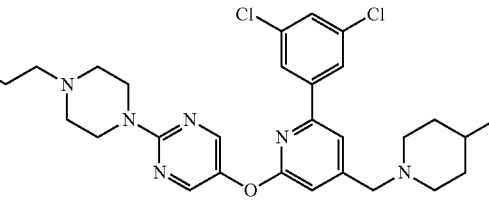<br>4-(4-(5-((6-(3,5-dichlorophenyl)-4-((4-(2-hydroxyethyl)piperidin-1-yl)methyl)pyridin-2-yl)oxy)pyrimidin-2-yl)piperazin-1-yl)-2-methylbutanoic acid | ¹H NMR (400 MHz, CD$_3$OD) δ ppm 8.46 (s, 2H), 7.95-7.81 (m, 3H), 7.51 (s, 1H), 7.32 (s, 1H), 4.96 (s, 2H), 4.43 (s, 2H), 3.71 (d, J = 12.3 Hz, 2H), 3.66-3.53 (m, 4H), 3.38 (s, 2H), 3.26 (d, J = 8.8 Hz, 2H), 3.22-3.03 (m, 4H), 2.61-2.51 (m, 1H), 2.20-2.08 (m, 1H), 2.02 (d, J = 12.8 Hz, 2H), 1.96-1.88 (m, 1H), 1.81 (s, 1H), 1.53 (q, J = 6.3 Hz, 4H), 1.27 (d, J = 7.3 Hz, 3H) | ES-LCMS m/z 643.3, 645.3 [M + H]⁺. |
| 58 | 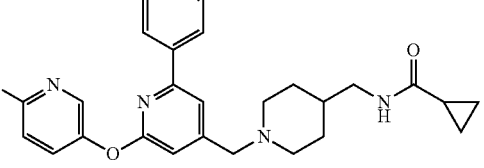<br>3-(4-(5-((4-((4-(cyclopropanecarboxamido methyl)piperidin-1-yl)methyl)-6-(3,5-dichlorophenyl)pyridin-2-yl)oxy)pyridin-2-yl)piperazin-1-yl)propanoic acid | ¹H NMR (400 MHz, CD$_3$OD) δ ppm 8.18 (d, J = 2.6 Hz, 1H), 7.92-7.86 (m, 3H), 7.81 (dd, J = 2.8, 9.4 Hz, 1H), 7.51 (t, J = 1.9 Hz, 1H), 7.30 (s, 1H), 7.26 (d, J = 9.5 Hz, 1H), 4.86-4.84 (m, 2H), 4.43 (s, 2H), 3.60 (d, J = 12.3 Hz, 2H), 3.56-3.52 (m, 2H), 3.40-3.32 (m, 6H), 3.20-3.04 (m, 4H), 2.94 (t, J = 7.1 Hz, 2H), 2.00 (d, J = 13.7 Hz, 2H), 1.85 (s, 1H), 1.63-1.52 (m, 3H), 0.85-0.80 (m, 2H), 0.76 (td, J = 3.1, 7.9 Hz, 2H) | ES-LCMS m/z 667.3, 669.3 [M + H]⁺. |

TABLE 2-continued

| Example | Structure/Name | ¹H NMR | LCMS |
|---|---|---|---|
| 59 | 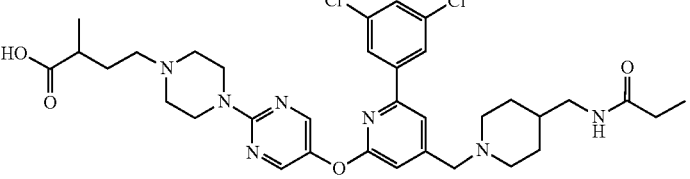<br>4-(4-(5-((6-(3,5-dichlorophenyl)-4-((4-(propionamidomethyl)piperidin-1-yl)methyl)pyridin-2-yl)oxy)pyrimidin-2-yl)piperazin-1-yl)-2-methylbutanoic acid | ¹H NMR (400 MHz, CD₃OD) δ ppm 8.50 (s, 2H), 8.02 (s, 1H), 7.87 (s, 2H), 7.46 (s, 1H), 7.38 (s, 1H), 4.91 (br d, J = 14.1 Hz, 2H), 4.47 (brs, 2H), 3.73 (d, J = 11.5 Hz, 2H), 3.59 (d, J = 10.4 Hz, 2H), 3.49 (t, J = 12.9 Hz, 2H), 3.36 (brs, 1H), 3.24-3.09 (m, 6H), 2.64-2.54 (m, 1H), 2.25 (q, J = 7.5 Hz, 2H), 2.16 (t, J = 6.4 Hz, 1H), 2.07-1.75 (m, 5H), 1.66 (d, J = 11.7 Hz, 2H), 1.31-1.23 (m, 3H), 1.20-1.08 (m, 3H) | ES-LCMS m/z 684.4, 686.3 [M + H]⁺ |
| 60 | 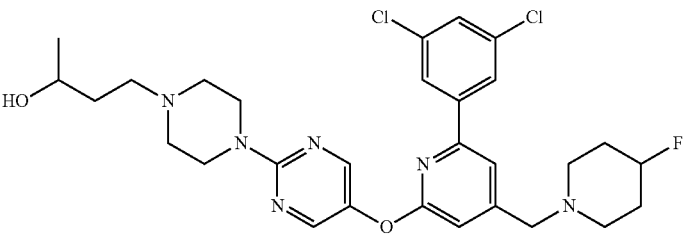 [SMILES: CC(O)CCN1CCN(c2ncc(Oc3cc(CN4CCC(F)CC4)cc(-c4cc(Cl)cc(Cl)c4)n3)cn2)CC1]<br>4-(4-(5-((6-(3,5-dichlorophenyl)-4-((4-fluoropiperidin-1-yl)methyl)pyridin-2-yl)oxy)pyrimidin-2-yl)piperazin-1-yl)butan-2-ol | ¹H NMR (400 MHz, CD₃OD) δ ppm 8.51 (s, 2H), 8.04-7.99 (m, 1H), 7.93-7.90 (m, 2H), 7.52 (s, 1H), 7.41-7.38 (m, 1H), 5.09 (s, 1H), 4.96 (s, 2H), 4.51 (s, 2H), 3.96-3.88 (m, 1H), 3.75 (t, J = 13.4 Hz, 2H), 3.55-3.35 (m, 7H), 3.31-3.15 (m, 3H), 2.35-2.09 (m, 4H), 2.02-1.85 (m, 2H), 1.28 (d, J = 6.3 Hz, 3H) | ES-LCMS m/z 589.1, 591.1 [M + H]⁺ |
| 61 | 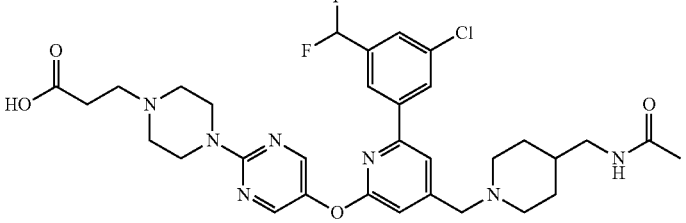<br>3-(4-(5-((4-((4-(acetamidomethyl)piperidin-1-yl)methyl)-6-(3-chloro-5-(difluoromethyl)phenyl)pyridin-2-yl)oxy)pyrimidin-2-yl)piperazin-1-yl)propanoic acid | ¹H NMR (400 MHz, CD₃OD) δ ppm 8.49 (s, 2H), 8.11-8.00 (m, 3H), 7.60 (s, 1H), 7.41-7.28 (m, 1H), 7.05-6.63 (m, 1H), 4.55-4.43 (m, 2H), 3.79-3.74 (m, 2H), 3.70-3.68 (m, 2H), 3.58-3.49 (m, 6H), 3.27-3.05 (m, 6H), 2.94 (t, J = 7.1 Hz, 2H), 2.04-1.96 (m, 5H), 1.87 (d, J = 3.1 Hz, 1H), 1.76-1.50 (m, 2H) | ES-LCMS m/z 658.3, 660.3 [M + H]⁺ |

Example 62: 3-(4-(5-((6-(3,5-Dichlorophenyl)-4-1 (4-(((methoxycarbonyl)amino)methyl)piperidin-1-yl) methyl)pyridin-2-yl)oxy)pyrimidin-2-yl)piperazin-1-yl)propanoic acid, 4 hydrochloride

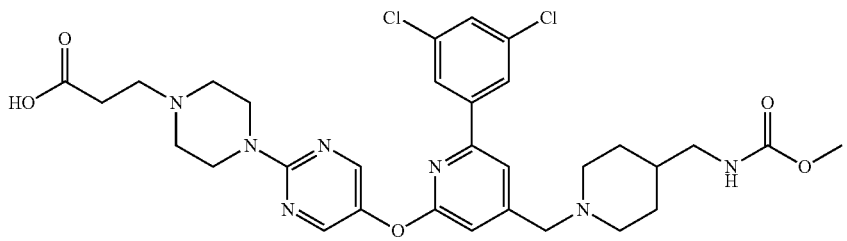 [SMILES: COC(=O)NCC1CCN(Cc2cc(Oc3cnc(N4CCN(CCC(=O)O)CC4)nc3)nc(-c3cc(Cl)cc(Cl)c3)c2)CC1]

Step 1: tert-Butyl 4-(5-((6-(3,5-dichlorophenyl)-4-((4-(((methoxycarbonyl)amino)methyl)piperidin-1-yl)methyl)pyridin-2-yl)oxy)pyrimidin-2-yl)piperazine-1-carboxylate

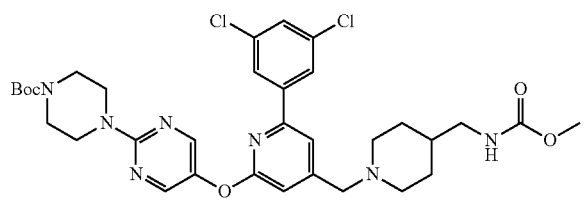 [SMILES: COC(=O)NCC1CCN(Cc2cc(Oc3cnc(N4CCN(C(=O)OC(C)(C)C)CC4)nc3)nc(-c3cc(Cl)cc(Cl)c3)c2)CC1]

To a solution of tert-butyl 4-(5-((6-(3,5-dichlorophenyl)-4-(((methylsulfonyl)oxy)methyl)pyridin-2-yl)oxy)pyrimidin-2-yl)piperazine-1-carboxylate (5 g, 7.78 mmol) in DMF (10 mL) was added K$_2$CO$_3$ (3.23 g, 23.34 mmol) and methyl(piperidin-4-ylmethyl)carbamate, hydrochloride (2.56 g, 11.67 mmol). The reaction was stirred at 25° C. for 5 h then filtered, concentrated and purified by silica gel column chromatography (DCM/MeOH=10/1). All fractions found to contain product by TLC analysis (DCM/MeOH=10/1, R$_f$=0.5) were combined and concentrated to yield a yellow solid of tert-butyl 4-(5-((6-(3,5-dichlorophenyl)-4-((4-(((methoxycarbonyl)amino)methyl)piperidin-1-yl)methyl)pyridin-2-yl)oxy)pyrimidin-2-yl)piperazine-1-carboxylate (6 g, 6.55 mmol, 84.0% yield): $^1$H NMR (400 MHz, CD$_3$OD) δ ppm 8.29 (s, 2H), 7.73 (d, J=2.2 Hz, 2H), 7.56 (s, 1H), 7.35 (t, J=1.8 Hz, 1H), 6.96 (s, 1H), 3.80-3.77 (m, 4H), 3.61 (s, 3H), 3.54 (s, 2H), 3.48 (br. s, 4H), 2.89 (d, J=11.0 Hz, 2H), 2.10-1.92 (m, 4H), 1.69 (d, J=11.9 Hz, 2H), 1.48 (s, 9H), 1.28-1.14 (m, 3H); LC-MS m/z 686.3, 688.3 [M+H]$^+$.

Step 2: Methyl((1-((2-(3,5-dichlorophenyl)-6-((2-(piperazin-1-yl)pyrimidin-5-yl)oxy)pyridine-4-yl)methyl)piperidin-4-yl)methyl)carbamate

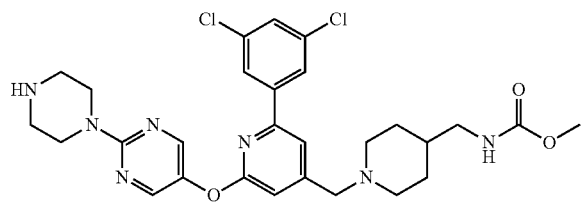

To a mixture of tert-butyl 4-(5-((6-(3,5-dichlorophenyl)-4-((4-(((methoxycarbonyl)amino)methyl)piperidin-1-yl)methyl)pyridin-2-yl)oxy)pyrimidin-2-yl)piperazine-1-carboxylate (6 g, 6.55 mmol) in EtOAc (100 mL) was added HCl solution (4.0 M in EtOAc, 20 mL, 80 mmol). The reaction was stirred at 25° C. for 0.5 h then saturated aqueous NaHCO$_3$ solution (200 mL) was added. The mixture was extracted with DCM (200 mL×2) and the combined organic layers were dried over Na$_2$SO$_4$, filtered and concentrated to yield a yellow solid of methyl((1-((2-(3,5-dichlorophenyl)-6-((2-(piperazin-1-yl)pyrimidin-5-yl)oxy)pyridin-4-yl)methyl)piperidin-4-yl)methyl)carbamate (4 g, 5.80 mmol, 88.0% yield): $^1$H NMR (400 MHz, CD$_3$OD) δ ppm 8.41-8.24 (m, 2H), 7.80 (d, J=1.8 Hz, 2H), 7.62 (s, 1H), 7.41 (t, J=1.8 Hz, 1H), 7.02 (s, 1H), 3.83-3.79 (m, 4H), 3.63-3.58 (m, 5H), 3.00 (d, J=6.2 Hz, 2H), 2.94-2.85 (m, 6H), 2.07 (t, J=10.8 Hz, 2H), 1.71 (d, J=11.5 Hz, 2H), 1.49 (s, 1H), 1.37-1.22 (m, 2H); LC-MS m/z 586.3, 588.3 [M+H]$^+$.

Step 3: Ethyl 3-(4-(5-((6-(3,5-dichlorophenyl)-4-((4-(((methoxycarbonyl)amino)methyl)piperidin-1-yl)methyl)pyridin-2-yl)oxy)pyrimidin-2-yl)piperazin-1-yl)propanoate

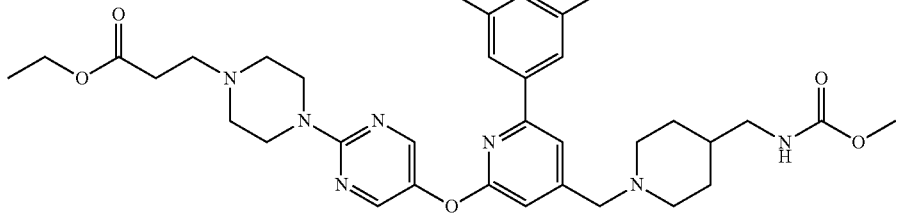

To a mixture of methyl((1-((2-(3,5-dichlorophenyl)-6-((2-(piperazin-1-yl)pyrimidin-5-yl)oxy)pyridin-4-yl)methyl)piperidin-4-yl)methyl)carbamate (250 mg, 0.341 mmol) in DML (5 mL) was added DIEA (0.179 mL, 1.023 mmol) and ethyl 3-bromopropanoate (93 mg, 0.511 mmol). The reaction was stirred at 25° C. for 5 hr. Water (20 mL) was added and the mixture was extracted with DCM (20 mL×2), the combine organic layers was dried over Na$_2$SO$_4$, filtered and concentrated to yield a yellow oil of ethyl 3-(4-(5-((6-(3,5-dichlorophenyl)-4-((4-(((methoxycarbonyl)amino)methyl)piperidin-1-yl)methyl)pyridin-2-yl)oxy)pyrimidin-2-yl)piperazin-1-yl)propanoate (200 mg, 0.204 mmol, 59.8% yield): $^1$H NMR (400 MHz, CD$_3$OD) δ ppm 8.39-8.36 (m, 2H), 7.88-7.81 (m, 3H), 7.49-7.45 (m, 1H), 7.25-7.11 (m, 1H), 4.20-4.16 (m, 2H), 3.98-3.91 (m, 6H), 3.69 (m, 3H), 3.63 (m, 2H), 3.07-3.03 (m, 2H), 2.92-2.86 (m, 2H), 2.79-2.72 (m, 4H), 2.71-2.64 (m, 2H), 2.53-2.46 (m, 2H), 1.89-1.82 (m, 2H), 1.70-1.61 (m, 1H), 1.60-1.53 (m, 2H), 1.29-1.25 (m, 3H); LC-MS m/z 686.3, 688.3[M+H]$^+$.

Step 4: 3-(4-(5-((6-(3,5-Dichlorophenyl)-4-((4-(((methoxycarbonyl)amino)methyl)piperidin-1-yl)methyl)pyridin-2-yl)oxy)pyrimidin-2-yl)piperazin-1-yl)propanoic acid, 4 hydrochloride

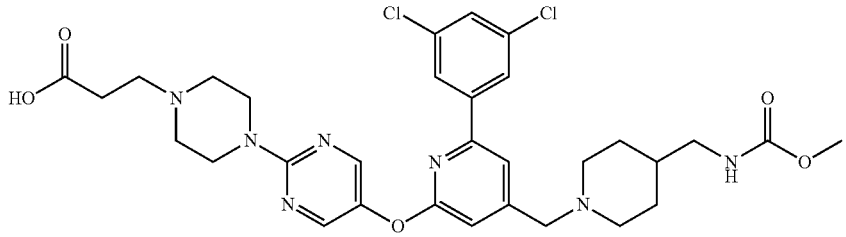 [SMILES: COC(=O)NCC1CCN(Cc2cc(Oc3cnc(N4CCN(CCC(=O)O)CC4)nc3)nc(-c3cc(Cl)cc(Cl)c3)c2)CC1]

To a mixture of ethyl 3-(4-(5-((6-(3,5-dichlorophenyl)-4-((4-(((methoxycarbonyl)amino)methyl)piperidin-1-yl)methyl)pyridin-2-yl)oxy)pyrimidin-2-yl)piperazin-1-yl)propanoate (200 mg, 0.204 mmol) in MeOH (5 mL) and water (1 mL) was added LiOH·H$_2$O (25.7 mg, 0.612 mmol). The reaction was stirred at 25° C. for 2 h. The mixture was filtered, concentrated and purified by preparative HPLC (MeCN/H$_2$O as eluents, acidic condition) and dried by lyophilization to yield a white solid of 3-(4-(5-((6-(3,5-dichlorophenyl)-4-((4-(((methoxycarbonyl)amino)methyl)piperidin-1-yl)methyl)pyridin-2-yl)oxy)pyrimidin-2-yl)piperazin-1-yl)propanoic acid, 4 hydrochloride (76.12 mg, 0.093 mmol, 45.5% yield): $^1$H NMR (400 MHz, CD$_3$OD) δ ppm 8.48 (s, 2H), 7.94 (s, 1H), 7.89 (d, J=1.5 Hz, 2H), 7.52 (s, 1H), 7.34 (s, 1H), 4.46 (br. s, 2H), 3.71-3.33 (m, 15H), 3.09 (br. s, 4H), 2.94 (t, J=7.0 Hz, 2H), 2.01 (d, J=13.6 Hz, 2H), 1.86 (br. s, 1H), 1.61 (br. s, 2H); LC-MS m/z 658.3, 660.3 [M+H]$^+$.

Example 63: Methyl ((1-1(2-(3,5-dichlorophenyl)-6-((2-(4-methylpiperazin-1-yl)pyrimidin-5-yl)oxy)pyridin-4-yl)methyl)piperidin-4-yl)methyl)carbamate, 4 hydrochloride

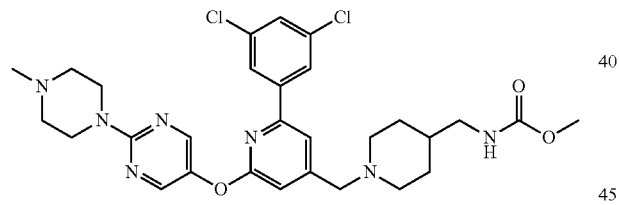

To a solution of methyl ((1-((2-(3,5-dichlorophenyl)-6-((2-(piperazin-1-yl)pyrimidin-5-yl)oxy)pyridin-4-yl)methyl)piperidin-4-yl)methyl)carbamate (400 mg, 0.587 mmol) and paraformaldehyde (35.2 mg, 1.173 mmol) in MeOH (10 mL) was added formic acid (2.70 mg, 0.059 mmol) and 4 Å molecular sieves (0.587 mmol). The reaction was stirred at 25° C. for 5 h under N$_2$ atmosphere. Then NaBH$_3$CN (111 mg, 1.760 mmol) was added and the reaction was stirred at 25° C. for another 2 h. The mixture was filtered, concentrated and purified by preparative HPLC (MeCN/H$_2$O as eluents, acidic condition) and dried by lyophilization to yield a white solid of methyl ((1-((2-(3,5-dichlorophenyl)-6-((2-(4-methylpiperazin-1-yl)pyrimidin-5-yl)oxy)pyridin-4-yl)ethyl)piperidin-4-yl)methyl)carbamate, 4 hydrochloride (114.54 mg, 0.150 mmol, 25.6% yield): $^1$H NMR (400 MHz, CD$_3$OD) δ ppm 8.45 (s, 2H), 7.96 (s, 1H), 7.86 (d, J=1.8 Hz, 2H), 7.47 (t, J=1.8 Hz, 1H), 7.38-7.32 (m, 1H), 4.93 (d, J=14.6 Hz, 2H), 4.59-4.40 (m, 2H), 3.69-3.54 (m, 6H), 3.46-3.34 (m, 3H), 3.25-3.15 (m, 2H), 3.11 (t, J=12.3 Hz, 2H), 3.05 (d, J=6.6 Hz, 2H), 2.97 (s, 3H), 2.05-1.92 (m, 2H), 1.83 (d, J=3.5 Hz, 1H), 1.67-1.52 (m, 2H); LC-MS m/z 600.2, 602.2 [M+H]$^+$.

Examples 64-72 (Table 3) were prepared by procedures analogous to those described for example 63.

TABLE 3

| Example | Structure/Name | $^1$H NMR | LCMS |
|---|---|---|---|
| 64 | ![structure] <br> N-((1-((2-(3,5-dichlorophenyl)-6-((2-(4-methylpiperazin-1-yl)pyrimidin-5-yl)oxy)pyridin-4-yl)methyl)piperidin-4-yl)methyl)acetamide | $^1$H NMR (400 MHz, CD$_3$OD) δ ppm 8.49 (s, 2H), 7.95 (s, 1H), 7.90 (d, J = 1.5 Hz, 2H), 7.53 (s, 1H), 7.35 (s, 1H), 5.00-4.93 (m, 2H), 4.46 (s, 2H), 3.70-3.56 (m, 4H), 3.46-3.34 (m, 3H), 3.27-3.17 (m, 2H), 3.16-3.08 (m, 3H), 2.99 (s, 3H), 2.07-1.95 (m, 5H), 1.87 (br. s, 1H), 1.72-1.53 (m, 2H) | ES-LCMS m/z 584.3, 586.3 [M + H]$^+$. |

TABLE 3-continued

| Example | Structure/Name | ¹H NMR | LCMS |
|---|---|---|---|
| 65 | 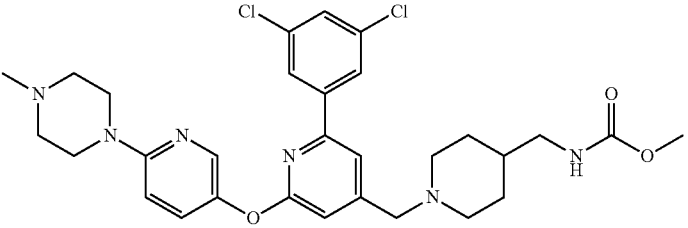<br>methyl ((1-((2-(3,5-dichlorophenyl)-6-((6-(4-methylpiperazin-1-yl)pyridin-3-yl)oxy)pyridin-4-yl)methyl)piperidin-4-yl)methyl)carbamate | ¹H NMR (400 MHz, CD₃OD) δ ppm 8.26-8.19 (m, 2H), 8.00 (s, 1H), 7.89 (d, J = 1.8 Hz, 2H), 7.61 (d, J = 9.3 Hz, 1H), 7.51 (s, 1H), 7.42 (s, 1H), 4.52-4.43 (m, 4H), 3.73 (br. s, 4H), 3.65-3.59 (m, 4H), 3.37 (d, J = 15.4 Hz, 3H), 3.11 (t, J = 12.3 Hz, 2H), 3.07-2.99 (m, 5H), 1.98 (d, J = 13.7 Hz, 2H), 1.83 (br. s, 1H), 1.68-1.56 (m, | ES-LCMS m/z 599.3, 601.3 [M + H]⁺. |
| 66 | 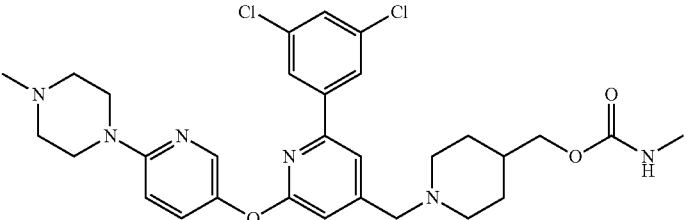<br>(1-((2-(3,5-dichlorophenyl)-6-((2-(4-methylpiperazin-1-yl)pyrimidin-5-yl)oxy)pyridin-4-yl)methyl)piperidin-4-yl)methyl methylcarbamate | ¹H NMR (400 MHz, CD₃OD) δ ppm 8.53 (s, 2H), 8.00 (s, 1H), 7.89 (d, J = 1.3 Hz, 2H), 7.49 (s, 1H), 7.37 (s, 1H), 4.46 (s, 2H), 3.96 (d, J = 5.3 Hz, 2H), 3.62 (t, J = 13.0 Hz, 4H), 3.46 (t, J = 13.5 Hz, 2H), 3.34 (br. s, 1H), 3.26-3.09 (m, 4H), 3.02-2.92 (m, 3H), 2.73-2.64 (m, 3H), 1.99 (d, J = 12.8 Hz, 4H), 1.79-1.64 (m, 2H) | ES-LCMS m/z 600.3, 602.3 [M + H]⁺. |
| 67 | 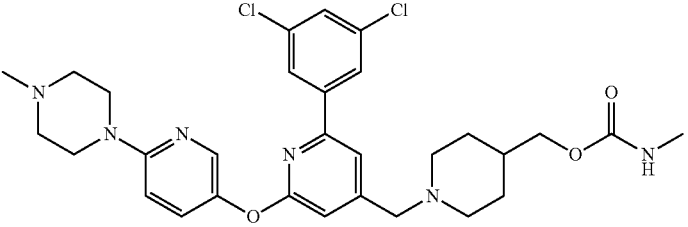<br>(1-((2-(3,5-dichlorophenyl)-6-((6-(4-methylpiperazin-1-yl)pyridin-3-yl)oxy)pyridin-4-yl)methyl)piperidin-4-yl)methyl methylcarbamate | ¹H NMR (400 MHz, CD₃OD) δ ppm 8.25 (d, J = 2.0 Hz, 1H), 8.15 (dd, J = 2.5, 9.5 Hz, 1H), 8.06 (s, 1H), 7.90 (s, 2H), 7.56 (d, J = 9.5 Hz, 1H), 7.51 (s, 1H), 7.44 (s, 1H), 4.61-4.43 (m, 4H), 3.98 (d, J = 4.5 Hz, 2H), 3.81-3.58 (m, 6H), 3.40 (br. s, 2H), 3.18 (t, J = 12.0 Hz, 2H), 3.03 (s, 3H), 2.77-2.67 (m, 3H), 2.02 (d, J = 13.1 Hz, 3H), 1.92-1.42 (m, 2H) | ES-LCMS m/z 599.3, 601.3 [M + H]⁺. |

| Example | Structure/Name | ¹H NMR | LCMS |
|---|---|---|---|
| 68 | 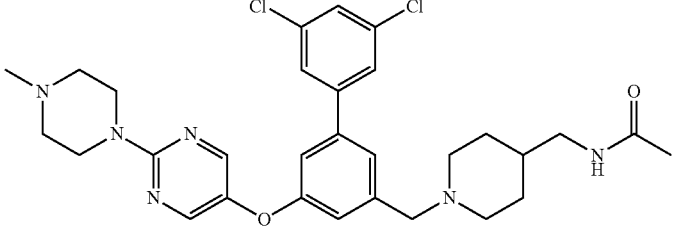 [SMILES: CC(=O)NCC1CCN(Cc2cc(Oc3cnc(N4CCN(C)CC4)nc3)cc(-c3cc(Cl)cc(Cl)c3)c2)CC1]<br>N-((1-((3',5'-dichloro-5-((2-(4-methylpiperazin-1-yl)pyrimidin-5-yl)oxy)-[1,1'-biphenyl]-3-yl)methyl)piperidin-4-yl)methyl)acetamide | ¹H NMR (400 MHz, CD$_3$OD) δ ppm 8.40 (s, 2H), 7.66 (d, J = 1.5 Hz, 2H), 7.57 (s, 1H), 7.52 (s, 1H), 7.41 (s, 1H), 7.32 (s, 1H), 4.93 (d, J = 15.1 Hz, 2H), 4.36 (s, 2H), 3.61 (d, J = 12.0 Hz, 2H), 3.54 (d, J = 12.5 Hz, 2H), 3.45-3.35 (m, 2H), 3.28-3.19 (m, 2H), 3.13 (d, J = 7.0 Hz, 2H), 3.08-2.97 (m, 5H), 2.01-1.95 (m, 5H), 1.84 (br. s, 1H), 1.61-1.46 (m, 2H) | ES-LCMS m/z 583.3, 585.3 [M + H]⁺. |
| 69 | 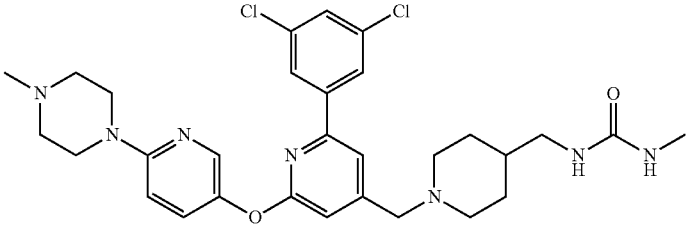<br>1-((1-((2-(3,5-dichlorophenyl)-6-((6-(4-methylpiperazin-1-yl)pyridin-3-yl)oxy)pyridin-4-yl)methyl)piperidin-4-yl)methyl)-3-methylurea | ¹H NMR (400 MHz, CD$_3$OD) δ ppm 8.26-8.17 (m, 2H), 7.98 (s, 1H), 7.88 (d, J = 1.3 Hz, 2H), 7.58 (d, J = 9.7 Hz, 1H), 7.52 (s, 1H), 7.40 (s, 1H), 4.52-4.38 (m, 4H), 3.79-3.53 (m, 6H), 3.37 (br. s, 2H), 3.19-3.05 (m, 4H), 3.01 (s, 3H), 2.71 (s, 3H), 1.98 (d, J = 13.7 Hz, 2H), 1.83 (br. s, 1H), 1.66-1.53 (m 2H) | ES-LCMS m/z 598.3, 600.3 [M + H]⁺. |
| 70 | 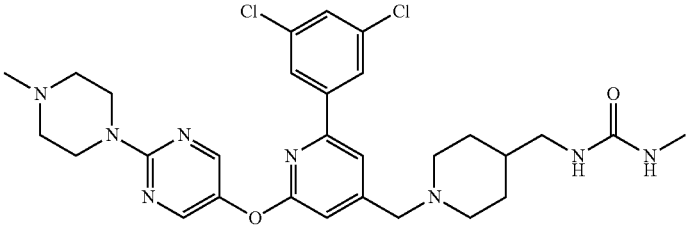<br>1-((1-((2-(3,5-dichlorophenyl)-6-((2-(4-methylpiperazin-1-yl)pyrimidin-5-yl)oxy)pyridin-4-yl)methyl)piperidin-4-yl)methyl)-3-methylurea | ¹H NMR (400 MHz, CD$_3$OD) δ ppm 8.49 (br. s, 2H), 7.98 (br. s, 1H), 7.88 (d, J = 1.3 Hz, 2H), 7.50 (s, 1H), 7.35 (br. s, 1H), 4.44 (s, 2H), 3.61 (t, J = 12.1 Hz, 4H), 3.48-3.33 (m, 4H), 3.21 (d, J = 11.9 Hz, 2H), 3.17-3.08 (m, 4H), 2.96 (s, 3H), 2.75 (br. s, 3H), 1.98 (d, J = 13.7 Hz, 2H), 1.87 (br. s, 1H), 1.64 (br. s, 2H) | ES-LCMS m/z 599.3, 601.3 [M + H]⁺. |

TABLE 3-continued

| Example | Structure/Name | ¹H NMR | LCMS |
|---|---|---|---|
| 71 | 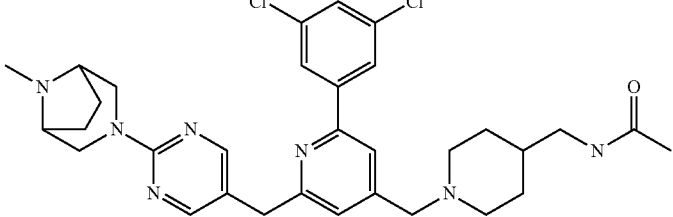<br>N-((1-((2-(3,5-dichlorophenyl)-6-((2-(8-methyl-3,8-diazabicyclo[3.2.1]octan-3-yl)pyrimidin-5-yl)oxy)pyridin-4-yl)methyl)piperidin-4-yl)methyl)acetamide | ¹H NMR (400 MHz, CD₃OD) δ ppm 8.33-8.24 (m, 2H), 7.80 (d, J = 1.8 Hz, 2H), 7.63 (s, 1H), 7.41 (t, J = 1.9 Hz, 1H), 7.02 (s, 1H), 4.33-4.24 (m, 2H), 3.60 (s, 2H), 3.33-3.31 (m, 2H), 3.19 (d, J = 12.3 Hz, 2H), 3.07 (d, J = 6.8 Hz, 2H), 2.92 (d, J = 11.5 Hz, 2H), 2.36 (s, 3H), 2.14-2.02 (m, 4H), 1.93 (s, 3H), 1.76-1.67 (m, 4H), 1.57-1.48 (m, 1H), 1.38-1.26 (m, 2H) | ES-LCMS m/z 610.3, 612.3 [M + H]⁺. |
| 72 | 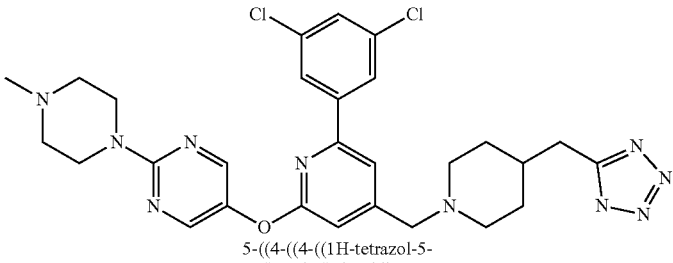<br>5-((4-((4-((1H-tetrazol-5-yl)methyl)piperidin-1-yl)methyl)-6-(3,5-dichlorophenyl)pyridin-2-yl)oxy)-2-(4-methylpiperazin-1-yl)pyrimidine | ¹H NMR (400 Hz, CD₃OD) δ 8.45 (s, 2H), 7.93 (s, 1H), 7.87 (d, J = 2.0 Hz, 2H), 7.49 (t, J = 1.8 Hz, 1H), 7.32 (s, 1H), 4.94 (br d, J = 14.8 Hz, 2H), 4.44 (s, 2H), 3.63-3.57 (m, 4H), 3.41-3.35 (m, 2H), 3.21-3.12 (m, 4H), 2.99-2.95 (m, 5H), 2.19 (br d, J = 4.2 Hz, 1H), 2.00 (br d, J = 13.9 Hz, 2H), 1.78-1.69 (m, 2H) | ES-LCMS m/z 595.3, 597.3 [M + H]⁺. |

Example 73: (1-((2-(3,5-Dichlorophenyl)-6-((2-(piperazin-1-yl)pyrimidin-5-yl)oxy)pyridin-4-yl)methyl)piperidin-4-yl)methyl methylcarbamate

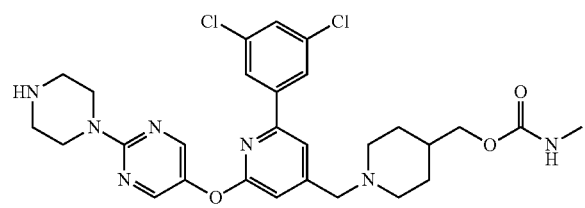 [SMILES: CNC(=O)OCC1CCN(Cc2cc(Oc3cnc(N4CCNCC4)nc3)nc(-c3cc(Cl)cc(Cl)c3)c2)CC1]

Step 1: tert-Butyl 4-(5-((6-(3,5-dichlorophenyl)-4-((4-(hydroxymethyl)piperidin-1-yl)methyl)pyridin-2-yl)oxy)pyrimidin-2-yl)piperazine-1-carboxylate

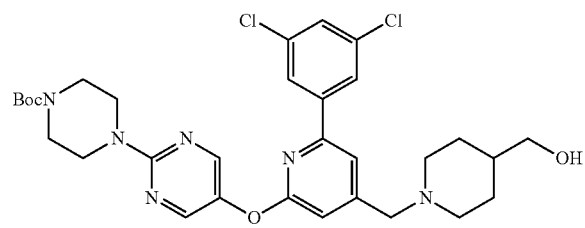

To a mixture of tert-butyl 4-(5-((6-(3,5-dichlorophenyl)-4-(((methylsulfonyl)oxy)methyl)pyridin-2-yl)oxy)pyrimidin-2-yl)piperazine-1-carboxylate (5 g, 6.45 mmol) in DMF (80 mL) was added K₂CO₃ (2.68 g, 19.36 mmol) and piperidin-4-ylmethanol (1.115 g, 9.68 mmol). The reaction was stirred at 25° C. for 5 h then water (100 mL) was added and the mixture was extracted with DCM (100 mL×2). The combined organic layers were dried over Na₂SO₄, filtered, concentrated and purified by silica gel column chromatography (DCM/MeOH=10/1). All fractions found to contain product by TLC (DCM/MeOH=10/1, R_f=0.7) were combined and concentrated to yield a yellow solid of tert-butyl 4-(5-((6-(3,5-dichlorophenyl)-4-((4-(hydroxymethyl)piperidin-1-yl)methyl)pyridin-2-yl)oxy)pyrimidin-2-yl)piperazine-1-carboxylate (4 g, 5.90 mmol, 91.0% yield): ¹H NMR (400 MHz, CDCl₃) δ ppm 8.29 (s, 2H), 7.71 (s, 2H), 7.41 (s, 1H), 7.32 (br. s, 1H), 6.90 (s, 1H), 3.81 (br. s, 4H), 2.94 (s, 4H), 2.87 (s, 4H), 2.04 (t, J=11.2 Hz, 2H), 1.74 (d, J=12.3 Hz, 2H), 1.66 (m, 4H), 1.48 (s, 9H), 1.37-1.30 (m, 2H); ES-LCMS m/z 629.3 631.3 [M+H]⁺.

Step 2: tert-Butyl 4-(5-((6-(3,5-dichlorophenyl)-4-((4-(((methylcarbamoyl)oxy)methyl)piperidin-1-yl)methyl)pyridin-2-yl)oxy)pyrimidin-2-yl)piperazine-1-carboxylate

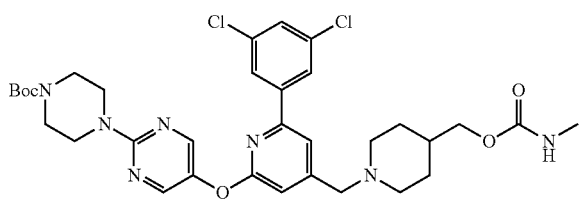 [SMILES: CNC(=O)OCC1CCN(Cc2cc(Oc3cnc(N4CCN(C(=O)OC(C)(C)C)CC4)nc3)nc(-c3cc(Cl)cc(Cl)c3)c2)CC1]

To a mixture of tert-butyl 4-(5-((6-(3,5-dichlorophenyl)-4-((4-(hydroxymethyl)piperidin-1-yl)methyl)pyridin-2-yl)oxy)pyrimidin-2-yl)piperazine-1-carboxylate (4 g, 5.90 mmol) in DCM (40 mL) was added DIEA (5.15 mL, 29.5 mmol) and CDI (2.390 g, 14.74 mmol). The reaction was stirred at 25° C. for 5 h. The methanamine, (30 wt % in ethanol, 12.21 g, 118 mmol) was added. The reaction was stirred at 25° C. for 2 h then concentrated and purified by silica gel column chromatography (DCM/MeOH=10/1). All fractions found to contain product by TLC (DCM/MeOH=10/1, R$_f$=0.6) were combined and concentrated to yield a yellow solid of tert-butyl 4-(5-((6-(3,5-dichlorophenyl)-4-((4-(((methylcarbamoyl)oxy)methyl)piperidin-1-yl)methyl)pyridin-2-yl)oxy)pyrimidin-2-yl)piperazine-1-carboxylate (4 g, 5.46 mmol, 93.0% yield): $^1$H NMR (400 MHz, CD$_3$OD) δ ppm 8.32 (s, 2H), 7.80 (d, J=1.8 Hz, 2H), 7.62 (s, 1H), 7.41 (t, J=1.8 Hz, 1H), 7.03 (s, 1H), 3.90 (d, J=6.2 Hz, 2H), 3.82 (s, 2H), 3.62-3.59 (m, 2H), 3.51 (br. s, 2H), 2.99 (s, 2H), 2.93 (d, J=11.0 Hz, 2H), 2.86 (s, 2H), 2.68 (s, 3H), 2.09 (t, J=11.0 Hz, 2H), 1.73 (d, J=12.8 Hz, 2H), 1.49 (s, 9H), 1.43-1.32 (m, 2H), 1.24-1.14 (m, 1H); ES-LCMS m/z 686.3, 688.3 [M+H]$^+$.

Step 3: (1-((2-(3,5-Dichlorophenyl)-6-((2-(piperazin-1-yl)pyrimidin-5-yl)oxy)pyridin-4-yl)methyl)piperidin-4-yl)methyl methylcarbamate, 4 hydrochloride

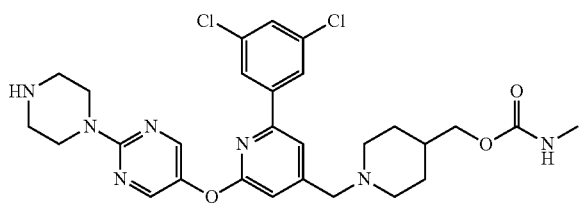 [SMILES: CNC(=O)OCC1CCN(Cc2cc(Oc3cnc(N4CCNCC4)nc3)nc(-c3cc(Cl)cc(Cl)c3)c2)CC1]

To a mixture of tert-butyl 4-(5-((6-(3,5-dichlorophenyl)-4-((4-(((methylcarbamoyl)oxy)methyl)piperidin-1-yl)methyl)pyridin-2-yl)oxy)pyrimidin-2-yl)piperazine-1-carboxylate (4 g, 5.46 mmol) in EtOAc (20 mL) was added HCl solution (4.0 M in EtOAc, 20 mL, 80.00 mmol). The reaction was stirred at 25° C. for 0.5 h then saturated aqueous NaHCO$_3$ solution (100 mL) was added and the mixture was extracted with DCM (100 mL×2). The combined organic layers were dried over Na$_2$SO$_4$, filtered, and concentrated to yield a yellow solid of (1-((2-(3,5-dichlorophenyl)-6-((2-(piperazin-1-yl)pyrimidin-5-yl)oxy)pyridin-4-yl)methyl)piperidin-4-yl)methyl methylcarbamate (3.4 g, 5.36 mmol, 98.0% yield). Taking 150 mg (0.243 mmol) of the material to purified with preparative HPLC (MeCN/H$_2$O as eluents, acidic condition) then dried by lyophilization to yield a white solid of (1-((2-(3,5-dichlorophenyl)-6-((2-(piperazin-1-yl)pyrimidin-5-yl)oxy)pyridin-4-yl)methyl)piperidin-4-yl)methyl methylcarbamate, 4 hydrochloride (53.51 mg, 0.072 mmol, 29.6% yield): $^1$H NMR (400 MHz, CD$_3$OD) δ ppm 8.49 (d, J=3.1 Hz, 2H), 8.00 (br. s, 1H), 7.87 (s, 2H), 7.48 (br. s, 1H), 7.36 (br. s, 1H), 4.46 (br. s, 2H), 4.14 (br. s, 4H), 3.96 (d, J=5.3 Hz, 2H), 3.61 (d, J=11.9 Hz, 2H), 3.35 (br. s, 4H), 3.14 (t, J=11.9 Hz, 2H), 2.72-2.65 (m, 3H), 2.00 (d, J=12.3 Hz, 3H), 1.71 (br. s, 2H); ES-LCMS m/z 586.2, 588.3 [M+H]$^+$.

Example 74: (1-((2-(3,5-Dichlorophenyl)-6-((6-(piperazin-1-yl)pyridin-3-yl)oxy)pyridin-4-yl)methyl)piperidin-4-yl)methyl methylcarbamate, 4 hydrochloride

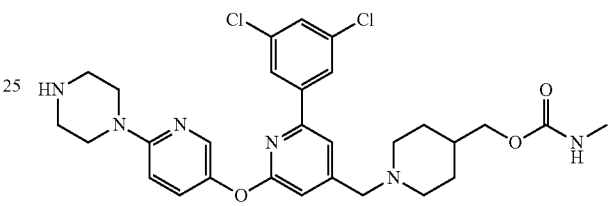

Step 1: tert-Butyl 4-(5-((6-(3,5-dichlorophenyl)-4-((4-(hydroxymethyl)piperidin-1-yl)methyl)pyridin-2-yl)oxy)pyridin-2-yl)piperazine-1-carboxylate

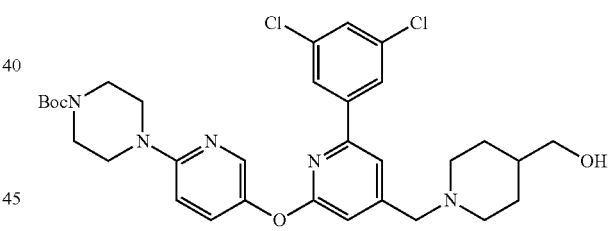

To a mixture of tert-butyl 4-(5-((6-(3,5-dichlorophenyl)-4-(((methylsulfonyl)oxy)methyl)pyridin-2-yl)oxy)pyridin-2-yl)piperazine-1-carboxylate (5 g, 6.94 mmol) in DMF (80 mL) was added piperidin-4-ylmethanol (1.199 g, 10.41 mmol) and K$_2$CO$_3$ (2.88 g, 20.82 mmol). The reaction was stirred at 25° C. for 5 h then water (200 mL) was added. The mixture was extracted with DCM (300 mL×2) and the combined organic layers were dried over Na$_2$SO$_4$, filtered, concentrated and purified by silica gel column chromatography (DCM/MeOH=10/1). All fractions found to contain product by TLC (DCM/MeOH=10/1, R$_f$=0.7) were combined and concentrated to yield a yellow solid of tert-butyl 4-(5-((6-(3,5-dichlorophenyl)-4-((4-(hydroxymethyl)piperidin-1-yl)methyl)pyridin-2-yl)oxy)pyridin-2-yl)piperazine-1-carboxylate (4 g, 4.77 mmol, 68.8% yield): $^1$H NMR (400 MHz, CD$_3$OD) δ ppm 8.02-7.95 (m, 2H), 7.74 (d, J=1.8 Hz, 1H), 7.54 (s, 1H), 7.45 (dd, J=2.9, 9.0 Hz, 1H), 7.34 (t, J=1.8 Hz, 1H), 6.96-6.86 (m, 2H), 3.59-3.48 (m, 10H), 3.39 (d, J=6.2 Hz, 2H), 2.90 (d, J=11.5 Hz, 2H), 2.85-2.78 (m, 2H), 2.04-1.93 (m, 2H), 1.74 (br. s, 1H), 1.48 (s, 9H), 1.29-1.22 (m, 2H); ES-LCMS m/z 628.3, 630.3 [M+H]⁺.

Step 2: tert-Butyl 4-(5-((6-(3,5-dichlorophenyl)-4-((4-(((methylcarbamoyl)oxy)methyl)piperidin-1-yl)methyl)pyridin-2-yl)oxy)pyridin-2-yl)piperazine-1-carboxylate

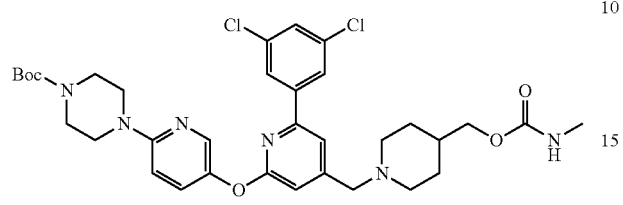

To a mixture of tert-butyl 4-(5-((6-(3,5-dichlorophenyl)-4-((4-(hydroxymethyl)piperidin-1-yl)methyl)pyridin-2-yl)oxy)pyridin-2-yl)piperazine-1-carboxylate (4 g, 4.77 mmol) in DCM (100 mL) was added DIEA (4.17 mL, 23.86 mmol) and CDI (3.10 g, 19.09 mmol). The reaction was stirred at 25° C. for 5 h then methanamine (30 wt % in ethanol, 9.88 g, 95 mmol) was added. The reaction was stirred at 25° C. for 2 h. The mixture was concentrated and purified by silica gel column chromatography (DCM/MeOH=10/1). All fractions found to contain product by TLC (DCM/MeOH=10/1, $R_f$=0.6) were combined and concentrated to yield a yellow solid of tert-butyl 4-(5-((6-(3,5-dichlorophenyl)-4-((4-(((methylcarbamoyl)oxy)methyl)piperidin-1-yl)methyl)pyridin-2-yl)oxy)pyridin-2-yl)piperazine-1-carboxylate (3.5 g, 4.44 mmol, 93.0% yield): ¹H NMR (400 MHz, CD₃OD) δ ppm 8.02 (d, J=2.6 Hz, 1H), 7.75 (d, J=1.8 Hz, 2H), 7.53 (s, 1H), 7.45 (dd, J=2.9, 9.0 Hz, 1H), 7.35 (t, J=1.8 Hz, 1H), 6.93-6.85 (m, 2H), 3.87 (d, J=5.7 Hz, 2H), 3.54-3.46 (m, 10H), 2.94-2.81 (m, 4H), 2.68 (s, 3H), 1.69 (d, J=12.8 Hz, 2H), 1.48 (s, 9H), 1.35 (br. s, 1H), 1.26-1.12 (m, 2H); ES-LCMS m/z 685.3, 687.3 [M+H]⁺.

Step 3: (1-((2-(3,5-dichlorophenyl)-6-((6-(piperazin-1-yl)pyridin-3-yl)oxy)pyridin-4-yl)methyl)piperidin-4-yl)methyl methylcarbamate, 4 hydrochloride

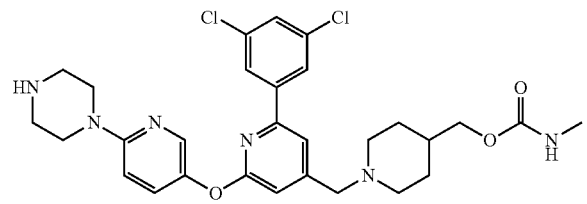 [SMILES: CNC(=O)OCC1CCN(Cc2cc(Oc3ccc(N4CCNCC4)nc3)nc(-c3cc(Cl)cc(Cl)c3)c2)CC1]

To a mixture of tert-butyl 4-(5-((6-(3,5-dichlorophenyl)-4-((4-(((methylcarbamoyl)oxy)methyl)piperidin-1-yl)methyl)pyridin-2-yl)oxy)pyridin-2-yl)piperazine-1-carboxylate (5 g, 6.20 mmol) in EtOAc (50 mL) was added HCl solution (4.0 M in EtOAc, 20 mL, 80 mmol). The reaction was stirred at 25° C. for 0.5 h then saturated aqueous NaHCO₃ solution (200 mL) was added. The mixture was extracted with DCM (200 mL×2) and the combined organic layers were dried over Na₂SO₄, filtered and concentrated to yield a yellow solid of (1-((2-(3,5-dichlorophenyl)-6-((6-(piperazin-1-yl)pyridin-3-yl)oxy)pyridin-4-yl)methyl)piperidin-4-yl)methyl methylcarbamate (3.5 g, 5.43 mmol, 88.0% yield). Taking 200 mg (0.34 mmol) of the material to purify with preparative HPLC (MeCN/H₂O as eluents, acidic condition) then dried by lyophilization to yield a white solid of (1-((2-(3,5-dichlorophenyl)-6-((6-(piperazin-1-yl)pyridin-3-yl)oxy)pyridin-4-yl)methyl)piperidin-4-yl)methylmethylcarbamate, 4 hydrochloride (54.17 mg, 0.073 mmol, 1.17% yield): ¹H NMR (400 MHz, CD₃OD) δ ppm 8.21 (br. s, 1H), 8.13-7.99 (m, 2H), 7.88 (br. s, 2H), 7.55-7.37 (m, 3H), 4.50 (br. s, 2H), 4.10-3.94 (m, 6H), 3.63 (d, J=11.5 Hz, 2H), 3.50 (br. s, 4H), 3.19 (t, J=12.3 Hz, 2H), 2.71 (br. s, 3H), 2.03 (d, J=12.5 Hz, 3H), 1.75 (br. s, 2H); ES-LCMS m/z 585.3, 587.3 [M+H]⁺.

Example 75: 1-((1-((2-(3,5-Dichlorophenyl)-6-((2-(piperazin-1-yl)pyrimidin-5-yl)oxy)pyridin-4-yl)methyl)piperidin-4-yl)methyl)-3-methylurea, 4 hydrochloride

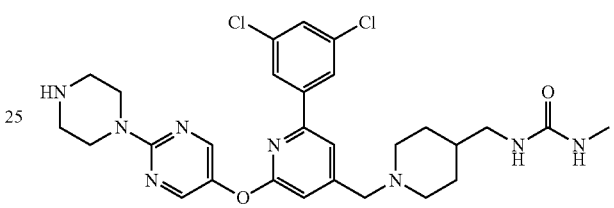

Step 1: tert-Butyl 4-(5-((6-(3,5-dichlorophenyl)-4-((4-((3-methylureido)methyl)piperidin-1-yl)methyl)pyridin-2-yl)oxy)pyrimidin-2-yl)piperazine-1-carboxylate

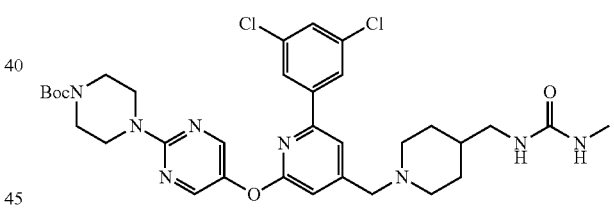

To a mixture of tert-butyl 4-(5-((6-(3,5-dichlorophenyl)-4-(((methylsulfonyl)oxy)methyl)pyridin-2-yl)oxy)pyrimidin-2-yl)piperazine-1-carboxylate (3 g, 3.87 mmol) and K₂CO₃ (1.605 g, 11.62 mmol) in DMF (50 mL) was added 1-methyl-3-(piperidin-4-ylmethyl)urea, hydrochloride (1.177 g, 4.65 mmol). The mixture was stirred at 20° C. for 10 h then concentrated to yield the crude product which was purified by silica gel column chromatography (DCM/MeOH=10/1). All fractions found to contain product by TLC (DCM/MeOH=10/1, $R_f$=0.6) were combined and concentrated to yield a yellow solid tert-butyl 4-(5-((6-(3,5-dichlorophenyl)-4-((4-((3-methylureido)methyl)piperidin-1-yl)methyl)pyridin-2-yl)oxy)pyrimidin-2-yl)piperazine-1-carboxylate (1.8 g, 2.510 mmol, 64.8% yield): ¹H NMR (400 MHz, CDCl₃) δ ppm 8.30 (s, 2H), 7.72 (d, J=1.3 Hz, 2H), 7.40 (s, 1H), 7.33 (s, 1H), 6.90 (s, 1H), 4.54-4.11 (m, 4H), 3.82 (d, J=4.9 Hz, 4H), 3.52 (br. s, 6H), 3.09 (t, J=6.2 Hz, 2H), 2.88 (d, J=11.0 Hz, 2H), 2.78 (d, J=4.9 Hz, 3H), 2.02 (t, J=10.8 Hz, 2H), 1.49 (s, 9H); ES-LCMS m/z 685.2, 687.2 [M+H]⁺.

Step 2: 1-((1-((2-(3,5-Dichlorophenyl)-6-((2-(piperazin-1-yl)pyrimidin-5-yl)oxy)pyridin-4-yl)methyl)piperidin-4-yl)methyl)-3-methylurea, 4 hydrochloride

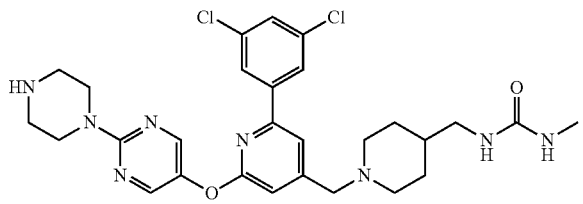 [SMILES: CNC(=O)NCC1CCN(Cc2cc(Oc3cnc(N4CCNCC4)nc3)nc(-c3cc(Cl)cc(Cl)c3)c2)CC1]

A solution of tert-butyl 4-(5-(((6-(3,5-dichlorophenyl)-4-((4-((3-methylureido)methyl)piperidin-1-yl)methyl)pyridin-2-yl)oxy)pyrimidin-2-yl)piperazine-1-carboxylate (250 mg, 0.349 mmol) in HCl solution (4.0 M in EtOAc, 5 mL, 20.00 mmol) was stirred at 20° C. for 15 min. The reaction mixture was concentrated to yield crude product which was purified by preparative HPLC (MeCN/H$_2$O as eluents, acidic condition) and dried by lyophilization yielded a yellow solid 1-((1-((2-(3,5-dichlorophenyl)-6-((2-(piperazin-1-yl)pyrimidin-5-yl)oxy)pyridin-4-yl)methyl)piperidin-4-yl)methyl)-3-methylurea, 4 hydrochloride (56.94 mg, 0.078 mmol, 22.3% yield): $^1$H NMR (400 MHz, CD$_3$OD) δ ppm 8.47 (s, 2H), 7.95 (br. s, 1H), 7.88 (d, J=1.3 Hz, 2H), 7.50 (s, 1H), 7.33 (br. s, 1H), 4.43 (s, 2H), 4.17-4.10 (m, 4H), 3.59 (d, J=11.9 Hz, 2H), 3.36-3.31 (m, 4H), 3.16-3.04 (m, 4H), 2.72 (br. s, 3H), 1.98 (d, J=13.7 Hz, 2H), 1.84 (br. s, 1H), 1.59 (d, J=12.8 Hz, 2H); ES-LCMS m/z 585.3, 587.3 [M+H]$^+$.

Example 76: Methyl 1(1-((2-(3,5-dichlorophenyl)-6-((6-(piperazin-1-yl)pyridin-3-yl)oxy)pyridin-4-yl)methyl)piperidin-4-yl)methyl)carbamate, 4 hydrochloride

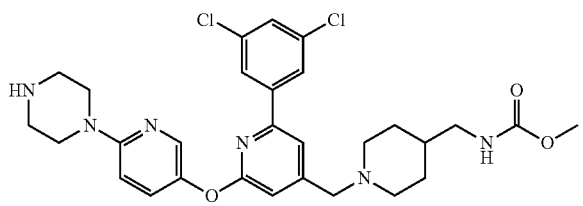 [SMILES: COC(=O)NCC1CCN(Cc2cc(Oc3ccc(N4CCNCC4)nc3)nc(-c3cc(Cl)cc(Cl)c3)c2)CC1]

Step 1: tert-Butyl 4-(5-((6-(3,5-dichlorophenyl)-4-((4-(((methoxycarbonyl)amino)methyl)piperidin-1-yl)methyl)pyridin-2-yl)oxy)pyridin-2-yl)piperazine-1-carboxylate

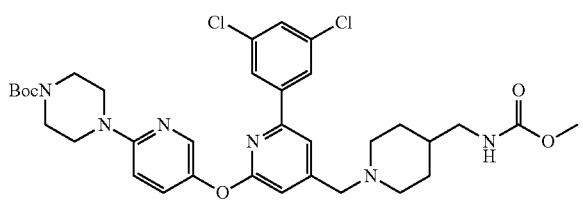 [SMILES: COC(=O)NCC1CCN(Cc2cc(Oc3ccc(N4CCN(C(=O)OC(C)(C)C)CC4)nc3)nc(-c3cc(Cl)cc(Cl)c3)c2)CC1]

To a solution of tert-butyl 4-(5-((6-(3,5-dichlorophenyl)-4-(((methylsulfonyl)oxy)methyl)pyridin-2-yl)oxy)pyridin-2-yl)piperazine-1-carboxylate (11 g, 14.98 mmol) and methyl (piperidin-4-ylmethyl)carbamate hydrochloride (3.95 g, 17.97 mmol) in DMF (200 mL) was added K$_2$CO$_3$ (10.17 g, 44.9 mmol). The mixture was stirred at 80° C. for 2 h then filtered and concentrated. The crude product was distributed between DCM (200 mL) and saturated aqueous NaHCO$_3$ (50 mL) solution. The aqueous phase was extracted with DCM (50 mL×2). The combined organic extracts were washed with brine (50 mL), dried over Na$_2$SO$_4$, filtered and concentrated. The residue was purified by silica gel column chromatography (PE/EtOAc=1/1). All fractions found to contain product by TLC (PE/EtOAc=1/1, R$_f$=0.6) were combined and concentrated to yield a brown solid of tert-butyl 4-(5-(((6-(3,5-dichlorophenyl)-4-(((4-(((methoxycarbonyl)amino)methyl)piperidin-1-yl)methylpyridin-2-yl)oxy)pyridin-2-yl)piperazine-1-carboxylate (10 g, 12.25 mmol, 82.0% yield): $^1$H NMR (400 MHz, CD$_3$OD) δ ppm 7.97 (s, 2H), 7.80 (d, J=1.8 Hz, 2H), 7.60 (s, 1H), 7.49 (dd, J=2.9, 9.0 Hz, 1H), 7.40 (t, J=1.8 Hz, 1H), 6.96 (d, J=2.6 Hz, 1H), 3.61 (s, 3H), 3.59-3.47 (m, 10H), 3.08-3.00 (m, 2H), 2.92 (d, J=11.5 Hz, 2H), 2.12-2.02 (m, 2H), 1.71 (d, J=11.9 Hz, 2H), 1.50-1.45 (m, 9H), 1.35-1.21 (m, 3H); ES-LCMS m/z 685.3, 687.3 [M+H]$^+$.

Step 2: Methyl ((1-((2-(3,5-dichlorophenyl)-6-((6-(piperazin-1-yl)pyridin-3-yl)oxy)pyridin-4-yl)methyl)piperidin-4-yl)methyl)carbamate, 4 hydrochloride

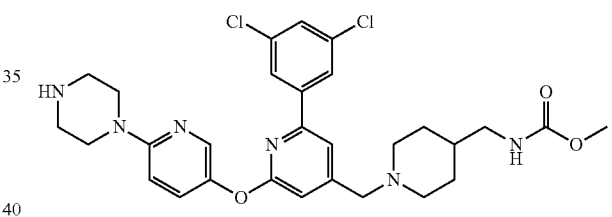

To a solution of tert-butyl 4-(5-(((6-(3,5-dichlorophenyl)-4-((4-(((methoxycarbonyl)amino)methyl)piperidin-1-yl)methyl)pyridin-2-yl)oxy)pyridin-2-yl)piperazine-1-carboxylate (10 g, 12.25 mmol) in MeOH (40 mL) was added HCl solution (4.0 M in EtOAc, 20 mL, 80 mmol). The mixture was stirred at 20° C. for 0.5 h then concentrated and distributed between DCM (200 mL) and saturated aqueous NaHCO$_3$ (200 mL) solution. The aqueous phase was extracted with DCM (100 mL×2). The combined organic extracts were washed with brine (50 mL), dried over Na$_2$SO$_4$, filtered and concentrated to yield a yellow solid of methyl ((1-((2-(3,5-dichlorophenyl)-6-((6-(piperazin-1-yl)pyridin-3-yl)oxy)pyridin-4-yl)methyl)piperidin-4-yl)methyl)carbamate (8.0 g, 12.16 mmol, 99% yield). Taking 0.2 g of the material to purify with preparative HPLC (MeCN/H$_2$O as eluents, acidic condition) then lyophilize yielded a white solid of methyl((1-((2-(3,5-dichlorophenyl)-6-((6-(piperazin-1-yl)pyridin-3-yl)oxy)pyridin-4-yl)methyl)piperidin-4-yl)methyl)carbamate, 4 hydrochloride (128.41 mg, 0.175 mmol, 1.40% yield): $^1$H NMR (400 MHz, CD$_3$OD) δ ppm 8.22 (d, J=2.6 Hz, 1H), 8.16 (dd, J=2.6, 9.7 Hz, 1H), 7.98 (s, 1H), 7.88 (d, J=1.8 Hz, 2H), 7.58-7.49 (m, 2H), 7.40 (s, 1H), 4.45 (s, 2H), 4.07-3.98 (m, 4H), 3.66-3.55 (m, 5H), 3.53-3.46 (m, 4H), 3.16-3.02 (m, 4H), 1.98 (d, J=13.7 Hz, 2H), 1.83 (br. s, 1H), 1.65-1.53 (m, 2H); ES-LCMS m/z 585.3, 587.3 [M+H]$^+$.

Example 77: 3-(4-(5-((6-(3,5-Dichlorophenyl)-4-((4-(((methylcarbamoyl)oxy)methyl)piperidin-1-yl)methyl)pyridin-2-yl)oxy)pyridin-2-yl)piperazin-1-yl)propanoic acid, 4 hydrochloride

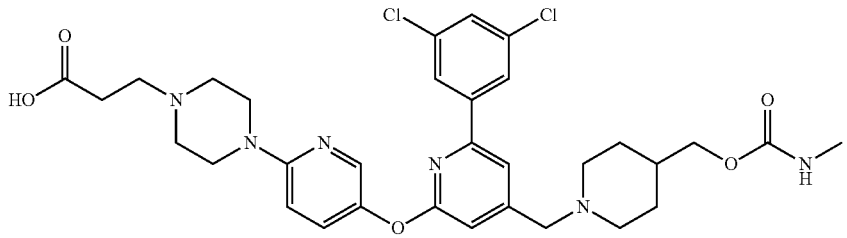 [SMILES: CNC(=O)OCC1CCN(Cc2cc(Oc3ccc(N4CCN(CCC(=O)O)CC4)nc3)nc(-c3cc(Cl)cc(Cl)c3)c2)CC1]

Step 1: Ethyl 3-(4-(5-((6-(3,5-dichlorophenyl)-4-((4-(hydroxymethyl)piperidin-1-yl)methyl)pyridin-2-yl)oxy)pyridin-2-yl)piperazin-1-yl)propanoate

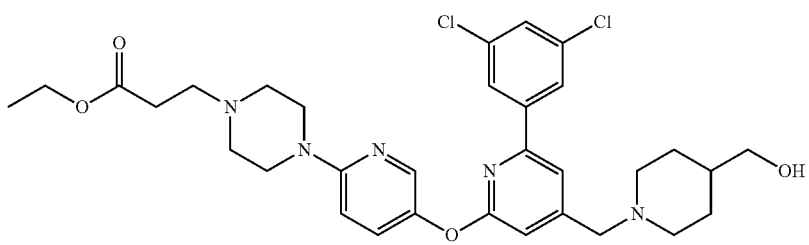 [SMILES: CCOC(=O)CCN1CCN(c2ccc(Oc3cc(CN4CCC(CO)CC4)cc(-c4cc(Cl)cc(Cl)c4)n3)cn2)CC1]

To a solution of ethyl 3-(4-(5-((6-(3,5-dichlorophenyl)-4-(((methylsulfonyl)oxy)methyl)pyridin-2-yl)oxy)pyridin-2-yl)piperazin-1-yl)propanoate (300 mg, 0.391 mmol) in DMF (5 mL) was added K$_2$CO$_3$ (270 mg, 1.956 mmol) and piperidin-4-ylmethanol (67.6 mg, 0.587 mmol). The mixture was stirred at 80° C. for 10 h then filtered and concentrated to yield crude product which was purified by silica gel column chromatography (DCM/MeOH=10/1). All fractions found to contain product by TLC (DCM/MeOH=10/1, R$_f$=0.6) were combined and concentrated to yield a light yellow solid of ethyl3-(4-(5-((6-(3,5-dichlorophenyl)-4-((4-(hydroxymethyl)piperidin-1-yl)methyl)pyridin-2-yl)oxy)pyridin-2-yl)piperazin-1-yl)propanoate (200 mg, 0.224 mmol, 57.2% yield): $^1$H NMR (400 MHz, CD$_3$OD) δ ppm 8.05 (d, J=3.0 Hz, 1H), 7.84 (d, J=1.5 Hz, 2H), 7.63 (s, 1H), 7.51 (dd, J=3.0, 9.0 Hz, 1H), 7.43 (s, 1H), 6.99 (s, 1H), 6.95 (d, J=9.0 Hz, 1H), 4.21-4.15 (m, 2H), 3.61 (s, 2H), 3.59-3.54 (m, 5H), 3.43 (d, J=6.5 Hz, 4H), 2.96 (d, J=11.0 Hz, 2H), 2.76 (d, J=7.0 Hz, 2H), 2.68 (s, 1H), 2.65 (br. s, 2H), 2.61 (d, J=7.0 Hz, 2H), 2.11 (t, J=11.0 Hz, 3H), 1.78 (d, J=11.0 Hz, 4H), 1.55-1.47 (m, 1H); ES-LCMS m/z 628.3, 630.3 [M+H]$^+$.

Step 2: Ethyl 3-(4-(5-((6-(3,5-dichlorophenyl)-4-((4-(((methylcarbamoyl)oxy)methyl)piperidin-1-yl)methyl)pyridin-2-yl)oxy)pyridin-2-yl)piperazin-1-yl)propanoate

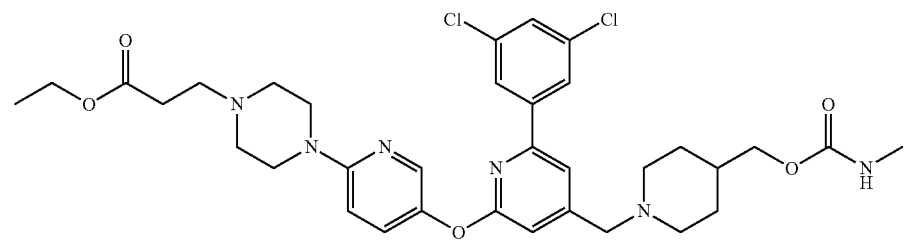 [SMILES: CCOC(=O)CCN1CCN(c2ccc(Oc3cc(CN4CCC(COC(=O)NC)CC4)cc(-c4cc(Cl)cc(Cl)c4)n3)cn2)CC1]

To a mixture of ethyl 3-(4-(5-((6-(3,5-dichlorophenyl)-4-((4-(hydroxymethyl)piperidin-1-yl)methyl)pyridin-2-yl)oxy)pyridin-2-yl)piperazin-1-yl)propanoate (150 mg, 0.168 mmol) and DIEA (0.146 mL, 0.839 mmol) in DCM (15 mL) was added CDI (32.6 mg, 0.201 mmol). The mixture was stirred at 25° C. for 3 h then methanamine (30 wt % in ethanol, 45.7 mg, 0.201 mmol) was added and the mixture was stirred at 25° C. for another 7 h. The mixture was concentrated to yield a brown solid ethyl 3-(4-(5-((6-(3,5-dichlorophenyl)-4-((4-(((methylcarbamoyl)oxy)methyl)piperidin-1-yl)methyl)pyridin-2-yl)oxy)pyridin-2-yl)piperazin-1-yl)propanoate (120 mg, 0.126 mmol, 75.0% yield): $^1$H NMR (400 MHz, CD$_3$OD) δ ppm 8.05 (s, 1H), 7.95 (s, 1H), 7.70 (d, J=1.8 Hz, 2H), 7.49 (br. s, 1H), 7.33 (s, 2H), 7.27 (s, 1H), 4.22 (br. s, 2H), 4.11-4.05 (m, 4H), 3.89 (br. s, 3H), 3.67 (m, 4H), 3.48 (m, 4H), 3.43 (m, 4H), 2.56-2.54 (m, 2H), 2.36 (m, 2H), 1.97 (d, J=10.6 Hz, 4H), 1.66-1.64 (m, 1H), 1.22 (br. s, 3H); ES-LCMS m/z 685.3, 687.3 [M+H]$^+$.

Step 3: 3-(4-(5-((6-(3,5-Dichlorophenyl)-4-((4-(((methylcarbamoyl)oxy)methyl)piperidin-1-yl)methyl)pyridin-2-yl)oxy)pyridin-2-yl)piperazin-1-yl)propanoic acid, 4 hydrochloride

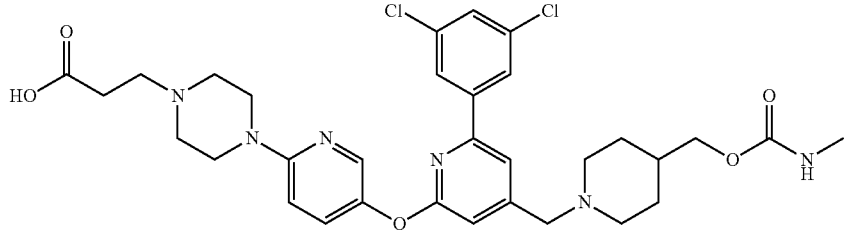 [SMILES: CNC(=O)OCC1CCN(Cc2cc(Oc3ccc(N4CCN(CCC(=O)O)CC4)nc3)nc(-c3cc(Cl)cc(Cl)c3)c2)CC1]

To a solution of ethyl 3-(4-(5-((6-(3,5-dichlorophenyl)-4-((4-(((methylcarbamoyl)oxy)methyl)piperidin-1-yl)methyl)pyridin-2-yl)oxy)pyridin-2-yl)piperazin-1-yl)propanoate (100 mg, 0.105 mmol) in THF (2 mL) and water (2 mL) was added LiOH·H$_2$O (22.03 mg, 0.525 mmol). The mixture was stirred at 25° C. for 12 h then concentrated to yield crude product which was purified by preparative HPLC (MeCN/H$_2$O as eluents, acidic condition) and dried by lyophilization to yield a white solid of 3-(4-(5-((6-(3,5-dichlorophenyl)-4-((4-(((methylcarbamoyl)oxy)methyl)piperidin-1-yl)methyl)pyridin-2-yl)oxy)pyridin-2-yl)piperazin-1-yl)propanoic acid, 4 hydrochloride (48.29 mg, 0.060 mmol, 57.2% yield): $^1$H NMR (400 MHz, CD$_3$OD) δ ppm 8.24 (br. s, 1H), 8.13 (br. s, 1H), 8.03 (br. s, 1H), 7.91 (s, 2H), 7.53 (br. s, 2H), 7.43 (br. s, 1H), 4.49 (br. s, 2H), 3.98 (d, J=5.0 Hz, 2H), 3.67-3.54 (m, 8H), 3.37-3.34 (m, 2H), 3.20-3.14 (m, 2H), 2.98 (d, J=6.5 Hz, 3H), 2.74-2.69 (m, 4H), 2.03 (d, J=11.5 Hz, 4H), 1.73 (br. s, 1H); ES-LCMS m/z 657.3, 659.3 [M+H]$^+$.

Example 78: 3-(4-(5-((4-((4-(3-Amino-3-oxopropyl)piperazin-1-yl)methyl)-6-(3,5-dichlorophenyl)pyridin-2-yl)oxy)pyrimidin-2-yl)piperazin-1-yl)propanoic acid

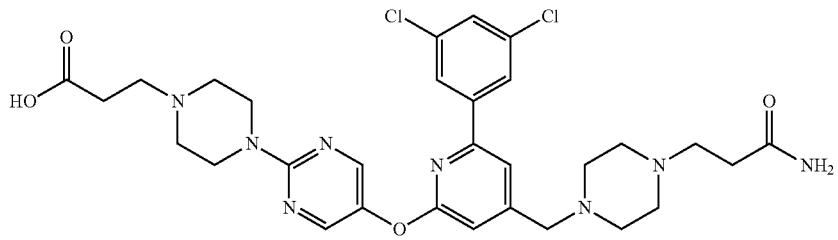 [SMILES: NC(=O)CCN1CCN(Cc2cc(Oc3cnc(N4CCN(CCC(=O)O)CC4)nc3)nc(-c3cc(Cl)cc(Cl)c3)c2)CC1]

343

Step 1: tert-Butyl 4-((2-(3,5-dichlorophenyl)-6-((2-(4-(3-ethoxy-3-oxopropyl)piperazin-1-yl)pyrimidin-5-yl)oxy)pyridin-4-yl)methyl)piperazine-1-carboxylate

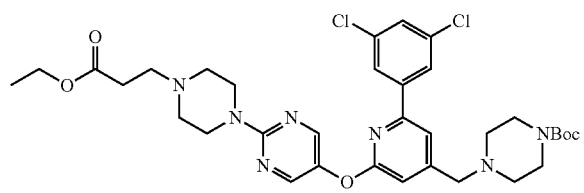 [SMILES: CCOC(=O)CCN1CCN(c2ncc(Oc3cc(CN4CCN(C(=O)OC(C)(C)C)CC4)cc(-c4cc(Cl)cc(Cl)c4)n3)cn2)CC1]

To a mixture of ethyl 3-(4-(5-(((6-(3,5-dichlorophenyl)-4-(((methylsulfonyl)oxy)methyl)pyridin-2-yl)oxy)pyrimidin-2-yl)piperazin-1-yl)propanoate (0.48 g, 0.676 mmol) and tert-butyl piperazine-1-carboxylate (0.151 g, 0.811 mmol) in DMF (5 mL) was added $K_2CO_3$ (0.280 g, 2.028 mmol). The mixture was stirred at 80° C. for 6 h then filtered and concentrated. The crude product was distributed between DCM (30 mL) and saturated aqueous $NaHCO_3$ (20 mL) solution. The aqueous phase was washed with DCM (20 mL×2). The combined organic extract was washed with brine (20 mL), dried over $Na_2SO_4$, filtered and concentrated. The crude product was purified by silica gel column chromatography (PE/EtOAc=1/1). All fractions found to contain product by TLC (PE/EtOAc=1/1, $R_f$=0.6) were combined and concentrated to yield a light yellow solid of tert-butyl 4-((2-(3,5-dichlorophenyl)-6-((2-(4-(3-ethoxy-3-oxopropyl)piperazin-1-yl)pyrimidin-5-yl)oxy)pyridin-4-yl)methyl)piperazine-1-carboxylate (0.4 g, 0.377 mmol, 55.7% yield): $^1$H NMR (400 MHz, $CD_3OD$) δ ppm 8.35-8.26 (m, 2H), 7.78 (d, J=1.8 Hz, 2H), 7.61 (s, 1H), 7.43-7.38 (m, 1H), 7.04 (s, 1H), 4.19-4.10 (m, 2H), 3.86-3.79 (m, 2H), 3.44 (d, J=16.8 Hz, 8H), 3.33-3.28 (m, 2H), 2.76-2.70 (m, 2H), 2.60-2.54 (m, 4H), 2.47 (d, J=4.4 Hz, 2H), 2.43-2.38 (m, 2H), 1.45 (s, 9H), 1.29-1.22 (m, 3H); ES-LCMS m/z 700.2, 702.2 [M+H]$^+$.

344

Step 2: Ethyl 3-(4-(5-((6-(3,5-dichlorophenyl)-4-(piperazin-1-ylmethyl)pyridin-2-yl)oxy)pyrimidin-2-yl)piperazin-1-yl)propanoate

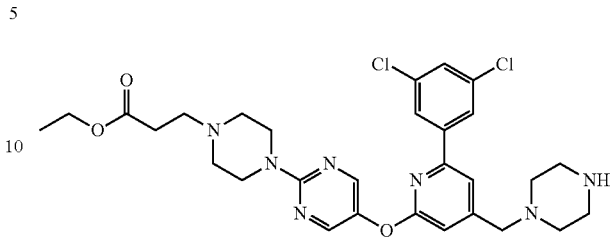

To a solution of tert-butyl 4-((2-(3,5-dichlorophenyl)-6-((2-(4-(3-ethoxy-3-oxopropyl)piperazin-1-yl)pyrimidin-5-yl)oxy)pyridin-4-yl)methyl)piperazine-1-carboxylate (400 mg, 0.377 mmol) in MeOH (10 mL) was added HCl solution (4.0 M in MeOH, 2 mL, 8.00 mmol). The mixture was stirred at 20° C. for 1 h then concentrated and distributed between DCM (30 mL) and saturated aqueous $NaHCO_3$ solution (20 mL). The aqueous phase was extracted with DCM (10 mL×2). The combined organic extracts were washed with brine (20 mL), dried over $Na_2SO_4$, filtered and concentrated to yield a yellow solid of ethyl 3-(4-(5-((6-(3,5-dichlorophenyl)-4-(piperazin-1-ylmethyl)pyridin-2-yl)oxy)pyrimidin-2-yl)piperazin-1-yl)propanoate (240 mg, 0.364 mmol, 97.0% yield): $^1$H NMR (400 MHz, $CD_3OD$) δ ppm 8.46-8.44 (m, 2H), 8.04 (s, 1H), 7.92-7.85 (m, 2H), 7.51-7.46 (m, 1H), 7.39 (s, 1H), 4.56 (s, 2H), 4.20 (q, J=7.2 Hz, 2H), 3.73-3.58 (m, 8H), 3.54-3.49 (m, 4H), 3.41 (t, J=13.0 Hz, 2H), 3.25-3.21 (m, 4H), 2.95-2.93 (m, 2H), 1.28 (t, J=7.2 Hz, 3H); ES-LCMS m/z 600.4, 602.4 [M+H]$^+$.

Step 3: Ethyl 3-(4-(5-((4-((4-(3-amino-3-oxopropyl)piperazin-1-yl)methyl)-6-(3,5-dichlorophenyl)pyridin-2-yl)oxy)pyrimidin-2-yl)piperazin-1-yl)propanoate

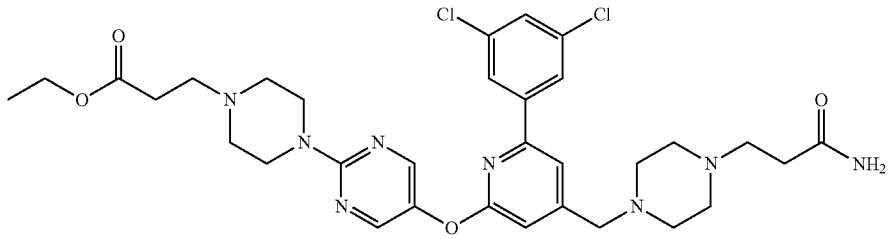 [SMILES: CCOC(=O)CCN1CCN(c2ncc(Oc3cc(CN4CCN(CCC(N)=O)CC4)cc(-c4cc(Cl)cc(Cl)c4)n3)cn2)CC1]

To a mixture of ethyl 3-(4-(5-((6-(3,5-dichlorophenyl)-4-(piperazin-1-ylmethyl)pyridin-2-yl)oxy)pyrimidin-2-yl)piperazin-1-yl)propanoate (0.23 g, 0.349 mmol) and 3-chloropropanamide (0.075 g, 0.697 mmol) in DML (10 mL) was added KI (0.116 g, 0.697 mmol) and $K_2CO_3$ (0.193 g, 1.394 mmol). The mixture was stirred at 80° C. for 6 h then filtered and concentrated to yield a brown solid of ethyl 3-(4-(5-((4-((4-(3-amino-3-oxopropyl)piperazin-1-yl)methyl)-6-(3,5-dichlorophenyl)pyridin-2-yl)oxy)pyrimidin-2-yl)piperazin-1-yl)propanoate (160 mg, 0.152 mmol, 43.7% yield): $^1$H NMR (400 MHz, $CD_3OD$) δ ppm 8.47-8.42 (m, 2H), 8.05 (s, 1H), 7.88 (d, J=1.8 Hz, 2H), 7.50-7.43 (m, 1H), 7.38 (s, 1H), 4.57 (s, 2H), 4.20 (q, J=7.1 Hz, 2H), 4.15-4.09 (m, 4H), 3.88-3.66 (m, 8H), 3.60 (t, J=7.1 Hz, 2H), 3.37-3.30 (m, 8H), 3.02-2.93 (m, 2H), 1.27 (t, J=7.1 Hz, 3H); ES-LCMS m/z 671.3, 673.3 [M+H]$^+$.

Step 4: 3-(4-(5-((4-((4-(3-Amino-3-oxopropyl)piper-azin-1-yl)methyl)-6-(3,5-dichlorophenyl)pyridin-2-yl)oxy)pyrimidin-2-yl)piperazin-1-yl)propanoic acid, 5 hydrochloride

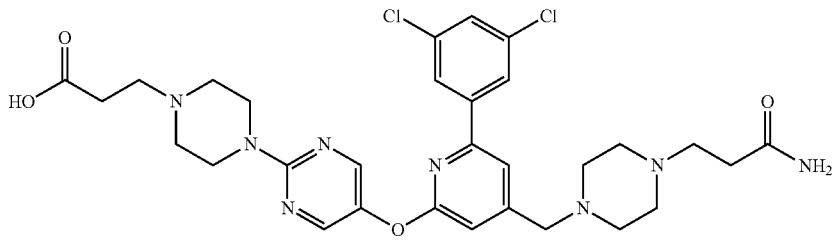 [SMILES: NC(=O)CCN1CCN(Cc2cc(Oc3cnc(N4CCN(CCC(=O)O)CC4)nc3)nc(-c3cc(Cl)cc(Cl)c3)c2)CC1]

To a mixture of ethyl 3-(4-(5-((4-((4-(3-amino-3-oxopropyl)piperazin-1-yl)methyl)-6-(3,5-dichlorophenyl)pyridin-2-yl)oxy)pyrimidin-2-yl)piperazin-1-yl)propanoate (0.15 g, 0.143 mmol) in MeOH (10 mL) and water (10 mL) was added LiOH·H₂O (0.018 g, 0.429 mmol). The mixture was stirred at 20° C. for 8 h then concentrated. The crude product was purified by preparative HPLC (MeCN/H₂O as eluents, acidic condition) and lyophilized to yield a white solid of 3-(4-(5-((4-((4-(3-amino-3-oxopropyl)piperazin-1-yl)methyl)-6-(3,5-dichlorophenyl)pyridin-2-yl)oxy)pyrimidin-2-yl)piperazin-1-yl)propanoic acid, 5 hydrochloride (60 mg, 0.073 mmol, 50.8% yield): $^1$H NMR (400 MHz, CD$_3$OD) δ ppm 8.46-8.37 (m, 2H), 7.90-7.77 (m, 3H), 7.49 (t, J=1.8 Hz, 1H), 7.27 (s, 1H), 4.20 (br. s, 2H), 3.70 (d, J=12.3 Hz, 2H), 3.62 (br. s, 4H), 3.55-3.47 (m, 4H), 3.40 (d, J=14.1 Hz, 8H), 3.27-3.15 (m, 2H), 2.91 (t, J=7.1 Hz, 2H), 2.80 (t, J=6.6 Hz, 2H); ES-LCMS m/z 643.3, 645.3 [M+H]$^+$.

Examples 79-85 (Table 4) were prepared by procedures analogous to those described for example 78.

TABLE 4

| Example | Structure/Name | $^1$H NMR | LCMS |
|---|---|---|---|
| 79 | 3-(4-(5-((4-((4-(2-amino-2-oxoethyl)piperazin-1-yl)methyl)-6-(3,5-dichlorophenyl)pyridin-2-yl)oxy)pyrimidin-2-yl)piperazin-1-yl)propanoic acid | $^1$H NMR (400 MHz, CD$_3$OD) δ ppm 8.47 (s, 2H), 7.96 (s, 1H), 7.90 (d, J = 1.0 Hz, 2H), 7.51 (s, 1H), 7.34 (s, 1H), 4.37 (br. s, 2H), 4.06 (s, 2H), 3.78-3.66 (m, 6H), 3.57-3.43 (m, 8H), 3.32-3.22 (m, 4H), 2.94 (t, J = 7.0 Hz, 2H) | ES-LCMS m/z 629.2, 631.2 [M + H]$^+$. |
| 80 | 3-(4-(5-((6-(3,5-dichlorophenyl)-4-(((1R,7S,8r)-8-(methylsulfonamido)-4-azabicyclo[5.1.0]octan-4-yl)methyl)pyridin-2-yl)oxy)pyrimidin-2-yl)piperazin-1-yl)propanoic acid | $^1$H NMR (400 MHz, CD$_3$OD) δ ppm 8.44 (s, 2H), 7.94-7.79 (m, 3H), 7.49 (s, 1H), 7.31 (s, 1H), 4.91 (brs, 2H), 4.58-4.40 (m, 2H), 3.69 (d, J = 12.13 Hz, 2H), 3.59 (dd, J = 5.29, 12.57 Hz, 2H), 3.49 (t, J = 6.95 Hz, 2H), 3.41 (t, J = 12.90 Hz, 2H), 3.28-3.08 (m, 4H), 2.95 (s, 3H), 2.90 (t, J = 7.06 Hz, 2H), 2.55-2.35 (m, 3H), 1.75-1.61 (m, 2H), 1.44 (brs, 2H) | ES-LCMS m/z 690.2, 692.2 [M + H]$^+$. |

TABLE 4-continued

| Example | Structure/Name | ¹H NMR | LCMS |
|---|---|---|---|
| 81 | <br>4-(4-(5-((6-(3,5-dichlorophenyl)-4-(((1R,7S,8r)-8-(methylsulfonamido)-4-azabicyclo[5.1.0]octan-4-yl)methyl)pyridin-2-yl)oxy)pyrimidin-2-yl)piperazin-1-yl)-2-methylbutanoic acid | ¹H NMR (400 MHz, CD$_3$OD) δ ppm 8.44 (s, 2H), 7.97-7.80 (m, 3H), 7.49 (s, 1H), 7.31 (s, 1H), 4.92 (d, J = 14.11 Hz, 2H), 4.47 (s, 2H), 3.69 (d, J = 11.91 Hz, 2H), 3.60 (dd, J = 5.29, 12.35 Hz, 2H), 3.49-3.31 (m, 4H), 3.27-3.21 (m, 2H), 3.21-3.07 (m, 2H), 2.95 (s, 3H), 2.63-2.43 (m, 3H), 2.40 (brs, 1H), 2.18-2.05 (m, 1H), 1.96-1.84 (m, 1H), 1.67 (brs, 2H), 1.44 (brs, 2H), 1.26 (d, J = 7.06 Hz, 3H) | ES-LCMS m/z 718.2, 720.2 [M + H]$^+$. |
| 82 | 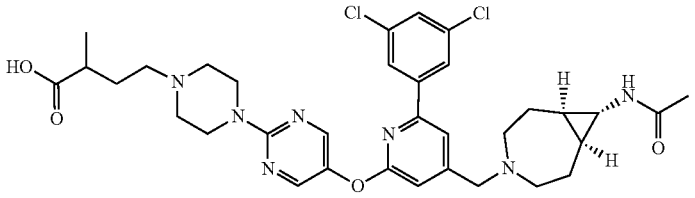 [SMILES: CC(=O)N[C@H]1[C@@H]2CCN(Cc3cc(Oc4cnc(N5CCN(CCC(C)C(=O)O)CC5)nc4)nc(-c4cc(Cl)cc(Cl)c4)c3)CC[C@@H]21]<br>4-(4-(5-((4-(((1R,7S,8r)-8-acetamido-4-azabicyclo[5.1.0]octan-4-yl)methyl)-6-(3,5-dichlorophenyl)pyridin-2-yl)oxy)pyrimidin-2-yl)piperazin-1-yl)-2-methylbutanoic acid | ¹H NMR (400 MHz, CD$_3$OD) δ ppm 8.45 (s, 2H), 7.97-7.80 (m, 3H), 7.50 (t, J = 1.87 Hz, 1H), 7.31 (s, 1H), 4.93 (d, J = 14.11 Hz, 2H), 4.48 (s, 2H), 3.70 (d, J = 11.91 Hz, 2H), 3.61 (dd, J = 5.95, 12.57 Hz, 2H), 3.44-3.30 (m, 5H), 3.28-3.23 (m, 2H), 3.22-3.10 (m, 2H), 2.62-2.48 (m, 3H), 2.17-2.08 (m, 1H), 1.98-1.91 (m, 1H), 1.90-1.85 (m, 3H), 1.74-1.58 (m, 2H), 1.27 (d, J = 7.28 Hz, 5H) | ES-LCMS m/z 682.3, 684.3 [M + H]$^+$. |
| 83 | 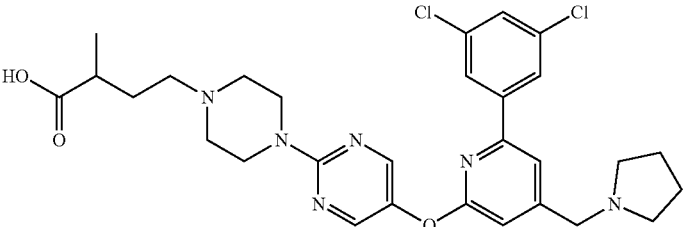<br>4-(4-(5-((6-(3,5-dichlorophenyl)-4-(pyrrolidin-1-ylmethyl)pyridin-2-yl)oxy)pyrimidin-2-yl)piperazin-1-yl)-2-methylbutanoic acid | ¹H NMR (400 MHz, CD$_3$OD) δ ppm 8.35 (s, 2H), 7.80 (d, J = 2.0 Hz, 2H), 7.67 (s, 1H), 7.42 (t, J = 1.9 Hz, 1H), 7.06-7.05 (m, 1H), 3.99-3.95 (m, 4H), 3.79 (s, 2H), 2.98-2.92 (m, 4H), 2.86-2.79 (m, 2H), 2.67 (br s, 4H), 2.48-2.41 (m, 1H), 1.91-1.83 (m, | ES-LCMS m/z 585.2, 587.3 [M + H]$^+$. |
| 84 | 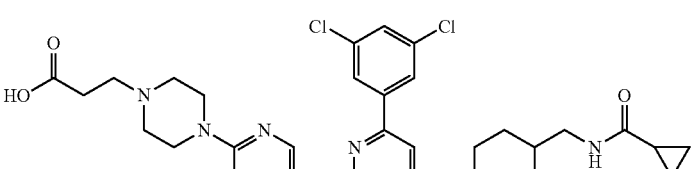<br>3-(4-(5-((4-((4-(cyclopropanecarboxamido-methyl)piperidin-1-yl)methyl)-6-(3,5-dichlorophenyl)pyridin-2-yl)oxy)pyrimidin-2-yl)piperazin-1-yl)propanoic acid | ¹H NMR (400 MHz, CD$_3$OD) δ ppm 8.46 (s, 2H), 7.87 (s, 3H), 7.52 (s, 1H), 7.31 (s, 1H), 4.87-4.86 (m, 2H), 4.43 (s, 2H), 3.70 (s, 2H), 3.61 (d, J = 12.6 Hz, 2H), 3.55-3.37 (m, 6H), 3.23 (s, 1H), 3.15 (d, J = 6.6 Hz, 2H), 3.12-3.05 (m, 1H), 2.96-2.88 (m, 2H), 2.00 (d, J = 14.3 Hz, 2H), 1.85 (s, 1H), 1.57 (s, 3H), 0.87-0.82 (m, 2H), 0.79-0.73 (m, 2H) | ES-LCMS m/z 668.3, 670.3 [M + H]$^+$. |

TABLE 4-continued

| Example | Structure/Name | $^1$H NMR | LCMS |
|---|---|---|---|
| 85 | 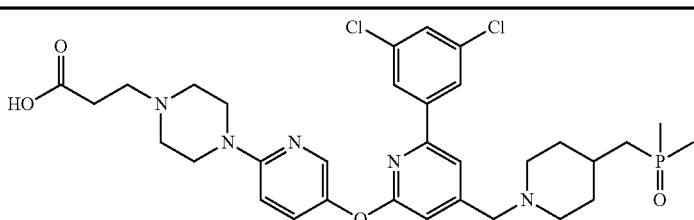3-(4-(5-((6-(3,5-dichlorophenyl)-4-((4-((dimethylphosphoryl)methyl)piperidin-1-yl)methyl)pyridin-2-yl)oxy)pyridin-2-yl)piperazin-1-yl)propanoic acid | $^1$H NMR (400 MHz, D$_2$O) δ ppm 8.01 (d, J = 2.9 Hz, 1H), 7.88-7.79 (m, 1H), 7.60-7.55 (m, 2H), 7.53 (s, 1H), 7.41-7.35 (m, 1H), 7.25-7.16 (m, 1H), 7.07 (s, 1H), 4.27 (s, 2H), 3.85 (br s, 2H), 3.43 (t, J = 6.8 Hz, 10H), 3.01 (t, J = 13.1 Hz, 2H), 2.82 (t, J = 6.9 Hz, 2H), 2.05-1.92 (m, 3H), 1.78 (dd, J = 6.5, 11.8 Hz, 2H), 1.59-1.48 (m, 2H), 1.45 (d, J = 13.0 Hz, 6H) | ES-LCMS m/z 660.3, 662.3 [M + H]$^+$. |

Example 86: 2-(1-((2-(3,5-Dichlorophenyl)-6-((2-(piperazin-1-yl)pyrimidin-5-yl)oxy)pyridine-4-yl)methyl)piperidin-4-yl)acetamide, 4 hydrochloride

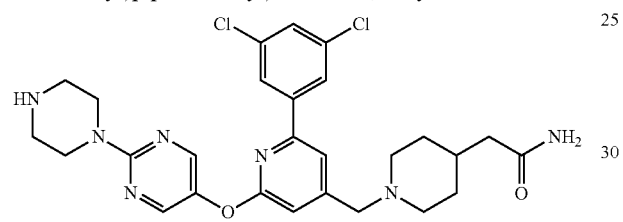

To a mixture of methyl 2-(1-((2-(3,5-dichlorophenyl)-6-((2-(piperazin-1-yl)pyrimidin-5-yl)oxy)pyridin-4-yl)methyl)piperidin-4-yl)acetate, 4 hydrochloride (300 mg, 0.335 mmol) was added ammonia in MeOH (5 mL). The mixture was stirred at 80° C. for 5 h then concentrated to yield the crude product which was purified by preparative HPLC (MeCN/H$_2$O as eluents, acidic condition) and dried by lyophilization to yield a white solid of 2-(1-((2-(3,5-dichlorophenyl)-6-((2-(piperazin-1-yl)pyrimidin-5-yl)oxy)pyridin-4-yl)methyl)piperidin-4-yl)acetamide, 4 hydrochloride (22.32 mg, 0.032 mmol, 9.50% yield): $^1$H NMR (400 MHz, CD$_3$OD) δ ppm 8.45 (s, 2H), 7.92 (s, 1H), 7.87 (d, J=1.8 Hz, 2H), 7.50 (s, 1H), 7.31 (s, 1H), 4.59-4.39 (m, 2H), 4.18-4.08 (m, 4H), 3.58 (d, J=11.9 Hz, 2H), 3.33 (d, J=5.3 Hz, 4H), 3.12 (t, J=11.9 Hz, 2H), 2.22 (d, J=6.6 Hz, 2H), 2.02 (d, J=14.6 Hz, 3H), 1.71-1.56 (m, 2H); ES-LCMS m/z 556.3, 558.2 [M+H]$^+$.

Example 87: 2-(1-((2-(3,5-Dichlorophenyl)-6-((2-(4-methylpiperazin-1-yl)pyrimidin-5-yl)oxy)pyridin-4-yl)methyl)piperidin-4-yl)ethanesulfonamide, 4 hydrochloride

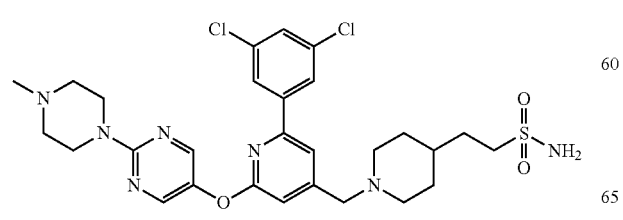

Step 1: (2-(3,5-Dichlorophenyl)-6-((2-(piperazin-1-yl)pyrimidin-5-yl)oxy)pyridin-4-yl)methanol, 3 hydrochloride

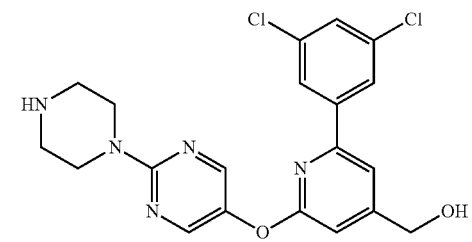

To a solution of tert-butyl 4-(5-((6-(3,5-dichlorophenyl)-4-(hydroxymethyl)pyridin-2-yl)oxy)pyrimidin-2-yl)piperazine-1-carboxylate (1 g, 1.503 mmol) in MeOH (20 mL) was added HCl solution (4.0 M in MeOH, 20 mL, 80 mmol). The reaction was stirred at 20° C. for 0.5 h then concentrated to yield a brown solid of (2-(3,5-dichlorophenyl)-6-((2-(piperazin-1-yl)pyrimidin-5-yl)oxy)pyridin-4-yl)methanol, 3 hydrochloride (820 mg, 1.317 mmol, 88.0% yield): $^1$H NMR (400 MHz, CD$_3$OD) δ ppm 8.70 (br. s, 2H), 7.82 (br. s, 2H), 7.67 (s, 1H), 7.47 (s, 1H), 7.20-7.13 (m, 1H), 4.78 (br. s, 2H), 4.24 (br. s, 4H), 3.44 (br. s, 4H); ES-LCMS m/z 432.1, 434.0 [M+H]$^+$.

Step 2: (2-(3,5-Dichlorophenyl)-6-((2-(4-methylpiperazin-1-yl)pyrimidin-5-yl)oxy)pyridin-4-yl)methanol and (2-(3,5-Dichlorophenyl)-6-((2-(4-methylpiperazin-1-yl)pyrimidin-5-yl)oxy)pyridin-4-yl)methyl formate

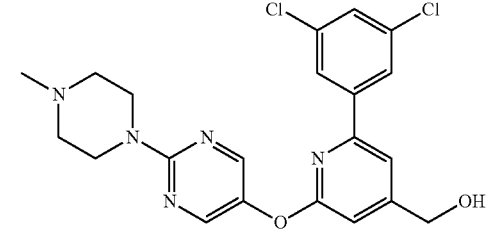 [SMILES: CN1CCN(c2ncc(Oc3cc(CO)cc(-c4cc(Cl)cc(Cl)c4)n3)cn2)CC1]

-continued

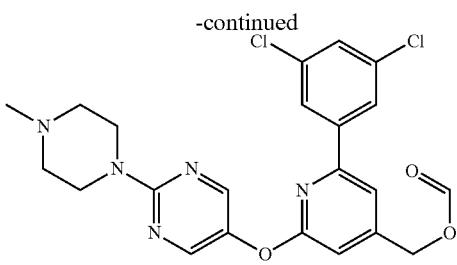

To a mixture of (2-(3,5-dichlorophenyl)-6-((2-(piperazin-1-yl)pyrimidin-5-yl)oxy)pyridin-4-yl)methanol, 3 hydrochloride (0.8 g, 1.285 mmol) in formic acid (5 mL) was added formaldehyde (37% in H₂O, 3.09 g, 25.7 mmol). The solution was stirred at 100° C. for 2 h then concentrated and distributed between DCM (50 mL) and saturated aqueous NaHCO₃ (30 mL) solution. The aqueous layer was extracted with DCM (50 mL×2). The combined organic extract was washed with brine (20 mL), dried over Na₂SO₄, filtered and concentrated to yield a mixture of (2-(3,5-dichlorophenyl)-6-((2-(4-methylpiperazin-1-yl)pyrimidin-5-yl)oxy)pyridin-4-yl)methanol (0.8 g, 1.144 mmol, 89.0% yield) and (2-(3,5-dichlorophenyl)-6-((2-(4-methylpiperazin-1-yl)pyrimidin-5-yl)oxy)pyridin-4-yl)methyl formate (0.8 g, 0.234 mmol, 18.2% yield) as a brown solid: ¹H NMR (400 MHz, CD₃OD) δ ppm 8.46 (s, 2H), 7.83 (s, 2H), 7.68-7.63 (m, 1H), 7.47 (s, 1H), 7.10 (s, 1H), 4.76 (br. s, 2H), 3.75 (s, 4H), 3.26 (s, 4H), 2.98 (s, 3H); ES-LCMS m/z 446.1, 448.1 [M+H]⁺ and ES-LCMS m/z 474.1, 476.1 [M+H]⁺.

Step 3: Ethyl 3-(4-(5-((6-(3,5-dichlorophenyl)-4-(((methylsulfonyl)oxy)methyl)pyridin-2-yl)oxy)pyrimidin-2-yl)piperazin-1-yl)propanoate

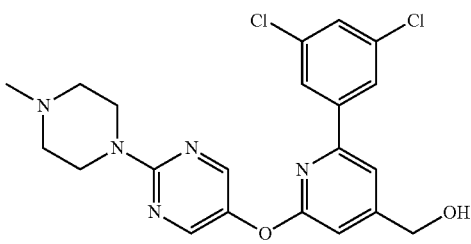

To a solution of (2-(3,5-dichlorophenyl)-6-((2-(4-methylpiperazin-1-yl)pyrimidin-5-yl)oxy)pyridin-4-yl)methyl formate (0.8 g, 0.234 mmol) and (2-(3,5-dichlorophenyl)-6-((6-(4-methylpiperazin-1-yl)pyridin-3-yl)oxy)pyridin-4-yl)methanol (0.8 g, 1.505 mmol) in MeOH (30 mL) and water (10 mL) was added K₂CO₃ (0.162 g, 1.172 mmol). The mixture was stirred at 20° C. for 1 h then concentrated and distributed between DCM (50 mL) and water (40 mL) solution. The aqueous phase was extracted with DCM (50 mL×3). The combined organic extract was dried over Na₂SO₄, filtered and concentrated to yield a white solid of (2-(3,5-dichlorophenyl)-6-((2-(4-methylpiperazin-1-yl)pyrimidin-5-yl)oxy)pyridin-4-yl)methanol (0.65 g, 1.188 mmol, 50.7% yield): ¹H NMR (400 MHz, CDCl₃) δ ppm 8.11 (s, 2H), 7.57 (s, 2H), 7.16 (s, 2H), 6.75 (s, 1H), 4.55 (s, 2H), 3.69 (br. s, 4H), 2.38 (br. s, 4H), 2.19 (s, 3H); LCMS m/z 446.1, 448.1 [M+H]⁺.

Step 4: (2-(3,5-Dichlorophenyl)-6-((2-(4-methylpiperazin-1-yl)pyrimidin-5-yl)oxy)pyridin-4-yl)methyl methanesulfonate

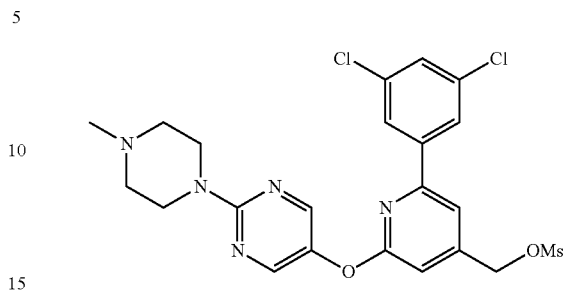

To a solution of (2-(3,5-dichlorophenyl)-6-((2-(4-methylpiperazin-1-yl)pyrimidin-5-yl)oxy)pyridin-4-yl)methanol (0.15 g, 0.274 mmol) and DIEA (0.146 mL, 0.823 mmol) in DCM (20 mL) was added MsCl (0.045 mL, 0.548 mmol). The solution was stirred at 20° C. for 0.5 h then washed with water (20 mL×3). The organic layer was dried over Na₂SO₄, filtered and concentrated. The mixture was concentrated to yield brown oil of (2-(3,5-dichlorophenyl)-6-((2-(4-methylpiperazin-1-yl)pyrimidin-5-yl)oxy)pyridin-4-yl)methyl methanesulfonate (180 mg, 0.235 mmol, 86.0% yield): ¹H NMR (400 MHz, CDCl₃) δ ppm 8.38 (d, J=17.6 Hz, 2H), 7.69 (br. s, 2H), 7.44 (br. s, 1H), 7.39 (br. s, 1H), 7.00 (br. s, 1H), 5.31 (br. s, 2H), 3.92 (s, 3H), 3.77 (br. s, 4H), 3.57 (br. s, 4H), 2.91-2.77 (m, 3H); LCMS m/z 524.0, 526.0 [M+H]⁺.

Step 5: 2-(1-((2-(3,5-Dichlorophenyl)-6-((2-(4-methylpiperazin-1-yl)pyrimidin-5-yl)oxy)pyridin-4-yl)methyl)piperidin-4-yl)ethanesulfonamide, 4 hydrochloride

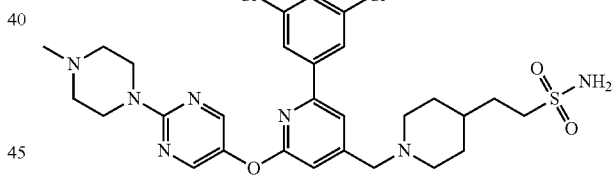

To a mixture of (2-(3,5-dichlorophenyl)-6-((2-(4-methylpiperazin-1-yl)pyrimidin-5-yl)oxy)pyridin-4-yl)methyl methanesulfonate (180 mg, 0.235 mmol), K₂CO₃ (97 mg, 0.704 mmol) in DMF (5 mL) was added 2-(piperidin-4-yl)ethanesulfonamide (67.7 mg, 0.282 mmol). The mixture was stirred at 25° C. for 2 h then concentrated. The residue was diluted with DCM (50 mL) and water (50 mL), extracted with DCM (50 mL×2). The combined organic extract was dried over Na₂SO₄, filtered and concentrated. The crude product was purified by silica gel column chromatography (DCM/MeOH=10/1, R_f=0.5) to yield a brown solid of 2-(1-((2-(3,5-dichlorophenyl)-6-((2-(4-methylpiperazin-1-yl)pyrimidin-5-yl)oxy)pyridin-4-yl)methyl)piperidin-4-yl)ethanesulfonamide, 4 hydrochloride (10.07 mg, 0.013 mmol, 5.5% yield): ¹H NMR (400 MHz, CD₃OD) δ ppm 8.49-8.42 (m, 2H), 7.90 (s, 1H), 7.87 (d, J=1.8 Hz, 2H), 7.51 (d, J=1.8 Hz, 1H), 7.31 (s, 1H), 4.43 (s, 2H), 3.59 (d, J=7.5 Hz, 5H), 3.39 (br. s, 2H), 3.25-3.04 (m, 7H), 2.97 (s, 3H), 2.05 (d, J=13.2 Hz, 2H), 1.88-1.78 (m, 3H), 1.56 (d, J=13.7 Hz, 2H); ES-LCMS m/z 620.2, 622.2 [M+H]⁺.

Example 88: 3-(4-(5-((4-((4-(Acetamidomethyl)piperidin-1-yl)methyl)-6-(3,5-dichlorophenyl)pyridin-2-yl)oxy)pyrimidin-2-yl)piperazin-1-yl)propanamide

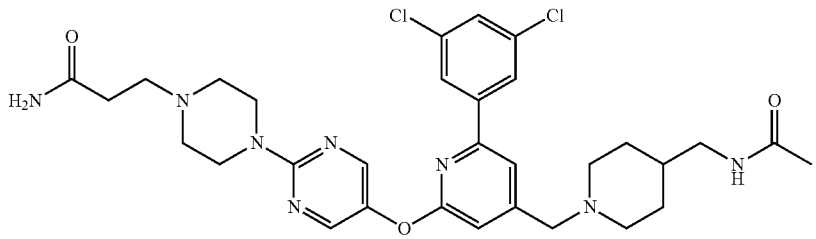

To a mixture of N-((1-((2-(3,5-dichlorophenyl)-6-((2-(piperazin-1-yl)pyrimidin-5-yl)oxy)pyridin-4-yl)methyl)piperidin-4-yl)methyl)acetamide, 4 hydrochloride (250 mg, 0.279 mmol) in MeCN (5 mL) was added DIEA (180 mg, 1.396 mmol) and 3-bromopropanamide (46.7 mg, 0.307 mmol). The reaction was stirred at 15° C. for 10 h under $N_2$ atmosphere. The mixture was concentrated to yield crude product which was purified by preparative HPLC (MeCN/$H_2O$ as eluents, basic condition) and dried by lyophilization to yield a white solid of 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanamide (39.31 mg, 0.060 mmol, 21.5% yield): $^1$H NMR (400 MHz, $CD_3OD$) δ ppm 8.34 (s, 2H), 7.85 (d, J=1.5 Hz, 2H), 7.68 (s, 1H), 7.46 (s, 1H), 7.07 (s, 1H), 3.95-3.84 (m, 4H), 3.64 (s, 2H), 3.10 (d, J=6.5 Hz, 2H), 2.96 (d, J=12.0 Hz, 2H), 2.79-2.72 (m, 2H), 2.62 (t, J=4.8 Hz, 4H), 2.49 (t, J=7.3 Hz, 2H), 2.17-2.06 (m, 2H), 1.96 (s, 3H), 1.75 (d, J=11.5 Hz, 2H), 1.42-1.23 (m, 3H); ES-LCMS m/z 641.3, 643.3 [M+H]$^+$.

Example 89: N-((1-((2-(3,5-Dichlorophenyl)-6-((6-(piperazin-1-yl)pyridin-3-yl)oxy) pyrimidin-4-yl)methyl) piperidin-4-yl)methyl)acetamide, 4 hydrochloride

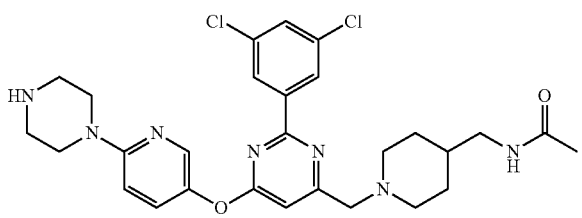

Step 1: Methyl 6-((6-(4-(tert-butoxycarbonyl)piperazin-1-yl)pyridin-3-yl)oxy)-2-chloropyrimidine-4-carboxylate

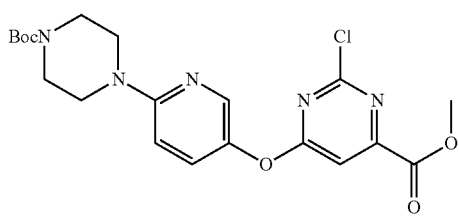 [SMILES: COC(=O)c1cc(Oc2ccc(N3CCN(C(=O)OC(C)(C)C)CC3)nc2)nc(Cl)n1]

To a mixture of methyl 2,6-dichloropyrimidine-4-carboxylate (600 mg, 2.90 mmol) in MeCN (100 mL) was added tert-butyl 4-(5-hydroxypyridin-2-yl)piperazine-1-carboxylate (972 mg, 3.48 mmol), $K_2CO_3$ (1202 mg, 8.70 mmol). The mixture was stirred at 30° C. for 12 h then filtered and concentrated to yield crude product which was purified by silica gel column chromatography (MeOH/DCM=10/1, $R_f$=0.4) to yield a brown solid of methyl 6-((6-(4-(tert-butoxycarbonyl)piperazin-1-yl)pyridin-3-yl)oxy)-2-chloropyrimidine-4-carboxylate (500 mg, 0.889 mmol, 30.7% yield): $^1$H NMR (400 MHz, $CDCl_3$) δ ppm 8.01 (d, J=2.65 Hz, 1H), 7.46 (s, 1H), 7.29 (dd, J=2.87, 9.04 Hz, 1H), 6.64 (d, J=9.04 Hz, 1H), 3.96 (s, 3H), 3.49 (s, 8H), 1.43 (s, 9H); ES-LCMS m/z 450.1 [M+H]$^+$.

Step 2: Methyl 6-((6-(4-(tert-butoxycarbonyl)piperazin-1-yl)pyridin-3-yl)oxy)-2-(3,5-dichlorophenyl)pyrimidine-4-carboxylate

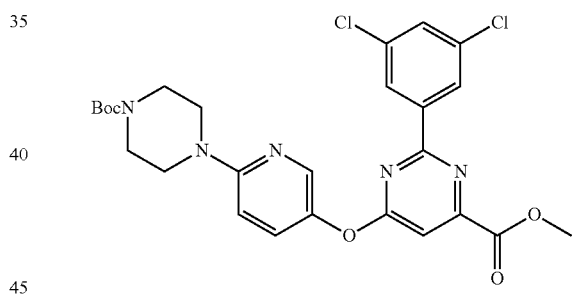

To a mixture of methyl 6-((6-(4-(tert-butoxycarbonyl)piperazin-1-yl)pyridin-3-yl)oxy)-2-chloropyrimidine-4-carboxylate (500 mg, 1.111 mmol), (3,5-dichlorophenyl)boronic acid (212 mg, 1.111 mmol), $K_2CO_3$ (461 mg, 3.33 mmol) in 1,4-dioxane (100 mL) was added $PdCl_2$(dppf) (81 mg, 0.111 mmol). The mixture was stirred at 80° C. for 3 h under $N_2$ atmosphere. The reaction mixture was concentrated and the residue was partitioned between DCM (100 mL) and water (100 mL), extracted with DCM (100 mL×2). The combined organic layers were dried over $Na_2SO_4$, filtered and concentrated to yield crude product. The crude product was purified by silica gel column chromatography (DCM/MeOH=20/1 to 10/1, DCM/MeOH=10/1, $R_f$=0.5) to yield a brown solid of methyl 6-((6-(4-(tert-butoxycarbonyl)piperazin-1-yl)pyridin-3-yl)oxy)-2-(3,5-dichlorophenyl)pyrimidine-4-carboxylate (400 mg, 0.571 mmol, 51.4% yield): $^1$H NMR (400 MHz, $CDCl_3$) δ ppm 8.19 (d, J=1.71 Hz, 1H), 8.12 (d, J=2.69 Hz, 1H), 7.52-7.38 (m, 3H), 7.27-7.21 (m, 1H), 6.78-6.72 (m, 1H), 4.04 (s, 3H), 3.57 (m, 8H), 1.48 (s, 9H); ES-LCMS m/z 560.1, 562.1 [M+H]$^+$.

Step 3: tert-Butyl 4-(5-((2-(3,5-dichlorophenyl)-6-(hydroxymethyl)pyrimidin-4-yl)oxy)pyridine-2-yl)piperazine-1-carboxylate

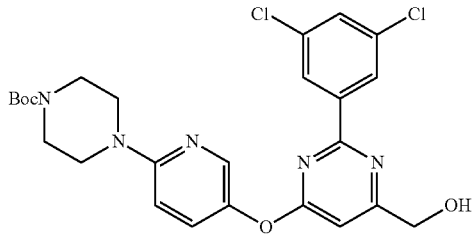

To a solution of methyl 6-((6-(4-(tert-butoxycarbonyl)piperazin-1-yl)pyridin-3-yl)oxy)-2-(3,5-dichlorophenyl)pyrimidine-4-carboxylate (500 mg, 0.892 mmol) in EtOH (100 mL) was added NaBH$_4$ (675 mg, 17.84 mmol). The mixture was stirred at 70° C. for 1 h then concentrated. The residue was dissolved in DCM (100 mL) and the mixture was washed with water (100 mL×3). The organic phase was dried over Na$_2$SO$_4$, filtered and concentrated to yield a brown solid of tert-butyl 4-(5-((2-(3,5-dichlorophenyl)-6-(hydroxymethyl)pyrimidin-4-yl)oxy)pyridin-2-yl)piperazine-1-carboxylate (400 mg, 0.601 mmol, 67.4% yield): $^1$H NMR (400 MHz, CDCl$_3$) δ ppm 8.18 (d, J=2.01 Hz, 2H), 8.12 (d, J=2.51 Hz, 1H), 7.45-7.39 (m, 2H), 6.84-6.79 (m, 1H), 6.75 (d, J=9.03 Hz, 1H), 4.79 (d, J=4.52 Hz, 2H), 3.58 (br. s, 8H), 1.50-1.48 (m, 9H); ES-LCMS m/z 532.2, 534.2 [M+H]$^+$.

Step 4: tert-Butyl 4-(5-((2-(3,5-dichlorophenyl)-6-(((methylsulfonyl)oxy)methyl)pyrimidin-4-yl)oxy)pyridin-2-yl)piperazine-1-carboxylate

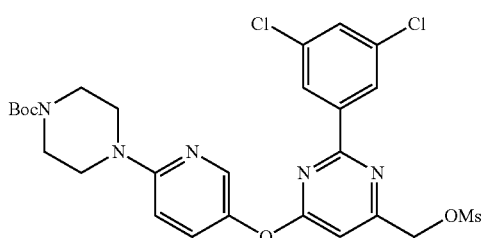

To a mixture of tert-butyl 4-(5-((2-(3,5-dichlorophenyl)-6-(hydroxymethyl)pyrimidin-4-yl)oxy)pyridin-2-yl)piperazine-1-carboxylate (300 mg, 0.563 mmol) in DCM (50 mL) was added MsCl (2.041 mL, 26.2 mmol), Et$_3$N (2.356 mL, 16.90 mmol) at 30° C. The mixture was stirred at 30° C. for 1 h then concentrated. The resulting crude was dissolved in DCM (50 mL) and the mixture was washed with water (50 mL×3). The organic layer was dried over Na$_2$SO$_4$, filtered, and concentrated to yield brown oil tert-butyl 4-(5-((2-(3,5-dichlorophenyl)-6-(((methylsulfonyl)oxy)methyl)pyrimidin-4-yl)oxy)pyridin-2-yl)piperazine-1-carboxylate (400 mg, 0.524 mmol, 93.0% yield): $^1$H NMR (400 MHz, CDCl$_3$) δ ppm 8.16 (d, J=1.51 Hz, 1H), 8.13-8.09 (m, 2H), 7.44 (d, J=2.01 Hz, 2H), 7.00 (s, 1H), 6.75 (d, J=9.03 Hz, 1H), 5.29 (s, 2H), 3.68 (td, J=6.34, 12.92 Hz, 8H), 3.18 (s, 3H), 1.42 (s, 9H); ES-LCMS m/z 610.2, 612.2 [M+H]$^+$.

Step 5: tert-Butyl 4-(5-((6-((4-(acetamidomethyl)piperidin-1-yl)methyl)-2-(3,5-dichlorophenyl)pyrimidin-4-yl)oxy)pyridin-2-yl)piperazine-1-carboxylate

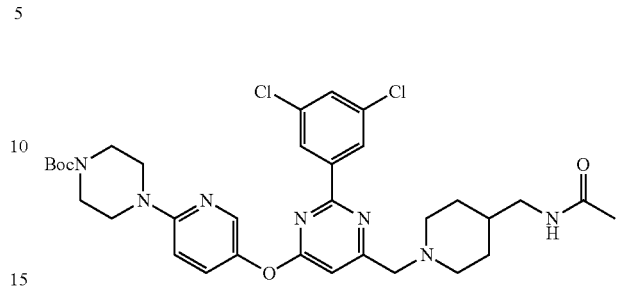

To a mixture of tert-butyl 4-(5-((2-(3,5-dichlorophenyl)-6-(((methylsulfonyl)oxy)methyl)pyrimidin-4-yl)oxy)pyridin-2-yl)piperazine-1-carboxylate (400 mg, 0.655 mmol) in DMF (100 mL) was added N-(piperidin-4-ylmethyl)acetamide, hydrochloride (151 mg, 0.786 mmol) and K$_2$CO$_3$ (272 mg, 1.966 mmol). The mixture was stirred at 80° C. for 5 h then cooled down, filtered and concentrated to yield the crude product which was purified by silica gel column chromatography (MeOH:DCM=10/1, R$_f$=0.4) to yield a brown solid of tert-butyl 4-(5-((6-((4-(acetamidomethyl)piperidin-1-yl)methyl)-2-(3,5-dichlorophenyl)pyrimidin-4-yl)oxy)pyridin-2-yl)piperazine-1-carboxylate (300 mg, 0.358 mmol, 54.6% yield): $^1$H NMR (400 MHz, CDCl$_3$) δ ppm 8.19 (d, J=1.96 Hz, 1H), 8.10-8.05 (m, 2H), 7.37-7.31 (m, 2H), 6.94 (s, 1H), 6.72-6.66 (m, 1H), 3.80-3.70 (m, 2H), 3.51 (br. s, 8H), 3.14-3.07 (m, 4H), 2.15-2.10 (m, 2H), 1.93 (s, 5H), 1.65 (d, J=12.72 Hz, 3H), 1.44-1.40 (m, 9H); ES-LCMS m/z 670.3, 672.3 [M+H]$^+$.

Step 6: N-((1-((2-(3,5-Dichlorophenyl)-6-((6-(piperazin-1-yl)pyridin-3-yl)oxy)pyrimidin-4-yl)methyl)piperidin-4-yl)methyl)acetamide, 4 hydrochloride

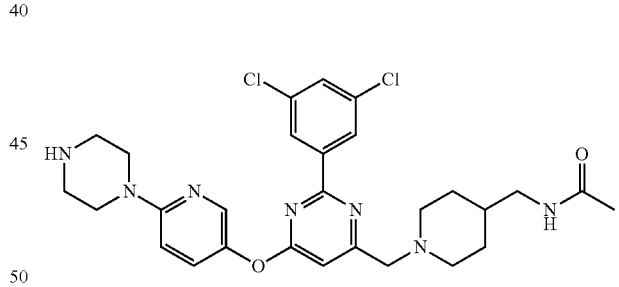

To a solution of tert-butyl 4-(5-((6-((4-(acetamidomethyl)piperidin-1-yl)methyl)-2-(3,5-dichlorophenyl)pyrimidin-4-yl)oxy)pyridin-2-yl)piperazine-1-carboxylate (290 mg, 0.432 mmol) in DCM (20 mL) was added TFA (5 mL, 64.9 mmol). The reaction was stirred at 20° C. for 1 h. The mixture was concentrated and purified by preparative HPLC (MeCN/H$_2$O as eluents, acidic condition) to yield a white solid of N-((1-((2-(3,5-dichlorophenyl)-6-((6-(piperazin-1-yl)pyridin-3-yl)oxy)pyrimidin-4-yl)methyl)piperidin-4-yl)methyl)acetamide, 4 hydrochloride (78.88 mg, 0.109 mmol, 25.1% yield): $^1$H NMR (400 MHz, CD$_3$OD) δ ppm 8.34-8.25 (m, 3H), 8.14 (dd, J=2.51, 9.54 Hz, 1H), 7.65 (s, 1H), 7.54 (d, J=10.04 Hz, 1H), 7.41-7.31 (m, 1H), 4.63 (s, 2H), 4.11-3.99 (m, 4H), 3.76 (d, J=12.55 Hz, 2H), 3.54-3.46 (m, 4H), 3.27-3.11 (m, 4H), 2.13-1.95 (m, 5H), 1.92 (br. s, 1H), 1.72-1.53 (m, 2H); ES-LCMS m/z 570.2, 572.2 [M+H]$^+$.

Example 90: N-((1-((6-(3,5-Dichlorophenyl)-2-((6-(piperazin-1-yl)pyridin-3-yl)oxy)pyrimidin-4-yl)methyl)piperidin-4-yl)methyl)acetamide

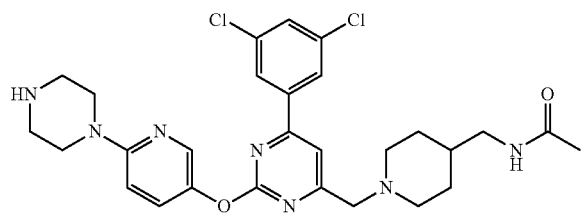 [SMILES: CC(=O)NCC1CCN(Cc2cc(-c3cc(Cl)cc(Cl)c3)nc(Oc3ccc(N4CCNCC4)nc3)n2)CC1]

Step 1: Methyl 2-chloro-6-(3,5-dichlorophenyl)pyrimidine-4-carboxylate

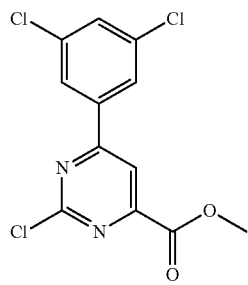 [SMILES: COC(=O)c1cc(-c2cc(Cl)cc(Cl)c2)nc(Cl)n1]

To a solution of methyl 2,6-dichloropyrimidine-4-carboxylate (5 g, 24.15 mmol) and K₂CO₃ (6.68 g, 48.3 mmol) in 1,4-dioxane (200 mL) was added (3,5-dichlorophenyl)boronic acid (5.53 g, 29.0 mmol) and PdCl₂(dppf) (1.767 g, 2.42 mmol) under N₂ atmosphere. The mixture was stirred at 80° C. for 12 h then concentrated and distributed between DCM (300 mL) and saturated aqueous NaHCO₃ (100 mL) solution. The combined organic extract was washed with brine (100 mL), dried over Na₂SO₄, filtered and concentrated. The crude material was purified by silica gel column chromatography (PE/EtOAc=3/1). All fractions found to contain product by TLC (PE/EtOAc=3/1, R_f=0.6) were combined and concentrated to yield a light yellow solid of methyl 2-chloro-6-(3,5-dichlorophenyl) pyrimidine-4-carboxylate (4 g, 11.34 mmol, 46.9% yield): ¹H NMR (400 MHz, CDCl₃) δ ppm 8.31 (s, 1H), 8.06 (d, J=2.0 Hz, 2H), 7.57 (t, J=1.9 Hz, 1H), 4.08 (s, 3H); ES-LCMS m/z 316.9, 318.9[M+H]⁺.

Step 2: Methyl 2-((6-(4-(tert-butoxycarbonyl)piperazin-1-yl)pyridin-3-yl)oxy)-6-(3,5-dichlorophenyl)pyrimidine-4-carboxylate

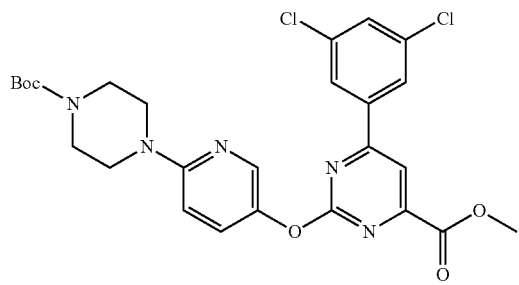 [SMILES: COC(=O)c1cc(-c2cc(Cl)cc(Cl)c2)nc(Oc2ccc(N3CCN(C(=O)OC(C)(C)C)CC3)nc2)n1]

To a mixture of methyl 2-chloro-6-(3,5-dichlorophenyl) pyrimidine-4-carboxylate (1 g, 3.15 mmol) and K₂CO₃ (0.870 g, 6.30 mmol) in DMF (20 mL) was added tert-butyl 4-(5-hydroxypyridin-2-yl)piperazine-1-carboxylate (0.880 g, 3.15 mmol). The mixture was stirred at 80° C. for 12 h. The solution was concentrated and distributed between DCM (50 mL) and saturated aqueous NaHCO₃ (30 mL) solution. The combined organic extract was washed with brine (20 mL), dried over Na₂SO₄, filtered and concentrated. The crude material was purified by silica gel column chromatography (PE/EtOAc=1/1). All fractions found to contain product by TLC (PE/EtOAc=1/1, R_f=0.3) were combined and concentrated to yield a light yellow solid of methyl 2-((6-(4-(tert-butoxycarbonyl)piperazin-1-yl)pyridin-3-yl)oxy)-6-(3,5-dichlorophenyl)pyrimidine-4-carboxylate (1.2 g, 1.328 mmol, 42.2% yield): ¹H NMR (400 MHz, CD₃OD) δ ppm 8.25 (s, 1H), 8.11 (d, J=2.6 Hz, 1H), 8.02 (d, J=1.8 Hz, 2H), 7.65-7.60 (m, 1H), 7.56 (dd, J=2.8, 9.2 Hz, 1H), 6.95 (d, J=9.3 Hz, 1H), 4.02-3.96 (m, 3H), 3.56 (s, 8H), 1.49 (s, 9H); ES-LCMS m/z 560.1, 562.1 [M+H]⁺.

Step 3: tert-Butyl 4-(5-((4-(3,5-dichlorophenyl)-6-(hydroxymethyl)pyrimidin-2-yl)oxy)pyridin-2-yl)piperazine-1-carboxylate

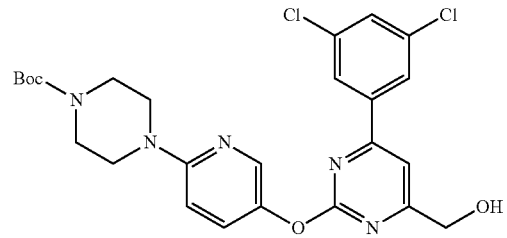 [SMILES: CC(C)(C)OC(=O)N1CCN(c2ccc(Oc3nc(CO)cc(-c4cc(Cl)cc(Cl)c4)n3)cn2)CC1]

To a solution of methyl 2-((6-(4-(tert-butoxycarbonyl)piperazin-1-yl)pyridin-3-yl)oxy)-6-(3,5-dichlorophenyl)pyrimidine-4-carboxylate (1.2 g, 2.141 mmol) in MeOH (50 mL) was added NaBH₄ (0.243 g, 6.42 mmol). The solution was stirred at 20° C. for 2 h. Saturated aqueous NH₄Cl (10 mL) was added and the solution was concentrated. Then crude product was added saturated aqueous NaHCO₃ (50 mL) solution, extracted with DCM (50 mL×2). The combined organic extract was washed with brine (50 mL), dried over Na₂SO₄, filtered and concentrated. The crude material was purified by silica gel column chromatography (PE/EtOAc=1/1). All fractions found to contain product by TLC (PE/EtOAc=1/1, R_f=0.6) were combined and concentrated to yield light yellow oil of tert-butyl 4-(5-((4-(3,5-dichlorophenyl)-6-(hydroxymethyl)pyrimidin-2-yl)oxy)pyridin-2-yl)piperazine-1-carboxylate (1 g, 1.127 mmol, 52.6% yield): ¹H NMR (400 MHz, CD₃OD) δ ppm 7.98 (d, J=1.8 Hz, 2H), 7.74 (d, J=2.9 Hz, 2H), 7.60 (t, J=1.8 Hz, 1H), 7.52 (dd, J=2.9, 9.0 Hz, 1H), 6.98-6.92 (m, 1H), 4.65 (s, 2H), 3.55 (br. s, 8H), 1.51-1.48 (m, 9H); ES-LCMS m/z 532.2, 534.2 [M+H]⁺.

Step 4: tert-Butyl 4-(5-((4-(3,5-dichlorophenyl)-6-(((methylsulfonyl)oxy)methyl)pyrimidin-2-yl)oxy)pyridin-2-yl)piperazine-1-carboxylate

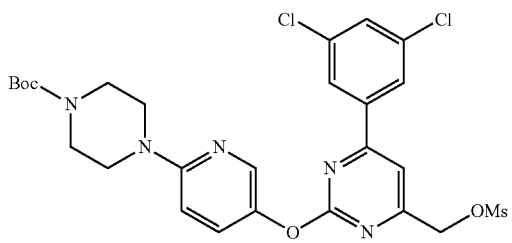 [SMILES: CC(C)(C)OC(=O)N1CCN(c2ccc(Oc3nc(COS(C)(=O)=O)cc(-c4cc(Cl)cc(Cl)c4)n3)cn2)CC1]

To a mixture of tert-butyl 4-(5-((4-(3,5-dichlorophenyl)-6-(hydroxymethyl)pyrimidin-2-yl)oxy)pyridin-2-yl)piperazine-1-carboxylate (1 g, 1.878 mmol) and DIEA (0.485 g, 3.76 mmol) in DCM (20 mL) was added MsCl (0.258 g, 2.254 mmol). The mixture was stirred at 20° C. for 10 min then concentrated and distributed between DCM (50 mL) and saturated aqueous NaHCO$_3$ (30 mL) solution. The combined organic extract was washed with brine (20 mL), dried over Na$_2$SO$_4$, filtered and concentrated to yield a light yellow solid of tert-butyl 4-(5-((4-(3,5-dichlorophenyl)-6-(((methylsulfonyl)oxy)methyl)pyrimidin-2-yl)oxy)pyridin-2-yl)piperazine-1-carboxylate (0.6 g, 0.865 mmol, 46.0% yield): $^1$H NMR (400 MHz, CD$_3$OD) δ ppm 8.08 (d, J=2.6 Hz, 2H), 8.04 (d, J=1.8 Hz, 1H), 7.53 (dd, J=2.9, 9.3 Hz, 2H), 6.86 (d, J=9.3 Hz, 2H), 5.30 (s, 2H), 3.55 (br. s, 8H), 3.21-3.11 (m, 3H), 1.48 (s, 9H); ES-LCMS m/z 610.1, 612.1 [M+H]$^+$.

Step 5: tert-Butyl 4-(5-((4-((4-(acetamidomethyl)piperidin-1-yl)methyl)-6-(3,5-dichlorophenyl)pyrimidin-2-yl)oxy)pyridin-2-yl)piperazine-1-carboxylate

To a mixture of tert-butyl 4-(5-((4-(3,5-dichlorophenyl)-6-(((methylsulfonyl)oxy)methyl)pyrimidin-2-yl)oxy)pyridin-2-yl)piperazine-1-carboxylate (0.6 g, 0.983 mmol) and K$_2$CO$_3$ (0.272 g, 1.966 mmol) in DMF (10 mL) was added N-(piperidin-4-ylmethyl)acetamide hydrochloride (0.189 g, 0.983 mmol). The mixture was stirred at 80° C. for 12 h then concentrated and distributed between DCM (50 mL) and saturated aqueous NaHCO$_3$ (30 mL) solution. The combined organic extract was washed with brine (20 mL), dried over Na$_2$SO$_4$, filtered and concentrated. The crude was purified by silica gel column chromatography (PE/EtOAc=1/1). All fractions found to contain product by TLC (PE/EtOAc=1/1, R$_f$=0.3) were combined and concentrated to yield a light yellow solid of tert-butyl 4-(5-((4-((4-(acetamidomethyl)piperidin-1-yl)methyl)-6-(3,5-dichlorophenyl)pyrimidin-2-yl)oxy)pyridin-2-yl)piperazine-1-carboxylate (0.3 g, 0.358 mmol, 36.4% yield): $^1$H NMR (400 MHz, CDCl$_3$) δ ppm 8.10 (d, J=2.9 Hz, 1H), 7.87 (d, J=1.8 Hz, 1H), 7.45 (dd, J=2.9, 9.3 Hz, 3H), 6.63 (d, J=9.3 Hz, 2H), 3.65-3.55 (m, 8H), 3.21-3.14 (m, 4H), 2.86-2.75 (m, 4H), 2.10-2.08 (m, 5H), 1.82-1.81 (m, 1H), 1.69-1.67 (m, 2H), 1.48 (s, 9H); ES-LCMS m/z 670.2, 672.2 [M+H]$^+$.

Step 6: N-((1-((6-(3,5-Dichlorophenyl)-2-((6-(piperazin-1-yl)pyridin-3-yl)oxy)pyrimidin-4-yl)methyl)piperidin-4-yl)methyl)acetamide, 4 hydrochloride

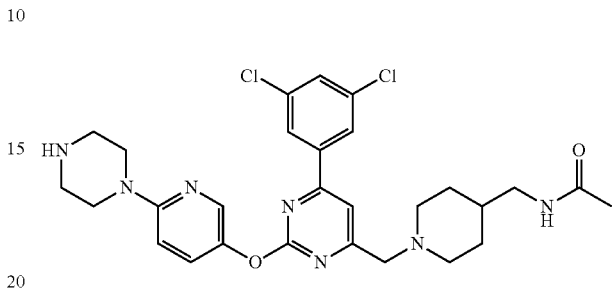

To a solution of tert-butyl 4-(5-((4-((4-(acetamidomethyl)piperidin-1-yl)methyl)-6-(3,5-dichlorophenyl)pyrimidin-2-yl)oxy)pyridin-2-yl)piperazine-1-carboxylate (300 mg, 0.447 mmol) in DCM (10 mL) was added TFA (2.0 g, 17.9 mmol). The solution was stirred at 20° C. for 0.5 h then concentrated. The residue was purified by preparative HPLC (MeCN/H$_2$O as eluents, acidic condition) to yield a light yellow solid of N-((1-((6-(3,5-dichlorophenyl)-2-((6-(piperazin-1-yl)pyridin-3-yl)oxy)pyrimidin-4-yl)methyl)piperidin-4-yl)methyl)acetamide, 4 hydrochloride (26 mg, 0.036 mmol, 8.1% yield): $^1$H NMR (400 MHz, CD$_3$OD) δ ppm 8.28 (d, J=2.3 Hz, 1H), 8.25 (dd, J=2.5, 9.8 Hz, 1H), 8.10 (d, J=1.5 Hz, 2H), 8.03-7.97 (m, 1H), 7.71 (s, 1H), 7.61 (d, J=9.8 Hz, 1H), 4.60 (s, 2H), 4.13-4.05 (m, 4H), 3.74 (d, J=12.0 Hz, 2H), 3.59-3.50 (m, 4H), 3.23-3.07 (m, 4H), 2.01-1.99 (m, 5H), 1.88 (br. s, 1H), 1.70-1.55 (m, 2H); ES-LCMS m/z 570.2, 572.2 [M+H]$^+$.

Example 91: N-((1-((2-(3,5-Dichlorophenyl)-6-((5-fluoro-6-(piperazin-1-yl)pyridin-3-yl)oxy)pyridin-4-yl)methyl)-4-hydroxypiperidin-4-yl)methyl)acetamide, 4 hydrochloride

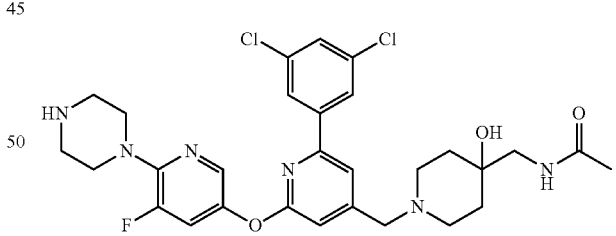

Step 1: tert-Butyl 4-(acetamidomethyl)-4-((tert-butyldimethylsilyl)oxy)piperidine-1-carboxylate

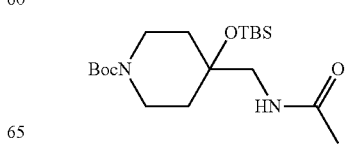

To a solution of tert-butyl 4-(aminomethyl)-4-((tert-butyldimethylsilyl)oxy)piperidine-1-carboxylate (15 g, 43.5 mmol) and DIEA (11.25 g, 87 mmol) in DCM (300 mL) was added acetyl chloride (5.13 g, 65.3 mmol). The reaction mixture was stirred at 20° C. for 12 h. Water (50 mL) was added then extracted with DCM (300 mL×2). The combined organic layers were dried over Na$_2$SO$_4$, concentrated to get the crude product which was purified by silica gel column chromatography (PE/EtOAc=5/1). All fractions found to contain product by TLC (PE/EA=3/1, R$_f$=0.4) were combined and concentrated to yield a light yellow solid of tert-butyl 4-(acetamidomethyl)-4-((tert-butyldimethylsilyl)oxy)piperidine-1-carboxylate (6 g, 13.97 mmol, 32.1% yield): $^1$H NMR (400 MHz, CD$_3$OD) δ ppm 3.58 (td, J=3.8, 13.2 Hz, 2H), 3.06 (br. s, 2H), 1.80 (s, 3H), 1.49-1.23 (m, 15H), 0.77 (s, 9H), 0.00 (s, 6H); ES-LCMS m/z 409.2 [M+Na]$^+$.

Step 2: N-((4-((tert-Butyldimethylsilyl)oxy)piperidin-4-yl)methyl)acetamide

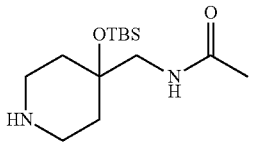

To a solution of tert-butyl 4-(acetamidomethyl)-4-((tert-butyldimethylsilyl)oxy)piperidine-1-carboxylate (6 g, 15.52 mmol) in DCM (20 mL) was added TFA (3 mL, 38.9 mmol). The reaction mixture was stirred at 20° C. for 0.5 h then concentrated to yield a yellow oil of N-((4-((tert-butyldimethylsilyl)oxy)piperidin-4-yl/methyl/acetamide as the TFA salt (4 g, 11.17 mmol, 72.0% yield): $^1$H NMR (400 MHz, CD$_3$OD) δ ppm 3.39 (s, 2H), 3.31-3.24 (m, 4H), 2.01 (s, 3H), 1.97-1.88 (m, 2H), 1.78 (br. s, 2H), 0.97 (s, 9H), 0.23 (s, 6H); ES-LCMS m/z 287.0 [M+H]$^+$.

Step 3: tert-Butyl 4-(5-((4-((4-(acetamidomethyl)-4-hydroxypiperidin-1-yl)methyl)-6-(3,5-dichlorophenyl)pyridin-2-yl)oxy)-3-fluoropyridin-2-yl)piperazine-1-carboxylate

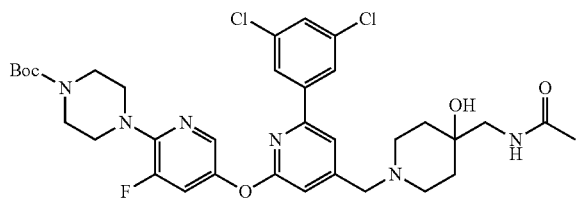 [SMILES: CC(=O)NCC1(O)CCN(Cc2cc(Oc3cnc(N4CCN(C(=O)OC(C)(C)C)CC4)c(F)c3)nc(-c3cc(Cl)cc(Cl)c3)c2)CC1]

A mixture of tert-butyl 4-(5-((6-(3,5-dichlorophenyl)-4-(((methylsulfonyl)oxy)methyl)pyridin-2-yl)oxy)-3-fluoropyridin-2-yl)piperazine-1-carboxylate (500 mg, 0.797 mmol), N-((4-((tert-butyldimethylsilyl)oxy)piperidin-4-yl)methyl)acetamide (457 mg, 1.594 mmol) and K$_2$CO$_3$ (330 mg, 2.390 mmol) in DMF (10 mL) was heated to 90° C. for 12 h under N$_2$ atmosphere. The reaction mixture was filtered and concentrated to yield the crude product which was purified by silica gel column chromatography (DCM/MeOH=9/1). All fractions found to contain product by TLC (DCM/MeOH=10/1, R$_f$=0.5) were combined and concentrated to yield a yellow solid of tert-butyl 4-(5-((4-((4-(acetamidomethyl)-4-hydroxypiperidin-1-yl)methyl)-6-(3,5-dichlorophenyl)pyridin-2-yl)oxy)-3-fluoropyridin-2-yl)piperazine-1-carboxylate (400 mg, 0.512 mmol, 64.2% yield): $^1$H NMR (400 MHz, CD$_3$OD) δ ppm 7.82-7.71 (m, 3H), 7.65 (s, 1H), 7.48 (dd, J=2.2, 12.8 Hz, 1H), 7.41 (s, 1H), 7.06-6.97 (m, 1H), 3.66-3.61 (m, 2H), 3.57 (br. s, 4H), 3.40 (d, J=4.9 Hz, 4H), 3.21 (s, 2H), 2.63 (d, J=11.5 Hz, 2H), 2.54-2.41 (m, 2H), 1.96 (s, 3H), 1.57 (d, J=12.8 Hz, 4H), 1.47 (s, 9H); ES-LCMS m/z 703.2, 705.2 [M+H]$^+$.

Step 4: N-((1-((2-(3,5-Dichlorophenyl)-6-((5-fluoro-6-(piperazin-1-yl)pyridin-3-yl)oxy)pyridin-4-yl)methyl)-4-hydroxypiperidin-4-yl)methyl)acetamide, 4 hydrochloride

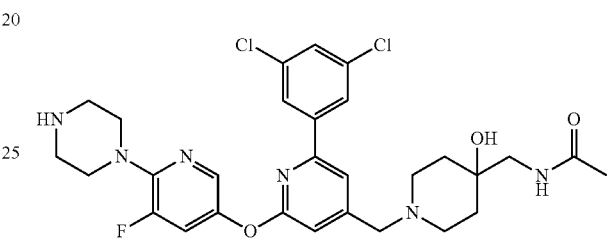

A mixture of tert-butyl 4-(5-((4-((4-(acetamidomethyl)-4-hydroxypiperidin-1-yl)methyl)-6-(3,5-dichlorophenyl)pyridin-2-yl)oxy)-3-fluoropyridin-2-yl)piperazine-1-carboxylate (400 mg, 0.568 mmol) and TFA (10% in DCM, 10 mL) was stirred at 15° C. for 0.5 h. Solution was concentrated to yield the crude product which was purified by preparative HPLC (MeCN/H$_2$O as eluents, acidic condition) to yield a white solid of N-((1-((2-(3,5-dichlorophenyl)-6-((5-fluoro-6-(piperazin-1-yl)pyridin-3-yl)oxy)pyridin-4-yl)methyl)-4-hydroxypiperidin-4-yl)methyl)acetamide, 4 hydrochloride (216.99 mg, 0.290 mmol, 50.9% yield): $^1$H NMR (400 MHz, CD$_3$OD) δ ppm 8.08 (d, J=2.2 Hz, 1H), 7.99 (s, 1H), 7.88 (d, J=1.8 Hz, 2H), 7.64 (dd, J=2.2, 12.8 Hz, 1H), 7.49 (t, J=1.8 Hz, 1H), 7.34 (s, 1H), 4.58-4.43 (m, 2H), 3.78-3.70 (m, 4H), 3.48-3.34 (m, 8H), 3.27 (s, 2H), 2.06-1.95 (m, 5H), 1.86-1.77 (m, 2H); ES-LCMS m/z 603.2, 605.2 [M+H]$^+$.

Example 92: N-((1-((2-(3,5-Dichlorophenyl)-6-((2-(piperazin-1-yl)pyrimidin-5-yl)oxy)pyridin-4-yl)methyl)piperidin-4-yl)methyl)acetamide

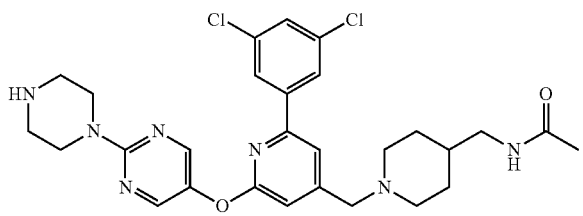 [SMILES: CC(=O)NCC1CCN(Cc2cc(Oc3cnc(N4CCNCC4)nc3)nc(-c3cc(Cl)cc(Cl)c3)c2)CC1]

Step 1: tert-Butyl 4-(5-((4-((4-(acetamidomethyl)piperidin-1-yl)methyl)-6-(3,5-dichlorophenyl)pyridin-2-yl)oxy)pyrimidin-2-yl)piperazine-1-carboxylate

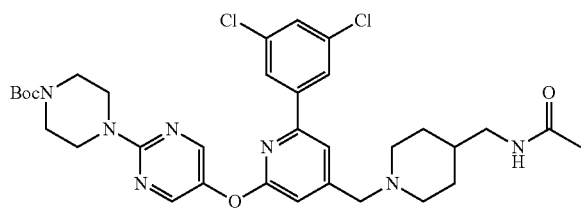

To a mixture of tert-butyl 4-(5-((6-(3,5-dichlorophenyl)-4-(((methylsulfonyl)oxy)methyl)pyridin-2-yl)oxy)pyrimidin-2-yl)piperazine-1-carboxylate (200 mg, 0.328 mmol), N-(piperidin-4-ylmethyl)acetamide hydrochloride (127 mg, 0.655 mmol) in DMF (5 mL) was added $K_2CO_3$ (181 mg, 1.310 mmol). The reaction was stirred at 50° C. for 8 h under $N_2$ atmosphere then concentrated. Saturated aqueous $NaHCO_3$ solution (15 mL) was added and the aqueous layer was extracted with DCM (150 mL×2). The combined extracts were washed with brine (15 mL×2), dried over $Na_2SO_4$, filtered and concentrated to yield a yellow oil of tert-butyl 4-(5-((4-((4-(acetamidomethyl)piperidin-1-yl)methyl)-6-(3,5-dichlorophenyl)pyridin-2-yl)oxy)pyrimidin-2-yl)piperazine-1-carboxylate (200 mg, 0.18 mmol, 54.6% yield): $^1$H NMR (400 MHz, $CDCl_3$) δ ppm 8.33-8.21 (m, 3H), 7.78-7.64 (m, 2H), 7.48-7.28 (m, 2H), 3.82 (br. s, 4H), 3.52 (br. s, 4H), 3.25-3.07 (m, 4H), 2.85-2.90 (m, 4H), 1.99 (d, J=2.5 Hz, 3H), 1.90-1.80 (m, 5H), 1.49-1.40 (m, 9H); ES-LCMS m/z 670.3, 672.3 [M+H]$^+$.

Step 2: N-((1-((2-(3,5-Dichlorophenyl)-6-((2-(piperazin-1-yl)pyrimidin-5-yl)oxy)pyridin-4-yl)methyl)piperidin-4-yl)methyl)acetamide, 4 hydrochloride

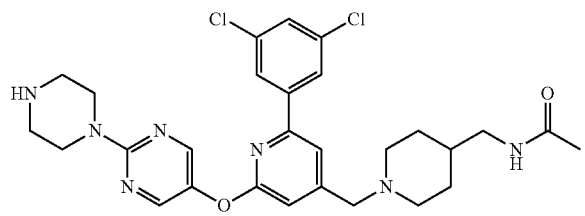

To a mixture of tert-butyl 4-(5-((4-((4-(acetamidomethyl)piperidin-1-yl)methyl)-6-(3,5-dichlorophenyl)pyridin-2-yl)oxy)pyrimidin-2-yl)piperazine-1-carboxylate (100 mg, 0.149 mmol) in DCM (10 mL) was added TFA (0.287 mL, 3.73 mmol). The reaction was stirred at 15° C. for 10 min under $N_2$ atmosphere then concentrated and purified by preparative HPLC (MeCN/$H_2O$ as eluents, acidic condition) to yield a yellow solid of N-((1-((2-(3,5-dichlorophenyl)-6-((2-(piperazin-1-yl)pyrimidin-5-yl)oxy)pyridine-4-yl)methyl)piperidin-4-yl)methyl)acetamide, 4 hydrochloride (5.39 mg, 7.45 μmol, 5.0% yield): $^1$H NMR (400 MHz, $CD_3OD$) δ ppm 8.45 (s, 2H), 7.91 (s, 1H), 7.87 (d, J=1.8 Hz, 2H), 7.51 (t, J=1.8 Hz, 1H), 7.34-7.27 (m, 1H), 4.43 (s, 2H), 4.15-4.10 (m, 4H), 3.60 (d, J=12.3 Hz, 2H), 3.34 (d, J=5.3 Hz, 4H), 3.14-3.05 (m, 4H), 2.02-1.94 (m, 5H), 1.85 (br. s, 1H), 1.62-1.51 (m, 2H); ES-LCMS m/z 570.3, 572.3 [M+H]$^+$.

Example 93: N-((1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)methyl)acetamide, 4 hydrochloride

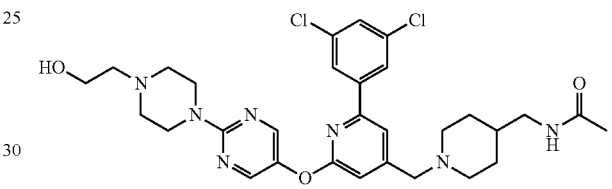

Step 1: Ethyl 2-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)acetate

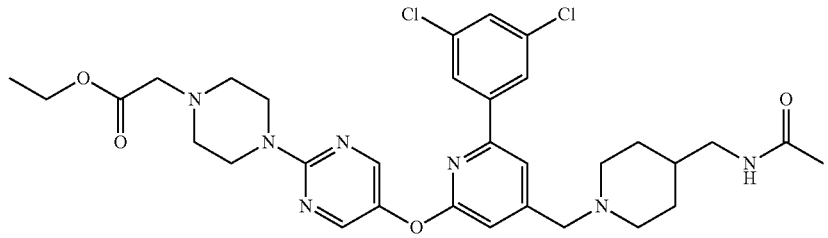 [SMILES: CCOC(=O)CN1CCN(c2ncc(Oc3cc(CN4CCC(CNC(C)=O)CC4)cc(-c4cc(Cl)cc(Cl)c4)n3)cn2)CC1]

To a mixture of N-((1-((2-(3,5-dichlorophenyl)-6-((2-(piperazin-1-yl)pyrimidin-5-yl)oxy)pyridin-4-yl)methyl)piperidin-4-yl)methyl)acetamide, 4 hydrochloride (400 mg, 0.447 mmol) in MeCN (5 mL) was added DIEA (289 mg, 2.234 mmol) and ethyl 2-bromoacetate (82 mg, 0.491 mmol). The reaction was stirred at 15° C. for 10 h under $N_2$ atmosphere then filtered and concentrated to yield a yellow solid of ethyl 2-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)acetate (350 mg, 0.426 mmol, 95.0% yield): $^1$H NMR (400 MHz, $CDCl_3$) δ ppm 8.23 (s, 2H), 7.95 (s, 2H), 7.68 (s, 2H), 7.22 (s, 1H), 4.13 (q, J=5.7 Hz, 2H), 3.84 (d, J=4.4 Hz, 4H), 3.76 (s, 2H), 3.67-3.63 (m, 4H), 3.08 (d, J=6.6 Hz, 4H), 2.60 (d, J=4.4 Hz, 4H), 1.94 (d, J=5.7 Hz, 6H), 1.76-1.66 (m, 2H), 1.21 (t, J=3.7 Hz, 3H); ES-LCMS m/z 656.3, 658.3 [M+H]$^+$.

Step 2: N-((1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)methyl)acetamide, 4 hydrochloride

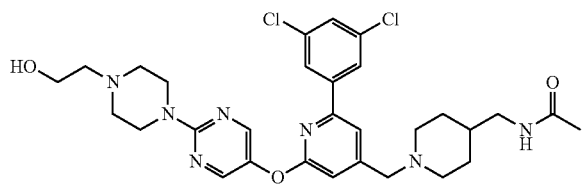 [SMILES: CC(=O)NCC1CCN(Cc2cc(Oc3cnc(N4CCN(CCO)CC4)nc3)nc(-c3cc(Cl)cc(Cl)c3)c2)CC1]

To a mixture of ethyl 2-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)acetate (250 mg, 0.305 mmol) in THF (10 mL) was added LiAlH$_4$ (17.34 mg, 0.457 mmol) at −20° C. The reaction was stirred at −20° C. for 10 h under N$_2$ atmosphere then quenched by 1 mL of water. The mixture was filtered and concentrated followed by purifying with preparative HPLC (MeCN/H$_2$O as eluents, acidic condition) and dried by lyophilization to yield a white solid N-((1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)methyl)acetamide, 4 hydrochloride (48.42 mg, 0.063 mmol, 20.8% yield): $^1$H NMR (400 MHz, CD$_3$OD) δ ppm 8.48 (s, 2H), 7.94-7.85 (m, 3H), 7.54 (s, 1H), 7.33 (s, 1H), 4.93 (br. s, 2H), 4.45 (s, 2H), 4.01-3.91 (m, 2H), 3.75 (d, J=12.5 Hz, 2H), 3.62 (d, J=12.0 Hz, 2H), 3.48 (t, J=12.3 Hz, 2H), 3.40-3.35 (m, 3H), 3.31-3.21 (m, 2H), 3.17-3.07 (m, 3H), 2.06-1.94 (m, 5H), 1.87 (br. s, 1H), 1.64-1.50 (m, 2H); ES-LCMS m/z 614.3, 616.3 [M+H]$^+$.

Example 94: 3-(4-(5-((4-((4-(Acetamidomethyl)piperidin-1-yl)methyl)-6-(3,5-dichlorophenyl)pyridin-2-yl)oxy)pyrimidin-2-yl)piperazin-1-yl)-N-methylpropanamide, 4 hydrochloride

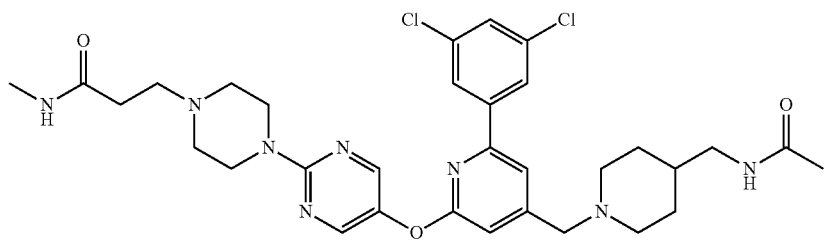 [SMILES: CNC(=O)CCN1CCN(c2ncc(Oc3cc(CN4CCC(CNC(C)=O)CC4)cc(-c4cc(Cl)cc(Cl)c4)n3)cn2)CC1]

Step 1: Ethyl 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoate and 3-(4-(5-((4-((4-(Acetamidomethyl)piperidin-1-yl)methyl)-6-(3,5-dichlorophenyl)pyridin-2-yl)oxy)pyrimidin-2-yl)piperazin-1-yl)propanoic acid

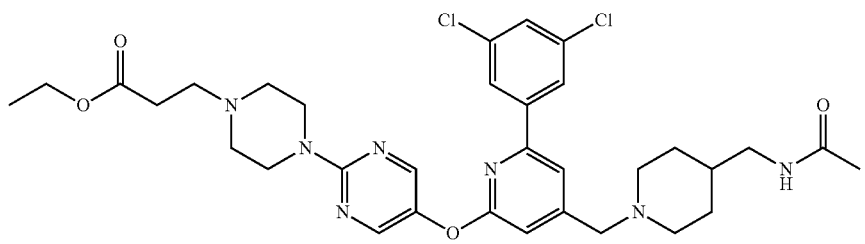

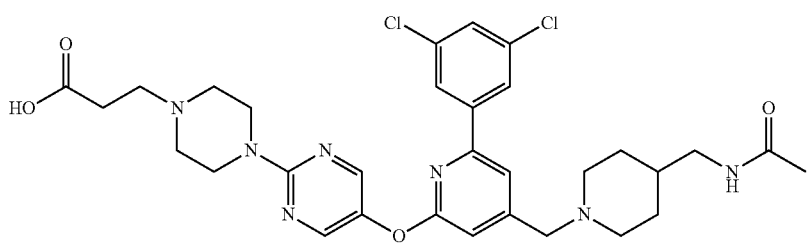

To a mixture of N-((1-((2-(3,5-dichlorophenyl)-6-((2-(piperazin-1-yl)pyrimidin-5-yl)oxy)pyridin-4-yl)methyl)piperidin-4-yl)methyl)acetamide (300 mg, 0.479 mmol) and $K_2CO_3$ (397 mg, 2.87 mmol) in DMF (15 mL) was added ethyl 3-bromopropanoate (173 mg, 0.957 mmol). Then, the mixture was stirred at 80° C. for 12 h. The mixture was cooled down and filtered. The filtrate was concentrated to yield a mixture of ethyl 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoate (350 mg, 0.089 mmol, 18.5% yield) and 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoic acid (350 mg, 0.234 mmol, 48.9% yield) as a brown solid: $^1$H NMR (400 MHz, CDCl$_3$) δ ppm 8.10-8.04 (m, 2H), 7.88 (d, J=1.3 Hz, 2H), 7.60 (d, J=8.8 Hz, 1H), 7.47 (s, 1H), 7.28 (s, 1H), 4.47 (s, 2H), 4.43-4.32 (m, 4H), 4.24-4.07 (m, 4H), 3.88-3.77 (m, 4H), 3.63-3.47 (m, 6H), 3.18-3.12 (m, 2H), 2.02-1.95 (m, 5H), 1.88 (br. s, 1H), 1.63 (d, J=11.9 Hz, 2H), 1.30-1.25 (m, 3H); ES-LCMS m/z 670.2, 672.2 [M+H]$^+$; ES-LCMS m/z 642.2, 644.2 [M+H]$^+$.

Step 2: 3-(4-(5-((4-((4-(Acetamidomethyl)piperidin-1-yl)methyl)-6-(3,5-dichloro phenyl)pyridin-2-yl)oxy)pyrimidin-2-yl)piperazin-1-yl)propanoic acid

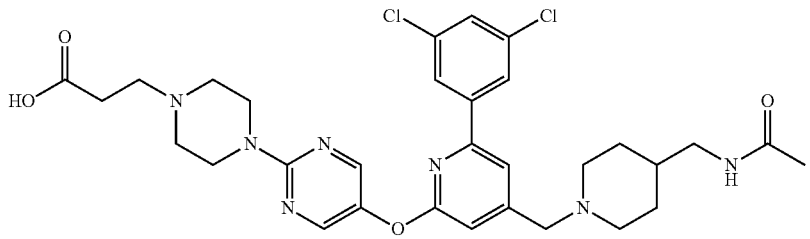

To a mixture of ethyl 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoate (350 mg, 0.089 mmol) and 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoic acid (350 mg, 0.234 mmol) in THF (5 mL) and Water (5 mL) was added LiOH·H$_2$O (30 mg, 0.715 mmol). Then the mixture was stirred at 30° C. for 3 h. The reaction was concentrated and this reaction mixture was diluted with DCM (100 mL) and water (100 mL), extracted with H$_2$O (100 mL×2). The combined water layers were adjusted to pH to 6-7 with 10% HCl aqueous solution. Then the mixture was concentrated to yield a brown solid of 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoic acid (250 mg, 0.311 mmol, 96.0% yield): $^1$H NMR (400 MHz, CDCl$_3$) δ ppm 8.09 (dd, J=2.6, 8.4 Hz, 2H), 7.83 (s, 1H), 7.71 (s, 2H), 7.43 (br. s, 1H), 7.05 (d, J=5.7 Hz, 1H), 3.83-3.74 (m, 4H), 3.44-3.37 (m, 6H), 3.20-3.13 (m, 4H), 3.11-3.01 (m, 4H), 2.57 (d, J=6.2 Hz, 2H), 1.96-1.90 (m, 5H), 1.78 (d, J=11.5 Hz, 1H), 1.43-1.33 (m, 2H); ES-LCMS m/z 642.2, 644.2 [M+H]$^+$.

Step 3: Methyl 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoate, 4 hydrochloride

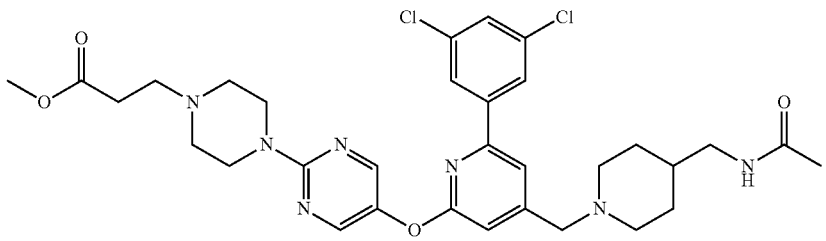 [SMILES: COC(=O)CCN1CCN(c2ncc(Oc3cc(CN4CCC(CNC(C)=O)CC4)cc(-c4cc(Cl)cc(Cl)c4)n3)cn2)CC1]

To a solution of 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoic acid (200 mg, 0.249 mmol) in MeOH (20 mL) was added HCl solution (4.0 M in MeOH, 10 mL, 40 mmol). The mixture was stirred at 30° C. for 0.5 h then concentrated. The reaction mixture was diluted with H₂O (50 mL), then washed with DCM (50 mL×3). The aqueous phase was concentrated to yield a brown solid of methyl 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoate, 4 hydrochloride (220 mg, 0.172 mmol, 69.1% yield): ¹H NMR (400 MHz, CDCl₃) δ ppm 8.32 (s, 2H), 7.82 (d, J=1.8 Hz, 2H), 7.66 (s, 1H), 7.44 (s, 1H), 7.05 (s, 1H), 4.63 (s, 4H), 3.87-3.81 (m, 3H), 3.69 (s, 3H), 3.63 (s, 2H), 3.08 (d, J=7.1 Hz, 2H), 2.95 (d, J=11.9 Hz, 3H), 2.79-2.72 (m, 2H), 2.63-2.57 (m, 4H), 2.14-2.07 (m, 3H), 1.73 (d, J=11.9 Hz, 2H), 1.30 (d, J=17.2 Hz, 3H); ES-LCMS m/z 656.2, 658.3 [M+H]⁺.

Step 4: 3-(4-(5-((4-((4-(Acetamidomethyl)piperidin-1-yl)methyl)-6-(3,5-dichlorophenyl)pyridin-2-yl)oxy)pyrimidin-2-yl)piperazin-1-yl)-N-methylpropanamide, 4 hydrochloride

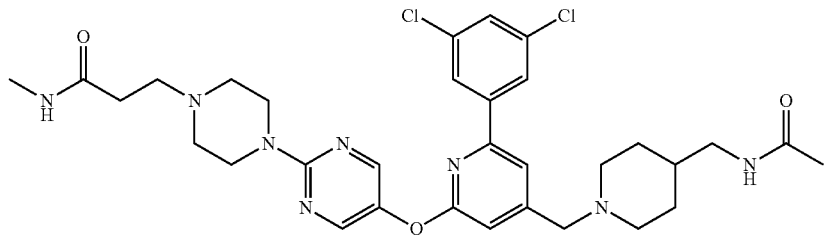 [SMILES: CNC(=O)CCN1CCN(c2ncc(Oc3cc(CN4CCC(CNC(C)=O)CC4)cc(-c4cc(Cl)cc(Cl)c4)n3)cn2)CC1]

A solution of methyl 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoate, 4 hydrochloride (180 mg, 0.141 mmol) and methanamine (30% in ethanol, 10 mL) was stirred at 70° C. for 16 h in autoclave. The mixture was concentrated and purified by preparative HPLC (MeCN/H₂O as eluents, acidic condition) and dried by lyophilization to yield a yellow solid of 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-N-methyl propanamide, 4 hydrochloride (50.39 mg, 0.062 mmol, 44.1% yield): ¹H NMR (400 MHz, CD₃OD) δ ppm 8.47 (s, 2H), 7.93 (s, 1H), 7.87 (d, J=1.8 Hz, 2H), 7.50 (s, 1H), 7.33 (s, 1H), 4.43 (s, 2H), 3.70 (d, J=11.9 Hz, 2H), 3.59 (d, J=11.9 Hz, 2H), 3.53-3.40 (m, 4H), 3.36-3.31 (m, 2H), 3.27-3.03 (m, 6H), 2.83-2.72 (m, 5H), 2.02-1.94 (m, 5H), 1.85 (br. s, 1H), 1.65-1.52 (m, 2H); ES-LCMS m/z 655.3, 657.3 [M+H]⁺.

Example 95: 3-(4-(5-((4-((4-(Acetamidomethyl)piperidin-1-yl)methyl)-6-(3,5-dichlorophenyl)pyridin-2-yl)oxy)pyrimidin-2-yl)piperazin-1-yl)butanamide, 4 hydrochloride

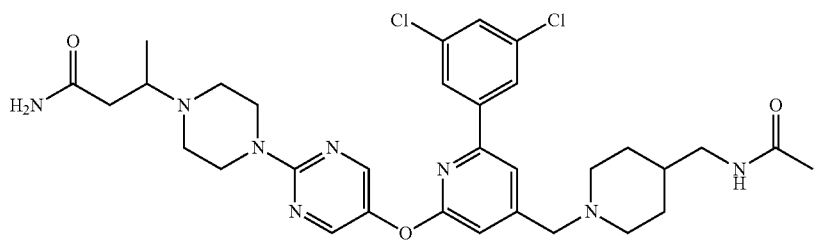 [SMILES: CC(=O)NCC1CCN(Cc2cc(Oc3cnc(N4CCN(C(C)CC(N)=O)CC4)nc3)nc(-c3cc(Cl)cc(Cl)c3)c2)CC1]

Step 1: Ethyl 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)butanoate

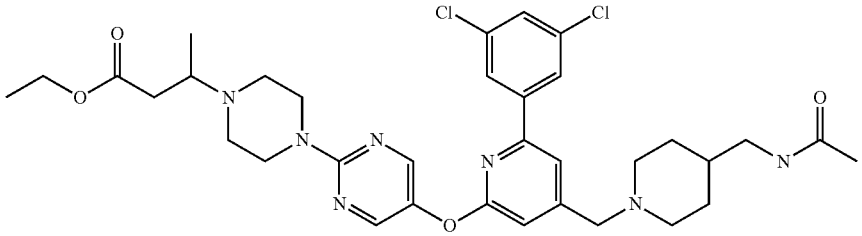 [SMILES: CCOC(=O)CC(C)N1CCN(c2ncc(Oc3cc(CN4CCC(CNC(C)=O)CC4)cc(-c4cc(Cl)cc(Cl)c4)n3)cn2)CC1]

To a suspension of N-((1-((2-(3,5-dichlorophenyl)-6-((2-(piperazin-1-yl)pyrimidin-5-yl)oxy)pyridin-4-yl)methyl)piperidin-4-yl)methyl)acetamide (300 mg, 0.479 mmol) and (E)-ethyl but-2-enoate (1092 mg, 9.57 mmol) was added DIEA (309 mg, 2.393 mmol). The reaction mixture was stirred at 150° C. for 3 h under microwave. This reaction mixture was concentrated to yield crude. The crude product was purified by silica column chromatography (DCM/MeOH=9/1). All fractions found to contain product by TLC (DCM/MeOH=10/1, $R_f$=0.5) were combined and concentrated to yield brown gum of ethyl 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)butanoate (280 mg, 0.290 mmol, 60.5% yield): $^1$H NMR (400 MHz, CDCl$_3$) δ ppm 8.22 (s, 2H), 7.66 (d, J=1.8 Hz, 2H), 7.34 (br. s, 1H), 7.27 (s, 1H), 6.82 (s, 1H), 5.47 (br. s, 1H), 4.15-4.05 (q, J=7.1 Hz, 2H), 3.81-3.65 (m, 4H), 3.52 (s, 3H), 3.17 (t, J=6.3 Hz, 2H), 2.89-2.71 (d, J=10.4 Hz, 3H), 2.67-2.57 (m, 4H), 2.28 (dd, J=7.8, 14.4 Hz, 1H), 2.08-2.00 (m, 3H), 1.99 (s, 3H), 1.42-1.29 (m, 4H), 1.26 (t, J=7.1 Hz, 3H), 1.08 (d, J=6.6 Hz, 3H); ES-LCMS m/z 684.3, 686.2 [M+H]$^+$.

Step 2: 3-(4-(5-((4-((4-(Acetamidomethyl)piperidin-1-yl)methyl)-6-(3,5-dichlorophenyl)pyridin-2-yl)oxy)pyrimidin-2-yl)piperazin-1-yl)butanamide, 4 hydrochloride

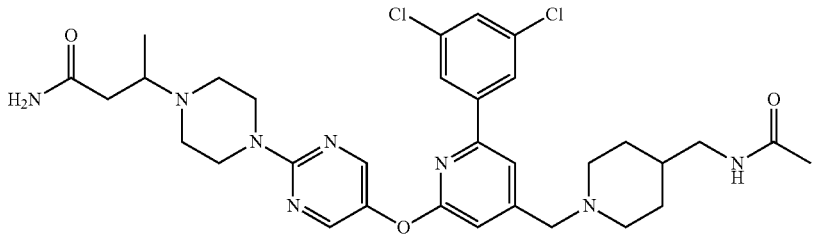 [SMILES: CC(=O)NCC1CCN(Cc2cc(Oc3cnc(N4CCN(C(C)CC(N)=O)CC4)nc3)nc(-c3cc(Cl)cc(Cl)c3)c2)CC1]

Ammonia gas was bubbled into a suspension of ethyl 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)butanoate (280 mg, 0.290 mmol) in MeOH (5 mL) for 0.5 h under −78° C. The reaction mixture was stirred in a sealed tube at 70° C. for 48 h. After cooling to room temperature, the reaction mixture was concentrated to yield crude product which was purified by preparative HPLC (MeCN/H$_2$O as eluents, acidic condition) and the desired fraction was lyophilized to yield a white solid of 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)butanamide, 4 hydrochloride (21.96 mg, 0.027 mmol, 9.4% yield): $^1$H NMR (400 MHz, CD$_3$OD) δ ppm 8.45 (s, 2H), 7.93 (s, 1H), 7.87 (d, J=1.3 Hz, 2H), 7.49 (s, 1H), 7.32 (s, 1H), 5.01 (d, J=13.7 Hz, 2H), 4.53-4.40 (m, 2H), 3.85 (qd, J=6.6, 13.2 Hz, 1H), 3.72-3.54 (m, 4H), 3.45-3.34 (m, 3H), 3.26-3.03 (m, 5H), 2.85 (dd, J=6.4, 16.1 Hz, 1H), 2.71-2.63 (m, 1H), 2.05-1.92 (m, 5H), 1.85 (br. s, 1H), 1.67-1.51 (m, 2H), 1.42 (d, J=6.6 Hz, 3H); ES-LCMS m/z 655.2, 657.3 [M+H]$^+$.

Example 96: 4-(4-(5-((4-((4-(Acetamidomethyl)
piperidin-1-yl)methyl)-6-(3,5-dichlorophenyl)pyri-
din-2-yl)oxy)pyrimidin-2-yl)piperazin-1-yl)butana-
mide

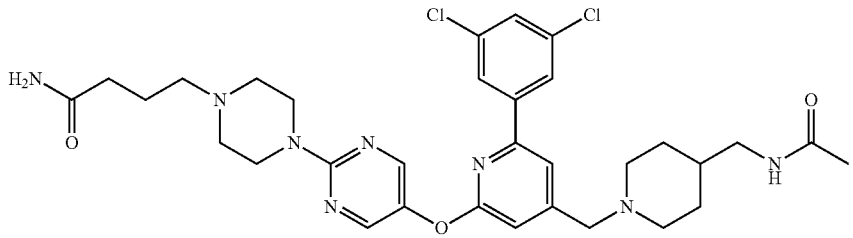 [SMILES: CC(=O)NCC1CCN(Cc2cc(Oc3cnc(N4CCN(CCCC(N)=O)CC4)nc3)nc(-c3cc(Cl)cc(Cl)c3)c2)CC1]

Step 1: Ethyl 4-(4-(5-((4-((4-(acetamidomethyl)
piperidin-1-yl)methyl)-6-(3,5-dichlorophenyl)pyri-
din-2-yl)oxy)pyrimidin-2-yl)piperazin-1-yl)butano-
ate

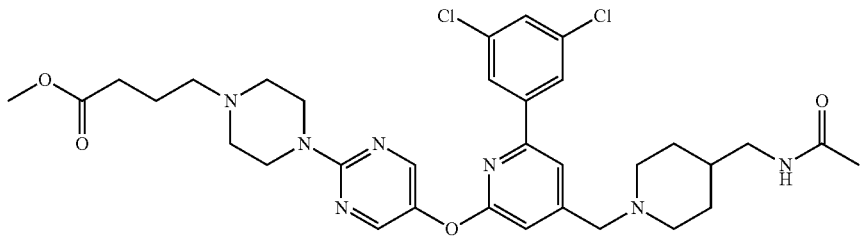 [SMILES: COC(=O)CCCN1CCN(c2ncc(Oc3cc(CN4CCC(CNC(C)=O)CC4)cc(-c4cc(Cl)cc(Cl)c4)n3)cn2)CC1]

To a solution of N-((1-((2-(3,5-dichlorophenyl)-6-((2-(piperazin-1-yl)pyrimidin-5-yl)oxy)pyridin-4-yl)methyl)piperidin-4-yl)methyl)acetamide (1 g, 1.578 mmol) and methyl 4-bromobutanoate (0.857 g, 4.73 mmol) in MeCN (50 mL) was added $K_2CO_3$ (0.872 g, 6.31 mmol). The reaction mixture was stirred at 80° C. for 5 h then filtered, concentrated and purified by flash chromatography (DCM/MeOH=100 to 10/1). All fractions found to contain product by TLC (DCM/MeOH=10/1, $R_f$=0.5) were combined and concentrated to yield a brown solid methyl 4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)butanoate (0.8 g, 0.852 mmol, 54.0% yield): $^1$H NMR (400 MHz, $CDCl_3$) δ ppm 8.27 (s, 2H), 7.95 (br. s, 2H), 7.88 (br. s, 1H), 7.55-7.45 (br. s, 1H), 7.29 (br. s, 1H), 3.75 (s, 2H), 3.65 (s, 3H), 3.40 (s, 4H), 3.29-3.10 (m, 6H), 3.09-3.00 (m, 6H), 2.39 (s, 2H), 2.05 (d, J=9.1 Hz, 5H), 1.95 (br. s, 1H), 1.85-1.75 (m, 2H), 1.59-1.55 (m, 2H); ES-LCMS m/z 670.2, 672.2 [M+H]$^+$.

Step 2: 4-(4-(5-((4-((4-(Acetamidomethyl)piperidin-
1-yl)methyl)-6-(3,5-dichlorophenyl)pyridin-2-yl)
oxy)pyrimidin-2-yl)piperazin-1-yl)butanamide, 4
hydrochloride

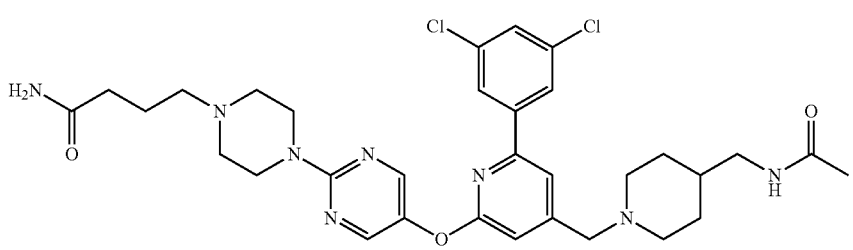 [SMILES: CC(=O)NCC1CCN(Cc2cc(Oc3cnc(N4CCN(CCCC(N)=O)CC4)nc3)nc(-c3cc(Cl)cc(Cl)c3)c2)CC1]

Ammonia gas was bubbled into a suspension of methyl 4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)butanoate (0.5 g, 0.533 mmol) in MeOH (10 mL) for 0.5 h under −78° C. Then the reaction mixture was stirred at 80° C. for 72 h in sealed tube. The solution was concentrated to yield the crude product which was purified by preparative HPLC (MeCN/H$_2$O as eluents, acidic condition) and lyophilized to yield a brown solid of 4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)butanamide, 4 hydrochloride (48.75 mg, 0.061 mmol, 11.4% yield): $^1$H NMR (400 MHz, $CD_3OD$) δ ppm 8.65-8.53 (m, 2H), 8.03 (s, 1H), 7.89 (d, J=1.3 Hz, 2H), 7.48 (s, 1H), 7.40 (s, 1H), 4.90 (d, J=14.6 Hz, 2H), 4.46 (s, 2H), 3.75 (d, J=11.9 Hz, 2H), 3.65-3.31 (m, 6H), 3.29-3.06 (m, 6H), 2.58-2.45 (m, 2H), 2.16-2.05 (m, 5H), 2.03-1.80 (m, 3H), 1.79-1.57 (m, 2H); ES-LCMS m/z 655.3, 657.3 [M+H]$^+$.

Example 97: 1-(5-((3',5'-Dichloro-5-(((2-methoxy-
ethyl)amino)methyl)-[1,1'-biphenyl]-3-yl)oxy)pyri-
din-2-yl)-N-methylpiperidin-4-amine

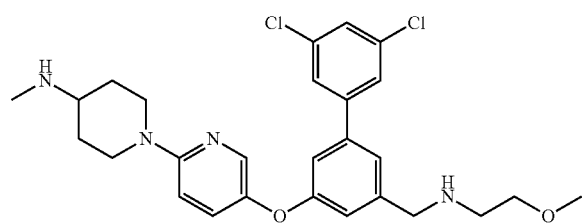

Step 1: 1-(5-Bromopyridin-2-yl)piperidin-4-one

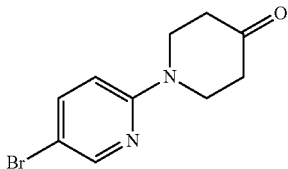

5-Bromo-2-fluoropyridine (2.130 g, 12.11 mmol), piperidin-4-one (1.0 g, 10.09 mmol) and K$_2$CO$_3$ (4.18 g, 30.3 mmol) were suspended in DMF (20 mL). The reaction mixture was stirred at 100° C. for 4 h under N$_2$ atmosphere then concentrated to yield crude product, which was purified by silica gel column chromatography (PE/EtOAc=1/0 to 1/1). All fractions found to contain product by TLC (PE/EtOAc=3/1, R$_f$=0.4) were combined and concentrated to yield a yellow solid of 1-(5-bromopyridin-2-yl)piperidin-4-one (1.3 g, 4.59 mmol, 45.5% yield): $^1$H NMR (400 MHz, CDCl$_3$) δ ppm 8.22 (d, J=2.2 Hz, 1H), 7.58 (dd, J=2.4, 9.0 Hz, 1H), 6.65 (d, J=9.0 Hz, 1H), 3.88 (t, J=6.1 Hz, 4H), 2.58-2.43 (m, 4H); ES-LCMS m/z 254.9, 256.9 [M+H]$^+$.

Step 2: tert-Butyl (1-(5-bromopyridin-2-yl)piperidin-4-yl)(methyl)carbamate

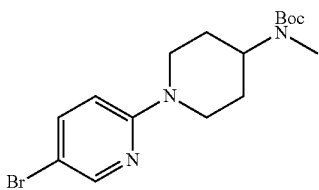 [SMILES: CN(C(=O)OC(C)(C)C)C1CCN(c2ccc(Br)cn2)CC1]

Methanamine (30% in EtOH, 2.0 mL, 5.10 mmol), 1-(5-bromopyridin-2-yl)piperidin-4-one (1.3 g, 5.10 mmol) and 3 Å molecular sieves were suspended in 1,2-dichloroethane (50 mL) and stirred at 40° C. for 12 h. NaBH(OAc)$_3$ (5.40 g, 25.5 mmol) was added and stirred for 5 h. Then DIEA (2.67 mL, 15.29 mmol) and Boc$_2$O (2.366 mL, 10.19 mmol) were added, and the mixture was stirred for another 3 h. The reaction was quenched with saturated aqueous NaHCO$_3$ solution. Separation and the organic layer was washed by water, brine, dried over MgSO$_4$ and concentrated to yield crude product which was purified by silica gel column chromatography (PE/EtOAc=1/0 to 1/1). All fractions found to contain product by TLC (PE/EtOAc=5/1, R$_f$=0.3) were combined and concentrated to yield a yellow oil of tert-butyl (1-(5-bromopyridin-2-yl)piperidin-4-yl)(methyl)carbamate (1.12 g, 2.12 mmol, 47.5% yield): $^1$H NMR (400 MHz, CDCl$_3$) δ ppm 8.17 (d, J=2.2 Hz, 1H), 7.51 (dd, J=2.4, 9.0 Hz, 1H), 6.57 (d, J=9.0 Hz, 1H), 4.12 (dd, J=2.4, 9.0 Hz, 2H), 2.92-2.81 (m, 2H), 2.70 (s, 3H), 1.70-1.67 (m, 5H), 1.46 (s, 9H); ES-LCMS m/z 370.1, 372.1 [M+H]$^+$.

Step 3: N-((3',5'-Dichloro-5-(methoxymethoxy)-[1,1'-biphenyl]-3-yl)methyl)-2-methoxyethanamine

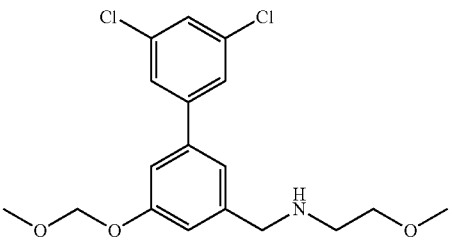

2-Methoxyethanamine (0.288 g, 3.83 mmol), (3',5'-dichloro-5-(methoxymethoxy)-[1,1'-biphenyl]-3-yl)methyl methanesulfonate (1 g, 2.56 mmol) and K$_2$CO$_3$ (1.060 g, 7.67 mmol) were suspended in MeCN (30 mL). The mixture was stirred at 80° C. for 6 h then concentrated to yield crude product, which was purified by silica gel column chromatography (PE/EtOAc=1/0 to 2/1). All fractions found to contain product by TLC (PE/EtOAc=3/1, R$_f$=0.5) were combined and concentrated to yield a yellow oil of N-((3',5'-dichloro-5-(methoxymethoxy)-[1,1'-biphenyl]-3-yl)methyl)-2-methoxyethanamine (980 mg, 2.382 mmol, 93.0% yield): $^1$H NMR (400 MHz, CDCl$_3$) δ ppm 7.49-7.42 (m, 2H), 7.31 (t, 7=1.6 Hz, 1H), 7.17-7.12 (m, 1H), 7.08-6.99 (m, 2H), 5.26-5.18 (m, 2H), 3.87-3.81 (m, 2H), 3.55-3.44 (m, 6H), 3.38-3.31 (m, 2H), 2.88-2.77 (m, 2H); ES-LCMS m/z 370.1, 372.1 [M+H]$^+$.

Step 4: 3',5'-Dichloro-5-(((2-methoxyethyl)amino)methyl)-[1,1'-biphenyl]-3-ol

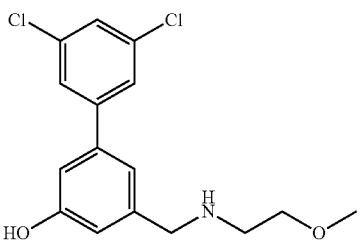 [SMILES: COCCNCc1cc(O)cc(-c2cc(Cl)cc(Cl)c2)c1]

To a solution of N-((3',5'-dichloro-5-(methoxymethoxy)-[1,1'-biphenyl]-3-yl)methyl)-2-methoxyethanamine (0.98 g, 2.65 mmol) in DCM (10 mL) was added 2 M HCl solution (2 mL, 4.00 mmol) solution in one portion. The reaction mixture was stirred at 25° C. for 6 h then concentrated to yield a yellow oil of 3',5'-dichloro-5-(((2-methoxyethyl)amino)methyl)-[1,1'-biphenyl]-3-ol (880 mg, 2.158 mmol, 82.0% yield); ES-LCMS m/z 326.0, 328.0 [M+H]$^+$.

Step 5: tert-Butyl ((3',5'-dichloro-5-hydroxy-[1,1'-biphenyl]-3-yl)methyl)(2-methoxyethyl)carbamate

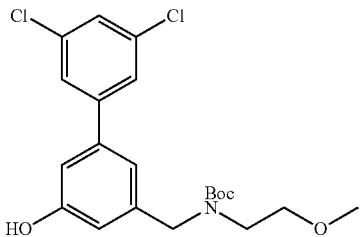 [SMILES: COCCN(Cc1cc(O)cc(-c2cc(Cl)cc(Cl)c2)c1)C(=O)OC(C)(C)C]

3',5'-Dichloro-5-(((2-methoxyethyl)amino)methyl)-[1,1'-biphenyl]-3-ol (1.28 g, 3.92 mmol), Boc$_2$O (1.822 mL, 7.85 mmol) and DIEA (2.056 mL, 11.77 mmol) were suspended in DCM (20 mL). The reaction was stirred at 20° C. for 6 h then concentrated to yield crude product which was purified by silica gel column chromatography (PE/EtOAc=1/0 to 1/1). All fractions found to contain product by TLC (PE/EtOAc=1/1, R$_f$=0.4) were combined and concentrated to yield a yellow oil of tert-butyl((3',5'-dichloro-5-hydroxy-[1,1'-biphenyl]-3-yl)methyl)(2-methoxyethyl)carbamate (1.13 g, 2.12 mmol, 54.0% yield): $^1$H NMR (400 MHz, CDCl$_3$) δ ppm 7.42 (d, J=1.7 Hz, 2H), 7.33 (s, 1H), 7.28-7.26 (m, 1H), 7.23 (s, 1H), 7.07 (br. s, 1H), 4.55 (br. s, 2H), 3.47-3.40 (m, 2H), 3.36-3.28 (m, 5H), 1.48-1.40 (m, 9H); ES-LCMS m/z 448.1, 450.1 [M+Na]$^+$.

Step 6: tert-Butyl ((5-((6-(4-((tert-butoxycarbonyl)(methyl)amino)piperidin-1-yl)pyridin-3-yl)oxy)-3',5'-dichloro-[1,1'-biphenyl]-3-yl)methyl)(2-methoxyethyl)carbamate

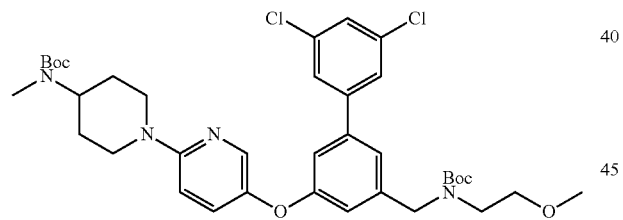

tert-Butyl (1-(5-bromopyridin-2-yl)piperidin-4-yl)(methyl)carbamate (521 mg, 1.407 mmol), CuI (44.7 mg, 0.235 mmol), tert-butyl ((3',5'-dichloro-5-hydroxy-[1,1'-biphenyl]-3-yl)methyl)(2-methoxyethyl)carbamate (500 mg, 1.173 mmol), picolinic acid (57.8 mg, 0.469 mmol) and K$_3$PO$_4$ (747 mg, 3.52 mmol) were suspended in DMSO (20 mL). The reaction mixture was stirred at 130° C. for 20 h under N$_2$ atmosphere then filtered. The filtrate was diluted with DCM (200 mL) then washed by water (20 mL×3), brine (20 mL×3) and dried over MgSO$_4$. Solid was removed by filtration and the filtrate was concentrated to yield crude product which was purified by silica gel column chromatography (PE/EtOAc=1/0 to 1/1). All fractions found to contain product by TLC (PE/EtOAc=1/1, R$_f$=0.6) were combined and concentrated to yield a yellow oil of tert-butyl ((5-((6-(4-((tert-butoxycarbonyl)(methyl)amino)piperidin-1-yl)pyridin-3-yl)oxy)-3',5'-dichloro-[1,1'-biphenyl]-3-yl)methyl)(2-methoxyethyl)carbamate (320 mg, 0.402 mmol, 34.3% yield): $^1$H NMR (400 MHz, CDCl$_3$) δ ppm 8.03 (d, J=2.6 Hz, 1H), 7.38-7.30 (m, 3H), 7.25-7.21 (m, 1H), 7.05 (s, 1H), 6.94 (d, J=10.1 Hz, 1H), 6.82 (br. s, 1H), 6.69 (d, J=9.0 Hz, 1H), 4.33 (d, J=12.8 Hz, 2H), 3.54-3.38 (m, 4H), 3.30 (s, 4H), 2.93-2.77 (m, 4H), 2.73 (br. s, 3H), 1.74 (br. s, 4H), 1.47 (s, 18H); ES-LCMS m/z 715.3, 717.3 [M+H]$^+$.

Step 7: 1-(5-((3',5'-Dichloro-5-(((2-methoxyethyl)amino)methyl)-[1,1'-biphenyl]-3-yl)oxy)pyridin-2-yl)-N-methylpiperidin-4-amine, 3 hydrochloride

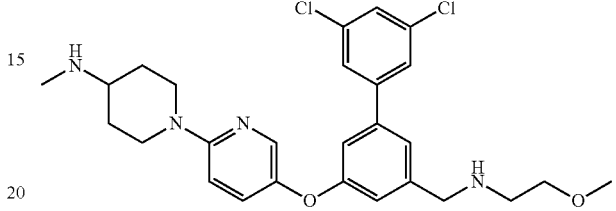

To a solution of tert-butyl ((5-((6-(4-((tert-butoxycarbonyl)(methyl)amino)piperidin-1-yl)pyridin-3-yl)oxy)-3',5'-dichloro-[1,1'-biphenyl]-3-yl)methyl)(2-methoxyethyl)carbamate (320 mg, 0.447 mmol) in DCM (15 mL) was added TFA (5.0 mL, 64.9 mmol). The reaction was stirred at 20° C. for 2 h then concentrated and purified by preparative HPLC (MeCN/H$_2$O as eluents, acidic condition) and dried by lyophilization to yield a white solid of 1-(5-((3',5'-dichloro-5-(((2-methoxyethyl)amino)methyl)-[1,1'-biphenyl]-3-yl)oxy)pyridin-2-yl)-N-methylpiperidin-4-amine, 3 hydrochloride (38.46 mg, 0.062 mmol, 13.7% yield): $^1$H NMR (400 MHz, CD$_3$OD) δ ppm 7.97 (dd, J=2.7, 9.8 Hz, 1H), 7.88 (d, J=2.7 Hz, 1H), 7.66 (d, J=1.7 Hz, 2H), 7.61 (s, 1H), 7.55 (d, J=10.0 Hz, 1H), 7.49 (t, J=1.7 Hz, 1H), 7.45 (s, 1H), 7.39 (s, 1H), 4.35 (d, J=14.2 Hz, 2H), 4.30 (s, 2H), 3.72-3.66 (m, 2H), 3.54-3.35 (m, 6H), 3.28-3.24 (m, 2H), 2.80-2.72 (m, 3H), 2.31 (d, J=11.0 Hz, 2H), 1.85 (dq, J=3.8, 12.2 Hz, 2H); ES-LCMS m/z 515.2, 517.2 [M+H]$^+$.

Example 98: 1-(3',5'-Dichloro-5-((6-(piperazin-1-yl)pyridin-3-yl)oxy)-[1,1'-biphenyl]-3-yl)-N-methylmethanamine, 3 hydrochloride

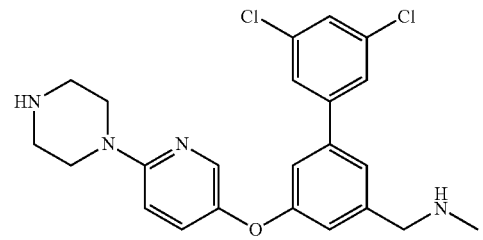 [SMILES: CNCc1cc(Oc2ccc(N3CCNCC3)nc2)cc(-c2cc(Cl)cc(Cl)c2)c1]

To a mixture of tert-butyl ((5-((6-bromopyridin-3-yl)oxy)-3',5'-dichloro-[1,1'-biphenyl]-3-yl)methyl)(methyl)carbamate (0.2 g, 0.372 mmol) and K$_2$CO$_3$ (0.103 g, 0.743 mmol) in NMP (3 mL) was added tert-butyl piperazine-1-carboxylate (0.138 g, 0.743 mmol). The reaction was stirred at 160° C. for 3 h under microwave then filtered, concentrated. The residue was purified by preparative HPLC (MeCN/H$_2$O as eluents, acidic condition) and dried by lyophilization to yield 1-(3',5'-dichloro-5-((6-(piperazin-1-yl)pyridin-3-yl)oxy)-[1,1'-biphenyl]-3-yl)-N-methylmethanamine, 3 hydrochloride (61.53 mg, 0.111 mmol, 30.0% yield): ¹H NMR (400 MHz, CD₃OD) δ ppm 8.00 (d, J=2.7 Hz, 1H), 7.97-7.85 (m, 1H), 7.63 (s, 2H), 7.56 (br. s, 1H), 7.49 (s, 1H), 7.48-7.37 (m, 2H), 7.31 (br. s, 1H), 4.25 (s, 2H), 3.97 (br. s, 4H), 3.46 (br. s, 4H), 2.74 (s, 3H); ES-LCMS m/z 443.1, 445.1 [M+H]⁺.

Example 99: N¹-(5-((3',5'-Dichloro-5-(morpholinomethyl))-[1,1'-biphenyl]-3-yl)oxy)pyridin-2-yl) ethane-1,2-diamine, 3 hydrochloride

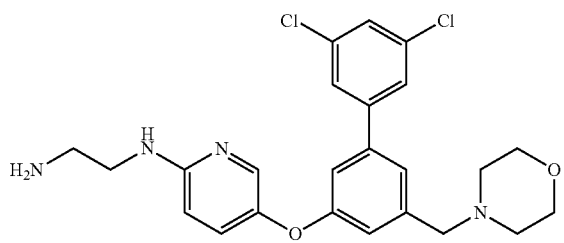 [SMILES: NCCNc1ccc(Oc2cc(CN3CCOCC3)cc(-c3cc(Cl)cc(Cl)c3)c2)cn1]

Step 1: tert-Butyl (2-((5-bromopyridin-2-yl)amino) ethyl)carbamate

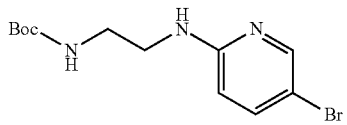 [SMILES: CC(C)(C)OC(=O)NCCNc1ccc(Br)cn1]

To a solution of 5-bromo-2-fluoropyridine (1 g, 5.68 mmol) and tert-butyl (2-aminoethyl)carbamate (0.910 g, 5.68 mmol) in MeCN (10 mL) was added K₂CO₃ (0.785 g, 5.68 mmol). The reaction mixture was stirred at 100° C. for 16 h then filtered and concentrated. The crude product was purified by silica gel column chromatography (PE/EtOAc=1/1). All fractions found to contain product were combined and concentrated to yield a white solid of tert-butyl (2-((5-bromopyridin-2-yl)amino)ethyl)carbamate (1.5 g, 4.74 mmol, 83.0% yield): ¹H NMR (400 MHz, CDCl₃) δ ppm 8.08 (d, J=2.2 Hz, 1H), 7.43 (dd, J=2.4, 8.8 Hz, 1H), 6.31 (d, J=8.8 Hz, 1H), 4.89 (br. s, 1H), 3.41 (q, J=5.5 Hz, 2H), 3.33 (d, J=5.4 Hz, 2H), 1.42 (s, 9H); ES-LCMS m/z 316.0, 318.0 [M+H]⁺.

Step 2: 4-((3',5'-Dichloro-5-(methoxymethoxy)-[1, 1'-biphenyl]-3-yl)methyl)morpholine

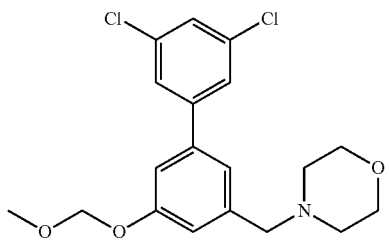 [SMILES: COCOc1cc(CN2CCOCC2)cc(-c2cc(Cl)cc(Cl)c2)c1]

To a solution of (3',5'-dichloro-5-(methoxymethoxy)-[1, 1'-biphenyl]-3-yl)methyl methanesulfonate (3 g, 7.67 mmol) and K₂CO₃ (3.18 g, 23.00 mmol) in MeCN (50 mL) was added morpholine (1.336 g, 15.33 mmol). The mixture was stirred at 80° C. for 12 h then filtered and concentrated. The crude material was purified by silica gel column chromatography (PE/EtOAc=5/1). All fractions found to contain product by TLC (PE/EA=5/1, R_f=0.6) were combined and concentrated to yield a light yellow solid of 4-((3',5'-dichloro-5-(methoxymethoxy)-[1,1'-biphenyl]-3-yl)methyl) morpholine (2 g, 4.97 mmol, 64.8% yield): ¹H NMR (400 MHz, CDCl₃) δ ppm 7.37 (d, J=1.5 Hz, 2H), 7.26 (d, J=1.5 Hz, 1H), 7.07 (s, 1H), 7.00 (d, J=15.0 Hz, 2H), 5.15 (s, 2H), 3.64-3.60 (m, 2H), 3.44 (m, 4H), 3.42 (s, 3H), 2.41 (m, 4H); ES-LCMS m/z 382.0, 384.0 [M+H]⁺.

Step 3: 3',5'-Dichloro-5-(morpholinomethyl)-[1,1'-biphenyl]-3-ol

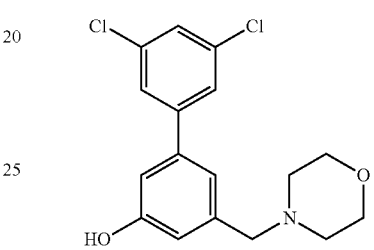

To a solution of 4-((3',5'-dichloro-5-(methoxymethoxy)-[1,1'-biphenyl]-3-yl)methyl)morpholine (2.2 g, 5.75 mmol) in DCM (100 mL) was added concentrated HCl (2 mL, 24.6 mmol). The mixture was stirred at 20° C. for 12 h then concentrated to yield 3',5'-dichloro-5-(morpholinomethyl)-[1,1'-biphenyl]-3-ol (2 g, 5.32 mmol, 92.0% yield): ¹H NMR (400 MHz, CD₃OD) δ ppm 7.60 (d, J=1.8 Hz, 2H), 7.46-7.42 (m, 1H), 7.30 (s, 1H), 7.12 (t, J=1.9 Hz, 1H), 7.04 (s, 1H), 4.38-4.32 (m, 2H), 4.03 (dd, J=2.9, 13.0 Hz, 2H), 3.84-3.76 (m, 2H), 3.40 (d, J=12.6 Hz, 2H), 3.27-3.18 (m, 2H), ES-LCMS m/z 338.0, 340.0 [M+H]⁺.

Step 4: tert-Butyl (2-((5-((3',5'-dichloro-5-(morpholinomethyl)-[1,1'-biphenyl]-3-yl)oxy)pyridin-2-yl)amino)ethyl)carbamate

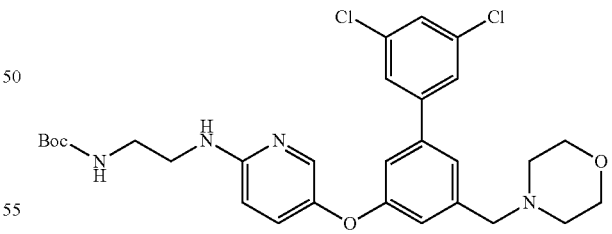

To a suspension of tert-butyl (2-((5-bromopyridin-2-yl) amino)ethyl)carbamate (300 mg, 0.949 mmol), 3',5'-dichloro-5-(morpholinomethyl)-[1,1'-biphenyl]-3-ol (289 mg, 0.854 mmol), Cs₂CO₃ (618 mg, 1.898 mmol) and 2-(dimethylamino)acetic acid (19.57 mg, 0.190 mmol) in 1,4-dioxane (10 mL) was added CuI (36.1 mg, 0.190 mmol). The reaction mixture was stirred at 110° C. for 16 h under N₂ atmosphere then filtered and concentrated. The crude product was purified by silica gel column chromatography (PE/EtOAc=4/1). All fractions found to contain product were combined and concentrated to yield a yellow oil of tert-butyl(2-((5-((3',5'-dichloro-5-(morpholinomethyl)-[1,1'-biphenyl]-3-yl)oxy)pyridin-2-yl)amino)ethyl)carbamate (220 mg, 0.384 mmol, 40.4% yield): $^1$H NMR (400 MHz, CDCl$_3$) δ ppm 7.94 (d, J=2.6 Hz, 1H), 7.41-7.29 (m, 3H), 7.22-7.13 (m, 2H), 6.94 (s, 2H), 6.46 (d, J=8.8 Hz, 1H), 3.70 (t, J=4.4 Hz, 4H), 3.52-3.42 (m, 4H), 3.38 (d, J=5.1 Hz, 2H), 2.45 (br. s, 4H), 1.43 (s, 9H); ES-LCMS m/z 573.2, 575.2 [M+H]$^+$.

Step 5; N$^1$-(5-((3',5'-Dichloro-5-(morpholinomethyl)-[1,1'-biphenyl]-3-yl)oxy)pyridin-2-yl)ethane-1,2-diamine, 3 hydrochloride

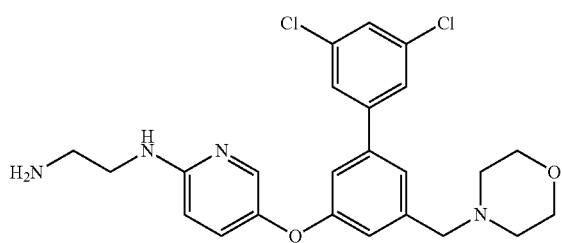

To a solution of tert-butyl (2-((5-((3',5'-dichloro-5-(morpholinomethyl)-[1,1'-biphenyl]-3-yl)oxy)pyridin-2-yl)amino)ethyl)carbamate (180 mg, 0.314 mmol) and 2,6-dimethylpyridine (0.366 mL, 3.14 mmol) in DCM (0.5 mL) was added tert-butyldimethylsilyl trifluoromethanesulfonate (0.721 mL, 3.14 mmol) dropwise. The reaction mixture was stirred at 20° C. for 8 h under N$_2$ atmosphere then concentrated and purified by preparative HPLC (MeCN/H$_2$O as eluents, acidic condition) and dried by lyophilization to yield N$^1$-(5-((3',5'-dichloro-5-(morpholinomethyl)-[1,1'-biphenyl]-3-yl)oxy)pyridin-2-yl)ethane-1,2-diamine, 3 hydrochloride (54.01 mg, 0.091 mmol, 29.0% yield): $^1$H NMR (400 MHz, CD$_3$OD) δ ppm 7.95 (dd, J=2.6, 9.7 Hz, 1H), 7.88 (d, J=2.4 Hz, 1H), 7.67 (d, J=1.7 Hz, 2H), 7.63 (s, 1H), 7.50 (d, J=1.7 Hz, 2H), 7.45 (s, 1H), 7.25 (d, J=9.8 Hz, 1H), 4.41 (s, 2H), 4.03 (d, J=10.5 Hz, 2H), 3.90-3.73 (m, 4H), 3.39 (d, J=12.2 Hz, 2H), 3.31 (br. s, 2H), 3.27-3.18 (m, 2H); ES-LCMS m/z 473.1, 475.1 [M+H]$^+$.

Example 100: 1-(5-((3',5'-Dichloro-5-((methylamino)methyl)-[1,1'-biphenyl]-3-yl)oxy)pyridin-2-yl)piperidin-4-amine, 3 hydrochloride

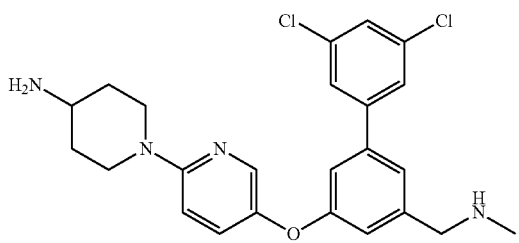 [SMILES: CNCc1cc(Oc2ccc(N3CCC(N)CC3)nc2)cc(-c2cc(Cl)cc(Cl)c2)c1]

Step 1: tert-Butyl ((5-((6-(4-((tert-butoxycarbonyl)amino)piperidin-1-yl)pyridin-3-yl)oxy)-3',5'-dichloro-[1,1'-biphenyl]-3-yl)methyl)(methyl)carbamate

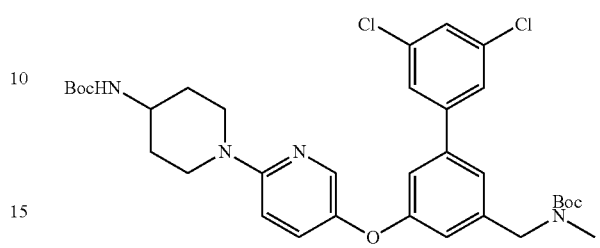

To a solution of tert-butyl ((5-((6-bromopyridin-3-yl)oxy)-3',5'-dichloro-[1,1'-biphenyl]-3-yl)methyl)(methyl)carbamate (0.2 g, 0.372 mmol) and tert-butyl piperidin-4-ylcarbamate (0.089 g, 0.446 mmol) in NMP (50 mL) was added Cs$_2$CO$_3$ (0.363 g, 1.115 mmol). The mixture was stirred at 160° C. for 2 h under microwave. The organic layer was filtered and the filtrate was concentrated to yield tert-Butyl ((5-((6-(4-((tert-butoxycarbonyl)amino)piperidin-1-yl)pyridin-3-yl)oxy)-3',5'-dichloro-[1,1'-biphenyl]-3-yl)methyl)(methyl)carbamate (0.2 g, 0.182 mmol, 49.1% yield): $^1$H NMR (400 MHz, CDCl$_3$) δ ppm 8.06-8.00 (m, 1H), 7.42-7.36 (m, 2H), 7.34-7.27 (m, 2H), 7.26-7.22 (m, 2H), 7.16 (s, 1H), 6.69 (d, J=9.3 Hz, 1H), 3.68 (d, J=13.0 Hz, 2H), 3.42-3.32 (m, 2H), 3.01-2.95 (m, 2H), 2.93-2.87 (m, 3H), 2.74-2.64 (m, 3H), 1.89-1.82 (m, 4H), 1.46-1.44 (m, 18H).

Step 2: 1-(5-((3',5'-Dichloro-5-((methylamino)methyl)-[1,1'-biphenyl]-3-yl)oxy)pyridin-2-yl)piperidin-4-amine, 3 hydrochloride

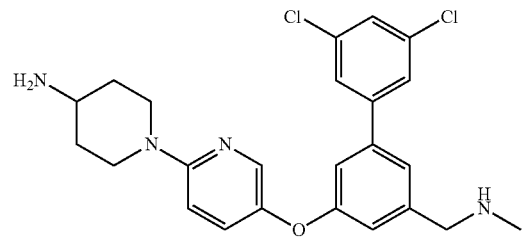 [SMILES: CNCc1cc(Oc2ccc(N3CCC(N)CC3)nc2)cc(-c2cc(Cl)cc(Cl)c2)c1]

To a solution of tert-butyl ((5-((6-(4-((tert-butoxycarbonyl)amino)piperidin-1-yl)pyridine-3-yl)oxy)-3',5'-dichloro-[1,1'-biphenyl]-3-yl)methyl)(methyl)carbamate (150 mg, 0.228 mmol) in DCM (10 mL) was added TFA (1300 mg, 11.4 mmol). The mixture was stirred at 20° C. for 1 h then concentrated and purified by preparative HPLC (MeCN/H$_2$O as eluents, acidic condition) and dried by lyophilization to yield 1-(5-((3',5'-dichloro-5-((methylamino)methyl)-[1,1'-biphenyl]-3-yl)oxy)pyridin-2-yl)piperidin-4-amine, 3 hydrochloride (60 mg, 0.106 mmol, 46.4% yield): $^1$H NMR (400 MHz, DMSO-d$_6$) δ ppm 9.29 (s, 2H), 8.22 (s, 3H), 7.98 (s, 1H), 7.78 (s, 2H), 7.68 (m, 1H), 7.64 (m, 1H), 7.53 (m, 1H), 7.44 (m, 1H), 7.13 (m, 1H), 7.05 (m, 2H), 4.30-4.27 (m, 2H), 4.10-4.09 (m, 2H), 3.27 (m, 1H), 2.94 (m, 2H), 2.51 (s, 3H), 1.98-1.95 (m, 2H), 1.57-1.54 (m, 2H); ES-LCMS m/z 456.9, 458.7 [M+H]$^+$.

Example 101: $N^1$-(5-((3',5'-Dichloro-5-((methyl-amino)methyl)-[1,1'-biphenyl]-3-yl)oxy)pyridin-2-yl)propane-1,3-diamine

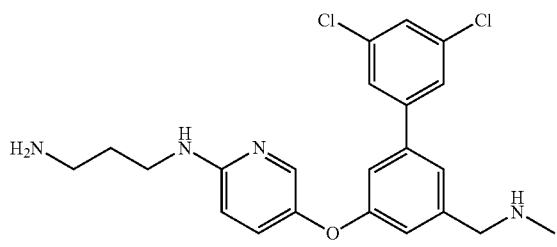 [SMILES: CNCc1cc(Oc2ccc(NCCCN)nc2)cc(-c2cc(Cl)cc(Cl)c2)c1]

Step 1: tert-Butyl (3-((5-bromopyridin-2-yl)amino)propyl)carbamate

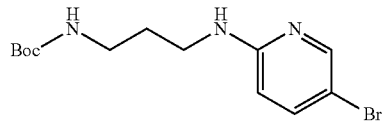

To a mixture of 5-bromo-2-fluoropyridine (5 g, 28.4 mmol) in MeOH (100 mL) was added $K_2CO_3$ (11.78 g, 85 mmol) and tert-butyl (3-aminopropyl)carbamate (9.90 g, 56.8 mmol). The mixture was stirred at 80° C. for 16 h then filtered. The filtrate was concentrated to yield crude product which was purified by silica gel column chromatography (PE/EtOAc=2/1). All fractions found to contain product by TLC (PE/EtOAc=2/1, $R_f$=0.4) were combined and concentrated to yield a white solid of tert-butyl (3-((5-bromopyridin-2-yl)amino)propyl)carbamate (3 g, 8.18 mmol, 28.8% yield): $^1$H NMR (400 MHz, $CDCl_3$) δ ppm 8.07 (d, J=2.21 Hz, 1H), 7.41 (dd, J=2.09, 8.71 Hz, 1H), 6.29 (d, J=8.82 Hz, 1H), 3.34 (q, J=6.39 Hz, 2H), 3.19 (q, J=5.88 Hz, 2H), 1.71 (q, J=6.39 Hz, 2H), 1.43 (s, 9H); ES-LCMS m/z 330.1 $[M+H]^+$.

Step 2: tert-Butyl ((5-((6-((3-((tert-butoxycarbonyl)amino)propyl)amino)pyridin-3-yl)oxy)-3',5'-dichloro-[1,1'-biphenyl]-3-yl)methyl)(methyl)carbamate

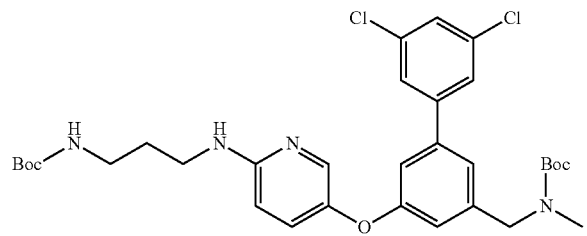 [SMILES: CN(Cc1cc(Oc2ccc(NCCCNC(=O)OC(C)(C)C)nc2)cc(-c2cc(Cl)cc(Cl)c2)c1)C(=O)OC(C)(C)C]

To a mixture of tert-butyl ((3',5'-dichloro-5-hydroxy-[1,1'-biphenyl]-3-yl)methyl)(methyl)carbamate (800 mg, 2.093 mmol) in 1,4-dioxane (120 mL) was added tert-butyl (3-((5-bromopyridin-2-yl)amino)propyl)carbamate (1037 mg, 3.14 mmol), 2-(dimethylamino)acetic acid (86 mg, 0.837 mmol), CuI (80 mg, 0.419 mmol) and $Cs_2CO_3$ (1364 mg, 4.19 mmol). The mixture was stirred under $N_2$ atmosphere at 120° C. for 48 h then filtered. The filtrate was concentrated to yield crude product which was purified by silica gel column chromatography (PE/EtOAc=3/2). All fractions found to contain product by TLC (PE/EtOAc=3/2, $R_f$=0.4) were combined and concentrated to yield a white solid of tert-butyl ((5-((6-((3-((tert-butoxycarbonyl)amino)propyl)amino)pyridin-3-yl)oxy)-3',5'-dichloro-[1,1'-biphenyl]-3-yl)methyl)(methyl)carbamate (1 g, 1.583 mmol, 76.0% yield): $^1$H NMR (400 MHz, $CD_3OD$) δ ppm 7.77 (s, 1H), 7.53 (s, 2H), 7.43 (s, 1H), 7.25 (dd, J=2.69, 9.05 Hz, 1H), 7.15 (s, 2H), 6.76 (br. s, 1H), 6.57 (d, J=9.05 Hz, 1H), 4.41 (s, 2H), 3.32 (J=6.85 Hz, 2H), 3.14 (t, J=6.85 Hz, 2H), 2.81 (s, 3H), 1.75 (t, J=6.72 Hz, 2H), 1.46-1.36 (m, 18H); ES-LCMS m/z 631.2, 633.2 $[M+H]^+$.

Step 3: $N^1$-(5-((3',5'-Dichloro-5-((methylamino)methyl)-[1,1'-biphenyl]-3-yl)oxy)pyridin-2-yl)propane-1,3-diamine, 3 hydrochloride

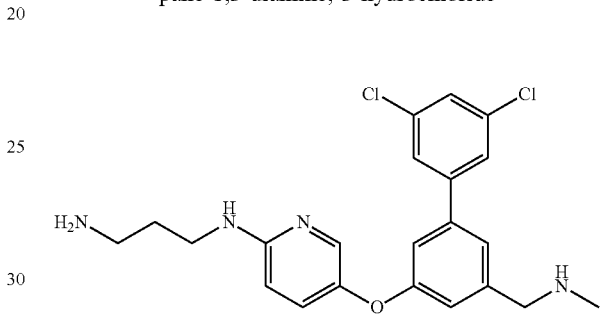

To a mixture of tert-butyl ((5-((6-((3-((tert-butoxycarbonyl)amino)propyl)amino)pyridin-3-yl)oxy)-3',5'-dichloro-[1,1'-biphenyl]-3-yl)methyl)(methyl)carbamate (1.1 g, 1.742 mmol) in DCM (40 mL) was added TFA (5 mL) slowly. The mixture was stirred at 25° C. for 0.5 h then filtered. The filtrate was concentrated to yield crude product which was purified by preparative HPLC (MeCN/$H_2O$ as eluents, acidic condition) and dried by lyophilization to yield an off white solid of N-(5-((3',5'-dichloro-5-((methyl-amino)methyl)-[1,1'-biphenyl]-3-yl)oxy)pyridin-2-yl)propane-1,3-diamine, 3 hydrochloride (371.86 mg, 0.688 mmol, 39.5% yield): $^1$H NMR (400 MHz, $CD_3OD$) δ ppm 7.89 (dd, J=2.76, 9.79 Hz, 1H), 7.82 (d, J=2.51 Hz, 1H), 7.68 (d, J=2.01 Hz, 2H), 7.61 (s, 1H), 7.54-7.52 (m, 1H), 7.47 (s, 1H), 7.37 (s, 1H), 7.24 (d, J=9.54 Hz, 1H), 4.29 (s, 2H), 3.57 (t, J=7.03 Hz, 2H), 3.17-3.11 (m, 2H), 2.78 (s, 3H), 2.13 (q, J=7.28 Hz, 2H); ES-LCMS m/z 431.1, 433.1 $[M+H]^+$.

Example 102: 1-(3',5'-Dichloro-5-((6-(3,3-dimethylpiperazin-1-yl)pyridin-3-yl)oxy)-[1,1'-biphenyl]-3-yl)-N-methylmethanamine, 3 hydrochloride

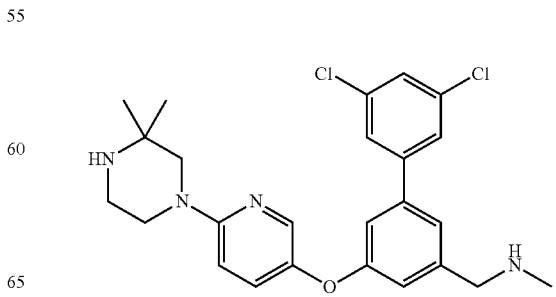

A mixture of tert-butyl ((5-(((6-bromopyridin-3-yl)oxy)-3',5'-dichloro-[1,1'-biphenyl]-3-yl)methyl)(methyl)carbamate (300 mg, 0.557 mmol), tert-butyl 2,2-dimethylpiperazine-1-carboxylate (500 mg, 2.333 mmol) and Cs₂CO₃ (545 mg, 1.672 mmol) in NMP (5 mL) was stirred at 190° C. under microwave for 1.5 h then filtered. The filtrate was concentrated and the residue was purified by preparative HPLC (MeCN/H₂O as eluents, acidic condition) and dried by lyophilization to yield a light yellow solid of 1-(3',5'-dichloro-5-((6-(3,3-dimethylpiperazin-1-yl)pyridin-3-yl)oxy)-[1,1'-biphenyl]-3-yl)-N-methylmethanamine, 3 hydrochloride (10.01 mg, 0.017 mmol, 3.1% yield): $^1$H NMR (400 MHz, CD₃OD) δ ppm 8.02-7.93 (m, 2H), 7.64 (d, J=2.0 Hz, 2H), 7.59 (s, 1H), 7.52 (d, J=10.5 Hz, 1H), 7.49 (t, J=1.7 Hz, 1H), 7.43 (s, 1H), 7.34 (s, 1H), 4.25 (s, 2H), 4.01-3.95 (m, 2H), 3.86 (s, 2H), 3.54-3.47 (m, 2H), 2.75 (s, 3H), 1.56-1.48 (m, 6H); ES-LCMS m/z 471.1, 473.2 [M+H]⁺.

Examples 103-104 (Table 5) were prepared by procedures analogous to those described for example 102.

Step 1: tert-Butyl (1-((5-bromopyridin-2-yl)amino)-2-methylpropan-2-yl)carbamate

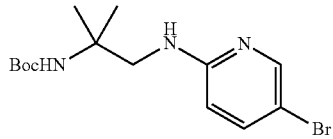 [SMILES: CC(C)(CNc1ccc(Br)cn1)NC(=O)OC(C)(C)C]

To a solution of 2-methylpropane-1,2-diamine (2.3 g, 26.1 mmol) and pyridine (2.53 mL, 31.3 mmol) in NMP (0.5 mL) was added 5-bromo-2-fluoropyridine (3.67 g, 20.87 mmol). The reaction was stirred for 16 h at 100° C. Then Boc₂O (12.12 mL, 52.2 mmol) was added and the mixture was concentrated and purified by silica gel column chromatography (PE/EtOAc=1/0 to 3/1) to yield tert-butyl (1-((5-bromopyridin-2-yl)amino)-2-methylpropan-2-yl)carbamate (1.8 g, 5.23 mmol, 20.0% yield): $^1$H NMR (400 MHz, CDCl₃) δ ppm 8.05 (d, J=2.0 Hz, 1H), 7.48-7.35 (m, 1H), 6.41-6.31 (m, 1H), 3.46 (d, J=6.1 Hz, 2H), 1.46-1.37 (m, 9H), 1.31 (s, 6H); ES-LCMS m/z 344.0, 346.0 [M+H]⁺.

Step 2: tert-Butyl (1-((5-((5-((4-(acetamidomethyl)piperidin-1-yl)methyl)-3',5'-dichloro-[1,1'-biphenyl]-3-yl)oxy)pyridin-2-yl)amino)-2-methylpropan-2-yl)carbamate

TABLE 5

| Example | Structure/Name | $^1$H NMR | LCMS |
|---|---|---|---|
| 103 | (structure) yl)pyridin-3-yl)oxy)-3',5'-dichloro-[1,1'-biphenyl]-3-yl)-N-methylmethanamine | $^1$H NMR (400 MHz, CD₃OD) δ ppm 7.98-7.91 (m, 2H), 7.64 (d, J = 1.8 Hz, 2H), 7.55 (s, 1H), 7.50 (t, J = 1.7 Hz, 1H), 7.46-7.39 (m, 2H), 7.34 (s, 1H), 4.25 (s, 2H), 4.16-4.10 (m, 2H), 3.87 (t, J = 5.8 Hz, 2H), 3.58-3.51 (m, 2H), 3.49-3.42 (m, 2H), 2.74 (s, 3H), 2.34 (d, J = 4.9 Hz, 2H) | ES-LCMS m/z 457.1, 459.2 [M + H]⁺. |
| 104 | (structure) 1-(3',5'-dichloro-5-((6-(4-methylpiperazin-1-yl)pyridin-3-yl)oxy)-[1,1'-biphenyl]-3-yl)-N-methylmethanamine | $^1$H NMR (400 MHz, CD₃OD) δ ppm 8.10-8.08 (m, 1H), 8.00 (s, 1H), 7.67-7.62 (m, 4H), 7.47 (s, 2H), 7.41 (s, 1H), 4.50 (d, J = 14.0 Hz, 2H), 4.29 (s, 2H), 3.82-3.73 (m, 4H), 3.50-3.44 (m, 2H), 3.03 (s, 3H), 2.84-2.72 (m, 3H) | ES-LCMS m/z 457.2, 459.2 [M + H]⁺. |

Example 105: N-((1-((5-((6-(((2-Amino-2-methylpropyl)amino)pyridin-3-yl)oxy)-3',5'-dichloro-[1,1'-biphenyl]-3-yl)methyl)piperidin-4-yl)methyl)acetamide, 3 hydrochloride

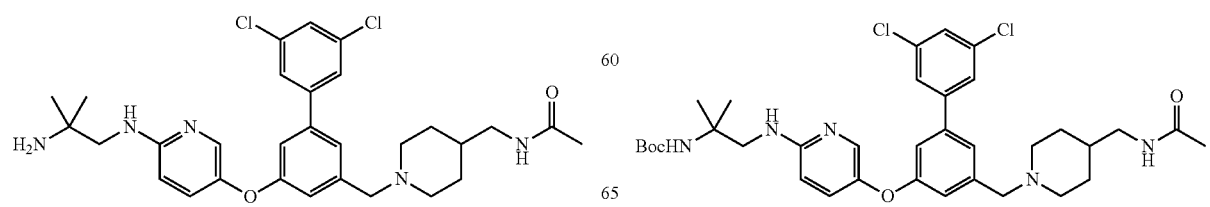

To a mixture of N-((1-((3',5'-dichloro-5-hydroxy-[1,1'-biphenyl]-3-yl)methyl)piperidin-4-yl)methyl)acetamide (0.5 g, 1.227 mmol), tert-butyl (1-((5-bromopyridin-2-yl)amino)-2-methyl-propan-2-yl)carbamate (0.423 g, 1.227 mmol), Cs$_2$CO$_3$ (0.400 g, 1.227 mmol) and 2-(dimethylamino)acetic acid (0.040 mL, 0.368 mmol) in 1,4-dioxane (30 mL) was added CuI (0.024 mL, 0.123 mmol). The reaction was stirred for 16 h at 100° C. under N$_2$ atmosphere then filtered, concentrated and purified by silica gel column chromatography (DCM/MeOH=1/0 to 5/1). All fractions found to contain product by TLC (DCM/MeOH=3/1, R$_f$=0.5) were combined and concentrated to yield a brown solid of tert-butyl (1-((5-((5-((4-(acetamidomethyl)piperidin-1-yl)methyl)-3',5'-dichloro-[1,1'-biphenyl]-3-yl)oxy)pyridin-2-yl)amino)-2-methylpropan-2-yl)carbamate (150 mg, 0.179 mmol, 14.6% yield): $^1$H NMR (400 MHz, CDCl$_3$) δ ppm 7.91 (d, J=2.7 Hz, 1H), 7.43-7.29 (m, 2H), 7.19-7.15 (m, 3H), 6.89-6.78 (m, 2H), 6.56-6.48 (m, 1H), 4.27-4.08 (m, 2H), 3.51 (m, 2H), 3.49-3.45 (m, 2H), 3.16-3.13 (m, 2H), 2.89-2.78 (m, 2H), 1.97-1.90 (m, 5H), 1.85-1.80 (m, 1H), 1.50 (m, 2H), 1.41 (s, 9H), 1.35 (s, 6H); ES-LCMS m/z 670.1, 672.1 [M+H]$^+$.

Step 3: N-((1-((5-((6-((2-amino-2-methylpropyl)amino)pyridin-3-yl)oxy)-3',5'-dichloro-[1,1'-biphenyl]-3-yl)methyl)piperidin-4-yl)methyl)acetamide, 3 hydrochloride

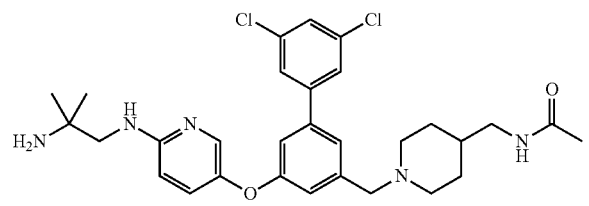 [SMILES: CC(=O)NCC1CCN(Cc2cc(Oc3ccc(NCC(C)(C)N)nc3)cc(-c3cc(Cl)cc(Cl)c3)c2)CC1]

To a solution of tert-butyl (1-((5-((5-((4-(acetamidomethyl)piperidin-1-yl)methyl)-3',5'-dichloro-[1,1'-biphenyl]-3-yl)oxy)pyridin-2-yl)amino)-2-methylpropan-2-yl)carbamate (150 mg, 0.224 mmol) in DCM (20 mL) was added TFA (2 mL, 0.224 mmol). The reaction was stirred for 4 h at 30° C. then concentrated and purified by preparative HPLC (MeCN/H$_2$O as eluents, acidic condition) and dried by lyophilization to yield a pale yellow solid of N-((1-((5-((6-((2-amino-2-methylpropyl)amino)pyridin-3-yl)oxy)-3',5'-dichloro-[1,1'-biphenyl]-3-yl)methyl)piperidin-4-yl)methyl)acetamide, 3 hydrochloride (51.13 mg, 0.072 mmol, 32.1% yield): $^1$H NMR (400 MHz, CD$_3$OD) δ ppm 7.99 (dd, J=2.5, 9.8 Hz, 1H), 7.87 (d, J=2.4 Hz, 1H), 7.68 (d, J=1.8 Hz, 2H), 7.66-7.60 (m, 1H), 7.53-7.43 (m, 3H), 7.38 (d, J=9.7 Hz, 1H), 4.42-4.29 (m, 2H), 3.77 (s, 2H), 3.52 (d, J=11.9 Hz, 2H), 3.13 (d, J=6.4 Hz, 2H), 3.03 (t, J=12.2 Hz, 2H), 2.03-1.91 (m, 5H), 1.84 (br. s, 1H), 1.68-1.53 (m, 2H), 1.49 (s, 6H); ES-LCMS m/z 570.2, 572.3 [M+H]$^+$.

Example 106: N-((1-((5-((6-((r/3)-4-Amino-3-fluoropiperidin-1-yl)pyridin-3-yl)oxy)-3',5'-dichloro-[1,1'-biphenyl]-3-yl)methyl)piperidin-4-yl)methyl)acetamide, 3 hydrochloride

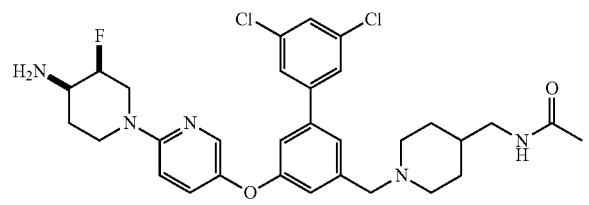

Step 1: tert-Butyl 4-(benzylamino)-3-fluoropiperidine-1-carboxylate

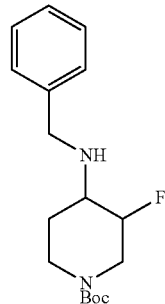 [SMILES: CC(C)(C)OC(=O)N1CCC(NCc2ccccc2)C(F)C1]

A mixture of phenylmethanamine (4.93 g, 46.0 mmol), tert-butyl 3-fluoro-4-oxopiperidine-1-carboxylate (2.0 g, 9.21 mmol) and 4 Å molecular sieve (2 g, 9.21 mmol) were suspended in DCE (150 mL) and stirred at 40° C. for 15 h. sodium triacetoxyborohydride (9.76 g, 46.0 mmol) was added and stirred at 40° C. for 5 h under N$_2$ atmosphere. The reaction was quenched slowly with saturated aqueous. NaHCO$_3$ solution (100 mL) and extracted with EtOAc (200 mL). The organic layer was washed with H$_2$O (200 mL×2), brine (200 mL), dried with anhydrous Na$_2$SO$_4$, filtered and concentrated in vacuum to afford the crude. The crude material was purified on silica gel column chromatography (from pure PE to PE/EA=10/1-1/1, TLC: PE/EA=1/1, R$_f$=0.3) and concentrated to yield tert-butyl 4-(benzylamino)-3-fluoropiperidine-1-carboxylate (2.1 g, 6.40 mmol, 69.5% yield) as a white solid: $^1$H NMR (400 MHz, CDCl$_3$) δ ppm 7.30-7.27 (m, 3H), 7.25-7.12 (m, 2H), 4.76-4.57 (m, 1H), 4.25 (br d, J=7.1 Hz, 1H), 4.16-3.83 (m, 2H), 3.01-2.47 (m, 4H), 1.76-1.57 (m, 2H), 1.39 (s, 9H); ES-LCMS m/z 309.2 [M+H]$^+$.

Step 2: tert-Butyl 4-amino-3-fluoropiperidine-1-carboxylate

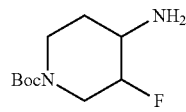

To a solution of tert-butyl 4-(benzylamino)-3-fluoropiperidine-1-carboxylate (2.0 g, 6.10 mmol) in methanol (100 mL) was added 20% Pd(OH)$_2$ (0.428 g, 0.610 mmol) under N$_2$ atmosphere. The reaction mixture was stirred at 50° C. under 50 psi H$_2$ atmosphere 16 h. Then the mixture was filtered and the filtrate was concentrated to yield tert-butyl 4-amino-3-fluoropiperidine-1-carboxylate (1.1 g, 4.79 mmol, 79.0% yield) as light yellow oil: $^1$H NMR (400 MHz, CDCl$_3$) δ ppm 4.65-4.44 (m, 1H), 4.28 (br d, J=7.7 Hz, 1H), 4.15-3.83 (m, 1H), 3.06-2.77 (m, 3H), 1.71-1.61 (m, 2H), 1.44 (s, 9H); ES-LCMS m/z 163.2 [M−t−Bu+H]$^+$.

Step 3: tert-Butyl 4-acetamido-3-fluoropiperidine-1-carboxylate

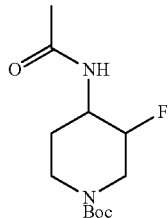

To a solution of tert-butyl 4-amino-3-fluoropiperidine-1-carboxylate (1 g, 4.35 mmol) in DCM (50 mL) was added acetyl chloride (0.410 g, 5.22 mmol) dropwise, followed by addition of DIEA (1.520 mL, 8.70 mmol). The reaction mixture was stirred at 20° C. for 12 h under $N_2$ atmosphere. The reaction was quenched slowly with saturated aqueous $NaHCO_3$ solution (100 mL) and extracted with EtOAc (200 mL). The organic layer was washed with $H_2O$ (200 mL×2), brine (200 mL), dried with anhydrous $Na_2SO_4$, filtered and concentrated in vacuum to afford the crude. The crude material was purified by flash chromatography (from pure PE to PE/EtOAc=1/1). All fractions found to contain product by TLC (PE/EtOAc=1/1, $R_f$=0.3) were combined and concentrated to yield a yellow oil of tert-butyl 4-acetamido-3-fluoropiperidine-1-carboxylate (850 mg, 3.10 mmol, 71.3% yield) as a white solid: $^1H$ NMR (400 MHz, $CDCl_3$) δ ppm 4.72-4.55 (m, 1H), 4.43-4.11 (m, 2H), 4.09-3.99 (m, 1H), 3.04-2.69 (m, 2H), 2.00 (s, 3H), 1.73-1.66 (m, 2H), 1.44 (s, 9H); ES-LCMS m/z 205.2 [M−t−Bu+H]$^+$.

Step 4: N-(3-fluoropiperidin-4-yl)acetamide, trifluoroacetic acid salt

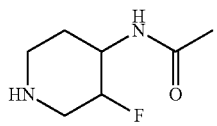

tert-Butyl 4-acetamido-3-fluoropiperidine-1-carboxylate (800 mg, 3.08 mmol) was dissolved in TFA/DCM (20%, 20 mL). The reaction mixture was stirred at 25° C. for 3 h then concentrated to yield brown oil of N-(3-fluoropiperidin-4-yl)acetamide, trifluoroacetic acid salt (700 mg, 1.53 mmol, 49.7% yield): $^1H$ NMR (400 MHz, $CDCl_3$) δ ppm 4.18-3.94 (m, 1H), 3.61-3.48 (m, 1H), 3.47-2.83 (m, 4H), 2.18-1.93 (m, 1H), 1.93-1.88 (m, 3H), 1.85-1.67 (m, 1H).

Step 5: N-((cis)-1-(5-bromopyridin-2-yl)-3-fluoropiperidin-4-yl)acetamide

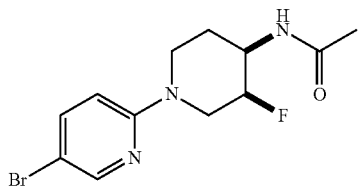 [SMILES: CC(=O)N[C@@H]1CCN(c2ccc(Br)cn2)C[C@@H]1F]

A suspension of 5-bromo-2-fluoropyridine (900 mg, 5.11 mmol), N-(3-fluoropiperidin-4-yl)acetamide, trifluoroacetic acid salt (1683 mg, 6.14 mmol) and DIEA (1.786 mL, 10.23 mmol) in NMP (2.0 mL) was stirred in the microwave at 160° C. for 3 h. After cooling to room temperature, the mixture was added DCM (100 mL) and washed by water (100×5 mL). The organic layer was dried over $MgSO_4$ then concentrated. The crude product was purified by silica gel column chromatography (DCM/MeOH=20/1 to 5/1). All fractions found to contain product by TLC (DCM/MeOH=10/1, $R_f$=0.7) were combined and concentrated to yield a yellow solid of N-((cis)-1-(5-bromopyridin-2-yl)-3-fluoropiperidin-4-yl)acetamide (1.2 g, 3.04 mmol, 59.4% yield): $^1H$ NMR (400 MHz, $CDCl_3$) δ ppm 8.07 (d, J=2.5 Hz, 1H), 7.47 (dd, J=2.5, 9.0 Hz, 1H), 6.55 (d, J=9.0 Hz, 1H), 4.83-4.65 (m, 1H), 4.58-4.51 (m, 1H), 4.30-4.23 (m, 1H), 4.15-4.01 (m, 1H), 3.10-2.94 (m, 1H), 2.92-2.84 (m, 1H), 1.94 (s, 3H), 1.81-1.74 (m, 2H); ES-LCMS m/z 316.2, 318.2 [M+H]$^+$.

Step 6: tert-Butyl ((cis)-1-(5-bromopyridin-2-yl)-3-fluoropiperidin-4-yl)carbamate

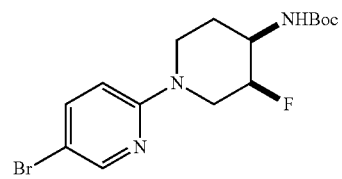 [SMILES: CC(C)(C)OC(=O)N[C@@H]1CCN(c2ccc(Br)cn2)C[C@@H]1F]

To a solution of N-((cis)-1-(5-bromopyridin-2-yl)-3-fluoropiperidin-4-yl)acetamide (600 mg, 1.898 mmol) in 1,4-dioxane (20 mL) was added aqueous HCl (2.0 M, 4.74 mL, 9.49 mmol). The reaction mixture was stirred at 120° C. under $N_2$ atmosphere for 16 h. NaOH (759 mg, 18.98 mmol) was added, followed by addition of $Boc_2O$ (0.881 mL, 3.80 mmol). The reaction mixture was stirred for another 4 h and concentrated to yield the residue which was dissolved in DCM (200 mL) and washed with brine (20 mL×2), dried over $Na_2SO_4$, filtered and concentrated. The crude product was purified by silica gel column chromatography (PE/EtOAc=2/1). All fractions found to contain product by TLC (PE/EtOAc=1/1, $R_f$=0.5) were combined and concentrated to yield a white solid of tert-butyl ((cis)-1-(5-bromopyridin-2-yl)-3-fluoropiperidin-4-yl)carbamate (250 mg, 0.601 mmol, 31.7% yield): $^1H$ NMR (400 MHz, $CDCl_3$) δ ppm 8.20-8.13 (m, 1H), 7.56-7.48 (m, 1H), 6.59 (d, J=9.0 Hz, 1H), 4.70-4.60 (m, 1H), 4.37-4.23 (m, 1H), 3.29-3.21 (m, 1H), 3.13-2.95 (m, 1H), 2.94-2.81 (m, 2H), 1.93-1.77 (m, 2H), 1.46-1.45 (m, 9H); ES-LCMS m/z 374.0, 376.0 [M+H]$^+$.

Step 7: tert-Butyl ((cis)-1-(5-((5-((4-(acetamidomethyl)piperidin-1-yl)methyl)-3',5'-dichloro-[1,1'-biphenyl]-3-yl)oxy)pyridin-2-yl)-3-fluoropiperidin-4-yl)carbamate

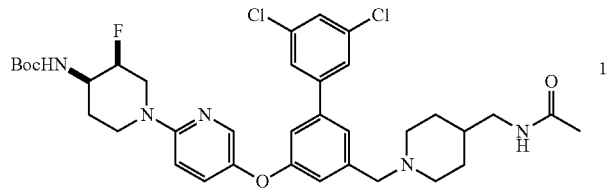

A mixture of tert-butyl ((cis)-1-(5-bromopyridin-2-yl)-3-fluoropiperidin-4-yl)carbamate (70 mg, 0.187 mmol), N-((1-((3',5'-dichloro-5-hydroxy-[1,1'-biphenyl]-3-yl)methyl)piperidin-4-yl)methyl)acetamide (76 mg, 0.187 mmol), CuI (3.31 mg, 0.017 mmol), 2-(dimethylamino)acetic acid (3.05 mg, 0.030 mmol) and $Cs_2CO_3$ (78.35 mg, 0.240 mmol) in 1,4-dioxane (3 mL) was stirred under $N_2$ atmosphere at 100° C. for 18 h. Then the mixture was filtered through a Celite® pad and the filtrate was concentrated to yield the crude product which was purified by preparative TLC (DCM/MeOH=10/1, $R_f$=3.5) to yield a faint yellow solid of tert-butyl ((cis)-1-(5-((5-((4-(acetamidomethyl)piperidin-1-yl)methyl)-3',5'-dichloro-[1,1'-biphenyl]-3-yl)oxy)pyridin-2-yl)-3-fluoropiperidin-4-yl)carbamate (30 mg, 0.039 mmol, 20.6% yield): $^1$H NMR (400 MHz, $CDCl_3$) δ ppm 8.01 (d, J=2.6 Hz, 1H), 7.42 (s, 3H), 7.33 (s, 1H), 7.30-7.27 (m, 1H), 7.05 (s, 2H), 6.75 (d, J=9.3 Hz, 1H), 4.95-4.90 (m, 1H), 4.85-4.80 (m, 1H), 3.80 (s, 2H), 3.48 (s, 2H), 3.20-3.10 (m, 4H), 2.95-1.85 (m, 2H), 2.55-1.45 (m, 2H), 2.01-1.98 (m, 5H), 1.83 (br. s, 1H), 1.69-1.65 (m, 2H), 1.59-1.55 (m, 2H), 1.43 (s, 9H); ES-LCMS m/z 700.1, 702.1 [M+H]$^+$.

Step 8: N-((1-((5-((6-(((ds)-4-Amino-3-fluoropiperidin-1-yl)pyridin-3-yl)oxy)-3',5'-dichloro-[1,1'-biphenyl]-3-yl)methyl)piperidin-4-yl)methyl)acetamide, 3 hydrochloride

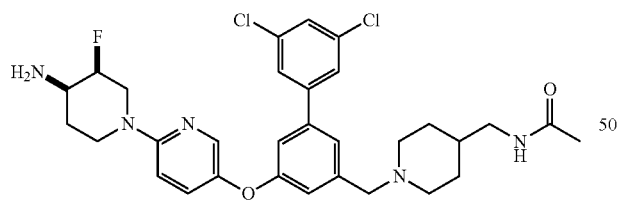

To a solution of tert-butyl ((cis)-1-(5-((5-((4-(acetamidomethyl)piperidin-1-yl)methyl)-3',5'-dichloro-[1,1'-biphenyl]-3-yl)oxy)pyridin-2-yl)-3-fluoropiperidin-4-yl)carbamate (30 mg, 0.043 mmol) in DCM (5 mL) was added TFA (1 mL, 12.98 mmol). The reaction mixture was stirred at 30° C. for 2 h then concentrated to yield the crude product, which was purified by preparative HPLC (MeCN/$H_2O$ as eluents, acidic condition) and dried by lyophilization to yield a yellow solid of N-((1-((5-((6-(((cis)-4-amino-3-fluoropiperidin-1-yl)pyridin-3-yl)oxy)-3',5'-dichloro-[1,1'-biphenyl]-3-yl)methyl)piperidin-4-yl)methyl)acetamide, 3 hydrochloride (11.04 mg, 0.015 mmol, 35.3% yield): $^1$H NMR (400 MHz, $CD_3OD$) δ ppm 8.03 (br. s, 1H), 7.93 (br. s, 1H), 7.68 (br. s, 3H), 7.59 (d, J=7.3 Hz, 1H), 7.50-7.45 (m, 3H), 5.30-5.12 (m, 1H), 4.70 (br. s, 1H), 4.46-4.32 (m, 3H), 3.93-3.63 (m, 2H), 3.51 (br. s, 3H), 3.25-2.86 (m, 4H), 2.14 (br. s, 2H), 1.94 (s, 5H), 1.83 (br. s, 1H), 1.59 (br. s, 2H); ES-LCMS m/z 600.3, 602.3 [M+H]$^+$.

Example 107: N-((1-((3',5'-Dichloro-5-((6-(3-oxohexahydroimidazo[1,5-a]pyrazin-7(1H)-yl)pyridin-3-yl)oxy)-[1,1'-biphenyl]-3-yl)methyl)piperidin-4-yl)methyl)acetamide, 2 hydrochloride

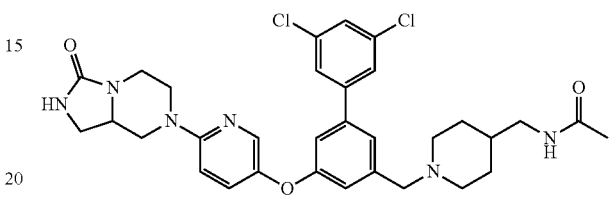

Step 1: 4-Benzyl 1-tert-butyl 2-(hydroxymethyl)piperazine-1,4-dicarboxylate

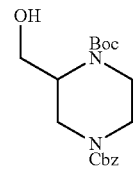

A mixture of tert-butyl 2-(hydroxymethyl)piperazine-1-carboxylate (5 g, 23.12 mmol), CbzCl (3.47 mL, 24.27 mmol) and $Et_3N$ (9.67 mL, 69.4 mmol) in DCM (75 mL) was stirred at 25° C. for 12 h. The mixture was washed successively with saturated aqueous citric acid solution (50 mL), saturated aqueous $NaHCO_3$ solution (50 mL) and brine (50 mL). The organic extract was dried over $Na_2SO_4$, filtered and concentrated to yield light yellow oil of 4-benzyl 1-tert-butyl 2-(hydroxymethyl)piperazine-1,4-dicarboxylate (6.3 g, 14.38 mmol, 62.2% yield): $^1$H NMR (400 MHz, $CDCl_3$) δ ppm 7.45-7.26 (m, 5H), 5.14 (br. s, 2H), 4.24-3.95 (m, 3H), 3.84 (br. s, 1H), 3.57 (br. s, 2H), 2.98 (br. s, 3H), 1.44 (s, 9H); ES-LCMS m/z 251.1 [M−Boc+H]$^+$.

Step 2: 4-Benzyl 1-tert-butyl 2-((1,3-dioxoisoindolin-2-yl)methyl)piperazine-1,4-dicarboxylate

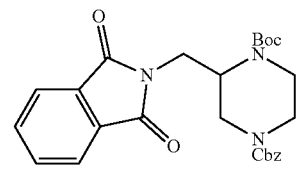

A mixture of 4-benzyl 1-tert-butyl 2-(hydroxymethyl)piperazine-1,4-dicarboxylate (4.3 g, 12.27 mmol), isoindoline-1,3-dione (1.805 g, 12.27 mmol), $PPh_3$ (3.86 g, 14.73 mmol) and DIAD (3.58 mL, 18.41 mmol) in DCM (80 mL) was stirred at 25° C. under $N_2$ atmosphere for 16 h. The mixture was washed with brine (30 mL×2), dried over Na$_2$SO$_4$, filtered and concentrated. The crude material was purified by silica gel column chromatography (PE/EtOAc=4/1). All fractions found to contain product by TLC (PE/EA=5/1, R$_f$=0.3) were combined and concentrated to yield a yellow solid of 4-benzyl 1-tert-butyl 2-((1,3-dioxoisoindolin-2-yl)methyl)piperazine-1,4-dicarboxylate (4.6 g, 8.63 mmol, 70.4% yield): $^1$H NMR (400 MHz, CD$_3$OD) δ ppm 7.85-7.74 (m, 5H), 7.44-7.21 (m, 4H), 5.18 (br. s, 2H), 4.21-4.09 (m, 3H), 4.05-3.70 (m, 3H), 3.61-3.46 (m, 1H), 3.11 (br. s, 1H), 2.91 (br. s, 1H), 1.13-0.95 (m, 9H); ES-LCMS m/z 380.2 [M−Boc+H]$^+$.

Step 3: tert-Butyl 2-((1,3-dioxoisoindolin-2-yl)methyl)piperazine-1-carboxylate

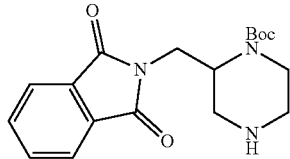 [SMILES: CC(C)(C)OC(=O)N1CCNCC1CN1C(=O)c2ccccc2C1=O]

A mixture of 4-benzyl 1-tert-butyl 2-((1,3-dioxoisoindolin-2-yl)methyl)piperazine-1,4-dicarboxylate (4.6 g, 9.59 mmol) and Pd/C (10 wt %, 0.5 g, 0.470 mmol) in DMF (60 mL) was stirred at 25° C. under 50 psi H$_2$ atmosphere for 16 h. The mixture was filtered and the filtrate was concentrated to yield a light yellow solid of tert-butyl 2-((1,3-dioxoisoindolin-2-yl)methyl)piperazine-1-carboxylate (2.8 g, 6.89 mmol, 71.8% yield): $^1$H NMR (400 MHz, CDCl$_3$) δ ppm 7.91-7.59 (m, 3H), 7.57-7.38 (m, 1H), 4.87-4.60 (m, 1H), 4.59-4.35 (m, 1H), 4.25-4.07 (m, 1H), 3.72-3.51 (m, 2H), 3.49-3.16 (m, 2H), 2.85-2.73 (m, 2H), 1.59-0.93 (m, 9H); ES-LCMS m/z 346.1 [M+H]$^+$.

Step 4: N-((1-((5-((6-Bromopyridin-3-yl)oxy)-3',5'-dichloro-[1,1'-biphenyl]-3-yl)methyl)piperidin-4-yl)methyl)acetamide

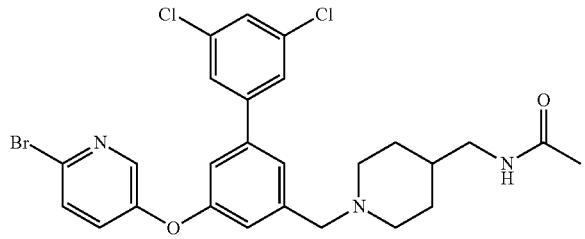 [SMILES: CC(=O)NCC1CCN(Cc2cc(Oc3ccc(Br)nc3)cc(-c3cc(Cl)cc(Cl)c3)c2)CC1]

A mixture of N-((1-((3',5'-dichloro-5-hydroxy-[1,1'-biphenyl]-3-yl)methyl)piperidin-4-yl)methyl)acetamide (2 g, 4.91 mmol), 2-bromo-5-fluoropyridine (4.32 g, 24.55 mmol) and Cs$_2$CO$_3$ (8.00 g, 24.55 mmol) in DMF (30 mL) was stirred at 130° C. for 24 h. The mixture was concentrated and the residue was diluted with H$_2$O (100 mL) and extracted with EtOAc (100 mL×3). The organic layers were combined, dried over Na$_2$SO$_4$ and filtered and concentrated. The resulting mixture was purified by silica gel column chromatography (DCM/MeOH=1/0 to 10/1). All fractions found to contain product by TLC (DCM/MeOH=20/1, R$_f$=0.3) were combined and concentrated to yield a yellow solid of N-((1-((5-((6-bromopyridin-3-yl)oxy)-3',5'-dichloro-[1,1'-biphenyl]-3-yl)methyl)piperidin-4-yl)methyl)acetamide (1.3 g, 1.962 mmol, 40.0% yield): $^1$H NMR (400 MHz, CD$_3$OD) δ ppm 8.14 (d, J=2.9 Hz, 1H), 7.62-7.52 (m, 3H), 7.46-7.41 (m, 2H), 7.39 (dd, J=8.7, 3.1, Hz, 1H), 7.28 (s, 1H), 7.09 (s, 1H), 3.62-3.52 (m, 2H), 3.08-2.99 (m, 2H), 2.91 (d, J=11.5 Hz, 2H), 2.03 (t, J=10.8 Hz, 2H), 1.91 (s, 3H), 1.76-1.62 (m, 2H), 1.50 (d, J=3.7 Hz, 1H), 1.30-1.21 (m, 2H); ES-LCMS m/z 564.1, 566.1 [M+H]$^+$.

Step 5: N-((1-((3',5'-Dichloro-5-((6-(3-oxohexahydroimidazo[1,5-a]pyrazin-7(1H)-yl)pyridin-3-yl)oxy)-[1,1'-biphenyl]-3-yl)methyl)piperidin-4-yl)methyl)acetamide, 2 hydrochloride

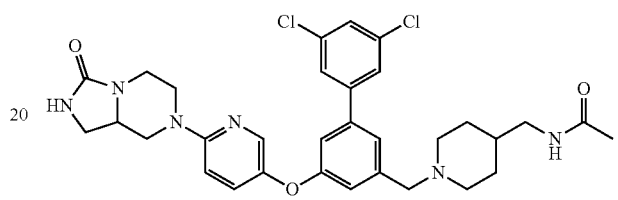

A mixture of N-((1-((5-((6-bromopyridin-3-yl)oxy)-3',5'-dichloro-[1,1'-biphenyl]-3-yl)methyl)piperidin-4-yl)methyl)acetamide (150 mg, 0.266 mmol), tert-butyl 2-((1,3-dioxoisoindolin-2-yl)methyl)piperazine-1-carboxylate (110 mg, 0.320 mmol), sodium tert-butoxide (77 mg, 0.799 mmol), (±)-BINAP (6.63 mg, 10.65 μmol), 18-crown-6 (211 mg, 0.799 mmol) and Pd$_2$(dba)$_3$ (4.88 mg, 5.33 μmol) in THF (10 mL) was stirred at 65° C. under N$_2$ atmosphere for 16 h. The mixture was concentrated and the residue was partitioned between DCM (50 mL) and H$_2$O (50 mL). The organic layer was washed with brine (50 mL×2), dried over Na$_2$SO$_4$, filtered and the filtrate was concentrated. The crude product was suspended in PE (50 mL) and filtered. The solid was collected and further purified by preparative HPLC (MeCN/H$_2$O as eluents, acidic condition) and dried by lyophilization to yield a pale yellow solid of N-((1-((3',5'-dichloro-5-((6-(3-oxohexahydroimidazo[1,5-a]pyrazin-7(1H)-yl)pyridin-3-yl)oxy)-[1,1'-biphenyl]-3-yl)methyl)piperidin-4-yl)methyl)acetamide, 2 hydrochloride (47.97 mg, 0.067 mmol, 25.1% yield): $^1$H NMR (400 MHz, CD$_3$OD) δ ppm 8.20 (d, J=2.4 Hz, 1H), 8.10 (d, J=9.3 Hz, 1H), 7.80 (dd, J=9.3, 2.6 Hz, 1H), 7.68-7.58 (m, 3H), 7.50 (s, 1H), 7.45-7.39 (m, 1H), 7.32 (br. s, 1H), 4.35 (s, 2H), 4.33-4.25 (m, 1H), 4.24-4.12 (m, 2H), 3.88 (dd, J=10.5, 4.5 Hz, 1H), 3.63-3.49 (m, 3H), 3.48-3.34 (m, 2H), 3.15-3.08 (m, 3H), 3.02 (t, J=12.1 Hz, 2H), 2.02-1.90 (m, 5H), 1.82 (br. s, 1H), 1.57-1.43 (m, 2H); ES-LCMS m/z 623.2, 625.2 [M+H]$^+$.

Example 108: 1-(5-((6-(3-Chloro-5-methylphenyl)-4-((methylamino)methyl)pyridin-2-yl)oxy)pyridin-2-yl)piperidin-4-amine, 4 hydrochloride

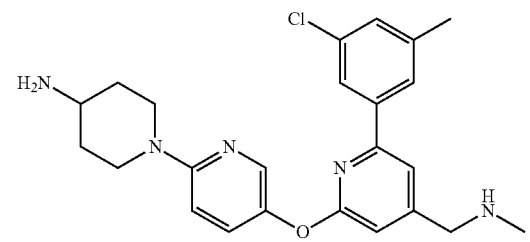 [SMILES: CNCc1cc(Oc2ccc(N3CCC(N)CC3)nc2)nc(-c2cc(C)cc(Cl)c2)c1]

Step 1: (2,6-Dichloropyridin-4-yl)methyl methanesulfonate

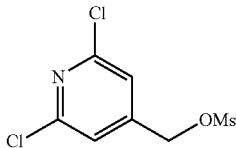 [SMILES: CS(=O)(=O)OCc1cc(Cl)nc(Cl)c1]

To a solution of (2,6-dichloropyridin-4-yl)methanol (6 g, 33.7 mmol) and DIEA (8.71 g, 67.4 mmol) in DCM (100 mL) was added MsCl (3.86 g, 33.7 mmol). Then the reaction was heated to 25° C. for 1 h. Then the solution was concentrated and distributed between DCM (50 mL×2) and water (50 mL). The combined organic extract was washed with brine (50 mL), dried over $Na_2SO_4$, filtered and concentrated to yield (2,6-dichloropyridin-4-yl)methyl methanesulfonate (6 g, 18.74 mmol, 55.6% yield): $^1$H NMR (400 MHz, $CDCl_3$) δ ppm 7.28 (s, 2H), 5.18 (s, 2H), 3.12 (s, 3H); ES-LCMS m/z 256.0 $[M+H]^+$.

Step 2: 1-(2,6-Dichloropyridin-4-yl)-N-methylmethanamine

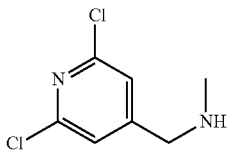

To a solution of (2,6-dichloropyridin-4-yl)methyl methanesulfonate (6 g, 23.43 mmol) in AcOH (50 mL) was added methanamine (181 g, 2343 mmol). Then the reaction was heated to 25° C. for 2 h. Then the solution was concentrated and purified by silica column chromatography (PE/EtOAc=2/1). All fractions found to contain product by TLC (PE/EtOAc=2/1, $R_f$=0.3) were combined and concentrated to yield a light yellow solid of 1-(2,6-dichloropyridin-4-yl)-N-methylmethanamine (5 g, 22.24 mmol, 95.0% yield): $^1$H NMR (400 MHz, $CD_3OD$) δ ppm 7.25 (s, 2H), 3.74 (s, 2H), 2.43 (s, 3H); ES-LCMS m/z 191.0 $[M+H]^+$.

Step 3: tert-Butyl ((2,6-dichloropyridin-4-yl)methyl)(methyl)carbamate

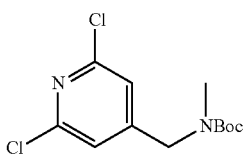

To a solution of 1-(2,6-dichloropyridin-4-yl)-N-methylmethanamine (3 g, 15.70 mmol) in DCM (50 mL) was added $Boc_2O$ (3.43 g, 15.70 mmol). Then the reaction was heated to 25° C. for 8 h. Then the solution was concentrated and purified by silica column chromatography (PE/EtOAc=10/1). All fractions found to contain product by TLC (PE/EtOAc=5/1, $R_f$=0.5) were combined and concentrated to yield a light yellow oil of tert-butyl ((2,6-dichloropyridin-4-yl)methyl)(methyl)carbamate (3.9 g, 12.05 mmol, 77.0% yield): $^1$H NMR (400 MHz, $CDCl_3$) δ ppm 7.09 (s, 2H), 4.38 (br. s, 2H), 2.88 (d, J=15.4 Hz, 3H), 1.51-1.41 (m, 9H); ES-LCMS m/z 291.0 $[M+H]^+$.

Step 4: tert-Butyl (1-(5-(benzyloxy)pyridin-2-yl)piperidin-4-yl)carbamate

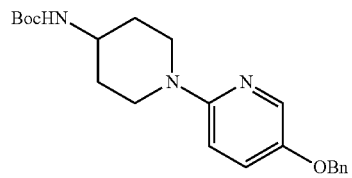 [SMILES: CC(C)(C)OC(=O)NC1CCN(c2ccc(OCc3ccccc3)cn2)CC1]

A mixture of 5-(benzyloxy)-2-bromopyridine (2 g, 7.57 mmol), tert-butyl piperidin-4-ylcarbamate (1.668 g, 8.33 mmol), (±)-BINAP (0.094 g, 0.151 mmol), t-BuONa (1.092 g, 11.36 mmol) and $Pd_2(dba)_3$ (0.069 g, 0.076 mmol) in toluene (30 mL) was stirred at 65° C. for 15 h under $N_2$ atmosphere. The mixture was concentrated and purified by silica gel column chromatography (PE/EtOAc=4/1). All fractions found to contain product by preparative TLC (PE/EA=3/1, $R_f$=0.5) were combined and concentrated to yield a light yellow solid tert-butyl (1-(5-(benzyloxy)pyridin-2-yl)piperidin-4-yl)carbamate (400 mg, 0.939 mmol, 12.4% yield): $^1$H NMR (400 MHz, $CDCl_3$) δ ppm 7.95 (d, J=2.9 Hz, 1H), 7.43-7.29 (m, 5H), 7.17 (d, J=6.6 Hz, 1H), 6.63 (d, J=9.0 Hz, 1H), 5.08-4.97 (m, 2H), 4.44 (br. s, 1H), 4.11-3.95 (m, 2H), 3.70-3.51 (m, 2H), 2.89 (t, J=11.6 Hz, 2H), 2.01 (d, J=13.9 Hz, 2H), 1.44 (s, 9H); ES-LCMS m/z 384.1 $[M+H]^+$.

Step 5: tert-Butyl (1-(5-hydroxypyridin-2-yl)piperidin-4-yl)carbamate

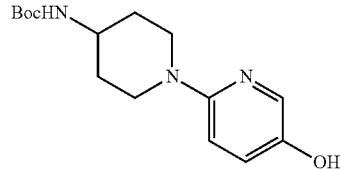 [SMILES: CC(C)(C)OC(=O)NC1CCN(c2ccc(O)cn2)CC1]

A mixture of tert-butyl (1-(5-(benzyloxy)pyridin-2-yl)piperidin-4-yl)carbamate (600 mg, 1.565 mmol), Pd/C (10 wt %, 1665 mg, 1.565 mmol) in MeOH (10 mL) was stirred at 25° C. for 10 h under $H_2$ atmosphere (15 psi). The reaction mixture was filtered and concentrated. The crude was purified by silica gel column chromatography (PE/EtOAc=2/1). All fractions found to contain product by TLC (PE/EA=1/1, $R_f$=0.5) were combined and concentrated to yield light yellow oil of tert-butyl (1-(5-hydroxypyridin-2-yl)piperidin-4-yl)carbamate (400 mg, 1.254 mmol, 80.0% yield): $^1$H NMR (400 MHz, $CDCl_3$) δ ppm 7.81 (d, J=2.9 Hz, 1H), 7.04 (dd, J=2.9, 9.0 Hz, 1H), 6.56 (d, J=9.0 Hz, 1H), 4.42 (br. s, 1H), 4.09-3.80 (m, 2H), 3.57 (br. s, 2H), 2.91-2.69 (m, 2H), 1.95 (d, J=10.8 Hz, 2H), 1.38 (s, 9H); ES-LCMS m/z 294.1 $[M+H]^+$.

Step 6: tert-Butyl ((2-((6-(4-((tert-butoxycarbonyl)amino)piperidin-1-yl)pyridin-3-yl)oxy)-6-chloropyridin-4-yl)methyl)(methyl)carbamate

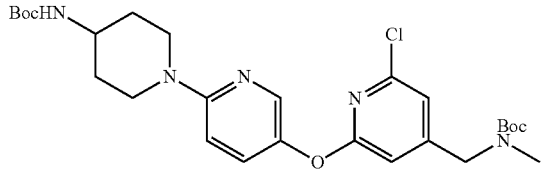 [SMILES: CN(Cc1cc(Cl)nc(Oc2ccc(N3CCC(NC(=O)OC(C)(C)C)CC3)nc2)c1)C(=O)OC(C)(C)C]

To a mixture of tert-butyl ((2,6-dichloropyridin-4-yl)methyl)(methyl)carbamate (328 mg, 1.125 mmol) and K$_2$CO$_3$ (424 mg, 3.07 mmol) in MeCN (10 mL) was added tert-butyl (1-(5-hydroxypyridin-2-yl)piperidin-4-yl)carbamate (300 mg, 1.023 mmol). The reaction was stirred at 80° C. for 14 h under N$_2$ atmosphere then filtered and concentrated to get the crude product which was purified by silica gel column chromatography (PE/EtOAc=9/1). All fractions found to contain product by TLC (PE/EA=3/1, R$_f$=0.5) were combined and concentrated to yield a light yellow solid of tert-butyl ((2-((6-(4-((tert-butoxycarbonyl)amino)piperidin-1-yl)pyridin-3-yl)oxy)-6-chloropyridin-4-yl)methyl)(methyl)carbamate (200 mg, 0.343 mmol, 33.5% yield): $^1$H NMR (400 MHz, CDCl$_3$) δ ppm 8.04 (d, J=2.9 Hz, 1H), 7.32 (dd, J=2.8, 9.2 Hz, 1H), 6.84 (s, 1H), 6.69 (d, J=9.3 Hz, 1H), 6.58 (br. s, 1H), 4.49 (br. s, 1H), 4.36 (d, J=19.2 Hz, 2H), 4.21-4.10 (m, 2H), 3.68 (br. s, 2H), 2.98 (t, J=11.5 Hz, 2H), 2.86 (d, J=12.1 Hz, 3H), 2.04 (t, J=5.0 Hz, 2H), 1.52-1.38 (m, 18H); ES-LCMS m/z 548.1, 550.2 [M+H]$^+$.

Step 7: tert-Butyl ((2-((6-(4-((tert-butoxycarbonyl)amino)piperidin-1-yl)pyridin-3-yl)oxy)-6-(3-chloro-5-methylphenyl)pyridin-4-yl)methyl)(methyl)carbamate

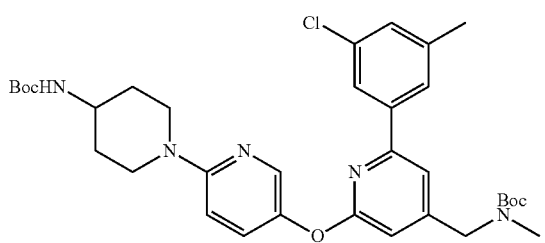 [SMILES: Cc1cc(Cl)cc(-c2cc(CN(C)C(=O)OC(C)(C)C)cc(Oc3ccc(N4CCC(NC(=O)OC(C)(C)C)CC4)nc3)n2)c1]

To a solution of tert-butyl ((2-((6-(4-((tert-butoxycarbonyl)amino)piperidin-1-yl)pyridin-3-yl)oxy)-6-(3-chloro-5-methylphenyl)pyridin-4-yl)methyl)(methyl)carbamate (180 mg, 0.282 mmol) in 1,4-dioxane (10 mL) was added (3-chloro-5-methylphenyl)boronic acid (96 mg, 0.564 mmol), K$_2$CO$_3$ (78 mg, 0.564 mmol) and PdCl$_2$(dppf) (10.32 mg, 0.014 mmol) under N$_2$ atmosphere at 20° C. The reaction was then degassed and filled with N$_2$ for three times then stirred at 80° C. for 15 h. The reaction mixture was concentrated. The crude was purified by silica gel column chromatography (PE/EtOAc=4/1). All fractions found to contain product by preparative TLC (PE/EA=3/1, R$_f$=0.5) were combined and concentrated to yield light yellow oil of tert-butyl ((2-((6-(4-((tert-butoxycarbonyl)amino)piperidin-1-yl)pyridin-3-yl)oxy)-6-(3-chloro-5-methylphenyl)pyridin-4-yl)methyl)(methyl)carbamate (100 mg, 0.139 mmol, 49.4% yield): $^1$H NMR (400 MHz, CDCl$_3$) δ ppm 8.05 (d, J=2.6 Hz, 1H), 7.58 (br. s, 1H), 7.50 (s, 1H), 7.35 (dd, J=2.8, 9.2 Hz, 1H), 7.10 (br. s, 1H), 6.72-6.62 (m, 2H), 6.55 (br. s, 1H), 4.39 (br. s, 1H), 4.37 (d, J=17.0 Hz, 4H), 4.11 (d, J=13.2 Hz, 2H), 3.63 (br. s, 1H), 3.42 (s, 3H), 2.82 (br. s, 4H), 2.29 (s, 3H), 1.39 (s, 18H); ES-LCMS m/z 638.2, 640.2 [M+H]$^+$.

Step 8: 1-(5-((6-(3-Chloro-5-methylphenyl)-4-((methylamino)methyl)pyridin-2-yl)oxy)pyridin-2-yl)piperidin-4-amine, 4 hydrochloride

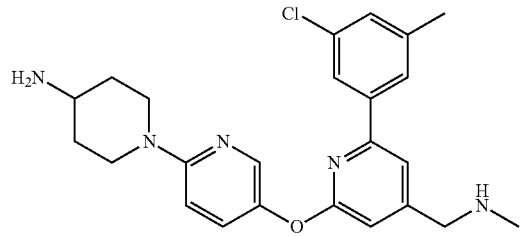 [SMILES: CNCc1cc(Oc2ccc(N3CCC(N)CC3)nc2)nc(-c2cc(C)cc(Cl)c2)c1]

A solution of tert-butyl ((2-((6-(4-((tert-butoxycarbonyl)amino)piperidin-1-yl)pyridin-3-yl)oxy)-6-(3-chloro-5-methylphenyl)pyridin-4-yl)methyl)(methyl)carbamate (100 mg, 0.157 mmol) in TFA (10% in DCM, 10 mL) was stirred at 20° C. for 0.5 h. The reaction was concentrated and the residue was purified by preparative HPLC (MeCN/H$_2$O as eluents, acidic condition) then dried by lyophilization to yield a white solid of 1-(5-((6-(3-chloro-5-methylphenyl)-4-((methylamino)methyl)pyridin-2-yl)oxy)pyridin-2-yl)piperidin-4-amine, 4 hydrochloride (27.69 mg, 0.047 mmol, 30.3% yield): $^1$H NMR (400 MHz, D$_2$O) δ ppm 7.80-7.78 (m, 2H), 7.43 (s, 1H), 7.31 (d, J=5.5 Hz, 2H), 7.21 (d, J=9.7 Hz, 1H), 7.08 (s, 1H), 6.92 (s, 1H), 4.14 (s, 2H), 4.03 (d, J=13.9 Hz, 2H), 3.45 (t, J=11.4 Hz, 1H), 3.18 (t, J=12.3 Hz, 2H), 2.62 (s, 3H), 2.19-2.04 (m, 5H), 1.62 (dq, J=3.7, 12.2 Hz, 2H); ES-LCMS m/z 438.0, 440.0 [M+H]$^+$.

Example 109: N-((1-((2-(3,5-Dichlorophenyl)-6-((5-(piperazin-1-yl)pyrazin-2-yl)oxy)pyridin-4-yl)methyl)piperidin-4-yl)methyl)acetamide

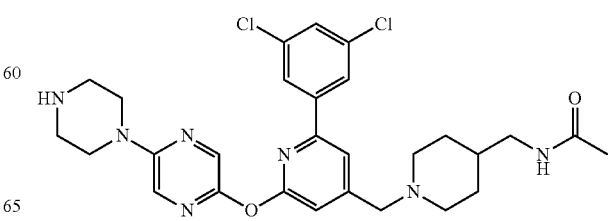

Step 1: N-((1-((2-((5-Chloropyrazin-2-yl)oxy)-6-(3,5-dichlorophenyl)pyridin-4-yl)methyl)piperidin-4-yl)methyl)acetamide

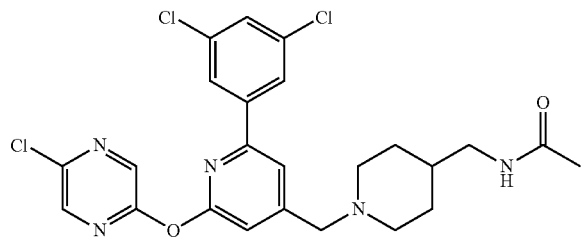

To a solution of 2,5-dichloropyrazine (0.952 g, 6.39 mmol) and N-((1-((2-(3,5-dichlorophenyl)-6-hydroxypyridin-4-yl)methyl)piperidin-4-yl)methyl)acetamide (1.5 g, 3.20 mmol) in DMF (30 mL) was added $K_2CO_3$ (0.883 g, 6.39 mmol). The reaction mixture was stirred at 120° C. for 12 h then filtered and concentrated to yield the crude product which was purified by silica gel (DCM/MeOH=1/0 to 10/1). All fractions found to contain product by TLC (DCM/MeOH=10/1, $R_f$=0.6) to yield a yellow solid of N-((1-((2-((5-chloropyrazin-2-yl)oxy)-6-(3,5-dichlorophenyl)pyridin-4-yl)methyl)piperidin-4-yl)methyl)acetamide (1.2 g, 2.130 mmol, 66.6% yield): $^1$H NMR (400 MHz, $CDCl_3$) δ ppm 8.36 (s, 1H), 8.26 (s, 1H), 7.71 (d, J=1.3 Hz, 2H), 7.53 (s, 1H), 7.34 (s, 1H), 7.06 (s, 1H), 5.61 (s, 1H), 3.56 (s, 2H), 3.15 (t, J=6.4 Hz, 2H), 2.88 (d, J=9.7 Hz, 2H), 2.08-2.00 (m, 2H), 1.97 (s, 3H), 1.69 (d, J=12.3 Hz, 2H), 1.52 (td, J=3.7, 7.2 Hz, 1H), 1.36-1.26 (m, 2H); ES-LCMS m/z 520.2, 522.2 $[M+H]^+$.

Step 2: tert-Butyl 4-(5-((4-((4-(acetamidomethyl)piperidin-1-yl)methyl)-6-(3,5-dichlorophenyl)pyridin-2-yl)oxy)pyrazin-2-yl)piperazine-1-carboxylate

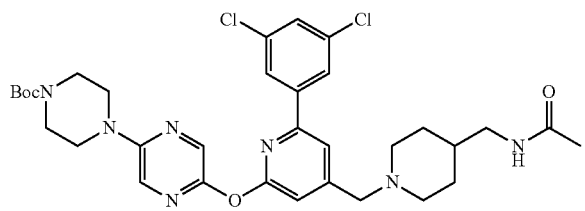 [SMILES: CC(=O)NCC1CCN(Cc2cc(Oc3cnc(N4CCN(C(=O)OC(C)(C)C)CC4)cn3)nc(-c3cc(Cl)cc(Cl)c3)c2)CC1]

A mixture of N-((1-((3',5'-dichloro-5-((5-chloropyrazin-2-yl)oxy)-[1,1'-biphenyl]-3-yl)methyl)piperidin-4-yl)methyl)acetamide (1.2 g, 2.134 mmol), tert-butylpiperazine-1-carboxylate (0.795 g, 4.27 mmol), Xantphos (0.025 g, 0.043 mmol), $Cs_2CO_3$ (2.086 g, 6.40 mmol) in THF (15 mL) was added $Pd_2(dba)_3$ (0.098 g, 0.107 mmol). The reaction was stirred at 80° C. for 6 h under $N_2$ atmosphere then filtered and concentrated to yield the crude product which was purified by silica gel (DCM/MeOH=1/0 to 10/1). All fractions found to contain product by TLC (DCM/MeOH=10/1, $R_f$=0.5) to yield a yellow solid of tert-butyl 4-(5-((4-((4-(acetamidomethyl)piperidin-1-yl)methyl)-6-(3,5-dichlorophenyl)pyridin-2-yl)oxy)pyrazin-2-yl)piperazine-1-carboxylate (1.3 g, 1.547 mmol, 72.5% yield): $^1$H NMR (400 MHz, $CDCl_3$) δ ppm 8.12 (s, 1H), 7.84 (s, 1H), 7.70 (d, J=1.3 Hz, 2H), 7.42 (s, 1H), 7.32 (s, 1H), 6.95 (s, 1H), 5.52 (br. s, 1H), 3.58 (d, J=3.1 Hz, 8H), 3.56 (s, 2H), 3.16 (t, J=6.2 Hz, 2H), 2.88 (d, J=11.0 Hz, 2H), 2.03-1.95 (m, 5H), 1.68 (d, J=11.9 Hz, 2H), 1.57-1.52 (m, 1H), 1.50-1.42 (m, 9H), 1.34-1.24 (m, 2H); ES-LCMS m/z 670.3, 672.4 $[M+H]^+$.

Step 3: N-((1-((2-(3,5-Dichlorophenyl)-6-((5-(piperazin-1-yl)pyrazin-2-yl)oxy)pyridin-4-yl)methyl)piperidin-4-yl)methyl)acetamide

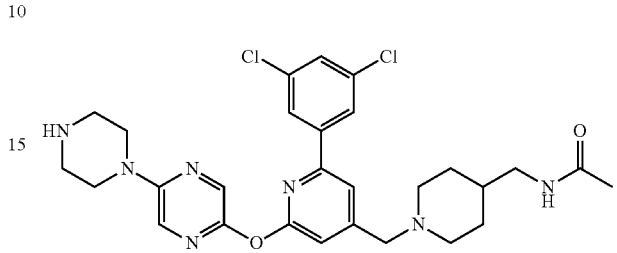

To a solution of tert-butyl 4-(5-((4-((4-(acetamidomethyl)piperidin-1-yl)methyl)-6-(3,5-dichlorophenyl)pyridin-2-yl)oxy)pyrazin-2-yl)piperazine-1-carboxylate (350 mg, 0.470 mmol) in DCM (8 mL) was added TFA (2 mL, 26.0 mmol). The reaction mixture was stirred at 25° C. for 0.1 h then concentrated to yield the crude product which was purified by preparative HPLC (MeCN/$H_2O$ as eluents, basic condition) and lyophilized to yield a pale yellow solid of N-((1-((2-(3,5-dichlorophenyl)-6-((5-(piperazin-1-yl)pyrazin-2-yl)oxy)pyridin-4-yl)methyl)piperidin-4-yl)methyl)acetamide (191.81 mg, 0.332 mmol, 70.7% yield): $^1$H NMR (400 MHz, $CD_3OD$) δ ppm 8.11 (d, J=1.3 Hz, 1H), 7.96 (s, 1H), 7.78 (d, J=1.8 Hz, 2H), 7.66 (s, 1H), 7.43 (t, J=1.8 Hz, 1H), 7.04 (s, 1H), 3.69-3.52 (m, 6H), 3.13-3.04 (m, 2H), 3.02-2.83 (m, 6H), 2.08 (t, J=10.8 Hz, 2H), 1.93 (s, 3H), 1.72 (d, J=11.9 Hz, 2H), 1.54-1.46 (m, 1H), 1.37-1.26 (m, 2H); ES-LCMS m/z 570.2, 572.2 $[M+H]^+$.

Example 110: N-((1-((2-(3,5-Dichlorophenyl)-6-((5-(4-methylpiperazin-1-yl)pyrazin-2-yl)oxy)pyridin-4-yl)methyl)piperidin-4-yl)methyl)acetamide

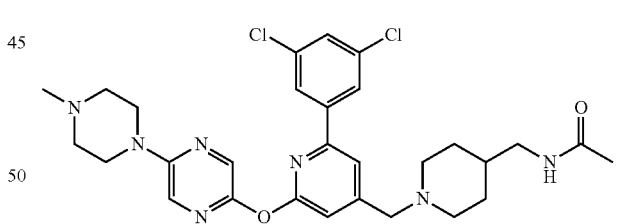

To a solution of N-((1-((2-(3,5-dichlorophenyl)-6-((5-(piperazin-1-yl)pyrazin-2-yl)oxy)pyridin-4-yl)methyl)piperidin-4-yl)methyl)acetamide, 4 trifluoroacetic acid salt (300 mg, 0.244 mmol) in MeOH (5 mL) was added paraformaldehyde (366 mg, 12.18 mmol) and formic acid (11.21 mg, 0.244 mmol). After stirring at 20° C. for 20 h, $NaBH_3CN$ (77 mg, 1.218 mmol) was added and the mixture was stirred for another 4 h. Saturated aqueous $NaHCO_3$ (50 mL) was added and extracted with DCM (30 mL×3). The combined organic layers were dried over $Na_2SO_4$ and concentrated to yield the crude product which was purified by preparative HPLC (MeCN/$H_2O$ as eluents, basic condition) and lyophilized to yield a white solid of N-((1-((2-(3,5-dichlorophenyl)-6-((5-(4-methylpiperazin-1-yl)pyrazin-2- yl)oxy)pyridin-4-yl)methyl)piperidin-4-yl)methyl)acetamide (106.34 mg, 0.180 mmol, 73.8% yield): $^1$H NMR (400 MHz, CD$_3$OD) δ ppm 8.12 (s, 1H), 7.98 (s, 1H), 7.78 (s, 2H), 7.66 (s, 1H), 7.43 (s, 1H), 7.04 (s, 1H), 3.65 (s, 4H), 3.62 (s, 2H), 3.07 (d, J=6.6 Hz, 2H), 2.94 (d, J=11.5 Hz, 2H), 2.61 (s, 4H), 2.37 (s, 3H), 2.08 (t, J=11.5 Hz, 2H), 1.93 (s, 3H), 1.72 (d, J=12.3 Hz, 2H), 1.53 (s, 1H), 1.35-1.26 (m, 2H); ES-LCMS m/z 584.3, 586.3 [M+H]$^+$.

Example 111: 3-(4-(5-((4-((4-(Acetamidomethyl) piperidin-1-yl)methyl)-6-(3,5-dichlorophenyl)pyridin-2-yl)oxy)pyrazin-2-yl)piperazin-1-yl)propanoic acid

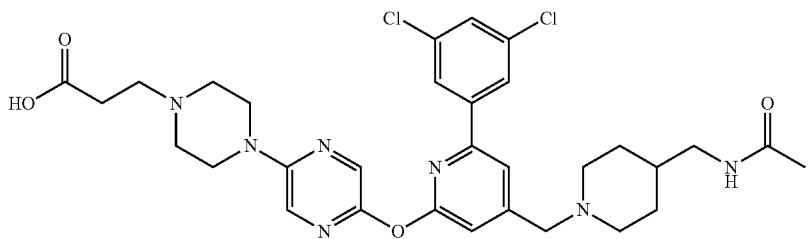 [SMILES: CC(=O)NCC1CCN(Cc2cc(Oc3cnc(N4CCN(CCC(=O)O)CC4)cn3)nc(-c3cc(Cl)cc(Cl)c3)c2)CC1]

Step 1: N-((1-((2-(3,5-Dichlorophenyl)-6-((5-(piperazin-1-yl)pyrazin-2-yl)oxy)pyridin-4-yl)methyl)piperidin-4-yl)methyl)acetamide

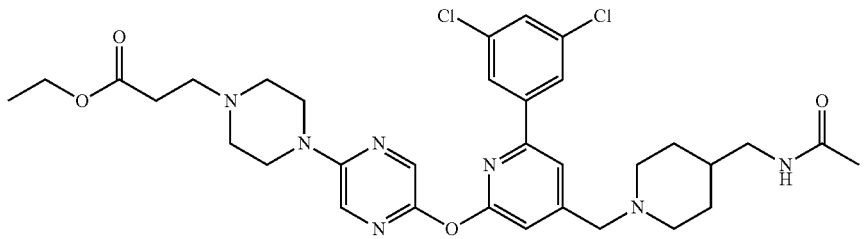 [SMILES: CCOC(=O)CCN1CCN(c2cnc(Oc3cc(CN4CCC(CNC(C)=O)CC4)cc(-c4cc(Cl)cc(Cl)c4)n3)cn2)CC1]

To a solution of N-((1-((2-(3,5-dichlorophenyl)-6-((5-(piperazin-1-yl)pyrazin-2-yl)oxy)pyridin-4-yl)methyl)piperidin-4-yl)methyl)acetamide, 4 trifluoroacetic acid salt (350 mg, 0.307 mmol) and ethyl 3-bromopropanoate (167 mg, 0.921 mmol) in DMF (12 mL) was added K$_2$CO$_3$ (212 mg, 1.534 mmol). The reaction mixture was stirred at 80° C. for 12 h then filtered and concentrated to yield a pale yellow solid of ethyl 3-(4-(5-((4-((4-(acetamidomethyl)piperidin-1-yl)methyl)-6-(3,5-dichlorophenyl)pyridin-2-yl)oxy) pyrazin-2-yl)piperazin-1-yl)propanoate (210 mg, 0.282 mmol, 92.0% yield): $^1$H NMR (400 MHz, CD$_3$OD) δ ppm 8.11 (s, 1H), 7.84 (s, 1H), 7.71 (d, J=1.8 Hz, 2H), 7.43 (s, 1H), 7.32 (s, 1H), 6.94 (s, 1H), 5.54 (s, 1H), 4.16 (q, J=7.1 Hz, 2H), 3.64-3.56 (m, 4H), 3.53 (s, 2H), 3.16 (t, J=6.2 Hz, 2H), 2.89 (d, J=11.0 Hz, 2H), 2.77 (t, J=7.3 Hz, 2H), 2.66-2.59 (m, 4H), 2.57-2.51 (m, 4H), 2.04-1.95 (m, 5H), 1.53 (s, 1H), 1.35-1.24 (m, 5H); ES-LCMS m/z 670.2, 672.2 [M+H]$^+$.

Step 2: 3-(4-(5-((4-((4-(Acetamidomethyl)piperidin-1-yl)methyl)-6-(3,5-dichlorophenyl)pyridin-2-yl) oxy)pyrazin-2-yl)piperazin-1-yl)propanoic acid

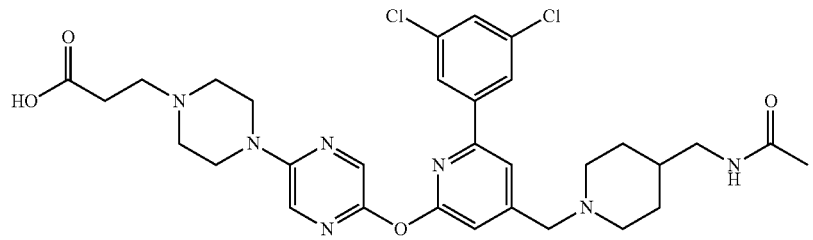 [SMILES: CC(=O)NCC1CCN(Cc2cc(Oc3cnc(N4CCN(CCC(=O)O)CC4)cn3)nc(-c3cc(Cl)cc(Cl)c3)c2)CC1]

To a solution of ethyl 3-(4-(5-((4-((4-(acetamidomethyl)piperidin-1-yl)methyl)-6-(3,5-dichlorophenyl)pyridin-2-yl)oxy)pyrazin-2-yl)piperazin-1-yl)propanoate (210 mg, 0.282 mmol) in THF (5 mL) was added LiOH·H$_2$O (23.65 mg, 0.564 mmol) in water (1 mL). The reaction mixture was stirred at 25° C. for 12 h. 1N HCl was added to adjust pH to 6 then solution was concentrated to yield the crude product which was purified by preparative HPLC (MeCN/H$_2$O as eluents, acidic condition) and lyophilized to yield a white solid of 3-(4-(5-((4-((4-(acetamidomethyl)piperidin-1-yl)methyl)-6-(3,5-dichlorophenyl)pyridine-2-yl)oxy)pyrazin-2-yl)piperazin-1-yl)propanoic acid (107.28 mg, 0.165 mmol, 58.6% yield): $^1$H NMR (400 MHz, CD$_3$OD) δ ppm 8.16 (d, J=0.9 Hz, 1H), 8.04 (d, J=0.9 Hz, 1H), 7.78 (d, J=1.8 Hz, 2H), 7.68 (s, 1H), 7.44 (t, J=1.8 Hz, 1H), 7.07 (s, 1H), 3.85-3.73 (m, 4H), 3.68 (s, 2H), 3.24-3.04 (m, 8H), 2.99 (d, J=11.5 Hz, 2H), 2.58 (t, J=6.8 Hz, 2H), 2.20-2.13 (m, 2H), 1.93 (s, 3H), 1.74 (d, J=11.9 Hz, 2H), 1.55 (s, 1H), 1.38-1.28 (m, 2H); ES-LCMS m/z 642.2, 644.2 [M+H]$^+$.

Example 112: 2-(1-((2-(3,5-Dichlorophenyl)-6-((5-(piperazin-1-yl)pyrazin-2-yl)oxy)pyridin-4-yl)methyl)piperidin-4-yl)acetic acid

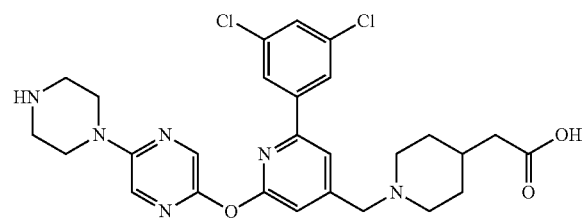

Step 1: Methyl 2-(1-((2-((5-chloropyrazin-2-yl)oxy)-6-(3,5-dichlorophenyl)pyridin-4-yl)methyl)piperidin-4-yl)acetate

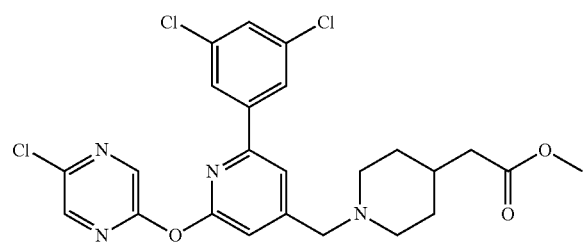 [SMILES: COC(=O)CC1CCN(Cc2cc(Oc3cnc(Cl)cn3)nc(-c3cc(Cl)cc(Cl)c3)c2)CC1]

To a solution of 2,5-dichloropyrazine (371 mg, 2.492 mmol) and methyl 2-(1-((2-(3,5-dichlorophenyl)-6-hydroxypyridin-4-yl)methyl)piperidin-4-yl)acetate (400 mg, 0.831 mmol) in DMF (10 mL) was added K$_2$CO$_3$ (230 mg, 1.661 mmol). The reaction mixture was stirred at 80° C. for 12 h then filtered and concentrated to yield the crude product which was purified by flash chromatography (DCM/MeOH=1/0 to 10/1, DCM/MeOH=10/1, R$_f$=0.55) to yield a pale yellow solid of methyl 2-(1-((2-((5-chloropyrazin-2-yl)oxy)-6-(3,5-dichlorophenyl)pyridin-4-yl)methyl)piperidin-4-yl)acetate (450 mg, 0.763 mmol, 92.0% yield): $^1$H NMR (400 MHz, CDCl$_3$) δ ppm 8.26 (s, 1H), 7.73 (s, 2H), 7.57-7.51 (m, 1H), 7.39-7.32 (m, 2H), 7.07 (s, 1H), 3.72-3.64 (m, 3H), 3.56 (s, 2H), 2.86 (d, J=11.0 Hz, 2H), 2.30-2.22 (m, 2H), 2.12-2.01 (m, 2H), 1.82 (ddd, J=4.0, 7.5, 11.0 Hz, 1H), 1.72 (d, J=12.3 Hz, 1H), 1.41-1.29 (m, 2H); ES-LCMS m/z 521.1, 523.1 [M+H]$^+$.

Step 2: tert-Butyl 4-(5-((4-((4-(acetamidomethyl)piperidin-1-yl)methyl)-6-(3,5-dichlorophenyl)pyridin-2-yl)oxy)pyrazin-2-yl)piperazine-1-carboxylate

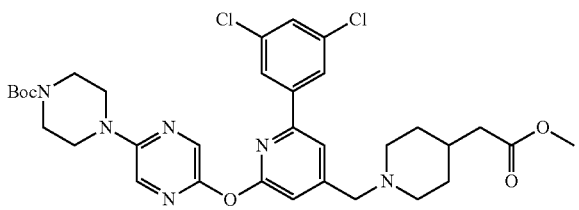 [SMILES: COC(=O)CC1CCN(Cc2cc(Oc3cnc(N4CCN(C(=O)OC(C)(C)C)CC4)cn3)nc(-c3cc(Cl)cc(Cl)c3)c2)CC1]

A mixture of methyl 2-(1-((2-((5-chloropyrazin-2-yl)oxy)-6-(3,5-dichlorophenyl)pyridin-4-yl)methyl)piperidin-4-yl)acetate (450 mg, 0.763 mmol), tert-butyl piperazine-1-carboxylate (142 mg, 0.763 mmol), Xantphos (44.1 mg, 0.076 mmol), Cs$_2$CO$_3$ (745 mg, 2.288 mmol) in THF (20 mL) was added Pd$_2$(dba)$_3$ (69.8 mg, 0.076 mmol). The reaction was stirred at 80° C. for 2 h under N$_2$ atmosphere. The solid was filtered off and solvent was removed in vacuo to give the crude product which was purified by flash chromatography (from DCM:MeOH=1:0 to DCM:MeOH=10:1 for 30 minutes, DCM:MeOH=10:1 (R$_f$=0.50)) to afford tert-butyl 4-(5-((6-(3,5-dichlorophenyl)-4-((4-(2-methoxy-2-oxoethyl)piperidin-1-yl)methyl)pyridin-2-yl)oxy)pyrazin-2-yl)piperazine-1-carboxylate (420 mg, 0.501 mmol, 65.6% yield) as a yellow solid: $^1$H NMR (400 MHz, CDCl$_3$) δ ppm 8.14-8.10 (m, 1H), 7.85 (s, 1H), 7.72-7.67 (m, 2H), 7.43 (s, 1H), 7.32 (s, 1H), 6.95 (s, 1H), 3.67 (s, 3H), 3.58 (d, J=4.0 Hz, 8H), 3.52 (s, 2H), 2.88-2.84 (m, 2H), 2.26 (d, J=7.1 Hz, 2H), 2.05 (t, J=10.6 Hz, 2H), 1.83-1.78 (m, 1H), 1.71 (d, J=12.8 Hz, 2H), 1.55-1.44 (m, 9H), 1.35 (d, J=12.3 Hz, 2H); ES-LCMS m/z 671.3, 673.3 [M+H]$^+$.

Step 3: Methyl 2-(1-((2-(3,5-dichlorophenyl)-6-((5-(piperazin-1-yl)pyrazin-2-yl)oxy)pyridin-4-yl)methyl)piperidin-4-yl)acetate, 4 trifluoroacetic acid salt

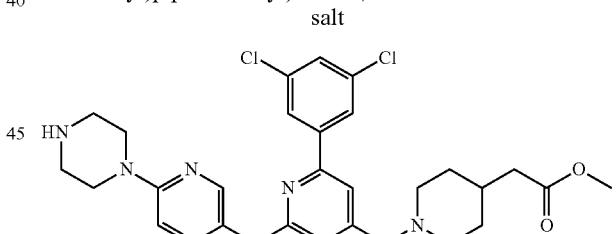

To a solution of tert-butyl 4-(5-((6-(3,5-dichlorophenyl)-4-((4-(2-methoxy-2-oxoethyl)piperidin-1-yl)methyl)pyridin-2-yl)oxy)pyrazin-2-yl)piperazine-1-carboxylate (200 mg, 0.238 mmol) in DCM (8 mL) was added TFA (2 mL, 26.0 mmol). The reaction mixture was stirred at 25° C. for 10 min then concentrated to yield a yellow solid of methyl 2-(1-((2-(3,5-dichlorophenyl)-6-((5-(piperazin-1-yl)pyrazin-2-yl)oxy)pyridin-4-yl)methyl)piperidin-4-yl)acetate, 4 trifluoroacetic acid salt (210 mg, 0.163 mmol, 68.6% yield): $^1$H NMR (400 MHz, CD$_3$OD) δ ppm 8.12 (s, 1H), 7.87-7.83 (m, 1H), 7.82-7.76 (m, 2H), 7.50 (t, J=1.8 Hz, 1H), 7.27 (s, 1H), 4.43 (s, 2H), 4.01-3.79 (m, 4H), 3.66 (s, 3H), 3.59 (d, J=10.6 Hz, 2H), 3.47-3.32 (m, 4H), 3.12 (t, J=12.3 Hz, 2H), 2.36 (d, J=5.7 Hz, 2H), 2.04 (d, J=15.0 Hz, 3H), 1.63-1.50 (m, 2H); ES-LCMS m/z 571.3, 573.3 [M+H]$^+$.

Step 4: 2-(1-((2-(3,5-Dichlorophenyl)-6-((5-(piperazin-1-yl)pyrazin-2-yl)oxy)pyridin-4-yl)methyl)piperidin-4-yl)acetic acid

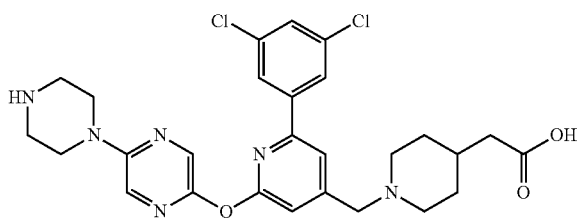 [SMILES: O=C(O)CC1CCN(Cc2cc(Oc3cnc(N4CCNCC4)cn3)nc(-c3cc(Cl)cc(Cl)c3)c2)CC1]

To a solution of methyl 2-(1-((2-(3,5-dichlorophenyl)-6-((5-(piperazin-1-yl)pyrazin-2-yl)oxy)pyridin-4-yl)methyl)piperidin-4-yl)acetate, 4 trifluoroacetic acid salt (210 mg, 0.163 mmol) in THF (5 mL) was added LiOH·H$_2$O (68.6 mg, 1.635 mmol) in water (1 mL). The reaction mixture was stirred at 25° C. for 12 h then 1 N HCl was added to adjust pH to 8. Concentration to yield the crude product which was purified by preparative HPLC (MeCN/H$_2$O as eluents, acidic condition) and lyophilized to yield a white solid of 2-(1-((2-(3,5-dichlorophenyl)-6-((5-(piperazin-1-yl)pyrazin-2-yl)oxy)pyridin-4-yl)methyl)piperidin-4-yl)acetic acid (34.86 mg, 0.062 mmol, 37.7% yield): $^1$H NMR (400 MHz, D$_2$O) δ ppm 8.16 (s, 1H), 8.01 (s, 1H), 7.80 (d, J=1.3 Hz, 2H), 7.75 (s, 1H), 7.51 (s, 1H), 7.22 (s, 1H), 4.29 (s, 2H), 3.85-3.72 (m, 4H), 3.47 (d, J=11.9 Hz, 2H), 3.36-3.23 (m, 4H), 3.01 (t, J=12.6 Hz, 2H), 2.28 (d, J=6.6 Hz, 2H), 2.08-1.96 (m, 3H), 1.52 (d, J=13.2 Hz, 2H); ES-LCMS m/z 557.2, 559.2 [M+H]$^+$.

Example 113: N-((1-((3',5'-Dichloro-5-((2-(4-(3-hydroxypropyl)piperazin-1-yl)pyrimidin-5-yl)oxy)-[1,1'-biphenyl]-3-yl)methyl)piperidin-4-yl)methyl)acetamide

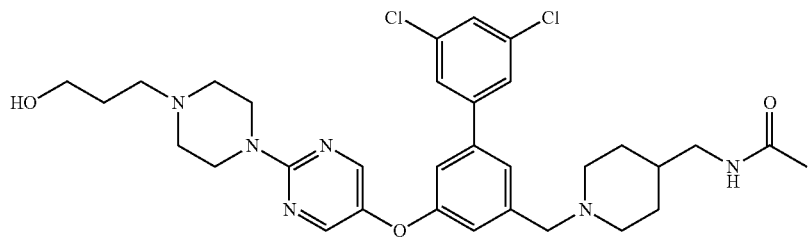 [SMILES: CC(=O)NCC1CCN(Cc2cc(Oc3cnc(N4CCN(CCCO)CC4)nc3)cc(-c3cc(Cl)cc(Cl)c3)c2)CC1]

Step 1: Ethyl 3-(4-(5-((5-((4-(acetamidomethyl)piperidin-1-yl)methyl)-3',5'-dichloro-[1,1'-biphenyl]-3-yl)oxy)pyrimidin-2-yl)piperazin-1-yl)propanoate

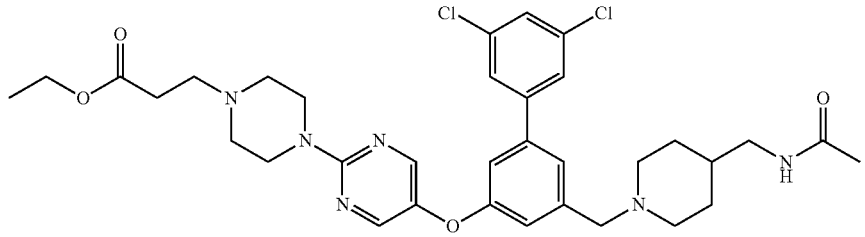 [SMILES: CCOC(=O)CCN1CCN(c2ncc(Oc3cc(CN4CCC(CNC(C)=O)CC4)cc(-c4cc(Cl)cc(Cl)c4)c3)cn2)CC1]

To a mixture of N-((1-((3',5'-dichloro-5-((2-(piperazin-1-yl)pyrimidin-5-yl)oxy)-[1,1'-biphenyl]-3-yl)methyl)piperidin-4-yl)methyl)acetamide, 3 hydrochloride (200 mg, 0.221 mmol) in Me$_3$CN (5 mL) was added DIEA (143 mg, 1.105 mmol) and ethyl 3-bromopropanoate (0.031 mL, 0.243 mmol). The reaction was stirred at 80° C. for 10 h under N$_2$ atmosphere then concentrated to yield brown oil of ethyl 3-(4-(5-((5-((4-(acetamidomethyl)piperidin-1-yl)methyl)-3',5'-dichloro-[1,1'-biphenyl]-3-yl)oxy)pyrimidin-2-yl)piperazin-1-yl)propanoate (250 mg, 0.187 mmol, 84.0% yield): $^1$H NMR (400 MHz, CD$_3$OD) δ ppm 8.26 (s, 2H), 7.60 (s, 2H), 7.46 (s, 1H), 7.37 (br. s, 1H), 7.20 (br. s, 1H), 7.02 (br. s, 1H), 4.25-4.13 (m, 2H), 3.83 (br. s, 6H), 3.59-3.43 (m, 2H), 3.08 (d, J=6.5 Hz, 3H), 3.02-2.97 (m, 2H), 2.80-2.71 (m, 2H), 2.63-2.51 (m, 4H), 2.18 (br. s, 2H), 1.95 (s, 3H), 1.75 (d, J=11.0 Hz, 2H), 1.55 (d, J=6.5 Hz, 2H), 1.24-1.15 (m, 3H); ES-LCMS m/z 669.4, 671.3 [M+H]$^+$.

Step 2: N-((1-((3',5'-Dichloro-5-((2-(4-(3-hydroxy-propyl)piperazin-1-yl)pyrimidin-5-yl)oxy)-[1,1'-biphenyl]-3-yl)methyl)piperidin-4-yl)methyl)acetamide, 3 hydrochloride

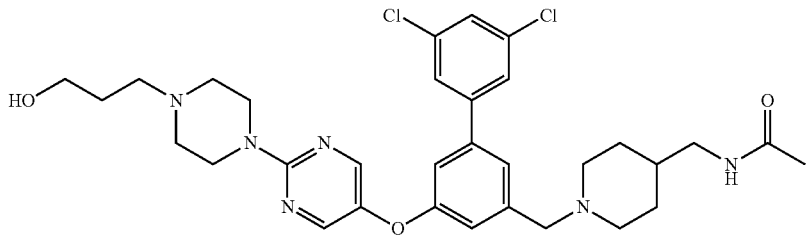 [SMILES: CC(=O)NCC1CCN(Cc2cc(Oc3cnc(N4CCN(CCCO)CC4)nc3)cc(-c3cc(Cl)cc(Cl)c3)c2)CC1]

To a mixture of ethyl 3-(4-(5-((5-((4-(acetamidomethyl)piperidin-1-yl)methyl-3',5'-dichloro-[1,1'-biphenyl]-3-yl)oxy)pyrimidin-2-yl)piperazin-1-yl)propanoate (250 mg, 0.187 mmol) in THF (10 mL) was added LiAlH$_4$ (10.63 mg, 0.280 mmol). The reaction was stirred at −20° C. for 10 min under N$_2$ atmosphere then quenched with 1 mL of water. The mixture was filtered, concentrated and purified by preparative HPLC (MeCN/H$_2$O as eluents, acidic condition) then dried by lyophilized to yield a white solid N-((1-((3',5'-dichloro-5-((2-(4-(3-hydroxypropyl)piperazin-1-yl)pyrimidin-5-yl)oxy)-[1,1'-biphenyl]-3-yl)methyl)piperidin-4-yl)methyl)acetamide, 3 hydrochloride (11.75 mg, 0.015 mmol, 8.1% yield): $^1$H NMR (400 MHz, CD$_3$OD) δ ppm 8.40 (s, 2H), 7.66 (d, J=1.5 Hz, 2H), 7.57 (s, 1H), 7.52 (s, 1H), 7.41 (s, 1H), 7.32 (s, 1H), 4.94 (br. s, 2H), 4.36 (s, 2H), 4.12 (t, J=5.0 Hz, 1H), 3.77-3.69 (m, 2H), 3.54 (d, J=12.0 Hz, 2H), 3.47-3.34 (m, 6H), 3.29-3.18 (m, 2H), 3.13 (d, J=6.5 Hz, 2H), 3.09-2.99 (m, 2H), 2.09-1.94 (m, 6H), 1.84 (br. s, 1H), 1.61-1.46 (m, 2H); LCMS m/z 627.3, 629.4 [M+H]$^+$.

Example 114: 3-(1-((3',5'-Dichloro-5-((2-(4-(2-hydroxyethyl)piperazin-1-yl)pyrimidin-5-yl)oxy)-[1,1'-biphenyl]-3-yl)methyl)piperidin-4-yl)propanoic acid To a solution of tert-butyl 4-(5-((3',5'-dichloro-5-(((methylsulfonyl)oxy)methyl)-[1,1'-biphenyl]-3-yl)oxy)pyrimidin-2-yl)piperazine-1-carboxylate (950 mg, 1.403 mmol) and ethyl 3-(piperidin-4-yl)propanoate (433 mg, 2.104 mmol) in DMF (10 mL) was added K$_2$CO$_3$ (582 mg, 4.21 mmol). The reaction mixture was stirred at 25° C. for 12 h then filtered and concentrated to yield the crude product which was purified by flash chromatography (DCM/MeOH=1/0 to 10/1). All fractions found to contain product by TLC (DCM/MeOH=10/1, R$_f$=0.45) were combined and concentrated to yield a pale yellow solid of tert-butyl 4-(5-((3',5'-dichloro-5-((4-(3-ethoxy-3-oxopropyl)piperidin-1-yl)methyl)-[1,1'-biphenyl]-3-yl)oxy)pyrimidin-2-yl)piperazine-1-carboxylate (900 mg, 1.159 mmol, 83.0% yield): $^1$H NMR (400 MHz, CD$_3$OD) δ ppm 8.28 (s, 2H), 7.59 (d, J=2.0 Hz, 2H), 7.46 (s, 1H), 7.37-7.28 (m, 1H), 7.18 (s, 1H), 7.04-6.95 (m, 1H), 4.61 (s, 2H), 4.16-4.10 (m, 2H), 3.88-3.75 (m, 4H), 3.53 (s, 4H), 2.96-2.90 (m, 2H), 2.35 (t, J=7.8 Hz, 2H), 2.05 (d, J=10.5 Hz, 2H), 1.73 (d, J=11.5 Hz, 2H), 1.65-1.54 (m, 3H), 1.51 (s, 9H), 1.31-1.23 (m, 5H); ES-LCMS m/z 698.3, 700.3 [M+H]$^+$.

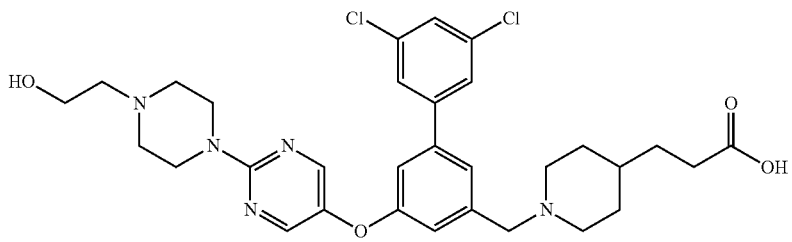 [SMILES: O=C(O)CCC1CCN(Cc2cc(Oc3cnc(N4CCN(CCO)CC4)nc3)cc(-c3cc(Cl)cc(Cl)c3)c2)CC1]

Step 1: tert-Butyl 4-(5-((3',5'-dichloro-5-((4-(3-ethoxy-3-oxopropyl)piperidin-1-yl)methyl)-[1,1'-biphenyl]-3-yl)oxy)pyrimidin-2-yl)piperazine-1-carboxylate Step 2: Ethyl 3-(1-((3',5'-dichloro-5-((2-(piperazin-1-yl)pyrimidin-5-yl)oxy)-[1,1'-biphenyl]-3-yl)methyl)piperidin-4-yl)propanoate, 3 hydrochloride

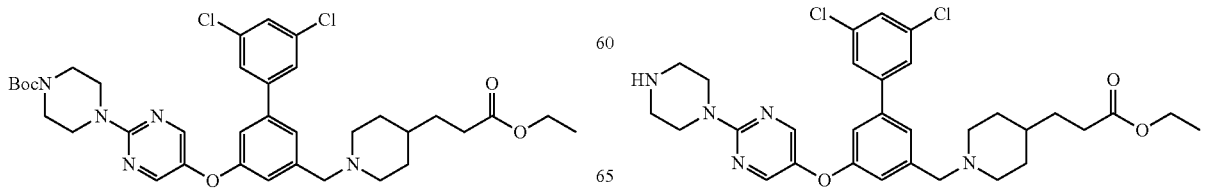

tert-Butyl 4-(5-((3',5'-dichloro-5-((4-(3-ethoxy-3-oxopropyl)piperidin-1-yl)methyl)-[1,1'-biphenyl]-3-yl)oxy)pyrimidin-2-yl)piperazine-1-carboxylate (900 mg, 1.159 mmol) was dissolved in HCl solution (4.0 M in EtOAc, 12 mL, 48.00 mmol). The reaction mixture was stirred at 25° C. for 10 min then concentrated to yield a pale yellow solid of ethyl 3-(1-((3',5'-dichloro-5-((2-(piperazin-1-yl)pyrimidin-5-yl)oxy)-[1,1'-biphenyl]-3-yl)methyl)piperidin-4-yl)propanoate, 3 hydrochloride (910 mg, 1.157 mmol, 100.0% yield): $^1$H NMR (400 MHz, CD$_3$OD) δ ppm 8.40 (s, 2H), 7.66 (d, J=1.5 Hz, 2H), 7.57 (s, 1H), 7.52 (s, 1H), 7.40 (s, 1H), 7.30 (s, 1H), 4.35 (s, 2H), 4.19-4.05 (m, 8H), 3.52 (d, J=12.5 Hz, 2H), 3.06 (s, 2H), 2.39 (t, J=7.0 Hz, 2H), 1.98 (s, 2H), 1.63 (s, 3H), 1.56-1.39 (m, 4H), 1.26 (t, J=7.0 Hz, 3H); ES-LCMS m/z 598.3, 600.3 [M+H]$^+$.

Step 3: Ethyl 3-(1-((3',5'-dichloro-5-((2-(4-(2-hydroxyethyl)piperazin-1-yl)pyrimidin-5-yl)oxy)-[1,1'-biphenyl]-3-yl)methyl)piperidin-4-yl)propanoate

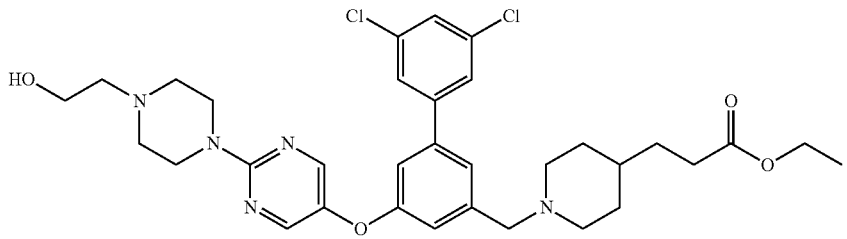 [SMILES: CCOC(=O)CCC1CCN(Cc2cc(Oc3cnc(N4CCN(CCO)CC4)nc3)cc(-c3cc(Cl)cc(Cl)c3)c2)CC1]

To a solution of ethyl 3-(1-((3',5'-dichloro-5-((2-(piperazin-1-yl)pyrimidin-5-yl)oxy)-[1,1'-biphenyl]-3-yl)methyl)piperidin-4-yl)propanoate, 3 hydrochloride (140 mg, 0.178 mmol) and DIEA (138 mg, 1.068 mmol) in MeOH (20 mL) was added oxirane (39.2 mg, 0.890 mmol) in MeOH (1 mL). The reaction mixture was stirred at 80° C. for 12 h then concentrated to yield a pale yellow solid of ethyl 3-(1-((3',5'-dichloro-5-((2-(4-(2-hydroxyethyl)piperazin-1-yl)pyrimidin-5-yl)oxy)-[1,1'-biphenyl]-3-yl)methyl)piperidin-4-yl)propanoate (125 mg, 0.097 mmol, 54.6% yield): $^1$H NMR (400 MHz, CDCl$_3$) δ ppm 8.25-8.15 (m, 2H), 7.38 (d, J=1.3 Hz, 2H), 7.32 (s, 1H), 7.22 (s, 1H), 6.99 (d, J=7.1 Hz, 2H), 4.09 (d, J=7.1 Hz, 2H), 3.89 (s, 4H), 3.75-3.70 (m, 2H), 3.46 (s, 2H), 3.03-2.94 (m, 4H), 2.74-2.65 (m, 6H), 2.27 (d, J=7.5 Hz, 2H), 2.11 (d, J=11.0 Hz, 2H), 1.68 (d, J=11.9 Hz, 3H), 1.27-1.18 (m, 5H); ES-LCMS m/z 642.3, 644.3 [M+H]$^+$.

Step 4: 3-(1-((3',5'-Dichloro-5-((2-(4-(2-hydroxyethyl)piperazin-1-yl)pyrimidin-5-yl)oxy)-[1,1'-biphenyl]-3-yl)methyl)piperidin-4-yl)propanoic acid

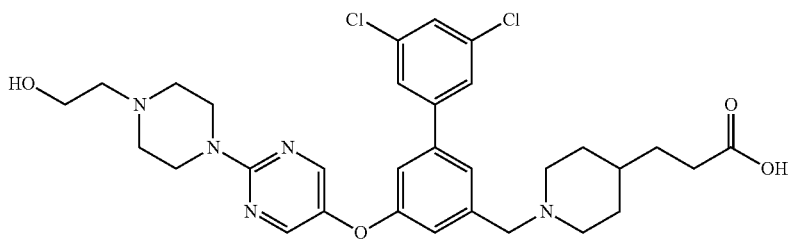 [SMILES: O=C(O)CCC1CCN(Cc2cc(Oc3cnc(N4CCN(CCO)CC4)nc3)cc(-c3cc(Cl)cc(Cl)c3)c2)CC1]

To a solution of ethyl 3-(1-(((3',5'-dichloro-5-((2-(4-(2-hydroxyethyl)piperazin-1-yl)pyrimidin-5-yl)oxy)-[1,1'-biphenyl]-3-yl)methyl)piperidin-4-yl)propanoate (125 mg, 0.097 mmol) in THF (5 mL) was added NaOH (7.78 mg, 0.195 mmol) in H₂O (1 mL). The reaction mixture was stirred at 25° C. for 12 h then 1 N HCl was added to adjust pH to 45 followed by concentration to yield the crude product, which was purified by preparative HPLC (MeCN/H₂O as eluents, basic condition) and lyophilized to yield a white solid of 3-(1-(((3',5'-dichloro-5-((2-(4-(2-hydroxyethyl)piperazin-1-yl)pyrimidin-5-yl)oxy)-[1,1'-biphenyl]-3-yl)methyl)piperidin-4-yl)propanoic acid (21.96 mg, 0.036 mmol, 36.6% yield): ¹H NMR (400 MHz, CD₃OD) δ ppm 8.28 (s, 2H), 7.61 (d, J=1.8 Hz, 2H), 7.47 (s, 1H), 7.43 (s, 1H), 7.31 (s, 1H), 7.06 (s, 1H), 4.01 (s, 2H), 3.95-3.80 (m, 4H), 3.76 (t, J=5.7 Hz, 2H), 3.23 (d, J=11.9 Hz, 2H), 2.87-2.55 (m, 8H), 2.24 (t, J=7.5 Hz, 2H), 1.88 (d, J=13.2 Hz, 2H), 1.65-1.55 (m, 2H), 1.49 (s, 1H), 1.40-1.29 (m, 2H); ES-LCMS m/z 614.3, 616.2 [M+H]⁺.

Example 115: 3-(4-(5-((4-((4-(Acetamidomethyl)piperidin-1-yl)methyl)-6-(3-chloro-5-fluorophenyl)pyridin-2-yl)oxy)pyridin-2-yl)piperazin-1-yl)propanoic acid, 4 hydrochloride

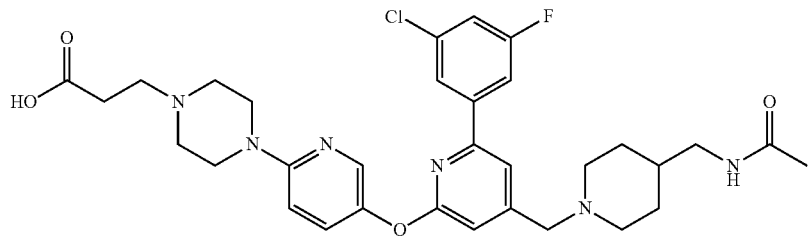 [SMILES: CC(=O)NCC1CCN(Cc2cc(Oc3ccc(N4CCN(CCC(=O)O)CC4)nc3)nc(-c3cc(F)cc(Cl)c3)c2)CC1]

Step 1: tert-Butyl 4-(5-(((6-(3-chloro-5-fluorophenyl)-4-(methoxycarbonyl)pyridin-2-yl)oxy)pyridin-2-yl)piperazine-1-carboxylate

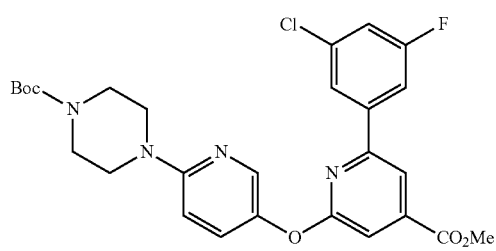 [SMILES: COC(=O)c1cc(Oc2ccc(N3CCN(C(=O)OC(C)(C)C)CC3)nc2)nc(-c2cc(F)cc(Cl)c2)c1]

To a suspension of tert-butyl 4-(5-((6-chloro-4-(methoxycarbonyl)pyridin-2-yl)oxy)pyridin-2-yl)piperazine-1-carboxylate (1 g, 1.559 mmol), (3-chloro-5-fluorophenyl)boronic acid (0.408 g, 2.339 mmol) and K₂CO₃ (0.647 g, 4.68 mmol) in 1,4-dioxane (30 mL) was added PdCl₂(dppf) (0.114 g, 0.156 mmol). The reaction mixture was stirred at 80° C. for 12 h then filtered and concentrated to yield crude product which was purified by silica gel column chromatography (PE/EtOAc=3/1). All fractions found to contain product by TLC (PE/EtOAc=3/1, R_f=0.5) were combined and concentrated to yield a yellow gum of tert-butyl 4-(5-((6-(3-chloro-5-fluorophenyl)-4-(methoxycarbonyl)pyridin-2-yl)oxy)pyridin-2-yl)piperazine-1-carboxylate (1 g, 1.565 mmol, 100.0% yield): ¹H NMR (400 MHz, CDCl₃) δ ppm 8.13 (d, J=2.6 Hz, 1H), 7.94 (s, 1H), 7.69 (s, 1H), 7.52 (d, J=9.7 Hz, 1H), 7.46-7.37 (m, 2H), 7.10 (d, J=7.9 Hz, 1H), 6.73 (d, J=8.8 Hz, 1H), 4.02-3.93 (m, 3H), 3.56 (d, J=6.2 Hz, 8H), 1.48 (s, 9H); ES-LCMS m/z 543.2, 545.2 [M+H]⁺.

Step 2: tert-Butyl 4-(5-(((6-(3-chloro-5-fluorophenyl)-4-(hydroxymethyl)pyridin-2-yl)oxy)pyridin-2-yl)piperazine-1-carboxylate

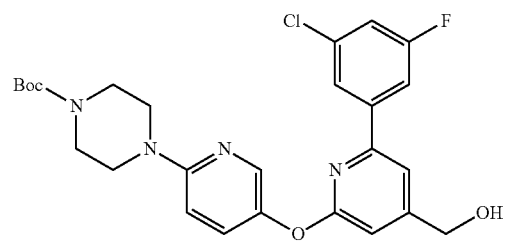 [SMILES: CC(C)(C)OC(=O)N1CCN(c2ccc(Oc3cc(CO)cc(-c4cc(F)cc(Cl)c4)n3)cn2)CC1]

To a suspension of tert-butyl 4-(5-(((6-(3-chloro-5-fluorophenyl)-4-(methoxycarbonyl)pyridin-2-yl)oxy)pyridin-2-yl)piperazine-1-carboxylate (1 g, 1.565 mmol) in THF (20 mL) stirred under N₂ atmosphere at −20° C. was added LiAlH₄ (0.089 g, 2.348 mmol) in portions. The reaction mixture was stirred at −20° C. for 20 min until TLC (PE/EtOAc=3/1, R_f=0.1) showed this reaction was completed. This reaction mixture was quenched with 10% NaOH (0.1 mL) and water (0.2 mL), then filtered. The filtrated was dried over MgSO₄, filtered and concentrated to yield a yellow gum of tert-butyl 4-(5-(((6-(3-chloro-5-fluorophenyl)-4-(hydroxymethyl)pyridin-2-yl)oxy)pyridin-2-yl)piperazine-1-carboxylate (900 mg, 1.398 mmol, 89.0% yield): ¹H NMR (400 MHz, CDCl₃) δ ppm 8.05 (d, J=2.6 Hz, 1H), 7.61 (s, 1H), 7.44 (d, J=9.7 Hz, 1H), 7.39-7.28 (m, 2H), 7.01 (d, J=8.4 Hz, 1H), 6.79 (s, 1H), 6.66 (d, J=8.8 Hz, 1H), 4.79-4.65 (m, 2H), 3.49 (dd, J=5.7, 16.3 Hz, 8H), 1.43 (s, 9H); ES-LCMS m/z 515.3 [M+H]⁺.

Step 3: tert-Butyl 4-(5-(((6-(3-chloro-5-fluorophenyl)-4-(((methylsulfonyl)oxy)methyl)pyridin-2-yl)oxy)pyridin-2-yl)piperazine-1-carboxylate

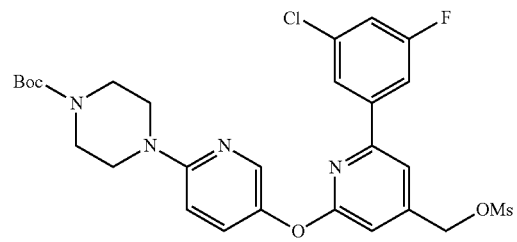 [SMILES: CC(C)(C)OC(=O)N1CCN(c2ccc(Oc3cc(COS(C)(=O)=O)cc(-c4cc(F)cc(Cl)c4)n3)cn2)CC1]

To a suspension of tert-butyl 4-(5-((6-(3-chloro-5-fluorophenyl)-4-(hydroxymethyl)pyridin-2-yl)oxy)pyridin-2-yl)piperazine-1-carboxylate (900 mg, 1.398 mmol) and Et$_3$N (0.585 mL, 4.19 mmol) in DCM (20 mL) stirred under N$_2$ atmosphere at 0° C. was added MsCl (0.142 mL, 1.818 mmol). The reaction mixture was stirred at 0° C. for 0.5 h until TLC (PE/EtOAc=3/1, R$_f$=0.65) showed this reaction was completed. The mixture was added with water (50 mL) then extracted with DCM (30 mL×3). The combined organic layers were combined and dried over Na$_2$SO$_4$, filtered and concentrated to yield a yellow oil of tert-butyl 4-(5-((6-(3-chloro-5-fluorophenyl)-4-(((methylsulfonyl)oxy)methyl)pyridin-2-yl)oxy)pyridin-2-yl)piperazine-1-carboxylate (900 mg, 1.214 mmol, 87.0% yield): $^1$H NMR (400 MHz, CDCl$_3$) δ ppm 8.11 (d, J=2.6 Hz, 1H), 7.64 (s, 1H), 7.52-7.33 (m, 3H), 7.09 (d, J=8.4 Hz, 1H), 6.89 (s, 1H), 6.72 (d, J=9.3 Hz, 1H), 5.26 (s, 2H), 3.55 (d, J=8.4 Hz, 8H), 3.10 (s, 3H), 1.48 (s, 9H); ES-LCMS m/z 593.1, 595.1 [M+H]$^+$.

Step 4: tert-Butyl 4-(5-((4-((4-(acetamidomethyl)piperidin-1-yl)methyl)-6-(3-chloro-5-fluorophenyl)pyridin-2-yl)oxy)pyridin-2-yl)piperazine-1-carboxylate

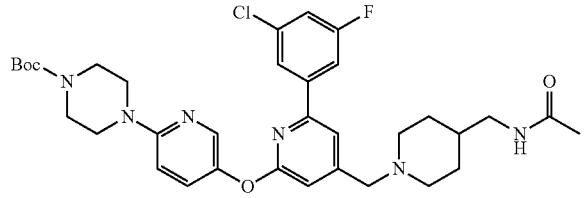 [SMILES: CC(=O)NCC1CCN(Cc2cc(Oc3ccc(N4CCN(C(=O)OC(C)(C)C)CC4)nc3)nc(-c3cc(F)cc(Cl)c3)c2)CC1]

To a suspension of tert-butyl 4-(5-((6-(3-chloro-5-fluorophenyl)-4-(((methylsulfonyl)oxy)methyl)pyridin-2-yl)oxy)pyridin-2-yl)piperazine-1-carboxylate (900 mg, 1.214 mmol) and N-(piperidin-4-ylmethyl)acetamide, hydrochloride (295 mg, 1.457 mmol) in DMF (20 mL) was added K$_2$CO$_3$ (336 mg, 2.428 mmol). The reaction mixture was stirred at 50° C. for 12 h then filtered and concentrated to yield crude product which was purified by silica gel column (DCM/MeOH=10/1, R$_f$=0.5) to yield a pale yellow solid of tert-butyl 4-(5-((4-((4-(acetamidomethyl)piperidin-1-yl)methyl)-6-(3-chloro-5-fluorophenyl)pyridin-2-yl)oxy)pyridin-2-yl)piperazine-1-carboxylate (700 mg, 0.857 mmol, 70.6% yield): $^1$H NMR (400 MHz, CDCl$_3$) δ ppm 8.14 (d, J=2.6 Hz, 1H), 7.67 (s, 1H), 7.50 (d, J=9.7 Hz, 1H), 7.47-7.39 (m, 2H), 7.07 (d, J=7.9 Hz, 1H), 6.85 (s, 1H), 6.74 (d, J=9.3 Hz, 1H), 5.56 (s, 1H), 3.67-3.42 (m, 8H), 3.17 (t, J=6.4 Hz, 2H), 2.89 (s, 4H), 2.11-1.94 (m, 4H), 1.75-1.60 (m, 5H), 1.50 (s, 9H), 1.41-1.21 (m, 2H); ES-LCMS m/z 653.4, 655.4 [M+H]$^+$.

Step 5: N-((1-((2-(3-Chloro-5-fluorophenyl)-6-((6-(piperazin-1-yl)pyridin-3-yl)oxy)pyridin-4-yl)methyl)piperidin-4-yl)methyl)acetamide

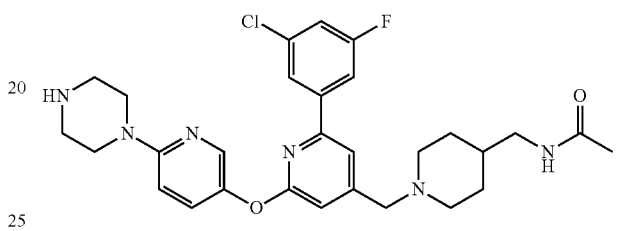

To a suspension of tert-butyl 4-(5-((4-((4-(acetamidomethyl)piperidin-1-yl)methyl)-6-(3-chloro-5-fluorophenyl)pyridin-2-yl)oxy)pyridin-2-yl)piperazine-1-carboxylate (0.7 g, 0.857 mmol) in DCM (10 mL) was added TFA (3 mL, 38.9 mmol). The reaction mixture was stirred at 15° C. for 12 h then concentrated. The residue was diluted with DCM (50 mL) and adjusted pH to 8 with saturated aqueous NaHCO$_3$ solution, extracted with DCM (30 mL×3). The combined organic layers were dried over Na$_2$SO$_4$, filtered and evaporated to yield a pale yellow gum of N-((1-((2-(3-chloro-5-fluorophenyl)-6-((6-(piperazin-1-yl)pyridin-3-yl)oxy)pyridin-4-yl)methyl)piperidin-4-yl)methyl)acetamide (550 mg, 0.788 mmol, 92.0% yield): $^1$H NMR (400 MHz, CDCl$_3$) δ ppm 8.14 (d, J=2.2 Hz, 1H), 7.68 (s, 1H), 7.52 (d, J=10.1 Hz, 1H), 7.46-7.36 (m, 2H), 7.08 (d, J=8.4 Hz, 1H), 6.83 (s, 1H), 6.74 (d, J=8.8 Hz, 1H), 5.54 (s, 1H), 3.65-3.54 (m, 4H), 3.52 (s, 2H), 3.17 (t, J=6.4 Hz, 2H), 3.12-3.02 (m, 4H), 2.87 (s, 1H), 2.11-1.94 (m, 5H), 1.70 (d, J=12.3 Hz, 2H), 1.54 (s, 1H), 1.39-1.23 (m, 4H); ES-LCMS m/z 553.4 [M+H]$^+$.

Step 6: Ethyl 3-(4-(5-((4-((4-(acetamidomethyl)piperidin-1-yl)methyl)-6-(3-chloro-5-fluorophenyl)pyridin-2-yl)oxy)pyridin-2-yl)piperazin-1-yl)propanoate

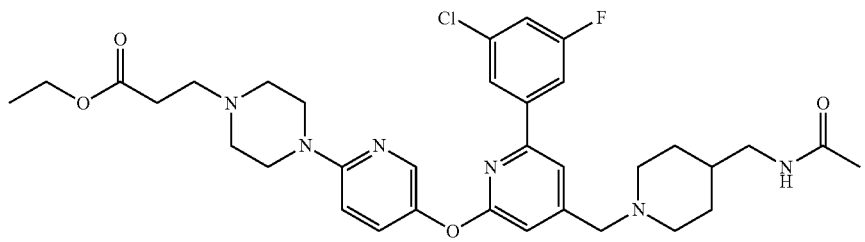 [SMILES: CCOC(=O)CCN1CCN(c2ccc(Oc3cc(CN4CCC(CNC(C)=O)CC4)cc(-c4cc(F)cc(Cl)c4)n3)cn2)CC1]

To a suspension of N-((1-((2-(3-chloro-5-fluorophenyl)-6-((6-(piperazin-1-yl)pyridin-3-yl)oxy)pyridin-4-yl)methyl)piperidin-4-yl)methyl)acetamide (200 mg, 0.287 mmol) and ethyl 3-bromopropanoate (78 mg, 0.430 mmol) in MeCN (10 mL) was added $K_2CO_3$ (119 mg, 0.860 mmol). The reaction mixture was stirred at 80° C. for 12 h then filtered and concentrated to yield a pale yellow gum of ethyl 3-(4-(5-((4-((4-(acetamidomethyl)piperidin-1-yl)methyl)-6-(3-chloro-5-fluorophenyl)pyridin-2-yl)oxy)pyridin-2-yl)piperazin-1-yl)propanoate (250 mg, 0.275 mmol, 96.0% yield): $^1$H NMR (400 MHz, CDCl$_3$) δ ppm 8.11 (d, J=2.6 Hz, 1H), 7.66 (s, 1H), 7.49 (d, J=9.7 Hz, 1H), 7.43-7.35 (m, 2H), 7.06 (d, J=7.9 Hz, 1H), 6.81 (s, 1H), 6.71 (d, J=8.8 Hz, 1H), 5.50 (s, 1H), 4.15 (q, J=7.4 Hz, 2H), 3.57-3.51 (m, 4H), 3.15 (t, J=6.4 Hz, 2H), 2.92-2.81 (m, 2H), 2.79-2.71 (m, 2H), 2.66-2.57 (m, 4H), 2.56-2.47 (m, 2H), 1.99 (d, J=7.1 Hz, 5H), 1.67 (d, J=11.9 Hz, 3H), 1.37-1.21 (m, 7H); ES-LCMS m/z 653.4, 655.4 [M+H]$^+$.

Step 7: 3-(4-(5-((4-((4-(Acetamidomethyl)piperidin-1-yl)methyl)-6-(3-chloro-5-fluorophenyl)pyridin-2-yl)oxy)pyridin-2-yl)piperazin-1-yl)propanoic acid, 4 hydrochloride

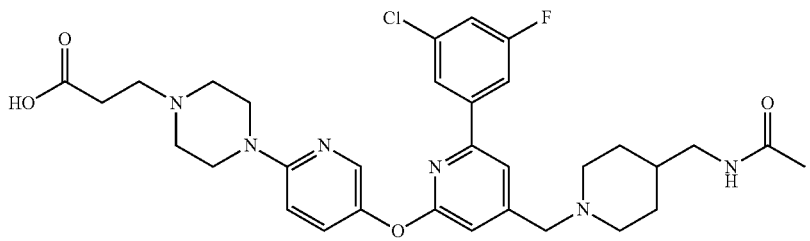 [SMILES: CC(=O)NCC1CCN(Cc2cc(Oc3ccc(N4CCN(CCC(=O)O)CC4)nc3)nc(-c3cc(F)cc(Cl)c3)c2)CC1]

To a suspension of ethyl 3-(4-(5-((4-((4-(acetamidomethyl)piperidin-1-yl)methyl)-6-(3-chloro-5-fluorophenyl)pyridin-2-yl)oxy)pyridin-2-yl)piperazin-1-yl)propanoate (250 mg, 0.275 mmol) in THF (10 mL) and H$_2$O (3 mL) was added LiOH·H$_2$O (57.8 mg, 1.377 mmol). The reaction mixture was stirred at 15° C. for 2 h then concentrated. The residue was dissolved in DMSO (10 mL), adjusted pH to 4 with 1 N HCl then purified by preparative HPLC (MeCN/ H$_2$O as eluents, acidic condition) and lyophilized to yield a white solid of 3-(4-(5-((4-((4-(acetamidomethyl)piperidin-1-yl)methyl)-6-(3-chloro-5-fluorophenyl)pyridin-2-yl)oxy)pyridin-2-yl)piperazin-1-yl)propanoic acid, 4 hydrochloride (116.78 mg, 0.148 mmol, 53.8% yield): $^1$H NMR (400 MHz, CD$_3$OD) δ ppm 8.25 (s, 1H), 8.17 (s, 1H), 8.01 (s, 1H), 7.83 (s, 1H), 7.65 (d, J=9.5 Hz, 1H), 7.58 (d, J=9.8 Hz, 1H), 7.41 (s, 1H), 7.31 (d, J=8.5 Hz, 1H), 4.48 (s, 2H), 3.78 (s, 3H), 3.65-3.33 (m, 9H), 3.24-3.05 (m, 4H), 2.98 (t, J=6.9 Hz, 2H), 2.06-1.94 (m, 5H), 1.88 (s, 1H), 1.63 (d, J=12.0 Hz, 2H); ES-LCMS m/z 625.3 [M+H]$^+$.

Example 116: 3-(4-(5-((4-((4-(Acetamidomethyl) piperidin-1-yl)methyl)-6-(3-bromo-5-fluorophenyl) pyridin-2-yl)oxy)pyridin-2-yl)piperazin-1-yl)propanoic acid, 4 hydrochloride

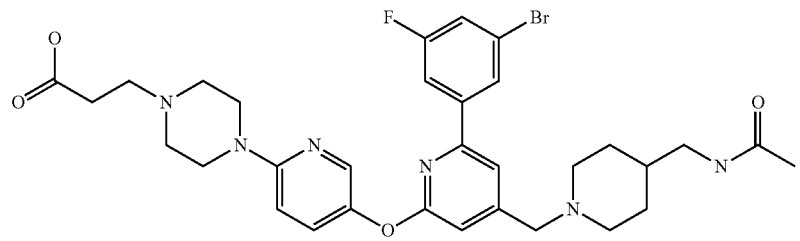 [SMILES: CC(=O)NCC1CCN(Cc2cc(Oc3ccc(N4CCN(CCC(=O)O)CC4)nc3)nc(-c3cc(F)cc(Br)c3)c2)CC1]

Step 1: tert-Butyl 4-(5-((6-(3-bromo-5-fluorophenyl)-4-(methoxycarbonyl)pyridin-2-yl)oxy)pyridin-2-yl)piperazine-1-carboxylate

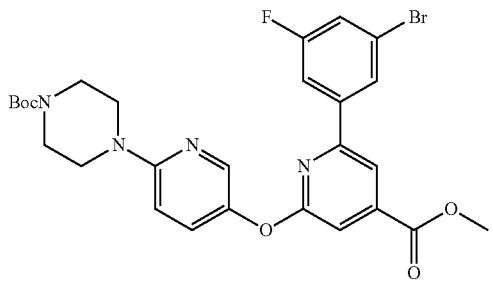 [SMILES: COC(=O)c1cc(Oc2ccc(N3CCN(C(=O)OC(C)(C)C)CC3)nc2)nc(-c2cc(F)cc(Br)c2)c1]

To a mixture of tert-butyl 4-(5-((6-chloro-4-(methoxycarbonyl)pyridin-2-yl)oxy)pyridin-2-yl)piperazine-1-carboxylate (5 g, 7.80 mmol) and (3-bromo-5-fluorophenyl)boronic acid (1.365 g, 6.24 mmol) in DMF (150 mL) was added K₂CO₃ (3.23 g, 23.39 mmol) and PdCl₂(dppf) (0.285 g, 0.390 mmol). The reaction was stirred at 80° C. under N₂ atmosphere for 2 h then filtered and concentrated to yield the crude product, which was purified by silica gel column chromatography (PE/EtOAc=5/1). All fractions found to contain product by TLC analysis (PE/EA=5/1, R$_f$=0.6) were combined and concentrated to yield a yellow oil. The yellow oil was purified by preparative HPLC (MeCN/H₂O as eluents, acidic condition) and lyophilized to yield a pale yellow solid. The solid was dissolved in DCM (100 mL) followed by washing with saturated aqueous NaHCO₃ solution, brine (20 mL) then dried over Na₂SO₄, filtered and concentrated to yield a brown solid of tert-butyl 4-(5-((6-(3-bromo-5-fluorophenyl)-4-(methoxycarbonyl)pyridin-2-yl)oxy)pyridin-2-yl)piperazine-1-carboxylate (650 mg, 0.996 mmol, 12.8% yield): ¹H NMR (400 MHz, CDCl₃) δ ppm 8.17 (d, J=2.6 Hz, 1H), 8.04-7.90 (m, 2H), 7.85 (s, 1H), 7.56 (d, J=9.7 Hz, 1H), 7.48 (dd, J=2.6, 9.3 Hz, 1H), 7.44 (s, 1H), 6.77 (d, J=9.3 Hz, 1H), 3.99 (s, 3H), 3.59 (d, J=3.1 Hz, 8H), 1.49 (s, 9H); ES-LCMS m/z 587.2, 589.2 [M+H]⁺.

Step 2: 2-(3-Bromo-5-fluorophenyl)-6-((6-(4-(tert-butoxycarbonyl)piperazin-1-yl)pyridin-3-yl)oxy)isonicotinic acid

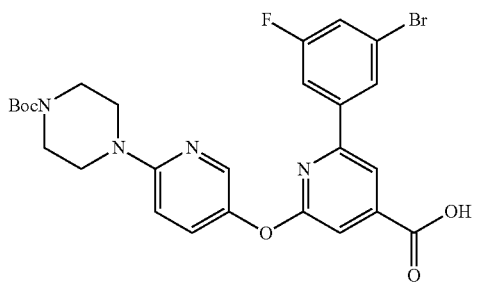 [SMILES: CC(C)(C)OC(=O)N1CCN(c2ccc(Oc3cc(C(=O)O)cc(-c4cc(F)cc(Br)c4)n3)cn2)CC1]

A mixture of tert-butyl 4-(5-((6-(3-bromo-5-fluorophenyl)-4-(methoxycarbonyl)pyridin-2-yl)oxy)pyridin-2-yl)piperazine-1-carboxylate (650 mg, 0.996 mmol) and NaOH (80 mg, 1.992 mmol) in MeOH (10 mL) and H₂O (1 mL) was stirred at 25° C. for 2 h. The reaction was adjusted pH to 6 with 1 N HCl. The mixture was concentrated to yield the residue which was washed with water then concentrated to yield a white solid of 2-(3-bromo-5-fluorophenyl)-6-((6-(4-(tert-butoxycarbonyl)piperazin-1-yl)pyridin-3-yl)oxy)isonicotinic acid (600 mg, 0.921 mmol, 92.0% yield): ¹H NMR (400 MHz, CD₃OD) δ ppm 8.06 (d, J=2.6 Hz, 1H), 8.02 (s, 1H), 7.90 (s, 1H), 7.62 (d, J=9.7 Hz, 1H), 7.51 (dd, J=3.1, 9.3 Hz, 1H), 7.38 (s, 1H), 7.33 (d, J=7.9 Hz, 1H), 6.96 (d, J=9.3 Hz, 1H), 3.72 (t, J=6.6 Hz, 2H), 3.59-3.50 (m, 6H), 1.65-1.33 (m, 9H); ES-LCMS m/z 572.9, 574.9 [M+H]⁺.

Step 3: tert-Butyl 4-(5-((6-(3-bromo-5-fluorophenyl)-4-(hydroxymethyl)pyridin-2-yl)oxy)pyridin-2-yl)piperazine-1-carboxylate

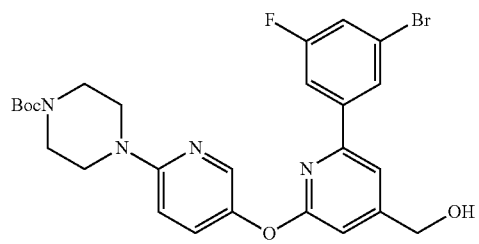 [SMILES: CC(C)(C)OC(=O)N1CCN(c2ccc(Oc3cc(CO)cc(-c4cc(F)cc(Br)c4)n3)cn2)CC1]

A mixture of 2-(3-bromo-5-fluorophenyl)-6-((6-(4-(tert-butoxycarbonyl)piperazin-1-yl)pyridin-3-yl)oxy)isonicotinic acid (450 mg, 0.691 mmol) in THF (5 mL) was added BH₃·DMS (2 mL, 20.00 mmol) at 25° C. in portions. The reaction was stirred at 50° C. for 2 h then quenched with MeOH (2 mL), filtered and concentrated to yield the crude product, which was purified by silica gel column chromatography (DCM/MeOH=95:5). All fractions found to contain product by TLC (DCM/MeOH=20/1, R$_f$=0.5) were combined and concentrated to yield a pale yellow solid of tert-butyl 4-(5-((6-(3-bromo-5-fluorophenyl)-4-(hydroxymethyl)pyridin-2-yl)oxy)pyridin-2-yl)piperazine-1-carboxylate (390 mg, 0.679 mmol, 98.0% yield): ¹H NMR (400 MHz, CDCl₃) δ ppm 8.06 (d, J=2.6 Hz, 1H), 7.76 (s, 1H), 7.48 (d, J=9.7 Hz, 1H), 7.39-7.31 (m, 2H), 7.16 (d, J=7.9 Hz, 1H), 6.79 (s, 1H), 6.66 (d, J=9.3 Hz, 1H), 4.77-4.69 (m, 2H), 3.51 (d, J=5.7 Hz, 4H), 3.47 (d, J=5.7 Hz, 4H), 1.43 (s, 9H); ES-LCMS m/z 558.9, 560.9 [M+H]⁺.

Step 4: tert-Butyl 4-(5-((6-(3-bromo-5-fluorophenyl)-4-(((methylsulfonyl)oxy)methyl)pyridin-2-yl)oxy)pyridin-2-yl)piperazine-1-carboxylate

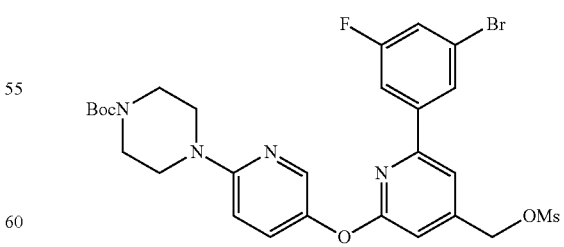

To a solution of tert-butyl 4-(5-((6-(3-bromo-5-fluorophenyl)-4-(hydroxymethyl)pyridin-2-yl)oxy)pyridin-2-yl)piperazine-1-carboxylate (400 mg, 0.696 mmol) and DIEA (0.365 mL, 2.089 mmol) in DCM (10 mL) was added MsCl (0.081 mL, 1.045 mmol) at 25° C. The reaction mixture was stirred at 25° C. for 20 min then DCM (50 mL) and saturated aqueous NaHCO₃ (20 mL) was added. The aqueous phase was extracted with DCM (100 mL×2). The combined organic layer was washed with brine (20 mL), dried over Na₂SO₄ and concentrated to yield a brown solid of tert-butyl 4-(5-((6-(3-bromo-5-fluorophenyl)-4-(((methylsulfonyl)oxy)methyl)pyridin-2-yl)oxy)pyridin-2-yl)piperazine-1-carboxylate (400 mg, 0.605 mmol, 87.0% yield): ¹H NMR (400 MHz, CDCl₃) δ ppm 8.12 (d, J=2.6 Hz, 1H), 7.81 (s, 1H), 7.53 (d, J=9.3 Hz, 1H), 7.46-7.39 (m, 2H), 7.23 (d, J=1.8 Hz, 1H), 6.88 (s, 1H), 6.73 (d, J=8.8 Hz, 1H), 4.57 (s, 2H), 3.56 (d, J=8.4 Hz, 8H), 2.78 (s, 3H), 1.49 (s, 9H); ES-LCMS m/z 631.2, 639.2 [M+H]⁺.

Step 5: tert-Butyl 4-(5-((4-((4-(acetamidomethyl)piperidin-1-yl)methyl)-6-(3-bromo-5-fluorophenyl)pyridin-2-yl)oxy)pyridin-2-yl)piperazine-1-carboxylate

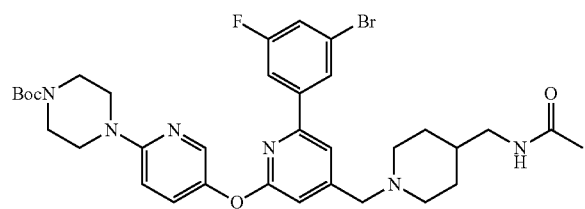 [SMILES: CC(=O)NCC1CCN(Cc2cc(Oc3ccc(N4CCN(C(=O)OC(C)(C)C)CC4)nc3)nc(-c3cc(F)cc(Br)c3)c2)CC1]

A mixture of tert-butyl 4-(5-((6-(3-bromo-5-fluorophenyl)-4-(((methylsulfonyl)oxy)methyl)pyridin-2-yl)oxy)pyridin-2-yl)piperazine-1-carboxylate (400 mg, 0.605 mmol), N-(piperidin-4-ylmethyl)acetamide, hydrochloride (184 mg, 0.908 mmol) and K₂CO₃ (251 mg, 1.816 mmol) in DMF (10 mL) was stirred at 80° C. for 6 h under N₂ atmosphere. The mixture was filtered and concentrated to yield the crude product which was purified by silica gel column chromatography (DCM/MeOH=95/5). All fractions found to contain product by TLC (DCM/MeOH=10/1, R_f=0.5) were combined and concentrated to yield a light yellow solid of tert-butyl 4-(5-((4-((4-(acetamidomethyl)piperidin-1-yl)methyl)-6-(3-bromo-5-fluorophenyl)pyridin-2-yl)oxy)pyridin-2-yl)piperazine-1-carboxylate (380 mg, 0.514 mmol, 85.0% yield). ¹H NMR (400 MHz, CDCl₃) δ ppm 8.13 (d, J=2.6 Hz, 1H), 8.01 (s, 1H), 7.81 (s, 1H), 7.53 (d, J=10.6 Hz, 1H), 7.46-7.37 (m, 2H), 7.22 (d, J=7.9 Hz, 1H), 6.83 (s, 1H), 6.73 (d, J=9.3 Hz, 1H), 5.52 (br. s, 1H), 3.61-3.50 (m, 8H), 3.16 (t, J=6.4 Hz, 2H), 2.88 (s, 4H), 2.06-1.96 (m, 5H), 1.69 (d, J=12.8 Hz, 2H), 1.49 (s, 9H), 1.32 (d, J=10.6 Hz, 2H); ES-LCMS m/z 697.0, 698.9 [M+H]⁺.

Step 6: N-((1-((2-(3-bromo-5-fluorophenyl)-6-((6-(piperazin-1-yl)pyridin-3-yl)oxy)pyridin-4-yl)methyl)piperidin-4-yl)methyl)acetamide, 4 hydrochloride

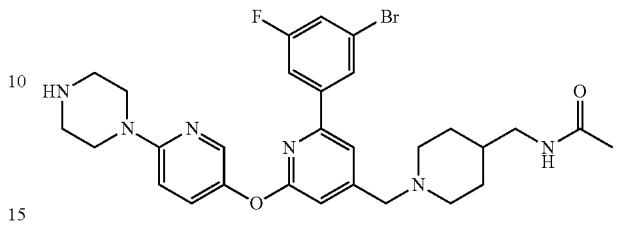

A mixture of tert-butyl 4-(5-((4-((4-(acetamidomethyl)piperidin-1-yl)methyl)-6-(3-bromo-5-fluorophenyl)pyridin-2-yl)oxy)pyridin-2-yl)piperazine-1-carboxylate (530 mg, 0.717 mmol) and HCl solution (4.0 M in EtOAc, 5 mL, 20.00 mmol) in EtOAc (10 mL) was stirred at 25° C. for 0.5 h then filtered. The filtered cake was washed with EtOAc (50 mL) and concentrated to yield a yellow solid of N-((1-((2-(3-bromo-5-fluorophenyl)-6-((6-(piperazin-1-yl)pyridin-3-yl)oxy)pyridin-4-yl)methyl)piperidin-4-yl)methyl)acetamide, 4 hydrochloride (480 mg, 0.610 mmol, 85.0% yield): ¹H NMR (400 MHz, CD₃OD) δ ppm 8.27-8.20 (m, 2H), 7.99 (s, 1H), 7.95 (s, 1H), 7.67 (d, J=9.3 Hz, 1H), 7.63-7.57 (m, 1H), 7.46-7.39 (m, 2H), 4.58-4.43 (m, 2H), 4.06-4.03 (m, 2H), 3.64-3.56 (m, 2H), 3.53-3.47 (m, 3H), 3.17-3.10 (m, 3H), 3.03-2.96 (m, 2H), 2.87 (s, 2H), 1.99-1.95 (m, 3H), 1.85 (d, J=3.5 Hz, 1H), 1.68-1.57 (m, 4H); ES-LCMS m/z 597.0, 599.0 [M+H]⁺.

Step 7: Ethyl 3-(4-(5-((4-((4-(acetamidomethyl)piperidin-1-yl)methyl)-6-(3-bromo-5-fluorophenyl)pyridin-2-yl)oxy)pyridin-2-yl)piperazin-1-yl)propanoate

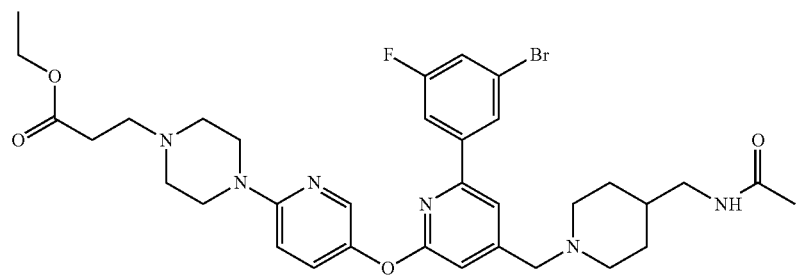 [SMILES: CCOC(=O)CCN1CCN(c2ccc(Oc3cc(CN4CCC(CNC(C)=O)CC4)cc(-c4cc(F)cc(Br)c4)n3)cn2)CC1]

A mixture of ethyl 3-bromopropanoate (92 mg, 0.508 mmol) and N-((1-((2-(3-bromo-5-fluorophenyl)-6-((6-(piperazin-1-yl)pyridin-3-yl)oxy)pyridin-4-yl)methyl)piperidin-4-yl)methyl)acetamide, 4 hydrochloride (200 mg, 0.254 mmol) and DIEA (0.222 mL, 1.270 mmol) in DMF (10 mL) was stirred at 26° C. for 2 h under N₂ atmosphere then concentrated to yield a brown solid of ethyl 3-(4-(5-((4-((4-(acetamidomethyl)piperidin-1-yl)methyl)-6-(3-bromo-5-fluorophenyl)pyridin-2-yl)oxy)pyridin-2-yl)piperazin-1-yl)propanoate (250 mg, 0.187 mmol, 73.5% yield): ¹H NMR (400 MHz, CD₃OD) δ ppm 8.08 (d, J=2.5 Hz, 1H), 7.94 (s, 1H), 7.81 (s, 1H), 7.67 (d, J=10.0 Hz, 1H), 7.55 (d, J=9.0 Hz, 1H), 7.38 (d, J=8.0 Hz, 1H), 7.13 (s, 1H), 7.01 (d, J=9.0 Hz, 1H), 4.62 (s, 1H), 4.01 (s, 2H), 3.67 (s, 4H), 3.16-3.05 (m, 4H), 3.03-2.95 (m, 3H), 2.88 (s, 5H), 2.71 (t, J=7.0 Hz, 3H), 2.59 (s, 2H), 2.00 (s, 1H), 1.86 (d, J=13.6 Hz, 2H), 1.71 (s, 1H), 1.56 (d, J=6.0 Hz, 2H), 1.25 (d, J=6.0 Hz, 3H); ES-LCMS m/z 697.3, 699.3 [M+H]⁺.

421

Step 8: 3-(4-(5-((4-((4-(Acetamidomethyl)piperidin-1-yl)methyl)-6-(3-bromo-5-fluorophenyl)pyridin-2-yl)oxy)pyridin-2-yl)piperazin-1-yl)propanoic acid, 4 hydrochloride

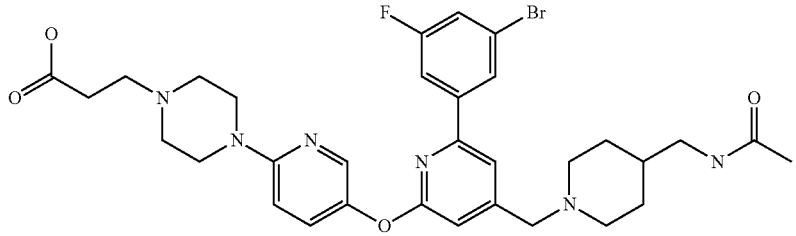 [SMILES: CC(=O)NCC1CCN(Cc2cc(Oc3ccc(N4CCN(CCC(=O)O)CC4)nc3)nc(-c3cc(F)cc(Br)c3)c2)CC1]

A mixture of ethyl 3-(4-(5-((4-((4-(acetamidomethyl)piperidin-1-yl)methyl)-6-(3-bromo-5-fluorophenyl)pyridin-2-yl)oxy)pyridin-2-yl)piperazin-1-yl)propanoate (320 mg, 0.239 mmol) and NaOH (28.7 mg, 0.717 mmol) in MeOH (10 mL) and H₂O (2 mL) was stirred at 25° C. for 2 h then concentrated. The residue was purified by preparative HPLC (MeCN/H₂O as eluents, acidic condition) and lyophilized to yield a white solid of 3-(4-(5-((4-((4-(acetamidomethyl)piperidin-1-yl)methyl)-6-(3-bromo-5-fluorophenyl)pyridin-2-yl)oxy)pyridin-2-yl)piperazin-1-yl)propanoic acid, 4 hydrochloride (131.32 mg, 0.161 mmol, 67.4% yield): $^1$H NMR (400 MHz, CD₃OD) δ ppm 8.22 (d, J=2.6 Hz, 1H), 8.13 (dd, J=2.6, 9.7 Hz, 1H), 7.96 (d, J=10.1 Hz, 2H), 7.66 (d, J=9.3 Hz, 1H), 7.52 (d, J=9.7 Hz, 1H), 7.45-7.41 (m, 1H), 7.39 (s, 1H), 4.59-4.30 (m, 4H), 3.86-3.65 (m, 3H), 3.64-3.52 (m, 5H), 3.48 (s, 2H), 3.21-3.05 (m, 4H), 2.96 (t, J=6.8 Hz, 2H), 2.05-1.94 (m, 5H), 1.86 (s, 1H), 1.68-1.54 (m, 2H); ES-LCMS m/z 669.3, 671.2 [M+H]⁺.

Example 117: 2-(1-((3',5'-Dichloro-5-((2-(4-methylpiperazin-1-yl)pyrimidin-5-yl)oxy)-[1,1'-biphenyl]-3-yl)methyl)piperidin-4-yl)acetic acid

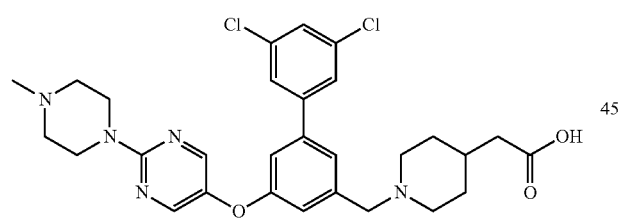

Step 1: 5-((2-(4-(tert-Butoxycarbonyl)piperazin-1-yl)pyrimidin-5-yl)oxy)-3',5'-dichloro-[1,1'-biphenyl]-3-carboxylic acid

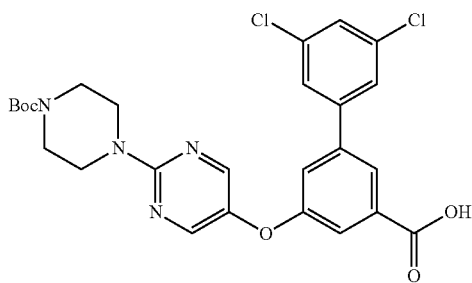 [SMILES: CC(C)(C)OC(=O)N1CCN(c2ncc(Oc3cc(C(=O)O)cc(-c4cc(Cl)cc(Cl)c4)c3)cn2)CC1]

422

To a mixture of tert-butyl 4-(5-bromopyrimidin-2-yl)piperazine-1-carboxylate (1.129 g, 2.96 mmol) and methyl 3',5'-dichloro-5-hydroxy-[1,1'-biphenyl]-3-carboxylate (1 g, 2.69 mmol) in DMSO (15 mL) was added CuI (0.026 g, 0.135 mmol), picolinic acid (0.331 g, 2.69 mmol) and K₃PO₄ (1.715 g, 8.08 mmol). The solution was stirred at 130° C. for 10 h under N₂ atmosphere then saturated aqueous NH₄Cl (40 mL) was added. The mixture was concentrated and the residue was distributed between DCM (200 mL) and saturated aqueous NaHCO₃ (100 mL) solution. The combined organic extract was washed with brine (200 mL), dried over Na₂SO₄, filtered and concentrated. The crude material was purified by silica gel column chromatography (DCM/MeOH=1/1). All fractions found to contain product by preparative TLC (DCM/MeOH=10/1, R$_f$=0.5) were combined and concentrated to yield brown oil of 5-((2-(4-(tert-butoxycarbonyl)piperazin-1-yl)pyrimidin-5-yl)oxy)-3',5'-dichloro-[1,1'-biphenyl]-3-carboxylic acid (1 g, 1.100 mmol, 40.9% yield): $^1$H NMR (400 MHz, DMSO-d₆) δ ppm 8.43-8.38 (m, 2H), 7.92-7.87 (m, 1H), 7.79-7.74 (m, 2H), 7.64 (d, J=2.0 Hz, 2H), 7.40 (br. s, 1H), 3.74-3.70 (m, 4H), 3.47-3.45 (m, 4H), 1.43 (s, 9H); ES-LCMS m/z 489.1, 491.0 [M−t−Bu+H]⁺.

Step 2: Methyl 3',5'-dichloro-5-((2-(piperazin-1-yl)pyrimidin-5-yl)oxy)-[1,1'-biphenyl]-3-carboxylate

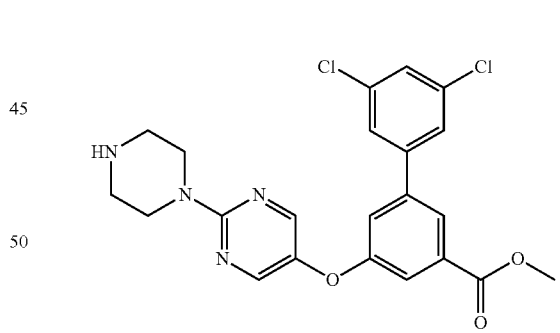

To a mixture of 5-((2-(4-(tert-butoxycarbonyl)piperazin-1-yl)pyrimidin-5-yl)oxy)-3',5'-dichloro-[1,1'-biphenyl]-3-carboxylic acid (1 g, 1.100 mmol) in MeOH (15 mL) was added SOCl₂ (0.131 g, 1.100 mmol) slowly. The reaction was stirred at 40° C. for 10 h then concentrated to yield brown oil of methyl 3',5'-dichloro-5-((2-(piperazin-1-yl)pyrimidin-5-yl)oxy)-[1,1'-biphenyl]-3-carboxylate, 2 hydrochloride (900 mg, 1.015 mmol, 92.0% yield): $^1$H NMR (400 MHz, DMSO-d₆) δ ppm 8.45 (s, 2H), 7.94-7.88 (m, 2H), 7.69-7.67 (m, 1H), 7.63 (s, 2H), 7.42 (s, 1H), 3.96 (d, J=5.0 Hz, 4H), 3.84 (s, 3H), 3.18-3.15 (m, 4H); ES-LCMS m/z 459.2, 461.2 [M+H]⁺.

423

Step 3: Methyl 3',5'-dichloro-5-((2-(4-methylpiper-azin-1-yl)pyrimidin-5-yl)oxy)-[1,1'-biphenyl]-3-carboxylate

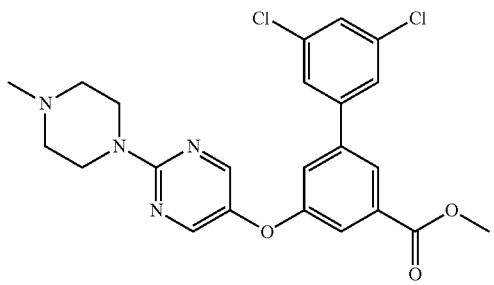

To a mixture of methyl 3',5'-dichloro-5-((2-(piperazin-1-yl)pyrimidin-5-yl)oxy)-[1,1'-biphenyl]-3-carboxylate, 2 hydrochloride (1.7 g, 1.916 mmol) in MeOH (20 mL) was added formaldehyde (37% in $H_2O$, 1.244 g, 9.58 mmol) and formic acid (0.441 g, 9.58 mmol). The reaction was stirred at 15° C. for 8 h under $N_2$ atmosphere then $NaBH(OAc)_3$ (2.437 g, 11.50 mmol) was added and stirred for another 2 h. The solution was concentrated and saturated aqueous $NaHCO_3$ solution (150 mL) was added. The aqueous layer was extracted with DCM (150 mL×2) and the combined extracts were washed with brine (15 mL×2), dried over $Na_2SO_4$, filtered and concentrated. The crude product was purified by silica gel column chromatography (DCM/MeOH=5/1). All fractions found to contain product by TLC (DCM/MeOH=10/1, $R_f$=0.5) were combined and concentrated to yield brown oil of methyl 3',5'-dichloro-5-((2-(4-methylpiperazin-1-yl)pyrimidin-5-yl)oxy)-[1,1'-biphenyl]-3-carboxylate (600 mg, 1.039 mmol, 54.2% yield): $^1H$ NMR (400 MHz, $CD_3OD$) δ ppm 8.29 (d, J=5.5 Hz, 2H), 7.97 (s, 1H), 7.61 (d, J=1.5 Hz, 2H), 7.54 (s, 1H), 7.52 (s, 1H), 7.49 (s, 1H), 3.94 (s, 3H), 3.86-3.82 (m, 4H), 3.37-3.32 (m, 4H), 2.62 (s, 3H); ES-LCMS m/z 473.1, 475.1 [M+H]$^+$.

Step 4: (3',5'-Dichloro-5-((2-(4-methylpiperazin-1-yl)pyrimidin-5-yl)oxy)-[1,1'-biphenyl]-3-yl)methanol

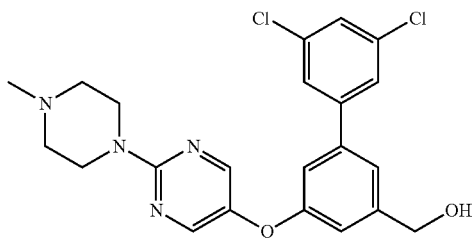 [SMILES: CN1CCN(c2ncc(Oc3cc(CO)cc(-c4cc(Cl)cc(Cl)c4)c3)cn2)CC1]

To a mixture of methyl 3',5'-dichloro-5-((2-(4-methylpiperazin-1-yl)pyrimidin-5-yl)oxy)-[1,1'-biphenyl]-3-carboxylate (600 mg, 1.039 mmol) in THF (10 mL) was added $LiAlH_4$ (79 mg, 2.079 mmol) at −20° C. The reaction was stirred at −20° C. for 10 min under $N_2$ atmosphere then quenched with 1 mL of water. The mixture was filtered and concentrated then diluted with additional DCM (50 mL) and washed with saturated aqueous $NaHCO_3$ solution (30 mL×2). The organic phase was dried over $Na_2SO_4$, filtered and concentrated to yield brown oil of (3',5'-dichloro-5-((2-

424

(4-methylpiperazin-1-yl)pyrimidin-5-yl)oxy)-[1,1'-biphenyl]-3-yl)methanol (550 mg, 0.753 mmol, 72.5% yield): $^1H$ NMR (400 MHz, $CD_3OD$) δ ppm 8.29-8.24 (m, 2H), 7.58 (d, J=1.8 Hz, 2H), 7.46 (s, 1H), 7.34 (s, 1H), 7.16 (s, 1H), 7.00 (s, 1H), 4.67-4.65 (m, 2H), 3.92-3.77 (m, 8H), 2.64 (s, 3H); ES-LCMS m/z 445.2, 447.2 [M+H]$^+$.

Step 5: (3',5'-Dichloro-5-((2-(4-methylpiperazin-1-yl)pyrimidin-5-yl)oxy)-[1,1'-biphenyl]-3-yl)methyl methanesulfonate

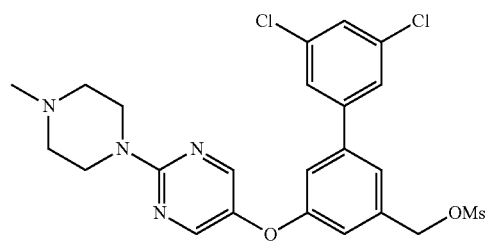 [SMILES: CN1CCN(c2ncc(Oc3cc(COS(C)(=O)=O)cc(-c4cc(Cl)cc(Cl)c4)c3)cn2)CC1]

To a mixture of (3',5'-dichloro-5-((2-(4-methylpiperazin-1-yl)pyrimidin-5-yl)oxy)-[1,1'-biphenyl]-3-yl)methanol (550 mg, 0.753 mmol) and DIEA (292 mg, 2.260 mmol) in DCM (10 mL) was added MsCl (0.088 mL, 1.130 mmol). The reaction was stirred at 15° C. for 10 h. The reaction mixture was diluted with additional DCM (50 mL) and washed with saturated aqueous $NaHCO_3$ solution (50 mL×2). The organic phase was dried over $Na_2SO_4$, filtered and concentrated to yield brown oil of (3',5'-dichloro-5-((2-(4-methylpiperazin-1-yl)pyrimidin-5-yl)oxy)-[1,1'-biphenyl]-3-yl)methyl methanesulfonate (600 mg, 0.550 mmol, 73.0% yield): $^1H$ NMR (400 MHz, $CD_3OD$) δ ppm 8.37-8.33 (m, 2H), 7.57 (d, J=1.8 Hz, 2H), 7.47 (s, 1H), 7.44-7.40 (m, 1H), 7.19 (s, 1H), 7.10-7.06 (m, 1H), 4.69 (s, 2H), 4.01-3.94 (m, 2H), 3.65-3.54 (m, 2H), 3.37 (s, 3H), 3.30 (s, 3H), 2.68 (s, 4H); ES-LCMS m/z 523.2, 525.2 [M+H]$^+$.

Step 6: Methyl 2-(1-((3',5'-dichloro-5-((2-(4-methylpiperazin-1-yl)pyrimidin-5-yl)oxy)-[1,1'-biphenyl]-3-yl)methyl)piperidin-4-yl)acetate

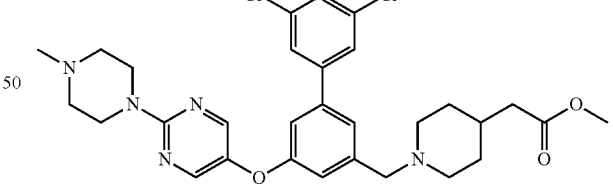

To a mixture of (3',5'-dichloro-5-((2-(4-methylpiperazin-1-yl)pyrimidin-5-yl)oxy)[1,1'-iphenyl]3-yl)methyl methanesulfonate (200 mg, 0.183 mmol) in DML (5 mL) was added $K_2CO_3$ (101 mg, 0.734 mmol) and methyl 2-(piperidin-4-yl)acetate, hydrochloride (79 mg, 0.367 mmol). The reaction was stirred at 15° C. for 10 h under $N_2$ atmosphere then concentrated and saturated $NaHCO_3$ solution (150 mL) was added. The aqueous layer was extracted with DCM (300 mL×2) and the combined extracts were washed with brine (150 mL×2), dried over $Na_2SO_4$, filtered and concentrated to yield brown oil of methyl 2-(1-((3',5'-dichloro-5-((2-(4-methylpiperazin-1-yl)pyrimidin-5-yl)oxy)-[1,1'-biphenyl]-

3-yl)methyl)piperidin-4-yl)acetate (200 mg, 0.154 mmol, 84.0% yield): ¹H NMR (400 MHz, CD₃OD) δ ppm 8.32-8.29 (m, 1H), 8.28-8.26 (m, 1H), 7.60 (s, 2H), 7.47 (s, 1H), 7.35 (s, 1H), 7.19 (s, 1H), 7.07-6.99 (m, 1H), 3.85 (s, 4H), 3.56 (s, 2H), 3.37 (s, 4H), 3.34-3.34 (m, 4H), 2.37 (d, J=1.5 Hz, 2H), 2.29 (s, 3H), 2.18-2.16 (m, 2H), 1.96-1.93 (m, 4H) 1.75 (s, 2H); ES-LCMS m/z 584.3, 586.3 [M+H]⁺.

Step 7: 2-(1-((3',5'-Dichloro-5-((2-(4-methylpiperazin-1-yl)pyrimidin-5-yl)oxy)-[1,1'-biphenyl]-3-yl)methyl)piperidin-4-yl)acetic acid

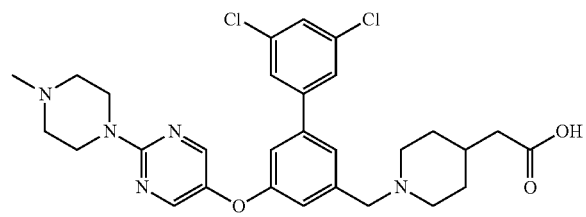 [SMILES: CN1CCN(c2ncc(Oc3cc(CN4CCC(CC(=O)O)CC4)cc(-c4cc(Cl)cc(Cl)c4)c3)cn2)CC1]

To a solution of methyl 2-(1-((3',5'-dichloro-5-((2-(4-methylpiperazin-1-yl)pyrimidin-5-yl)oxy)-[1,1'-biphenyl]-3-yl)methyl)piperidin-4-yl)acetate (200 mg, 0.154 mmol) in THF (3 mL) and H₂O (1 mL) was added LiOH·H₂O (32.3 mg, 0.770 mmol). The reaction was stirred at 15° C. for 15 min under N₂ atmosphere then concentrated and purified by preparative HPLC (MeCN/H₂O as eluents, acidic condition) and lyophilized to yield a white solid of 2-(1-((3',5'-dichloro-5-((2-(4-methylpiperazin-1-yl)pyrimidin-5-yl)oxy)-[1,1'-biphenyl]-3-yl)methyl)piperidin-4-yl)acetic acid, 3 hydrochloride (9.53 mg, 0.014 mmol, 9.1% yield): ¹H NMR (400 MHz, D₂O) δ ppm 7.97 (s, 2H), 7.28 (s, 3H), 7.03-6.87 (m, 3H), 4.48 (d, J=13.6 Hz, 2H), 4.10 (s, 2H), 3.50 (d, J=11.0 Hz, 2H), 3.34-3.18 (m, 4H), 3.07 (d, J=11.0 Hz, 2H), 2.86 (s, 5H), 2.20 (d, J=5.0 Hz, 2H), 1.94-1.69 (m, 3H), 1.39 (d, J=11.0 Hz, 2H); ES-LCMS m/z 570.2, 572.2 [M+H]⁺.

Example 118: N-((1-((2-((2-(1,4-Biazepan-1-yl)pyrimidin-5-yl)oxy)-6-(3,5-dichlorophenyl)pyridin-4-yl)methyl)piperidin-4-yl)methyl)acetamide, 4 hydrochloride

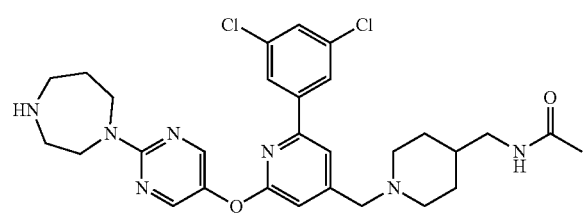 [SMILES: CC(=O)NCC1CCN(Cc2cc(Oc3cnc(N4CCCNCC4)nc3)nc(-c3cc(Cl)cc(Cl)c3)c2)CC1]

Step 1: tert-Butyl 4-(5-((4-((4-(acetamidomethyl)piperidin-1-yl)methyl)-6-(3,5-dichlorophenyl)pyridin-2-yl)oxy)pyrimidin-2-yl)-1,4-diazepane-1-carboxylate

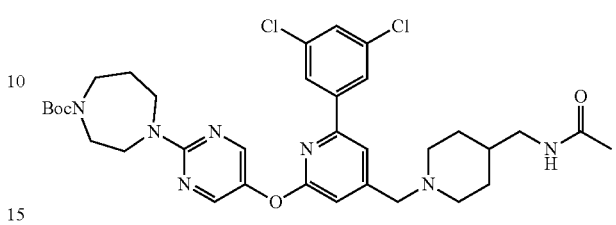

To a solution of tert-butyl 4-(5-((6-(3,5-dichlorophenyl)-4-(((methylsulfonyl)oxy)methyl)pyridin-2-yl)oxy)pyrimidin-2-yl)-1,4-diazepane-1-carboxylate (1.25 g, 1.629 mmol) and N-(piperidin-4-ylmethyl)acetamide, hydrochloride (0.496 g, 2.444 mmol) in DMF (20 mL) was added K₂CO₃ (0.675 g, 4.89 mmol). The reaction mixture was stirred at 80° C. for 12 h then filtered and concentrated to yield the crude product which was purified by flash chromatography on silica gel (DCM/MeOH=1/0 to 10/1). All fractions found to contain product by TLC (DCM/MeOH=10/1, R_f=0.55) were combined and concentrated to yield a yellow solid of tert-butyl 4-(5-((4-((4-(acetamidomethyl)piperidin-1-yl)methyl)-6-(3,5-dichlorophenyl)pyridine-2-yl)oxy)pyrimidin-2-yl)-1,4-diazepane-1-carboxylate (1.05 g, 1.316 mmol, 81.0% yield): ¹H NMR (400 MHz, CDCl₃) δ ppm 8.28 (s, 2H), 8.01 (s, 1H), 7.73 (d, J=1.3 Hz, 2H), 7.41 (s, 1H), 7.33 (s, 1H), 6.90 (s, 1H), 5.58 (s, 1H), 3.95-3.86 (m, 2H), 3.84-3.67 (m, 4H), 3.58 (d, J=4.4 Hz, 2H), 3.53-3.47 (m, 2H), 3.39-3.27 (m, 2H), 3.16 (t, J=6.4 Hz, 2H), 2.90 (s, 2H), 2.07-1.95 (m, 7H), 1.86-1.83 (m, 1H), 1.45 (d, J=7.1 Hz, 9H), 1.39-1.28 (m, 2H); ES-LCMS m/z 684.3, 686.3 [M+H]⁺.

Step 2: N-((1-((2-((2-(1,4-Diazepan-1-yl)pyrimidin-5-yl)oxy)-6-(3,5-dichlorophenyl)pyridin-4-yl)methyl)piperidin-4-yl)methyl)acetamide, 4 hydrochloride

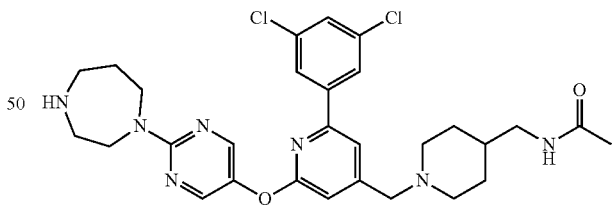

tert-Butyl 4-(5-((4-((4-(acetamidomethyl)piperidin-1-yl)methyl)-6-(3,5-dichlorophenyl)pyridin-2-yl)oxy)pyrimidin-2-yl)-1,4-diazepane-1-carboxylate (250 mg, 0.313 mmol) was dissolved in HCl solution (4 M in MeOH, 8 mL, 32.0 mmol). The reaction mixture was stirred at 25° C. for 0.5 h then concentrated to yield crude product which was purified by preparative HPLC (MeCN/H₂O as eluents, acidic condition) and lyophilized to yield a pale yellow solid of N-((1-((2-((2-(1,4-diazepan-1-yl)pyrimidin-5-yl)oxy)-6-(3,5-dichlorophenyl)pyridin-4-yl)methyl)piperidin-4-yl)methyl)acetamide, 4 hydrochloride (94.61 mg, 0.128 mmol, 40.7% yield): ¹H NMR (400 MHz, CD₃OD) δ ppm 8.73-

8.66 (m, 2H), 8.01 (s, 1H), 7.93 (d, J=1.8 Hz, 2H), 7.53-7.50 (m, 1H), 7.43 (s, 1H), 4.46 (s, 2H), 4.29-4.23 (m, 2H), 4.00 (t, J=6.0 Hz, 2H), 3.59 (d, J=11.9 Hz, 2H), 3.53-3.47 (m, 2H), 3.45-3.39 (m, 2H), 3.19-3.06 (m, 4H), 2.34-2.27 (m, 2H), 2.04-1.94 (m, 5H), 1.89 (s, 1H), 1.70-1.60 (m, 2H); ES-LCMS m/z 584.3, 586.3 [M+H]$^+$.

Examples 119-125 (Table 6) were prepared by procedures analogous to those described for example 118.

TABLE 6

| Example | Structure/Name | $^1$H NMR | LCMS |
|---|---|---|---|
| 119 | 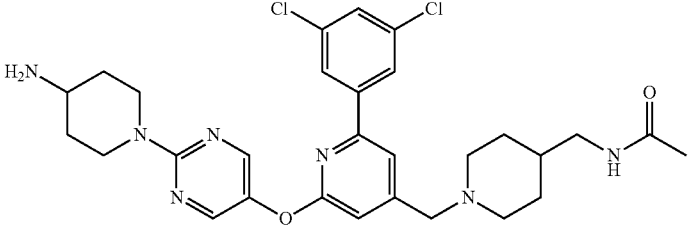 [SMILES: CC(=O)NCC1CCN(Cc2cc(Oc3cnc(N4CCC(N)CC4)nc3)nc(-c3cc(Cl)cc(Cl)c3)c2)CC1]<br>N-((1-((2-((2-(4-aminopiperidin-1-yl)pyrimidin-5-yl)oxy)-6-(3,5-dichlorophenyl)pyridin-4-yl)methyl)piperidin-4-yl)methyl)acetamide | $^1$H NMR (400 MHz, CD$_3$OD) δ ppm 8.72 (br s, 2H), 8.05 (br s, 1H), 7.92 (s, 2H), 7.50 (s, 1H), 7.44 (br s, 1H), 4.83-4.73 (m, 2H), 4.48 (br s, 2H), 3.67-3.50 (m, 3H), 3.35 (br d, J = 7.9 Hz, 2H), 3.15 (br s, 4H), 2.22 (br d, J = 11.2 Hz, 2H), 2.05-1.95 (m, 4H), 1.88 (br s, 1H), 1.82-1.59 (m, 4H) | ES-LCMS m/z 584.2, 586.2 [M + H]$^+$. |
| 120 | 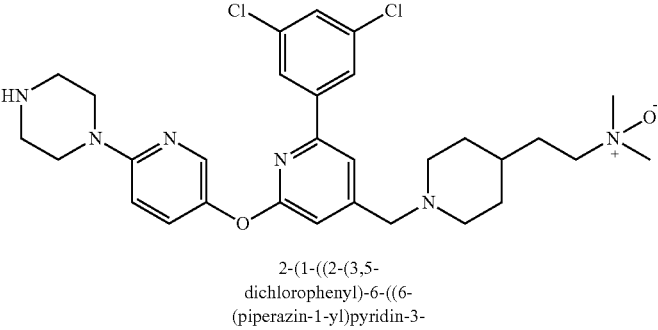<br>2-(1-((2-(3,5-dichlorophenyl)-6-((6-(piperazin-1-yl)pyridin-3-yl)oxy)pyridin-4-yl)methyl)piperidin-4-yl)-N,N-dimethylethanamine oxide | $^1$H NMR (400 MHz, CD$_3$OD) δ ppm 8.23 (d, J = 2.5 Hz, 1H), 8.10 (dd, J = 2.5, 9.5 Hz, 1H), 8.06 (s, 1H), 7.92 (d, J = 1.5 Hz, 2H), 7.54 (s, 1H), 7.49 (d, J = 9.5 Hz, 1H), 7.43 (s, 1H), 4.49 (s, 2H), 4.08-3.96 (m, 4H), 3.83-3.72 (m, 2H), 3.66-3.57 (m, 2H), 3.53 (s, 6H), 3.50-3.47 (m, 4H), 3.19 (t, J = 12.0 Hz, 2H), 2.06 (m, 2H), 1.94 (m, 2H), 1.80 (m, 3H) | ES-LCMS m/z 585.3, 587.3 [M + H]$^+$. |
| 121 | 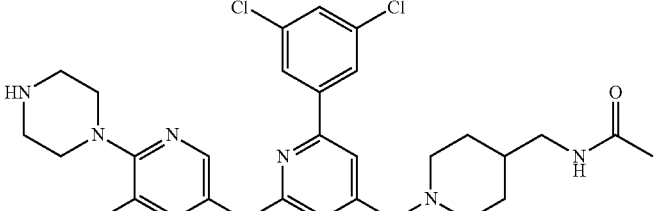<br>N-((1-((2-(3,5-dichlorophenyl)-6-((5-fluoro-6-(piperazin-1-yl)pyridin-3-yl)oxy)pyridin-4-yl)methyl)piperidin-4-yl)methyl)acetamide | $^1$H NMR (400 MHz, CD$_3$OD) δ ppm 8.11 (d, J = 2.0 Hz, 1H), 8.01 (s, 1H), 7.91 (d, J = 1.5 Hz, 2H), 7.68 (dd, J = 1.8, 12.8 Hz, 1H), 7.52 (s, 1H), 7.35 (s, 1H), 4.67-4.39 (m, 2H), 3.85-3.72 (m, 4H), 3.62 (d, J = 11.5 Hz, 2H), 3.49-3.40 (m, 4H), 3.21-3.07 (m, 4H), 2.09-1.97 (m, 5H), 1.90 (br. s, 1H), 1.74-1.56 (m, 2H) | ES-LCMS m/z 587.3, 589.3 [M + H]$^+$. |

TABLE 6-continued

| Example | Structure/Name | ¹H NMR | LCMS |
|---|---|---|---|
| 122 | 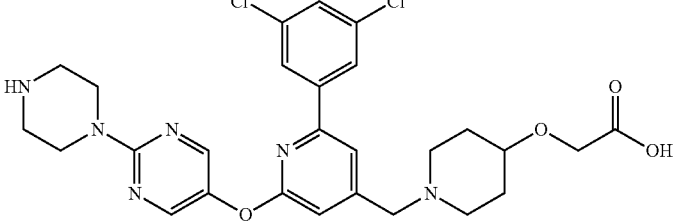<br>dichlorophenyl)-6-((2-(piperazin-1-yl)pyrimidin-5-yl)oxy)pyridin-4-yl)methyl)piperidin-4-yl)oxy)acetic acid | ¹H NMR (400 MHz, CD₃OD) δ ppm 8.44 (s, 2H), 7.98-7.92 (m, 1H), 7.87 (d, J = 1.8 Hz, 2H), 7.48 (s, 1H), 7.35-7.31 (m, 1H), 4.49-4.43 (m, 2H), 4.23-4.17 (m, 2H), 4.14-4.11 (m, 4H), 3.85 (s, 1H), 3.78-3.58 (m, 1H), 3.48-3.40 (m, 2H), 3.34 (d, J = 5.3 Hz, 4H), 3.18 (t, J =0 12.0 Hz, 1H), 2.36-2.15 (m, 2H), 2.11-1.80 (m, 2H) | ES-LCMS: m/z 573.2, 575.2 [M + H]⁺. |
| 123 | 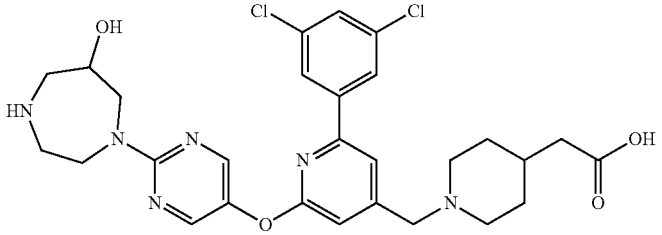 [SMILES: O=C(O)CC1CCN(Cc2cc(Oc3cnc(N4CCNCC(O)C4)nc3)nc(-c3cc(Cl)cc(Cl)c3)c2)CC1]<br>2-(1-((2-(3,5-dichlorophenyl)-6-((2-(6-hydroxy-1,4-diazepan-1-yl)pyrimidin-5-yl)oxy)pyridin-4-yl)methyl)piperidin-4-yl)acetic acid | ¹H NMR (400 Hz CD₃OD) δ = 8.42 (s, 2H), 7.94-7.82 (m, 3H), 7.50 (s, 1H), 7.32 (s, 1H), 4.45-4.35 (m, 3H), 4.31-4.03 (m, 5H), 3.58 (br d, J = 11.5 Hz, 3H), 3.46-3.36 (m, 2H), 3.14 (br t, J = 12.3 Hz, 2H), 2.32 (br d, J = 6.7 Hz, 2H), 2.06 (br d, J = 13.3 Hz, 3H), 1.71-1.56 (m, 2H) | ES-LCMS: m/z 587.2, 589.2 [M + H]⁺. |
| 124 | 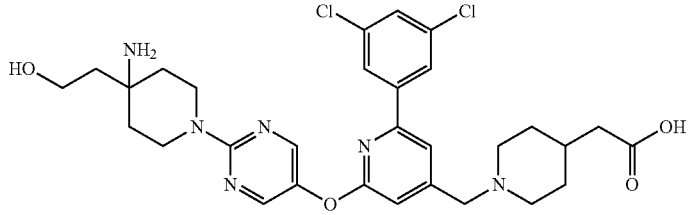 [SMILES: NC1(CCO)CCN(c2ncc(Oc3cc(CN4CCC(CC(=O)O)CC4)cc(-c4cc(Cl)cc(Cl)c4)n3)cn2)CC1]<br>2-(1-((2-((2-(4-amino-4-(2-hydroxyethyl)piperidin-1-yl)pyrimidin-5-yl)oxy)-6-(3,5-dichlorophenyl)pyridin-4-yl)methyl)piperidin-4-yl)acetic acid | ¹H NMR (400 MHz, CD₃OD) δ ppm 8.44 (s, 2H), 7.90 (s, 1H), 7.89-7.86 (m, 2H), 7.50 (t, J = 1.8 Hz, 1H), 7.30 (s, 1H), 4.42 (s, 2H), 4.38-4.31 (m, 2H), 3.89 (t, J = 5.7 Hz, 2H), 3.65-3.54 (m, 4H), 3.17-3.07 (m, 2H), 2.31 (d, J = 6.6 Hz, 2H), 2.06 (t, J = 5.5 Hz, 7H), 1.90 (dd, J = 4.2, 9.9 Hz, 2H), 1.68-1.56 (m, 2H) | ES-LCMS m/z 615.4, 617.4 [M + H]⁺. |
| 125 | 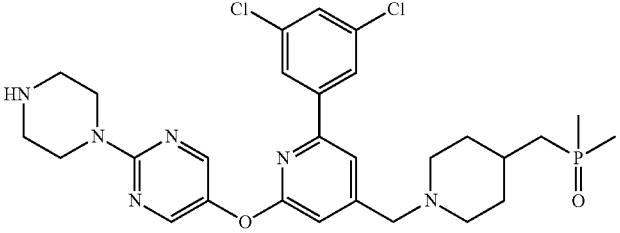 [SMILES: CP(C)(=O)CC1CCN(Cc2cc(Oc3cnc(N4CCNCC4)nc3)nc(-c3cc(Cl)cc(Cl)c3)c2)CC1]<br>((1-(2-(3,5-dichlorophenyl)-6-((2-(piperazin-1-yl)pyrimidin-5-yl)oxy)pyridin-4-yl)methyl)piperidin-4-yl)methyl)dimethylphosphine oxide | ¹H NMR (400 MHz, D₂O) δ ppm 8.30 (s, 2H), 7.46 (d, J = 1.3 Hz, 3H), 7.28-7.21 (m, 1H), 7.03 (s, 1H), 4.24 (s, 2H), 3.94-3.83 (m, 4H), 3.43 (d, J = 11.9 Hz, 2H), 3.26-3.21 (m, 4H), 3.01 (t, J = 12.2 Hz, 2H), 2.00 (d, J = 13.0 Hz, 3H), 1.77 (dd, J = 6.1, 12.0 Hz, 2H), 1.51 (d, J = 14.1 Hz, 2H), 1.45 (d, J = 13.0 Hz, 6H) | ES-LCMS m/z 589.2, 591.3 [M + H]⁺. |

Example 126: 2-(1-((2-(3,5-Dichlorophenyl)-6-((2-(4-methyl-1,4-diazepan-1-yl)pyrimidin-5-yl)oxy)pyridin-4-yl)methyl)piperidin-4-yl)acetic acid, 4 hydrochloride

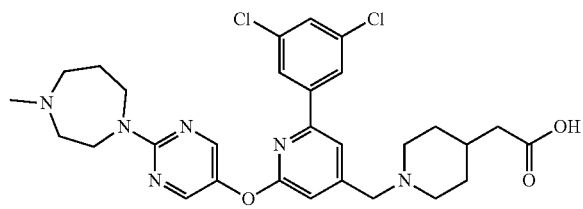 [SMILES: CN1CCCN(c2ncc(Oc3cc(CN4CCC(CC(=O)O)CC4)cc(-c4cc(Cl)cc(Cl)c4)n3)cn2)CC1]

Step 1: tert-Butyl 4-(5-((6-(3,5-dichlorophenyl)-4-((4-(2-methoxy-2-oxoethyl)piperidin-1-yl)methyl)pyridin-2-yl)oxy)pyrimidin-2-yl)-1,4-diazepane-1-carboxylate

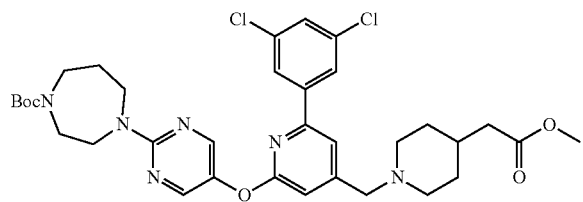

To a solution of tert-butyl 4-(5-((6-(3,5-dichlorophenyl)-4-(((methylsulfonyl)oxy)methyl)pyridin-2-yl)oxy)pyrimidin-2-yl)-1,4-diazepane-1-carboxylate (1.25 g, 1.601 mmol) and methyl 2-(piperidin-4-yl)acetate, hydrochloride (0.490 g, 2.402 mmol) in DMF (20 mL) was added K$_2$CO$_3$ (0.664 g, 4.80 mmol). The reaction mixture was stirred at 80° C. for 1 h then filtered and concentrated to yield the crude product which was purified by flash chromatography on silica gel (PE/EtOAc=1/0 to 1/1). All fractions found to contain product by TLC (DCM/MeOH=10/1, R$_f$=0.65) were combined and concentrated to yield a pale yellow solid of tert-butyl 4-(5-((6-(3,5-dichlorophenyl)-4-((4-(2-methoxy-2-oxoethyl)piperidin-1-yl)methyl)pyridin-2-yl)oxy)pyrimidin-2-yl)-1,4-diazepane-1-carboxylate (1.25 g, 1.550 mmol, 97.0% yield): $^1$H NMR (400 MHz, CDCl$_3$) δ ppm 8.27 (s, 2H), 7.97 (s, 1H), 7.96 (d, J=1.8 Hz, 2H), 7.32 (s, 1H), 7.02 (s, 1H), 3.88-3.86 (m, 2H), 3.82-3.78 (m, 4H), 3.66 (s, 3H), 3.38-3.36 (m, 2H), 3.24-3.18 (m, 2H), 3.08-3.06 (m, 2H), 2.30-2.28 (m, 2H), 2.21-2.03 (m, 2H), 1.98-1.94 (m, 4H), 1.62 (s, 3H), 1.46 (s, 9H); ES-LCMS m/z 685.4, 687.3 [M+H]$^+$.

Step 2: Methyl 2-(1-((2-((2-(1,4-diazepan-1-yl)pyrimidin-5-yl)oxy)-6-(3,5-dichlorophenyl)pyridin-4-yl)methyl)piperidin-4-yl)acetate

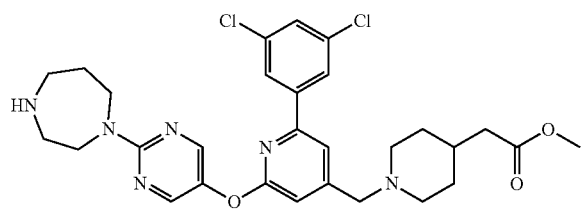 [SMILES: COC(=O)CC1CCN(Cc2cc(Oc3cnc(N4CCCNCC4)nc3)nc(-c3cc(Cl)cc(Cl)c3)c2)CC1]

tert-Butyl 4-(5-((6-(3,5-dichlorophenyl)-4-((4-(2-methoxy-2-oxoethyl)piperidin-1-yl)methyl)pyridin-2-yl)oxy)pyrimidin-2-yl)-1,4-diazepane-1-carboxylate (1.25 g, 1.550 mmol) was dissolved in HCl solution (4.0 M in MeOH, 15 mL, 60.0 mmol). The reaction mixture was stirred at 20° C. for 0.5 h then concentrated to yield a pale yellow solid of methyl 2-(1-((2-((2-(1,4-diazepan-1-yl)pyrimidin-5-yl)oxy)-6-(3,5-dichlorophenyl)pyridin-4-yl)methyl)piperidin-4-yl)acetate, 4 hydrochloride (1.3 g, 1.338 mmol, 86.0% yield): $^1$H NMR (400 MHz, CD$_3$OD) δ ppm 8.63 (s, 2H), 7.99 (s, 1H), 7.92 (d, J=1.8 Hz, 2H), 7.51 (t, J=1.8 Hz, 1H), 7.40 (s, 1H), 4.45 (s, 2H), 4.23 (d, J=5.7 Hz, 2H), 4.00 (t, J=6.2 Hz, 2H), 3.66 (s, 3H), 3.57 (d, J=7.1 Hz, 2H), 3.50-3.47 (m, 2H), 3.40 (d, J=5.3 Hz, 2H), 3.18-3.10 (m, 2H), 2.29 (d, J=5.7 Hz, 2H), 2.13-2.08 (m, 1H), 2.05-2.01 (m, 2H), 1.73-1.64 (m, 2H); ES-LCMS m/z 585.3, 587.3 [M+H]$^+$.

Step 3: Methyl 2-(1-((2-(3,5-dichlorophenyl)-6-((2-(4-methyl-1,4-diazepan-1-yl)pyrimidin-5-yl)oxy)pyridin-4-yl)methyl)piperidin-4-yl)acetate

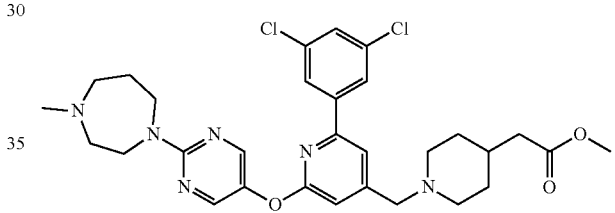

To a solution of methyl 2-(1-((2-((2-(1,4-diazepan-1-yl)pyrimidin-5-yl)oxy)-6-(3,5-dichlorophenyl)pyridin-4-yl)methyl)piperidin-4-yl)acetate, 4 hydrochloride (250 mg, 0.257 mmol) in MeOH (5 mL) was added paraformaldehyde (386 mg, 12.86 mmol) and formic acid (11.84 mg, 0.257 mmol) in MeOH (5 mL). After stirring at 20° C. for 24 h, NaBH$_3$CN (81 mg, 1.286 mmol) was added and the mixture was stirred at 20° C. for another 2 h. Saturated aqueous NaHCO$_3$ (50 mL) was added and extracted with DCM (30 mL×3). The combined organic layers were dried over Na$_2$SO$_4$ and concentrated to yield a pale yellow solid of methyl 2-(1-((2-(3,5-dichlorophenyl)-6-((2-(4-methyl-1,4-diazepan-1-yl)pyrimidin-5-yl)oxy)pyridin-4-yl)methyl)piperidin-4-yl)acetate (210 mg, 0.245 mmol, 95.0% yield): $^1$H NMR (400 MHz, CD$_3$OD) δ ppm 8.35-8.20 (m, 2H), 7.82-7.66 (m, 2H), 7.46-7.38 (m, 1H), 7.33 (s, 1H), 6.89 (s, 1H), 4.02-3.92 (m, 2H), 3.84 (t, J=6.4 Hz, 2H), 3.69-3.64 (m, 3H), 3.57-3.48 (m, 2H), 2.86 (d, J=11.5 Hz, 2H), 2.76-2.68 (m, 2H), 2.63-2.53 (m, 2H), 2.44-2.36 (m, 3H), 2.30-2.23 (m, 2H), 2.16-1.97 (m, 4H), 1.83 (d, J=11.5 Hz, 1H), 1.72 (d, J=12.8 Hz, 2H), 1.41-1.29 (m, 2H); ES-LCMS m/z 599.3, 601.3 [M+H]$^+$.

Step 4: 2-(1-((2-(3,5-Dichlorophenyl)-6-((2-(4-methyl-1,4-diazepan-1-yl)pyrimidin-5-yl)oxy)pyridin-4-yl)methyl)piperidin-4-yl)acetic acid

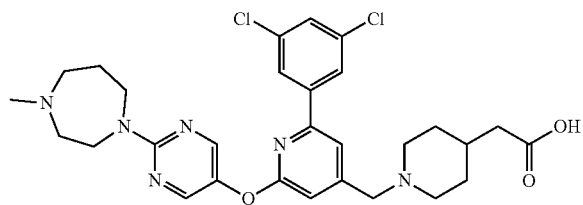 [SMILES: CN1CCCN(c2ncc(Oc3cc(CN4CCC(CC(=O)O)CC4)cc(-c4cc(Cl)cc(Cl)c4)n3)cn2)CC1]

To a solution of methyl 2-(1-((2-(3,5-dichlorophenyl)-6-((2-(4-methyl-1,4-diazepan-1-yl)pyrimidin-5-yl)oxy)pyridin-4-yl)methyl)piperidin-4-yl)acetate, 4 hydrochloride (210 mg, 0.197 mmol) in THF (5 mL) was added LiOH·H$_2$O (41.4 mg, 0.986 mmol) in water (1 mL). The reaction mixture was stirred at 50° C. for 12 h then 1 N HCl was added to adjust pH to 67. The reaction mixture was concentrated and the residue was purified by preparative HPLC (MeCN/H$_2$O as eluents, acidic condition) then lyophilized to yield a white solid of 2-(1-((2-(3,5-dichlorophenyl)-6-((2-(4-methyl-1,4-diazepan-1-yl)pyrimidin-5-yl)oxy)pyridin-4-yl)methyl)piperidin-4-yl)acetic acid, 4 hydrochloride (90.09 mg, 0.122 mmol, 61.9% yield): $^1$H NMR (400 MHz, CD$_3$OD) δ ppm 8.55 (s, 2H), 7.97 (s, 1H), 7.91 (d, J=1.8 Hz, 2H), 7.51 (s, 1H), 7.38 (s, 1H), 4.55-4.48 (m, 1H), 4.45 (s, 2H), 4.02-3.91 (m, 3H), 3.75 (dd, J=5.3, 13.2 Hz, 1H), 3.58 (d, J=12.3 Hz, 3H), 3.42-3.33 (m, 2H), 3.15 (t, J=12.1 Hz, 2H), 2.96 (s, 3H), 2.40-2.29 (m, 4H), 2.12-2.00 (m, 3H), 1.74-1.62 (m, 2H); ES-LCMS m/z 585.3, 587.3 [M+H]$^+$.

Examples 127-155 (Table 7) were prepared by procedures analogous to those described for example 126.

TABLE 7

| Example | Structure/Name | $^1$H NMR | LCMS |
|---|---|---|---|
| 127 | 3-(1-((2-(3,5-dichlorophenyl)-6-((2-(4-methylpiperazin-1-yl)pyrimidin-5-yl)oxy)pyridin-4-yl)methyl)azetidin-3-yl)butanoic acid | $^1$H NMR (400 MHz, DMSO-d$_6$) δ ppm 8.41 (s, 2H), 7.88 (d, J = 1.5 Hz, 2H), 7.72 (s, 1H), 7.64 (s, 1H), 6.98 (s, 1H), 3.85-3.67 (m, 5H), 3.49-3.30 (m, 2H), 2.83 (t, J = 6.8 Hz, 2H), 2.38 (t, J = 4.8 Hz, 5H), 2.27-2.14 (m, 5H), 2.03-1.81 (m, 2H), 0.82 (d, J = 6.5 Hz, 3H) | ES-LCMS m/z 571.3, 573.3 [M + H]$^+$. |
| 128 | 2-((1-((2-(3,5-dichlorophenyl)-6-((2-(4-methylpiperazin-1-yl)pyrimidin-5-yl)oxy)pyridin-4-yl)methyl)pyrrolidin-3-yl)oxy)acetic acid | $^1$H NMR (400 MHz, CD$_3$OD) δ ppm 8.47 (s, 2H), 8.01-7.82 (m, 3H), 7.50 (br. s, 1H), 7.34 (d, J = 12.3 Hz, 1H), 4.94 (d, J = 15.0 Hz, 2H), 4.70-4.52 (m, 2H), 4.46 (d, J = 15.0 Hz, 1H), 4.31-4.14 (m, 2H), 3.86-3.69 (m, 2H), 3.62 (d, J = 12.3 Hz, 2H), 3.56-3.48 (m, 1H), 3.45-3.34 (m, 3H), 3.19 (dt, J = 2.9, 12.2 Hz, 2H), 2.97 (s, 3H), 2.53-2.37 (m, 1H), 2.30-2.13 (m, 1H) | ES-LCMS m/z 573.3, 575.3 [M + H]$^+$. |

TABLE 7-continued

| Example | Structure/Name | $^1$H NMR | LCMS |
|---|---|---|---|
| 129 | 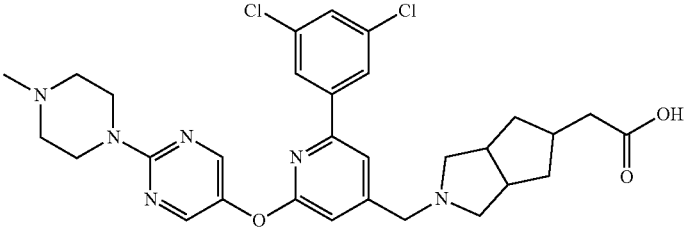 [SMILES: CN1CCN(c2ncc(Oc3cc(CN4CC5CC(CC(=O)O)CC5C4)cc(-c4cc(Cl)cc(Cl)c4)n3)cn2)CC1]<br>2-(2-((2-(3,5-dichlorophenyl)-6-((2-(4-methylpiperazin-1-yl)pyrimidin-5-yl)oxy)pyridin-4-yl)methyl)octahydrocyclopenta[c]pyrrol-5-yl)acetic acid | $^1$H NMR (400 MHz, CD$_3$OD) (δ ppm 8.46 (s, 2H), 7.99-7.88 (m, 1H), 7.85 (d, J = 1.3 Hz, 2H), 7.49 (s, 1H), 7.40-7.28 (m, 1H), 4.87 (d, J = 15.0 Hz, 2H), 4.50 (d, J = 10.6 Hz, 2H), 3.77 (s, 1H), 3.61 (d, J = 12.3 Hz, 2H), 3.50-3.31 (m, 5H), 3.22-3.12 (m, 2H), 3.04 (s, 3H), 2.95 (s, 3H), 2.47-2.37 (m, 2H), 2.19 (s, 2H), 1.28 (s, 2H); ES-LCMS (m/z) | ES-LCMS m/z 597.3, 599.3 [M + H]$^+$. |
| 130 | 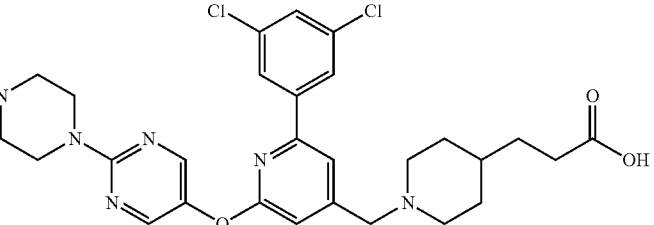<br>3-(1-((2-(3,5-dichlorophenyl)-6-((2-(4-methylpiperazin-1-yl)pyrimidin-5-yl)oxy)pyridin-4-yl)methyl)piperidin-4-yl)propanoic acid | $^1$H NMR (400 MHz, CD$_3$CN) δ ppm 8.43 (s, 2H), 7.85 (d, J = 1.8 Hz, 2H), 7.80 (s, 1H), 7.54 (t, J = 1.8 Hz, 1H), 7.25 (s, 1H), 4.77 (d, J =14.6 Hz, 2H), 4.29 (s, 2H), 3.57-3.47 (m, 4H), 3.36 (d, J = 12.8 Hz, 2H), 3.11-3.04 (m, 2H), 2.96 (t, J = 12.1 Hz, 2H), 2.86 (s, 3H), 2.33 (t, J =7.1 Hz, 2H), 1.90 (br. s, 2H), 1.61-1.48 (m, 5H) | ES-LCMS m/z 585.4, 587.4 [M + H]$^+$. |
| 131 | 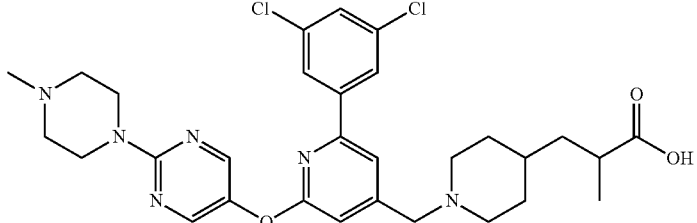<br>3-(1-((2-(3,5-dichlorophenyl)-6-((2-(4-methylpiperazin-1-yl)pyrimidin-5-yl)oxy)pyridin-4-yl)methyl)piperidin-4-yl)-2-methylpropanoic acid | $^1$H NMR (400 MHz, CD$_3$OD) δ ppm 8.46 (s, 2H), 7.93 (s, 1H), 7.87 (d, J = 1.8 Hz, 2H), 7.50 (t, J = 1.8 Hz, 1H), 7.32 (s, 1H), 4.47-4.37 (m, 2H), 3.65-3.52 (m, 4H), 3.41-3.34 (m, 2H), 3.22-3.07 (m, 4H), 3.01-2.93 (m, 3H), 2.54-2.48 (m, 1H), 2.13-1.90 (m, 3H), 1.74-1.64 (m, 2H), 1.62-1.50 (m, 2H), 1.44-1.27 (m, 2H), 1.20-1.11 (m, 3H) | ES-LCMS m/z 599.2; 601.2 [M + H]$^+$. |
| 132 | 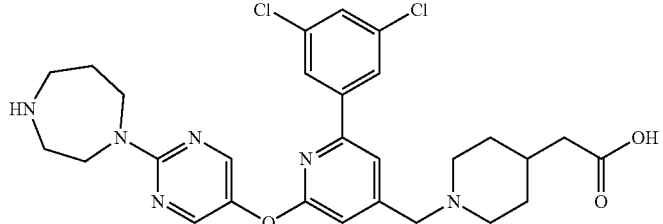<br>2-(1-((2-((2-(1,4-diazepan-1-yl)pyrimidin-5-yl)oxy)-6-(3,5-dichlorophenyl)pyridin-4-yl)methyl)piperidin-4-yl)acetic acid | $^1$H NMR (400 MHz, CD$_3$OD) δ ppm 8.54 (d, J = 7.1 Hz, 2H), 8.06-7.79 (m, 3H), 7.56-7.45 (m, 1H), 7.36 (s, 1H), 4.44 (s, 2H), 4.19 (s, 2H), 4.00 (t, J = 6.0 Hz, 2H), 3.57 (d, J = 11.9 Hz, 2H), 3.47 (s, 2H), 3.37 (s, 2H), 3.14 (t, J = 12.3 Hz, 2H), 2.32 (d, J = 6.2 Hz, 2H), 2.24 (s, 2H), 2.05 (d, J = 12.8 Hz, 3H), 1.66 (d, J = 11.5 Hz, 2H) | ES-LCMS m/z 571.3, 573.3 [M + H]$^+$. |

TABLE 7-continued

| Example | Structure/Name | $^1$H NMR | LCMS |
|---|---|---|---|
| 133 | 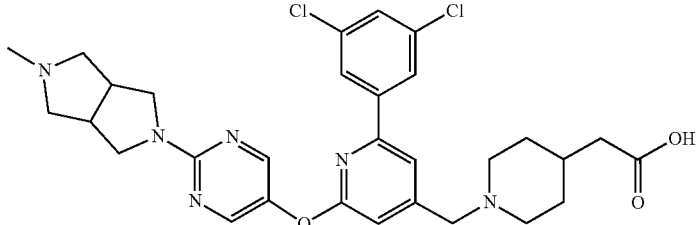<br>2-(1-((2-(3,5-dichlorophenyl)-6-((2-(5-methylhexahydropyrrolo[3,4-c]pyrrol-2(1H)-yl)pyrimidin-5-yl)oxy)pyridin-4-yl)methyl)piperidin-4-yl)acetic acid | $^1$H NMR (400 MHz, CD$_3$OD) δ ppm 8.57 (d, J = 9.5 Hz, 2H), 7.96 (br. s, 1H), 7.91 (s, 2H), 7.54 (s, 1H), 7.38 (s, 1H), 4.58-4.43 (s, 2H), 4.02-3.72 (m, 6H), 3.61 (d, J = 12.5 Hz, 2H), 3.53-3.46 (m, 2H), 3.27-3.07 (m, 4H), 2.99 (d, J = 12.5 Hz, 3H), 2.35 (d, J = 6.5 Hz, 2H), 2.09 (d, J = 14.1 Hz, 3H), 1.79-1.54 (m, 2H) | ES-LCMS m/z 597.4, 599.4 [M + H]$^+$. |
| 134 | 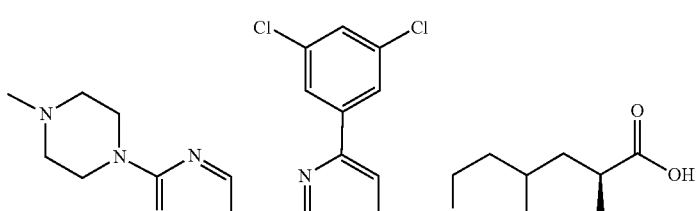<br>dichlorophenyl)-6-((2-(4-methylpiperazin-1-yl)pyrimidin-5-yl)oxy)pyridin-4-yl)methyl)piperidin-4-yl)-2-methylpropanoic acid | $^1$H NMR (400 MHz, CD$_3$OD) δ ppm 8.45 (s, 2H), 7.96 (br.s., 1H), 7.87 (s, 2H), 7.48 (br.s., 1H), 7.33 (s, 1H), 4.93 (d, J = 14.6 Hz, 2H), 4.43 (s, 2H), 3.66-3.52 (m, 4H), 3.43-3.35 (m, 2H), 3.23-3.07 (m, 4H), 2.97 (s, 3H), 2.66-2.55 (m, 1H), 2.04-1.90 (m, 2H), 1.74-1.54 (m, 4H), 1.41-1.32 (m, 1H), 1.21-1.11 (m, 3H) | LC-MS m/z 599.2; 601.3 [M + H]$^+$. |
| 135 | 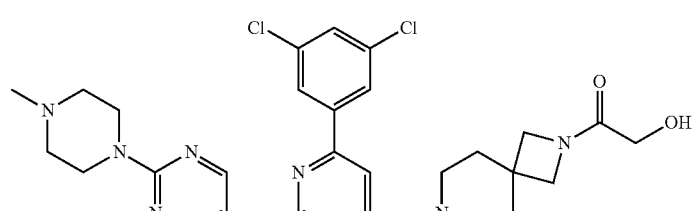<br>1-(7-((2-(3,5-dichlorophenyl)-6-((2-(4-methylpiperazin-1-yl)pyrimidin-5-yl)oxy)pyridin-4-yl)methyl)-2,7-diazaspiro[3.5]nonan-2-yl)-2-hydroxyethanone | $^1$H NMR (400 MHz, CD$_3$OD) δ ppm 8.46 (s, 2H), 7.93 (d, J = 3.5 Hz, 1H), 7.88 (d, J = 1.8 Hz, 2H), 7.51 (t, J = 1.8 Hz, 1H), 7.32 (s, 1H), 4.95 (d, J = 15.0 Hz, 2H), 4.45 (s, 2H), 4.17 (s, 1H), 4.09 (d, J = 8.8 Hz, 2H), 4.04 (s, 1H), 3.90 (s, 1H), 3.78 (s, 1H), 3.61 (d, J = 12.3 Hz, 2H), 3.54 (d, J = 11.9 Hz, 2H), 3.43-3.34 (m, 2H), 3.22-3.11 (m, 4H), 2.97 (s, 3H), 2.26-2.18 (m, 2H), 2.13 (d, J = 7.1 Hz, 2H) | ES-LCMS m/z 612.2, 614.2 [M + H]$^+$. |

TABLE 7-continued

| Example | Structure/Name | ¹H NMR | LCMS |
|---|---|---|---|
| 136 | 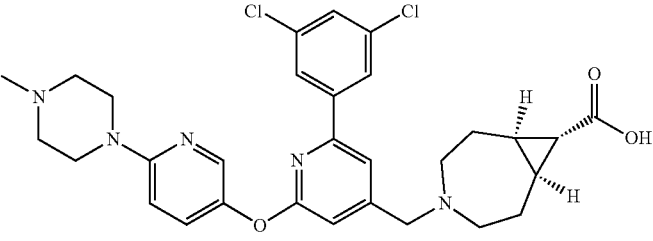 [SMILES: CN1CCN(c2ccc(Oc3cc(CN4CC[C@@H]5[C@H](CC4)[C@H]5C(=O)O)cc(-c4cc(Cl)cc(Cl)c4)n3)cn2)CC1]<br>(1R,7S,8r)-4-((2-(3,5-dichlorophenyl)-6-((6-(4-methylpiperazin-1-yl)pyridin-3-yl)oxy)pyridin-4-yl)methyl)-4-azabicyclo[5.1.0]octane-8-carboxylic acid | ¹H NMR (400 MHz, CD₃OD) δ ppm 8.20 (d, J = 2.6 Hz, 1H), 8.05 (dd, J = 2.6, 9.7 Hz, 1H), 7.99-7.93 (m, 1H), 7.87 (d, J = 1.8 Hz, 2H), 7.50 (t, J = 1.9 Hz, 1H), 7.46 (d, J = 9.7 Hz, 1H), 7.39-7.33 (m, 1H), 4.57-4.39 (m, 4H), 3.76-3.45 (m, 6H), 3.33 (br d, J = 11.5 Hz, 4H), 2.99 (s, 3H), 2.48 (br d, J = 15.2 Hz, 2H), 1.88-1.70 (m, 4H), 1.56 (br s, 1H) | ES-LCMS m/z 582.3, 584.2 [M + H]⁺. |
| 137 | 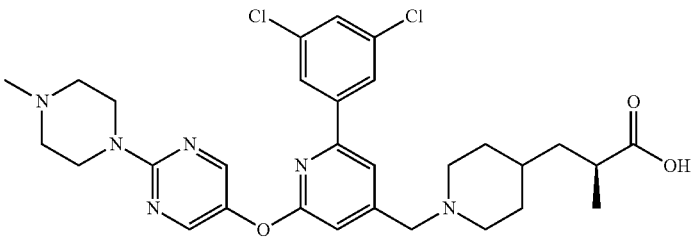 [SMILES: C[C@@H](CC1CCN(Cc2cc(Oc3cnc(N4CCN(C)CC4)nc3)nc(-c3cc(Cl)cc(Cl)c3)c2)CC1)C(=O)O]<br>(R)-3-(1-((2-(3,5-dichlorophenyl)-6-((2-(4-methylpiperazin-1-yl)pyrimidin-5-yl)oxy)pyridin-4-yl)methyl)piperidin-4-yl)-2-methylpropanoic acid | ¹H NMR (400 MHz, CD₃OD) δ ppm 8.45 (s, 2H), 7.92 (s, 1H), 7.87 (d, J = 2.0 Hz, 2H), 7.49 (t, J = 1.8 Hz, 1H), 7.32 (s, 1H), 4.94 (d, J = 14.6 Hz, 2H), 4.42 (s, 2H), 3.64-3.55 (m, 4H), 3.41-3.35 (m, 2H), 3.22-3.06 (m, 4H), 2.96 (s, 3H), 2.55-2.48 (m, 1H), 2.07-1.94 (m, 2H), 1.77-1.64 (m, 2H), 1.63-1.48 (m, 2H), 1.39-1.29 (m, 1H), 1.22-1.12 (m, 3H) | ES-LCMS m/z 599.3, 601.3 [M + H]⁺. |
| 138 | 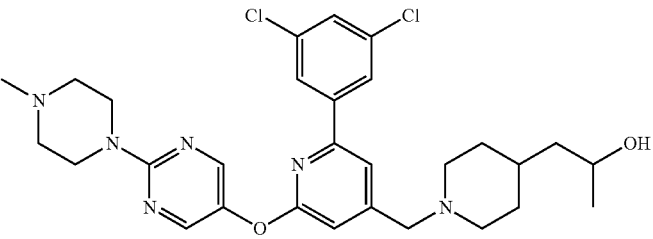<br>1-(1-((2-(3,5-dichlorophenyl)-6-((2-(4-methylpiperazin-1-yl)pyrimidin-5-yl)oxy)pyridin-4-yl)methyl)piperidin-4-yl)propan-2-ol | ¹H NMR (400 MHz, CD₃OD) δ ppm 8.48-8.43 (m, 2H), 8.00 (s, 1H), 7.86 (d, J = 1.6 Hz, 2H), 7.45 (s, 1H), 7.37-7.36 (m, 1H), 4.95-4.91 (m, 2H), 4.46 (s, 2H), 3.88-3.81 (m, 1H), 3.64-3.52 (m, 4H), 3.43-3.39 (m, 2H), 3.20-3.16 (m, 4H), 2.97 (s, 3H), 2.04-1.94 (m, 2H), 1.85-1.84 (m, 1H), 1.63-1.60 (m, 2H), 1.46-1.45 (m, 1H), 1.38-1.28 (m, 1H), 1.17 (d, J = 6.0 Hz, 3H) | ES-LCMS m/z 571.3, 573.3 [M + H]⁺. |

TABLE 7-continued

| Example | Structure/Name | ¹H NMR | LCMS |
|---|---|---|---|
| 139 | 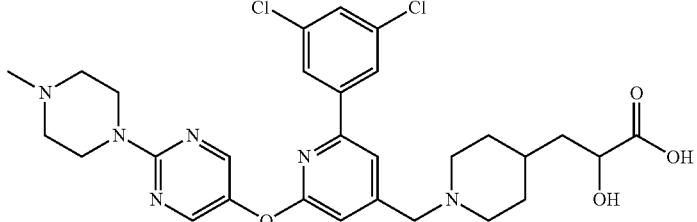<br>3-(1-((2-(3,5-dichlorophenyl)-6-((2-(4-methylpiperazin-1-yl)pyrimidin-5-yl)oxy)pyridin-4-yl)methyl)piperidin-4-yl)-2-hydroxypropanoic acid | ¹H NMR (400 MHz, CD$_3$OD) δ ppm 8.45 (s, 2H), 7.95-7.81 (m, 3H), 7.50 (s, 1H), 7.30 (s, 1H), 4.94 (d, J = 14.6 Hz, 2H), 4.42 (s, 2H), 4.20 (s, 1H), 3.66-3.53 (m, 4H), 3.44-3.34 (m, 2H), 3.25-3.05 (m, 4H), 2.96 (s, 3H), 2.17-2.01 (m, 2H), 1.91 (s, 1H), 1.77-1.47 (m, 4H) | ES-LCMS m/z 601.2, 603.2 [M + H]⁺. |
| 140 | 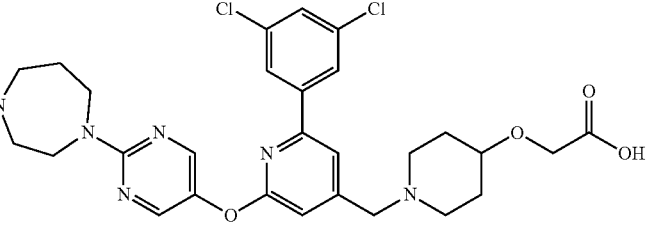<br>2-((1-((2-(3,5-dichlorophenyl)-6-((2-(4-methyl-1,4-diazepan-1-yl)pyrimidin-5-yl)oxy)pyridin-4-yl)methyl)piperidin-4-yl)oxy)acetic acid | ¹H NMR (400 Hz, CD$_3$OD) δ ppm 8.36-8.34 (m, 2H), 7.77 (d, J = 2.0 Hz, 2H), 7.61 (s, 1H), 7.38 (t, J = 1.9 Hz, 1H), 7.01 (s, 1H), 4.14-4.09 (m, 2H), 3.94-3.90 (m, 4H), 3.67 (s, 2H), 3.47 (td, J = 4.1, 7.7 Hz, 1H), 3.34-3.31 (m, 2H), 3.24-3.20 (m, 2H), 2.91-2.84 (m, 2H), 2.79 (s, 3H), 2.35 (t, J = 9.0 Hz, 2H), 2.26-2.18 (m, 2H), 1.99-1.91 (m, 2H), 1.75-1.64 (m, 2H) | ES-LCMS m/z 601.2, 603.2 [M + H]⁺. |
| 141 | 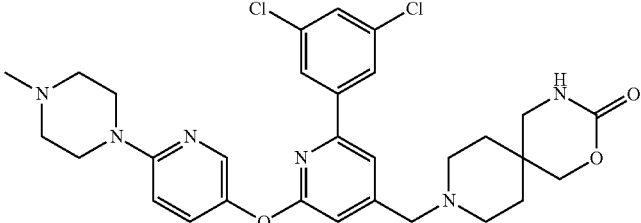<br>9-((2-(3,5-dichlorophenyl)-6-((6-(4-methylpiperazin-1-yl)pyridin-3-yl)oxy)pyridin-4-yl)methyl)-2-oxa-4,9-diazaspiro[5.5]undecan-3-one | ¹H NMR (400 MHz, CD$_3$OD) δ ppm 8.03 (d J = 2.6 Hz 1H), 7.81 (d, J = 1.8 Hz, 2H), 7.61 (s, 1H), 7.49 (dd, J = 2.8, 9.2 Hz, 1H), 7.43-7.39 (m, 1H), 6.99-6.91 (m, 2H), 4.10 (s, 2H), 3.63 (s, 2H), 3.59-3.54 (m, 4H), 3.16 (s, 2H), 2.62-2.56 (m, 6H), 2.50-2.42 (m, 2H), 2.36 (s, 3H), 1.64 (s, 4H) | ES-LCMS m/z 597.3, 599.3 [M + H]⁺. |
| 142 | 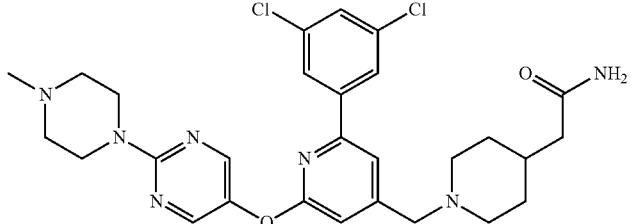<br>2-(1-((2-(3,5-dichlorophenyl)-6-((2-(4-methylpiperazin-1-yl)pyrimidin-5-yl)oxy)pyridin-4-yl)methyl)piperidin-4-yl)acetamide | ¹H NMR (400 MHz, CD$_3$OD) δ ppm 8.55 (s, 2H), 8.01 (s, 1H), 7.88 (d, J = 1.8 Hz, 2H), 7.48 (s, 1H), 7.38 (s, 1H), 4.92 (brs, 2H), 4.44 (s, 2H), 3.67-3.42 (m, 6H), 3.26-3.10 (m, 4H), 2.96 (s, 3H), 2.27 (d, J = 7.1 Hz, 2H), 2.16-1.93 (m, 3H), 1.80-1.64 (m, 2H) | ES-LCMS m/z 570.3, 572.4 [M + H]⁺. |

TABLE 7-continued

| Example | Structure/Name | $^1$H NMR | LCMS |
|---|---|---|---|
| 143 | 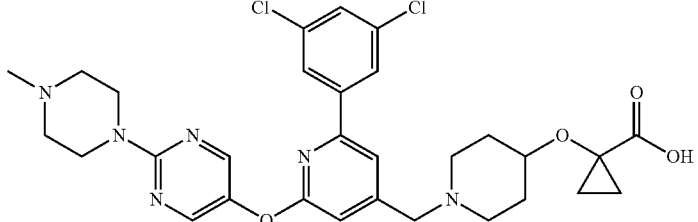<br>1-((1-((2-(3,5-dichlorophenyl)-6-((2-(4-methylpiperazin-1-yl)pyrimidin-5-yl)oxy)pyridin-4-yl)methyl)piperidin-4-yl)oxy)cyclopropanecarboxylic acid | $^1$H NMR (400 MHz, CD$_3$OD) δ ppm 8.31 (s, 2H), 7.79 (d, J = 1.8 Hz, 2H), 7.62 (s, 1H), 7.41 (s, 1H), 7.03 (s, 1H), 3.87 (br s, 4H), 3.62 (s, 2H), 3.30 (s, 4H), 2.56 (t, J = 5.0 Hz, 4H), 2.42 (d, J = 8.8 Hz, 1H), 2.36 (s, 3H), 1.94 (d, J = 12.6 Hz, 2H), 1.80-1.69 (m, 2H), 1.28-1.22 (m, 2H), 1.09-1.01 (m, 2H) | ES-LCMS m/z 613.2, 615.2 [M + H]$^+$. |
| 144 | 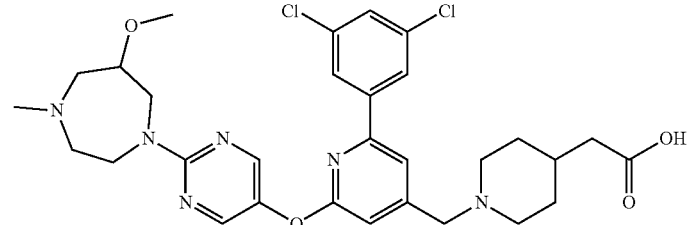<br>2-(1-((2-(3,5-dichlorophenyl)-6-((2-(6-methoxy-4-methyl-1,4-diazepan-1-yl)pyrimidin-5-yl)oxy)pyridin-4-yl)methyl)piperidin-4-yl)acetic acid | 1H NMR (400 MHz, CD$_3$OD) δ ppm 8.43 (s, 2H), 7.88 (s, 1H), 7.85 (d, J = 1.8 Hz, 2H), 7.48 (t, J = 1.8 Hz, 1H), 7.30 (s, 1H), 4.55-4.49 (m, 1H), 4.40 (s, 2H), 4.13 (t, J = 5.3 Hz, 2H), 3.96 (br s, 1H), 3.83 (dd, J = 3.6, 15.1 Hz, 1H), 3.69 (d, J = 7.1 Hz, 1H), 3.66-3.62 (m, 2H), 3.55 (br s, 1H), 3.53 (s, 3H), 3.30 (br s, 2H), 3.10 (t, J = 11.9 Hz, 2H), 2.91 (s, 3H), 2.32-2.25 (m, 2H), 2.06-1.99 (m, 3H), 1.68-1.53 (m, 2H) | ES-LCMS m/z 615.3, 617.3 [M + H]$^+$. |
| 145 | 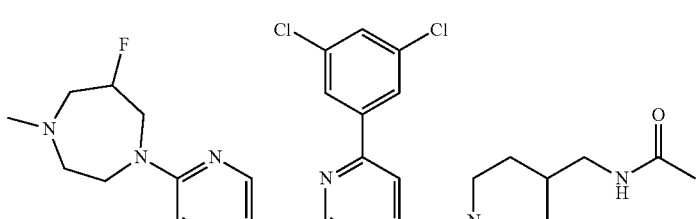<br>N-((1-((2-(3,5-dichlorophenyl)-6-((6-(6-fluoro-4-methyl-1,4-diazepan-1-yl)pyridin-3-yl)oxy)pyridin-4-yl)methyl)piperidin-4-yl)methyl)acetamide | $^1$H NMR (400 MHz, CD$_3$OD) δ ppm 8.27 (d, J = 9.7 Hz, 1H), 8.21 (s, 1H), 8.03 (s, 1H), 7.89 (d, J = 1.5 Hz, 2H), 7.63 (d, J = 9.7 Hz, 1H), 7.49 (s, 1H), 7.44 (s, 1H), 5.53-5.37 (m, 1H), 4.58-4.44 (m, 3H), 4.30-4.10 (m, 3H), 4.03-3.89 (m, 3H), 3.74 (br s, 1H), 3.58 (d, J = 11.0 Hz, 2H), 3.34 (d, J = 5.7 Hz, 1H), 3.14 (d, J = 6.2 Hz, 3H), 3.09 (s, 3H), 2.01-1.94 (m, 5H), 1.90-1.81 (m, 1H), 1.87 (br s, 1H), 1.72-1.58 (m, 2H) | ES-LCMS m/z 615.4, 617.4 [M + H]$^+$. |

TABLE 7-continued

| Example | Structure/Name | ¹H NMR | LCMS |
|---|---|---|---|
| 146 | 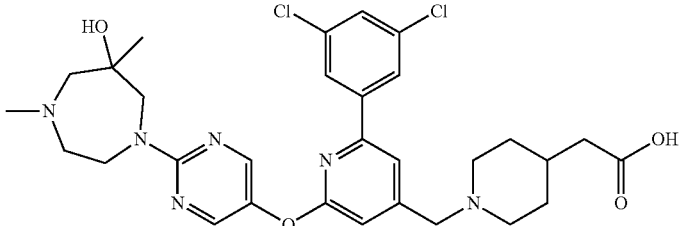<br>2-(1-((2-(3,5-dichlorophenyl)-6-((2-(6-hydroxy-4,6-dimethyl-1,4-diazepan-1-yl)pyrimidin-5-yl)oxy)pyridin-4-yl)methyl)piperidin-4-yl)acetic acid | ¹H NMR (400 MHz, CD₃OD) δ ppm 8.61-8.47 (m, 2H), 7.97 (br s, 1H), 7 91 (d, J = 1.5 Hz, 2H), 7.54-7.49 (m, 1H), 7.39 (br s, 1H), 4.43-4.34 (m, 1H), 4.53-4.30 (m, 3H), 4.09-3.97 (m, 1H), 3.88-3.75 (m, 2H), 3.70 (d, J = 14.8 Hz, 1H), 3.59 (d, J = 12.0 Hz, 2H), 3.36 (d, J = 12.8 Hz, 1H), 3.26-3.09 (m, 3H), 2.95 (s, 3H), 2.34 (d, J = 6.5 Hz, 2H), 2.06 (d, J = 14.3 Hz, 3H), 1.78-1.62 (m, 2H), 1.41 (s, 3H) | ES-LCMS m/z 615.2, 617.2 [M + H]⁺. |
| 147 | 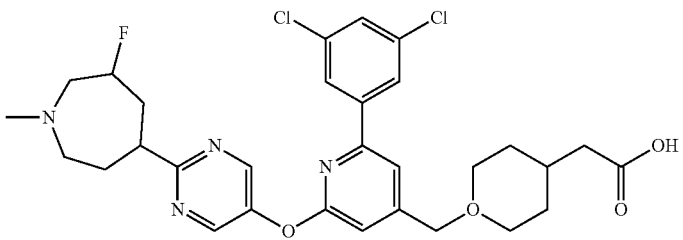<br>2-(1-((2-(3,5-dichlorophenyl)-6-((2-(6-fluoro-4-methyl-1,4-diazepan-1-yl)pyrimidin-5-yl)oxy)pyridin-4-yl)methyl)piperidin-4-yl)acetic acid | ¹H NMR (400 MHz, CD₃OD) δ 8.47-8.44 (m, 2H), 7.94 (s, 1H), 7.89 (d, J = 2.0 Hz, 2H), 7.50 (t, J = 1.9 Hz, 1H), 7.35 (s, 1H), 5.40-5.27 (m, 1H), 4.60-4.48 (m, 2H), 4.44 (s, 2H), 4.31-4.25 (m, 1H), 4.21 (brd, J = 3.7 Hz, 1H), 4.13-4.05 (m, 1H), 3.90-3.82 (m, 2H), 3.77 (brd, J = 4.2 Hz, 1H), 3.57 (brd, J = 12.6 Hz, 2H), 3.46-3.40 (m, 1H), 3.19-3.10 (m, 2H), 3.02 (s, 3H), 2.32 (d, J = 6.6 Hz, 2H), 2.05 (brd, J = 14.1 Hz, 2H), 1.73-1.62 (m, 2H) | ES-LCMS m/z 603.3, 605.3 [M + H]⁺. |
| 148 | 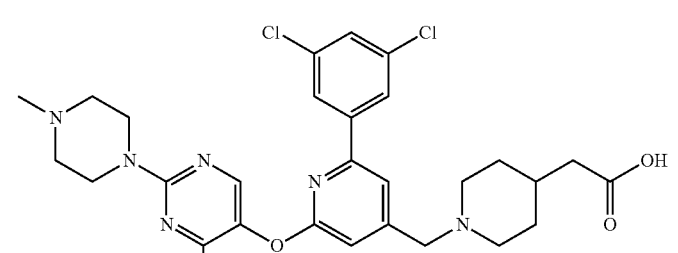<br>2-(1-((2-(3,5-dichlorophenyl)-6-((4-methyl-2-(4-methylpiperazin-1-yl)pyrimidin-5-yl)oxy)pyridin-4-yl)methyl)piperidin-4-yl)acetic acid | ¹H NMR (400 MHz, CD₃OD) δ ppm 8.24 (s, 1H), 7.87 (s, 1H), 7.79 (d, J = 1.8 Hz, 2H), 7.49-7.44 (m, 1H), 7.33 (s, 1H), 4.93 (br s, 2H), 4.42 (s, 2H), 3.58 (br t, J = 13.3 Hz, 4H), 3.40-3.31 (m, 2H), 3.22-3.07 (m, 4H), 2.94 (s, 3H), 2.32 (br d, J = 6.2 Hz, 2H), 2.27 (s, 3H), 2.12-1.95 (m, 3H), 1.62 (br d, J = 12.1 Hz, 2H) | ES-LCMS m/z 585.3, 587.3 [M + H]⁺. |

TABLE 7-continued

| Example | Structure/Name | ¹H NMR | LCMS |
|---|---|---|---|
| 149 | 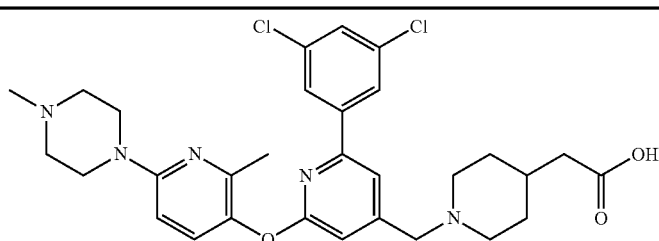<br>2-(1-((2-(3,5-dichlorophenyl)-6-((2-methyl-6-(4-methylpiperazin-1-yl)pyridin-3-yl)oxy)pyridin-4-yl)methyl)piperidin-4-yl)acetic acid | ¹H NMR (400 MHz, CD₃CN:H₂O = 1:1) δ ppm 7.90 (d, J = 9.5 Hz, 1H), 7.82-7.72 (m, 3H), 7.45 (d, J = 2.0 Hz, 1H), 7.23 (s, 1H), 7.16 (d, J = 9.0 Hz, 1H), 4.48-4.23 (m, 4H), 3.80-3.37 (m, 6H), 3.23 (t, J = 11.8 Hz, 2H), 3.01 (t, J = 12.1 Hz, 2H), 2.91 (s, 3H), 2.42 (s, 3H), 2.28 (d, J = 6.4 Hz, 2H), 2.03-1.92 (m, 3H), 1.68-1.38 (m, 2H) | ES-LCMS m/z 584.3, 586.3 [M + H]⁺. |
| 150 | 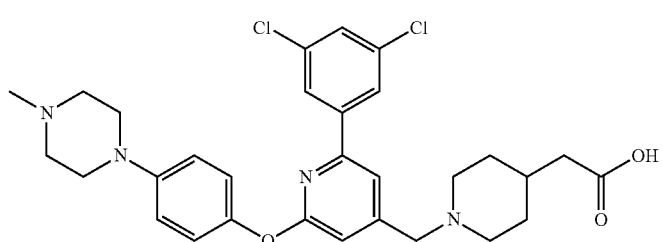<br>2-(1-((2-(3,5-dichlorophenyl)-6-(4-(4-methylpiperazin-1-yl)phenoxy)pyridin-4-yl)methyl)piperidin-4-yl)acetic acid | ¹H NMR (400 MHz, CD₃OD) δ ppm 7.87 (d, J = 1.1 Hz, 3H), 7.46 (s, 1H), 7.17 (s, 1H), 7.15 (s, 4H), 4.40 (s, 2H), 3.84 (br d, J = 13.2 Hz, 2H), 3.64 (br d, J = 12.1 Hz, 2H), 3.56 (br d, J = 12.1 Hz, 2H), 3.35 (br s, 2H), 3.13 (br t, J = 12.5 Hz, 4H), 2.98 (s, 3H), 2.32 (d, J = 6.4 Hz, 2H), 2.05 (br d, J = 13.5 Hz, 3H), 1.70-1.58 (m, 2H) | ES-LCMS m/z 569.3, 571.3 [M + H]⁺. |
| 151 | 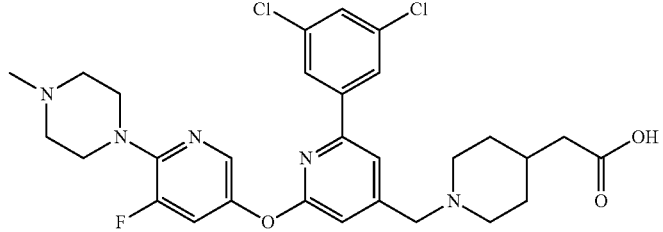 [SMILES: CN1CCN(c2ncc(Oc3cc(CN4CCC(CC(=O)O)CC4)cc(-c4cc(Cl)cc(Cl)c4)n3)cc2F)CC1]<br>2-(1-((2-(3,5-dichlorophenyl)-6-((5-fluoro-6-(4-methylpiperazin-1-yl)pyridin-3-yl)oxy)pyridin-4-yl)methyl)piperidin-4-yl)acetic acid | ¹H NMR (400 MHz, CD₃OD) d ppm 8.08 (d, J = 2.2 Hz, 1H), 7.92 (s 1H) 7.87 (d, J = 1.8 Hz 2H), 7.63 (dd, J = 2.3, 12.7 Hz, 1H), 7.50 (t, J = 1.9 Hz, 1H), 7.30 (s, 1H), 4.43 (s, 2H), 4.29-4.12 (m, 2H), 3.69-3.53 (m, 4H), 3.38-3.32 (m, 3H), 3.30 (br s, 1H), 3.14 (br t, J = 12.1 Hz, 2H), 2.97 (s, 3H), 2.32 (d, J = 6.6 Hz, 2H), 2.20-1.98 (m, 3H), 1.63 (q, J = 12.6 Hz, 2H) | ES-LCMS m/z: 588.2, 590.2 [M + H]⁺. |
| 152 | 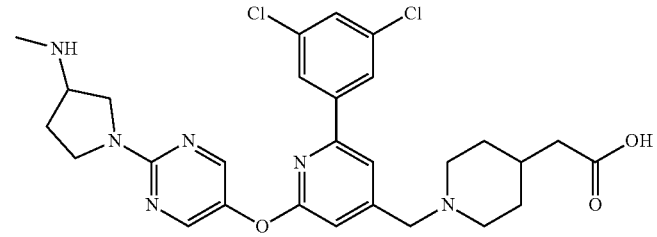 [SMILES: CNC1CCN(c2ncc(Oc3cc(CN4CCC(CC(=O)O)CC4)cc(-c4cc(Cl)cc(Cl)c4)n3)cn2)C1]<br>2-(1-((2-(3,5-dichlorophenyl)-6-((2-(3-(methylamino)pyrrolidin-1-yl)pyrimidin-5-yl)oxy)pyridin-4-yl)methyl)piperidin-4-yl)acetic acid | ¹H NMR (400 MHz, D₂O) δ ppm 8.55-8.31 (m, 2H), 7.45 (s, 3H), 7.22 (s 1H), 7.06-6.93 (m, 1H), 4.17 (s, 2H), 3.96-3.81 (m, 2H), 3.78-3.52 (m, 3H), 3.41-3.26 (m, 2H), 2.89 (t, J = 12.1Hz, 2H), 2.61 (s, 3H), 2.47-2.34 (m, 1H), 2.24-2.05 (m, 3H), 1.93-1.72 (m, 3H), 1.41-1.27 (m, 2H) | ES-LCMS m/z 571.3, 573.3 [M + H]⁺. |

TABLE 7-continued

| Example | Structure/Name | $^1$H NMR | LCMS |
|---|---|---|---|
| 153 | 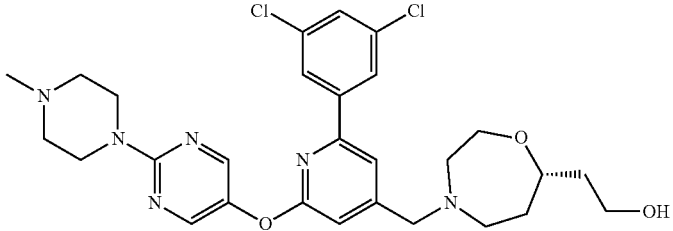 [SMILES: CN1CCN(c2ncc(Oc3cc(CN4CCO[C@H](CCO)CC4)cc(-c4cc(Cl)cc(Cl)c4)n3)cn2)CC1]<br><br>(S)-2-(4-((2-(3,5-dichlorophenyl)-6-((2-(4-methylpiperazin-1-yl)pyrimidin-5-yl)oxy)pyridin-4-yl)methyl)-1,4-oxazepan-7-yl)ethanol | $^1$H NMR (400 MHz, CD$_3$OD) δ ppm 8.50 (s, 2H), 8.00 (d, J = 6.6 Hz, 1H), 7.88 (s, 2H), 7.49 (t, J = 1.8 Hz, 1H), 7.37 (s, 1H), 4.93 (br s, 2H), 4.61-4.49 (m, 2H), 4.13-3.77 (m, 3H), 3.70-3.36 (m, 10H), 3.25-3.15 (m, 2H), 2.96 (s, 3H), 2.26-2.00 (m, 2H), 1.86-1.70 (m, 1H), 1.67-1.56 (m, 1H) | ES-LCMS m/z 573.3, 575.3 [M + H]$^+$. |
| 154 | 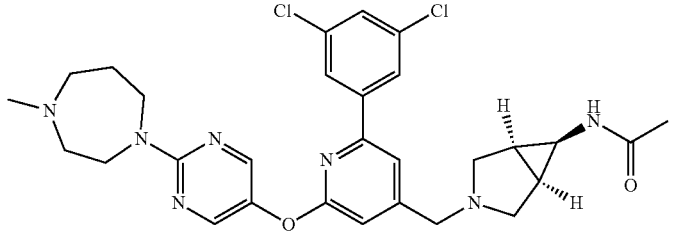 [SMILES: CC(=O)N[C@@H]1[C@@H]2CN(Cc3cc(Oc4cnc(N5CCCN(C)CC5)nc4)nc(-c4cc(Cl)cc(Cl)c4)c3)C[C@@H]21]<br><br>N-((1R,5S,6r)-3-((2-(3,5-dichlorophenyl)-6-((2-(4-methyl-1,4-diazepan-1-yl)pyrimidin-5-yl)oxy)pyridin-4-yl)methyl)-3-azabicyclo[3.1.0]hexan-6-yl)acetamide | $^1$H NMR (400 MHz, CD$_3$OD) δ ppm 8.69 (s, 2H), 8.11-7.98 (m, 1H), 7.90 (s, 2H), 7.52-7.41 (m, 2H), 4.95-4.92 (m, 2H), 4.62-4.50 (m, 2H), 4.05 (dd, J = 7.5, 14.8 Hz, 1H), 3.95 (s, 3H), 3.74 (t, J = 14.6 Hz, 2H), 3.67-3.54 (m, 2H), 3.49-3.36 (m, 2H), 3.02 (d, J = 11.9 Hz, 1H), 2.95 (s, 3H), 2.46 (s, 1H), 2.40-2.24 (m, 3H), 2.13 (d, J = 17.2 Hz, 3H) | ES-LCMS m/z: 582.2, 584.2 [M + H]$^+$. |
| 155 | 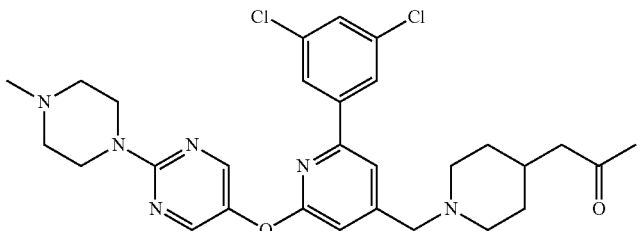<br><br>1-(1-((2-(3,5-dichlorophenyl)-6-((2-(4-methylpiperazin-1-yl)pyrimidin-5-yl)oxy)pyridin-4-yl)methyl)piperidin-4-yl)propan-2-one | $^1$H NMR (400 MHz, CD$_3$OD) δ ppm 8.29 (s, 2H), 7.77 (s, 2H), 7.60 (s, 1H), 7.39 (s, 1H), 7.00 (s, 1H), 3.84 (s, 4H), 3.56 (s, 2H), 2.87 (d, J =10.4 Hz, 2H), 2.52 (s, 4H), 2.41 (d, J = 5.7 Hz, 2H), 2.33 (s, 3H), 2.10 (s, 4H), 1.82 (s, 1H), 1.67 (d, J = 11.5 Hz, 2H), 1.28 (d, J = 13.0 Hz, 3H) | ES-LCMS: m/z 569.2, 571.2 [M + H]$^+$. |

Example 156: 2-(1-((2-(3,5-Dichlorophenyl)-6-((6-(4-methyl-1,4-diazepan-1-yl)pyridin-3-yl)oxy)pyridin-4-yl)methyl)piperidin-4-yl)acetic acid

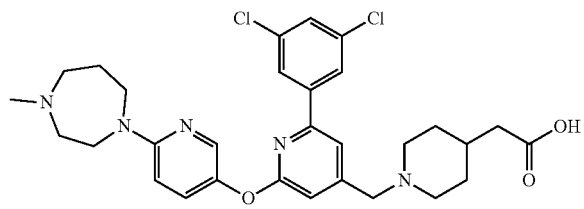 [SMILES: CN1CCCN(c2ccc(Oc3cc(CN4CCC(CC(=O)O)CC4)cc(-c4cc(Cl)cc(Cl)c4)n3)cn2)CC1]

Step 1: Methyl 2-(1-((2-((6-(1,4-diazepan-1-yl)pyridin-3-yl)oxy)-6-(3,5-dichlorophenyl)pyridin-4-yl)methyl)piperidin-4-yl)acetate

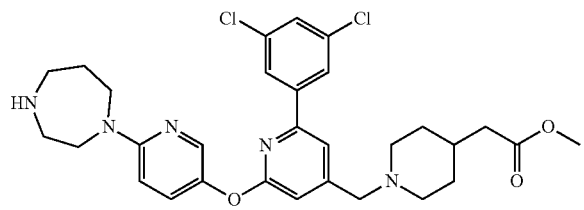 [SMILES: COC(=O)CC1CCN(Cc2cc(Oc3ccc(N4CCCNCC4)nc3)nc(-c3cc(Cl)cc(Cl)c3)c2)CC1]

To a mixture of methyl 2-(1-((2-((6-bromopyridin-3-yl)oxy)-6-(3,5-dichlorophenyl)pyridin-4-yl)methyl)piperidin-4-yl)acetate (500 mg, 0.885 mmol), 1,4-diazepane (133 mg, 1.327 mmol), Xantphos (51.2 mg, 0.088 mmol), Cs$_2$CO$_3$ (865 mg, 2.65 mmol) in THF (10 mL) was added Pd$_2$(dba)$_3$ (81 mg, 0.088 mmol). The reaction was stirred at 75° C. for 24 h under N$_2$ atmosphere then filtered and concentrated. The crude product was purified by silica gel column chromatography (DCM/MeOH=1/0 to 8/1, TLC: DCM/MeOH=10/1, R$_f$=0.3) to yield a yellow solid of methyl 2-(1-((2-((6-(1,4-diazepan-1-yl)pyridin-3-yl)oxy)-6-(3,5-dichlorophenyl)pyridin-4-yl)methyl)piperidin-4-yl)acetate (300 mg, 0.462 mmol, 52.2% yield): $^1$H NMR (400 MHz, CD$_3$OD) δ ppm 8.00 (s, 1H), 7.83 (s, 2H), 7.61 (s, 1H), 7.47 (d, J=7.6 Hz, 1H), 7.42 (s, 1H), 6.97 (s, 1H), 6.81 (d, J=9.6 Hz, 1H), 3.90 (s, 2H), 3.77 (t, J=5.6 Hz, 2H), 3.64 (s, 3H), 3.60-3.58 (m, 2H), 3.21-3.19 (m, 2H), 3.06-3.04 (m, 2H), 2.92-2.89 (m, 2H), 2.27 (d, J=6.4 Hz, 2H), 2.16-2.03 (m, 4H), 1.75-1.72 (m, 3H), 1.40-1.29 (m, 2H); ES-LCMS m/z 584.3, 586.3 [M+H]$^+$.

Step 2: Methyl 2-(1-((2-(3,5-dichlorophenyl)-6-((6-(4-methyl-1,4-diazepan-1-yl)pyridin-3-yl)oxy)pyridin-4-yl)methyl)piperidin-4-yl)acetate

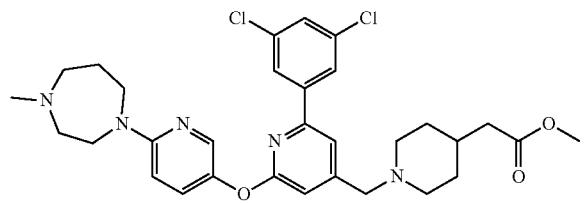

To a solution of methyl 2-(1-((2-((6-(1,4-diazepan-1-yl)pyridin-3-yl)oxy)-6-(3,5-dichlorophenyl)pyridin-4-yl)methyl)piperidin-4-yl)acetate (300 mg, 0.462 mmol) in MeOH (5 mL) was added paraformaldehyde (693 mg, 23.10 mmol) and formic acid (21.26 mg, 0.462 mmol) in MeOH (5 mL). After stirring at 30° C. for 20 h, NaBH$_3$CN (145 mg, 2.310 mmol) was added and the mixture was stirred at 30° C. for 8 h. The mixture was concentrated, added with DCM/MeOH (10/1, 50 mL) and washed with saturated aqueous NaHCO$_3$ (50 mL) solution. The aqueous layer was extracted with DCM (30 mL×2). The combined organic layers were dried over Na$_2$SO$_4$ and concentrated to yield a yellow solid of methyl 2-(1-((2-(3,5-dichlorophenyl)-6-((6-(4-methyl-1,4-diazepan-1-yl)pyridin-3-yl)oxy)pyridin-4-yl)methyl)piperidin-4-yl)acetate (250 mg, 0.360 mmol, 78.0% yield): $^1$H NMR (400 MHz, CD$_3$OD) δ ppm 7.99 (d, J=2.8 Hz, 1H), 7.86 (d, J=2.0 Hz, 2H), 7.63 (s, 1H), 7.48-7.44 (m, 2H), 6.98 (s, 1H), 6.77 (d, J=8.8 Hz, 1H), 3.86-3.85 (m, 2H), 3.71-3.69 (m, 2H), 3.67 (s, 3H), 3.61 (s, 2H), 2.95-2.93 (m, 2H), 2.85-2.78 (m, 2H), 2.71-2.63 (m, 2H), 2.42 (s, 3H), 2.30 (d, J=7.2 Hz, 2H), 2.13-2.10 (m, 4H), 1.87-1.71 (m, 3H), 1.38-1.31 (m, 2H); ES-LCMS m/z 598.3, 600.4 [M+H]$^+$.

Step 3: 2-(1-((2-(3,5-Dichlorophenyl)-6-((6-(4-methyl-1,4-diazepan-1-yl)pyridin-3-yl)oxy)pyridin-4-yl)methyl)piperidin-4-yl)acetic acid

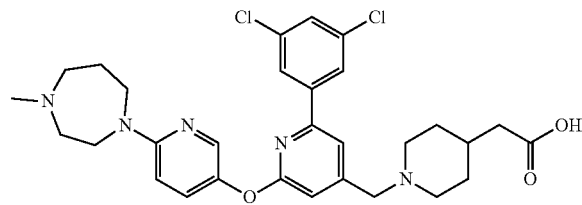 [SMILES: CN1CCCN(c2ccc(Oc3cc(CN4CCC(CC(=O)O)CC4)cc(-c4cc(Cl)cc(Cl)c4)n3)cn2)CC1]

To a solution of methyl 2-(1-((2-(3,5-dichlorophenyl)-6-((6-(4-methyl-1,4-diazepan-1-yl)pyridin-3-yl)oxy)pyridin-4-yl)methyl)piperidin-4-yl)acetate (250 mg, 0.360 mmol) in THF (5 mL) and water (1 mL) was added LiOH·H$_2$O (60.4 mg, 1.440 mmol). The mixture was stirred at 20° C. for 30 h. The mixture was acidified with 1 N HCl to pH=5-6 then concentrated. The residue was purified by preparative HPLC (MeCN/H$_2$O as eluents, acidic condition) and dried by lyophilization to yield a pale yellow solid of 2-(1-((2-(3,5-dichlorophenyl)-6-((6-(4-methyl-1,4-diazepan-1-yl)pyridin-3-yl)oxy)pyridin-4-yl)methyl) piperidin-4-yl)acetic acid, 4 hydrochloride (161.91 mg, 0.222 mmol, 61.6% yield): $^1$H NMR (400 MHz, CD$_3$OD) δ ppm 8.17-8.13 (m, 2H), 7.95 (s, 1H), 7.90 (d, J=1.6 Hz, 2H), 7.53 (s, 1H), 7.48-0.45 (m, 1H), 7.39 (s, 1H), 4.45 (s, 2H), 4.32-4.21 (m, 1H), 4.15-4.05 (m, 1H), 3.87 (s, 1H), 3.81-3.78 (m, 2H), 3.70-3.68 (m, 1H), 3.60-3.57 (m, 2H), 3.46-3.42 (m, 2H), 3.14 (t, J=12.0 Hz, 2H), 2.99 (s, 3H), 2.55-2.40 (m, 2H), 2.33-2.31 (m, 2H), 2.08-2.05 (m, 3H), 1.67-1.64 (m, 2H); ES-LCMS m/z 584.3, 586.3 [M+H]$^+$.

Example 157: N-((1-((2-(3,5-dichlorophenyl)-6-((6-(4-methylpiperazin-1-yl)pyridazin-3-yl)oxy)pyridin-4-yl)methyl)piperidin-4-yl)methyl)acetamide

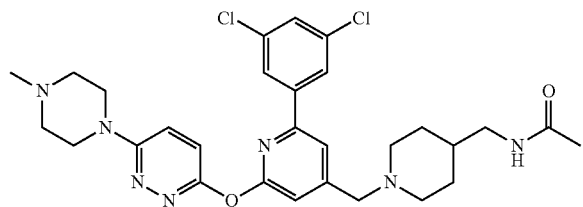 [SMILES: CC(=O)NCC1CCN(Cc2cc(Oc3ccc(N4CCN(C)CC4)nn3)nc(-c3cc(Cl)cc(Cl)c3)c2)CC1]

Step 1: N-((1-((2-((6-Chloropyridazin-3-yl)oxy)-6-(3,5-dichlorophenyl)pyridin-4-yl)methyl)piperidin-4-yl)methyl)acetamide

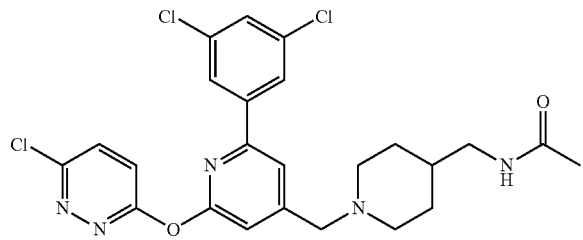 [SMILES: CC(=O)NCC1CCN(Cc2cc(Oc3ccc(Cl)nn3)nc(-c3cc(Cl)cc(Cl)c3)c2)CC1]

To a suspension of N-((1-((2-(3,5-dichlorophenyl)-6-hydroxypyridin-4-yl)methyl)piperidin-4-yl)methyl)acetamide (3 g, 6.39 mmol) and 3,6-dichloropyridazine (1.428 g, 9.59 mmol) in DMF (50 mL) was added Cs$_2$CO$_3$ (6.25 g, 19.18 mmol). The reaction mixture was stirred at 130° C. for 12 h then filtered and concentrated. The residue was purified by ISCO (DCM/MeOH=10/1, R$_f$=0.5) and the desired fraction was concentrated to yield a brown solid of N-((1-((2-((6-chloropyridazin-3-yl)oxy)-6-(3,5-dichlorophenyl)pyridin-4-yl)methyl)piperidin-4-yl)methyl)acetamide (700 mg, 1.259 mmol, 19.7% yield): $^1$H NMR (400 MHz, CDCl$_3$) δ ppm 7.73 (d, J=1.8 Hz, 2H), 7.59 (d, J=9.3 Hz, 1H), 7.55 (s, 1H), 7.40 (d, J=8.8 Hz, 1H), 7.36 (d, J=1.8 Hz, 1H), 7.17-7.12 (m, 1H), 5.56 (br. s, 1H), 3.57 (s, 2H), 3.21-3.12 (m, 3H), 2.94-2.84 (m, 3H), 2.08-2.03 (m, 2H), 2.00-1.98 (m, 3H), 1.58-1.48 (m, 1H), 1.35-1.26 (m, 2H); ES-LCMS m/z 520.2, 522.2 [M+H]$^+$.

Step 2: tert-Butyl 4-(6-((4-((4-(acetamidomethyl)piperidin-1-yl)methyl)-6-(3,5-dichlorophenyl)pyridin-2-yl)oxy)pyridazin-3-yl)piperazine-1-carboxylate

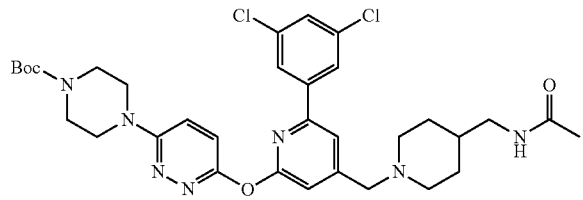 [SMILES: CC(=O)NCC1CCN(Cc2cc(Oc3ccc(N4CCN(C(=O)OC(C)(C)C)CC4)nn3)nc(-c3cc(Cl)cc(Cl)c3)c2)CC1]

To a suspension of N-((1-((2-((6-chloropyridazin-3-yl)oxy)-6-(3,5-dichlorophenyl)pyridin-4-yl)methyl)piperidin-4-yl)methyl)acetamide (540 mg, 0.971 mmol), tert-butyl piperazine-1-carboxylate (271 mg, 1.456 mmol) and Cs$_2$CO$_3$ (949 mg, 2.91 mmol) in THF (10 mL) stirred under N$_2$ atmosphere was added Xantphos (56.2 mg, 0.097 mmol) and Pd$_2$(dba)$_3$ (89 mg, 0.097 mmol). The reaction mixture was stirred at 80° C. for 12 h under N$_2$ atmosphere then filtered and concentrated to yield crude product which was purified by silica gel column chromatography (DCM/MeOH=1/0 to 20/1). All fractions found to contain product by TLC (DCM/MeOH=10/1, R$_f$=0.4) were combined and concentrated to yield a brown solid of tert-butyl 4-(6-((4-((4-(acetamidomethyl)piperidin-1-yl)methyl)-6-(3,5-dichlorophenyl)pyridin-2-yl)oxy)pyridazin-3-yl)piperazine-1-carboxylate (300 mg, 0.164 mmol, 16.9% yield): $^1$H NMR (400 MHz, CDCl$_3$) δ ppm 7.67 (br. s, 2H), 7.44-7.37 (m, 1H), 7.28 (d, J=6.2 Hz, 1H), 7.13-7.08 (m, 1H), 7.03 (d, J=10.6 Hz, 1H), 6.82 (d, J=9.7 Hz, 1H), 5.58-5.44 (m, 2H), 4.28 (d, J=12.8 Hz, 2H), 3.56-3.50 (m, 4H), 3.15-3.05 (m, 4H), 2.88-2.76 (m, 4H), 1.93 (d, J=3.5 Hz, 5H), 1.64 (br. s, 1H), 1.53-1.33 (m, 9H), 1.27-1.21 (m, 2H); ES-LCMS m/z 670.2, 672.3 [M+H]$^+$.

Step 3: N-((1-((2-(3,5-Dichlorophenyl)-6-((6-(piperazin-1-yl)pyridazin-3-yl)oxy)pyridin-4-yl)methyl)piperidin-4-yl)methyl)acetamide, 4 trifluoroacetic acid salt

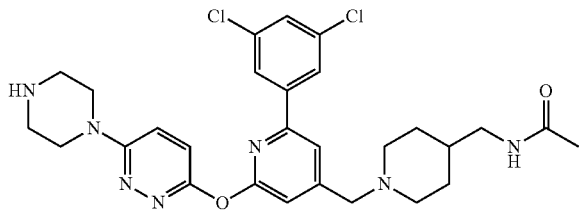 [SMILES: CC(=O)NCC1CCN(Cc2cc(Oc3ccc(N4CCNCC4)nn3)nc(-c3cc(Cl)cc(Cl)c3)c2)CC1]

To a suspension of tert-butyl 4-(6-((4-((4-(acetamidomethyl)piperidin-1-yl)methyl)-6-(3,5-dichlorophenyl)pyridin-2-yl)oxy)pyridazin-3-yl)piperazine-1-carboxylate (300 mg, 0.164 mmol) in DCM (10 mL) was added TFA (2.5 mL, 32.4 mmol). The reaction mixture was stirred at 15° C. for 5 h then concentrated to yield brown gum crude of N-((1-((2-(3,5-dichlorophenyl)-6-((6-(piperazin-1-yl)pyridazin-3-yl)oxy)pyridin-4-yl)methyl)piperidin-4-yl)methyl)acetamide, 4 trifluoroacetic acid salt (300 mg, 0.148 mmol, 91.0% yield): $^1$H NMR (400 MHz, CDCl$_3$) δ ppm 7.96-7.90 (m, 1H), 7.89-7.81 (m, 3H), 7.72-7.66 (m, 1H), 7.64 (s, 1H), 7.48 (br. s, 1H), 4.43 (br. s, 2H), 4.27 (d, J=13.2 Hz, 2H), 3.92 (br. s, 2H), 3.60 (br. s, 3H), 3.39 (br. s, 3H), 3.23-3.16 (m, 2H), 2.01 (br. s, 5H), 1.83-1.76 (m, 1H), 1.35 (br. s, 2H); ES-LCMS m/z 570.3, 572.3 [M+H]$^+$.

Step 4: N-((1-((2-(3,5-Dichlorophenyl)-6-((6-(4-methylpiperazin-1-yl)pyridazin-3-yl)oxy)pyridin-4-yl)methyl)piperidin-4-yl)methyl)acetamide

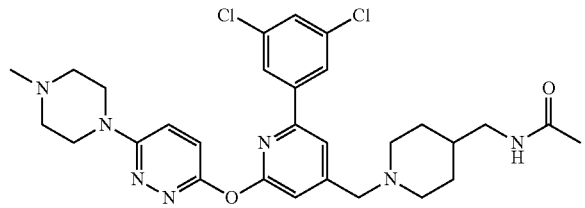 [SMILES: CC(=O)NCC1CCN(Cc2cc(Oc3ccc(N4CCN(C)CC4)nn3)nc(-c3cc(Cl)cc(Cl)c3)c2)CC1]

To a suspension of N-((1-((2-(3,5-dichlorophenyl)-6-((6-(piperazin-1-yl)pyridazin-3-yl)oxy)pyridin-4-yl)methyl)piperidin-4-yl)methyl)acetamide, 4 trifluoroacetic acid salt (300 mg, 0.148 mmol) and paraformaldehyde (44.6 mg, 1.484 mmol) in MeOH (10 mL) was added formic acid (0.017 mL, 0.445 mmol). The reaction mixture was stirred at 40° C. for 30 h. To this reaction mixture was added NaBH$_3$CN (28.0 mg, 0.445 mmol). This reaction mixture was stirred at 40° C. for 10 h then filtered. The filtrate was diluted with water (50 mL), extracted with DCM (30 mL×3). The combined organic layers were dried over Na$_2$SO$_4$, filtered and concentrated to yield crude product which was purified by preparative HPLC (MeCN/H$_2$O as eluents, neutral condition) and the desired fraction was lyophilized to yield a white solid of N-((1-((2-(3,5-dichlorophenyl)-6-((6-(4-methylpiperazin-1-yl)pyridazin-3-yl)oxy)pyridin-4-yl)methyl)piperidin-4-yl)methyl)acetamide (37.59 mg, 0.061 mmol, 40.9% yield): $^1$H NMR (400 MHz, CD$_3$OD) δ ppm 7.82-7.75 (m, 2H), 7.71 (s, 1H), 7.52 (d, J=9.7 Hz, 1H), 7.46-7.37 (m, 2H), 7.13 (s, 1H), 3.76-3.62 (m, 6H), 3.07 (d, J=6.6 Hz, 2H), 2.97 (d, J=11.5 Hz, 2H), 2.70 (t, J=4.9 Hz, 4H), 2.43 (s, 3H), 2.17-2.09 (m, 2H), 1.93 (s, 3H), 1.73 (d, J=12.3 Hz, 2H), 1.60-1.47 (m, 1H), 1.38-1.27 (m, 2H); ES-LCMS m/z 584.3, 586.3 [M+H]$^+$.

Example 158: 2-(1-((2-((2-(4-Aminopiperidin-1-yl)pyrimidin-5-yl)oxy)-6-(3,5-dichlorophenyl)pyridin-4-yl)methyl)piperidin-4-yl)acetic acid, 4 hydrochloride

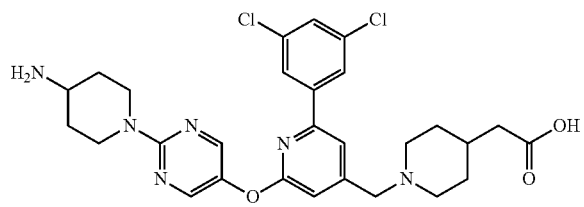 [SMILES: NC1CCN(c2ncc(Oc3cc(CN4CCC(CC(=O)O)CC4)cc(-c4cc(Cl)cc(Cl)c4)n3)cn2)CC1]

Step 1: Methyl 2-(1-((2-((2-(4-((tert-butoxycarbonyl)amino)piperidin-1-yl)pyrimidin-5-yl)oxy)-6-(3,5-dichlorophenyl)pyridin-4-yl)methyl)piperidin-4-yl)acetate

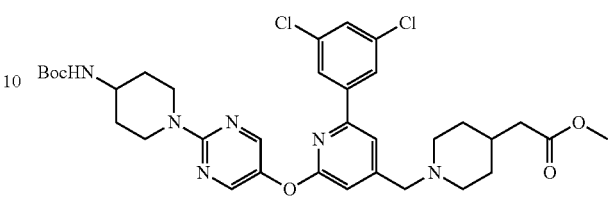

A mixture of (2-((2-(4-((tert-butoxycarbonyl)amino)piperidin-1-yl)pyrimidin-5-yl)oxy)-6-(3,5-dichlorophenyl)pyridin-4-yl)methyl methanesulfonate (300 mg, 0.336 mmol), methyl 2-(piperidin-4-yl)acetate, hydrochloride (163 mg, 0.672 mmol) and K$_2$CO$_3$ (139 mg, 1.009 mmol) in DMF (10 mL) was heated to 90° C. for 10 h under N$_2$ atmosphere. The reaction mixture was filtered and concentrated to yield the crude product which was purified by silica gel column chromatography (DCM/MeOH=1/0 to 9/1). All fractions found to contain product by TLC (DCM/MeOH=10/1, R$_f$=0.5) were combined and concentrated to yield oil of methyl 2-(1-((2-((2-(4-((tert-butoxycarbonyl)amino)piperidin-1-yl)pyrimidin-5-yl)oxy)-6-(3,5-dichlorophenyl)pyridin-4-yl)methyl)piperidin-4-yl)acetate (200 mg, 0.265 mmol, 79.0% yield): $^1$H NMR (400 MHz, CDCl$_3$) δ ppm 8.33-8.20 (m, 2H), 7.74-7.69 (m, 2H), 7.41-7.37 (m, 1H), 7.35-7.28 (m, 1H), 6.92-6.85 (m, 1H), 4.62 (d, J=13.7 Hz, 2H), 4.47 (br. s, 1H), 3.81-3.69 (m, 1H), 3.65 (s, 2H), 3.50 (s, 2H), 3.09 (t, J=11.5 Hz, 2H), 2.84 (d, J=11.5 Hz, 2H), 2.28-2.23 (m, 2H), 2.08-1.98 (m, 4H), 1.84-1.76 (m, 1H), 1.74-1.63 (m, 4H), 1.48-1.42 (m, 9H), 1.41-1.32 (m, 3H); ES-LCMS m/z 685.2, 687.2 [M+H]$^+$.

Step 2: 2-(1-((2-((2-(4-((tert-Butoxycarbonyl)amino)piperidin-1-yl)pyrimidin-5-yl)oxy)-6-(3,5-dichlorophenyl)pyridin-4-yl)methyl)piperidin-4-yl)acetic acid

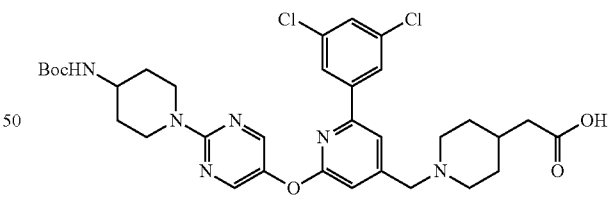

A mixture of methyl 2-(1-((2-((2-(4-((tert-butoxycarbonyl)amino)piperidin-1-yl)pyrimidin-5-yl)oxy)-6-(3,5-dichlorophenyl)pyridin-4-yl)methyl)piperidin-4-yl)acetate (200 mg, 0.265 mmol) and NaOH (21.23 mg, 0.531 mmol) in MeOH (10 mL) and H$_2$O (1 mL) was stirred at 25° C. for 10 h. The reaction was adjusted pH to 7 with 1 N HCl then extracted with DCM (50 mL×3). The organic layer was washed by brine (30 mL), dried over Na$_2$SO$_4$, filtered and concentrated to yield a yellow solid of 2-(1-((2-((2-(4-((tert-butoxycarbonyl)amino)piperidin-1-yl)pyrimidin-5-yl)oxy)-6-(3,5-dichlorophenyl)pyridin-4-yl)methyl)piperidin-4-yl)acetic acid (230 mg, 0.240 mmol, 90.0% yield): $^1$H NMR (400 MHz, CDCl$_3$) δ ppm 8.28-8.17 (m, 1H), 8.08 (s, 2H), 7.12 (br. s, 2H), 6.93 (s, 1H), 6.71 (br. s, 1H), 4.48 (d, J=12.8 Hz, 2H), 3.66-3.58 (m, 2H), 3.27 (br. s, 2H), 3.00-2.88 (m, 3H), 2.68 (br. s, 4H), 1.97 (br. s, 3H), 1.86 (br. s, 3H), 1.55 (d, J=8.4 Hz, 3H), 1.42-1.33 (m, 9H); ES-LCMS m/z 671.2, 673.2 [M+H]$^+$.

Step 3: 2-(1-((2-((2-(4-Aminopiperidin-1-yl)pyrimidin-5-yl)oxy)-6-(3,5-dichlorophenyl)pyridin-4-yl)methyl)piperidin-4-yl)acetic acid, 4 hydrochloride

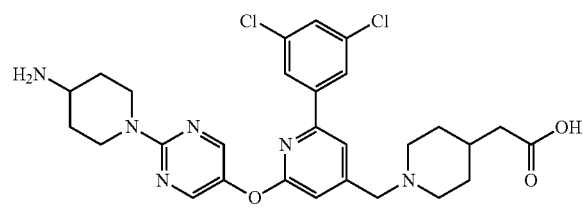 [SMILES: NC1CCN(c2ncc(Oc3cc(CN4CCC(CC(=O)O)CC4)cc(-c4cc(Cl)cc(Cl)c4)n3)cn2)CC1]

A mixture of 2-(1-((2-((2-(4-((tert-butoxycarbonyl)amino)piperidin-1-yl)pyrimidin-5-yl)oxy)-6-(3,5-dichlorophenyl)pyridin-4-yl)methyl)piperidin-4-yl)acetic acid (230 mg, 0.240 mmol) and TFA (2 mL, 26.0 mmol) in DCM (10 mL) was stirred at 25° C. for 0.5 h. The reaction mixture was filtered and concentrated to yield the crude product which was purified by preparative HPLC (MeCN/H$_2$O as eluents, acidic condition) and dried by lyophilization to yield a pale yellow solid of 2-(1-((2-((2-(4-aminopiperidin-1-yl)pyrimidin-5-yl)oxy)-6-(3,5-dichlorophenyl)pyridin-4-yl)methyl)piperidin-4-yl)acetic acid, 4 hydrochloride (76.54 mg, 0.104 mmol, 43.3% yield): $^1$H NMR (400 MHz, CD$_3$OD) δ ppm 8.61 (s, 2H), 8.10-8.01 (m, 1H), 7.92 (d, J=1.0 Hz, 2H), 7.55-7.48 (m, 1H), 7.43 (s, 1H), 4.83 (d, J=13.6 Hz, 2H), 4.66-4.41 (m, 2H), 3.68-3.48 (m, 3H), 3.31-3.12 (m, 4H), 2.41-2.26 (m, 2H), 2.20 (d, J=12.0 Hz, 2H), 2.14-1.98 (m, 3H), 1.84-1.64 (m, 4H); ES-LCMS m/z 571.2, 573.2 [M+H]$^+$.

Example 159: (S)-2-(1-((2-(3,5-Dichlorophenyl)-6-((2-(3-methylpiperazin-1-yl)pyrimidin-5-yl)oxy)pyridin-4-yl)methyl)piperidin-4-yl)acetic acid, 4 hydrochloride

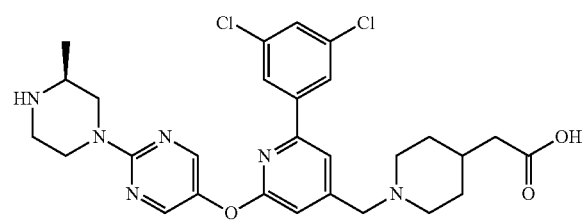 [SMILES: C[C@H]1CN(c2ncc(Oc3cc(CN4CCC(CC(=O)O)CC4)cc(-c4cc(Cl)cc(Cl)c4)n3)cn2)CCN1]

Step 1: (S)-tert-Butyl 4-(5-((6-(3,5-dichlorophenyl)-4-((4-(2-methoxy-2-oxoethyl)piperidin-1-yl)methyl)pyridin-2-yl)oxy)pyrimidin-2-yl)-2-methylpiperazine-1-carboxylate

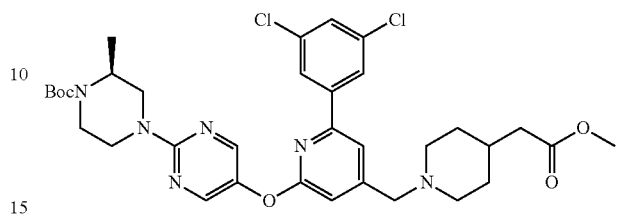

To a solution of (S)-tert-butyl 4-(5-((6-(3,5-dichlorophenyl)-4-(((methylsulfonyl)oxy)methyl)pyridin-2-yl)oxy)pyrimidin-2-yl)-2-methylpiperazine-1-carboxylate (1 g, 1.078 mmol) in DMF (30 mL) was added K$_2$CO$_3$ (0.447 g, 3.23 mmol) and methyl 2-(piperidin-4-yl)acetate (0.282 g, 1.616 mmol). The reaction was stirred at 20° C. for 2 h then concentrated and purified by silica gel column chromatography (PE/EtOAc=1/1). All fractions found to contain product by TLC (PE/EtOAc=1/1, R$_f$=0.5) were combined and concentrated to yield a yellow solid of (S)-tert-butyl 4-(5-((6-(3,5-dichlorophenyl)-4-((4-(2-methoxy-2-oxoethyl)piperidin-1-yl)methyl)pyridin-2-yl)oxy)pyrimidin-2-yl)-2-methylpiperazine-1-carboxylate (1 g, 0.948 mmol, 88.0% yield): $^1$H NMR (400 MHz, CD$_3$OD) δ ppm 8.31 (s, 2H), 7.80 (s, 2H), 7.62 (s, 1H), 7.41 (s, 1H), 7.06-7.04 (m, 1H), 7.03 (s, 1H), 4.63-4.54 (m, 2H), 4.32-4.29 (m, 1H), 3.82-3.78 (m, 1H), 3.66 (s, 3H), 3.64 (s, 2H), 3.29-3.22 (m, 3H), 3.11-2.80 (m, 4H), 2.29 (d, J=6.5 Hz, 2H), 2.13-2.10 (m, 2H), 1.76-1.73 (m, 3H), 1.50 (s, 9H), 1.18 (d, J=6.5 Hz, 3H); ES-LCMS m/z 685.3, 687.3 [M+H]$^+$.

Step 2: (S)-Methyl 2-(1-((2-(3,5-dichlorophenyl)-6-((2-(3-methylpiperazin-1-yl)pyrimidin-5-yl)oxy)pyridin-4-yl)methyl)piperidin-4-yl)acetate

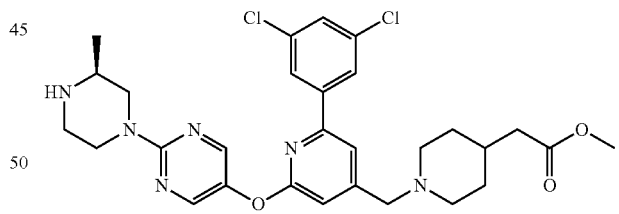

To a mixture of (S)-tert-butyl 4-(5-((6-(3,5-dichlorophenyl)-4-((4-(2-methoxy-2-oxoethyl)piperidin-1-yl)methyl)pyridin-2-yl)oxy)pyrimidin-2-yl)-2-methylpiperazine-1-carboxylate (1 g, 0.948 mmol) in EtOAc (20 mL) was added HCl solution (4.0 M in EtOAc, 5 mL, 20.0 mmol). The reaction was stirred at 20° C. for 0.5 h then saturated aqueous NaHCO$_3$ solution (200 mL) was added and extracted with DCM (200 mL×2). The combined organic layers were dried over Na$_2$SO$_4$, filtered and concentrated to yield a yellow solid of (S)-methyl 2-(1-((2-(3,5-dichlorophenyl)-6-((2-(3-methylpiperazin-1-yl)pyrimidin-5-yl)oxy)pyridin-4-yl)methyl)piperidin-4-yl)acetate (700 mg, 0.921 mmol, 97.0% yield): $^1$H NMR (400 MHz, CD$_3$OD) δ ppm 8.53 (br. s, 2H), 8.00 (s, 1H), 7.90 (br. s, 2H), 7.51 (m, 1H), 7.38 (m, 1H), 4.86 (m, 2H), 4.47 (s, 2H), 3.68-3.48 (m, 10H), 3.28-3.22 (m, 4H), 2.03 (m, 3H), 1.78-1.58 (m, 2H), 1.25-1.17 (m, 3H); ES-LCMS m/z 585.3, 587.3 [M+H]+.

Step 3: (S)-2-(1-((2-(3,5-Dichlorophenyl)-6-((2-(3-methylpiperazin-1-yl)pyrimidin-5-yl)oxy)pyridin-4-yl)methyl)piperidin-4-yl)acetic acid, 4 hydrochloride

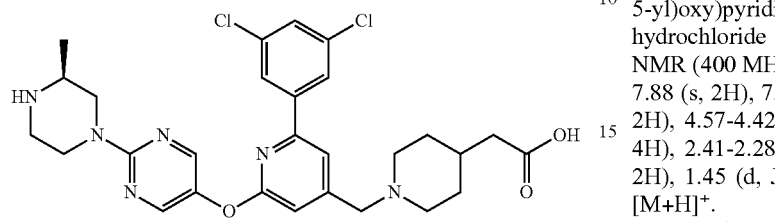

To a mixture of (S)-methyl 2-(1-((2-(3,5-dichlorophenyl)-6-((2-(3-methylpiperazin-1-yl)pyrimidin-5-yl)oxy)pyridin-4-yl)methyl)piperidin-4-yl)acetate (400 mg, 0.526 mmol) in MeOH (10 mL) and water (2 mL) was added NaOH (63.1 mg, 1.578 mmol). The reaction was stirred at 20° C. for 5 h then concentrated and purified by preparative HPLC (MeCN/H2O as eluents, acidic condition) and dried by lyophilization to yield a white solid of (S)-2-(1-((2-(3,5-dichlorophenyl)-6-((2-(3-methylpiperazin-1-yl)pyrimidin-5-yl)oxy)pyridin-4-yl)methyl)piperidin-4-yl)acetic acid, 4 hydrochloride (75.97 mg, 0.105 mmol, 19.9% yield): 1H NMR (400 MHz, CD3OD) δ ppm 8.50 (s, 2H), 8.03 (s, 1H), 7.88 (s, 2H), 7.48 (s, 1H), 7.39 (s, 1H), 4.85 (d, J=13.6 Hz, 2H), 4.57-4.42 (m, 2H), 3.63-3.44 (m, 5H), 3.29-3.16 (m, 4H), 2.41-2.28 (m, 2H), 2.17-2.01 (m, 3H), 1.90-1.59 (m, 2H), 1.45 (d, J=6.5 Hz, 3H); ES-LCMS m/z 571.3, 573.3 [M+H]+.

Examples 160-165 (Table 8) were prepared by procedures analogous to those described for example 159

TABLE 8

| Example | Structure/Name | 1H NMR | LCMS |
|---|---|---|---|
| 160 | ![structure] 2-(1-((2-(3,5-dichlorophenyl)-6-((2-(3,3-dimethylpiperazin-1-yl)pyrimidin-5-yl)oxy)pyridin-4-yl)methyl)piperidin-4-yl)acetic acid | 1H NMR (400 MHz, CD3OD) δ ppm 8.42 (s, 2H), 7.93 (s, 1H), 7.86 (d, J = 1.3 Hz, 2H), 7.49 (s, 1H), 7.32 (s, 1H), 4.43 (s, 2H), 4.15 (t, J = 5.3 Hz, 2H), 3.99 (s, 2H), 3.58 (d, J = 12.3 Hz, 2H), 3.40-3.34 (m, 2H), 3.14 (t, J = 12.3 Hz, 2H), 2.36-2.28 (m, 2H), 2.06 (d, J = 14.1 Hz, 3H), 1.71-1.57 (m, 2H), 1.45 (s, 6H) | ES-LCMS m/z 585.3, 587.3 [M + H]+. |
| 161 | ![structure] 2-(1-((2-(3,5-dichlorophenyl)-6-((2-(hexahydropyrrolo[3,4-c]pyrrol-2(1H)-yl)pyrimidin-5-yl)oxy)pyridin-4-yl)methyl)piperidin-4-yl)acetic acid | 1H NMR (400 MHz, D2O) δ ppm 8.30 (s, 2H), 7.54 (br. s, 2H), 7.49 (br. s, 1H), 7.34 (br. s, 1H), 7.05 (br. s, 1H), 4.26 (br. s, 2H), 3.70 (br. s, 2H), 3.52 (d, J = 11.0 Hz, 4H), 3.44 (d, J = 11.9 Hz, 2H), 3.27-3.15 (m, 4H), 3.02-2.94 (m, 2H), 2.57 (s, 1H), 2.25 (d, J = 6.2 Hz, 2H), 1.91 (m, 2H), 1.41 (m, 2H) | ES-LCMS m/z 583.3, 585.2 [M + H]+. |

| Example | Structure/Name | ¹H NMR | LCMS |
|---|---|---|---|
| 162 | 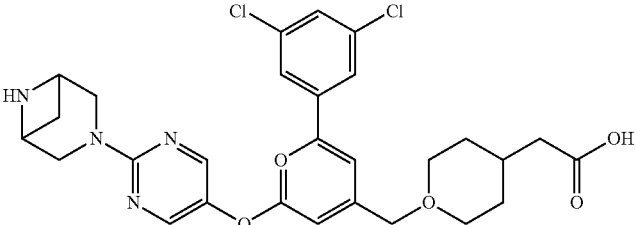<br>2-(1-((2-((2-(3,6-diazabicyclo[3.1.1]heptan-3-yl)pyrimidin-5-yl)oxy)-6-(3,5-dichlorophenyl)pyridin-4-yl)methyl)piperidin-4-yl)acetic acid | ¹H NMR (400 MHz, CD₃OD) δ ppm 8.50 (s, 2H), 7.91 (s, 1H), 7.88 (d, J = 1.8 Hz, 2H), 7.51 (t, J = 1.8 Hz, 1H), 7.33 (s, 1H), 4.62-4.53 (m, 2H), 4.44 (s, 2H), 4.28-4.20 (m, 2H), 4.16-4.08 (m, 2H), 3.59 (d, J = 12.3 Hz, 2H), 3.21-3.03 (m, 3H), 2.33 (d, J = 6.6 Hz, 2H), 2.14-1.99 (m, 4H), 1.69-1.57 (m, 2H) | ES-LCMS m/z 569.3, 571.2 [M + H]⁺. |
| 163 | 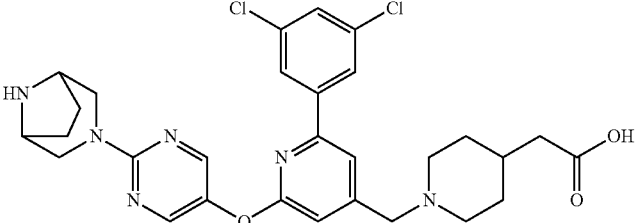<br>2-(1-((2-((2-(3,8-diazabicyclo[3.2.1]octan-3-yl)pyrimidin-5-yl)oxy)-6-(3,5-dichlorophenyl)pyridin-4-yl)methyl)piperidin-4-yl)acetic acid | ¹H NMR (400 MHz, CD₃OD) δ ppm 8.44 (s, 2H), 7.93 (br. s, 1H), 7.89 (s, 2H), 7.53 (s, 1H), 7.33 (s, 1H), 4.72 (d, J = 14.1 Hz, 2H), 4.46 (br. s, 2H), 4.23 (br. s, 2H), 3.61 (d, J = 10.5 Hz, 2H), 3.40 (d, J = 14.6 Hz, 2H), 3.22-3.09 (m, 2H), 2.35 (d, J = 6.0 Hz, 2H), 2.19-2.01 (m, 7H), 1.64-1.62 (m, 2H) | ES-LCMS m/z 583.4, 585.3 [M + H]⁺. |
| 164 | 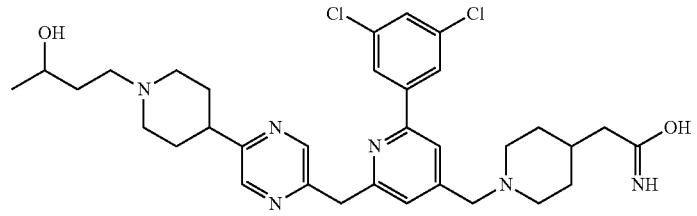<br>2-(1-((2-((2-(4,7-diazaspiro[2.5]octan-7-yl)pyrimidin-5-yl)oxy)-6-(3,5-dichlorophenyl)pyridin-4-yl)methyl)piperidin-4-yl)acetic acid | ¹H NMR (400 MHz, CD₃OD) δ ppm 8.42 (s, 2H), 7.90 (s, 1H), 7.87 (d, J = 1.8 Hz, 2H), 7.51 (t, J = 1.8 Hz, 1H), 7.30 (s, 1H), 4.43 (s, 2H), 4.29-4.18 (m, 2H), 4.08 (s, 2H), 3.59 (d, J = 12.3 Hz, 2H), 3.47-3.39 (m, 2H), 3.14 (t, J = 12.1 Hz, 2H), 2.33 (d, J = 6.6 Hz, 2H), 2.07 (d, J = 13.2 Hz, 3H), 1.66-1.55 (m, 2H), 1.16-1.01 (m, 4H) | ES-LCMS m/z 583.2, 585.2 [M + H]⁺. |
| 165 | 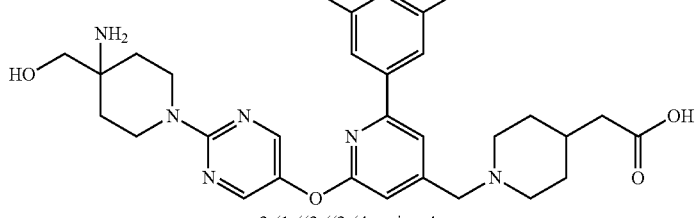<br>2-(1-((2-((2-(4-amino-4-(hydroxymethyl)piperidin-1-yl)pyrimidin-5-yl)oxy)-6-(3,5-dichlorophenyl)pyridin-4-yl)methyl)piperidin-4-yl)acetic acid | ¹H NMR (400 MHz, CD₃OD) δ ppm 8.65 (s, 2H), 8.00 (s, 1H), 7.90 (d, J = 1.8 Hz, 2H), 7.49 (s, 1H), 7.40 (s, 1H), 4.45 (s, 2H), 4.31-4.23 (m, 2H), 3.81-3.73 (m, 4H), 3.56 (d, J = 11.2 Hz, 2H), 3.14 (t, J = 12.0 Hz, 2H), 2.36-2.28 (m, 2H), 2.11-2.02 (m, 4H), 2.00-1.87 (m, 3H), 1.74-1.61 (m, 2H) | ES-LCMS m/z: 601.4, 603.3 [M + H]⁺. |

Example 166: 2-(1-((2-((6-(1,4-Diazepan-1-yl)pyridin-3-yl)oxy)-6-(3,5-dichlorophenyl)pyridin-4-yl)methyl)piperidin-4-yl)acetic acid

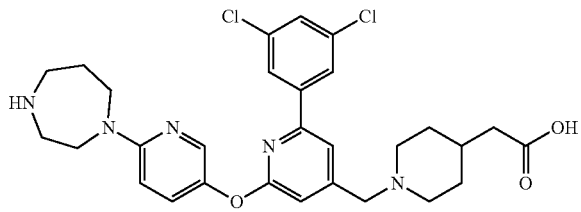 [SMILES: O=C(O)CC1CCN(Cc2cc(Oc3ccc(N4CCCNCC4)nc3)nc(-c3cc(Cl)cc(Cl)c3)c2)CC1]

To a solution of methyl 2-(1-((2-((6-(1,4-diazepan-1-yl)pyridin-3-yl)oxy)-6-(3,5-dichlorophenyl)pyridin-4-yl)methyl)piperidin-4-yl)acetate (230 mg, 0.326 mmol) in THF (2 mL) and H$_2$O (2 mL) was added LiOH·H$_2$O (54.7 mg, 1.303 mmol). The mixture was stirred at 20° C. for 10 h then acidified with 1 N HCl to pH=5-6 then concentrated. The residue was purified by preparative HPLC (MeCN/H$_2$O as eluents, acidic condition) and dried by lyophilization to yield a white solid of 2-(1-((2-((6-(1,4-diazepan-1-yl)pyridin-3-yl)oxy)-6-(3,5-dichlorophenyl)pyridin-4-yl)methyl)piperidin-4-yl)acetic acid, 4 hydrochloride (114.38 mg, 0.160 mmol, 49.0% yield): $^1$H NMR (400 MHz, CD$_3$OD) δ ppm 8.19-8.17 (m, 2H), 7.98 (s, 1H), 7.91 (s, 2H), 7.53-7.51 (m, 2H), 7.41 (s, 1H), 4.46 (s, 2H), 4.18-4.15 (m, 2H), 3.92-3.89 (m, 2H), 3.63-3.57 (m, 4H), 3.47-3.45 (m, 2H), 3.15 (t, J=12.0 Hz, 2H), 2.37-2.32 (m, 4H), 2.07-2.04 (m, 3H), 1.69-1.66 (m, 2H); ES-LCMS m/z 570.3, 572.3 [M+H]$^+$.

Example 167: N-((1-((3',5'-Dichloro-5-((2-(4-(2-(methylsulfonyl)ethyl)piperazin-1-yl)pyrimidin-5-yl)oxy)-[1,1'-biphenyl]-3-yl)methyl)piperidin-4-yl)methyl)acetamide To a mixture of tert-butyl 4-(5-bromopyrimidin-2-yl)piperazine-1-carboxylate (0.756 g, 1.983 mmol) and N-((1-((3',5'-dichloro-5-hydroxy-[1,1'-biphenyl]-3-yl)methyl)piperidin-4-yl)methyl)acetamide, hydrochloride (1 g, 1.803 mmol) in DMSO (10 mL) was added CuI (0.017 g, 0.090 mmol), picolinic acid (0.011 g, 0.090 mmol) and K$_3$PO$_4$ (1.148 g, 5.41 mmol). The mixture was stirred at 130° C. for 10 h. Saturated aqueous NH$_4$Cl (40 mL) was added and the solution was concentrated. The crude product was distributed between DCM (500 mL) and saturated aqueous NaHCO$_3$ (300 mL) solution, extracted with DCM (500 mL×2). The combined organic extract was washed with brine (200 mL), dried over Na$_2$SO$_4$, filtered and concentrated. The crude material was purified by silica gel (DCM/MeOH=1/0 to 1/1). All fractions found to contain product by TLC (DCM/MeOH=15/1, R$_f$=0.5) were combined and concentrated to yield brown oil of tert-butyl 4-(5-((5-((4-(acetamidomethyl)piperidin-1-yl)methyl)-3',5'-dichloro-[1,1'-biphenyl]-3-yl)oxy)pyrimidin-2-yl)piperazine-1-carboxylate (1.4 g, 1.673 mmol, 93.0% yield): $^1$H NMR (400 MHz, CD$_3$OD) δ ppm 8.26 (s, 2H), 7.56 (d, J=1.5 Hz, 2H), 7.43 (s, 1H), 7.33 (s, 1H), 7.15 (s, 1H), 6.99 (s, 1H), 3.83-3.79 (m, 4H), 3.56 (s, 2H), 3.53 (br. s, 4H), 3.07 (d, J=7.0 Hz, 2H), 2.94 (d, J=11.5 Hz, 2H), 2.06 (t, J=10.8 Hz, 2H), 1.94 (s, 3H), 1.72 (d, J=12.5 Hz, 2H), 1.51 (s, 10H), 1.33-1.23 (m, 2H); ES-LCMS m/z 669.4, 671.3 [M+H]$^+$.

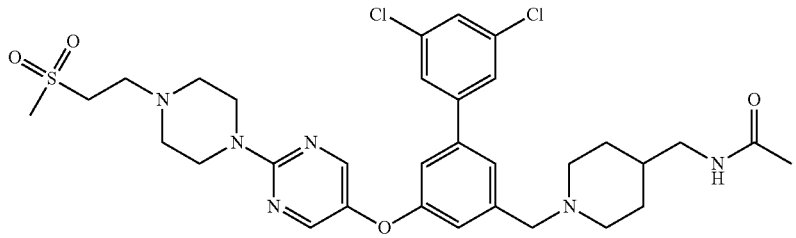 [SMILES: CC(=O)NCC1CCN(Cc2cc(Oc3cnc(N4CCN(CCS(C)(=O)=O)CC4)nc3)cc(-c3cc(Cl)cc(Cl)c3)c2)CC1]

Step 1: tert-Butyl 4-(5-((5-((4-(acetamidomethyl)piperidin-1-yl)methyl)-3',5'-dichloro-[1,1'-biphenyl]-3-yl)oxy)pyrimidin-2-yl)piperazine-1-carboxylate Step 2: N-((1-((3',5'-Dichloro-5-((2-(piperazin-1-yl)pyrimidin-5-yl)oxy)-[1,1'-biphenyl]-3-yl)methyl)piperidin-4-yl)methyl)acetamide, 3 hydrochloride

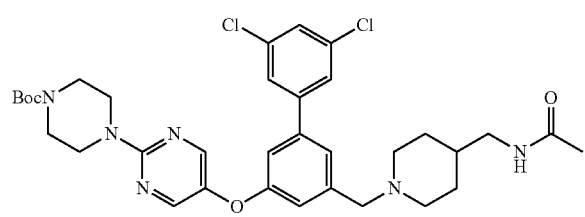
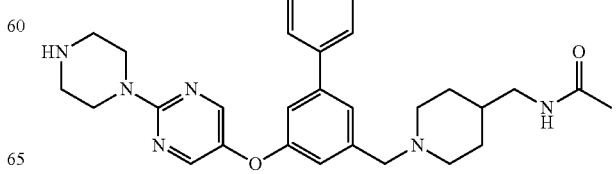

To a mixture of tert-butyl 4-(5-((5-((4-(acetamidomethyl) piperidin-1-yl)methyl)-3',5'-dichloro-[1,1'-biphenyl]-3-yl) oxy)pyrimidin-2-yl)piperazine-1-carboxylate (1.4 g, 1.673 mmol) in DCM (8 mL) was added HCl solution (4.0 M in EtOAc, 5 mL, 20 mmol). The reaction was stirred at 15° C. for 0.5 h under $N_2$ atmosphere then concentrated to yield brown oil of N-((1-((3',5'-dichloro-5-((2-(piperazin-1-yl)pyrimidin-5-yl)oxy)-[1,1 biphenyl]-3-yl)methyl)piperidin-4-yl)methyl)acetamide, 3 hydrochloride (1.4 g, 1.547 mmol, 92.0% yield): $^1$H NMR (400 MHz, $CD_3OD$) δ ppm 8.61 (s, 2H), 7.74-7.67 (m, 3H), 7.56-7.48 (m, 3H), 4.39 (s, 2H), 4.22 (br. s, 4H), 3.54 (d, J=10.5 Hz, 2H), 3.46 (br. s, 4H), 3.24 (d, J=5.5 Hz, 2H), 3.14-3.04 (m, 2H), 2.15 (s, 3H), 1.99 (d, J=13.6 Hz, 3H), 1.66 (d, J=12.5 Hz, 2H); ES-LCMS m/z 569.3, 571.3 $[M+H]^+$.

Step 3: N-((1-((3',5'-Dichloro-5-((2-(4-(2-(methylsulfonyl)ethyl)piperazin-1-yl)pyrimidin-5-yl)oxy)-[1,1'-biphenyl]-3-yl)methyl)piperidin-4-yl)methyl) acetamide

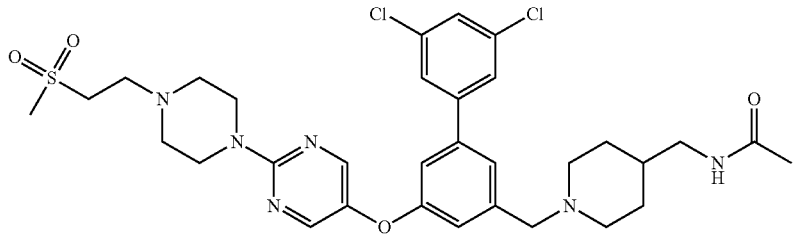 [SMILES: CC(=O)NCC1CCN(Cc2cc(Oc3cnc(N4CCN(CCS(C)(=O)=O)CC4)nc3)cc(-c3cc(Cl)cc(Cl)c3)c2)CC1]

To a mixture of N-((1-((3',5'-dichloro-5-((2-(piperazin-1-yl)pyrimidin-5-yl)oxy)-[1,1'-biphenyl]-3-yl)methyl)piperidin-4-yl)methyl)acetamide, 3 hydrochloride (200 mg, 0.221 mmol) in DCM (8 mL) was added (methylsulfonyl)ethene (70.4 mg, 0.663 mmol) and DIEA (114 mg, 0.884 mmol). The reaction was stirred at 15° C. for 10 h under $N_2$ atmosphere then filtered and concentrated. The mixture was purified by preparative HPLC (MeCN/$H_2O$ as eluents, basic condition) and dried by lyophilization to yield an off white solid of N-((1-((3',5'-dichloro-5-((2-(4-(2-(methylsulfonyl) ethyl)piperazin-1-yl)pyrimidin-5-yl)oxy)-[1,1'-biphenyl]-3-yl)methyl)piperidin-4-yl)methyl)acetamide (15.19 mg, 0.022 mmol, 9.8% yield): $^1$H NMR (400 MHz, $CD_3OD$) δ ppm 8.26 (s, 2H), 7.60 (d, J=1.5 Hz, 2H), 7.46 (s, 1H), 7.35 (s, 1H), 7.19 (s, 1H), 7.00 (s, 1H), 3.85 (br. s, 4H), 3.58 (br. s, 2H), 3.39-3.36 (m, 2H), 3.11 (s, 3H), 3.07 (d, J=6.5 Hz, 2H), 3.01-2.87 (m, 4H), 2.63 (t, J=4.8 Hz, 4H), 2.16-2.00 (m, 2H), 1.95 (s, 3H), 1.73 (d, J=12.0 Hz, 2H), 1.54 (br. s, 1H), 1.34-1.22 (m, 2H); ES-LCMS m/z 675.2, 677.2 $[M+H]^+$.

Example 168: 3-(4-(5-((5-((4-(Acetamidomethyl) piperidin-1-yl)methyl)-3',5'-dichloro-[1,1'-biphenyl]-3-yl)oxy)pyrimidin-2-yl)piperazin-1-yl)propanoic acid, 3 hydrochloride

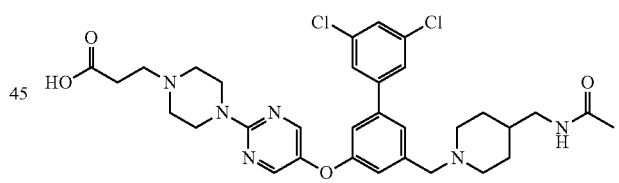

Step 1: Ethyl 3-(4-(5-((5-((4-(acetamidomethyl) piperidin-1-yl)methyl)-3',5'-dichloro-[1,1'-biphenyl]-3-yl)oxy)pyrimidin-2-yl)piperazin-1-yl)propanoate

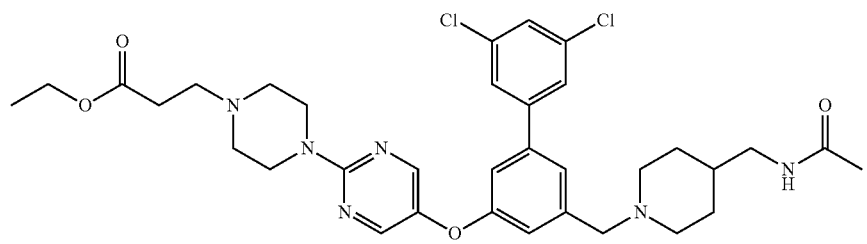

To a mixture of N-((1-((3',5'-dichloro-5-((2-(piperazin-1-yl)pyrimidin-5-yl)oxy)-[1,1'-biphenyl]-3-yl)methyl)piperidin-4-yl)methyl)acetamide, 3 hydrochloride (300 mg, 0.354 mmol) in MeCN (5 mL) was added DIEA (228 mg, 1.768 mmol) and ethyl 3-bromopropanoate (0.050 mL, 0.389 mmol). The reaction was stirred at 80° C. for 10 h under N₂ atmosphere then concentrated to yield brown oil of ethyl 3-(4-(5-((5-((4-(acetamidomethyl)piperidin-1-yl)methyl)-3',5'-dichloro-[1,1'-biphenyl]-3-yl)oxy)pyrimidin-2-yl)piperazin-1-yl)propanoate (300 mg, 0.269 mmol, 76.0% yield): ¹H NMR (400 MHz, CD₃OD) δ ppm 8.35 (s, 2H), 7.69 (d, J=1.5 Hz, 2H), 7.60 (s, 1H), 7.51 (s, 1H), 7.42 (s, 1H), 7.29 (s, 1H), 4.35 (br. s, 2H), 4.25-4.18 (m, 2H), 3.55-3.42 (m, 4H), 3.32-3.21 (m, 4H), 3.13-3.10 (m, 6H), 2.87-2.78 (m, 4H), 1.97 (s, 6H), 1.56 (t, J=6.1 Hz, 2H), 1.26-1.23 (m, 3H); ES-LCMS m/z 669.3, 671.4 [M+H]⁺.

Step 2: 3-(4-(5-((5-((4-(Acetamidomethyl)piperidin-1-yl)methyl)-3',5'-dichloro-[1,1'-biphenyl]-3-yl)oxy)pyrimidin-2-yl)piperazin-1-yl)propanoic acid, 3 hydrochloride

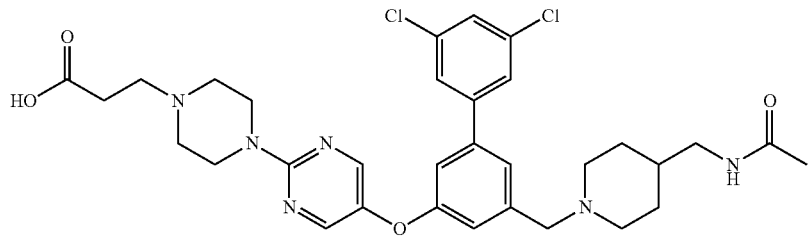 [SMILES: CC(=O)NCC1CCN(Cc2cc(Oc3cnc(N4CCN(CCC(=O)O)CC4)nc3)cc(-c3cc(Cl)cc(Cl)c3)c2)CC1]

To a mixture of ethyl 3-(4-(5-((5-((4-(acetamidomethyl)piperidin-1-yl)methyl)-3',5'-dichloro-[1,1'-biphenyl]-3-yl)oxy)pyrimidin-2-yl)piperazin-1-yl)propanoate (300 mg, 0.358 mmol) in MeOH (5 mL) and H₂O (3 mL) was added LiOH·H₂O (75 mg, 1.792 mmol). The reaction was stirred at 15° C. for 10 min then concentrated and purified by preparative HPLC (MeCN/H₂O as eluents, acidic condition) and dried by lyophilization to yield a yellow solid of 3-(4-(5-((5-((4-(acetamidomethyl)piperidin-1-yl)methyl)-3',5'-dichloro-[1,1'-biphenyl]-3-yl)oxy)pyrimidin-2-yl)piperazin-1-yl)propanoic acid, 3 hydrochloride (28.43 mg, 0.037 mmol, 10.3% yield): ¹H NMR (400 MHz, CD₃OD) δ ppm 8.41 (s, 2H), 7.67 (d, J=1.5 Hz, 2H), 7.57 (s, 1H), 7.52 (s, 1H), 7.41 (s, 1H), 7.33 (br. s, 1H), 4.36 (s, 2H), 3.70 (d, J=12.0 Hz, 2H), 3.58-3.39 (m, 6H), 3.28 (br. s, 4H), 3.14 (d, J=6.5 Hz, 2H), 3.09-2.98 (m, 2H), 2.94 (t, J=6.8 Hz, 2H), 2.02-1.94 (m, 5H), 1.85 (br. s, 1H), 1.63-1.47 (m, 2H); ES-LCMS m/z 641.3, 643.3 [M+H]⁺.

Examples 169-177 (Table 9) were prepared by procedures analogous to those described for example 168.

TABLE 9

| Example | Structure/Name | ¹H NMR | LCMS |
|---|---|---|---|
| 169 | ![structure]<br><br>3-(4-(6-((4-((4-(acetamidomethyl)piperidin-1-yl)methyl)-6-(3,5-dichlorophenyl)pyridin-2-yl)oxy)pyridazin-3-yl)piperazin-1-yl)propanoic acid | ¹H NMR (400 MHz, CD₃OD) δ ppm 7.80 (d, J = 1.8 Hz, 2H), 7.73 (s, 1H), 7.57 (d, J = 9.7 Hz, 1H), 7.48-7.42 (m, 2H), 7.15 (s, 1H), 4.64 (br.s, 2H), 3.81 (br. s, 4H), 3.70 (s, 2H), 3.12-3.03 (m, 6H), 2.99 (d, J = 11.9 Hz, 2H), 2.58 (t, J = 6.8 Hz, 2H), 2.17 (t, J = 11.0 Hz, 2H), 1.93 (s, 3H), 1.75 (d, J = 13.2 Hz, 2H), 1.55 (br. s, 1H), 1.40-1.29 (m, 2H) | ES-LCMS m/z 642.1, 644.1 [M + H]⁺. |

TABLE 9-continued

| Example | Structure/Name | ¹H NMR | LCMS |
|---|---|---|---|
| 170 | 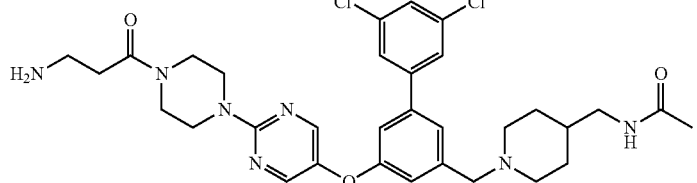 3-(4-(5-((5-((4-(acetamidomethyl)piperidin-1-yl)methyl)-3',5'-dichloro-[1,1'-biphenyl]-3-yl)oxy)pyrimidin-2-yl)piperazin-1-yl)propanamide | ¹H NMR (400 MHz, CD₃OD) δ ppm 8.26 (s, 2H), 7.60 (d, J = 1.5 Hz, 2H), 7.46 (s, 1H), 7.34 (s, 1H), 7.18 (s, 1H), 7.00 (s, 1H), 3.84 (d, J = 4.5 Hz, 4H), 3.55 (s, 2H), 3.07 (d, J = 7.0 Hz, 2H), 2.93 (d, J = 11.5 Hz, 2H), 2.75 (t, J = 7.3 Hz, 2H), 2.60 (t, J = 4.5 Hz, 4H), 2.48 (t, J = 7.3 Hz, 2H), 2.04 (t, J = 11.3 Hz, 2H), 1.95 (s, 3H), 1.72 (d, J = 12.5 Hz, 2H), 1.53 (br. s, 1H), 1.35-1.17 (m, 2H) | ES-LCMS m/z 640.3, 642.3 [M + H]⁺. |
| 171 | 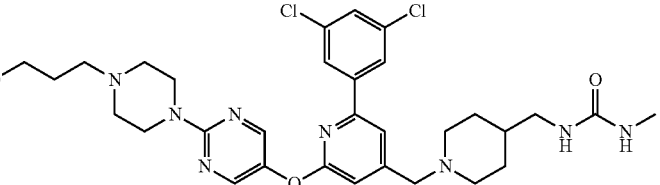 1-((1-((2-(3,5-dichlorophenyl)-6-((2-(4-(3-hydroxypropyl)piperazin-1-yl)pyrimidin-5-yl)oxy)pyridin-4-yl)methyl)piperidin-4-yl)methyl)-3-methylurea | ¹H NMR (400 MHz, D₂O) δ ppm 8.37 (s, 2H), 7.58-7.50 (m, 3H), 7.36 (s, 1H), 7.10 (s, 1H), 4.61 (d, J = 15.1 Hz, 2H), 4.30 (s, 2H), 3.74-3.59 (m, 4H), 3.50 (d, J = 12.0 Hz, 2H), 3.35 (t, J = 12.5 Hz, 2H), 3.27-3.19 (m, 2H), 3.15-3.04 (m, 2H), 3.03-2.90 (m, 4H), 2.57 (s, 3H), 2.02-1.81 (m, 4H), 1.72 (brs., 1H), 1.44-1.28 (m, 2H) | LC-MS m/z 643.3, 645.3 [M + H]⁺. |
| 172 | 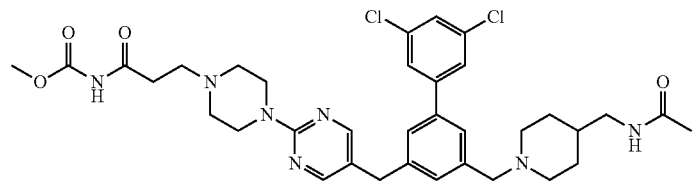 methyl (3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoyl)carbamate | ¹H NMR (400 MHz, CDCl₃) δ ppm 8.32 (s, 2H), 7.73 (d, J = 1.8 Hz, 2H), 7.42 (s, 1H), 7.35 (t, J = 1.9 Hz, 1H), 6.92 (s, 1H), 5.55 (t, J = 5.5 Hz, 1H), 3.97-3.89 (m, 4H), 3.78 (s, 3H), 3.54 (s, 2H), 3.18 (t, J = 6.4 Hz, 2H), 2.90 (d, J = 11.7 Hz, 2H), 2.78-2.72 (m, 2H), 2.67 (t, J = 5.0 Hz, 6H), 2.10-2.01 (m, 2H), 2.00 (s, 3H), 1.78-1.62 (m, 3H), 1.41-1.28 (m, 2H) | ES-LCMS m/z 699.2, 701.2 [M + H]⁺. |
| 173 | 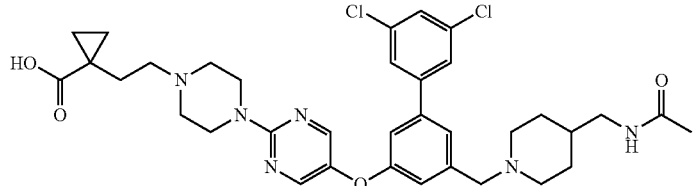 1-(2-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)ethyl)cyclopropanecarboxylic acid | ¹H NMR (400 MHz, D₂O) δ ppm 8.29 (s, 2H), 7.48-7.40 (m, 3H), 7.22 (s, 1H), 7.03 (s, 1H), 4.60-4.51 (m, 2H), 4.38-4.30 (m, 1H), 4.26-4.14 (m, 3H), 3.60 (d, J = 11.9 Hz, 2H), 3.44 (d, J = 11.9 Hz, 2H), 3.37-3.24 (m, 3H), 3.17 (dt, J = 4.6, 12.2 Hz, 1H), 3.07-2.91 (m, 5H), 2.80-2.68 (m, 1H), 2.38-2.36 (m, 1H), 2.22-2.07 (m, 1H), 2.02-1.80 (m, 7H), 1.71 (br s, 1H), 1.33 (q, J = 11.8 Hz, 2H) | ES-LCMS m/z 682.3, 684.3 [M + H]⁺. |

TABLE 9-continued

| Example | Structure/Name | ¹H NMR | LCMS |
|---|---|---|---|
| 174 | 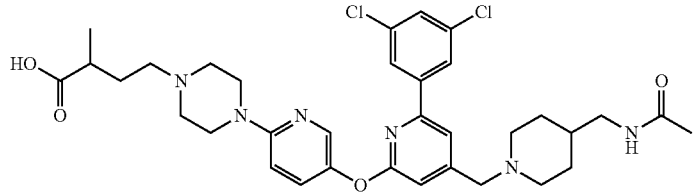 [SMILES: CC(=O)NCC1CCN(Cc2cc(Oc3ccc(N4CCN(CCC(C)C(=O)O)CC4)nc3)nc(-c3cc(Cl)cc(Cl)c3)c2)CC1]<br>4-(4-(5-((4-((4-(acetamidomethyl)piperidin-1-yl)methyl)-6-(3,5-dichlorophenyl)pyridin-2-yl)oxy)pyridin-2-yl)piperazin-1-yl)-2-methylbutanoic acid | ¹H NMR (400 MHz, CD₃OD) δ ppm 8.07 (d, J = 2.4 Hz, 1H), 7.80 (d, J = 1.8 Hz, 2H), 7.61 (s, 1H), 7.52 (dd, J = 2.9, 9.3 Hz, 1H), 7.41 (t, J = 1.9 Hz, 1H), 7.00-6.96 (m, 2H), 3.73 (s, 4H), 3.62 (s, 2H), 3.20-3.09 (m, 4H), 3.07 (d, J = 6.8 Hz, 2H), 3.01-2.89 (m, 4H), 2.54-2.46 (m, 1H), 2.16-2.07 (m, 2H), 1.97-1.90 (m, 4H), 1.86-1.78 (m, 1H), 1.72 (d, J = 12.3 Hz, 2H), 1.58-1.47 (m, 1H), 1.37-1.26 (m, 2H), 1.22 (d, J = 7.3 Hz, 3H) | ES-LCMS m/z 669.3, 671.3 [M + H]⁺. |
| 175 | 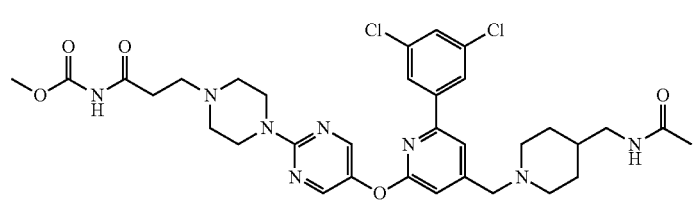 [SMILES: COC(=O)NC(=O)CCN1CCN(c2ncc(Oc3cc(CN4CCC(CNC(C)=O)CC4)cc(-c4cc(Cl)cc(Cl)c4)n3)cn2)CC1]<br>methyl (3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoyl)carbamate | ¹H NMR (400 MHz, CD₃OD) δ ppm 8.49 (s, 2H), 8.00 (s, 1H), 7.89 (d, J = 1.8 Hz, 2H), 7.49 (s, 1H), 7.37 (s, 1H), 4.48 (s, 2H), 3.79 (s, 3H), 3.74 (d, J = 11.8 Hz, 2H), 3.68-3.44 (m, 7H), 3.37 (s, 1H), 3.31-3.21 (m, 4H), 3.19-3.08 (m, 4H), 2.05-1.96 (m, 5H), 1.92-1.82 (m, 1H), 1.73-1.58 (m, 2H) | ES-LCMS m/z 699.3, 701.3 [M + H]⁺. |
| 176 | 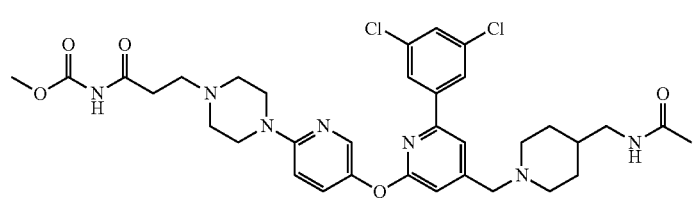 [SMILES: COC(=O)NC(=O)CCN1CCN(c2ccc(Oc3cc(CN4CCC(CNC(C)=O)CC4)cc(-c4cc(Cl)cc(Cl)c4)n3)cn2)CC1]<br>methyl (3-(4-(5-((4-((4-(acetamidomethyl)piperidin-1-yl)methyl)-6-(3,5-dichlorophenyl)pyridin-2-yl)oxy)pyridin-2-yl)piperazin-1-yl)propanoyl)carbamate | ¹H NMR (400 MHz, CD₃OD) δ ppm 8.19 (d, J = 2.6 Hz, 1H), 8.06-7.92 (m, 2H), 7.87-7.82 (m, 2H), 7.51-7.38 (m, 2H), 7.37 (s, 1H), 4.57-4.39 (m, 4H), 3.75 (s, 3H), 3.67 (d, J = 4.4 Hz, 7H), 3.31 (s, 3H), 3.27-3.21 (m, 2H), 3.11 (d, J = 6.6 Hz, 4H), 1.98-1.93 (m, 5H), 1.84 (s, 1H), 1.61 (d, J = 12.1 Hz, 2H) | ES-LCMS m/z 698.3, 700.3 [M + H]⁺. |
| 177 | 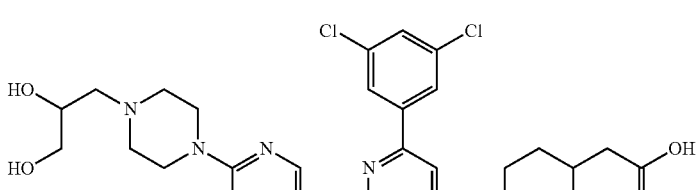<br>2-(1-((2-(3,5-dichlorophenyl)-6-((2-(4-(2,3-dihydroxypropyl)piperazin-1-yl)pyrimidin-5-yl)oxy)pyridin-4-yl)methyl)piperidin-4-yl)acetic acid | ¹H NMR (400 MHz, CD₃OD) δ ppm 8.47 (s, 2H), 7.97 (s, 1H), 7.88 (d, J = 2.2 Hz, 2H), 7.49 (t, J = 1.8 Hz, 1H), 7.35 (s, 1H), 4.91 (br. s., 2H), 4.45 (s, 2H), 4.14 (dt, J = 3.1, 5.1 Hz, 1H), 3.76 (d, J = 10.1 Hz, 2H), 3.64-3.49 (m, 6H), 3.34 (d, J = 3.1 Hz, 2H), 3.30-3.23 (m, 2H), 3.20-3.08 (m, 2H), 2.38-2.29 (m, 2H), 2.13-2.01 (m, 3H), 1.75-1.63 (m, 2H) | ES-LCMS m/z: 631.2, 633.2 [M + H]⁺. |

Example 178: 4-(5-((4-((4-(Acetamidomethyl)piperidin-1-yl)methyl)-6-(3,5-dichlorophenyl)pyridin-2-yl)oxy)pyridin-2-yl)-1-methylpiperazine 1-oxide, 3 hydrochloride

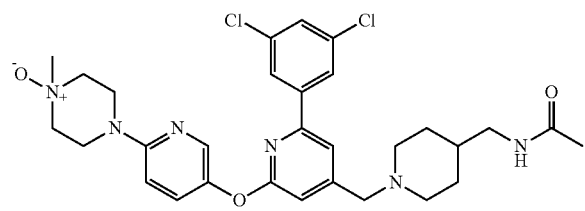 [SMILES: CC(=O)NCC1CCN(Cc2cc(Oc3ccc(N4CC[N+](C)(O)CC4)nc3)nc(-c3cc(Cl)cc(Cl)c3)c2)CC1]

Step 1: tert-Butyl 4-methylpiperazine-1-carboxylate

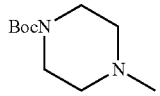

To a solution of 1-methylpiperazine (3 g, 30.0 mmol) and DIEA (10.46 mL, 59.9 mmol) in DCM (100 mL) was added Boc$_2$O (8.34 mL, 35.9 mmol). The mixture was stirred at 25° C. for 1 h then concentrated and washed with PE (20 mL×2) to yield a colorless oil tert-butyl 4-methylpiperazine-1-carboxylate (4 g, 17.98 mmol, 60.0% yield): $^1$H NMR (400 MHz, CDCl$_3$) δ ppm 3.50-3.29 (m, 4H), 2.31 (br. s, 4H), 2.26 (s, 3H), 1.43 (s, 9H); ES-LCMS m/z 201.2 [M+H]$^+$.

Step 2: 4-(tert-Butoxycarbonyl)-1-methylpiperazine 1-oxide

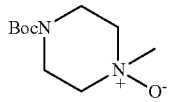

To a solution of tert-butyl 4-methylpiperazine-1-carboxylate (4 g, 19.97 mmol) in DCM (100 mL) was added 3-chlorobenzoperoxoic acid (15.10 mL, 100 mmol) in portions. The reaction was stirred at 30° C. for 12 h. The mixture was quenched with saturated Na$_2$S$_2$O$_3$ solution (100 mL) and stirred at 30° C. for 0.5 h. The organic phase was concentrated and purified by flash chromatography (MeOH/DCM=0/1 to 1/5). All fractions found to contain product by TLC (MeOH/DCM=1/10, R$_f$=0.25) were combined and concentrated to yield a white solid of 4-(tert-butoxycarbonyl)-1-methylpiperazine 1-oxide (2.5 g, 8.09 mmol, 40.5% yield): $^1$H NMR (400 MHz, CD$_3$OD) δ ppm 4.01-3.97 (m, 2H), 3.60-3.57 (m, 2H), 3.48-3.42 (m, 2H), 3.27-3.25 (m, 3H), 3.23-3.20 (m, 2H), 1.44 (s, 9H); ES-LCMS m/z 217.2 [M+H]$^+$.

Step 3: 1-Methylpiperazine 1-oxide, hydrochloride

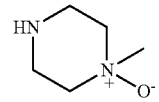

4-(tert-Butoxycarbonyl)-1-methylpiperazine 1-oxide (2 g, 9.25 mmol) was dissolved in HCl solution (4.0 M in EtOAc, 30 mL, 120 mmol). The reaction was stirred at 25° C. for 2 h and white solid formed. The mixture was filtered to yield a white solid of (1-methylpiperazine 1-oxide, hydrochloride (1.3 g, 7.67 mmol, 83.0% yield): $^1$H NMR (400 MHz, CD$_3$OD) δ ppm 4.27-4.08 (m, 4H), 3.88-3.68 (m, 7H).

Step 4: 4-(5-((4-((4-(Acetamidomethyl)piperidin-1-yl)methyl)-6-(3,5-dichlorophenyl)pyridin-2-yl)oxy)pyridin-2-yl)-1-methylpiperazine 1-oxide, 3 hydrochloride

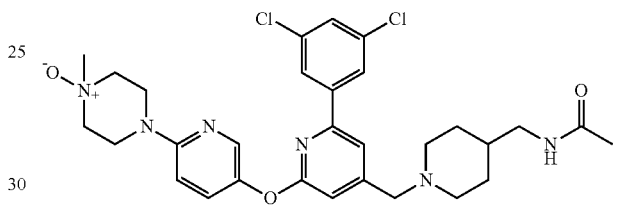

A mixture of N-((1-((2-((6-bromopyridin-3-yl)oxy)-6-(3,5-dichlorophenyl)pyridin-4-yl)methyl)piperidin-4-yl)methyl)acetamide (150 mg, 0.266 mmol), 1-methylpiperazine 1-oxide, hydrochloride (81 mg, 0.532 mmol), Pd$_2$(dba)$_3$ (12.17 mg, 0.013 mmol), (±)-BINAP (33.1 mg, 0.053 mmol), 18-crown-6 (211 mg, 0.797 mmol) and sodium tert-butoxide (25.5 mg, 0.266 mmol) in THF (15 mL) was heated to 65° C. for 12 h under N$_2$ atmosphere. The mixture was concentrated and purified by preparative HPLC (MeCN/H$_2$O as eluents, acidic condition) to yield a white solid of 4-(5-((4-(acetamidomethyl)piperidin-1-yl)methyl)-6-(3,5-dichlorophenyl)pyridin-2-yl)oxy)pyridin-2-yl)-1-methylpiperazine 1-oxide, 3 hydrochloride (21.98 mg, 0.031 mmol, 11.5% yield): $^1$H NMR (400 MHz, CD$_3$OD) δ ppm 8.18 (d, J=2.6 Hz, 1H), 7.91-7.83 (m, 4H), 7.50 (s, 1H), 7.36-7.26 (m, 2H), 4.42 (s, 2H), 4.37 (d, J=14.1 Hz, 2H), 3.97-3.84 (m, 4H), 3.83-3.72 (m, 2H), 3.63 (s, 3H), 3.58 (d, J=12.3 Hz, 2H), 3.15-3.02 (m, 4H), 2.03-1.95 (m, 3H), 1.94-1.76 (m, 3H), 1.63-1.44 (m, 2H); ES-LCMS m/z 599.3, 601.3 [M+H]$^+$.

Example 179: 1-(4-(5-((4-((4-(Acetamidomethyl)piperidin-1-yl)methyl)-6-(3,5-dichlorophenyl)pyridin-2-yl)oxy)pyridin-2-yl)-1-(2-hydroxyethyl)piperazin-1-ium-1-yl)-2-hydroxyethan-1-ide, chloride

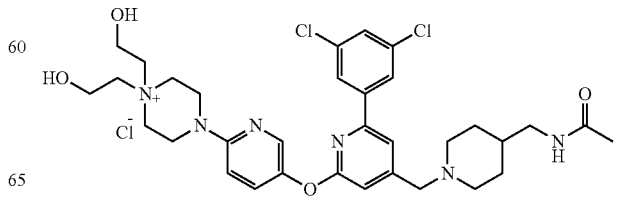

Example 180: N-((1-((2-(3,5-Dichlorophenyl)-6-((6-(4-(2-hydroxyethyl)piperazin-1-yl)pyridin-3-yl)oxy)pyridin-4-yl)methyl)piperidin-4-yl)methyl)acetamide, 4 hydrochloride

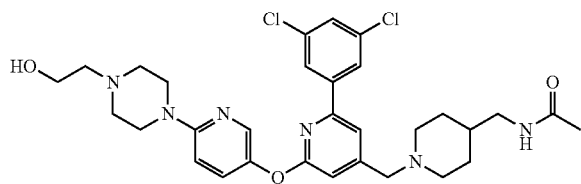 [SMILES: CC(=O)NCC1CCN(Cc2cc(Oc3ccc(N4CCN(CCO)CC4)nc3)nc(-c3cc(Cl)cc(Cl)c3)c2)CC1]

To a solution of N-((1-((2-(3,5-dichlorophenyl)-6-((6-(piperazin-1-yl)pyridin-3-yl)oxy)pyridin-4-yl)methyl)piperidin-4-yl)methyl)acetamide, 4 hydrochloride (1 g, 1.328 mmol) in MeCN (40 mL) was added 2-bromoethanol (0.249 g, 1.992 mmol) and K$_2$CO$_3$ (0.551 g, 3.98 mmol). The mixture was stirred at 80° C. for 12 h then filtered and concentrated. The mixture was purified by preparative HPLC (MeCN/H$_2$O as eluents, acidic condition) to yield a yellow solid which was purified by preparative SFC to yield a white solid of N-((1-((2-(3,5-dichlorophenyl)-6-((6-(4-(2-hydroxyethyl)piperazin-1-yl)pyridin-3-yl)oxy)pyridin-4-yl)methyl)piperidin-4-yl)methyl)acetamide, 4 hydrochloride (0.044 g, 0.071 mmol, 41.3%): $^1$H NMR (400 MHz, CD$_3$OD) δ ppm 8.30-8.22 (m, 2H), 8.01 (s, 1H), 7.89 (d, J=1.8 Hz, 2H), 7.64 (d, J=9.7 Hz, 1H), 7.52 (s, 1H), 7.43 (s, 1H), 4.59-4.40 (m, 4H), 4.00-3.93 (m, 2H), 3.90-3.77 (m, 3H), 3.60 (d, J=11.9 Hz, 2H), 3.54-3.36 (m, 5H), 3.19-3.05 (m, 4H), 2.05-1.97 (m, 5H), 1.87 (br. s, 1H), 1.69-1.55 (m, 2H); ES-LCMS m/z 613.2, 615.2 [M+H]$^+$ and 4-(5-((4-((4-(acetamidomethyl)piperidin-1-yl)methyl)-6-(3,5-dichlorophenyl)pyridin-2-yl)oxy)pyridin-2-yl)-1,1-bis(2-hydroxyethyl)piperazin-1-ium chloride (31.30 mg, 0.043 mmol, 26.6%): $^1$H NMR (400 MHz, CD$_3$OD) δ ppm 8.07 (d, J=2.6 Hz, 1H), 7.83 (d, J=1.8 Hz, 2H), 7.65 (s, 1H), 7.53 (dd, J=2.9, 9.0 Hz, 1H), 7.44 (t, J=1.8 Hz, 1H), 7.02-6.96 (m, 2H), 4.08-3.91 (m, 1H), 3.90-3.73 (m, 4H), 3.72-3.64 (m, 6H), 3.62-3.55 (m, 2H), 3.08 (d, J=6.6 Hz, 3H), 3.00 (d, J=7.9 Hz, 5H), 2.18 (br. s, 2H), 1.93 (s, 3H), 1.75 (d, J=12.3 Hz, 2H), 1.56 (br. s, 1H), 1.42-1.25 (m, 3H); ES-LCMS m/z 657.2, 659.2 [M]$^+$.

Example 181: 4-(5-((4-((4-(Acetamidomethyl)piperidin-1-yl)methyl)-6-(3,5-dichlorophenyl)pyridin-2-yl)oxy)pyridin-2-yl)-1,1-dimethylpiperazin-1-ium chloride, 3 hydrochloride

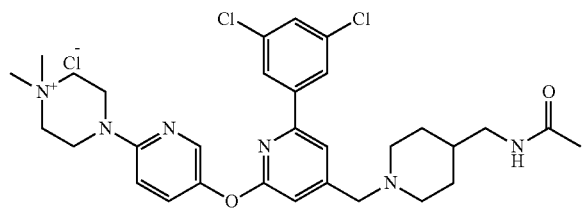

Step 1: 4-(tert-Butoxycarbonyl)-1,1-dimethylpiperazin-1-ium iodide

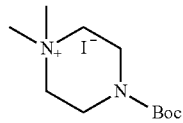

A mixture of tert-butyl piperazine-1-carboxylate (3 g, 16.11 mmol), iodomethane (11.43 g, 81 mmol) and K$_2$CO$_3$ (4.45 g, 32.2 mmol) in THF (100 mL) was stirred at 25° C. for 12 h. The mixture was filtered and concentrated to yield a white solid of A-(ten-butoxycarbonyl)-1,1-dimethylpiperazin-1-ium iodide (3 g, 8.33 mmol, 51.7% yield): $^1$H NMR (400 MHz, CD$_3$OD) δ ppm 3.79 (br. s, 4H), 3.48 (t, J=5.3 Hz, 4H), 3.25 (s, 6H), 1.52-1.41 (m, 9H); ES-LCMS m/z 215.1 [M]$^+$.

Step 2: 1,1-Dimethylpiperazin-1-ium chloride, hydrochloride

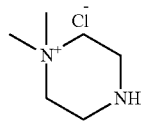

4-(tert-Butoxycarbonyl)-1,1-dimethylpiperazin-1-ium iodide (3 g, 8.77 mmol) was dissolved in HCl solution (4.0 M in EtOAc, 30 mL, 120 mmol). The reaction was stirred at 25° C. for 2 h until TLC analysis (DCM/MeOH=10/1, R$_f$=0.04) showed the reaction was completed. The mixture was concentrated to yield a brown solid of 1,1-dimethylpiperazin-1-ium chloride, hydrochloride (1.8 g, 9.68 mmol, 73.0% yield): $^1$H NMR (400 MHz, CD$_3$OD) δ ppm 3.89-3.79 (m, 4H), 3.74 (d, J=4.6 Hz, 4H), 3.38 (s, 6H).

Step 3: 4-(5-((4-((4-(Acetamidomethyl)piperidin-1-yl)methyl)-6-(3,5-dichlorophenyl)pyridin-2-yl)oxy)pyridin-2-yl)-1,1-dimethylpiperazin-1-ium chloride, 3 hydrochloride

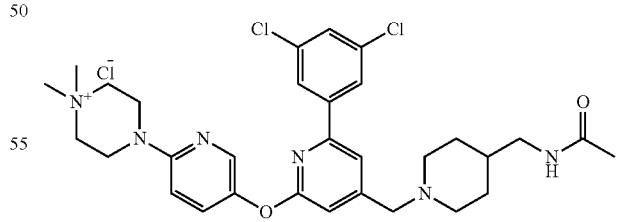

A mixture of N-((1-((2-((6-bromopyridin-3-yl)oxy)-6-(3,5-dichlorophenyl)pyridin-4-yl)methyl)piperidin-4-yl)methyl)acetamide (150 mg, 0.266 mmol), 1,1-dimethylpiperazin-1-ium chloride, hydrochloride (81 mg, 0.435 mmol), Pd$_2$(dba)$_3$ (12.17 mg, 0.013 mmol), (±)-BINAP (33.1 mg, 0.053 mmol), 18-crown-6 (211 mg, 0.797 mmol) and sodium tert-butoxide (128 mg, 1.329 mmol) in THF (15 mL) was heated to 65° C. for 12 h under N$_2$ atmosphere. The mixture was concentrated to yield the crude product which was purified by preparative HPLC (MeCN/H₂O as eluents, acidic condition) to yield a brown solid of 4-(5-((4-((4-(acetamidomethyl)piperidin-1-yl)methyl)-6-(3,5-dichlorophenyl)pyridin-2-yl)oxy)pyridin-2-yl)-1,1-dimethylpiperazin-1-ium, hydrochloride, chloride (13.85 mg, 0.026 mmol, 8.7% yield): $^1$H NMR (400 MHz, CD₃OD) δ ppm 8.27 (br. s, 2H), 8.07 (br. s, 1H), 7.88 (br. s, 2H), 7.69 (br. s, 1H), 7.54-7.38 (m, 2H), 4.48 (br. s, 2H), 4.19 (br. s, 4H), 3.81 (br. s, 4H), 3.64 (br. s, 2H), 3.37 (br. s, 6H), 3.18 (br. s, 4H), 2.05 (s, 3H), 1.98 (d, J=12.8 Hz, 3H), 1.79-1.53 (m, 2H); ES-LCMS m/z 597.3, 599.3 [M]⁺.

Example 182: N-((1-((2-((6-(cis)-4-amino-3-fluoropiperidin-1-yl)pyridin-3-yl)oxy)-6-(3,5-dichlorophenyl)pyridin-4-yl)methyl)piperidin-4-yl)methyl)acetamide, 4 hydrochloride

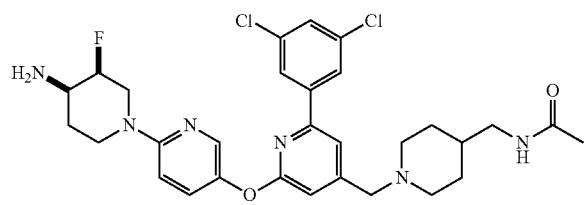 [SMILES: CC(=O)NCC1CCN(Cc2cc(Oc3ccc(N4CC[C@@H](N)[C@@H](F)C4)nc3)nc(-c3cc(Cl)cc(Cl)c3)c2)CC1]

Step 1: (cis)-tert-butyl 4-(benzylamino)-3-fluoropiperidine-1-carboxylate

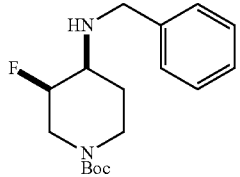

To a solution of tert-butyl 3-fluoro-4-oxopiperidine-1-carboxylate (16.83 mL, 81 mmol) in methanol (200 mL) and acetic acid (2.419 g, 40.3 mmol) was added phenylmethanamine (9.50 g, 89 mmol) at 15° C. The reaction was stirred at 15° C. for 15 h under N₂ atmosphere. NaBH₃CN (5.06 g, 81 mmol) was added and stirred for another 3 h. Then the solution was concentrated and saturated aqueous NaHCO₃ solution (15 mL) was added. The aqueous layer was extracted with DCM (55 mL×2), and the combined extracts were washed with brine (15 mL×2), dried over Na₂SO₄, filtered and concentrated to afford crude product. The crude material was purified by flash chromatography (PE/EtOAc=2/1). All fractions found to contain product by TLC analysis (PE/EA=2/1, R$_f$=0.2) were combined and concentrated to yield light yellow oil of (cis)-tert-butyl 4-(benzylamino)-3-fluoropiperidine-1-carboxylate (10 g, 19.46 mmol, 24.1% yield): $^1$H NMR (400 MHz, CD₃OD) δ ppm 7.45-7.21 (m, 5H), 4.43-4.35 (m, 1H), 4.12 (d, J=7.5 Hz, 1H), 3.88-3.83 (m, 2H), 2.84-2.65 (m, 2H), 1.99-1.88 (m, 1H), 1.64 (dq, J=4.3, 12.5 Hz, 1H), 1.47 (s, 9H); ES-LCMS m/z 309.2, [M+H]⁺.

Step 2: (cis)-tert-Butyl 4-amino-3-fluoropiperidine-1-carboxylate

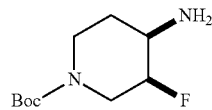 [SMILES: CC(C)(C)OC(=O)N1CC[C@@H](N)[C@@H](F)C1]

To a solution of (cis)-tert-butyl 4-(benzylamino)-3-fluoropiperidine-1-carboxylate (2.5 g, 8.11 mmol) in MeOH (50 mL) stirred under N₂ was added Pd/C, (10 wt %, 1.725 g, 1.621 mmol) in one portion. Then the suspension was degassed under vacuum and purged with H₂ three times. The mixture was stirred under 30 psi of H₂ at 40° C. for 10 h. The reaction mixture was filtered through a pad of Celite® and the filtercake was washed with MeOH (30 mL). The combined filtrates were concentrated to dryness to yield a yellow oil of (cis)-tert-butyl 4-amino-3-fluoropiperidine-1-carboxylate (1.5 g, 5.50 mmol, 67.8% yield): $^1$H NMR (400 MHz, CDCl₃) δ ppm 4.58 (s, 2H), 4.27 (s, 2H), 4.10-3.83 (m, 2H), 3.07-2.72 (m, 4H), 1.42 (s, 9H);

Step 3: (cis)-tert-Butyl 4-(((benzyloxy)carbonyl)amino)-3-fluoropiperidine-1-carboxylate

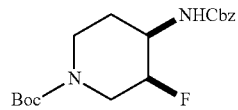 [SMILES: CC(C)(C)OC(=O)N1CC[C@@H](NC(=O)OCc2ccccc2)[C@@H](F)C1]

To a solution of (cis)-tert-butyl 4-amino-3-fluoropiperidine-1-carboxylate (400 mg, 1.833 mmol) in DCM (10 mL) was added CbzCl (469 mg, 2.75 mmol) and DIEA (711 mg, 5.50 mmol). The reaction mixture was stirred at 30° C. for 1 h. H₂O (20 mL) was added and extracted with DCM (20 mL×2). The combine organic layers were dried over Na₂SO₄, filtered and concentrated to yield the crude product which was purified by preparative TLC (EA/PE=1/5, R$_f$=0.3) to yield a yellow solid of (cis)-tert-butyl 4-(((benzyloxy)carbonyl)amino)-3-fluoropiperidine-1-carboxylate (350 mg, 0.795 mmol, 43.4% yield): $^1$H NMR (400 MHz, CDCl₃) δ ppm 7.40-7.27 (m, 5H), 5.10 (s, 2H), 4.75-4.07 (m, 4H), 3.89-3.67 (m, 1H), 3.03-2.73 (m, 2H), 1.71-1.66 (m, 2H), 1.44 (s, 9H); ES-LCMS m/z 375.1 [M+Na]⁺.

Step 2: Benzyl ((cis)-3-fluoropiperidin-4-yl)carbamate

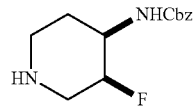 [SMILES: O=C(N[C@@H]1CCNC[C@@H]1F)OCc1ccccc1]

To a solution of (cis)-tert-butyl 4-(((benzyloxy)carbonyl)amino)-3-fluoropiperidine-1-carboxylate (350 mg, 0.993 mmol) in DCM (10 mL) was added 2,2,2-trifluoroacetic acid (2 mL, 27.0 mmol). The reaction mixture was stirred at 30° C. for 1 h then concentrated to yield a yellow solid of benzyl ((cis)-3-fluoropiperidin-4-yl)carbamate (193 mg, 0.612 mmol, 61.6% yield): $^1$H NMR (400 MHz, CD₃OD) δ ppm 7.47-7.03 (m, 5H), 5.15-5.03 (m, 2H), 4.68-4.54 (m, 1H), 3.76-3.61 (m, 1H), 3.19 (t, J=12.0 Hz, 1H), 3.02 (d, J=13.2 Hz, 1H), 2.84-2.58 (m, 2H), 1.80-1.63 (m, 2H); ES-LCMS m/z 253.1 [M+H]⁺.

Step 3: N-((1-((2-((6-((cis)-4-amino-3-fluoropiperidin-1-yl)pyridin-3-yl)oxy)-6-(3,5-dichlorophenyl)pyridin-4-yl)methyl)piperidin-4-yl)methyl)acetamide, 4 hydrochloride

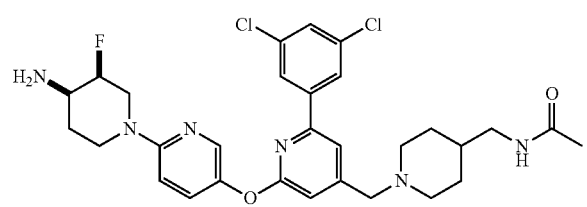 [SMILES: CC(=O)NCC1CCN(Cc2cc(Oc3ccc(N4CC[C@@H](N)[C@@H](F)C4)nc3)nc(-c3cc(Cl)cc(Cl)c3)c2)CC1]

To a solution of N-((1-((2-((6-bromopyridin-3-yl)oxy)-6-(3,5-dichlorophenyl)pyridin-4-yl)methyl)piperidin-4-yl)methyl)acetamide (150 mg, 0.266 mmol) in THF (2 mL) was added 18-crown-6 (211 mg, 0.797 mmol), (±)-BINAP (16.55 mg, 0.027 mmol), Pd₂(dba)₃ (24.34 mg, 0.027 mmol), benzyl ((cis)-3-fluoropiperidin-4-yl)carbamate (67.1 mg, 0.266 mmol) and sodium 2-methylpropan-2-olate (153 mg, 1.595 mmol). The reaction mixture was stirred at 70° C. for 10 h. H₂O (20 mL) was added, extracted with DCM (20 mL×2). The combined organic layers were dried over Na₂SO₄, filtered and concentrated to yield the crude product, which was purified by preparative TLC (DCM/MeOH=10/1, R$_f$=0.3) to yield the crude product. The crude product was purified by preparative HPLC (MeCN/H₂O as eluents, acidic condition) and dried by lyophilization to yield a white solid of N-((1-((2-((6-((cis)-4-amino-3-fluoropiperidin-1-yl)pyridin-3-yl)oxy)-6-(3,5-dichlorophenyl)pyridin-4-yl)methyl)piperidin-4-yl)methyl)acetamide, 4 hydrochloride (7.89 mg, 10.52 μmol, 3.96% yield): ¹H NMR (400 MHz, CD₃OD) δ ppm 8.32-7.76 (m, 5H), 7.64 (br. s, 1H), 7.52-7.27 (m, 2H), 5.35-5.12 (m, 2H), 4.67 (s, 2H), 4.46 (br. s, 2H), 4.01-3.45 (m, 5H), 3.13 (br. s, 3H), 2.69 (br. s, 2H), 2.16 (br. s, 2H), 1.95 (br. s, 4H), 1.64 (br. s, 2H); ES-LCMS m/z 601.2, 603.2 [M+H]⁺.

Example 183: N-((1-((2-(3,5-Dichlorophenyl)-6-((6-((1S,4S)-5-(2-(methylsulfonyl)ethyl)-2,5-diazabicyclo[2.2.1]heptan-2-yl)pyridin-3-yl)oxy)pyridin-4-yl)methyl)piperidin-4-yl)methyl)acetamide, 4 Hydrochloride

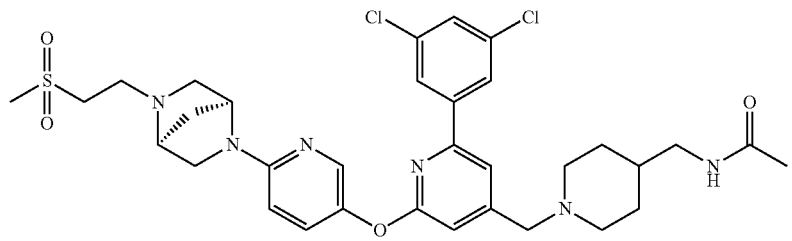

Step 1: (1-Butyl 5-(5-((4-((4-(acetamidomethyl)piperidin-1-yl)methyl)-6-(3,5-dichlorophenyl)pyridin-2-yl)oxy)pyridin-2-yl)-2,5-diazabicyclo[2.2.1]heptane-2-carboxylate

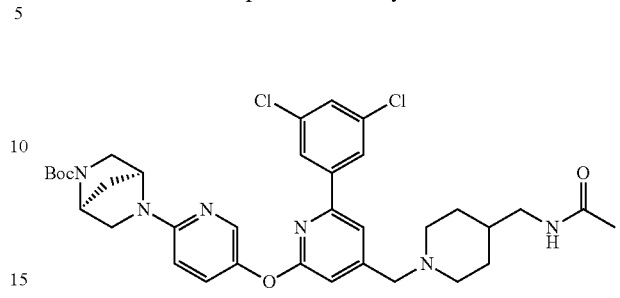

To a mixture of N-((1-((2-((6-bromopyridin-3-yl)oxy)-6-(3,5-dichlorophenyl)pyridin-4-yl)methyl)piperidin-4-yl)methyl)acetamide (500 mg, 0.797 mmol) in THF (10 mL) was added (1S,4S)-tert-butyl 2,5-diazabicyclo[2.2.1]heptane-2-carboxylate (237 mg, 1.196 mmol), Xantphos (231 mg, 0.399 mmol), Pd₂(dba)₃ (146 mg, 0.159 mmol) and Cs₂CO₃ (779 mg, 2.392 mmol). The reaction was stirred at 80° C. for 5 h under N₂ atmosphere. Saturated aqueous NaHCO₃ solution (50 mL) was added and the mixture was extracted with DCM (50 mL×2). The combined organic layers were dried over Na₂SO₄, filtered, concentrated and purified by silica gel column chromatography (DCM/MeOH=10/1). All fractions found to contain product by TLC (DCM/MeOH=10/1, R$_f$=0.5) were combined and concentrated to yield a yellow solid of (1S,4S)-tert-butyl 5-(5-((4-((4-(acetamidomethyl)piperidin-1-yl)methyl)-6-(3,5-dichlorophenyl)pyridin-2-yl)oxy)pyridin-2-yl)-2,5-diazabicyclo[2.2.1]heptane-2-carboxylate (600 mg, 0.643 mmol, 81.0% yield): ¹H NMR (400 MHz, CD₃OD) δ ppm 7.96 (d, J=2.6 Hz, 1H), 7.80 (br. s, 2H), 7.58 (s, 1H), 7.46 (dd, J=2.9, 9.0 Hz, 1H), 7.41-7.36 (m, 1H), 6.94 (s, 1H), 6.63 (t, J=9.3 Hz, 1H), 4.79 (br. s, 1H), 4.58 (d, J=4.9 Hz, 1H), 3.65-3.57 (m, 4H), 3.48-3.36 (m, 4H), 3.06 (d, J=6.6 Hz, 2H), 2.99-2.90 (m, 2H), 2.10-1.98 (m, 3H), 1.93 (s, 3H), 1.71 (d, J=11.9 Hz, 2H), 1.57-1.41 (m, 9H), 1.36-1.23 (m, 2H); ES-LCMS m/z 681.3, 683.3 [M+H]⁺.

Step 2: N-((1-((2-((6-((1S,4S)-2,5-Diazabicyclo [2.2.1]heptan-2-yl)pyridin-3-yl)oxy)-6-(3,5-dichlorophenyl)pyridin-4-yl)methyl)piperidin-4-yl)methyl) acetamide

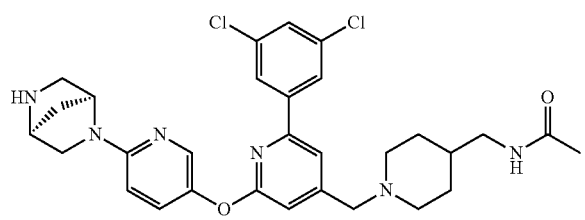

To a mixture of (1S,4S)-tert-butyl 5-(5-((4-((4-(acetamidomethyl)piperidin-1-yl)methyl)-6-(3,5-dichlorophenyl)pyridin-2-yl)oxy)pyridin-2-yl)-2,5-diazabicyclo[2.2.1]heptane-2-carboxylate (600 mg, 0.643 mmol) in EtOAc (10 mL) was added HCl solution (4.0 M in EtOAc, 5 mL, 20.0 mmol). The reaction was stirred at 25° C. for 0.5 h. Saturated aqueous NaHCO₃ solution (50 mL) was added and the mixture was extracted with DCM (50 mL×2). The combined organic layers were dried over Na₂SO₄, filtered, concentrated to yield a yellow solid of N-((1-((2-((6-((1S,4S)-2,5-diazabicyclo[2.2.1]heptan-2-yl)pyridin-3-yl)oxy)-6-(3,5-dichlorophenyl)pyridin-4-yl)methyl)piperidin-4-yl)methyl) acetamide (400 mg, 0.585 mmol, 91.0% yield): ¹H NMR (400 MHz, CD₃OD) δ ppm 8.22 (d, J=9.7 Hz, 1H), 8.16 (d, J=2.2 Hz, 1H), 8.01 (s, 1H), 7.90 (d, J=1.3 Hz, 2H), 7.51 (s, 1H), 7.46-7.41 (m, 2H), 5.25 (br. s, 1H), 4.75 (s, 1H), 4.46 (s, 2H), 4.08-3.94 (m, 2H), 3.66-3.55 (m, 4H), 3.12 (d, J=5.7 Hz, 4H), 2.44-2.27 (m, 1H), 2.25-2.22 (m, 1H), 1.99-1.95 (m, 5H), 1.94-1.77 (m, 1H), 1.72-1.59 (m, 2H); ES-LCMS m/z 581.3, 583.3 [M+H]⁺.

Step 3: N-((1-((2-(3,5-Dichlorophenyl)-6-((6-((1S,4S)-5-(2-(methylsulfonyl)ethyl)-2,5-diazabicyclo [2.2.1]heptan-2-yl)pyridin-3-yl)oxy)pyridin-4-yl) methyl)piperidin-4-yl)methyl)acetamide, 4 hydrochloride

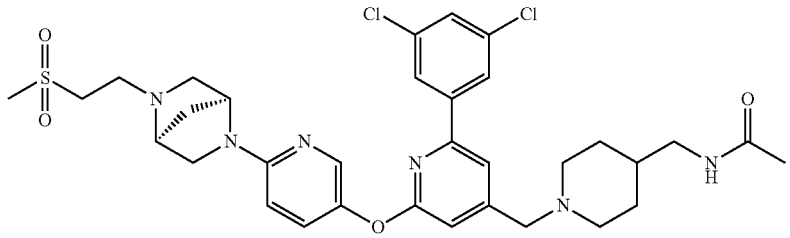

To a mixture of N-((1-((2-((6-((1S,4S)-2,5-diazabicyclo [2.2.1]heptan-2-yl)pyridin-3-yl)oxy)-6-(3,5-dichlorophenyl)pyridin-4-yl)methyl)piperidin-4-yl)methyl) acetamide (150 mg, 0.219 mmol) in DCM (5 mL) was added (methylsulfonyl)ethene (69.8 mg, 0.658 mmol) and DIEA (0.191 mL, 1.096 mmol). The reaction was stirred at 25° C. for 5 h then concentrated and purified by preparative HPLC (MeCN/H₂O as eluents, acidic condition) and dried by lyophilization to yield an off white solid of N-((1-((2-(3,5-dichlorophenyl)-6-((6-((1S,4S)-5-(2-(methyl sulfonyl) ethyl)-2,5-diazabicyclo[2.2.1]heptan-2-yl)pyridin-3-yl)oxy) pyridin-4-yl)methyl)piperidin-4-yl)methyl)acetamide, 4 hydrochloride (82.23 mg, 0.098 mmol, 44.9% yield): ¹H NMR (400 MHz, CD₃OD) δ ppm 8.21-8.16 (m, 2H), 7.97 (s, 1H), 7.89 (d, J=1.8 Hz, 2H), 7.52 (s, 1H), 7.41-7.37 (m, 2H), 5.26 (br. s, 1H), 4.85 (s, 1H), 4.45 (s, 2H), 4.17 (d, J=11.5 Hz, 1H), 4.12-3.95 (m, 3H), 3.93-3.77 (m, 4H), 3.59 (d, J=11.9 Hz, 2H), 3.16-3.08 (m, 7H), 2.68-2.42 (m, 2H), 2.00-1.94 (m, 5H), 1.85 (br. s, 1H), 1.68-1.50 (m, 2H); ES-LCMS m/z 687.3, 689.3 [M+H]⁺.

Example 184: N-((1-((2-((6-(trans-3-(Aminomethyl)-4-hydroxypyrrolidin-1-yl)pyridin-3-yl)oxy)-6-(3,5-dichlorophenyl)pyridin-4-yl)methyl)piperidin-4-yl)methyl)acetamide, 4 hydrochloride

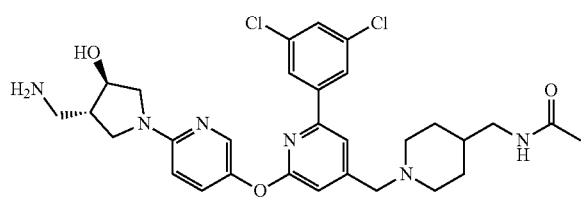 [SMILES: CC(=O)NCC1CCN(Cc2cc(Oc3ccc(N4C[C@H](CN)[C@@H](O)C4)nc3)nc(-c3cc(Cl)cc(Cl)c3)c2)CC1]

Step 1: tert-Butyl 3-cyano-4-hydroxypyrrolidine-1-carboxylate

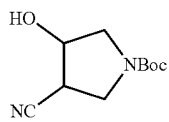

The tert-butyl 3-cyano-4-oxopyrrolidine-1-carboxylate (10 g, 47.6 mmol) in EtOH (500 mL) was cooled to 0° C. (ice bath), and to this solution was added NaBH₄ (3.60 g, 95 mmol) over a period of 0.1 h portion wise. The reaction mixture was stirred for 0.5 h at the same temperature and concentrated. The residue was diluted with EtOAc (200 mL), washed with water (200 mL×3), dried over Na₂SO₄, and filtered. The filtrate was concentrated to yield a residue which was purified by column chromatography (silica gel, PE/EtOAc=1/1) to yield a colorless oil of tert-butyl 3-cyano-4-hydroxypyrrolidine-1-carboxylate (10 g, 37.7 mmol, 79.0% yield): ¹H NMR (400 MHz, CD₃OD) δ ppm 4.57-4.45 (m, 1H), 3.85-3.45 (m, 3H), 3.41-3.25 (m, 2H), 1.50 (s, 9H).

Step 2: tert-Butyl 3-(aminomethyl)-4-hydroxypyrrolidine-1-carboxylate

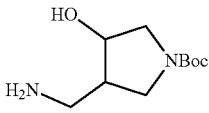

To a solution of tert-butyl 3-cyano-4-hydroxypyrrolidine-1-carboxylate (10 g, 47.1 mmol) in DMF (150 mL) was added Raney nickel (1.383 g, 23.56 mmol). Then the reaction was stirred at 40° C. for 12 h under $H_2$ atmosphere (50 psi). The reaction mixture was filtered and the filtrate was concentrated to yield light yellow oil of tert-butyl 3-(aminomethyl)-4-hydroxypyrrolidine-1-carboxylate (10 g, 37.0 mmol, 79.0% yield): $^1$H NMR (400 MHz, $CD_3OD$) δ ppm 4.39-3.99 (m, 1H), 3.72-3.07 (m, 5H), 2.79-2.54 (m, 1H), 2.44-2.18 (m, 1H), 1.48 (br. s, 9H).

Step 3: trans-tert-Butyl 3-((((benzyloxy)carbonyl)amino)methyl)-4-hydroxypyrrolidine-1-carboxylate

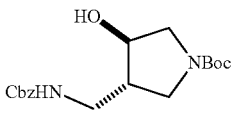

To a mixture of tert-butyl 3-(aminomethyl)-4-hydroxypyrrolidine-1-carboxylate (10 g, 46.2 mmol) and DIEA (24.56 mL, 139 mmol) in DCM (100 mL) was added CbzCl (9.47 g, 55.5 mmol) dropwise at 0° C. The mixture was stirred at 0° C. for 1 h under $N_2$ atmosphere then concentrated and purified by preparative HPLC (MeCN/$H_2O$ as eluents, acidic condition) and dried by lyophilization to yield light oil of trans-tert-butyl 3-((((benzyloxy)carbonyl)amino)methyl)-4-hydroxypyrrolidine-1-carboxylate (4 g, 9.13 mmol, 19.8% yield): $^1$H NMR (400 MHz, $CD_3OD$) δ ppm 7.35-7.27 (m, 5H), 5.08-5.05 (m, 2H), 4.08-4.02 (m, 1H), 3.58-3.49 (m, 2H), 3.22-3.12 (m, 3H), 3.05 (dd, J=3.9, 7.6 Hz, 1H), 2.24 (dd, J=3.7, 6.8 Hz, 1H), 1.44 (s, 9H); ES-LCMS m/z 295.1 [M−t−Bu+H]$^+$.

Step 4: Benzyl ((trans-4-hydroxypyrrolidin-3-yl)methyl/carbamate, trifluoroacetate

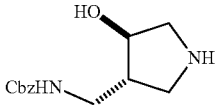

To a suspension of trans-tert-butyl 3-((((benzyloxy)carbonyl)amino)methyl)-4-hydroxypyrrolidine-1-carboxylate (2 g, 5.71 mmol) in DCM (10 mL) was added trifluoroacetic acid (2 mL, 26.9 mmol). The mixture was stirred at 20° C. for 0.5 h under $N_2$ atmosphere then concentrated to yield a brown solid of benzyl ((trans-4-hydroxypyrrolidin-3-yl)methyl)carbamate, trifluoroacetate (1.5 g, 3.30 mmol, 57.9% yield): $^1$H NMR (400 MHz, $CD_3OD$) δ 7.33 (d, J=4.2 Hz, 5H), 5.07 (s, 2H), 4.28-4.22 (m, 1H), 3.51 (dd, J=7.7, 12.1 Hz, 1H), 3.35 (dd, J=4.5, 12.3 Hz, 1H), 3.21-2.95 (m, 4H), 2.43 (dd, J=3.7, 6.8 Hz, 1H); ES-LCMS m/z 251.1 [M+H]$^+$.

Step 5: Benzyl ((trans-1-(5-((4-((4-(acetamidomethyl)piperidin-1-yl)methyl)-6-(3,5-dichlorophenyl)pyridin-2-yl)oxy)pyridin-2-yl)-4-hydroxypyrrolidin-3-yl)methyl)carbamate

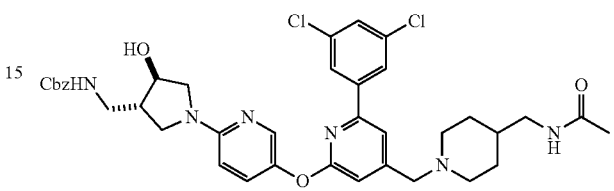

To a suspension of benzyl ((trans-4-hydroxypyrrolidin-3-yl)methyl/carbamate (133 mg, 0.532 mmol), $Pd_2(dba)_3$ (24.34 mg, 0.027 mmol) and dicyclohexyl(2',4',6'-triisopropyl-[1,1'-biphenyl]-2-yl)phosphine (12.67 mg, 0.027 mmol) in THF (5 mL) was added N-((1-((2-((6-bromopyridin-3-yl)oxy)-6-(3,5-dichlorophenyl)pyridin-4-yl)methyl)piperidin-4-yl)methyl) acetamide (150 mg, 0.266 mmol) and $Cs_2CO_3$ (173 mg, 0.532 mmol). The reaction mixture was stirred at 70° C. for 12 h under $N_2$ atmosphere then filtered and concentrated to yield a light yellow solid of benzyl ((trans-1-(5-((4-((4-(acetamidomethyl)piperidin-1-yl)methyl)-6-(3,5-dichlorophenyl)pyridin-2-yl)oxy)pyridin-2-yl)-4-hydroxypyrrolidin-3-yl)methyl)carbamate (100 mg, 0.095 mmol, 35.9% yield): $^1$H NMR (400 MHz, $CD_3OD$) δ ppm 7.97 (d, J=2.5 Hz, 1H), 7.89-7.80 (m, 2H), 7.77-7.73 (m, 1H), 7.63 (s, 1H), 7.49-7.43 (m, 2H), 7.42-7.25 (m, 6H), 5.13 (s, 2H), 3.75-3.67 (m, 4H), 3.55 (s, 2H), 3.41-3.38 (m, 1H), 3.09 (d, J=6.5 Hz, 4H), 2.95 (d, J=11.0 Hz, 2H), 2.14 (s, 2H), 1.98 (s, 3H), 1.74 (d, J=10.5 Hz, 2H), 1.55 (br. s, 1H), 1.41-1.20 (m, 3H); ES-LCMS m/z 1332, 735.2 [M+H]$^+$.

Step 6: N-((1-((2-((6-(trans-3-(Aminomethyl)-4-hydroxypyrrolidin-1-yl)pyridin-3-yl)oxy)-6-(3,5-dichlorophenyl)pyridin-4-yl)methyl)piperidin-4-yl)methyl)acetamide, 4 hydrochloride

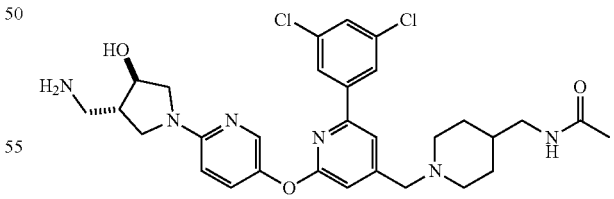

A solution of benzyl ((trans-1-(5-((4-((4-(acetamidomethyl)piperidin-1-yl)methyl)-6-(3,5-dichlorophenyl)pyridin-2-yl)oxy)pyridin-2-yl)-4-hydroxypyrrolidin-3-yl)methyl)carbamate (100 mg, 0.136 mmol) in TFA (5 mL, 67.3 mmol) was stirred at 40° C. for 2 h then concentrated and purified by preparative HPLC (MeCN/$H_2O$ as eluents, acidic condition) and dried by lyophilization to yield a yellow solid of N-((1-((2-((6-(trans-3-(aminomethyl)-4-hydroxypyrrolidin-1-yl)pyridin-3-yl)oxy)-6-(3,5-dichlorophenyl)pyridin-4-yl)methyl)piperidin-4-yl)methyl)acetamide, 4 hydrochloride (33.75 mg, 0.045 mmol, 33.2% yield): $^1$H NMR (400 MHz, CD$_3$OD) δ ppm 8.17 (dd, J=2.1, 9.8 Hz, 1H), 8.08 (d, J=2.2 Hz, 1H), 7.99 (s, 1H), 7.89 (d, J=1.8 Hz, 2H), 7.52 (s, 1H), 7.40 (s, 1H), 7.27 (d, J=9.9 Hz, 1H), 4.46 (s, 2H), 4.07-3.97 (m, 2H), 3.63-3.51 (m, 4H), 3.35 (dd, J=2.0, 3.7 Hz, 1H), 3.25-3.07 (m, 6H), 2.75-2.68 (m, 1H), 2.04-1.94 (m, 5H), 1.86 (br. s, 1H), 1.69-1.54 (m, 2H); ES-LCMS m/z 599.2, 601.3 [M+H]$^+$.

Example 185: 3-(3-(5-((4-((4-(Acetamidomethyl) piperidin-1-yl)methyl)-6-(3,5-dichlorophenyl)pyridin-2-yl)oxy)pyridin-2-yl)-3,8-diazabicyclo[3.2.1] octan-8-yl)propanoic acid, 4 hydrochloride

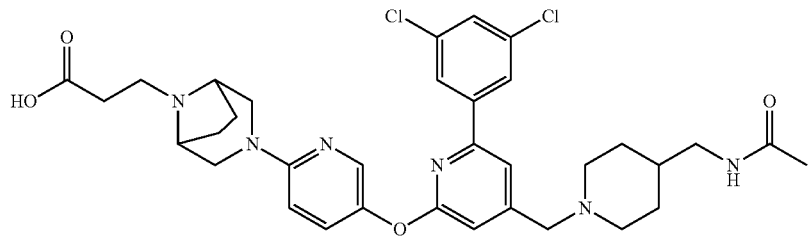 [SMILES: CC(=O)NCC1CCN(Cc2cc(Oc3ccc(N4CC5CCC(C4)N5CCC(=O)O)nc3)nc(-c3cc(Cl)cc(Cl)c3)c2)CC1]

Step 1: tert-Butyl 8-(5-((4-((4-(acetamidomethyl) piperidin-1-yl)methyl)-6-(3,5-dichlorophenyl)pyridin-2-yl)oxy)pyridin-2-yl)-3,8-diazabicyclo[3.2.1] octane-3-carboxylate

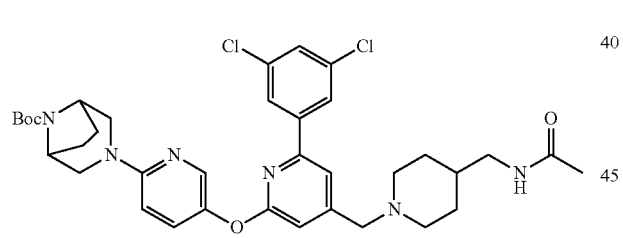

To a mixture of N-((1-((2-((6-bromopyridin-3-yl)oxy)-6-(3,5-dichlorophenyl)pyridin-4-yl)methyl)piperidin-4-yl) methyl)acetamide (300 mg, 0.478 mmol) and tert-butyl 3,8-diazabicyclo[3.2.1]octane-8-carboxylate (102 mg, 0.478 mmol) in THF (10 mL) was added Xantphos (27.7 mg, 0.048 mmol), Pd$_2$(dba)$_3$ (43.8 mg, 0.048 mmol) and Cs$_2$CO$_3$ (468 mg, 1.435 mmol). The reaction was stirred at 70° C. for 8 h under N$_2$ atmosphere. Water (20 mL) was added and the mixture was extracted with DCM (20 mL×2). The combined organic layers were dried over Na$_2$SO$_4$, filtered, concentrated and purified by silica gel column chromatography (DCM/MeOH=10/1). All fractions found to contain product by TLC (DCM/MeOH=10/1, R$_f$=0.3) were combined and concentrated to yield a light yellow solid of tert-butyl 8-(5-((4-((4-(acetamidomethyl)piperidin-1-yl)methyl)-6-(3,5-dichlorophenyl)pyridin-2-yl)oxy)pyridin-2-yl)-3,8-diazabicyclo[3.2.1]octane-3-carboxylate (250 mg, 0.180 mmol, 37.6% yield): $^1$H NMR (400 MHz, CD$_3$OD) δ ppm 8.32 (d, J=2.2 Hz, 2H), 8.01 (d, J=2.6 Hz, 1H), 7.47 (dd, J=3.1, 9.3 Hz, 1H), 7.09 (s, 2H), 6.96 (s, 1H), 6.85 (d, J=9.3 Hz, 1H), 3.97-3.92 (m, 2H), 3.62 (s, 2H), 3.59 (s, 2H), 3.08 (br. s, 4H), 2.95 (br. s, 4H), 1.95-1.85 (m, 5H), 1.74-1.71 (m, 3H), 1.49 (s, 9H), 1.35-1.31 (m, 4H); ES-LCMS m/z 695.3, 697.3 [M+H]$^+$.

Step 2: N-((1-((2-((6-(3,8-Diazabicyclo[3.2.1]octan-8-yl)pyridin-3-yl)oxy)-6-(3,5-dichlorophenyl)pyridin-4-yl)methyl)piperidin-4-yl)methyl)acetamide

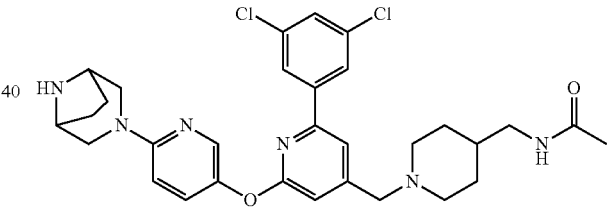

To a mixture of tert-butyl 8-(5-((4-((4-(acetamidomethyl) piperidin-1-yl)methyl)-6-(3,5-dichlorophenyl)pyridin-2-yl) oxy)pyridin-2-yl)-3,8-diazabicyclo[3.2.1]octane-3-carboxylate (250 mg, 0.180 mmol) in EtOAc (5 mL) was added HCl solution (4.0 M in EtOAc, 5 mL, 20.0 mmol). The reaction was stirred at 25° C. for 0.5 h. Saturated aqueous NaHCO$_3$ solution (50 mL) was added and the mixture was extracted with DCM (50 mL×2). The combined organic layers were dried over Na$_2$SO$_4$, filtered and concentrated to yield a yellow solid of N-((1-((2-((6-(3,8-diazabicyclo[3.2.1]octan-8-yl)pyridin-3-yl)oxy)-6-(3,5-dichlorophenyl)pyridin-4-yl) methyl)piperidin-4-yl)methyl)acetamide (200 mg, 0.168 mmol, 93.0% yield): $^1$H NMR (400 MHz, CD$_3$OD) δ ppm 8.35 (d, J=2.2 Hz, 1H), 8.24 (br. s, 1H), 8.03 (d, J=5.3 Hz, 2H), 7.75-7.67 (m, 2H), 7.51-7.44 (m, 2H), 4.50 (s, 2H), 4.21 (s, 1H), 3.79-3.75 (m, 1H), 3.60 (d, J=7.1 Hz, 4H), 3.18-3.08 (m, 6H), 2.38-2.11 (m, 3H), 1.98 (s, 6H), 1.87 (br. s, 1H), 1.65 (d, J=12.3 Hz, 2H); ES-LCMS m/z 595.3, 597.3 [M+H]$^+$.

Step 3: Ethyl 3-(8-(5-((4-((4-(acetamidomethyl)piperidin-1-yl)methyl)-6-(3,5-dichlorophenyl)pyridin-2-yl)oxy)pyridin-2-yl)-3,8-diazabicyclo[3.2.1]octan-3-yl)propanoate

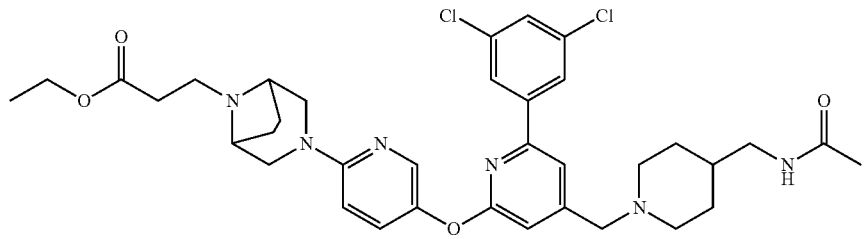 [SMILES: CCOC(=O)CCN1C2CCC1CN(c1ccc(Oc3cc(CN4CCC(CNC(C)=O)CC4)cc(-c4cc(Cl)cc(Cl)c4)n3)cn1)C2]

To a mixture of N-((1-((2-((6-(3,8-diazabicyclo[3.2.1]octan-8-yl)pyridin-3-yl)oxy)-6-(3,5-dichlorophenyl)pyridin-4-yl)methyl)piperidin-4-yl)methyl)acetamide (200 mg, 0.168 mmol) in DMF (5 mL) was added ethyl 3-bromopropanoate (0.038 mL, 0.252 mmol) and $K_2CO_3$ (69.6 mg, 0.504 mmol). The reaction was stirred at 60° C. for 5 h. Water (20 mL) was added and the mixture was extracted with DCM (20 mL×2). The combined organic layers were dried over $Na_2SO_4$, filtered and concentrated to yield a yellow of ethyl 3-(8-(5-((4-((4-(acetamidomethyl)piperidin-1-yl)methyl)-6-(3,5-dichlorophenyl)pyridin-2-yl)oxy)pyridin-2-yl)-3,8-diazabicyclo[3.2.1]octan-3-yl)propanoate (200 mg, 0.144 mmol, 86.0% yield): $^1$H NMR (400 MHz, $CD_3OD$) δ ppm 8.32 (s, 1H), 7.82-7.77 (m, 3H), 7.52 (s, 1H), 7.48-7.36 (m, 2H), 7.09 (s, 1H), 4.15 (d, J=7.1 Hz, 2H), 3.80 (d, J=11.9 Hz, 2H), 3.67-3.56 (m, 4H), 3.20-3.03 (m, 6H), 2.97-2.89 (m, 6H), 2.15-2.01 (m, 5H), 1.79-1.69 (m, 4H), 1.61-1.45 (m, 1H), 1.35-1.25 (m, 5H); ES-LCMS m/z 695.3, 697.3 $[M+H]^+$.

Step 4: 3-(3-(5-((4-((4-(Acetamidomethyl)piperidin-1-yl)methyl)-6-(3,5-dichlorophenyl)pyridin-2-yl)oxy)pyridin-2-yl)-3,8-diazabicyclo[3.2.1]octan-8-yl)propanoic acid, 4 hydrochloride

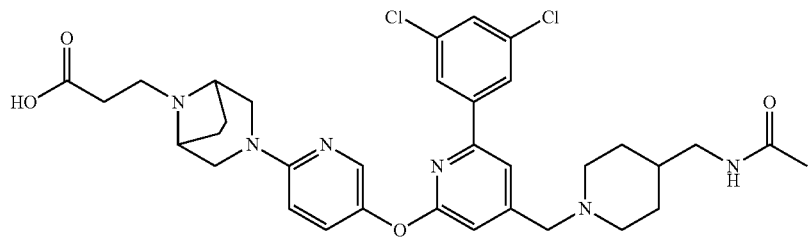 [SMILES: CC(=O)NCC1CCN(Cc2cc(Oc3ccc(N4CC5CCC(C4)N5CCC(=O)O)nc3)nc(-c3cc(Cl)cc(Cl)c3)c2)CC1]

To a mixture of ethyl 3-(3-(5-((4-((4-(acetamidomethyl)piperidin-1-yl)methyl)-6-(3,5-dichlorophenyl)pyridin-2-yl)oxy)pyridin-2-yl)-3,8-diazabicyclo[3.2.1]octan-8-yl)propanoate (200 mg, 0.144 mmol) in MeOH (10 mL) and water (1 mL) was added NaOH (5.75 mg, 0.144 mmol). The reaction was stirred at 20° C. for 2 h then concentrated and purified by preparative HPLC (MeCN/$H_2O$ as eluents, acidic condition) and dried by lyophilization to yield a light yellow solid of 3-(3-(5-((4-((4-(acetamidomethyl)piperidin-1-yl)methyl)-6-(3,5-dichlorophenyl)pyridin-2-yl)oxy)pyridin-2-yl)-3,8-diazabicyclo[3.2.1]octan-8-yl)propanoic acid, 4 hydrochloride (16.51 mg, 0.020 mmol, 14.1% yield): $^1$H NMR (400 MHz, $CD_3OD$) δ ppm 8.19 (s, 1H), 8.03-7.93 (m, 2H), 7.87 (d, J=1.3 Hz, 2H), 7.51 (s, 1H), 7.35 (s, 2H), 4.44 (s, 2H), 4.39-4.23 (m, 4H), 3.71 (d, J=11.9 Hz, 1H), 3.60 (d, J=11.9 Hz, 1H), 3.46 (br. s, 1H), 3.18-3.07 (m, 4H), 3.00 (t, J=6.8 Hz, 2H), 2.39 (br. s, 2H), 2.19 (d, J=8.4 Hz, 2H), 2.09-1.92 (m, 7H), 1.85 (br. s, 1H), 1.67-1.55 (m, 2H); ES-LCMS m/z 667.2, 669.2 $[M+H]^+$.

Examples 186-189 (Table 10) were prepared by procedures analogous to those described for example 185.

TABLE 10

| Example | Structure/Name | ¹H NMR | LCMS |
|---|---|---|---|
| 186 | 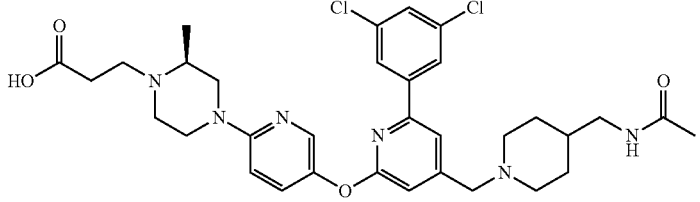 [SMILES: CC(=O)NCC1CCN(Cc2cc(Oc3ccc(N4CCN(CCC(=O)O)[C@@H](C)C4)nc3)nc(-c3cc(Cl)cc(Cl)c3)c2)CC1]<br>(S)-3-(4-(5-((4-((4-(acetamidomethyl)piperidin-1-yl)methyl)-6-(3,5-dichlorophenyl)pyridin-2-yl)oxy)pyridin-2-yl)-2-methylpiperazin-1-yl)propanoic acid | ¹H NMR (400 MHz, CD₃OD) δ ppm 8.28 (d, J = 9.7 Hz, 1H), 8.23 (d, J = 1.8 Hz, 1H), 8.11 (s, 1H), 7.89 (d, J = 1.3 Hz, 2H), 7.70 (d, J = 9.7 Hz, 1H), 7.47 (s, 2H), 4.51 (br. s, 3H), 4.05-3.35 (m, 10H), 3.26-3.12 (m, 4H), 3.02-2.94 (m, 2H), 2.14 (s, 3H), 1.99 (d, J = 13.2 Hz, 3H), 1.72 (d, J = 11.9 Hz, 2H), 1.60 (br. s, 3H) | ES-LCMS m/z 655.2, 657.2 [M + H]⁺. |
| 187 | 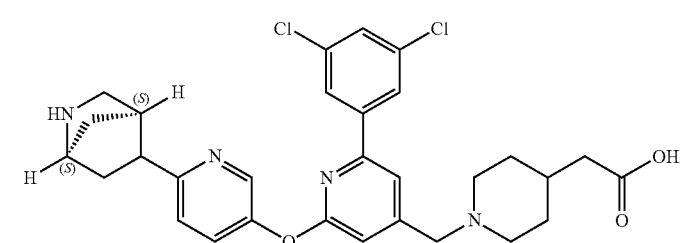<br>2-(1-((2-((6-((1S,4S)-2,5-diazabicyclo[2.2.1]heptan-2-yl)pyridin-3-yl)oxy)-6-(3,5-dichlorophenyl)pyridin-4-yl)methyl)piperidin-4-yl)acetic acid | ¹H NMR (400 MHz, CD₃OD) δ ppm 8.23-8.12 (m, 2H), 7.97 (s, 1H), 7.89 (s, 2H), 7.52 (s, 1H), 7.40 (s, 2H), 5.22 (s, 1H), 4.74 (s, 1H), 4.45 (s, 2H), 4.00-3.89 (m, 2H), 3.66-3.50 (m, 4H), 3.14 (t, J = 12.1 Hz, 2H), 2.43 (d, J = 11.5 Hz, 1H), 2.32 (d, J = 6.2 Hz, 2H), 2.25 (d, J = 11.5 Hz, 1H), 2.05 (d, J = 13.7 Hz, 3H), 1.75-1.59 (m, 2H) | ES-LCMS m/z 568.3, 570.3 [M + H]⁺. |
| 188 | 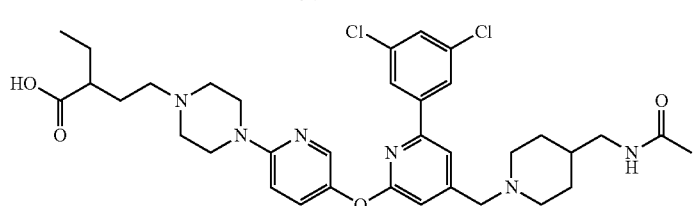<br>4-(4-(5-((4-((4-(acetamidomethyl)piperidin-1-yl)methyl)-6-(3,5-dichlorophenyl)pyridin-2-yl)oxy)pyridin-2-yl)piperazin-1-yl)-2-ethylbutanoic acid | ¹H NMR (400 Hz, CD₃OD) δ ppm 8.16 (s, 1H), 7.89 (br s, 1H), 7.85 (d, J = 2.0 Hz, 3H), 7.49 (t, J = 1.9 Hz, 1H), 7.29 (brs, 2H), 4.56-4.27 (m, 4H), 3.74 (brs, 2H), 3.58 (d, J = 11.5 Hz, 2H), 3.51-3.31 (m, 5H), 3.27-3.19 (m, 2H), 3.15-2.98 (m, 3H), 2.48-2.34 (m, 1H), 2.17-2.06 (m, 1H), 2.02-1.91 (m, 6H), 1.83 (br s, 1H), 1.76-1.62 (m, 2H), 1.62-1.47 (m, 2H), 0.98 (t, J = 7.4 Hz, 3H) | ES-LCMS m/z 683.3, 685.3 [M + H]⁺. |
| 189 | 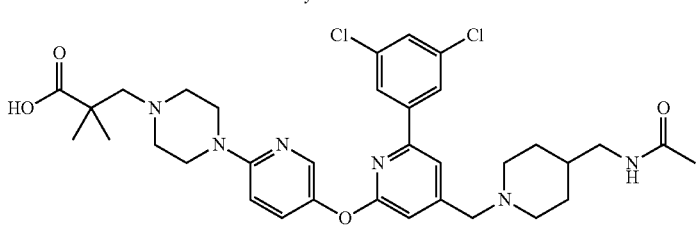<br>3-(4-(5-((4-((4-(acetamidomethyl)piperidin-1-yl)methyl)-6-(3,5-dichlorophenyl)pyridin-2-yl)oxy)pyridin-2-yl)piperazin-1-yl)-2,2-dimethylpropanoic acid | ¹H NMR (400 MHz, CD₃OD) δ ppm 8.20 (d, J = 2.6 Hz, 1H), 8.03 (dd, J = 2.5, 9.4 Hz, 1H), 7.95 (s, 1H), 7.88 (d, J = 1.8 Hz, 2H), 7.51 (t, J = 1.9 Hz, 1H), 7.43 (d, J = 9.7 Hz, 1H), 7.36 (s, 1H), 4.58-4.38 (m, 2H), 4.18 (br s, 2H), 3.81-3.53 (m, 6H), 3.48 (s, 2H), 3.38-3.31 (m, 2H), 3.21-3.01 (m, 4H), 2.06-1.93 (m, 5H), 1.85 (br s, 1H), 1.66-1.53 (m, 2H), 1.42 (s, 6H) | ES-LCMS m/z 669.3, 671.3 [M + H]⁺. |

Example 190: 3-(4-(5-((4-((4-(Acetamidomethyl) piperidin-1-yl)methyl)-6-(3,5-dichlorophenyl)pyridin-2-yl)oxy)pyridin-2-yl)-1,4-diazepan-1-yl)propanoic acid, 4 hydrochloride

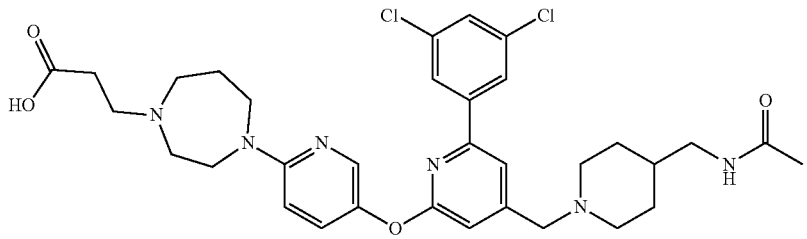 [SMILES: CC(=O)NCC1CCN(Cc2cc(Oc3ccc(N4CCCN(CCC(=O)O)CC4)nc3)nc(-c3cc(Cl)cc(Cl)c3)c2)CC1]

Step 1: tert-Butyl 4-(5-((4-((4-(acetamidomethyl) piperidin-1-yl)methyl)-6-(3,5-dichlorophenyl)pyridin-2-yl)oxy)pyridin-2-yl)-1,4-diazepane-1-carboxylate Step 2: N-((1-((2-((6-(1,4-Diazepan-1-yl)pyridin-3-yl)oxy)-6-(3,5-dichlorophenyl)pyridin-4-yl)methyl) piperidin-4-yl)methyl)acetamide, 4 hydrochloride

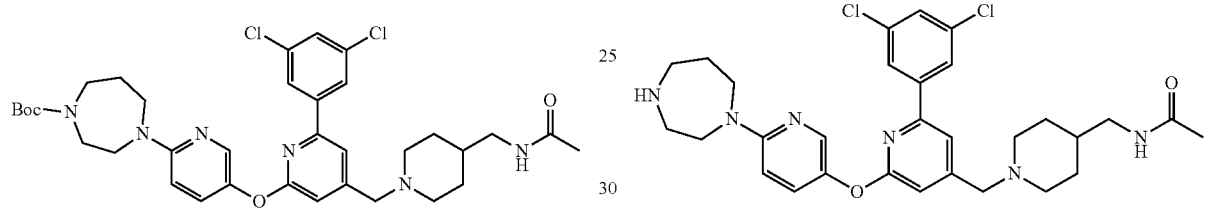

To a suspension of N-((1-((2-((6-bromopyridin-3-yl)oxy)-6-(3,5-dichlorophenyl)pyridin-4-yl)methyl)piperidin-4-yl)methyl)acetamide (500 mg, 0.797 mmol), tert-butyl 1,4-diazepane-1-carboxylate (240 mg, 1.196 mmol), (±)-BINAP (99 mg, 0.159 mmol), 18-crown-6 (211 mg, 0.797 mmol) and t-BuONa (230 mg, 2.392 mmol) in THF (20 mL) stirred under N₂ atmosphere was added Pd₂(dba)₃ (73.0 mg, 0.080 mmol). The reaction mixture was stirred at 70° C. for 12 h under N₂ atmosphere then filtered and concentrated to yield crude product, which was purified by column chromatography (DCM/MeOH=10/1, R$_f$=0.6). The desired fraction was concentrated to yield brown gum of tert-butyl 4-(5-((4-((4-(acetamidomethyl)piperidin-1-yl)methyl)-6-(3,5-dichlorophenyl)pyridin-2-yl)oxy)pyridin-2-yl)-1,4-diazepane-1-carboxylate (350 mg, 0.372 mmol, 46.6% yield): ¹H NMR (400 MHz, CDCl₃) δ ppm 8.06 (d, J=2.6 Hz, 1H), 7.76 (d, J=1.8 Hz, 2H), 7.42-7.34 (m, 2H), 7.32 (s, 1H), 6.81 (s, 1H), 6.57 (d, J=9.3 Hz, 1H), 5.54 (br. s, 1H), 3.79 (t, J=5.1 Hz, 2H), 3.61-3.60 (m, 4H), 3.59 (d, J=4.4 Hz, 2H), 3.53-3.46 (m, 2H), 3.35 (br. s, 1H), 3.30-3.23 (m, 1H), 3.16 (t, J=6.4 Hz, 2H), 2.87 (d, J=11.0 Hz, 2H), 2.06-1.94 (m, 7H), 1.53 (br. s, 1H), 1.43 (d, J=11.0 Hz, 9H), 1.37-1.22 (m, 2H); ES-LCMS m/z 683.3, 685.3 [M+H]⁺.

To a suspension of tert-butyl 4-(5-((4-((4-(acetamidomethyl)piperidin-1-yl)methyl)-6-(3,5-dichlorophenyl)pyridin-2-yl)oxy)pyridin-2-yl)-1,4-diazepane-1-carboxylate (630 mg, 0.675 mmol) in EtOAc (5 mL) was added HCl solution (4.0 M in EtOAc, 20 mL, 80 mmol). The reaction mixture was stirred at 25° C. for 0.5 h then concentrated to yield brown gum of N-((1-((2-((6-(1,4-diazepan-1-yl)pyridin-3-yl)oxy)-6-(3,5-dichlorophenyl)pyridin-4-yl)methyl) piperidin-4-yl)methyl)acetamide, 4 hydrochloride (500 mg, 0.544 mmol, 81.0% yield): ¹H NMR (400 MHz, CD₃OD) δ ppm 8.27-8.20 (m, 1H), 8.17 (d, J=2.6 Hz, 1H), 8.00 (s, 1H), 7.91 (d, J=1.8 Hz, 2H), 7.59 (d, J=10.1 Hz, 1H), 7.53 (s, 1H), 7.43 (s, 1H), 4.46 (s, 2H), 4.22-4.13 (m, 2H), 3.90 (t, J=5.7 Hz, 2H), 3.62-3.54 (m, 4H), 3.51-3.43 (m, 2H), 3.19-3.05 (m, 4H), 2.38 (br. s, 2H), 2.07-1.93 (m, 5H), 1.87 (br. s, 1H), 1.69-1.57 (m, 2H); ES-LCMS m/z 583.3, 585.3 [M+H]⁺.

Step 3: Ethyl 3-(4-(5-((4-((4-(acetamidomethyl) piperidin-1-yl)methyl)-6-(3,5-dichlorophenyl)pyridin-2-yl)oxy)pyridin-2-yl)-1,4-diazepan-1-yl)propanoate

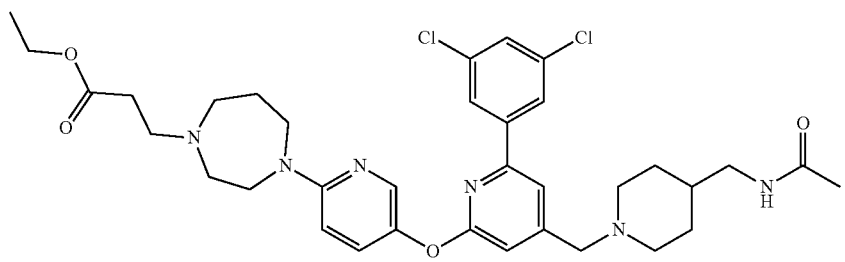 [SMILES: CCOC(=O)CCN1CCCN(c2ccc(Oc3cc(CN4CCC(CNC(C)=O)CC4)cc(-c4cc(Cl)cc(Cl)c4)n3)cn2)CC1]

To a suspension of N-((1-((2-((6-(1,4-diazepan-1-yl)pyridin-3-yl)oxy)-6-(3,5-dichlorophenyl)pyridin-4-yl)methyl)piperidin-4-yl)methyl)acetamide, 4 hydrochloride (500 mg, 0.544 mmol) and ethyl 3-bromopropanoate (492 mg, 2.72 mmol) in DMF (20 mL) was added K$_2$CO$_3$ (451 mg, 3.26 mmol). The reaction mixture was stirred at 80° C. for 10 h then filtered and concentrated to yield crude product, which was purified by ISCO (DCM/MeOH=10/1, R$_f$=0.6) and the desired fraction was concentrated to yield a pale yellow solid of ethyl 3-(4-(5-((4-((4-(acetamidomethyl)piperidin-1-ylmethyl)-6-(3,5-dichlorophenyl)pyridin-2-yl)oxy)pyridin-2-yl)-1,4-diazepan-1-yl)propanoate (250 mg, 0.303 mmol, 55.7% yield): $^1$H NMR (400 MHz, CD$_3$OD) δ ppm 8.05 (d, J=3.1 Hz, 1H), 7.86 (d, J=1.8 Hz, 2H), 7.75 (br. s, 1H), 7.53 (dd, J=2.9, 9.0 Hz, 1H), 7.48 (s, 1H), 7.13 (br. s, 1H), 6.85 (d, J=9.3 Hz, 1H), 4.61 (br. s, 2H), 4.24-4.15 (m, 2H), 4.11 (br. s, 4H), 3.76-3.67 (m, 2H), 3.56-3.37 (m, 6H), 3.11 (d, J=5.3 Hz, 2H), 2.85 (t, J=6.6 Hz, 2H), 2.69 (s, 2H), 2.29 (br. s, 2H), 1.94 (s, 3H), 1.89 (d, J=13.7 Hz, 2H), 1.74 (br. s, 1H), 1.47 (br. s, 2H), 1.27 (t, J=7.3 Hz, 3H); ES-LCMS m/z 683.4, 685.3 [M+H]$^+$.

Step 4: 3-(4-(5-((4-((4-(Acetamidomethyl)piperidin-1-yl)methyl)-6-(3,5-dichlorophenyl)pyridin-2-yl)oxy)pyridin-2-yl)-1,4-diazepan-1-yl)propanoic acid, 4 hydrochloride

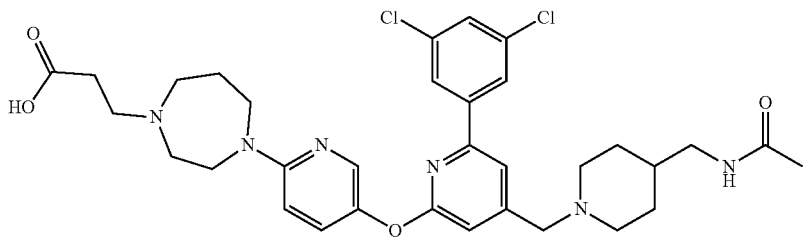 [SMILES: CC(=O)NCC1CCN(Cc2cc(Oc3ccc(N4CCCN(CCC(=O)O)CC4)nc3)nc(-c3cc(Cl)cc(Cl)c3)c2)CC1]

To a suspension of ethyl 3-(4-(5-((4-((4-(acetamidomethyl)piperidin-1-yl)methyl)-6-(3,5-dichlorophenyl)pyridin-2-yl)oxy)pyridin-2-yl)-1,4-diazepan-1-yl)propanoate (250 mg, 0.303 mmol) in THF (10 mL) was added LiOH·H$_2$O (38.2 mg, 0.909 mmol) in H$_2$O (3 mL). The reaction mixture was stirred at 25° C. for 10 h then was adjusted pH to 7 with 1 N HCl and evaporated to yield crude product, which was purified by preparative HPLC (MeCN/H$_2$O as eluents, acidic condition). The desired fraction was lyophilized to yield a white solid of 3-(4-(5-((4-((4-(acetamidomethyl)piperidin-1-yl)methyl)-6-(3,5-dichlorophenyl)pyridin-2-yl)oxy)pyridin-2-yl)-1,4-diazepan-1-yl)propanoic acid, 4 hydrochloride (106.1 mg, 0.129 mmol, 42.7% yield): $^1$H NMR (400 MHz, CD$_3$OD) δ ppm 8.28-8.20 (m, 1H), 8.17 (d, J=2.2 Hz, 1H), 8.03 (s, 1H), 7.91 (d, J=1.8 Hz, 2H), 7.58 (d, 7=9.7 Hz, 1H), 7.50 (s, 1H), 7.44 (s, 1H), 4.47 (s, 2H), 4.25 (br. s, 2H), 3.97-3.70 (m, 4H), 3.66-3.32 (m, 7H), 3.23-3.07 (m, 3H), 2.97 (t, 7=7.1 Hz, 2H), 2.64-2.37 (m, 2H), 2.10-1.92 (m, 5H), 1.88 (br. s, 1H), 1.66 (q, 7=11.9 Hz, 2H); ES-LCMS m/z 655.3, 657.3 [M+H]$^+$.

Examples 191-203 (Table 11) were prepared by procedures analogous to those described for example 190.

TABLE 11

| Example | Structure/Name | $^1$H NMR | LCMS |
|---|---|---|---|
| 191 | 3-(4-(5-((4-((4-(acetamidomethyl)piperidin-1-yl)methyl)-6-(3,5-dichlorophenyl)pyridin-2-yl)oxy)pyridin-2-yl)-2,2-dimethylpiperazin-1-yl)propanoic acid | $^1$H NMR (400 MHz, CD$_3$OD) δ ppm 8.18 (d, J = 2.6 Hz 1H), 8.07 (dd, J = 2.6, 9.7 Hz, 1H), 7.96 (s, 1H), 7.88 (d, J = 1.8 Hz, 2H), 7.53-7.48 (m, 2H), 7.37 (s, 1H), 4.45 (s, 2H), 3.94-3.43 (m, 10H), 3.16-3.05 (m, 4H), 2.95 (t, J = 6.4 Hz, 2H), 2.02-1.93 (m, 5H), 1.85 (s, 1H), 1.70-1.49 (m, 8H) | ES-LCMS m/z 669.4, 671.4 [M + H]$^+$. |

TABLE 11-continued

| Example | Structure/Name | ¹H NMR | LCMS |
|---|---|---|---|
| 192 | N-((1-((2-((6-(1,4-diazepan-1-yl)pyridin-3-yl)oxy)-6-(3,5-dichlorophenyl)pyridin-4-yl)methyl)piperidin-4-yl)methyl)acetamide | ¹H NMR (400 MHz, CD₃OD) δ ppm 7.96 (d, J = 2.6 Hz, 1H), 7.83 (d, J = 1.8 Hz, 2H), 7.60 (s, 1H), 7.48-7.37 (m, 2H), 6.95 (s, 1H), 6.77 (d, J = 9.3 Hz, 1H), 4.76-4.52 (m, 2H), 3.87-3.68 (m, 4H), 3.18-3.01 (m, 4H), 2.97-2.78 (m, 4H), 2.14-1.96 (m, 4H), 1.93 (s, 3H), 1.72 (d, J = 11.9 Hz, 2H), 1.55-1.46 (m, 1H), 1.37-1.23 (m, 2H) | ES-LCMS m/z 583.3, 585.3 [M + H]⁺. |
| 193 | N-((1-((2-(3,5-dichlorophenyl)-6-((6-(4-(methylamino)piperidin-1-yl)pyridin-3-yl)oxy)pyridin-4-yl)methyl)piperidin-4-yl)methyl)acetamide | ¹H NMR (400 MHz, CD₃OD) δ ppm 8.19 (d, J = 9.0 Hz, 1H), 8.12 (br. s, 1H), 8.02 (s, 1H), 7.89 (s, 2H), 7.62 (d, J = 9.3 Hz, 1H), 7.50 (s, 1H), 7.42 (s, 1H), 4.54-4.31 (m, 4H), 3.62-3.30 (m, 7H), 3.13 (d, J = 6.0 Hz, 3H), 2.76 (s, 3H), 2.35 (d, J = 11.7 Hz, 2H), 2.03-1.94 (m, 4H), 1.85 (d, J = 10.6 Hz, 3H), 1.64 (d, J = 12.1 Hz, 2H) | ES-LCMS m/z 597.1, 599.0 [M + H]⁺. |
| 194 | N-((1-((2-(3,5-dichlorophenyl)-6-((6-(hexahydropyrrolo[3,4-c]pyrrol-2(1H)-yl)pyridin-3-yl)oxy)pyridin-4-yl)methyl)piperidin-4-yl)methyl)acetamide | ¹H NMR (400 MHz, CD₃OD) δ ppm 8.15 (d, J = 9.0 Hz, 1H), 8.09 (s, 1H), 7.98 (s, 1H), 7.87 (d, J = 1.5 Hz, 2H), 7.50 (s, 1H), 7.39 (s, 1H), 7.28 (d, J = 9.5 Hz, 1H), 4.56-4.38 (m, 2H), 3.95 (d, J = 6.1 Hz, 2H), 3.78 (d, J = 10.5 Hz, 2H), 3.69-3.54 (m, 4H), 3.49-3.32 (m, 5H), 3.11 (d, J = 5.9 Hz, 3H), 2.02-1.93 (m, 5H), 1.84 (br. s, 1H), 1.69-1.52 (m, 2H) | ES-LCMS m/z 595.2, 597.2 [M + H]⁺. |
| 195 | N-((1-((2-(3,5-dichlorophenyl)-6-((6-(3-(hydroxymethyl)piperazin-1-yl)pyridin-3-yl)oxy)pyridin-4-yl)methyl)piperidin-4-yl)methyl)acetamide | ¹H NMR (400 MHz, CD₃OD) δ ppm 8.19 (d, J = 1.7 Hz, 1H), 8.08 (d, J = 7.8 Hz, 1H), 7.97 (s, 1H), 7.87 (d, J = 1.5 Hz, 2H), 7.53-7.47 (m, 2H), 7.38 (s, 1H), 4.47-4.36 (m, 4H), 3.91 (dd, J = 3.5, 11.9 Hz, 1H), 3.79 (dd, J = 5.4, 12.0 Hz, 1H), 3.64-3.51 (m, 5H), 3.40 (d, J = 10.0 Hz, 2H), 3.16-3.04 (m, 4H), 2.00-1.93 (m, 5H), 1.84 (br. s, 1H), 1.67-1.57 (m, 2H) | ES-LCMS m/z 599.3, 601.3 [M + H]⁺. |

TABLE 11-continued

| Example | Structure/Name | ¹H NMR | LCMS |
|---|---|---|---|
| 196 | 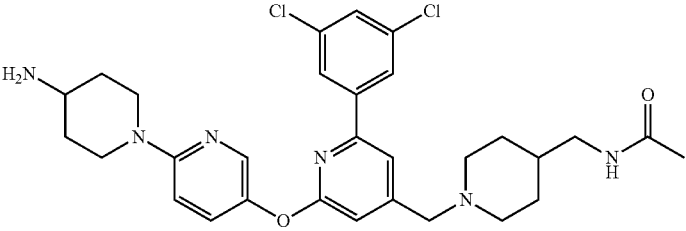 [SMILES: CC(=O)NCC1CCN(Cc2cc(Oc3ccc(N4CCC(N)CC4)nc3)nc(-c3cc(Cl)cc(Cl)c3)c2)CC1]<br>N-((1-((2-((6-(4-aminopiperidin-1-yl)pyridin-3-yl)oxy)-6-(3,5-dichlorophenyl)pyridin-4-yl)methyl)piperidin-4-yl)methyl)acetamide | ¹H NMR (400 MHz, CD₃OD) δ ppm 8.18 (d, J = 9.3 Hz, 1H), 8.11 (s, 1H), 8.02 (s, 1H), 7.89 (d, J = 1.3 Hz, 2H), 7.62 (d, J = 9.7 Hz, 1H), 7.50 (s, 1H), 7.42 (s, 1H), 4.46 (s, 2H), 4.36 (d, J = 13.9 Hz, 2H), 3.58 (d, J = 11.0 Hz, 3H), 3.45 (t, J = 12.6 Hz, 2H), 3.21-3.02 (m, 4H), 2.27 (d, J = 11.5 Hz, 2H), 2.05-1.93 (m, 5H), 1.84 (d, J = 11.5 Hz, 3H), 1.70-1.57 (m, 2H) | ES-LCMS m/z 583.3, 585.3 [M + H]⁺. |
| 197 | 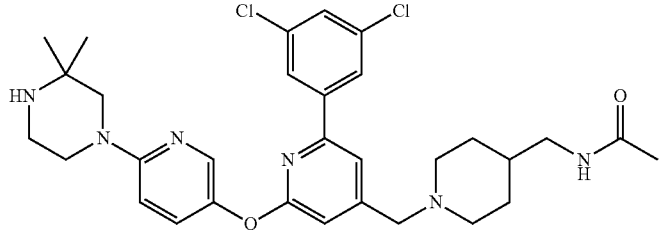 [SMILES: CC(=O)NCC1CCN(Cc2cc(Oc3ccc(N4CCNC(C)(C)C4)nc3)nc(-c3cc(Cl)cc(Cl)c3)c2)CC1]<br>N-((1-((2-(3,5-dichlorophenyl)-6-((6-(3,3-dimethylpiperazin-1-yl)pyridin-3-yl)oxy)pyridin-4-yl)methyl)piperidin-4-yl)methyl)acetamide | ¹H NMR (400 MHz, CD₃OD) δ ppm 8.17 (br. s, 2H), 7.95-7.84 (m, 3H), 7.51 (s, 1H), 7.35 (br. s, 2H), 4.44 (br. s, 2H), 4.00-3.81 (m, 4H), 3.59 (d, J = 11.7 Hz, 2H), 3.48 (br. s, 2H), 3.35 (br. s, 2H), 3.12 (d, J = 6.6 Hz, 2H), 2.05-1.92 (m, 5H), 1.84 (br. s, 1H), 1.68-1.43 (m, 8H) | ES-LCMS m/z 597.3, 599.3 [M + H]⁺. |
| 198 | 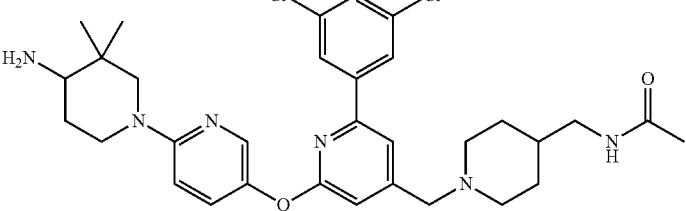<br>N-((1-((2-((6-(4-amino-3,3-dimethylpiperidin-1-yl)pyridin-3-yl)oxy)-6-(3,5-dichlorophenyl)pyridin-4-yl)methyl)piperidin-4-yl)methyl)acetamide | ¹H NMR (400 MHz, D₂O) δ ppm 7.96-7.89 (m, 2H), 7.55 (s, 1H), 7.46-7.37 (m, 3H), 7.21-7.16 (m, 1H), 7.10 (s, 1H), 4.30 (s, 2H), 4.14 (d, J = 14.1 Hz, 1H), 3.85 (d, J = 14.6 Hz, 1H), 3.47 (d, J = 11.5 Hz, 2H), 3.40-3.30 (m, 2H), 3.19-3.12 (m, 1H), 3.00 (d, J = 6.5 Hz, 3H), 2.10-2.00 (m, 1H), 1.92-1.85 (m, 6H), 1.75 (d, J = 7.5 Hz, 1H), 1.39 (q, J = 12.0 Hz, 2H), 1.10 (s, 3H), 1.06 (d, J = 6.5 Hz, 1H), 0.97 (s, 3H) | ES-LCMS m/z 611.2, 613.2 [M + H]⁺. |
| 199 | 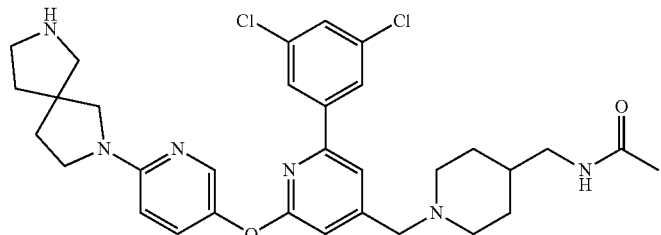<br>N-((1-((2-((6-(2,7-diazaspiro[4.4]nonan-2-yl)pyridin-3-yl)oxy)-6-(3,5-dichlorophenyl)pyridin-4-yl)methyl)piperidin-4-yl)methyl)acetamide | ¹H NMR (400 MHz, CD₃OD) δ ppm 8.14 (dd, J = 2.4, 9.8 Hz, 1H), 8.06 (d, J = 2.2 Hz, 1H), 7.96 (s, 1H), 7.87 (d, J = 1.7 Hz, 2H), 7.51 (s, 1H), 7.39 (s, 1H), 7.26 (d, J = 9.8 Hz, 1H), 4.44 (s, 2H), 3.85-3.71 (m, 4H), 3.59 (d, J = 12.0 Hz, 2H), 3.50 (t, J = 7.3 Hz, 2H), 3.44-3.36 (m, 2H), 3.14-3.06 (m, 4H), 2.36-2.14 (m, 4H), 2.04-1.91 (m, 5H), 1.84 (br. s, 1H), 1.68-1.52 (m, 2H) | ES-LCMS m/z 609.2, 611.2 [M + H]⁺. |

TABLE 11-continued

| Example | Structure/Name | ¹H NMR | LCMS |
|---|---|---|---|
| 200 | 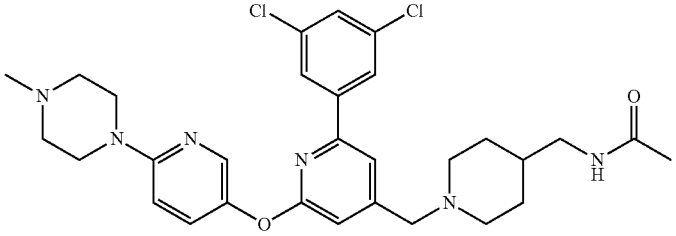<br>N-((1-((2-(3,5-dichlorophenyl)-6-((6-(4-methylpiperazin-1-yl)pyridin-3-yl)oxy)pyridin-4-yl)methyl)piperidin-4-yl)methyl)acetamide | ¹H NMR (400 MHz, CD₃OD) δ ppm 8.21 (d, J = 2.4 Hz, 1H), 8.05 (dd, J = 2.6, 9.5 Hz, 1H), 7.94 (s, 1H), 7.87 (d, J = 1.8 Hz, 2H), 7.51 (t, J = 1.8 Hz, 1H), 7.46 (d, J = 9.7 Hz, 1H), 7.36 (s, 1H), 4.53-4.35 (m, 4H), 3.69 (br. s, 2H), 3.59 (d, J = 12.1 Hz, 4H), 3.35 (br. s, 2H), 3.17-3.04 (m, 4H), 3.00 (s, 3H), 2.03-1.92 (m, 5H), 1.84 (br. s, 1H), 1.64-1.50 (m, 2H) | ES-LCMS m/z 583.1, 585.2 [M + H]⁺. |
| 201 | 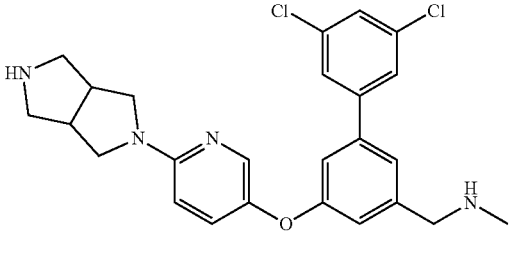 [SMILES: CNCc1cc(Oc2ccc(N3CC4CNCC4C3)nc2)cc(-c2cc(Cl)cc(Cl)c2)c1]<br>1-(3',5'-dichloro-5-((6-(hexahydropyrrolo[3,4-c]pyrrol-2(1H)-yl)pyridin-3-yl)oxy)-[1,1'-biphenyl]-3-yl)-N-methylmethanamine | ¹H NMR (400 MHz, CD₃OD) δ ppm 7.97 (dd, J = 2.6, 9.9 Hz, 1H), 7.88 (d, J = 2.4 Hz, 1H), 7.65 (d, J = 1.8 Hz, 2H), 7.59 (s, 1H), 7.49 (t, J =0 1.8 Hz, 1H), 7.43 (s, 1H), 7.34 (s, 1H), 7.24 (d, J = 9.7 Hz, 1H), 4.26 (s, 2H), 4.00-3.89 (m, 2H), 3.78 (dd, J = 2.5, 11.1 Hz, 2H), 3.69-3.58 (m, 2H), 3.50-3.36 (m, 4H), 2.75 (s, 3H) | ES-LCMS m/z 469.1, 471.2 [M + H]⁺. |
| 202 | 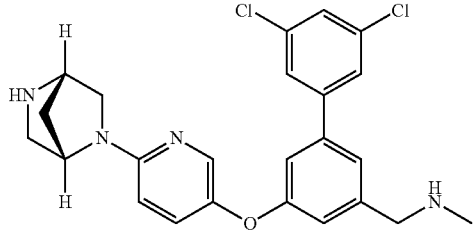 [SMILES: CNCc1cc(Oc2ccc(N3C[C@@H]4C[C@H]3CN4)nc2)cc(-c2cc(Cl)cc(Cl)c2)c1]<br>1-(5-((6-((1S,4S)-2,5-diazabicyclo[2.2.1]heptan-2-yl)pyridin-3-yl)oxy)-3',5'-dichloro-[1,1'-biphenyl]-3-yl)-N-methylmethanamine | ¹H NMR (400 MHz, CD₃OD) δ ppm 8.06-7.91 (m, 2H), 7.66 (br. s, 2H), 7.58 (br. s, 1H), 7.53-7.42 (m, 2H), 7.36 (br. s, 2H), 5.18 (br. s, 1H), 4.73 (br. s, 1H), 4.27 (br. s, 2H), 4.00-3.87 (m, 2H), 3.74-3.61 (m, 1H), 3.57-3.47 (m, 0.5H), 3.14 (br. s, 0.5H), 2.76 (d, J = 3.3 Hz, 3H), 2.43 (d, J = 12.1 Hz, 1H), 2.29-2.19 (m, 1H) | ES-LCMS: m/z 455.0, 457.0 [M + H]⁺. |
| 203 | 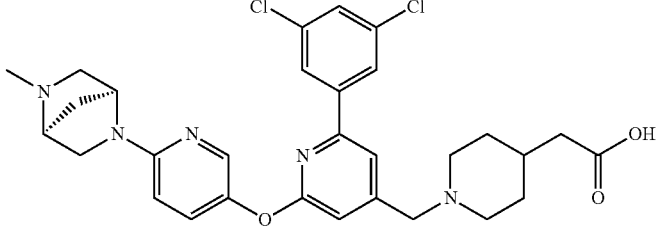 [SMILES: CN1C[C@@H]2C[C@H]1CN2c1ccc(Oc2cc(CN3CCC(CC(=O)O)CC3)cc(-c3cc(Cl)cc(Cl)c3)n2)cn1]<br>2-(1-((2-(3,5-dichlorophenyl)-6-((6-((1S,4S)-5-methyl-2,5-diazabicyclo[2.2.1]heptan-2-yl)pyridin-3-yl)oxy)pyridin-4-yl)methyl)piperidin-4-yl)acetic acid | ¹H NMR (400 MHz, CD₃OD) δ ppm 8.23 (dd, J = 2.2, 9.7 Hz, 1H), 8.17 (d, J = 2.0 Hz, 1H), 8.05 (s, 1H), 7.90 (d, J = 1.8 Hz, 2H), 7.50 (s, 1H), 7.48-7.41 (m, 2H), 5.31-5.19 (m, 1H), 4.77-4.64 (m, 1H), 4.49 (s, 2H), 4.18-4.10 (m, 1H), 4.09-3.93 (m, 2H), 3.59 (br d, J = 11.5 Hz, 2H), 3.42 (br d, J = 11.9 Hz, 1H), 3.18 (br t, J = 12.0 Hz, 2H), 3.09 (s, 3H), 2.66 (br d, J = 12.3 Hz, 1H), 2.46 (br d, J = 11.7 Hz, 1H), 2.39-2.28 (m, 2H), 2.17-1.98 (m, 3H), 1.72 (q, J = 12.0 Hz, 2H) | ES-LCMS m/z 582.3, 584.3 [M + H]⁺. |

Example 204: 2-(1-((2-(3,5-Dichlorophenyl)-6-((2-(4-(3-(methylsulfinyl)butyl)piperazin-1-yl)pyrimidin-5-yl)oxy)pyridin-4-yl)methyl)piperidin-4-yl)acetic acid

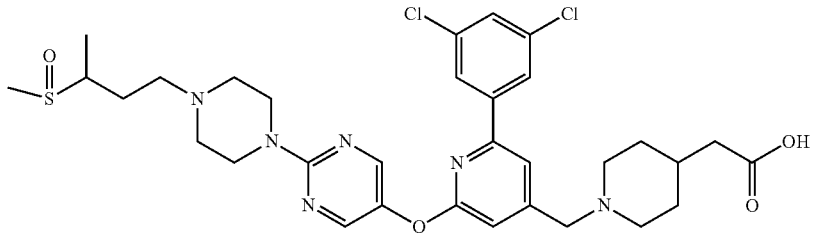 [SMILES: CC(CCN1CCN(c2ncc(Oc3cc(CN4CCC(CC(=O)O)CC4)cc(-c4cc(Cl)cc(Cl)c4)n3)cn2)CC1)S(C)=O]

Step 1: ten-Butyl 4-(5-((6-(3,5-dichlorophenyl)-4-((4-(2-methoxy-2-oxoethyl)piperidin-1-yl)methyl)pyridin-2-yl)oxy)pyrimidin-2-yl)piperazine-1-carboxylate

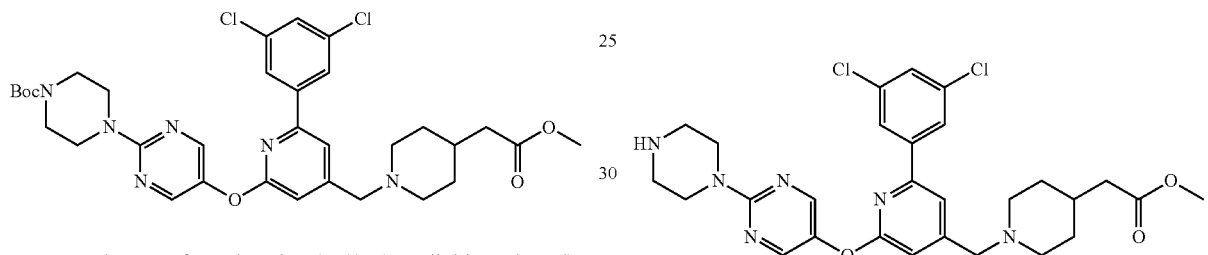

To a mixture of tert-butyl 4-(5-((6-(3,5-dichlorophenyl)-4-(((methylsulfonyl)oxy)methyl)pyridin-2-yl)oxy)pyrimidin-2-yl)piperazine-1-carboxylate (2 g, 2.80 mmol) and methyl 2-(piperidin-4-yl)acetate, hydrochloride (1.207 g, 5.61 mmol) in DMF (30 mL) was added K$_2$CO$_3$ (1.550 g, 11.22 mmol). The reaction was stirred at 15° C. for 2 h under N$_2$ atmosphere then concentrated. Saturated aqueous NaHCO$_3$ solution (150 mL) was added and the aqueous layer was extracted with DCM (500 mL×2), and the combined extracts were washed with brine (150 mL×2), dried over Na$_2$SO$_4$, filtered and concentrated. The crude material was purified by silica gel column chromatography (DCM/MeOH=5/1). All fractions found to contain product by TLC analysis (DCM/MeOH=10/1, R$_f$=0.5) were combined and concentrated to yield a yellow oil of tert-butyl 4-(5-((6-(3,5-dichlorophenyl)-4-((4-(2-methoxy-2-oxoethyl)piperidin-1-yl)methyl)pyridin-2-yl)oxy)pyrimidin-2-yl)piperazine-1-carboxylate (1.6 g, 2.168 mmol, 77.0% yield): $^1$H NMR (400 MHz, CDCl$_3$) δ ppm 8.31 (s, 2H), 7.72 (d, J=1.5 Hz, 2H), 7.41 (s, 1H), 7.34 (s, 1H), 6.92-6.87 (m, 1H), 3.86-3.79 (m, 4H), 3.67 (s, 3H), 3.56-3.51 (m, 6H), 2.86 (d, J=11.0 Hz, 2H), 2.27 (d, J=7.0 Hz, 2H), 2.11-2.02 (m, 2H), 1.82 (ddd, J=3.8, 7.3, 11.0 Hz, 1H), 1.72 (d, J=12.5 Hz, 2H), 1.50 (s, 9H), 1.42-1.29 (m, 2H); ES-CMS m/z 671.3, 673.3 [M+H]$^+$.

Step 2: Methyl 2-(1-((2-(3,5-dichlorophenyl)-6-((2-(piperazin-1-yl)pyrimidin-5-yl)oxy)pyridin-4-yl)methyl)piperidin-4-yl)acetate, 4 hydrochloride

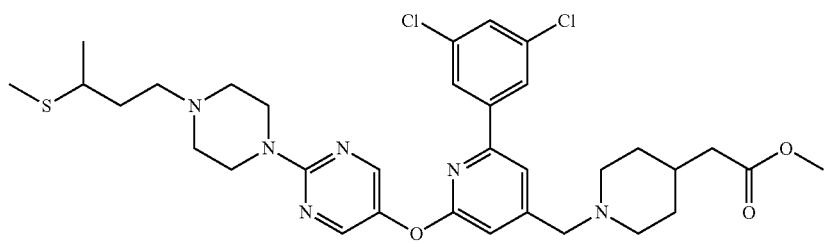

To a mixture of tert-butyl 4-(5-((6-(3,5-dichlorophenyl)-4-((4-(2-methoxy-2-oxoethyl)piperidin-1-yl)methyl)pyridin-2-yl)oxy)pyrimidin-2-yl)piperazine-1-carboxylate (1.6 g, 2.168 mmol) in DCM (10 mL) was added HCl solution (4.0 M in EtOAc, 5.42 mL, 21.68 mmol). The reaction was stirred at 15° C. for 2 h under N$_2$ atmosphere then concentrated to yield a yellow solid of methyl 2-(1-((2-(3,5-dichlorophenyl)-6-((2-(piperazin-1-yl)pyrimidin-5-yl)oxy)pyridin-4-yl)methyl)piperidin-4-yl)acetate, 4 hydrochloride (1.5 g, 1.882 mmol, 87.0% yield): $^1$H NMR (400 MHz, CD$_3$OD) δ ppm 8.69-8.47 (m, 2H), 8.10-7.96 (m, 1H), 7.90 (s, 2H), 7.57-7.36 (m, 2H), 4.47 (d, J=8.0 Hz, 2H), 4.17 (d, J=5.0 Hz, 4H), 3.68 (s, 3H), 3.60 (d, J=12.0 Hz, 2H), 3.43-3.37 (m, 4H), 3.24-3.11 (m, 2H), 2.39 (d, J=6.5 Hz, 2H), 2.19-2.00 (m, 3H), 1.70 (t, J=12.8 Hz, 2H); ES-LCMS m/z 571.3, 573.3 [M+H]$^+$.

Step 3: Methyl 2-(1-((2-(3,5-dichlorophenyl)-6-((2-(4-(3-(methylthio)butyl)piperazin-1-yl)pyrimidin-5-yl)oxy)pyridin-4-yl)methyl)piperidin-4-yl)acetate To a solution of 3-(methylthio)butanal (0.445 g, 3.76 mmol), acetic acid (7.18 μL, 0.125 mmol), methyl 2-(1-((2-(3,5-dichlorophenyl)-6-((2-(piperazin-1-yl)pyrimidin-5-yl)oxy)pyridine-4-yl)methyl)piperidin-4-yl)acetate, 4 hydrochloride (1 g, 1.255 mmol) in MeOH (10 mL) was added 4 Å molecular sieves (100 mg, 1.255 mmol). The reaction mixture was stirred at 25° C. for 12 h under N₂ atmosphere. Then, NaBH₃CN (0.237 g, 3.76 mmol) was added to the mixture and the mixture was stirred at 25° C. for 2 h. The reaction mixture was concentrated and diluted with DCM (300 mL) and washed with saturated aqueous NaHCO₃ solution (50 mL×2). The organic phase was dried over Na₂SO₄, filtered and concentrated then purified by silica gel column chromatography (DCM/MeOH=10/1). All fractions found to contain product by TLC (DCM/MeOH=20/1, $R_f$=0.6) were combined and concentrated to yield light yellow oil of methyl 2-(1-((2-(3,5-dichlorophenyl)-6-((2-(4-(3-(methylthio)butyl)piperazin-1-yl)pyrimidin-5-yl)oxy)pyridin-4-yl)methyl)piperidin-4-yl)acetate (1.2 g, 1.247 mmol, 99.0% yield): ¹H NMR (400 MHz, CDCl₃) δ ppm 8.29 (s, 2H), 7.73 (d, J=1.5 Hz, 2H), 7.43-7.39 (m, 1H), 7.34 (s, 1H), 6.89 (s, 1H), 3.87-3.72 (m, 6H), 3.67 (s, 3H), 3.52 (s, 2H), 2.88-2.83 (m, 4H), 2.57-2.53 (m, 4H), 2.27 (d, J=7.0 Hz, 2H), 2.07 (m, 5H), 1.72 (d, J=10.0 Hz, 4H), 1.70-1.65 (m, 1H), 1.43-1.40 (m, 2H), 1.39-1.34 (m, 3H); ES-LCMS m/z 673.3, 675.3 [M+H]⁺.

Step 4: Methyl 2-(1-((2-(3,5-dichlorophenyl)-6-((2-(4-(3-(methylsulfinyl)butyl)piperazin-1-yl)pyrimidin-5-yl)oxy)pyridin-4-yl)methyl)piperidin-4-yl)acetate

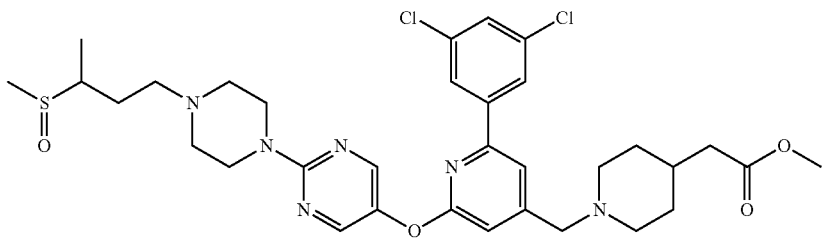

To a solution of methyl 2-(1-((2-(3,5-dichlorophenyl)-6-((2-(4-(3-(methylthio)butyl)piperazin-1-yl)pyrimidin-5-yl)oxy)pyridin-4-yl)methyl)piperidin-4-yl)acetate (650 mg, 0.675 mmol) in MeOH (6 mL) and H₂O (2 mL) was added Oxone (374 mg, 0.608 mmol). The reaction was stirred at 25° C. for 12 h then quenched with sat. Na₂SO₃ (aq., 3 mL). The solution was concentrated and saturated aqueous NaHCO₃ solution (15 mL) was added. The aqueous layer was extracted with DCM (150 mL×2), and the combined extracts were washed with brine (15 mL×2), dried over Na₂SO₄, filtered and concentrated to yield a colorless oil of methyl 2-(1-((2-(3,5-dichlorophenyl)-6-((2-(4-(3-(methylsulfinyl)butyl)piperazin-1-yl)pyrimidin-5-yl)oxy)pyridin-4-yl)methyl)piperidin-4-yl)acetate (650 mg, 0.660 mmol, 98.0% yield): ¹H NMR (400 MHz, CD₃OD) δ ppm 8.33 (s, 2H), 7.83 (d, J=1.5 Hz, 2H), 7.65 (s, 1H), 7.45 (s, 1H), 7.05 (s, 1H), 3.88 (t, J=4.8 Hz, 4H), 3.70 (s, 3H), 3.62 (s, 2H), 2.97-2.87 (m, 3H), 2.63-2.58 (m, 9H), 2.30 (d, J=6.5 Hz, 2H), 2.19-2.05 (m, 2H), 1.75-1.62 (m, 5H), 1.46-1.34 (m, 2H), 1.32-1.29 (m, 3H); ES-LCMS m/z 689.2, 691.2 [M+H]⁺.

Step 5: 2-(1-((2-(3,5-Dichlorophenyl)-6-((2-(4-(3-(methylsulfinyl)butyl)piperazin-1-yl)pyrimidin-5-yl)oxy)pyridin-4-yl)methyl)piperidin-4-yl)acetic acid

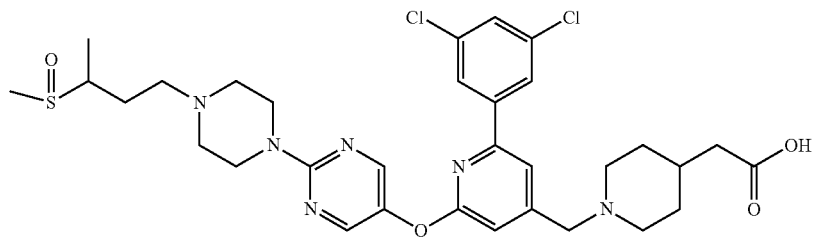 [SMILES: CC(CCN1CCN(c2ncc(Oc3cc(CN4CCC(CC(=O)O)CC4)cc(-c4cc(Cl)cc(Cl)c4)n3)cn2)CC1)S(C)=O]

To a solution of methyl 2-(1-((2-(3,5-dichlorophenyl)-6-((2-(4-(3-(methylsulfinyl)butyl)piperazin-1-yl)pyrimidin-5-yl)oxy)pyridin-4-yl)methyl)piperidin-4-yl)acetate (350 mg, 0.355 mmol) in THF (9 mL) and H$_2$O (3 mL) was added LiOH·H$_2$O (74.5 mg, 1.776 mmol). The reaction mixture was stirred at 25° C. for 0.5 h. The solution was concentrated and purified by preparative HPLC (MeCN/H$_2$O as eluents, acidic condition) and dried by lyophilization to yield an off white solid of 2-(1-((2-(3,5-dichlorophenyl)-6-((2-(4-(3-(methylsulfinyl)butyl)piperazin-1-yl)pyrimidin-5-yl)oxy)pyridin-4-yl)methyl)piperidin-4-yl)acetic acid (89.52 mg, 0.132 mmol, 37.3% yield): $^1$H NMR (400 MHz, CD$_3$OD) δ ppm 8.34 (s, 2H), 7.84 (d, J=1.5 Hz, 2H), 7.69 (s, 1H), 7.45 (s, 1H), 7.08 (s, 1H), 3.95-3.84 (m, 4H), 3.73 (s, 2H), 3.08-2.85 (m, 3H), 2.68-2.60 (m, 9H), 2.27 (t, J=11.3 Hz, 2H), 2.21 (d, J=6.5 Hz, 2H), 2.18-2.06 (m, 1H), 1.83 (d, J=10.5 Hz, 4H), 1.47-1.35 (m, 2H), 1.34-1.29 (m, 3H); ES-LCMS m/z 675.3, 677.3 [M+H]$^+$.

Example 205: 2-(1-((2-(3,5-Dichlorophenyl)-6-((2-(4-(3-(methylsulfonyl)butyl)piperazin-1-yl)pyrimidin-5-yl)oxy)pyridin-4-yl)methyl)piperidin-4-yl)acetic acid Methyl 2-(1-((2-(3,5-dichlorophenyl)-6-((2-(4-(3-(methylsulfinyl)butyl)piperazin-1-yl)pyrimidin-5-yl)oxy)pyridin-4-yl)methyl)piperidin-4-yl)acetate (250 mg, 0.254 mmol) was dissolved in HCl solution (4.0 M in MeOH, 2 mL, 8.00 mmol) and concentrated. Then, the mixture was dissolved in MeOH (3 mL) and H$_2$O (1 mL) then Oxone (140 mg, 0.228 mmol) was added. The reaction was stirred at 25° C. for 4 h then quenched with saturated Na$_2$SO$_3$ solution (3 mL). The solution was concentrated and saturated aqueous NaHCO$_3$ solution (15 mL) was added. The aqueous layer was extracted with DCM (150 mL×2), and the combined extracts were washed with brine (15 mL×2), dried over Na$_2$SO$_4$, filtered and concentrated to yield a yellow oil of methyl 2-(1-((2-(3,5-dichlorophenyl)-6-((2-(4-(3-(methylsulfonyl)butyl)piperazin-1-yl)pyrimidin-5-yl)oxy)pyridin-4-yl)methyl)piperidin-4-yl)acetate (230 mg, 0.228 mmol, 90.0% yield): $^1$H NMR (400 MHz, CDCl$_3$) δ ppm 8.29 (s, 2H), 7.74-7.69 (m, 2H), 7.43-7.39 (m, 1H), 7.33 (s, 1H), 6.92-6.86 (m, 1H), 3.84 (br. s, 4H), 3.67 (s, 3H), 3.52 (s, 2H),

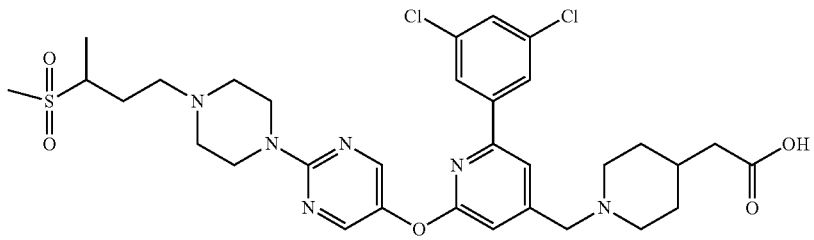 [SMILES: CC(CCN1CCN(c2ncc(Oc3cc(CN4CCC(CC(=O)O)CC4)cc(-c4cc(Cl)cc(Cl)c4)n3)cn2)CC1)S(C)(=O)=O]

Step 1: Methyl 2-(1-((2-(3,5-dichlorophenyl)-6-((2-(4-(3-(methylsulfonyl)butyl)piperazin-1-yl)pyrimidin-5-yl)oxy)pyridin-4-yl)methyl)piperidin-4-yl)acetate 3.29-3.13 (m, 1H), 2.87-2.84 (m, 5H), 2.65-2.44 (m, 6H), 2.43-2.23 (m, 4H), 2.07 (t, J=10.8 Hz, 2H), 1.72 (d, J=13.2 Hz, 3H), 1.42-1.29 (m, 5H); ES-LCMS m/z 353.6, 354.5 [1/2M+H]$^+$.

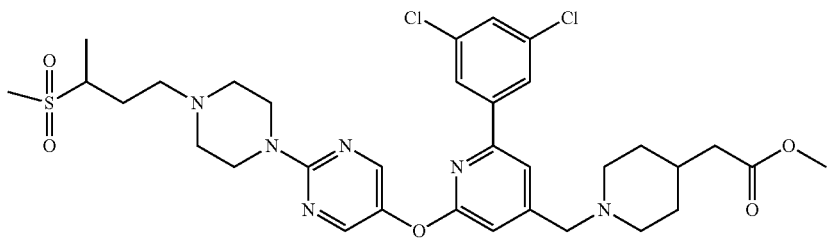

Step 2: 2-(1-((2-(3,5-Dichlorophenyl)-6-((2-(4-(3-(methylsulfonyl)butyl)piperazin-1-yl)pyrimidin-5-yl)oxy)pyridin-4-yl)methyl)piperidin-4-yl)acetic acid

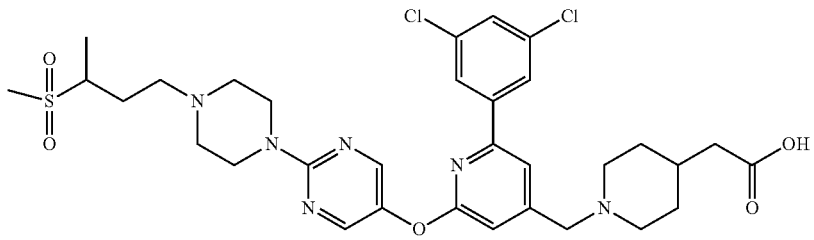 [SMILES: CC(CCN1CCN(c2ncc(Oc3cc(CN4CCC(CC(=O)O)CC4)cc(-c4cc(Cl)cc(Cl)c4)n3)cn2)CC1)S(C)(=O)=O]

To a solution of methyl 2-(1-((2-(3,5-dichlorophenyl)-6-((2-(4-(3-(methylsulfonyl)butyl)piperazin-1-yl)pyrimidin-5-yl)oxy)pyridin-4-yl)methyl)piperidin-4-yl)acetate (230 mg, 0.228 mmol) in THF (9 mL) and H$_2$O (3 mL) was added LiOH·H$_2$O (47.9 mg, 1.141 mmol). The reaction was stirred at 25° C. for 0.5 h. Then the solution was concentrated and purified by preparative HPLC (MeCN/H$_2$O as eluents, basic condition) and dried by lyophilization to yield an off white solid of 2-(1-((2-(3,5-dichlorophenyl)-6-((2-(4-(3-(methylsulfonyl)butyl)piperazin-1-yl)pyrimidin-5-yl)oxy)pyridin-4-yl)methyl)piperidin-4-yl)acetic acid (26.41 mg, 0.037 mmol, 16.3% yield): $^1$H NMR (400 MHz, CD$_3$OD) δ ppm 8.35 (s, 2H), 7.85 (d, J=1.5 Hz, 2H), 7.69 (s, 1H), 7.46 (s, 1H), 7.08 (s, 1H), 3.89 (t, J=4.8 Hz, 4H), 3.69 (s, 2H), 3.01-2.94 (m, 5H), 2.71 (s, 3H), 2.69-2.53 (m, 6H), 2.35-2.17 (m, 4H), 1.82 (d, J=11.5 Hz, 3H), 1.47-1.32 (m, 5H); ES-LCMS m/z 691.2, 693.2 [M+H]$^+$.

Example 206: 2-(1-((2-(3,5-Dichlorophenyl)-6-((2-(piperazin-1-yl)pyrimidin-5-yl)oxy)pyridin-4-yl)methyl)piperidin-4-yl)acetic acid, 4 hydrochloride

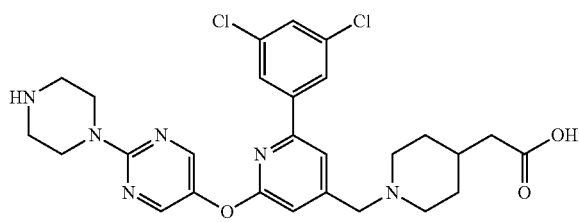 [SMILES: O=C(O)CC1CCN(Cc2cc(Oc3cnc(N4CCNCC4)nc3)nc(-c3cc(Cl)cc(Cl)c3)c2)CC1]

A mixture of methyl 2-(1-((2-(3,5-dichlorophenyl)-6-((2-(piperazin-1-yl)pyrimidin-5-yl)oxy)pyridin-4-yl)methyl)piperidin-4-yl)acetate, 4 hydrochloride (250 mg, 0.279 mmol) and NaOH (33.5 mg, 0.836 mmol) in MeOH (10 mL) and H$_2$O (2 mL) was stirred at 25° C. for 0.5 h then concentrated to yield the crude product which was purified by preparative HPLC (MeCN/H$_2$O as eluents, acidic condition) and dried by lyophilization to yield a white solid of 2-(1-((2-(3,5-dichlorophenyl)-6-((2-(piperazin-1-yl)pyrimidin-5-yl)oxy)pyridin-4-yl)methyl)piperidin-4-yl)acetic acid, 4 hydrochloride (118.36 mg, 0.167 mmol, 59.9% yield): $^1$H NMR (400 MHz, CD$_3$OD) δ ppm 8.46-8.43 (m, 2H), 7.89 (s, 1H), 7.87 (d, J=1.8 Hz, 2H), 7.51 (t, J=1.9 Hz, 1H), 7.31 (s, 1H), 4.43 (s, 2H), 4.16-4.09 (m, 4H), 3.56 (s, 2H), 3.33 (d, J=5.3 Hz, 4H), 3.14 (s, 2H), 2.33 (s, 2H), 2.06 (d, J=14.1 Hz, 3H), 1.62 (d, J=13.0 Hz, 2H); ES-LCMS m/z 557.1, 559.1 [M+H]$^+$.

Example 207: 2-(1-((2-(3,5-Dichlorophenyl)-6-((2-(4-methylpiperazin-1-yl)pyrimidin-5-yl)oxy)pyridin-4-yl)methyl)piperidin-4-yl)acetic acid, 4 hydrochloride

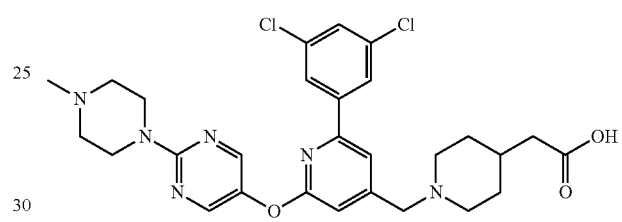

Step 1: Methyl 2-(1-((2-(3,5-dichlorophenyl)-6-((2-(4-methylpiperazin-1-yl)pyrimidin-5-yl)oxy)pyridin-4-yl)methyl)piperidin-4-yl)acetate

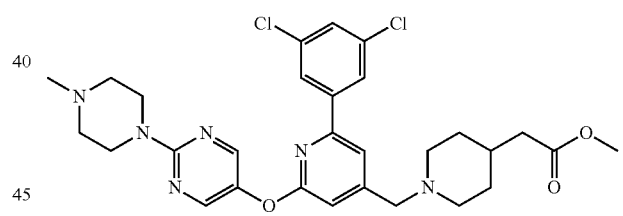

To a mixture of methyl 2-(1-((2-(3,5-dichlorophenyl)-6-((2-(piperazin-1-yl)pyrimidin-5-yl)oxy)pyridin-4-yl)methyl)piperidin-4-yl)acetate, 4 hydrochloride (3,000 mg, 3.52 mmol), and formic acid (0.675 mL, 17.60 mmol) in MeOH (50 mL) was added paraformaldehyde (528 mg, 17.60 mmol). The solution was stirred at 20° C. for 5 h then NaBH$_3$CN (2,212 mg, 35.2 mmol) was added. The reaction was stirred at 20° C. for 1 h then concentrated and distributed between DCM (100 mL) and saturated aqueous NaHCO$_3$ (50 mL) solution. The organic extract was washed with brine (50 mL), dried over Na$_2$SO$_4$, filtered and concentrated to yield a white solid of methyl 2-(1-((2-(3,5-dichlorophenyl)-6-((2-(4-methylpiperazin-1-yl)pyrimidin-5-yl)oxy)pyridin-4-yl)methyl)piperidin-4-yl)acetate (2500 mg, 3.29 mmol, 93.0% yield): $^1$H NMR (400 MHz, CDCl$_3$) δ ppm 8.30 (s, 2H), 7.73 (d, J=1.5 Hz, 2H), 7.41 (s, 1H), 7.34 (d, J=2.0 Hz, 1H), 6.89 (s, 1H), 3.89-3.81 (m, 4H), 3.71-3.64 (m, 3H), 3.52 (s, 2H), 2.86 (d, J=11.5 Hz, 2H), 2.52 (t, J=5.0 Hz, 4H), 2.36 (s, 3H), 2.30-2.24 (m, 2H), 2.07 (t, J=10.8 Hz, 2H), 1.82-1.78 (m, 1H), 1.72 (d, J=12.5 Hz, 2H), 1.42-1.30 (m, 2H); ES-LCMS m/z 585.3, 587.3 [M+H]$^+$.

Step 2: 2-(1-((2-(3,5-Dichlorophenyl)-6-((2-(4-methylpiperazin-1-yl)pyrimidin-5-yl)oxy)pyridin-4-yl)methyl)piperidin-4-yl)acetic acid, 4 hydrochloride

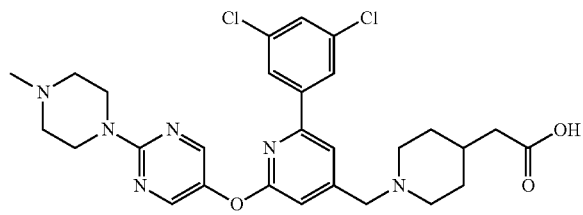 [SMILES: CN1CCN(c2ncc(Oc3cc(CN4CCC(CC(=O)O)CC4)cc(-c4cc(Cl)cc(Cl)c4)n3)cn2)CC1]

To a mixture of methyl 2-(1-((2-(3,5-dichlorophenyl)-6-((2-(4-methylpiperazin-1-yl)pyrimidin-5-yl)oxy)pyridin-4-yl)methyl)piperidin-4-yl)acetate (2.5 g, 3.29 mmol) in THF (30 mL) and water (10 mL) was added NaOH (0.263 g, 6.58 mmol). The mixture was stirred at 50° C. for 5 h. The mixture pH was adjusted to 5-7 with HCl solution (aq., 2 M). The mixture was concentrated to yield the crude product which was purified by preparative HPLC (MeCN/H$_2$O as eluents, acidic condition) and dried by lyophilization to yield a white solid of 2-(1-((2-(3,5-dichlorophenyl)-6-((2-(4-methylpiperazin-1-yl)pyrimidin-5-yl)oxy)pyridin-4-yl)methyl)piperidin-4-yl)acetic acid, 4 hydrochloride (1406.92 mg, 1.956 mmol, 59.5% yield): $^1$H NMR (400 MHz, CD$_3$OD) δ ppm 8.45 (s, 2H), 7.91-7.84 (m, 3H), 7.51 (s, 1H), 7.30 (s, 1H), 4.95 (d, J=14.6 Hz, 2H), 4.43 (s, 2H), 3.60 (t, J=11.7 Hz, 4H), 3.35-3.42 (m, 2H), 3.23-3.07 (m, 4H), 2.97 (s, 3H), 2.32 (d, J=6.6 Hz, 2H), 2.07 (d, J=12.3 Hz, 3H), 1.66-1.53 (m, 2H); ES-LCMS m/z 571.2, 573.2 [M+H]$^+$.

Examples 208-233 (Table 12) were prepared by procedures analogous to those described for example 207.

TABLE 12

| Example | Structure/Name | $^1$H NMR | LCMS |
|---|---|---|---|
| 208 | 4-(4-(5-((6-(3,5-dichlorophenyl)-4-(((methylcarbamoyl)oxy)ethyl)piperidin-1-yl)methyl)pyridin-2-yl)oxy)pyrimidin-2-yl)piperazin-1-yl)pentanoic acid | $^1$H NMR (400 MHz, CD$_3$OD) δ ppm 8.45 (s, 2H), 7.94 (br. s, 1H), 7.87 (d, J = 1.3 Hz, 2H), 7.49 (s, 1H), 7.33 (s, 1H), 4.99 (d, J = 14.1 Hz, 2H), 4.44 (s, 2H), 3.95 (d, J = 4.9 Hz, 2H), 3.60 (d, J = 9.7 Hz, 4H), 3.55-3.34 (m, 4H), 3.13 (t, J = 12.1 Hz, 2H), 2.73-2.66 (m, 3H), 2.61-2.41 (m, 3H), 2.31-2.20 (m, 1H), 2.07-1.94 (m, 3H), 1.90-1.79 (m, 1H), 1.68 (d, J = 11.9 Hz, 2H), 1.40 (d, J = 6.6 Hz, 3H) | ES-LCMS m/z 686.3, 688.3 [M + H]$^+$. |
| 209 | (1-((2-(3,5-dichlorophenyl)-6-((2-(4-(4-hydroxybutan-2-yl)piperazin-1-yl)pyrimidin-5-yl)oxy)pyridin-4-yl)methyl)piperidin-4-yl)methyl methylcarbamate | $^1$H NMR (400 MHz, CD$_3$OD) δ ppm 8.46 (s, 2H), 7.94 (s, 1H), 7.88 (s, 2H), 7.50 (t, J = 1.6 Hz, 1H), 7.33 (s, 1H), 5.05-4.90 (m, 2H), 4.45 (s, 2H), 3.96 (d, J = 5.2 Hz, 2H), 3.77-3.66 (m, 2H), 3.61 (d, J = 11.9 Hz, 4H), 3.42-3.34 (m, 3H), 3.21-3.08 (m, 4H), 2.71-2.67 (m, 3H), 2.07-1.94 (m, 4H), 1.77-1.57 (m, 3H), 1.26 (d, J = 6.2 Hz, 3H) | ES-LCMS m/z 658.4, 660.4 [M + H]$^+$. |
| 210 | (1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)methyl methylcarbamate | $^1$H NMR (400 MHz, CD$_3$OD) δ ppm 8.37 (s, 2H), 7.84 (d, J = 1.3 Hz, 2H), 7.78 (s, 1H), 7.46 (s, 1H), 7.18 (s, 1H), 4.09 (br. s, 2H), 4.02-3.92 (m, 6H), 3.28-3.23 (m, 4H), 3.01 (s, 3H), 2.94 (br. s, 6H), 2.68 (s, 5H), 2.21-2.12 (m, 2H), 1.89 (d, J = 12.8 Hz, 3H), 1.54 (d, J = 12.3 Hz, 2H) | ES-LCMS m/z 706.1, 708.1 [M + H]$^+$. |

TABLE 12-continued

| Example | Structure/Name | $^1$H NMR | LCMS |
|---|---|---|---|
| 211 | 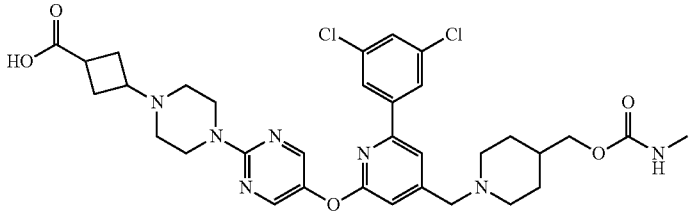 [SMILES: CNC(=O)OCC1CCN(Cc2cc(Oc3cnc(N4CCN(C5CC(C(=O)O)C5)CC4)nc3)nc(-c3cc(Cl)cc(Cl)c3)c2)CC1]<br>3-(4-(5-((6-(3,5-dichlorophenyl)-4-(((methylcarbamoyl)oxy)methyl)piperidin-1-yl)methyl)pyridin-2-yl)oxy)pyrimidin-2-yl)piperazin-1-yl)cyclobutanecarboxylic acid | $^1$H NMR (400 MHz, D$_2$O) δ ppm 8.34-8.23 (m, 2H), 7.58-7.30 (m, 4H), 7.02 (br. s, 1H), 4.59 (br. s, 3H), 4.24 (br. s, 2H), 3.81 (br. s, 2H), 3.59 (br. s, 1H), 3.46 (br. s, 4H), 3.23 (br. s, 2H), 3.01-2.78 (m, 5H), 2.54 (m, 5H), 2.40-2.30 (m, 2H), 1.85 (m, 2H), 1.41 (d, J = 11.5 Hz, 2H) | ES-LCMS m/z 684.2, 686.2 [M + H]$^+$. |
| 212 | 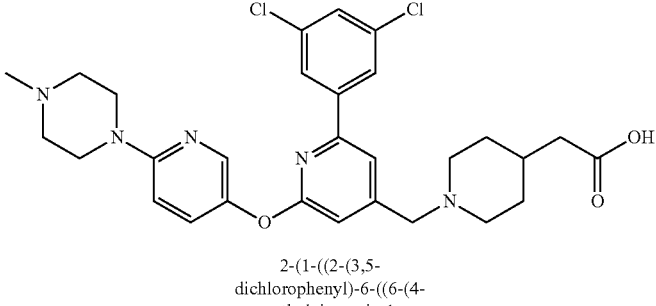<br>2-(1-((2-(3,5-dichlorophenyl)-6-((6-(4-methylpiperazin-1-yl)pyridin-3-yl)oxy)pyridin-4-yl)methyl)piperidin-4-yl)acetic acid | $^1$H NMR (400 MHz, D$_2$O) δ ppm 8.08 (d, J = 2.6 Hz, 1H), 7.82 (dd, J = 2.6, 9.7 Hz, 1H), 7.63 (d, J = 1.8 Hz, 2H), 7.58 (s, 1H), 7.45 (t, J = 1.8 Hz, 1H), 7.21 (d, J = 9.7 Hz, 1H), 7.11 (s, 1H), 4.37-4.25 (m, 4H), 3.64 (d, J = 12.3 Hz, 2H), 3.51 (d, J = 11.5 Hz, 2H), 3.41 (t, J = 13.2 Hz, 2H), 3.30-3.18 (m, 2H), 3.06 (t, J =12.1 Hz, 2H), 2.93 (s, 3H), 2.32 (d, J = 6.6 Hz, 2H), 1.98 (d, J =13.2 Hz, 3H), 1.48 (q, J = 11.9 Hz, 2H) | ES-LCMS m/z 570.2, 572.2 [M + H]$^+$. |
| 213 | 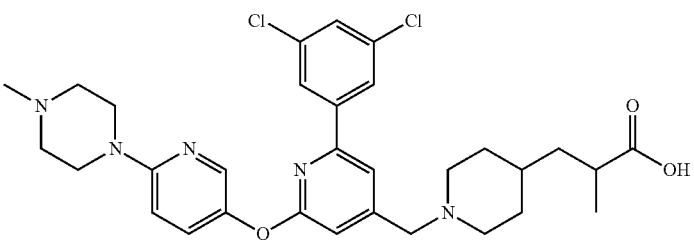 [SMILES: CC(CC1CCN(Cc2cc(Oc3ccc(N4CCN(C)CC4)nc3)nc(-c3cc(Cl)cc(Cl)c3)c2)CC1)C(=O)O]<br>3-(1-((2-(3,5-dichlorophenyl)-6-((6-(4-methylpiperazin-1-yl)pyridin-3-yl)oxy)pyridin-4-yl)methyl)piperidin-4-yl)-2-methylpropanoic acid | $^1$H NMR (400 MHz, CD$_3$OD) δ ppm 8.20 (d, J = 2.2 Hz, 1H), 8.02 (dd, J = 2.6, 9.3 Hz, 1H), 7.96 (s, 1H), 7.88 (d, J = 1.8 Hz, 2H), 7.50 (t, J = 1.8 Hz, 1H), 7.44 (d, J = 9.7 Hz, 1H), 7.36 (s, 1H), 4.61-4.36 (m, 4H), 3.82-3.48 (m, 6H), 3.34 (br. s, 2H), 3.18-3.04 (m, 2H), 3.03-2.94 (m, 3H), 2.61-2.47 (m, 1H), 2.10-1.90 (m, 2H), 1.77-1.47 (m, 4H), 1.44-1.25 (m, 1H), 1.23-1.11 (m, 3H) | ES-LCMS m/z 598.2, 600.2 [M + H]$^+$. |

TABLE 12-continued

| Example | Structure/Name | $^1$H NMR | LCMS |
|---|---|---|---|
| 214 | 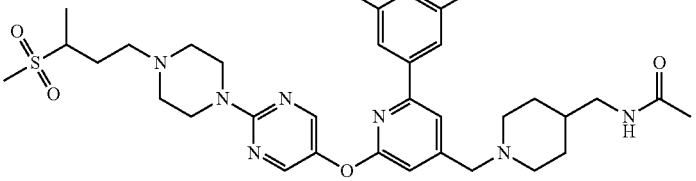<br>N-((1-((2-(3,5-dichlorophenyl)-6-((2-(4-(3-(methylsulfonyl)butyl)piperazin-1-yl)pyrimidin-5-yl)oxy)pyridin-4-yl)methyl)piperidin-4-yl)methyl)acetamide | $^1$H NMR (400 MHz, CD$_3$OD) ppm 8.53 (s, 2H), 8.03 (s, 1H), 7.86 (d, J = 1.3 Hz, 2H), 7.45 (s, 1H), 7.39 (s, 1H), 4.91 (d, J = 14.1 Hz, 2H), 4.48 (br. s, 2H), 3.77 (d, J = 11.0 Hz, 2H), 3.62-3.44 (m, 6H), 3.40-3.32 (m, 2H), 3.23-3.11 (m, 5H), 3.04-2.97 (m, 3H), 2.51 (dd, J = 6.0, 14.3 Hz, 1H), 2.19-2.09 (m, 1H), 2.05 (s, 3H), 2.02-1.90 (m, 3H), 1.75-1.64 (m, 2H), 1.45 (d, J = 7.1 Hz, 3H) | ES-LCMS m/z 704.2, 706.2 [M + H]$^+$. |
| 215 | 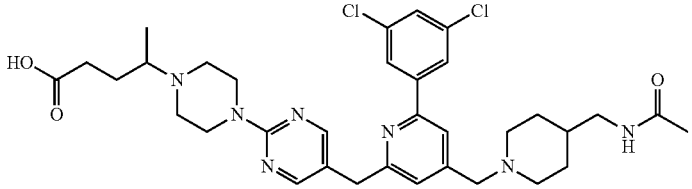 [SMILES: CC(=O)NCC1CCN(Cc2cc(Cc3cnc(N4CCN(C(C)CCC(=O)O)CC4)nc3)nc(-c3cc(Cl)cc(Cl)c3)c2)CC1]<br>4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)pentanoic acid | $^1$H NMR (400 MHz, CD$_3$OD) δ ppm 8.56 (s, 2H), 8.03 (s, 1H), 7.88 (d, J = 1.3 Hz, 2H), 7.47 (s, 1H), 7.40 (s, 1H), 4.94 (br. s, 2H), 4.47 (s, 2H), 3.78-3.48 (m, 7H), 3.35 (d, J = 11.9 Hz, 2H), 3.26-3.05 (m, 4H), 2.64-2.43 (m, 2H), 2.36-2.24 (m, 1H), 2.11-2.02 (m, 3H), 1.98 (d, J = 14.1 Hz, 2H), 1.93-1.79 (m, 2H), 1.76-1.60 (m, 2H), 1.48-1.33 (m, 3H) | ES-LCMS m/z 670.4, 672.3 [M + H]$^+$. |
| 216 | 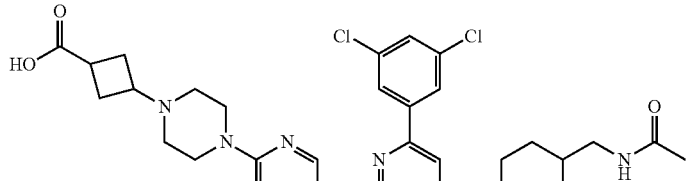<br>3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)cyclobutanecarboxylic acid | $^1$H NMR (400 MHz, D$_2$O) δ ppm 8.24 (s, 2H), 7.43 (s, 1H), 7.35 (br. s, 2H), 7.08 (br. s, 1H), 7.00 (s, 1H), 4.54-4.47 (m, 2H), 4.21 (br. s, 2H), 3.43 (dd, J = 11.2, 19.6 Hz, 4H), 3.24-3.17 (m, 2H), 2.98-2.91 (m, 4H), 2.83-2.72 (m, 2H), 2.63-2.45 (m, 4H), 2.39-2.30 (m, 2H), 1.86-1.79 (m, 5H), 1.69 (br. s, 1H), 1.37-1.27 (m, 2H) | ES-LCMS m/z 668.4, 670.4 [M + H]$^+$. |
| 217 | 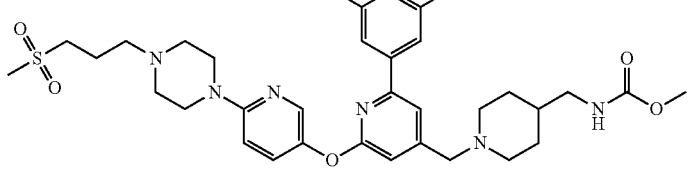<br>methyl ((1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)methyl)carbamate | $^1$H NMR (400 MHz, CDCl$_3$) δ ppm 8.12 (d, J = 3.0 Hz, 1H), 7.76 (d, J = 2.0 Hz, 2H), 7.43 (dd, J = 3.0, 9.0 Hz, 1H), 7.40 (s, 1H), 7.33 (s, 1H), 6.82 (s, 1H), 6.73 (d, J = 9.0 Hz, 1H), 4.76 (br. s, 1H), 3.66 (s, 3H), 3.58-3.53 (m, 4H), 3.50 (s, 2H), 3.20-3.13 (m, 2H), 3.09 (t, J = 6.0 Hz, 2H), 2.94 (s, 3H), 2.88 (d, J = 11.0 Hz, 2H), 2.66-2.50 (m, 6H), 2.13-1.97 (m, 4H), 1.68-1.65 (m, 4H), 1.51 (br. s, 1H), 1.37-1.23 (m, 2H) | ES-LCMS m/z 705.3, 707.3 [M + H]$^+$. |

TABLE 12-continued

| Example | Structure/Name | $^1$H NMR | LCMS |
|---|---|---|---|
| 218 | 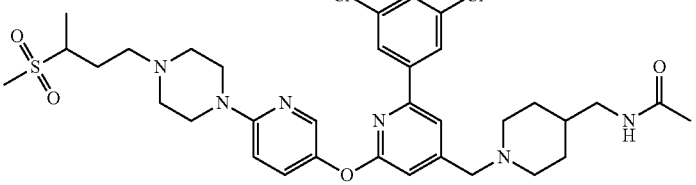<br>N-((1-((2-(3,5-dichlorophenyl)-6-((6-(4-(3-(methylsulfonyl)butyl)piperazin-1-yl)pyridin-3-yl)oxy)pyridin-4-yl)methyl)piperidin-4-yl)methyl)acetamide | $^1$H NMR (400 MHz, CD$_3$OD) δ ppm 8.22 (d, J = 2.2 Hz, 1H), 8.10 (d, J = 9.3 Hz, 1H), 7.96 (s, 1H), 7.87 (d, J = 1.8 Hz, 2H), 7.53-7.48 (m, 2H), 7.38 (s, 1H), 4.45 (s, 2H), 3.87-3.55 (m, 7H), 3.52-3.46 (m, 2H), 3.38-3.33 (m, 2H), 3.16-3.06 (m, 4H), 3.00 (s, 3H), 2.60-2.41 (m, 2H), 2.26-2.09 (m, 2H), 2.00-1.92 (m, 5H), 1.85 (br. s, 1H), 1.67-1.53 (m, 2H), 1.46 (d, J = 7.1 Hz, 3H) | ES-LCMS m/z 703.3, 705.3 [M + H]$^+$. |
| 219 | 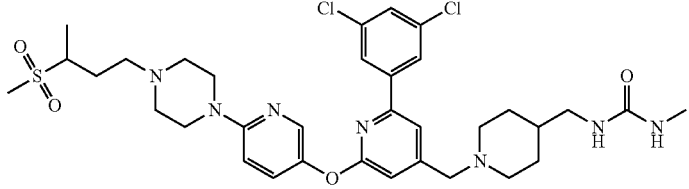<br>1-((1-((2-(3,5-dichlorophenyl)-6-((6-(4-(3-(methylsulfonyl)butyl)piperazin-1-yl)pyridin-3-yl)oxy)pyridin-4-yl)methyl)piperidin-4-yl)methyl)-3-methylurea | $^1$H NMR (400 MHz, CD$_3$OD) δ ppm 8.27-8.16 (m, 2H), 7.99 (br. s, 1H), 7.88 (d, J = 1.3 Hz, 2H), 7.59 (br. s, 1H), 7.52 (s, 1H), 7.41 (br. s, 1H), 4.46 (s, 2H), 3.80-3.75 (m, 5H), 3.60 (d, J = 12.3 Hz, 2H), 3.53-3.47 (m, 2H), 3.40-3.34 (m, 2H), 3.16-3.06 (m, 4H), 3.01 (s, 3H), 2.71 (s, 3H), 2.57-2.42 (m, 2H), 2.18-2.12 (m, 1H), 1.99 (d, J = 13.7 Hz, 2H), 1.85-1.80 (m, 2H), 1.60 (d, J = 12.8 Hz, 2H), 1.47 (d, J = 7.1 Hz, 3H) | ES-LCMS m/z 718.3, 720.3 [M + H]$^+$. |
| 220 | 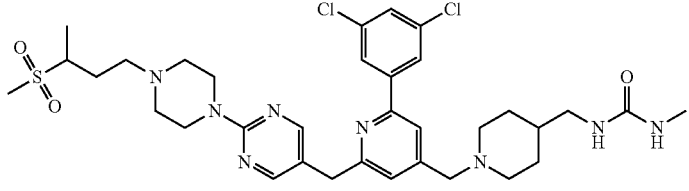<br>1-((1-((2-(3,5-dichlorophenyl)-6-((2-(4-(3-(methylsulfonyl)butyl)piperazin-1-yl)pyrimidin-5-yl)oxy)pyridin-4-yl)methyl)piperidin-4-yl)methyl)-3-methylurea | $^1$H NMR (400 MHz, CD$_3$OD) δ ppm 8.47 (s, 2H), 8.00 (s, 1H), 7.86 (d, J = 1.8 Hz, 2H), 7.45 (t, J = 1.8 Hz, 1H), 7.39-7.32 (m, 1H), 4.46 (s, 2H), 3.75 (d, J = 11.5 Hz, 2H), 3.59 (d, J = 11.9 Hz, 2H), 3.54-3.40 (m, 4H), 3.37-3.30 (m, 3H), 3.28-3.07 (m, 6H), 3.01 (s, 3H), 2.74 (s, 3H), 2.60-2.43 (m, 1H), 2.20-2.07 (m, 1H), 1.99 (d, J = 13.7 Hz, 2H), 1.87 (br. s, 1H), 1.74-1.56 (m, 2H), 1.50-1.39 (m, 3H) | ES-LCMS m/z 719.3, 721.3 [M + H]$^+$. |
| 221 | 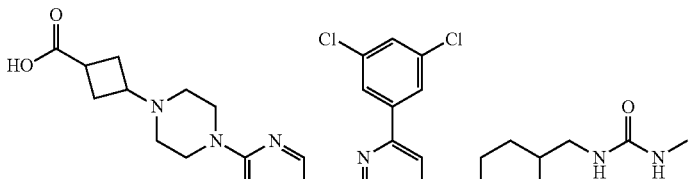<br>3-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)cyclobutanecarboxylic acid | $^1$H NMR (400 MHz, CD$_3$OD) δ ppm 8.46 (s, 2H), 7.90-7.84 (m, 3H), 7.51 (s, 1H), 7.30 (s, 1H), 5.03-4.98 (m, 2H), 4.42 (s, 2H), 3.75-3.69 (m, 1H), 3.59 (d, J = 9.3 Hz, 4H), 3.42-3.32 (m, 4H), 3.06 (d, J = 7.1 Hz, 3H), 3.03-2.94 (m, 2H), 2.74-2.60 (m, 5H), 2.55-2.44 (m, 2H), 1.99 (d, J = 14.6 Hz, 2H), 1.79 (s, 1H), 1.58-1.47 (m, 2H) | ES-LCMS m/z 683.4, 685.4 [M + H]$^+$. |

TABLE 12-continued

| Example | Structure/Name | ¹H NMR | LCMS |
|---|---|---|---|
| 222 | 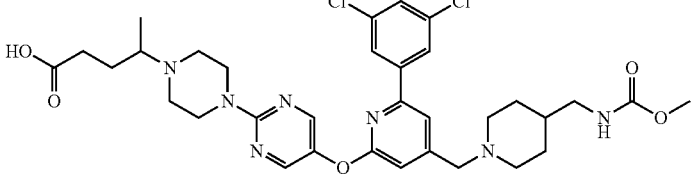<br>4-(4-(5-((6-(3,5-dichlorophenyl)-4-((4-(((methoxycarbonyl)amino)methyl)piperidin-1-yl)methyl)pyridin-2-yl)oxy)pyrimidin-2-yl)piperazin-1-yl)pentanoic acid | ¹H NMR (400 MHz, CD₃OD) δ ppm 8.48 (s, 2H), 7.98 (s, 1H), 7.86 (d, J = 1.8 Hz, 2H), 7.47 (t, J = 1.8 Hz, 1H), 7.35 (s, 1H), 4.98 (d, J = 13.7 Hz, 2H), 4.45 (s, 2H), 3.69-3.41 (m, 8H), 3.38-3.19 (m, 5H), 3.12 (t, J = 11.9 Hz, 2H), 3.04 (d, J = 6.2 Hz, 1H), 2.61-2.42 (m, 2H), 2.33-2.22 (m, 1H), 2.04-1.92 (m, 2H), 1.90-1.76 (m, 2H), 1.69-1.53 (m, 2H), 1.47-1.38 (m, 3H) | ES-LCMS m/z 686.3, 688.3 [M + H]⁺. |
| 223 | 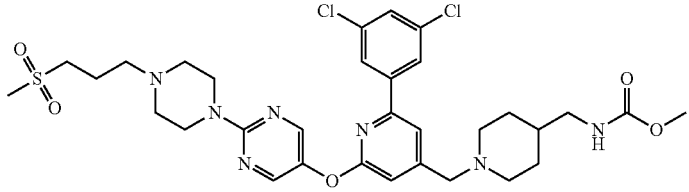<br>methyl ((1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)methyl)carbamate | ¹H NMR (400 MHz, CD₃OD) δ ppm 8.30 (s, 2H), 7.77 (d, J = 1.8 Hz, 2H), 7.60 (s, 1H), 7.39 (s, 1H), 7.00 (s, 1H), 3.88-3.79 (m, 4H), 3.66-3.53 (m, 5H), 3.23-3.16 (m, 2H), 3.04-2.96 (m, 5H), 2.91 (d, J = 11.0 Hz, 2H), 2.61-2.50 (m, 6H), 2.13-1.99 (m, 4H), 1.70 (d, J = 11.9 Hz, 2H), 1.49 (br. s, 1H), 1.39-1.20 (m, 2H) | ES-LCMS m/z 706.2, 708.3 [M + H]⁺. |
| 224 | 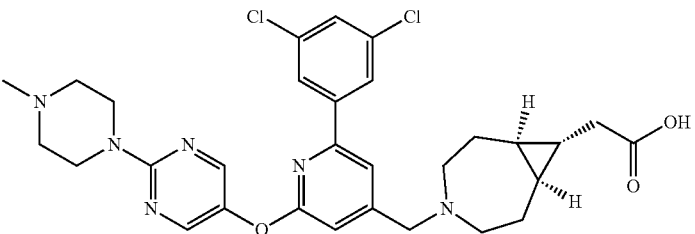 [SMILES: CN1CCN(c2ncc(Oc3cc(CN4CC[C@@H]5[C@H](CC4)[C@H]5CC(=O)O)cc(-c4cc(Cl)cc(Cl)c4)n3)cn2)CC1]<br>2-((1R,7S,8r)-4-((2-(3,5-dichlorophenyl)-6-((2-(4-methylpiperazin-1-yl)pyrimidin-5-yl)oxy)pyridin-4-yl)methyl)-4-azabicyclo[5.1.0]octan-8-yl)acetic acid | ¹H NMR (400 MHz, D2O + CD3CN) δ ppm 8.80 (s, 2H), 8.16 (s, 2H), 8.08 (s, 1H), 7.87 (s, 1H), 7.58 (s, 1H), 5.08 (d, J = 14.8 Hz, 2H), 4.73 (br s, 2H), 3.99-3.82 (m, 4H), 3.78-3.68 (m, 2H), 3.60-3.40 (m, 4H), 3.26 (s, 3H), 2.85-2.59 (m, 4H), 1.98-1.78 (m, 2H), 1.31 (br s, 3H) | ES-LCMS m/z 597.3, 599.3 [M + H]⁺. |

TABLE 12-continued

| Example | Structure/Name | ¹H NMR | LCMS |
|---|---|---|---|
| 225 | 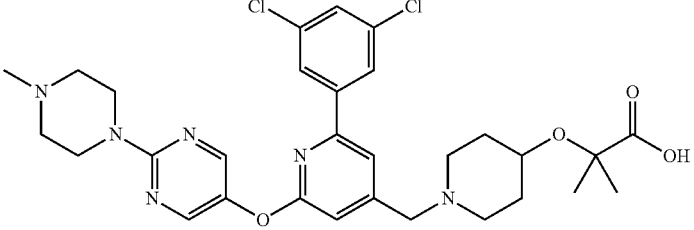 [SMILES: CN1CCN(c2ncc(Oc3cc(CN4CCC(OC(C)(C)C(=O)O)CC4)cc(-c4cc(Cl)cc(Cl)c4)n3)cn2)CC1]  2-((1-((2-(3,5-dichlorophenyl)-6-((2-(4-methylpiperazin-1-yl)pyrimidin-5-yl)oxy)pyridin-4-yl)methyl)piperidin-4-yl)oxy)-2-methylpropanoic acid | ¹H NMR (400 MHz, CD₃OD) δ δ ppm 8.52-8.47 (m, 2H), 8.00-7.93 (m, 1H), 7.90-7.86 (m, 2H), 7.50 (s, 1H), 7.38-7.32 (m, 1H), 4.49-4.42 (m, 2H), 3.99 (br s, 1H), 3.68-3.51 (m, 4H), 3.45-3.36 (m, 5H), 3.24-3.14 (m, 3H), 2.97 (s, 3H), 2.27 (d, J = 11.5 Hz, 1H), 2.09 (br s, 2H), 1.95-1.82 (m, 1H), 1.47-1.42 (m, 6H) | ES-LCMS m/z 615.3, 617.3 [M + H]⁺. |
| 226 | 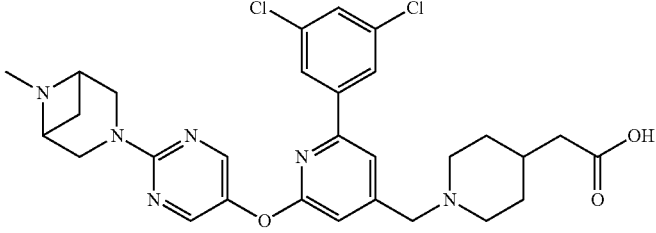  2-(1-((2-(3,5-dichlorophenyl)-6-((2-(6-hydroxy-4-methyl-1,4-diazepan-1-yl)pyrimidin-5-yl)oxy)pyridin-4-yl)methyl)piperidin-4-yl)acetic acid | ¹H NMR (400 MHz, CD₃OD) δ 8.47 (s, 2H), 7.95-7.85 (m, 3H), 7.51 (t, J = 1.9 Hz, 1H), 7.34 (s, 1H), 4.43 (s, 3H), 4.32 (ddd, J = 3.4, 6.5, 15.4 Hz, 1H), 4.19-4.03 (m, 3H), 3.74-3.61 (m, 2H), 3.61-3.43 (m, 4H), 3.14 (br t, J = 12.3 Hz, 2H), 2.95 (s, 3H), 2.32 (d, J = 6.5 Hz, 2H), 2.05 (br d, J = 13.7 Hz, 3H), 1.72-1.58 (m, 2H) | ES-LCMS m/z 601.3, 603.2 [M + H]⁺. |
| 227 | 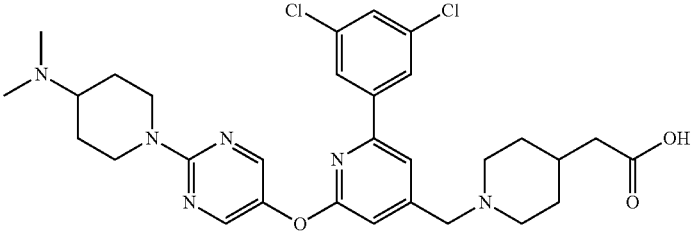 [SMILES: CN(C)C1CCN(c2ncc(Oc3cc(CN4CCC(CC(=O)O)CC4)cc(-c4cc(Cl)cc(Cl)c4)n3)cn2)CC1]  2-(1-((2-(3,5-dichlorophenyl)-6-((2-(4-(dimethylamino)piperidin-1-yl)pyrimidin-5-yl)oxy)pyridin-4-yl)methyl)piperidin-4-yl)acetic acid | ¹H NMR (400 MHz, CD₃OD) δ ppm 8.38 (s, 2H), 7.86 (m, 3H), 7.50 (s, 1H), 7.26 (s, 1H), 5.04-4.93 (m, 2H), 4.41 (s, 2H), 3.63-3.44 (m, 3H), 3.12 (t, J = 12.3 Hz, 2H), 3.01(t, J = 12.6 Hz, 2H), 2.88 (s, 6H), 2.31 (d, J = 6.2 Hz, 2H), 2.21-2.12 (m, 2H), 2.12-1.99 (m, 3H), 1.78-1.51 (m, 4H) | ES-LCMS m/z 599.3, 601.3 [M + H]⁺. |

TABLE 12-continued

| Example | Structure/Name | $^1$H NMR | LCMS |
| --- | --- | --- | --- |
| 228 | 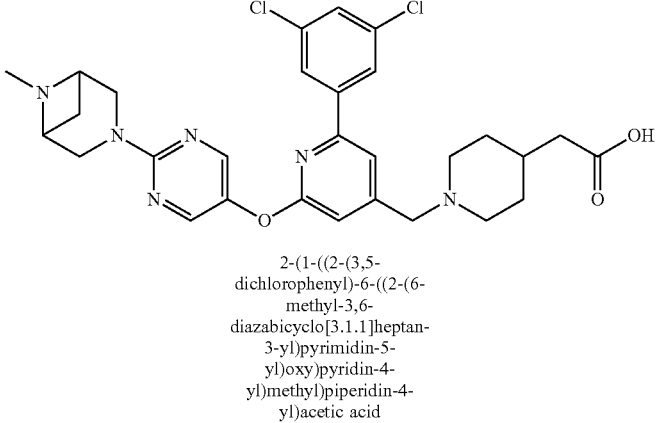<br>2-(1-((2-(3,5-dichlorophenyl)-6-((2-(6-methyl-3,6-diazabicyclo[3.1.1]heptan-3-yl)pyrimidin-5-yl)oxy)pyridin-4-yl)methyl)piperidin-4-yl)acetic acid | $^1$H NMR (400 MHz, D$_2$O) δ ppm 8.31 (s, 2H), 7.46-7.37 (m, 7.17 (td, J = 1.7, 9.2 Hz, 1H), 7.02 (d, J = 3.1 Hz, 1H), 4.47 (br d, J = 6.2 Hz, 1H), 4.31 (br d, J = 6.4 Hz, 1H), 4.23 (s, 2H), 4.07-3.96 (m, 3H), 3.93-3.85 (m, 1H), 3.41 (br d, J = 11.5 Hz, 2H), 2.96 (br t, J = 12.8 Hz, 3H), 2.77-2.33 (m, 3H), 2.22 (br d, J = 6.6 Hz, 2H), 1.96-1.84 (m, 4H), 1.46-1.32 (m, 2H) | ES-LCMS m/z 583.2, 585.2 [M + H]$^+$. |
| 229 | 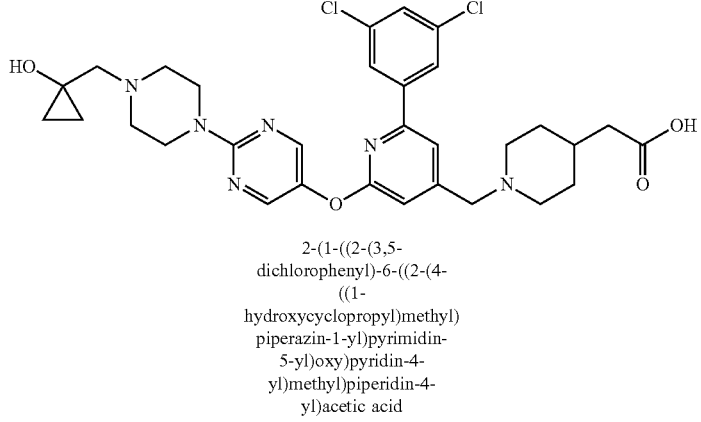<br>2-(1-((2-(3,5-dichlorophenyl)-6-((2-(4-((1-hydroxycyclopropyl)methyl)piperazin-1-yl)pyrimidin-5-yl)oxy)pyridin-4-yl)methyl)piperidin-4-yl)acetic acid | $^1$H NMR (400 MHz, CD$_3$OD) δ 8.46 (s, 2H), 7.93 (s, 1H), 7.87 (d, J = 1.6 Hz, 2H), 7.50 (s, 1H), 7.33 (s, 1H), 4.91 (br. s., 2H), 4.43 (s, 2H), 3.82 (d, J = 12.5 Hz, 2H), 3.60-3.46 (m, 4H), 3.35 (s, 2H), 3.29-3.22 (m, 2H), 3.14 (t, J = 12.1 Hz, 2H), 2.32 (d, J = 6.7 Hz, 2H), 2.06 (d, J = 13.3 Hz, 3H), 1.71-1.59 (m, 2H), 0.98-0.92 (m, 2H), 0.80-0.74 (m, 2H) | ES-LCMS m/z 627.3, 629.3 [M + H]$^+$. |
| 230 | 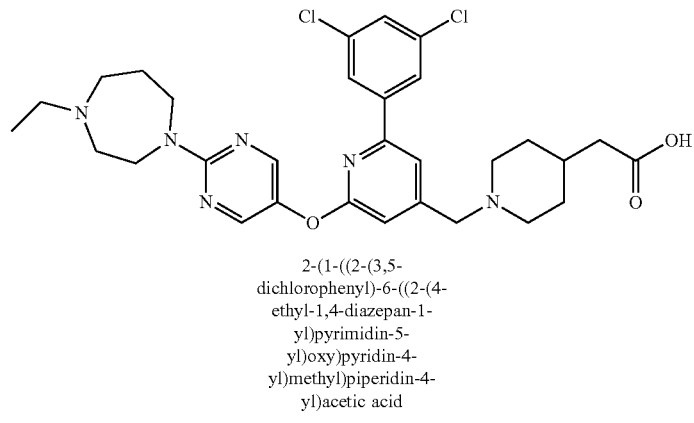<br>2-(1-((2-(3,5-dichlorophenyl)-6-((2-(4-ethyl-1,4-diazepan-1-yl)pyrimidin-5-yl)oxy)pyridin-4-yl)methyl)piperidin-4-yl)acetic acid | $^1$H NMR (400 MHz, CD$_3$OD) δ 8.55-8.44 (m, 2H), 7.96-7.87 (m, 3H), 7.54-7.47 (m, 1H), 7.35 (br d, J = 6.1 Hz, 1H), 4.43 (s, 2H), 4.01-3.95 (m, 2H), 3.82-3.64 (m, 2H), 3.58 (br d, J = 12.9 Hz, 2H), 3.31-3.31 (m, 2H), 3.29-3.24 (m, 2H), 3.14 (br t, J = 12.4 Hz, 2H), 2.36-2.24 (m, 4H), 2.05 (br d, J = 13.3 Hz, 4H), 1.68 (br s, 3H), 1.38 (t, J = 7.3 Hz, 3H) | ES-LCMS m/z 599.3; 601.3 [M + H]$^+$. |

TABLE 12-continued

| Example | Structure/Name | ¹H NMR | LCMS |
|---|---|---|---|
| 231 | 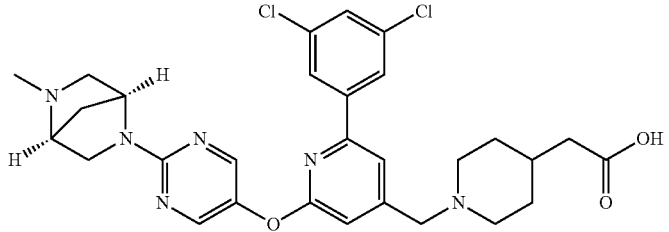 [SMILES: CN1C[C@@H]2C[C@H]1CN2c1ncc(Oc2cc(CN3CCC(CC(=O)O)CC3)cc(-c3cc(Cl)cc(Cl)c3)n2)cn1]<br>2-(1-((2-(3,5-dichlorophenyl)-6-((2-((1S,4S)-5-methyl-2,5-diazabicyclo[2.2.1]heptan-2-yl)pyrimidin-5-yl)oxy)pyridin-4-yl)methyl)piperidin-4-yl)acetic acid | ¹H NMR (400 MHz, CD₃OD) δ ppm 8.70-8.62 (m, 2H), 8.02 (s, 1H), 7.90 (d, J = 1.8 Hz, 2H), 7.50 (d, J = 1.5 Hz, 1H), 7.44-7.38 (m, 1H), 5.26 (s, 1H), 4.59-4.51 (m, 1H), 4.47 (s, 2H), 4.04 (d, J = 12.1 Hz, 1H), 3.99-3.87 (m, 2H), 3.58 (d, J = 11.5 Hz, 2H), 3.35 (d, J = 10.1 Hz, 1H), 3.16 (t, J = 11.9 Hz, 2H), 3.04 (s, 3H), 2.59-2.45 (m, 1H), 2.41-2.28 (m, 3H), 2.18-1.97 (m, 3H), 1.78-1.61 (m, 2H) | ES-LCMS m/z 583.3, 585.3 [M + H]⁺. |
| 232 | 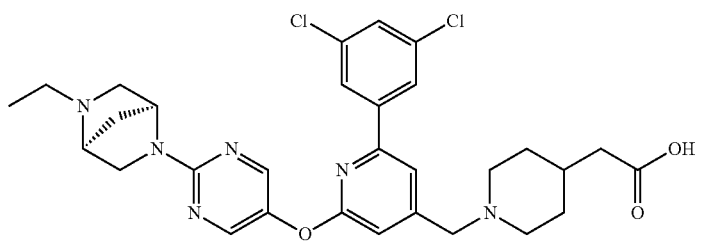 [SMILES: CCN1C[C@@H]2C[C@H]1CN2c1ncc(Oc2cc(CN3CCC(CC(=O)O)CC3)cc(-c3cc(Cl)cc(Cl)c3)n2)cn1]<br>2-(1-((2-(3,5-dichlorophenyl)-6-((2-((1S,4S)-5-ethyl-2,5-diazabicyclo[2.2.1]heptan-2-yl)pyrimidin-5-yl)oxy)pyridin-4-yl)methyl)piperidin-4-yl)acetic acid | ¹H NMR (400 MHz, CD₃OD) δ ppm 8.38 (s, 2H), 7.82 (d, J = 2.0 Hz, 2H), 7.64 (s, 1H), 7.44 (s, 1H), 7.04 (s, 1H), 5.04 (s, 1H), 4.59 (s, 1H), 4.33 (s, 1H), 3.87 (d, J = 11.9 Hz, 1H), 3.77-3.59 (m, 4H), 3.43 (d, J = 10.8 Hz, 2H), 3.26-3.02 (m, 2H), 2.93 (d, J = 9.9 Hz, 2H), 2.24 (s, 2H), 2.21-2.18 (m, 1H), 2.16 (d, J = 6.6 Hz, 2H), 1.76 (d, J = 9.9 Hz, 2H), 1.40-1.32 (m, 2H), 1.28 (t, J = 7.2 Hz, 3H) | ES-LCMS m/z 597.2, 599.3 [M + H]⁺. |
| 233 | 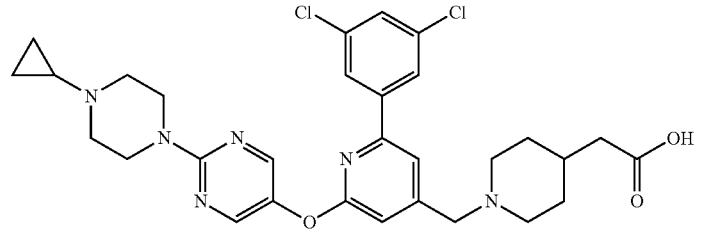 [SMILES: O=C(O)CC1CCN(Cc2cc(Oc3cnc(N4CCN(C5CC5)CC4)nc3)nc(-c3cc(Cl)cc(Cl)c3)c2)CC1]<br>2-(1-((2-((2-(4-cyclopropylpiperazin-1-yl)pyrimidin-5-yl)oxy)-6-(3,5-dichlorophenyl)pyridin-4-yl)methyl)piperidin-4-yl)acetic acid | ¹H NMR (400 MHz, CD₃OD) δ ppm 8.47 (s, 2H), 7.89-7.87 (m, 3H), 7.52 (s, 1H), 7.31 (s, 1H), 4.44 (s, 2H), 3.60-3.47 (m, 8H), 3.18-3.14 (m, 2H), 2.94-2.90 (m, 1H), 2.34 (s, 2H), 2.09-2.06 (m, 4H), 1.64-1.63 (m, 3H), 1.11-1.08 (m, 2H), 1.03-1.01 (m, 2H) | ES-LCMS m/z 597.3, 599.2 [M + H]⁺. |

Example 234: 2-(1-((2-(3,5-Dichlorophenyl)-6-((2-(4-ethylpiperazin-1-yl)pyrimidin-5-yl)oxy)pyridin-4-yl)methyl)piperidin-4-yl)acetic acid

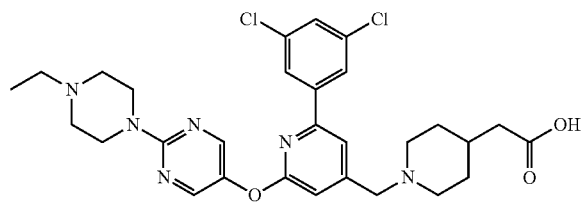 [SMILES: CCN1CCN(c2ncc(Oc3cc(CN4CCC(CC(=O)O)CC4)cc(-c4cc(Cl)cc(Cl)c4)n3)cn2)CC1]

Step 1: Methyl 2-(1-((2-(3,5-dichlorophenyl)-6-((2-(4-ethylpiperazin-1-yl)pyrimidin-5-yl)oxy)pyridin-4-yl)methyl)piperidin-4-yl)acetate

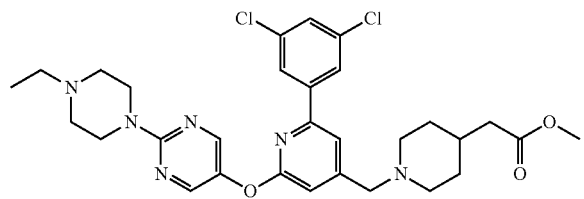 [SMILES: CCN1CCN(c2ncc(Oc3cc(CN4CCC(CC(=O)OC)CC4)cc(-c4cc(Cl)cc(Cl)c4)n3)cn2)CC1]

A mixture of methyl 2-(1-((2-(3,5-dichlorophenyl)-6-((2-(piperazin-1-yl)pyrimidin-5-yl)oxy)pyridin-4-yl)methyl)piperidin-4-yl)acetate (0.5 g, 0.694 mmol), acetaldehyde (0.037 g, 0.833 mmol), 4 Å molecular sieves (200 mg, 0.694 mmol) and acetic acid (0.042 g, 0.694 mmol) in MeOH (5 mL) was stirred at 20° C. for 10 min then NaBH$_3$CN (0.436 g, 6.94 mmol) was added. The reaction was stirred at 20° C. for 20 min then concentrated to yield a brown solid of methyl 2-(1-((2-(3,5-dichlorophenyl)-6-((2-(4-ethylpiperazin-1-yl)pyrimidin-5-yl)oxy)pyridin-4-yl)methyl)piperidin-4-yl)acetate (0.4 g, 0.428 mmol, 61.6% yield): $^1$H NMR (400 MHz, CDCl$_3$) δ ppm 8.57 (s, 2H), 7.97 (s, 2H), 7.84 (s, 1H), 7.59-7.55 (m, 2H), 3.91 (s, 2H), 3.61 (s, 3H), 3.57-3.55 (m, 4H), 3.37-3.35 (m, 6H), 2.70 (s, 2H), 3.54-3.52 (m, 2H), 2.09-2.06 (m, 4H), 1.77-1.63 (m, 4H), 1.48-1.43 (m, 2H); ES-LCMS m/z 599.3, 601.3 [M+H]$^+$.

Step 2: 2-(1-((2-(3,5-Dichlorophenyl)-6-((2-(4-ethylpiperazin-1-yl)pyrimidin-5-yl)oxy)pyridin-4-yl)methyl)piperidin-4-yl)acetic acid

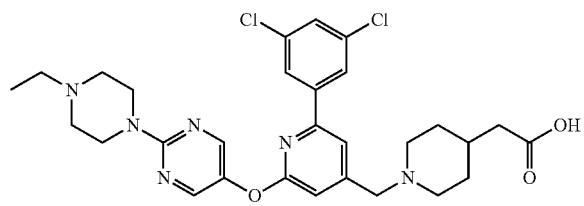

To a solution of methyl 2-(1-((2-(3,5-dichlorophenyl)-6-((2-(4-ethylpiperazin-1-yl)pyrimidin-5-yl)oxy)pyridin-4-yl)methyl)piperidin-4-yl)acetate (0.4 g, 0.428 mmol) in THF (10 mL) and H$_2$O (5.00 mL) was added LiOH·H$_2$O (0.036 g, 0.855 mmol). The reaction mixture was stirred at 25° C. for 6 h then 1 N HCl was added to adjust pH to 6-7. The mixture was concentrated, purified by preparative HPLC (MeCN/H$_2$O as eluents, acidic condition) and lyophilized to yield a white solid of 2-(1-((2-(3,5-dichlorophenyl)-6-((2-(4-ethylpiperazin-1-yl)pyrimidin-5-yl)oxy)pyridin-4-yl)methyl)piperidin-4-yl)acetic acid (65.5 mg, 0.112 mmol, 26.2% yield): $^1$H NMR (400 MHz, DMSO-Je) δ ppm 8.42 (s, 2H), 7.88 (s, 2H), 7.75 (s, 1H), 7.65 (s, 1H), 7.04 (s, 1H), 3.74 (br. s, 4H), 3.56 (s, 2H), 2.82 (d, J=11.0 Hz, 2H), 2.43 (d, J=4.5 Hz, 4H), 2.38-2.33 (m, 2H), 2.15 (d, J=6.0 Hz, 2H), 2.01 (t, J=11.3 Hz, 2H), 1.65 (d, J=10.0 Hz, 3H), 1.30-1.18 (m, 2H), 1.04 (t, J=7.0 Hz, 3H); ES-LCMS m/z 585.2, 587.2 [M+H]$^+$.

Example 235: 2-(1-((2-(3,5-Dichlorophenyl)-6-((2-(4-isopropylpiperazin-1-yl)pyrimidin-5-yl)oxy)pyridin-4-yl)methyl)piperidin-4-yl)acetic acid, 4 hydrochloride

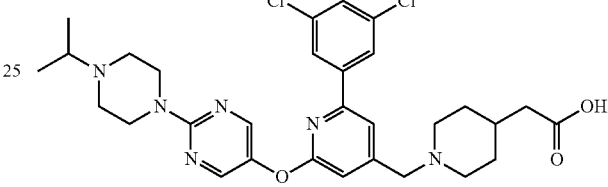

Step 1: Methyl 2-(1-((2-(3,5-dichlorophenyl)-6-((2-(4-isopropylpiperazin-1-yl)pyrimidin-5-yl)oxy)pyridin-4-yl)methyl)piperidin-4-yl)acetate

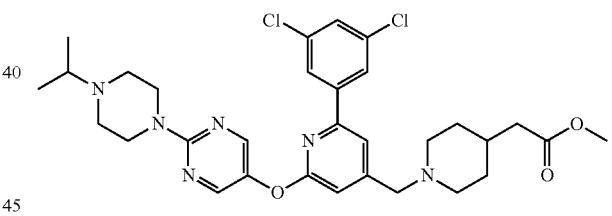

A mixture of methyl 2-(1-((2-(3,5-dichlorophenyl)-6-((2-(piperazin-1-yl)pyrimidin-5-yl)oxy)pyridin-4-yl)methyl)piperidin-4-yl)acetate (2 g, 3.19 mmol), propan-2-one (0.556 g, 9.57 mmol), 4 Å molecular sieves (200 mg, 3.19 mmol) and acetic acid (0.192 g, 3.19 mmol) was stirred at 20° C. for 10 h. Then, NaBH$_3$CN (2.005 g, 31.9 mmol) was added and the reaction was stirred at 20° C. for 4 h. The mixture was concentrated and distributed between DCM (150 mL) and saturated aqueous NaHCO$_3$ (30 mL) solution. The organic extract was washed with brine (50 mL), dried over Na$_2$SO$_4$, filtered and concentrated to yield a brown solid of methyl 2-(1-((2-(3,5-dichlorophenyl)-6-((2-(4-isopropylpiperazin-1-yl)pyrimidin-5-yl)oxy)pyridine-4-yl)methyl)piperidin-4-yl)acetate (1.2 g, 1.748 mmol, 54.8% yield): $^1$H NMR (400 MHz, CDCl$_3$) δ ppm 8.34-8.26 (m, 2H), 7.73 (d, J=2.0 Hz, 2H), 7.40 (s, 1H), 7.33 (t, J=1.9 Hz, 1H), 6.88 (s, 1H), 3.93-3.83 (m, 4H), 3.66 (s, 3H), 3.51 (s, 2H), 2.85 (d, J=11.5 Hz, 2H), 2.75 (m, 1H), 2.67-2.57 (m, 4H), 2.26 (d, J=7.1 Hz, 2H), 2.11-2.00 (m, 2H), 1.81 (tdd, J=3.9, 7.5, 14.9 Hz, 1H), 1.76-1.65 (m, 2H), 1.43-1.29 (m, 2H), 1.09 (d, J=6.6 Hz, 6H); ES-LCMS m/z 613.3, 615.3 [M+H]$^+$.

Step 2: 2-(1-((2-(3,5-Dichlorophenyl)-6-((2-(4-isopropylpiperazin-1-yl)pyrimidin-5-yl)oxy)pyridin-4-yl)methyl)piperidin-4-yl)acetic acid, 4 hydrochloride

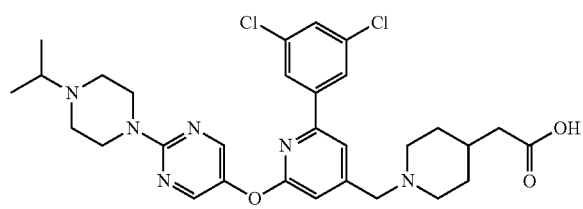 [SMILES: CC(C)N1CCN(c2ncc(Oc3cc(CN4CCC(CC(=O)O)CC4)cc(-c4cc(Cl)cc(Cl)c4)n3)cn2)CC1]

Methyl 2-(1-((2-(3,5-dichlorophenyl)-6-((2-(4-isopropylpiperazin-1-yl)pyrimidin-5-yl)oxy)pyridin-4-yl)methyl)piperidin-4-yl)acetate (1.2 g, 1.748 mmol) was dissolved in concentrated HCl (10 mL, 122 mmol). The reaction was stirred at 80° C. for 2 h then concentrated and purified by preparative HPLC (MeCN/H$_2$O as eluents, acidic condition) and dried by lyophilization to yield a white solid of 2-(1-((2-(3,5-dichlorophenyl)-6-((2-(4-isopropylpiperazin-1-yl)pyrimidin-5-yl)oxy)pyridin-4-yl)methyl)piperidin-4-yl)acetic acid, 4 hydrochloride (737.95 mg, 0.990 mmol, 56.6% yield): $^1$H NMR (400 MHz, CD$_3$OD) δ ppm 8.45 (s, 2H), 7.94 (s, 1H), 7.87 (d, J=2.0 Hz, 2H), 7.49 (d, J=1.5 Hz, 1H), 7.33 (s, 1H), 4.99 (d, J=14.8 Hz, 2H), 4.44 (s, 2H), 3.64-3.56 (m, 4H), 3.49-3.33 (m, 3H), 3.27-3.08 (m, 4H), 2.38-2.25 (m, 2H), 2.05 (d, J=12.3 Hz, 3H), 1.71-1.56 (m, 2H), 1.42 (d, J=6.6 Hz, 6H); ES-LCMS m/z 599.2, 601.2 [M+H]$^+$.

Example 236: 2-(1-((2-(3,5-Dichlorophenyl)-6-((2-(4-(2-fluoroethyl)piperazin-1-yl)pyrimidin-5-yl)oxy)pyridin-4-yl)methyl)piperidin-4-yl)acetic acid

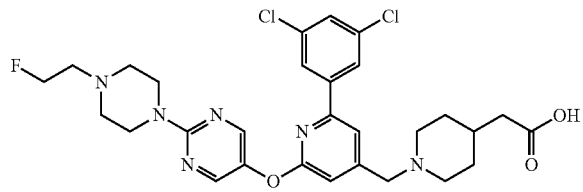 [SMILES: O=C(O)CC1CCN(Cc2cc(Oc3cnc(N4CCN(CCF)CC4)nc3)nc(-c3cc(Cl)cc(Cl)c3)c2)CC1]

Step 1: Methyl 2-(1-((2-(3,5-dichlorophenyl)-6-((2-(4-(2-fluoroethyl)piperazin-1-yl)pyrimidin-5-yl)oxy)pyridin-4-yl)methyl)piperidin-4-yl)acetate

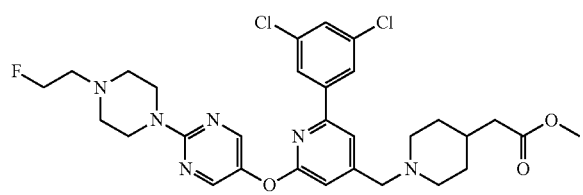 [SMILES: COC(=O)CC1CCN(Cc2cc(Oc3cnc(N4CCN(CCF)CC4)nc3)nc(-c3cc(Cl)cc(Cl)c3)c2)CC1]

To a mixture of K$_2$CO$_3$ (294 mg, 2.126 mmol), 1-bromo-2-fluoroethane (270 mg, 2.126 mmol) in DMF (50 mL) was added methyl 2-(1-((2-(3,5-dichlorophenyl)-6-((2-(piperazin-1-yl)pyrimidin-5-yl)oxy)pyridin-4-yl)methyl)piperidin-4-yl)acetate (500 mg, 0.709 mmol). The mixture was stirred at 130° C. for 16 h then filtered and concentrated to yield the crude product, which was purified by silica gel column chromatography (DCM/MeOH=20/1, R$_f$=0.5) to yield a brown solid of methyl 2-(1-((2-(3,5-dichlorophenyl)-6-((2-(4-(2-fluoroethyl)piperazin-1-yl)pyrimidin-5-yl)oxy)pyridin-4-yl)methyl)piperidin-4-yl)acetate (400 mg, 0.473 mmol, 66.7% yield): $^1$H NMR (400 MHz, CD$_3$OD) δ ppm 8.45 (br. s, 2H), 7.88 (br. s, 2H), 7.49 (s, 1H), 7.21 (s, 1H), 6.71 (s, 1H), 4.43 (s, 2H), 4.18-4.04 (m, 4H), 3.80 (s, 3H), 3.51 (br. s, 3H), 3.16 (br. s, 4H), 2.99 (s, 2H), 2.91-2.81 (m, 3H), 2.48 (s, 2H), 2.35 (s, 2H), 1.66 (s, 3H); ES-LCMS m/z 617.4, 619.3 [M+H]$^+$.

Step 2: 2-(1-((2-(3,5-Dichlorophenyl)-6-((2-(4-(2-fluoroethyl)piperazin-1-yl)pyrimidin-5-yl)oxy)pyridin-4-yl)methyl)piperidin-4-yl)acetic acid, 4 hydrochloride

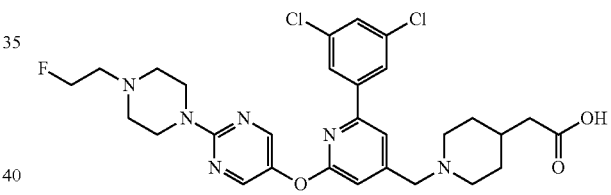

A solution of methyl 2-(1-((2-(3,5-dichlorophenyl)-6-((2-(4-(2-fluoroethyl)piperazin-1-yl)pyrimidin-5-yl)oxy)pyridin-4-yl)methyl)piperidin-4-yl)acetate (395 mg, 0.467 mmol) was added concentrated HCl (10 mL, 122 mmol) and stirred at 80° C. for 2 h. The mixture was concentrated and purified by preparative HPLC (MeCN/H$_2$O as eluents, acidic condition) and dried by lyophilization to yield a white solid of 2-(1-((2-(3,5-dichlorophenyl)-6-((2-(4-(2-fluoroethyl)piperazin-1-yl)pyrimidin-5-yl)oxy)pyridin-4-yl)methyl)piperidin-4-yl)acetic acid, 4 hydrochloride (105.7 mg, 0.141 mmol, 30.2% yield): $^1$H NMR (400 MHz, CD$_3$OD) δ ppm 8.46 (s, 2H), 7.90 (s, 1H), 7.87 (d, J=2.2 Hz, 2H), 7.51 (t, J=1.8 Hz, 1H), 7.31 (s, 1H), 5.00-4.88 (m, 4H), 4.43 (s, 2H), 3.74 (br. s, 2H), 3.68-3.65 (m, 1H), 3.63-3.52 (m, 4H), 3.46 (d, J=12.3 Hz, 3H), 3.14 (t, J=12.1 Hz, 2H), 2.32 (d, J=6.2 Hz, 2H), 2.07 (d, J=13.2 Hz, 3H), 1.68-1.58 (m, 2H); ES-LCMS m/z 603.2, 605.1 [M+H]$^+$.

Example 237: 2-(1-((2-(3,5-Dichlorophenyl)-6-((2-(4-(3-hydroxybutyl)piperazin-1-yl)pyrimidin-5-yl)oxy)pyridin-4-yl)methyl)piperidin-4-yl)acetic acid

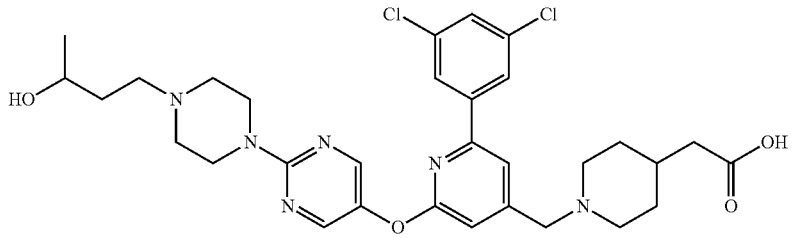 [SMILES: CC(O)CCN1CCN(c2ncc(Oc3cc(CN4CCC(CC(=O)O)CC4)cc(-c4cc(Cl)cc(Cl)c4)n3)cn2)CC1]

Step 1: Methyl 2-(1-((2-(3,5-dichlorophenyl)-6-((2-(4-(3-oxobutyl)piperazin-1-yl)pyrimidin-5-yl)oxy)pyridin-4-yl)methyl)piperidin-4-yl)acetate

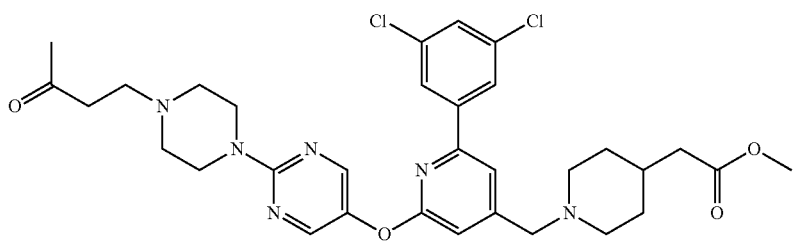 [SMILES: COC(=O)CC1CCN(Cc2cc(Oc3cnc(N4CCN(CCC(C)=O)CC4)nc3)nc(-c3cc(Cl)cc(Cl)c3)c2)CC1]

To a mixture of methyl 2-(1-((2-(3,5-dichlorophenyl)-6-((2-(piperazin-1-yl)pyrimidin-5-yl)oxy)pyridin-4-yl)methyl)piperidin-4-yl)acetate (600 mg, 0.850 mmol) in MeOH (1 mL) was added DIEA (2.97 mL, 17.01 mmol) and but-3-en-2-one (0.64 g, 9.13 mmol). The reaction was stirred at 80° C. for 7 h then concentrated and purified by silica gel column chromatography (DCM/MeOH=10/1). All fractions found to contain product by TLC (DCM/MeOH=10/1, $R_f$=0.6) were combined and concentrated to yield a yellow oil of methyl 2-(1-((2-(3,5-dichlorophenyl)-6-((2-(4-(3-oxobutyl)piperazin-1-yl)pyrimidin-5-yl)oxy)pyridin-4-yl)methyl)piperidin-4-yl)acetate (400 mg, 0.405 mmol, 47.7% yield): $^1$H NMR (400 MHz, CDCl$_3$) δ ppm 8.30 (s, 2H), 7.71 (s, 2H), 7.44 (br. s, 1H), 7.34 (s, 1H), 6.91 (s, 1H), 3.86 (m, 4H), 3.67 (s, 3H), 3.57 (m, 4H), 3.00-2.74 (m, 8H), 2.27 (m, 2H), 2.21 (s, 3H), 2.18-2.02 (m, 2H), 1.91-1.71 (m, 3H), 1.50-1.33 (m, 2H); ES-LCMS m/z 641.4, 643.3 [M+H]$^+$.

Step 2: 2-(1-((2-(3,5-Dichlorophenyl)-6-((2-(4-(3-oxobutyl)piperazin-1-yl)pyrimidin-5-yl)oxy)pyridin-4-yl)methyl)piperidin-4-yl)acetic acid

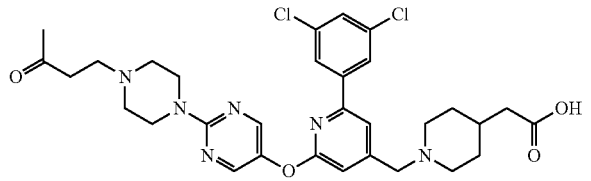 [SMILES: CC(=O)CCN1CCN(c2ncc(Oc3cc(CN4CCC(CC(=O)O)CC4)cc(-c4cc(Cl)cc(Cl)c4)n3)cn2)CC1]

To a solution of methyl 2-(1-((2-(3,5-dichlorophenyl)-6-((2-(4-(3-oxobutyl)piperazin-1-yl)pyrimidin-5-yl)oxy)pyridin-4-yl)methyl)piperidin-4-yl)acetate (400 mg, 0.405 mmol) in water (10 mL) and MeOH (10.00 mL) was added LiOH·H$_2$O (51.0 mg, 1.216 mmol). The reaction mixture was stirred at 20° C. for 0.5 h then adjusted pH to 7 with 1 N HCl solution. The mixture was concentrated to yield the residue which was distributed between DCM (30 mL) and H$_2$O (20 mL), separation then the aqueous phase was extracted with DCM (30 mL×2). The combined organic layers were washed with brine (20 mL), dried over Na$_2$SO$_4$, filtered and concentrated to yield a brown solid of 2-(1-((2-(3,5-dichlorophenyl)-6-((2-(4-(3-oxobutyl)piperazin-1-yl)pyrimidin-5-yl)oxy)pyridin-4-yl)methyl)piperidin-4-yl)acetic acid (290 mg, 0.397 mmol, 98.0% yield): $^1$H NMR (400 MHz, CD$_3$OD) δ ppm 8.36-8.26 (m, 2H), 7.81 (s, 2H), 7.67 (s, 1H), 7.43 (br. s, 1H), 7.07 (br. s, 1H), 3.87 (br. s, 4H), 3.78-3.51 (m, 4H), 3.02 (d, J=11.0 Hz, 2H), 2.78 (s, 2H), 2.65 (br. s, 4H), 2.29 (t, J=11.5 Hz, 2H), 2.22-2.09 (m, 5H), 1.81 (m, 3H), 1.39 (m, 2H), LC-MS m/z 627.3, 629.4 [M+H]$^+$.

Step 3: 2-(1-((2-(3,5-Dichlorophenyl)-6-((2-(4-(3-hydroxybutyl)piperazin-1-yl)pyrimidin-5-yl)oxy)pyridin-4-yl)methyl)piperidin-4-yl)acetic acid

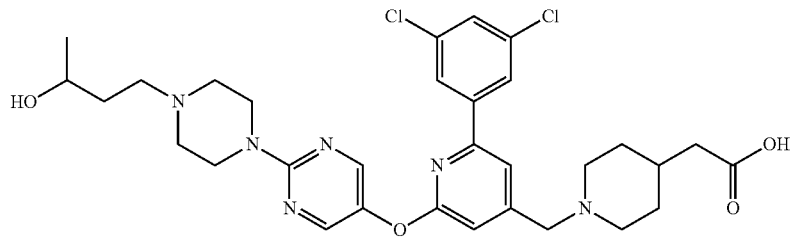 [SMILES: CC(O)CCN1CCN(c2ncc(Oc3cc(CN4CCC(CC(=O)O)CC4)cc(-c4cc(Cl)cc(Cl)c4)n3)cn2)CC1]

To a solution of 2-(1-((2-(3,5-dichlorophenyl)-6-((2-(4-(3-oxobutyl)piperazin-1-yl)pyrimidin-5-yl)oxy)pyridin-4-yl)methyl)piperidin-4-yl)acetic acid (240 mg, 0.329 mmol) in MeOH (10 mL) was added NaBH$_4$ (12.44 mg, 0.329 mmol). The reaction mixture was stirred at 20° C. for 0.5 h. Saturated aqueous NH$_4$Cl solution (10 mL) was added then concentrated to yield the residue which was distributed between DCM (30 mL) and H$_2$O (20 mL), extracted with DCM (30 mL×2). The combined organic layers were combined and washed with brine (20 mL), dried over Na$_2$SO$_4$, filtered and concentrated. The crude product was purified by preparative HPLC (MeCN/H$_2$O as eluents, basic condition) and lyophilized to yield a white solid of 2-(1-((2-(3,5-dichlorophenyl)-6-((2-(4-(3-hydroxybutyl)piperazin-1-yl)pyrimidin-5-yl)oxy)pyridin-4-yl)methyl)piperidin-4-yl)acetic acid (56.61 mg, 0.090 mmol, 27.3% yield): $^1$H NMR (400 MHz, CD$_3$OD) δ ppm 8.35 (s, 2H), 7.82 (s, 2H), 7.67 (s, 1H), 7.44 (br. s, 1H), 7.07 (s, 1H), 3.95-3.83 (m, 5H), 3.71 (br. s, 2H), 2.99 (d, J=11.0 Hz, 2H), 2.85-2.69 (m, 6H), 2.29-2.18 (m, 4H), 1.85-1.67 (m, 5H), 1.37 (d, J=11.0 Hz, 2H), 1.20 (d, J=6.2 Hz, 3H); LC-MS m/z 629.3, 631.4 [M+H]$^+$.

Example 238: 2-(1-((2-(3,5-Dichlorophenyl)-6-((2-(4-(4-hydroxybutan-2-yl)piperazin-1-yl)pyrimidin-5-yl)oxy)pyridin-4-yl)methyl)piperidin-4-yl)acetic acid

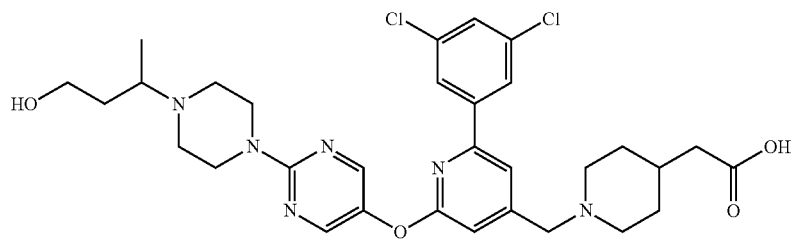 [SMILES: CC(CCO)N1CCN(c2ncc(Oc3cc(CN4CCC(CC(=O)O)CC4)cc(-c4cc(Cl)cc(Cl)c4)n3)cn2)CC1]

Step 1: Methyl 2-(1-((2-(3,5-dichlorophenyl)-6-((2-(4-(4-hydroxybutan-2-yl)piperazin-1-yl)pyrimidin-5-yl)oxy)pyridin-4-yl)methyl)piperidin-4-yl)acetate

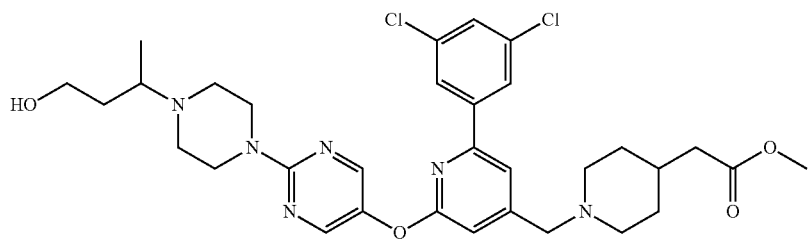 [SMILES: COC(=O)CC1CCN(Cc2cc(Oc3cnc(N4CCN(C(C)CCO)CC4)nc3)nc(-c3cc(Cl)cc(Cl)c3)c2)CC1]

A mixture of methyl 2-(1-((2-(3,5-dichlorophenyl)-6-((2-(4-piperazin-1-yl)pyrimidin-5-yl)oxy)pyridin-4-yl)methyl)piperidin-4-yl)acetate (2 g, 2.83 mmol), 4-hydroxybutan-2-one (3.75 g, 42.5 mmol) and acetic acid (0.170 g, 2.83 mmol) in MeOH (20 mL) was added 4 Å molecular sieves (100 mg, 2.83 mmol). After stirring at 30° C. for 24 h, NaBH$_3$CN (1.781 g, 28.3 mmol) was added and the reaction was stirred at 30° C. for 20 h. The mixture was filtered and the filtrate was diluted with DCM (60 mL), washed with saturated aqueous NaHCO$_3$ solution (50 mL). The organic layer was dried over Na$_2$SO$_4$, filtered and concentrated. The crude material was purified on silica gel column chromatography (DCM/MeOH=1/0 to 10/1). All fractions found to contain product by TLC (DCM/MeOH=10/1, R$_f$=0.5) were combined and concentrated to yield a colorless oil of methyl 2-(1-((2-(3,5-dichlorophenyl)-6-((2-(4-(4-hydroxybutan-2-yl)piperazin-1-yl)pyrimidin-5-yl)oxy)pyridin-4-yl)methyl)piperidin-4-yl)acetate (2.3 g, 2.62 mmol, 92.0% yield): $^1$H NMR (400 MHz, CD$_3$OD) δ ppm 8.37-8.32 (m, 2H), 7.85 (d, J=1.5 Hz, 2H), 7.67 (s, 1H), 7.46 (s, 1H), 7.07 (s, 1H), 3.96-3.89 (m, 4H), 3.78-3.71 (m, 2H), 3.68 (br s, 4H), 3.66-3.61 (m, 3H), 2.94 (d, J=10.0 Hz, 2H), 2.78 (br s, 2H), 2.71-2.63 (m, 3H), 2.31 (d, J=7.0 Hz, 2H), 2.18-2.09 (m, 2H), 1.76 (d, J=13.6 Hz, 3H), 1.43-1.33 (m, 2H), 1.10 (d, J=6.5 Hz, 3H); ES-LCMS m/z 643.4, 645.4 [M+H]$^+$.

Step 2: 2-(1-((2-(3,5-Dichlorophenyl)-6-((2-(4-(4-hydroxybutan-2-yl)piperazin-1-yl)pyrimidin-5-yl)oxy)pyridin-4-yl)methyl)piperidin-4-yl)acetic acid

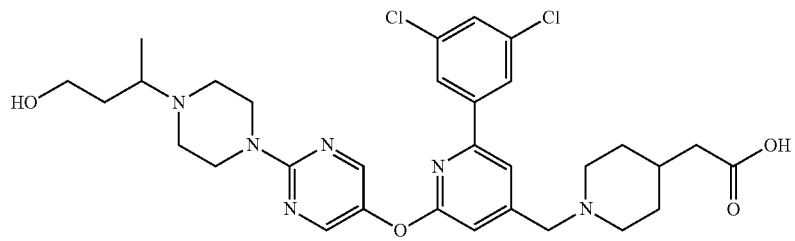 [SMILES: CC(CCO)N1CCN(c2ncc(Oc3cc(CN4CCC(CC(=O)O)CC4)cc(-c4cc(Cl)cc(Cl)c4)n3)cn2)CC1]

To a solution of methyl (1-((2-(3,5-dichlorophenyl)-6-((2-(4-(4-hydroxybutan-2-yl)piperazin-1-yl)pyrimidin-5-yl)oxy)pyridin-4-yl)methyl)piperidin-4-yl)acetate (400 mg, 0.456 mmol) in THF (5 mL) and water (1 mL) was added LiOH·H$_2$O (76 mg, 1.822 mmol). The mixture was stirred at 20° C. for 48 h. The mixture was acidified with 1 N HCl to pH=5-6 then concentrated. The residue was purified by preparative HPLC (MeCN/H$_2$O as eluents, acidic condition) and dried by lyophilization to yield a white solid of 2-(1-((2-(3,5-dichlorophenyl)-6-((2-(4-(4-hydroxybutan-2-yl)piperazin-1-yl)pyrimidin-5-yl)oxy)pyridin-4-yl)methyl)piperidin-4-yl)acetic acid, 4 hydrochloride (237.73 mg, 0.307 mmol, 67.3% yield): $^1$H NMR (400 MHz, CD$_3$OD) δ ppm 8.46 (s, 2H), 7.92 (s, 1H), 7.88 (s, 2H), 7.51 (s, 1H), 7.33 (s, 1H), 5.04-4.95 (m, 2H), 4.44 (s, 2H), 3.94-3.80 (m, 1H), 3.78-3.65 (m, 2H), 3.63-3.60 (m, 3H), 3.43-3.34 (m, 2H), 3.28-3.10 (m, 4H), 2.33 (d, J=6.4 Hz, 2H), 2.19-2.01 (m, 4H), 1.97-1.76 (m, 2H), 1.71-1.56 (m, 2H), 1.43 (d, J=7.2 Hz, 2H), 1.26 (d, J=6.0 Hz, 1H); ES-LCMS m/z 629.3, 631.4 [M+H]$^+$.

Example 239: 2-(1-((2-(3,5-Dichlorophenyl)-6-((2-(4-(4-(methylamino)butan-2-yl)piperazin-1-yl)pyrimidin-5-yl)oxy)pyridin-4-yl)methyl)piperidin-4-yl)acetic acid

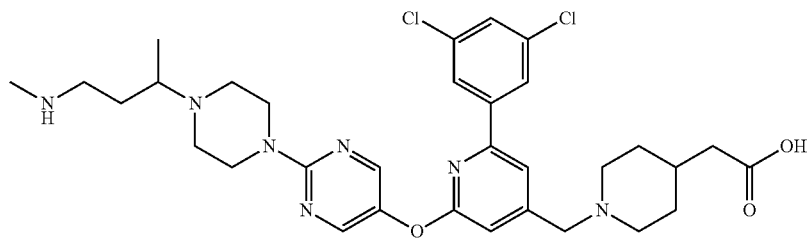 [SMILES: CNCCC(C)N1CCN(c2ncc(Oc3cc(CN4CCC(CC(=O)O)CC4)cc(-c4cc(Cl)cc(Cl)c4)n3)cn2)CC1]

Step 1: Methyl 2-(1-((2-(3,5-dichlorophenyl)-6-((2-(4-(4-((methylsulfonyl)oxy)butan-2-yl)piperazin-1-yl)pyrimidin-5-yl)oxy)pyridin-4-yl)methyl)piperidin-4-yl)acetate

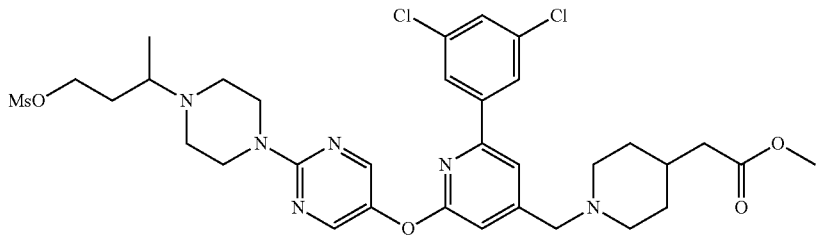 [SMILES: COC(=O)CC1CCN(Cc2cc(Oc3cnc(N4CCN(C(C)CCOS(C)(=O)=O)CC4)nc3)nc(-c3cc(Cl)cc(Cl)c3)c2)CC1]

To a mixture of methyl 2-(1-((2-(3,5-dichlorophenyl)-6-((2-(4-(4-hydroxybutan-2-yl)piperazin-1-yl)pyrimidin-5-yl)oxy)pyridin-4-yl)methyl)piperidin-4-yl)acetate (400 mg, 0.456 mmol) in DCM (15 mL) was added DIEA (0.095 mL, 0.547 mmol). Then MsCl (0.177 mL, 2.278 mmol) was added and the reaction was stirred at 0° C. for 5 min under $N_2$ atmosphere. Saturated aqueous $NaHCO_3$ solution (150 mL) was added and the aqueous layer was extracted with DCM (150 mL×2). The combined extracts were washed with brine (150 mL×2), dried over $Na_2SO_4$, filtered and concentrated to yield a yellow oil of methyl 2-(1-((2-(3,5-dichlorophenyl)-6-((2-(4-(4-((methylsulfonyl)oxy)butan-2-yl)piperazin-1-yl)pyrimidin-5-yl)oxy)pyridin-4-yl)methyl)piperidin-4-yl)acetate (400 mg, 0.333 mmol, 73.0% yield): $^1$H NMR (400 MHz, $CDCl_3$) δ ppm 8.42-8.29 (m, 2H), 8.01 (d, J=15.1 Hz, 1H), 7.91-7.77 (m, 2H), 7.37 (br. s, 2H), 5.04-4.88 (m, 2H), 4.58-4.20 (m, 4H), 3.67 (d, J=5.0 Hz, 3H), 3.59 (m 4H), 3.49 (s, 2H), 3.14-3.07 (m, 4H), 3.06-3.01 (m, 4H), 2.35 (m, 2H), 1.77 (m, 3H), 1.39-1.28 (m, 2H), 1.23 (d, J=7.0 Hz, 3H); ES-LCMS m/z 721.3, 723.3 [M+H]$^+$.

Step 2: Methyl 2-(1-((2-(3,5-dichlorophenyl)-6-((2-(4-(4-(methylamino)butan-2-yl)piperazin-1-yl)pyrimidin-5-yl)oxy)pyridin-4-yl)methyl)piperidin-4-yl)acetate

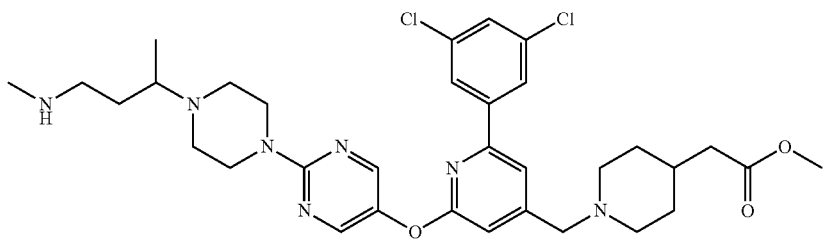

To a solution of methyl 2-(1-((2-(3,5-dichlorophenyl)-6-((2-(4-(4-((methylsulfonyl)oxy)butan-2-yl)piperazin-1-yl)pyrimidin-5-yl)oxy)pyridin-4-yl)methyl)piperidin-4-yl)acetate (400 mg, 0.333 mmol) in DCM (15 mL) was added methanamine (30% in ethanol, 466 mg, 1.995 mmol). The reaction was stirred at 15° C. for min under $N_2$ atmosphere then concentrated to yield a yellow oil of methyl 2-(1-((2-(3,5-dichlorophenyl)-6-((2-(4-(4-(methylamino)butan-2-yl)piperazin-1-yl)pyrimidin-5-yl)oxy)pyridin-4-yl)methyl)piperidin-4-yl)acetate (350 mg, 0.251 mmol, 75.0% yield): $^1$H NMR (400 MHz, $CDCl_3$) δ ppm 8.31 (s, 2H), 7.73 (s, 1H), 7.46 (br. s, 2H), 7.24-7.18 (m, 2H), 3.67 (s, 3H), 3.59 (s, 2H), 3.17 (d, J=9.5 Hz, 6H), 3.09-3.08 (m, 2H), 2.45-2.41 (m, 6H), 2.28 (m, 6H), 2.21-2.17 (m, 2H), 1.92 (m, 3H), 1.39-1.28 (m, 2H), 1.13 (m, 3H); ES-LCMS m/z 656.4, 658.4 [M+H]$^+$.

Step 3: 2-(1-((2-(3,5-Dichlorophenyl)-6-((2-(4-(4-(methylamino)butan-2-yl)piperazin-1-yl)pyrimidin-5-yl)oxy)pyridin-4-yl)methyl)piperidin-4-yl)acetic acid

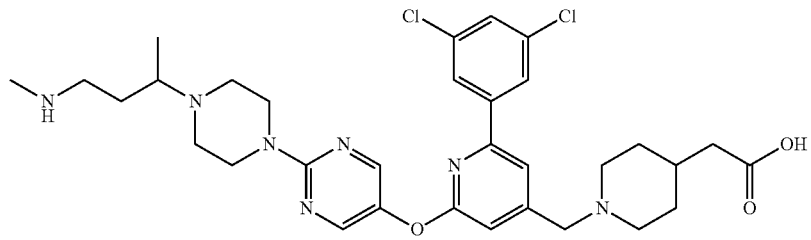 [SMILES: CNCCC(C)N1CCN(c2ncc(Oc3cc(CN4CCC(CC(=O)O)CC4)cc(-c4cc(Cl)cc(Cl)c4)n3)cn2)CC1]

To a solution of methyl 2-(1-((2-(3,5-dichlorophenyl)-6-((2-(4-(4-(methylamino)butan-2-yl)piperazin-1-yl)pyrimidin-5-yl)oxy)pyridin-4-yl)methyl)piperidin-4-yl)acetate (350 mg, 0.251 mmol) in THF (5 mL) and water (1 mL) was added LiOH·H$_2$O (105 mg, 2.505 mmol). The reaction was stirred at 25° C. for 0.5 h then concentrated and purified by preparative HPLC (MeCN/H$_2$O as eluents, basic condition) and dried by lyophilization to yield a yellow solid of 2-(1-((2-(3,5-dichlorophenyl)-6-((2-(4-(4-(methylamino)butan-2-yl)piperazin-1-yl)pyrimidin-5-yl)oxy)pyridin-4-yl)methyl)piperidin-4-yl)acetic acid (63.36 mg, 0.096 mmol, 38.4% yield): $^1$H NMR (400 MHz, CD$_3$OD) δ ppm 8.30 (s, 2H), 7.79 (d, J=1.8 Hz, 2H), 7.62 (s, 1H), 7.41 (t, J=1.8 Hz, 1H), 7.00 (s, 1H), 4.60 (br. s, 2H), 3.91-3.77 (m, 4H), 3.59 (s, 2H), 3.22-3.06 (m, 2H), 2.90 (d, J=10.1 Hz, 3H), 2.77-2.71 (m, 5H), 2.63-2.50 (m, 2H), 2.13 (s, 2H), 2.02-1.89 (m, 1H), 1.77 (d, J=9.7 Hz, 3H), 1.69-1.58 (m, 1H), 1.39-1.28 (m, 2H), 1.06 (d, J=6.6 Hz, 3H); ES-LCMS m/z 642.3, 644.3 [M+H]$^+$.

Example 240: 2-(1-((2-(3,5-Dichlorophenyl)-6-((2-(4-(4-(dimethylamino)butan-2-yl)piperazin-1-yl)pyrimidin-5-yl)oxy)pyridin-4-yl)methyl)piperidin-4-yl)acetic acid

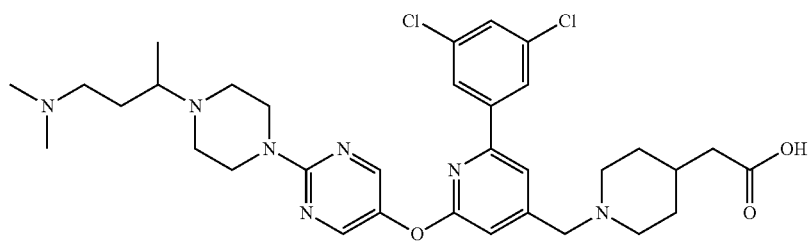 [SMILES: CC(CCN(C)C)N1CCN(c2ncc(Oc3cc(CN4CCC(CC(=O)O)CC4)cc(-c4cc(Cl)cc(Cl)c4)n3)cn2)CC1]

Example 240 was prepared by procedures analogous to those described for example 239. With dimethylamine substituted for the methylamine and reacted with the piperazine intermediate generated the final target in good yield: $^1$H NMR (400 MHz, D$_2$O) δ ppm 8.33 (s, 2H), 7.49 (s, 1H), 7.42 (d, J=1.0 Hz, 2H), 7.20 (s, 1H), 7.06 (s, 1H), 4.27 (s, 2H), 3.56-3.42 (m, 5H), 3.37-3.14 (m, 7H), 3.01 (t, J=12.3 Hz, 2H), 2.84 (s, 6H), 2.77 (d, J=5.0 Hz, 1H), 2.33-2.20 (m, 3H), 2.08-1.88 (m, 4H), 1.52-1.36 (m, 2H), 1.32 (d, J=6.5 Hz, 3H); ES-LCMS m/z 656.3, 658.4 [M+H]$^+$.

Example 241: 2-(1-((2-(3,5-Dichlorophenyl)-6-((2-(4-(2-((methylcarbamoyl)oxy)ethyl)piperazin-1-yl)pyrimidin-5-yl)oxy)pyridin-4-yl)methyl)piperidin-4-yl)acetic acid

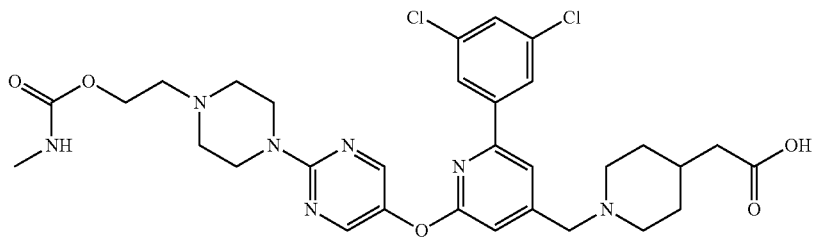 [SMILES: CNC(=O)OCCN1CCN(c2ncc(Oc3cc(CN4CCC(CC(=O)O)CC4)cc(-c4cc(Cl)cc(Cl)c4)n3)cn2)CC1]

Step 1: Methyl 2-(1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)acetate

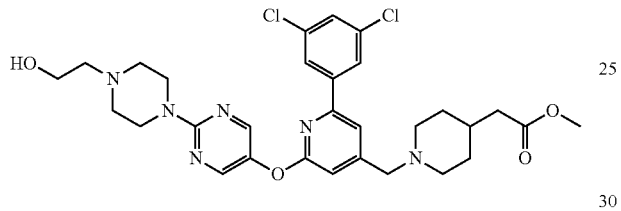

To a solution of methyl 2-(1-((2-(3,5-dichlorophenyl)-6-((2-(piperazin-1-yl)pyrimidin-5-yl)oxy)pyridin-4-yl)methyl)piperidin-4-yl)acetate (1 g, 1.557 mmol) in MeOH (40 mL) was added oxirane (0.274 g, 6.23 mmol) and DIEA (1.632 mL, 9.34 mmol) at −78° C. The mixture was stirred at 20° C. for 8 h then concentrated. The crude product was purified by silica gel column chromatography (PE/EtOAc=3/1). All fractions found to contain product by TLC (PE/EtOAc=3/1, $R_f$=0.6) were combined and concentrated to yield a light yellow solid of methyl 2-(1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)acetate (0.3 g, 0.434 mmol, 27.9% yield): $^1$H NMR (400 MHz, CD$_3$OD) δ ppm 8.30 (s, 2H), 7.78 (s, 2H), 7.60 (s, 1H), 7.40 (s, 1H), 7.00 (s, 1H), 3.89-3.81 (m, 4H), 3.73 (t, J=6.0 Hz, 2H), 3.67-3.61 (m, 3H), 3.57 (s, 2H), 2.89 (d, J=11.5 Hz, 2H), 2.66-2.54 (m, 6H), 2.27 (d, J=7.1 Hz, 2H), 2.09 (t, J=11.2 Hz, 2H), 1.82-1.68 (m, 3H), 1.42-1.26 (m, 3H); ES-LCMS m/z 615.0, 617.0 [M+H]$^+$.

Step 2: Methyl 2-(1-((2-(3,5-dichlorophenyl)-6-((2-(4-(2-((methylcarbamoyl)oxy)ethyl)piperazin-1-yl)pyrimidin-5-yl)oxy)pyridin-4-yl)methyl)piperidin-4-yl)acetate

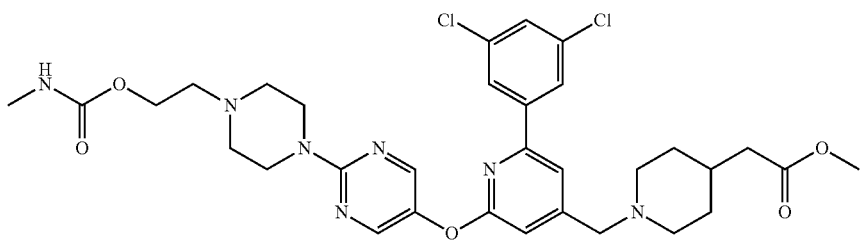

To a mixture of methyl 2-(1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)acetate (0.3 g, 0.434 mmol) in DCM (20 mL) was added DIEA (0.227 mL, 1.301 mmol) and CDI (0.141 g, 0.868 mmol). The reaction was stirred at 25° C. for 5 h then methanamine (30% in ethanol, 0.898 g, 8.68 mmol) was added. The reaction was stirred at 25° C. for another 2 h then concentrated and purified by silica gel column chromatography (DCM/MeOH=10/1). All fractions found to contain product by TLC (DCM/MeOH=10/1, $R_f$=0.6) were combined and concentrated to yield a yellow solid of methyl 2-(1-((2-(3,5-dichlorophenyl)-6-((2-(4-(2-((methylcarbamoyl)oxy)ethyl)piperazin-1-yl)pyrimidin-5-yl)oxy)pyridin-4-yl)methyl)piperidin-4-yl)acetate (0.2 g, 0.274 mmol, 63.1% yield): $^1$H NMR (400 MHz, CD$_3$OD) δ ppm 8.31 (s, 2H), 7.80 (d, J=1.8 Hz, 2H), 7.62 (s, 1H), 7.42 (s, 1H), 7.02 (s, 1H), 4.26-4.18 (m, 2H), 3.90-3.81 (m, 4H), 3.65 (s, 3H), 3.63 (s, 2H), 2.96-2.87 (m, 2H), 2.76-2.65 (m, 5H), 2.65-2.53 (m, 4H), 2.27 (d, J=6.6 Hz, 2H), 2.11 (t, J=11.0 Hz, 2H), 1.86-1.69 (m, 3H), 1.39-1.33 (m, 2H); ES-LCMS m/z 672.0, 674.0 [M+H]$^+$.

Step 3: 2-(1-((2-(3,5-Dichlorophenyl)-6-((2-(4-(2-((methylcarbamoyl)oxy)ethyl)piperazin-1-yl)pyrimidin-5-yl)oxy)pyridin-4-yl)methyl)piperidin-4-yl) acetic acid

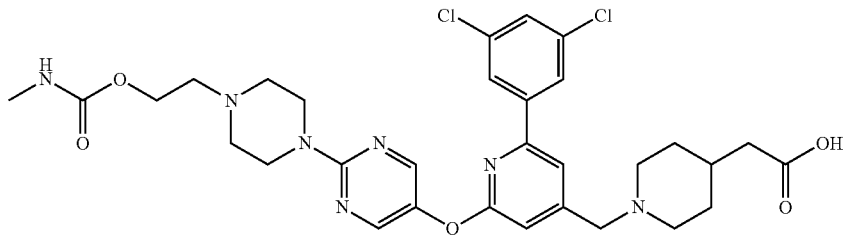 [SMILES: CNC(=O)OCCN1CCN(c2ncc(Oc3cc(CN4CCC(CC(=O)O)CC4)cc(-c4cc(Cl)cc(Cl)c4)n3)cn2)CC1]

To a mixture of methyl 2-(1-((2-(3,5-dichlorophenyl)-6-((2-(4-(2-((methylcarbamoyl)oxy)ethyl)piperazin-1-yl)pyrimidin-5-yl)oxy)pyridin-4-yl)methyl)piperidin-4-yl)acetate (190 mg, 0.260 mmol) in THF (5 mL) and water (5 mL) was added LiOH·H$_2$O (32.7 mg, 0.780 mmol). The mixture was stirred at 20° C. for 4 h then concentrated. The crude product was purified by preparative HPLC (MeCN/H$_2$O as eluents, acidic condition) and lyophilized to yield a white solid of 2-(1-((2-(3,5-dichlorophenyl)-6-((2-(4-(2-((methylcarbamoyl)oxy)ethyl)piperazin-1-yl)pyrimidin-5-yl)oxy)pyridin-4-yl)methyl)piperidin-4-yl)acetic acid, 4 hydrochloride (190.29 mg, 0.233 mmol, 90.0% yield): $^1$H NMR (400 MHz, CD$_3$OD) δ ppm 8.31 (s, 2H), 7.80 (d, J=1.8 Hz, 2H), 7.62 (s, 1H), 7.42 (s, 1H), 7.02 (s, 1H), 4.26-4.18 (m, 2H), 3.90-3.81 (m, 4H), 3.65 (s, 3H), 3.63 (s, 2H), 2.96-2.87 (m, 2H), 2.76-2.65 (m, 5H), 2.64-2.53 (m, 4H), 2.27 (d, J=6.6 Hz, 2H), 2.11 (t, J=11.0 Hz, 2H), 1.86-1.69 (m, 3H), 1.39-1.33 (m, 2H); ES-LCMS m/z 672.0, 674.0 [M+H]$^+$.

Example 242: 2-(1-((2-(3,5-Dichlorophenyl)-6-((2-(4-(3-(methylsulfonyl)propyl)piperazin-1-yl)pyrimidin-5-yl)oxy)pyridin-4-yl)methyl)piperidin-4-yl) acetic acid, 4 hydrochloride

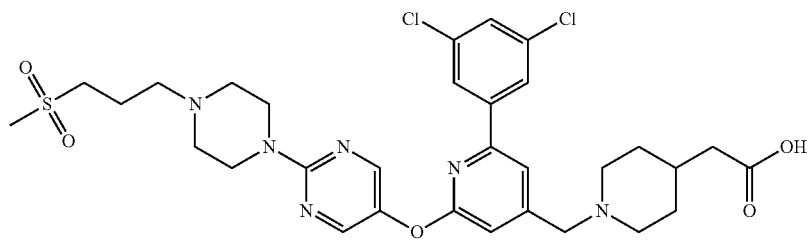 [SMILES: CS(=O)(=O)CCCN1CCN(c2ncc(Oc3cc(CN4CCC(CC(=O)O)CC4)cc(-c4cc(Cl)cc(Cl)c4)n3)cn2)CC1]

Step 1: Methyl 2-(1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)acetate

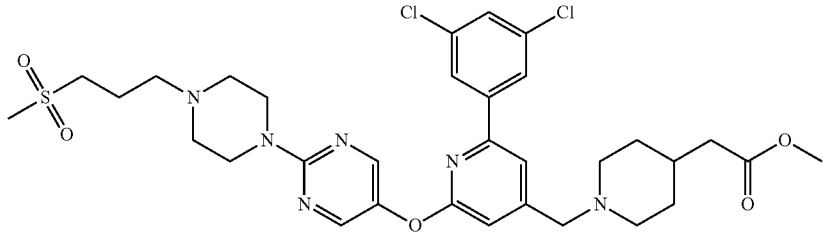

A mixture of methyl 2-(1-((2-(3,5-dichlorophenyl)-6-((2-(piperazin-1-yl)pyrimidin-5-yl)oxy)pyridin-4-yl)methyl)piperidin-4-yl)acetate, 4 hydrochloride (5 g, 5.55 mmol), 3-(methylsulfonyl)propylmethanesulfonate (4.50 g, 16.65 mmol) and DIEA (5.82 mL, 33.3 mmol) in MeCN (100 mL) was heated to 40° C. for 10 h under $N_2$ atmosphere. The reaction was concentrated to yield the crude product which was purified by silica gel column chromatography (MeOH/DCM=1/19). All fractions found to contain product by TLC (DCM/MeOH=20/1, $R_f$=0.4) were combined and concentrated to yield a yellow solid of methyl 2-(1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)acetate (4.5 g, 4.92 mmol, 89.0% yield): $^1$H NMR (400 MHz, CDCl$_3$) δ ppm 8.32-8.24 (m, 2H), 7.75 (br. s, 2H), 7.67 (d, J=1.8 Hz, 1H), 7.32 (br. s, 1H), 7.04 (br. s, 1H), 3.96 (br. s, 3H), 3.45 (s, 3H), 3.22-3.17 (m, 5H), 3.04 (s, 4H), 2.75 (s, 8H), 2.36-2.26 (m, 6H), 2.21 (br. s, 2H), 1.77 (br. s, 2H); ES-LCMS m/z 691.3, 693.3 [M+H]$^+$.

Step 2: 2-(1-((2-(3,5-Dichlorophenyl)-6-((2-(4-(3-(methylsulfonyl)propyl)piperazin-1-yl)pyrimidin-5-yl)oxy)pyridin-4-yl)methyl)piperidin-4-yl)acetic acid, 4 hydrochloride

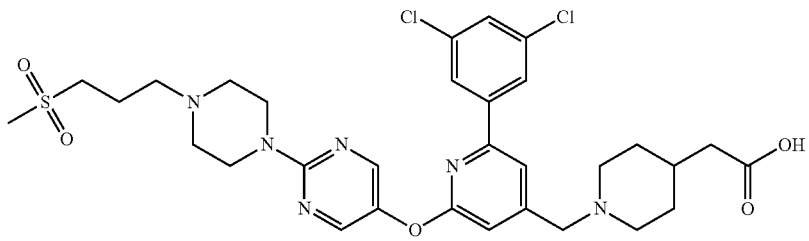 [SMILES: CS(=O)(=O)CCCN1CCN(c2ncc(Oc3cc(CN4CCC(CC(=O)O)CC4)cc(-c4cc(Cl)cc(Cl)c4)n3)cn2)CC1]

A mixture of methyl 2-(1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)acetate (4.5 g, 4.92 mmol) and LiOH·H$_2$O (1.033 g, 24.61 mmol) in THF (30 mL) and H$_2$O (5 mL) was stirred at 25° C. for 2 h. The reaction was concentrated to yield the crude product then purified by preparative HPLC (MeCN/H$_2$O as eluents, acidic condition). The fractions were combined and adjusted pH to 2 with 1 N HCl solution then dried by lyophilization to yield a pink solid of 2-(1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)acetic acid, 4 hydrochloride (1790.91 mg, 2.169 mmol, 44.1% yield): $^1$H NMR (400 MHz, CD$_3$OD) δ ppm 8.46 (s, 2H), 7.89-7.78 (m, 3H), 7.50 (t, J=1.9 Hz, 1H), 7.32 (s, 1H), 5.01-4.87 (m, 2H), 4.49-4.38 (m, 2H), 3.73 (br s, 1H), 3.57 (d, J=11.9 Hz, 3H), 3.47-3.37 (m, 4H), 3.36-3.32 (m, 3H), 3.27-3.11 (m, 3H), 3.08 (s, 3H), 2.42-2.30 (m, 4H), 2.06 (d, J=14.8 Hz, 2H), 1.68-1.55 (m, 2H); ES-LCMS m/z 677.3, 679.3 [M+H]$^+$.

Examples 243-280 (Table 13) were prepared by procedures analogous to those described for example 242

TABLE 13

| Example | Structure/Name | ¹H NMR | LCMS |
| --- | --- | --- | --- |
| 243 | 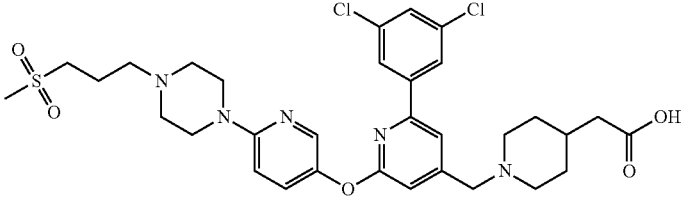 [SMILES: CS(=O)(=O)CCCN1CCN(c2ccc(Oc3cc(CN4CCC(CC(=O)O)CC4)cc(-c4cc(Cl)cc(Cl)c4)n3)cn2)CC1]<br>2-(1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)acetic acid | ¹H NMR (400 MHz, CD₃OD) δ ppm 8.20 (d, J = 2.4 Hz, 1H), 8.05 (d, J = 7.5 Hz, 1H), 7.98 (s, 1H), 7.87 (d, J = 1.8 Hz, 2H), 7.51-7.45 (m, 2H), 7.38 (s, 1H), 4.86 (br s, 2H), 4.46 (s, 2H), 4.12-3.99 (m, 1H), 3.83-3.51 (m, 6H), 3.49-3.42 (m, 2H), 3.40-3.32 (m, 3H), 3.16 (t, J = 12.0 Hz, 2H), 3.07 (s, 3H), 2.45-2.35 (m, 2H), 2.33 (d, J = 6.4 Hz, 2H), 2.16-1.98 (m, 3H), 1.76-1.60 (m, 2H) | ES-LCMS m/z 676.1, 678.1 [M + H]⁺. |
| 244 | 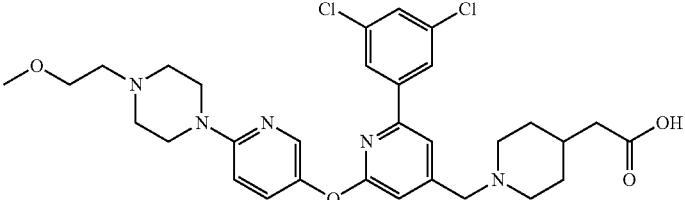<br>2-(1-((2-(3,5-dichlorophenyl)-6-((6-(4-(2-methoxyethyl)piperazin-1-yl)pyridin-3-yl)oxy)pyridin-4-yl)methyl)piperidin-4-yl)acetic acid | ¹H NMR (400 MHz, CD₃OD) δ ppm 8.24-8.18 (m, 2H), 8.01 (s, 1H), 7.88 (d, J = 1.8 Hz, 2H), 7.60 (d, J = 9.3 Hz, 1H), 7.50 (s, 1H), 7.42 (s, 1H), 4.46 (s, 2H), 3.94-3.70 (m, 6H), 3.58 (d, J = 11.9 Hz, 2H), 3.54 (s, 3H), 3.53-3.48 (m, 2H), 3.43 (s, 4H), 3.15 (t, J = 12.1 Hz, 2H), 2.36-2.27 (m, 2H), 2.14-2.00 (m, 3H), 1.77-1.62 (m, 2H) | ES-LCMS m/z 614.2, 616.2 [M + H]⁺. |
| 245 | 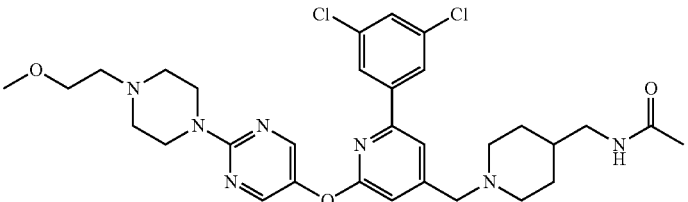<br>N-((1-((2-(3,5-dichlorophenyl)-6-((2-(4-(2-methoxyethyl)piperazin-1-yl)pyrimidin-5-yl)oxy)pyridin-4-yl)methyl)piperidin-4-yl)methyl)acetamide | ¹H NMR (400 MHz, CD₃OD) δ ppm 8.46 (s, 2H), 7.91 (s, 1H), 7.87 (d, J = 1.8 Hz, 2H), 7.51 (s, 1H), 7.32 (s, 1H), 4.43 (s, 2H), 3.81-3.75 (m, 2H), 3.70 (d, J = 12.8 Hz, 2H), 3.59 (d, J = 12.3 Hz, 2H), 3.48 (m, 2H), 3.44 (s, 3H), 3.43 (d, J = 5.3 Hz, 2H), 3.37-3.32 (m, 4H), 3.24 (d, J = 11.9 Hz, 2H), 3.12 (d, J = 6.6 Hz, 2H), 3.10-3.04 (m, 2H), 2.00 (s, 2H), 1.95 (s, 3H), 1.84 (m, 1H), 1.57 (m, 2H) | ES-LCMS m/z 628.4, 630.4 [M + H]⁺. |
| 246 | 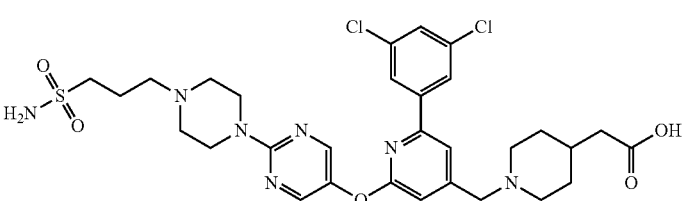<br>2-(1-((2-(3,5-dichlorophenyl)-6-((2-(4-(3-sulfamoylpropyl)piperazin-1-yl)pyrimidin-5-yl)oxy)pyridin-4-yl)methyl)piperidin-4-yl)acetic acid | ¹H NMR (400 MHz, CD₃OD) δ ppm 8.46 (s, 2H), 7.96-7.78 (m, 3H), 7.50 (s, 1H), 7.31 (s, 1H), 4.95 (s, 2H), 4.43 (s, 2H), 3.71 (d, J = 11.9 Hz, 2H), 3.58 (d, J = 12.3 Hz, 2H), 3.42-3.36 (m, 4H), 3.26-3.10 (m, 6H), 2.36-2.26 (m, 4H), 2.06 (d, J = 12.8 Hz, 3H), 1.69-1.52 (m, 2H) | ES-LCMS m/z 678.3, 680.2 [M + H]+. |

TABLE 13-continued

| Example | Structure/Name | 1H NMR | LCMS |
|---|---|---|---|
| 247 | 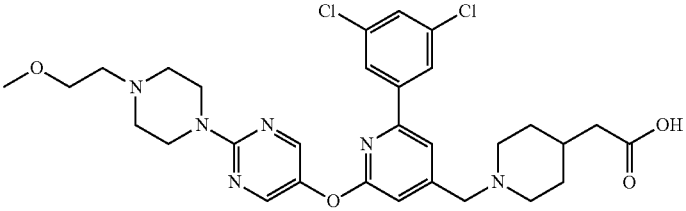 [SMILES: COCCN1CCN(c2ncc(Oc3cc(CN4CCC(CC(=O)O)CC4)cc(-c4cc(Cl)cc(Cl)c4)n3)cn2)CC1]<br>2-(1-((2-(3,5-dichlorophenyl)-6-((2-(4-(2-methoxyethyl)piperazin-1-yl)pyrimidin-5-yl)oxy)pyridin-4-yl)methyl)piperidin-4-yl)acetic acid | 1H NMR (400 MHz, CD3OD) δ ppm 8.46 (s, 2H), 7.95 (br. s, 1H), 7.87 (d, J = 1.8 Hz, 2H), 7.49 (s, 1H), 7.34 (s, 1H), 4.44 (s, 2H), 3.81-3.76 (m, 2H), 3.70 (d, J = 12.3 Hz, 2H), 3.57 (d, J = 11.9 Hz, 2H), 3.46 (br. s, 2H), 3.44 (s, 3H), 3.24 (d, J = 12.3 Hz, 4H), 3.18-3.09 (m, 4H), 2.32 (d, J = 6.6 Hz, 2H), 2.05 (d, J = 13.2 Hz, 3H), 1.73-1.62 (m, 2H) | ES-LCMS m/z 615.3, 617.3 [M + H]+. |
| 248 | 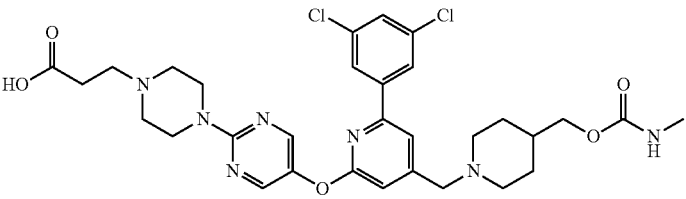<br>3-(4-(5-((6-(3,5-dichlorophenyl)-4-((4-(((methylcarbamoyl)oxy)methyl)piperidin-1-yl)methyl)pyridin-2-yl)oxy)pyrimidin-2-yl)piperazin-1-yl)propanoic acid | 1H NMR (400 MHz, CD3OD) δ ppm 8.49 (s, 2H), 7.98 (s, 1H), 7.90 (s, 2H), 7.52 (s, 1H), 7.36 (s, 1H), 4.47 (s, 2H), 3.98 (d, J = 4.5 Hz, 2H), 3.73 (d, J = 12.0 Hz, 2H), 3.63 (d, J = 11.5 Hz, 2H), 3.57-3.45 (m, 4H), 3.32-3.13 (m, 6H), 2.95 (t, J = 7.0 Hz, 2H), 2.71 (s, 3H), 2.02 (d, J = 12.5 Hz, 3H), 1.82-1.60 (m, 2H) | ES-LCMS m/z 658.3, 660.3 [M + H]+. |
| 249 | 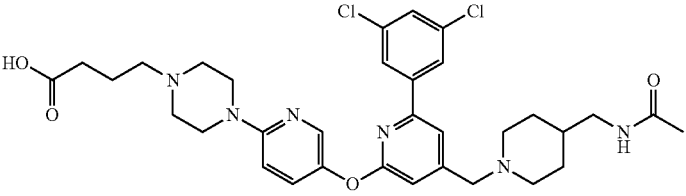 [SMILES: CC(=O)NCC1CCN(Cc2cc(Oc3ccc(N4CCN(CCCC(=O)O)CC4)nc3)nc(-c3cc(Cl)cc(Cl)c3)c2)CC1]<br>4-(4-(5-((4-((4-(acetamidomethyl)piperidin-1-yl)methyl)-6-(3,5-dichlorophenyl)pyridin-2-yl)oxy)pyridin-2-yl)piperazin-1-yl)butanoic acid | 1H NMR (400 MHz, CD3OD) δ ppm 8.19 (d, J = 2.2 Hz, 1H), 7.96-7.78 (m, 4H), 7.52 (s, 1H), 7.31 (br. s, 2H), 4.54-4.37 (m, 4H), 3.77 (br. s, 4H), 3.60 (d, J = 11.9 Hz, 2H), 3.48 (br. s, 4H), 3.23-2.97 (m, 4H), 2.50 (t, J = 6.8 Hz, 2H), 2.15-2.05 (m, 2H), 2.04-1.89 (m, 5H), 1.85 (br. s, 1H), 1.55 (d, J = 11.7 Hz, 2H) | ES-LCMS m/z 655.3, 657.3 [M + H]+. |
| 250 | 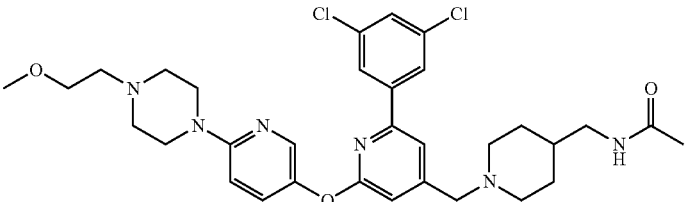<br>N-((1-((2-(3,5-dichlorophenyl)-6-((6-(4-(2-methoxyethyl)piperazin-1-yl)pyridin-3-yl)oxy)pyridin-4-yl)methyl)piperidin-4-yl)methyl)acetamide | 1H NMR (400 MHz, CD3OD) δ ppm 8.24 (s, 1H), 8.12 (d, J = 8.8 Hz, 1H), 7.98 (s, 1H), 7.90 (s, 2H), 7.56-7.49 (m, 2H), 7.40 (s, 1H), 4.47 (br. s, 2H), 3.83 (br. s, 4H), 3.62 (d, J = 10.5 Hz, 4H), 3.51 (br. s, 2H), 3.47 (s, 3H), 3.34 (br. s, 4H), 3.15 (d, J = 6.0 Hz, 4H), 2.05-2.00 (m, 2H), 1.98 (s, 3H), 1.88 (br. s, 1H), 1.62 (d, J = 12.0 Hz, 2H) | ES-LCMS m/z 627.3, 629.3 [M + H]+. |

TABLE 13-continued

| Example | Structure/Name | ¹H NMR | LCMS |
|---|---|---|---|
| 251 | 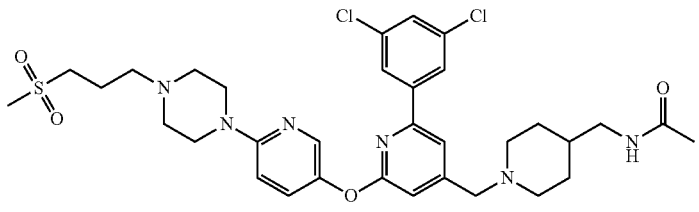 [SMILES: CC(=O)NCC1CCN(Cc2cc(Oc3ccc(N4CCN(CCCS(C)(=O)=O)CC4)nc3)nc(-c3cc(Cl)cc(Cl)c3)c2)CC1]<br>N-((1-((2-(3,5-dichlorophenyl)-6-((6-(4-(3-(methylsulfonyl)propyl)piper-azin-1-yl)pyridin-3-yl)oxy)pyridin-4-yl)methyl)piperidin-4-yl)methyl)acetamide | ¹H NMR (400 MHz, CD₃OD) δ ppm 8.24 (d, J = 2.5 Hz, 1H), 8.07 (dd, J = 2.3, 9.8 Hz, 1H), 7.98 (s, 1H), 7.90 (d, J = 1.5 Hz, 2H), 7.53 (s, 1H), 7.48 (d, J = 10.0 Hz, 1H), 7.39 (s, 1H), 4.58-4.43 (m, 3H), 3.75 (t, J = 6.5 Hz, 3H), 3.62 (d, J = 12.0 Hz, 3H), 3.52-3.43 (m, 3H), 3.39-3.35 (m, 2H), 3.29 (d, J = 8.0 Hz, 1H), 3.15 (d, J = 6.5 Hz, 3H), 3.08 (s, 3H), 3.04-2.98 (m, 2H), 2.41 (d, J = 7.6, 15.4 Hz, 2H), 2.35-2.24 (m, 1H), 2.06-1.95 (m, 5H), 1.88 (br. s, 2H), 1.70-1.51 (m, 2H) | ES-LCMS m/z 689.2, 691.2 [M + H]⁺. |
| 252 | 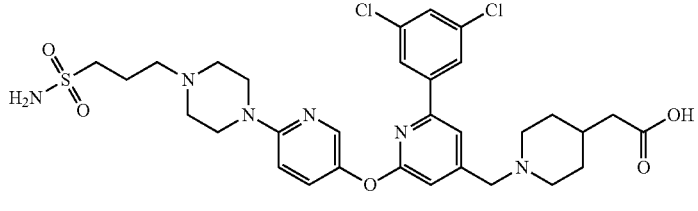<br>2-(1-((2-(3,5-dichlorophenyl)-6-((6-(4-(3-sulfamoylpropyl)piperazin-1-yl)pyridin-3-yl)oxy)pyridin-4-yl)methyl)piperidin-4-yl)acetic acid | ¹H NMR (400 MHz, CD₃OD) δ ppm 8.18 (d, J = 2.6 Hz, 1H), 7.90 (s, 1H), 7.88-7.82 (m, 3H), 7.51 (t, J = 1.8 Hz, 1H), 7.33-7.27 (m, 2H), 4.43 (s, 2H), 3.77 (br. s, 4H), 3.58 (d, J = 12.8 Hz, 3H), 3.53-3.38 (m, 5H), 3.25 (t, J =7.1 Hz, 2H), 3.14 (t, J = 12.3 Hz, 2H), 2.40-2.28 (m, 4H), 2.07 (d, J = 13.7 Hz, 3H), 1.66-1.57 (m, 2H) | ES-LCMS m/z 677.2, 679.2 [M + H]⁺. |
| 253 | 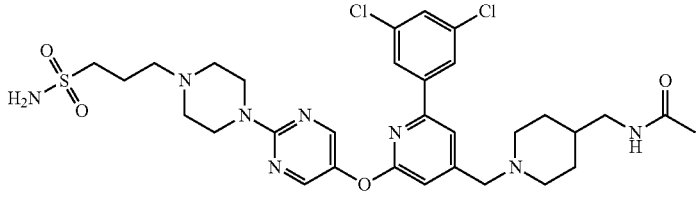 [SMILES: CC(=O)NCC1CCN(Cc2cc(Oc3cnc(N4CCN(CCCS(N)(=O)=O)CC4)nc3)nc(-c3cc(Cl)cc(Cl)c3)c2)CC1]<br>N-((1-((2-(3,5-dichlorophenyl)-6-((2-(4-(3-sulfamoylpropyl)piperazin-1-yl)pyrimidin-5-yl)oxy)pyridin-4-yl)methyl)piperidin-4-yl)methyl)acetamide | ¹H NMR (400 MHz, CD₃OD) δ ppm 8.48 (s, 2H), 7.96 (s, 1H), 7.87 (d, J = 1.8 Hz, 2H), 7.49 (s, 1H), 7.34 (s, 1H), 4.56-4.40 (m, 2H), 3.72 (t, J = 6.4 Hz, 3H), 3.59 (d, J = 12.3 Hz, 2H), 3.53-3.34 (m, 5H), 3.28-3.17 (m, 5H), 3.16-3.09 (m, 3H), 2.35 (q, J = 7.7 Hz, 2H), 2.04-1.94 (m, 5H), 1.86 (br. s, 1H), 1.69-1.54 (m, 2H) | ES-LCMS m/z 691.2, 693.2 [M + H]⁺. |
| 254 | 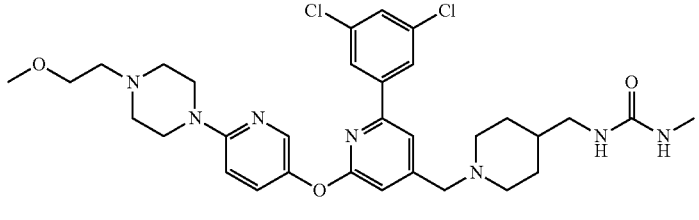<br>1-((1-((2-(3,5-dichlorophenyl)-6-((6-(4-(2-methoxyethyl)piperazin-1-yl)pyridin-3-yl)oxy)pyridin-4-yl)methyl)piperidin-4-yl)methyl)-3-methylurea | ¹H NMR (400 MHz, CD₃OD) δ ppm 8.31-8.23 (m, 2H), 8.05 (s, 1H), 7.91 (d, J = 1.5 Hz, 2H), 7.66 (d, J = 9.5 Hz, 1H), 7.54 (s, 1H), 7.48-7.44 (m, 1H), 4.49 (s, 4H), 3.93-3.73 (m, 6H), 3.62 (d, J = 12.0 Hz, 2H), 3.57-3.50 (m, 3H), 3.47 (s, 4H), 3.20-3.10 (m, 4H), 2.76 (s, 3H), 2.01 (d, J = 13.6 Hz, 2H), 1.88 (br. s, 1H), 1.73-1.58 (m, 2H) | ES-LCMS m/z 642.3, 644.3 [M + H]⁺. |

TABLE 13-continued

| Example | Structure/Name | $^1$H NMR | LCMS |
|---|---|---|---|
| 255 | 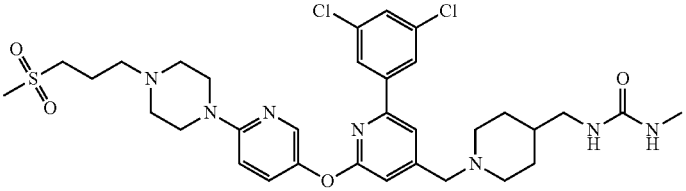<br>1-((1-((2-(3,5-dichlorophenyl)-6-((6-(4-(3-(methylsulfonyl)propyl)piper-azin-1-yl)pyridin-3-yl)oxy)pyridin-4-yl)methyl)piperidin-4-yl)methyl)-3-methylurea | $^1$H NMR (400 MHz, CD$_3$OD) δ ppm 8.23 (d, J = 2.5 Hz, 1H), 8.04 (dd, J = 2.5, 9.5 Hz, 1H), 7.96 (s, 1H), 7.93-7.87 (m, 2H), 7.54 (s, 1H), 7.45 (d, J = 9.5 Hz, 1H), 7.41-7.34 (m, 1H), 4.56-4.41 (m, 3H), 3.75 (t, J = 6.3 Hz, 3H), 3.62 (d, J = 12.0 Hz, 2H), 3.51-3.43 (m, 3H), 3.38-3.35 (m, 2H), 3.28 (s, 1H), 3.17-3.10 (m, 2H), 3.08 (s, 3H), 3.03-2.98 (m, 4H), 2.40 (d, J = 7.6, 15.4 Hz, 2H), 2.33-2.24 (m, 3H), 2.08-1.95 (m, 2H), 1.83 (m, 1H), 1.66-1.53 (m, 2H) | ES-LCMS m/z 704.2, 706.2 [M + H]$^+$. |
| 256 | 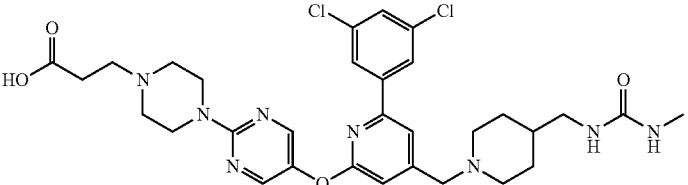<br>3-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)propanoic acid | $^1$H NMR (400 MHz, CD$_3$OD) δ ppm 8.46 (s, 2H), 7.93 (s, 1H), 7.87 (d, J = 1.8 Hz, 2H), 7.53-7.47 (m, 1H), 7.32 (s, 1H), 4.43 (s, 2H), 3.71 (d, J = 12.3 Hz, 2H), 3.59 (d, J = 11.9 Hz, 2H), 3.54-3.33 (m, 5H), 3.28-3.16 (m, 3H), 3.15-3.03 (m, 4H), 2.92 (t, J = 7.1 Hz, 2H), 2.76-2.67 (m, 3H), 2.02-1.95 (m, 2H), 1.82 (m, 1H), 1.65-1.53 (m, 2H) | ES-LCMS m/z 657.2, 659.2 [M + H]$^+$. |
| 257 | 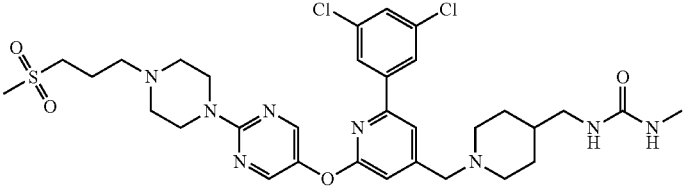<br>1-((1-((2-(3,5-dichlorophenyl)-6-((2-(4-(3-(methylsulfonyl)propyl)piper-1-yl)pyrimidin-5-yl)oxy)pyridin-4-yl)methyl)piperidin-4-yl)methyl)-3-methylurea | $^1$H NMR (400 MHz, CD$_3$OD) δ ppm 8.48-8.43 (m, 2H), 7.91-7.84 (m, 3H), 7.51 (s, 1H), 7.31 (s, 1H), 4.97 (br s, 2H), 4.55-4.40 (m, 2H), 4.12 (br s, 1H), 3.73 (d, J = 12.3 Hz, 2H), 3.59 (d, J = 9.9 Hz, 3H), 3.49-3.35 (m, 5H), 3.23 (d, J = 12.8 Hz, 2H), 3.14-3.01 (m, 6H), 2.68 (s, 3H), 2.41-2.30 (m, 2H), 1.99 (d, J = 14.1 Hz, 2H), 1.81 (br s, 1H), 1.61-1.47 (m, 2H) | ES-LCMS m/z 705.2, 707.2 [M + H]$^+$. |
| 258 | 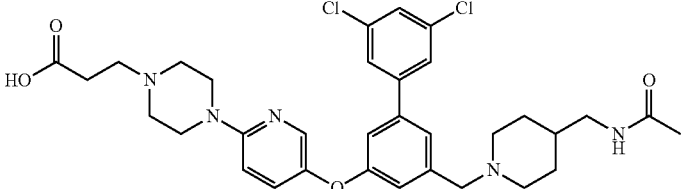<br>3-(4-(5-((5-((4-(acetamidomethyl)piperidin-1-yl)methyl)-3',5'-dichloro-[1,1'-biphenyl]-3-yl)oxy)pyridin-2-yl)piperazin-1-yl)propanoic acid | $^1$H NMR (400 MHz, CD$_3$OD) (δ ppm 8.05 (d, J = 2.21 Hz, 1H), 7.81 (d, J = 9.26 Hz, 1H), 7.63 (d, J = 1.76 Hz, 2H), 7.56 (s, 1H), 7.49 (s, 1H), 7.40 (s, 1H), 7.36-7.28 (m, 2H), 4.42 (br. s, 1H), 4.33 (s, 2H), 4.02 (br. s, 1H), 3.93 (br. s, 1H), 3.68 (br. s, 2H), 3.57-3.39 (m, 6H), 3.09 (d, J = 6.62 Hz, 2H), 3.06-2.96 (m, 3H), 2.92 (t, J = 7.06 Hz, 2H), 2.00-1.90 (m, 5H), 1.80 (br. s, 1 H), 1.59-1.44 (m, 2 H) | ES-LCMS m/z 640.3, 642.3 [M + H]$^+$. |

TABLE 13-continued

| Example | Structure/Name | ¹H NMR | LCMS |
|---|---|---|---|
| 259 | 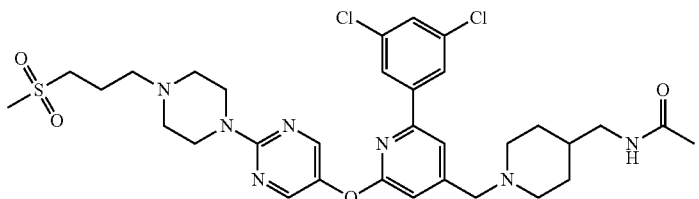<br>N-((1-((2-(3,5-dichlorophenyl)-6-((2-(4-(3-(methylsulfonyl)propyl)piper-azin-1-yl)pyrimidin-5-yl)oxy)pyridin-4-yl)methyl)piperidin-4-yl)methyl)acetamide | ¹H NMR (400 MHz, CD₃OD) δ ppm 8.47 (s, 2H), 7.93 (s, 1H), 7.87 (d, J = 1.8 Hz, 2H), 7.50 (t, J = 1.8 Hz, 1H), 7.32 (s, 1H), 4.95 (d, J = 13.7 Hz, 2H), 4.60-4.37 (m, 3H), 3.78-3.69 (m, 2H), 3.59 (d, J = 11.9 Hz, 2H), 3.49-3.35 (m, 5H), 3.26-3.18 (m, 2H), 3.15-3.09 (m, 3H), 3.05 (s, 3H), 3.00-2.95 (m, 1H), 2.36 (d, J = 7.9, 15.5 Hz, 2H), 2.08-1.94 (m, 5H), 1.85 (br. s, 1H), 1.66-1.51 (m, 2H) | ES-LCMS m/z 690.3, 692.3 [M + H]⁺. |
| 260 | 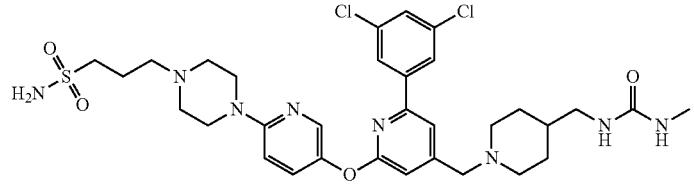<br>3-(4-(5-((6-(3,5-dichlorophenyl)-4-((4-((3-methylureido)methyl)piperidin-1-yl)methyl)pyridin-2-yl)oxy)pyridin-2-yl)piperazin-1-yl)propane-1-sulfonamide | ¹H NMR (400 MHz, CD₃OD) δ ppm 8.18 (d, J = 2.6 Hz, 1H), 7.90 (s, 1H), 7.88-7.82 (m, 3H), 7.51 (t, J = 1.8 Hz, 1H), 7.33-7.27 (m, 2H), 4.43 (s, 2H), 3.77 (br. s, 4H), 3.58 (d, J = 12.8 Hz, 3H), 3.53-3.38 (m, 5H), 3.25 (t, J = 7.1 Hz, 2H), 3.14 (t, J = 12.3 Hz, 2H), 2.40-2.28 (m, 4H), 2.07 (d, J = 13.7 Hz, 3H), 1.66-1.57 (m, 2H) | ES-LCMS m/z 677.2, 679.2 [M + H]⁺. |
| 261 | 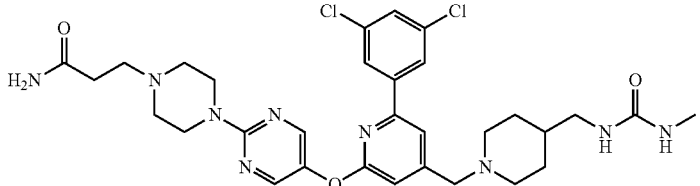<br>3-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)propanamide | ¹H NMR (400 MHz, CD₃OD) δ ppm 8.51-8.45 (m, 2H), 8.01 (s, 1H), 7.86 (d, J = 1.5 Hz, 2H), 7.46 (s, 1H), 7.40-7.33 (m, 1H), 4.87 (br s, 2H), 4.47 (s, 2H), 4.18-4.11 (m, 1H), 3.72 (d, J = 11.5 Hz, 1H), 3.59 (d, J = 10.8 Hz, 2H), 3.54-3.43 (m, 3H), 3.40-3.32 (m, 2H), 3.28-3.09 (m, 5H), 2.99-2.82 (m, 2H), 2.75 (s, 3H), 2.02-1.93 (m, 2H), 1.88 (br s, 1H), 1.74-1.57 (m, 2H) | ES-LCMS m/z 656.2, 658.2 [M + H]⁺. |
| 262 | 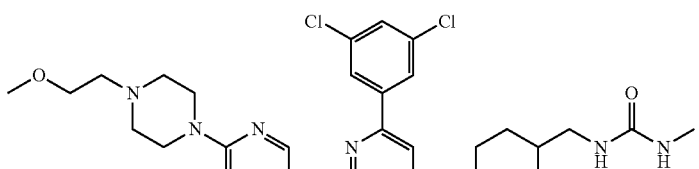<br>1-((1-((2-(3,5-dichlorophenyl)-6-((2-(4-(2-methoxyethyl)piperazin-1-yl)pyrimidin-5-yl)oxy)pyridin-4-yl)methyl)piperidin-4-yl)methyl)-3-methylurea | ¹H NMR (400 MHz, CD₃OD) δ ppm 8.47 (s, 2H), 7.95 (s, 1H), 7.88 (d, J = 1.3 Hz, 2H), 7.49 (s, 1H), 7.35-7.32 (m, 1H), 4.44 (s, 2H), 3.81-3.76 (m, 2H), 3.70 (d, J = 12.3 Hz, 2H), 3.59 (d, J = 11.9 Hz, 2H), 3.52-3.46 (m, 2H), 3.44 (s, 3H), 3.34 (s, 4H), 3.26-3.20 (m, 2H), 3.15-3.05 (m, 4H), 2.72 (s, 3H), 1.98 (d, J = 13.7 Hz, 2H), 1.84 (br. s, 1H), 1.66-1.56 (m, 2H) | ES-LCMS m/z 643.3, 645.3 [M + H]⁺. |

TABLE 13-continued

| Example | Structure/Name | ¹H NMR | LCMS |
|---|---|---|---|
| 263 | 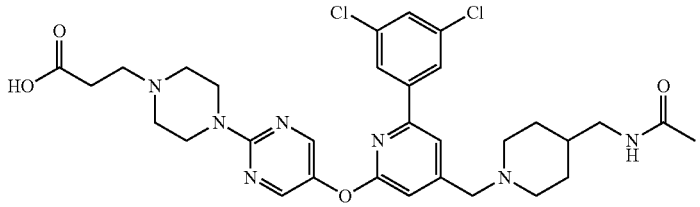 [SMILES: CC(=O)NCC1CCN(Cc2cc(Oc3cnc(N4CCN(CCC(=O)O)CC4)nc3)nc(-c3cc(Cl)cc(Cl)c3)c2)CC1]<br>3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoic acid | ¹H NMR (400 MHz, CD₃OD) δ ppm 8.41 (s, 2H), 7.83 (d, J = 1.5 Hz, 2H), 7.68 (s, 1H), 7.47 (s, 1H), 7.09 (s, 1H), 4.07 (br. s, 4H), 3.68 (s, 2H), 3.22-3.08 (m, 8H), 3.00 (d, J = 11.5 Hz, 2H), 2.62 (t, J = 6.5 Hz, 2H), 2.17 (t, J = 11.0 Hz, 2H), 1.96 (s, 3H), 1.77 (d, J = 12.0 Hz, 2H), 1.57 (br. s, 1H), 1.43-1.27 (m, 2H) | ES-LCMS m/z 642.3, 644.3 [M + H]⁺. |
| 264 | 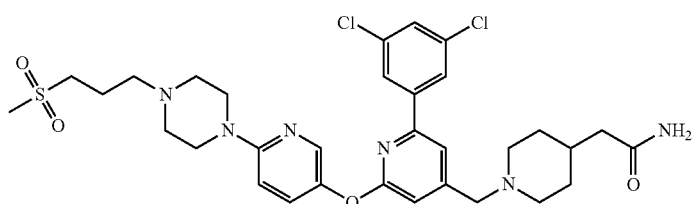<br>2-(1-((2-(3,5-dichlorophenyl)-6-((6-(4-(3-(methylsulfonyl)propyl)piper-azin-1-yl)pyridin-3-yl)oxy)pyridin-4-yl)methyl)piperidin-4-yl)acetamide | ¹H NMR (400 MHz, CD₃OD) δ ppm 8.22 (d, J = 2.6 Hz, 1H), 8.11 (dd, J = 2.6, 9.7 Hz, 1H), 7.97 (s, 1H), 7.88 (d, J = 1.8 Hz, 2H), 7.56-7.47 (m, 2H), 7.38 (s, 1H), 4.44 (s, 2H), 3.77 (br. s, 4H), 3.58 (d, J = 11.9 Hz, 3H), 3.51-3.41 (m, 3H), 3.40-3.31 (m, 4H), 3.13 (t, J = 12.1 Hz, 2H), 3.05 (s, 3H), 2.38 (td, J = 7.6, 15.7 Hz, 2H), 2.22 (d, J = 6.6 Hz, 2H), 2.14-1.96 (m, 3H), 1.74-1.60 (m, 2H) | ES-LCMS m/z 675.2, 677.2 [M + H]⁺. |
| 265 | 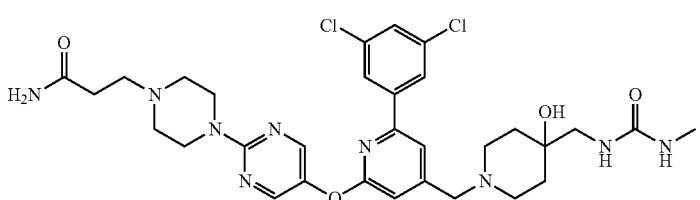<br>3-(4-(5-((6-(3,5-dichlorophenyl)-4-((4-hydroxy-4-((3-methylureido)methyl)piperidin-1-yl)methyl)pyridin-2-yl)oxy)pyrimidin-2-yl)piperazin-1-yl)propanamide | ¹H NMR (400 MHz, CD₃OD) δ ppm 8.51 (s, 2H), 8.01 (s, 1H), 7.93-7.86 (m, 2H), 7.51 (s, 1H), 7.39 (s, 1H), 4.60-4.46 (m, 2H), 3.73 (d, J = 11.5 Hz, 2H), 3.61-3.34 (m, 10H), 3.25 (s, 4H), 2.86 (t, J = 7.0 Hz, 2H), 2.78-2.72 (m, 3H), 2.07-1.96 (m, 2H), 1.83 (d, J = 14.1 Hz, 2H) | ES-LCMS m/z 672.3, 674.3 [M + H]⁺. |
| 266 | 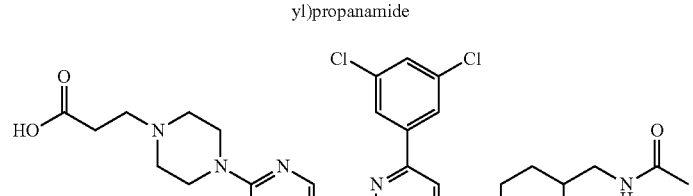<br>3-(4-(5-((4-((4-(acetamidomethyl)piperidin-1-yl)methyl)-6-(3,5-dichlorophenyl)pyridin-2-yl)oxy)-3-fluoropyridin-2-yl)piperazin-1-yl)propanoic acid | ¹H NMR (400 MHz, CD₃OD) δ ppm 8.11 (d, J = 2.0 Hz, 1H), 7.96 (s, 1H), 7.90 (d, J = 1.5 Hz, 2H), 7.65 (dd, J = 2.0, 12.5 Hz, 1H), 7.52 (s, 1H), 7.33 (s, 1H), 4.61-4.43 (m, 2H), 4.22 (d, J = 11.0 Hz, 2H), 3.73 (d, J = 9.0 Hz, 2H), 3.62 (d, J = 12.0 Hz, 2H), 3.54 (t, J = 7.0 Hz, 2H), 3.46-3.36 (m, 5H), 3.16-3.09 (m, 3H), 2.94 (t, J = 7.0 Hz, 2H), 2.04-1.96 (m, 5H), 1.87 (br. s, 1H), 1.70-1.52 (m, 2H) | ES-LCMS m/z 661.2, 659.2 [M + H]⁺. |

TABLE 13-continued

| Example | Structure/Name | ¹H NMR | LCMS |
|---|---|---|---|
| 267 | 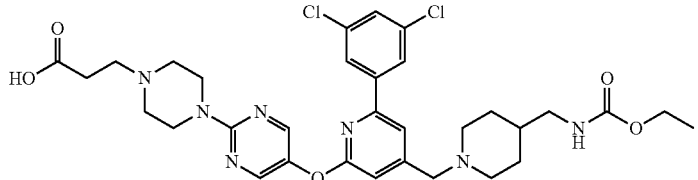<br>3-(4-(5-((6-(3,5-dichlorophenyl)-4-((4-(((ethoxycarbonyl)amino)methyl)piperidin-1-yl)methyl)pyridin-2-yl)oxy)pyrimidin-2-yl)piperazin-1-yl)propanoic acid | ¹H NMR (400 MHz, CD₃OD) δ ppm 8.45 (s, 2H), 7.98 (s, 1H), 7.85 (d, J = 1.3 Hz, 2H), 7.45 (s, 1H), 7.35 (s, 1H), 4.58-4.43 (m, 2H), 4.18-3.98 (m, 3H), 3.71 (d, J = 11.9 Hz, 2H), 3.59 (d, J = 11.9 Hz, 2H), 3.54-3.42 (m, 4H), 3.34 (s, 1H), 3.27-3.19 (m, 2H), 3.12 (t, J = 12.3 Hz, 2H), 3.04 (d, J = 6.2 Hz, 2H), 2.95 (t, J = 7.1 Hz, 2H), 1.97 (d, J = 13.7 Hz, 2H), 1.83 (br. s, 1H), 1.69-1.54 (m, 2H), 1.21 (t, J = 6.8 Hz, 3H) | ES-LCMS m/z 672.3, 674.3 [M + H]⁺. |
| 268 | 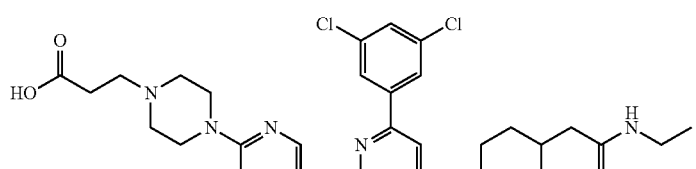<br>3-(4-(5-((6-(3,5-dichlorophenyl)-4-((4-(2-(ethylamino)-2-oxoethyl)piperidin-1-yl)methyl)pyridin-2-yl)oxy)pyrimidin-2-yl)piperazin-1-yl)propanoic acid | ¹H NMR (400 MHz, CD₃OD) δ ppm 8.46 (s, 2H), 7.94 (s, 1H), 7.87 (d, J = 1.8 Hz, 2H), 7.50 (s, 1H), 7.32 (s, 1H), 4.42 (s, 2H), 3.70 (d, J = 11.9 Hz, 2H), 3.57 (d, J = 12.3 Hz, 2H), 3.53-3.31 (m, 6H), 3.27-3.04 (m, 6H), 2.92 (t, J = 7.1 Hz, 2H), 2.18 (d, J = 7.1 Hz, 2H), 2.06 (d, J = 10.1 Hz, 1H), 1.97 (d, J = 14.6 Hz, 2H), 1.71-1.58 (m, 2H), 1.10 (t, J = 7.3 Hz, 3H) | ES-LCMS m/z 656.2, 658.2 [M + H]⁺. |
| 269 | 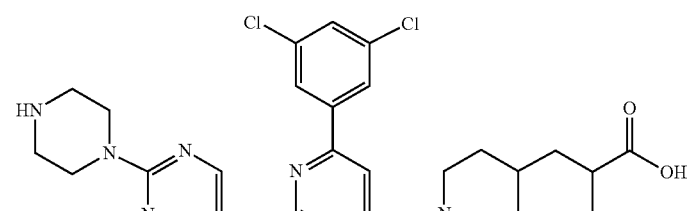<br>3-(1-((2-(3,5-dichlorophenyl)-6-((2-(piperazin-1-yl)pyrimidin-5-yl)oxy)pyridin-4-yl)methyl)piperidin-4-yl)-2-methylpropanoic acid | ¹H NMR (400 MHz, CD₃OD) δ ppm 8.48 (s, 2H), 7.97 (s, 1H), 7.88 (d, J = 1.8 Hz, 2H), 7.49 (s, 1H), 7.34 (s, 1H), 4.44 (s, 2H), 4.19-4.06 (m, 4H), 3.55 (br. s, 2H), 3.40-3.32 (m, 4H), 3.11 (t, J = 12.1 Hz, 2H), 2.53 (dd, J = 6.8, 13.5 Hz, 1H), 2.08-1.92 (m, 2H), 1.73-1.51 (m, 4H), 1.39-1.29 (m, 1H), 1.21-1.07 (m, 3H) | ES-LCMS m/z 585.2; 587.2 [M + H]⁺. |
| 270 | 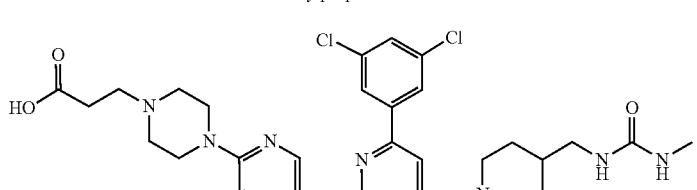<br>3-(4-(5-((6-(3,5-dichlorophenyl)-4-((4-((3-methylureido)methyl)piperidin-1-yl)methyl)pyridin-2-yl)oxy)-3-fluoropyridin-2-yl)piperazin-1-yl)propanoic acid | ¹H NMR (400 MHz, CD₃OD) δ ppm 8.08 (d, J = 2.2 Hz, 1H), 7.93-7.78 (m, 3H), 7.63 (dd, J = 2.2, 12.3 Hz, 1H), 7.51 (t, J = 1.8 Hz, 1H), 7.28 (s, 1H), 4.55-4.35 (m, 2H), 4.18 (br. s, 2H), 3.71 (br. s, 2H), 3.59 (d, J = 12.3 Hz, 2H), 3.52 (t, J = 7.1 Hz, 2H), 3.34 (br. s, 4H), 3.17-3.03 (m, 3H), 2.91 (t, J = 7.1 Hz, 2H), 2.72-2.68 (m, 2H), 2.07-1.90 (m, 3H), 1.79 (br. s, 2H), 1.58-1.45 (m, 2H) | ES-LCMS m/z 674.2, 676.2 [M + H]⁺. |

| Example | Structure/Name | ¹H NMR | LCMS |
|---|---|---|---|
| 271 | 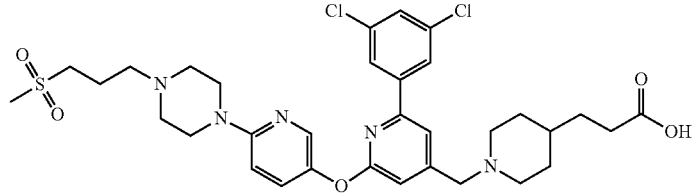 [SMILES: CS(=O)(=O)CCCN1CCN(c2ccc(Oc3cc(CN4CCC(CCC(=O)O)CC4)cc(-c4cc(Cl)cc(Cl)c4)n3)cn2)CC1]<br>3-(1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)propanoic acid | ¹H NMR (400 MHz, D₂O) δ ppm 8.03-7.92 (m, 2H), 7.51 (s, 1H), 7.39-7.27 (m, 3H), 7.08-6.88 (m, 2H), 4.34-4.16 (m, 2H), 3.70 (s., 2H), 3.57-3.48 (m, 4H), 3.37-3.29 (m, 3H), 3.25 (d, J = 7.5 Hz, 2H), 3.20 (d, J = 4.9 Hz, 2H), 2.99 (s, 2H), 2.90 (d, J = 6.6 Hz, 4H), 2.20 (d, J = 7.1 Hz, 3H), 2.11-2.02 (m, 2H), 1.79 (d, J = 13.2 Hz, 2H), 1.48-1.22 (m, 4H) | ES-LCMS m/z 690.3, 692.3 [M + H]⁺. |
| 272 | 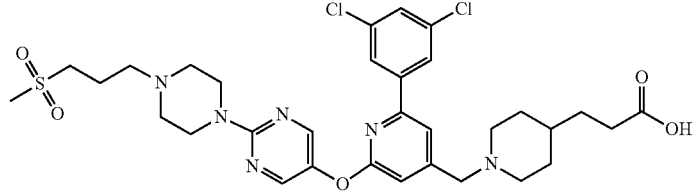 [SMILES: CS(=O)(=O)CCCN1CCN(c2ncc(Oc3cc(CN4CCC(CCC(=O)O)CC4)cc(-c4cc(Cl)cc(Cl)c4)n3)cn2)CC1]<br>3-(1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)propanoic acid | ¹H NMR (400 MHz, CD₃OD) δ ppm 8.50-8.37 (m, 2H), 7.97 (s, 1H), 7.82 (s, 2H), 7.44-7.32 (m, 2H), 4.89 (s., 2H), 4.64-4.38 (m, 2H), 3.82-3.68 (m, 2H), 3.62-3.48 (m, 4H), 3.45-3.38 (m, 2H), 3.35 (t, J = 7.1 Hz, 2H), 3.27-3.09 (m, 4H), 3.07 (s, 2H), 3.03-2.95 (m, 1H), 2.45-2.33 (m, 3H), 2.29-2.21 (m, 1H), 1.99 (d, J = 12.8 Hz, 2H), 1.81 (s., 1H), 1.61 (d, J = 6.6 Hz, 4H) | ES-LCMS m/z 691.2, 693.2 [M + H]⁺. |
| 273 | 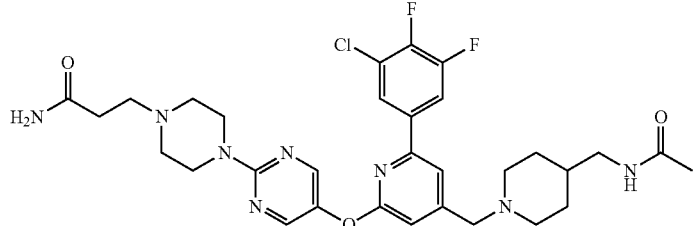<br>3-(4-(5-((4-((4-(acetamidomethyl)piperidin-1-yl)methyl)-6-(3-chloro-4,5-difluorophenyl)pyridin-2-yl)oxy)pyrimidin-2-yl)piperazin-1-yl)propanamide | ¹H NMR (400 MHz, D₂O) δ ppm 8.31 (s, 2H), 7.55-7.29 (m, 3H), 7.05 (s, 1H), 4.56 (d, J = 14.6 Hz, 1H), 4.26 (s, 2H), 3.91 (s., 2H), 3.62 (d, J = 11.0 Hz, 1H), 3.50-3.31 (m, 5H), 3.27 (d, J = 4.5 Hz, 2H), 3.09 (s., 1H), 3.03-2.80 (m, 5H), 2.76 (t, J = 6.8 Hz, 1H), 1.91-1.85 (m, 5H), 1.74 (s., 1H), 1.45-1.30 (m, 2H) | ES-LCMS m/z 643.3, 645.3 [M + H]⁺. |
| 274 | 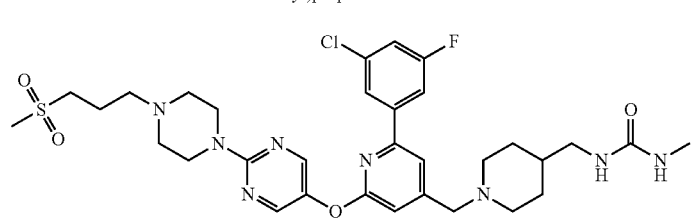<br>1-((1-((2-(3-chloro-5-fluorophenyl)-6-((2-(4-(3-(methylsulfonyl)propyl)piperazin-1-yl)pyrimidin-5-yl)oxy)pyridin-4-yl)methyl)piperidin-4-yl)methyl)-3-methylurea | ¹H NMR (400 MHz, CD₃OD) δ ppm 8.49 (s, 2H), 8.00 (s, 1H), 7.80 (s, 1H), 7.62 (d, J = 9.3 Hz, 1H), 7.36 (s, 1H), 7.25 (d, J = 8.4 Hz, 1H), 4.62-4.37 (m, 3H), 4.14 (s, 1H), 3.74 (d, J = 11.0 Hz, 2H), 3.59 (d, J = 10.6 Hz, 2H), 3.54-3.45 (m, 2H), 3.44-3.38 (m, 2H), 3.37-3.31 (m, 3H), 3.25 (d, J = 11.9 Hz, 2H), 3.13 (s., 3H), 3.06 (s, 3H), 2.83-2.62 (m, 3H), 2.37 (s., 2H), 1.99 (d, J = 12.8 Hz, 2H), 1.87 (s., 1H), 1.64 (d, J = 11.5 Hz, 2H) | ES-LCMS m/z 689.2, 691.2 [M + H]⁺. |

TABLE 13-continued

| Example | Structure/Name | $^1$H NMR | LCMS |
|---|---|---|---|
| 275 | 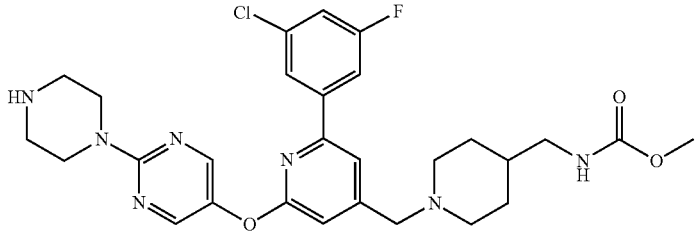 [SMILES: COC(=O)NCC1CCN(Cc2cc(Oc3cnc(N4CCNCC4)nc3)nc(-c3cc(F)cc(Cl)c3)c2)CC1]<br>methyl ((1-((2-(3-chloro-5-fluorophenyl)-6-((2-(piperazin-1-yl)pyrimidin-5-yl)oxy)pyridin-4-yl)methyl)piperidin-4-yl)methyl)carbamate | $^1$H NMR (400 MHz, CD$_3$OD) ppm 8.44 (s, 2H), 7.90 (s, 1H), 7.78 (s, 1H), 7.60 (d, J = 9.3 Hz, 1H), 7.34-7.23 (m, 2H), 4.52 (s, 2H), 4.16-4.04 (m, 4H), 3.72-3.51 (m, 5H), 3.33 (m, 4H), 3.11-3.04 (m, 4H), 2.03-1.93 (m, 2H), 1.82 (m, 1H), 1.61-1.49 (m, 2H) | ES-LCMS m/z 570.3, 572.3 [M + H]$^+$. |
| 276 | 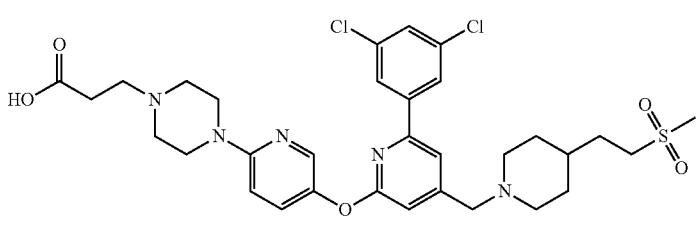 [SMILES: CS(=O)(=O)CCC1CCN(Cc2cc(Oc3ccc(N4CCN(CCC(=O)O)CC4)nc3)nc(-c3cc(Cl)cc(Cl)c3)c2)CC1]<br>3-(4-(5-((6-(3,5-dichlorophenyl)-4-((4-(2-(methylsulfonyl)ethyl)piperidin-1-yl)methyl)pyridin-2-yl)oxy)pyridin-2-yl)piperazin-1-yl)propanoic acid | $^1$H NMR (400 MHz, CD$_3$OD) ppm 8.20 (br. s, 1H), 7.99-7.86 (m, 4H), 7.53 (s, 1H), 7.35 (d, J = 11.5 Hz, 2H), 4.46 (s, 2H), 3.83-3.35 (m, 10H), 3.32-3.27 (m, 2H), 3.25-3.19 (m, 2H), 3.14 (t, J = 11.8 Hz, 2H), 3.05-2.87 (m, 5H), 2.08 (d, J = 14.1 Hz, 2H), 1.93-1.76 (m, 3H), 1.62 (s, 2H) | ES-LCMS m/z 676.2, 678.2 [M + H]$^+$. |
| 277 | 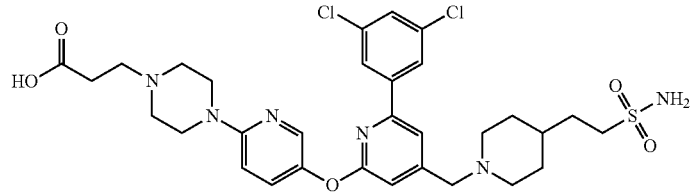 [SMILES: NS(=O)(=O)CCC1CCN(Cc2cc(Oc3ccc(N4CCN(CCC(=O)O)CC4)nc3)nc(-c3cc(Cl)cc(Cl)c3)c2)CC1]<br>3-(4-(5-((6-(3,5-dichlorophenyl)-4-((4-(2-sulfamoylethyl)piperidin-1-yl)methyl)pyridin-2-yl)oxy)pyridin-2-yl)piperazin-1-yl)propanoic acid | $^1$H NMR (400 MHz, CD$_3$OD) δ ppm 8.20 (d, J = 2.2 Hz, 1H), 8.02-7.95 (m, 2H), 7.88 (d, J = 1.8 Hz, 2H), 7.51 (s, 1H), 7.44-7.34 (m, 2H), 4.48-4.42 (m, 2H), 3.94-3.66 (m, 4H), 3.64-3.45 (m, 6H), 3.39-3.32 (m, 2H), 3.20-3.08 (m, 4H), 2.95 (t, J = 7.1 Hz, 2H), 2.04 (d, J = 14.1 Hz, 2H), 1.82 (d, J = 6.2 Hz, 3H), 1.62 (d, J = 11.9 Hz, 2H) | ES-LCMS m/z 677.1, 679.1 [M + H]$^+$. |
| 278 | 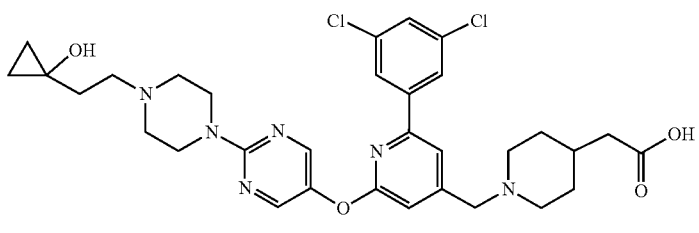 [SMILES: O=C(O)CC1CCN(Cc2cc(Oc3cnc(N4CCN(CCC5(O)CC5)CC4)nc3)nc(-c3cc(Cl)cc(Cl)c3)c2)CC1]<br>2-(1-((2-(3,5-dichlorophenyl)-6-((2-(4-(2-(1-hydroxycyclopropyl)ethyl)piperazin-1-yl)pyrimidin-5-yl)oxy)pyridin-4-yl)methyl)piperidin-4-yl)acetic acid | $^1$H NMR (400 MHz, CD$_3$OD) δ ppm 8.46 (s, 2H), 7.94 (s, 1H), 7.88 (d, J = 1.2 Hz, 2H), 7.50 (s, 1H), 7.34 (s, 1H), 4.90 (d, J = 15.3 Hz, 2H), 4.44 (s, 2H), 3.73-3.64 (m, 2H), 3.59 (d, J = 11.7 Hz, 2H), 3.51-3.38 (m, 4H), 3.24-3.06 (m, 6H), 2.59 (q, J = 7.4 Hz, 2H), 2.36-2.29 (m, 2H), 2.13-2.03 (m, 3H), 1.71-1.63 (m, 2H), 1.08 (t, J = 7.2 Hz, 2H) | ES-LCMS m/z: 641.3, 643.3 [M + H]$^+$. |

TABLE 13-continued

| Example | Structure/Name | $^1$H NMR | LCMS |
|---|---|---|---|
| 279 | 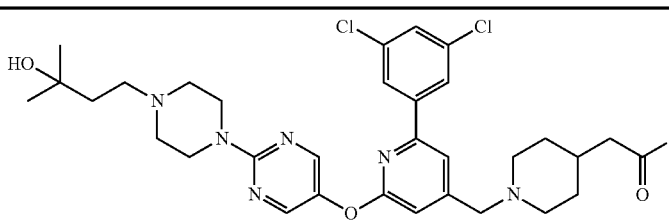<br>2-(1-((2-(3,5-dichlorophenyl)-6-((2-(4-(3-hydroxy-3-methylbutyl)piperazin-1-yl)pyrimidin-5-yl)oxy)pyridin-4-yl)methyl)piperidin-4-yl)acetic acid | $^1$H NMR (400 MHz, CD$_3$OD) δ 8.49-8.44 (m, 2H), 7.96-7.87 (m, 3H), 7.52 (t, J = 1.9 Hz, 1H), 7.34 (s, 1H), 4.94 (d, J = 14.8 Hz, 2H), 4.45 (s, 2H), 3.73 (d, J = 12.3 Hz, 2H), 3.59 (d, J = 11.5 Hz, 2H), 3.45-3.35 (m, 4H), 3.17 (q, J = 11.8 Hz, 4H), 2.34 (d, J = 6.5 Hz, 2H), 2.07 (d, J = 14.3 Hz, 3H), 2.00-1.90 (m, 2H), 1.73-1.55 (m, 2H), 1.30 (s, 6H) | ES-LCMS m/z 643.3, 645.4 [M + H]$^+$. |
| 280 | 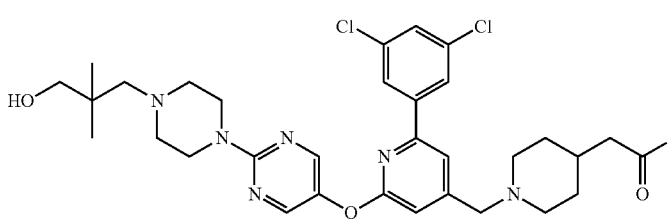<br>2-(1-((2-(3,5-dichlorophenyl)-6-((2-(4-(3-hydroxy-2,2-dimethylpropyl)piperazin-1-yl)pyrimidin-5-yl)oxy)pyridin-4-yl)methyl)piperidin-4-yl)acetic acid | $^1$H NMR (400 MHz, CD$_3$OD) δ ppm 8.45 (s, 2H), 7.86-7.89 (m, 3H), 7.51 (t, J =1.8 Hz, 1H), 7.30 (s, 1H), 4.43 (s, 2H), 4.11-4.14 (m, 5H), 3.89 (s, 2H), 3.59 (d, J = 12.3 Hz, 2H), 3.34 (d, J = 5.73 Hz, 5H), 3.11-3.17 (m, 2H), 2.36-2.39 (m, 2H), 2.06 (d, J = 15.44 Hz, 3H), 1.57-1.63 (m, 2H), 0.90 (s, 6H) | ES-LCMS m/z 643.3, 645.3 [M + H]$^+$. |

Example 281: 3-(4-(5-((4-((4-(Acetamidomethyl) piperidin-1-yl)methyl)-6-(3,5-dichlorophenyl)pyridin-2-yl)oxy)pyridin-2-yl)piperazin-1-yl)butanoic acid, 4 hydrochloride

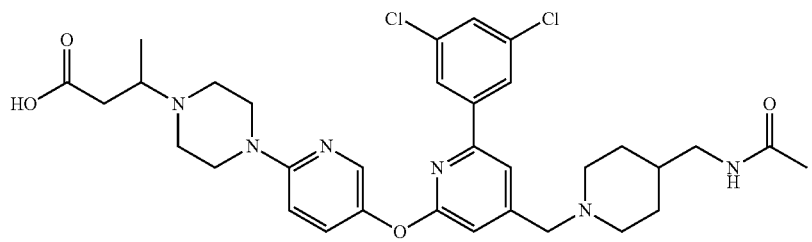

Step 1: Ethyl 3-(4-(5-((4-((4-(acetamidomethyl) piperidin-1-yl)methyl)-6-(3,5-dichlorophenyl)pyridin-2-yl)oxy)pyridin-2-yl)piperazin-1-yl)butanoate

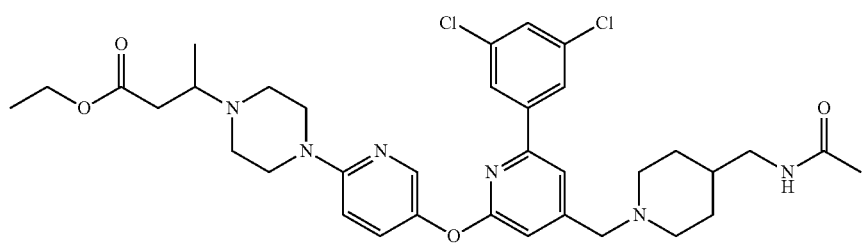 [SMILES: CCOC(=O)CC(C)N1CCN(c2ccc(Oc3cc(CN4CCC(CNC(C)=O)CC4)cc(-c4cc(Cl)cc(Cl)c4)n3)cn2)CC1]

To a mixture of N-((1-((2-(3,5-dichlorophenyl)-6-((6-(piperazin-1-yl)pyridin-3-yl)oxy)pyridin-4-yl)methyl)piperidin-4-yl)methyl)acetamide, 4 hydrochloride (200 mg, 0.252 mmol) and (S)-ethylbut-2-enoate (862 mg, 7.55 mmol) was added DIEA (220 µl, 1.258 mmol). The reaction mixture was stirred at 150° C. for 2 h under microwave then concentrated to yield brown oil of ethyl 3-(4-(5-((4-((4-

(acetamidomethyl)piperidin-1-yl)methyl)-6-(3,5-dichlorophenyl)pyridin-2-yl)oxy)pyridin-2-yl)piperazin-1-yl)butanoate (200 mg, 0.205 mmol, 81.0% yield): $^1$H NMR (400 MHz, CD$_3$OD) δ ppm 8.12-8.01 (m, 1H), 7.74-7.60 (m, 2H), 7.44-7.30 (m, 2H), 7.27 (s, 1H), 6.96-6.83 (m, 2H), 4.15-4.09 (m, 4H), 3.79-3.51 (m, 5H), 3.46 (d, J=5.7 Hz, 4H), 3.10 (t, J=6.0 Hz, 2H), 2.83 (d, J=10.1 Hz, 2H), 2.67-2.51 (m, 3H), 1.99-1.90 (m, 5H), 1.62 (d, J=11.9 Hz, 2H), 1.48 (br. s, 1H), 1.25-1.20 (m, 8H); ES-LCMS m/z 683.3, 685.3 [M+H]$^+$.

Step 2: 3-(4-(5-((4-((4-(Acetamidomethyl)piperidin-1-yl)methyl)-6-(3,5-dichlorophenyl)pyridin-2-yl)oxy)pyridin-2-yl)piperazin-1-yl)butanoic acid, 4 hydrochloride

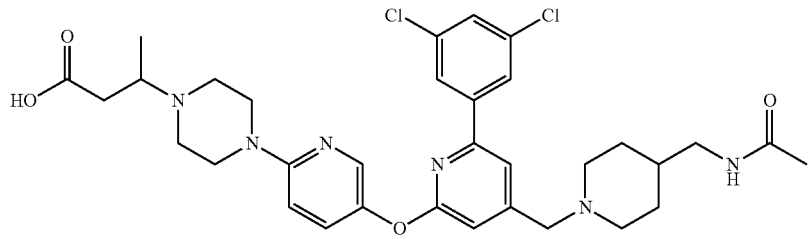 [SMILES: CC(=O)NCC1CCN(Cc2cc(Oc3ccc(N4CCN(C(C)CC(=O)O)CC4)nc3)nc(-c3cc(Cl)cc(Cl)c3)c2)CC1]

To a suspension of ethyl 3-(4-(5-((4-((4-(acetamidomethyl)piperidin-1-yl)methyl)-6-(3,5-dichlorophenyl)pyridin-2-yl)oxy)pyridin-2-yl)piperazin-1-yl)butanoate (200 mg, 0.205 mmol) in THF (5 mL) and water (3 mL) was added LiOH·H$_2$O (25.8 mg, 0.614 mmol). The reaction mixture was stirred at 20° C. for 3 h then adjusted pH to 5 with 1 N HCl and concentrated to yield crude product which was purified by preparative HPLC (MeCN/H$_2$O as eluents, acidic condition) and lyophilized to yield a white solid of 3-(4-(5-((4-((4-(acetamidomethyl)piperidin-1-yl)methyl)-6-(3,5-dichlorophenyl)pyridin-2-yl)oxy)pyridin-2-yl)piperazin-1-yl)butanoic acid, 4 hydrochloride (23.26 mg, 0.028 mmol, 13.7% yield): $^1$H NMR (400 MHz, CD$_3$OD) δ ppm 8.20 (br. s, 1H), 8.04 (br. s, 1H), 7.96 (br. s, 1H), 7.88 (d, J=1.3 Hz, 2H), 7.51 (s, 1H), 7.46 (d, J=9.3 Hz, 1H), 7.37 (br. s, 1H), 4.45 (s, 2H), 3.92 (d, J=4.4 Hz, 2H), 3.83-3.31 (m, 10H), 3.20-2.98 (m, 4H), 2.78 (dd, J=8.4, 17.2 Hz, 1H), 2.11-1.91 (m, 5H), 1.85 (br. s, 1H), 1.75-1.41 (m, 5H); ES-LCMS m/z 655.3, 657.3 [M+H]$^+$.

Examples 282-297 (Table 14) were prepared by procedures analogous to those described for example 281.

TABLE 14

| Example | Structure/Name | $^1$H NMR | LCMS |
|---|---|---|---|
| 282 | 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)butanoic acid | $^1$H NMR (400 MHz, D$_2$O) δ ppm 8.28 (s, 2H), 7.44 (s, 3H), 7.22 (s, 1H), 7.02 (s, 1H), 4.22 (br. s, 2H), 3.72 (dd, J = 6.6, 12.3 Hz, 1H), 3.42 (d, J = 11.9 Hz, 5H), 3.32-3.05 (m, 5H), 2.98-2.84 (m, 4H), 2.79 (dd, J = 5.1, 17.0 Hz, 1H), 2.63 (d, J = 7.9 Hz, 1H), 1.93-1.76 (m, 5H), 1.69 (br. s, 1H), 1.40-1.22 (m, 5H) | ES-LCMS m/z 656.3, 658.3 [M + H]$^+$. |

TABLE 14-continued

| Example | Structure/Name | 1H NMR | LCMS |
|---|---|---|---|
| 283 | 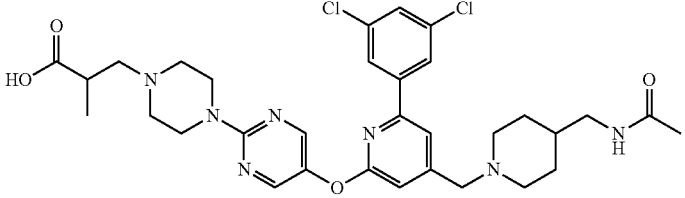
3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-methylpropanoic acid | 1H NMR (400 MHz, CD3OD) δ ppm 8.49 (s, 2H), 8.00 (s, 1H), 7.90 (d, J = 1.5 Hz, 2H), 7.50 (s, 1H), 7.37 (s, 1H), 4.47 (s, 2H), 3.82-3.69 (m, 2H), 3.63-3.54 (m, 4H), 3.35-3.25 (m, 7H), 3.16 (d, J = 6.5 Hz, 4H), 2.03-1.98 (m, 5H), 1.89 (br. s, 1H), 1.78-1.55 (m, 2H), 1.37 (d, J = 7.0 Hz, 3H) | ES-LCMS m/z 656.3, 658.3 [M + H]+. |
| 284 | 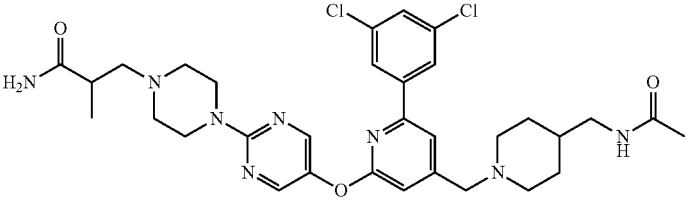 [SMILES: CC(=O)NCC1CCN(Cc2cc(Oc3cnc(N4CCN(CC(C)C(N)=O)CC4)nc3)nc(-c3cc(Cl)cc(Cl)c3)c2)CC1]
3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-methylpropanamide | 1H NMR (400 MHz, CD3OD) δ pm 8.33-8.27 (m, 2H), 7.81 (d, J = 1.8 Hz, 2H), 7.64 (s, 1H), 7.43 (t, J =1.8 Hz, 1H), 7.04 (s, 1H), 3.86-3.80 (m, 4H), 3.64 (s, 2H), 3.08 (d, J = 6.6 Hz, 2H), 2.96 (d, J = 11.5 Hz, 2H), 2.74-2.62 (m, 4H), 2.58-2.49 (m, 2H), 2.32 (d, J = 7.5 Hz, 1H), 2.12 (t, J = 11.0 Hz, 2H), 1.93 (s, 3H), 1.73 (d, J = 12.3 Hz, 2H), 1.53 (d, J = 11.0 Hz, 1H), 1.36-1.28 (m, 2H), 1.13 (d, J = 6.6 Hz, 3H) | ES-LCMS m/z 655.1, 657.1 [M + H]+. |
| 285 | 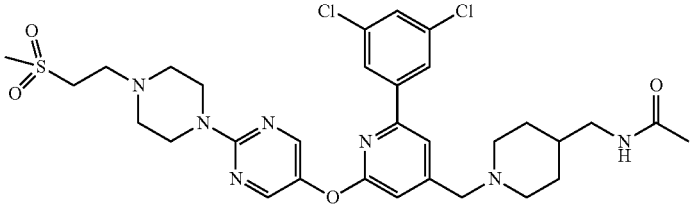 [SMILES: CC(=O)NCC1CCN(Cc2cc(Oc3cnc(N4CCN(CCS(C)(=O)=O)CC4)nc3)nc(-c3cc(Cl)cc(Cl)c3)c2)CC1]
N-((1-((2-(3,5-dichlorophenyl)-6-((2-(4-(2-(methylsulfonyl)ethyl)piper-azin-1-yl)pyrimidin-5-yl)oxy)pyridin-4-yl)methyl)piperidin-4-yl)methyl)acetamide | 1H NMR (400 MHz, CD3OD) δ ppm 8.47 (s, 2H), 7.94 (s, 1H), 7.87 (d, J = 1.8 Hz, 2H), 7.49 (d, J = 1.8 Hz, 1H), 7.33 (s, 1H), 4.44 (s, 2H), 3.87-3.68 (m, 6H), 3.59 (d, J = 12.3 Hz, 3H), 3.40-3.31 (m, 5H), 3.17-3.03 (m, 7H), 2.05-1.92 (m, 5H), 1.86 (br. s, 1H), 1.67-1.52 (m, 2H) | ES-LCMS m/z 676.2, 678.2 [M + H]+. |
| 286 | 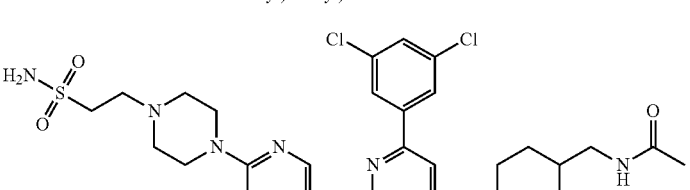
N-((1-((2-(3,5-dichlorophenyl)-6-((2-(4-(2-sulfamoylethyl)piperazin-1-yl)pyrimidin-5-yl)oxy)pyridin-4-yl)methyl)piperidin-4-yl)methyl)acetamide | 1H NMR (400 MHz, CD3OD) δ ppm 8.34 (s, 2H), 7.84 (d, J = 1.5 Hz, 2H), 7.67 (s, 1H), 7.46 (s, 1H), 7.07 (s, 1H), 3.92-3.86 (m, 4H), 3.66 (s, 2H), 3.39-3.34 (m, 2H), 3.10 (d, J = 6.5 Hz, 2H), 3.01-2.88 (m, 4H), 2.65 (t, J = 5.0 Hz, 4H), 2.14 (t, J = 11.0 Hz, 2H), 1.96 (s, 3H), 1.76 (d, J = 12.0 Hz, 2H), 1.57 (br. s, 1H), 1.36 (br. s, 2H) | ES-LCMS m/z 677.2, 679.2 [M + H]+. |

TABLE 14-continued

| Example | Structure/Name | ¹H NMR | LCMS |
| --- | --- | --- | --- |
| 287 | 2-(4-(5-((4-((4-(acetamidomethyl)piperidin-1-yl)methyl)-6-(3,5-dichlorophenyl)pyridin-2-yl)oxy)pyridin-2-yl)piperazin-1-yl)ethanesulfonic acid | ¹H NMR (400 MHz, CD$_3$OD) (δ ppm 8.29-8.20 (m, 2H), 8.00 (s, 1H), 7.88 (d, J = 1.8 Hz, 2H), 7.64-7.60 (m, 1H), 7.50 (t, J = 1.8 Hz, 1H), 7.42 (s, 1H), 4.47 (s, 2H), 3.96-3.52 (m, 10H), 3.41-3.31 (m, 4H), 3.20-3.06 (m, 4H), 2.03-1.94 (m, 5H), 1.87 (br. s, 1H), 1.70-1.56 (m, 2H) | ES-LCMS m/z 677.3, 679.2 [M + H]⁺. |
| 288 | 2-((4-(5-((4-((4-(acetamidomethyl)piperidin-1-yl)methyl)-6-(3,5-dichlorophenyl)pyridin-2-yl)oxy)pyridin-2-yl)piperazin-1-yl)methyl)butanoic acid | ¹H NMR (400 MHz, CD³OD) δ ppm 8.17 (d, J = 2.6 Hz, 1H), 7.97-7.83 (m, 3H), 7.80 (s., 1H), 7.50 (s, 1H), 7.30 (s, 1H), 7.25 (d, J = 8.8 Hz, 1H), 4.61-4.28 (m, 4H), 3.97-3.36 (m, 10H), 3.21-2.87 (m, 5H), 2.09-1.91 (m, 5H), 1.79 (qd, J = 7.5, 15.0 Hz, 3H), 1.65-1.50 (m, 2H), 1.11-0.95 (m, 3H) | ES-LCMS m/z 669.3, 671.3 [M + H]⁺. |
| 289 | N-((1-((2-(3,5-dichlorophenyl)-6-((6-(4-(2-sulfamoylethyl)piperazin-1-yl)pyridin-3-yl)oxy)pyridin-4-yl)methyl)piperidin-4-yl)methyl)acetamide | ¹H NMR (400 MHz, CD³OD) δ ppm 8.11 (d, J = 2.6 Hz, 1H), 7.92 (dd, J = 2.4, 9.5 Hz, 1H), 7.85 (s, 1H), 7.78 (d, J +32 1.8 Hz, 2H), 7.42 (s, 1H), 7.34 (d, J = 9.3 Hz, 1H), 7.26 (s, 1H), 4.35 (s, 2H), 3.90 (br. s, 4H), 3.67-3.45 (m, 9H), 3.25 (br. s, 1H), 3.09-2.95 (m, 4H), 1.94-1.83 (m, 5H), 1.76 (br. s, 1H), 1.56-1.43 (m, 2H) | ES-LCMS m/z 676.3, 678.2 [M + H]⁺. |
| 290 | 1-((1-((2-(3,5-dichlorophenyl)-6-((6-(4-(2-(methylsulfonyl)ethyl)piperazin-1-yl)pyridin-3-yl)oxy)pyridin-4-yl)methyl)piperidin-4-yl)methyl)-3-methylurea | ¹H NMR (400 MHz, CD³OD) δ ppm 8.23 d, J = 2.6 Hz 1H), 8.14 (dd, J = 2.2, 9.7 Hz, 1H), 7.97 (s, 1H), 7.88 (d, J = 1.8 Hz, 2H), 7.57-7.48 (m, 2H), 7.43-7.37 (m, 1H), 4.50-4.41 (m, 2H), 4.28-3.99 (m, 4H), 3.81 (dd, J = 3.7, 10.8 Hz, 5H), 3.72-3.57 (m, 5H), 3.19-2.95 (m, 7H), 2.78-2.62 (m, 3H), 1.98 (d, J = 13.7 Hz, 2H), 1.82 (br. s, 1H), 1.66-1.52 (m, 2H) | ES-LCMS m/z 690.3, 692.3 [M + H]⁺. |

TABLE 14-continued

| Example | Structure/Name | ¹H NMR | LCMS |
|---|---|---|---|
| 291 | 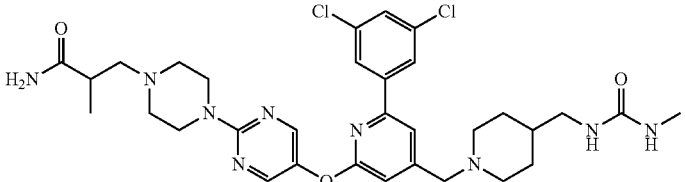<br>3-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)-2-methylpropanamide | ¹H NMR (400 MHz, CD³OD) δ ppm 8.48 (s, 2H), 7.95 (s, 1H), 7.89 (d, J = 2.0 Hz, 2H), 7.52 (s, 1H), 7.40-7.29 (m, 1H), 4.46 (s, 2H), 3.83-3.43 (m, 7H), 3.32-3.03 (m, 10H), 2.77-2.67 (m, 3H), 2.01 (d, J = 14.1 Hz, 2H), 1.84 (br. s, 1H), 1.65-1.50 (m, 2H), 1.32 (d, J = 7.0 Hz, 3H) | ES-LCMS m/z 670.3, 672.3 [M + H]⁺. |
| 292 | 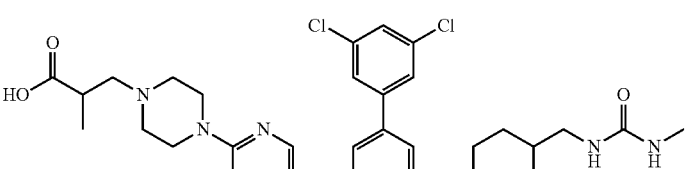<br>3-(4-(5-((3',5'-dichloro-5-((4-((3-methylureido)methyl)piperidin-1-yl)methyl)-[1,1'-biphenyl]-3-yl)oxy)pyrimidin-2-yl)piperazin-1-yl)-2-methylpropanoic acid | ¹H NMR (400 MHz, CD₃OD) δ ppm 8.40 (s, 2H), 7.66 (d, J = 1.5 Hz, 2H), 7.57 (s, 1H), 7.52 (s, 1H), 7.40 (s, 1H), 7.31 (br. s, 1H), 4.35 (s, 2H), 3.71 (br. s, 2H), 3.61 (dd, J = 9.8, 13.3 Hz, 2H), 3.53 (d, J = 11.0 Hz, 3H), 3.40-3.34 (m, 2H), 3.31-3.21 (m, 4H), 3.13 (br. s, 1H), 3.08 (d, J = 6.5 Hz, 2H), 3.04-2.99 (m, 1H), 2.74-2.68 (m, 3H), 1.98 (d, J = 13.6 Hz, 2H), 1.80 (br. s, 1H), 1.58-1.47 (m, 2H), 1.36 (d, J = 7.5 Hz, 3H) | ES-LCMS m/z 670.3, 672.3 [M + H]⁺. |
| 293 | 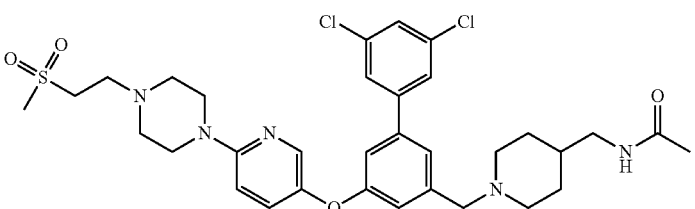<br>N-((1-((3',5'-dichloro-5-((6-(4-(2-(methylsulfonyl)ethyl)piper-1-yl)pyridin-3-yl)oxy)-[1,1'-biphenyl]-3-yl)methyl)piperidin-4-yl)methyl)acetamide | ¹H NMR (400 MHz, CD₃OD) δ ppm 8.05 (d, J = 2.65 Hz, 1H), 7.90 (dd, J = 9.48, 2.87 Hz, 1H), 7.64 (d, J = 1.76 Hz, 2H), 7.57 (s, 1H), 7.50 (s, 1H), 7.45-7.40 (m, 2H), 7.38 (s, 1H), 4.33 (s, 2H), 3.97 (br. s, 4H), 3.82-3.75 (m, 4H), 3.63 (br. s, 4H), 3.50 (d, J = 12.35 Hz, 2H), 3.13 (s, 3H), 3.09 (d, J = 6.62 Hz, 2H), 3.01 (t, J = 12.13 Hz, 2H), 1.99-1.91 (m, 5H), 1.80 (br. s, 1H), 1.59-1.46 (m, 2H) | ES-LCMS m/z 674.3, 676.3 [M + H]⁺. |
| 294 | 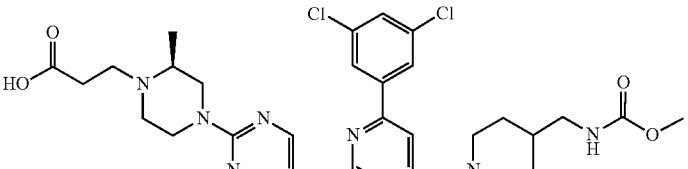<br>(S)-3-(4-(5-((6-(3,5-dichlorophenyl)-4-((4-(((methoxycarbonyl)amino)methyl)piperidin-1-yl)methyl)pyridin-2-yl)oxy)pyrimidin-2-yl)-2-methylpiperazin-1-yl)propanoic acid | ¹H NMR (400 MHz, CD₃OD) δ ppm 8.48-8.42 (m, 2H), 7.96 (s, 1H), 7.86 (d, J = 1.3 Hz, 2H), 7.47 (s, 1H), 7.34 (s, 1H), 4.87 (m, 1H), 4.83-4.67 (m, 1H), 4.45 (s, 2H), 3.86-3.72 (m, 2H), 3.70-3.38 (m, 10H), 3.25-3.00 (m, 4H), 2.95-2.90 (m, 2H), 1.97 (d, J = 13.7 Hz, 2H), 1.83 (d, J = 3.5 Hz, 1H), 1.64-1.52 (m, 4H), 1.42 (d, J = 6.2 Hz, 1H) | ES-LCMS m/z 672.3, 674.4 [M + H]⁺. |

TABLE 14-continued

| Example | Structure/Name | $^1$H NMR | LCMS |
|---|---|---|---|
| 295 | 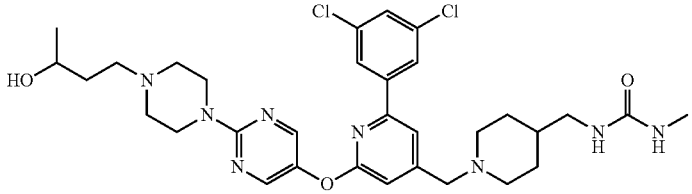 [SMILES: CNC(=O)NCC1CCN(Cc2cc(Oc3cnc(N4CCN(CCC(C)O)CC4)nc3)nc(-c3cc(Cl)cc(Cl)c3)c2)CC1]

1-((1-((2-(3,5-dichlorophenyl)-6-((2-(4-(3-hydroxybutyl)piperazin-1-yl)pyrimidin-5-yl)oxy)pyridin-4-yl)methyl)piperidin-4-yl)methyl)-3-methylurea | $^1$H NMR (400 MHz, D$_2$O) δ ppm 8.34 (s, 2H), 7.51 (s, 1H), 7.46 (s, 2H), 7.23 (s, 1H), 7.08 (s, 1H), 4.59 (d, J = 14.6 Hz, 2H), 4.29 (s, 2H), 3.95-3.80 (m, 1H), 3.65 (d, J = 11.0 Hz, 2H), 3.49 (d, J = 11.5 Hz, 2H), 3.39-3.21 (m, 4H), 3.12-2.91 (m, 6H), 2.58 (s, 3H), 1.99-1.79 (m, 4H), 1.73 (br.s., 1H), 1.51-1.29 (m, 2H), 1.17 (d, J = 6.0 Hz, 3H) | LC-MS m/z 657.3, 659.3 [M + H]$^+$. |
| 296 | 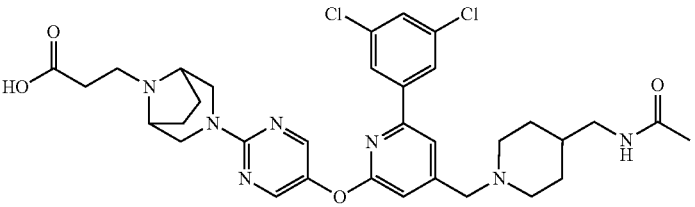 [SMILES: CC(=O)NCC1CCN(Cc2cc(Oc3cnc(N4CC5CCC(C4)N5CCC(=O)O)nc3)nc(-c3cc(Cl)cc(Cl)c3)c2)CC1]

3-(3-(5-((4-((4-(acetamidomethyl)piperidin-1-yl)methyl)-6-(3,5-dichlorophenyl)pyridin-2-yl)oxy)pyrimidin-2-yl)-3,8-diazabicyclo[3.2.1]octan-8-yl)propanoic acid | $^1$H NMR (400 MHz, CD$_3$OD) δ ppm 8.42 (s, 2H), 7.84 (d, J = 2.0 Hz, 2H), 7.69 (s, 1H), 7.47 (t, J = 2.0 Hz, 1H), 7.10 (s, 1H), 4.75 (d, J = 12.0 Hz, 2H), 4.15 (br s, 2H), 3.67 (s, 2H), 3.52-3.41 (m, 2H), 3.31-3.27 (m, 2H), 3.16-3.09 (m, 2H), 2.98 (br d, J = 12.0 Hz, 2H), 2.65 (t, J = 6.5 Hz, 2H), 2.33-2.25 (m, 2H), 2.19-2.09 (m, 2H), 2.06-2.00 (m, 2H), 1.96 (s, 3H), 1.76 (d, J = 12.0 Hz, 2H), 1.61-1.50 (m, 1H), 1.43-1.30 (m, 2H) | ES-LCMS m/z 668.3, 670.3 [M + H]$^+$. |
| 297 | 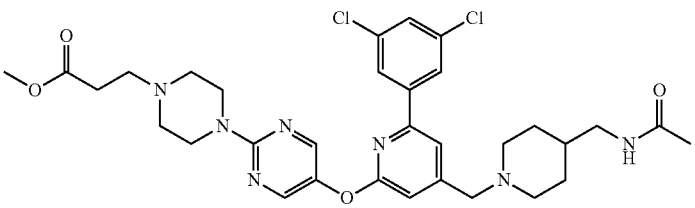 [SMILES: COC(=O)CCN1CCN(c2ncc(Oc3cc(CN4CCC(CNC(C)=O)CC4)cc(-c4cc(Cl)cc(Cl)c4)n3)cn2)CC1]

methyl 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoate | $^1$H NMR (400 MHz, CDCl$_3$) δ ppm 8.27 (s, 2H), 7.71 (d, J = 1.98 Hz, 2H), 7.39 (s, 1H), 7.32 (t, J = 1.87 Hz, 1H), 6.87 (s, 1H), 5.51 (s, 1H), 3.89-3.76 (m, 4H), 3.69 (s, 3H), 3.50 (s, 2H), 3.15 (t, J = 6.39 Hz, 2H), 2.87 (d, J = 11.47 Hz, 2H), 2.78-2.67 (m, 2H), 2.61-2.49 (m, 6H), 2.06-1.94 (m, 5H), 1.68 (d, J = 11.03 Hz, 2H), 1.53 (s, 1H), 1.38-1.19 (m, 2H) | ES-LCMS m/z 656.3, 658.3 [M + H]$^+$. |

Example 298: (R)-2-(1-((2-(3,5-Dichlorophenyl)-6-((2-(4-(2-hydroxypropyl)piperazin-1-yl)pyrimidin-5-yl)oxy)pyridin-4-yl)methyl)piperidin-4-yl)acetic acid, 4 hydrochloride Step 1: (R)-Methyl 2-(1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)acetate

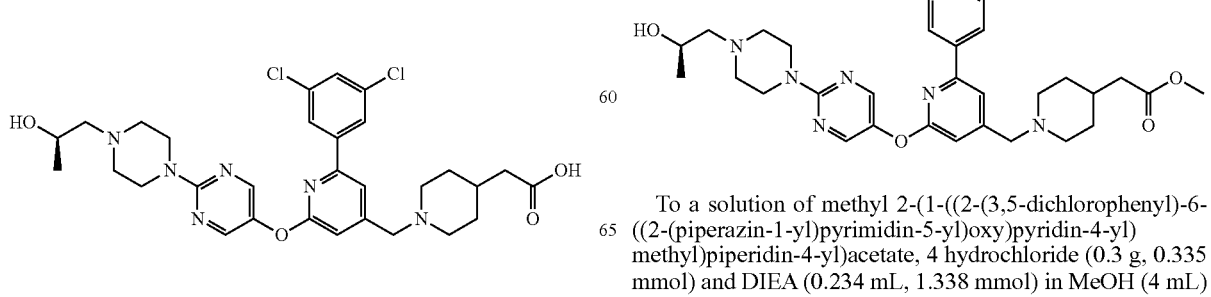

To a solution of methyl 2-(1-((2-(3,5-dichlorophenyl)-6-((2-(piperazin-1-yl)pyrimidin-5-yl)oxy)pyridin-4-yl)methyl)piperidin-4-yl)acetate, 4 hydrochloride (0.3 g, 0.335 mmol) and DIEA (0.234 mL, 1.338 mmol) in MeOH (4 mL)

was added (R)-2-methyloxirane (0.039 g, 0.669 mmol). The reaction mixture was stirred at 25° C. for 8 h then concentrated to yield a brown solid of (R)-methyl 2-(1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)acetate (0.25 g, 0.291 mmol, 87.0% yield): $^1$H NMR (400 MHz, CDCl$_3$) δ ppm 8.36-8.26 (m, 2H), 7.77-7.68 (m, 2H), 7.46 (br. s, 1H), 7.32 (s, 1H), 6.92 (s, 1H), 3.68-3.63 (m, 6H), 3.11-3.05 (m, 4H), 2.90 (d, J=10.6 Hz, 4H), 2.70-2.47 (m, 6H), 2.16-2.05 (m, 3H), 1.54 (s, 5H), 1.17 (d, J=6.2 Hz, 2H); ES-LCMS m/z 629.2, 631.2 [M+H]$^+$.

Step 2: (R)-2-(1-((2-(3,5-Dichlorophenyl)-6-((2-(4-(2-hydroxypropyl)piperazin-1-yl)pyrimidin-5-yl)oxy)pyridin-4-yl)methyl)piperidin-4-yl)acetic acid, 4 hydrochloride

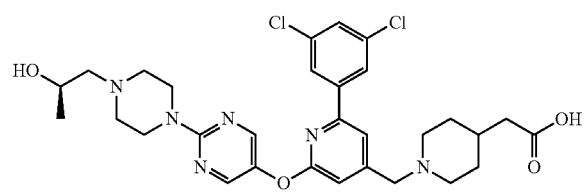 [SMILES: C[C@@H](O)CN1CCN(c2ncc(Oc3cc(CN4CCC(CC(=O)O)CC4)cc(-c4cc(Cl)cc(Cl)c4)n3)cn2)CC1]

To a solution of (R)-methyl 2-(1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)acetate (0.25 g, 0.291 mmol) in THF (10 mL) and H$_2$O (10.00 mL) was added LiOH·H$_2$O (0.021 g, 0.872 mmol). The reaction mixture was stirred at 30° C. for 6 h then concentrated to yield the crude product which was purified by preparative HPLC (MeCN/H$_2$O as eluents, acidic condition) and lyophilized to yield a white solid of (R)-2-(1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)acetic acid, 4 hydrochloride (117.52 mg, 0.154 mmol, 53.0% yield): $^1$H NMR (400 MHz, CD$_3$OD) δ ppm 8.47-8.44 (m, 2H), 7.93 (s, 1H), 7.87 (d, J=1.8 Hz, 2H), 7.49 (t, J=1.9 Hz, 1H), 7.33 (s, 1H), 4.80 (m, 2H), 4.43 (s, 2H), 4.35-4.17 (m, 1H), 3.72 (t, J=13.0 Hz, 2H), 3.61-3.44 (m, 4H), 3.27-3.07 (m, 6H), 2.32 (d, J=6.6 Hz, 2H), 2.19-1.97 (m, 3H), 1.71-1.58 (m, 2H), 1.25 (d, J=6.2 Hz, 3H); ES-LCMS m/z 615.2; 617.2 [M+H]$^+$.

Examples 299-317 (Table 15) were prepared by procedures analogous to those described for example 298.

TABLE 15

| Example | Structure/Name | $^1$H NMR | LCMS |
|---|---|---|---|
| 299 | (R)-2-(1-((2-(3,5-dichlorophenyl)-6-((6-(4-(2-hydroxypropyl)piperazin-1-yl)pyridin-3-yl)oxy)pyridin-4-yl)methyl)piperidin-4-yl)acetic acid | $^1$H NMR (400 MHz, CD$_3$OD) δ ppm 8.31-8.23 (m, 2H), 8.07 (s, 1H), 7.91 (d, J = 1.0 Hz, 2H), 7.67 (d, J = 10.0 Hz, 1H), 7.52 (s, 1H), 7.47 (s, 1H), 4.56-4.19 (m, 5H), 3.89 (br. s, 4H), 3.67-3.45 (m, 4H), 3.20 (d, J = 7.5 Hz, 2H), 2.78-2.50 (m, 2H), 2.40-2.27 (m, 2H), 2.17-2.04 (m, 3H), 1.73 (q, J = 12.0 Hz, 2H), 1.29 (d, J = 6.0 Hz, 3H) | ES-LCMS m/z 614.2, 616.3 [M + H]$^+$. |
| 300 | 2-(1-((2-(3,5-dichlorophenyl)-6-((6-(4-(2-hydroxyethyl)piperazin-1-yl)pyridin-3-yl)oxy)pyridin-4-yl)methyl)piperidin-4-yl)acetic acid | $^1$H NMR (400 MHz, CD$_3$OD) δ ppm 8.04 (d, J = 2.6 Hz, 1H), 7.79 (d, J = 2.2 Hz, 2H), 7.61 (s, 1H), 7.50 (dd, J = 2.9, 9.0 Hz, 1H), 7.39 (t, J = 1.8 Hz, 1H), 6.98-6.93 (m, 2H), 3.79 (t, J = 5.7 Hz, 2H), 3.71 (s, 2H), 3.67-3.61 (m, 4H), 3.00 (d, J = 11.9 Hz, 2H), 2.93-2.88 (m, 4H), 2.80 (t, J = 5.7 Hz, 2H), 2.29-2.16 (m, 4H), 1.79 (d, J = 12.8 Hz, 3H), 1.38 (m, 2H) | ES-LCMS m/z 600.3, 602.3 [M + H]$^+$. |

| Example | Structure/Name | ¹H NMR | LCMS |
|---|---|---|---|
| 301 | 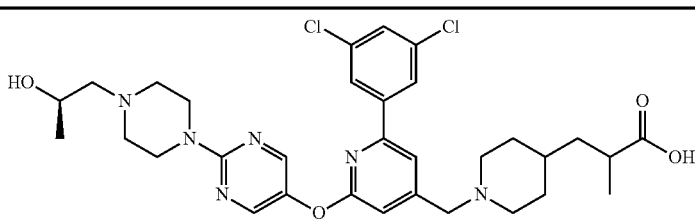<br>3-(1-((2-(3,5-dichlorophenyl)-6-((2-(4-((R)-2-hydroxypropyl)piperazin-1-yl)pyrimidin-5-yl)oxy)pyridin-4-yl)methyl)piperidin-4-yl)-2-methylpropanoic acid | ¹H NMR (400 MHz, CD₃OD) δ ppm 8.45 (s, 2H), 8.00 (s, 1H), 7.85 (d, J = 1.3 Hz, 2H), 7.42 (s, 1H), 7.36 (s, 1H), 4.88-4.76 (m, 2H), 4.42 (s, 2H), 4.33-4.08 (m, 1H), 3.73 (d, J = 12.3 Hz, 2H), 3.64-3.40 (m, 4H), 3.29-3.16 (m, 3H), 3.16-2.98 (m, 3H), 2.61-2.51 (m, 1H), 2.09-1.80 (m, 2H), 1.77-1.55 (m, 4H), 1.38-1.30 (m, 1H), 1.25 (d, J = 5.7 Hz, 3H), 1.14 (d, J = 6.6 Hz, 3H) | ES-LCMS m/z 643.3, 645.3 [M + H]⁺. |
| 302 | 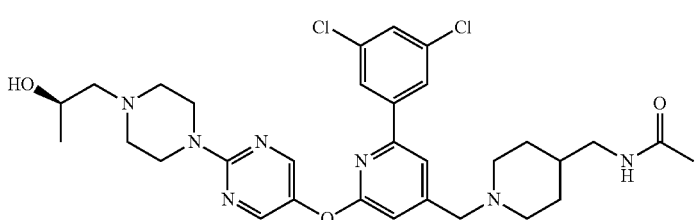<br>(R)-N-((14(2-(3,5-dichlorophenyl)-6-((2-(4-(2-hydroxypropyl)piperazin-1-yl)pyrimidin-5-yl)oxy)pyridin-4-yl)methyl)piperidin-4-yl)methyl)acetamide | ¹H NMR (400 MHz, CD₃OD) δ ppm 8.47 (s, 2H), 7.94 (s, 1H), 7.88 (d, J = 1.8 Hz, 2H), 7.53-7.48 (m, 1H), 7.33 (s, 1H), 4.86-4.76 (m, 2H), 4.55-4.40 (m, 2H), 4.30-4.20 (m, 1H), 3.79-3.67 (m, 2H), 3.63-3.46 (m, 4H), 3.27-3.18 (m, 3H), 3.17-3.03 (m, 5H), 2.00-1.95 (m, 5H), 1.85 (br. s, 1H), 1.67-1.52 (m, 2H), 1.25 (d, J = 6.2 Hz, 3H) | ES-LCMS m/z 628.3, 630.3 [M + H]⁺. |
| 303 | 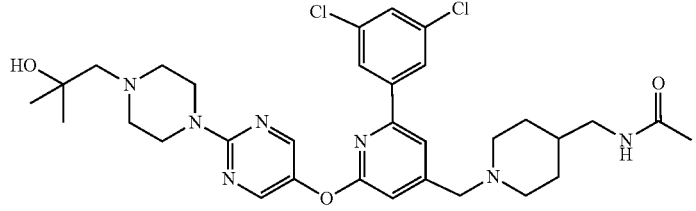 [SMILES: CC(=O)NCC1CCN(Cc2cc(Oc3cnc(N4CCN(CC(C)(C)O)CC4)nc3)nc(-c3cc(Cl)cc(Cl)c3)c2)CC1]<br>N-((1-((2-(3,5-dichlorophenyl)-6-((2-(4-(2-hydroxy-2-methylpropyl)piperazin-1-yl)pyrimidin-5-yl)oxy)pyridin-4-yl)methyl)piperidin-4-yl)methyl)acetamide | ¹H NMR (400 MHz, CD₃OD) δ ppm 8.47 (s, 2H), 7.94 (s, 1H), 7.88 (d, J = 1.8 Hz, 2H), 7.51 (d, J = 1.8 Hz, 1H), 7.33 (s, 1H), 4.66 (d, J = 14.6 Hz, 2H), 4.44 (s, 2H), 3.83-3.69 (m, 5H), 3.59 (d, J = 11.9 Hz, 3H), 3.28 (s, 2H), 3.17-3.04 (m, 4H), 2.03-1.95 (m, 5H), 1.86 (br. s, 1H), 1.64-1.55 (m, 2H), 1.39 (s, 6H) | ES-LCMS m/z 642.3, 644.3 [M + H]⁺. |
| 304 | 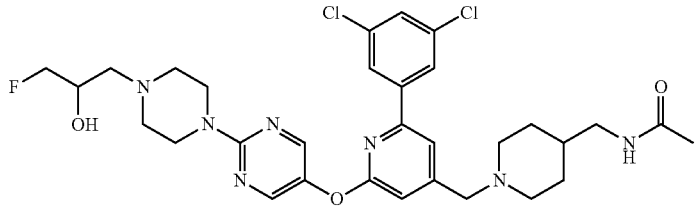 [SMILES: CC(=O)NCC1CCN(Cc2cc(Oc3cnc(N4CCN(CC(O)CF)CC4)nc3)nc(-c3cc(Cl)cc(Cl)c3)c2)CC1]<br>N-((1-((2-(3,5-dichlorophenyl)-6-((2-(4-(3-fluoro-2-hydroxypropyl)piperazin-1-yl)pyrimidin-5-yl)oxy)pyridin-4-yl)methyl)piperidin-4-yl)methyl)acetamide | ¹H NMR (400 MHz, CD₃OD) δ ppm 8.46 (s, 2H), 7.91 (s, 1H), 7.87 (d, J = 1.8 Hz, 2H), 7.51 (s, 1H), 7.32 (s, 1H), 4.55-4.48 (m, 1H), 4.43 (s, 2H), 4.40-4.27 (m, 2H), 3.74 (d, J = 11.5 Hz, 2H), 3.64-3.42 (m, 5H), 3.39-3.32 (m, 4H), 3.28-3.18 (m, 1H), 3.16-3.03 (m, 4H), 2.02-1.92 (m, 5H), 1.84 (br. s, 1H), 1.63-1.49 (m, 2H) | ES-LCMS m/z 646.3, 648.3 [M + H]⁺. |

TABLE 15-continued

| Example | Structure/Name | $^1$H NMR | LCMS |
|---|---|---|---|
| 305 | 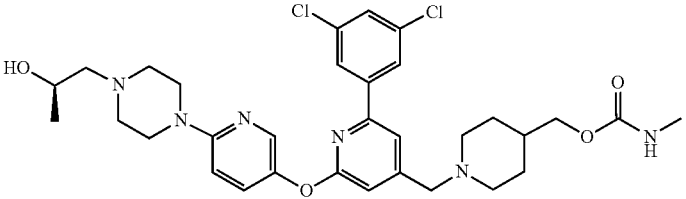 [SMILES: CNC(=O)OCC1CCN(Cc2cc(Oc3ccc(N4CCN(C[C@@H](C)O)CC4)nc3)nc(-c3cc(Cl)cc(Cl)c3)c2)CC1]<br>(R)-(1-((2-(3,5-dichlorophenyl)-6-((6-(4-(2-hydroxypropyl)piperazin-1-yl)pyridin-3-yl)oxy)pyridin-4-yl)methyl)piperidin-4-yl)methyl methylcarbamate | $^1$H NMR (400 MHz, CD$_3$OD) δ ppm 8.01 (s, 1H), 7.75 (s, 2H), 7.53 (s, 1H), 7.46-7.43 (m, 1H), 7.35 (s, 1H), 6.90 (s, 1H), 6.88-6.86 (m, 1H), 3.97-3.88 (m, 3H), 3.52 (s, 6H), 2.89 (d, J = 10.8 Hz, 2H), 2.68-2.63 (m, 7H), 2.61-2.60 (m, 2H), 2.03 (m, 2H), 1.67-1.70 (m, 3H), 1.17 (m, 2H), 1.15 (d, J = 6.0 Hz, 3H) | ES-LCMS m/z 643.3, 645.3 [M + H]$^+$. |
| 306 | 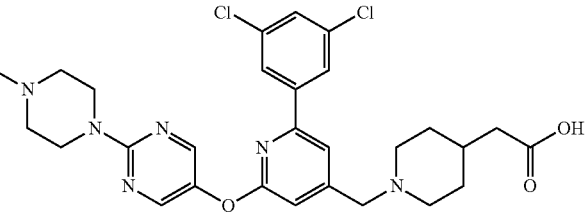<br>2-(1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)acetic acid | $^1$H NMR (400 MHz, D$_2$O) δ ppm 8.31 (br. s, 2H), 7.49 (d, J = 17.6 Hz, 3H), 7.33 (br. s, 1H), 7.04 (br. s, 1H), 4.55 (br. s, 2H), 4.24 (br. s, 2H), 3.85-3.80 (m, 2H), 3.59 (br. s, 2H), 3.46-3.33 (m, 4H), 3.25-3.21 (m, 2H), 3.10 (br. s, 2H), 2.97 (t, J = 12.3 Hz, 2H), 2.22 (d, J = 6.2 Hz, 2H), 1.89 (d, J = 13.7 Hz, 3H), 1.39 (d, J = 12.8 Hz, 2H) | ES-LCMS m/z 601.3, 603.3 [M + H]$^+$. |
| 307 | 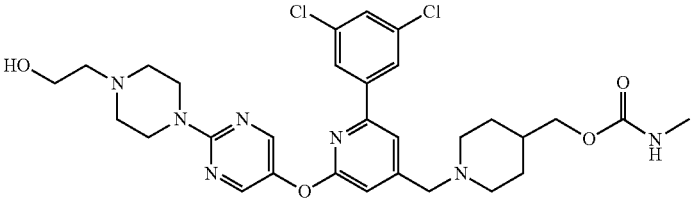 [SMILES: CNC(=O)OCC1CCN(Cc2cc(Oc3cnc(N4CCN(CCO)CC4)nc3)nc(-c3cc(Cl)cc(Cl)c3)c2)CC1]<br>(1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)methyl methylcarbamate | $^1$H NMR (400 MHz, CD$_3$OD) δ ppm 8.33-8.27 (m, 2H), 7.81 (d, J = 1.3 Hz, 2H), 7.64 (s, 1H), 7.43 (s, 1H), 7.03 (s, 1H), 3.90 (d, J = 6.2 Hz, 2H), 3.88-3.83 (m, 4H), 3.73 (t, J = 6.0 Hz, 2H), 3.61 (s, 2H), 2.94 (d, J = 10.6 Hz, 2H), 2.68 (s, 3H), 2.64-2.56 (m, 6H), 2.10 (t, J = 11.5 Hz, 2H), 1.73 (d, J = 12.8 Hz, 2H), 1.66 (br. s, 1H), 1.44-1.35 (m, 2H) | ES-LCMS m/z 630.2, 632.3 [M + H]$^+$. |
| 308 | 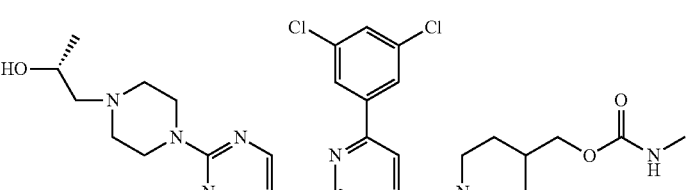<br>(R)-(1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)methyl methylcarbamate | $^1$H NMR (400 MHz, CD$_3$OD) δ ppm 8.48 (s, 2H), 8.00 (s, 1H), 7.87 (d, J = 1.8 Hz, 2H), 7.47 (t, J = 1.8 Hz, 1H), 7.36 (s, 1H), 4.88-4.78 (m, 2H), 4.46 (s, 2H), 4.31-4.22 (m, 1H), 3.95 (d, J = 5.3 Hz, 2H), 3.74 (t, J = 10.8 Hz, 2H), 3.65-3.43 (m, 4H), 3.30-3.06 (m, 6H), 2.75-2.65 (m, 3H), 1.99 (d, J = 12.8 Hz, 3H), 1.80-1.65 (m, 2H), 1.25 (d, J = 6.2 Hz, 3H) | ES-LCMS m/z 644.5, 646.5 [M + H]$^+$. |

TABLE 15-continued

| Example | Structure/Name | ¹H NMR | LCMS |
|---|---|---|---|
| 309 | 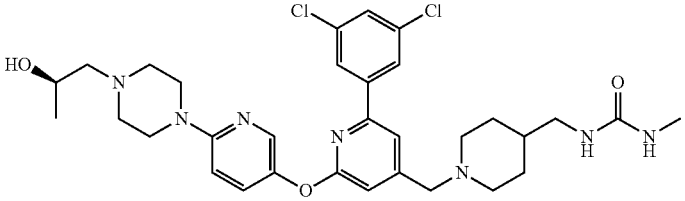 [SMILES: CNC(=O)NCC1CCN(Cc2cc(Oc3ccc(N4CCN(C[C@@H](C)O)CC4)nc3)nc(-c3cc(Cl)cc(Cl)c3)c2)CC1]<br>(R)-1-((1-((2-(3,5-dichlorophenyl)-6-((6-(4-(2-hydroxypropyl)piperazin-1-yl)pyridin-3-yl)oxy)pyridin-4-yl)methyl)piperidin-4-yl)methyl)-3-methylurea | ¹H NMR (400 MHz, CD₃OD) δ ppm 8.25 (d, J = 2.5 Hz, 1H), 8.19 (dd, J = 2.5, 9.5 Hz, 1H), 8.00 (s, 1H), 7.91 (d, J = 1.0 Hz, 2H), 7.60-7.52 (m, 2H), 7.44-7.40 (m, 1H), 4.48 (s, 4H), 4.34-4.24 (m, 1H), 3.93-3.68 (m, 4H), 3.62 (d, J = 12.0 Hz, 2H), 3.46 (br. s, 3H), 3.24-3.05 (m, 5H), 2.76-2.69 (m, 3H), 2.01 (d, J = 13.6 Hz, 2H), 1.85 (br. s, 1H), 1.68-1.54 (m, 2H), 1.29 (d, J = 6.0 Hz, 3H) | ES-LCMS m/z 642.3, 644.3 [M + H]⁺. |
| 310 | 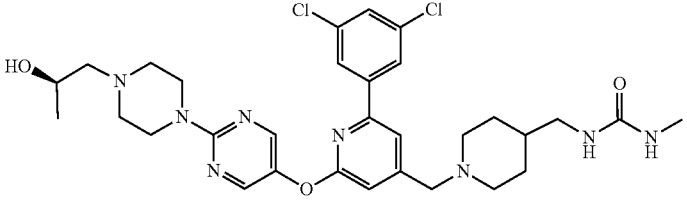 [SMILES: CNC(=O)NCC1CCN(Cc2cc(Oc3cnc(N4CCN(C[C@@H](C)O)CC4)nc3)nc(-c3cc(Cl)cc(Cl)c3)c2)CC1]<br>(R)-1-((1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)methyl)-3-methylurea | ¹H NMR (400 MHz, CD₃OD) δ ppm 8.45 (s, 2H), 7.92 (br. s, 1H), 7.87 (s, 2H), 7.50 (br. s, 1H), 7.32 (br. s, 1H), 4.43 (s, 2H), 4.25 (br. s, 2H), 3.77-3.67 (m, 2H), 3.59 (d, J = 11.9 Hz, 2H), 3.54-3.43 (m, 2H), 3.23 (d, J = 13.2 Hz, 3H), 3.15-3.03 (m, 5H), 2.71-2.65 (m, 3H), 1.98 (d, J = 13.7 Hz, 2H), 1.82-1.80 (m, 1H), 1.57-1.55 (m, 2H), 1.25 (d, J = 6.2 Hz, 3H) | ES-LCMS m/z 643.2 645.2 [M + H]⁺. |
| 311 | 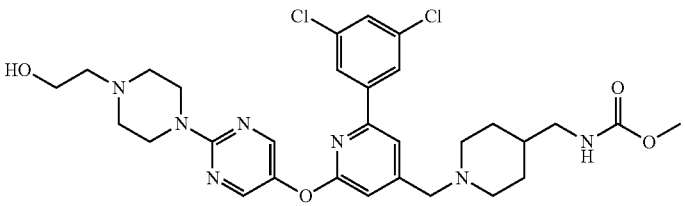 [SMILES: COC(=O)NCC1CCN(Cc2cc(Oc3cnc(N4CCN(CCO)CC4)nc3)nc(-c3cc(Cl)cc(Cl)c3)c2)CC1]<br>methyl ((1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)methyl)carbamate | ¹H NMR (400 MHz, CD₃OD) δ ppm 8.31 (s, 2H), 7.81 (d, J = 1.3 Hz, 2H), 7.63 (s, 1H), 7.42 (s, 1H), 7.03 (s, 1H), 3.88-3.84 (m, 4H), 3.73 (t, J = 6.0 Hz, 2H), 3.61-3.59 (m, 5H), 3.00 (d, J = 6.6 Hz, 2H), 2.93 (d, J = 11.5 Hz, 2H), 2.64-2.57 (m, 6H), 2.07 (t, J = 10.8 Hz, 2H), 1.71 (d, J = 12.3 Hz, 2H), 1.50 (d, J = 3.1 Hz, 1H), 1.33-1.26 (m, 2H) | ES-LCMS m/z 630.3, 632.3 [M + H]⁺. |
| 312 | 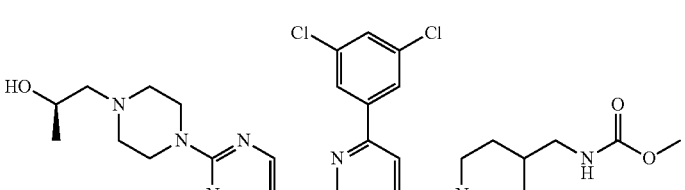<br>(R)-methyl ((1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)methyl)carbamate | ¹H NMR (400 MHz, CD₃OD) δ ppm 8.47 (s, 2H), 7.97 (s, 1H), 7.89 (d, J = 1.0 Hz, 2H), 7.51 (s, 1H), 7.35 (s, 1H), 4.60-4.41 (m, 2H), 4.36-4.21 (m, 1H), 3.82-3.50 (m, 9H), 3.32-3.05 (m, 10H), 2.00 (d, J = 13.6 Hz, 2H), 1.85 (br. s, 1H), 1.70-1.49 (m, 2H), 1.28 (d, J = 6.0 Hz, 3H) | ES-LCMS m/z 644.3, 646.3 [M + H]⁺. |

TABLE 15-continued

| Example | Structure/Name | ¹H NMR | LCMS |
|---|---|---|---|
| 313 | 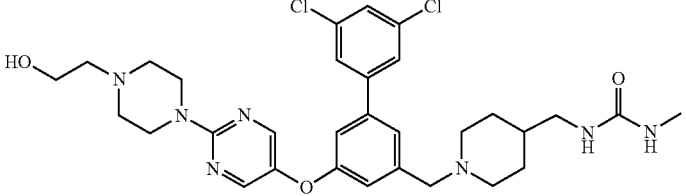 [SMILES: CNC(=O)NCC1CCN(Cc2cc(Oc3cnc(N4CCN(CCO)CC4)nc3)cc(-c3cc(Cl)cc(Cl)c3)c2)CC1]<br>1-((1-((3',5'-dichloro-5-((2-(4-(2-hydroxyethyl)piperazin-1-yl)pyrimidin-5-yl)oxy)-[1,1'-biphenyl]-3-yl)methyl)piperidin-4-yl)methyl)-3-methylurea | ¹H NMR (400 MHz, CD$_3$OD) δ ppm 8.47-8.41 (m, 2H), 7.68 (d, J = 1.5 Hz, 2H), 7.63 (br. s, 1H), 7.50 (s, 1H), 7.43 (s, 1H), 7.38 (br. s, 1H), 4.87 (d, J = 14.6 Hz, 2H), 4.37 (s, 2H), 4.18-4.13 (m, 1H), 3.99-3.96 (m, 1H), 3.74 (d, J = 12.0 Hz, 2H), 3.63-3.46 (m, 4H), 3.45-3.34 (m, 4H), 3.17-3.01 (m, 4H), 2.77 (s, 3H), 1.98 (d, J = 13.6 Hz, 2H), 1.87 (m, 1H), 1.60 (m, 2H) | ES-LCMS m/z 628.3, 630.3 [M + H]⁺. |
| 314 | 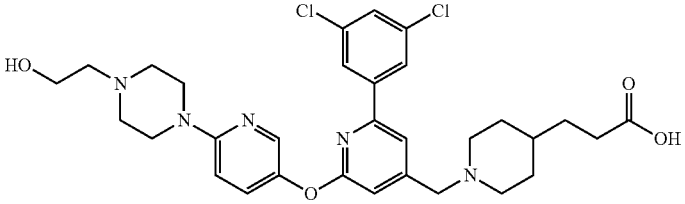 [SMILES: O=C(O)CCC1CCN(Cc2cc(Oc3ccc(N4CCN(CCO)CC4)nc3)nc(-c3cc(Cl)cc(Cl)c3)c2)CC1]<br>3-(1-((2-(3,5-dichlorophenyl)-6-((6-(4-(2-hydroxyethyl)piperazin-1-yl)pyridin-3-yl)oxy)pyridin-4-yl)methyl)piperidin-4-yl)propanoic acid | ¹H NMR (400 MHz, CD$_3$OD) δ ppm 8.24 (d, J = 2.5 Hz, 1H), 8.20-8.10 (m, 1H), 8.00 (s, 1H), 7.91 (d, J = 1.5 Hz, 2H), 7.60-7.49 (m, 2H), 7.42 (s, 1H), 4.47 (s, 2H), 4.14-3.95 (m, 4H), 3.94-3.60 (m, 5H), 3.57-3.34 (m, 5H), 3.13 (t, J = 11.8 Hz, 2H), 2.48-2.31 (m, 2H), 2.03 (m, 2H), 1.85-1.57 (m, 5H) | ES-LCMS m/z 614.2, 616.2 [M + H]⁺. |
| 315 | 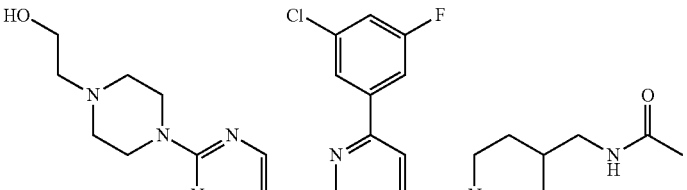<br>N-((1-((2-(3-chloro-5-fluorophenyl)-6-((2-(4-(2-hydroxyethyl)piperazin-1-yl)pyrimidin-5-yl)oxy)pyridin-4-yl)methyl)piperidin-4-yl)methyl)acetamide | ¹H NMR (400 MHz, CD$_3$OD) δ ppm 8.53 (s, 2H), 8.06 (s, 1H), 7.79 (s, 1H), 7.62 (d, J = 9.3 Hz, 1H), 7.40 (s, 1H), 7.22 (d, J = 7.9 Hz, 1H), 4.86 (d, J = 14.6 Hz, 2H), 4.60-4.44 (m, 2H), 4.00-3.93 (m, 2H), 3.77 (d, J = 11.9 Hz, 2H), 3.64-3.53 (m, 4H), 3.42-3.31 (m, 4H), 3.17 (d, J = 5.3 Hz, 4H), 2.04 (s, 3H), 2.02-1.88 (m, 3H), 1.84-1.30 (m, 2H) | ES-LCMS m/z 598.3, 600.2 [M + H]⁺. |
| 316 | 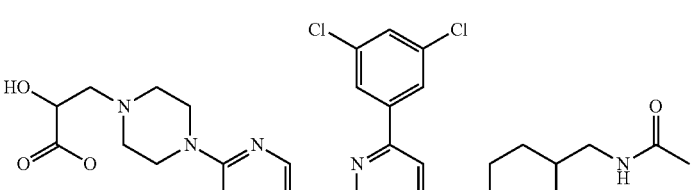<br>3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-hydroxypropanoic acid | ¹H NMR (400 MHz, DMSO-d$_6$) δ ppm 8.58-8.33 (m, 2H), 7.88-7.81 (m, 3H), 7.76 (s, 1H), 7.64 (d, J = 1.8 Hz, 1H), 7.08-6.99 (m, 1H), 4.24-4.06 (m, 1H), 3.83-3.57 (m, 8H), 3.42-3.38 (m, 2H), 2.91 (d, J = 6.2 Hz, 2H), 2.64 (d, J = 7.1 Hz, 6H), 1.78 (s, 4H), 1.62 (d, J = 11.5 Hz, 2H), 1.26-1.09 (m, 2H) | LC-MS m/z 658.3, 660.3 [M + H]⁺. |

TABLE 15-continued

| Example | Structure/Name | ¹H NMR | LCMS |
|---|---|---|---|
| 317 | 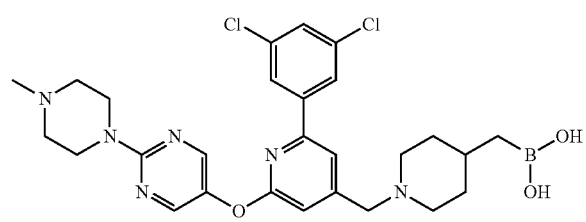<br>(R)-2-((1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)oxy)acetic acid | ¹H NMR (400 MHz, CD$_3$OD) δ 8.51-8.43 (m, 2H), 7.95-7.87 (m, 3H), 7.50 (d, J = 1.8 Hz, 1H), 7.39-7.28 (m, 1H), 4.81 (br s, 2H), 4.47-4.40 (m, 2H), 4.33-4.05 (m, 4H), 3.88-3.41 (m, 8H), 3.28-3.03 (m, 5H), 2.34-2.15 (m, 2H), 2.09-1.83 (m, 2H), 1.25 (d, J = 6.2 Hz, 3H) | ES-LCMS m/z 631.3, 633.3 [M + H]$^+$. |

Example 318: ((1-((2-(3,5-Dichlorophenyl)-6-((2-(4-methylpiperazin-1-yl)pyrimidin-5-yl)oxy)pyridin-4-yl)methyl)piperidin-4-yl)methyl)boronic acid, 4 hydrochloride

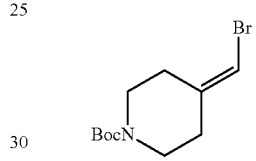

Step 1: tert-Butyl 4-(dibromomethylene)piperidine-1-carboxylate

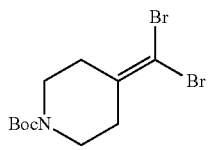

To a mixture of tert-butyl 4-oxopiperidine-1-carboxylate (30 g, 151 mmol) and PPh$_3$ (79 g, 301 mmol) in DCM (800 mL) was added CBr$_4$ (100 g, 301 mmol) at 0° C., the reaction mixture was stirred at 0° C. for 1 h under N$_2$ atmosphere then at 20° C. for 12 h under N$_2$ atmosphere. The mixture was filtered and concentrated. The crude material was purified by flash chromatography (from pure PE to PE/EtOAc=10/1, TLC: PE/EtOAc=5/1, R$_f$=0.7) to yield tert-butyl 4-(dibromomethylene)piperidine-1-carboxylate (10 g, 25.9 mmol, 17.2% yield) as a white solid: ¹H NMR (400 MHz, CD$_3$OD) δ ppm 3.43 (t, J=5.7 Hz, 4H), 2.52-2.46 (m, 4H), 1.47-1.43 (m, 9H); ES-LCMS m/z 299.9, 301.9 [M−t−Bu+H]$^+$.

Step 2: tert-Butyl 4-(bromomethylene)piperidine-1-carboxylate

A mixture of tert-butyl 4-(dibromomethylene)piperidine-1-carboxylate (9.5 g, 24.62 mmol) and ammonium chloride (10.53 g, 197 mmol) in MeOH (200 mL) and THF (100 mL) was stirred at 0° C. for 1 h under N$_2$ atmosphere, Zn (6.44 g, 98 mmol) was added, the reaction mixture was stirred at 20° C. for 12 h under N$_2$ atmosphere. The mixture was filtered and concentrated. The crude material was purified by flash chromatography (from pure PE to PE/EtOAc=10/1, TLC: PE/EtOAc=5/1, R$_f$=0.65) to yield tert-butyl 4-(bromomethylene)piperidine-1-carboxylate (6 g, 19.77 mmol, 80.0% yield) as a pale yellow solid: ¹H NMR (400 MHz, CD$_3$OD) δ ppm 6.12 (s, 1H), 3.45-3.39 (m, 4H), 2.40-2.36 (m, 2H), 2.27-2.24 (m, 2H), 1.45 (s, 9H); ES-LCMS m/z 220.1, 222.1 [M−t−Bu+H]$^+$.

Step 3: tert-Butyl 4-((4,4,5,5-tetramethyl-1,3,2-dioxaborolan-2-yl)methylene)piperidine-1-carboxylate

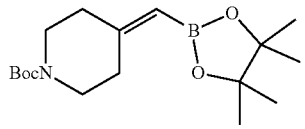 [SMILES: CC(C)(C)OC(=O)N1CCC(=CB2OC(C)(C)C(C)(C)O2)CC1]

A mixture of tert-butyl 4-(bromomethylene)piperidine-1-carboxylate (4 g, 13.18 mmol), 4,4,4',4',5,5,5',5'-octamethyl-2,2'-bi(1,3,2-dioxaborolane) (6.69 g, 26.4 mmol), Ph$_3$P (0.346 g, 1.318 mmol), Pd$_2$(dba)$_3$ (1.207 g, 1.318 mmol) and KOAc (3.88 g, 39.5 mmol) in toluene (120 mL) was stirred at 110° C. for 12 h under N$_2$ atmosphere. The mixture was filtered and concentrated. The crude material was purified by flash chromatography (from pure PE to PE/EtOAc=8/1, TLC: PE/EtOAc=5/1, R$_f$=0.6) to yield tert-butyl 4-((4,4,5, 5-tetramethyl-1,3,2-dioxaborolan-2-yl)methylene)piperidine-1-carboxylate (3 g, 7.05 mmol, 53.5% yield) as a pale yellow solid: ¹H NMR (400 MHz, CD₃OD) δ ppm 5.09 (s, 1H), 3.48-3.37 (m, 4H), 2.63-2.56 (m, 2H), 2.24 (t, J=5.4 Hz, 2H), 1.45 (s, 9H), 1.23 (s, 12H); ES-LCMS m/z 224.1 [M−Boc+H]⁺.

Step 4: tert-Butyl 4-((4,4,5,5-tetramethyl-1,3,2-dioxaborolan-2-yl)methyl)piperidine-1-carboxylate

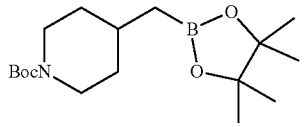 [SMILES: CC(C)(C)OC(=O)N1CCC(CB2OC(C)(C)C(C)(C)O2)CC1]

A mixture of tert-butyl 4-((4,4,5,5-tetramethyl-1,3,2-dioxaborolan-2-yl)methylene)piperidine-1-carboxylate (2.9 g, 6.82 mmol) in MeOH (40 mL) was added Pd/C (10 wt %, 1.5 g, 1.41 mmol). The mixture was stirred at 20° C. for 15 min under H₂ atmosphere (15 psi). The solid was filtered off and solvent was concentrated to afford crude product of tert-butyl 4-((4,4,5,5-tetramethyl-1,3,2-dioxaborolan-2-yl)methyl)piperidine-1-carboxylate (2.5 g, 5.76 mmol, 85.0% yield) as pale yellow oil: ¹H NMR (400 MHz, CD₃OD) δ ppm 2.84-2.61 (m, 4H), 1.71-1.52 (m, 4H), 1.43 (s, 9H), 1.22 (s, 12H), 1.12-1.06 (m, 1H), 0.71 (d, J=6.6 Hz, 2H); ES-LCMS m/z 226.1 [M−Boc+H]⁺.

Step 5: 4-((4,4,5,5-Tetramethyl-1,3,2-dioxaborolan-2-yl)methyl)piperidine, trifluoroacetic acid salt

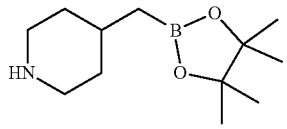 [SMILES: CC1(C)OB(CC2CCNCC2)OC1(C)C]

tert-Butyl 4-((4,4,5,5-tetramethyl-1,3,2-dioxaborolan-2-yl)methyl)piperidine-1-carboxylate (2.4 g, 5.53 mmol) was dissolved in TFA (4 mL, 51.9 mmol) and DCM (16 mL). The mixture was stirred at 20° C. for 1 h. The reaction mixture was concentrated to yield 4-((4,4,5,5-tetramethyl-1,3,2-dioxaborolan-2-yl)methyl)piperidine, trifluoroacetic acid (2.3 g, 4.75 mmol, 86.0% yield) as pale yellow oil: ¹H NMR (400 MHz, CD₃OD) δ ppm 2.99-2.91 (m, 2H), 2.84-2.60 (m, 2H), 1.93 (d, J=14.1 Hz, 2H), 1.78 (m, J=3.7, 7.3, 11.1 Hz, 1H), 1.44-1.32 (m, 2H), 1.22-1.18 (m, 12H), 0.79 (d, J=7.1 Hz, 2H); ES-LCMS m/z 226.1 [M+H]⁺.

Step 6: 5-((6-(3,5-Dichlorophenyl)-4-((4-((4,4,5,5-tetramethyl-1,3,2-dioxaborolan-2-yl)methyl)piperidin-1-yl)methyl)pyridin-2-yl)oxy)-2-(4-methylpiperazin-1-yl)pyrimidine

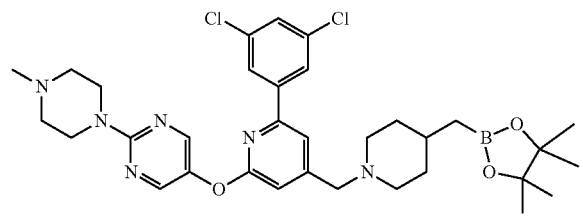

To a solution of (2-(3,5-dichlorophenyl)-6-((2-(4-methylpiperazin-1-yl)pyrimidin-5-yl)oxy)pyridin-4-yl)methyl methanesulfonate (150 mg, 0.257 mmol) and 4-((4,4,5,5-tetramethyl-1,3,2-dioxaborolan-2-yl)methyl)piperidine, trifluoroacetic acid (499 mg, 1.030 mmol) in DMF (10 mL) was added DIEA (0.450 mL, 2.57 mmol). Then the reaction mixture was stirred at 40° C. for 12 h. Solvent was concentrated to give the crude product. The crude material was purified by flash chromatography (DCM/MeOH=50/1 to 10/1, TLC: DCM/MeOH=10/1, R_f=0.7) to afford 5-((6-(3,5-dichlorophenyl)-4-((4-((4,4,5,5-tetramethyl-1,3,2-dioxaborolan-2-yl)methyl)piperidin-1-yl)methyl)pyridin-2-yl)oxy)-2-(4-methylpiperazin-1-yl)pyrimidine (160 mg, 0.171 mmol, 66.6% yield) as a pale yellow solid: ¹H NMR (400 MHz, CD₃OD) δ ppm 8.40 (s, 2H), 7.96 (s, 2H), 7.82 (d, J=2.0 Hz, 1H), 7.47 (br s, 1H), 7.15 (br s, 1H), 4.59 (br s, 2H), 3.73-3.67 (m, 4H), 3.33 (s, 3H), 3.24-3.20 (m, 4H), 2.99-2.86 (m, 4H), 1.98-1.95 (m, 2H), 1.81-1.78 (m, 1H), 1.55-1.50 (m, 2H), 1.20 (d, J=18.3 Hz, 12H), 0.79 (d, J=7.1 Hz, 2H); LCMS m/z 653.0, 655.0 [M+H]⁺.

Step 7: ((1-((2-(3,5-Dichlorophenyl)-6-((2-(4-methylpiperazin-1-yl)pyrimidin-5-yl)oxy)pyridin-4-yl)methyl)piperidin-4-yl)methyl)boronic acid, 4 hydrochloride

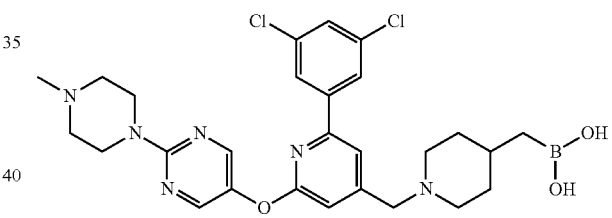

A mixture of 5-((6-(3,5-dichlorophenyl)-4-((4-((4,4,5,5-tetramethyl-1,3,2-dioxaborolan-2-yl)methyl)piperidin-1-yl)methyl)pyridin-2-yl)oxy)-2-(4-methylpiperazin-1-yl)pyrimidine (150 mg, 0.161 mmol) in HCl (12 N, 3 mL, 36 mmol) and water (3 mL) was stirred at 80° C. for 20 min. The solvent was concentrated to give the crude product. The crude product was purified by preparative HPLC (MeCN/H₂O as eluents, acidic condition) and lyophilized to afford ((1-((2-(3,5-dichlorophenyl)-6-((2-(4-methylpiperazin-1-yl)pyrimidin-5-yl)oxy)pyridin-4-yl)methyl)piperidin-4-yl)methyl)boronic acid, 4 hydrochloride (74.37 mg, 0.103 mmol, 63.9% yield) as a white solid: ¹H NMR (400 MHz, CD₃OD) δ ppm 8.44 (s, 2H), 7.87 (s, 1H), 7.88-7.86 (m, 1H), 7.85 (d, J=1.8 Hz, 2H), 7.50 (t, J=1.9 Hz, 1H), 7.28 (s, 1H), 4.93 (d, J=14.3 Hz, 2H), 4.39 (s, 2H), 3.60 (d, J=12.1 Hz, 2H), 3.52 (d, J=12.6 Hz, 2H), 3.34 (br s, 2H), 3.21-3.14 (m, 2H), 3.11-3.04 (m, 2H), 2.95 (s, 3H), 2.00 (d, J=14.6 Hz, 2H), 1.81 (br s, 1H), 1.55-1.47 (m, 2H), 0.83 (d, J=6.8 Hz, 2H); LCMS m/z 571.0, 572.9 [M+H]⁺.

Example 319: (2-(4-(5-((4-((4-(Acetamidomethyl)
piperidin-1-yl)methyl)-6-(3,5-dichlorophenyl)pyri-
din-2-yl)oxy)pyrimidin-2-yl)piperazin-1-yl)ethyl)
boronic acid, 4 hydrochloride

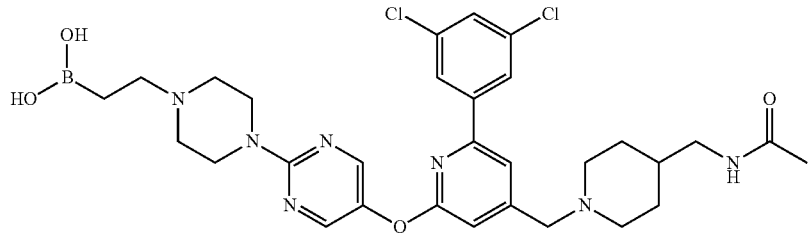 [SMILES: CC(=O)NCC1CCN(Cc2cc(Oc3cnc(N4CCN(CCB(O)O)CC4)nc3)nc(-c3cc(Cl)cc(Cl)c3)c2)CC1]

Step 1: (2-Bromoethyl)boronic acid

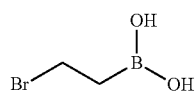

To a solution of 1,2-dibromoethane (8 g, 42.6 mmol) in THF (100 mL) was added n-BuLi (2.5 M in hexane) (18.74 mL, 46.8 mmol) dropwise at −78° C. under $N_2$ atmosphere. The reaction mixture was stirred at −78° C. for 1 h. Then trimethyl borate (11.06 g, 106 mmol) was added. The reaction mixture was stirred at 25° C. for 12 h. Then HCl (4 M in EtOAc) (5 mL, 20.00 mmol) was added. Then the mixture was concentrated to yield (2-bromoethyl)boronic acid (18 g, 35.3 mmol, 83.0% yield) as a white solid: $^1$H NMR (400 MHz, $CD_3OD$) δ ppm 3.48 (t, J=6.7 Hz, 2H), 1.71-1.65 (m, 2H).

Step 2: (2-(4-(5-((4-((4-(Acetamidomethyl)piperi-
din-1-yl)methyl)-6-(3,5-dichlorophenyl)pyridin-2-yl)
oxy)pyrimidin-2-yl)piperazin-1-yl)ethyl)boronic
acid, 4 hydrochloride

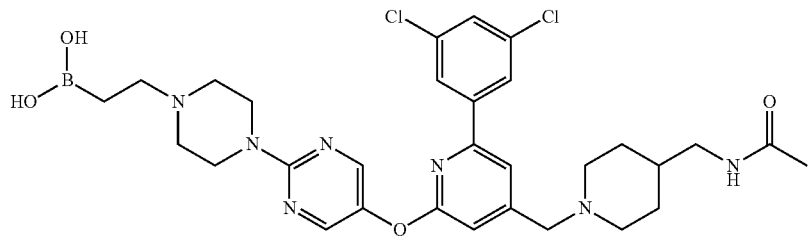 [SMILES: CC(=O)NCC1CCN(Cc2cc(Oc3cnc(N4CCN(CCB(O)O)CC4)nc3)nc(-c3cc(Cl)cc(Cl)c3)c2)CC1]

To a mixture of N-((1-((2-(3,5-dichlorophenyl)-6-((2-(piperazin-1-yl)pyrimidin-5-yl)oxy)pyridin-4-yl)methyl)piperidin-4-yl)methyl)acetamide, 4 trifluoroacetic acid salt (400 mg, 0.381 mmol) and DIEA (0.684 mL, 3.81 mmol) in DMF (30 mL) was added (2-bromoethyl)boronic acid (1941 mg, 3.81 mmol). Then, the mixture was stirred at 25° C. for 24 h. The reaction was diluted with DCM (20 mL) and water (20 mL). The mixture extracted with DCM (50 mL×3). The combined organic layers were concentrated. The crude product was purified by preparative HPLC (MeCN/$H_2O$ as eluents, basic condition) and dried by lyophilization to yield (crude product: 14.55 mg) as a white solid. The crude product was purified by preparative HPLC (MeCN/$H_2O$ as eluents, acidic condition) and dried by lyophilization to yield (2-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)ethyl)boronic acid, 4 hydrochloride (8.68 mg, 10.49 μmol, 2.7% yield) as a white solid: $^1$H NMR (400 MHz, $CD_3OD$) δ ppm 8.47 (s, 2H), 7.88 (s, 1H), 7.88 (d, J=1.8 Hz, 2H), 7.52 (t, J=1.8 Hz, 1H), 7.32 (s, 1H), 4.99-4.95 (m, 2H), 4.44 (s, 2H), 3.74-3.54 (m, 6H), 3.43-3.35 (m, 2H), 3.26-3.18 (m, 2H), 3.16-3.08 (m, 4H), 2.03-1.98 (m, 2H), 1.96 (s, 3H), 1.94-1.84 (m, 2H), 1.66 (d, J=7.3 Hz, 1H), 1.63-1.47 (m, 2H); ES-LCMS m/z 642.3, 644.3 [M+H]$^+$.

Example 320: ((1-((2-(3,5-Dichlorophenyl)-6-((2-(4-methylpiperazin-1-yl)pyrimidin-5-yl)oxy)pyridin-4-yl)methyl)piperidin-4-yl)methyl)dimethylphosphine oxide, 4 hydrochloride

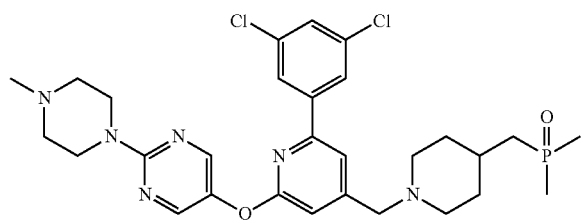

To a solution of (2-(3,5-dichlorophenyl)-6-((2-(4-methylpiperazin-1-yl)pyrimidin-5-yl)oxy)pyridin-4-yl)methyl methanesulfonate (100 mg, 0.172 mmol) and DIEA (111 mg, 0.858 mmol) in DMF (3 mL) was added dimethyl(piperidin-4-ylmethyl)phosphine oxide (90 mg, 0.308 mmol). Then the reaction mixture was stirred at 25° C. for 30 h. The reaction mixture was concentrated to afford crude product. The crude product was purified by preparative HPLC (MeCN/H$_2$O as eluents, acidic condition) and dried by lyophilization to yield a white solid of ((1-((2-(3,5-dichlorophenyl)-6-((2-(4-methylpiperazin-1-yl)pyrimidin-5-yl)oxy)pyridin-4-yl)methyl)piperidin-4-yl)methyl)dimethylphosphine oxide, 4 hydrochloride (28.2 mg, 0.037 mmol, 21.7% yield): $^1$H NMR (400 MHz, CD$_3$OD) δ ppm 8.51 (s, 2H), 8.01 (s, 1H), 7.88 (d, J=1.8 Hz, 2H), 7.47 (t, J=1.9 Hz, 1H), 7.38 (s, 1H), 4.89 (br s, 2H), 4.46 (s, 2H), 3.63 (d, J=12.6 Hz, 2H), 3.57 (d, J=11.7 Hz, 2H), 3.49-3.43 (m, 2H), 3.24-3.16 (m, 4H), 2.96 (s, 3H), 2.21-2.13 (m, 3H), 1.95 (br s, 2H), 1.81 (d, J=11.9 Hz, 2H), 1.65 (d, J=12.8 Hz, 6H); ES-LCMS m/z 603.2, 605.2 [M+H]$^+$.

Examples 321-329 (Table 16) were prepared by procedures analogous to those described for example 320.

TABLE 16

| Example | Structure/Name | $^1$H NMR | LCMS |
|---|---|---|---|
| 321 | (1R,7S,8r)-4-((2-(3,5-dichlorophenyl)-6-((2-(4-methylpiperazin-1-yl)pyrimidin-5-yl)oxy)pyridin-4-yl)methyl)-4-azabicyclo[5.1.0]octane-8-carboxylic acid | $^1$H NMR (400 MHz, D$_2$O/CD$_3$CN = 4/1) δ ppm 8.47 (s, 2H), 7.77 (d, J = 1.8 Hz, 2H), 7.71 (s, 1H), 7.50 (t, J = 1.9 Hz, 1H), 7.24 (s, 1H), 4.72 (d, J = 14.8 Hz, 2H), 4.43 (s, 2H), 3.69-3.49 (m, 4H), 3.46-3.35 (m, 2H), 3.29 (t, J = 12.2 Hz, 2H), 3.14 (dt, J = 3.2, 12.4 Hz, 2H), 2.94 (s, 3H), 2.50 (d, J = 15.7 Hz, 2H), 2.03 (td, J = 2.5, 5.0 Hz, 1H), 1.76 (br s, 2H), 1.63 (br s, 2H) | ES-LCMS m/z 583.3, 585.2 [M + H]$^+$. |
| 322 | ((1-((2-(3,5-dichlorophenyl)-6-((2-(4-methyl-1,4-diazepan-1-yl)pyrimidin-5-yl)oxy)pyridin-4-yl)methyl)piperidin-4-yl)methyl)boronic acid | $^1$H NMR (400 MHz, CD$_3$OD) δ ppm 8.47 (s, 2H), 7.90 (s, 1H), 7.88 (d, J = 1.8 Hz, 2H), 7.50 (t, J = 1.8 Hz, 1H), 7.32 (s, 1H), 4.49-4.43 (m, 1H), 4.40 (s, 2H), 4.10-3.85 (m, 4H), 3.74-3.69 (m, 1H), 3.57-3.51 (m, 1H), 3.54 (br d, J = 9.5 Hz, 1H), 3.40-3.33 (m, 2H), 3.07 (br t, J = 11.8 Hz, 2H), 2.94 (s, 3H), 2.33-2.28 (m, 2H), 1.99 (br d, J = 14.1 Hz, 2H), 1.81 (br d, J = 2.6 Hz, 1H), 1.58-1.48 (m, 2H), 0.83 (br d, J = 6.8 Hz, 2H) | LCMS m/z 584.9, 586.9 [M + H]$^+$. |

TABLE 16-continued

| Example | Structure/Name | ¹H NMR | LCMS |
|---|---|---|---|
| 323 | 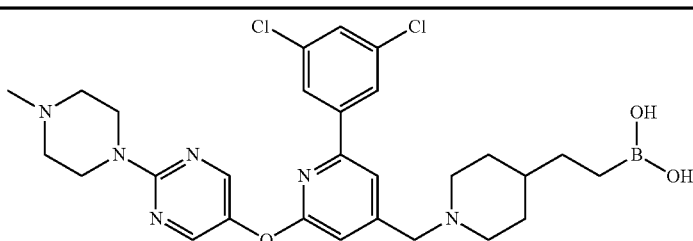<br>(2-(1-((2-(3,5-dichlorophenyl)-6-((2-(4-methylpiperazin-1-yl)pyrimidin-5-yl)oxy)pyridin-4-yl)methyl)piperidin-4-yl)ethyl)boronic acid | ¹H NMR (400 MHz, CD₃OD) δ ppm 8.44 (s, 2H), 7.95 (s, 1H), 7.86 (d, J = 2.0 Hz, 2H), 7.47 (t, J = 1.9 Hz, 1H), 7.33 (s, 1H), 4.96-4.89 (m, 2H), 4.43 (s, 2H), 3.64-3.52 (m, 4H), 3.43-3.35 (m, 2H), 3.18 (dt, J = 3.0, 12.3 Hz, 2H), 3.09 (t, J = 11.5 Hz, 2H), 2.96 (s, 3H), 2.04-1.94 (m, 2H), 1.52 (s, 3H), 1.41-1.34 (m, 2H), 0.78 (s, 2H) | ES-LCMS m/z 585.2, 587.2 [M + H]⁺. |
| 324 | 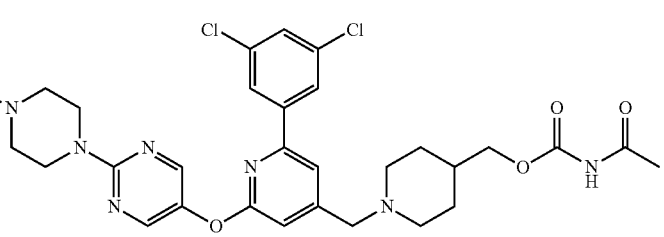<br>(1-((2-(3,5-dichlorophenyl)-6-((6-(4-methylpiperazin-1-yl)pyridin-3-yl)oxy)pyridin-4-yl)methyl)piperidin-4-yl)methyl acetylcarbamate | ¹H NMR (400 MHz,CD₃OD) δ ppm 8.48-8.41 (m, 2H), 7.93 (s, 1H), 7.89-7.84 (m, 2H), 7.53-7.48 (m, 1H), 7.36-7.30 (m, 1H), 4.98-4.91 (m, 2H), 4.44 (s, 2H), 4.15-4.03 (m, 2H), 3.70-3.54 (m, 4H), 3.42-3.34 (m, 2H), 3.25-3.04 (m, 4H), 2.96 (s, 3H), 2.24-2.15 (m, 3H), 2.12-1.95 (m, 3H), 1.83-1.61 (m, 2H) | ES-LCMS m/z 628.3, 630.3 [M + H]⁺. |
| 325 | 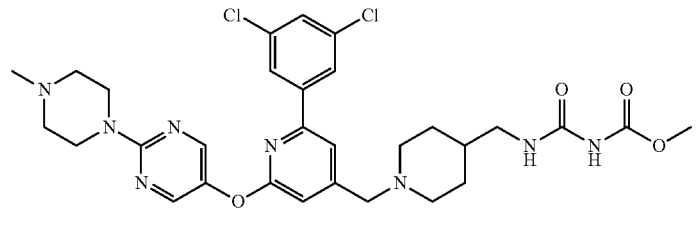<br>N-14(14(2(3,5-dichlorophenyl)-6-((2-(4-methylpiperazin-1-yl)pyrimidin-5-yl)oxy)pyridin-4-yl)methyl)piperidin-4-yl)methyl)-N'-methoxylcarbonylurea | ¹H NMR (400 MHz, CD₃OD) δ ppm 8.49 (s, 2H), 7.98-7.91 (m, 1H), 7.88-7.82 (m, 2H), 7.48 (t, J = 1.9 Hz, 1H), 7.36-7.31 (m, 1H), 4.95-4.91 (m, 2H), 4.53-4.38 (m, 2H), 3.75-3.67 (m, 3H), 3.65-3.54 (m, 4H), 3.45-3.36 (m, 2H), 3.27-3.02 (m, 6H), 2.95 (s, 3H), 1.97 (d, J = 4.3 Hz, 2H), 1.89 (d, J = 3.5 Hz, 1H), 1.70-1.51 (m, 2H) | ES-LCMS m/z 643.4, 645.3 [M + H]⁺. |
| 326 | 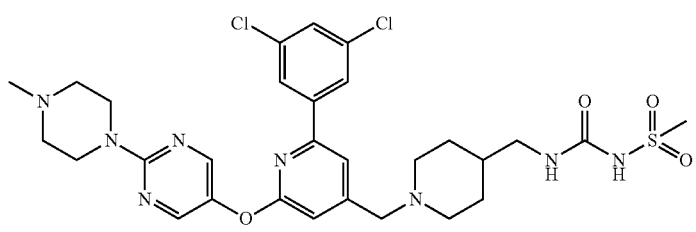<br>N-(((1-((2-(3,5-dichlorophenyl)-6-((2-(4-methylpiperazin-1-yl)pyrimidin-5-yl)oxy)pyridin-4-yl)methyl)piperidin-4-yl)methyl)carbamoyl)methanesulfonamide | ¹H NMR (400 MHz, CD3OD) δ ppm 8.51-8.47 (m, 2H), 7.94 (s, 1H), 7.89-7.83 (m, 2H), 7.48 (t, J = 1.8 Hz, 1H), 7.35-7.32 (m, 1H), 4.93 (d, J = 1.3 Hz, 2H), 4.49-4.38 (m, 2H), 3.65-3.54 (m, 4H), 3.46-3.36 (m, 4H), 3.32-3.22 (m, 3H), 2.95 (s, 4H), 2.12-2.01 (m, 3H), 2.00-1.94 (m, 2H), 1.88 (d, J = 3.5 Hz, 1H), 1.70-1.54 (m, 2H) | ES-LCMS m/z 663.3, 665.3 [M + H]⁺. |

TABLE 16-continued

| Example | Structure/Name | ¹H NMR | LCMS |
|---|---|---|---|
| 327 | 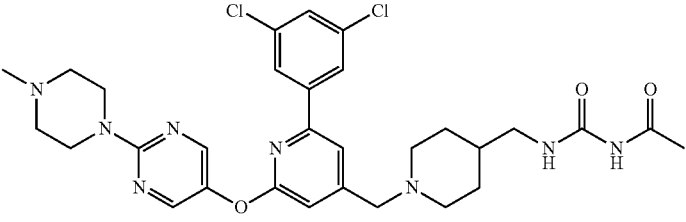 [SMILES: CC(=O)NC(=O)NCC1CCN(Cc2cc(Oc3cnc(N4CCN(C)CC4)nc3)nc(-c3cc(Cl)cc(Cl)c3)c2)CC1]<br>N-(((1-(2-3,5-dichlorophenyl)-6-((2-(4-methylpiperazin-1-yl)pyrimidin-5-yl)oxy)pyridin-4-yl)methyl)piperidin-4-yl)methyl)carbamoyl)acetamide | ¹H NMR (400 MHz, CD₃OD) δ ppm 8.51-8.47 (m, 2H), 7.94 (s, 1H), 7.89-7.83 (m, 2H), 7.48 (t, J = 1.8 Hz, 1H), 7.35-7.32 (m, 1H), 4.93 (d, J = 1.3 Hz, 2H), 4.49-4.38 (m, 2H), 3.65-3.54 (m, 4H), 3.46-3.37 (m, 2H), 3.24-3.05 (m, 6H), 2.95 (s, 3H), 2.12-2.01 (m, 3H), 2.00-1.94 (m, 2H), 1.88 (br d, J = 3.5 Hz, 1H), 1.70-1.54 (m, 2H) | ES-LCMS m/z 627.4, 629.4 [M + H]⁺. |
| 328 | 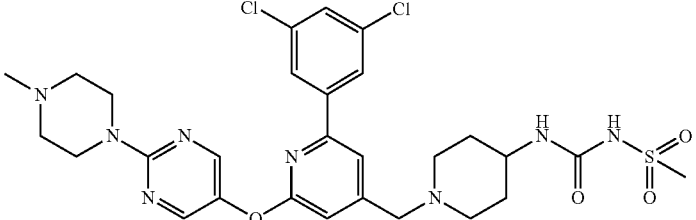<br>N-((1-((2-(3,5-dichlorophenyl)-6-((2-(4-methylpiperazin-1-yl)pyrimidin-5-yl)oxy)pyridin-4-yl)methyl)piperidin-4-yl)carbamoyl)methanesulfonamide | ¹H NMR (400 MHz, CD₃OD) δ ppm: 8.46 (s, 2H), 7.99-7.94 (m, 1H), 7.87 (d, J = 1.8 Hz, 2H), 7.48 (t, J = 1.9 Hz, 1H), 7.34 (s, 1H), 4.93 (d, J = 14.8 Hz, 2H), 4.45 (s, 2H), 3.86 (d, J = 2.9 Hz, 1H), 3.61 (d, J = 12.8 Hz, 4H), 3.50-3.33 (m, 3H), 3.28-3.23 (m, 1H), 3.22 (s, 3H), 3.21-3.13 (m, 2H), 2.96 (s, 3H), 2.24-2.09 (m, 2H), 1.94 (d, J = 12.1 Hz, 2H) | ES-LCMS m/z 649.2, 651.2 [M + H]⁺. |
| 329 | 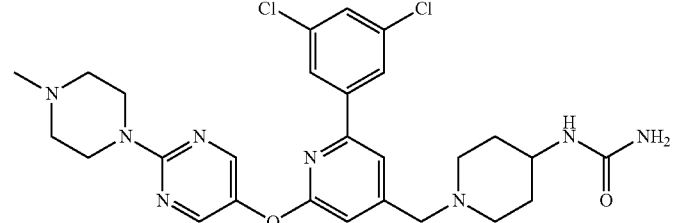<br>1-(1-((2-(3,5-dichlorophenyl)-6-((2-(4-methylpiperazin-1-yl)pyrimidin-5-yl)oxy)pyridin-4-yl)methyl)piperidin-4-yl)urea | ¹H NMR (400 MHz, CD₃OD) δ ppm 8.46 (s, 2H), 8.01 (s, 1H), 7.86 (d, J = 1.8 Hz, 2H), 7.45 (t, J = 1.8 Hz, 1H), 7.39-7.34 (m, 1H), 4.90-4.86 (m, 2H), 4.54-4.43 (m, 2H), 3.87-3.74 (m, 1H), 3.61 (d, J = 12.1 Hz, 4H), 3.48-3.35 (m, 3H), 3.27-3.13 (m, 3H), 2.95 (s, 3H), 2.17 (d, J = 13.7 Hz, 2H), 2.09-1.87 (m, 2H) | ES-LCMS m/z 571.2, 573.2 [M + H]⁺. |

Example 330: (S)-(4-((2-(3,5-Dichlorophenyl)-6-((2-(4-methylpiperazin-1-yl)pyrimidin-5-yl)oxy)pyridin-4-yl)methyl)-1,4-oxazepan-7-yl)methanol, 4 hydrochloride

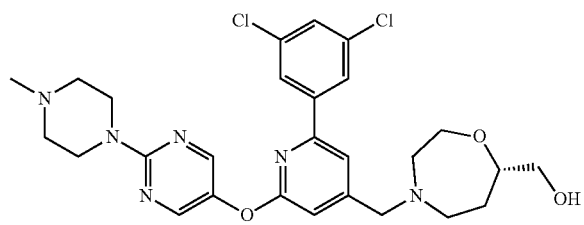 [SMILES: CN1CCN(c2ncc(Oc3cc(CN4CCO[C@H](CO)CC4)cc(-c4cc(Cl)cc(Cl)c4)n3)cn2)CC1]

Step 1: (S)-4-(Benzylamino)-2-hydroxybutanoic acid

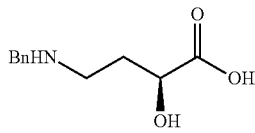

To a solution of (S)-4-amino-2-hydroxybutanoic acid (13.5 g, 113 mmol), NaOH (4.85 g, 121 mmol) in water (120 mL) was added benzaldehyde (12.26 mL, 121 mmol) at 25° C. Then the mixture was stirred at 25° C. for 30 min. The mixture was cooled to 0° C. and NaBH$_4$ (2.92 g, 77 mmol) was added during 30 min. The mixture was stirred for 11 h at 25° C. The mixture was washed with EtOAc (100 mL). The aqueous phase was acidified to pH=6 with 12 M HCl solution and the solid was collected and dried to yield 0S')-4-(benzylamino)-2-hydroxybutanoic acid (23 g, 33.0 mmol, 29.1% yield) as a white solid: $^1$H NMR (400 MHz, CD$_3$OD) δ ppm 7.40-7.20 (m, 5H), 4.01-3.91 (m, 1H), 3.82-3.72 (m, 2H), 2.90-2.71 (m, 2H), 2.08-1.94 (m, 1H), 1.89-1.75 (m, 1H); ES-LCMS m/z 210.2 [M+H]$^+$.

Step 2: (S)-4-Benzyl-3-oxo-1,4-oxazepane-7-carboxylic acid

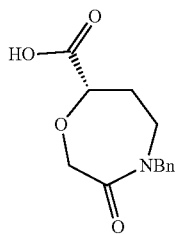 [SMILES: O=C(O)[C@@H]1CCN(Cc2ccccc2)C(=O)CO1]

To a solution of (S)-4-(benzylamino)-2-hydroxybutanoic acid (23 g, 33.0 mmol), NaOH (14 g, 350 mmol) in water (150 mL) was added 2-chloroacetyl chloride (11.2 mL, 141 mmol) dropwise at 0° C. Then the mixture was stirred at 25° C. for 12 h. The reaction mixture was extracted with DCM (15 mL×2), the aqueous phase was acidified to pH=3 with 12 M HCl solution. The solid was filtered and dried to yield light oil, which was purified by preparative HPLC (MeCN/H$_2$O as eluents, acidic condition) followed by lyophilization to yield (S)-4-benzyl-3-oxo-1,4-oxazepane-7-carboxylic acid (7 g, 27.1 mmol, 82.0% yield) as colorless oil: $^1$H NMR (400 MHz, CD$_3$OD) δ ppm 7.40-7.21 (m, 5H), 4.61 (d, J=2.4 Hz, 2H), 4.52-4.36 (m, 2H), 4.29 (dd, J=4.6, 9.5 Hz, 1H), 3.64-3.44 (m, 2H), 2.32-2.18 (m, 1H), 2.05-1.92 (m, 1H); ES-LCMS m/z 250.3 [M+H]$^+$.

Step 3: (S)-Methyl 4-benzyl-3-oxo-1,4-oxazepane-7-carboxylate

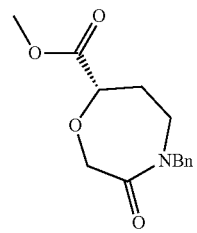 [SMILES: COC(=O)[C@@H]1CCN(Cc2ccccc2)C(=O)CO1]

To a solution of (S)-4-benzyl-3-oxo-1,4-oxazepane-7-carboxylic acid (950 mg, 3.68 mmol) in MeOH (15 mL) was added SOCl$_2$ (0.8 mL, 10.96 mmol) dropwise at 0° C. Then the mixture was stirred at 30° C. for 12 h. The mixture was concentrated to yield (S)-methyl 4-benzyl-3-oxo-1,4-oxazepane-7-carboxylate (910 mg, 3.05 mmol, 83.0% yield) as light yellow oil: $^1$H NMR (400 MHz, CDCl$_3$) δ ppm 7.36-7.24 (m, 5H), 4.70-4.57 (m, 2H), 4.57-4.43 (m, 1H), 4.37-4.29 (m, 1H), 4.27-4.17 (m, 1H), 3.76 (s, 3H), 3.52-3.35 (m, 2H), 2.28-2.06 (m, 2H); ES-LCMS m/z 264.0 [M+H]$^+$.

Step 4: (S)-(4-Benzyl-1,4-oxazepan-7-yl)methanol

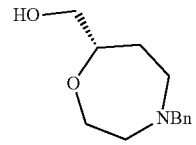

To a solution of (S)-methyl 4-benzyl-3-oxo-1,4-oxazepane-7-carboxylate (700 mg, 2.348 mmol) in THF (30 mL) was added LAH (267 mg, 7.04 mmol) portion wise at 0° C. Then the mixture was stirred at 25° C. for 12 h. The mixture was quenched by H$_2$O (0.267 mL), followed by 10% aqueous NaOH solution (0.267 mL) at 0° C. Then the mixture was filtered and the filtrate was concentrated to yield (S)-(4-benzyl-1,4-oxazepan-7-yl)methanol (450 mg, 1.220 mmol, 52.0% yield) as colorless oil: $^1$H NMR (400 MHz, CDCl$_3$) δ ppm 7.39-7.24 (m, 5H), 3.90 (m, 1H), 3.76-3.57 (m, 4H), 3.54-3.40 (m, 2H), 2.78-2.60 (m, 4H), 1.89-1.81 (m, 1H), 1.70-1.58 (m, 1H); ES-LCMS m/z 222.2 [M+H]$^+$.

Step 5: (S)-(1,4-Oxazepan-7-yl)methanol

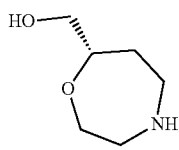

To a solution of (S)-(4-benzyl-1,4-oxazepan-7-yl)methanol (350 mg, 0.949 mmol) in MeOH (15 mL) was added Pd/C (10 wt %, 101 mg, 0.095 mmol) under $N_2$ atmosphere. Then the mixture was stirred at 25° C. under $H_2$ atmosphere (50 psi) for 12 h. Then the mixture was filtered and the filtrate was concentrated to yield (S)-(1,4-oxazepan-7-yl)methanol (150 mg, 0.686 mmol, 72.3% yield) as colorless oil: $^1$H NMR (400 MHz, $CD_3OD$) δ ppm 3.95 (d, J=13.1 Hz, 1H), 3.78-3.58 (m, 2H), 3.54-3.41 (m, 2H), 3.06-2.75 (m, 4H), 1.97-1.84 (m, 1H), 1.72-1.58 (m, 1H).

Step 6: (S)-tert-Butyl 4-(5-((6-(3,5-dichlorophenyl)-4-((7-(hydroxymethyl)-1,4-oxazepan-4-yl)methyl)pyridin-2-yl)oxy)pyrimidin-2-yl)piperazine-1-carboxylate

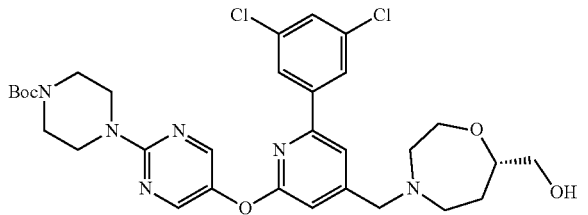

To a solution of tert-butyl 4-(5-((6-(3,5-dichlorophenyl)-4-(((methylsulfonyl)oxy)methyl)pyridin-2-yl)oxy)pyrimidin-2-yl)piperazine-1-carboxylate (600 mg, 0.885 mmol) and (S)-(1,4-oxazepan-7-yl)methanol (150 mg, 0.686 mmol) in DMF (10 mL) was added DIEA (0.630 mL, 3.54 mmol). Then the mixture was stirred at 50° C. for 3 h. Then the mixture was concentrated to yield the residue. The residue was purified by flash chromatography (DCM/MeOH=100/1 to 20/1, TLC: DCM/MeOH=10/1, $R_f$=0.6) to yield (S)-tert-butyl 4-(5-((6-(3,5-dichlorophenyl)-4-((7-(hydroxymethyl)-1,4-oxazepan-4-yl)methyl)pyridin-2-yl)oxy)pyrimidin-2-yl)piperazine-1-carboxylate (450 mg, 0.686 mmol, 78.0% yield) as a yellow oil: $^1$H NMR (400 MHz, $CD_3OD$) δ ppm 8.34 (s, 2H), 7.82 (s, 2H), 7.67 (s, 1H), 7.44 (d, J=1.6 Hz, 1H), 7.09 (s, 1H), 3.96-3.78 (m, 9H), 3.53-3.45 (m, 6H), 2.77-2.75 (m, 4H), 1.94-1.93 (m, 1H), 1.78-1.76 (m, 1H), 1.49 (s, 9H); ES-LCMS m/z 645.3, 647.3 [M+H]$^+$.

Step 7: (S)-(4-((2-(3,5-Dichlorophenyl)-6-((2-(piperazin-1-yl)pyrimidin-5-yl)oxy)pyridin-4-yl)methyl)-1,4-oxazepan-7-yl)methanol, 4 trifluoroacetic acid

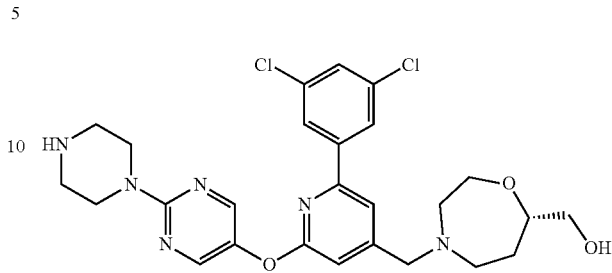

To a solution of (S)-tert-butyl 4-(5-((6-(3,5-dichlorophenyl)-4-((7-(hydroxymethyl)-1,4-oxazepan-4-yl)methyl)pyridin-2-yl)oxy)pyrimidin-2-yl)piperazine-1-carboxylate (450 mg, 0.686 mmol) in DCM (8 mL) was added TFA (2 mL, 26.0 mmol) and then the mixture was stirred at 25° C. for 0.5 h. Then the mixture was concentrated to yield 0S')-(4-((2-(3,5-dichlorophenyl)-6-((2-(piperazin-1-yl)pyrimidin-5-yl)oxy)pyridin-4-yl)methyl)-1,4-oxazepan-7-yl)methanol, 4 trifluoroacetic acid (500 mg, 0.639 mmol, 93.0% yield) as light yellow oil. $^1$H NMR (400 MHz, $CD_3OD$) δ ppm 8.45 (s, 2H), 7.85 (d, J=1.8 Hz, 3H), 7.52 (t, J=1.8 Hz, 1H), 7.30 (s, 1H), 4.61-4.48 (m, 3H), 4.20-4.06 (m, 6H), 3.95-3.82 (m, 2H), 3.67 (br. s, 1H), 3.61-3.51 (m, 3H), 3.47 (br. s, 2H), 3.35 (br. s, 2H), 2.22 (d, J=19.0 Hz, 2H); ES-LCMS m/z 545.2, 547.2 [M+H]$^+$.

Step 8: (S)-(4-((2-(3,5-Dichlorophenyl)-6-((2-(4-methylpiperazin-1-yl)pyrimidin-5-yl)oxy)pyridin-4-yl)methyl)-1,4-oxazepan-7-yl)methanol, 4 hydrochloride

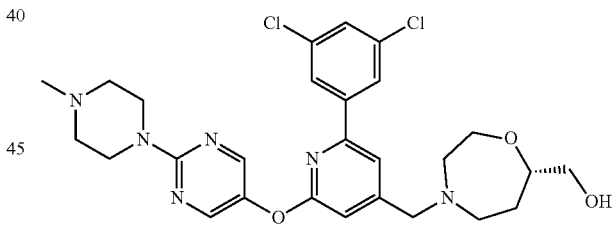

A mixture of paraformaldehyde (253 mg, 8.42 mmol), (S)-(4-((2-(3,5-dichlorophenyl)-6-((2-(piperazin-1-yl)pyrimidin-5-yl)oxy)pyridin-4-yl)methyl)-1,4-oxazepan-7-yl)methanol, 4 trifluoroacetic acid salt (500 mg, 0.421 mmol) in MeOH (10 mL) was stirred at 25° C. for 10 h. Then $NaBH_3CN$ (79 mg, 1.263 mmol) was added to above mixture and stirred for 2 h. Then the solution of saturated aqueous $NaHCO_3$ (20 mL) was added. The mixture was extracted with DCM (50 mL×3). The combined organic layers were washed with brine (20 mL), dried over $Na_2SO_4$, filtered and concentrated to yield a residue, which was purified by preparative HPLC (MeCN/$H_2O$ as eluents, acidic condition) followed by lyophilization to yield (S)-(4-((2-(3,5-dichlorophenyl)-6-((2-(4-methylpiperazin-1-yl)pyrimidin-5-yl)oxy)pyridin-4-yl)methyl)-1,4-oxazepan-7-yl)methanol, 4 hydrochloride (93.32 mg, 0.132 mmol, 31.4% yield) as a white solid: $^1$H NMR (400 MHz, $CD_3OD$) δ ppm 8.46 (s, 2H), 7.97 (d, J=7.3 Hz, 1H), 7.88 (d, J=1.1 Hz, 2H), 7.51 (t, J=1.8 Hz, 1H), 7.36 (s, 1H), 4.97 (br. s, 2H), 4.55 (d, J=5.5 Hz, 2H), 4.22-4.03 (m, 1H), 3.98-3.84 (m, 2H), 3.75-3.47 (m, 8H), 3.41-3.35 (m, 2H), 3.24-3.13 (m, 2H), 2.97 (s, 3H), 2.52-2.10 (m, 2H); ES-LCMS m/z 559.3, 561.2 [M+H]⁺. ¹H NMR (400 MHz, CD₃OD+Na₂CO₃) δ ppm 8.32 (s, 2H), 7.81 (d, J=1.8 Hz, 2H), 7.66 (s, 1H), 7.43 (t, J=1.8 Hz, 1H), 7.08 (s, 1H), 3.99-3.80 (m, 6H), 3.77 (s, 2H), 3.69 (d, J=5.0, 13.0 Hz, 1H), 3.55-3.39 (m, 2H), 2.88-2.64 (m, 4H), 2.54 (t, J=5.0 Hz, 4H), 2.35 (s, 3H), 2.02-1.90 (m, 1H), 1.82-1.70 (m, 1H).

Example 331: (1-((2-(3,5-Dichlorophenyl)-6-((2-(4-methylpiperazin-1-yl)pyrimidin-5-yl)oxy)pyridin-4-yl)methyl)piperidin-4-yl)dimethylphosphine oxide, 4 hydrochloride

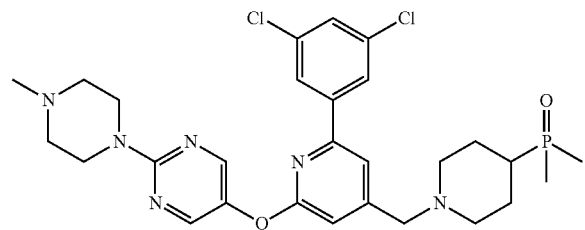

To a solution of (2-(3,5-dichlorophenyl)-6-((2-(4-methylpiperazin-1-yl)pyrimidin-5-yl)oxy)pyridin-4-yl)methyl methanesulfonate (100 mg, 0.172 mmol) and dimethyl(piperidin-4-yl)phosphine oxide (70 mg, 0.304 mmol) in DMF (20 mL) was added DIEA (111 mg, 0.858 mmol). The mixture was stirred at 40° C. for 5 h. The reaction mixture was concentrated to afford crude product, which was purified by preparative HPLC (MeCN/H₂O as eluents, acidic condition) and dried by lyophilization to yield a white solid of (1-((2-(3,5-dichlorophenyl)-6-((2-(4-methylpiperazin-1-yl)pyrimidin-5-yl)oxy)pyridin-4-yl)methyl)piperidin-4-yl)dimethylphosphine oxide, 4 hydrochloride (23.31 mg, 0.031 mmol, 18.3% yield): ¹H NMR (400 MHz, CD₃OD) δ ppm 8.46 (s, 2H), 7.97 (s, 1H), 7.87 (d, J=1.8 Hz, 2H), 7.49-7.46 (m, 1H), 7.35 (s, 1H), 4.93 (br s, 2H), 4.48 (s, 2H), 3.68 (d, J=12.1 Hz, 2H), 3.61 (d, J=12.1 Hz, 2H), 3.43-3.36 (m, 2H), 3.23-3.14 (m, 4H), 2.95 (s, 3H), 2.16 (br s, 3H), 2.01 (d, J=6.6 Hz, 2H), 1.56 (d, J=12.8 Hz, 6H); ES-LCMS m/z 589.3, 591.2 [M+H]⁺.

Example 332: 2-(1-((2-(3,5-Dichlorophenyl)-6-((2-(4-methylpiperazin-1-yl)pyrimidin-5-yl)amino)pyridin-4-yl)methyl)piperidin-4-yl)acetic acid, 4 hydrochloride

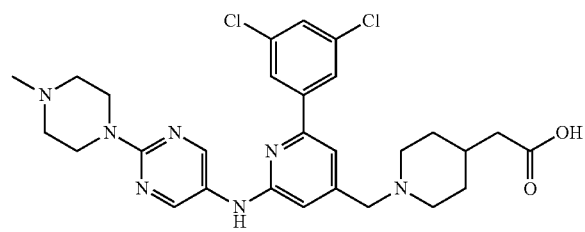 [SMILES: CN1CCN(c2ncc(Nc3cc(CN4CCC(CC(=O)O)CC4)cc(-c4cc(Cl)cc(Cl)c4)n3)cn2)CC1]

Step 1: (2-(3,5-Dichlorophenyl)-6-((2-(methylthio)pyrimidin-5-yl)amino)pyridin-4-yl)methanol

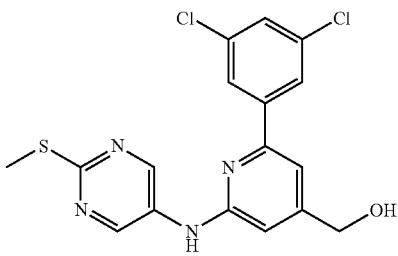 [SMILES: CSc1ncc(Nc2cc(CO)cc(-c3cc(Cl)cc(Cl)c3)n2)cn1]

To a solution of methyl 2-(3,5-dichlorophenyl)-6-((2-(methylthio)pyrimidin-5-yl)amino)isonicotinate (100 mg, 0.190 mmol) in THF (8 mL) was added LiAlH₄ (10.81 mg, 0.285 mmol) in portions at −40° C. Then the reaction mixture was stirred at −40° C. for 20 min. The reaction mixture was quenched by the addition of water (0.1 mL) and 1 N aqueous NaOH solution (0.1 mL) at −10° C., then MgSO₄ (500 mg) was added. The mixture was filtered and concentrated. The crude material was purified by flash chromatography (from pure DCM to DCM/MeOH=20/1, TLC: DCM/MeOH=20/1, R_f=0.45) to yield (2-(3,5-dichlorophenyl)-6-((2-(methylthio)pyrimidin-5-yl)amino)pyridin-4-yl)methanol (80 mg, 0.177 mmol, 93.0% yield) as a pale yellow solid: ¹H NMR (400 MHz, CD₃OD) δ ppm 9.04 (s, 2H), 7.92 (d, J=2.0 Hz, 2H), 7.45 (t, J=1.9 Hz, 1H), 7.28 (s, 1H), 6.85 (d, J=0.9 Hz, 1H), 4.64 (s, 2H), 2.56 (s, 3H); ES-LCMS m/z 393.0, 395.0 [M+H]⁺.

Step 2: (2-(3,5-Dichlorophenyl)-6-((2-(methylthio)pyrimidin-5-yl)amino)pyridin-4-yl)methyl methanesulfonate

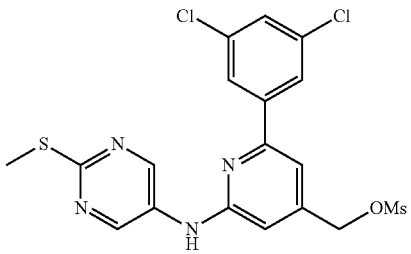 [SMILES: CSc1ncc(Nc2cc(COS(C)(=O)=O)cc(-c3cc(Cl)cc(Cl)c3)n2)cn1]

To a solution of (2-(3,5-dichlorophenyl)-6-((2-(methylthio)pyrimidin-5-yl)amino)pyridin-4-yl)methanol (80 mg, 0.177 mmol) and DIEA (0.093 mL, 0.531 mmol) in DCM (5.00 mL) was added MsCl (0.018 mL, 0.230 mmol) at 0° C. Then the reaction mixture was stirred at 0° C. for 10 min. Water (20 mL) was added and extracted with DCM (15 mL×2). The combined organic layers were dried over Na₂SO₄ and concentrated to yield a yellow solid of (2-(3,5-dichlorophenyl)-6-((2-(methylthio)pyrimidin-5-yl)amino)pyridin-4-yl)methyl methanesulfonate (110 mg, 0.161 mmol, 91.0% yield): ¹H NMR (400 MHz, CDCl₃) δ ppm 8.94 (s, 2H), 7.81 (s, 2H), 7.40-7.40 (m, 1H), 7.14 (s, 1H), 6.85 (s, 1H), 4.52 (s, 2H), 3.11 (s, 3H), 2.60 (s, 3H); LCMS m/z 471.1, 473.1 [M+H]⁺.

Step 3: Methyl 2-(1-((2-(3,5-dichlorophenyl)-6-((2-(methylthio)pyrimidin-5-yl)amino)pyridin-4-yl)methyl)piperidin-4-yl)acetate

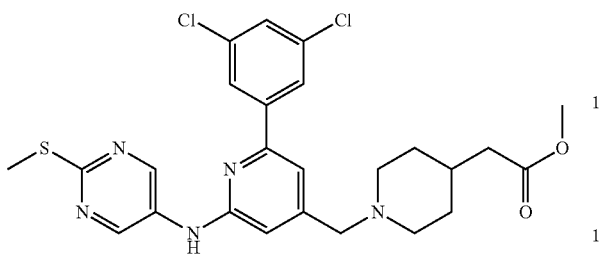

To a solution of (2-(3,5-dichlorophenyl)-6-((2-(methylthio)pyrimidin-5-yl)amino)pyridin-4-yl)methyl methanesulfonate (110 mg, 0.161 mmol) and methyl 2-(piperidin-4-yl)acetate (36.6 mg, 0.209 mmol) in DML (8 mL) was added DIEA (0.141 mL, 0.805 mmol). Then the reaction mixture was stirred at 20° C. for 12 h. Solvent was concentrated to give the crude product. The crude material was purified by flash chromatography (from DCM/MeOH=20/1 to 10/1, TLC: DCM/MeOH=10/1, $R_f$=0.65) to yield a pale yellow solid of methyl 2-(1-((2-(3,5-dichlorophenyl)-6-((2-(methylthio)pyrimidin-5-yl)amino)pyridin-4-yl)methyl)piperidin-4-yl)acetate (85 mg, 0.144 mmol, 89.0% yield): $^1$H NMR (400 MHz, CD$_3$OD) δ ppm 9.02 (s, 2H), 7.91 (d, J=1.8 Hz, 2H), 7.45-7.43 (m, 1H), 7.31 (s, 1H), 6.79 (s, 1H), 3.66-3.61 (m, 5H), 2.56 (s, 3H), 2.27 (s, 2H), 2.19-2.11 (m, 2H), 1.83-1.79 (m, 1H), 1.75 (br s, 2H), 1.42-1.34 (m, 2H), 1.21 (s, 2H); LCMS m/z 532.1, 534.1 [M+H]$^+$.

Step 4: Methyl 2-(1-((2-(3,5-dichlorophenyl)-6-((2-(methylsulfonyl)pyrimidin-5-yl)amino)pyridin-4-yl)methyl)piperidin-4-yl)acetate

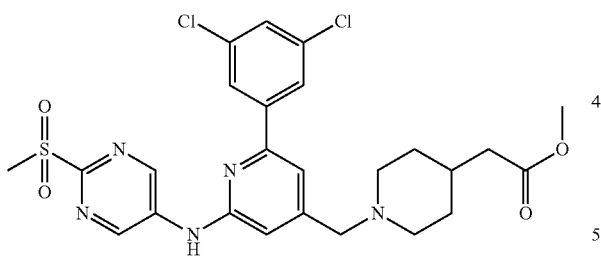

To a solution methyl 2-(1-((2-(3,5-dichlorophenyl)-6-((2-(methylthio)pyrimidin-5-yl)amino)pyridin-4-yl)methyl)piperidin-4-yl)acetate (85 mg, 0.144 mmol) in MeOH (10 mL) was added Oxone (79 mg, 0.129 mmol). Then the mixture was stirred at 25° C. for 12 h. The solid was filtered off and saturated aqueous Na$_2$SO$_3$ (15 mL) solution was added and extracted with DCM (15 mL×3). The combined organic layers were combined, dried over Na$_2$SO$_4$, filtered and concentrated in vacuo to yield the crude product. The crude material was purified by flash chromatography (from DCM/MeOH=20/1 to 10/1, TLC: DCM/MeOH=10/1, $R_f$=0.55) to yield methyl 2-(1-((2-(3,5-dichlorophenyl)-6-((2-(methylsulfonyl)pyrimidin-5-yl)amino)pyridin-4-yl)piperidin-4-yl)acetate (80 mg, 0.099 mmol, 69.1% yield) as a pale yellow solid: $^1$H NMR (400 MHz, CD$_3$OD) δ ppm 9.38 (s, 2H), 7.92 (d, J=1.8 Hz, 2H), 7.45-7.44 (m, 1H), 7.42 (s, 1H), 6.90 (s, 1H), 5.47 (s, 2H), 3.63 (s, 3H), 2.96-2.95 (m, 3H), 2.90 (br s, 2H), 2.27 (s, 2H), 2.14 (br s, 2H), 1.81 (d, J=4.2 Hz, 1H), 1.74 (br s, 2H), 1.38 (br s, 2H); LCMS m/z 564.2, 566.1 [M+H]$^+$.

Step 5: Methyl 2-(1-((2-(3,5-dichlorophenyl)-6-((2-(4-methylpiperazin-1-yl)pyrimidin-5-yl)amino)pyridin-4-yl)methyl)piperidin-4-yl)acetate

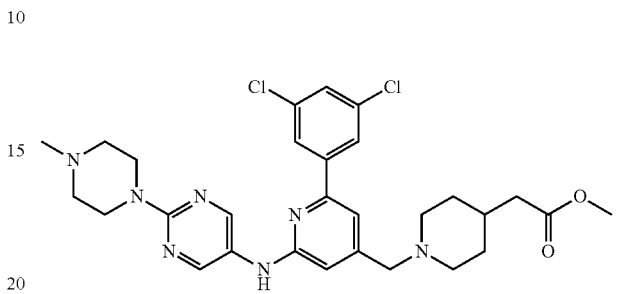

A mixture of methyl 2-(1-((2-(3,5-dichlorophenyl)-6-((2-(methylsulfonyl)pyrimidin-5-yl)amino)pyridin-4-yl)methyl)piperidin-4-yl)acetate (80 mg, 0.099 mmol), 1-methylpiperazine (49.7 mg, 0.496 mmol) and DIEA (64.1 mg, 0.496 mmol) in t-BuOH (0.1 mL) was stirred at 150° C. for 1.5 h under microwave. The solvent was concentrated to give the crude product of methyl 2-(1-((2-(3,5-dichlorophenyl)-6-((2-(4-methylpiperazin-1-yl)pyrimidin-5-yl)amino)pyridin-4-yl)methyl)piperidin-4-yl)acetate (80 mg, 0.096 mmol, 97.0% yield) as a yellow oil: $^1$H NMR (400 MHz, CD$_3$OD) δ ppm 8.68 (s, 2H), 7.92 (d, J=1.8 Hz, 2H), 7.43 (t, J=2.0 Hz, 1H), 7.27-7.22 (m, 1H), 6.68 (s, 1H), 4.00 (s, 2H), 3.79 (br s, 4H), 3.63 (s, 3H), 2.92 (d, J=12.1 Hz, 2H), 2.75-2.72 (m, 4H), 2.35 (s, 3H), 2.12-2.06 (m, 2H), 1.74 (br s, 3H), 1.34 (d, J=12.8 Hz, 4H); LCMS m/z 584.3, 586.3 [M+H]$^+$.

Step 6: 2-(1-((2-(3,5-Dichlorophenyl)-6-((2-(4-methylpiperazin-1-yl)pyrimidin-5-yl)amino)pyridin-4-yl)methyl)piperidin-4-yl)acetic acid, 4 hydrochloride

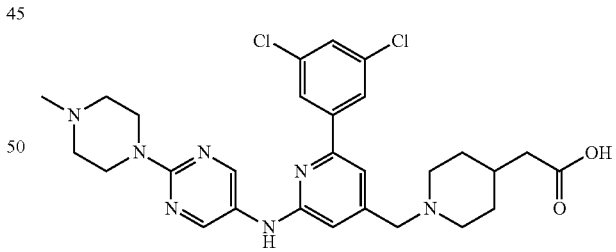

A mixture of methyl 2-(1-((2-(3,5-dichlorophenyl)-6-((2-(4-methylpiperazin-1-yl)pyrimidin-5-yl)amino)pyridin-4-yl)methyl)piperidin-4-yl)acetate (75 mg, 0.090 mmol) in concentrated HCl (1 mL, 8.15 mmol) and water (1 mL). The mixture was stirred at 80° C. for 15 min. The solvent was concentrated to give the crude product, the crude product was purified by preparative HPLC (MeCN/H$_2$O as eluents, acidic condition) and lyophilized to afford 2-(1-((2-(3,5-dichlorophenyl)-6-((2-(4-methylpiperazin-1-yl)pyrimidin-5-yl)amino)pyridin-4-yl)methyl)piperidin-4-yl)acetic acid, 4 hydrochloride (28.83 mg, 0.040 mmol, 44.8% yield) as a yellow solid: $^1$H NMR (400 MHz, CD$_3$OD) δ ppm 8.82 (s, 2H), 7.96 (d, J=2.0 Hz, 2H), 7.51 (t, J=1.9 Hz, 1H), 7.45 (s, 1H), 6.92 (s, 1H), 4.84 (br s, 2H), 4.30 (s, 2H), 3.59 (d, J=13.5 Hz, 4H), 3.36-3.32 (m, 2H), 3.20-3.07 (m, 4H), 2.95 (s, 3H), 2.30 (d, J=6.6 Hz, 2H), 2.04 (d, J=13.7 Hz, 3H), 1.64-1.55 (m, 2H); ES-LCMS m/z 570.2, 572.2 [M+H]$^+$.

Example 333: 2-(1-((6-(3,5-Dichlorophenyl)-3-methyl-2-((5-(4-methylpiperazin-1-yl)pyrazin-2-yl)oxy)pyridin-4-yl)methyl)piperidin-4-yl)acetic acid

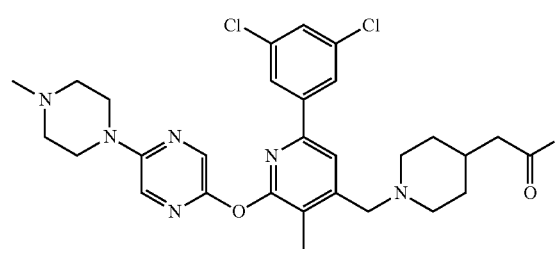

Step 1: 2-((4-(((tert-Butyldimethylsilyl)oxy)methyl)-6-(3,5-dichlorophenyl)-3-methylpyridin-2-yl)oxy)-5-chloropyrazine

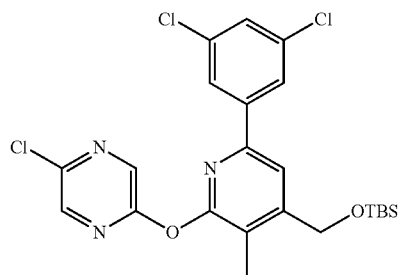 [SMILES: Cc1c(CO[Si](C)(C)C(C)(C)C)cc(-c2cc(Cl)cc(Cl)c2)nc1Oc1cnc(Cl)cn1]

A mixture of 4-(((tert-butyldimethylsilyl)oxy)methyl)-6-(3,5-dichlorophenyl)-3-methylpyridin-2-ol (500 mg, 1.130 mmol), 2,5-dichloropyrazine (505 mg, 3.39 mmol), 18-crown-6 (149 mg, 0.565 mmol) and K$_2$CO$_3$ (468 mg, 3.39 mmol) in DMF (15 mL) was stirred at 80° C. for 5 h. After filtration, the filtrate was concentrated. The crude material was purified by flash chromatography (from pure PE to PE/EtOAc=5/1, TLC: PE/EtOAc=5/1, R$_f$=0.6) to yield 2-((4-(((tert-butyldimethylsilyl)oxy)methyl)-6-(3,5-dichlorophenyl)-3-methylpyridin-2-yl)oxy)-5-chloropyrazine (400 mg, 0.733 mmol, 64.9% yield) as a white solid: $^1$H NMR (400 MHz, CDCl$_3$) δ ppm 8.37 (s, 1H), 8.25 (s, 1H), 7.77 (s, 1H), 7.69 (d, J=1.8 Hz, 2H), 7.34 (s, 1H), 4.79 (s, 2H), 2.23 (s, 3H), 1.01 (s, 9H), 0.18 (s, 6H); ES-LCMS m/z: 510.1, 512.1 [M+H]$^+$.

Step 2: tert-Butyl 4-(5-((4-(((tert-butyldimethylsilyl)oxy)methyl)-6-(3,5-dichlorophenyl)-3-methylpyridin-2-yl)oxy)pyrazin-2-yl)piperazine-1-carboxylate

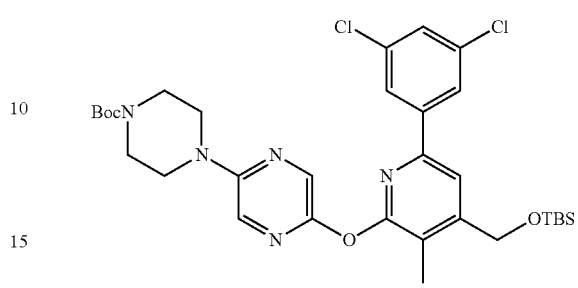

A mixture of 2-((4-(((tert-butyldimethylsilyl)oxy)methyl)-6-(3,5-dichlorophenyl)-3-methylpyridin-2-yl)oxy)-5-chloropyrazine (340 mg, 0.623 mmol), Xantphos (72.1 mg, 0.125 mmol), Cs$_2$CO$_3$ (609 mg, 1.869 mmol), Pd$_2$(dba)$_3$ (57.0 mg, 0.062 mmol) and tert-butyl piperazine-1-carboxylate (580 mg, 3.11 mmol) in 1,4-dioxane (10 mL) was stirred at 90° C. for 14 h under N$_2$ atmosphere. After filtration, the filtrate was concentrated. The crude material was purified by flash chromatography (from PE/EtOAc=5/1 to 2/1, TLC: PE/EtOAc=3/1, R$_f$=0.5) to yield tert-butyl 4-(5-((4-(((tert-butyldimethylsilyl)oxy)methyl)-6-(3,5-dichlorophenyl)-3-methylpyridin-2-yl)oxy)pyrazin-2-yl)piperazine-1-carboxylate (300 mg, 0.409 mmol, 65.6% yield) as a yellow oil: NMR (400 MHz, CDCl$_3$) δ ppm 8.12 (d, J=1.3 Hz, 1H), 7.85 (d, J=1.3 Hz, 1H), 7.67-7.58 (m, 3H), 7.31-7.26 (m, 1H), 4.78 (s, 2H), 3.63-3.49 (m, 8H), 2.28 (s, 3H), 1.50 (s, 9H), 1.00 (s, 9H), 0.18-0.13 (m, 6H); ES-LCMS m/z 660.3, 662.3 [M+H]$^+$.

Step 3: tert-Butyl 4-(5-((6-(3,5-dichlorophenyl)-4-(hydroxymethyl)-3-methylpyridin-2-yl)oxy)pyrazin-2-yl)piperazine-1-carboxylate

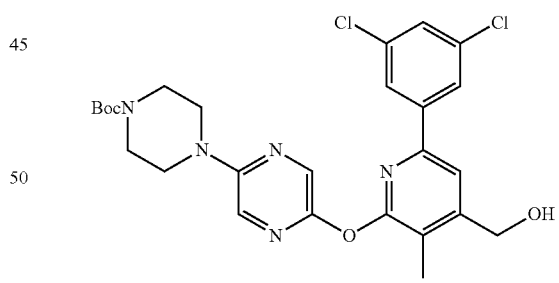

A mixture of tert-butyl 4-(5-((4-(((tert-butyldimethylsilyl)oxy)methyl)-6-(3,5-dichlorophenyl)-3-methylpyridin-2-yl)oxy)pyrazin-2-yl)piperazine-1-carboxylate (300 mg, 0.409 mmol) and TBAF (1 M in THF) (3 mF, 3.00 mmol) in THF (10 mF) was stirred at 20° C. for 30 min. The mixture was concentrated to give the crude product. The crude material was purified by flash chromatography (from pure DCM to DCM/MeOH=5/1, TFC: DCM/MeOH=20/1, R$_f$=0.6) to yield tert-butyl 4-(5-((6-(3,5-dichlorophenyl)-4-(hydroxymethyl)-3-methylpyridin-2-yl)oxy)pyrazin-2-yl)piperazine-1-carboxylate (350 mg, 0.320 mmol, 78.0% yield) as a yellow oil: $^1$H NMR (400 MHz, CDCl$_3$) δ ppm 8.11 (d, J=1.5 Hz, 1H), 7.86 (d, J=1.5 Hz, 1H), 7.73 (d, J=2.0 Hz, 1H), 7.65 (d, J=2.0 Hz, 3H), 4.86 (s, 2H), 3.58 (d, J=4.4 Hz, 8H), 2.27 (s, 3H), 1.50 (s, 9H); ES-FCMS m/z 546.2, 548.2 [M+H]$^+$.

Step 4: tert-Butyl 4-(5-((6-(3,5-dichlorophenyl)-3-methyl-4-(((methylsulfonyl)oxy)methyl)pyridin-2-yl)oxy)pyrazin-2-yl)piperazine-1-carboxylate

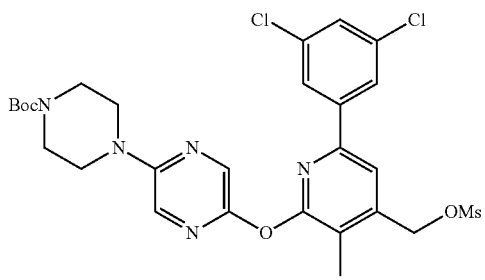 [SMILES: Cc1c(COS(C)(=O)=O)cc(-c2cc(Cl)cc(Cl)c2)nc1Oc1cnc(N2CCN(C(=O)OC(C)(C)C)CC2)cn1]

To a mixture of tert-butyl 4-(5-((6-(3,5-dichlorophenyl)-4-(hydroxymethyl)-3-methylpyridin-2-yl)oxy)pyrazin-2-yl)piperazine-1-carboxylate (300 mg, 0.275 mmol) and DIEA (106 mg, 0.824 mmol) in DCM (20 mL) was added MsCl (47.2 mg, 0.412 mmol). The mixture was stirred at 0° C. for 15 min. The mixture was added H$_2$O (15 mL), extracted with DCM (15 mL×2). The combined organic layers were washed with brine (20 mL), dried over Na$_2$SO$_4$, filtered and concentrated to yield tert-butyl 4-(5-((6-(3,5-dichlorophenyl)-3-methyl-4-(((methylsulfonyl)oxy)methyl)pyridin-2-yl)oxy)pyrazin-2-yl)piperazine-1-carboxylate (300 mg, 0.240 mmol, 87.0% yield) as a brown solid: $^1$H NMR (400 MHz, CDCl$_3$) δ ppm 8.13 (d, J=1.3 Hz, 1H), 7.68 (d, J=1.8 Hz, 2H), 7.62 (d, J=2.0 Hz, 3H), 5.33 (s, 2H), 3.61-3.59 (m, 8H), 3.13 (s, 3H), 2.39-2.36 (m, 3H), 1.46 (d, J=0.9 Hz, 9H); ES-LCMS m/z 624.2, 626.2 [M+H]$^+$.

Step 5: tert-Butyl 4-(5-((6-(3,5-dichlorophenyl)-4-((4-(2-methoxy-2-oxoethyl)piperidin-1-yl)methyl)-3-methylpyridin-2-yl)oxy)pyrazin-2-yl)piperazine-1-carboxylate

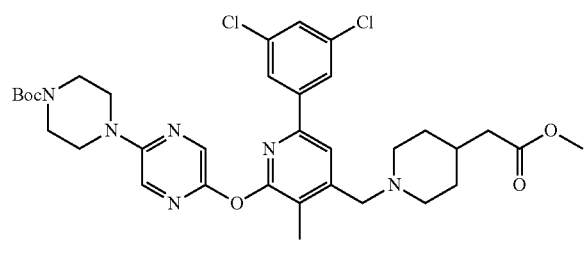 [SMILES: COC(=O)CC1CCN(Cc2cc(-c3cc(Cl)cc(Cl)c3)nc(Oc3cnc(N4CCN(C(=O)OC(C)(C)C)CC4)cn3)c2C)CC1]

To a mixture of tert-butyl 4-(5-((6-(3,5-dichlorophenyl)-3-methyl-4-(((methylsulfonyl)oxy)methyl)pyridin-2-yl)oxy)pyrazin-2-yl)piperazine-1-carboxylate (350 mg, 0.280 mmol) and methyl 2-(piperidin-4-yl)acetate, hydrochloride (72.4 mg, 0.336 mmol) in DML (10 mL) was added DIEA (181 mg, 1.401 mmol). The mixture was stirred at 20° C. for 12 h. After filtration, the filtrate was concentrated. The residue was purified by flash chromatography (from PE/EtOAc=5/1 to 2/1 to DCM/MeOH=10/1, TLC: PE/EtOAc=3/1, R$_f$=0.5) to yield tert-butyl 4-(5-((6-(3,5-dichlorophenyl)-4-((4-(2-methoxy-2-oxoethyl)piperidin-1-yl)methyl)-3-methylpyridin-2-yl)oxy)pyrazin-2-yl)piperazine-1-carboxylate (300 mg, 0.219 mmol, 78.0% yield) as a yellow oil: $^1$H NMR (400 MHz, CDCl$_3$) δ ppm 8.10 (s, 1H), 7.86-7.82 (m, 1H), 7.67 (s, 1H), 7.63-7.55 (m, 3H), 3.80 (s, 2H), 3.67 (s, 3H), 3.56 (d, J=5.1 Hz, 8H), 3.13-3.03 (m, 2H), 2.64 (d, J=13.7 Hz, 2H), 2.35 (s, 3H), 2.08-2.05 (m, 2H), 1.83 (br s, 2H), 1.66-1.63 (m, 3H), 1.48 (s, 9H); ES-LCMS m/z 685.3, 687.3 [M+H]$^+$.

Step 6: Methyl 2-(1-((6-(3,5-dichlorophenyl)-3-methyl-2-((5-(piperazin-1-yl)pyrazin-2-yl)oxy)pyridin-4-yl)methyl)piperidin-4-yl)acetate, 4 trifluoroacetic acid salt

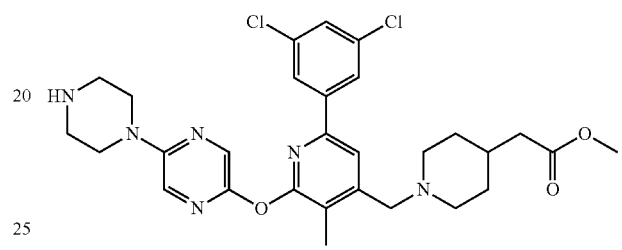

A solution of tert-butyl 4-(5-((6-(3,5-dichlorophenyl)-4-((4-(2-methoxy-2-oxoethyl)piperidin-1-yl)methyl)-3-methylpyridin-2-yl)oxy)pyrazin-2-yl)piperazine-1-carboxylate (270 mg, 0.197 mmol) and TFA (0.5 mL, 6.49 mmol) in DCM (2 mL) was stirred at 20° C. for 1 h. Then the mixture was concentrated to yield methyl 2-(1-((6-(3,5-dichlorophenyl)-3-methyl-2-((5-(piperazin-1-yl)pyrazin-2-yl)oxy)pyridin-4-yl)methyl)piperidin-4-yl)acetate, 4 trifluoroacetic acid salt (350 mg, 0.168 mmol, 85.0% yield) as a yellow oil: $^1$H NMR (400 MHz, CDCl$_3$) δ ppm 8.22 (s, 1H), 7.93 (s, 1H), 7.60 (s, 1H), 7.54 (d, J=1.8 Hz, 2H), 7.34 (br s, 1H), 4.40 (br s, 2H), 3.91 (br s, 4H), 3.77 (br s, 4H), 3.68 (s, 3H), 2.88-2.78 (m, 4H), 2.45 (s, 3H), 2.02 (br s, 2H), 1.58 (d, J=11.0 Hz, 3H), 1.42-1.34 (m, 2H); ES-LCMS m/z 585.2, 587.2 [M+H]$^+$.

Step 7: Methyl 2-(1-((6-(3,5-dichlorophenyl)-3-methyl-2-((5-(4-methylpiperazin-1-yl)pyrazin-2-yl)oxy)pyridin-4-yl)methyl)piperidin-4-yl)acetate

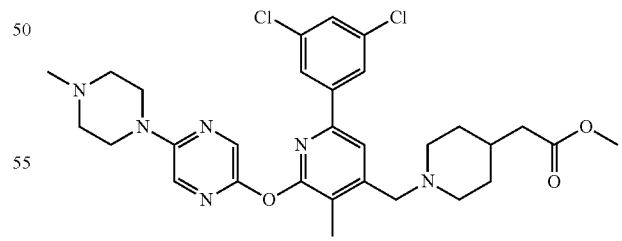

A mixture of paraformaldehyde (50.4 mg, 1.680 mmol) and methyl 2-(1-((6-(3,5-dichlorophenyl)-3-methyl-2-((5-(piperazin-1-yl)pyrazin-2-yl)oxy)pyridin-4-yl)methyl)piperidin-4-yl)acetate, 4 trifluoroacetic acid salt (350 mg, 0.168 mmol) in MeOH (15 mL) was stirred at 30° C. for 10 h. Then to the mixture was added NaBH$_3$CN (52.8 mg, 0.840 mmol). The whole mixture was stirred at 30° C. for another 2 h. The mixture was added saturated aqueous Na$_2$CO$_3$ solution (20 mL), extracted with DCM (20 mL×3). The combined organic layers were washed with brine (30 mL), dried over Na₂SO₄, filtered and concentrated. The residue was purified with preparative TLC (DCM/MeOH=10/1, R$_f$=0.5) to afford methyl 2-(1-((6-(3,5-dichlorophenyl)-3-methyl-2-((5-(4-methylpiperazin-1-yl)pyrazin-2-yl)oxy)pyridin-4-yl)methyl)piperidin-4-yl)acetate (70 mg, 0.097 mmol, 57.5% yield) as a yellow oil: $^1$H NMR (400 MHz, CDCl₃) δ ppm 8.03 (d, J=1.3 Hz, 1H), 7.79 (d, J=1.3 Hz, 1H), 7.56 (d, J=2.0 Hz, 2H), 7.40 (s, 1H), 7.21-7.20 (m, 1H), 3.63-3.59 (m, 5H), 3.56-3.52 (m, 4H), 3.43 (s, 2H), 2.83-2.75 (m, 2H), 2.52-2.49 (m, 4H), 2.31-2.29 (m, 6H), 2.21-2.19 (m, 2H), 1.73-1.61 (m, 3H), 1.33-1.23 (m, 2H); ES-LCMS m/z: 599.3, 601.3 [M+H]⁺.

Step 8: 2-(1-((6-(3,5-Dichlorophenyl)-3-methyl-2-((5-(4-methylpiperazin-1-yl)pyrazin-2-yl)oxy)pyridin-4-yl)methyl)piperidin-4-yl)acetic acid

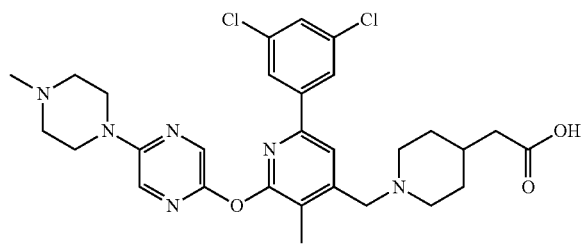 [SMILES: Cc1c(CN2CCC(CC(=O)O)CC2)cc(-c2cc(Cl)cc(Cl)c2)nc1Oc1cnc(N2CCN(C)CC2)cn1]

To a solution of methyl 2-(1-((6-(3,5-dichlorophenyl)-3-methyl-2-((5-(4-methylpiperazin-1-yl)pyrazin-2-yl)oxy)pyridin-4-yl)methyl)piperidin-4-yl)acetate (70 mg, 0.097 mmol) in THF (5.00 mL) and water (1 mL) was added LiOH·H₂O (40.6 mg, 0.967 mmol). The mixture was stirred at 50° C. for 5 h. The mixture was concentrated. To the residue was added MeCN (6 mL) and H₂O (2 mL), and acidified with 1 N HCl to pH=7-7.5. The mixture was purified by preparative HPLC (MeCN/H₂O as eluents, basic condition) followed by lyophilization to yield 2-(1-((6-(3,5-dichlorophenyl)-3-methyl-2-((5-(4-methylpiperazin-1-yl)pyrazin-2-yl)oxy)pyridin-4-yl)methyl)piperidin-4-yl)acetic acid (35.04 mg, 0.059 mmol, 60.6% yield) as a white solid: $^1$H NMR (400 MHz, CD₃OD) δ ppm 8.12 (d, J=1.3 Hz, 1H), 8.00 (d, J=1.3 Hz, 1H), 7.71-7.64 (m, 3H), 7.37 (t, J=1.9 Hz, 1H), 3.78 (s, 2H), 3.73-3.64 (m, 4H), 3.04 (d, J=11.9 Hz, 2H), 2.78 (t, J=5.1 Hz, 4H), 2.49 (s, 3H), 2.41 (s, 3H), 2.36 (t, J=10.9 Hz, 2H), 2.20 (d, J=6.6 Hz, 2H), 1.89-1.75 (m, 3H), 1.44-1.29 (m, 2H); ES-LCMS m/z: 585.3, 587.2 [M+H]⁺.

Example 334: 2-(1-((2-((2-(1,4-Diazabicyclo[3.2.1]octan-4-yl)pyrimidin-5-yl)oxy)-6-(3,5-dichlorophenyl)pyridin-4-yl)methyl)piperidin-4-yl)acetic acid, 4 hydrochloride

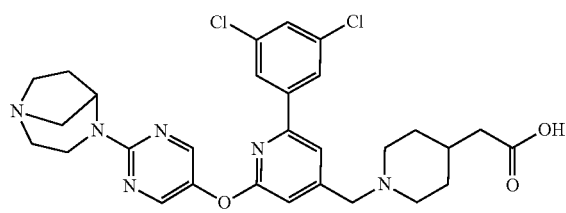 [SMILES: O=C(O)CC1CCN(Cc2cc(Oc3cnc(N4CCN5CCC4C5)nc3)nc(-c3cc(Cl)cc(Cl)c3)c2)CC1]

Step 1: Methyl 2-(1-((2-((2-(1,4-diazabicyclo[3.2.1]octan-4-yl)pyrimidin-5-yl)oxy)-6-(3,5-dichlorophenyl)pyridin-4-yl)methyl)piperidin-4-yl)acetate

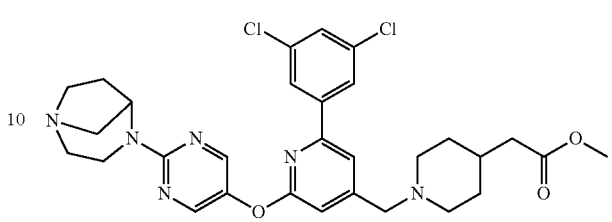

A mixture of methyl 2-(1-((2-(3,5-dichlorophenyl)-6-((2-(methylsulfinyl)pyrimidin-5-yl)oxy)pyridin-4-yl)methyl)piperidin-4-yl)acetate (500 mg, 0.728 mmol), 1,4-diazabicyclo[3.2.1]octane (576 mg, 4.37 mmol) and DIEA (941 mg, 7.28 mmol) in t-BuOH (3 mL) was stirred at 150° C. for 30 min under microwave. The reaction mixture was concentrated to afford the crude, which was purified by flash chromatography (from pure DCM to DCM/MeOH=50/1, TLC: DCM/MeOH=10/1, R$_f$=0.6) to yield methyl 2-(1-((2-((2-(1,4-diazabicyclo[3.2.1]octan-4-yl)pyrimidin-5-yl)oxy)-6-(3,5-dichlorophenyl)pyridin-4-yl)methyl)piperidin-4-yl)acetate (148 mg, 0.198 mmol, 27.2% yield) as a yellow oil: $^1$H NMR (400 MHz, CD₃OD) δ ppm 8.39-8.36 (m, 2H), 7.79 (d, J=1.8 Hz, 2H), 7.63 (s, 1H), 7.42 (t, J=1.9 Hz, 1H), 7.04 (s, 1H), 3.64 (s, 3H), 3.61 (s, 2H), 3.47-3.39 (m, 2H), 3.39-3.33 (m, 3H), 3.27-3.22 (m, 1H), 3.17-3.08 (m, 2H), 2.91 (d, J=11.9 Hz, 2H), 2.27 (d, J=6.8 Hz, 2H), 2.20-1.97 (m, 4H), 1.73 (d, J=13.2 Hz, 2H), 1.37-1.35 (m, 2H), 1.34-1.24 (m, 2H); ES-LCMS m/z 597.3, 599.3 [M+H]⁺.

Step 2: 2-(1-((2-((2-(1,4-Diazabicyclo[3.2.1]octan-4-yl)pyrimidin-5-yl)oxy)-6-(3,5-dichlorophenyl)pyridin-4-yl)methyl)piperidin-4-yl)acetic acid, 4 hydrochloride

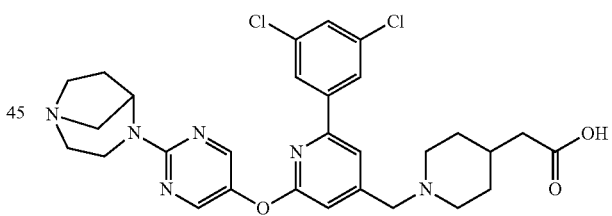

A solution of methyl 2-(1-((2-((2-(1,4-diazabicyclo[3.2.1]octan-4-yl)pyrimidin-5-yl)oxy)-6-(3,5-dichlorophenyl)pyridin-4-yl)methyl)piperidin-4-yl)acetate (650 mg, 0.870 mmol) in 3 N HCl solution (12 mL, 36.0 mmol) was stirred at 80° C. for 10 min. The mixture was concentrated to yield the residue. The residue was purified by preparative HPLC (MeCN/H₂O as eluents, acidic condition) followed by lyophilization to yield 2-(1-((2-((2-(1,4-diazabicyclo[3.2.1]octan-4-yl)pyrimidin-5-yl)oxy)-6-(3,5-dichlorophenyl)pyridin-4-yl)methyl)piperidin-4-yl)acetic acid, 4 hydrochloride (496.96 mg, 0.681 mmol, 78.0% yield) as a white solid: $^1$H NMR (400 MHz, D₂O/CD₃CN=10/1) δ ppm 8.52 (s, 2H), 7.84 (d, J=1.8 Hz, 2H), 7.76 (s, 1H), 7.59 (t, J=1.8 Hz, 1H), 7.29 (s, 1H), 5.63 (d, J=6.2 Hz, 1H), 4.59-4.52 (m, 1H), 4.42 (s, 2H), 3.76-3.67 (m, 2H), 3.66-3.53 (m, 4H), 3.53-3.44 (m, 3H), 3.13 (t, J=12.2 Hz, 2H), 2.61-2.53 (m, 1H), 2.42 (d, J=6.6 Hz, 2H), 2.28-2.17 (m, 1H), 2.08 (td, J=2.5, 5.0 Hz, 3H), 1.65-1.54 (m, 2H); ES-LCMS m/z 583.3, 585.3 [M+H]+.

Examples 335-338 (Table 17) were prepared by procedures analogous to those described for example 334.

TABLE 17

| Example | Structure/Name | 1H NMR | LCMS |
|---|---|---|---|
| 335 | 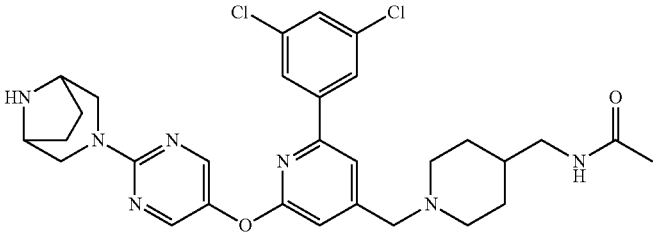 [SMILES: CC(=O)NCC1CCN(Cc2cc(Oc3cnc(N4CC5CCC(C4)N5)nc3)nc(-c3cc(Cl)cc(Cl)c3)c2)CC1]<br>N-((1-((2-((2-(3,8-diazabicyclo[3.2.1]octan-3-yl)pyrimidin-5-yl)oxy)-6-(3,5-dichlorophenyl)pyridin-4-yl)methyl)piperidin-4-yl)methyl)acetamide | 1H NMR (400 MHz, CD3OD) δ ppm 8.42 (s, 2H), 7.94 (br s, 1H), 7.87 (d, J = 1.8 Hz, 2H), 7.49 (br s, 1H), 7.32 (br s, 1H), 4.69 (br d, J = 3.9 Hz, 2H), 4.43 (s, 2H), 4.21 (br s, 2H), 3.61-3.58 (m, 2H), 3.39 (br d, J = 14.3 Hz, 2H), 3.18-3.02 (m, 4H), 2.13 (br d, J = 5.1 Hz, 2H), 2.04-1.93 (m, 7H), 1.85 (br s, 1H), 1.56 (br s, 2H) | ES-LCMS m/z 596.3, 598.3 [M + H]+. |
| 336 | 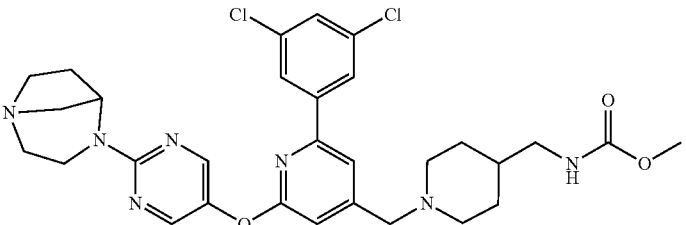<br>methyl ((1-((2-((2-(1,4-diazabicyclo[3.2.1]octan-4-yl)pyrimidin-5-yl)oxy)-6-(3,5-dichlorophenyl)pyridin-4-yl)methyl)piperidin-4-yl)methyl)carbamate | 1H NMR (400 MHz, CD3OD) δ ppm 8.45 (s, 2H), 7.94 (s, 1H), 7.86 (d, J = 1.8 Hz, 2H), 7.49 (t, J = 1.9 Hz, 1H), 7.32 (s, 1H), 5.77 (dd, J = 3.0, 5.6 Hz, 1H), 4.70 (d, J = 9.5 Hz, 1H), 4.43 (s, 2H), 3.70-3.52 (m, 9H), 3.51-3.38 (m, 4H), 3.14-3.02 (m, 3H), 2.58-2.46 (m, 1H), 2.19 (d, J = 6.8, 13.6 Hz, 1H), 1.98 (d, J = 13.5 Hz, 2H), 1.82 (brs, 1H), 1.64-1.50 (m, 2H) | ES-LCMS: m/z 612.3, 614.3 [M + H]+. |
| 337 | 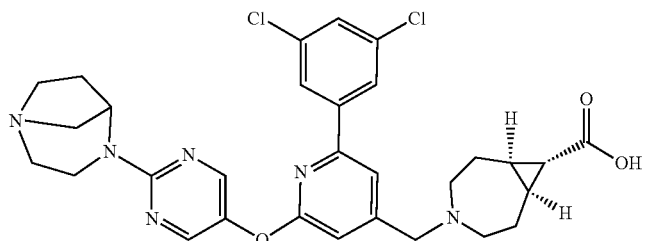<br>(1R,7S,8r)-4-((2-((2-(1,4-diazabicyclo[3.2.1]octan-4-yl)pyrimidin-5-yl)oxy)-6-(3,5-dichlorophenyl)pyridin-4-yl)methyl)-4-azabicyclo[5.1.0]octane-8-carboxylic acid | 1H NMR (400 MHz, D2O) δ ppm 8.35 (s, 2H), 7.55-7.44 (m, 3H), 7.30 (s, 1H), 7.09 (s, 1H), 5.45 (d, J = 5.5 Hz, 1H), 4.73-4.71 (m, 1H), 4.39-4.38 (m, 1H), 4.35-4.31 (m, 3H), 3.64-3.54 (m, 2H), 3.53-3.43 (m, 3H), 3.39 (s, 3H), 3.20 (s, 2H), 2.44 (ddd, J = 13.7, 10.1, 7.0 Hz, 3H), 2.12 (dt, J = 13.2, 6.8 Hz, 1H), 2.07-1.96 (m, 2H), 1.68 (s, 2H | ES-LCMS m/z 595.2, 597.2 [M + H]+. |

TABLE 17-continued

| Example | Structure/Name | $^1$H NMR | LCMS |
|---|---|---|---|
| 338 | 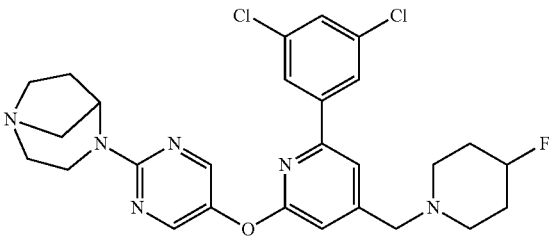 [SMILES: FC1CCN(Cc2cc(Oc3cnc(N4CCN5CCC4C5)nc3)nc(-c3cc(Cl)cc(Cl)c3)c2)CC1]<br>4-(5-((6-(3,5-dichlorophenyl)-4-((4-fluoropiperidin-1-yl)methyl)pyridin-2-yl)oxy)pyrimidin-2-yl)-1,4-diazabicyclo[3.2.1]octane | $^1$H NMR (400 MHz, CD$_3$OD) δ ppm 8.44 (s, 2H), 7.95 (s, 1H), 7.86 (d, J = 1.8 Hz, 2H), 7.49 (t, J = 1.8 Hz, 1H), 7.33 (s, 1H), 5.77 (dd, J = 3.2, 5.8 Hz, 1H), 5.08-4.92 (m, 1H), 4.69 (d, J = 9.3 Hz, 1H), 4.47 (s, 2H), 3.71-3.61 (m, 3H), 3.53 (d, J = 6.6 Hz, 2H), 3.50-3.44 (m, 4H), 3.39 (d, J = 7.9 Hz, 2H), 2.60-2.31 (m, 2H), 2.28-2.18 (m, 4H) | ES-LCMS m/z 543.1, 545.0 [M + H]$^+$. |

Example 339: 2-(1-((2-(3,5-Dichlorophenyl)-6-((5-(4-methylpiperazin-1-yl)pyrazin-2-yl)oxy)pyridin-4-yl)methyl)piperidin-4-yl)acetic acid

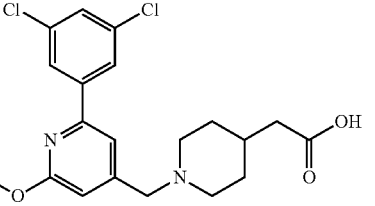

Step 1: Ethyl 2-(1-((2-((5-chloropyrazin-2-yl)oxy)-6-(3,5-dichlorophenyl)pyridin-4-yl)methyl)piperidin-4-yl)acetate

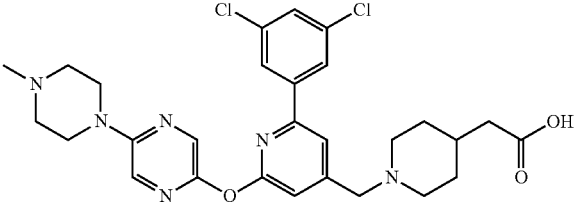 [SMILES: CN1CCN(c2cnc(Oc3cc(CN4CCC(CC(=O)O)CC4)cc(-c4cc(Cl)cc(Cl)c4)n3)cn2)CC1]

To a solution of ethyl 2-(1-((2-(3,5-dichlorophenyl)-6-hydroxypyridin-4-yl)methyl)piperidin-4-yl)acetate (5 g, 10.04 mmol) and 2,5-dichloropyrazine (2.243 g, 15.06 mmol) in DMF (120 mL) was added K$_2$CO$_3$ (2.77 g, 20.08 mmol). Then the reaction mixture was stirred at 80° C. for 12 h. The solid was filtered off and solvent was removed in vacuo to give the crude product which was purified by flash chromatography (from pure PE to PE/EtOAc=3/1, TLC: PE/EtOAc=2/1, R$_f$=0.45) to afford ethyl 2-(1-((2-((5-chloropyrazin-2-yl)oxy)-6-(3,5-dichlorophenyl)pyridin-4-yl)methyl)piperidin-4-yl)acetate (4.3 g, 7.22 mmol, 71.9% yield) as a yellow oil: $^1$H NMR (400 MHz, CDCl$_3$) δ ppm 8.37 (d, J=1.1 Hz, 1H), 8.27 (d, J=1.1 Hz, 1H), 7.73 (d, J=1.8 Hz, 2H), 7.54 (s, 1H), 7.36 (t, J=1.8 Hz, 1H), 7.07 (s, 1H), 4.20-4.12 (m, 2H), 3.57 (s, 2H), 2.86 (d, J=11.5 Hz, 2H), 2.25 (d, J=7.1 Hz, 2H), 2.11-2.05 (m, 2H), 1.82 (ddd, J=3.9, 7.3, 11.1 Hz, 1H), 1.73 (d, J=12.6 Hz, 2H), 1.42-1.31 (m, 2H), 1.26-1.19 (m, 3H); ES-LCMS m/z 535.1, 537.2 [M+H]$^+$.

Step 2: tert-Butyl 4-(5-((6-(3,5-dichlorophenyl)-4-((4-(2-ethoxy-2-oxoethyl)piperidin-1-yl)methyl)pyridin-2-yl)oxy)pyrazin-2-yl)piperazine-1-carboxylate

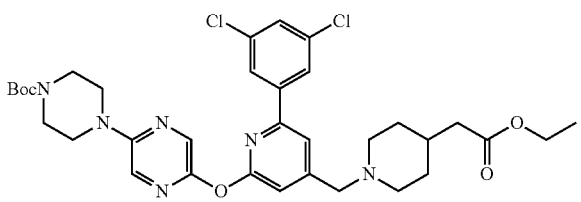 [SMILES: CCOC(=O)CC1CCN(Cc2cc(Oc3cnc(N4CCN(C(=O)OC(C)(C)C)CC4)cn3)nc(-c3cc(Cl)cc(Cl)c3)c2)CC1]

To a mixture of ethyl 2-(1-((2-((5-chloropyrazin-2-yl)oxy)-6-(3,5-dichlorophenyl)pyridin-4-yl)methyl)piperidin-4-yl)acetate (4.3 g, 7.22 mmol), tert-butyl piperazine-1-carboxylate (4.04 g, 21.67 mmol), Xantphos (0.209 g, 0.361 mmol) and Cs$_2$CO$_3$ (7.06 g, 21.67 mmol) in THF (100 mL) was added Pd$_2$(dba)$_3$ (0.331 g, 0.361 mmol). The reaction was stirred at 80° C. for 6 h under N$_2$ atmosphere. The solid was filtered off and solvent was removed in vacuo to give the crude product which was purified by flash chromatography (from pure PE to PE:EtOAc=1:1, TLC: PE:EtOAc=1:1, R$_f$=0.35) to afford tert-butyl 4-(5-((6-(3,5-dichlorophenyl)-4-((4-(2-ethoxy-2-oxoethyl)piperidin-1-yl)methyl)pyridin-2-yl)oxy)pyrazin-2-yl)piperazine-1-carboxylate (4.15 g, 5.45 mmol, 75.0% yield) as a pale yellow solid: $^1$H NMR (400 MHz, CDCl$_3$) δ ppm 8.13 (d, J=1.3 Hz, 1H), 7.85 (d, J=1.3 Hz, 1H), 7.71 (d, J=2.0 Hz, 2H), 7.44 (s, 1H), 7.32 (t, J=1.9 Hz, 1H), 6.96 (s, 1H), 4.14-4.10 (m, 2H), 3.58 (d, J=4.0 Hz, 8H), 3.52 (s, 2H), 2.86 (d, J=11.5 Hz, 2H), 2.24 (d, J=7.1 Hz, 2H), 2.06-2.00 (m, 2H), 1.80 (tdd, J=3.8, 7.4, 11.2 Hz, 1H), 1.71 (d, J=12.8 Hz, 2H), 1.49 (s, 9H), 1.40-1.30 (m, 2H), 1.27-1.20 (m, 3H); ES-LCMS m/z 685.3, 687.3 [M+H]$^+$.

Step 3: Ethyl 2-(1-((2-(3,5-dichlorophenyl)-6-((5-(piperazin-1-yl)pyrazin-2-yl)oxy)pyridin-4-yl)methyl)piperidin-4-yl)acetate, 4 trifluoroacetic acid

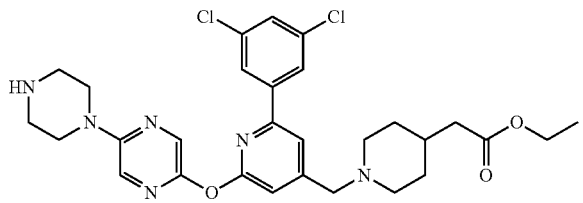 [SMILES: CCOC(=O)CC1CCN(Cc2cc(Oc3cnc(N4CCNCC4)cn3)nc(-c3cc(Cl)cc(Cl)c3)c2)CC1]

To a solution of tert-butyl 4-(5-((6-(3,5-dichlorophenyl)-4-((4-(2-ethoxy-2-oxoethyl)piperidin-1-yl)methyl)pyridin-2-yl)oxy)pyrazin-2-yl)piperazine-1-carboxylate (2.6 g, 3.41 mmol) in DCM (30 mL) was added TFA (6 mL, 78 mmol). Then the reaction mixture was stirred at 25° C. for 30 min. The solvent was removed in vacuo to give ethyl 2-(1-((2-(3,5-dichlorophenyl)-6-((5-(piperazin-1-yl)pyrazin-2-yl)oxy)pyridin-4-yl)methyl)piperidin-4-yl)acetate, 4 trifluoroacetic acid (3.8 g, 3.28 mmol, 96.0% yield) as a yellow oil: $^1$H NMR (400 MHz, CD$_3$OD) δ ppm 8.22 (d, J=1.1 Hz, 1H), 8.12 (d, J=1.1 Hz, 1H), 7.84 (s, 1H), 7.80 (d, J=2.0 Hz, 2H), 7.50 (t, J=1.9 Hz, 1H), 7.28 (s, 1H), 4.46-4.36 (m, 2H), 4.13 (q, J=7.1 Hz, 2H), 3.94-3.83 (m, 4H), 3.62-3.53 (m, 2H), 3.42-3.36 (m, 4H), 3.12 (t, J=12.7 Hz, 2H), 2.34 (d, J=6.2 Hz, 2H), 2.04 (d, J=14.6 Hz, 3H), 1.62-1.49 (m, 2H), 1.31-1.18 (m, 3H); ES-LCMS m/z 585.3, 587.3 [M+H]$^+$.

Step 4: Ethyl 2-(1-((2-(3,5-dichlorophenyl)-6-((5-(4-methylpiperazin-1-yl)pyrazin-2-yl)oxy)pyridin-4-yl)methyl)piperidin-4-yl)acetate

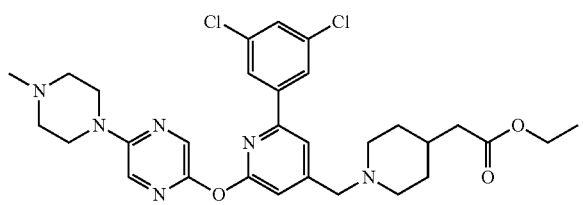 [SMILES: CCOC(=O)CC1CCN(Cc2cc(Oc3cnc(N4CCN(C)CC4)cn3)nc(-c3cc(Cl)cc(Cl)c3)c2)CC1]

To a solution of ethyl 2-(1-((2-(3,5-dichlorophenyl)-6-((5-(piperazin-1-yl)pyrazin-2-yl)oxy)pyridin-4-yl)methyl)piperidin-4-yl)acetate, 4 trifluoroacetic acid (3.8 g, 3.28 mmol) in MeOH (12 mL) was added paraformaldehyde (4.93 g, 164 mmol). After stirring at 25° C. for 12 h, NaBH$_3$CN (2.063 g, 32.8 mmol) was added. Then the mixture was stirred for another 3 h. Saturated aqueous NaHCO$_3$ solution (100 mL) was added and extracted with DCM (50 mL×3). The combined organic layers were dried over Na$_2$SO$_4$ and concentrated in vacuo to give ethyl 2-(1-((2-(3,5-dichlorophenyl)-6-((5-(4-methylpiperazin-1-yl)pyrazin-2-yl)oxy)pyridin-4-yl)methyl)piperidin-4-yl)acetate (2.1 g, 3.15 mmol, 96.0% yield) as a pale yellow solid: $^1$H NMR (400 MHz, CD$_3$OD) δ ppm 8.11 (d, J=1.3 Hz, 1H), 7.98 (d, J=1.3 Hz, 1H), 7.77 (d, J=1.8 Hz, 2H), 7.65 (s, 1H), 7.42 (t, J=1.9 Hz, 1H), 7.04 (s, 1H), 4.11 (q, J=7.1 Hz, 2H), 3.69-3.62 (m, 4H), 3.60 (s, 2H), 2.91 (d, J=11.7 Hz, 2H), 2.36 (s, 3H), 2.59 (t, J=5.0 Hz, 4H), 2.26 (d, J=6.8 Hz, 2H), 2.15-2.06 (m, 2H), 1.83-1.77 (m, 1H), 1.73 (d, J=13.0 Hz, 2H), 1.40-1.31 (m, 2H), 1.23 (t, J=7.1 Hz, 3H); ES-LCMS m/z 599.3, 601.3 [M+H]$^+$.

Step 5: 2-(1-((2-(3,5-Dichlorophenyl)-6-((5-(4-methylpiperazin-1-yl)pyrazin-2-yl)oxy)pyridin-4-yl)methyl)piperidin-4-yl)acetic acid

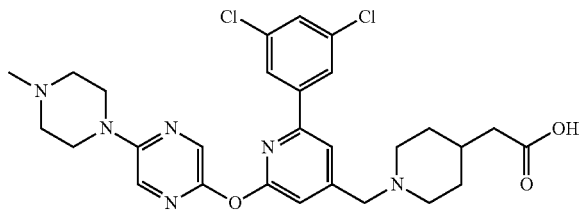 [SMILES: CN1CCN(c2cnc(Oc3cc(CN4CCC(CC(=O)O)CC4)cc(-c4cc(Cl)cc(Cl)c4)n3)cn2)CC1]

To a solution of ethyl 2-(1-((2-(3,5-dichlorophenyl)-6-((5-(4-methylpiperazin-1-yl)pyrazin-2-yl)oxy)pyridin-4-yl)methyl)piperidin-4-yl)acetate (2.1 g, 3.15 mmol) in THF (50 mL) and water (5 mL) was added LiOH·H$_2$O (0.661 g, 15.76 mmol). Then the reaction mixture was stirred at 25° C. for 12 h. 1 N HCl solution was added to adjust pH=6-7. The solvent was removed in vacuo to give the crude product which was purified by preparative HPLC (MeCN/H$_2$O as eluents, basic condition) and lyophilized to afford 2-(1-((2-(3,5-dichlorophenyl)-6-((5-(4-methylpiperazin-1-yl)pyrazin-2-yl)oxy)pyridin-4-yl)methyl)piperidin-4-yl)acetic acid (1511.38 mg, 2.62 mmol, 83.0% yield) as a white solid: $^1$H NMR (400 MHz, CD$_3$OD) δ ppm 8.15 (s, 1H), 8.06 (s, 1H), 7.85 (d, J=1.8 Hz, 2H), 7.76 (s, 1H), 7.63 (s, 1H), 7.00 (s, 1H), 3.54 (br s, 6H), 2.79 (d, J=10.8 Hz, 2H), 2.42 (d, J=4.6 Hz, 4H), 2.21 (s, 3H), 2.13 (d, J=6.4 Hz, 2H), 2.02-1.93 (m, 2H), 1.63 (d, J=11.2 Hz, 3H), 1.21 (d, J=10.8 Hz, 2H); ES-LCMS m/z 571.3, 573.2 [M+H]$^+$.

Examples 340-366 (Table 18) were prepared by procedures analogous to those described for example 339.

TABLE 18

| Example | Structure/Name | $^1$H NMR | LCMS |
|---|---|---|---|
| 340 | 2-(1-((2-(3,5-dichlorophenyl)-6-((5-(4-methyl-1,4-diazepan-1-yl)pyrazin-2-yl)oxy)pyridin-4-yl)methyl)piperidin-4-yl)acetic acid | $^1$H NMR (400 MHz, CD$_3$OD) δ = 8.12 (d, J = 1.3 Hz, 1H), 7.88 (d, J = 1.3 Hz, 1H), 7.82 (d, J = 1.8 Hz, 2H), 7.69 (s, 1H), 7.45 (t, J = 1.9 Hz, 1H), 7.06 (s, 1H), 4.04-3.97 (m, 2H), 3.77 (t, J = 6.1 Hz, 2H), 3.71 (s, 2H), 3.17-3.11 (m, 2H), 3.08-3.02 (m, 2H), 2.99 (d, J = 11.8 Hz, 2H), 2.67 (s, 3H), 2.29-2.15 (m, 6H), 1.81 (d, J = 10.3 Hz, 3H), 1.45-1.31 (m, 2H) | ES-LCMS m/z: 585.3, 587.3 [M + H]+. |

TABLE 18-continued

| Example | Structure/Name | ¹H NMR | LCMS |
|---|---|---|---|
| 341 | 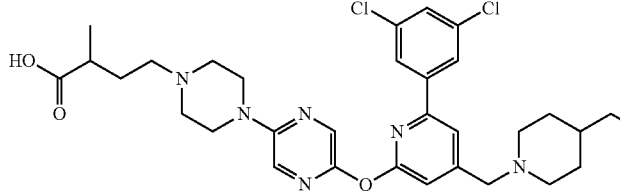<br>4-(4-(5-((6-(3,5-dichlorophenyl)-4-((4-(2-hydroxyethyl)piperidin-1-yl)methyl)pyridin-2-yl)oxy)pyrazin-2-yl)piperazin-1-yl)-2-methylbutanoic acid | ¹H NMR (400 MHz, CDCl₃) δ ppm 8.13 (s, 1H), 7.84 (s, 1H), 7.71 (s, 2H), 7.45 (s, 1H), 7.33 (s, 1H), 6.96 (s, 1H), 3.70 (t, J = 5.8 Hz, 6H), 3.54 (s, 2H), 2.89 (d, J = 10.6 Hz, 4H), 2.82-2.74 (m, 3H), 2.72-2.64 (m, 1H), 2.61-2.53 (m, 1H), 2.03 (t, J = 11.1 Hz, 2H), 1.96-1.85 (m, 1H), 1.82-1.74 (m, 1H), 1.70 (d, J = 12.1 Hz, 2H), 1.54 (q, J = 6.4 Hz, 2H), 1.46 (s, 1H), 1.39-1.29 (m, 2H), 1.26 (d, J = 7.1 Hz, 3H) | ES-LCMS m/z: 643.2, 645.2 [M + H]⁺. |
| 342 | 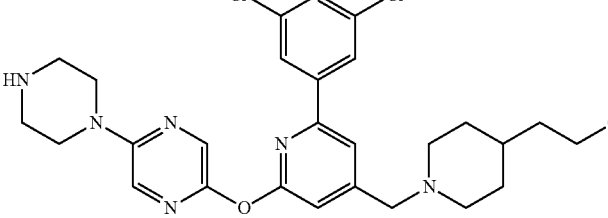<br>2-(1-((2-(3,5-dichlorophenyl)-6-((5-(piperazin-1-yl)pyrazin-2-yl)oxy)pyridin-4-yl)methyl)piperidin-4-yl)ethanol | ¹H NMR (400 MHz, CD₃OD) δ ppm 8.11 (s, 1H), 7.96 (s, 1H), 7.77 (d, J = 1.5 Hz, 2H), 7.65 (s, 1H), 7.41 (s, 1H), 7.03 (s, 1H), 3.63-3.56 (m, 8H), 3.02-2.95 (m, 4H), 2.91 (d, J = 11.5 Hz, 2H), 2.14-2.02 (m, 2H), 1.73 (d, J = 12.1 Hz, 2H), 1.48 (brs, 3H), 1.37-1.21 (m, 2H) | ES-LCMS: m/z 543.3, 545.3 [M + H]⁺. |
| 343 | 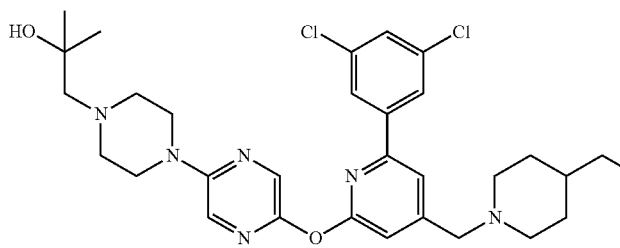<br>2-(1-((2-(3,5-dichlorophenyl)-6-((5-(4-(2-hydroxy-2-methylpropyl)piperazin-1-yl)pyrazin-2-yl)oxy)pyridin-4-yl)methyl)piperidin-4-yl)acetic acid | ¹H NMR (400 MHz, CDCl₃) δ ppm 8.12 (d, J = 1.1 Hz, 1H), 7.84 (s, 1H), 7.71 (d, J = 2.0 Hz, 2H), 7.49 (s, 1H), 7.33 (t, J = 1.9 Hz, 1H), 6.91 (s, 1H), 3.61 (s, 6H), 3.01 (d, J = 11.2 Hz, 2H), 2.83-2.80 (m, 4H), 2.43 (s, 2H), 2.34 (d, J = 5.7 Hz, 2H), 2.12 (t, J = 10.8 Hz, 2H), 1.75 (d, J = 13.5 Hz, 3H), 1.64-1.53 (m, 2H), 1.22 (s, 6H) | ES-LCMS m/z 629.2, 631.2 (M + H)⁺. |
| 344 | 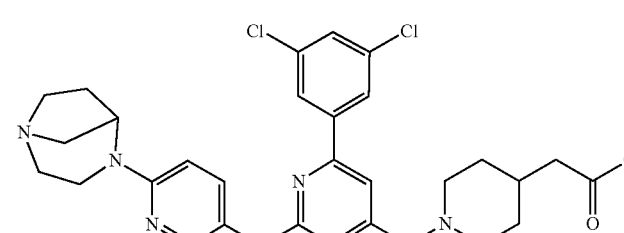<br>2-(1-((2-((6-(1,4-diazabicyclo[3.2.1]octan-4-yl)pyridazin-3-yl)oxy)-6-(3,5-dichlorophenyl)pyridin-4-yl)methyl)piperidin-4-yl)acetic acid | ¹H NMR (400 MHz, D₂O) δ ppm 7.57-7.51 (m, 2H), 7.48-7.42 (m, 1H), 7.38 (d, J = 1.8 Hz, 2H), 7.33-7.29 (m, 1H), 7.13 (s, 1H), 5.13 (br s, 1H), 4.28 (s, 2H), 4.10-4.03 (m, 1H), 3.57-3.51 (m, 3H), 3.49-3.41 (m, 4H), 3.38-3.31 (m, 2H), 2.99 (t, J = 12.0 Hz, 2H), 2.45-2.32 (m, 1H), 2.22 (d, J = 6.6 Hz, 2H), 2.16-2.06 (m, 1H), 1.90 (d, J = 13.5 Hz, 3H), 1.47-1.34 (m, 2H) | ES-LCMS m/z 583.3, 585.2 [M + H]⁺. |

TABLE 18-continued

| Example | Structure/Name | ¹H NMR | LCMS |
|---|---|---|---|
| 345 | 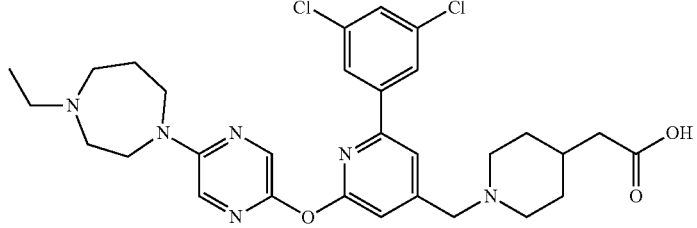 [SMILES: CCN1CCCN(c2cnc(Oc3cc(CN4CCC(CC(=O)O)CC4)cc(-c4cc(Cl)cc(Cl)c4)n3)cn2)CC1]<br>2-(1-((2-(3,5-dichlorophenyl)-6-((5-(4-ethyl-1,4-diazepan-1-yl)pyrazin-2-yl)oxy)pyridin-4-yl)methyl)piperidin-4-yl)acetic acid | ¹H NMR (400 MHz, CD₃OD) δ ppm 8.11 (s, 1H), 7.87 (s, 1H), 7.80 (d, J =2.0 Hz, 2H), 7.67 (s, 1H), 7.44 (s, 1H), 7.04 (s, 1H), 4.04-3.97 (m, 2H), 3.78-3.74 (m, 2H), 3.67 (s, 2H), 3.22-3.18 (m, 2H), 3.12-3.09 (m, 2H), 2.99-2.94 (m, 4H), 2.21-2.13 (m, 6H), 1.78 (d, J = 10.4 Hz, 3H), 1.40-1.33 (m, 2H), 1.25 (t, J = 7.3 Hz, 3H) | ES-LCMS m/z 559.3, 601.3 [M + H]⁺. |
| 346 | 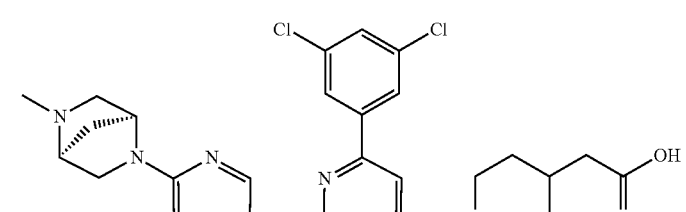<br>2-(1-((2-(3,5-dichlorophenyl)-6-((5-((1S,4S)-5-methyl-2,5-diazabicyclo+2.2.1+heptan-2-yl)pyrazin-2-yl)oxy)pyridin-4-yl)methyl)piperidin-4-yl)acetic acid | ¹H NMR (400 MHz, CD₃OD) δ ppm 8.09 (d, J = 1.3 Hz, 1H), 7.81 (d, J = 2.0 Hz, 2H), 7.75 (d, J = 1.3 Hz, 1H), 7.63 (s, 1H), 7.43 (t, J = 1.9 Hz, 1H), 6.97 (s, 1H), 4.83-4.77 (m, 1H), 4.08 (s, 1H), 3.79-3.71 (m, 1H), 3.71-3.56 (m, 3H), 3.35 (d, J = 11.2 Hz, 1H), 3.12 (dd, J = 1.7, 10.9 Hz, 1H), 2.97-2.86 (m, 2H), 2.74 (s, 3H), 2.31-2.24 (m, 1H), 2.24-2.06 (m, 5H), 1.71 (d, J = 12.1 Hz, 3H), 1.46-1.26 (m, 2H) | ES-LCMS m/z 583.2, 585.2 [M + H]⁺. |
| 347 | 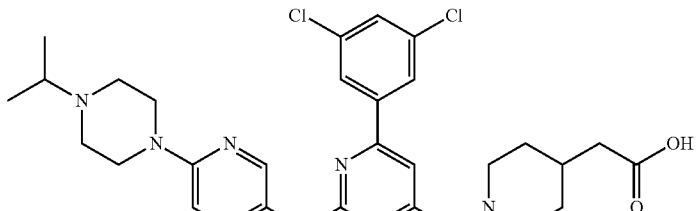<br>2-(1-((2-(3,5-dichlorophenyl)-6-((5-(4-isopropylpiperazin-1-yl)pyrazin-2-yl)oxy)pyridin-4-yl)methyl)piperidin-4-yl)acetic acid | ¹H NMR (400 MHz, CD₃OD) δ ppm 8.15 (d, J = 1.3 Hz, 1H), 8.02 (d, J = 1.1 Hz, 1H), 7.79 (d, J = 1.8 Hz, 2H), 7.68 (s, 1H), 7.44 (t, J = 1.9 Hz, 1H), 7.06 (s, 1H), 3.76-3.72 (m, 4H), 3.71 (brs, 2H), 3.09-3.03 (m, 1H), 3.01-2.95 (m, 6H), 2.24 (t, J = 11.1 Hz, 2H), 2.18 (d, J = 6.6 Hz, 2H), 1.79 (brd, J = 12.3 Hz, 2H), 1.43-1.30 (m, 3H), 1.23 (d, J = 6.6 Hz, 6H) | ES-LCMS m/z 599.2, 601.2 [M + H]⁺. |
| 348 | 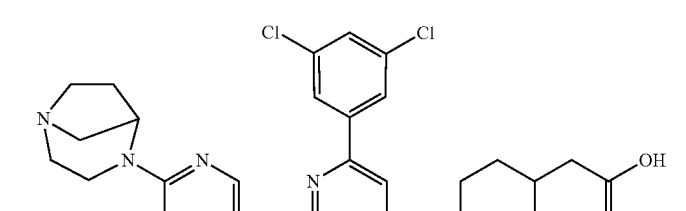<br>2-(1-((2-((5-(1,4-diazabicyclo[3.2.1]octan-4-yl)pyrazin-2-yl)oxy)-6-(3,5-dichlorophenyl)pyridin-4-yl)methyl)piperidin-4-yl)acetic acid | ¹H NMR (400 MHz, DMSO-d₆) δ ppm 8.14 (s, 1H), 7.94 (s, 1H), 7.85 (d, J = 1.8 Hz, 2H), 7.72 (s, 1H), 7.57 (s, 1H), 7.01 (s, 1H), 4.90 (br s, 1H), 3.66 (d, J = 7.0 Hz, 1H), 3.59 (s, 2H), 2.91-2.73 (m, 6H), 2.58 (br s, 1H), 2.17 (d, J = 6.3 Hz, 2H), 2.09 (t, J = 11.4 Hz, 2H), 1.93 (br s, 1H), 1.80 (br s, 1H), 1.69 (d, J = 8.8 Hz, 2H), 1.35-1.24 (m, 5H) | ES-LCMS: m/z 583.2, 585.3 [M + H]⁺. |

TABLE 18-continued

| Example | Structure/Name | ¹H NMR | LCMS |
|---|---|---|---|
| 349 | 2-(1-((2-(3,5-dichlorophenyl)-6-((5-(4-(3-hydroxybutyl)piperazin-1-yl)pyrazin-2-yl)oxy)pyridin-4-yl)methyl)piperidin-4-yl)acetic acid | ¹H NMR (400 MHz, CD₃OD) δ ppm 8.13 (s, 1H), 7.99 (s, 1H), 7.77 (d, J = 2.0 Hz, 2H), 7.68 (s, 1H), 7.42-7.41 (m, 1H), 7.07 (s, 1H), 3.86-3.85 (m, 1H), 3.75 (s, 2H), 3.69-3.67 (m, 4H), 3.02 (d, J = 11.6 Hz, 2H), 2.87-2.73 (m, 5H), 2.71-2.61 (m, 1H), 2.30-2.29 (m, 2H), 2.19 (d, J = 6.4 Hz, 2H), 1.82-1.80 (m, 3H), 1.76-1.67 (m, 2H), 1.40-1.38 (m, 2H), 1.20 (d, J = 6.4 Hz, 3H) | ES-LCMS m/z 629.3, 631.3 [M + H]⁺. |
| 350 | 2-(1-((2-(3,5-dichlorophenyl)-6-((5-(4-methylpiperazin-1-yl)pyrazin-2-yl)oxy)pyridin-4-yl)methyl)piperidin-4-yl)ethanol | ¹H NMR (400 MHz, CD₃OD) δ ppm 8.10 (s, 1H), 7.96 (s, 1H), 7.74 (s, 2H), 7.62 (s, 1H), 7.38 (s, 1H), 7.00 (s, 1H), 3.69-3.53 (m, 8H), 2.90 (d, J = 11.0 Hz, 2H), 2.59 (brs, 4H), 2.35 (s, 3H), 2.07 (t, J = 11.0 Hz, 2H), 1.72 (d, J = 12.3 Hz, 2H), 1.47 (brs, 3H), 1.28 (d, J = 9.9 Hz, 2H) | ES-LCMS m/z 557.2, 559.3 [M + H]⁺. |
| 351 | 3-(1-((2-(3,5-dichlorophenyl)-6-((5-(4-methyl-1,4-diazepan-1-yl)pyrazin-2-yl)oxy)pyridin-4-yl)methyl)piperidin-4-yl)-2-methylpropanoic acid | ¹H NMR (400 MHz, DMSO-d₆) δ ppm 8.08 (d, J = 1.1 Hz, 1H), 7.86-7.83 (m, 3H), 7.72 (s, 1H), 7.60 (t, J = 1.8 Hz, 1H), 6.96 (s, 1H), 3.78-3.71 (m, 2H), 3.66-3.60 (m, 6H), 2.78 (br d, J = 9.0 Hz, 2H), 2.65-2.59 (m, 2H), 2.41-2.33 (m, 1H), 2.25 (s, 3H), 1.96-1.83 (m, 4H), 1.69-1.49 (m, 3H), 1.22-1.06 (m, 4H), 1.01 (d, J = 6.8 Hz, 3H) | ES-LCMS m/z 613.2, 615.2 [M + H]⁺. |
| 352 | 2-(1-((2-(3,5-dichlorophenyl)-6-((5-(6-methyl-3,6-diazabicyclo[3.1.1]heptan-3-yl)pyrazin-2-yl)oxy)pyridin-4-yl)methyl)piperidin-4-yl)acetic acid | ¹H NMR (400 MHz, DMSO-d₆) δ ppm 8.18 (s, 1H), 7.87 (s, 1H), 7.84 (d, J = 1.1 Hz, 2H), 7.74 (s, 1H), 7.61 (s, 1H), 6.98 (s, 1H), 3.65 (d, J = 11.9 Hz, 2H), 3.58 (d, J = 6.0 Hz, 2H), 3.53 (s, 2H), 3.47 (d, J = 11.9 Hz, 3H), 2.79 (d, J = 10.8 Hz, 2H), 2.12 (d, J = 6.2 Hz, 2H), 2.05 (s, 3H), 1.98 (t, J = 11.1 Hz, 2H), 1.62 (d, J = 10.4 Hz, 3H), 1.54 (d, J = 8.6 Hz, 1H), 1.28-1.12 (m, 2H) | ES-LCMS m/z 583.2, 585.2 [M + H]⁺. |

TABLE 18-continued

| Example | Structure/Name | ¹H NMR | LCMS |
|---|---|---|---|
| 353 | 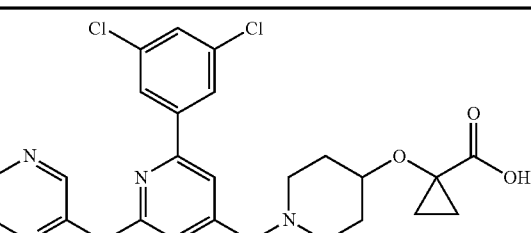<br>1-((1-((2-(3,5-dichlorophenyl)-6-((5-(4-methylpiperazin-1-yl)pyrazin-2-yl)oxy)pyridin-4-yl)methyl)piperidin-4-yl)oxy)cyclopropanecarboxylic acid | ¹H NMR (400 MHz, CD₃OD) δ ppm 8.11 (d, J = 1.3 Hz, 1H), 7.98 (d, J = 1.1 Hz, 1H), 7.77 (d, J = 2.0 Hz, 2H), 7.65 (s, 1H), 7.42 (t, J = 1.9 Hz, 1H), 7.05 (s, 1H), 4.60 (s, 1H), 3.68-3.61 (m, 6H), 2.77-2.68 (m, 1H), 2.72 (br s, 1H), 2.61 (t, J = 5.1 Hz, 4H), 2.41 (t, J = 9.0 Hz, 2H), 2.36 (s, 3H), 1.99-1.89 (m, 2H), 1.75 (dq, J = 3.9, 8.3 Hz, 2H), 1.27-1.22 (m, 2H), 1.08-1.01 (m, 2H) | ES-LCMS m/z: 613.1, 615.1 [M + H]⁺. |
| 354 | 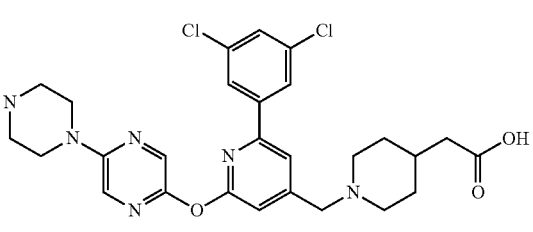<br>2-(1-((2-(3,5-dichlorophenyl)-6-((5-(4-(3-(methylsulfonyl)propyl)piperazin-1-yl)pyrazin-2-yl)oxy)pyridin-4-yl)methyl)piperidin-4-yl)acetic acid | ¹H NMR (400 MHz, CD₃OD) δ ppm 8.12 (d, J = 1.1 Hz, 1H), 7.98 (d, J = 1.1 Hz, 1H), 7.78 (d, J = 1.8 Hz, 2H), 7.70 (s, 1H), 7.44 (t, J = 1.8 Hz, 1H), 7.08 (s, 1H), 3.80 (s, 2H), 3.68-3.61 (m, 4H), 3.27-3.19 (m, 2H), 3.07 (, J = 11.7 Hz, 2H), 2.99 (s, 3H), 2.69-2.64 (m, 4H), 2.60 (t, J = 7.2 Hz, 2H), 2.36 (t, J = 11.4 Hz, 2H), 2.21 (d, J = 6.6 Hz, 2H), 2.06 (quin, J = 7.5 Hz, 2H), 1.83 (d, J = 11.7 Hz, 3H), 1.47-1.34 (m, 2H) | ;ES-LCMS m/z 677.1, 679.1 [M + H]⁺. |
| 355 | 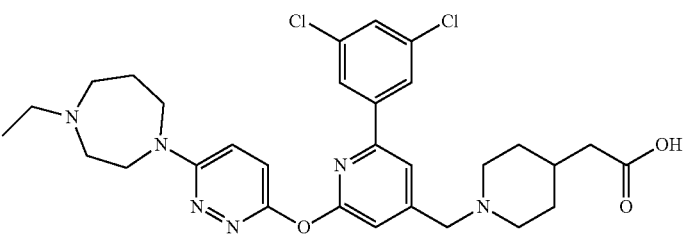 [SMILES: CCN1CCCN(c2ccc(Oc3cc(CN4CCC(CC(=O)O)CC4)cc(-c4cc(Cl)cc(Cl)c4)n3)nn2)CC1]<br>2-(1-((2-(3,5-dichlorophenyl)-6-((6-(4-ethyl-1,4-diazepan-1-yl)pyridazin-3-yl)oxy)pyridin-4-yl)methyl)piperidin-4-yl)acetic acid | ¹H NMR (400 MHz, CD₃OD) δ ppm 7.74 (d, J = 1.5 Hz, 2 H), 7.66 (s, 1 H), 7.36 (s, 3 H), 7.08 (s, 1 H), 4.06-3.95 (m, 2 H), 3.73 (t, J = 6.0 Hz, 2 H), 3.69-3.62 (m, 2 H), 3.25-3.16 (m, 2 H), 3.15-3.03 (m, 2 H), 3.01-2.89 (m, 4 H), 2.22-2.11 (m, 6 H), 1.75 (d, J = 12.1 Hz, 3 H), 1.39-1.29 (m, 2 H), 1.22 (t, J = 7.2 Hz, 3 H) | ES-LCMS m/z 599.3, 601.3 [M + H]⁺. |
| 356 | 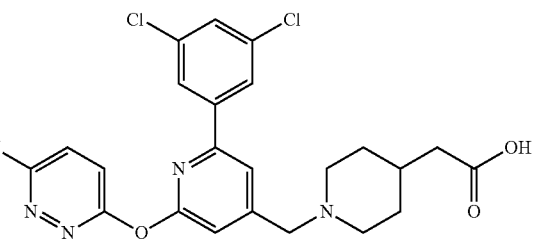<br>2-(1-((2-(3,5-dichlorophenyl)-6-((6-(4-methyl-1,4-diazepan-1-yl)pyridazin-3-yl)oxy)pyridin-4-yl)methyl)piperidin-4-yl)acetic acid | ¹H NMR (400 MHz, CD₃OD) δ ppm 8.12-8.07 (m, 2H), 8.02-7.97 (m, 1H), 7.93 (d, J = 1.8 Hz, 2H), 7.54 (t, J = 1.8 Hz, 1H), 7.52 (s, 1H), 4.48 (s, 2H), 4.37-4.25 (m, 1H), 4.21-4.08 (m, 1H), 3.90 (br s, 1H), 3.80 (br d, J = 12.3 Hz, 2H), 3.69 (br s, 1H), 3.59 (br d, J = 12.1 Hz, 2H), 3.52-3.41 (m, 2H), 3.16 (br t, J = 12.5 Hz, 2H), 2.99 (s, 3H), 2.57-2.40 (m, 2H), 2.32 (d, J = 6.4 Hz, 2H), 2.06 (br d, J = 13.2 Hz, 3H), 1.77-1.59 (m, 2H) | ES-LCMS m/z 585.3, 587.2 [M + H]⁺, |

TABLE 18-continued

| Example | Structure/Name | ¹H NMR | LCMS |
|---|---|---|---|
| 357 | 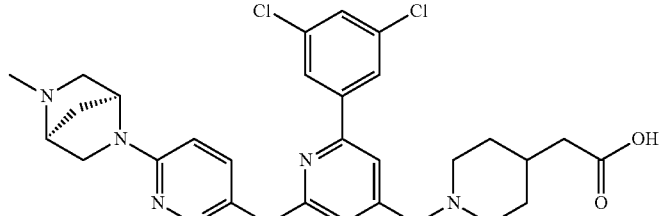<br>2-(1-((2-(3,5-dichlorophenyl)-6-((6-((1S,4S)-5-methyl-2,5-diazabicyclo[2.2.1]heptan-2-yl)pyridazin-3-yl)oxy)pyridin-4-yl)methyl)piperidin-4-yl)acetic acid | ¹H NMR (400 MHz, CD₃OD) δ ppm 8.12 (s, 1H), 8.01-7.93 (m, 2H), 7.92 (d, J = 2.0 Hz, 2H), 7.53 (d, J = 1.5 Hz, 2H), 5.29 (s, 1H), 4.72-4.57 (m, 1H), 4.50 (s, 2H), 4.17-3.97 (m, 3H), 3.59 (d, J = 11.9 Hz, 2H), 3.39 (d, J = 8.8 Hz, 1H), 3.17 (t, J = 12.2 Hz, 2H), 3.07 (s, 3H), 2.71-2.58 (m, 1H), 2.45 (s, 1H), 2.32 (d, J = 6.6 Hz, 2H), 2.05 (d, J = 14.1 Hz, 3H), 1.76-1.61 (m, 2H) | ES-LCMS m/z 583.3, 585.3 [M + H]⁺. |
| 358 | 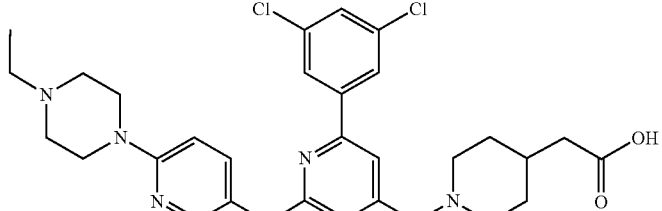<br>2-(1-((2-(3,5-dichlorophenyl)-6-((6-(4-ethylpiperazin-1-yl)pyridazin-3-yl)oxy)pyridin-4-yl)methyl)piperidin-4-yl)acetic acid | ¹H NMR (400 MHz, CDCl₃) δ ppm 7.74 (d, J = 1.8 Hz, 2H), 7.49 (s, 1H) 7.32 (t, J = 1.8 Hz, 1H), 7.23-7.19 (m, 1H), 7.13-7.09 (m, 1H), 7.02 (s, 1H), 3.71-3.66 (m, 4H), 3.58 (s, 2H), 2.93 (d, J = 11.5 Hz, 2H), 2.73-2.69 (m, 4H), 2.57 (d, J = 7.3 Hz, 2H), 2.27 (d, J = 6.2 Hz, 2H), 2.08 (t, J = 11.0 Hz, 2H), 1.83-1.70 (m, 3H), 1.51-1.40 (m, 2H), 1.16 (t, J = 7.2 Hz, 3H) | ES-LCMS m/z: 585.3, 587.3 [M + H]⁺. |
| 359 | 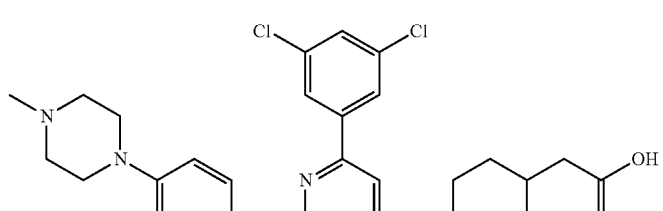<br>2-(1-((2-(3,5-dichlorophenyl)-6-((6-(4-methylpiperazin-1-yl)pyridazin-3-yl)oxy)pyridin-4-yl)methyl)piperidin-4-yl)acetic acid | ¹H NMR (400 MHz, CD₃OD) δ ppm 7.89 (d, J = 1.6 Hz, 2H), 7.80 (s, 1H), 7.59-7.52 (m, 2H), 7.46 (d, J = 9.8 Hz, 1H), 7.18 (s, 1H), 3.76-3.66 (m, 5H), 2.97 (d, J = 11.0 Hz, 2H), 2.67 (d, J = 5.1 Hz, 4H), 2.42 (s, 3H), 2.29-2.10 (m, 5H), 1.80 (d, J = 10.6 Hz, 3H), 1.46-1.31 (m, 2H) | ES-LCMS m/z: 571.2, 573.1 [M + H]⁺. |

TABLE 18-continued

| Example | Structure/Name | ¹H NMR | LCMS |
|---|---|---|---|
| 360 | 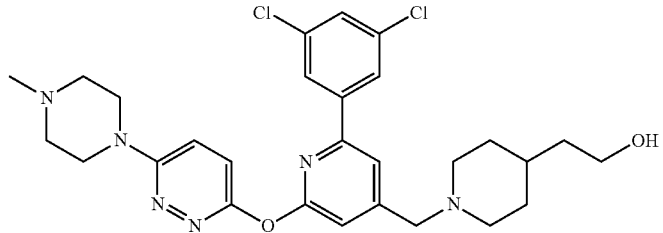 [SMILES: CN1CCN(c2ccc(Oc3cc(CN4CCC(CCO)CC4)cc(-c4cc(Cl)cc(Cl)c4)n3)nn2)CC1]<br>2-(1-((2-(3,5-dichlorophenyl)-6-((6-(4-methylpiperazin-1-yl)pyridazin-3-yl)oxy)pyridin-4-yl)methyl)piperidin-4-yl)ethanol | ¹H NMR (400 MHz, CDCl₃) δ ppm 7.74 (d, J =2.0 Hz, 2H), 7.48 (s, 1H), 7.33 (s, 1H), 7.23-7.18 (m, 1H), 7.13-7.06 (m, 2H), 3.72-3.63 (m, 6H), 3.53 (s, 2H), 2.86 (d, J = 11.2 Hz, 2H), 2.62-2.51 (m, 4H), 2.35 (s, 3H), 2.01 (t, J = 11.6 Hz, 2H), 1.70-1.68 (m, 2H), 1.53 (q, J = 6.6 Hz, 2H), 1.46 (d, J = 6.4 Hz, 1H), 1.38-1.28 (m, 2H); | ES-LCMS m/z: 557.2, 559.2 [M + H]⁺. |
| 361 | 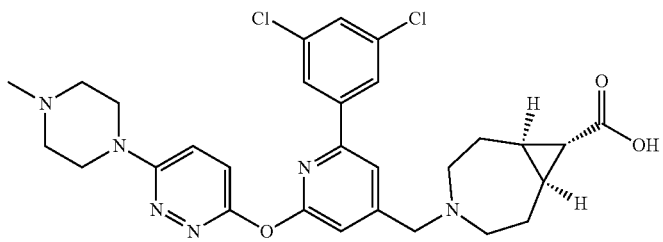 [SMILES: CN1CCN(c2ccc(Oc3cc(CN4CC[C@@H]5[C@H](CC4)[C@H]5C(=O)O)cc(-c4cc(Cl)cc(Cl)c4)n3)nn2)CC1]<br>(1R,7S,8r)-4-((2-(3,5-dichlorophenyl)-6-((6-(4-methylpiperazin-1-yl)pyridazin-3-yl)oxy)pyridin-4-yl)methyl)-4-azabicyclo[5.1.0]octane-8-carboxylic acid | ¹H NMR (400 MHz, CD₃OD) δ ppm 7.77 (d, J = 2.0 Hz, 2H), 7.69 (s, 1H), 7.52 (d, J = 9.7 Hz, 1H), 7.42 (t, J = 1.9 Hz, 1H), 7.41-7.38 (m, 1H), 7.13 (s, 1H), 3.79 (s, 2H), 3.72-3.68 (m, 4H), 2.89 (dd, J = 6.9, 12.9 Hz, 2H), 2.72 (t, J = 5.0 Hz, 4H), 2.62-2.55 (m, 2H), 2.45-2.42 (m, 3H), 2 27-2 19 (m, 2H) 1.57 (s, 4H), 1.46 (s, 1H); | ES-LCMS m/z 583.2, 585.2 [M + H]⁺. |
| 362 | 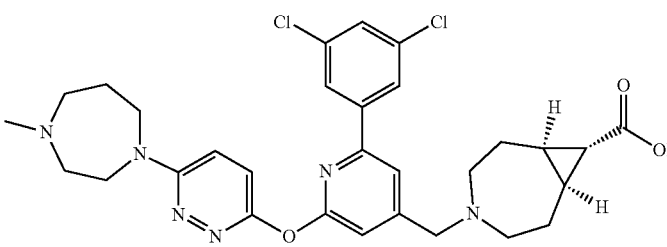<br>(1R,7S,8r)-4-((2-(3,5-dichlorophenyl)-6-((6-(4-methyl-1,4-diazepan-1-yl)pyridazin-3-yl)oxy)pyridin-4-yl)methyl)-4-azabicyclo[5.1.0]octane-8-carboxylic acid | ¹H NMR (400 MHz, DMSO-d₆)) δ ppm 7.85 (d, J = 2.0 Hz, 2H), 7.77 (s, 1H), 7.62 (t, J = 1.9 Hz, 1H), 7.39-7.33 (m, 1H), 7.32-7.26 (m, 1H), 7.05 (s, 1H), 3.77 (s, 2H), 3.70-3.62 (m, 2H), 2.77-2.58 (m, 4H), 2.50 (d, J = 1.8 Hz, 2H), 2.39 (d, J = 12.1 Hz, 2H), 2.33-2.21 (m, 3H), 2.11 (d, J = 9.9 Hz, 2H), 1.96-1.86 (m, 2H), 1.53-1.40 (m, 4H), 1.21 (s, 3H)); | ES-LCMS m/z 597.2, 599.1 [M + H]⁺. |

| Example | Structure/Name | ¹H NMR | LCMS |
|---|---|---|---|
| 363 | 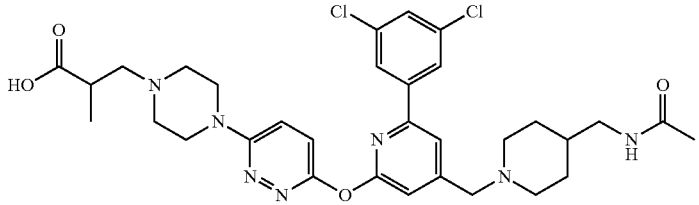 [SMILES: CC(=O)NCC1CCN(Cc2cc(Oc3ccc(N4CCN(CC(C)C(=O)O)CC4)nn3)nc(-c3cc(Cl)cc(Cl)c3)c2)CC1]<br>3-(4-(6-((4-((4-(acetamidomethyl)piperidin-1-yl)methyl)-6-(3,5-dichlorophenyl)pyridin-2-yl)oxy)pyridazin-3-yl)piperazin-1-yl)-2-methylpropanoic acid | ¹H NMR (400 MHz, CDCl₃) δ ppm 7.72 (d, J = 2.0 Hz, 2H), 7.47 (s, 1H), 7.33 (t, J = 1.8 Hz, 1H), 7.24 (s, 1H), 7.13 (d, J = 9.7 Hz, 1H), 7.07 (s, 1H), 5.68 (t, J = 5.8 Hz, 1H), 4.78 (s, 1H), 3.75 (d, J = 11.5 Hz, 4H), 3.54 (s, 2H), 3.15 (t, J = 6.4 Hz, 1H), 3.14-3.11 (m, 1H), 2.98 (d, J = 5.1 Hz, 2H), 2.88 (d, J = 11.2 Hz, 2H), 2.77-2.65 (m, 4H), 2.60 (d, J = 6.8 Hz, 1H), 2.05-2.00 (m, 2H), 1.98 (s, 3H), 1.68 (d, J = 12.1 Hz, 2H), 1.57-1.47 (m, 1H), 1.36-1.28 (m, 2H), 1.20 (d, J = 6.0 Hz, 3H); | ES-LCMS m/z 656.2, 658.2 [M + H]⁺. |
| 364 | 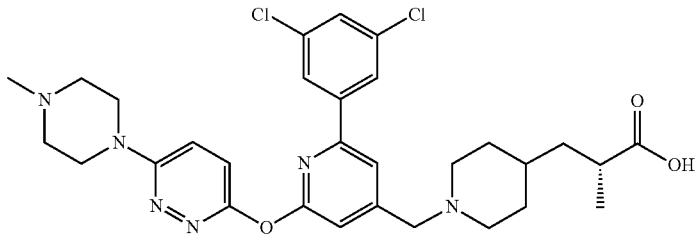<br>(R)-3-(1-((2-(3,5-dichlorophenyl)-6-((6-(4-methylpiperazin-1-yl)pyridazin-3-yl)oxy)pyridin-4-yl)methyl)piperidin-4-yl)-2-methylpropanoic acid | ¹H NMR (400 MHz, CDCl₃) δ ppm 7.72 (d, J = 2.0 Hz, 2H), 7.47 (s, 1H), 7.33 (t, J = 1.8 Hz, 1H), 7.24 (s, 1H), 7.13 (d, J = 9.7 Hz, 1H), 7.07 (s, 1H), 5.68 (t, J = 5.8 Hz, 1H), 4.78 (s, 1H), 3.75 (d, J = 11.5 Hz, 4H), 3.54 (s, 2H), 3.15 (t, J = 6.4 Hz, 1H), 3.14-3.11 (m, 1H), 2.98 (d, J = 5.1 Hz, 2H), 2.88 (d, J = 11.2 Hz, 2H), 2.77-2.65 (m, 4H), 2.60 (d, J = 6.8 Hz, 1H), 2.05-2.00 (m, 2H), 1.98 (s, 3H), 1.68 (d, J = 12.1 Hz, 2H), 1.57-1.47 (m, 1H), 1.36-1.28 (m, 2H), 1.20 (d, J = 6.0 Hz, 3H); | ES-LCMS m/z 656.2, 658.2 [M + H]⁺. |
| 365 | 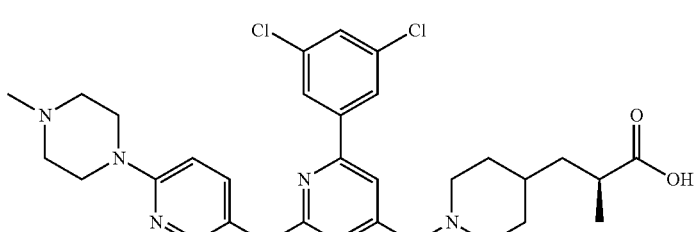<br>(S)-3-(1-((2-(3,5-dichlorophenyl)-6-((6-(4-methylpiperazin-1-yl)pyridazin-3-yl)oxy)pyridin-4-yl)methyl)piperidin-4-yl)-2-methylpropanoic acid | ¹H NMR (400 MHz, CD₃OD) δ ppm 7.80 (br s, 2H), 7.73 (s, 1H), 7.54 (d, J = 9.7 Hz, 1H), 7.46-7.37 (m, 2H), 7.14 (s, 1H), 3.73 (d, J = 8.4 Hz, 6H), 3.01 (s, 2H), 2.73 (s, 4H), 2.51-2.42 (m, 4H), 2.23 (t, J = 11.8 Hz, 2H), 1.85 (d, J = 13.0 Hz, 1H), 1.73 (d, J = 13.9 Hz, 1H), 1.68-1.60 (m, 1H), 1.40 (s, 1H), 1.34-1.21 (m, 3H), 1.12 (d, J = 6.8 Hz, 3H) | ES-LCMS m/z 599.3, 601.3 [M + H]⁺. |

TABLE 18-continued

| Example | Structure/Name | $^1$H NMR | LCMS |
|---|---|---|---|
| 366 | 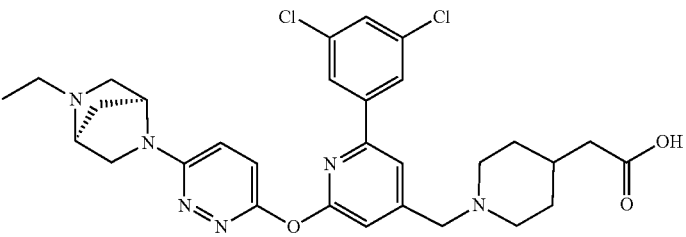 [SMILES: CCN1C[C@@H]2C[C@H]1CN2c1ccc(Oc2cc(CN3CCC(CC(=O)O)CC3)cc(-c3cc(Cl)cc(Cl)c3)n2)nn1]

2-(1-((2-(3,5-dichlorophenyl)-6-((6-((1S,4S)-5-ethyl-2,5-diazabicyclo[2.2.1]heptan-2-yl)pyridazin-3-yl)oxy)pyridin-4-yl)methyl)piperidin-4-yl)acetic acid | $^1$H NMR (400 MHz, CD$_3$OD) δ ppm 7.76 (d, J = 2.0 Hz, 2H), 7.68 (s, 1H), 7.43-7.38 (m, 2H), 7.26 (d, J = 9.5 Hz, 1H), 7.08 (s, 1H), 4.91-4.90 (m, 1H), 4.25 (s, 1H), 3.84 (d, J = 10.8 Hz, 1H), 3.72-3.63 (m, 3H), 3.39-3.34 (m, 1H), 3.24 (d, J = 9.5 Hz, 1H), 3.18-3.07 (m, 1H), 3.06-2.90 (m, 3H), 2.30-2.24 (m, 1H), 2.23-2.09 (m, 5H), 1.81-1.67 (m, 3H), 1.42-1.31 (m, 2H), 1.27 (t, J = 7.2 Hz, 3H) | ES-LCMS m/z 597.3, 599.4 [M + H]$^+$. |

Example 367: 3-(4-(5-((4-(((1R,7S,8r)-8-Acetamido-4-azabicyclo[5.1.0]octan-4-yl)methyl)-6-(3,5-dichlorophenyl)pyridin-2-yl)oxy)pyrimidin-2-yl)piperazin-1-yl)propanoic acid

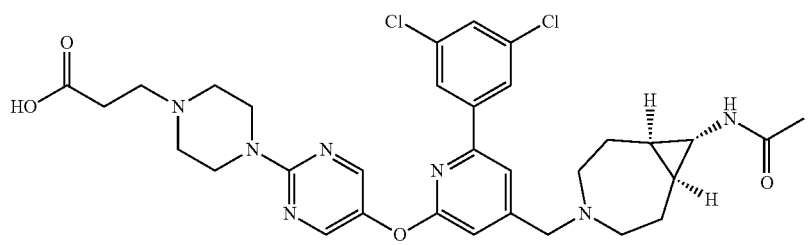 [SMILES: CC(=O)N[C@H]1[C@@H]2CCN(Cc3cc(Oc4cnc(N5CCN(CCC(=O)O)CC5)nc4)nc(-c4cc(Cl)cc(Cl)c4)c3)CC[C@@H]21]

Step 1: Methyl 3-(4-(5-((6-(3,5-dichlorophenyl)-4-(hydroxymethyl)pyridin-2-yl)oxy)pyrimidin-2-yl)piperazin-1-yl)propanoate Step 2: Methyl 3-(4-(5-((6-(3,5-dichlorophenyl)-4-(((methylsulfonyl)oxy)methyl)pyridin-2-yl)oxy)pyrimidin-2-yl)piperazin-1-yl)propanoate

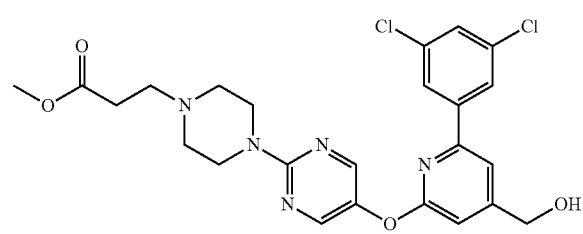 [SMILES: COC(=O)CCN1CCN(c2ncc(Oc3cc(CO)cc(-c4cc(Cl)cc(Cl)c4)n3)cn2)CC1]

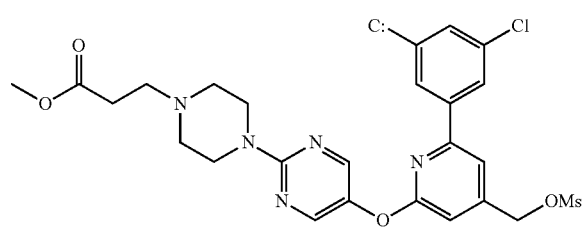

To a mixture of (2-(3,5-dichlorophenyl)-6-((2-(piperazin-1-yl)pyrimidin-5-yl)oxy)pyridin-4-yl)methanol, 3 hydrochloride (2.3 g, 4.05 mmol) and DIEA (3.54 mL, 20.27 mmol) in MeOH (30 mL) was added methyl acrylate (0.735 mL, 8.11 mmol). The reaction mixture was stirred at 25° C. for 12 h under N$_2$ atmosphere. Then the mixture was concentrated. The crude material was purified by flash chromatography (from pure DCM to DCM/MeOH=10/1, TLC: DCM/MeOH=10/1, R$_f$=0.5) to yield methyl 3-(4-(5-((6-(3,5-dichlorophenyl)-4-(hydroxymethyl)pyridin-2-yl)oxy)pyrimidin-2-yl)piperazin-1-yl)propanoate (2.3 g, 3.99 mmol, 98.0% yield) as a white solid: $^1$H NMR (400 MHz, CDCl$_3$) δ ppm 8.22 (s, 2H), 7.66 (d, J=1.8 Hz, 2H), 7.36 (s, 1H), 7.31-7.28 (m, 1H), 6.88 (s, 1H), 4.75 (s, 2H), 3.85-3.77 (m, 4H), 3.67 (s, 3H), 2.76-2.69 (m, 2H), 2.55-2.49 (m, 6H); ES-LCMS m/z: 518.2, 520.2 [M+H]$^+$.

To a mixture of methyl 3-(4-(5-((6-(3,5-dichlorophenyl)-4-(hydroxymethyl)pyridin-2-yl)oxy)pyrimidin-2-yl)piperazin-1-yl)propanoate (2.3 g, 3.99 mmol) and DIEA (2.092 mL, 11.98 mmol) in DCM (30 mL) was added MsCl (0.622 mL, 7.99 mmol). The reaction mixture was stirred at 0° C. for 0.5 h. The mixture was added H$_2$O (50 mL), extracted with DCM (100 mL×3). The combined organic layers were washed with brine (50 mL), dried over Na$_2$SO$_4$, filtered and concentrated to yield methyl 3-(4-(5-((6-(3,5-dichlorophenyl)-4-(((methylsulfonyl)oxy)methyl)pyridin-2-yl)oxy)pyrimidin-2-yl)piperazin-1-yl)propanoate (2.6 g, 3.92 mmol, 98.0% yield) as a white solid: $^1$H NMR (400 MHz, CDCl$_3$)

δ ppm 8.32-8.27 (m, 2H), 7.72 (dd, J=1.9, 4.1 Hz, 2H), 7.43-7.36 (m, 2H), 6.96 (d, J=3.1 Hz, 1H), 3.94-3.91 (m, 1H), 3.86 (d, J=3.3 Hz, 4H), 3.72-3.69 (m, 3H), 3.15-3.12 (m, 3H), 3.04-3.00 (m, 1H), 2.80-2.73 (m, 2H), 2.57 (d, J=3.7 Hz, 6H); ES-LCMS m/z 596.2, 598.2 [M+H]$^+$.

Step 3: Methyl 3-(4-(5-((4-(((1R,7S,8r)-8-acetamido-4-azabicyclo[5.1.0]octan-4-yl)methyl)-6-(3,5-dichlorophenyl)pyridin-2-yl)oxy)pyrimidin-2-yl)piperazin-1-yl)propanoate

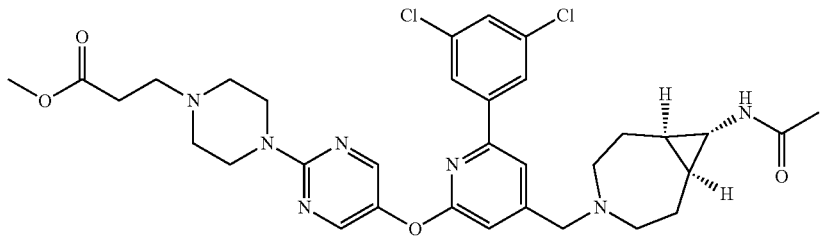 [SMILES: COC(=O)CCN1CCN(c2ncc(Oc3cc(CN4CC[C@@H]5[C@H](CC4)[C@H]5NC(C)=O)cc(-c4cc(Cl)cc(Cl)c4)n3)cn2)CC1]

To a solution of N-((1R,7S,8r)-4-azabicyclo[5.1.0]octan-8-yl)acetamide, trifluoroacetic acid (200 mg, 0.567 mmol) and methyl 3-(4-(5-((6-(3,5-dichlorophenyl)-4-(((methylsulfonyl)oxy)methyl)pyridin-2-yl)oxy)pyrimidin-2-yl)piperazin-1-yl)propanoate (250 mg, 0.377 mmol) in DMF (6 mL) was added DIEA (0.329 mL, 1.886 mmol). Then the reaction mixture was stirred at 20° C. for 12 h. Solvent was concentrated to give the crude product. Water (50 mL) was added and extracted with DCM (30 mL×2). The combined organic layers were dried over Na$_2$SO$_4$, filtered and concentrated to yield methyl 3-(4-(5-((4-(((1R,7S,8r)-8-acetamido-4-azabicyclo[5.1.0]octan-4-yl)methyl)-6-(3,5-dichlorophenyl)pyridin-2-yl)oxy)pyrimidin-2-yl)piperazin-1-yl)propanoate (300 mg, 0.337 mmol, 89.0% yield) as a yellow oil: $^1$H NMR (400 MHz, CDCl$_3$) δ ppm 8.25-8.16 (m, 2H), 7.69-7.61 (m, 2H), 7.30-7.22 (m, 2H), 6.85-6.74 (m, 1H), 3.81-3.71 (m, 4H), 3.63 (s, 3H), 3.58-3.51 (m, 2H), 2.75-2.63 (m, 4H), 2.50-2.34 (m, 7H), 2.23-2.09 (m, 2H), 1.89-1.74 (m, 3H), 1.51-1.36 (m, 2H), 1.32-1.15 (m, 2H), 1.04 (s, 2H); ES-LCMS m/z 668.2, 670.2 [M+H]$^+$.

Step 4: 4-(4-(5-((4-(((1R,7S,8r)-8-Acetamido-4-azabicyclo[5.1.0]octan-4-yl)methyl)-6-(3,5-dichlorophenyl)pyridin-2-yl)oxy)pyrimidin-2-yl)piperazin-1-yl)-2-methylbutanoic acid

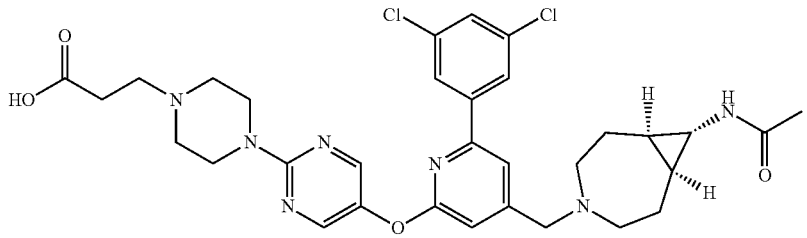 [SMILES: CC(=O)N[C@H]1[C@@H]2CCN(Cc3cc(Oc4cnc(N5CCN(CCC(=O)O)CC5)nc4)nc(-c4cc(Cl)cc(Cl)c4)c3)CC[C@@H]21]

To a solution of methyl 3-(4-(5-((4-(((1R,7S,8r)-8-acetamido-4-azabicyclo[5.1.0]octan-4-yl)methyl)-6-(3,5-dichlorophenyl)pyridin-2-yl)oxy)pyrimidin-2-yl)piperazin-1-yl)propanoate (300 mg, 0.337 mmol) in MeOH (6 mL) and water (0.5 mL) was added LiOH·H$_2$O (42.4 mg, 1.010 mmol). Then the reaction mixture was stirred at 25° C. for 12 h. 1 N HCl was added to adjust pH=6-7 and the mixture was concentrated to give the residue which was purified by preparative HPLC (MeCN/H$_2$O as eluents, basic condition) and lyophilized to yield a white solid of 3-(4-(5-((4-(((1R,7S,8r)-8-acetamido-4-azabicyclo[5.1.0]octan-4-yl)methyl)-6-(3,5-dichlorophenyl)pyridin-2-yl)oxy)pyrimidin-2-yl)piperazin-1-yl)propanoic acid (92.42 mg, 0.141 mmol, 42.0% yield): $^1$H NMR (400 MHz, CD$_3$OD) δ ppm 8.37 (s, 2H), 7.79 (d, J=1.98 Hz, 2H), 7.62 (s, 1H), 7.43 (t, J=1.87 Hz, 1H), 7.04 (s, 1H), 4.03 (s, 4H), 3.74 (s, 2H), 3.18-3.05 (m, 6H), 2.88 (dd, J=6.95, 12.68 Hz, 2H), 2.61-2.46 (m, 5H), 2.30-2.18 (m, 2H), 1.86 (s, 3H), 1.60-1.45 (m, 2H), 1.13 (s, 2H); ES-LCMS m/z 654.2, 656.2 [M+H]$^+$.

Example 368: methyl 4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-methylbutanoate

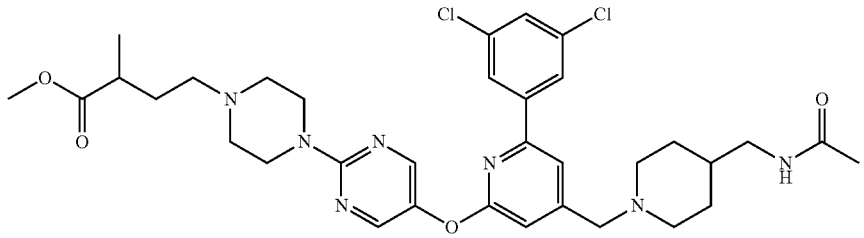 [SMILES: COC(=O)C(C)CCN1CCN(c2ncc(Oc3cc(CN4CCC(CNC(C)=O)CC4)cc(-c4cc(Cl)cc(Cl)c4)n3)cn2)CC1]

To a solution of N-((1-((2-(3,5-dichlorophenyl)-6-((2-(piperazin-1-yl)pyrimidin-5-yl)oxy)pyridin-4-yl)methyl)piperidin-4-yl)methyl)acetamide, 4 hydrochloride (3.3 g, 4.38 mmol) and methyl 4-bromo-2-methylbutanoate (2.85 g, 13.13 mmol) in DMF (50 mL) was added $K_2CO_3$ (4.84 g, 35.0 mmol). Then the reaction mixture was stirred at 80° C. for 12 h. The solid was filtered off and solvent was removed in vacuo to give the crude product which was purified by chromatography (from pure DCM to DCM/MeOH=10/1, TLC: DCM/MeOH=10/1, $R_f$=0.45) to yield a yellow solid of methyl 4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-methylbutanoate (2.3 g, 2.88 mmol, 65.9% yield): $^1$H NMR (400 MHz, $CDCl_3$) δ ppm 8.31-8.22 (m, 2H), 7.73-7.64 (m, 2H), 7.43-7.36 (m, 1H), 7.34-7.27 (m, 1H), 6.85 (s, 1H), 5.62 (t, J=5.4 Hz, 1H), 3.80 (t, J=4.7 Hz, 4H), 3.66 (s, 3H), 3.48 (s, 2H), 3.13 (t, J=6.3 Hz, 2H), 2.85 (d, J=11.2 Hz, 2H), 2.60-2.43 (m, 5H), 2.37 (t, J=7.2 Hz, 2H), 2.09-1.89 (m, 7H), 1.66 (d, J=12.1 Hz, 2H), 1.54-1.46 (m, 1H), 1.36-1.25 (m, 2H), 1.19-1.13 (m, 3H); ES-LCMS m/z 684.4, 686.4 $[M+H]^+$.

Example 369: 4-(4-(5-((4-((4-(Acetamidomethyl)piperidin-1-yl)methyl)-6-(3,5-dichlorophenyl)pyridin-2-yl)oxy)pyrimidin-2-yl)piperazin-1-yl)-2-methylbutanoic acid, 4 hydrochloride

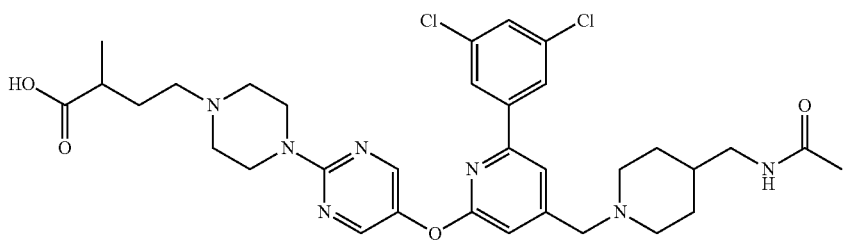 [SMILES: CC(=O)NCC1CCN(Cc2cc(Oc3cnc(N4CCN(CCC(C)C(=O)O)CC4)nc3)nc(-c3cc(Cl)cc(Cl)c3)c2)CC1]

To a solution of methyl 4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-methylbutanoate (1.7 g, 2.130 mmol) in MeOH (20 mL) and $H_2O$ (3 mL) was added LiOH (0.153 g, 6.39 mmol). Then the reaction mixture was stirred at 25° C. for 0.5 h. The solvent was removed in vacuo to give the crude product which was dissolved with MeCN (10 mL) and $H_2O$ (10 mL). 1 N HCl was added to adjust pH=6-7. The mixture was purified by preparative HPLC (MeCN/$H_2O$ as eluents, acidic condition) and lyophilized to yield 4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-methylbutanoic acid, 4 hydrochloride (1186.17 mg, 1.447 mmol, 67.9% yield) as a pale yellow solid: $^1$H NMR (400 MHz, $CD_3OD$) δ ppm 8.63 (s, 2H), 8.05 (s, 1H), 7.88 (d, J=1.8 Hz, 2H), 7.47 (s, 1H), 7.44-7.38 (m, 1H), 4.88 (d, J=14.6 Hz, 2H), 4.47 (s, 2H), 3.75 (d, J=12.1 Hz, 2H), 3.64-3.51 (m, 4H), 3.43-3.29 (m, 2H), 3.27-3.07 (m, 6H), 2.66-2.51 (m, 1H), 2.22-2.08 (m, 4H), 2.01-1.88 (m, 4H), 1.77-1.61 (m, 2H), 1.29-1.20 (m, 3H); ES-LCMS m/z 670.4, 672.4 $[M+H]^+$.

Example 370: 4-(4-(5-((4-((4-(Acetamidomethyl) piperidin-1-yl)methyl)-6-(3,5-dichlorophenyl)pyridin-2-yl)oxy)pyrimidin-2-yl)piperazin-1-yl)-2,2-dimethylbutanoic acid, 4 hydrochloride

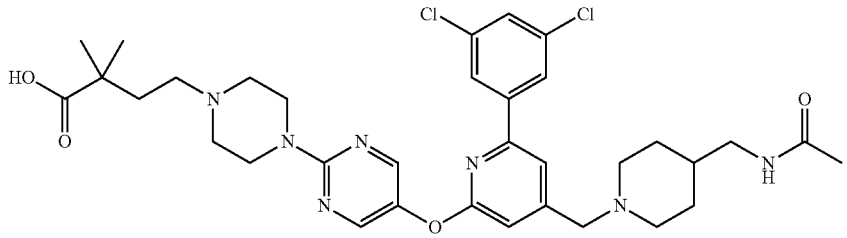 [SMILES: CC(=O)NCC1CCN(Cc2cc(Oc3cnc(N4CCN(CCC(C)(C)C(=O)O)CC4)nc3)nc(-c3cc(Cl)cc(Cl)c3)c2)CC1]

Step 1: 3,3-Dimethyldihydrofuran-2(3/7)-one

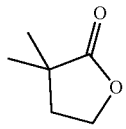

A mixture of NaH (5.81 g, 145 mmol) (60%) in THF (60 mL) was added CH₃I (13.07 mL, 209 mmol) and dihydrofuran-2(3/7)-one (5 g, 58.1 mmol) at 70° C. under N₂ atmosphere. Then the mixture was stirred at 70° C. for 2 h under N₂ atmosphere. The reaction mixture was quenched by the addition of saturated aqueous NH₄Cl solution (50 mL) at 0° C. The mixture was concentrated and then water (50 mL) was added. The mixture was extracted with EtOAc (10 mL×3). The combined organic layers were washed with brine (50 mL), dried over Na₂SO₄, filtered and concentrated. The crude material was purified by flash chromatography (from PE/EtOAc=50/1 to 10/1, TLC: PE/EtOAc=5/1, $R_f$=0.6) to yield 3,3-dimethyldihydrofuran-2(3/7)-one (1.3 g, 10.82 mmol, 18.6% yield) as a yellow oil: ¹H NMR (400 MHz, CDCl₃) δ ppm 4.27 (t, J=6.9 Hz, 2H), 2.12 (t, J=6.9 Hz, 2H), 1.27 (s, 6H); ES-LCMS m/z 115.2 [M+H]⁺.

Step 2: Methyl 4-bromo-2,2-dimethylbutanoate

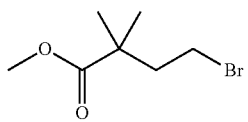

To a mixture of 3,3-dimethyldihydrofuran-2(3H)-one (500 mg, 4.16 mmol) in DCM (10 mL) was added BBr₃ (1.967 mL, 20.81 mmol) at 0° C. under N₂ atmosphere. Then the mixture was stirred at 25° C. for 8 h under N₂ atmosphere. MeOH (10.0 mL) was added to the mixture and stirred at 25° C. for 8 h. The reaction mixture was quenched by the addition of saturated aqueous NaHCO₃ solution (30 mL) at 0° C. The mixture was extracted with EtOAc (50 mL×3). The combined organic layers were washed with brine (30 mL), dried over Na₂SO₄, filtered and concentrated to give pale yellow oil of methyl 4-bromo-2,2-dimethylbutanoate (150 mg, 0.574 mmol, 13.8% yield): ¹H NMR (400 MHz, CDCl₃) δ ppm 3.65-3.59 (m, 3H), 3.31-3.22 (m, 2H), 2.11-2.05 (m, 2H), 1.17-1.12 (m, 6H).

Step 3: Methyl 4-(4-(5-((4-((4-(acetamidomethyl) piperidin-1-yl)methyl)-6-(3,5-dichlorophenyl)pyridin-2-yl)oxy)pyrimidin-2-yl)piperazin-1-yl)-2,2-dimethylbutanoate

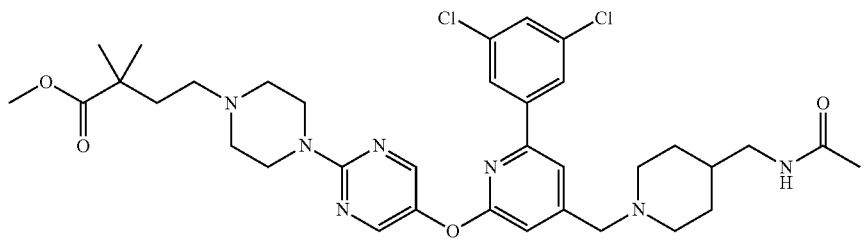 [SMILES: COC(=O)C(C)(C)CCN1CCN(c2ncc(Oc3cc(CN4CCC(CNC(C)=O)CC4)cc(-c4cc(Cl)cc(Cl)c4)n3)cn2)CC1]

A mixture of N-((1-((2-(3,5-dichlorophenyl)-6-((2-(piperazin-1-yl)pyrimidin-5-yl)oxy)pyridin-4-yl)methyl)piperidin-4-yl)methyl)acetamide, 4 hydrochloride (0.2 g, 0.251 mmol), methyl 4-bromo-2,2-dimethylbutanoate (0.131 g, 0.503 mmol) and K₂CO₃ (0.104 g, 0.754 mmol) in MeCN (5 mL) was stirred at 80° C. for 6 h. The mixture was filtered and concentrated. The crude material was purified by flash chromatography (from pure DCM to DCM/MeOH=10/1, TLC: DCM/MeOH=10/1, $R_f$=0.4) to yield methyl 4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2,2-dimethylbutanoate (120 mg, 0.086 mmol, 34.2% yield) as a yellow solid: ¹H NMR (400 MHz, CDCl₃) δ ppm 8.25-8.21 (m, 1H), 7.95 (s, 2H), 7.66 (d, J=1.8 Hz, 2H), 7.36 (s, 1H), 7.28 (s, 1H), 6.89-6.80 (m, 1H), 4.20 (t, J=6.9 Hz, 2H), 3.81 (d, J=6.8 Hz, 4H), 3.72-3.67 (m, 2H), 3.64-3.60 (m, 2H), 3.48 (br s, 2H), 3.10 (t, J=6.4 Hz, 2H), 2.56 (br s, 2H), 2.38 (br s, 1H), 1.97-1.91 (m, 10H), 1.83-1.75 (m, 2H), 1.64 (d, J=11.5 Hz, 2H), 1.20 (s, 6H); ES-LCMS m/z 698.0, 700.0 [M+H]⁺.

Step 4: 4-(4-(5-((4-((4-(Acetamidomethyl)piperidin-1-yl)methyl)-6-(3,5-dichlorophenyl)pyridin-2-yl)oxy)pyrimidin-2-yl)piperazin-1-yl)-2,2-dimethylbutanoic acid, 4 hydrochloride

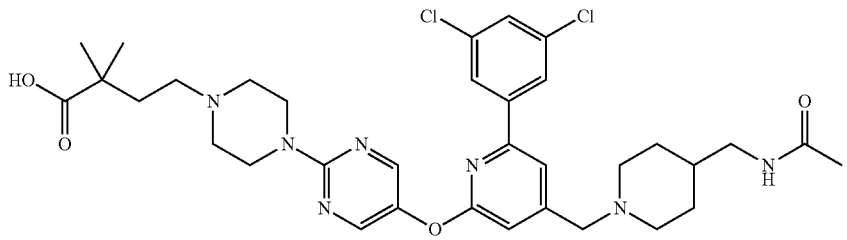 [SMILES: CC(=O)NCC1CCN(Cc2cc(Oc3cnc(N4CCN(CCC(C)(C)C(=O)O)CC4)nc3)nc(-c3cc(Cl)cc(Cl)c3)c2)CC1]

To a solution of methyl 4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2,2-dimethylbutanoate (100 mg, 0.072 mmol) in water (4 mL) was added concentrated HCl solution (2 mL, 24.00 mmol). Then, the mixture was stirred at 80° C. for 15 min. The reaction was evaporated to give the residue. The residue was purified by preparative HPLC (MeCN/H$_2$O as eluents, acidic condition) followed by lyophilization to yield 4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2,2-dimethylbutanoic acid, 4 hydrochloride (13.62 mg, 0.016 mmol, 22.8% yield) as a white solid: $^1$H NMR (400 MHz, D$_2$O) δ ppm 8.28 (s, 2H), 7.45 (s, 1H), 7.43 (d, J=1.8 Hz, 2H), 7.20 (t, J=1.9 Hz, 1H), 7.03 (s, 1H), 4.52 (s, J 20=15.0 Hz, 2H), 4.23 (s, 2H), 3.57 (d, J=12.3 Hz, 2H), 3.43 (d, J=11.7 Hz, 2H), 3.27 (t, J=12.6 Hz, 2H), 3.15-3.06 (m, 2H), 3.01-2.89 (m, 6H), 1.92-1.79 (m, 7H), 1.71 (br s, 1H), 1.43-1.24 (m, 2H), 1.10 (s, 6H); ES-LCMS m/z 684.3, 686.2 [M+H]$^+$.

Example 371: 2-(1-((6-(3,5-Dichlorophenyl)-3-methyl-2-((6-(4-methylpiperazin-1-yl)pyridazin-3-yl)oxy)pyridin-4-yl)methyl)piperidin-4-yl)acetic acid

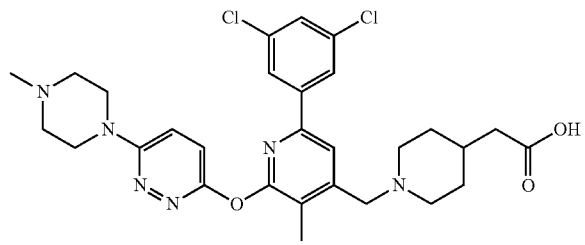 [SMILES: Cc1c(CN2CCC(CC(=O)O)CC2)cc(-c2cc(Cl)cc(Cl)c2)nc1Oc1ccc(N2CCN(C)CC2)nn1]

Step 1 (2-((6-Chloropyridazin-3-yl)oxy)-6-(3,5-dichlorophenyl)-3-methylpyridin-4-yl)methanol

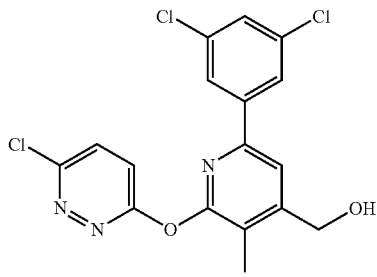 [SMILES: Cc1c(CO)cc(-c2cc(Cl)cc(Cl)c2)nc1Oc1ccc(Cl)nn1]

A mixture of 4-(((tert-butyldimethylsilyl)oxy)methyl)-6-(3,5-dichlorophenyl)-3-methylpyridin-2-ol (600 mg, 1.355 mmol), 3,6-dichloropyridazine (808 mg, 5.42 mmol), 18-crown-6 (179 mg, 0.678 mmol) and K$_2$CO$_3$ (562 mg, 4.07 mmol) in DMF (5 mL) was stirred at 80° C. for 5 h. After filtration, the filtrate was concentrated. The crude material was purified by flash chromatography (from PE/EtOAc=5/1 to 2/1, TLC: PE/EtOAc=5/1, R$_f$=0.6) to yield (2-((6-chloropyridazin-3-yl)oxy)-6-(3,5-dichlorophenyl)-3-methylpyridin-4-yl)methanol (300 mg, 0.681 mmol, 50.2% yield) as a yellow oil: $^1$H NMR (400 MHz, CDCl$_3$) δ ppm 7.77 (s, 1H), 7.70 (d, J=2.0 Hz, 2H), 7.60 (d, J=9.3 Hz, 1H), 7.39 (d, J=9.3 Hz, 1H), 7.32 (t, J=1.9 Hz, 1H), 4.83 (s, 2H), 2.25 (s, 3H); ES-LCMS m/z: 396.0, 398.0 [M+H]$^+$.

Step 2: (2-((6-Chloropyridazin-3-yl)oxy)-6-(3,5-dichlorophenyl)-3-methylpyridin-4-yl(methyl methanesulfonate

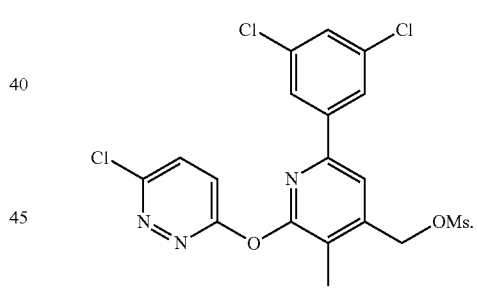

To a mixture of (2-((6-chloropyridazin-3-yl)oxy)-6-(3,5-dichlorophenyl)-3-methylpyridin-4-yl)methanol (280 mg, 0.635 mmol) and DIEA (246 mg, 1.906 mmol) in DCM cooled to 0° C. was added MsCl (109 mg, 0.953 mmol). The mixture was stirred at 0° C. for 0.2 h. Water (20 mL) was added. The mixture was extracted with DCM (15 mL×3). The combined organic layers were dried over Na$_2$SO$_4$, filtered and concentrated to yield (2-((6-chloropyridazin-3-yl)oxy)-6-(3,5-dichlorophenyl)-3-methylpyridin-4-yl)methyl methanesulfonate (300 mg, 0.569 mmol, 90.0% yield) as a yellow solid: $^1$H NMR (400 MHz, CDCl$_3$) δ ppm 7.81 (d, J=9.0 Hz, 1H), 7.61 (d, J=1.8 Hz, 2H), 7.53 (d, J=4.9 Hz, 2H), 7.34 (d, J=9.0 Hz, 1H), 4.58 (s, 2H), 2.71 (s, 3H), 2.35 (s, 3H); ES-LCMS m/z 474.0, 476.0, 478.0 [M+H]$^+$.

Step 3: Methyl 2-(1-((2-((6-chloropyridazin-3-yl)oxy)-6-(3,5-dichlorophenyl)-3-methylpyridin-4-yl)methyl)piperidin-4-yl)acetate

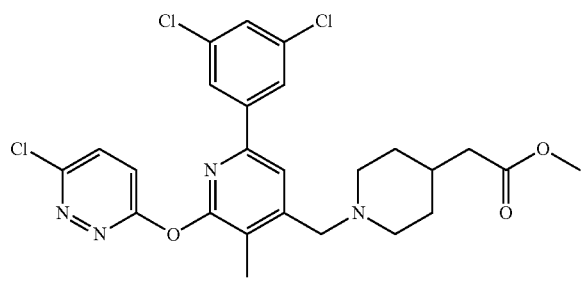 [SMILES: COC(=O)CC1CCN(Cc2cc(-c3cc(Cl)cc(Cl)c3)nc(Oc3ccc(Cl)nn3)c2C)CC1]

To a mixture of (2-((6-chloropyridazin-3-yl)oxy)-6-(3,5-dichlorophenyl)-3-methylpyridin-4-yl)methyl methanesulfonate (300 mg, 0.569 mmol) and DIEA (368 mg, 2.84 mmol) in DMF (10 mL) was added methyl 2-(piperidin-4-yl)acetate, hydrochloride (245 mg, 1.137 mmol). The mixture was stirred at 30° C. for 10 h. After filtration, the filtrate was concentrated. The residue was purified by preparative TLC (PE/EtOAc=3/1, $R_f$=0.6) to afford methyl 2-(1-((2-((6-chloropyridazin-3-yl)oxy)-6-(3,5-dichlorophenyl)-3-methylpyridin-4-yl)methyl)piperidin-4-yl)acetate (250 mg, 0.420 mmol, 73.8% yield) as a yellow solid: $^1$H NMR (400 MHz, CDCl$_3$) δ ppm 7.67 (d, J=1.8 Hz, 2H), 7.62-7.54 (m, 2H), 7.37 (d, J=9.0 Hz, 1H), 7.31 (s, 1H), 3.66 (s, 3H), 3.51 (s, 2H), 2.90-2.80 (m, 2H), 2.31 (s, 3H), 2.26 (d, J=11 Hz, 2H), 2.09 (t, J=11.4 Hz, 2H), 1.91-1.66 (m, 3H), 1.40-1.29 (m, 2H); ES-LCMS m/z 535.1, 537.1 [M+H]$^+$.

Step 4: tert-Butyl 4-(6-((6-(3,5-dichlorophenyl)-4-((4-(2-methoxy-2-oxoethyl)piperidin-1-yl)methyl)-3-methylpyridin-2-yl)oxy)pyridazin-3-yl)piperazine-1-carboxylate

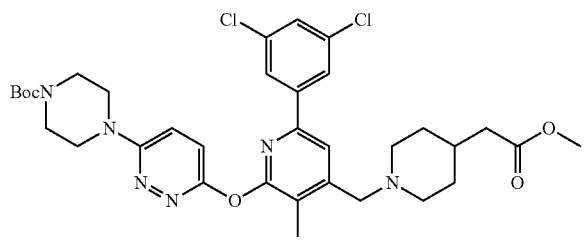 [SMILES: COC(=O)CC1CCN(Cc2cc(-c3cc(Cl)cc(Cl)c3)nc(Oc3ccc(N4CCN(C(=O)OC(C)(C)C)CC4)nn3)c2C)CC1]

A mixture of methyl 2-(1-((2-((6-chloropyridazin-3-yl)oxy)-6-(3,5-dichlorophenyl)-3-methylpyridin-4-yl)methyl)piperidin-4-yl)acetate (250 mg, 0.420 mmol), Xantphos (48.6 mg, 0.084 mmol), Cs$_2$CO$_3$ (410 mg, 1.260 mmol), Pd$_2$(dba)$_3$ (38.5 mg, 0.042 mmol) and tert-butyl piperazine-1-carboxylate (391 mg, 2.1 mmol) in THF (15 mL) was stirred at 80° C. for 20 h under N$_2$ atmosphere. Pd$_2$(dba)$_3$ (38.5 mg, 0.042 mmol) and tert-butyl piperazine-1-carboxylate (391 mg, 2.1 mmol) was added and the whole mixture was stirred at 80° C. for another 16 h under N$_2$ atmosphere. The mixture was cooled down and filtered. The filtrate was concentrated. The crude material was purified by prep-TLC (PE/EtOAc=3/1, $R_f$=0.3) to yield tert-butyl 4-(6-((6-(3,5-dichlorophenyl)-4-((4-(2-methoxy-2-oxoethyl)piperidin-1-yl)methyl)-3-methylpyridin-2-yl)oxy)pyridazin-3-yl)piperazine-1-carboxylate (300 mg, 0.185 mmol, 44.0% yield) as a yellow solid: $^1$H NMR (400 MHz, CDCl$_3$) δ ppm 7.66 (s, 2H), 7.51 (s, 1H), 7.39 (br s, 1H), 7.28 (br s, 1H), 7.10 (d, J=9.9 Hz, 1H), 3.66 (s, 3H), 3.57 (br s, 6H), 3.49 (s, 4H), 2.90-2.84 (m, 2H), 2.32 (s, 3H), 2.26 (d, J=7.5 Hz, 2H), 2.08 (d, J=9.0 Hz, 2H), 1.69-1.59 (m, 3H), 1.47 (br s, 9H), 1.26 (d, J=19.4 Hz, 2H); ES-LCMS m/z 685.3, 687.3 [M+H]$^+$.

Step 5: Methyl 2-(1-((6-(3,5-dichlorophenyl)-3-methyl-2-((6-(piperazin-1-yl)pyridazin-3-yl)oxy)pyridin-4-yl)methyl)piperidin-4-yl)acetate, 4 trifluoroacetic acid salt

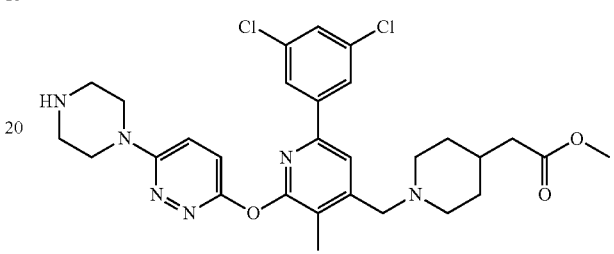

A solution of tert-butyl 4-(6-((6-(3,5-dichlorophenyl)-4-((4-(2-methoxy-2-oxoethyl)piperidin-1-yl)methyl)-3-methylpyridin-2-yl)oxy)pyridazin-3-yl)piperazine-1-carboxylate (300 mg, 0.185 mmol) and TFA (2 mL, 26.0 mmol) in DCM (10 mL) was stirred at 20° C. for 1 h. The mixture was concentrated to yield methyl 2-(1-((6-(3,5-dichlorophenyl)-3-methyl-2-((6-(piperazin-1-yl)pyridazin-3-yl)oxy)pyridin-4-yl)methyl)piperidin-4-yl)acetate, 4 trifluoroacetic acid salt (300 mg, 0.147 mmol, 80.0% yield) as a yellow oil: $^1$H NMR (400 MHz, CDCl$_3$) δ ppm 7.61 (s, 2H), 7.54 (d, J=1.5 Hz, 1H), 7.34 (br s, 2H), 7.14 (s, 1H), 4.04-3.72 (m, 2H), 3.68 (s, 3H), 3.25-3.20 (m, 2H), 2.89-2.62 (m, 6H), 2.48-2.35 (m, 4H), 2.28-3.20 (m, 3H), 2.02-1.95 (m, 3H), 1.68-1.50 (m, 2H), 1.31-1.27 (m, 2H); ES-LCMS m/z 585.3, 587.3 [M+H]$^+$.

Step 6: Methyl 2-(1-((6-(3,5-dichlorophenyl)-3-methyl-2-((6-(4-methylpiperazin-1-yl)pyridazin-3-yl)oxy)pyridin-4-yl)methyl)piperidin-4-yl)acetate

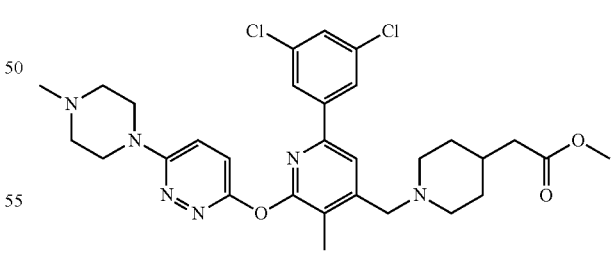

A mixture of methyl 2-(1-((6-(3,5-dichlorophenyl)-3-methyl-2-((6-(piperazin-1-yl)pyridazin-3-yl)oxy)pyridin-4-yl)methyl)piperidin-4-yl)acetate, 4 trifluoroacetic acid (300 mg, 0.147 mmol) and formaldehyde (44.1 mg, 1.469 mmol) in MeOH (10 mL) was stirred at 30° C. for 10 h. To the mixture was added NaBH$_3$CN (46.2 mg, 0.734 mmol). The whole mixture was stirred at 30° C. for another 2 h. The mixture was added saturated aqueous Na$_2$CO$_3$ solution (20 mL), extracted with DCM (20 mL×3). The combined organic layers were washed with brine (30 mL), dried over Na$_2$SO$_4$, filtered and concentrated to yield methyl 2-(1-((6-(3,5-dichlorophenyl)-3-methyl-2-((6-(4-methylpiperazin-1-yl)pyridazin-3-yl)oxy)pyridin-4-yl)methyl)piperidin-4-yl)acetate (160 mg, 0.133 mmol, 91.0% yield) as a yellow oil: $^1$H NMR (400 MHz, CDCl$_3$) δ ppm 7.62 (d, J=2.0 Hz, 2H), 7.46 (s, 1H), 7.23-7.21 (m, 2H), 7.06-7.05 (m, 1H), 3.61 (s, 3H), 3.60-3.55 (m, 4H), 3.47-3.40 (m, 2H), 2.79-2.71 (m, 4H), 2.60 (s, 3H), 2.50-2.47 (m, 4H), 2.27 (s, 3H), 2.02-1.95 (m, 2H), 1.67-1.50 (m, 3H), 1.32-1.27 (m, 2H); ES-LCMS m/z: 599.3, 601.3 [M+H]$^+$.

Step 7: 2-(1-((6-(3,5-Dichlorophenyl)-3-methyl-2-((6-(4-methylpiperazin-1-yl)pyridazin-3-yl)oxy)pyridin-4-yl)methyl)piperidin-4-yl)acetic acid

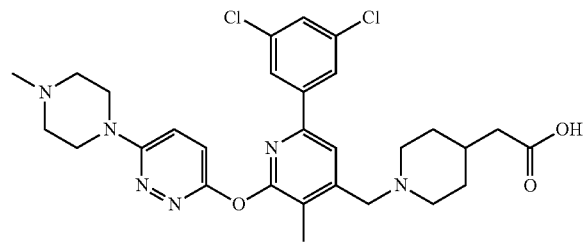 [SMILES: Cc1c(CN2CCC(CC(=O)O)CC2)cc(-c2cc(Cl)cc(Cl)c2)nc1Oc1ccc(N2CCN(C)CC2)nn1]

To a solution of methyl 2-(1-((6-(3,5-dichlorophenyl)-3-methyl-2-((6-(4-methylpiperazin-1-yl)pyridazin-3-yl)oxy)pyridin-4-yl)methyl)piperidin-4-yl/acetate (160 mg, 0.133 mmol) in THF (5.00 mL) and water (1 mL) was added LiOH·H$_2$O (56.0 mg, 1.334 mmol). The mixture was stirred at 50° C. for 5 h. The mixture was concentrated. The residue was added MeCN (6 mL) and H$_2$O (2 mL), acidified with 1 N HCl to pH=7-7.5. The mixture was purified by prep-HPLC (MeCN/H$_2$O as eluents, basic condition) followed by lyophilization to yield 2-(1-((6-(3,5-dichlorophenyl)-3-methyl-2-((6-(4-methylpiperazin-1-yl)pyridazin-3-yl)oxy)pyridin-4-yl)methyl)piperidin-4-yl)acetic acid (23.77 mg, 0.039 mmol, 29.0% yield) as a white solid: $^1$H NMR (400 MHz, CD$_3$OD) δ ppm 7.76-7.72 (m, 3H), 7.55 (d, J=9.8 Hz, 1H), 7.42 (d, J=9.3 Hz, 1H), 7.41-7.39 (m, 1H), 3.78-3.70 (m, 6H), 3.03 (d, J=11.5 Hz, 2H), 2.76 (t, J=5.1 Hz, 4H), 2.48 (s, 3H), 2.44 (s, 3H), 2.33 (t, J=11.0 Hz, 2H), 2.23 (d, J=6.8 Hz, 2H), 1.92-1.76 (m, 3H), 1.43-1.36 (m, 2H); ES-LCMS m/z: 585.3, 587.2 [M+H]$^+$.

Example 372: N-((1-((2-(3-Chloro-5-fluorophenyl)-6-((2-(4-(4-(methylsulfonyl)butan-2-yl)piperazin-1-yl)pyrimidin-5-yl)oxy)pyridin-4-yl)methyl)piperidin-4-yl)methyl)acetamide Step 1: tert-Butyl 4-(5-((4-((4-(acetamidomethyl)piperidin-1-yl)methyl)-6-(3-chloro-5-fluorophenyl)pyridin-2-yl)oxy)pyrimidin-2-yl)piperazine-1-carboxylate

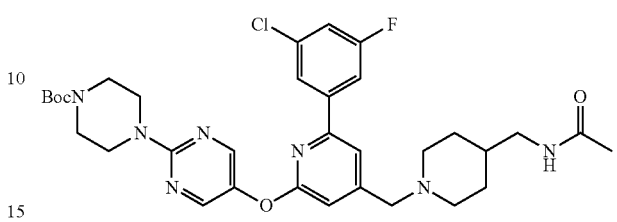

To a solution of tert-butyl 4-(5-((6-(3-chloro-5-fluorophenyl)-4-(((methylsulfonyl)oxy)methyl)pyridin-2-yl)oxy)pyrimidin-2-yl)piperazine-1-carboxylate (1.5 g, 2.146 mmol) and N-(piperidin-4-ylmethyl/acetamide, hydrochloride (0.871 g, 4.29 mmol) in DMF (15 mL) was added DIEA (1.528 mL, 8.59 mmol). Then the mixture was stirred at 50° C. for 3 h. Then the mixture was concentrated to give the residue which was distributed between DCM (30 mL) and H$_2$O (20 mL), extracted with DCM (30 mL×2). The combined organic layers were washed with brine (20 mL), dried over Na$_2$SO$_4$, filtered and concentrated. The crude product was purified by flash chromatography (from pure DCM to DCM/MeOH 8/1, TLC: DCM/MeOH=10/1, R$_f$=0.55) to yield a light yellow solid of tert-butyl 4-(5-((4-((4-(acetamidomethyl)piperidin-1-yl)methyl)-6-(3-chloro-5-fluorophenyl)pyridin-2-yl)oxy)pyrimidin-2-yl)piperazine-1-carboxylate (1.5 g, 2.112 mmol, 98.0% yield): $^1$H NMR (400 MHz, CD$_3$OD) δ ppm 8.33 (s, 2H), 7.71 (s, 1H), 7.63 (s, 1H), 7.58-7.52 (m, 1H), 7.19 (td, J=2.0, 8.4 Hz, 1H), 7.03 (s, 1H), 3.86-3.79 (m, 4H), 3.61 (s, 2H), 3.52 (br s, 4H), 3.07 (d, J=6.6 Hz, 2H), 2.93 (d, J=11.7 Hz, 2H), 2.08 (t, J=10.7 Hz, 2H), 1.72 (d, J=11.7 Hz, 2H), 1.53 (br s, 1H), 1.51 (br s, 3H), 1.49 (s, 9H), 1.37-1.25 (m, 2H); ES-LCMS m/z 654.0, 656.0 [M+H]$^+$.

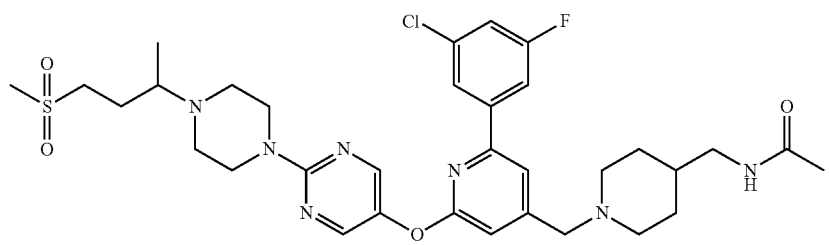 [SMILES: CC(=O)NCC1CCN(Cc2cc(Oc3cnc(N4CCN(C(C)CCS(C)(=O)=O)CC4)nc3)nc(-c3cc(F)cc(Cl)c3)c2)CC1]

Step 2: N-((1-((2-(3-Chloro-5-fluorophenyl)-6-((2-(piperazin-1-yl)pyrimidin-5-yl)oxy)pyridin-4-yl)methyl)piperidin-4-yl)methyl)acetamide, 4 hydrochloride

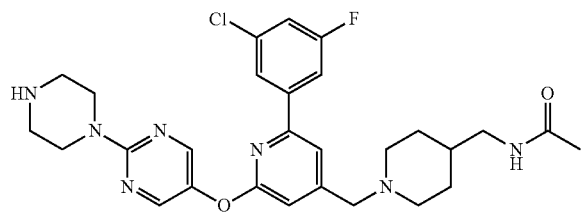 [SMILES: CC(=O)NCC1CCN(Cc2cc(Oc3cnc(N4CCNCC4)nc3)nc(-c3cc(F)cc(Cl)c3)c2)CC1]

A mixture of tert-butyl 4-(5-((4-((4-(acetamidomethyl)piperidin-1-yl)methyl)-6-(3-chloro-5-fluorophenyl)pyridin-2-yl)oxy)pyrimidin-2-yl)piperazine-1-carboxylate (730 mg, 1.028 mmol) in HCl solution (4 M in MeOH, 15 mL, 60.0 mmol) was stirred at 20° C. for 30 min. Then the mixture was concentrated to give N-((1-((2-(3-chloro-5-fluorophenyl)-6-((2-(piperazin-1-yl)pyrimidin-5-yl)oxy)pyridin-4-yl)methyl)piperidin-4-yl)methyl)acetamide, 4 hydrochloride (800 mg, 0.954 mmol, 93.0% yield) as a pale yellow solid: $^1$H NMR (400 MHz, CD$_3$OD) δ ppm 8.48 (s, 2H), 7.95 (br s, 1H), 7.80 (s, 1H), 7.61 (d, J=9.7 Hz, 1H), 7.33 (br s, 1H), 7.27 (d, J=8.2 Hz, 1H), 4.44 (br s, 2H), 4.13 (br s, 4H), 3.59 (br s, 2H), 3.34 (br s, 4H), 3.14 (br s, 4H), 1.98 (s, 5H), 1.87 (br s, 1H), 1.63 (br s, 2H); ES-LCMS m/z 554.0, 556.1 [M+H]$^+$.

Step 3: N-((1-((2-(3-Chloro-5-fluorophenyl)-6-((2-(4-(4-(methylthio)butan-2-yl)piperazin-1-yl)pyrimidin-5-yl)oxy)pyridin-4-yl)methyl)piperidin-4-yl)methyl/acetamide

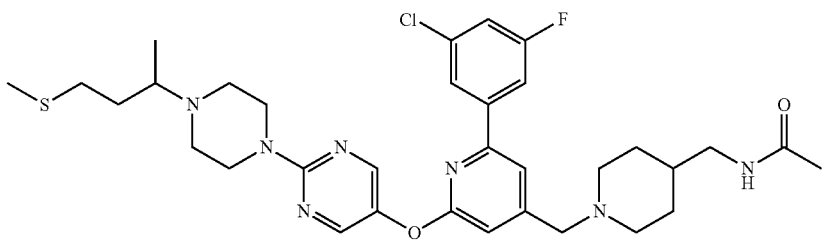 [SMILES: CSCCC(C)N1CCN(c2ncc(Oc3cc(CN4CCC(CNC(C)=O)CC4)cc(-c4cc(F)cc(Cl)c4)n3)cn2)CC1]

To a solution of 4-(methylthio)butan-2-one (564 mg, 4.77 mmol), N-((1-((2-(3-chloro-5-fluorophenyl)-6-((2-(piperazin-1-yl)pyrimidin-5-yl)oxy)pyridin-4-yl)methyl)piperidin-4-yl)methyl)acetamide, 4 hydrochloride (800 mg, 0.954 mmol) in MeOH (15 mL) was added 4 Å molecular sieve (0.2 g, 0.954 mmol) and stirred at 50° C. for 84 h under N$_2$ atmosphere. Then NaBH$_3$CN (300 mg, 4.77 mmol) was added to the mixture and the mixture was stirred at 50° C. for 12 h. The crude material was purified by flash chromatography (from DCM/MeOH=100/1 to 15/1, TLC: DCM/MeOH=20/1, R$_f$=0.35) to yield an off white solid of N-((1-((2-(3-chloro-5-fluorophenyl)-6-((2-(4-(4-(methylthio)butan-2-yl)piperazin-1-yl)pyrimidin-5-yl)oxy)pyridin-4-yl)methyl)piperidin-4-yl)methyl/acetamide (480 mg, 0.626 mmol, 65.6% yield): $^1$H NMR (400 MHz, CD$_3$OD) δ ppm 8.31 (s, 2H), 7.73 (s, 1H), 7.64 (d, J=9.9 Hz, 1H), 7.20 (d, J=8.4 Hz, 1H), 7.03 (s, 1H), 3.83 (d, J=2.4 Hz, 4H), 3.61 (s, 2H), 3.07 (d, J=6.8 Hz, 2H), 2.93 (d, J=10.8 Hz, 2H), 2.84-2.77 (m, 1H), 2.71-2.64 (m, 2H), 2.63-2.50 (m, 4H), 2.11-2.04 (m, 5H), 1.93 (s, 3H), 1.91-1.85 (m, 1H), 1.72 (d, J=12.6 Hz, 2H), 1.64-1.48 (m, 2H), 1.37-1.28 (m, 2H), 1.05 (d, J=6.6 Hz, 3H); ES-LCMS m/z 656.2, 658.0 [M+H]$^+$.

Step 4: N-((1-((2-(3-Chloro-5-fluorophenyl)-6-((2-(4-(4-(methylsulfonyl)butan-2-yl)piperazin-1-yl)pyrimidin-5-yl)oxy)pyridin-4-yl)methyl)piperidin-4-yl)methyl)acetamide

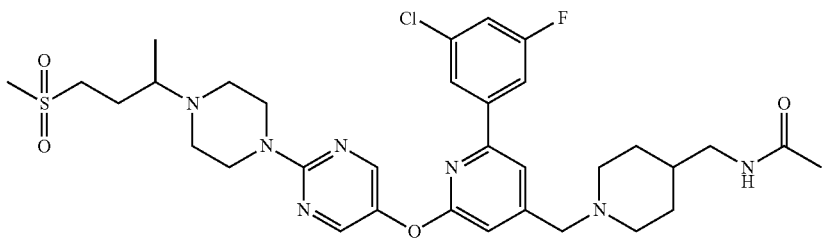 [SMILES: CC(=O)NCC1CCN(Cc2cc(Oc3cnc(N4CCN(C(C)CCS(C)(=O)=O)CC4)nc3)nc(-c3cc(F)cc(Cl)c3)c2)CC1]

To a solution of N-((1-((2-(3-chloro-5-fluorophenyl)-6-((2-(4-(4-(methyl thio)butan-2-yl)piperazin-1-yl)pyrimidin-5-yl)oxy)pyridin-4-yl)methyl)piperidin-4-yl)methyl)acetamide (400 mg, 0.522 mmol) in MeOH (15 mL) was added Oxone (240 mg, 0.390 mmol) and stirred at 25° C. for 12 h. Saturated Na₂SO₃ solution (30 mL) was added to above mixture and the mixture was concentrated to give the residue which was distributed between DCM (30 mL) and H₂O (20 mL), extracted with DCM (30 mL×2). The combined organic layers were washed with brine (20 mL), dried over Na₂SO₄, filtered and concentrated. The crude product was purified by preparative HPLC (MeCN/H₂O as eluents, basic condition). The desired fraction was lyophilized to afford a white solid of N-((1-((2-(3-chloro-5-fluorophenyl)-6-((2-(4-(4-(methylsulfonyl)butan-2-yl)piperazin-1-yl)pyrimidin-5-yl)oxy)pyridin-4-yl)methyl)piperidin-4-yl)methyl)acetamide (123.07 mg, 0.177 mmol, 33.9% yield): ¹H NMR (400 MHz, CD₃OD) δ 8.31 (s, 2H), 7.73 (s, 1H), 7.64 (s, 1H), 7.59-7.53 (m, 1H), 7.20 (td, J=2.0, 8.3 Hz, 1H), 7.03 (s, 1H), 3.90-3.76 (m, 4H), 3.61 (s, 2H), 3.29-3.17 (m, 2H), 3.07 (d, J=6.6 Hz, 2H), 2.98 (s, 3H), 2.94 (br d, J=11.5 Hz, 2H), 2.87-2.78 (m, 1H), 2.74-2.65 (m, 2H), 2.58-2.50 (m, 2H), 2.13-1.97 (m, 3H), 1.93 (s, 3H), 1.90-1.80 (m, 1H), 1.72 (br d, J=12.3 Hz, 2H), 1.53 (br d, J=3.3 Hz, 1H), 1.37-1.25 (m, 2H), 1.06 (d, J=6.6 Hz, 3H); ES-LCMS m/z 688.3, 690.3 [M+H]⁺.

Examples 373-374 (Table 19) were prepared by procedures analogous to those described for example 372.

TABLE 19

| Example | Structure/Name | ¹H NMR | LCMS |
|---|---|---|---|
| 373 | 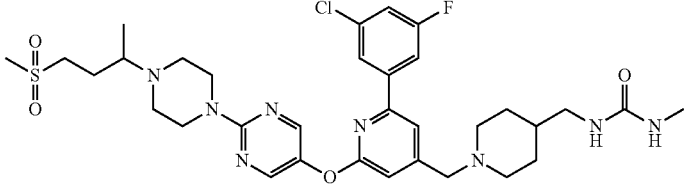<br>1-((1-((2-(3-chloro-5-fluorophenyl)-6-((2-(4-(4-(methylsulfonyl)butan-2-yl)piperazin-1-yl)pyrimidin-5-yl)oxy)pyridin-4-yl)methyl)piperidin-4-yl)methyl)-3-methylurea | ¹H NMR (400 MHz, CD₃OD) δ ppm 8.47 (br.s., 2H), 7.93 (br.s., 1H), 7.79 (br.s., 1H), 7.61 (d, J = 9.7 Hz, 1H), 7.33 (br.s., 1H), 7.27 (d, J = 7.9 Hz, 1H), 5.01 (d, J = 13.2 Hz, 2H), 4.44 (br.s., 2H), 3.75-3.55 (m, 6H), 3.47-3.36 (m, 4H), 3.16-3.04 (m, 6H), 2.72 (d, J = 4.0 Hz, 2H), 2.48 (br.s., 2H), 2.19-2.07 (m, 2H), 1.99 (d, J = 14.1 Hz, 2H), 1.84 (br.s., 2H), 1.59 (br.s., 2H), 1.47 (d, J = 6.6 Hz, 3H) | ES-LCMS m/z 703.3, .705.3 [M + H]⁺. |
| 374 | 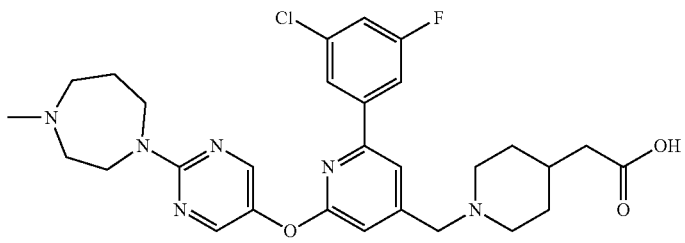 [SMILES: CN1CCCN(c2ncc(Oc3cc(CN4CCC(CC(=O)O)CC4)cc(-c4cc(F)cc(Cl)c4)n3)cn2)CC1]<br>2-(1-((2-(3-chloro-5-fluorophenyl)-6-((2-(4-methyl-1,4-diazepan-1-yl)pyrimidin-5-yl)oxy)pyridin-4-yl)methyl)piperidin-4-yl)acetic acid | ¹H NMR (400 MHz, D₂O) δ ppm 8.32-8.23 (m, 2H), 7.50-7.44 (m, 1H), 7.38 (s, 1H), 7.25 (s, 1H), 7.01 (s, 2H), 4.26-4.12 (m, 3H), 3.76-3.52 (m, 5H), 3.47-3.37 (m, 3H), 3.16 (s, 2H), 2.96 (t, J = 12.2 Hz, 2H), 2.79 (s, 3H), 2.22 (d, J = 6.4 Hz, 2H), 2.18-2.07 (m, 2H), 1.88 (d, J = 13.5 Hz, 2H), 1.39 (q, J = 12.6 Hz, 2H) | ES-LCMS: m/z 569.3, 571.3 [M + H]⁺. |

Example 375: 2-(1-((2-(3,5-Dichlorophenyl)-6-(isopropyl(2-(4-methylpiperazin-1-yl)pyrimidin-5-yl)amino)pyridin-4-yl)methyl)piperidin-4-yl)acetic acid

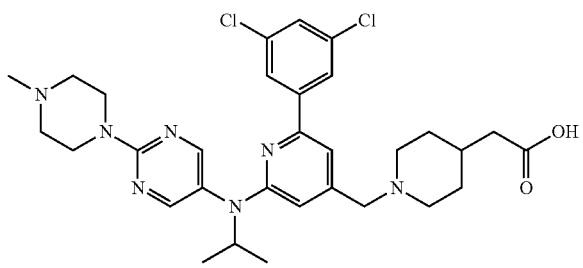 [SMILES: CC(C)N(c1cnc(N2CCN(C)CC2)nc1)c1cc(CN2CCC(CC(=O)O)CC2)cc(-c2cc(Cl)cc(Cl)c2)n1]

Example 375 was prepared by procedures analogous to those described for example 388: ¹H NMR (400 MHz, CD₃OD) δ ppm 8.53 (br s, 2H), 7.99 (br s, 2H), 7.52 (s, 1H), 7.47 (br s, 1H), 7.01 (br s, 1H), 5.26 (br s, 1H), 4.97 (br d, J=13.2 Hz, 2H), 4.28 (br s, 2H), 3.67 (br s, 4H), 3.48 (br s, 4H), 3.10 (br s, 2H), 3.02 (br s, 3H), 2.36-2.21 (m, 2H), 2.10-1.92 (m, 3H), 1.71 (br s, 2H), 1.27 (br d, J=4.9 Hz, 6H); LCMS m/z 612.3, 614.2 [M+H]⁺.

Example 376: 2-(1-((3',5'-dichloro-4-fluoro-5-((2-(4-methylpiperazin-1-yl)pyrimidin-5-yl)oxy)-[1,1'-biphenyl]-3-yl)methyl)piperidin-4-yl)acetic acid

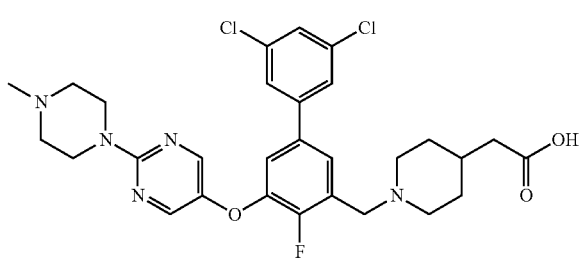 [SMILES: CN1CCN(c2ncc(Oc3cc(-c4cc(Cl)cc(Cl)c4)cc(CN4CCC(CC(=O)O)CC4)c3F)cn2)CC1]

Step 1: 2-Fluoro-3-methyl-5-(4,4,5,5-tetramethyl-1,3,2-dioxaborolan-2-yl)phenol

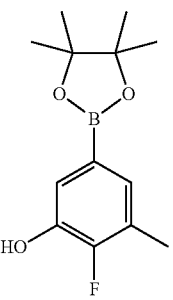

A mixture of 2-fluoro-3-methylphenol (4.5 g, 35.7 mmol), 4,4,4',4',5,5,5',5'-octamethyl-2,2'-bi(1,3,2-dioxaborolane) (22.65 g, 89 mmol), 2,9-dimethyl-1,10-phenanthroline (1.486 g, 7.14 mmol) and [Ir(COD)OMe]₂ (0.904 g, 1.784 mmol) in THF (300 mL) was stirred at 80° C. for 12 h under N₂ atmosphere. The mixture was concentrated to give the crude product. The crude material was purified by flash chromatography (from pure PE to PE/EtOAc=5/1, TLC: PE/EtOAc=4/1, R_f=0.5) to yield 2-fluoro-3-methyl-5-(4,4,5,5-tetramethyl-1,3,2-dioxaborolan-2-yl)phenol (6 g, 21.42 mmol, 60.0% yield) as a brown solid: ¹H NMR (400 MHz, CD₃OD) δ ppm 7.12-7.03 (m, 2H), 2.23 (d, J=2.2 Hz, 3H), 1.32 (s, 12H); ES-LCMS m/z 253.2 [M+H]⁺.

Step 2: 3',5'-Dichloro-4-fluoro-5-methyl-[1,1'-biphenyl]-3-ol

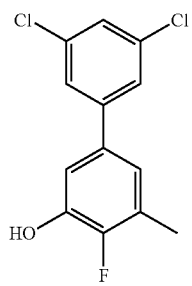

To a solution of 2-fluoro-3-methyl-5-(4,4,5,5-tetramethyl-1,3,2-dioxaborolan-2-yl)phenol (3 g, 10.71 mmol) and 1-bromo-3,5-dichlorobenzene (2.90 g, 12.85 mmol) in 1,4-dioxane (250 mL) and water (50.00 mL) was added K₂CO₃ (4.44 g, 32.1 mmol) and PdCl₂(dppf) (0.784 g, 1.071 mmol) under N₂ atmosphere. Then the reaction mixture was stirred at 80° C. for 2 h. After filtration, the filtrate was concentrated. The residue was purified by flash chromatography (from pure PE to PE/EtOAc=4/1, TLC: PE/EtOAc=4/1, R_f=0.5) to yield 3',5'-dichloro-4-fluoro-5-methyl-[1,1'-biphenyl]-3-ol (2.5 g, 8.30 mmol, 77.0% yield) as a yellow solid: ¹H NMR (400 MHz, CD₃OD) δ ppm 7.48 (d, J=2.0 Hz, 2H), 7.37 (t, J=1.9 Hz, 1H), 6.97-6.90 (m, 2H), 2.30 (d, J=2.2 Hz, 3H).

Step 3: 5-((3',5'-Dichloro-4-fluoro-5-methyl-[1,1'-biphenyl]-3-yl)oxy)-2-(methylthio)pyrimidine

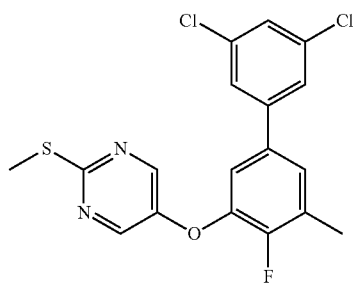 [SMILES: CSc1ncc(Oc2cc(-c3cc(Cl)cc(Cl)c3)cc(C)c2F)cn1]

To a mixture of 3',5'-dichloro-4-fluoro-5-methyl-[1,1'-biphenyl]-3-ol (2400 mg, 7.97 mmol) and 5-bromo-2-(methylthio)pyrimidine (2451 mg, 11.95 mmol) in 1,4-dioxane (170 mL) was added 2-(dimethylamino)acetic acid (82 mg, 0.797 mmol), Cs₂CO₃ (7788 mg, 23.90 mmol) and CuI (152 mg, 0.797 mmol). The mixture was stirred at 90° C. for 72 h. The mixture was filtered, concentrated to give the residue which was distributed between DCM (500 mL) and H₂O (500 mL), extracted with DCM (300 mL×2). The combined organic layers were washed with brine (400 mL), dried over Na₂SO₄, filtered and concentrated. The crude product was purified by flash chromatography (from pure PE to EtOAc/PE=1/1, TLC: PE/EtOAc=2/1, R_f=0.5) to yield 5-((3',5'-dichloro-4-fluoro-5-methyl-[1,1'-biphenyl]-3-yl)oxy)-2-(methylthio)pyrimidine (1.6 g, 3.04 mmol, 38.1% yield) as pale yellow oil: ¹H NMR (400 MHz, CD₃OD) δ ppm 7.88 (s, 1H), 7.55-7.52 (m, 2H), 7.35 (s, 2H), 7.12 (d, J=8.5 Hz, 2H), 2.53 (s, 3H), 2.40 (m, 3H); ES-LCMS m/z 395.0, 397.0 [M+H]⁺.

Step 4: 5-((3',5'-Dichloro-4-fluoro-5-methyl-[1,1'-biphenyl]-3-yl)oxy)-2-(methylsulfonyl)pyrimidine

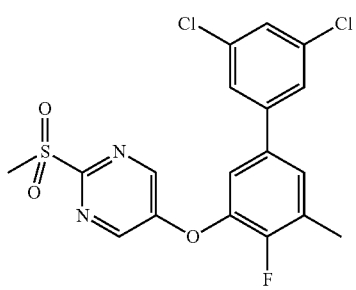 [SMILES: Cc1cc(-c2cc(Cl)cc(Cl)c2)cc(Oc2cnc(S(C)(=O)=O)nc2)c1F]

To a solution of 5-((3',5'-dichloro-4-fluoro-5-methyl-[1,1'-biphenyl]-3-yl)oxy)-2-(methylthio)pyrimidine (1.5 g, 2.85 mmol) in MeOH (50 mL) was added Oxone (1.925 g, 3.13 mmol). Then the reaction mixture was stirred at 15° C. for 2 h. The solid was filtered off and the filtrate was concentrated. The crude material was purified by flash chromatography (from pure DCM to DCM/MeOH=10/1, TLC: DCM/MeOH=10/1, R_f=0.7) to yield 5-((3',5'-dichloro-4-fluoro-5-methyl-[1,1'-biphenyl]-3-yl)oxy)-2-(methylsulfonyl)pyrimidine (1.4 g, 2.457 mmol, 86.0% yield) as a pale yellow solid: ¹H NMR (400 MHz, CD₃OD) δ ppm 8.70 (s, 2H), 7.59-7.55 (m, 1H), 7.61-7.55 (m, 1H), 7.53-7.45 (m, 2H), 7.43 (t, J=1.9 Hz, 1H), 2.98 (s, 3H), 2.43 (d, J=2.0 Hz, 3H); ES-LCMS m/z 426.9, 428.9 [M+H]⁺.

Step 5: 5-((5-(Bromomethyl)-3',5'-dichloro-4-fluoro-[1,1'-biphenyl]-3-yl)oxy)-2-(methylsulfonyl)pyrimidine

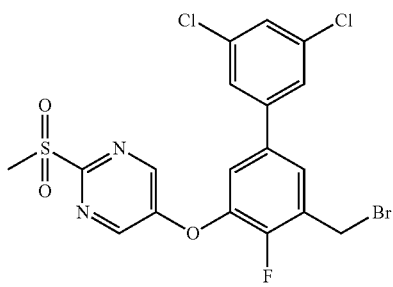 [SMILES: CS(=O)(=O)c1ncc(Oc2cc(-c3cc(Cl)cc(Cl)c3)cc(CBr)c2F)cn1]

A mixture of 5-((3',5'-dichloro-4-fluoro-5-methyl-[1,1'-biphenyl]-3-yl)oxy)-2-(methylsulfonyl)pyrimidine (380 mg, 0.667 mmol), NBS (190 mg, 1.067 mmol) and AIBN (10.95 mg, 0.067 mmol) in CCl₄ (10 mL) was stirred at 85° C. for 12 h. The mixture was concentrated to give the crude product. The crude material was purified by flash chromatography (from PE/EtOAc=3/1 to 1/1, TLC: PE/EtOAc=1/1, R_f=0.6) to yield 5-((5-(bromomethyl)-3',5'-dichloro-4-fluoro-[1,1'-biphenyl]-3-yl)oxy)-2-(methylsulfonyl)pyrimidine (380 mg, 0.526 mmol, 79.0% yield) as a yellow oil: ¹H NMR (400 MHz, CD₃OD) δ ppm 8.77-8.70 (m, 2H), 7.47 (ddd, J=2.3, 6.7, 18.3 Hz, 2H), 7.65-7.62 (m, 1H), 7.65-7.62 (m, 1H), 7.47 (t, J=1.8 Hz, 1H), 4.69 (s, 2H), 3.36-3.35 (m, 3H); ES-LCMS m/z 504.9, 506.9 [M+H]⁺.

Step 6: Methyl 2-(1-((3',5'-dichloro-4-fluoro-5-((2-(methylsulfonyl)pyrimidin-5-yl)oxy)-[1,1'-biphenyl]-3-yl)methyl)piperidin-4-yl)acetate

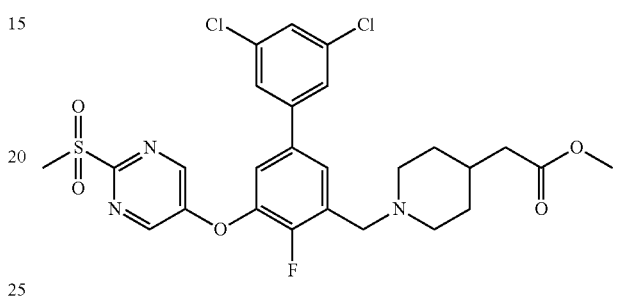

To a solution of 5-((5-(bromomethyl)-3',5'-dichloro-4-fluoro-[1,1'-biphenyl]-3-yl)oxy)-2-(methylsulfonyl)pyrimidine (380 mg, 0.526 mmol) and methyl 2-(piperidin-4-yl)acetate (138 mg, 0.788 mmol) in DMF (10 mL) was added K₂CO₃ (218 mg, 1.577 mmol). The mixture was stirred at 80° C. for 12 h. The mixture was filtered off and solvent was removed in vacuo to give the crude product. The crude material was purified by flash chromatography (from PE/EtOAc=5/1 to 1/1, TLC: PE/EtOAc=1/1, R_f=0.6) to yield methyl 2-(1-((3',5'-dichloro-4-fluoro-5-((2-(methylsulfonyl)pyrimidin-5-yl)oxy)-[1,1'-biphenyl]-3-yl)methyl)piperidin-4-yl)acetate (350 mg, 0.466 mmol, 89.0% yield) as a yellow oil: ¹H NMR (400 MHz, CD₃OD) δ ppm 8.73 (s, 2H), 7.68 (dd, J=3.7, 6.4 Hz, 2H), 7.64 (d, J=1.8 Hz, 2H), 7.45 (t, J=1.8 Hz, 1H), 3.70 (s, 2H), 3.63 (s, 3H), 3.35 (s, 3H), 3.00-2.98 (m, 2H), 2.25 (d, J=6.6 Hz, 2H), 2.17 (t, J=11.0 Hz, 2H), 1.73 (d, J=12.3 Hz, 3H), 1.32 (d, J=12.1 Hz, 2H); ES-LCMS m/z 582.2, 584.2 [M+H]⁺.

Step 7: Methyl 2-(1-((3',5'-dichloro-4-fluoro-5-((2-(4-methylpiperazin-1-yl)pyrimidin-5-yl)oxy)-[1,1'-biphenyl]-3-yl)methyl)piperidin-4-yl)acetate

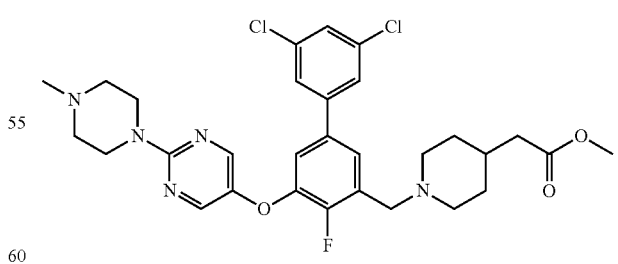

A mixture of 1-methylpiperazine (466 mg, 4.66 mmol), methyl 2-(1-((3',5'-dichloro-4-fluoro-5-((2-(methylsulfonyl)pyrimidin-5-yl)oxy)-[1,1'-biphenyl]-3-yl)methyl)piperidin-4-yl)acetate (350 mg, 0.466 mmol) and DIEA (301 mg, 2.328 mmol) in t-BuOH (0.5 mL) was stirred at 155° C. for 2 h under microwave. The mixture was concentrated to give the crude product. The crude material was purified by flash chromatography (from PE/EtOAc=3/1 to 1/1, TLC: PE/EtOAc=1/1, R$_f$=0.5) to yield methyl 2-(1-((3',5'-dichloro-4-fluoro-5-((2-(4-methylpiperazin-1-yl)pyrimidin-5-yl)oxy)-[1,1'-biphenyl]-3-yl)methyl)piperidin-4-yl)acetate (300 mg, 0.443 mmol, 95.0% yield) as a yellow oil: $^1$H NMR (400 MHz, CD$_3$OD) δ ppm 8.23 (s, 2H), 7.53 (d, J=1.8 Hz, 2H), 7.45-7.43 (m, 1H), 7.41 (t, J=1.9 Hz, 1H), 7.23 (dd, J=2.2, 7.3 Hz, 1H), 3.79 (br s, 2H), 3.65 (s, 2H), 3.63 (s, 3H), 3.51 (br s, 4H), 2.94 (d, J=11.5 Hz, 2H), 2.51 (br s, 2H), 2.32 (s, 3H), 2.25 (d, J=6.8 Hz, 2H), 2.17-2.10 (m, 2H), 1.72 (d, J=12.3 Hz, 3H), 1.31 (d, J=10.1 Hz, 2H); ES-LCMS m/z 602.3, 604.3 [M+H]$^+$.

Step 8: 2-(1-((3',5'-Dichloro-4-fluoro-5-((2-(4-methylpiperazin-1-yl)pyrimidin-5-yl)oxy)-[1,1'-biphenyl]-3-yl)methyl)piperidin-4-yl)acetic acid, 3 hydrochloride

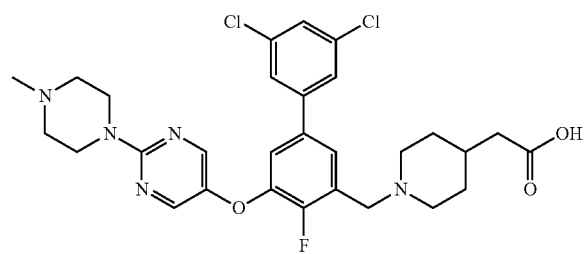 [SMILES: CN1CCN(c2ccc(Oc3nc(-c4cc(Cl)cc(Cl)c4)cc(CN4CCC(CC(=O)O)CC4)c3F)cn2)CC1]

A mixture of methyl 2-(1-((3',5'-dichloro-4-fluoro-5-((2-(4-methylpiperazin-1-yl)pyrimidin-5-yl)oxy)-[1,1'-biphenyl]-3-yl)methyl)piperidin-4-yl)acetate (280 mg, 0.414 mmol) in concentrated HCl (8 mL, 65.2 mmol). The mixture was stirred at 80° C. for 20 min. The solvent was concentrated to give the crude product, the crude product was purified by preparative HPLC (MeCN/H$_2$O as eluents, acidic condition) and lyophilized to afford 2-(1-((3',5'-dichloro-4-fluoro-5-((2-(4-methylpiperazin-1-yl)pyrimidin-5-yl)oxy)-[1,1'-biphenyl]-3-yl)methyl)piperidin-4-yl)acetic acid, 3 hydrochloride (85.15 mg, 0.118 mmol, 28.6% yield) as a pale yellow solid: $^1$H NMR (400 MHz, CD$_3$OD) δ ppm 8.40 (s, 2H), 7.72 (d, J=4.0 Hz, 1H), 7.63 (d, J=1.5 Hz, 2H), 7.49-7.42 (m, 2H), 4.88 (br s, 2H), 4.50 (s, 2H), 3.65-3.58 (m, 4H), 3.40-3.34 (m, 2H), 3.23-3.12 (m, 4H), 2.96 (s, 3H), 2.37-2.27 (m, 2H), 2.07 (d, J=12.6 Hz, 3H), 1.73-1.52 (m, 2H); ES-LCMS m/z 588.2, 590.2 [M+H]$^+$.

Example 377: 2-(1-((6-(3,5-Dichlorophenyl)-3-fluoro-2-((6-(4-methylpiperazin-1-yl)pyridin-3-yl)oxy)pyridin-4-yl)methyl)piperidin-4-yl)acetic acid, 4 hydrochloride

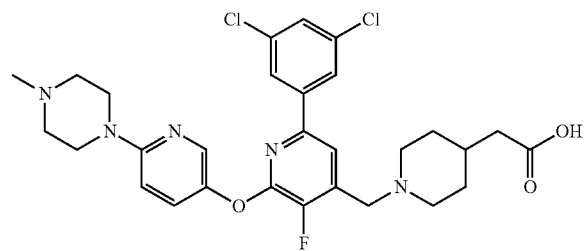

Step 1: tert-Butyl 4-(5-((4-(((tert-butyldimethylsilyl)oxy)methyl)-6-(3,5-dichlorophenyl)-3-fluoropyridin-2-yl)oxy)pyridin-2-yl)piperazine-1-carboxylate

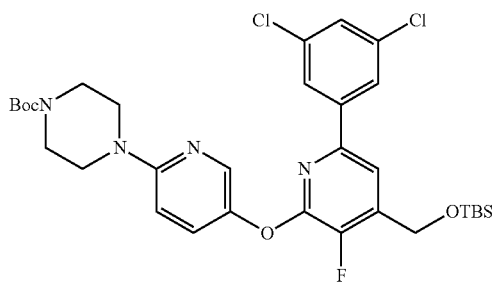 [SMILES: CC(C)(C)OC(=O)N1CCN(c2ccc(Oc3nc(-c4cc(Cl)cc(Cl)c4)cc(CO[Si](C)(C)C(C)(C)C)c3F)cn2)CC1]

A mixture of 4-(((tert-butyldimethylsilyl)oxy)methyl)-2-chloro-6-(3,5-dichlorophenyl)-3-fluoropyridine (600 mg, 1.212 mmol), tert-butyl 4-(5-hydroxypyridin-2-yl)piperazine-1-carboxylate (635 mg, 2.182 mmol), CuI (23.08 mg, 0.121 mmol), Cs$_2$CO$_3$ (1185 mg, 3.64 mmol) and 2-(dimethylamino)acetic acid (12.50 mg, 0.121 mmol) in 1,4-dioxane (5 mL) was stirred at 110° C. for 24 h under N$_2$ atmosphere. The mixture was filtered and the filtrate was concentrated to afford the crude. The crude material was purified by flash chromatography (from PE/EtOAc=5/1 to 3/1, TLC: PE/EtOAc=3/1, R$_f$=0.6) to yield tert-butyl 4-(5-((4-(((tert-butyldimethylsilyl)oxy)methyl)-6-(3,5-dichlorophenyl)-3-fluoropyridin-2-yl)oxy)pyridin-2-yl)piperazine-1-carboxylate (180 mg, 0.231 mmol, 19.0% yield) as a yellow oil: $^1$H NMR (400 MHz, CDCl$_3$) δ ppm 8.16 (d, J=2.8 Hz, 1H), 7.62 (d, J=1.8 Hz, 2H), 7.58 (d, J=3.5 Hz, 1H), 7.47 (m, J=2.8, 9.0 Hz, 1H), 7.41 (t, J=1.8 Hz, 1H), 7.32-7.29 (m, 1H), 4.89 (s, 2H), 3.57-3.53 (m, 8H), 1.49 (s, 9H), 0.99 (s, 9H), 0.17 (s, 6H); ES-LCMS m/z 663.2, 665.2 [M+H]$^+$.

Step 2: tert-Butyl 4-(5-((6-(3,5-dichlorophenyl)-3-fluoro-4-(hydroxymethyl)pyridin-2-yl)oxy)pyridin-2-yl)piperazine-1-carboxylate

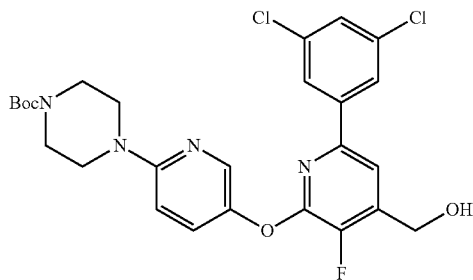 [SMILES: CC(C)(C)OC(=O)N1CCN(c2ccc(Oc3nc(-c4cc(Cl)cc(Cl)c4)cc(CO)c3F)cn2)CC1]

To a solution of tert-butyl 4-(5-((4-(((tert-butyldimethylsilyl)oxy)methyl)-6-(3,5-dichlorophenyl)-3-fluoropyridin-2-yl)oxy)pyridin-2-yl)piperazine-1-carboxylate (230 mg, 0.295 mmol) in THF (5 mL) was added TBAF (231 mg, 0.884 mmol) and the mixture was stirred at 25° C. for 15 min. The crude material was purified by flash chromatography (from PE/EtOAc=5/1 to 3/1, TLC: PE/EtOAc=3/1, R$_f$=0.6) to yield tert-butyl 4-(5-((6-(3,5-dichlorophenyl)-3-fluoro-4-(hydroxymethyl)pyridin-2-yl)oxy)pyridin-2-yl)piperazine-1-carboxylate (180 mg, 0.278 mmol, 95.0% yield) as a yellow oil: ¹H NMR (400 MHz, CDCl₃) δ ppm 8.16 (d, J=2.9 Hz, 1H), 7.65 (d, J=1.8 Hz, 2H), 7.60 (d, J=4.0 Hz, 1H), 7.47 (dd, J=3.0, 9.2 Hz, 1H), 7.31 (t, J=1.9 Hz, 1H), 6.74 (d, J=8.6 Hz, 1H), 4.93 (d, J=4.4 Hz, 2H), 3.59-3.56 (m, 4H), 3.56-3.53 (m, 4H), 1.50 (s, 9H); ES-LCMS m/z 549.2, 551.2 [M+H]⁺.

Step 3: tert-Butyl 4-(5-((6-(3,5-dichlorophenyl)-3-fluoro-4-(((methylsulfonyl)oxy)methyl)pyridin-2-yl)oxy)pyridin-2-yl)piperazine-1-carboxylate

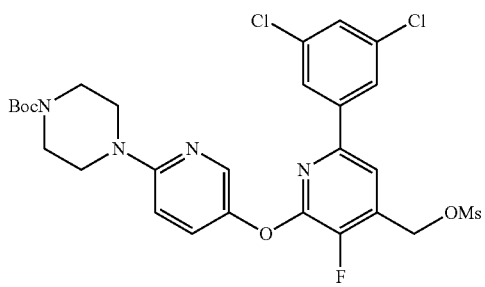 [SMILES: CC(C)(C)OC(=O)N1CCN(c2ccc(Oc3nc(-c4cc(Cl)cc(Cl)c4)cc(COS(C)(=O)=O)c3F)cn2)CC1]

To a solution of tert-butyl 4-(5-((6-(3,5-dichlorophenyl)-3-fluoro-4-(hydroxymethyl)pyridin-2-yl)oxy)pyridin-2-yl)piperazine-1-carboxylate (170 mg, 0.263 mmol) in DCM (4 mL) was added DIE A (0.138 mL, 0.789 mmol) and MsCl (0.027 mL, 0.342 mmol) and the mixture was stirred at 29° C. for 15 min. Saturated aqueous NaHCO₃ (20 mL) solution was added. The mixture was extracted with DCM (20 mL×3). The combined organic layers were washed with brine (20 mL), dried over Na₂SO₄, filtered and concentrated to yield tert-butyl 4-(5-((6-(3,5-dichlorophenyl)-3-fluoro-4-(((methylsulfonyl)oxy)methyl)pyridin-2-yl)oxy)pyridin-2-yl)piperazine-1-carboxylate (160 mg, 0.229 mmol, 87.0% yield) as a yellow oil: ¹H NMR (400 MHz, CDCl₃) δ ppm 8.21 (d, J=2.6 Hz, 1H), 7.57 (t, J=2.2 Hz, 1H), 7.54 (d, J=2.0 Hz, 2H), 7.43 (d, J=3.7 Hz, 1H), 7.28 (t, J=1.9 Hz, 1H), 6.78 (d, J=9.5 Hz, 1H), 5.33 (s, 2H), 3.09 (s, 3H), 2.77 (s, 8H), 1.42 (s, 9H); ES-LCMS m/z 627.2, 629.2 [M+H]⁺.

Step 4: tert-Butyl 4-(5-((6-(3,5-dichlorophenyl)-3-fluoro-4-((4-(2-methoxy-2-oxoethyl)piperidin-1-yl)methyl)pyridin-2-yl)oxy)pyridin-2-yl)piperazine-1-carboxylate

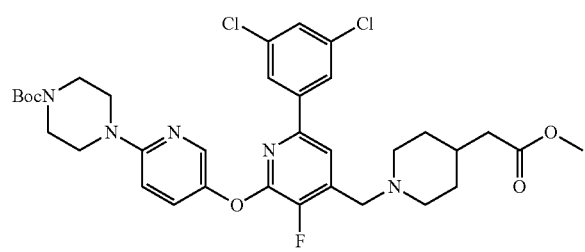 [SMILES: COC(=O)CC1CCN(Cc2cc(-c3cc(Cl)cc(Cl)c3)nc(Oc3ccc(N4CCN(C(=O)OC(C)(C)C)CC4)nc3)c2F)CC1]

To a solution of tert-butyl 4-(5-((6-(3,5-dichlorophenyl)-3-fluoro-4-(((methylsulfonyl)oxy)methyl)pyridin-2-yl)oxy) pyridin-2-yl)piperazine-1-carboxylate (130 mg, 0.186 mmol) and methyl 2-(piperidin-4-yl)acetate, hydrochloride (80 mg, 0.373 mmol) DMF (4 mL) was added DIEA (0.163 mL, 0.932 mmol) and the mixture was stirred at 28° C. for 12 h. The reaction mixture was concentrated to yield the residue. The crude material was purified by flash chromatography (from pure DCM to DCM/MeOH=10/1, TLC: DCM/MeOH=10/1, R_f=0.4) to yield tert-butyl 4-(5-((6-(3,5-dichlorophenyl)-3-fluoro-4-((4-(2-methoxy-2-oxoethyl)piperidin-1-yl)methyl)pyridin-2-yl)oxy)pyridin-2-yl)piperazine-1-carboxylate (120 mg, 0.160 mmol, 86.0% yield) as a yellow oil: ¹H NMR (400 MHz, CDCl₃) δ ppm 8.16 (d, J=2.8 Hz, 1H), 7.63 (d, J=1.8 Hz, 2H), 7.52-7.45 (m, 2H), 7.31 (s, 1H), 6.73 (d, J=9.3 Hz, 1H), 3.67 (s, 3H), 3.57 (br s, 4H), 3.56-3.53 (m, 4H), 2.92 (m, 2H), 2.28 (d, J=7.0 Hz, 2H), 2.24-2.11 (m, 2H), 1.87-1.69 (m, 5H), 1.39 (d, J=11.8 Hz, 2H), 0.07 (s, 9H); ES-LCMS m/z 688.2, 690.2 [M+H]⁺.

Step 5: Methyl 2-(1-((6-(3,5-dichlorophenyl)-3-fluoro-2-((6-(piperazin-1-yl)pyridin-3-yl)oxy)pyridin-4-yl)methyl)piperidin-4-yl)acetate, 4 trifluoroacetic acid salt

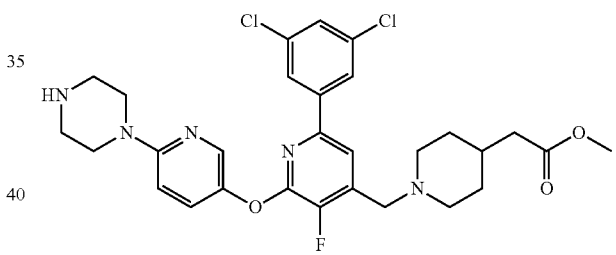

To a solution of tert-butyl 4-(5-((6-(3,5-dichlorophenyl)-3-fluoro-4-((4-(2-methoxy-2-oxoethyl)piperidin-1-yl)methyl)pyridin-2-yl)oxy)pyridin-2-yl)piperazine-1-carboxylate (130 mg, 0.173 mmol) in DCM (3 mL) was added TFA (0.3 mL, 3.89 mmol) and the mixture was stirred at 28° C. for 20 min. The reaction mixture was concentrated to yield methyl 2-(1-((6-(3,5-dichlorophenyl)-3-fluoro-2-((6-(piperazin-1-yl)pyridin-3-yl)oxy)pyridin-4-yl)methyl)piperidin-4-yl)acetate, 4 trifluoroacetic acid salt (140 mg, 0.120 mmol, 69.2% yield) as a yellow oil: ¹H NMR (400 MHz, CDCl₃) δ ppm 8.11 (d, J=2.9 Hz, 1H), 7.71 (d, J=3.5 Hz, 1H), 7.54 (d, J=1.8 Hz, 2H), 7.49 (dd, J=2.9, 9.3 Hz, 1H), 7.26 (t, J=1.8 Hz, 1H), 6.78 (d, J=9.3 Hz, 1H), 4.33 (s, 2H), 3.79-3.74 (m, 4H), 3.61 (s, 3H), 3.60-3.53 (m, 2H), 3.32 (d, J=1.8 Hz, 4H), 2.89 (d, J=14.3 Hz, 2H), 2.31-2.25 (m, 2H), 2.01-1.90 (m, 3H), 1.69 (q, J=11.8 Hz, 2H): ES-LCMS m/z 588.2, 590.2 [M+H]⁺.

Step 6: Methyl 2-(1-((6-(3,5-dichlorophenyl)-3-fluoro-2-((6-(4-methylpiperazin-1-yl)pyridin-3-yl)oxy)pyridin-4-yl)methyl)piperidin-4-yl)acetate Step 7: 2-(1-((6-(3,5-Dichlorophenyl)-3-fluoro-2-((6-(4-methylpiperazin-1-yl)pyridin-3-yl)oxy)pyridin-4-yl)methyl)piperidin-4-yl)acetic acid, 4 hydrochloride

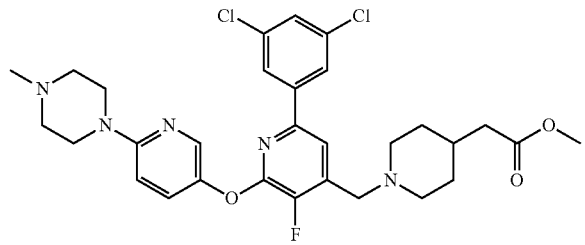

To a solution of methyl 2-(1-((6-(3,5-dichlorophenyl)-3-fluoro-2-((6-(piperazin-1-yl)pyridin-3-yl)oxy)pyridin-4-yl)methyl)piperidin-4-yl)acetate, 4 trifluoroacetic acid salt (130 mg, 0.111 mmol) in MeOH (5 mL) was added formic acid (0.1 mL, 2.61 mmol) and paraformaldehyde (16.68 mg, 0.556 mmol) and the mixture was stirred at 28° C. for 15.5 h. NaBH₃CN (34.9 mg, 0.556 mmol) was added and the whole mixture was stirred at 28° C. for 0.5 h. Saturated aqueous NaHCO₃ solution (20 mL) was added and the mixture was extracted with DCM (20 mL×3). The combined organic layers were washed with brine (20 mL), dried over Na₂SO₄, filtered and concentrated to yield methyl 2-(1-((6-(3,5-dichlorophenyl)-3-fluoro-2-((6-(4-methylpiperazin-1-yl)pyridin-3-yl)oxy)pyridin-4-yl)methyl)piperidin-4-yl)acetate (70 mg, 0.103 mmol, 93.0% yield) as a yellow oil: ¹H NMR (400 MHz, CDCl₃) δ ppm 8.09 (d, J=2.6 Hz, 1H), 7.56 (d, J=1.8 Hz, 2H), 7.42-7.37 (m, 2H), 7.23 (t, J=1.9 Hz, 1H), 6.66 (d, J=9.3 Hz, 1H), 3.60 (s, 3H), 3.57 (s, 2H), 3.52-3.50 (m, 4H), 2.84 (br s, 2H), 2.51-2.48 (m, 4H), 2.29 (s, 3H), 2.20 (d, J=7.1 Hz, 2H), 2.11-2.05 (m, 2H), 1.73-1.65 (m, 5H); ES-LCMS m/z 602.2, 604.2 [M+H]⁺.

A solution of methyl 2-(1-((6-(3,5-dichlorophenyl)-3-fluoro-2-((6-(4-methylpiperazin-1-yl)pyridin-3-yl)oxy)pyridin-4-yl)methyl)piperidin-4-yl)acetate (65 mg, 0.096 mmol) in 4 N HCl (3 mL, 12.00 mmol) was stirred at 80° C. for 0.5 h. The reaction mixture was concentrated. The residue was purified by preparative HPLC (MeCN/H₂O as eluents, acidic condition) followed by lyophilization to yield 2-(1-((6-(3,5-dichlorophenyl)-3-fluoro-2-((6-(4-methylpiperazin-1-yl)pyridin-3-yl)oxy)pyridin-4-yl)methyl)piperidin-4-yl)acetic acid, 4 hydrochloride (33.96 mg, 0.046 mmol, 48.2% yield) as a white solid: ¹H NMR (400 MHz, CD₃OD) δ ppm 8.18 (d, J=2.9 Hz, 1H), 7.92 (d, J=3.5 Hz, 1H), 7.77 (d, J=1.8 Hz, 2H), 7.69 (dd, J=2.8, 9.4 Hz, 1H), 7.46 (t, J=1.9 Hz, 1H), 7.13 (d, J=9.0 Hz, 1H), 4.55-4.46 (m, 4H), 3.68-3.59 (m, 4H), 3.49-3.30 (m, 2H), 3.23 (d, J=14.6 Hz, 4H), 2.96 (s, 3H), 2.31 (d, J=6.6 Hz, 2H), 2.06 (d, J=12.8 Hz, 3H), 1.69-1.54 (m, 2H); ES-LCMS m/z 588.2, 590.2 [M+H]⁺.

Examples 378-384 (Table 20) were prepared by procedures analogous to those described for example 377.

TABLE 20

| Example | Structure/Name | ¹H NMR | LCMS |
|---|---|---|---|
| 378 | 2-(1-((6-(3,5-dichlorophenyl)-3-fluoro-2-((2-(8-methyl-3,8-diazabicyclo[3.2.1]octan-3-yl)pyrimidin-5-yl)oxy)pyridin-4-yl)methyl)piperidin-4-yl)acetic acid | ¹H NMR (400 MHz, CD₃OD) δ ppm 8.50-8.47 (m, 2H), 8.00 (d, J = 3.5 Hz, 1H), 7.80 (d, J = 1.8 Hz, 2H), 7.48 (t, J = 1.7 Hz, 1H), 4.78 (d, J = 13.2 Hz, 2H), 4.55 (s, 2H), 4.11 (s, 2H), 3.66 (d, J = 11.9 Hz, 2H), 3.47 (d, J = 14.1 Hz, 2H), 3.23 (t, J = 12.6 Hz, 2H), 2.90 (s, 3H), 2.37-2.29 (m, 4H), 2.12-1.99 (m, 5H), 1.72-1.58 (m, 2H) | ES-LCMS m/z 615.3, 617.3 [M + H]⁺. |

TABLE 20-continued

| Example | Structure/Name | ¹H NMR | LCMS |
|---|---|---|---|
| 379 | 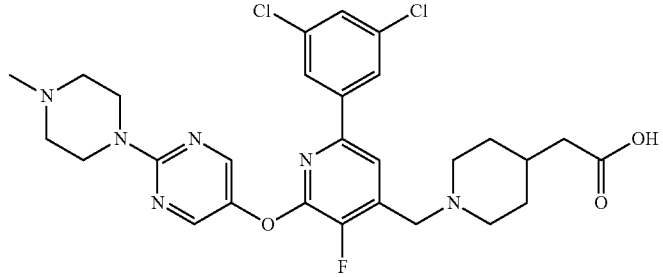 [SMILES: CN1CCN(c2ncc(Oc3nc(-c4cc(Cl)cc(Cl)c4)cc(CN4CCC(CC(=O)O)CC4)c3F)cn2)CC1]<br>2-(1-((6-(3,5-dichlorophenyl)-3-fluoro-2-((2-(4-methylpiperazin-1-yl)pyrimidin-5-yl)oxy)pyridin-4-yl)methyl)piperidin-4-yl)acetic acid | ¹H NMR (400 MHz, CD$_3$CN:D$_2$O = 3:1) δ ppm 8.55 (s, 2H) 7.83 (d J = 2.0 Hz, 2H) 7.79 (d, J = 3.7 Hz, 1H), 7.60 (t, J = 1.9 Hz, 1H), 4.82 (br d, J = 14.1 Hz, 2H), 4.49 (br s, 2H), 3.63 (br d, J = 12.3 Hz, 4H), 3.47-3.40 (m, 2H), 3.20-3.11 (m, 4H), 2.95 (s, 3H), 2.39 (br s, 2H), 2.13-2.08 (m, 3H), 1.59 (br s, 2H) | ES-LCMS m/z 589.2, 591.3 [M + H]⁺. |
| 380 | 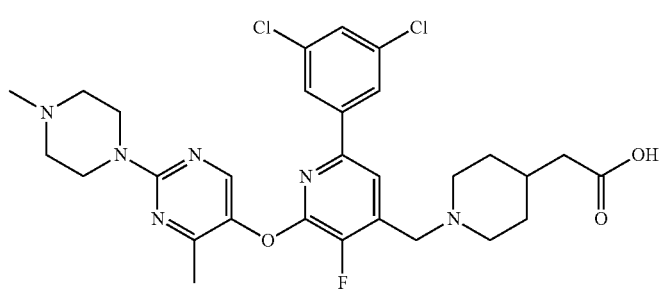 [SMILES: Cc1nc(N2CCN(C)CC2)ncc1Oc1nc(-c2cc(Cl)cc(Cl)c2)cc(CN2CCC(CC(=O)O)CC2)c1F]<br>2-(1-((6-(3,5-dichlorophenyl)-3-fluoro-2-((4-methyl-2-(4-methylpiperazin-1-yl)pyrimidin-5-yl)oxy)pyridin-4-yl)methyl)piperidin-4-yl)acetic acid | ¹H NMR (400 MHz, CD3OD) δ ppm 8.18 (s, 1H), 7.72 (d, J = 3.75 Hz, 1H), 7.69 (d, J = 1.76 Hz, 2H), 7.39 (t, J = 1.87 Hz, 1H), 3.90 (brs, 4H), 3.73 (s, 2H), 2.97 (d, J = 11.25 Hz, 2H), 2.62 (t, J = 4.96 Hz, 4H), 2.41 (s, 3H), 2.24 (s, 3H), 2.23-2.11 (m, 4H), 1.78 (d, J = 10.80 Hz, 3H), 1.35 (q, J = 11.54 Hz, 2H) | ES-LCMS m/z 603.2, 605.2 [M + H]⁺. |
| 381 | 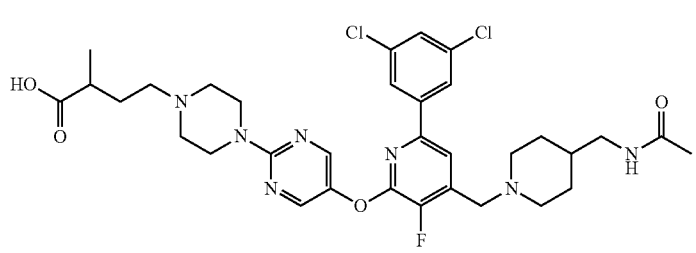 [SMILES: CC(=O)NCC1CCN(Cc2cc(-c3cc(Cl)cc(Cl)c3)nc(Oc3cnc(N4CCN(CCC(C)C(=O)O)CC4)nc3)c2F)CC1]<br>4-(4-(5-((4-((4-(acetamidomethyl)piperidin-1-yl)methyl)-6-(3,5-dichlorophenyl)-3-fluoropyridin-2-yl)oxy)pyrimidin-2-yl)piperazin-1-yl)-2-methylbutanoic acid | ¹H NMR (400 MHz, CD$_3$OD) δ ppm 8.49 (s, 2H), 7.93 (d, J = 3.7 Hz, 1H), 7.78 (d, J = 2.0 Hz, 2H), 7.48 (t, J = 1.8 Hz, 1H), 4.94 (br d, J = 14.8 Hz, 2H), 4.52 (s, 2H), 3.67 (br t, J = 14.4 Hz, 4H), 3.39 (br d, J = 11.7 Hz, 2H), 3.24 (d, J = 8.4 Hz, 2H), 3.19-3.11 (m, 4H), 2.56 (dd, J = 7.5, 13.0 Hz, 1H), 2.18-2.06 (m, 1H), 2.03-1.95 (m, 3H), 1.93 (s, 3H), 1.85 (br d, J = 13.5 Hz, 1H), 1.62-1.48 (m, 2H), 1.26 (d, J = 7.1 Hz, 3H) | ES-LCMS m/z 688.0, 689.9 [M + H]⁺. |

TABLE 20-continued

| Example | Structure/Name | ¹H NMR | LCMS |
|---|---|---|---|
| 382 | 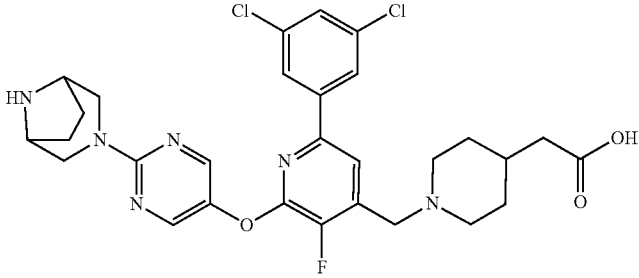 [SMILES: O=C(O)CC1CCN(Cc2cc(-c3cc(Cl)cc(Cl)c3)nc(Oc3cnc(N4CC5CCC(C4)N5)nc3)c2F)CC1]<br>2-(1-((2-((2-(3,8-diazabicyclo[3.2.1]octan-3-yl)pyrimidin-5-yl)oxy)-6-(3,5-dichlorophenyl)-3-fluoropyridin-4-yl)methyl)piperidin-4-yl)acetic acid | ¹H NMR (400 MHz, CD₃OD) δ ppm 8.48 (s, 2H), 8.04 (d, J = 3.3 Hz, 1H), 7.81 (d, J = 1.8 Hz, 2H), 7.49-7.45 (m, 1H), 4.71 (d, J = 12.8 Hz, 2H), 4.55 (s, 2H), 4.22 (s, 2H), 3.66 (d, J = 11.2 Hz, 2H), 3.41 (d, J = 13.9 Hz, 2H), 3.23 (t, J = 12.0 Hz, 2H), 2.33 (d, J = 6.6 Hz, 2H), 2.18-2.11 (m, 2H), 2.10-1.96 (m, 5H), 1.74-1.61 (m, 2H) | ES-LCMS m/z 601.3, 603.3 [M + H]⁺. |
| 383 | 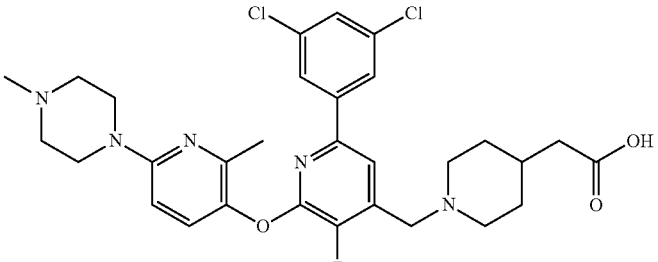<br>2-(1-((6-(3,5-dichlorophenyl)-3-fluoro-2-((2-methyl-6-(4-methylpiperazin-1-yl)pyridin-3-yl)oxy)pyridin-4-yl)methyl)piperidin-4-yl)acetic acid | ¹H NMR (400 MHz, CD₃OD) δ ppm 8.08 (d, J = 3.8 Hz, 1H), 8.01 (d, J = 9.3 Hz, 1H), 7.80 (d, J = 2.0 Hz, 2H), 7.50 (t, J = 1.8 Hz, 1H), 7.29 (d, J = 9.5 Hz, 1H), 4.64-4.46 (m, 4H), 3.70 (d, J = 11.3 Hz, 4H), 3.58 (t, J = 12.2 Hz, 2H), 3.42-3.34 (m, 2H), 3.27 (t, J = 11.9 Hz, 2H), 3.03 (s, 3H), 2.53 (s, 3H), 2.35 (d, J = 6.5 Hz, 2H), 2.10 (d, J = 13.1 Hz, 3H), 1.80-1.61 (m, 2H) | ES-LCMS m/z: 602.2, 604.2 [M + H]⁺. |
| 384 | 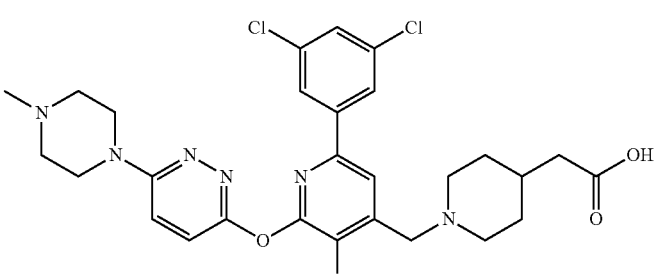<br>2-(1-((6-(3,5-dichlorophenyl)-3-fluoro-2-((6-(4-methylpiperazin-1-yl)pyridazin-3-yl)oxy)pyridin-4-yl)methyl)piperidin-4-yl)acetic acid | ¹H NMR (400 MHz, CD₃OD:CDCl₃ = 1:1) δ ppm m/z 7.75 (d, J = 3.7 Hz, 1H), 7.74 (d, J = 2.0 Hz, 2H), 7.62 (s, 1H), 7.39-7.37 (m, 2H), 3.72 (s, 2H), 3.71-3.66 (m, 4H), 3.01-2.95 (m, 2H), 2.66 (t, J = 5.1 Hz, 4H), 2.41 (s, 3H), 2.26 (d, J = 6.6 Hz, 2H), 2.24-2.18 (m, 2H), 1.82 (d, J = 10.1 Hz, 3H), 1.46-1.35 (m, 2H) | ES-LCMS 589.1, 591.1 [M + H]⁺. |

Example 385: Methyl 3-(4-(5-((4-((4-(Acetamidomethyl)piperidin-1-yl)methyl)-6-(3,5-dichlorophenyl)pyridin-2-yl)oxy)pyridin-2-yl)piperazin-1-yl)propanoate

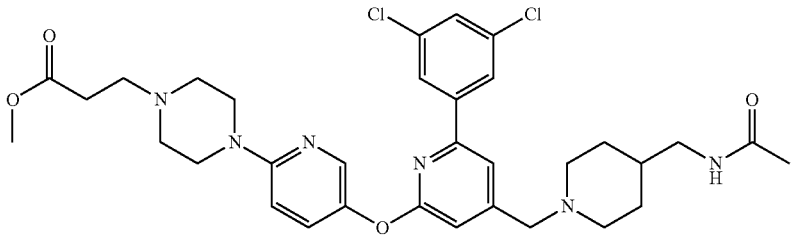 [SMILES: COC(=O)CCN1CCN(c2ccc(Oc3cc(CN4CCC(CNC(C)=O)CC4)cc(-c4cc(Cl)cc(Cl)c4)n3)cn2)CC1]

3-(4-(5-((4-((4-(Acetamidomethyl)piperidin-1-yl)methyl)-6-(3,5-dichlorophenyl)pyridin-2-yl)oxy)pyridin-2-yl)piperazin-1-yl)propanoic acid, 4 hydrochloride, 5H$_2$O (135 mg, 0.154 mmol) was dissolved in HCl solution (4 M in MeOH, 5 mL, 20.00 mmol). Then the reaction mixture was stirred at 20° C. for 12 h. The solvent was concentrated to give the crude which was purified by preparative HPLC and the solution was adjust pH=7-8 with aqueous NaOH solution (1 M). The mixture was extracted with DCM (30 mL×3). The combined organic layers were dried over Na$_2$SO$_4$, filtered and concentrated to give methyl 3-(4-(5-((4-((4-(acetamidomethyl)piperidin-1-yl)methyl)-6-(3,5-dichlorophenyl)pyridin-2-yl)oxy)pyridin-2-yl)piperazin-1-yl)propanoate (54.2 mg, 0.080 mmol, 52.0% yield) as a pale yellow solid: $^1$H NMR (400 MHz, CD$_3$OD) δ ppm 8.01 (d, J=2.65 Hz, 1H), 7.80 (d, J=1.98 Hz, 2H), 7.60 (s, 1H), 7.47 (dd, J=2.87, 9.26 Hz, 1H), 7.40 (t, J=1.87 Hz, 1H), 6.96 (s, 1H), 6.92 (d, J=9.04 Hz, 1H), 3.67 (s, 3H), 3.60 (s, 2H), 3.56-3.50 (m, 4H), 3.06 (d, J=6.61 Hz, 2H), 2.93 (d, J=11.91 Hz, 2H), 2.78-2.72 (m, 2H), 2.65-2.55 (m, 6H), 2.09 (t, J=10.80 Hz, 2H), 1.92 (s, 3H), 1.71 (d, J=11.91 Hz, 2H), 1.52 (brs, 1H), 1.30-1.22 (m, 2H); ES-LCMS m/z 655.0, 657.0 [M+H]$^+$.

Example 386: 2-(1-((6-(3,5-Dichlorophenyl)-3-methyl-2-((6-(4-methylpiperazin-1-yl)pyridin-3-yl)oxy)pyridin-4-yl)methyl)piperidin-4-yl)acetic acid, 4 hydrochloride

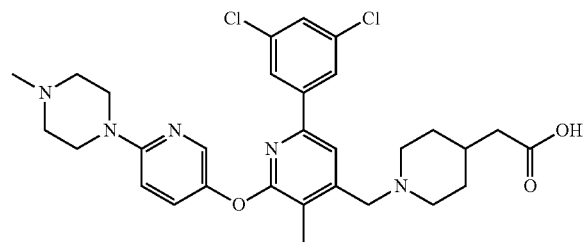 [SMILES: Cc1c(CN2CCC(CC(=O)O)CC2)cc(-c2cc(Cl)cc(Cl)c2)nc1Oc1ccc(N2CCN(C)CC2)nc1]

Step 1: 2-(Benzyloxy)-4-(((tert-butyldimethylsilyl)oxy)methyl)-6-(3,5-dichlorophenyl)-3-methylpyridine

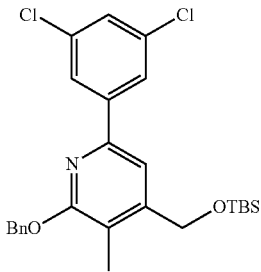 [SMILES: Cc1c(CO[Si](C)(C)C(C)(C)C)cc(-c2cc(Cl)cc(Cl)c2)nc1OCc1ccccc1]

To a mixture of 18-crown-6 (0.388 g, 1.468 mmol), K$_2$CO$_3$ (1.218 g, 8.81 mmol) and BnBr (1.005 g, 5.87 mmol) in DMF (10 mL) was added 4-(((tert-butyldimethylsilyl)oxy)methyl)-6-(3,5-dichlorophenyl)-3-methylpyridin-2-ol (1.3 g, 2.94 mmol). The mixture was stirred at 80° C. for 5 h. After filtration, the filtrate was concentrated to yield 2-(benzyloxy)-4-(((tert-butyldimethylsilyl)oxy)methyl)-6-(3,5-dichlorophenyl)-3-methylpyridine (1.6 g, 2.62 mmol, 89.0% yield) as a yellow solid: $^1$H NMR (400 MHz, CDCl$_3$) δ ppm 7.86 (d, J=1.8 Hz, 2H), 7.73 (dd, J=1.5, 7.9 Hz, 3H), 7.45-7.43 (m, 3H), 7.39 (d, J=1.3 Hz, 1H), 5.50 (s, 2H), 4.72 (s, 2H), 2.16 (s, 3H), 0.99-0.97 (m, 9H), 0.15-0.13 (m, 6H); ES-LCMS m/z 488.2, 490.2 [M+H]$^+$.

Step 2: (2-(Benzyloxy)-6-(3,5-dichlorophenyl)-3-methylpyridin-4-yl)methanol

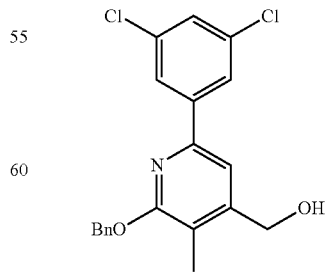

To a solution of 2-(benzyloxy)-4-(((tert-butyldimethylsilyl)oxy)methyl)-6-(3,5-dichlorophenyl)-3-methylpyridine (1.5 g, 2.456 mmol) in THF (15 mL) was added TBAF (1 M in THF, 5 mL, 5.00 mmol). The mixture was stirred at 30° C. for 30 min. The mixture was concentrated. The crude material was purified by flash chromatography (from PE/EtOAc=10/1 to 3/1 to DCM/MeOH=10/1, TLC: PE/EtOAc=3/1, $R_f$=0.3) to yield (2-(benzyloxy)-6-(3,5-dichlorophenyl)-3-methylpyridin-4-yl)methanol (0.95 g, 2.335 mmol, 95.0% yield) as an off white solid: $^1$H NMR (400 MHz, CDCl$_3$) δ ppm 7.87 (d, J=1.8 Hz, 2H), 7.53-7.43 (m, 3H), 7.41-7.31 (m, 4H), 5.49 (s, 2H), 4.75 (s, 2H), 2.20 (s, 3H); ES-LCMS m/z 374.1, 376.0 [M+H]$^+$.

Step 3: (2-(Benzyloxy)-6-(3,5-dichlorophenyl)-3-methylpyridin-4-yl)methyl methanesulfonate

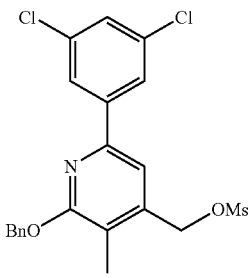 [SMILES: Cc1c(COS(C)(=O)=O)cc(-c2cc(Cl)cc(Cl)c2)nc1OCc1ccccc1]

To a mixture of (2-(benzyloxy)-6-(3,5-dichlorophenyl)-3-methylpyridin-4-yl)methanol (0.95 g, 2.335 mmol) and DIEA (1.240 mL, 7.01 mmol) in DCM (30 mL) was added MsCl (0.401 g, 3.50 mmol). The mixture was stirred at 0° C. for 15 min. The mixture was added H$_2$O (15 mL), extracted with DCM (15 mL×2). The combined organic layers were washed with brine (20 mL), dried over Na$_2$SO$_4$, filtered and concentrated to yield (2-(benzyloxy)-6-(3,5-dichlorophenyl)-3-methylpyridin-4-yl)methyl methanesulfonate (1.1 g, 2.189 mmol, 94.0% yield) as a yellow solid: $^1$H NMR (400 MHz, CDCl$_3$) δ ppm 7.79 (d, J=2.0 Hz, 2H), 7.44 (d, J=7.7 Hz, 2H), 7.35-7.31 (m, 3H), 7.27-7.22 (m, 2H), 5.44 (d, J=3.7 Hz, 2H), 4.53 (s, 2H), 2.71 (s, 3H), 2.27-2.21 (m, 3H); ES-LCMS m/z 452.0, 454.1 [M+H]$^+$.

Step 4: Methyl 2-(1-((2-(benzyloxy)-6-(3,5-dichlorophenyl)-3-methylpyridin-4-yl)methyl)piperidin-4-yl)acetate

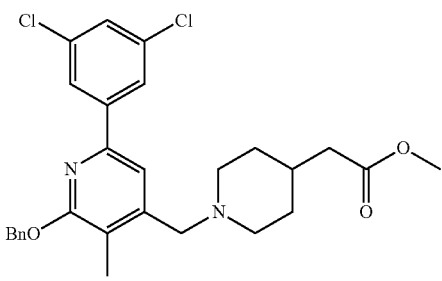 [SMILES: COC(=O)CC1CCN(Cc2cc(-c3cc(Cl)cc(Cl)c3)nc(OCc3ccccc3)c2C)CC1]

To a mixture of (2-(benzyloxy)-6-(3,5-dichlorophenyl)-3-methylpyridin-4-yl)methyl methanesulfonate (1.1 g, 2.189 mmol) and DIEA (1.937 mL, 10.94 mmol) in DML (10 mL) was added methyl 2-(piperidin-4-yl)acetate, hydrochloride (0.942 g, 4.38 mmol). The mixture was stirred at 50° C. for 10 h. The mixture was concentrated. The residue was purified by flash chromatography (from PE/EtOAc=10/1 to 2/1, TLC: PE/EtOAc=5/1, $R_f$=0.6) to yield methyl 2-(1-((2-(benzyloxy)-6-(3,5-dichlorophenyl)-3-methylpyridin-4-yl)methyl)piperidin-4-yl)acetate (1.15 g, 2.061 mmol, 94.0% yield) as a yellow solid: $^1$H NMR (400 MHz, CDCl$_3$) δ ppm 8.01 (br s, 2H), 7.51 (d, J=7.3 Hz, 2H), 7.47-7.37 (m, 3H), 7.36-7.30 (m, 2H), 5.49 (s, 2H), 4.13 (br s, 2H), 3.66 (s, 3H), 3.44 (br s, 2H), 2.78-2.53 (m, 2H), 2.32 (br s, 5H), 1.87 (br s, 3H), 1.44 (d, J=5.0 Hz, 2H); ES-LCMS m/z 513.2, 515.2 [M+H]$^+$.

Step 5: Methyl 2-(1-((6-(3,5-dichlorophenyl)-2-hydroxy-3-methylpyridin-4-yl)methyl)piperidin-4-yl)acetate

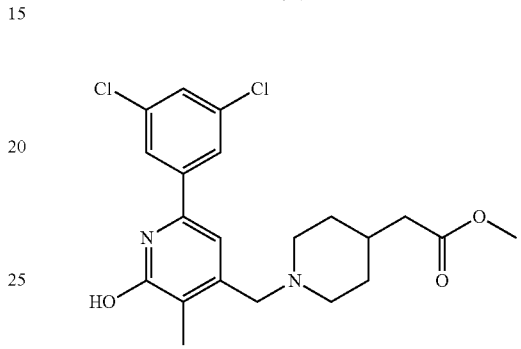

A solution of methyl 2-(1-((2-(benzyloxy)-6-(3,5-dichlorophenyl)-3-methylpyridin-4-yl)methyl)piperidin-4-yl)acetate (1 g, 1.792 mmol) in TFA (5 mL, 64.9 mmol) was stirred at 50° C. for 4 h. The reaction mixture was concentrated. The residue was added DCM/MeOH (100 mL, 10/1), neutralized with saturated aqueous Na$_2$CO$_3$ solution (50 mL) to pH=8-9. The mixture was extracted with DCM/MeOH (50 mL, 10/1). The combined organic layers were washed with brine (50 mL), dried over Na$_2$SO$_4$, filtered and concentrated to yield methyl 2-(1-((6-(3,5-dichlorophenyl)-2-hydroxy-3-methylpyridin-4-yl)methyl)piperidin-4-yl)acetate (1 g, 1.677 mmol, 94.0% yield) as a yellow solid: $^1$H NMR (400 MHz, CDCl$_3$) δ ppm 7.72 (d, J=1.8 Hz, 2H), 7.36 (d, J=0.9 Hz, 1H), 7.30 (s, 1H), 3.66 (s, 3H), 3.39 (s, 2H), 2.83 (d, J=11.7 Hz, 2H), 2.26 (d, J=7.1 Hz, 2H), 2.20 (s, 3H), 2.09-2.03 (m, 2H), 1.84-1.78 (m, 1H), 1.70 (d, J=12.6 Hz, 2H), 1.36-1.31 (m, 2H); ES-LCMS m/z 423.1, 425.1 [M+H]$^+$.

Step 6: Methyl 2-(1-((2-((6-bromopyridin-3-yl)oxy)-6-(3,5-dichlorophenyl)-3-methylpyridin-4-yl)methyl)piperidin-4-yl)acetate

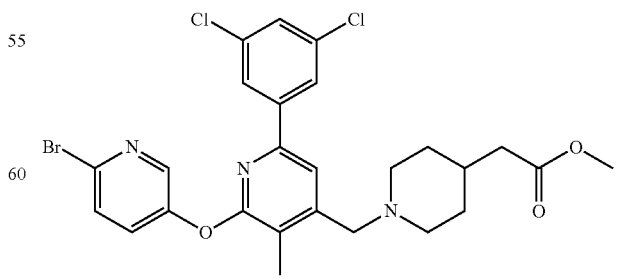

To a mixture of methyl 2-(1-((6-(3,5-dichlorophenyl)-2-hydroxy-3-methylpyridin-4-yl)methyl)piperidin-4-yl)acetate (600 mg, 1.006 mmol) and 2-bromo-5-fluoropyridine (885 mg, 5.03 mmol) in NMP (30 mL) was added K₂CO₃ (834 mg, 6.04 mmol). The mixture was stirred at 160° C. for 5 h. After filtration, the filtrate was concentrated. The crude material was purified by flash chromatography (from pure PE to PE/EA=5/1, TLC: PE/EA=5/1, $R_f$=0.6) to yield methyl 2-(1-((2-((6-bromopyridin-3-yl)oxy)-6-(3,5-dichlorophenyl)-3-methylpyridin-4-yl)methyl)piperidin-4-yl)acetate (290 mg, 0.355 mmol, 35.3% yield) as a yellow solid: ¹H NMR (400 MHz, CDCl₃) δ ppm 8.31 (d, J=2.9 Hz, 1H), 7.64 (d, J=2.0 Hz, 2H), 7.51 (d, J=5.5 Hz, 2H), 7.38 (s, 1H), 7.30-7.29 (m, 1H), 3.67-3.65 (m, 2H), 3.51 (s, 3H), 2.86 (d, J=12.6 Hz, 4H), 2.36 (s, 3H), 2.13-2.09 (m, 2H), 1.85-1.72 (m, 3H), 1.36 (br s, 2H); ES-LCMS m/z 578.0, 580.0, 582.0 [M+H]⁺.

Step 7: tert-Butyl 4-(5-((6-(3,5-dichlorophenyl)-4-((4-(2-methoxy-2-oxoethyl)piperidin-1-yl)methyl)-3-methylpyridin-2-yl)oxy)pyridin-2-yl)piperazine-1-carboxylate

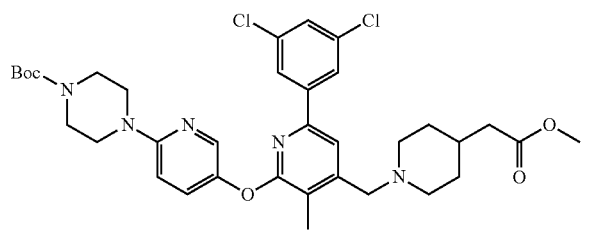 [SMILES: COC(=O)CC1CCN(Cc2cc(-c3cc(Cl)cc(Cl)c3)nc(Oc3ccc(N4CCN(C(=O)OC(C)(C)C)CC4)nc3)c2C)CC1]

A mixture of methyl 2-(1-((2-((6-bromopyridin-3-yl)oxy)-6-(3,5-dichlorophenyl)-3-methylpyridin-4-yl)methyl)piperidin-4-yl)acetate (290 mg, 0.355 mmol), tert-butyl piperazine-1-carboxylate (331 mg, 1.777 mmol), Xantphos (20.57 mg, 0.036 mmol) and Cs₂CO₃ (347 mg, 1.066 mmol) in THF (15 mL) was added Pd₂(dba)₃ (32.5 mg, 0.036 mmol) under N₂ atmosphere. The mixture was stirred at 75° C. for 36 h under N₂ atmosphere. The mixture was filtered and the filtrate was concentrated. The residue was purified by prep-TLC (PE/EtOAc=4/1, $R_f$=0.2) were combined and concentrated to yield tert-butyl 4-(5-((6-(3,5-dichlorophenyl)-4-((4-(2-methoxy-2-oxoethyl)piperidin-1-yl)methyl)-3-methylpyridin-2-yl)oxy)pyridin-2-yl)piperazine-1-carboxylate (100 mg, 0.099 mmol, 27.9% yield) as a yellow oil: ¹H NMR (400 MHz, CDCl₃) δ ppm 7.62-7.51 (m, 2H), 7.37-7.29 (m, 2H), 7.21 (dd, J=2.1, 3.9 Hz, 2H), 6.72-6.57 (m, 1H), 3.60 (s, 2H), 3.59 (s, 3H), 3.49-3.44 (m, 4H), 2.88-2.72 (m, 4H), 2.39-2.25 (m, 3H), 2.24-2.14 (m, 4H), 2.06-1.99 (m, 2H), 1.76-1.64 (m, 3H), 1.47-1.25 (m, 11H); ES-LCMS m/z: 684.3, 686.3 [M+H]⁺.

Step 8: Methyl 2-(1-((6-(3,5-dichlorophenyl)-3-methyl-2-((6-(piperazin-1-yl)pyridin-3-yl)oxy)pyridin-4-yl)methyl)piperidin-4-yl)acetate, 4 trifluoroacetic acid

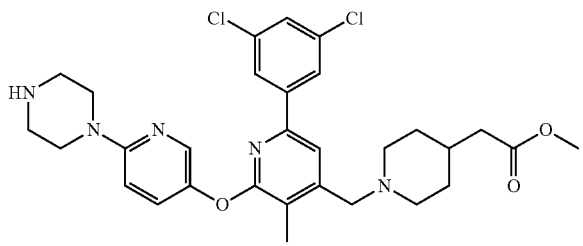 [SMILES: COC(=O)CC1CCN(Cc2cc(-c3cc(Cl)cc(Cl)c3)nc(Oc3ccc(N4CCNCC4)nc3)c2C)CC1]

A solution of tert-butyl 4-(5-((6-(3,5-dichlorophenyl)-4-((4-(2-methoxy-2-oxoethyl)piperidin-1-yl)methyl)-3-methylpyridin-2-yl)oxy)pyridin-2-yl)piperazine-1-carboxylate (100 mg, 0.099 mmol) and TFA (3 mL, 38.9 mmol) in DCM (15 mL) was stirred at 20° C. for 1 h. Then the mixture was concentrated to yield methyl 2-(1-((6-(3,5-dichlorophenyl)-3-methyl-2-((6-(piperazin-1-yl)pyridin-3-yl)oxy)pyridin-4-yl)methyl)piperidin-4-yl)acetate, 4 trifluoroacetic acid (140 mg, 0.094 mmol, 95.0% yield) as a yellow oil: ¹H NMR (400 MHz, CDCl₃) δ ppm 7.81-7.57 (m, 3H), 7.46 (br s, 2H), 7.10-7.07 (m, 1H), 7.02-6.92 (m, 1H), 4.10-4.01 (m, 2H), 3.97 (t, J=6.9 Hz, 2H), 3.58-3.41 (m, 5H), 2.99-2.73 (m, 2H), 2.54 (br s, 2H), 2.13 (br s, 3H), 1.96-1.72 (m, 6H), 1.63-1.40 (m, 2H), 1.39-1.17 (m, 3H); ES-LCMS m/z 584.2, 586.2 [M+H]⁺.

Step 9: Methyl 2-(1-((6-(3,5-dichlorophenyl)-3-methyl-2-((6-(4-methylpiperazin-1-yl)pyridin-3-yl)oxy)pyridin-4-yl)methyl)piperidin-4-yl)acetate

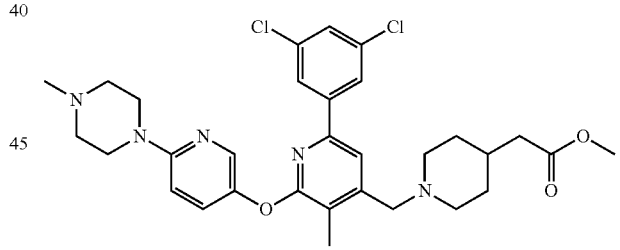

A mixture of methyl 2-(1-((6-(3,5-dichlorophenyl)-3-methyl-2-((6-(piperazin-1-yl)pyridin-3-yl)oxy)pyridin-4-yl)methyl)piperidin-4-yl)acetate, 4 trifluoroacetic acid (140 mg, 0.094 mmol) and formaldehyde (28.3 mg, 0.942 mmol) in MeOH was stirred at 30° C. for 10 h. Then to the mixture was added NaBH₃CN (29.6 mg, 0.471 mmol). The whole mixture was stirred at 30° C. for another 2 h. The mixture was added saturated aqueous Na₂CO₃ solution (20 mL), extracted with DCM (30 mL×3). The combined organic layers were washed with brine (50 mL), dried over Na₂SO₄, filtered and concentrated to yield methyl 2-(1-((6-(3,5-dichlorophenyl)-3-methyl-2-((6-(4-methylpiperazin-1-yl)pyridin-3-yl)oxy)pyridin-4-yl)methyl)piperidin-4-yl)acetate (70 mg, 0.082 mmol, 87.0% yield) as a yellow oil: ¹H NMR (400 MHz, CDCl₃) δ ppm 7.70-7.48 (m, 2H), 7.39-7.33 (m, 1H), 7.27-7.20 (m, 3H), 7.19-7.13 (m, 1H), 3.60 (s, 2H), 3.54-3.41 (m, 4H), 3.40 (br s, 3H), 2.79 (td, J=3.8, 7.6 Hz, 2H), 2.61-2.42 (m, 2H), 2.41-2.13 (m, 6H), 2.10-1.96 (m, 2H), 1.90 (dt, J=2.3, 11.7 Hz, 2H), 1.76-1.70 (m, 1H), 1.69-1.53 (m, 4H), 1.31-1.24 (m, 2H); ES-LCMS m/z: 598.3, 600.3 [M+H]$^+$.

Step 10: 2-(1-(((6-(3,5-Dichlorophenyl)-3-methyl-2-((6-(4-methylpiperazin-1-yl)pyridin-3-yl)oxy)pyridin-4-yl)methyl)piperidin-4-yl)acetic acid, 4 hydrochloride

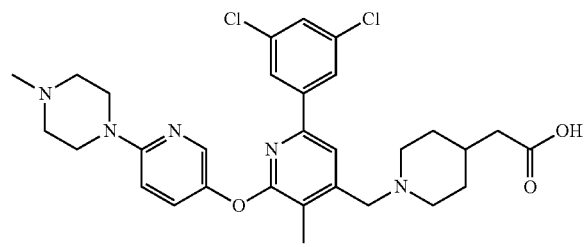 [SMILES: Cc1c(CN2CCC(CC(=O)O)CC2)cc(-c2cc(Cl)cc(Cl)c2)nc1Oc1ccc(N2CCN(C)CC2)nc1]

A solution of methyl 2-(1-(((6-(3,5-dichlorophenyl)-3-methyl-2-((6-(4-methylpiperazin-1-yl)pyridin-3-yl)oxy)pyridin-4-yl)methyl)piperidin-4-yl)acetate (70 mg, 0.082 mmol) and concentrated HCl (2 mL, 24.35 mmol) was stirred at 60° C. for 0.5 h. The mixture was concentrated. The residue was purified by preparative HPLC (MeCN/H$_2$O as eluents, acidic condition) followed by lyophilization to yield 2-(1-(((6-(3,5-dichlorophenyl)-3-methyl-2-((6-(4-methylpiperazin-1-yl)pyridin-3-yl)oxy)pyridin-4-yl)methyl)piperidin-4-yl)acetic acid, 4 hydrochloride (4.97 mg, 6.75 μmol, 8.25% yield) as a white solid: $^1$H NMR (400 MHz, D$_2$O/CD$_3$CN=1/1) δ ppm 8.05 (d, J=2.6 Hz, 1H), 7.72 (d, J=1.8 Hz, 2H), 7.64-7.59 (m, 2H), 7.46-7.43 (m, 1H), 7.02 (d, J=9.3 Hz, 1H), 4.34 (s, 2H), 4.26 (d, J=15.4 Hz, 2H), 3.58-3.44 (m, 4H), 3.21 (d, J=11.7 Hz, 2H), 3.14-3.01 (m, 4H), 2.85 (s, 3H), 2.38 (s, 3H), 2.27 (d, J=6.4 Hz, 2H), 2.04-1.96 (m, 3H), 1.49 (d, J=13.0 Hz, 2H); ES-LCMS m/z: 584.2, 586.3 [M+H]$^+$.

Example 387: 2-(1-((2-((2-(4-((1H-1,2,3-Triazol-5-yl)methyl)piperazin-1-yl)pyrimidin-5-yl)oxy)-6-(3,5-dichlorophenyl)pyridin-4-yl)methyl)piperidin-4-yl)acetic acid

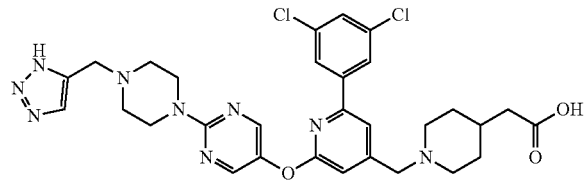 [SMILES: O=C(O)CC1CCN(Cc2cc(Oc3cnc(N4CCN(Cc5cnn[nH]5)CC4)nc3)nc(-c3cc(Cl)cc(Cl)c3)c2)CC1]

Step 1: Ethyl 2-(1-((2-(3,5-dichlorophenyl)-6-((2-(4-(prop-2-yn-1-yl)piperazin-1-yl) pyrimidin-5-yl)oxy)pyridin-4-yl(methyl)piperidin-4-yl)acetate

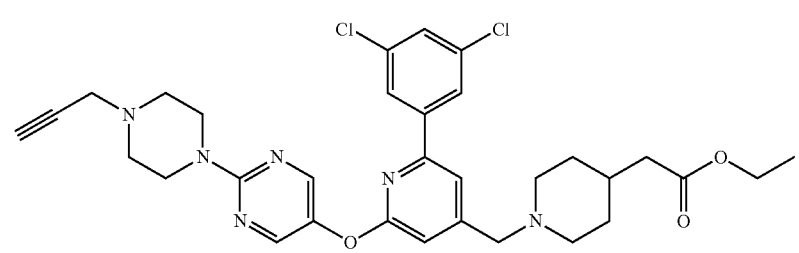 [SMILES: C#CCN1CCN(c2ncc(Oc3cc(CN4CCC(CC(=O)OCC)CC4)cc(-c4cc(Cl)cc(Cl)c4)n3)cn2)CC1]

To a mixture of K$_2$CO$_3$ (115 mg, 0.832 mmol) and ethyl 2-(1-((2-(3,5-dichlorophenyl)-6-((2-(piperazin-1-yl)pyrimidin-5-yl)oxy)pyridin-4-yl)methyl)piperidin-4-yl)acetate (500 mg, 0.757 mmol) in DCE (20 mL) was added 3-bromoprop-1-yne (80% in toluene) (0.159 mL, 0.832 mmol) dropwise. Then the mixture was stirred at 25° C. for 5 h. The mixture was added water (50 mL), extracted with DCM (30 mL×3). The combined organic layers were washed with brine (50 mL), dried over Na$_2$SO$_4$, filtered and concentrated. The residue was purified by flash chromatography (from PE/EtOAc=3/1 to 2/1, TLC: PE/EtOAc=2/1, R$_f$=0.4) to yield ethyl 2-(1-((2-(3,5-dichlorophenyl)-6-((2-(4-(prop-2-yn-1-yl)piperazin-1-yl)pyrimidin-5-yl)oxy)pyridin-4-yl)methyl)piperidin-4-yl)acetate (350 mg, 0.524 mmol, 69.2% yield) as a yellow solid: $^1$H NMR (400 MHz, CDCl$_3$) δ ppm 8.30 (s, 2H), 7.73 (d, J=1.8 Hz, 2H), 7.41 (s, 1H), 7.34 (t, J=1.8 Hz, 1H), 6.89 (s, 1H), 4.16-4.10 (m, 2H), 3.94-3.85 (m, 4H), 3.52 (s, 2H), 3.37 (d, J=2.4 Hz, 2H), 2.90-2.82 (m, 2H), 2.73-2.61 (m, 4H), 2.30-2.21 (m, 3H), 2.11-2.04 (m, 2H), 1.80 (d, J=10.6 Hz, 1H), 1.72 (d, J=13.2 Hz, 2H), 1.42-1.30 (m, 2H), 1.25 (t, J=7.2 Hz, 3H); ES-LCMS m/z: 623.3, 625.3 [M+H]$^+$.

Step 2: 2-(1-((2-((2-(4-((1H-1,2,3-Triazol-5-yl)methyl)piperazin-1-yl)pyrimidin-5-yl)oxy)-6-(3,5-dichlorophenyl)pyridin-4-yl)methyl)piperidin-4-yl)acetic acid To a mixture of ethyl 2-(1-((2-(3,5-dichlorophenyl)-6-((2-(4-(prop-2-yn-1-yl)piperazin-1-yl)pyrimidin-5-yl)oxy)pyridin-4-yl)methyl)piperidin-4-yl)acetate (300 mg, 0.449 mmol), 3,3',3''-(4,4',4''-(nitrilotris(methylene))tris(1H-1,2,3-triazole-4,1-diyl))tris(propan-1-ol) (78 mg, 0.180 mmol), (R)-2-((S)-1,2-dihydroxyethyl)-4-hydroxy-5-oxo-2,5-dihydrofuran-3-olate, sodium salt (89 mg, 0.449 mmol) and CuSO$_4$ (14.33 mg, 0.090 mmol) in t-BuOH (1 mL), DMSO (1 mL) and water (1 mL) was added TMS-N$_3$ (56.9 mg, 0.494 mmol). Then the reaction mixture was stirred at 25° C. for 12 h. To the mixture was added LiOH·H$_2$O (56.5 mg, 1.346 mmol) and stirred at 25° C. for 4 h. The mixture was acidified with 1 N HCl to pH=5. The mixture was purified by preparative HPLC (MeCN/H$_2$O as eluents, acidic condition), followed by lyophilization to yield a residue, which was purified by preparative HPLC (MeCN/H$_2$O as eluents, basic condition), followed by lyophilization to yield 2-(1-((2-((2-(4-((1H-1,2,3-triazol-5-yl)methyl)piperazin-1-yl)pyrimidin-5-yl)oxy)-6-(3,5-dichlorophenyl)pyridin-4-yl)methyl)piperidin-4-yl)acetic acid (55.42 mg, 0.085 mmol, 19.0% yield) as a white solid: $^1$H NMR (400 MHz, CD$_3$OD) δ ppm 8.30 (s, 2H), 7.80 (d, J=2.0 Hz, 2H), 7.77 (s, 1H), 7.65 (s, 1H), 7.42 (t, J=1.9 Hz, 1H), 7.04 (s, 1H), 3.89-3.80 (m, 4H), 3.75 (s, 2H), 3.68 (s, 2H), 2.97 (d, J=11.7 Hz, 2H), 2.59 (t, J=5.0 Hz, 4H), 2.28-2.12 (m, 4H), 1.79 (d, J=10.4 Hz, 3H), 1.44-1.29 (m, 2H); ES-LCMS m/z 638.3, 640.3 [M+H]$^+$.

Example 388: 2-(1-((2-(3,5-Dichlorophenyl)-6-(methyl(2-(4-methylpiperazin-1-yl)pyrimidin-5-yl)amino)pyridin-4-yl)methyl)piperidin-4-yl)acetic acid, 4 hydrochloride

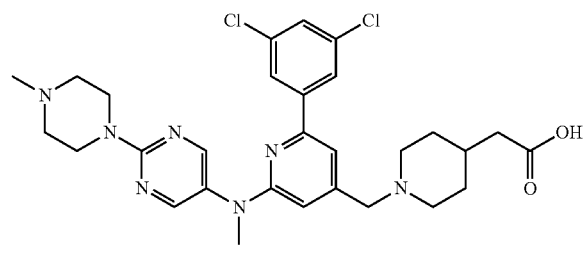 [SMILES: CN1CCN(c2ncc(N(C)c3cc(CN4CCC(CC(=O)O)CC4)cc(-c4cc(Cl)cc(Cl)c4)n3)cn2)CC1]

Step 1: Methyl 2-(3,5-dichlorophenyl)-6-(methyl(2-(methylthio)pyrimidin-5-yl)amino)isonicotinate

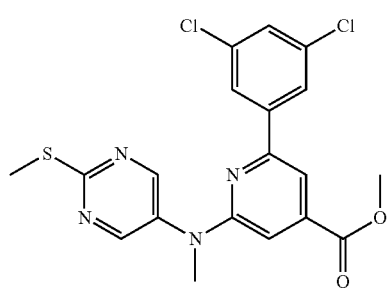

To a mixture of methyl 2-(3,5-dichlorophenyl)-6-((2-(methylthio)pyrimidin-5-yl)amino)isonicotinate (500 mg, 0.949 mmol), MeI (1078 mg, 7.60 mmol) in DMF (5 mL) was added t-BuOK (320 mg, 2.85 mmol). The mixture was stirred at 20° C. for 1 h. The mixture was filtered and concentrated. The crude material was purified by flash chromatography (from pure PE to PE/EA=5/1, TLC: PE/EA=5/1, R$_f$=0.7) to yield methyl 2-(3,5-dichlorophenyl)-6-(methyl(2-(methylthio)pyrimidin-5-yl)amino)isonicotinate (400 mg, 0.735 mmol, 77.0% yield) as a pale yellow solid: $^1$H NMR (400 MHz, CDCl$_3$) δ ppm 8.55 (s, 2H), 7.88 (d, J=1.8 Hz, 2H), 7.67 (s, 1H), 7.38 (d, J=2.0 Hz, 1H), 7.09 (s, 1H), 3.92 (s, 3H), 3.57 (s, 3H), 2.61 (s, 3H); ES-LCMS m/z 435.0, 437.0 [M+H]$^+$.

Step 2: (2-(3,5-Dichlorophenyl)-6-(methyl(2-(methylthio)pyrimidin-5-yl)amino)pyridin-4-yl)methanol

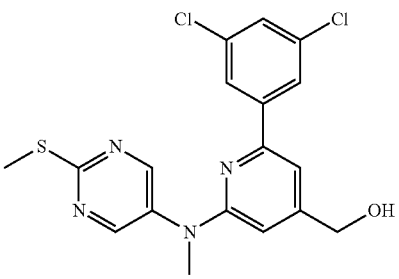 [SMILES: CSc1ncc(N(C)c2cc(CO)cc(-c3cc(Cl)cc(Cl)c3)n2)cn1]

To a solution of methyl 2-(3,5-dichlorophenyl)-6-(methyl(2-(methylthio)pyrimidin-5-yl)amino)isonicotinate (380 mg, 0.698 mmol) in THF (12 mL) was added LiAlH$_4$ (39.8 mg, 1.047 mmol) in portions at −40° C. Then the reaction mixture was stirred at −40° C. for 10 min. The reaction mixture was quenched by the addition of water (1 mL) and 1 M aqueous NaOH solution (1 mL) at −10° C., then MgSO$_4$ (1.5 g) was added. The mixture was filtered and concentrated. The crude material was purified by flash chromatography (from pure DCM to DCM/MeOH=20/1, TLC: DCM/MeOH=20/1, R$_f$=0.45) to yield (2-(3,5-dichlorophenyl)-6-(methyl(2-(methylthio)pyrimidin-5-yl)amino)pyridin-4-yl)methanol (330 mg, 0.567 mmol, 81.0% yield) as a pale yellow solid: $^1$H NMR (400 MHz, CD$_3$OD) δ ppm 8.65 (s, 2H), 7.90 (d, J=2.0 Hz, 2H), 7.47-7.42 (m, 1H), 7.30 (s, 1H), 6.79 (d, J=0.7 Hz, 1H), 4.63 (s, 2H), 3.54 (s, 3H), 2.60 (s, 3H); ES-LCMS m/z 407.1, 409.0 [M+H]$^+$.

Step 3: (2-(3,5-Dichlorophenyl)-6-(methyl(2-(methylthio)pyrimidin-5-yl)amino)pyridin-4-yl)methyl methanesulfonate

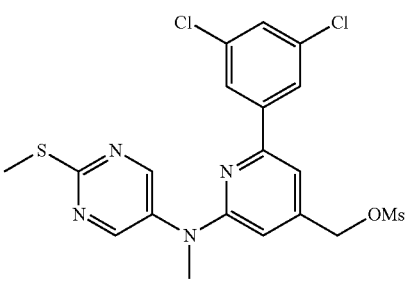 [SMILES: CSc1ncc(N(C)c2cc(COS(C)(=O)=O)cc(-c3cc(Cl)cc(Cl)c3)n2)cn1]

To a solution of (2-(3,5-dichlorophenyl)-6-(methyl(2-(methylthio)pyrimidin-5-yl)amino)pyridin-4-yl)methanol (330.000 mg, 0.567 mmol) and DIEA (0.594 mL, 3.40 mmol) in DCM (10.00 mL) was added MsCl (0.080 mL, 1.021 mmol) at 20° C. Then the reaction mixture was stirred at 20° C. for 15 min. Water (80 mL) was added and extracted with DCM (50 mL×2). The combined organic layers were dried over Na$_2$SO$_4$ and concentrated to yield (2-(3,5-dichlorophenyl)-6-(methyl(2-(methylthio)pyrimidin-5-yl)amino)pyridin-4-yl)methyl methanesulfonate (340 mg, 0.490 mmol, 86.0% yield) as a yellow solid: $^1$H NMR (400 MHz, CDCl$_3$) δ ppm 8.54 (s, 2H), 7.83 (d, J=2.0 Hz, 2H), 7.40-7.36 (m, 1H), 7.14 (s, 1H), 6.51 (s, 1H), 5.13 (s, 2H), 3.54 (s, 3H), 3.05 (s, 3H), 2.62-2.60 (m, 3H); ES-LCMS m/z 485.1, 487.0 [M+H]$^+$.

Step 4: Methyl 2-(1-((2-(3,5-dichlorophenyl)-6-(methyl(2-(methylthio)pyrimidin-5-yl)amino)pyridin-4-yl)methyl)piperidin-4-yl)acetate

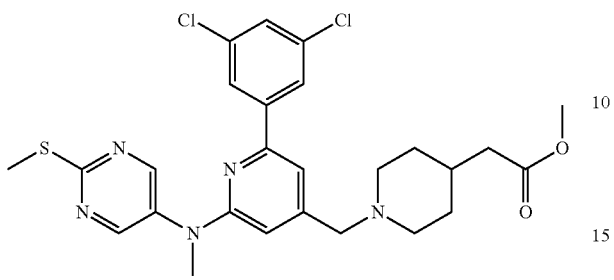

To a solution of (2-(3,5-dichlorophenyl)-6-(methyl(2-(methylthio)pyrimidin-5-yl)amino)pyridin-4-yl)methyl methanesulfonate (340 mg, 0.490 mmol) and methyl 2-(piperidin-4-yl)acetate (111 mg, 0.637 mmol) in DMF (10 mL) was added DIEA (0.428 mL, 2.452 mmol). Then the reaction mixture was stirred at 20° C. for 12 h. Solvent was concentrated to give the crude product. The crude material was purified by flash chromatography (DCM/MeOH=20/1 to 10/1, TLC: DCM/MeOH=10/1, $R_f$=0.65) to yield methyl 2-(1-((2-(3,5-dichlorophenyl)-6-(methyl(2-(methylthio)pyrimidin-5-yl)amino)pyridin-4-yl)methyl)piperidin-4-yl)acetate (300 mg, 0.439 mmol, 90.0% yield) as a pale yellow solid: $^1$H NMR (400 MHz, CDCl$_3$) δ ppm 8.57 (s, 2H), 8.04-8.01 (m, 1H), 7.86 (s, 2H), 7.37 (br s, 1H), 7.24-7.19 (m, 1H), 3.68 (s, 2H), 3.57 (s, 3H), 2.97 (s, 3H), 2.65-2.48 (m, 5H), 2.28 (br s, 2H), 2.07 (d, J=16.1 Hz, 3H), 1.74 (br s, 4H); ES-LCMS m/z 546.2, 548.2 [M+H]$^+$.

Step 5: Methyl 2-(1-((2-(3,5-dichlorophenyl)-6-(methyl(2-(methylsulfinyl)pyrimidin-5-yl)amino)pyridin-4-yl)methyl)piperidin-4-yl)acetate

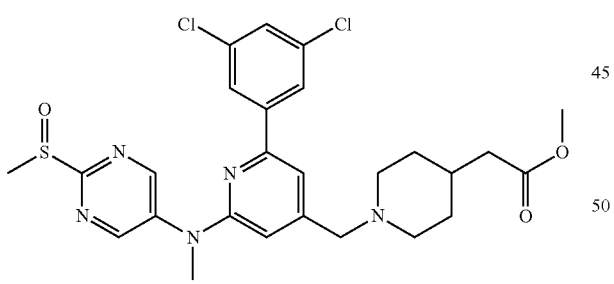

To a solution of methyl 2-(1-((2-(3,5-dichlorophenyl)-6-(methyl(2-(methylthio)pyrimidin-5-yl)amino)pyridin-4-yl)methyl)piperidin-4-yl)acetate (300 mg, 0.439 mmol) in MeOH (15 mL) was added Oxone (216 mg, 0.351 mmol). Then the mixture was stirred at 25° C. for 1 h. The solid was filtered off and saturated aqueous Na$_2$SO$_3$ (50 mL) was added and extracted with DCM (30 mL×3). The combined organic layers were combined, dried over Na$_2$SO$_4$, filtered and concentrated to yield the crude product. The crude material was purified by flash chromatography (from DCM/MeOH=20/1 to 10/1, TLC: DCM/MeOH=10/1, $R_f$=0.55) to yield methyl 2-(1-((2-(3,5-dichlorophenyl)-6-(methyl(2-(methylsulfinyl)pyrimidin-5-yl)amino)pyridin-4-yl)methyl)piperidin-4-yl)acetate (290 mg, 0.412 mmol, 94.0% yield) as a pale yellow solid: $^1$H NMR (400 MHz, CDCl$_3$) δ ppm 8.91 (s, 2H), 7.81 (br s, 2H), 7.51 (br s, 1H), 7.40 (d, J=17.3 Hz, 1H), 7.33 (s, 1H), 4.08 (d, J=9.3 Hz, 2H), 3.49 (s, 3H), 3.02-2.77 (m, 6H), 2.35-2.25 (m, 4H), 2.04-1.95 (m, 3H), 1.88-1.84 (m, 2H), 1.32-1.16 (m, 2H); ES-LCMS m/z 562.2, 564.2 [M+H]$^+$.

Step 6: Methyl 2-(1-((2-(3,5-dichlorophenyl)-6-(methyl(2-(4-methylpiperazin-1-yl)pyrimidin-5-yl)amino)pyridin-4-yl)methyl)piperidin-4-yl)acetate

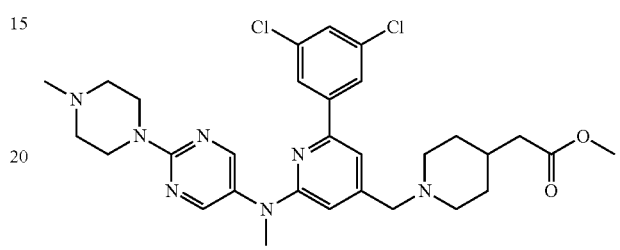

A mixture of methyl 2-(1-((2-(3,5-dichlorophenyl)-6-(methyl(2-(methylsulfinyl)pyrimidin-5-yl)amino)pyridin-4-yl)methyl)piperidin-4-yl)acetate (280 mg, 0.398 mmol), 1-methylpiperazine (199 mg, 1.991 mmol) and DIEA (257 mg, 1.991 mmol) in t-BuOH (1.5 mL) was stirred at 150° C. for 1.5 h under microwave. The solvent was concentrated to give the crude product of methyl 2-(1-((2-(3,5-dichlorophenyl)-6-(methyl(2-(4-methylpiperazin-1-yl)pyrimidin-5-yl)amino)pyridin-4-yl)methyl)piperidin-4-yl)acetate (310 mg, 0.373 mmol, 94.0% yield) as a yellow oil: $^1$H NMR (400 MHz, CDCl$_3$) δ ppm 8.24-8.19 (m, 2H), 7.84 (d, J=2.0 Hz, 2H), 7.28 (t, J=1.9 Hz, 1H), 7.03 (s, 1H), 6.26 (s, 1H), 3.85-3.81 (m, 4H), 3.59 (s, 3H), 3.42 (s, 3H), 3.27 (s, 2H), 2.74 (br s, 2H), 2.45 (t, J=5.0 Hz, 4H), 2.30 (s, 3H), 2.17 (d, J=7.1 Hz, 2H), 1.94-1.87 (m, 2H), 1.70 (d, J=3.7 Hz, 3H), 1.25-1.20 (m, 2H); ES-LCMS m/z 598.3, 600.3 [M+H]$^+$.

Step 7: 2-(1-((2-(3,5-Dichlorophenyl)-6-(methyl(2-(4-methylpiperazin-1-yl)pyrimidin-5-yl)amino)pyridin-4-yl)methyl)piperidin-4-yl)acetic acid, 4 hydrochloride

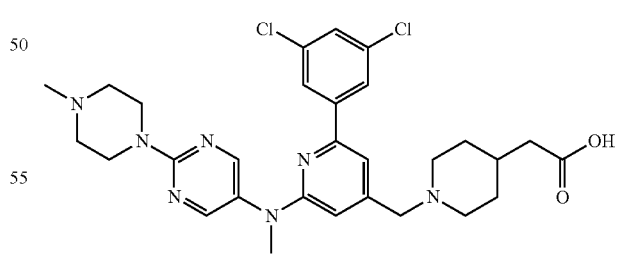

A mixture of methyl 2-(1-((2-(3,5-dichlorophenyl)-6-(methyl(2-(4-methylpiperazin-1-yl)pyrimidin-5-yl)amino)pyridin-4-yl)methyl)piperidin-4-yl)acetate (300 mg, 0.361 mmol) in concentrated HCl (1 mL, 8.15 mmol) and water (4 mL). The mixture was stirred at 80° C. for 15 min. The solvent was concentrated to give the crude product which was purified by preparative HPLC (MeCN/H$_2$O as eluents, acidic condition) and lyophilized to afford 2-(1-((2-(3,5- dichlorophenyl)-6-(methyl(2-(4-methylpiperazin-1-yl)pyrimidin-5-yl)amino)pyridin-4-yl)methyl)piperidin-4-yl)acetic acid, 4 hydrochloride (239.05 mg, 0.327 mmol, 91.0% yield) as a yellow solid: $^1$H NMR (400 MHz, CD$_3$OD) δ ppm 8.48 (s, 2H), 7.99 (d, J=1.8 Hz, 2H), 7.49 (t, J=1.9 Hz, 1H), 7.43-7.41 (m, 1H), 6.87 (s, 1H), 4.98 (br s, 2H), 4.24 (s, 2H), 3.60 (d, J=13.0 Hz, 2H), 3.54 (s, 3H), 3.50 (d, J=12.8 Hz, 2H), 3.39 (br s, 2H), 3.27-3.20 (m, 2H), 3.05 (t, J=11.8 Hz, 2H), 2.98 (s, 3H), 2.30 (d, J=6.6 Hz, 2H), 2.02 (d, J=13.9 Hz, 3H), 1.65-1.55 (m, 2H); ES-LCMS m/z 584.2, 586.2 [M+H]$^+$.

Example 389: 2-(1-((2-(3,5-Dichlorophenyl)-6-(ethyl(2-(4-methylpiperazin-1-yl)pyrimidin-5-yl)amino)pyridin-4-yl)methyl)piperidin-4-yl)acetic acid

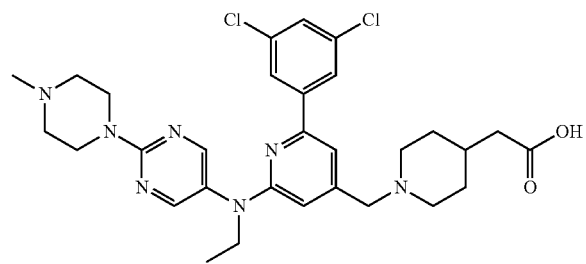 [SMILES: CCN(c1cnc(N2CCN(C)CC2)nc1)c1cc(CN2CCC(CC(=O)O)CC2)cc(-c2cc(Cl)cc(Cl)c2)n1]

Example 389 was prepared by procedures analogous to those described for example 388: $^1$H NMR (400 MHz, CD$_3$OD) δ ppm 8.45 (s, 2H), 8.01 (d, J=2.0 Hz, 2H), 7.50 (t, J=1.9 Hz, 1H), 7.38 (s, 1H), 6.78 (s, 1H), 4.98 (d, J=14.6 Hz, 2H), 4.21 (s, 2H), 4.05 (q, J=7.2 Hz, 2H), 3.61 (d, J=12.3 Hz, 2H), 3.51-3.39 (m, 4H), 3.29-3.23 (m, 2H), 3.08-3.00 (m, 2H), 2.99 (s, 3H), 2.30 (d, J=6.6 Hz, 2H), 2.01 (d, J=12.6 Hz, 3H), 1.66-1.53 (m, 2H), 1.31 (t, J=7.1 Hz, 3H); LCMS m/z 598.3, 600.3 [M+H]$^+$.

Example 390: 2-(1-((6-(3,5-Dichlorophenyl)-3-fluoro-2-((5-(4-methylpiperazin-1-yl)pyrazin-2-yl)oxy)pyridin-4-yl)methyl)piperidin-4-yl)acetic acid

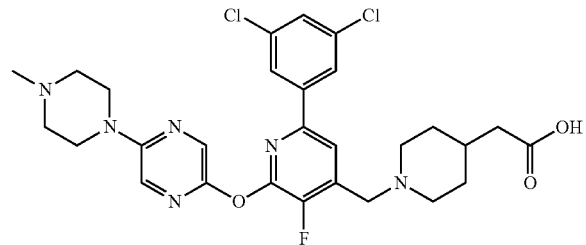 [SMILES: CN1CCN(c2cnc(Oc3nc(-c4cc(Cl)cc(Cl)c4)cc(CN4CCC(CC(=O)O)CC4)c3F)cn2)CC1]

Step 1: Methyl 2-acetoxy-6-(3,5-dichlorophenyl)-3-fluoroisonicotinate

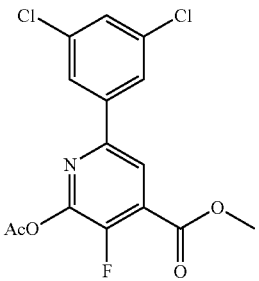 [SMILES: COC(=O)c1cc(-c2cc(Cl)cc(Cl)c2)nc(OC(C)=O)c1F]

A solution of 2-(3,5-dichlorophenyl)-5-fluoro-4-(methoxycarbonyl)pyridine 1-oxide (8 g, 20.25 mmol) in Ac$_2$O (80 mL, 848 mmol) was stirred at 110° C. for 12 h. The reaction mixture was concentrated to afford the crude product. The crude material was purified by flash chromatography (from PE/EtOAc=5/1 to 2/1, TLC: PE/EtOAc=3/1, R$_f$=0.8) to yield methyl 2-acetoxy-6-(3,5-dichlorophenyl)-3-fluoroisonicotinate (3.5 g, 8.65 mmol, 42.7% yield) as a white solid: $^1$H NMR (400 MHz, CDCl$_3$) 8.03 (d, J=3.7 Hz, 1H), 7.79 (s, 2H), 7.35 (s, 1H), 3.95 (s, 3H), 2.37 (s, 3H); ES-LCMS m/z 316.0, 318.0 [M+H-Ac]$^+$.

Step 2: 6-(3,5-Dichlorophenyl)-3-fluoro-4-(hydroxymethyl)pyridin-2-ol

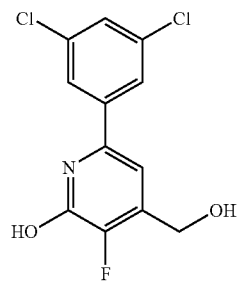 [SMILES: OCc1cc(-c2cc(Cl)cc(Cl)c2)nc(O)c1F]

To a solution of methyl 2-acetoxy-6-(3,5-dichlorophenyl)-3-fluoroisonicotinate (2600 mg, 6.42 mmol) in THF (100 mL) was added LiAlH$_4$ (1219 mg, 32.1 mmol) in portions at 25° C. Then the reaction mixture was stirred at 25° C. for 30 min. Aqueous NaOH (1.2 mL, 10%) solution and H$_2$O (1.2 mL) was added to quench the reaction. The solid was filtered off and solvent was removed in vacuo to give 6-(3,5-dichlorophenyl)-3-fluoro-4-(hydroxymethyl)pyridin-2-ol (2000 mg, 5.40 mmol, 84.0% yield) as a white solid: $^1$H NMR (400 MHz, CDCl$_3$) δ ppm 7.83 (d, J=2.0 Hz, 2H), 7.31 (t, J=1.9 Hz, 1H), 6.88 (d, J=4.0 Hz, 1H), 4.64 (d, J=1.1 Hz, 2H); ES-LCMS m/z 288.0, 290.1 [M+H]$^+$.

Step 3: (2-(Benzyloxy)-6-(3,5-dichlorophenyl)-3-fluoropyridin-4-yl)methanol

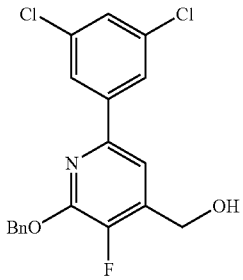

To a solution of 6-(3,5-dichlorophenyl)-3-fluoro-4-(hydroxymethyl)pyridin-2-ol (2000 mg, 5.40 mmol) and (bromomethyl)benzene (1847 mg, 10.80 mmol) in DMF (50 mL) was added K$_2$CO$_3$ (2239 mg, 16.20 mmol). Then the reaction mixture was stirred at 25° C. for 2 h. The solid was filtered off and solvent was removed in vacuo to give the crude product. The crude material was purified by flash chromatography (from PE/EtOAc=50/1 to 3/1, TLC: PE/EtOAc=5/1, R$_f$=0.7) to yield (2-(benzyloxy)-6-(3,5-dichlorophenyl)-3-fluoropyridin-4-yl)methanol (2000 mg, 4.71 mmol, 87.0% yield) as a yellow solid: $^1$H NMR (400 MHz, CDCl$_3$) δ ppm 7.79 (d, J=1.8 Hz, 2H), 7.50 (d, J=5.1 Hz, 2H), 7.47-7.42 (m, 1H), 7.41-7.32 (m, 4H), 5.54 (d, J=2.6 Hz, 2H), 4.83 (s, 2H); ES-LCMS m/z 378.1, 380.1 [M+H]$^+$.

Step 4: (2-(Benzyloxy)-6-(3,5-dichlorophenyl)-3-fluoropyridin-4-yl)methyl methanesulfonate

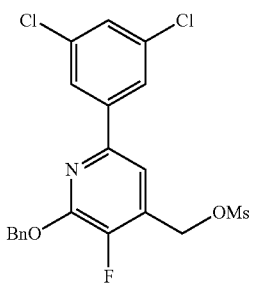 [SMILES: CS(=O)(=O)OCc1cc(-c2cc(Cl)cc(Cl)c2)nc(OCc2ccccc2)c1F]

To a mixture of (2-(benzyloxy)-6-(3,5-dichlorophenyl)-3-fluoropyridin-4-yl)methanol (2000 mg, 4.71 mmol), DIEA (1216 mg, 9.41 mmol) in DCM (80 mL) was added MsCl (647 mg, 5.65 mmol). Then, the mixture was stirred at 20° C. for 20 min. The reaction was diluted with DCM (20 mL) and water (20 mL), extracted with DCM (30 mL×2). The combined organic layers were dried over Na$_2$SO$_4$, filtered and evaporated to give (2-(benzyloxy)-6-(3,5-dichlorophenyl)-3-fluoropyridin-4-yl)methyl methanesulfonate (2300 mg, 4.31 mmol, 92.0% yield) as a yellow solid: $^1$H NMR (400 MHz, CDCl$_3$) δ ppm 7.72 (d, J=1.8 Hz, 2H), 7.45 (d, J=7.1 Hz, 2H), 7.35 (s, 1H), 7.34-7.25 (m, 5H), 5.49 (s, 2H), 5.26 (s, 2H), 3.04 (s, 3H); ES-LCMS m/z 456.1, 458.1 [M+H]$^+$.

Step 5: Methyl 2-(1-((2-(benzyloxy)-6-(3,5-dichlorophenyl)-3-fluoropyridin-4-yl)methyl)piperidin-4-yl)acetate

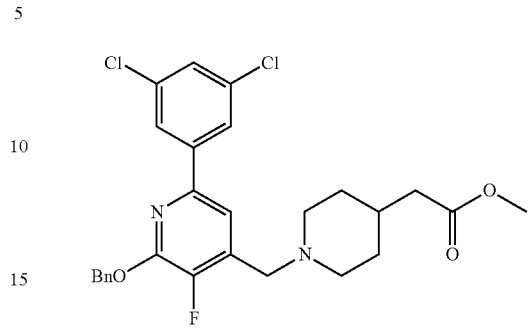

To a solution of (2-(benzyloxy)-6-(3,5-dichlorophenyl)-3-fluoropyridin-4-yl)methyl methanesulfonate (2300 mg, 4.31 mmol) and methyl 2-(piperidin-4-yl)acetate, hydrochloride (1857 mg, 8.63 mmol) in DMF (80 mL) was added DIEA (2788 mg, 21.57 mmol). The mixture was stirred at 40° C. for 5 h. The crude material was purified by flash chromatography (from pure DCM to DCM/MeOH=20/1, TLC: DCM/MeOH=20/1, R$_f$=0.6) to yield methyl 2-(1-((2-(benzyloxy)-6-(3,5-dichlorophenyl)-3-fluoropyridin-4-yl)methyl)piperidin-4-yl)acetate (2100 mg, 3.57 mmol, 83.0% yield) as a brown solid: $^1$H NMR (400 MHz, CD$_3$OD) δ ppm 7.83 (d, J=1.8 Hz, 2H), 7.68 (s, 1H), 7.51 (d, J=7.5 Hz, 2H), 7.42-7.36 (m, 2H), 7.36-7.29 (m, 2H), 5.53 (s, 2H), 3.84 (s, 2H), 3.65 (s, 3H), 3.11 (s, 2H), 2.36 (s, 2H), 2.28 (d, J=7.1 Hz, 2H), 1.88 (s, 1H), 1.79 (d, =13.2 Hz, 2H), 1.62 (s, 2H); ES-LCMS m/z 517.1, 519.2 [M+H]$^+$.

Step 6: Methyl 2-(1-((6-(3,5-dichlorophenyl)-3-fluoro-2-hydroxypyridin-4-yl)methyl)piperidin-4-yl)acetate

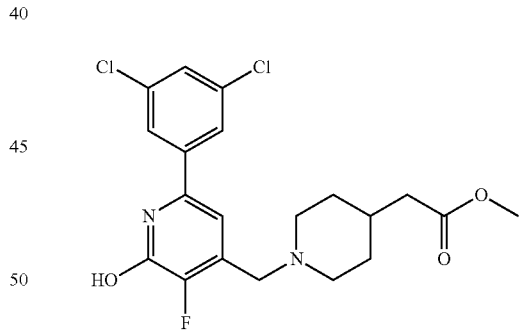

A solution of methyl 2-(1-((2-(benzyloxy)-6-(3,5-dichlorophenyl)-3-fluoropyridin-4-yl)methyl)piperidin-4-yl)acetate (2000 mg, 3.40 mmol) in TFA (20 mL, 260 mmol) was stirred at 50° C. for 4 h. The mixture was concentrated and then saturated aqueous NaHCO$_3$ solution (80 mL) was added. The mixture was extracted with DCM (100 mL×3). The combined organic layers were washed with brine (50 mL), dried over Na$_2$SO$_4$, filtered and concentrated. The crude material was purified by flash chromatography (from pure DCM to DCM/MeOH=10/1, TLC: DCM/MeOH=10/1, R$_f$=0.6) to yield methyl 2-(1-((6-(3,5-dichlorophenyl)-3-fluoro-2-hydroxypyridin-4-yl)methyl)piperidin-4-yl)acetate (1300 mg, 2.80 mmol, 82.0% yield) as a yellow solid: $^1$H NMR (400 MHz, CDCl$_3$) δ ppm 7.61 (s, 2H), 7.41 (s, 1H), 6.69 (s, 1H), 3.68-3.61 (m, 5H), 3.01-2.95 (m, 2H), 2.26 (d, J=7.1 Hz, 4H), 1.84 (s, 1H), 1.75 (d, J=12.3 Hz, 2H), 1.47-1.33 (m, 2H); ES-LCMS m/z 427.1, 429.1 [M+H]⁺.

Step 7: Methyl 2-(1-((2-((5-chloropyrazin-2-yl)oxy)-6-(3,5-dichlorophenyl)-3-fluoropyridin-4-yl)methyl)piperidin-4-yl)acetate

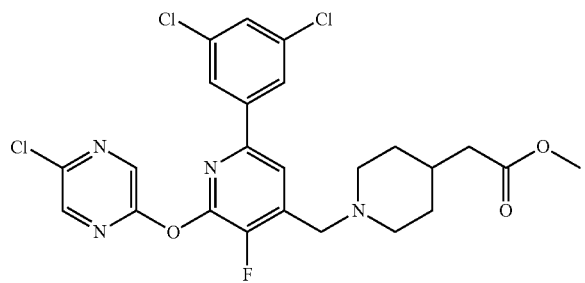 [SMILES: COC(=O)CC1CCN(Cc2cc(-c3cc(Cl)cc(Cl)c3)nc(Oc3cnc(Cl)cn3)c2F)CC1]

To a mixture of methyl 2-(1-(((6-(3,5-dichlorophenyl)-3-fluoro-2-hydroxypyridin-4-yl)methyl)piperidin-4-yl)acetate (400 mg, 0.861 mmol) and 2,5-dichloropyrazine (1283 mg, 8.61 mmol) in DMF (10 mL) was added K₃PO₄ (914 mg, 4.31 mmol). The reaction mixture was stirred at 120° C. for 16 h. The mixture was cooled down and filtered. The filtrate was concentrated to give the crude product. The crude material was purified by flash chromatography (from pure PE to PE/EtOAc=3/1, TLC: PE/EtOAc=3/1, R$_f$=0.6) to yield methyl 2-(1-((2-((5-chloropyrazin-2-yl)oxy)-6-(3,5-dichlorophenyl)-3-fluoropyridin-4-yl)methyl)piperidin-4-yl)acetate (300 mg, 0.453 mmol, 52.6% yield) as a yellow solid: ¹H NMR (400 MHz, CDCl₃) δ ppm 8.33 (d, J=1.3 Hz, 1H), 8.10 (d, J=1.3 Hz, 1H), 7.66 (d, J=2.0 Hz, 3H), 7.30 (t, J=1.9 Hz, 1H), 3.61 (s, 3H), 3.59 (s, 2H), 2.85-2.81 (m, 2H), 2.22 (s, 2H), 2.09 (t, J=11.1 Hz, 2H), 1.77 (dd, J=3.7, 7.5 Hz, 1H), 1.70 (s, 2H), 1.39-1.29 (m, 2H); ES-LCMS m/z 539.1, 541.1 [M+H]⁺.

Step 8: tert-Butyl 4-(5-((6-(3,5-dichlorophenyl)-3-fluoro-4-((4-(2-methoxy-2-oxoethyl)piperidin-1-yl)methyl)pyridin-2-yl)oxy)pyrazin-2-yl)piperazine-1-carboxylate

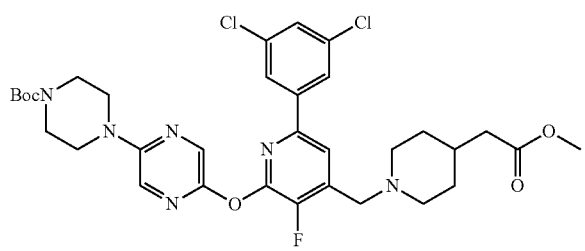 [SMILES: COC(=O)CC1CCN(Cc2cc(-c3cc(Cl)cc(Cl)c3)nc(Oc3cnc(N4CCN(C(=O)OC(C)(C)C)CC4)cn3)c2F)CC1]

A mixture of methyl 2-(1-((2-((5-chloropyrazin-2-yl)oxy)-6-(3,5-dichlorophenyl)-3-fluoropyridin-4-yl)methyl)piperidin-4-yl)acetate (200 mg, 0.302 mmol), Cs₂CO₃ (500 mg, 1.535 mmol), tert-butyl piperazine-1-carboxylate (112 mg, 0.604 mmol), Xantphos (20 mg, 0.035 mmol) and Pd₂(dba)₃ (20 mg, 0.022 mmol) in THF (30 mL) was stirred at 80° C. for 14 h under N₂ atmosphere. The mixture was cooled down and filtered. The filtrate was concentrated to give the crude product. The crude material was purified by flash chromatography (from PE/EtOAc=10/1 to 3/1, TLC: PE/EtOAc=3/1, R$_f$=0.4) to yield tert-butyl 4-(5-((6-(3,5-dichlorophenyl)-3-fluoro-4-((4-(2-methoxy-2-oxoethyl)piperidin-1-yl)methyl)pyridin-2-yl)oxy)pyrazin-2-yl)piperazine-1-carboxylate (150 mg, 0.208 mmol, 68.9% yield) as a yellow solid: ¹H NMR (400 MHz, CDCl₃) δ ppm 8.15 (d, J=1.3 Hz, 1H), 7.79 (d, J=1.3 Hz, 1H), 7.64 (d, J=1.8 Hz, 2H), 7.57 (d, J=3.7 Hz, 1H), 7.31 (t, J=1.9 Hz, 1H), 3.67 (s, 3H), 3.64 (s, 2H), 3.57 (d, J=5.3 Hz, 8H), 2.88 (d, J=11.2 Hz, 2H), 2.27 (d, J=11 Hz, 2H), 2.17-2.11 (m, 2H), 1.88-1.81 (m, 1H), 1.73 (d, J=13.0 Hz, 2H), 1.49 (s, 9H), 1.36 (d, J=9.9 Hz, 2H); ES-LCMS m/z 689.3, 691.3 [M+H]⁺.

Step 9: Methyl 2-(1-(((6-(3,5-dichlorophenyl)-3-fluoro-2-((5-(piperazin-1-yl)pyrazin-2-yl)oxy)pyridin-4-yl)methyl)piperidin-4-yl)acetate, 4 trifluoroacetic acid salt

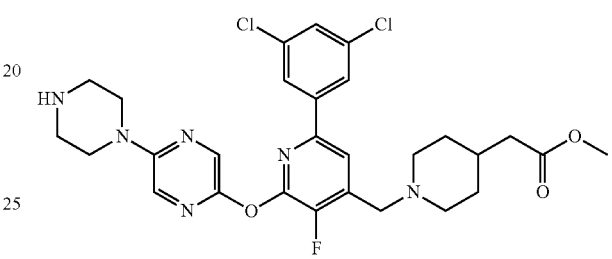

To a mixture of tert-butyl 4-(5-((6-(3,5-dichlorophenyl)-3-fluoro-4-((4-(2-methoxy-2-oxoethyl)piperidin-1-yl)methyl)pyridin-2-yl)oxy)pyrazin-2-yl)piperazine-1-carboxylate (150 mg, 0.208 mmol) in DCM (15 mL) was added TFA (5 mL, 64.9 mmol). Then, the mixture was stirred at 20° C. for 10 min. The reaction was concentrated to give methyl 2-(1-(((6-(3,5-dichlorophenyl)-3-fluoro-2-((5-(piperazin-1-yl)pyrazin-2-yl)oxy)pyridin-4-yl)methyl)piperidin-4-yl)acetate, 4 trifluoroacetic acid (220 mg, 0.168 mmol, 81.0% yield) as a brown solid: ¹H NMR (400 MHz, CD₃OD) δ ppm 8.27 (d, J=1.3 Hz, 1H), 8.10 (d, J=1.3 Hz, 1H), 7.91 (d, J=3.7 Hz, 1H), 7.74 (d, J=1.8 Hz, 2H), 7.49 (t, J=1.9 Hz, 1H), 4.54 (s, 2H), 3.89 (d, J=5.3 Hz, 4H), 3.67 (s, 3H), 3.63 (s, 2H), 3.39 (d, J=5.3 Hz, 4H), 3.27-3.11 (m, 2H), 2.36 (s, 2H), 2.19-2.09 (m, 1H), 2.05 (d, J=14.6 Hz, 2H), 1.58 (d, J=14.3 Hz, 2H); ES-LCMS m/z 589.2, 591.2 [M+H]⁺.

Step 10: Methyl 2-(1-(((6-(3,5-Dichlorophenyl)-3-fluoro-2-((5-(4-methylpiperazin-1-yl)pyrazin-2-yl)oxy)pyridin-4-yl)methyl)piperidin-4-yl)acetate

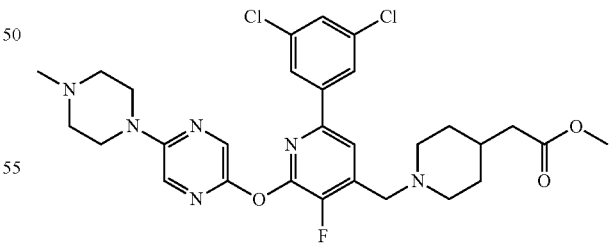

To a mixture of methyl 2-(1-(((6-(3,5-dichlorophenyl)-3-fluoro-2-((5-(piperazin-1-yl)pyrazin-2-yl)oxy)pyridin-4-yl)methyl)piperidin-4-yl)acetate, 4 trifluoroacetic acid salt (220 mg, 0.168 mmol), formic acid (0.032 mL, 0.842 mmol) in MeOH (10 mL) was added paraformaldehyde (25.3 mg, 0.842 mmol). The solution was stirred at 20° C. for 10 h. Then, to the reaction mixture was added NaBH₃CN (178 mg, 0.842 mmol) followed by stirring at 20° C. for 2 h. The reaction mixture was quenched by the addition of saturated aqueous NaHCO$_3$ solution (30 mL). The aqueous layer was separated and extracted with DCM (30 mL×2). The combined organic layers were dried over Na$_2$SO$_4$, filtered and evaporated to afford methyl 2-(1-((6-(3,5-dichlorophenyl)-3-fluoro-2-((5-(4-methylpiperazin-1-yl)pyrazin-2-yl)oxy)pyridin-4-yl)methyl)piperidin-4-yl)acetate (110 mg, 0.157 mmol, 93.0% yield) as a brown solid: $^1$H NMR (400 MHz, CDCl$_3$) δ ppm 8.07 (d, J=1.3 Hz, 1H), 7.73 (d, J=1.3 Hz, 1H), 7.58 (d, J=2.0 Hz, 2H), 7.50 (d, J=3.5 Hz, 1H), 7.27-7.24 (m, 1H), 3.60 (s, 3H), 3.57 (s, 2H), 3.54 (d, J=4.9 Hz, 4H), 2.83 (d, J=7.5 Hz, 4H), 2.50 (d, J=5.1 Hz, 4H), 2.30 (s, 3H), 2.21 (s, 2H), 2.11-2.04 (m, 3H), 1.67 (d, J=11.7 Hz, 2H); ES-LCMS m/z 603.2, 605.2 [M+H]$^+$.

Step 11: 2-(1-((6-(3,5-Dichlorophenyl)-3-fluoro-2-((5-(4-methylpiperazin-1-yl)pyrazin-2-yl)oxy)pyridin-4-yl)methyl)piperidin-4-yl)acetic acid

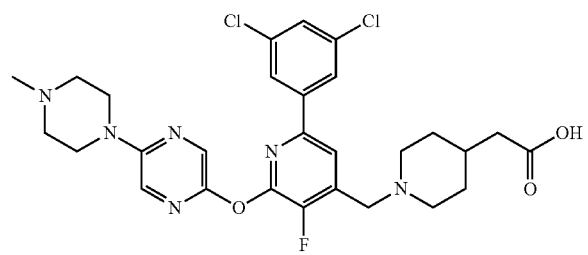 [SMILES: CN1CCN(c2cnc(Oc3nc(-c4cc(Cl)cc(Cl)c4)cc(CN4CCC(CC(=O)O)CC4)c3F)cn2)CC1]

A solution of methyl 2-(1-((6-(3,5-dichlorophenyl)-3-fluoro-2-((5-(4-methylpiperazin-1-yl)pyrazin-2-yl)oxy)pyridin-4-yl)methyl)piperidin-4-yl)acetate (110 mg, 0.157 mmol), LiOH·H$_2$O (65.8 mg, 1,567 mmol) in THF (5 mL) and H$_2$O (1.00 mL) was stirred at 20° C. for 30 h. The mixture was adjusted pH to 5-6 with 2 N HCl and the reaction mixture was concentrated to afford crude product. The crude product was purified by preparative HPLC (MeCN/H$_2$O as eluents, neutral condition) and dried by lyophilization to yield 2-(1-((6-(3,5-dichlorophenyl)-3-fluoro-2-((5-(4-methylpiperazin-1-yl)pyrazin-2-yl)oxy)pyridin-4-yl)methyl)piperidin-4-yl)acetic acid (48.41 mg, 0.080 mmol, 51.2% yield) as a white solid: $^1$H NMR (400 MHz, DMSO-d$_6$) δ ppm 8.22 (d, J=1.1 Hz, 1H), 8.01 (s, 1H), 7.86 (d, J=4.0 Hz, 1H), 7.77 (d, J=1.8 Hz, 2H), 7.60 (t, J=1.8 Hz, 1H), 3.57 (s, 2H), 3.52-3.49 (m, 4H), 2.77 (d, J=10.6 Hz, 2H), 2.40-2.37 (m, 4H), 2.18 (s, 3H), 1.99-1.94 (m, 2H), 1.74 (d, J=6.6 Hz, 2H), 1.61 (d, J=12.3 Hz, 3H), 1.13-1.05 (m, 2H); ES-LCMS m/z 589.2, 591.2 [M+H]$^+$.

Examples 391-396 (Table 21) were prepared by procedures analogous to those described for example 390.

TABLE 21

| Example | Structure/Name | $^1$H NMR | LCMS |
|---|---|---|---|
| 391 | 3-(4-(5-((4-((4-(acetamidomethyl)piperidin-1-yl)methyl)-6-(3,5-dichlorophenyl)pyridin-2-yl)oxy)pyrazin-2-yl)piperazin-1-yl)propanamide | $^1$H NMR (400 MHz, CD$_3$OD:CDCl$_3$ = 1:1) δ ppm 8.08 (d, J = 1.3 Hz, 1H), 7.89 (d, J = 1.1 Hz, 1H), 7.71 (d, J = 2.0 Hz, 2H), 7.56 (s, 1H), 7.34 (t, J = 1.9 Hz, 1H), 6.97 (s, 1H), 3.64-3.58 (m, 4H), 3.56 (s, 2H), 3.04 (d, J = 6.8 Hz, 2H), 2.90 (d, J = 11.5 Hz, 2H), 2.72 (t, J = 7.1 Hz, 2H), 2.67-2.60 (m, 4H), 2.47-2.40 (m, 2H), 2.11-1.99 (m, 2H), 1.91 (s, 3H), 1.70 (d, J = 12.1 Hz, 2H), 1.50 (br s, 1H), 1.35-1.20 (m, 2H) | ES-LCMS m/z 641.4, 643.4 [M + H]$^+$. |
| 392 | 4-(4-(5-((6-(3,5-dichlorophenyl)-4-((4-(propionamidomethyl)piperidin-1-yl)methyl)pyridin-2-yl)oxy)pyrazin-2-yl)piperazin-1-yl)-2-methylbutanoic acid | $^1$H NMR (400 MHz, CD$_3$OD) δ ppm 8.16 (d, J = 1.1 Hz, 1H), 8.04 (s, 1H), 7.78 (d, J = 1.8 Hz, 2H), 7.68 (s, 1H), 7.44 (s, 1H), 7.07 (s, 1H), 3.79 (brs, 4H), 3.67 (s, 2H), 3.08 (d, J = 6.6 Hz, 6H), 2.97 (d, J = 11.0 Hz, 2H), 2.93-2.84 (m, 2H), 2.57-2.46 (m, 1H), 2.23-2.10 (m, 4H), 1.99-1.88 (m, 1H), 1.80 (dd, J = 3.3, 10.8 Hz, 1H), 1.74 (d, J = 13.0 Hz, 2H), 1.55 (s, 1H), 1.37-1.26 (m, 2H), 1.22 (d, J = 7.1 Hz, 3H), 1.12 (t, J = 7.6 Hz, 3H) | ES-LCMS m/z: 684.4, 686.3 [M + H]$^+$. |

TABLE 21-continued

| Example | Structure/Name | $^1$H NMR | LCMS |
|---|---|---|---|
| 393 | 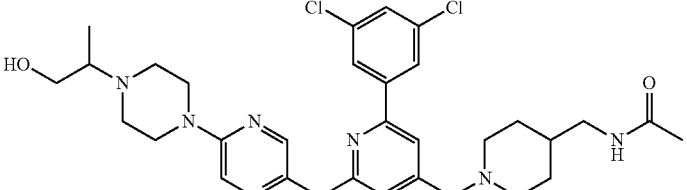<br>N-((1-((2-(3,5-dichlorophenyl)-6-((5-(4-(1-hydroxypropan-2-yl)piperazin-1-yl)pyrazin-2-yl)oxy)pyridin-4-yl)methyl)piperidin-4-yl)methyl)acetamide | $^1$H NMR (400 MHz, CD$_3$OD) δ ppm 8.10 (d, J = 0.9 Hz, 1H), 7.95 (s, 1H), 7.85-7.75 (m, 2H), 7.64 (s, 1H), 7.48-7.36 (m, 1H), 7.03 (s, 1H), 4.61 (br s, 2H), 3.66-3.59 (m, 6H), 3.50 (dd, J = 5.7, 11.0 Hz, 1H), 3.07 (br d, J = 6.6 Hz, 2H), 2.92 (br d, J = 11.2 Hz, 2H), 2.83-2.75 (m, 2H), 2.74-2.68 (m, 2H), 2.07 (br t, J = 10.7 Hz, 2H), 1.93 (s, 3H), 1.72 (br d, J = 12.1 Hz, 2H), 1.52 (br s, 1H), 1.39-1.24 (m, 2H), 1.07 (d, J = 6.6 Hz, 3H) | ES-LCMS m/z 628.2, 630.2 [M + H]$^+$. |
| 394 | 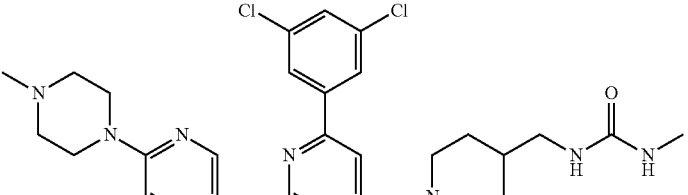<br>1-((1-((2-(3,5-dichlorophenyl)-6-((5-(4-methylpiperazin-1-yl)pyrazin-2-yl)oxy)pyridin-4-yl)methyl)piperidin-4-yl)methyl)-3-methylurea | $^1$H NMR (400 MHz, CD$_3$OD) δ ppm 8.21 (d, J = 1.1 Hz, 1H), 8.13 (d, J = 1.1 Hz, 1H), 7.99 (s, 1H), 7.83 (d, J = 2.0 Hz, 2H), 7.47 (t, J = 1.9 Hz, 1H), 7.36-7.33 (m, 1H), 4.53 (d, J = 14.3 Hz, 2H), 4.44 (s, 2H), 3.66-3.55 (m, 4H), 3.40-3.32 (m, 2H), 3.28-3.21 (m, 2H), 3.16-3.07 (m, 4H), 2.96 (s, 3H), 2.76 (s, 3H), 1.98 (d, J = 13.9 Hz, 2H), 1.87 (brs, 1H), 1.69-1.56 (m, 2H) | ES-LCMS m/z 599.4, 601.4 [M + H]$^+$. |
| 395 | 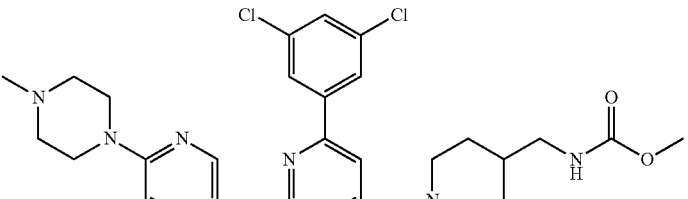<br>methyl ((1-((2-(3,5-dichlorophenyl)-6-((5-(4-methylpiperazin-1-yl)pyrazin-2-yl)oxy)pyridin-4-yl)methyl)piperidin-4-yl)methyl)carbamate | $^1$H NMR (400 MHz, CD$_3$OD) δ ppm 8.11 (d, J = 0.9 Hz, 1H), 7.97 (s, 1H), 7.76 (d, J = 1.5 Hz, 2H), 7.64 (s, 1H), 7.40 (s, 1H), 7.02 (s, 1H), 3.64 (d, J = 4.9 Hz, 4H), 3.61 (s, 3H), 3.59 (s, 2H), 2.99 (d, J = 6.6 Hz, 2H), 2.92 (d, J = 11.5 Hz, 2H), 2.59 (t, J = 5.0 Hz, 4H), 2.35 (s, 3H), 2.06 (t, J = 11.0 Hz, 2H), 1.70 (d, J = 12.3 Hz, 2H), 1.49 (s, 1H), 1.34-1.22 (m, 2H) | ES-LCMS m/z 600.3, 602.3 [M + H]$^+$. |
| 396 | 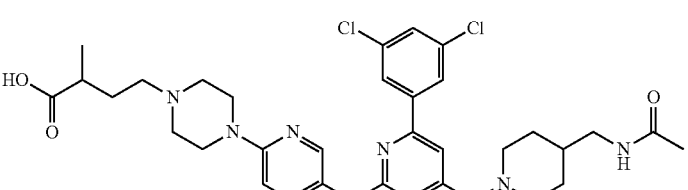<br>4-(4-(5-((4-((4-(acetamidomethyl)piperidin-1-yl)methyl)-6-(3,5-dichlorophenyl)pyridin-2-yl)oxy)pyrazin-2-yl)piperazin-1-yl)-2-methylbutanoic acid | $^1$H NMR (400 MHz, CD$_3$OD) δ ppm 8.16-8.12 (m, 1H), 8.07-7.99 (m, 1H), 7.84-7.73 (m, 2H), 7.68-7.59 (m, 1H), 7.47-7.34 (m, 1H), 7.14-6.98 (m, 1H), 3.76 (br t, J = 4.9 Hz, 4H), 3.65 (s, 2H), 3.07 (d, J = 6.6 Hz, 2H), 3.05-2.92 (m, 6H), 2.92-2.79 (m, 2H), 2.56-2.44 (m, 1H), 2.13 (br t, J = 11.2 Hz, 2H), 2.00-1.88 (m, 4H), 1.84-1.70 (m, 3H), 1.59-1.47 (m, 1H), 1.39-1.26 (m, 2H), 1.21 (d, J = 7.1 Hz, 3H) | ES-LCMS m/z 670.3, 672.3 [M + H]$^+$. |

Example 397: (1R,7S,8r)-4-((2-(3,5-Dichlorophenyl)-6-((2-(4-methyl-1,4-diazepan-1-yl)pyrimidin-5-yl)oxy)pyridin-4-yl)methyl)-4-azabicyclo[5.1.0]octane-8-carboxylic acid, 4 hydrochloride

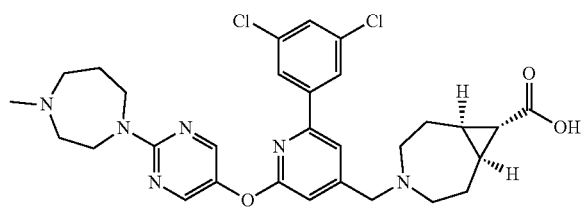 [SMILES: CN1CCCN(c2ncc(Oc3cc(CN4CC[C@@H]5[C@H](CC4)[C@H]5C(=O)O)cc(-c4cc(Cl)cc(Cl)c4)n3)cn2)CC1]

Step 1: (2-(3,5-Dichlorophenyl)-6-((2-(methylsulfinyl)pyrimidin-5-yl)oxy)pyridin-4-yl)methanol

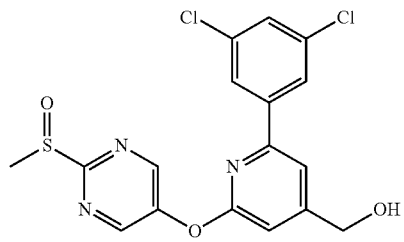 [SMILES: CS(=O)c1ncc(Oc2cc(CO)cc(-c3cc(Cl)cc(Cl)c3)n2)cn1]

To a solution of (2-(3,5-dichlorophenyl)-6-((2-(methylthio)pyrimidin-5-yl)oxy)pyridin-4-yl)methanol (2 g, 4.31 mmol) in MeOH (20 mL) and DCM (10 mL) was added Oxone (3.18 g, 5.17 mmol). Then the reaction mixture was stirred at 10° C. for 10 h. After filtration, the filtrate was concentrated. The crude product was purified by flash chromatography (from pure DCM to DCM/MeOH=10/1, TLC: DCM/MeOH=10/1, R$_f$=0.55) to yield (2-(3,5-dichlorophenyl)-6-((2-(methylsulfinyl)pyrimidin-5-yl)oxy)pyridin-4-yl)methanol (1.65 g, 3.43 mmol, 80.0% yield) as a yellow solid: $^1$H NMR (400 MHz, CDCl$_3$) δ ppm 9.07-9.01 (m, 2H), 7.82 (d, J=1.8 Hz, 2H), 7.74 (s, 1H), 7.47 (t, J=1.9 Hz, 1H), 7.24 (d, J=0.8 Hz, 1H), 4.80 (s, 2H), 3.04 (s, 3H); ES-LCMS m/z: 410.1, 412.0 [M+H]$^+$.

Step 2: tert-Butyl 4-(5-((6-(3,5-dichlorophenyl)-4-(hydroxymethyl)pyridin-2-yl)oxy)pyrimidin-2-yl)-1,4-diazepane-1-carboxylate

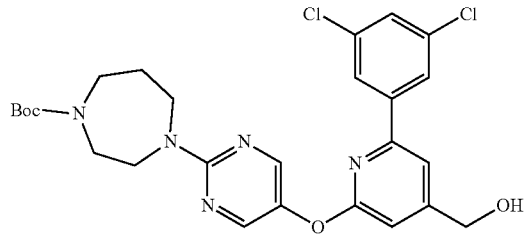 [SMILES: CC(C)(C)OC(=O)N1CCCN(c2ncc(Oc3cc(CO)cc(-c4cc(Cl)cc(Cl)c4)n3)cn2)CC1]

To a solution of (2-(3,5-dichlorophenyl)-6-((2-(methylsulfinyl)pyrimidin-5-yl)oxy)pyridin-4-yl)methanol (1 g, 2.082 mmol) and tert-butyl 1,4-diazepane-1-carboxylate (2.92 g, 14.57 mmol) in t-BuOH (15 mL) was added DIEA (3.64 mL, 20.82 mmol). Then the mixture was stirred and irradiated at 130° C. for 2 h under microwave. The mixture was concentrated. The residue was added DCM/MeOH (10/1, 100 mL), washed with 10% citric acid solution (50 mL×2) and brine (50 mL). The organic layer was concentrated. The residue was purified by flash chromatography (from pure DCM to DCM/MeOH=10/1, TLC: DCM/MeOH=10/1, R$_f$=0.5) to yield tert-butyl 4-(5-((6-(3,5-dichlorophenyl)-4-(hydroxymethyl)pyridin-2-yl)oxy)pyrimidin-2-yl)-1,4-diazepane-1-carboxylate (1 g, 1.647 mmol, 79.0% yield) as a yellow solid: $^1$H NMR (400 MHz, CDCl$_3$) δ ppm 8.28 (s, 2H), 7.76-7.71 (m, 2H), 7.43 (s, 1H), 7.34 (s, 1H), 6.93 (s, 1H), 4.82 (s, 2H), 3.94-3.86 (m, 2H), 3.84-3.74 (m, 2H), 3.58 (d, J=4.8 Hz, 2H), 3.40-3.35 (m, 1H), 3.30 (t, J=6.1 Hz, 1H), 2.03 (br s, 2H), 1.49-1.44 (m, 9H); ES-LCMS m/z 546.2, 548.2 [M+H]$^+$.

Step 3: (1R,7S,8r)-Ethyl 4-azabicyclo[5.1.0]octane-8-carboxylate, TFA salt

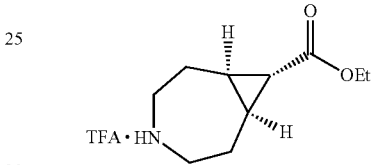

A solution of (1R,7S,8r)-4-benzyl 8-ethyl 4-azabicyclo[5.1.0]octane-4,8-dicarboxylate (2.6 g, 8.03 mmol) and TFA (15 mL) was stirred at 50° C. for 2 h. LCMS showed the reaction was completed. The mixture was concentrated to yield (1R,7S,8r)-ethyl 4-azabicyclo[5.1.0]octane-8-carboxylate, TFA (2.9 g, 7.83 mmol, 98.0% yield) as a yellow oil: $^1$H NMR (400 MHz, CDCl$_3$) δ ppm 4.20-4.10 (m, 2H), 3.51 (d, J=9.3 Hz, 2H), 3.19-3.04 (m, 2H), 2.51 (d, J=15.9 Hz, 2H), 1.82-1.59 (m, 5H), 1.32-1.24 (m, 3H); ES-FCMS m/z 184.1 [M+H]$^+$.

Step 4: tert-Butyl 4-(5-((6-(3,5-dichlorophenyl)-4-(((methylsulfonyl)oxy)methyl)pyridin-2-yl)oxy)pyrimidin-2-yl)-1,4-diazepane-1-carboxylate

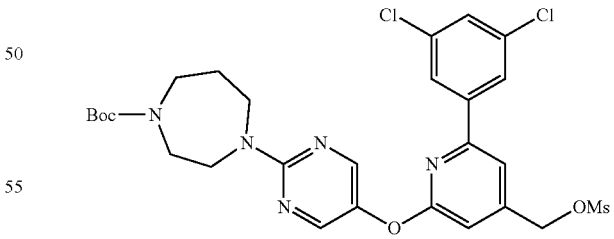

To a solution of tert-butyl 4-(5-((6-(3,5-dichlorophenyl)-4-(hydroxymethyl)pyridin-2-yl)oxy)pyrimidin-2-yl)-1,4-diazepane-1-carboxylate (500 mg, 0.824 mmol) and DIEA (0.437 mF, 2.471 mmol) in DCM (20 mF) was added MsCl (0.096 mF, 1.235 mmol). The mixture was stirred at 0° C. for 15 min. The mixture was added water (20 mF) and extracted with DCM (20 mF×2). The combined organic layers were dried over Na$_2$SO$_4$, filtered and evaporated to give tert-butyl 4-(5-((6-(3,5-dichlorophenyl)-4-(((methylsulfonyl)oxy)

methyl)pyridin-2-yl)oxy)pyrimidin-2-yl)-1,4-diazepane-1-carboxylate (500 mg, 0.721 mmol, 87.0% yield) as colorless oil: $^1$H NMR (400 MHz, CDCl$_3$) δ ppm 8.30 (s, 2H), 7.73 (d, J=2.0 Hz, 2H), 7.42 (s, 1H), 7.38 (t, J=1.9 Hz, 1H), 6.97 (s, 1H), 5.30 (s, 2H), 3.95-3.87 (m, 2H), 3.83-3.77 (m, 2H), 3.62-3.56 (m, 2H), 3.42-3.37 (m, 1H), 3.31 (t, J=6.0 Hz, 1H), 3.14 (s, 3H), 2.04 (br s, 2H), 1.47 (s, 9H); ES-LCMS m/z 624.2, 626.1 [M+H]$^+$.

Step 5: (1R,7S,8r)-Ethyl 4-((2-((2-(4-(tert-butoxycarbonyl)-1,4-diazepan-1-yl)pyrimidin-5-yl)oxy)-6-(3,5-dichlorophenyl)pyridin-4-yl)methyl)-4-azabicyclo[5.1.0]octane-8-carboxylate

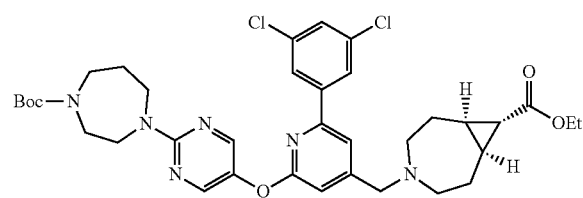 [SMILES: CCOC(=O)[C@H]1[C@@H]2CCN(Cc3cc(Oc4cnc(N5CCCN(C(=O)OC(C)(C)C)CC5)nc4)nc(-c4cc(Cl)cc(Cl)c4)c3)CC[C@@H]21]

To a solution of tert-butyl 4-(5-((6-(3,5-dichlorophenyl)-4-(((methylsulfonyl)oxy)methyl)pyridin-2-yl)oxy)pyrimidin-2-yl)-1,4-diazepane-1-carboxylate (500 mg, 0.721 mmol) and (1R,7S,8r)-ethyl 4-azabicyclo[5.1.0]octane-8-carboxylate, TFA (268 mg, 0.721 mmol) in DMF (15 mL) was added DIEA (0.513 mL, 2.88 mmol). Then the mixture was stirred at 20° C. for 10 h. The mixture was concentrated. The residue was purified by flash chromatography (from PE/EtOAc=5:1 to DCM/MeOH=10/1, TLC: DCM/MeOH=10/1, R$_f$=0.6) to yield (1R,7S,8r)-ethyl 4-((2-((2-(4-(tert-butoxycarbonyl)-1,4-diazepan-1-yl)pyrimidin-5-yl)oxy)-6-(3,5-dichlorophenyl)pyridin-4-yl)methyl)-4-azabicyclo[5.1.0]octane-8-carboxylate (350 mg, 0.443 mmol, 61.4% yield) as a yellow solid: $^1$H NMR (400 MHz, CD$_3$OD) δ ppm 8.31-8.25 (m, 2H), 7.81-7.76 (m, 3H), 7.66 (s, 1H), 7.11-7.07 (m, 1H), 4.17-4.07 (m, 4H), 3.92-3.87 (m, 2H), 3.80-3.78 (m, 2H), 3.62-3.55 (m, 2H), 3.35 (d, J=6.6 Hz, 2H), 3.21-3.19 (m, 2H), 2.35-2.33 (m, 2H), 1.96-1.94 (m, 1H), 1.69-1.65 (m, 6H), 1.46-1.41 (m, 2H), 1.38 (s, 9H), 1.26-1.22 (m, 3H); ES-LCMS m/z 711.3, 713.3 [M+H]$^+$.

Step 6: (1R,7S,8r)-Ethyl 4-((2-((2-(1,4-diazepan-1-yl)pyrimidin-5-yl)oxy)-6-(3,5-dichlorophenyl)pyridin-4-yl)methyl)-4-azabicyclo[5.1.0]octane-8-carboxylate

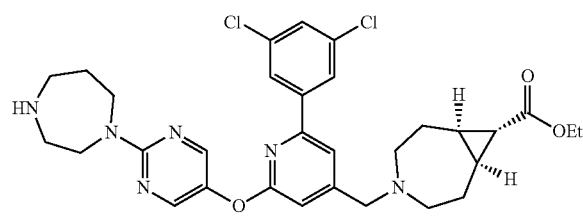 [SMILES: CCOC(=O)[C@H]1[C@@H]2CCN(Cc3cc(Oc4cnc(N5CCCNCC5)nc4)nc(-c4cc(Cl)cc(Cl)c4)c3)CC[C@@H]21]

To a solution of (1R,7S,8r)-ethyl 4-((2-((2-(4-(tert-butoxycarbonyl)-1,4-diazepan-1-yl)pyrimidin-5-yl)oxy)-6-(3,5-dichlorophenyl)pyridin-4-yl)methyl)-4-azabicyclo[5.1.0]octane-8-carboxylate (350 mg, 0.443 mmol) in DCM (15 mL) was added TFA (3 mL, 38.9 mmol). Then the mixture was stirred at 20° C. for 1 h. Then the mixture was concentrated. The residue was added DCM/MeOH (10/1, 50 mL), neutralized with 2 N NaOH to pH=7-8. The organic layer was washed with brine (50 mL), dried over Na$_2$SO$_4$, filtered and concentrated to yield (1R,7S,8r)-ethyl 4-((2-((2-(1,4-diazepan-1-yl)pyrimidin-5-yl)oxy)-6-(3,5-dichlorophenyl)pyridin-4-yl)methyl)-4-azabicyclo[5.1.0]octane-8-carboxylate (300 mg, 0.392 mmol, 89.0% yield) as a yellow oil: NMR (400 MHz, CD$_3$OD) δ ppm 8.41 (s, 2H), 7.85 (d, J=1.8 Hz, 2H), 7.51 (t, J=1.9 Hz, 1H), 7.49 (s, 1H), 7.25 (s, 1H), 4.48 (s, 2H), 4.16-4.10 (m, 4H), 4.03-3.96 (m, 4H), 3.59 (br s, 2H), 3.46-3.40 (m, 4H), 2.20-2.16 (m, 2H), 1.77-1.61 (m, 7H), 1.23-1.20 (m, 3H); ES-LCMS m/z 611.3, 613.3 [M+H]$^+$.

Step 7: (1R,7S,8r)-Ethyl 4-((2-(3,5-dichlorophenyl)-6-((2-(4-methyl-1,4-diazepan-1-yl)pyrimidin-5-yl)oxy)pyridin-4-yl)methyl)-4-azabicyclo[5.1.0]octane-8-carboxylate

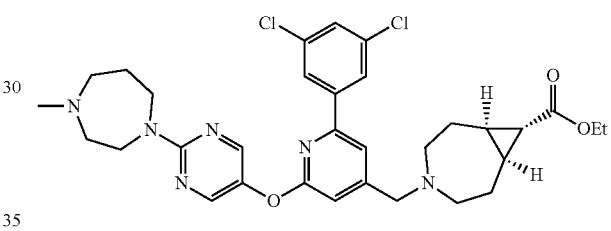

To a solution of (1R,7S,8r)-ethyl 4-((2-((2-(1,4-diazepan-1-yl)pyrimidin-5-yl)oxy)-6-(3,5-dichlorophenyl)pyridin-4-yl)methyl)-4-azabicyclo[5.1.0]octane-8-carboxylate (300 mg, 0.392 mmol) and formic acid (0.1 mL, 2.61 mmol) in MeOH (15 mL) was added paraformaldehyde (118 mg, 3.92 mmol) and stirred at 40° C. for 10 h. Then to the mixture was added NaBH$_3$CN (123 mg, 1.962 mmol). The whole mixture was stirred at 40° C. for another 2 h. The mixture was added saturated Na$_2$CO$_3$ solution (30 mL) and water (30 mL), extracted with DCM (50 mL×3). The combined organic layers were dried over Na$_2$SO$_4$, filtered and concentrated. The crude material was purified by flash chromatography (from pure DCM to DCM/MeOH=10/1, TLC: DCM/MeOH=10/1, R$_f$=0.4) to yield (1R,7S,8r)-ethyl 4-((2-(3,5-dichlorophenyl)-6-((2-(4-methyl-1,4-diazepan-1-yl)pyrimidin-5-yl)oxy)pyridin-4-yl)methyl)-4-azabicyclo[5.1.0]octane-8-carboxylate (200 mg, 0.256 mmol, 65.2% yield) as a yellow oil: $^1$H NMR (400 MHz, CDCl$_3$) δ ppm 8.22 (s, 2H), 7.66 (s, 2H), 7.32 (s, 1H), 7.26 (s, 1H), 6.81 (s, 1H), 4.04 (q, J=6.8 Hz, 2H), 3.89 (d, J=4.0 Hz, 2H), 3.78 (t, J=6.0 Hz, 2H), 3.55 (s, 2H), 2.74-2.64 (m, 4H), 2.59-2.51 (m, 2H), 2.46-2.37 (m, 2H), 2.34 (s, 3H), 2.22-2.10 (m, 2H), 1.99 (d, J=4.9 Hz, 2H), 1.58 (br s, 2H), 1.52-1.39 (m, 3H), 1.19 (t, J=7.1 Hz, 3H); ES-LCMS m/z: 625.3, 627.2 [M+H]$^+$.

Step 8: (1R,7S,8r)-4-((2-(3,5-Dichlorophenyl)-6-((2-(4-methyl-1,4-diazepan-1-yl)pyrimidin-5-yl)oxy)pyridin-4-yl)methyl)-4-azabicyclo[5.1.0]octane-8-carboxylic acid, 4 hydrochloride

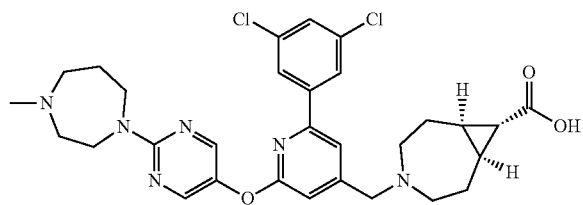 [SMILES: CN1CCCN(c2ncc(Oc3cc(CN4CC[C@@H]5[C@H](CC4)[C@H]5C(=O)O)cc(-c4cc(Cl)cc(Cl)c4)n3)cn2)CC1]

To a solution of (1R,7S,8r)-ethyl 4-((2-(3,5-dichlorophenyl)-6-((2-(4-methyl-1,4-diazepan-1-yl)pyrimidin-5-yl)oxy)pyridin-4-yl)methyl)-4-azabicyclo[5.1.0]octane-8-carboxylate (200 mg, 0.256 mmol) in THF (5 mL) and water (1 mL) was added LiOH·H$_2$O (32.2 mg, 0.767 mmol). The mixture was stirred at 50° C. for 5 h. LCMS showed the reaction was completed. The mixture was concentrated. The residue was added MeCN (6 mL) and H$_2$O (2 mL), acidified with 1 N HCl to pH=6.5-7. The mixture was purified by preparative HPLC (MeCN/H$_2$O as eluents, acidic condition) followed by lyophilization to yield (1R,7S,8r)-4-((2-(3,5-dichlorophenyl)-6-((2-(4-methyl-1,4-diazepan-1-yl)pyrimidin-5-yl)oxy)pyridin-4-yl)methyl)-4-azabicyclo[5.1.0]octane-8-carboxylic acid, 4 hydrochloride (77.1 mg, 0.101 mmol, 39.4% yield) as a white solid: $^1$H NMR (400 MHz, D$_2$O/CD$_3$CN=1/1) δ ppm 8.35 (s, 2H), 7.78 (d, J=1.8 Hz, 2H), 7.63 (s, 1H), 7.50 (t, J=1.7 Hz, 1H), 7.15 (s, 1H), 4.32 (br s, 2H), 3.87 (d, J=16.5 Hz, 1H), 3.77-3.64 (m, 2H), 3.58 (d, J=10.8 Hz, 1H), 3.46 (br s, 2H), 3.26-3.11 (m, 4H), 2.81 (s, 3H), 2.39 (d, J=15.0 Hz, 2H), 2.21 (br s, 2H), 1.95-1.93 (m, 3H), 1.65 (br s, 2H), 1.53 (br s, 2H); ES-LCMS m/z: 597.2, 599.2 [M+H]$^+$.

Examples 398-399 (Table 22) were prepared by procedures analogous to those described for example 397.

TABLE 22

| Example | Structure/Name | $^1$H NMR | LCMS |
|---|---|---|---|
| 398 | ![structure] 2-(1-((2-(3,5-dichlorophenyl)-6-((2-(8-methyl-3,8-diazabicyclo[3.2.1]octan-3-yl)pyrimidin-5-yl)oxy)pyridin-4-yl)methyl)piperidin-4-yl)acetic acid | $^1$H NMR (400 MHz, CD$_3$OD) δ ppm 8.41 (s, 2H), 7.87 (s, 1H), 7.85 (d, J = 2.0 Hz, 2H), 7.49 (t, J = 1.9 Hz, 1H), 7.29 (s, 1H), 4.75 (br d, J = 13.5 Hz, 2H), 4.42 (br s, 2H), 4.08 (br s, 2H), 3.55 (br s, 2H), 3.42 (br d, J = 14.3 Hz, 2H), 3.20-3.06 (m, 2H), 2.88 (s, 3H), 2.31 (br s, 4H), 2.14-1.99 (m, 5H), 1.62 (br s, 2H) | ES-LCMS m/z 597.3, 599.3 [M + H]$^+$. |
| 399 | ![structure] 2-(1-((2-(3,5-dichlorophenyl)-6-((2-(6-fluoro-1,4-diazepan-1-yl)pyrimidin-5-yl)oxy)pyridin-4-yl)methyl)piperidin-4-yl)acetic acid | $^1$H NMR (400 MHz, CD$_3$OD) δ ppm 8.45 (s, 2H), 7.88 (s, 1H), 7.85 (d, J = 2.0 Hz, 2H), 7.50 (t, J = 1.9 Hz, 1H), 7.30 (s, 1H), 4.85-4.80 (m, 2H), 4.76-4.65 (m, 1H), 4.42 (s, 2H), 3.67-3.50 (m, 4H), 3.48-3.31 (m, 4H), 3.12 (t, J = 12.2 Hz, 2H), 2.31 (d, J = 6.4 Hz, 2H), 2.05 (d, J = 13.2 Hz, 3H), 1.65-1.57 (m, 2H) | LCMS m/z 589.1, 591.1 [M + H]$^+$. |

Assay Protocol

Furin Enzyme Assay

Reactions were performed in black 384-well polystyrene low volume plates (Greiner). Furin (108-574-Tev-Flag-His) enzyme was expressed and purified from CHO cells. Compounds of the invention were dissolved in DMSO (1.0 mM) and serially diluted 1 to 3 with DMSO through eleven dilutions to provide a final compound concentration range from 0.00017 to 10 µM. 0.05 µL of each concentration was transferred to the corresponding well of an assay plate, and then 5 µL of 40 pM furin enzyme in assay buffer (100 mM HEPES pH7.5, 1 mM $CaCl_2$ and 0.005% Triton X-100) was added using a Multidrop Combi (Thermo) to the compound plates, and mixed by inversion. Following a 30 min preincubation of enzyme with compound at room temperature (22° C.), the substrate FAM-QRVRRAVGIDK-TAMRA (SEQ ID NO:1) (5 µL of a 1 pM solution in assay buffer) was added using a Multidrop Combi to the entire assay plate. The plates were centrifuged at 500×g for 1 minute and incubated at room temperature for two hours. Enzyme inhibition is then quantified using an Envision instrument (PerkinElmer). Data were normalized to maximal inhibition determined by 1 µM Decanoyl-Arg-Val-Arg-Lys-Chloromethylketone (SEQ ID NO:2) (Calbiochem #344930 or AnaSpec #808143).

Furin Cell-Based Assay

This assay uses an image-based platform to evaluate the intracellular activity of compounds of the invention. Reactions were performed in black 384-well, tissue culture-treated, clear bottom plates (Greiner). Compounds under analysis were dissolved in DMSO (1.0 mM) and serially diluted 1 to 3 with DMSO through eleven dilutions. This creates a final compound concentration range from 0.00017 to 10 µM, and 0.1 µL of each concentration was transferred to the corresponding well of the assay plate. Assays were initiated by the addition of U20S cells simultaneously transduced with a BacMam-delivered construct containing a Golgi-targeting sequence followed by a 12-amino acid furin/PCSK cleavage site from Bone Morphogenic Protein 10 (BMP10) and then GFP at the C terminus. The furin cleavage site sequence was flanked by glycine rich linkers (GalNAc-T2-GGGGS-DSTARIRRNAKG-GGGGS-GFP) (SEQ ID NOG). Briefly, frozen cells are thawed in assay media (Dulbecco's Modified Eagles Medium Nutritional Mixture F-12 (Ham) without phenol red containing 5% FBS) and diluted to deliver 6000 cells/well (50 µL) to the plate using a Multidrop Combi (Thermo).

After a 24-hour incubation period at 37° C., the cells are stained with Cell Mask Deep Red, fixed in paraformaldehyde and the nuclei stained using Ho33342. The Golgi-targeted GFP forms bright punctate clusters within the cell. In the absence of a furin inhibitor, the endogenous protease cleaves GFP from its N-acetylgalactosaminyltransferase-2 Golgi tether, releasing GFP into the Golgi lumen where fluorescence is diluted below the threshold of assay sensitivity. In the presence of a cell-permeable furin inhibitor, GFP fluorescence increases as intra-Golgi protease activity is reduced. Cellular GFP intensity is determined by image-based acquisition (Incell 2200, Perkin Elmer) at 40× magnification with 4 fields measured per well. Multi-scale tophat segmentation is used to identify the GFP-tagged puncta and to quantitate the average fluorescence of all puncta on a per cell basis. Cellular toxicity is determined in parallel.

Data were analyzed using AbaseXE 7.3, utilizing a four-parameter curve fit equation. The following values were used to define limits and/or constraints for each of the four parameters:
Minimum—limit −10 to 10
Maximum—90 to 110
Slope—limit 0.5 to 2.0
pXC50 confidence interval—10

Raw counts obtained from the respective plate reader (Perkin Elmer) were captured for data analysis. Curves were generated using the equation:

$$Y=A+[(B-A)/(1+(10^{C/x})^D)]$$

where: A=minimum response
B=maximum response
C=log 10*XC50
D=slope factor
x=log 10 compound concentration [M]

The results were recorded as $pXC_{50}$ values (−C in the above equation)

The exemplified compounds were generally tested according to the above or analogous assays and were found to be inhibitors of furin. Specific biological activities tested according to such assays are listed in the following table. Repeating the assay run(s) may result in somewhat different $pIC_{50}$ values.

TABLE I

Enzymatic and cellular data

| Example | furin enzyme $pIC_{50}$ | furin golgi cell $pXC_{50}$ |
|---|---|---|
| 1 | 8.3 | 8.8 |
| 2 | 8.8 | 7.4 |
| 3 | 8.9 | 7.3 |
| 4 | 8.7 | 7.5 |
| 5 | 9.1 | 7.2 |
| 6 | 8.5 | 8.1 |
| 7 | 9.2 | 7.1 |
| 8 | 8.9 | 6.7 |
| 9 | 9.2 | 8.1 |
| 10 | 8.7 | 6.9 |
| 11 | 9.6 | 7.6 |
| 12 | 8.3 | 7.6 |
| 13 | 9.1 | 8.1 |
| 14 | 9.5 | 6.2 |
| 15 | 8.5 | 7.6 |
| 16 | 9 | 8.9 |
| 17 | 10.5 | 8.7 |
| 18 | 10.7 | 9.3 |
| 19 | 10.2 | 9.4 |
| 20 | 9.6 | 9 |
| 21 | 9.9 | 8.2 |
| 22 | 9.5 | 8 |
| 23 | 8.3 | 7.8 |
| 24 | 8.6 | 7.9 |
| 25 | 8.2 | 7.9 |
| 26 | 9.9 | 8.8 |
| 27 | 9.6 | 8.5 |
| 28 | 9 | 8.7 |
| 29 | 9 | >9.1 |
| 30 | 9.1 | 6.3 |
| 31 | 9.1 | 8.2 |
| 32 | 8.7 | 8 |
| 33 | 8.5 | 7.4 |
| 34 | 9.4 | 8.3 |
| 35 | 8.8 | 8.5 |
| 36 | 9 | 8.3 |
| 37 | 8.5 | 7.9 |
| 38 | 9 | 6.9 |
| 39 | 8.3 | 7.1 |

TABLE I-continued

Enzymatic and cellular data

| Example | furin enzyme $pIC_{50}$ | furin golgi cell $pXC_{50}$ |
|---|---|---|
| 40 | 7.6 | 8 |
| 41 | 9.1 | 7.6 |
| 42 | 7.7 | 6.5 |
| 43 | 6 | |
| 44 | 9.5 | 7.6 |
| 45 | 7.2 | 6.4 |
| 46 | 7 | 6.3 |
| 47 | 8.9 | 8.4 |
| 48 | 9.4 | 8.6 |
| 49 | 9.1 | 7.7 |
| 50 | 8.1 | 6.9 |
| 51 | 8.2 | 6.8 |
| 52 | 9.8 | 8.9 |
| 53 | 8.7 | 7.8 |
| 54 | 8.2 | 6.8 |
| 55 | 8.2 | 6.6 |
| 56 | 10.5 | 8.3 |
| 57 | 10.3 | 8 |
| 58 | 9.2 | 7.8 |
| 59 | 8.9 | 8.2 |
| 60 | 7.6 | 7.8 |
| 61 | 9.2 | 6.8 |
| 62 | 9.8 | 7.5 |
| 63 | 10.8 | 8.1 |
| 64 | 9.1 | 8 |
| 65 | 8.7 | 7.7 |
| 66 | 8.8 | 8.1 |
| 67 | 10.4 | 7.9 |
| 68 | 9.6 | 7.9 |
| 69 | 9.1 | 8.3 |
| 70 | 10.5 | 8.4 |
| 71 | 9.7 | 8.8 |
| 72 | 8.8 | 8 |
| 73 | 8.9 | 8.2 |
| 74 | 8.4 | 8.2 |
| 75 | 9.1 | 8.5 |
| 76 | 8.4 | 8 |
| 77 | 9.1 | 7.2 |
| 78 | 8 | 7.2 |
| 79 | 8.3 | 7.1 |
| 80 | 9.5 | 8.1 |
| 81 | 9.4 | 8.2 |
| 82 | 9.3 | 8.3 |
| 83 | 8.9 | 7.3 |
| 84 | 9.3 | 8.1 |
| 85 | 8.1 | 6.8 |
| 86 | 8.9 | 8 |
| 87 | 9 | 8.4 |
| 88 | 9.1 | 8.3 |
| 89 | 8 | 7.9 |
| 90 | 8.5 | 8.1 |
| 91 | 8.4 | 7.4 |
| 92 | 8.9 | 8.5 |
| 93 | 8.9 | 8.3 |
| 94 | 8.9 | 8.3 |
| 95 | 9.9 | 8.8 |
| 96 | 9 | 8.8 |
| 97 | 8.4 | 7.6 |
| 98 | 8.7 | 7.4 |
| 99 | 7.2 | 6.6 |
| 100 | 8.8 | 7.1 |
| 101 | 8.6 | 5.5 |
| 102 | 9.2 | 7.8 |
| 103 | 8.9 | 7.2 |
| 104 | 8.5 | 7.6 |
| 105 | 9 | 6.9 |
| 106 | 9.4 | 8.5 |
| 107 | 9 | 8.3 |
| 108 | 7.5 | <4.3 |
| 109 | 9.6 | 7.8 |
| 110 | 10.3 | 8.6 |
| 111 | 9.7 | 6.8 |
| 112 | 8.9 | 6.9 |
| 113 | >9.8 | 7.9 |
| 114 | >9.8 | 7.7 |
| 115 | 8.3 | 6.6 |
| 116 | 10.4 | 6.7 |
| 117 | 9.2 | 7.5 |
| 118 | 8.7 | 7.8 |
| 119 | 9.3 | 7.6 |
| 120 | 8.7 | 7.8 |
| 121 | 8.6 | 7.5 |
| 122 | 8.5 | 7.1 |
| 123 | 8.7 | 7 |
| 124 | 8.8 | 7.7 |
| 125 | 8 | 7.3 |
| 126 | 9 | 8.2 |
| 127 | 8.8 | 6.3 |
| 128 | 7.9 | 6.2 |
| 129 | 8.2 | 7.1 |
| 130 | 8.7 | 8.1 |
| 131 | 8.7 | 7.5 |
| 132 | 8.8 | 7.2 |
| 133 | 8.3 | 7.4 |
| 134 | 9.5 | 7.6 |
| 135 | 9.2 | 8 |
| 136 | 9.8 | 7.8 |
| 137 | 9.1 | 8 |
| 138 | 9.1 | 8.1 |
| 139 | 9.3 | 8 |
| 140 | 8.8 | 8.1 |
| 141 | 8.6 | 8.3 |
| 142 | 8.8 | 8.2 |
| 143 | 8.4 | 7.7 |
| 144 | 8.5 | 8.1 |
| 145 | 8.9 | 8.7 |
| 146 | 8.5 | 7.8 |
| 147 | 9.2 | 7.5 |
| 148 | 8.3 | 7.2 |
| 149 | 8.3 | 7.1 |
| 150 | 8.2 | 7.2 |
| 151 | 8.2 | 7 |
| 152 | 8.2 | 7.5 |
| 153 | 7.9 | 7.8 |
| 154 | 7.8 | 7.3 |
| 155 | 8.1 | 7.8 |
| 156 | 8.8 | 7.8 |
| 157 | 10.8 | 8.9 |
| 158 | 8.8 | 7.1 |
| 159 | 8.5 | 7.6 |
| 160 | 8.8 | 7.6 |
| 161 | 8.3 | 7.4 |
| 162 | 8.4 | 7.1 |
| 163 | 8.7 | 8 |
| 164 | 8.4 | 7.6 |
| 165 | 8.4 | 7.5 |
| 166 | 8.5 | 7.2 |
| 167 | 8.3 | 7.3 |
| 168 | 9.3 | 7.6 |
| 169 | 10.5 | 5.9 |
| 170 | 9.1 | 7.9 |
| 171 | 10.7 | 8.7 |
| 172 | 9.6 | 8.7 |
| 173 | 9.4 | 8.9 |
| 174 | 9.2 | 7.7 |
| 175 | 9.2 | 8 |
| 176 | 9 | 8.4 |
| 177 | 9.2 | 7.7 |
| 178 | 8.9 | >8.6 |
| 179 | 8.8 | 7.9 |
| 180 | 9.1 | 8.5 |
| 181 | 9 | 7.1 |
| 182 | 9.3 | 8.8 |
| 183 | 10.6 | 7.9 |
| 184 | 9.6 | 7.8 |
| 185 | 9.5 | 7.5 |

TABLE I-continued

Enzymatic and cellular data

| Example | furin enzyme $pIC_{50}$ | furin golgi cell $pXC_{50}$ |
|---|---|---|
| 186 | 9.1 | 7.4 |
| 187 | 8.9 | 7.1 |
| 188 | 8.8 | 7.9 |
| 189 | 8.7 | 7.5 |
| 190 | 10.7 | 6.8 |
| 191 | 9.8 | 7.4 |
| 192 | 10.4 | 7.8 |
| 193 | 9 | 8.5 |
| 194 | 9.1 | 8.5 |
| 195 | 9.2 | 9 |
| 196 | 9.2 | 8.5 |
| 197 | 9.2 | 8.7 |
| 198 | 9.3 | 8.7 |
| 199 | 9.2 | 8.3 |
| 200 | 9.1 | 9.3 |
| 201 | 9.4 | 7.7 |
| 202 | 8.6 | 7.4 |
| 203 | 8.7 | 7.9 |
| 204 | 8.7 | 7.5 |
| 205 | 8.6 | 7.8 |
| 206 | 8.6 | 7.6 |
| 207 | 9.1 | 7.8 |
| 208 | 10.9 | 8 |
| 209 | 9.6 | 8.6 |
| 210 | 8.7 | 8.4 |
| 211 | 10.1 | 7.6 |
| 212 | 9 | 7.5 |
| 213 | 8.9 | 7.6 |
| 214 | 9.1 | 8.6 |
| 215 | 9.4 | 8 |
| 216 | 10.2 | 7.8 |
| 217 | 9.8 | 8.3 |
| 218 | 10.1 | 8.7 |
| 219 | 9.8 | 9.4 |
| 220 | 10.2 | 8.6 |
| 221 | 10.4 | 8.3 |
| 222 | 10.2 | 7.6 |
| 223 | 9.8 | 8.3 |
| 224 | 8.7 | 8.1 |
| 225 | 8.5 | 8 |
| 226 | 8.6 | 7.8 |
| 227 | 8.7 | 7.4 |
| 228 | 8.6 | 7.4 |
| 229 | 8.6 | 7.7 |
| 230 | 8.6 | 8 |
| 231 | 8.5 | 8 |
| 232 | 8.9 | 7.3 |
| 233 | 8.2 | 7 |
| 234 | 10.7 | 8 |
| 235 | 9.2 | 7.8 |
| 236 | 8.5 | 7.4 |
| 237 | 8.7 | 8.5 |
| 238 | 9.8 | 8 |
| 239 | 8 | 7.6 |
| 240 | 8.4 | 8.2 |
| 241 | 8.6 | 7.2 |
| 242 | 8.6 | 7.6 |
| 243 | 8.7 | 7.6 |
| 244 | 8.3 | 7.7 |
| 245 | 10 | 8.4 |
| 246 | 8.9 | 7.8 |
| 247 | 8.5 | 7.5 |
| 248 | 10.5 | 7.6 |
| 249 | 9.1 | 7.9 |
| 250 | 8.9 | >9.1 |
| 251 | >9.8 | 8.3 |
| 252 | 8.5 | 7.5 |
| 253 | 9.7 | 8.6 |
| 254 | 8.7 | 8.5 |
| 255 | 9.5 | 8.2 |
| 256 | 9.5 | 7.8 |
| 257 | 10.1 | 8.3 |
| 258 | 9.6 | 7.5 |
| 259 | 9.8 | 8.8 |
| 260 | 9.7 | 8.2 |
| 261 | 9.2 | 8 |
| 262 | 9 | 9.5 |
| 263 | 9.8 | 8 |
| 264 | 8.6 | 8.4 |
| 265 | 9.4 | 8.1 |
| 266 | 8.7 | 7.3 |
| 267 | 9.9 | 7.3 |
| 268 | 9.1 | 7.2 |
| 269 | 8.5 | 7.6 |
| 270 | 9.5 | 7.6 |
| 271 | 8.9 | 7.6 |
| 272 | 9.8 | 7.5 |
| 273 | 8.2 | 7.5 |
| 274 | 9 | 8.2 |
| 275 | 8.3 | 7 |
| 276 | 9 | 7.3 |
| 277 | 10.5 | 7.3 |
| 278 | 9.4 | 8 |
| 279 | 8.6 | 7.7 |
| 280 | 8.3 | 7.8 |
| 281 | 9.5 | 7.4 |
| 282 | 9.7 | 8.1 |
| 283 | 9.1 | 7.6 |
| 284 | 10.1 | 8.9 |
| 285 | 8.1 | 7.2 |
| 286 | 9.4 | 8.1 |
| 287 | 8.7 | 6.2 |
| 288 | 9.4 | 7.3 |
| 289 | 8.6 | 8.3 |
| 290 | 8.2 | 7.8 |
| 291 | 10.7 | 8.1 |
| 292 | 9.4 | 7.3 |
| 293 | 8.2 | 6.8 |
| 294 | 10.1 | 7.7 |
| 295 | 9.5 | 9.1 |
| 296 | 10.6 | 8 |
| 297 | 9.4 | 8.3 |
| 298 | 9.2 | 7.7 |
| 299 | 8.5 | 7.5 |
| 300 | 9.1 | 7.7 |
| 301 | 9.6 | 7.4 |
| 302 | 9.6 | 8.1 |
| 303 | 9.2 | 8.6 |
| 304 | 8.8 | 8.6 |
| 305 | 8.7 | 8 |
| 306 | 8.9 | 7.6 |
| 307 | 9.4 | 8.7 |
| 308 | 9.3 | 7.9 |
| 309 | 9.8 | 8.6 |
| 310 | 9.6 | 8.4 |
| 311 | 8.9 | 7.8 |
| 312 | 9.7 | 7.8 |
| 313 | >9.8 | 7.8 |
| 314 | 8.9 | 7.5 |
| 315 | 9.2 | 7.8 |
| 316 | 10.2 | 7 |
| 317 | 9.2 | 7.8 |
| 318 | 8.9 | 8 |
| 319 | 8.9 | 9 |
| 320 | 8.2 | 7.9 |
| 321 | 9.1 | 7.8 |
| 322 | 8.9 | 8.2 |
| 323 | 8.7 | 7.9 |
| 324 | 8.3 | 7.8 |
| 325 | 8.3 | 8.2 |
| 326 | 8.7 | 7.9 |
| 327 | 8.6 | 8.5 |
| 328 | 8.3 | 7.9 |
| 329 | 8.2 | 7.8 |
| 330 | 8 | 8 |
| 331 | 7.8 | 7.7 |

TABLE I-continued

Enzymatic and cellular data

| Example | furin enzyme pIC$_{50}$ | furin golgi cell pXC$_{50}$ |
|---|---|---|
| 332 | 8.3 | 7.3 |
| 333 | 8.7 | 7.9 |
| 334 | 8.9 | 7.7 |
| 335 | 9.2 | 8.9 |
| 336 | 9.1 | 8.4 |
| 337 | 9 | 8.1 |
| 338 | 8 | 7.9 |
| 339 | 8.7 | 7.3 |
| 340 | 8.8 | 7.7 |
| 341 | 8.8 | 8 |
| 342 | 8.7 | 8.3 |
| 343 | 8.7 | 7.2 |
| 344 | 8.4 | 7.1 |
| 345 | 8.6 | 7.9 |
| 346 | 8.5 | 7.9 |
| 347 | 8.5 | 7.8 |
| 348 | 8.4 | 7.3 |
| 349 | 8.6 | 8 |
| 350 | 8.6 | 8.9 |
| 351 | 9.4 | 7.6 |
| 352 | 8.2 | 7.3 |
| 353 | 8.1 | 7.6 |
| 354 | 8.1 | 7.6 |
| 355 | 8.6 | 8 |
| 356 | 8.6 | 7.5 |
| 357 | 8.5 | 7 |
| 358 | 9.1 | 7.7 |
| 359 | 9 | 7.2 |
| 360 | 9 | 7.9 |
| 361 | 9 | 7.3 |
| 362 | 10.5 | 7.6 |
| 363 | 9.7 | 6.2 |
| 364 | 9.7 | 7.5 |
| 365 | 9.9 | 6.9 |
| 366 | 8.8 | 7.5 |
| 367 | 10.1 | 8.6 |
| 368 | 8.3 | 8.4 |
| 369 | 9.3 | 8.3 |
| 370 | 9.2 | 8.2 |
| 371 | 8.9 | 7.5 |
| 372 | 8.8 | 8.4 |
| 373 | 8.9 | 8.3 |
| 374 | 7.9 | 6.8 |
| 375 | 7.9 | 6.6 |
| 376 | 8.7 | 7.6 |
| 377 | 8.6 | 7.6 |
| 378 | 8.7 | 8.2 |
| 379 | 8.7 | 7.7 |
| 380 | 9.6 | 7.2 |
| 381 | 8.9 | 8 |
| 382 | 8.6 | 8.2 |
| 383 | 8.4 | 7.2 |
| 384 | 8.4 | 7.6 |
| 385 | 8.4 | 7.9 |
| 386 | 8.4 | 8 |
| 387 | 8.5 | 7.6 |
| 388 | 8.1 | 7.3 |
| 389 | 8.2 | 7.2 |
| 390 | 8.3 | |
| 391 | 8.7 | 8.2 |
| 392 | 9 | 7.8 |
| 393 | 9.2 | 8.6 |
| 394 | 9 | 8.2 |
| 395 | 9.2 | 7.5 |
| 396 | 10.3 | 8 |
| 397 | 9 | 7.6 |
| 398 | 8.9 | 8.2 |
| 399 | 8.8 | 7.4 |

Bleomycin Induced Lung Fibrosis Model

Preclinical pulmonary fibrosis can be induced by single instillation of Bleomycin to the mouse lung. A 15-day Bleomycin protocol was developed to evaluate compounds of the invention in vivo for their ability to inhibit TGFβ secretion and collagen deposition in the mouse lung. On the day before Bleomycin instillation, compounds were administrated to mice based on the appropriate route and frequency. On the study initiation day, under Ketamine (80 mg/kg) and Xylazine (10 mg/kg) anesthesia, all the animals were cannulated oro-tracheally and 50 µL of normal saline (Sham control) or 0.03 U Bleomycin in 50 µL saline (all groups except sham control group) was delivered into the trachea. Compounds were dosed daily until the end of study on Day 15. On termination day, animals were euthanized using CO$_2$ inhalation. The right lung was collected, washed in normal saline, weighed, flash frozen in liquid nitrogen and stored at −80° C. for hydroxyproline (a specific marker for collagen) and TGFβ assays.

Flash frozen whole right lung tissues were homogenized in 500 µL of RIPA buffer containing PMSF and protease inhibitor cocktail using zirconium oxide bead based homogenizer (Bullet blender Gold, NextAdvance, Germany). Briefly, tissues were spun in the homogenizer at 4° C. for three cycles of 10 minutes each at 1000 g. A complete uniform tissue mixture was obtained using this procedure. The homogenate volume was made up to 1.5 mL by adding 1 mL of RIPA buffer containing PMSF and protease inhibitor cocktail to 500 µL of homogenate. The homogenate was stored as aliquots of 100-500 µL each at −80° C.

Hydroxyproline Assay:

Acid hydrolysis: 500 µL of the homogenized lung parenchyma was transferred to glass vials, and an equal volume of 12N HCl was added (final concentration of HCl: 6N). The vials were purged with nitrogen gas, sealed and incubated overnight (16 h) under anoxic conditions at 110° C.

Post incubation procedures: 35 µL of the sample from each tube or standard (prepared by serial dilution of hydroxyproline stock solution) was added onto a 96 well plate and the assay was performed as per the kit protocol (Quickzyme Biosciences: Cat #: QZBHYPR05). After the final color development, absorbance was measured by colorimetric analysis at 570 nm (using Thermoscan spectrum (Plate Reader) and results were recorded. Standard curve (linear graph) was generated by using hydroxyproline standards provided in the Quickzyme kit.

Tgfβ Assay:

Lung tissue homogenates (500 µL) were spun at 13,000 rpm for 20 minutes at 4° C. and supernatants were collected for TGFβ estimation. The assay was performed according to the manufacturer's manual (R&D systems: Cat #SMB100B). Briefly, the lung homogenates were activated by acid activation followed by neutralization to convert latent TGFβ to active TGFβ and the total TGFβ levels in supernatants were measured. Total protein levels in the lung supernatant were also determined.

TABLE II

Summary of compound effects on mouse lung TGFβ and hydroxyproline content in the Bleomycin-induced lung fibrosis mouse model.

| Example | Dose (mg/kg) | Route | Frequency | % inhibition of total TGFβ in lung | % inhibition of hydroxyproline in lung |
|---|---|---|---|---|---|
| 10 | 10 | Intraperitoneal | Twice Daily | 43* | 16 |
| 11 | 10 | Intraperitoneal | Twice daily | 69* | 67* |

TABLE II-continued

Summary of compound effects on mouse lung TGFβ and hydroxy-proline content in the Bleomycin-induced lung fibrosis mouse model.

| Example | Dose (mg/kg) | Route | Frequency | % inhibition of total TGFβ in lung | % inhibition of hydroxy-proline in lung |
|---|---|---|---|---|---|
| 12 | 30 | Oral | Once daily | 41* | 45* |
| 41 | 10 | Intra-peritoneal | Once daily | 67* | 39* |
| 62 | 30 | Oral | Once daily | 7 | −14 |
| 126 | 30 | Oral | Once daily | 34* | 36* |
| 137 | 10 | Oral | Once daily | 81* | 54* |
| 180 | 10 | Intra-peritoneal | Once daily | 60* | 56* |
| 206 | 10 | Oral | Once daily | −11 | 6 |
| 207 | 10 | Oral | Once daily | 66* | 46* |
| 242 | 10 | Oral | Once daily | 40* | −1 |
| 263 | 10 | Intra-peritoneal | Twice Daily | 86* | 60* |
| 298 | 10 | Oral | Once daily | 23* | 16* |
| 306 | 10 | Oral | Once daily | 31* | 11 |
| 334 | 30 | Oral | Once daily | 36* | 34* |
| 339 | 10 | Oral | Once daily | 22 | 4 |
| 340 | 30 | Oral | Once daily | 26* | 21* |
| 369 | 10 | Oral | Once daily | 75* | 62* |

% inhibition is reported relative to levels induced by Bleomycin in vehicle treated animals (*p < 0.05 (t-test)).

Transepithelial Electrical Resistance Assays

For Transepithelial Electrical Resistance (TEER) assays the epithelial sodium channel (ENaC) is active under basal conditions and affects the transepithelial resistance ($R_{TE}$) significantly with its function of transporting cations across the apical membrane. Primary cultures of CF delF508 or non-CF HBE cells are seeded onto permeable filter supports and grown for 12-14 days for a significant $R_{TE}$ to be measured for TEER assays.

When the ENaC is active under basal conditions (at least in part due to protease cleavage inside the cell or at the apical membrane), there is a finite $R_{TE}$ that is affected by the Na+ current flowing through ENaC heterotrimers (αβγ or δβγ).

When the ENaC is closed (inhibited) at the membrane or removed from the membrane, Na⁺ current does not flow and $R_{TE}$ increases (i.e., fewer holes in the apical membrane—it is the sum of the apical membrane resistance and basolateral membrane resistance that determines $R_{TE}$).

Figure 6:
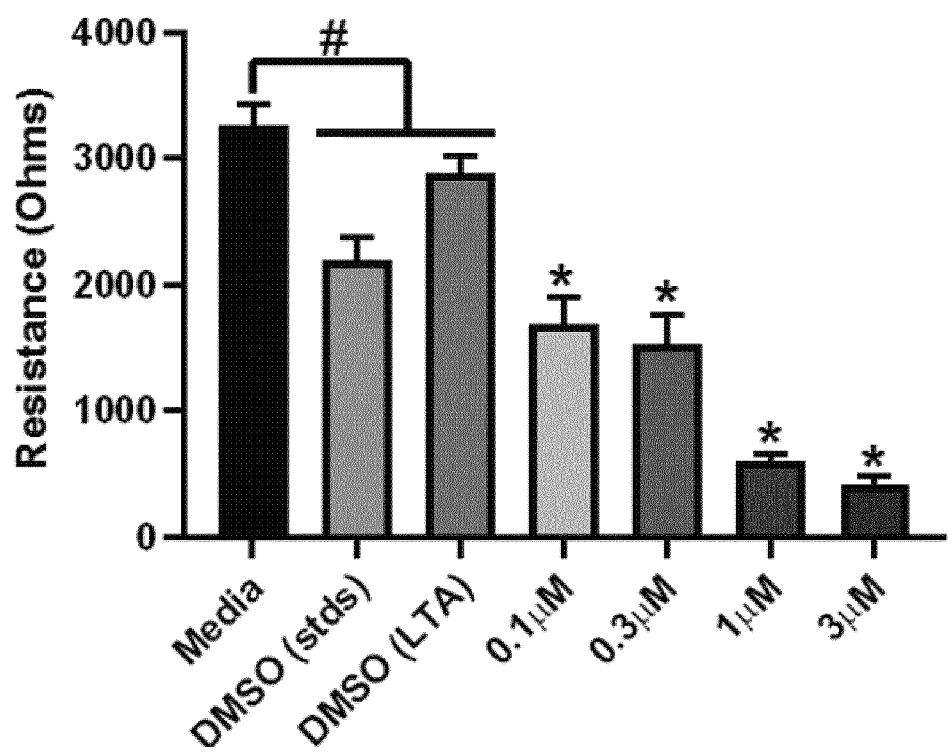
FIG. 6 shows the results of the TEER assay using polarized CF human bronchial epithelial cells (CF delF508) with Example 11.
Figure 7:
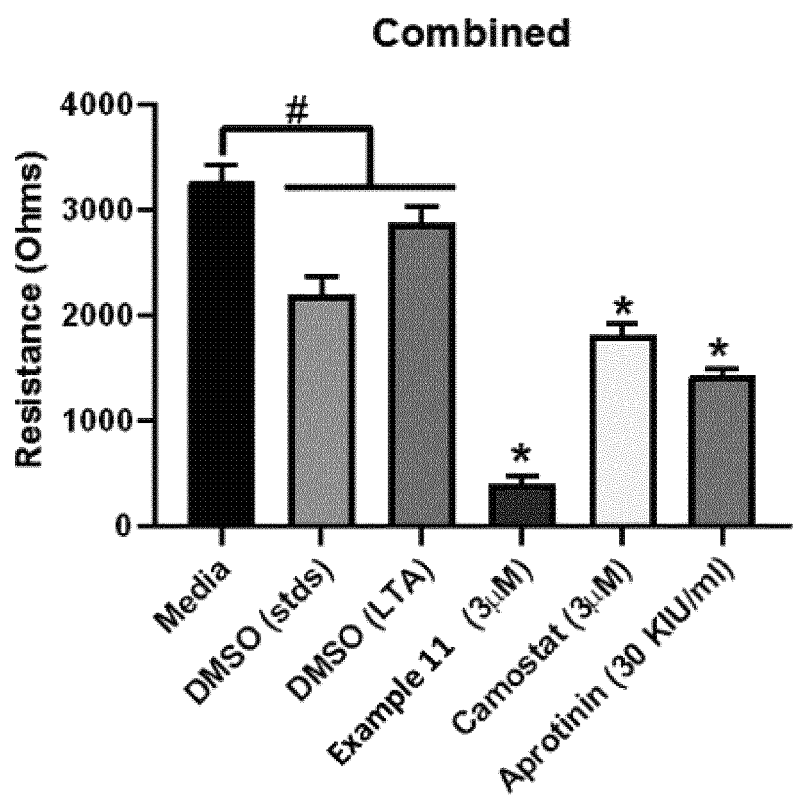
FIG. 7 shows the results of the TEER assay using polarized CF human bronchial epithelial cells (CF delF508) comparing Example 11 with Camostat and Aprotinin.
Figure 8:
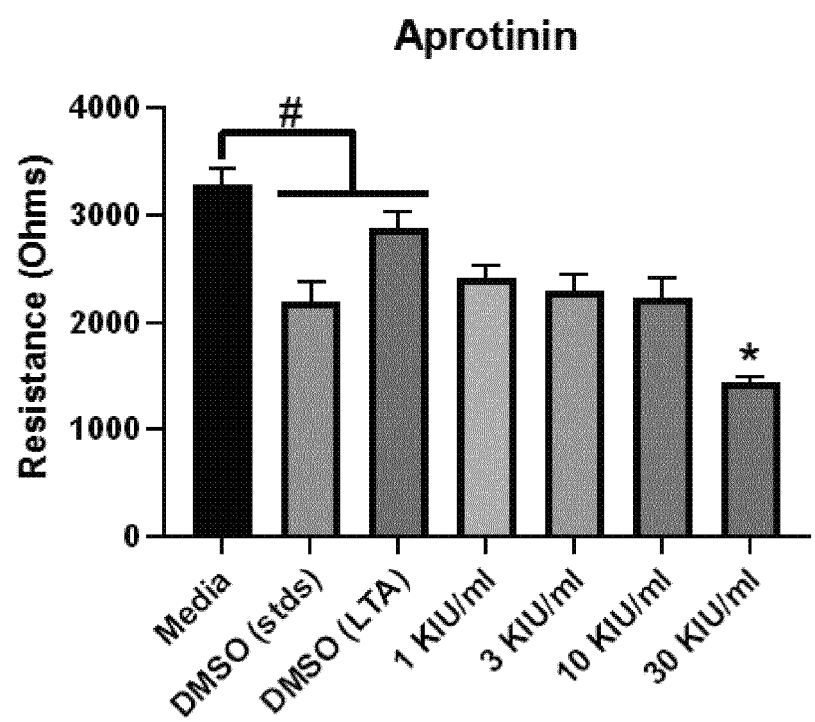
FIG. 8 shows the results of the TEER assay using polarized CF human bronchial epithelial cells (CF delF508) with Aprotinin.
Figure 9:
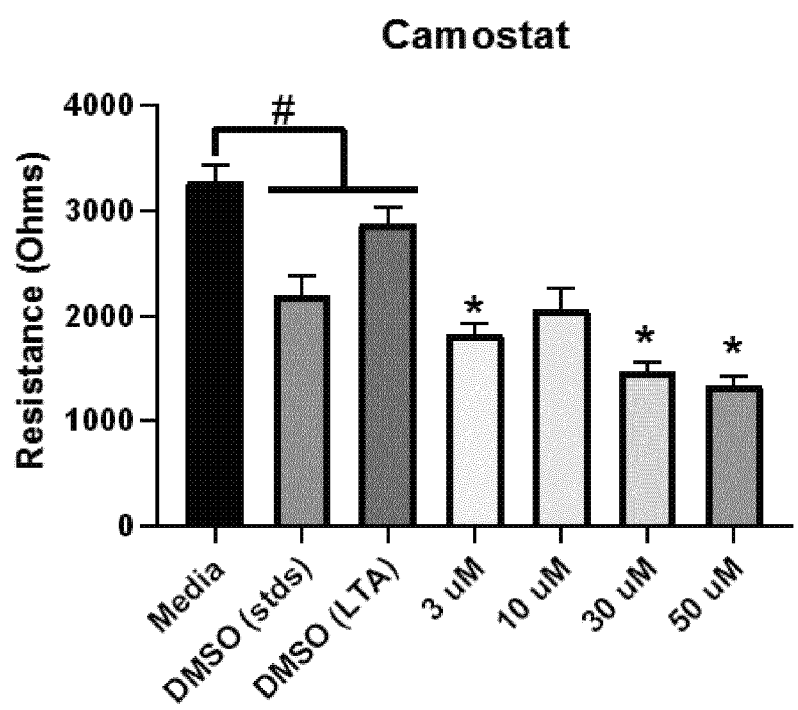
FIG. 9 shows the results of the TEER assay using polarized CF human bronchial epithelial cells (CF delF508) with Camostat.

As can be seen in FIG. 6, Example 11 shows a concentration-dependent reduction in amiloride-induced increase in $R_{TE}$ when compared to 'Media only' and 'DMSO (LTA)' controls (One-way ANOVA was performed followed by Tukey's HSD post-hoc analysis, *p<0.05). Example 11 is more effective when compared to Camostat at the same concentration and Aprotinin at ~10 μM (FIG. 7). The overlap in CRCs occurs only at 3 μM. The industry standards, Camostat mesylate and Aprotinin, are only partially inhibitory and modestly Inhibitory when compared to Example 11. Only mid-μM concentrations were partially effective (FIG. 8 and FIG. 9).

Figure 10:
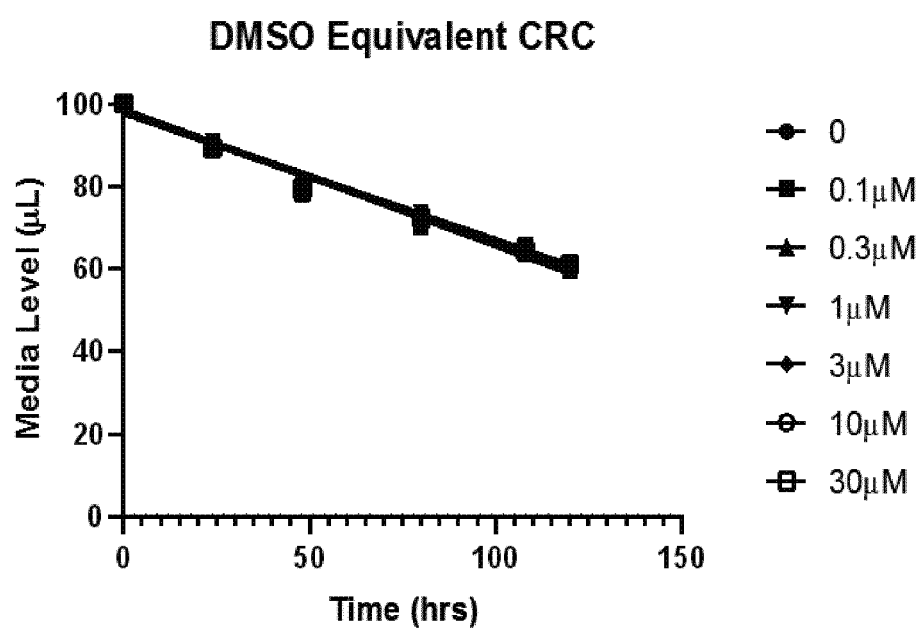
FIG. 10 shows the results of a fluid transport assay using polarized CF human bronchial epithelial cells (CF delF508) with DMSO (control).
Figure 11:
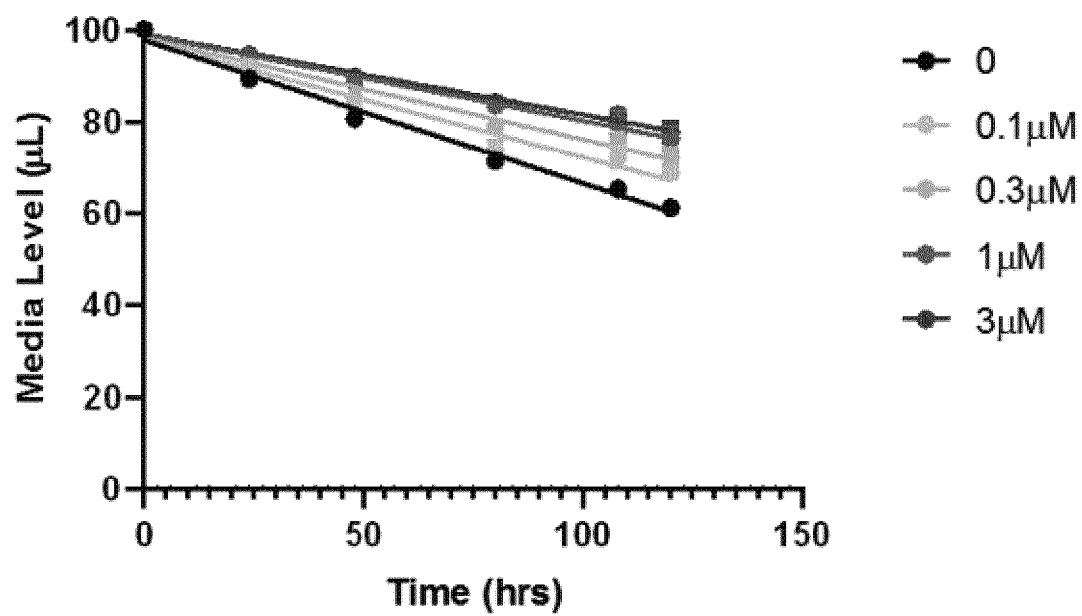
FIG. 11 shows the results of a fluid transport assay using polarized CF human bronchial epithelial cells (CF delF508) with Example 11.
Figure 12:
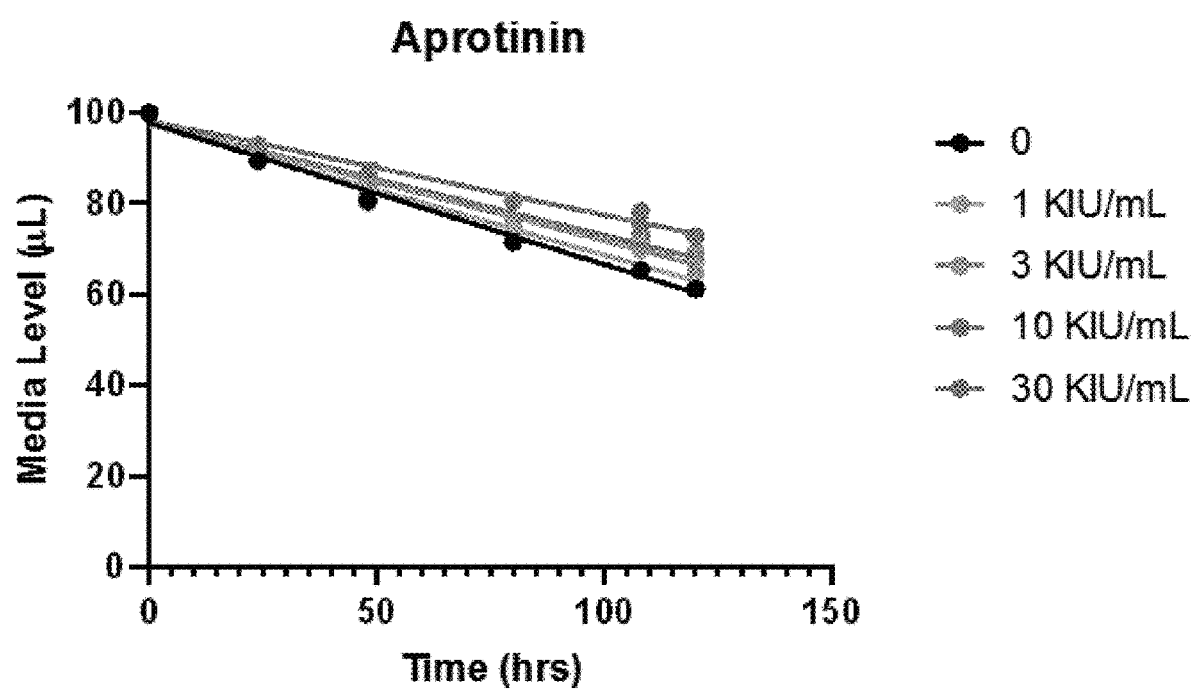
FIG. 12 shows the results of a fluid transport assay using polarized CF human bronchial epithelial cells (CF delF508) with Aprotinin.
Figure 13:
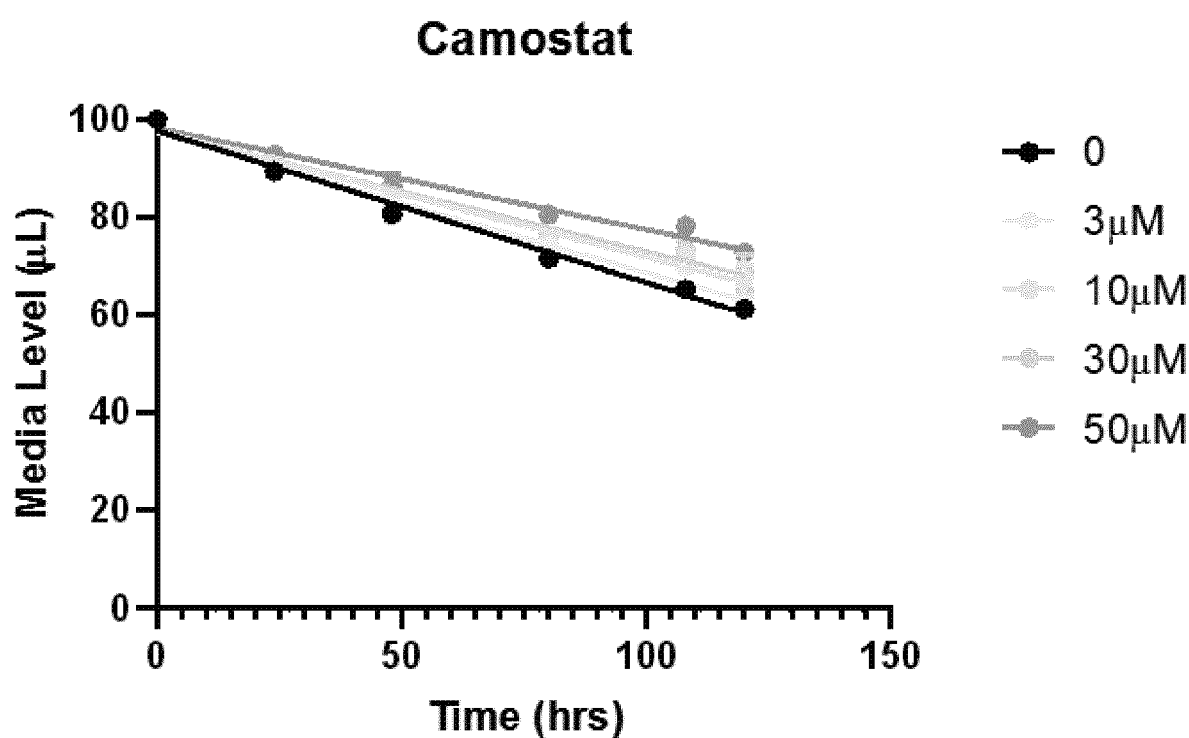
FIG. 13 shows the results of a fluid transport assay using polarized CF human bronchial epithelial cells (CF delF508) with Camostat.
Figure 14:
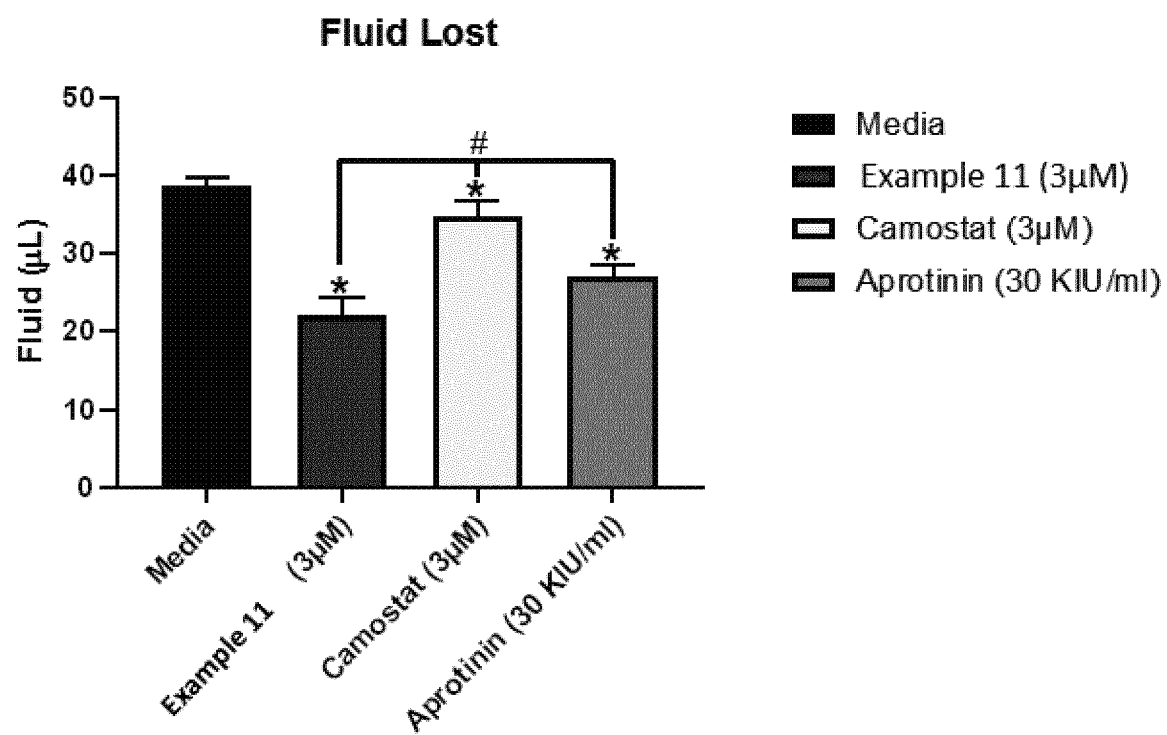
FIG. 14 shows the results of fluid loss between control (DMSO), Example 11, Camostat, and Aprotinin.
Figure 15:
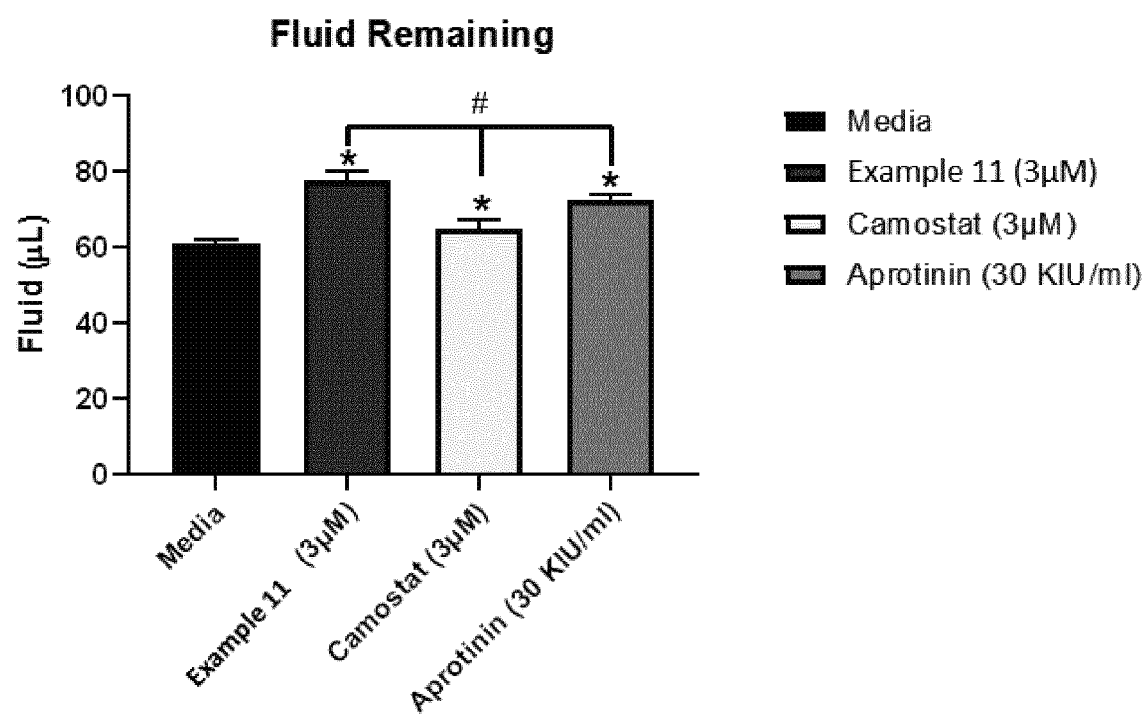
FIG. 15 shows the results of fluid loss between control (DMSO), Example 11, Camostat, and Aprotinin.
Figure 16:
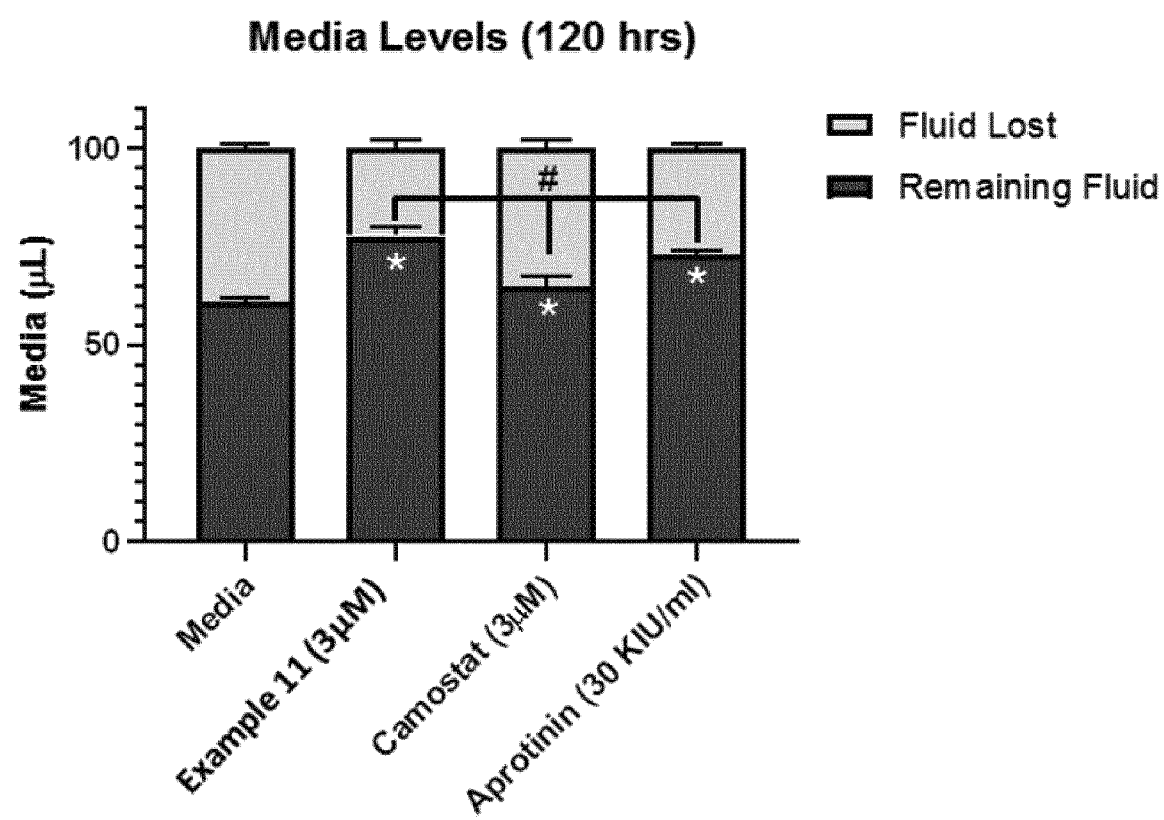
FIG. 16 shows the media levels of fluid loss and retention between control (DMSO), Example 11, Camostat, and Aprotinin.

Example 11 shows a concentration-dependent attenuation of absorptive fluid transport when compared to 'DMSO Equivalent' controls. The higher concentrations of 1 and 3 μM attenuated total fluid volume lost and rate of fluid lost by 50%. (FIG. 10 and FIG. 11) Similar data were obtained in non-CF HBE cell monolayers. By contrast, the industry standards only attenuated absorptive fluid transport by nearly 50% at the highest concentration of each protease inhibitor tested. (FIG. 12 and FIG. 13) Similar data were obtained in non-CF HBE cell monolayers.

Table III shows that Example 11 at 3 μM and Camostat at 50 μM had an equivalent inhibitory effect (P<0.05) on the amiloride-sensitive $R_{TE}$ delta (while aprotinin did not) with a chronic overnight treatment.

TABLE III

TEER Data for Chronic Treatment (overnight in the media prior to TEER assay) with Example 11 vs. Aprotinin or Camostat in Non-CF Polarized Human Lobar Bronchial Epithelial Cells.

|  | Before Amil | After Amil | Delta $R_{TE}$ |
|---|---|---|---|
| Media Only | 463 ± 23 | 666 ± 35 | +203 ± 13 |
| DMSO Eqviv | 578 ± 24 | 712 ± 30 | +135 ± 11 |
| Example 11 (n = 6 per) | | | |
| 0.1 μM | 517 ± 42 | 697 ± 57 | +181 ± 16 |
| 0.3 μM | 426 ± 10 | 548 ± 13 | +122 ± 6 |
| 1 μM | 472 ± 38 | 605 ± 49 | +133 ± 14 |
| 3 μM | 326 ± 16 | 390 ± 18 | +63 ± 7 |
| Aprotinin (n = 3 per) | | | |
| 1 KIU/ml | 439 ± 4 | 657 ± 19 | +219 ± 15 |
| 3 KIU/ml | 458 ± 29 | 690 ± 65 | +233 ± 36 |
| 10 KIU/ml | 500 ± 39 | 734 ± 65 | +234 ± 27 |
| 30 KIU/ml | 513 ± 9 | 729 ± 15 | +215 ± 5 |
| Camostat (n = 3 per) | | | |
| 3 μM | 443 ± 6 | 615 ± 26 | +172 ± 20 |
| 10 μM | 387 ± 11 | 506 ± 10 | +119 ± 1 |
| 30 μM | 472 ± 6 | 635 ± 13 | +163 ± 8 |
| 50 μM | 348 ± 4 | 446 ± 3 | +98 ± 2 |

Table IV shows the results of acute treatment with Example 11, demonstrating that Example 11 up to 3 μM had an equivalent acute effect to Aprotinin and a stronger effect than Camostat. Example 11 also inhibited amiloride-sensitive $R_{TE}$ delta modestly (remaining ENaC activity not inhibited already by the putative ENaC inhibitors, while Aprotinin and Camostat inhibited that parameter more strongly. However, the research tool protease inhibitors (Aprotonin and Camostat) are tested at much higher concentrations. Acute treatment data was generated with 50 ml additions of media to the apical side of the cell monolayer with or without ENaC inhibitors initially to affect $R_{TE}$. Then, amiloride was added to detect remaining ENaC activity not inhibited by the putative ENaC inhibitors.

TABLE IV

TEER Data for acute Treatment with Example 11 vs. Aprotinin or Camostat in Non-CF Polarized Human Lobar Bronchial Epithelial Cells.

|  | Delta $R_{TE}$ after Volume Additions | Delta $R_{TE}$ after Amil |
|---|---|---|
| Media Oniy | +56 ± 7 | +64 ± 3 |
| DMSO Equiv | +43 ± 6 | +61 ± 3 |
| Example 11 (n = 12 per) | | |
| 0.1 μM thru 3 μM | +148 ± 6 | +52 ± 3 |
| 0.1 μM thru 3 μM | +157 ± 9 | +51 ± 2 |
| Aprotinin (n = 12 per) | | |
| 1 KIU/ml thru 30 KIU/ml | +123 ± 3 | +20 ± 1 |
| Camostat (n = 12 per) | | |
| 3 μM thru 50 μM | +82 ± 4 | +15 ± 2 |

Transepithelial Fluid Transport Assays

Primary cultures of CF delF508 or non-CF HBE cells are seeded onto permeable filter supports and grown for 7 days for a significant $R_{TE}$ to be measured. Then, apical media is removed to initiate air-fluid interface (AFI) culture. When the cell monolayers are tight to fluid leak from basolateral to apical side of the cell monolayer, they are ready for fluid transport (fluid absorption) measurements.

Two methods are being used to challenge cell monolayers in AFI culture where there is no media in the apical side:

(1) A chronic overnight treatment was performed by adding the protease inhibitors (ENaC inhibitors) into the basolateral media. Then, 100 ml of cell culture media is added to the apical side of each monolayer and fluid absorption measured (by the loss of volume in mls).

(2) An acute treatment was performed when the protease inhibitors (ENaC inhibitors) are added in the apical media in that 100 ml volume (or media only or DMSO equivalents as controls).

In each case, fluid absorption is occurring against a 5× hydrostatic pressure gradient (i.e., there are 500 ml on the basolateral side and 100 µM on the apical side).

When the ENaC is active under basal conditions (at least in part due to protease cleavage inside the cell or at the apical membrane), the absorptive Na+ current flowing through ENaC heterotrimers ($\alpha\beta\gamma$ or $\delta\beta\gamma$) creates an osmotic driving force for fluid absorption.

When the ENaC is closed (inhibited) at the membrane or removed from the membrane, Na+ current does not flow and the absorptive driving force for fluid absorption is not present (i.e., there is less fluid absorption across the epithelium when ENaC is inhibited).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A compound according to Formula (I):

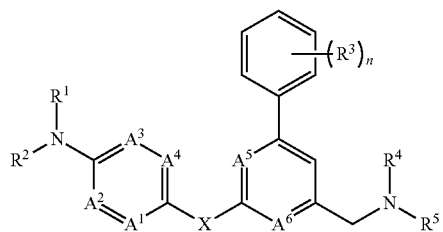

(I)

wherein:
$A^1$, $A^2$, $A^3$, $A^4$, $A^5$, and $A^6$ are each independently N, CH, or $CR^6$;
X is O or $NR^8$;
$R^1$ and $R^2$ are each independently hydrogen, $(C_1-C_4)$alkyl, or $H_2N(C_1-C_4)$alkyl-;
or $R^1$ and $R^2$ taken together with the nitrogen atom to which they are attached represent a 4-11 membered monocyclic or fused, bridged, or spiro bicyclic saturated ring, optionally containing one or two additional heteroatoms independently selected from oxygen, nitrogen, and sulfur, wherein said ring is optionally substituted by one, two, or three substituents independently selected from halogen, hydroxyl, oxo, —OCONR$^8$R$^9$, —CO$_2$R$^8$, —C(O)CO$_2$R$^8$, R$^7$, —OR$^7$, —NHR$^8$, —NR$^7$R$^8$, —C(O)R$^7$, —CONHR$^8$, —CONR$^7$R$^8$, and —SO$_2$R$^7$;

each $R^3$ is independently selected from the group consisting of halogen, methyl, fluoromethyl, difluoromethyl, and trifluoromethyl;

$R^4$ and $R^5$ are each independently hydrogen, $(C_1-C_4)$alkyl, or $(C_1-C_4)$alkoxy$(C_2-C_4)$alkyl-;

or $R^4$ and $R^5$ taken together with the nitrogen atom to which they are attached represent a 4-11 membered monocyclic or fused, bridged, or spiro bicyclic saturated ring, optionally containing one or two additional heteroatoms independently selected from oxygen, nitrogen, and sulfur, wherein said ring is optionally substituted by one, two, or three substituents independently selected from halogen, hydroxyl, oxo, —OCONR$^8$R$^9$, —CO$_2$R$^8$, —C(O)CO$_2$R$^8$, —SO$_2$(C$_1$-C$_4$)alkyl, R$^7$, —OR$^7$, —NHR$^8$, —NR$^7$R$^8$, —N(R$^8$)C (O)R⁹, —N(R⁸)SO₂R⁹, —N(R⁸)CONR⁸R⁹, —N(R⁸)CON(R⁸)SO₂R⁹, —C(O)R⁷, —CONHR⁸, —CONR⁷R⁸, and —P(O)R⁸R⁹;

each R⁶ is independently selected from the group consisting of halogen, —(C₁-C₄)alkyl, —halo(C₁-C₄)alkyl, —hydroxyl, and —(C₁-C₄)alkoxy;

each R⁷ is independently selected from the group consisting of (C₁-C₆)alkyl, (C₂-C₆)alkenyl, halo(C₁-C₆)alkyl, (C₃-C₆)cycloalkyl, and (C₃-C₆)cycloalkyl(C₁-C₄)alkyl-, each of which is optionally substituted by one or two substituents independently selected from triazolyl, tetrazolyl, —CO₂R⁸, —CONR⁸R⁹, —CON(R⁸)CO₂(C₁-C₄)alkyl, hydroxyl, oxo, (C₁-C₄)alkoxy, —OCONR⁸R⁹, —OCON(R⁸)C(O)R⁹, (C₁-C₄)alkyl, HO(C₁-C₄)alkyl-, —NR⁸R⁹, —N(O)R⁸R⁹, —N(R⁸)C(O)R⁹, —N(R⁸)CO₂(C₁-C₄)alkyl, —N(R⁸)CH₂CO₂R⁹, —N(R⁸)CONR⁸R⁹, —N(R⁸)CON(R⁸)C(O)R⁹, —N(R⁸)CON(R⁸)CO₂(C₁-C₄)alkyl, —N(R⁸)SO₂R⁹, —N(R⁸)CON(R⁸)SO₂R⁹, —SO(C₁-C₄)alkyl, —SO₂(C₁-C₄)alkyl, —SO₃R⁸, —SO₂NR⁸R⁹, —B(OH)₂, —P(O)R⁸R⁹, and —P(O)(OR⁸)(OR⁹);

each R⁸ and R⁹ is independently hydrogen, —(C₁-C₄)alkyl, or —(C₃-C₆)cycloalkyl; and n is 1, 2, 3, or 4;

or a pharmaceutically acceptable salt thereof.

2. The compound according to claim 1 represented by Formula (II):

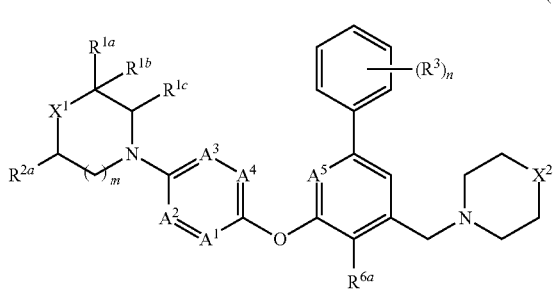

(II)

wherein:
A¹, A², A³, A⁴, and A⁵ are each independently N or CH, wherein one, two, or three of A¹, A², A³, A⁴, and A⁵ are N;
X¹ and X² are each independently NR¹⁰ or C(R¹¹)R¹²;
R¹ᵃ, R¹ᵇ, R¹ᶜ, and R²ᵃ are each independently hydrogen, fluoro, (C₁-C₄)alkyl, HO(C₁-C₄)alkyl-, hydroxyl, or —CONR⁸R⁹, wherein at least two of R¹ᵃ, R¹ᵇ, R¹ᶜ, and R²ᵃ are hydrogen;
or X¹ is NR¹⁰, R¹ᵃ and R²ᵃ taken together represent —CH₂— or —(CH₂)₂—, and R¹ᵇ and R¹ᶜ are each hydrogen;
or X¹ is NR¹⁰, R¹ᶜ and R²ᵃ taken together represent —CH₂— or —(CH₂)₂—, and R¹ᵃ and R¹ᵇ are each hydrogen;
or X¹ is NR¹⁰, R¹ᶜ and R¹⁰ taken together represent —CH₂— or —(CH₂)₂—, and R¹ᵃR¹ᵇ, and R²ᵃ are each hydrogen;
or X¹ is NR¹⁰, R¹ᵃ and R¹ᵇ taken together with the carbon atom to which they are attached represent (C₃-C₆)cycloalkyl, and R¹ and R²ᵃ are each hydrogen;
each R³ is independently selected from the group consisting of fluoro, chloro, methyl, fluoromethyl, difluoromethyl, and trifluoromethyl;

R⁶ᵃ is hydrogen, fluoro, chloro, or methyl;
each R⁷ is independently selected from the group consisting of (C₁-C₄)alkyl, (C₂-C₄)alkenyl, halo(C₁-C₄)alkyl, (C₃-C₆)cycloalkyl, and (C₃-C₆)cycloalkyl(C₁-C₂)alkyl-, each of which is optionally substituted by one or two substituents independently selected from —CO₂R⁸, —CONR⁸R⁹, hydroxyl, oxo, (C₁-C₄)alkoxy, —OCONR⁸R⁹, HO(C₁-C₄)alkyl-, —NR⁸R⁹, —N(R⁸)C(O)R⁹, —N(R⁸)CO₂(C₁-C₄)alkyl, —N(R⁸)CH₂CO₂R⁹, —N(R⁸)CONR⁸R⁹, —N(R⁸)SO₂R⁹, —SO(C₁-C₄)alkyl, —SO₂(C₁-C₄)alkyl, —SO₃R⁸, —SO₂NR⁸R⁹, and —P(O)(OR⁸)(OR⁹));

each R⁸ and R⁹ is independently hydrogen or (C₁-C₄)alkyl;

each R¹⁰ is independently selected from the group consisting of hydrogen, R⁷, —C(O)R⁷, —CONHR⁸, —CONR⁷R⁸, —C(O)CO₂R⁸, and —SO₂R⁷;

each R¹¹ is independently selected from the group consisting of hydrogen, —OR⁷, —NHR⁸, —NR⁷R⁸, and R⁷;

each R¹² is independently selected from the group consisting of hydrogen, halogen, hydroxyl, —CO₂R⁸, —CONHR⁸, and —CONR⁸R⁹, wherein when R¹² is hydroxyl, R¹¹ is hydrogen or R⁷;

m is 1 or 2; and n is 1, 2, or 3;

or a pharmaceutically acceptable salt thereof.

3. The compound according to claim 1 represented by Formula (III):

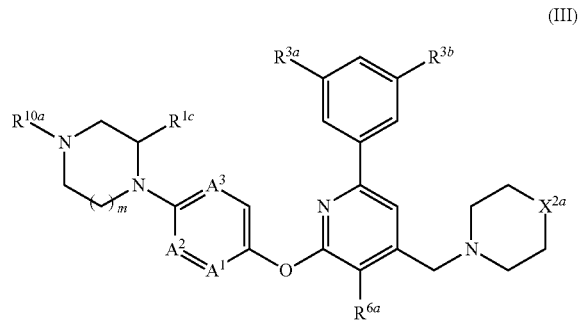

(III)

wherein:
A¹, A², and A³ are each independently N or CH, wherein one or two of A¹, A², and A³ are N;
X²ᵃ is NR¹⁰ᵇ or C(R¹¹ᵃ)R¹²ᵃ;
R¹ᶜ is hydrogen;
R³ᵃ and R³ᵇ are each independently fluoro or chloro;
R⁶ᵃ is hydrogen, fluoro, chloro, or methyl;
R¹⁰ᵃ is hydrogen, (C₁-C₄)alkyl, or (C₃-C₆)cycloalkyl, wherein said (C₁-C₄)alkyl or (C₃-C₆)cycloalkyl is optionally substituted by —CO₂H, —CONH₂, —CONH(C₁-C₄)alkyl, —CON((C₁-C₄)alkyl)((C₁-C₄)alkyl), hydroxyl, (C₁-C₄)alkoxy, —SO₂(C₁-C₄)alkyl, or —SO₂NH₂;
or R¹ᶜ and R¹⁰ᵃ taken together represent —CH₂— or —(CH₂)₂—;
R¹⁰ᵇ is (C₁-C₄)alkyl which is optionally substituted by —CONH₂, —CONH(C₁-C₄)alkyl, or —CON((C₁-C₄)alkyl)((C₁-C₄)alkyl);
R¹¹ᵃ is (C₁-C₄)alkyl or (C₁-C₄)alkoxy, each of which is optionally substituted by one or two substituents independently selected from —CO₂H, —CONH₂, —CONH(C₁-C₄)alkyl, —CON((C₁-C₄)alkyl)((C₁-C₄)

alkyl), hydroxyl, —OCONH($C_1$-$C_4$)alkyl, —NHCO($C_1$-$C_4$)alkyl, —NHCO$_2$($C_1$-$C_4$)alkyl, and —NHCONH($C_1$-$C_4$)alkyl;

$R^{12a}$ is hydrogen, hydroxyl, or fluoro, wherein when $R^{12a}$ is hydroxyl, $R^{11a}$ is ($C_1$-$C_4$)alkyl which is optionally substituted by one or two substituents independently selected from —CO$_2$H, —CONH$_2$, —CONH($C_1$-$C_4$)alkyl, —CON(($C_1$-$C_4$)alkyl)(($C_1$-$C_4$)alkyl), hydroxyl, —OCONH($C_1$-$C_4$)alkyl, —NHCO($C_1$-$C_4$)alkyl, —NHCO$_2$($C_1$-$C_4$)alkyl, and —NHCONH($C_1$-$C_4$)alkyl; and m is 1 or 2;

or a pharmaceutically acceptable salt thereof.

4. The compound or pharmaceutically acceptable salt thereof according to claim 1, wherein zero, one, two, or three of $A^1$, $A^2$, $A^3$, $A^4$, $A^5$, and $A^6$ are N.

5. The compound or pharmaceutically acceptable salt thereof according to claim 1, wherein X is O.

6. The compound or pharmaceutically acceptable salt thereof according to claim 1, wherein $R^1$ and $R^2$ taken together with the nitrogen atom to which they are attached represent a 4-11 membered monocyclic or fused, bridged, or spiro bicyclic saturated ring, optionally containing one or two additional nitrogen heteroatoms, wherein said ring is optionally substituted by one, two, or three substituents independently selected from halogen, hydroxyl, oxo, $R^7$, —OR$^7$, —NHR$^8$, —NR$^7$R$^8$, and —C(O)R$^7$.

7. The compound or pharmaceutically acceptable salt thereof according to claim 1, wherein each $R^3$ is independently selected from the group consisting of halogen, methyl, and difluoromethyl.

8. The compound or pharmaceutically acceptable salt thereof according to claim 1, wherein $R^4$ and $R^5$ taken together with the nitrogen atom to which they are attached represent a 4-11 membered monocyclic or fused, bridged, or spiro bicyclic saturated ring, optionally containing one or two additional heteroatoms independently selected from oxygen and nitrogen, wherein said ring is optionally substituted by one or two substituents independently selected from halogen, hydroxyl, oxo, —CO$_2$R$^8$, R$^7$, —OR$^7$, —NHR$^8$, —N(R$^8$)C(O)R$^9$, —N(R$^8$)SO$_2$R$^9$, —N(R$^8$)CONR$^8$R$^9$, —N(R$^8$)CON(R$^8$)SO$_2$R$^9$, —C(O)R$^7$, and —P(O)R$^8$R$^9$.

9. The compound or pharmaceutically acceptable salt thereof according to claim 1, wherein each $R^6$ is independently selected from the group consisting of halogen and ($C_1$-$C_4$)alkyl.

10. The compound or pharmaceutically acceptable salt thereof according to claim 1, wherein each $R^7$ is independently selected from the group consisting of ($C_1$-$C_6$)alkyl, halo($C_1$-$C_6$)alkyl, ($C_3$-$C_6$)cycloalkyl, and ($C_3$-$C_6$)cycloalkyl($C_1$-$C_4$)alkyl-, each of which is optionally substituted by one or two substituents independently selected from triazolyl, tetrazolyl, —CO$_2$R$^8$, —CONR$^8$R$^9$, —CON(R$^8$)CO$_2$($C_1$-$C_4$)alkyl, hydroxyl, ($C_1$-$C_4$)alkoxy, —OCONR$^8$R$^9$, —OCON(R$^8$)C(O)R$^9$, ($C_1$-$C_4$)alkyl, HO($C_1$-$C_4$)alkyl-, —NR$^8$R$^9$, —N(O)R$^8$R$^9$, —N(R$^8$)C(O)R$^9$, —N(R$^8$)CO$_2$($C_1$-$C_4$)alkyl, —N(R$^8$)CONR$^8$R$^9$, —N(R$^8$)CON(R$^8$)C(O)R$^9$, —N(R$^8$)CON(R$^8$)CO$_2$($C_1$-$C_4$)alkyl, —N(R$^8$)SO$_2$R$^9$, —N(R$^8$)CON(R$^8$)SO$_2$R$^9$, —SO($C_1$-$C_4$)alkyl, —SO$_2$($C_1$-$C_4$)alkyl, —SO$_3$R$^8$, —SO$_2$NR$^8$R$^9$, —B(OH)$_2$, —P(O)R$^8$R$^9$, and —P(O)(OR$^8$)(OR$^9$).

11. The compound or pharmaceutically acceptable salt thereof according to claim 1, wherein each $R^8$ and $R^9$ is independently hydrogen or ($C_1$-$C_4$)alkyl.

12. The compound or pharmaceutically acceptable salt thereof according to claim 1, wherein n is 2 or 3.

13. The compound or pharmaceutically acceptable salt thereof according to claim 2 wherein:

$A^1$, $A^2$, $A^3$, $A^4$, and $A^5$ are each independently N or CH, wherein two or three of $A^1$, $A^2$, $A^3$, $A^4$, and $A^5$ are N;

$X^1$ and $X^2$ are each independently NR$^{10}$ or C(R$^{11}$)R$^{12}$;

$R^{1a}$, $R^{1b}$, $R^{1c}$, and $R^{2a}$ are each hydrogen;

or $X^1$ is NR$^{10}$, $R^{1a}$ and $R^{2a}$ taken together represent —CH$_2$— or —(CH$_2$)$_2$—, and $R^{1b}$ and $R^{1c}$ are each hydrogen;

or $X^1$ is NR$^{10}$, $R^{1c}$ and $R^{2a}$ taken together represent —CH$_2$— or —(CH$_2$)$_2$—, and $R^{1a}$ and $R^{1b}$ are each hydrogen;

or $X^1$ is NR$^{10}$, $R^{1c}$ and $R^{10}$ taken together represent —CH$_2$— or —(CH$_2$)$_2$—, and $R^{1a}$, $R^{1b}$, and $R^{2a}$ are each hydrogen;

each $R^3$ is independently selected from the group consisting of halogen, methyl, and difluoromethyl;

$R^{6a}$ is hydrogen, fluoro, chloro, or methyl;

each $R^7$ is independently selected from the group consisting of ($C_1$-$C_4$)alkyl, ($C_2$-$C_4$)alkenyl, halo($C_1$-$C_4$)alkyl, ($C_3$-$C_6$)cycloalkyl, and ($C_3$-$C_6$)cycloalkyl($C_1$-$C_2$)alkyl-, each of which is optionally substituted by one or two substituents independently selected from —CO$_2$R$^8$, —CONR$^8$R$^9$, hydroxyl, ($C_1$-$C_4$)alkoxy, —OCONR$^8$R$^9$, HO($C_1$-$C_4$)alkyl-, —NR$^8$R$^9$, —N(R$^8$)C(O)R$^9$, —N(R$^8$)CO$_2$($C_1$-$C_4$)alkyl, —N(R$^8$)CONR$^8$R$^9$, —N(R$^8$)SO$_2$R$^9$, —SO($C_1$-$C_4$)alkyl, —SO$_2$($C_1$-$C_4$)alkyl, —SO$_3$R$^8$, —SO$_2$R$^8$R$^9$, and —P(O)(OR$^8$)(OR$^9$);

each $R^8$ and $R^9$ is independently hydrogen or ($C_1$-$C_4$)alkyl;

each $R^{10}$ is independently selected from the group consisting of hydrogen and R$^7$;

each $R^{11}$ is R$^7$;

each $R^{12}$ is independently selected from the group consisting of hydrogen, halogen, and hydroxyl;

m is 1 or 2; and n is 2 or 3.

14. The compound or pharmaceutically acceptable salt thereof according to claim 3 wherein:

$A^1$ and $A^2$ are each CH;

or one of $A^1$ and $A^2$ is N and the other is CH;

$A^3$ is N;

$X^{2a}$ is C(R$^{11a}$)R$^{12a}$;

$R^{1c}$ is hydrogen;

$R^{3a}$ and $R^{3b}$ are each chloro;

$R^{6a}$ is hydrogen or methyl;

$R^{10a}$ is ($C_1$-$C_4$)alkyl which is optionally substituted by —CO$_2$H, hydroxyl, or —SO$_2$($C_1$-$C_4$)alkyl;

or $R^{1c}$ and $R^{10a}$ taken together represent —CH$_2$— or —(CH$_2$)$_2$—;

$R^{11a}$ is ($C_1$-$C_4$)alkyl which is optionally substituted by one substituent which is —CO$_2$H or —NHCO($C_1$-$C_4$)alkyl;

$R^{12a}$ is hydrogen; and m is 1 or 2.

15. The compound according to claim 1, wherein the compound is selected from the group consisting of:

2-(4-((2-(3,5-dichlorophenyl)-6-((6-(piperazin-1-yl)pyridin-3-yl)oxy)pyridin-4-yl)methyl)piperazin-1-yl)-N-methylacetamide;

N-((1-((2-(3,5-dichlorophenyl)-6-((6-(piperazin-1-yl)pyridin-3-yl)oxy)pyridin-4-yl)methyl)-4-hydroxypiperidin-4-yl)methyl)acetamide;

3-(1-((2-(3,5-dichlorophenyl)-6-((6-(piperazin-1-yl)pyridin-3-yl)oxy)pyridin-4-yl)methyl)piperidin-4-yl)propanoic acid;

2-(1-((2-(3,5-dichlorophenyl)-6-((6-(piperazin-1-yl)pyridin-3-yl)oxy)pyridin-4-yl)methyl)piperidin-4-yl)acetic acid;

1-((1-((2-(3,5-dichlorophenyl)-6-((6-(piperazin-1-yl)pyridin-3-yl)oxy)pyridin-4-yl)methyl)-4-hydroxypiperidin-4-yl)methyl)-3-methylurea;

methyl ((1-((2-(3,5-dichlorophenyl)-6-((6-(piperazin-1-yl)pyridin-3-yl)oxy)pyridin-4-yl)methyl)-4-hydroxypiperidin-4-yl)methyl)carbamate;

2-(1-((2-(3,5-dichlorophenyl)-6-((6-(piperazin-1-yl)pyridin-3-yl)oxy)pyridin-4-yl)methyl)piperidin-4-yl)ethanesulfonic acid;

(1-((2-(3,5-dichlorophenyl)-6-((6-(piperazin-1-yl)pyridin-3-yl)oxy)pyridin-4-yl)methyl)piperidin-4-yl)methanesulfonic acid;

N-((1-((2-(3,5-dichlorophenyl)-6-((6-(piperazin-1-yl)pyridin-3-yl)oxy)pyridin-4-yl)methyl)piperidin-4-yl)methyl)acetamide;

2-(4-(5-((4-((4-(acetamidomethyl)piperidin-1-yl)methyl)-6-(3,5-dichlorophenyl)pyridin-2-yl)oxy)pyridin-2-yl)piperazin-1-yl)acetic acid;

3-(4-(5-((4-((4-(acetamidomethyl)piperidin-1-yl)methyl)-6-(3,5-dichlorophenyl)pyridin-2-yl)oxy)pyridin-2-yl)piperazin-1-yl)propanoic acid;

N-((1-((2-(3,5-dichlorophenyl)-6-((6-(4-(2-(methylsulfonyl)ethyl)piperazin-1-yl)pyridin-3-yl)oxy)pyridin-4-yl)methyl)piperidin-4-yl)methyl)acetamide;

3-(4-(5-((4-((4-(acetamidomethyl)piperidin-1-yl)methyl)-6-(3,5-dichlorophenyl)pyridin-2-yl)oxy)pyridin-2-yl)piperazin-1-yl)propanamide;

N-((1-((2-((6-(4-(2-(1H-tetrazol-5-yl)ethyl)piperazin-1-yl)pyridin-3-yl)oxy)-6-(3,5-dichlorophenyl)pyridin-4-yl)methyl)piperidin-4-yl)methyl)acetamide;

N-((1-((2-(3,5-dichlorophenyl)-6-((6-(4-(2-(methylsulfinyl)ethyl)piperazin-1-yl)pyridin-3-yl)oxy)pyridin-4-yl)methyl)piperidin-4-yl)methyl)acetamide;

N-((1-((2-(3,5-dichlorophenyl)-6-((6-(4-(4-(methylsulfonyl)butan-2-yl)piperazin-1-yl)pyridin-3-yl)oxy)pyridin-4-yl)methyl)piperidin-4-yl)methyl)acetamide;

1-((1-((2-(3,5-dichlorophenyl)-6-((2-(4-(3-(methyl sulfinyl)butyl)piperazin-1-yl)pyrimidin-5-yl)oxy)pyridin-4-yl)methyl)piperidin-4-yl)methyl)-3-methylurea;

1-((1-((2-(3,5-dichlorophenyl)-6-((2-(4-(4-(methylsulfonyl)butan-2-yl)piperazin-1-yl)pyrimidin-5-yl)oxy)pyridin-4-yl)methyl)piperidin-4-yl)methyl)-3-methylurea;

N-((1-((2-(3,5-dichlorophenyl)-6-((2-(4-(4-(methylsulfonyl)butan-2-yl)piperazin-1-yl)pyrimidin-5-yl)oxy)pyridin-4-yl)methyl)piperidin-4-yl)methyl)acetamide;

1-((1-((2-(3,5-dichlorophenyl)-6-((2-(4-(4-hydroxybutan-2-yl)piperazin-1-yl)pyrimidin-5-yl)oxy)pyridin-4-yl)methyl)piperidin-4-yl)methyl)-3-methylurea;

2-(1-((2-(3,5-dichlorophenyl)-6-((2-(4-(1-hydroxypropan-2-yl)piperazin-1-yl)pyrimidin-5-yl)oxy)pyridin-4-yl)methyl)piperidin-4-yl)acetic acid;

2-(1-((2-(3,5-dichlorophenyl)-6-((2-(4-(3-hydroxycyclobutyl)piperazin-1-yl)pyrimidin-5-yl)oxy)pyridin-4-yl)methyl)piperidin-4-yl)acetic acid;

2-(1-((2-(3,5-dichlorophenyl)-6-((2-(4-(1,3-dihydroxypropan-2-yl)piperazin-1-yl)pyrimidin-5-yl)oxy)pyridin-4-yl)methyl)piperidin-4-yl)acetic acid;

2-(1-((2-(3,5-dichlorophenyl)-6-((2-(4-((1s,3s)-3-hydroxy-3-methylcyclobutyl)piperazin-1-yl)pyrimidin-5-yl)oxy)pyridin-4-yl)methyl)piperidin-4-yl)acetic acid;

2-(1-((2-(3,5-dichlorophenyl)-6-((2-(4-((1r,3r)-3-hydroxy-3-methylcyclobutyl)piperazin-1-yl)pyrimidin-5-yl)oxy)pyridin-4-yl)methyl)piperidin-4-yl)acetic acid;

N-((1-((2-(3,5-dichlorophenyl)-6-((6-(4-((trans)-3-(methylsulfonamido)cyclobutyl)piperazin-1-yl)pyridin-3-yl)oxy)pyridin-4-yl)methyl)piperidin-4-yl)methyl)acetamide;

N-((1-((2-(3,5-dichlorophenyl)-6-((6-(4-((cis)-3-(methylsulfonamido)cyclobutyl)piperazin-1-yl)pyridin-3-yl)oxy)pyridin-4-yl)methyl)piperidin-4-yl)methyl)acetamide;

N-((1-((2-((6-(4-(2-aminoethyl)piperazin-1-yl)pyridin-3-yl)oxy)-6-(3,5-dichlorophenyl)pyridin-4-yl)methyl)piperidin-4-yl)methyl)acetamide;

N-((1-((2-(3,5-dichlorophenyl)-6-((6-(4-(2,4-dihydroxybutyl)piperazin-1-yl)pyridin-3-yl)oxy)pyridin-4-yl)methyl)piperidin-4-yl)methyl)acetamide;

(2-(4-(5-((4-((4-(acetamidomethyl)piperidin-1-yl)methyl)-6-(3,5-dichlorophenyl)pyridin-2-yl)oxy)pyridin-2-yl)piperazin-1-yl)ethyl)phosphonic acid;

2-(4-(5-((4-((4-(acetamidomethyl)piperidin-1-yl)methyl)-6-(3,5-dichlorophenyl)pyridin-2-yl)oxy)pyridin-2-yl)piperazin-1-yl)ethyl carbamate;

N-((1-((2-(3,5-dichlorophenyl)-6-((6-(4-(2-(N-methylmethylsulfonamido)ethyl)piperazin-1-yl)pyridin-3-yl)oxy)pyridin-4-yl)methyl)piperidin-4-yl)methyl)acetamide;

4-(4-(5-((4-((4-(acetamidomethyl)piperidin-1-yl)methyl)-6-(3,5-dichlorophenyl)pyridin-2-yl)oxy)pyridin-2-yl)piperazin-1-yl)-4-oxobutanoic acid;

N-((1-((2-(3,5-dichlorophenyl)-6-((6-(4-((1-(hydroxymethyl)cyclopropyl)methyl)piperazin-1-yl)pyridin-3-yl)oxy)pyridin-4-yl)methyl)piperidin-4-yl)methyl)acetamide;

N-((1-((2-(3,5-dichlorophenyl)-6-((6-(4-((1-hydroxycyclopropyl)methyl)piperazin-1-yl)pyridin-3-yl)oxy)pyridin-4-yl)methyl)piperidin-4-yl)methyl)acetamide;

2-(1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)-N-ethylacetamide;

1-(2-(3,5-dichlorophenyl)-6-((2-(4-(3-(methylsulfonyl)propyl)piperazin-1-yl)pyrimidin-5-yl)oxy)pyridin-4-yl)-N-methylmethanamine;

3-(4-(5-((6-(3,5-dichlorophenyl)-4-((4-(sulfamoylmethyl)piperidin-1-yl)methyl)pyridin-2-yl)oxy)pyridin-2-yl)piperazin-1-yl)propanoic acid;

3-(4-(5-((6-(3,5-dichlorophenyl)-4-((4-((methylsulfonyl)methyl)piperidin-1-yl)methyl)pyridin-2-yl)oxy)pyridin-2-yl)piperazin-1-yl)propanoic acid;

1-((1-((2-(3,5-dichlorophenyl)-6-((6-(4-(2-hydroxyethyl)piperazin-1-yl)pyridin-3-yl)oxy)pyridin-4-yl)methyl)piperidin-4-yl)methyl)-3-methylurea;

3-(4-(5-((6-(3,5-dichlorophenyl)-4-((4-((3-methylureido)methyl)piperidin-1-yl)methyl)pyridin-2-yl)oxy)pyridin-2-yl)piperazin-1-yl)propanoic acid;

N-((1-((5-(4-aminophenoxy)-3',5'-dichloro-[1,1'-biphenyl]-3-yl)methyl)piperidin-4-yl)methyl) acetamide;

N-((1-((5-((5-aminopyrimidin-2-yl)oxy)-3',5'-dichloro-[1,1'-biphenyl]-3-yl)methyl)piperidin-4-yl)methyl)acetamide;

3-(4-(5-((6-(3,5-dichlorophenyl)-4-((4-(methylsulfonamidoethyl)piperidin-1-yl)methyl)pyridin-2-yl)oxy)pyridin-2-yl)piperazin-1-yl)propanoic acid;

N-((1-((5-((5-aminopyridin-2-yl)oxy)-3',5'-dichloro-[1,1'-biphenyl]-3-yl)methyl)piperidin-4-yl)methyl)acetamide;

N-((1-((5-((6-amino-5-fluoropyridin-3-yl)oxy)-3',5'-dichloro-[1,1'-biphenyl]-3-yl)methyl)piperidin-4-yl)methyl)acetamide;

1-((1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)methyl)-3-methylurea;

3-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)propane-1-sulfonamide;

methyl ((1-((2-(3,5-dichlorophenyl)-6-((2-(piperazin-1-yl)pyrimidin-5-yl)oxy)pyridin-4-yl)methyl)piperidin-4-yl)methyl)carbamate;

3-(4-(5-((6-(3,5-dichlorophenyl)-4-((methylamino)methyl)pyridin-2-yl)oxy)pyridin-2-yl)piperazin-1-yl)propanoic acid;

3-(4-(5-((6-(3,5-dichlorophenyl)-4-((4-fluoro-4-(((methoxycarbonyl)amino)methyl)piperidin-1-yl)methyl)pyridin-2-yl)oxy)pyrimidin-2-yl)piperazin-1-yl)propanoic acid;

2-(1-((2-(3,5-dichlorophenyl)-6-((2-(4-methylpiperazin-1-yl)pyrimidin-5-yl)oxy)pyridin-4-yl)methyl)piperidin-4-yl)ethanol;

2-((1-((2-(3,5-dichlorophenyl)-6-((2-(4-methylpiperazin-1-yl)pyrimidin-5-yl)oxy)pyridin-4-yl)methyl)piperidin-4-yl)oxy)acetic acid;

3-(4-(5-((4-((4-(2-(carbamoyloxy)ethyl)piperazin-1-yl)methyl)-6-(3,5-dichlorophenyl)pyridin-2-yl)oxy)pyrimidin-2-yl)piperazin-1-yl)propanoic acid;

3-(4-(5-((4-((4-(2-(carbamoyloxy)ethyl)piperazin-1-yl)methyl)-6-(3,5-dichlorophenyl)pyridin-2-yl)oxy)pyridin-2-yl)piperazin-1-yl)propanoic acid;

3-(3-(5-((6-(3,5-dichlorophenyl)-4-((4-(((methoxycarbonyl)amino)methyl)piperidin-1-yl)methyl)pyridin-2-yl)oxy)pyrimidin-2-yl)-3,8-diazabicyclo[3.2.1]octan-8-yl)propanoic acid;

4-(4-(5-((6-(3,5-dichlorophenyl)-4-((4-(2-hydroxyethyl)piperidin-1-yl)methyl)pyridin-2-yl)oxy)pyrimidin-2-yl)piperazin-1-yl)-2-methylbutanoic acid;

3-(4-(5-((4-((4-(cyclopropanecarboxamidomethyl)piperidin-1-yl)methyl)-6-(3,5-dichlorophenyl)pyridin-2-yl)oxy)pyridin-2-yl)piperazin-1-yl)propanoic acid;

4-(4-(5-((6-(3,5-dichlorophenyl)-4-((4-(propionamidomethyl)piperidin-1-yl)methyl)pyridin-2-yl)oxy)pyrimidin-2-yl)piperazin-1-yl)-2-methylbutanoic acid;

4-(4-(5-((6-(3,5-dichlorophenyl)-4-((4-fluoropiperidin-1-yl)methyl)pyridin-2-yl)oxy)pyrimidin-2-yl)piperazin-1-yl)butan-1-ol;

3-(4-(5-((4-((4-(acetamidomethyl)piperidin-1-yl)methyl)-6-(3-chloro-5-(difluoromethyl)phenyl)pyridin-2-yl)oxy)pyrimidin-2-yl)piperazin-1-yl)propanoic acid;

3-(4-(5-((6-(3,5-dichlorophenyl)-4-((4-(((methoxycarbonyl)amino)methyl)piperidin-1-yl)methyl)pyridin-2-yl)oxy)pyrimidin-2-yl)piperazin-1-yl)propanoic acid;

methyl ((1-((2-(3,5-dichlorophenyl)-6-((2-(4-methylpiperazin-1-yl)pyrimidin-5-yl)oxy)pyridin-4-yl)methyl)piperidin-4-yl)methyl)carbamate;

N-((1-((2-(3,5-dichlorophenyl)-6-((2-(4-methylpiperazin-1-yl)pyrimidin-5-yl)oxy)pyridin-4-yl)methyl)piperidin-4-yl)methyl)acetamide;

methyl ((1-((2-(3,5-dichlorophenyl)-6-((6-(4-methylpiperazin-1-yl)pyridin-3-yl)oxy)pyridin-4-yl)methyl)piperidin-4-yl)methyl)carbamate;

(1-((2-(3,5-dichlorophenyl)-6-((2-(4-methylpiperazin-1-yl)pyrimidin-5-yl)oxy)pyridin-4-yl)methyl)piperidin-4-yl)methyl methylcarbamate;

(1-((2-(3,5-dichlorophenyl)-6-((6-(4-methylpiperazin-1-yl)pyridin-3-yl)oxy)pyridin-4-yl)methyl)piperidin-4-yl)methyl methylcarbamate;

N-((1-((3',5'-dichloro-5-((2-(4-methylpiperazin-1-yl)pyrimidin-5-yl)oxy)-[1,1'-biphenyl]-3-yl)methyl)piperidin-4-yl)methyl)acetamide;

1-((1-((2-(3,5-dichlorophenyl)-6-((6-(4-methylpiperazin-1-yl)pyridin-3-yl)oxy)pyridin-4-yl)methyl)piperidin-4-yl)methyl)-3-methylurea;

1-((1-((2-(3,5-dichlorophenyl)-6-((2-(4-methylpiperazin-1-yl)pyrimidin-5-yl)oxy)pyridin-4-yl)methyl)piperidin-4-yl)methyl)-3-methylurea;

N-((1-((2-(3,5-dichlorophenyl)-6-((2-(8-methyl-3,8-diazabicyclo[3.2.1]octan-3-yl)pyrimidin-5-yl)oxy)pyridin-4-yl)methyl)piperidin-4-yl)methyl)acetamide;

5-((4-((4-((1H-tetrazol-5-yl)methyl)piperidin-1-yl)methyl)-6-(3,5-dichlorophenyl)pyridin-2-yl)oxy)-2-(4-methylpiperazin-1-yl)pyrimidine;

(1-((2-(3,5-dichlorophenyl)-6-((2-(piperazin-1-yl)pyrimidin-5-yl)oxy)pyridin-4-yl)methyl)piperidin-4-yl)methyl methylcarbamate;

(1-((2-(3,5-dichlorophenyl)-6-((6-(piperazin-1-yl)pyridin-3-yl)oxy)pyridin-4-yl)methyl)piperidin-4-yl)methyl methylcarbamate;

1-((1-((2-(3,5-dichlorophenyl)-6-((2-(piperazin-1-yl)pyrimidin-5-yl)oxy)pyridin-4-yl)methyl)piperidin-4-yl)methyl)-3-methylurea;

methyl ((1-((2-(3,5-dichlorophenyl)-6-((6-(piperazin-1-yl)pyridin-3-yl)oxy)pyridin-4-yl)methyl)piperidin-4-yl)methyl)carbamate;

3-(4-(5-((6-(3,5-dichlorophenyl)-4-((4-(((methylcarbamoyl)oxy)methyl)piperidin-1-yl)methyl)pyridin-2-yl)oxy)pyridin-2-yl)piperazin-1-yl)propanoic acid;

3-(4-(5-((4-((4-(3-amino-3-oxopropyl)piperazin-1-yl)methyl)-6-(3,5-dichlorophenyl)pyridin-2-yl)oxy)pyrimidin-2-yl)piperazin-1-yl)propanoic acid;

3-(4-(5-((4-((4-(2-amino-2-oxoethyl)piperazin-1-yl)methyl)-6-(3,5-dichlorophenyl)pyridin-2-yl)oxy)pyrimidin-2-yl)piperazin-1-yl)propanoic acid;

3-(4-(5-((6-(3,5-dichlorophenyl)-4-(((1R,7S,8r)-8-(methylsulfonamido)-4-azabicyclo[5.1.0]octan-4-yl)methyl)pyridin-2-yl)oxy)pyrimidin-2-yl)piperazin-1-yl)propanoic acid;

4-(4-(5-((6-(3,5-dichlorophenyl)-4-(((1R,7S,8r)-8-(methylsulfonamido)-4-azabicyclo[5.1.0]octan-4-yl)methyl)pyridin-2-yl)oxy)pyrimidin-2-yl)piperazin-1-yl)-2-methylbutanoic acid;

4-(4-(5-((4-(((1R,7S,8r)-8-acetamido-4-azabicyclo[5.1.0]octan-4-yl)methyl)-6-(3,5-dichlorophenyl)pyridin-2-yl)oxy)pyrimidin-2-yl)piperazin-1-yl)-2-methylbutanoic acid;

4-(4-(5-((6-(3,5-dichlorophenyl)-4-(pyrrolidin-1-ylmethyl)pyridin-2-yl)oxy)pyrimidin-2-yl)piperazin-1-yl)-2-methylbutanoic acid;

3-(4-(5-((4-((4-(cyclopropanecarboxamidomethyl)piperidin-1-yl)methyl)-6-(3,5-dichlorophenyl)pyridin-2-yl)oxy)pyrimidin-2-yl)piperazin-1-yl)propanoic acid;

3-(4-(5-((6-(3,5-dichlorophenyl)-4-((4-((dimethylphosphoryl)methyl)piperidin-1-yl)methyl)pyridin-2-yl)oxy)pyridin-2-yl)piperazin-1-yl)propanoic acid;

2-(1-((2-(3,5-dichlorophenyl)-6-((2-(piperazin-1-yl)pyrimidin-5-yl)oxy)pyridin-4-yl)methyl)piperidin-4-yl)acetamide;

2-(1-((2-(3,5-dichlorophenyl)-6-((2-(4-methylpiperazin-1-yl)pyrimidin-5-yl)oxy)pyridin-4-yl)methyl)piperidin-4-yl)ethanesulfonamide;

3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanamide;

N-((1-((6-(3,5-dichlorophenyl)-2-((6-(piperazin-1-yl)
pyridin-3-yl)oxy)pyrimidin-4-yl)methyl)piperidin-4-
yl)methyl)acetamide;

N-((1-((2-(3,5-dichlorophenyl)-6-((5-fluoro-6-(piper-
azin-1-yl)pyridin-3-yl)oxy)pyridin-4-yl)methyl)-4-hy-
droxypiperidin-4-yl)methyl)acetamide;

N-((1-((2-(3,5-dichlorophenyl)-6-((2-(piperazin-1-yl)py-
rimidin-5-yl)oxy)pyridin-4-yl)methyl)piperidin-4-yl)
methyl)acetamide;

N-((1-((2-(3,5-dichlorophenyl)-6-((2-(4-(2-hydroxy-
ethyl)piperazin-1-yl)pyrimidin-5-yl)oxy)pyridin-4-yl)
methyl)piperidin-4-yl)methyl)acetamide;

3-(4-(5-((4-((4-(acetamidomethyl)piperidin-1-yl)
methyl)-6-(3,5-dichlorophenyl)pyridin-2-yl)oxy)py-
rimidin-2-yl)piperazin-1-yl)-N-methylpropanamide;

3-(4-(5-((4-((4-(acetamidomethyl)piperidin-1-yl)
methyl)-6-(3,5-dichlorophenyl)pyridin-2-yl)oxy)py-
rimidin-2-yl)piperazin-1-yl)butanamide;

4-(4-(5-((4-((4-(acetamidomethyl)piperidin-1-yl)
methyl)-6-(3,5-dichlorophenyl)pyridin-2-yl)oxy)py-
rimidin-2-yl)piperazin-1-yl)butanamide;

1-(5-((3',5'-dichloro-5-(((2-methoxyethyl)amino)
methyl)-[1,1'-biphenyl]-3-yl)oxy)pyridin-2-yl)-N-
methylpiperidin-4-amine;

1-(3',5'-dichloro-5-((6-(hexahydropyrrolo[3,4-c]pyrrol-2
(1H)-yl)pyridin-3-yl)oxy)-[1,1'-biphenyl]-3-yl)-N-
methylmethanamine;

N1-(5-((3',5'-dichloro-5-(morpholinomethyl)-[1,1'-biphe-
nyl]-3-yl)oxy)pyridin-2-yl)ethane-1,2-diamine;

1-(5-((3',5'-dichloro-5-((methylamino)methyl)-[1,1'-bi-
phenyl]-3-yl)oxy)pyridin-2-yl)piperidin-4-amine;

N1-(5-((3',5'-dichloro-5-((methylamino)methyl)-[1,1'-bi-
phenyl]-3-yl)oxy)pyridin-2-yl)propane-1,3-diamine;

1-(3',5'-dichloro-5-((6-(3,3-dimethylpiperazin-1-yl)pyri-
din-3-yl)oxy)-[1,1'-biphenyl]-3-yl)-N-methylmeth-
anamine;

1-(5-((6-(1,4-diazepan-1-yl)pyridin-3-yl)oxy)-3',5'-di-
chloro-[1,1'-biphenyl]-3-yl)-N-methylmethanamine;

1-(3',5'-dichloro-5-((6-(4-methylpiperazin-1-yl)pyridin-
3-yl)oxy)-[1,1'-biphenyl]-3-yl)-N-methylmeth-
anamine;

N-((1-((5-((6-((2-amino-2-methylpropyl)amino)pyridin-
3-yl)oxy)-3',5'-dichloro-[1,1'-biphenyl]-3-yl)methyl)
piperidin-4-yl)methyl)acetamide;

N-((1-((5-((6-((3S,4R)-4-amino-3-fluoropiperidin-1-yl)
pyridin-3-yl)oxy)-3',5'-dichloro-[1,1'-biphenyl]-3-yl)
methyl)piperidin-4-yl)methyl)acetamide;

N-((1-((3',5'-dichloro-5-((6-(3-oxohexahydroimidazo[1,
5-a]pyrazin-7(1H)-yl)pyridin-3-yl)oxy)-[1,1'-biphe-
nyl]-3-yl)methyl)piperidin-4-yl)methyl)acetamide;

1-(5-((6-(3-chloro-5-methylphenyl)-4-((methylamino)
methyl)pyridin-2-yl)oxy)pyridin-2-yl)piperidin-4-
amine;

N-((1-((2-(3,5-dichlorophenyl)-6-((5-(piperazin-1-yl)
pyrazin-2-yl)oxy)pyridin-4-yl)methyl)piperidin-4-yl)
methyl)acetamide;

N-((1-((2-(3,5-dichlorophenyl)-6-((5-(4-methylpiper-
azin-1-yl)pyrazin-2-yl)oxy)pyridin-4-yl)methyl)piperi-
din-4-yl)methyl)acetamide;

3-(4-(5-((4-((4-(acetamidomethyl)piperidin-1-yl)
methyl)-6-(3,5-dichlorophenyl)pyridin-2-yl)oxy)
pyrazin-2-yl)piperazin-1-yl)propanoic acid;

2-(1-((2-(3,5-dichlorophenyl)-6-((5-(piperazin-1-yl)
pyrazin-2-yl)oxy)pyridin-4-yl)methyl)piperidin-4-yl)
acetic acid;

N-((1-((3',5'-dichloro-5-((2-(4-(3-hydroxypropyl)piper-
azin-1-yl)pyrimidin-5-yl)oxy)-[1,1'-biphenyl]-3-yl)
methyl)piperidin-4-yl)methyl)acetamide;

3-(1-((3',5'-dichloro-5-((2-(4-(2-hydroxyethyl)piperazin-
1-yl)pyrimidin-5-yl)oxy)-[1,1'-biphenyl]-3-yl)methyl)
piperidin-4-yl)propanoic acid;

3-(4-(5-((4-((4-(acetamidomethyl)piperidin-1-yl)
methyl)-6-(3-chloro-5-fluorophenyl)pyridin-2-yl)oxy)
pyridin-2-yl)piperazin-1-yl)propanoic acid;

3-(4-(5-((4-((4-(acetamidomethyl)piperidin-1-yl)
methyl)-6-(3-bromo-5-fluorophenyl)pyridin-2-yl)oxy)
pyridin-2-yl)piperazin-1-yl)propanoic acid;

2-(1-((3',5'-dichloro-5-((2-(4-methylpiperazin-1-yl)py-
rimidin-5-yl)oxy)-[1,1'-biphenyl]-3-yl)methyl)piperi-
din-4-yl)acetic acid;

N-((1-((2-((2-(1,4-diazepan-1-yl)pyrimidin-5-yl)oxy)-6-
(3,5-dichlorophenyl)pyridin-4-yl)methyl)piperidin-4-
yl)methyl)acetamide;

N-((1-((2-((2-(4-aminopiperidin-1-yl)pyrimidin-5-yl)
oxy)-6-(3,5-dichlorophenyl)pyridin-4-yl)methyl)pip-
eridin-4-yl)methyl)acetamide;

2-(1-((2-(3,5-dichlorophenyl)-6-((6-(piperazin-1-yl)pyri-
din-3-yl)oxy)pyridin-4-yl)methyl)piperidin-4-yl)-N,N-
dimethylethanamine oxide;

N-((1-((2-(3,5-dichlorophenyl)-6-((5-fluoro-6-(piper-
azin-1-yl)pyridin-3-yl)oxy)pyridin-4-yl)methyl)piperi-
din-4-yl)methyl)acetamide;

2-((1-((2-(3,5-dichlorophenyl)-6-((2-(piperazin-1-yl)py-
rimidin-5-yl)oxy)pyridin-4-yl)methyl)piperidin-4-yl)
oxy)acetic acid;

2-(1-((2-(3,5-dichlorophenyl)-6-((2-(6-hydroxy-1,4-diaz-
epan-1-yl)pyrimidin-5-yl)oxy)pyridin-4-yl)methyl)pi-
peridin-4-yl)acetic acid;

2-(1-((2-((2-(4-amino-4-(2-hydroxyethyl)piperidin-1-yl)
pyrimidin-5-yl)oxy)-6-(3,5-dichlorophenyl)pyridin-4-
yl)methyl)piperidin-4-yl)acetic acid;

((1-((2-(3,5-dichlorophenyl)-6-((2-(piperazin-1-yl)py-
rimidin-5-yl)oxy)pyridin-4-yl)methyl)piperidin-4-yl)
methyl)dimethylphosphine oxide;

2-(1-((2-(3,5-dichlorophenyl)-6-((2-(4-methyl-1,4-diaz-
epan-1-yl)pyrimidin-5-yl)oxy)pyridin-4-yl)methyl)pi-
peridin-4-yl)acetic acid;

3-(1-((2-(3,5-dichlorophenyl)-6-((2-(4-methylpiperazin-
1-yl)pyrimidin-5-yl)oxy)pyridin-4-yl)methyl)azetidin-
3-yl)butanoic acid;

2-((1-((2-(3,5-dichlorophenyl)-6-((2-(4-methylpiperazin-
1-yl)pyrimidin-5-yl)oxy)pyridin-4-yl)methyl)pyrroli-
din-3-yl)oxy)acetic acid;

2-(2-((2-(3,5-dichlorophenyl)-6-((2-(4-methylpiperazin-
1-yl)pyrimidin-5-yl)oxy)pyridin-4-yl)methyl)octahy-
drocyclopenta[c]pyrrol-5-yl)acetic acid;

3-(1-((2-(3,5-dichlorophenyl)-6-((2-(4-methylpiperazin-
1-yl)pyrimidin-5-yl)oxy)pyridin-4-yl)methyl)piperi-
din-4-yl)propanoic acid;

3-(1-((2-(3,5-dichlorophenyl)-6-((2-(4-methylpiperazin-
1-yl)pyrimidin-5-yl)oxy)pyridin-4-yl)methyl)piperi-
din-4-yl)-2-methylpropanoic acid;

2-(1-((2-((2-(1,4-diazepan-1-yl)pyrimidin-5-yl)oxy)-6-
(3,5-dichlorophenyl)pyridin-4-yl)methyl)piperidin-4-
yl)acetic acid;

2-(1-((2-(3,5-dichlorophenyl)-6-((2-(5-methylhexahydro-
pyrrolo[3,4-c]pyrrol-2(1H)-yl)pyrimidin-5-yl)oxy)
pyridin-4-yl)methyl)piperidin-4-yl)acetic acid;

(S)-3-(1-((2-(3,5-dichlorophenyl)-6-((2-(4-methylpiper-
azin-1-yl)pyrimidin-5-yl)oxy)pyridin-4-yl)methyl)pip-
eridin-4-yl)-2-methylpropanoic acid;

1-(7-((2-(3,5-dichlorophenyl)-6-((2-(4-methylpiperazin-1-yl)pyrimidin-5-yl)oxy)pyridin-4-yl)methyl)-2,7-diazaspiro[3.5]nonan-2-yl)-2-hydroxyethanone;
(1R,7S,8r)-4-((2-(3,5-dichlorophenyl)-6-((6-(4-methylpiperazin-1-yl)pyridin-3-yl)oxy)pyridin-4-yl)methyl)-4-azabicyclo[5.1.0]octane-8-carboxylic acid;
(R)-3-(1-((2-(3,5-dichlorophenyl)-6-((2-(4-methylpiperazin-1-yl)pyrimidin-5-yl)oxy)pyridin-4-yl)methyl)piperidin-4-yl)-2-methylpropanoic acid;
1-(1-((2-(3,5-dichlorophenyl)-6-((2-(4-methylpiperazin-1-yl)pyrimidin-5-yl)oxy)pyridin-4-yl)methyl)piperidin-4-yl)propan-2-ol;
3-(1-((2-(3,5-dichlorophenyl)-6-((2-(4-methylpiperazin-1-yl)pyrimidin-5-yl)oxy)pyridin-4-yl)methyl)piperidin-4-yl)-2-hydroxypropanoic acid;
2-((1-((2-(3,5-dichlorophenyl)-6-((2-(4-methyl-1,4-diazepan-1-yl)pyrimidin-5-yl)oxy)pyridin-4-yl)methyl)piperidin-4-yl)oxy)acetic acid;
9-((2-(3,5-dichlorophenyl)-6-((6-(4-methylpiperazin-1-yl)pyridin-3-yl)oxy)pyridin-4-yl)methyl)-2-oxa-4,9-diazaspiro[5.5]undecan-3-one;
2-(1-((2-(3,5-dichlorophenyl)-6-((2-(4-methylpiperazin-1-yl)pyrimidin-5-yl)oxy)pyridin-4-yl)methyl)piperidin-4-yl)acetamide;
1-((1-((2-(3,5-dichlorophenyl)-6-((2-(4-methylpiperazin-1-yl)pyrimidin-5-yl)oxy)pyridin-4-yl)methyl)piperidin-4-yl)oxy)cyclopropanecarboxylic acid;
2-(1-((2-(3,5-dichlorophenyl)-6-((2-(6-methoxy-4-methyl-1,4-diazepan-1-yl)pyrimidin-5-yl)oxy)pyridin-4-yl)methyl)piperidin-4-yl)acetic acid;
N-((1-((2-(3,5-dichlorophenyl)-6-((6-(6-fluoro-4-methyl-1,4-diazepan-1-yl)pyridin-3-yl)oxy)pyridin-4-yl)methyl)piperidin-4-yl)methyl)acetamide;
2-(1-((2-(3,5-dichlorophenyl)-6-((2-(6-hydroxy-4,6-dimethyl-1,4-diazepan-1-yl)pyrimidin-5-yl)oxy)pyridin-4-yl)methyl)piperidin-4-yl)acetic acid;
2-(1-((2-(3,5-dichlorophenyl)-6-((2-(6-fluoro-4-methyl-1,4-diazepan-1-yl)pyrimidin-5-yl)oxy)pyridin-4-yl)methyl)piperidin-4-yl)acetic acid;
2-(1-((2-(3,5-dichlorophenyl)-6-((4-methyl-2-(4-methylpiperazin-1-yl)pyrimidin-5-yl)oxy)pyridin-4-yl)methyl)piperidin-4-yl)acetic acid;
2-(1-((2-(3,5-dichlorophenyl)-6-((2-methyl-6-(4-methylpiperazin-1-yl)pyridin-3-yl)oxy)pyridin-4-yl)methyl)piperidin-4-yl)acetic acid;
2-(1-((2-(3,5-dichlorophenyl)-6-(4-(4-methylpiperazin-1-yl)phenoxy)pyridin-4-yl)methyl)piperidin-4-yl)acetic acid;
2-(1-((2-(3,5-dichlorophenyl)-6-((5-fluoro-6-(4-methylpiperazin-1-yl)pyridin-3-yl)oxy)pyridin-4-yl)methyl)piperidin-4-yl)acetic acid;
2-(1-((2-(3,5-dichlorophenyl)-6-((2-(3-(methylamino)pyrrolidin-1-yl)pyrimidin-5-yl)oxy)pyridin-4-yl)methyl)piperidin-4-yl)acetic acid;
(S)-2-(4-((2-(3,5-dichlorophenyl)-6-((2-(4-methylpiperazin-1-yl)pyrimidin-5-yl)oxy)pyridin-4-yl)methyl)-1,4-oxazepan-7-yl)ethanol;
N-((1R,5S,6r)-3-((2-(3,5-dichlorophenyl)-6-((2-(4-methyl-1,4-diazepan-1-yl)pyrimidin-5-yl)oxy)pyridin-4-yl)methyl)-3-azabicyclo[3.1.0]hexan-6-yl)acetamide;
1-(1-((2-(3,5-dichlorophenyl)-6-((2-(4-methylpiperazin-1-yl)pyrimidin-5-yl)oxy)pyridin-4-yl)methyl)piperidin-4-yl)propan-2-one;
2-(1-((2-(3,5-dichlorophenyl)-6-((6-(4-methyl-1,4-diazepan-1-yl)pyridin-3-yl)oxy)pyridin-4-yl)methyl)piperidin-4-yl)acetic acid;
N-((1-((2-(3,5-dichlorophenyl)-6-((6-(4-methylpiperazin-1-yl)pyridazin-3-yl)oxy)pyridin-4-yl)methyl)piperidin-4-yl)methyl)acetamide;
2-(1-((2-((2-(4-aminopiperidin-1-yl)pyrimidin-5-yl)oxy)-6-(3,5-dichlorophenyl)pyridin-4-yl)methyl)piperidin-4-yl)acetic acid;
(S)-2-(1-((2-(3,5-dichlorophenyl)-6-((2-(3-methylpiperazin-1-yl)pyrimidin-5-yl)oxy)pyridin-4-yl)methyl)piperidin-4-yl)acetic acid;
2-(1-((2-(3,5-dichlorophenyl)-6-((2-(3,3-dimethylpiperazin-1-yl)pyrimidin-5-yl)oxy)pyridin-4-yl)methyl)piperidin-4-yl)acetic acid;
2-(1-((2-(3,5-dichlorophenyl)-6-((2-(hexahydropyrrolo[3,4-c]pyrrol-2(1H)-yl)pyrimidin-5-yl)oxy)pyridin-4-yl)methyl)piperidin-4-yl)acetic acid;
2-(1-((2-((2-(3,6-diazabicyclo[3.1.1]heptan-3-yl)pyrimidin-5-yl)oxy)-6-(3,5-dichlorophenyl)pyridin-4-yl)methyl)piperidin-4-yl)acetic acid;
2-(1-((2-((2-(3,8-diazabicyclo[3.2.1]octan-3-yl)pyrimidin-5-yl)oxy)-6-(3,5-dichlorophenyl)pyridin-4-yl)methyl)piperidin-4-yl)acetic acid;
2-(1-((2-((2-(4,7-diazaspiro[2.5]octan-7-yl)pyrimidin-5-yl)oxy)-6-(3,5-dichlorophenyl)pyridin-4-yl)methyl)piperidin-4-yl)acetic acid;
2-(1-((2-((2-(4-amino-4-(hydroxymethyl)piperidin-1-yl)pyrimidin-5-yl)oxy)-6-(3,5-dichlorophenyl)pyridin-4-yl)methyl)piperidin-4-yl)acetic acid;
2-(1-((2-((6-(1,4-diazepan-1-yl)pyridin-3-yl)oxy)-6-(3,5-dichlorophenyl)pyridin-4-yl)methyl)piperidin-4-yl)acetic acid;
N-((1-((3',5'-dichloro-5-((2-(4-(2-(methylsulfonyl)ethyl)piperazin-1-yl)pyrimidin-5-yl)oxy)-[1,1'-biphenyl]-3-yl)methyl)piperidin-4-yl)methyl) acetamide;
3-(4-(5-((5-((4-(acetamidomethyl)piperidin-1-yl)methyl)-3',5'-dichloro-[1,1'-biphenyl]-3-yl)oxy)pyrimidin-2-yl)piperazin-1-yl)propanoic acid;
3-(4-(6-((4-((4-(acetamidomethyl)piperidin-1-yl)methyl)-6-(3,5-dichlorophenyl)pyridin-2-yl)oxy)pyridazin-3-yl)piperazin-1-yl)propanoic acid;
3-(4-(5-((5-((4-(acetamidomethyl)piperidin-1-yl)methyl)-3',5'-dichloro-[1,1'-biphenyl]-3-yl)oxy)pyrimidin-2-yl)piperazin-1-yl)propanamide;
1-((1-((2-(3,5-dichlorophenyl)-6-((2-(4-(3-hydroxypropyl)piperazin-1-yl)pyrimidin-5-yl)oxy)pyridin-4-yl)methyl)piperidin-4-yl)methyl)-3-methylurea;
methyl (3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoyl)carbamate;
1-(2-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)ethyl)cyclopropanecarboxylic acid;
4-(4-(5-((4-((4-(acetamidomethyl)piperidin-1-yl)methyl)-6-(3,5-dichlorophenyl)pyridin-2-yl)oxy)pyridin-2-yl)piperazin-1-yl)-2-methylbutanoic acid;
methyl (3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoyl)carbamate;
methyl (3-(4-(5-((4-((4-(acetamidomethyl)piperidin-1-yl)methyl)-6-(3,5-dichlorophenyl)pyridin-2-yl)oxy)pyridin-2-yl)piperazin-1-yl)propanoyl)carbamate;
2-(1-((2-(3,5-dichlorophenyl)-6-((2-(4-(2,3-dihydroxypropyl)piperazin-1-yl)pyrimidin-5-yl)oxy)pyridin-4-yl)methyl)piperidin-4-yl)acetic acid;
4-(5-((4-((4-(acetamidomethyl)piperidin-1-yl)methyl)-6-(3,5-dichlorophenyl)pyridin-2-yl)oxy)pyridin-2-yl)-1-methylpiperazine 1-oxide;

4-(5-((4-((4-(acetamidomethyl)piperidin-1-yl)methyl)-6-(3,5-dichlorophenyl)pyridin-2-yl)oxy)pyridin-2-yl)-1,1-bis(2-hydroxyethyl)piperazin-1-ium;

N-((1-((2-(3,5-dichlorophenyl)-6-((6-(4-(2-hydroxyethyl)piperazin-1-yl)pyridin-3-yl)oxy)pyridin-4-yl)methyl)piperidin-4-yl)methyl)acetamide;

4-(5-((4-((4-(acetamidomethyl)piperidin-1-yl)methyl)-6-(3,5-dichlorophenyl)pyridin-2-yl)oxy)pyridin-2-yl)-1,1-dimethylpiperazin-1-ium;

N-((1-((2-((6-(4-amino-3-fluoropiperidin-1-yl)pyridin-3-yl)oxy)-6-(3,5-dichlorophenyl)pyridin-4-yl)methyl)piperidin-4-yl)methyl)acetamide;

N-((1-((2-(3,5-dichlorophenyl)-6-((6-((1S,4S)-5-(2-(methylsulfonyl)ethyl)-2,5-diazabicyclo[2.2.1]heptan-2-yl)pyridin-3-yl)oxy)pyridin-4-yl)methyl)piperidin-4-yl)methyl) acetamide;

N-((1-((2-((6-((3S,4R)-3-(aminomethyl)-4-hydroxypyrrolidin-1-yl)pyridin-3-yl)oxy)-6-(3,5-dichlorophenyl)pyridin-4-yl)methyl)piperidin-4-yl)methyl) acetamide;

3-((1R,5S)-3-(5-((4-((4-(acetamidomethyl)piperidin-1-yl)methyl)-6-(3,5-dichlorophenyl)pyridin-2-yl)oxy)pyridin-2-yl)-3,8-diazabicyclo[3.2.1]octan-8-yl)propanoic acid;

(S)-3-(4-(5-((4-((4-(acetamidomethyl)piperidin-1-yl)methyl)-6-(3,5-dichlorophenyl)pyridin-2-yl)oxy)pyridin-2-yl)-2-methylpiperazin-1-yl)propanoic acid;

2-(1-((2-((6-((1S,4S)-2,5-diazabicyclo[2.2.1]heptan-2-yl)pyridin-3-yl)oxy)-6-(3,5-dichlorophenyl)pyridin-4-yl)methyl)piperidin-4-yl)acetic acid;

4-(4-(5-((4-((4-(acetamidomethyl)piperidin-1-yl)methyl)-6-(3,5-dichlorophenyl)pyridin-2-yl)oxy)pyridin-2-yl)piperazin-1-yl)-2-ethylbutanoic acid;

3-(4-(5-((4-((4-(acetamidomethyl)piperidin-1-yl)methyl)-6-(3,5-dichlorophenyl)pyridin-2-yl)oxy)pyridin-2-yl)piperazin-1-yl)-2,2-dimethylpropanoic acid;

3-(4-(5-((4-((4-(acetamidomethyl)piperidin-1-yl)methyl)-6-(3,5-dichlorophenyl)pyridin-2-yl)oxy)pyridin-2-yl)-1,4-diazepan-1-yl)propanoic acid;

3-(4-(5-((4-((4-(acetamidomethyl)piperidin-1-yl)methyl)-6-(3,5-dichlorophenyl)pyridin-2-yl)oxy)pyridin-2-yl)-2,2-dimethylpiperazin-1-yl)propanoic acid;

N-((1-((2-((6-(1,4-diazepan-1-yl)pyridin-3-yl)oxy)-6-(3,5-dichlorophenyl)pyridin-4-yl)methyl)piperidin-4-yl)methyl)acetamide;

N-((1-((2-(3,5-dichlorophenyl)-6-((6-(4-(methylamino)piperidin-1-yl)pyridin-3-yl)oxy)pyridin-4-yl)methyl)piperidin-4-yl)methyl)acetamide;

N-((1-((2-(3,5-dichlorophenyl)-6-((6-(hexahydropyrrolo[3,4-c]pyrrol-2(1H)-yl)pyridin-3-yl)oxy)pyridin-4-yl)methyl)piperidin-4-yl)methyl)acetamide;

N-((1-((2-(3,5-dichlorophenyl)-6-((6-(3-(hydroxymethyl)piperazin-1-yl)pyridin-3-yl)oxy)pyridin-4-yl)methyl)piperidin-4-yl)methyl)acetamide;

N-((1-((2-((6-(4-aminopiperidin-1-yl)pyridin-3-yl)oxy)-6-(3,5-dichlorophenyl)pyridin-4-yl)methyl)piperidin-4-yl)methyl)acetamide;

N-((1-((2-(3,5-dichlorophenyl)-6-((6-(3,3-dimethylpiperazin-1-yl)pyridin-3-yl)oxy)pyridin-4-yl)methyl)piperidin-4-yl)methyl)acetamide;

N-((1-((2-((6-(4-amino-3,3-dimethylpiperidin-1-yl)pyridin-3-yl)oxy)-6-(3,5-dichlorophenyl)pyridin-4-yl)methyl)piperidin-4-yl)methyl)acetamide;

N-((1-((2-((6-(2,7-diazaspiro[4.4]nonan-2-yl)pyridin-3-yl)oxy)-6-(3,5-dichlorophenyl)pyridin-4-yl)methyl)piperidin-4-yl)methyl)acetamide;

N-((1-((2-(3,5-dichlorophenyl)-6-((6-(4-methylpiperazin-1-yl)pyridin-3-yl)oxy)pyridin-4-yl)methyl)piperidin-4-yl)methyl)acetamide;

1-(3',5'-dichloro-5-((6-(hexahydropyrrolo[3,4-c]pyrrol-2(1H)-yl)pyridin-3-yl)oxy)-[1,1'-biphenyl]-3-yl)-N-methylmethanamine;

1-(5-((6-((1S,4S)-2,5-diazabicyclo[2.2.1]heptan-2-yl)pyridin-3-yl)oxy)-3',5'-dichloro-[1,1'-biphenyl]-3-yl)-N-methylmethanamine;

2-(1-((2-(3,5-dichlorophenyl)-6-((6-((1S,4S)-5-methyl-2,5-diazabicyclo[2.2.1]heptan-2-yl)pyridin-3-yl)oxy)pyridin-4-yl)methyl)piperidin-4-yl)acetic acid;

2-(1-((2-(3,5-dichlorophenyl)-6-((2-(4-(3-(methylsulfinyl)butyl)piperazin-1-yl)pyrimidin-5-yl)oxy)pyridin-4-yl)methyl)piperidin-4-yl)acetic acid;

2-(1-((2-(3,5-dichlorophenyl)-6-((2-(4-(3-(methylsulfonyl)butyl)piperazin-1-yl)pyrimidin-5-yl)oxy)pyridin-4-yl)methyl)piperidin-4-yl)acetic acid;

2-(1-((2-(3,5-dichlorophenyl)-6-((2-(piperazin-1-yl)pyrimidin-5-yl)oxy)pyridin-4-yl)methyl)piperidin-4-yl)acetic acid;

2-(1-((2-(3,5-dichlorophenyl)-6-((2-(4-methylpiperazin-1-yl)pyrimidin-5-yl)oxy)pyridin-4-yl)methyl)piperidin-4-yl)acetic acid;

4-(4-(5-((6-(3,5-dichlorophenyl)-4-((4-(((methylcarbamoyl)oxy)methyl)piperidin-1-yl)methyl)pyridin-2-yl)oxy)pyrimidin-2-yl)piperazin-1-yl)pentanoic acid;

(1-((2-(3,5-dichlorophenyl)-6-((2-(4-(4-hydroxybutan-2-yl)piperazin-1-yl)pyrimidin-5-yl)oxy)pyridin-4-yl)methyl)piperidin-4-yl)methyl methylcarbamate;

(1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)methyl methylcarbamate;

3-(4-(5-((6-(3,5-dichlorophenyl)-4-((4-(((methylcarbamoyl)oxy)methyl)piperidin-1-yl)methyl)pyridin-2-yl)oxy)pyrimidin-2-yl)piperazin-1-yl)cyclobutanecarboxylic acid;

2-(1-((2-(3,5-dichlorophenyl)-6-((6-(4-methylpiperazin-1-yl)pyridin-3-yl)oxy)pyridin-4-yl)methyl)piperidin-4-yl)acetic acid;

3-(1-((2-(3,5-dichlorophenyl)-6-((6-(4-methylpiperazin-1-yl)pyridin-3-yl)oxy)pyridin-4-yl)methyl)piperidin-4-yl)-2-methylpropanoic acid;

N-((1-((2-(3,5-dichlorophenyl)-6-((2-(4-(3-(methylsulfonyl)butyl)piperazin-1-yl)pyrimidin-5-yl)oxy)pyridin-4-yl)methyl)piperidin-4-yl)methyl)acetamide;

4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)pentanoic acid;

3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)cyclobutanecarboxylic acid;

methyl ((1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)methyl/carbamate;

N-((1-((2-(3,5-dichlorophenyl)-6-((6-(4-(3-(methylsulfonyl)butyl)piperazin-1-yl)pyridin-3-yl)oxy)pyridin-4-yl)methyl)piperidin-4-yl)methyl)acetamide;

1-((1-((2-(3,5-dichlorophenyl)-6-((6-(4-(3-(methylsulfonyl)butyl)piperazin-1-yl)pyridin-3-yl)oxy)pyridin-4-yl)methyl)piperidin-4-yl)methyl)-3-methylurea;

1-((1-((2-(3,5-dichlorophenyl)-6-((2-(4-(3-(methyl sulfonyl)butyl)piperazin-1-yl)pyrimidin-5-yl)oxy)pyridin-4-yl)methyl)piperidin-4-yl)methyl)-3-methylurea;

3-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)cyclobutanecarboxylic acid;
4-(4-(5-((6-(3,5-dichlorophenyl)-4-((4-(((methoxycarbonyl)amino)methyl)piperidin-1-yl)methyl)pyridin-2-yl)oxy)pyrimidin-2-yl)piperazin-1-yl)pentanoic acid;
methyl ((1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)methyl)carbamate;
2-((1R,7S,8r)-4-((2-(3,5-dichlorophenyl)-6-((2-(4-methylpiperazin-1-yl)pyrimidin-5-yl)oxy)pyridin-4-yl)methyl)-4-azabicyclo[5.1.0]octan-8-yl)acetic acid;
2-((1-((2-(3,5-dichlorophenyl)-6-((2-(4-methylpiperazin-1-yl)pyrimidin-5-yl)oxy)pyridin-4-yl)methyl)piperidin-4-yl)oxy)-2-methylpropanoic acid;
2-(1-((2-(3,5-dichlorophenyl)-6-((2-(6-hydroxy-4-methyl-1,4-diazepan-1-yl)pyrimidin-5-yl)oxy)pyridin-4-yl)methyl)piperidin-4-yl)acetic acid;
2-(1-((2-(3,5-dichlorophenyl)-6-((2-(4-(dimethylamino)piperidin-1-yl)pyrimidin-5-yl)oxy)pyridin-4-yl)methyl)piperidin-4-yl)acetic acid;
2-(1-((2-(3,5-dichlorophenyl)-6-((2-(6-methyl-3,6-diazabicyclo[3.1.1]heptan-3-yl)pyrimidin-5-yl)oxy)pyridin-4-yl)methyl)piperidin-4-yl)acetic acid;
2-(1-((2-(3,5-dichlorophenyl)-6-((2-(4-((1-hydroxycyclopropyl)methyl)piperazin-1-yl)pyrimidin-5-yl)oxy)pyridin-4-yl)methyl)piperidin-4-yl)acetic acid;
2-(1-((2-(3,5-dichlorophenyl)-6-((2-(4-ethyl-1,4-diazepan-1-yl)pyrimidin-5-yl)oxy)pyridin-4-yl)methyl)piperidin-4-yl)acetic acid;
2-(1-((2-(3,5-dichlorophenyl)-6-((2-((1S,4S)-5-methyl-2,5-diazabicyclo[2.2.1]heptan-2-yl)pyrimidin-5-yl)oxy)pyridin-4-yl)methyl)piperidin-4-yl)acetic acid;
2-(1-((2-(3,5-dichlorophenyl)-6-((2-((1S,4S)-5-ethyl-2,5-diazabicyclo[2.2.1]heptan-2-yl)pyrimidin-5-yl)oxy)pyridin-4-yl)methyl)piperidin-4-yl)acetic acid;
2-(1-((2-((2-(4-cyclopropylpiperazin-1-yl)pyrimidin-5-yl)oxy)-6-(3,5-dichlorophenyl)pyridin-4-yl)methyl)piperidin-4-yl)acetic acid;
2-(1-((2-(3,5-dichlorophenyl)-6-((2-(4-ethylpiperazin-1-yl)pyrimidin-5-yl)oxy)pyridin-4-yl)methyl)piperidin-4-yl)acetic acid;
2-(1-((2-(3,5-dichlorophenyl)-6-((2-(4-isopropylpiperazin-1-yl)pyrimidin-5-yl)oxy)pyridin-4-yl)methyl)piperidin-4-yl)acetic acid;
2-(1-((2-(3,5-dichlorophenyl)-6-((2-(4-(2-fluoroethyl)piperazin-1-yl)pyrimidin-5-yl)oxy)pyridin-4-yl)methyl)piperidin-4-yl)acetic acid;
2-(1-((2-(3,5-dichlorophenyl)-6-((2-(4-(3-hydroxybutyl)piperazin-1-yl)pyrimidin-5-yl)oxy)pyridin-4-yl)methyl)piperidin-4-yl)acetic acid;
2-(1-((2-(3,5-dichlorophenyl)-6-((2-(4-(4-hydroxybutan-2-yl)piperazin-1-yl)pyrimidin-5-yl)oxy)pyridin-4-yl)methyl)piperidin-4-yl)acetic acid;
2-(1-((2-(3,5-dichlorophenyl)-6-((2-(4-(4-(methylamino)butan-2-yl)piperazin-1-yl)pyrimidin-5-yl)oxy)pyridin-4-yl)methyl)piperidin-4-yl)acetic acid;
2-(1-((2-(3,5-dichlorophenyl)-6-((2-(4-(4-(dimethylamino)butan-2-yl)piperazin-1-yl)pyrimidin-5-yl)oxy)pyridin-4-yl)methyl)piperidin-4-yl)acetic acid;
2-(1-((2-(3,5-dichlorophenyl)-6-((2-(4-(2-((methylcarbamoyl)oxy)ethyl)piperazin-1-yl)pyrimidin-5-yl)oxy)pyridin-4-yl)methyl)piperidin-4-yl)acetic acid;
2-(1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)acetic acid;
2-(1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)acetic acid;
2-(1-((2-(3,5-dichlorophenyl)-6-((6-(4-(2-methoxyethyl)piperazin-1-yl)pyridin-3-yl)oxy)pyridin-4-yl)methyl)piperidin-4-yl)acetic acid;
N-((1-((2-(3,5-dichlorophenyl)-6-((2-(4-(2-methoxyethyl)piperazin-1-yl)pyrimidin-5-yl)oxy)pyridin-4-yl)methyl)piperidin-4-yl)methyl)acetamide;
2-(1-((2-(3,5-dichlorophenyl)-6-((2-(4-(3-sulfamoylpropyl)piperazin-1-yl)pyrimidin-5-yl)oxy)pyridin-4-yl)methyl)piperidin-4-yl)acetic acid;
2-(1-((2-(3,5-dichlorophenyl)-6-((2-(4-(2-methoxyethyl)piperazin-1-yl)pyrimidin-5-yl)oxy)pyridin-4-yl)methyl)piperidin-4-yl)acetic acid;
3-(4-(5-((6-(3,5-dichlorophenyl)-4-((4-(((methylcarbamoyl)oxy)methyl)piperidin-1-yl)methyl)pyridin-2-yl)oxy)pyrimidin-2-yl)piperazin-1-yl)propanoic acid;
4-(4-(5-((4-((4-(acetamidomethyl)piperidin-1-yl)methyl)-6-(3,5-dichlorophenyl)pyridin-2-yl)oxy)pyridin-2-yl)piperazin-1-yl)butanoic acid;
N-((1-((2-(3,5-dichlorophenyl)-6-((6-(4-(2-methoxyethyl)piperazin-1-yl)pyridin-3-yl)oxy)pyridin-4-yl)methyl)piperidin-4-yl)methyl)acetamide;
N-((1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)methyl)acetamide;
2-(1-((2-(3,5-dichlorophenyl)-6-((6-(4-(3-sulfamoylpropyl)piperazin-1-yl)pyridin-3-yl)oxy)pyridin-4-yl)methyl)piperidin-4-yl)acetic acid;
N-((1-((2-(3,5-dichlorophenyl)-6-((2-(4-(3-sulfamoylpropyl)piperazin-1-yl)pyrimidin-5-yl)oxy)pyridin-4-yl)methyl)piperidin-4-yl)methyl)acetamide;
1-((1-((2-(3,5-dichlorophenyl)-6-((6-(4-(2-methoxyethyl)piperazin-1-yl)pyridin-3-yl)oxy)pyridin-4-yl)methyl)piperidin-4-yl)methyl)-3-methylurea;
1-((1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)methyl)-3-methylurea;
3-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)propanoic acid;
1-((1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)methyl)-3-methylurea;
3-(4-(5-((5-((4-(acetamidomethyl)piperidin-1-yl)methyl)-3',5'-dichloro-[1,1'-biphenyl]-3-yl)oxy)pyridin-2-yl)piperazin-1-yl)propanoic acid;
N-((1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)methyl)acetamide;
3-(4-(5-((6-(3,5-dichlorophenyl)-4-((4-((3-methylureido)methyl)piperidin-1-yl)methyl)pyridin-2-yl)oxy)pyridin-2-yl)piperazin-1-yl)propane-1-sulfonamide;
3-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)propanamide;
1-((1-((2-(3,5-dichlorophenyl)-6-((2-(4-(2-methoxyethyl)piperazin-1-yl)pyrimidin-5-yl)oxy)pyridin-4-yl)methyl)piperidin-4-yl)methyl)-3-methylurea;
3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoic acid;
2-(1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)acetamide;

3-(4-(5-((6-(3,5-dichlorophenyl)-4-((4-hydroxy-4-((3-methylureido)methyl)piperidin-1-yl)methyl)pyridin-2-yl)oxy)pyrimidin-2-yl)piperazin-1-yl)propanamide;
3-(4-(5-((4-((4-(acetamidomethyl)piperidin-1-yl)methyl)-6-(3,5-dichlorophenyl)pyridin-2-yl)oxy)-3-fluoropyridin-2-yl)piperazin-1-yl)propanoic acid;
3-(4-(5-((6-(3,5-dichlorophenyl)-4-((4-(((ethoxycarbonyl)amino)methyl)piperidin-1-yl)methyl)pyridin-2-yl)oxy)pyrimidin-2-yl)piperazin-1-yl)propanoic acid;
3-(4-(5-((6-(3,5-dichlorophenyl)-4-((4-(2-(ethylamino)-2-oxoethyl)piperidin-1-yl)methyl)pyridin-2-yl)oxy)pyrimidin-2-yl)piperazin-1-yl)propanoic acid;
3-(1-((2-(3,5-dichlorophenyl)-6-((2-(piperazin-1-yl)pyrimidin-5-yl)oxy)pyridin-4-yl)methyl)piperidin-4-yl)-2-methylpropanoic acid;
3-(4-(5-((6-(3,5-dichlorophenyl)-4-((4-((3-methylureido)methyl)piperidin-1-yl)methyl)pyridin-2-yl)oxy)-3-fluoropyridin-2-yl)piperazin-1-yl)propanoic acid;
3-(1-((2-(3,5-dichlorophenyl)-6-((6-(4-(3-(methylsulfonyl)propyl)piperazin-1-yl)pyridin-3-yl)oxy)pyridin-4-yl)methyl)piperidin-4-yl)propanoic acid;
3-(1-((2-(3,5-dichlorophenyl)-6-((2-(4-(3-(methylsulfonyl)propyl)piperazin-1-yl)pyrimidin-5-yl)oxy)pyridin-4-yl)methyl)piperidin-4-yl)propanoic acid;
3-(4-(5-((4-((4-(acetamidomethyl)piperidin-1-yl)methyl)-6-(3-chloro-4,5-difluorophenyl)pyridin-2-yl)oxy)pyrimidin-2-yl)piperazin-1-yl)propanamide;
1-((1-((2-(3-chloro-5-fluorophenyl)-6-((2-(4-(3-(methylsulfonyl)propyl)piperazin-1-yl)pyrimidin-5-yl)oxy)pyridin-4-yl)methyl)piperidin-4-yl)methyl)-3-methylurea;
methyl ((1-((2-(3-chloro-5-fluorophenyl)-6-((2-(piperazin-1-yl)pyrimidin-5-yl)oxy)pyridin-4-yl)methyl)piperidin-4-yl)methyl)carbamate;
3-(4-(5-((6-(3,5-dichlorophenyl)-4-((4-(2-(methylsulfonyl)ethyl)piperidin-1-yl)methyl)pyridin-2-yl)oxy)pyridin-2-yl)piperazin-1-yl)propanoic acid;
3-(4-(5-((6-(3,5-dichlorophenyl)-4-((4-(2-sulfamoylethyl)piperidin-1-yl)methyl)pyridin-2-yl)oxy)pyridin-2-yl)piperazin-1-yl)propanoic acid;
2-(1-((2-(3,5-dichlorophenyl)-6-((2-(4-(2-(1-hydroxycyclopropyl)ethyl)piperazin-1-yl)pyrimidin-5-yl)oxy)pyridin-4-yl)methyl)piperidin-4-yl)acetic acid;
2-(1-((2-(3,5-dichlorophenyl)-6-((2-(4-(3-hydroxy-3-methylbutyl)piperazin-1-yl)pyrimidin-5-yl)oxy)pyridin-4-yl)methyl)piperidin-4-yl)acetic acid;
2-(1-((2-(3,5-dichlorophenyl)-6-((2-(4-(3-hydroxy-2,2-dimethylpropyl)piperazin-1-yl)pyrimidin-5-yl)oxy)pyridin-4-yl)methyl)piperidin-4-yl)acetic acid;
3-(4-(5-((4-((4-(acetamidomethyl)piperidin-1-yl)methyl)-6-(3,5-dichlorophenyl)pyridin-2-yl)oxy)pyridin-2-yl)piperazin-1-yl)butanoic acid;
3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)butanoic acid;
3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-methylpropanoic acid;
3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-methylpropanamide;
N-((1-((2-(3,5-dichlorophenyl)-6-((2-(4-(2-(methylsulfonyl)ethyl)piperazin-1-yl)pyrimidin-5-yl)oxy)pyridin-4-yl)methyl)piperidin-4-yl)methyl)acetamide;
N-((1-((2-(3,5-dichlorophenyl)-6-((2-(4-(2-sulfamoylethyl)piperazin-1-yl)pyrimidin-5-yl)oxy)pyridin-4-yl)methyl)piperidin-4-yl)methyl)acetamide;
2-(4-(5-((4-((4-(acetamidomethyl)piperidin-1-yl)methyl)-6-(3,5-dichlorophenyl)pyridin-2-yl)oxy)pyridin-2-yl)piperazin-1-yl)ethanesulfonic acid;
2-((4-(5-((4-((4-(acetamidomethyl)piperidin-1-yl)methyl)-6-(3,5-dichlorophenyl)pyridin-2-yl)oxy)pyridin-2-yl)piperazin-1-yl)methyl)butanoic acid;
N-((1-((2-(3,5-dichlorophenyl)-6-((6-(4-(2-sulfamoylethyl)piperazin-1-yl)pyridin-3-yl)oxy)pyridin-4-yl)methyl)piperidin-4-yl)methyl)acetamide;
1-((1-((2-(3,5-dichlorophenyl)-6-((6-(4-(2-(methylsulfonyl)ethyl)piperazin-1-yl)pyridin-3-yl)oxy)pyridin-4-yl)methyl)piperidin-4-yl)methyl)-3-methylurea;
3-(4-(5-((6-(3,5-dichlorophenyl)-4-((4-((3-methylureido)methyl)piperidin-1-yl)methyl)pyridin-2-yl)oxy)pyrimidin-2-yl)piperazin-1-yl)-2-methylpropanamide;
3-(4-(5-((3',5'-dichloro-5-((4-((3-methylureido)methyl)piperidin-1-yl)methyl)-[1,1'-biphenyl]-3-yl)oxy)pyrimidin-2-yl)piperazin-1-yl)-2-methylpropanoic acid;
N-((1-((3',5'-dichloro-5-((6-(4-(2-(methylsulfonyl)ethyl)piperazin-1-yl)pyridin-3-yl)oxy)-[1,1'-biphenyl]-3-yl)methyl)piperidin-4-yl)methyl) acetamide;
(S)-3-(4-(5-((6-(3,5-dichlorophenyl)-4-((4-(((methoxycarbonyl)amino)methyl)piperidin-1-yl)methyl)pyridin-2-yl)oxy)pyrimidin-2-yl)-2-methylpiperazin-1-yl)propanoic acid;
1-((1-((2-(3,5-dichlorophenyl)-6-((2-(4-(3-hydroxybutyl)piperazin-1-yl)pyrimidin-5-yl)oxy)pyridin-4-yl)methyl)piperidin-4-yl)methyl)-3-methylurea;
3-(3-(5-((4-((4-(acetamidomethyl)piperidin-1-yl)methyl)-6-(3,5-dichlorophenyl)pyridin-2-yl)oxy)pyrimidin-2-yl)-3,8-diazabicyclo[3.2.1]octan-8-yl)propanoic acid;
methyl 3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)propanoate;
(R)-2-(1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)acetic acid;
(R)-2-(1-((2-(3,5-dichlorophenyl)-6-((6-(4-(2-hydroxypropyl)piperazin-1-yl)pyridin-3-yl)oxy)pyridin-4-yl)methyl)piperidin-4-yl)acetic acid;
2-(1-((2-(3,5-dichlorophenyl)-6-((6-(4-(2-hydroxyethyl)piperazin-1-yl)pyridin-3-yl)oxy)pyridin-4-yl)methyl)piperidin-4-yl)acetic acid;
3-(1-((2-(3,5-dichlorophenyl)-6-((2-(4-((R)-2-hydroxypropyl)piperazin-1-yl)pyrimidin-5-yl)oxy)pyridin-4-yl)methyl)piperidin-4-yl)-2-methylpropanoic acid;
(R)—N-((1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)methyl)acetamide;
N-((1-((2-(3,5-dichlorophenyl)-6-((2-(4-(2-hydroxy-2-methylpropyl)piperazin-1-yl)pyrimidin-5-yl)oxy)pyridin-4-yl)methyl)piperidin-4-yl)methyl)acetamide;
N-((1-((2-(3,5-dichlorophenyl)-6-((2-(4-(3-fluoro-2-hydroxypropyl)piperazin-1-yl)pyrimidin-5-yl)oxy)pyridin-4-yl)methyl)piperidin-4-yl)methyl)acetamide;
(R)-(1-((2-(3,5-dichlorophenyl)-6-((6-(4-(2-hydroxypropyl)piperazin-1-yl)pyridin-3-yl)oxy)pyridin-4-yl)methyl)piperidin-4-yl)methyl methylcarbamate;
2-(1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)acetic acid;
(1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)methyl methylcarbamate;

(R)-(1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)methyl methylcarbamate;

(R)-1-((1-((2-(3,5-dichlorophenyl)-6-((6-(4-(2-hydroxypropyl)piperazin-1-yl)pyridin-3-yl)oxy)pyridin-4-yl)methyl)piperidin-4-yl)methyl)-3-methylurea;

(R)-1-((1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)methyl)-3-methylurea;

methyl ((1-((2-(3,5-dichlorophenyl)-6-((2-(4-(2-hydroxyethyl)piperazin-1-yl)pyrimidin-5-yl)oxy)pyridin-4-yl)methyl)piperidin-4-yl)methyl)carbamate;

(R)-methyl ((1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)methyl)carbamate;

1-((1-((3',5'-dichloro-5-((2-(4-(2-hydroxyethyl)piperazin-1-yl)pyrimidin-5-yl)oxy)-[1,1'-biphenyl]-3-yl)methyl)piperidin-4-yl)methyl)-3-methylurea;

3-(1-((2-(3,5-dichlorophenyl)-6-((6-(4-(2-hydroxyethyl)piperazin-1-yl)pyridin-3-yl)oxy)pyridin-4-yl)methyl)piperidin-4-yl)propanoic acid;

N-((1-((2-(3-chloro-5-fluorophenyl)-6-((2-(4-(2-hydroxyethyl)piperazin-1-yl)pyrimidin-5-yl)oxy)pyridin-4-yl)methyl)piperidin-4-yl)methyl)acetamide;

3-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-hydroxypropanoic acid;

(R)-2-((1-((2-(3,5-dichlorophenyl)-6-((2-(4-(2-hydroxypropyl)piperazin-1-yl)pyrimidin-5-yl)oxy)pyridin-4-yl)methyl)piperidin-4-yl)oxy)acetic acid;

((1-((2-(3,5-dichlorophenyl)-6-((2-(4-methylpiperazin-1-yl)pyrimidin-5-yl)oxy)pyridin-4-yl)methyl)piperidin-4-yl)methyl)boronic acid;

(2-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)ethyl)boronic acid;

((1-((2-(3,5-dichlorophenyl)-6-((2-(4-methylpiperazin-1-yl)pyrimidin-5-yl)oxy)pyridin-4-yl)methyl)piperidin-4-yl)methyl)dimethylphosphine oxide;

(1R,7S,8r)-4-((2-(3,5-dichlorophenyl)-6-((2-(4-methylpiperazin-1-yl)pyrimidin-5-yl)oxy)pyridin-4-yl)methyl)-4-azabicyclo[5.1.0]octane-8-carboxylic acid;

((1-((2-(3,5-dichlorophenyl)-6-((2-(4-methyl-1,4-diazepan-1-yl)pyrimidin-5-yl)oxy)pyridin-4-yl)methyl)piperidin-4-yl)methyl)boronic acid;

(2-(1-((2-(3,5-dichlorophenyl)-6-((2-(4-methylpiperazin-1-yl)pyrimidin-5-yl)oxy)pyridin-4-yl)methyl)piperidin-4-yl)ethyl)boronic acid;

(1-((2-(3,5-dichlorophenyl)-6-((6-(4-methylpiperazin-1-yl)pyridin-3-yl)oxy)pyridin-4-yl)methyl)piperidin-4-yl)methyl acetylcarbamate;

N-1-((1-((2-(3,5-dichlorophenyl)-6-((2-(4-methylpiperazin-1-yl)pyrimidin-5-yl)oxy)pyridin-4-yl)methyl)piperidin-4-yl)methyl)-N'-methoxycarbonylurea;

N-(((1-((2-(3,5-dichlorophenyl)-6-((2-(4-methylpiperazin-1-yl)pyrimidin-5-yl)oxy)pyridin-4-yl)methyl)piperidin-4-yl)methyl)carbamoyl)methanesulfonamide;

N-(((1-((2-(3,5-dichlorophenyl)-6-((2-(4-methylpiperazin-1-yl)pyrimidin-5-yl)oxy)pyridin-4-yl)methyl)piperidin-4-yl)methyl)carbamoyl)acetamide;

N-((1-((2-(3,5-dichlorophenyl)-6-((2-(4-methylpiperazin-1-yl)pyrimidin-5-yl)oxy)pyridin-4-yl)methyl)piperidin-4-yl)carbamoyl)methanesulfonamide;

1-(1-((2-(3,5-dichlorophenyl)-6-((2-(4-methylpiperazin-1-yl)pyrimidin-5-yl)oxy)pyridin-4-yl)methyl)piperidin-4-yl)urea;

(S)-(4-((2-(3,5-dichlorophenyl)-6-((2-(4-methylpiperazin-1-yl)pyrimidin-5-yl)oxy)pyridin-4-yl)methyl)-1,4-oxazepan-7-yl)methanol;

(1-((2-(3,5-dichlorophenyl)-6-((2-(4-methylpiperazin-1-yl)pyrimidin-5-yl)oxy)pyridin-4-yl)methyl)piperidin-4-yl)dimethylphosphine oxide;

2-(1-((2-(3,5-dichlorophenyl)-6-((2-(4-methylpiperazin-1-yl)pyrimidin-5-yl)amino)pyridin-4-yl)methyl)piperidin-4-yl)acetic acid;

2-(1-((6-(3,5-dichlorophenyl)-3-methyl-2-((5-(4-methylpiperazin-1-yl)pyrazin-2-yl)oxy)pyridin-4-yl)methyl)piperidin-4-yl)acetic acid;

2-(1-((2-((2-(1,4-diazabicyclo[3.2.1]octan-4-yl)pyrimidin-5-yl)oxy)-6-(3,5-dichlorophenyl)pyridin-4-yl)methyl)piperidin-4-yl)acetic acid;

N-((1-((2-((2-(3,8-diazabicyclo[3.2.1]octan-3-yl)pyrimidin-5-yl)oxy)-6-(3,5-dichlorophenyl)pyridin-4-yl)methyl)piperidin-4-yl)methyl)acetamide;

methyl ((1-((2-((2-(1,4-diazabicyclo[3.2.1]octan-4-yl)pyrimidin-5-yl)oxy)-6-(3,5-dichlorophenyl)pyridin-4-yl)methyl)piperidin-4-yl)methyl)carbamate;

(1R,7S,8r)-4-((2-((2-(1,4-diazabicyclo[3.2.1]octan-4-yl)pyrimidin-5-yl)oxy)-6-(3,5-dichlorophenyl)pyridin-4-yl)methyl)-4-azabicyclo[5.1.0]octane-8-carboxylic acid;

4-(5-((6-(3,5-dichlorophenyl)-4-((4-fluoropiperidin-1-yl)methyl)pyridin-2-yl)oxy)pyrimidin-2-yl)-1,4-diazabicyclo[3.2.1]octane;

2-(1-((2-(3,5-dichlorophenyl)-6-((5-(4-methylpiperazin-1-yl)pyrazin-2-yl)oxy)pyridin-4-yl)methyl)piperidin-4-yl)acetic acid;

2-(1-((2-(3,5-dichlorophenyl)-6-((5-(4-methyl-1,4-diazepan-1-yl)pyrazin-2-yl)oxy)pyridin-4-yl)methyl)piperidin-4-yl)acetic acid;

4-(4-(5-((6-(3,5-dichlorophenyl)-4-((4-(2-hydroxyethyl)piperidin-1-yl)methyl)pyridin-2-yl)oxy)pyrazin-2-yl)piperazin-1-yl)-2-methylbutanoic acid;

2-(1-((2-(3,5-dichlorophenyl)-6-((5-(piperazin-1-yl)pyrazin-2-yl)oxy)pyridin-4-yl)methyl)piperidin-4-yl)ethanol;

2-(1-((2-(3,5-dichlorophenyl)-6-((5-(4-(2-hydroxy-2-methylpropyl)piperazin-1-yl)pyrazin-2-yl)oxy)pyridin-4-yl)methyl)piperidin-4-yl)acetic acid;

2-(1-((2-((6-(1,4-diazabicyclo[3.2.1]octan-4-yl)pyridazin-3-yl)oxy)-6-(3,5-dichlorophenyl)pyridin-4-yl)methyl)piperidin-4-yl)acetic acid;

2-(1-((2-(3,5-dichlorophenyl)-6-((5-(4-ethyl-1,4-diazepan-1-yl)pyrazin-2-yl)oxy)pyridin-4-yl)methyl)piperidin-4-yl)acetic acid;

2-(1-((2-(3,5-dichlorophenyl)-6-((5-((1S,4S)-5-methyl-2,5-diazabicyclo[2.2.1]heptan-2-yl)pyrazin-2-yl)oxy)pyridin-4-yl)methyl)piperidin-4-yl)acetic acid;

2-(1-((2-(3,5-dichlorophenyl)-6-((5-(4-isopropylpiperazin-1-yl)pyrazin-2-yl)oxy)pyridin-4-yl)methyl)piperidin-4-yl)acetic acid;

2-(1-((2-((5-(1,4-diazabicyclo[3.2.1]octan-4-yl)pyrazin-2-yl)oxy)-6-(3,5-dichlorophenyl)pyridin-4-yl)methyl)piperidin-4-yl)acetic acid;

2-(1-((2-(3,5-dichlorophenyl)-6-((5-(4-(3-hydroxybutyl)piperazin-1-yl)pyrazin-2-yl)oxy)pyridin-4-yl)methyl)piperidin-4-yl)acetic acid;

2-(1-((2-(3,5-dichlorophenyl)-6-((5-(4-methylpiperazin-1-yl)pyrazin-2-yl)oxy)pyridin-4-yl)methyl)piperidin-4-yl)ethanol;

3-(1-((2-(3,5-dichlorophenyl)-6-((5-(4-methyl-1,4-diazepan-1-yl)pyrazin-2-yl)oxy)pyridin-4-yl)methyl)piperidin-4-yl)-2-methylpropanoic acid;

2-(1-((2-(3,5-dichlorophenyl)-6-((5-(6-methyl-3,6-diazabicyclo[3.1.1]heptan-3-yl)pyrazin-2-yl)oxy)pyridin-4-yl)methyl)piperidin-4-yl)acetic acid;
1-((1-((2-(3,5-dichlorophenyl)-6-((5-(4-methylpiperazin-1-yl)pyrazin-2-yl)oxy)pyridin-4-yl)methyl)piperidin-4-yl)oxy)cyclopropanecarboxylic acid;
2-(1-((2-(3,5-dichlorophenyl)-6-((5-(4-(3-(methylsulfonyl)propyl)piperazin-1-yl)pyrazin-2-yl)oxy)pyridin-4-yl)methyl)piperidin-4-yl)acetic acid;
2-(1-((2-(3,5-dichlorophenyl)-6-((6-(4-ethyl-1,4-diazepan-1-yl)pyridazin-3-yl)oxy)pyridin-4-yl)methyl)piperidin-4-yl)acetic acid;
2-(1-((2-(3,5-dichlorophenyl)-6-((6-(4-methyl-1,4-diazepan-1-yl)pyridazin-3-yl)oxy)pyridin-4-yl)methyl)piperidin-4-yl)acetic acid;
2-(1-((2-(3,5-dichlorophenyl)-6-((6-((1S,4S)-5-methyl-2,5-diazabicyclo[2.2.1]heptan-2-yl)pyridazin-3-yl)oxy)pyridin-4-yl)methyl)piperidin-4-yl)acetic acid;
2-(1-((2-(3,5-dichlorophenyl)-6-((6-(4-ethylpiperazin-1-yl)pyridazin-3-yl)oxy)pyridin-4-yl)methyl)piperidin-4-yl)acetic acid;
2-(1-((2-(3,5-dichlorophenyl)-6-((6-(4-methylpiperazin-1-yl)pyridazin-3-yl)oxy)pyridin-4-yl)methyl)piperidin-4-yl)acetic acid;
2-(1-((2-(3,5-dichlorophenyl)-6-((6-(4-methylpiperazin-1-yl)pyridazin-3-yl)oxy)pyridin-4-yl)methyl)piperidin-4-yl)ethanol;
(1R,7S,8r)-4-((2-(3,5-dichlorophenyl)-6-((6-(4-methylpiperazin-1-yl)pyridazin-3-yl)oxy)pyridin-4-yl)methyl)-4-azabicyclo[5.1.0]octane-8-carboxylic acid;
(1R,7S,8r)-4-((2-(3,5-dichlorophenyl)-6-((6-(4-methyl-1,4-diazepan-1-yl)pyridazin-3-yl)oxy)pyridin-4-yl)methyl)-4-azabicyclo[5.1.0]octane-8-carboxylic acid;
3-(4-(6-((4-((4-(acetamidomethyl)piperidin-1-yl)methyl)-6-(3,5-dichlorophenyl)pyridin-2-yl)oxy)pyridazin-3-yl)piperazin-1-yl)-2-methylpropanoic acid;
(R)-3-(1-((2-(3,5-dichlorophenyl)-6-((6-(4-methylpiperazin-1-yl)pyridazin-3-yl)oxy)pyridin-4-yl)methyl)piperidin-4-yl)-2-methylpropanoic acid;
(S)-3-(1-((2-(3,5-dichlorophenyl)-6-((6-(4-methylpiperazin-1-yl)pyridazin-3-yl)oxy)pyridin-4-yl)methyl)piperidin-4-yl)-2-methylpropanoic acid;
2-(1-((2-(3,5-dichlorophenyl)-6-((6-((1S,4S)-5-ethyl-2,5-diazabicyclo[2.2.1]heptan-2-yl)pyridazin-3-yl)oxy)pyridin-4-yl)methyl)piperidin-4-yl)acetic acid;
3-(4-(5-((4-(((1R,7S,8r)-8-acetamido-4-azabicyclo[5.1.0]octan-4-yl)methyl)-6-(3,5-dichlorophenyl)pyridin-2-yl)oxy)pyrimidin-2-yl)piperazin-1-yl)propanoic acid;
methyl 4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-methylbutanoate;
4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2-methylbutanoic acid;
4-(4-(5-((4-((4-(acetamidomethyl)piperidin-1-yl)methyl)-6-(3,5-dichlorophenyl)pyridin-2-yl)oxy)pyrimidin-2-yl)piperazin-1-yl)-2,2-dimethylbutanoic acid;
2-(1-((6-(3,5-dichlorophenyl)-3-methyl-2-((6-(4-methylpiperazin-1-yl)pyridazin-3-yl)oxy)pyridin-4-yl)methyl)piperidin-4-yl)acetic acid;
N-((1-((2-(3-chloro-5-fluorophenyl)-6-((2-(4-(4-(methylsulfonyl)butan-2-yl)piperazin-1-yl)pyrimidin-5-yl)oxy)pyridin-4-yl)methyl)piperidin-4-yl)methyl) acetamide;
1-((1-((2-(3-chloro-5-fluorophenyl)-6-((2-(4-(4-(methylsulfonyl)butan-2-yl)piperazin-1-yl)pyrimidin-5-yl)oxy)pyridin-4-yl)methyl)piperidin-4-yl)methyl)-3-methylurea;
2-(1-((2-(3-chloro-5-fluorophenyl)-6-((2-(4-methyl-1,4-diazepan-1-yl)pyrimidin-5-yl)oxy)pyridin-4-yl)methyl)piperidin-4-yl)acetic acid;
2-(1-((2-(3,5-dichlorophenyl)-6-(isopropyl(2-(4-methylpiperazin-1-yl)pyrimidin-5-yl)amino)pyridin-4-yl)methyl)piperidin-4-yl)acetic acid;
2-(1-((3',5'-dichloro-4-fluoro-5-((2-(4-methylpiperazin-1-yl)pyrimidin-5-yl)oxy)-[1,1'-biphenyl]-3-yl)methyl)piperidin-4-yl)acetic acid;
2-(1-((6-(3,5-dichlorophenyl)-3-fluoro-2-((6-(4-methylpiperazin-1-yl)pyridin-3-yl)oxy)pyridin-4-yl)methyl)piperidin-4-yl)acetic acid;
2-(1-((6-(3,5-dichlorophenyl)-3-fluoro-2-((2-(8-methyl-3,8-diazabicyclo[3.2.1]octan-3-yl)pyrimidin-5-yl)oxy)pyridin-4-yl)methyl)piperidin-4-yl)acetic acid;
2-(1-((6-(3,5-dichlorophenyl)-3-fluoro-2-((2-(4-methylpiperazin-1-yl)pyrimidin-5-yl)oxy)pyridin-4-yl)methyl)piperidin-4-yl)acetic acid;
2-(1-((6-(3,5-dichlorophenyl)-3-fluoro-2-((4-methyl-2-(4-methylpiperazin-1-yl)pyrimidin-5-yl)oxy)pyridin-4-yl)methyl)piperidin-4-yl)acetic acid;
4-(4-(5-((4-((4-(acetamidomethyl)piperidin-1-yl)methyl)-6-(3,5-dichlorophenyl)-3-fluoropyridin-2-yl)oxy)pyrimidin-2-yl)piperazin-1-yl)-2-methylbutanoic acid;
2-(1-((2-((2-(3,8-diazabicyclo[3.2.1]octan-3-yl)pyrimidin-5-yl)oxy)-6-(3,5-dichlorophenyl)-3-fluoropyridin-4-yl)methyl)piperidin-4-yl)acetic acid;
2-(1-((6-(3,5-dichlorophenyl)-3-fluoro-2-((2-methyl-6-(4-methylpiperazin-1-yl)pyridin-3-yl)oxy)pyridin-4-yl)methyl)piperidin-4-yl)acetic acid;
2-(1-((6-(3,5-dichlorophenyl)-3-fluoro-2-((6-(4-methylpiperazin-1-yl)pyridazin-3-yl)oxy)pyridin-4-yl)methyl)piperidin-4-yl)acetic acid;
methyl 3-(4-(5-((4-((4-(acetamidomethyl)piperidin-1-yl)methyl)-6-(3,5-dichlorophenyl)pyridin-2-yl)oxy)pyridin-2-yl)piperazin-1-yl)propanoate;
2-(1-((6-(3,5-dichlorophenyl)-3-methyl-2-((6-(4-methylpiperazin-1-yl)pyridin-3-yl)oxy)pyridin-4-yl)methyl)piperidin-4-yl)acetic acid;
2-(1-((2-((2-(4-((1H-1,2,3-triazol-5-yl)methyl)piperazin-1-yl)pyrimidin-5-yl)oxy)-6-(3,5-dichlorophenyl)pyridin-4-yl)methyl)piperidin-4-yl)acetic acid;
2-(1-((2-(3,5-dichlorophenyl)-6-(methyl(2-(4-methylpiperazin-1-yl)pyrimidin-5-yl)amino)pyridin-4-yl)methyl)piperidin-4-yl)acetic acid;
2-(1-((2-(3,5-dichlorophenyl)-6-(ethyl(2-(4-methylpiperazin-1-yl)pyrimidin-5-yl)amino)pyridin-4-yl)methyl)piperidin-4-yl)acetic acid;
2-(1-((6-(3,5-dichlorophenyl)-3-fluoro-2-((5-(4-methylpiperazin-1-yl)pyrazin-2-yl)oxy)pyridin-4-yl)methyl)piperidin-4-yl)acetic acid;
3-(4-(5-((4-((4-(acetamidomethyl)piperidin-1-yl)methyl)-6-(3,5-dichlorophenyl)pyridin-2-yl)oxy)pyrazin-2-yl)piperazin-1-yl)propanamide;
4-(4-(5-((6-(3,5-dichlorophenyl)-4-((4-(propionamidomethyl)piperidin-1-yl)methyl)pyridin-2-yl)oxy)pyrazin-2-yl)piperazin-1-yl)-2-methylbutanoic acid;
N-((1-((2-(3,5-dichlorophenyl)-6-((5-(4-(1-hydroxypropan-2-yl)piperazin-1-yl)pyrazin-2-yl)oxy)pyridin-4-yl)methyl)piperidin-4-yl)methyl)acetamide;

1-((1-((2-(3,5-dichlorophenyl)-6-((5-(4-methylpiperazin-1-yl)pyrazin-2-yl)oxy)pyridin-4-yl)methyl)piperidin-4-yl)methyl)-3-methylurea;

methyl ((1-((2-(3,5-dichlorophenyl)-6-((5-(4-methylpiperazin-1-yl)pyrazin-2-yl)oxy)pyridin-4-yl)methyl)piperidin-4-yl)methyl)carbamate;

4-(4-(5-((4-((4-(acetamidomethyl)piperidin-1-yl)methyl)-6-(3,5-dichlorophenyl)pyridin-2-yl)oxy)pyrazin-2-yl)piperazin-1-yl)-2-methylbutanoic acid;

(1R,7S,8r)-4-((2-(3,5-dichlorophenyl)-6-((2-(4-methyl-1,4-diazepan-1-yl)pyrimidin-5-yl)oxy)pyridin-4-yl)methyl)-4-azabicyclo[5.1.0]octane-8-carboxylic acid;

2-(1-((2-(3,5-dichlorophenyl)-6-((2-(8-methyl-3,8-diazabicyclo[3.2.1]octan-3-yl)pyrimidin-5-yl)oxy)pyridin-4-yl)methyl)piperidin-4-yl)acetic acid; and 2-(1-((2-(3,5-dichlorophenyl)-6-((2-(6-fluoro-1,4-diazepan-1-yl)pyrimidin-5-yl)oxy)pyridin-4-yl)methyl)piperidin-4-yl)acetic acid;

and pharmaceutically acceptable salts thereof.

16. A pharmaceutical composition comprising the compound or pharmaceutically acceptable salt thereof according to claim 1, and a pharmaceutically acceptable excipient.

17. A method of treating pulmonary fibrosis comprising administering to a human in need thereof a therapeutically effective amount of the compound or pharmaceutically acceptable salt thereof according to claim 1.

18. A compound which is: N-((1-((2-(3,5-Dichlorophenyl)-6-((6-(piperazin-1-yl)pyridin-3-yl)oxy)pyrimidin-4-yl)methyl)piperidin-4-yl)methyl)acetamide, or a salt thereof.

19. The compound of claim 1, of the formula:

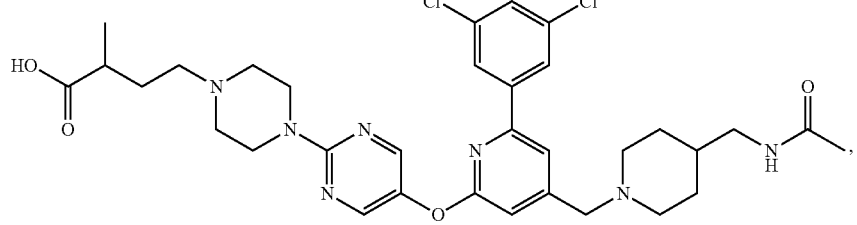

or a pharmaceutically acceptable salt thereof.

20. The compound of claim 1, of the formula:

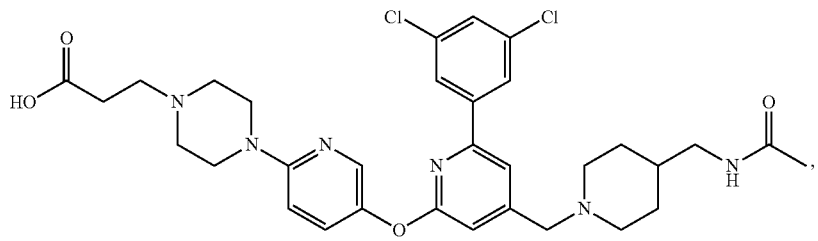 [SMILES: CC(=O)NCC1CCN(Cc2cc(Oc3ccc(N4CCN(CCC(=O)O)CC4)nc3)nc(-c3cc(Cl)cc(Cl)c3)c2)CC1]

or a pharmaceutically acceptable salt thereof.

21. A method of treating cystic fibrosis comprising administering to a human in need thereof a therapeutically effective amount of the compound or pharmaceutically acceptable salt thereof according to claim 1.

22. A method of treating cystic fibrosis comprising administering to a human in need thereof a therapeutically effective amount of the compound or pharmaceutically acceptable salt thereof according to claim 18.

* * * * *

SEQUENCE LISTING

```
<160> NUMBER OF SEQ ID NOS: 3

<210> SEQ ID NO 1
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Modified by FAM
<220> FEATURE:
<221> NAME/KEY: MISC_FEATURE
<222> LOCATION: (11)..(11)
<223> OTHER INFORMATION: Modified by TAMRA
```

```
<400> SEQUENCE: 1

Gln Arg Val Arg Arg Ala Val Gly Ile Asp Lys
1               5                   10

<210> SEQ ID NO 2
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Modified by decanoyl
<220> FEATURE:
<221> NAME/KEY: MISC_FEATURE
<222> LOCATION: (4)..(4)
<223> OTHER INFORMATION: Modified by chloromethylketone

<400> SEQUENCE: 2

Arg Val Arg Lys
1

<210> SEQ ID NO 3
<211> LENGTH: 22
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Modified by GalNAc-T2
<220> FEATURE:
<221> NAME/KEY: MISC_FEATURE
<222> LOCATION: (22)..(22)
<223> OTHER INFORMATION: Modified by GFP

<400> SEQUENCE: 3

Gly Gly Gly Gly Ser Asp Ser Thr Ala Arg Ile Arg Arg Asn Ala Lys
1               5                   10                  15

Gly Gly Gly Gly Gly Ser
            20
```